US008669066B2

(12) United States Patent
Moyer et al.

(10) Patent No.: US 8,669,066 B2
(45) Date of Patent: Mar. 11, 2014

(54) RATIONALE, METHODS, AND ASSAYS FOR IDENTIFYING HUMAN AND NON-HUMAN PRIMATE TASTE SPECIFIC GENES AND USE THEREOF IN TASTE MODULATOR AND THERAPEUTIC SCREENING ASSAYS

(75) Inventors: Bryan Moyer, San Deigo, CA (US); Albert Zlotnik, San Deigo, CA (US); Peter Hevezi, Encinitas, CA (US); Hortensia Soto, San Diego, CA (US); Dalia Kalabat, El Cajon, CA (US); Min Lu, San Diego, CA (US); Na Gao, San Diego, CA (US); Evan Carl White, Fair Oaks, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

(21) Appl. No.: 13/090,335

(22) Filed: Apr. 20, 2011

(65) Prior Publication Data

US 2011/0281753 A1 Nov. 17, 2011

Related U.S. Application Data

(62) Division of application No. 12/134,302, filed on Jun. 6, 2008, now Pat. No. 7,932,058.

(60) Provisional application No. 60/929,017, filed on Jun. 8, 2007, provisional application No. 60/929,007, filed on Jun. 8, 2007, provisional application No. 60/947,052, filed on Jun. 29, 2007, provisional application No. 60/935,297, filed on Aug. 3, 2007, provisional application No. 60/987,611, filed on Nov. 13, 2007, provisional application No. 60/988,938, filed on Nov. 19, 2007, provisional application No. 60/991,274, filed on Nov. 30, 2007, provisional application No. 60/991,289, filed on Nov. 30, 2007, provisional application No. 60/992,502, filed on Dec. 5, 2007, provisional application No. 60/992,517, filed on Dec. 5, 2007, provisional application No. 61/017,244, filed on Dec. 28, 2007, provisional application No. 61/021,437, filed on Jan. 16, 2008, provisional application No. 61/043,257, filed on Apr. 8, 2008, provisional application No. 61/053,310, filed on May 10, 2008.

(51) Int. Cl.
*G01N 33/567* (2006.01)
*C12Q 1/68* (2006.01)
*C07K 14/705* (2006.01)

(52) U.S. Cl.
USPC .......................... 435/7.21; 435/6.17; 436/501

(58) Field of Classification Search
None
See application file for complete search history.

(56) References Cited

U.S. PATENT DOCUMENTS

| | | | |
|---|---|---|---|
| 6,524,798 B1 | 2/2003 | Goldbard et al. | |
| 2005/0037369 A1 | 2/2005 | Neote et al. | |
| 2005/0048586 A1 | 3/2005 | Zuker et al. | |
| 2005/0177886 A1 | 8/2005 | Margolskee et al. | |
| 2005/0221394 A1 | 10/2005 | Wood et al. | |
| 2006/0089306 A1 | 4/2006 | Wallace et al. | |
| 2006/0223117 A1 | 10/2006 | Moyer et al. | |
| 2007/0071757 A1 | 3/2007 | Yu et al. | |
| 2007/0099251 A1 | 5/2007 | Zhang et al. | |

FOREIGN PATENT DOCUMENTS

WO 2007146120 A2 12/2007

OTHER PUBLICATIONS

LopezJimenez et al., Two novel genes, Gpr113, which encodes a family 2 G-protein-coupled receptor, and Trcg1, are selectively expressed in taste receptor cells, Apr. 2005, Genomics 85(4):472-482.*

Li et al., Expression and localization of amiloride-sensitive sodium channel indicate a role for non-taste cells in taste perception, Proc. Natl. Acad. Sci., vol. 91, No. 5, (1994), pp. 1814-1818.

* cited by examiner

*Primary Examiner* — John Ulm

(74) *Attorney, Agent, or Firm* — LeClairRyan, a Professional Corporation; Robin L. Teskin

(57) ABSTRACT

This invention relates to novel rationale and methods for identifying human and primate taste-specific genes, including genes involved in salty taste perception, especially human salty taste perception, but also genes involved in sweet, bitter, umami, and sour taste perception, and genes involved in other taste cell or taste receptor related activities such as digestive function and digestive related diseases, taste cell turnover, immunoregulation of the oral and digestive tract, and metabolic regulation such as in diabetes and obesity, the genes identified using these methods, and assays for identifying taste modulators (enhancers or blockers) and potential therapeutics using these genes. These compounds have potential application in modulating (enhancing or blocking) taste perception, especially salty taste perception and as potential therapeutics. In addition, this invention relates to novel methods for identifying taste-specific genes that can be used as markers for different taste cell types, including sweet, bitter, umami, sour, salty, and other taste cells in mammals as well as assays that measure the activity of the sweet, bitter, umami, or sour receptor in the presence of these genes to identify modulators of sweet, bitter, umami, and sour taste and to identify therapeutics especially for treating digestive or metabolic disorders, taste loss, and oral infections. Particularly, the genes identified herein and antibodies or oligos thereto can be used as markers to identify and/or purify specific taste cells e.g., from taste cell suspensions by use of FACS or magnetic bead cell selection or other known cell purification and isolation procedures.

9 Claims, 47 Drawing Sheets

SEQUENCE LISTING

<160> NUMBER OF SEQ ID NOS: 105

<210> SEQ ID NO 1
<211> LENGTH: 5311
<212> TYPE: DNA
<213> ORGANISM: Homo sapiens

<400> SEQUENCE: 1
agcataacct tcggtggcag gacaaatcag gccagcacgc agtctgccaa gtcctgctcg 60
ctccctgtca agaaaaacag ctggatccat ttctaatcaa cacttcccaa cgcaacactt 120
ctgagtctct gaaggagacc agagcttgaa actttccaga cttccaacag acatcgagtg 180
caaaaggata tttaggttgt ctttgcacaa atctggttga tttgagagat aaagggggg 240

-continued

```
ggaaccagtg tgactttcac ctaagaagtc acatgaacat atttcacatt tgaactacat    300
aatgaatgat ggttattgaa atagcccaaa cctctaccac agagcgaggg atatagctca    360
aggggcaacc aggcagtcgc agaaccaagg aatggatgac tacaagtatc aggacaatta    420
tgggggctat gctcccagtg atggctatta ccgcggcaat gagtccaacc cagaagaaga    480
tgcacagagt gatgtcaccg aaggccatga tgaggaagac gagatctatg agggcgagta    540
ccagggtatc cctcacccag atgatgtcaa ggccaagcag gccaagatgg cgccctccag    600
aatggacagc cttcggggcc agacagacct gatggctgag aggctggaag atgaggagca    660
gttggcccac cagtacgaga ccatcatgga tgagtgtggc catggccgct tccagtggat    720
cctctttttc gtcttgggtt tggccctgat ggccgatggg gtggaagtgt tcgtggtgag    780
ttttgccctg cccagtgcag agaaggacat gtgtctgtcc agttccaaaa aaggaatgct    840
agggatgata gtctacttgg gaatgatggc gggcgccttc atcctgggag gcctggctga    900
taagctggga aggaagcgag tcctcagcat gtctctggcc gtcaatgcct ccttcgcctc    960
cctctcttcc ttcgtgcagg gatatggagc cttcctcttc tgccgactca tctcaggcat   1020
cggtattggg ggtgctctac cgattgtttt tgcctatttt tctgaattct tgtctcggga   1080
gaagcgagga gaacacctca gttggctggg catcttctgg atgactgggg gcctgtacgc   1140
atctgccatg gcctggagca tcatcccaca ctatggctgg ggcttcagca tggggaccaa   1200
ttaccacttc catagctgga gagtgtttgt catcgtctgt gctctgccct gcaccgtgtc   1260
catggtggcc ctgaagttca tgccagagag cccaaggttt ctgctagaga tgggcaaaca   1320
tgatgaagcc tggatgattc tcaagcaagt ccatgacacc aacatgagag ctaaggggac   1380
cccagagaaa gtgttcacgg tttccaacat caaaactccc aagcaaatgg atgaattcat   1440
tgagatccaa agttcaacag gaacctggta ccagcgctgg ctggtcagat tcaagaccat   1500
tttcaagcag gtctgggata atgccctgta ctgtgtgatg gggccctaca gaatgaatac   1560
actgattctg gccgtggttt ggtttgccat ggcattcagt tactatggac tgacagtttg   1620
gtttcctgat atgatccgct attttcaaga tgaagaatac aagtctaaaa tgaaggtgtt   1680
ttttggtgag catgtgtacg gcgccacaat caacttcacg atggaaaatc agatccacca   1740
acatgggaaa cttgtgaatg ataagttcac aagaatgtac tttaaacatg tactctttga   1800
ggacacattc tttgacgagt gctattttga agacgtaaca tcaacagata cctacttcaa   1860
aaattgtacc attgaatcaa ccatctttta caacacagac ctctacgagc acaagttcat   1920
caactgtcgg tttatcaact ccaccttcct ggagcagaag gagggctgcc acatggactt   1980
ggagcaagat aatgacttcc tgatttacct cgtcagcttc ctgggcagcc tgtctgtctt   2040
acccgggaac atcatttctg ccctgctcat ggatagaatt ggaaggctca agatgattgg   2100
tggctccatg ctaatctctg cagtctgctg cttcttcctg ttttttggca acagtgagtc   2160
tgcaatgatc ggctggcagt gcctgttctg tgggacaagc attgcagcct ggaatgctct   2220
ggatgtgatc acagtggagc tgtatcccac caaccagaga gcaacagcct tcggcattct   2280
caatggatta tgcaaatttg gcgccatcct gggaaacacc atctttgctt cttttgttgg   2340
gataaccaaa gtggtcccca tccttctggc tgctgcttct ctggttgggg gtggcctgat   2400
tgcccttcga ctgccagaga ctcgagaaca ggtcctgatg tgaacaacct atgggaaaag   2460
gaaaggtcga gagaatcttg tccaggacac tgaaatgcat ccacacttcc tgcctatcac   2520
ggtccggagg acaccttgga tagcacggga ggagaagttg actttgtgac ccctagttta   2580
ggacccactt cagctgtcaa tatgtttgta actcaggtga ctgatttggg ggtgccctga   2640
```

-continued

```
gccacccctta gaatcacaga gctgcgtgtt taacttcaag tcttcccagt ccaaggcagg   2700
gagaggattc tccagtgagt gcacacacta tgcgaggagc aagcatttct ctaagtcaag   2760
tgcaaggact taacttgcgt ttgaaaagga attagagggt cagaaacacc caggttcctc   2820
cagaaagctc cttggagccc aacaacttaa caaatcaact tggctggaag ttagagtcat   2880
tatatgaaga ttgggcttga agtatatatt tttgcattta aaagtatcac ctatcatatt   2940
ttccactcga aaattgacat agtagcattg aggatactct gatctagaaa gccaagtatt   3000
tgagcaacat ctatagagat ctacttttct cctatgtctc ctaggctttc catgataatt   3060
aggtaataca tttaagaagg atatttattt ctgttttgct ctattcaaag aaacggaatg   3120
ggatagttat tctgtaaact aagtttgtat ataactttat ttgggtttaa tttccacaac   3180
tggtatctgc aaatattgcc agcattttag ccatattttg ggagaacttg gtgtttgagg   3240
tcccaggaaa tgaggtctga tcaaatgaaa tgcaagcaca atttcttaca gccatttaac   3300
tttctgttgg gaggatgaat taacaaactc acattgtgca gtctgcttaa tccaggcact   3360
tttctttgtg caggtgtagt gagtagttac ttctctccct tacacagatg acttgtgaaa   3420
ctcaagctca ccatcttcag tgctggcatt ttactttgcc actacccaaa aacaatgtga   3480
gatgtgttca gtggcctctg gtactctttg caggcaagaa tcaaacaaca tggggactga   3540
gggaaggatg gggaagtgta gccacagttc ttccaaatgt aaatactttt tgtttgttct   3600
agtggtaaaa tgcaaatgca atccatattt gttaggatgg tcaggtctca tgagaaatct   3660
atgctatgtg tccagagctt ttgaaacaga gtccattgga gtgggagtta gggagtgtag   3720
tggatgccaa atatgttttt cttcagtgct taagagaact gtttcctgaa gtccagcttt   3780
gaacataaac aggggtgtgg gttgggggag gagcttagga caaacctctc tgatgaaggt   3840
cagcaataga ctgaagtctt gactgcatgg aagaggaaaa acatcagaac tgtctgacaa   3900
tggaggggac agtgagctac gcacaactgc cagcggaggt gaacttgcac ctgcccaggc   3960
cggatgaaca tcagcctgca agaactagtt gtttgagttg atttgcagtg ctctcaatgg   4020
gcaagtgcca cattttccct ggcagagatc tccaaaaatt taaaacagaa taataatggc   4080
tatatcgagt gttttctcag tattggagaa atgcttaggt cctatgatag cttcgggaca   4140
tctttctgta attttcctca attaacgggt tggtaggggt aaatcttatg acacctttcc   4200
accgtcgatt tgagatcagt tttaatggtt aaaatgttta ctctccttct gtcaaccctc   4260
acctttttat ttacacccct cccttttttt ctgtacaggg agagaagaca tattgactct   4320
gactggacac cctgattcct ccaaatatat ataccactgt gtattaatct ttctctcagt   4380
gttttatagg agtactaaca tttattgctc tgtcaataat gaaaggctcg atgtaatata   4440
gctgtaattt actttccata tgaatacagt ggctaggttc ataaaagaga attgtgtgag   4500
tctgggatta ccacatctaa aacattattc tttaatggga taatacaatt cattgagcag   4560
ctaccactta aaaaacttgc aggacagtta gagcctgcat ttctagttaa gatggatctt   4620
gtaaatttaa aattggatta acattggagt gctggggtgg ctgcaataat ttgggggcta   4680
actccatttg gtttccaaga tctcacttct gcattatctt tatggctctt taaaccagcc   4740
acctagccaa tcaagggcaa ttcccatctc atccatcact caggtctttg taaagggtgc   4800
agccaagctc tgcagacttt tgcaggattg tctagcctga gtaccgggct acttcttaaa   4860
tgccgtcact cctgctgaga taaatgcgtc tttaaaaata gtctctgtgg caggtcactg   4920
ggggacaatg tacagcattc tggccatcca cttctttttc acttcatgtt ctaccccaag   4980
agactcccga tgtcggctgt ggagggttaa agggatgagg ctttcctttg tttagcaaat   5040
```

ctgttcacag ttcttgatga tgtattttat gatgcccagc ttggaaatag ttgctttcca 5100
tagtctcaac tgtattgtgt catctcctga tgctgatttt tgatcttttg ttttattaaa 5160
aataattagt gaaagaggtg tgcctatctg tgaagtttgt agtacatcat cctgaggtca 5220
tgtaacaagt aaaccccaac ccagcgttcc ctcctacgtt gtgttagttc attaaaacta 5280
aataataaaa ataactgtaa gaaaacctta a 5311

<210> SEQ ID NO 2
<211> LENGTH: 2482
<212> TYPE: DNA
<213> ORGANISM: Homo sapiens

<400> SEQUENCE: 2
cttctggcca gggaacgtgg aaggcgcacc gacagggatc cggccaggga gggcgagtga 60
aagaaggaaa tcagaaagga agggagttaa caaaataata aaaacagcct gagccacggc 120
tggagagacc gagacccggc gcaagagagc gcagccttag taggagagga acgcgagacg 180
cggcagagcg cgttcagcac tgacttttgc tgctgcttct gcttttttttt ttcttagaaa 240 caagaaggcg ccagcggcag cctcacacgc gagcgccacg cgaggctccc gaagccaacc 300
cgcgaaggga ggaggggagg gaggaggagg cggcgtgcag ggaggagaaa aagcattttc 360
actttttttg ctcccactct aagaagtctc ccggggattt tgtatatatt ttttaacttc 420
cgtcagggct cccgcttcat atttcctttt ctttccctct ctgttcctgc acccaagttc 480
tctctgtgtc cccctcgcgg gccccgcacc tcgcgtcccg gatcgctctg attccgcgac 540
tccttggccg ccgctgcgca tggaaagctc tgccaagatg gagagcggcg gcgccggcca 600
gcagccccag ccgcagcccc agcagccctt cctgccgccc gcagcctgtt tctttgccac 660
ggccgcagcc gcggcggccg cagccgccgc agcggcagcg cagagcgcgc agcagcagca 720
gcagcagcag cagcagcagc agcaggcgcc gcagctgaga ccggcggccg acggccagcc 780
ctcagggggc ggtcacaagt cagcgcccaa gcaagtcaag cgacagcgct cgtcttcgcc 840
cgaactgatg cgctgcaaac gccggctcaa cttcagcggc tttggctaca gcctgccgca 900
gcagcagccg gccgccgtgg cgcgccgcaa cgagcgcgag cgcaaccgcg tcaagttggt 960
caacctgggc tttgccaccc ttcgggagca cgtccccaac ggcgcggcca acaagaagat 1020
gagtaaggtg gagacactgc gctcggcggt cgagtacatc cgcgcgctgc agcagctgct 1080
ggacgagcat gacgcggtga gcgccgcctt ccaggcaggc gtcctgtcgc ccaccatctc 1140 cccaactac tccaacgact tgaactccat ggccggctcg ccggtctcat cctactcgtc 1200
ggacgagggc tcttacgacc cgctcagccc cgaggagcag gagcttctcg acttcaccaa 1260
ctggttctga ggggctcggc ctggtcaggc cctggtgcga atggactttg gaagcagggt 1320
gatcgcacaa cctgcatctt tagtgctttc ttgtcagtgg cgttgggagg gggagaaaag 1380
gaaaagaaaa aaaaaagaag aagaagaaga aaagagaaga agaaaaaaac gaaaacagtc 1440
aaccaacccc atcgccaact aagcgaggca tgcctgagag acatggcttt cagaaaacgg 1500
gaagcgctca gaacagtatc tttgcactcc aatcattcac ggagatatga agagcaactg 1560
ggacctgagt caatgcgcaa aatgcagctt gtgtgcaaaa gcagtgggct cctggcagaa 1620
gggagcagca cacgcgttat agtaactccc atcacctcta acacgcacag ctgaaagttc 1680
ttgctcgggt cccttcacct ccccgccctt tcttaaagtg cagttcttag ccctctagaa 1740
acgagttggt gtctttcgtc tcagtagccc ccacccccaat aagctgtaga cattggttta 1800
cagtgaaact atgctattct cagccctttg aaactctgct tctcctccag ggcccgattc 1860

-continued

```
ccaaacccca tggcttccct cacactgtct tttctaccat tttcattata gaatgcttcc   1920

aatcttttgt gaatttttta ttataaaaaa tctatttgta tctatcctaa ccagttcggg   1980

gatatattaa gatatttttg tacataagag agaaagagag agaaaaattt atagaagttt   2040

tgtacaaatg gtttaaaatg tgtatatctt gatactttaa catgtaatgc tattacctct   2100

gcatatttta gatgtgtagt tcaccttaca actgcaattt tccctatgtg gttttgtaaa   2160

gaactctcct cataggtgag atcaagaggc caccagttgt acttcagcac caatgtgtct   2220

tactttatag aaatgttgtt aatgtattaa tgatgttatt aaatactgtt caagaagaac   2280

aaagtttatg cagctactgt ccaaactcaa agtggcagcc agttggtttt gataggttgc   2340

cttttggaga tttctattac tgcctttttt ttcttactgt tttattacaa acttacaaaa   2400

atatgtataa ccctgtttta tacaaactag tttcgtaata aaactttttc cttttttttaa  2460

aatgaaaaaa aaaaaaaaaa aa                                             2482


<210> SEQ ID NO 3
<211> LENGTH: 1872
<212> TYPE: DNA
<213> ORGANISM: Homo sapiens

<400> SEQUENCE: 3

gttagattag tctgaagccg ccaccagccc caggcccccg tgcagaagaa aagcgggagg     60

gaacggcgga ggccgccgct gccctgcacc gccctcctgg aggccacttg gagagtccgg    120

ccccgaggag gccatggcca caagtgccca cagctggccc caggttgcca gcgtcgctac    180

agcccagacc aaggcagaat aatctccgga tgagctggtg gcaccgctga gcctttggtc    240

tcaccagggc ttcctgttgc tggcaggcgg ggtggagcgg agctgctggg aggctgctgg    300

ataggagagg ggtcacggct gcggaagagg aggttcttcg ggacacccgt ggatggacac    360

ggcaaggaaa caccaggcca accacagctg ggataaaat agcacaacca caccctgccg     420

tccagcgcct cccagcctgt gccccttcct agtaccacca gcaaccatca atcccgtctc    480

ctcctgcctc ctctcctgca atccaccccg ccacgactat cgccatggca gccctgatcg    540

cagagaactt ccgcttcctg tcacttttct tcaagagcaa ggatgtgatg attttcaacg    600

gcctggtggc actgggcacg gtgggcagcc aggagctgtt ctctgtggtg gccttccact    660

gcccctgctc gccggcccgg aactacctgt acgggctggc ggccatcggc gtgcccgccc    720

tggtgctctt catcattggc atcatcctca acaaccacac ctggaacctc gtggccgagt    780

gccagcaccg gaggaccaag aactgctccg ccgcccccac cttcctcctt ctaagctcca    840

tcctgggacg tgcggctgtg gcccctgtca cctggtctgt catctccctg ctgcgtggtg    900

aggcttatgt ctgtgctctc agtgagttcg tggacccttc ctcactcacg gccagggaag    960

agcacttccc atcagcccac gccactgaaa tcctggccag gttcccctgc aaggagaacc   1020

ctgacaacct gtcagacttc cgggaggagg tcagccgcag gctcaggtat gagtcccagc   1080

tctttggatg gctgctcatc ggcgtggtgg ccatcctggt gttcctgacc aagtgcctca   1140

agcattactg ctcaccactc agctaccgcc aggaggccta ctgggcgcag taccgcgcca   1200

atgaggacca gctgttccag cgcacggccg aggtgcactc tcgggtgctc gctgccaaca   1260

atgtgcgccg cttctttggc tttgtggcgc tcaacaagga tgatgaggaa ctgattgcca   1320

acttcccagt ggaaggcacg cagccacggc cacagtggaa tgccatcacc ggcgtctact   1380

tgtaccgtga gaaccagggc ctcccactct acagccgcct gcacaagtgg gcccagggtc   1440

tggcaggcaa cggcgcggcc cctgacaacg tggagatggc cctgctcccc tcctaaggag   1500
```

-continued gtgcttccca tgctctttgt aaatggcact acttggtccc aaactgaacc ccactgcttg 1560
ctcacatcca tatcagaagg ggatttttaa aaaactgtta tcttcttggc caggggaaag 1620
gaccacaagg caatctgggg tgtggacaga cccagtagac aatggaagcc cagccagcag 1680
ggccaggtga cagtgaagct caccagtggg ctcctttatg gtactctatg cagttaacat 1740
gtatctagct gcatagggac acccagcgca gcagtgcacc actgggaagt ggcctccagt 1800
gcagcctctg gccttatttt atatatttaa atttttgata aagtttttct tactaaaaaa 1860
aaaaaaaaaa aa 1872

<210> SEQ ID NO 4
<211> LENGTH: 3099
<212> TYPE: DNA
<213> ORGANISM: Homo sapiens

<400> SEQUENCE: 4
ctctgctctg agctctgttg gtcccagcca ggagagcccg agtcatgagg tgggcaccca 60
gtgggcaggg tgggcagcag gggccctctt ggaggcagca gtgagttggg aagaggaggc 120
cgggccccac agcgggcatg atggacaagt tccggatgat cttccagttc ctgcagtcca 180
accaggagtc cttcatgaat ggcatctgtg gcatcatggc cctggccagt gcccagatgt 240
actcggcctt cgacttcaac tgcccctgcc tgccgggcta caatgcggcc tacagcgcgg 300
gcatcctgct ggcgccaccc ctggtgctct ttctgcttgg cctggtcatg aacaacaacg 360
tgtccatgct ggccgaagag tggaagcggc caccgggccg ccgggccaag gaccccgctg 420
tgttgcgcta catgttctgc tccatggccc agcgcgccct catcgcgcct gtcgtctggg 480
tggccgtcac gctactcgac ggcaaatgct tcctctgtgc cttctgcact gccgtgcccg 540
tgagcgcact gggcaacggc agcctggcac ccggccttcc tgcccccgag ctcgcccgcc 600
tgctggcccg ggtgccctgc cctgagatct acgatggcga ctggctgttg gcccgagagg 660
tggccgtgcg ttacctccgc tgcatctccc aggcgctggg ctggtccttc gtgctgctga 720
ccactctgct ggcattcgtg gtgcgctctg tgcggccctg cttcacgcag gccgccttcc 780
tcaagagcaa gtactggtcc cactatatcg acatcgagcg caagctcttc gacgagacgt 840
gcacggagca cgccaaagcc tttgccaagg tctgcatcca gcagttcttc gaggccatga 900
accatgacct ggagctgggt cacaccaacg ggacactggc cacggcccct gcttccgcag 960
ctgcccccac gacccccgat ggtgcggagg aggaaaggga gaagctgcgt ggcatcacgg 1020
atcaaggcac catgaacagg ctgctcacga gctggcacaa atgcaaaccg cctctgcggc 1080
tgggccagga ggagccaccg ctgatgggca acggctgggc tgggggtggg ccccggcctc 1140
cgcgtaagga ggtggccacc tacttcagca aagtgtgagg cgtggccagc tgaagaggca 1200
ggaacgggga tctgagccca cagcccctcc aacccccaaa ccaggtggaa aaaggaaggg 1260
tttcggtgct gggcagtact cccctaggca gatccacact ccgtagcact cgcctgccca 1320
ttggaggcag gaaatttgga gctggaaggg gatctgatgc cttcaggtgt gacactgccc 1380
tggatggccc tagggcagtg ggcccatgag cagtattagt ctaaaggggt cggaactgtc 1440
atggcaggta cagggaccaa tggctcccct ctgcccagcc cttcccaggc tgatgttcac 1500
tgtctcctcc caggttcaac agacatccct gcaccagggt ccaccctcgt ctgtggctgt 1560
tcagtacctc tcttccttta tgctccgggc tcggggagtg ggaatcatca ggcgtctcat 1620
gaagtgggag ccctctgatt tgggcaagcg tgtcgtaggt gagactgggt gtgccggggc 1680
aggtccataa ggacatgaca cacagcctac atggtgtgac acacctgggg tgacaggcga 1740

```
tgagacaaga tgtcagaagc taggttcaca tggaagaggt cagagtgtgt ggtcaccatg   1800

ggggtcatgt gacaattgtc caggtggact gcatgtttat ttagcacaaa ccaagcacaa   1860

aagtcctcct gtagaggggt ctttgaaaaa ccaccttaat acccacgtca catccaggtc   1920

tccaggggaa atcagaccat ccccaaggct tgagaagtta gacacagaag ctgaagtctc   1980

tccatttttc tcaaagaccc cacctcttgg ggatggagtt ctaagaggct aagaggagct   2040

ccaaggctct agcccaggtg ggatgagggt ggaggagagc agtgtaaaga gaaagcagct   2100

cagattccag agtgagacag aactgggtca aatggtgtct ctaccactca caaaccctgt   2160

ccctgggcca gctgcatcac tgcctgtgcc ttcgtttctt catctataca atgaggatga   2220

ggcccccccg gcccgccatc atggggttgc tgtgtgtaaa agcacatggc acatagtagg   2280

cacccagcac agggtggcta atgtatttgt tgatttctga acctaaggac ttccttcctc   2340

ctcccctggg cagggatgag acagcaacac aaacactcga gcttccatct tgttgaggag   2400

gaaacagagg tacagatagg tttctcagca ccgccctcag ctctgagaca taagtcccaa   2460

gcatctaagg attcattttg atcttggcat gattccatcc ttttttatcc atccttccct   2520

ctattcccac ttctggggtc cagtttccct cctcttaatt atttgggagg agttgctcag   2580

atctttgtgg gccaaggtgg gctgggaggg ctcttccagg aggtaggagt tggtatgggc   2640

cctgaagtca gggaggatta ggatgagcaa aaaacaaggt gtatgttggt gggtggcagc   2700

acttccagtg ggaagagaag gcccggaggt atcaggaggt acaaatgtga tgaagagcaa   2760

agctttgggt caggcacacc tgagttcaaa taccagcact gcaggacttg tggccagtca   2820

cccagccact ctaagcctca gtgtgtctgt ctataaaatg gatattagaa gacctgcttg   2880

gccaggcgga gtggctcatg cctgtaatcc cagcacttgg gaggccaagg agggaggatc   2940

acttgagcct gggagttgga gaccagcctg ggcaacatag caagactctg tctctgtaaa   3000

gtaataataa taataataag aagaagaaga agaataaaga gaagatttat aattttaaaa   3060

aaaaaaaaaa aaaaaaaaaa aagaaaaaaa aaaaaaaaa                          3099
```

<210> SEQ ID NO 5
<211> LENGTH: 5917
<212> TYPE: DNA
<213> ORGANISM: Homo sapiens

<400> SEQUENCE: 5

```
agtgctgcgg ctgcctagtt gacgcaccca ttgagtcgct ggcttctttg cagcgcttca     60

gcgttttccc ctggagggcg cctccatcct tggaggccta gtgccgtcgg agagagagcg    120

ggagccgcgg acagagacgc gtgcgcaatt cggagccgac tctgggtgcg gactgtggga    180

gctgactctg ggtagccggc tgcgcgtggc tggggaggcg aggccggacg cacctctgtt    240

tgggggtcct cagagattaa tgattcatca agggatagtt gtacttgtct cgtgggaatc    300

acttcatcat gcgaaatctg aaattatttc ggaccctgga gttcagggat attcaaggtc    360

cagggaatcc tcagtgcttc tctctccgaa ctgaacaggg gacggtgctc attggttcag    420

aacatggcct gatagaagta gaccctgtct caagagaagt gaaaaatgaa gtttctttgg    480

tggcagaagg ctttctccca gaggatggaa gtggccgcat tgttggtgtt caggacttgc    540

tggatcagga gtctgtgtgt gtggccacag cctctggaga cgtcatactc tgcagtctca    600

gcacacaaca gctggagtgt gttgggagtg tagccagtgg tatctctgtt atgagttgga    660

gtcctgacca agagctggtg cttcttgcca caggtcaaca gaccctgatt atgatgacaa    720

aagattttga gccaatcctg gagcagcaga tccatcagga tgattttggt gaaagcaagt    780
```

-continued

```
ttatcactgt tggatggggt aggaaggaga cacagttcca tggatcagaa ggcagacaag     840
cagcttttca gatgcaaatg catgagtctg ctttgccctg ggatgaccat agaccacaag     900
ttacctggcg gggggatgga cagttttttg ctgtgagtgt tgtttgccca gaaacagggg     960
ctcggaaggt cagagtgtgg aaccgagagt ttgctttgca gtcaaccagt gagcctgtgg    1020
caggactggg accagccctg gcttggaaac cctcaggcag tttgattgca tctacacaag    1080
ataaacccaa ccagcaggat attgtgtttt ttgagaaaaa tggactcctt catggacact    1140
ttacacttcc cttccttaaa gatgaggtta aggtaaatga cttgctctgg aatgcagatt    1200
cctctgtgct tgcagtctgg ctggaagacc ttcagagaga agaaagctcc attccgaaaa    1260
cctgtgttca gctctggact gttggaaact atcactggta tctcaagcaa agtttatcct    1320
tcagcacctg tgggaagagc aagattgtgt ctctgatgtg ggaccctgtg accccatacc    1380
ggctgcatgt tctctgtcag ggctggcatt acctcgccta tgattggcac tggacgactg    1440
accggagcgt gggagataat tcaagtgact tgtccaatgt ggctgtcatt gatggaaaca    1500
gggtgttggt gacagtcttc cggcagactg tggttccgcc tcccatgtgc acctaccaac    1560
tgctgttccc acaccctgtg aatcaagtca cattcttagc acaccctcaa aagagtaatg    1620
accttgctgt tctagatgcc agtaaccaga tttctgttta taaatgtggt gattgtccaa    1680
gtgctgaccc tacagtgaaa ctgggagctg tgggtggaag tggatttaaa gtttgcctta    1740
gaactcctca tttggaaaag agatacaaaa tccagtttga gaataatgaa gatcaagatg    1800
taaacccgct gaaactaggc cttctcactt ggattgaaga agacgtcttc ctggctgtaa    1860
gccacagtga gttcagcccc cggtctgtca ttcaccattt gactgcagct tcttctgaga    1920
tggatgaaga gcatggacag ctcaatgtca gttcatctgc agcggtggat ggggtcataa    1980
tcagtctatg ttgcaattcc aagaccaagt cagtagtatt acagctggct gatggccaga    2040
tatttaagta cctttgggag tcaccttctc tggctattaa accatggaag aactctggtg    2100
gatttcctgt tcggtttcct tatccatgca cccagaccga attggccatg attggagaag    2160
aggaatgtgt ccttggtctg actgacaggt gtcgcttttt catcaatgac attgaggttg    2220
cgtcaaatat cacgtcattt gcagtatatg atgagttttt attgttgaca acccattccc    2280
atacctgcca gtgtttttgc ctgagggatg cttcatttaa aacattacag gccggcctga    2340
gcagcaatca tgtgtcccat ggggaagttc tgcggaaagt ggagaggggt tcacggattg    2400
tcactgttgt gccccaggac acaaagcttg tattacagat gccaagggga aacttagaag    2460
ttgttcatca tcgagccctg gttttagctc agattcggaa gtggttggac aaacttatgt    2520
ttaaagaggc atttgaatgc atgagaaagc tgagaatcaa tctcaatctg atttatgatc    2580
ataaccctaa ggtgtttctt ggaaatgtgg aaaccttcat taaacagata gattctgtga    2640
atcatattaa cttgtttttt acagaattga aagaagaaga tgtcacgaag accatgtacc    2700
ctgcaccagt taccagcagt gtctacctgt ccagggatcc tgacgggaat aaaatagacc    2760
ttgtctgcga tgctatgaga gcagtcatgg agagcataaa tcctcataaa tactgcctat    2820
ccatacttac atctcatgta aagaagacaa ccccagaact ggaaattgta ctgcaaaaag    2880
tacacgagct tcaaggaaat gctccctctg atcctgatgc tgtgagtgct gaagaggcct    2940
tgaaatattt gctgcatctg gtagatgtta atgaattata tgatcattct cttggcacct    3000
atgactttga tttggtcctc atggtagctg agaagtcaca gaaggatccc aaagaatatc    3060
ttccatttct taatacactt aagaaaatgg aaactaatta tcagcggttt actatagaca    3120
aatacttgaa acgatatgaa aaagccattg gccacctcag caaatgtgga cctgagtact    3180
```

-continued

```
tcccagaatg cttaaacttg ataaaagata aaaacttgta taacgaagct ctgaagttat   3240
attcaccaag ctcacaacag taccaggata tcagcattgc ttatggggag cacctgatgc   3300
aggagcacat gtatgagcca gcggggctca tgtttgcccg ttgcggtgcc cacgagaaag   3360
ctctctcagc ctttctgaca tgtggcaact ggaagcaagc cctctgtgtg gcagcccagc   3420
ttaactttac caaagaccag ctggtgggcc tcggcagaac tctggcagga aagctggttg   3480
agcagaggaa gcacattgat gcggccatgg ttttggaaga gtgtgcccag gattatgaag   3540
aagctgtgct cttgctgtta gaaggagctg cctgggaaga agctttgagg ctggtataca   3600
aatataacag actggatatt atagaaacca acgtaaagcc ttccatttta gaagcccaga   3660
aaaattatat ggcatttctg gactctcaga cagccacatt cagtcgccac aagaaacgtt   3720
tattggtagt tcgagagctc aaggagcaag cccagcaggc aggtctggat gatgaggtac   3780
cccacgggca agagtcagac ctcttctctg aaactagcag tgtcgtgagt ggcagtgaga   3840
tgagtggcaa atactcccat agtaactcca ggatatcagc gagatcatcc aagaatcgcc   3900
gaaaagcgga gcggaagaag cacagcctca aagaaggcag tccgctggag gacctggccc   3960
tcctggaggc actgagtgaa gtggtgcaga acactgaaaa cctgaaagat gaagtatacc   4020
atattttaaa ggtactcttt ctctttgagt ttgatgaaca aggaagggaa ttacagaagg   4080
cctttgaaga tacgctgcag ttgatggaaa ggtcacttcc agaaatttgg actcttactt   4140
accagcagaa ttcagctacc ccggttctag gtcccaattc tactgcaaat agtatcatgg   4200
catcttatca gcaacagaag acttcggttc ctgttcttga tgctgagctt tttataccac   4260
caaagatcaa cagaagaacc cagtggaagc tgagcctgct agactgagtg actgcagtta   4320
ggagggatcc gacagagaag accatttcca ctcattcctg ttgtcctacc accccttgct   4380
ctttgagggc tggctattga gaactggaaa gagtaaaatg ataacttacc ttagcattgc   4440
caagaacttc agcagacaac aagcaattct atttatttta tgttgtgtat acatcttgat   4500
cattagcaag acattaagct ttaaccatta tggcaccatt ttgtgagaat gattgttctt   4560
tcacttgggc tgtttgagag cataattatg gtaatcatga gattaatgtt tcatgatttc   4620
tacctccaaa gtgtgaagac aagtaaaaca atgtttctaa attgtcttat tttgttggcg   4680
gagaagatta caatggctat tagtgctaca tttggtcaaa tgtaatcact taaatagctt   4740
cttgtcacct taaactaaag cagaataaaa agtatccttt gaaattataa gccctccttt   4800
gctgacagct attattttgt aacatcttac caggtcatgt gctttcagtt ataactgggc   4860
tgagcctcct ataattacaa tgtctatagg gactgtttta ctgcctgtgt attttctgct   4920
agagagttag caatgttaga gctagaacag attagaattt ctaaacagta tcatgcacag   4980
ttggtgtgag tgatcagtgt gcattgtatg gcatgcatgg ttgtgaatta ttctctgttc   5040
tccaaatact gtttctttaa ctcagatatt tttgttagtg tctaggccac ttcatttatt   5100
tttcgtcatg gtactttact gacttctctt tattcaattc tccacgccct caccaaaaaa   5160
aactgtctca aaatgagaat attttatttt catggtgagt ctagaaaacg cccacttcat   5220
tctgattaaa aattcttcca tgttttaaat atcagaacca gacctttctt actgtgtatc   5280
ttagcccatt tgtgtctcta taacaacaac cagctttcaa aggaactaat agagtgaaaa   5340
ctcactcatt accacgagga tggcacaagc gattcacgta ggatctgccc ctgtgaccaa   5400
aacacctccc attgggcccc acttccaaca ctggtgatca catttcaaca tgaggtttag   5460
ggaaacaaat gcctaaacta cagcactgta cataaactaa caggaaatgc tgcttttgat   5520
cctcaaagaa gtgatatagc caaaattgta atttaagaag cctttgtcag tatagcaaga   5580
```

```
tgttaactat agaatcaatc taggagtatt cactgtaaaa ttcaactttt ctgtatgttt   5640

gaacattttc acaatctcat aggagttttt aaaaagaaga gaaagaagat atactttgct   5700

ttggagaaat ctactttttg acttacatgg gtttgctgta attaagtgcc caatattgaa   5760

aggctgcaag tactttgtaa tcactctttg gcatgggtaa ataagcatgg taacttatat   5820

tgaaatatag tgctcttgct ttggataact gtaaagggac ccatgctgat agactggaaa   5880

tagaagtaaa tgtgtttatt gaaaaaaaaa aaaaaaa                            5917
```

<210> SEQ ID NO 6
<211> LENGTH: 5035
<212> TYPE: DNA
<213> ORGANISM: Homo sapiens

<400> SEQUENCE: 6

```
gggagaaaaa gggctcagga ctgaggagtg aagagctcca gggatttcac tcttctttgt     60

gtgtgtgaag gaaggtttat ttgcaagatg ggtttgaggg aattaaggat aaagtctgct    120

gaaagtagca ccagcctctg gattaaaagg gatgtttgga tgaagcttca atctcaagaa    180

gaggcaagag aaaactaaag aaaaagaagg cagcaactgc tttcgggagc agctgaaggc    240

tggagataac atggacctcc atgatgagag ctggaatgaa gtaccagggc aagggagctg    300

cctggatgag gaaaccaagg ctatctcagt actgccaagg tgttttcatc attcatcaaa    360

atgcaaaagt aaacactggt gagaaaaacg atgttgatct cccaggcaag ccactttcca    420

ggagtgtggc tgattatttt caaatgctgc atcggaaagt tgcaggcccc ttggaaaatc    480

tgtcacccct gagagtgata ttattctaca gaaacaacac atcactggat gcctctcacc    540

atgcaatcct ctgtgcactt gagaagaaga caagactctc ctatttttag atgggaaagc    600

tgaggcaaaa cggatgcact tggcaaaat catttgataa aaatggaagc tgaacctcca     660

agtcctggca tcggtagctg cctcatgttc ctcccgcctc actccacctc agtgtacccg    720

cgactggagg gtgccacagg ctggagcaca caaaacactg tgtgcttcgt gattctgatg    780

tggggcgcca gatccggtgg aaggagggtg gctgcgtggg aacagatgct cgtgtcgcaa    840

ggagttgtct cttgtgggca aagcaagctg gaaagtgttt cgatttcttt attttcatgc    900

tctactcttg gtgcttcctt ctcctttgcc caccaatccc cccaatgcca ggcttctcct    960

tacctgggtg cagagagagg aacaacttgg aggtgggcag agagggactc agttcatggt   1020

gcttggaggt gggagagctc ccaggcaaaa tagagaggag actgtggaga tgccgtgggc   1080

aggtgtggag gagagggaga gcttgaacgg tgaaaaacaa gagatggaga gtctgggaga   1140

agggtgagca gccagaatgg ggatttccac agtagcttct gatgagctat gtctggtcag   1200

aactataacc ttagcttcct ttatttccct ggaggggtgg ggagatagga aggagaggag   1260

tatactagtc tcttccaaag ggagggccag agcaaaagcg tcctgtgatt aattactcac   1320

cacaaaaacc ctcttcaagg ctggagacct aggaggggct tggcacacag acaactcctc   1380

tgcagctgtt cagagaaaaa cagctcttcc catctcaagc cgcccacctg cccagtgtgc   1440

tgtctgtccc actggtcaca cactttccct agagtgcttc ttgcttctct cacagcaatt   1500

cccacctccg catgctggac caggcggccc cctctagatc ccatggtgaa gcatcaggtg   1560

cccacaggtc taagatgtct tcatttgttc aatggctaga gcaggcagct ggctgtccag   1620

atgcatgaat gaattcccta actctcacat gtctgcagga aactgctgta ggaagcctgc   1680

accagtggat tgccattcgg gcagatcctc tcaactttga gagcttaagg cttgcttttg   1740

agtatgtgat tatgatcctg cctgtgtgta tgtatgtcag aatcatagaa ctctagaggt   1800
```

-continued

```
catgttttaa ttaatttatt cattcattga ttcattaaca aatgcttatt gagtacctac   1860
tatgtgtcag gctgtgatct ggatactgag gcacagatca gtgagcaaaa cagaccaaaa   1920
gctctgtcat catgaagctt atattctaga gagaagagat atactatcat caaattaagt   1980
cagttatgta gcatattaga aagtgataag tccagtgggg taaaataaag gaggatgatg   2040
gggaatgtga ggggcggcat gcaattttaa atagaatgtt tgaggaaggc tttcatggga   2100
aagtgatatt tggtgcaaaa cgtgaaggcg gtaaagaggt gaattatgtg gctatgtcgg   2160
ggatggacat tacaggcaga agaattagtt agtcggggct ctgagcaggg agcaggtctg   2220
gcatgttccc atcccagcaa gtaggccagt gtggctctgg tggagtaagc aaggatggaa   2280
ttgcagcagg tgagtccaga agagtgataa tggacagcca gttgggggtg ccttccaggt   2340
gattgtggga actaggcttt attctgagtg tgatgggtag ccacttgggg ctttcaggac   2400
aggatggtaa aaaaaggatc atgctgcctg ctgtgttggg aacagactgt atgggaccag   2460
gtgaaagcaa agcagtcagc ctcaaataat tcaggtgagg gaaaacgtga cttgaataag   2520
attcactgta gaagtggtga gatataagtg gattctggat ataataaaaa tatagagcca   2580
gcaggatttt ctgatggatt agctaaggag tgtaaagaaa tagaggagtc agagtgactt   2640
tttttttcc ttgagcaaca ggaagtggag aggtatcatt acctgaaagg aggaaagcct   2700
caggtagaga aagttttaga ggaggtaaga tcagaggttt agtgcaagac atgctaagtt   2760
tgagatgtct attagatacc caagtggatc tgtctaatgg gtatttagac agatccactt   2820
ggatatctgt ctcaatggac atgtgatcta catgtagttc acaggataag tccagtttag   2880
agtaccaatt tgaagtcatc aaatgtaggt ggcatttaaa gtggtaaaac tggactgagc   2940
acagtggctt atgcctgtaa cccctgcatt ttgggaggct gaggtgggtg gataacttga   3000
ggtcaggagt tcgagaccag cttggccaac atggtgaaac cctatctcta ctaaaaatac   3060
aaaaaattag ccaggcatgg tggcacatgc ctataatctg agcctctcgg gaggctgagg   3120
caggagaatt gcttgaatcc aggaggcaga ggttgcagtg agccaagatc gtgcgactgc   3180
actccagcct gggtgacaga gtgagactcc atctcaaaaa aataaataaa taaataaata   3240
aataaaacaa aaataaaaaa taaagtgata aaactggaga tcactatgag aatgaggata   3300
gctagagaaa agaaggggtc cagaaggtta tccttgctgt gctccaaggt gcttgagttt   3360
ggaaacatga gacaaaacca gaaacagaga ccctgggaga gtctgtggtc tccatttttc   3420
cgctgagcaa accacaggct tgtgttctgc ctatctccca cttcgcacat gtacagcatt   3480
gtagaatatt tacatggaaa aggattctat gatatagtag agtgacttcc cctattgata   3540
acaaacaatt atgtcagtcc ctacacaact cttatgctaa aggtaatggg gagggttgaa   3600
tggtactcat ttgggcagct tttttttgg ctatgtatac tttcagaaag aatttacctc   3660
acctagatca catgactaaa tataggaata ttaataccca ctgtgtctaa ttggcagatt   3720
gttttgagat tttaaatgag atctattcat gaaaacattt tgttaatctt aaagcaccac   3780
accaatatca cctattatat tgtacagcca tgatcaacac aatttccaat ctagaagtcc   3840
ctctcaactt ttcctgggac cgagctttca ggacttagag ttccttctcc ttctcattct   3900
ttttctgcgc atagtctccc ggtaaagtga aaaccagctg agaaaagatt cgggctggac   3960
aggcctccgt ggcgattaag agtcacgaat gtgatgatat tattcgcaaa cagcagtgta   4020
gtcatggttc agaattttgg aaacagtgcc aggaggatct tggacataat tttcagggtg   4080
tataagccct gcactaaagt aaagtttacc agtgccaaga gtttgacgtt ttcttcttca   4140
tgttttcttt ggctggagcc tggctttagt tgaagagttc tgtcaacaaa tggaattctc   4200
```

-continued tatttgggac tgggattctt gattggtggt gcttctgtct cctcttgctg tgagtttcct 4260
caaacttaga gtcctgtggg atctgtgttt gaacagagac tggaaatgct tacctcatct 4320
ccacatttct tagccatttg tcaccagact gtagattgac tggtgggatg cctgtttcta 4380
gagagaaaag atactgcttt tctctgactc cagctgagaa gaggttggtt aaattacgaa 4440
tctgatgact atctatgaac ctaaggagga aaagttaatt tcttttgagg gtttgcataa 4500
tgttttaaaa caaatttata gaaatataga tgatggaaaa aagcaatagg gtaaacctaa 4560
attattaaaa ataaataata cataggaaat aaacagcata gaaaagaaac aaaaaagaga 4620
ttgttaccaa aaaccataag tttttttttt tttgaaaatt ctaagaaggt ggataaattt 4680
ctggaatttt caatgagcaa aaaagtgaaa agatacaaat gaataaaaaa tgaaaaggta 4740
gaaattaaaa taggtctagt agagattaaa aataataaaa gaatattatt aaaaagtatt 4800
ggtggataaa ataggcacat atctgaagat aaaagccgaa ttgacccccct aaaaagcaga 4860 aaacttacaa taacaatcat taatggcttt gaatggctat gaaaaaataa tatctctgcc 4920
ctcttcacta ctcccatgta aaataatttt acgggtagat tttaccaacg tttcaagaga 4980
gacatgattc ccaaatatta tgtaagtttt ttcagaaaaa aaaaaaaaaa aaaaa 5035

<210> SEQ ID NO 7
<211> LENGTH: 5280
<212> TYPE: DNA
<213> ORGANISM: Homo sapiens

<400> SEQUENCE: 7
gaatataagg ggaattactg gcgagagagc tgtagaccaa cttaacactg aacccattac 60
ttttccaaga ccagaaaaaa atattacatg aacaggaact acttctcctt cagataagaa 120
ttcaagcttt gacattgtaa accacagacg aattggagct tggcattgaa aggaggtgtt 180
ctgcaatgat ttttttttctt gtttagagaa gtttacttct acaagaagaa atctgaaaaa 240
tgacaggagc aaagaggaaa aagaaaagca tgctttggag caagatgcat accccccagt 300
gtgaagacat tatacagtgg tgtagaaggc gactgcccat tttggattgg gcaccacatt 360
acaatctgaa agaaaacttg cttccagaca ctgtgtctgg gataatgttg gcagttcaac 420
aggtgaccca aggattggcc tttgctgttc tctcatctgt gcacccagtg tttggtttat 480
atgggtctct gtttcctgcc ataatttatg ccatatttgg aatgggacat catgttgcca 540
caggcacctt tgccttgaca tccttaatat cagccaacgc cgtggaacgg attgtccctc 600
agaacatgca gaatctcacc acacagagta acacaagcgt gctgggctta tccgactttg 660
aaatgcaaag gatccacgtt gctgcagcag tttccttctt gggaggtgtg attcaggtgg 720
ccatgtttgt gctgcaactg ggcagtgcca catttgtggt cacagagcct gtgatcagcg 780
caatgacaac tggggctgcc acccatgtgg tgacttcaca agtcaaatat ctcttgggaa 840
tgaaaatgcc atatatatcc ggaccacttg gattctttta tatttatgca tatgtttttg 900
aaaacatcaa gtctgtgcga ctggaagcat tgcttttatc cttgctgagc attgtggtcc 960
ttgttcttgt taaagagctg aatgaacagt ttaaaaggaa aattaaagtt gttcttcctg 1020
tagatttagt tttgattatt gctgcatcat ttgcttgtta ttgcaccaat atggaaaaca 1080
catatggatt agaagtagtt ggtcatattc cacaaggaat tccctcacct agagctcccc 1140
cgatgaacat cctctctgcg gtgatcactg aagctttcgg agtggcactt gtaggctatg 1200
tggcctcact ggctcttgct caaggatctg ccaaaaaatt caaatattca attgatgaca 1260
accaggaatt tttggcccat ggcctcagca atatagtttc ttcatttttc ttctgcatac 1320

-continued

```
caagtgctgc tgccatggga aggacggctg gcctgtacag cacaggagcg aagacacagg   1380
tggcttgtct aatatcttgc attttcgtcc ttatagtcat ctatgcaata ggacctttgc   1440
tttactggct gcccatgtgt gtccttgcaa gcattattgt tgtgggactg aagggaatgc   1500
taatacagtt ccgagattta aaaaaatatt ggaatgtgga taaaatcgat tggggaatat   1560
gggtcagtac atatgtattt acaatatgct ttgctgccaa tgtgggactg ctgtttggtg   1620
ttgtttgtac catagctata gtgataggac gcttcccaag agcaatgact gtaagtataa   1680
aaaatatgaa agaaatggaa tttaaagtga agacagaaat ggacagtgaa accctgcagc   1740
aggtgaaaat tatctcaata aacaacccgc ttgttttcct gaatgcaaaa aaattttata   1800
ctgatttaat gaacatgatc caaaaggaaa atgcctgtaa tcagccactt gatgatatca   1860
gcaagtgtga acaaaacaca ttgcttaatt ccctatccaa tggcaactgc aatgaagaag   1920
cttcacagtc ctgccctaat gagaagtgtt atttaatcct ggattgcagt ggatttacct   1980
tttttgacta ttctggagtc tccatgcttg ttgaggttta catggactgt aaaggcagga   2040
gtgtggatgt attgttagcc cattgtacag cttccttgat aaaagcaatg acgtattatg   2100
gaaacctaga ctcagagaaa ccaatttttt ttgaatcggt atctgctgca ataagtcata   2160
tccattcaaa taagaatttg agcaaactca gtgaccacag tgaagtctga gacccttttg   2220
tcacagtaca gctcttgtct ttaccaactg cctgaagagg ccatatgctg gcattttgca   2280
caactttttg gttgtttaga tcctacagat gacctctgct acaataagta cgatgtgact   2340
tagtaactgc atagcagttg gaaagaactg ccaacttttt tttctcattt ttgttagtaa   2400
gaagattcgc ttagttattt tatgtaaaaa tcagtatgtg tttagtttta gtgtactgaa   2460
gggtaaacat ggttttattt tattttacca tattattttg tgttgtttta tttctattgt   2520
gctgtaagtt gatgtttaaa attgagaaat acttttgtca taggtaattt ggaacattta   2580
caagccattt gtaaaatttt aagataatct gtaactaata cataaaaaca acttagcaaa   2640
tgtgccattt tcacacaact tctctctgta taggcctctg aaatatcaat aaggctaaat   2700
attactttac acagtaagat gtgaaattca caaaaagtaa accaaacaaa acgaatgaaa   2760
aactggaaat aattcgtttc catatctttc catacatcca tttctgaagt attcaggaat   2820
gttttcataa tcgaaagaaa cggtatccaa aataaaacca agttcttgac attggtctgt   2880
tttgctgtga atattggaaa tgcttaggat cttcagaccc aatagctcta attttaacat   2940
ttctacccaa taagaggctc tgttttccac tgaagctttg ttggagaaag agaatatgaa   3000
aattacacat tttataattt ttagatgaga aaataccact agcagaatag ctttgtgcta   3060
ttccagtata agatgaactg taataatttt tgacttccct atttcagaga tagtcaatat   3120
aatatgttta tctatatcca tatggatgga taggtaggta gatcttcata gattttttt    3180
tcttttgtta gaggagagct tgatgtgatt atcttcaaac ccaccaaacc aacaggataa   3240
ttgacaaata aacgccatag gctaggctga actgtatgtt actgttttca tgcttataca   3300
tatattttca atcacataca agtacataga atttcacatt ttaatttagc aaattgattt   3360
acctaggaaa aaattatcac cttcaaagat aggcatagac acataattat gcttaagctt   3420
ttaacagcat tttaaccgct ctaaaaatta ccagagtaag aaaaagctag gtactttaaa   3480
gtgagtttga gaaacaagtt gaaactaaaa ttaaaatacc agccatttag gtgctttctc   3540
tggcatctat aaaagtaaat tctagtgcct gccaagtgat ggattataat ggtctctagc   3600
aaatgtgtgg taaacattca tatggccatt aattttaaca ttaaatcgta ggtagggcaa   3660
tgtagtaaaa tgaaagagaa ttaagaaagg ttttgaattc ttataacata tccagccatt   3720
```

```
tcaattttga ttgaaatgaa ctacaaagaa tagtgtttgt ccctatggta gcctcagtct   3780
ctttatcact aacttggatt gaaatgagtg aggccaactc acattcccat caaacactct   3840
tccaaggaaa agcagaagta ataattggag gtaaagtttc cttagagaaa ataattttat   3900
tctgctttgt ccaattaaat tattccaatg gcggatggta atattcacca tctctaattc   3960
attggtcact ggtaggtaag catgagttaa ggaaagtcaa aaatgaaaat atattttgct   4020
gtgtataaat tgatattttg ctatgcaact cctgtaattg aatttgtata atgcaggcac   4080
tttctaattt attagagatt atggatcagt tctgacatta aaatcatagt taattgatgg   4140
atggttttta tagtttgttg ataaagtgga cacagtattg tctgagcagt tatattttaa   4200
tgcatttcag tgtttatagt agaagtttag tggataaaac tttaagtcca ataacttggg   4260
ggtcaaatgc taatgtttta ttcaatgtaa aggaagacca aaccatgtac cttatgaaga   4320
cctttgtttt aagacttcca cacaccaagg ctacaatgac tgttaacctg gaggaagtct   4380
ctggtatgga gttctgagag cttaagagct aaacatgagt ttagacacac aagattctaa   4440
aatgcaaatg tttattttga agcaggcatt gacaacacaa aaactgtgta gtggtcttga   4500
tgctggattg tttctagagt cacaatgaat tatttttatg agattacctt atttttatat   4560
atgacaaact acttctataa tgcttattat ggtaaaataa aattggaaaa aattaaaact   4620
gacctataag agtgttaagg acctaataga gtgacatata taaattaagc ataaaatatg   4680
taaccaggaa aagactgtta acattacatt tatgcaaatt aaatgccctt aaatttcacc   4740
atttgtcttt cattttaaag gttatttgct cccgattata tgattcaagt gttataagtt   4800
ttagcttgaa ctactttgca gtaatttatt tgacagatct ctattctata aatgtgtaat   4860
gtgatgaaga aagagatctt tctttttttaa tgaaaacatt aatgtgttaa taccctgtat   4920
ggataatgct tgacatttag tggtttccaa aatatattag tatattgttg aacatacatt   4980
atgccttaga aatgcacatt ctgtattttg tgggatgata atctaattca gtatagaata   5040
tgctgtttgg caatgagttt gtggccagat ttcaaatagg gagttaagtg gtactttcac   5100
aatccaaaga tttttagtta aaaatcatgt agtctaatat gctgcagtta ttttttttata   5160
tttttcaatg catttaatta tcttttttat aattctttgt actaactcag catgtaacaa   5220
ccaatttaca tggaaataaa tcgaaatatg ataactatta tgcaaaaaaa aaaaaaaaaa   5280
```

<210> SEQ ID NO 8
<211> LENGTH: 3138
<212> TYPE: DNA
<213> ORGANISM: Homo sapiens

<400> SEQUENCE: 8

```
ctttctccct agggtggcgt gggttgcatc cctcggaaga gcgaaggaat gagccaggtc     60
ggggggcggg gagacaggtg cacacaggag gtccagggct tggtccatgg ggctggtgac    120
ctttctgctt cccttgcaga aaactctccc accatgtcgc agaatggata cttcgaggat    180
tcaagctact acaagtgtga cacagatgac accttcgaag cccgagagga gatcctgggg    240
gatgaggcct tcgacactgc caactcctcc atcgtgtctg gcgagagtat ccgttttttt    300
gtcaatgtca accttgagat gcaggccacc aacactgaga atgaagcgac ttccggtggc    360
tgtgtgctcc tgcacacctc ccgaaagtac ctgaagttaa agaacttcaa ggaagagatc    420
cgtgcgcacc gcgacctaga tggcttcctg gcgcaggcca gcatcgtcct gaacgagacg    480
gccacctccc tggataacgt gctgcggacc atgcttcgcc gcttcgccag ggaccctgac    540
aacaatgagc ccaactgcaa cctggacctg ctcatggcca tgctcttcac cgatgccggg    600
```

-continued

```
gcacccatgc ggggtaaagt ccacctgctg tcagatacca tccaaggggt caccgccaca    660
gtgacagggg tgcggtacca gcagtcgtgg ctctgcatca tctgtaccat gaaggcccta    720
cagaagcggc acgtgtgcat cagccgcctg gttcgcccac agaactgggg ggagaattcc    780
tgtgaggttc ggttcgtcat cctggtgctg gccccaccca agatgaaaag cactaagact    840
gcgatggagg tggcgcgcac gtttgccacc atgttctcgg atatcgcctt ccgccagaag    900
ctcctggaga cccgcacaga ggaggaattc aaggaggcct tggtgcatca gagacagctg    960
ctcaccatgg tgagccacgg tccagtggcg ccgagaacga aggaacgcag cacagtctcc   1020
ctccctgccc acagacaccc agagccccca aagtgcaagg actttgtccc ttttgggaag   1080
ggcatccggg aggacatcgc acgcaggttc cccttgtacc ccttggactt cactgatggc   1140
attattggga aaaacaaggc tgtgggcaaa tacatcacca ccaccctgtt cctctacttc   1200
gcctgcctcc tgcccaccat cgctttcggg tctctcaatg acgagaacac agacggggcc   1260
atcgacgtgc agaagaccat agccgggcag agcatcgggg gcctgctcta cgcgctcttc   1320
tctgggcagc cattggtgat tctgctgacc accgcgcccc tggcgctcta catccaggtg   1380
attcgtgtca tctgtgatga ctatgacctg gacttcaact ccttctacgc atggacgggc   1440
ctgtggaata gtttcttcct tgcgctttat gcctttttca acctcagcct ggtcatgagt   1500
ctcttcaaga ggtcgacgga ggagatcatc gccctcttca tttccatcac gtttgtgctg   1560
gatgccgtca agggcacggt taaaatcttc tggaagtact actatgggca ttacttggac   1620
gactatcaca caaaaaggac ttcatccctt gtcagcctgt caggcctcgg cgccagcctc   1680
aacgccagcc tccacactgc cctcaacgcc agcttcctcg ccagccccac ggagctgccc   1740
tcggccacac actcaggcca ggcgaccgcc gtgctcagcc tcctcatcat gctgggcacg   1800
ctctggctgg gctacaccct ctaccaattc aagaagagcc cctacctgca cccctgcgtg   1860
cgagagatcc tgtccgactg cgccctgccc atcgcggtgc tcgccttctc cctcatcagc   1920
tcccatggct tccgggaaat cgagatgagc aagttccgct acaaccccag cgagagcccc   1980
tttgcgatgg cgcagatcca gtcgctgtcc ctgagggccg tcagcggtgc catgggcctc   2040
ggcttcctgc tgtccatgct cttcttcatc gagcagaact tggtggccgc cttggtgaat   2100
gcaccggaga acaggctggt gaagggcact gcctaccact gggacctcct gctcctcgcc   2160
atcatcaaca cagggctgtc tctgtttggg ctgccttgga tccatgccgc ctacccccac   2220
tccccgctgc acgtgcgagc cctggcctta gtggaggagc gtgtggagaa cggacacatc   2280
tatgacacga ttgtgaacgt gaaggagacg cggctgacct cgctgggcgc cagcgtcctg   2340
gtgggcctgt ccctgttgct gctgccggtc ccgcttcagt ggatccccaa gcccgtgctc   2400
tatggcctct tcctctacat cgcgctcacc tccctcgatg gcaaccagct cgtccagcgc   2460
gtggccctgc tgctcaagga gcagactgcg taccccccga cacactacat ccggagggtg   2520
ccccagagga agatccacta cttcacgggc ctgcaggtgc ttcagctgct gctgctgtgt   2580
gccttcggca tgagctccct gccctacatg aagatgatct ttcccctcat catgatcgcc   2640
atgatcccca tccgctatat cctgctgccc cgaatcattg aagccaagta cttggatgtc   2700
atggacgctg agcacaggcc ttgactggca gaccctgccc acgccccatt cgccagccct   2760
ccacgtcctc ccaggctggc tctggagctg tgaggggagg tgtaggtgtg tgggtgactg   2820
ctctgtgctg cgccttctca tggctgactc aggcctgggg catctgggca ttgtaggggt   2880
gcagtggtat gtgcccaccc ctctcccatt atcctttagc tttaggccaa gagcgttgct   2940
cagggcagct tctgcccagg gtgggtggga ctgagcagga tggattttct tttgataaaa   3000
```

gagtcgatgc ctgaaagaga aaccatttcc ttgattgtgt aaggaacttg ctggacgcac 3060
attagagaat aaagctcctg tttctaggct cctaaaaaaa aaaaaaaaaa aaaaaaaaaa 3120
aaaaaaaaaa aaaaaaaa 3138

<210> SEQ ID NO 9
<211> LENGTH: 4443
<212> TYPE: DNA
<213> ORGANISM: Homo sapiens

<400> SEQUENCE: 9
ggacactccc aacttgagac tgaaagctgg gcgaaagcgg tttgtgaagc taacctaaaa 60
gacaaaatgg tctagagcca ccttttcccc gcaaataaca gaggattaag gatctgaaat 120
cttcaagcct ccaggaccac ggtgcaagcc ctcagcaaaa atttctgctg gaggccggag 180
cgccttttga tttcgggaga ctggcccagg aactctagtc acttggaagg cggaagagaa 240
ggtggtacct gagccaggta ggagccactc agaggcagcc cggggccgcc actcacctag 300
gagaggaggt ggagtccgat gacctggact gagaggaaac gcgagactga gtctaccagg 360
tgaggtaaaa aacacccacc tgctcacctc ggaaggggcg ggcgaggtgc ggctcccggt 420
gacccgcggg ggtgcagcgc acctgggcgg aggcggaact gggagggtgt gggcactgct 480
cgtagggcct ggaactaaac tcacctgtga cggaggcaga ggaggggccc gggcaaaaac 540
ccacctgagc tggcgggaaa cccgacccgc gagcagtccc cgggcttgcg cggcgcggag 600
agggaggcgc cccgcggcgg ggcccccact cggtcagccc gcgcgtcggt ccccgcgcgg 660
ccgccatgac ctggagcgcc acggcccggg gcgcccacca gcccgacaac accgccttca 720
ctcagcagcg cctccccgcc tggcagccgc tgctgtcggc cagcatcgcg ctgccgctct 780
tcttctgcgc gggcctggcc ttcatcggcc tgggcctggg cctctactac tcctccaacg 840
gcatcaagga gctggagtac gactatacag gcgacccggg caccggtaac tgctcggtgt 900
gcgccgcggc tggccagggc cgggcgctgc cgcccccctg ctcgtgcgcc tggtacttct 960
cgctgcccga gctcttccag ggcccagtgt acctctacta cgagctgacc aacttctacc 1020
agaacaaccg gcgctacggc gtgtcccgcg acgacgcgca gctgagcgga ctccccagcg 1080
cgctgcgcca ccctgtcaac gagtgcgccc cctaccagcg cagcgcggcc ggcctgccca 1140
tcgcgccctg cggcgccatc gccaacagcc tcttcaacga ctccttctcg ctttggcacc 1200
agcgccagcc cggcgggccc tacgtcgagg tgccgctcga ccgctccggc atcgcctggt 1260
ggaccgacta ccacgtcaag ttccgcaacc cgccgctggt caacggcagc ctggcgttgg 1320
ccttccaggg cacggcgccc ccgcccaact ggcgccggcc agtctacgag ctcagccccg 1380
accccaacaa caccggcttc atcaatcagg acttcgtggt gtggatgcgc acggcggcgc 1440
tgcccacgtt ccgcaaactg tacgcgcgca tccgccaggg caactactcg gccgggctgc 1500
cgcggggcgc ctaccgcgtc aacatcacct acaactaccc ggtgcgcgcg ttcggcggcc 1560
acaagctcct catcttcagc agcatctcgt ggatgggtgg caagaacccc ttcctgggca 1620
tcgcctacct ggtcgtcggc tccctctgca tcctcaccgg ctttgtcatg ctggtcgtct 1680
acattcgcta ccaggaccag gacgacgacg acgaggagtg attccggctt tccagggatc 1740
cctcctgctt cttgccaaaa ctcttgcaag gtgcttttgg catctcctcc tcgcccgtca 1800
cccaattcca acctcgccta gcttttcctc cctttgtgaa tgaggggacc agataaggga 1860
attacccccc ttgctcttgg ggggctgcta gactgtcttg ccgcggggag ggatgttgac 1920
tgcagagtga aacatccttg caaactcttc ccacctcctt cacgacactg agttgccatg 1980

-continued

```
tgaggttctt caagtctgag agtggaaggg atccctatgg agactcctat taaaccccta   2040
ttagaggaag agattgagag acctagcaat gtgaagtaac aaagatcagg cagctgcaag   2100
tgactcctga atcttgagtc cagggctttc gccactacag tacagtggtt ttcttttctt   2160
tggtcgggga gagtgggctg gaatggagag tgaggcccac aaattacctg cagagacgtg   2220
gaggcgtgag ggagaacatg cttgttaaat atgcaggtag attaggagac accaaacaga   2280
gattcagaca cagtaaggct gggatgagat cctcgaagct gtgttttaac aaactccact   2340
ggagagtccc atattccctc aaatttggga atcacgaccc tgaaccaggt tgggcctgaa   2400
gcagtcaact gaattcactt tttcggatag taatttgttc ccaggggcag tgacaaccat   2460
gatgttccag gtttggtctg gcactctgcc ttgaacgtag gaagctcttg atgatttgtg   2520
gaatgaattt ttaaaaaatt actatctggg gaaaactagt tggcatacag agttgtagga   2580
cagggtttat gtgattcatt tgatatttta gtattttggt gtaaaagcca acaggcaaac   2640
tttgccaggt actgtgtaga aactcgaaaa tgtgaggcca gtttgtacag ttcagaggaa   2700
atgctttaac gtagaatcag atagctggaa gagatcttcg agggaaagta agttccctaa   2760
agtcacatct atgtctccta gctcagtgtt ctttgtcatt gtgtgtgtgt gtgtgtgtgt   2820
gtgtgtgtgt gtgtgtgatt agaaagggct tcattcatac cttttccctt ggacctggaa   2880
aaaaaatttt ttttatcttt tcaaatgaaa tctattgatt tctagtaatc atatttgaat   2940
caatgttaaa gcatatatag tcttatatgt aaactagatt cttaagatta tttgaacctt   3000
tgagatgaag tttacactca actaaaatca ttccattgat tttattgatt aacatcaatc   3060
agtatgttta aagttattct aagaagcaat agtttatttt taaaaacctt gtatagcaaa   3120
ataacttaaa accctttgtg atatcatctt accagtttat ttggtaaaaa caaacagtta   3180
tttggtattt gtcagaattc ttcagtgcct gctattacag ctattttcca attactaact   3240
tgattatact cactcaaggc agtgcaagat cttgaagtac tttttagcag ttaagtaata   3300
ttgaattgta ttgaatagtt tacatagttt attctagtct ttgaaaatta ctgaacatgg   3360
acaatgtgca tgtcattgac atctgcctta gaacttctgg gacaatcctg attcgagaga   3420
ttctatccca ttatttacat ataccaaaaa tactttgtta atttaatgtg ttggcttccc   3480
aactcctgaa cacgacacaa ttttattatt agattttgta tggtgatttt aggctatgaa   3540
aacatgatca ttatatgtat atagatacat ttttatttgt tacaaatgtt tgagcagctc   3600
actagcccac ccctcctcta ttttgggtaa gagaatttac taccttttttt aactatgtag  3660
ttgagagcaa catgtatttt gttattttta gaatggtcag tatattgcta taaaatttta   3720
aatgagacta tgaaagttaa agtattctga ttctggttaa attaacgaat atggttccag   3780
gccctgttct ctgggttttt gagagagaat aaaggttatg tttgtcttac ctttgttatc   3840
gagtttgctg aattcttttg aacgatgatc ttaaaggcac aaacaccacc agccactttg   3900
ctaatttctt aatagcagat ttacattgca gcaagaaaac catcttttat agtaacattc   3960
agttaaaatg aactcaattc attgttaact tcctaaaaca gaatttgaac tttatcaacc   4020
tcaacgtgta tataaactag atagtcctca atactttatc aacctcaaca tgtatataaa   4080
ctagatagtc ctcaaatact gtttgaattt aataaatgtc aatttaaaaa tttttgtagt   4140
agtcttctgc attttacttc aattataaat tgcaattatt tattggatat tttggacttc   4200
aaagcagcag aaactttaaa actgaaatgg gaaacgtttt cctgcaatga tccctgtgct   4260
gtaacatttt gtctggtgtc tcaggcttcc aggttcttgt tggcctgaat tcccttgttg   4320
cccagtaaat gttcactagc tagaagtatc ttcaggaagt gagatagaaa agagtgaacc   4380
```

tcaacaattg gactggaaat gagctttgac ctaactttgt aaaataaaag cataaaagag 4440
aaa 4443

<210> SEQ ID NO 10
<211> LENGTH: 1613
<212> TYPE: DNA
<213> ORGANISM: Homo sapiens

<400> SEQUENCE: 10
gcgcctttcc aggtcttctc ccggtgaacc ggatgctctg tcagtctcct cctctgcgtc 60
ctcggccgcg gcccgggtcc ctcgcaaagc cgctgccatc ccggagggcc cagccagcgg 120
gctcccggag gctggccggg caggcgtggt gcgcggtagg agctgggcgc gcacggctac 180
cgcgcgtgga ggagacactg ccctgccgcg atgggggccc ggggcgctcc ttcacgccgt 240
aggcaagcgg ggcggcggct gcggtacctg cccaccggga gctttccctt ccttctcctg 300
ctgctgctgc tctgcatcca gctcggggga ggacagaaga aaaaggagaa tcttttagct 360
gaaaaagtag agcagctgat ggaatggagt tccagacgct caatcttccg aatgaatggt 420
gataaattcc gaaaatttat aaaggcacca cctcgaaact attccatgat tgttatgttc 480
actgctcttc agcctcagcg gcagtgttct gtgtgcaggc aagctaatga agaatatcaa 540
atactggcga actcctggcg ctattcatct gctttttgta acaagctctt cttcagtatg 600
gtggactatg atgaggggac agacgttttt cagcagctca acatgaactc tgctcctaca 660
ttcatgcatt ttcctccaaa aggcagacct aagagagctg atacttttga cctccaaaga 720
attggatttg cagctgagca actagcaaag tggattgctg acagaacgga tgttcatatt 780
cgggttttca gaccacccaa ctactctggt accattgctt tggccctgtt agtgtcgctt 840
gttggaggtt tgctttattt gagaaggaac aacttggagt tcatctataa caagactggt 900
tgggccatgg tgtctctgtg tatagtcttt gctatgactt ctggccagat gtggaaccat 960
atccgtggac ctccatatgc tcataagaac ccacacaatg gacaagtgag ctacattcat 1020
gggagcagcc aggctcagtt tgtggcagaa tcacacatta ttctggtact gaatgccgct 1080
atcaccatgg ggatggttct tctaaatgaa gcagcaactt cgaaaggcga tgttggaaaa 1140
agacggataa tttgcctagt gggattgggc ctggtggtct tcttcttcag ttttctactt 1200
tcaatatttc gttccaagta ccacggctat ccttatagtg atctggactt tgagtgagaa 1260
gatgtgattt ggaccatggc acttaaaaac tctataacct cagcttttta attaaatgaa 1320
gccaagtggg atttgcataa agtgaatgtt taccatgaag ataaactgtt cctgacttta 1380
tactattttg aattcattca tttcattgtg atcagctagc ttattcttgt gtactttttt 1440
taaactgtgg gttttcctag taaatttaat ttacagaaat caatggtagc atttagtaat 1500
ctacaaagga aatatcaaag tgtttttcaa gcctgttata ttcagtgtgt gccacaggat 1560
tgaaataaat gacaatgtaa ttatgaaaaa aaaaaaaaaa aaaaaaaaaa aaa 1613

<210> SEQ ID NO 11
<211> LENGTH: 8270
<212> TYPE: DNA
<213> ORGANISM: Homo sapiens

<400> SEQUENCE: 11
aagagctcgc ccagctctgc gggcgccgcc accttcgccg ccaccgctgc ctttctcctc 60
ctcctgtcgg cgtgcggggg ccgcgcccgg cggcagctct gccctaggtg ggcggcggcg 120
cggcccaggc tgcagctgag cgctctgcgc ggcgcagccg ggtctcccgc gtgtaccacg 180

-continued

```
ccgtgacagg tgcagagtcc gggctgagga cccacctgca gccgccgccg cgatgcccac    240
catgcggagg accgtgtcgg agatccgctc gcgcgccgaa ggttatgaga agacagatga    300
tgtttcagag aagacctcac tggctgacca ggaggaagta aggactattt tcatcaacca    360
gccccagctg acaaaattct gcaataacca tgtcagcact gcaaaataca acataatcac    420
attccttcca agatttctct actctcagtt cagaagagct gctaattcat tttttctctt    480
tattgcactg ctgcagcaaa tacctgatgt gtcaccaaca ggtcgttata caacactggt    540
tcctctctta tttattttag ctgtggcagc tatcaaagag ataatagaag atattaaacg    600
acataaagct gataatgcag tgaacaagaa acaaacgcaa gttttgagaa atggtgcttg    660
ggaaattgtc cactgggaaa aggtggcagt aggggagata gtgaaagtga ccaatgggga    720
acatctccca gcagatctca tcagtctgtc ctcaagtgag ccccaagcca tgtgctacat    780
tgaaacatcc aacttagatg gtgaaacaaa cttgaaaatt agacagggct taccagcaac    840
atcagatatc aaagacgttg acagtttgat gaggatttct ggcagaattg agtgtgaaag    900
tccaaacaga catctctacg attttgttgg aaacataagg cttgatggac atggcaccgt    960
tccactggga gcagatcaga ttcttcttcg aggagctcag ttgagaaata cacagtgggt   1020
tcatggaata gttgtctaca ctggacatga caccaagctg atgcagaatt caacaagtcc   1080
accacttaag ctctcaaatg tggaacggat tacaaatgta caaattttga ttttattttg   1140
tatcttaatt gccatgtctc ttgtctgttc tgtgggctca gccatttgga atcgaaggca   1200
ttctggaaaa gactggtatc tcaatctaaa ctatggtggc gctagtaatt ttggactgaa   1260
tttcttgacc ttcatcatcc ttttcaacaa tctcattcct atcagcttat tggttacatt   1320
agaagttgtg aaatttaccc aggcatactt cataaattgg gatcttgaca tgcactatga   1380
acccacagac actgctgcta tggctcgaac atctaatctg aatgaggaac ttggccaggt   1440
taaatacata ttttctgaca aaactggtac tctgacatgc aatgtaatgc agtttaagaa   1500
gtgcaccata gcgggagttg cttatggcca tgtccctgaa cctgaggatt atggctgctc   1560
tcctgatgaa tggcagaact cacagtttgg agatgaaaaa acatttagtg attcatcatt   1620
gctggaaaat ctccaaaata atcatccaac tgcacctata atatgtgaat ttcttacaat   1680
gatggcagtc tgtcacacag cagtgccaga gcgagaaggt gacaagatta tttatcaagc   1740
agcatctcca gatgagggag cattggtcag agcagccaag caattgaatt ttgttttcac   1800
tggaagaaca cccgactcgg tgattataga ttcactgggg caggaagaaa gatatgaatt   1860
gctcaatgtc ttggagttta ccagtgctag gaaaagaatg tcagtgattg ttcgcactcc   1920
atctggaaag ttacgactct actgcaaagg agctgacact gtaatttatg atcgactggc   1980
agagacgtca aaatacaaag aaattaccct aaaacattta gagcagtttg ctacagaagg   2040
gttaagaact ttatgttttg ctgtggctga gatttcagag agcgactttc aggagtggcg   2100
agcagtctat cagcgagcat ctacatctgt gcagaacagg ctactcaaac tcgaagagag   2160
ttatgagttg attgaaaaga atcttcagct acttggagca acagccattg aggataaatt   2220
acaagatcaa gtgcctgaaa ccatagaaac gctaatgaaa gcagacatca aaatctggat   2280
ccttacaggg gacaagcaag aaactgccat taacatcgga cactcctgca aactgttgaa   2340
gaagaacatg ggaatgattg ttataaatga aggctctctt gatggaacaa gggaaactct   2400
cagtcgtcac tgtactaccc ttggtgatgc tctccggaaa gagaatgatt ttgctcttat   2460
aattgatggg aaaaccctca aatatgcctt aacctttgga gtacgacagt atttcctgga   2520
cttagctttg tcatgcaaag ctgtcatttg ctgtcgggtt tctcctcttc aaaaatctga   2580
```

-continued

```
agttgttgag atggttaaga aacaagtcaa agtcgtaacg cttgcaatcg gtgatggagc   2640
aaatgatgtc agcatgatac agacagcgca cgttggtgtt ggtatcagtg gcaatgaagg   2700
cctgcaggca gctaattcct ctgactactc catagctcag ttcaaatatt tgaagaattt   2760
actgatgatt catggtgcct ggaactataa cagagtctcc aagtgcatct tatactgctt   2820
ctacaagaat atagtgctct atattatcga gatctggttt gcctttgtta atggcttttc   2880
tggacagatc ctctttgaaa gatggtgtat aggtctctat aacgtgatgt ttacagcaat   2940
gcctcctttta actcttggaa tatttgagag atcatgcaga aaagagaaca tgttgaagta   3000
ccctgaatta tacaaaacat ctcagaatgc cctggacttc aacaccaagg ttttctgggt   3060
tcattgttta aatggcctct tccactcagt tattctgttt tggtttccac taaaagccct   3120
tcagtatggt actgcatttg gaaatgggaa aacctcggat tatctgctac tgggaaactt   3180
tgtgtacact tttgtggtga taactgtgtg tttgaaagct ggattggaga catcatattg   3240
gacatggttc agccacatag cgatatgggg gagcatcgca ctctgggtgg tgttttttgg   3300
aatctactca tctctgtggc ctgccattcc gatggcccct gatatgtcag gagaggcagc   3360
catgttgttc agttctggag tcttttggat gggcttgtta ttcatccctg tggcatctct   3420
gctccttgat gtggtgtaca aggttatcaa gaggactgct tttaaaacat tggtcgatga   3480
agttcaggag ctggaggcaa aatctcaaga cccaggagca gttgtacttg gaaaaagcct   3540
gaccgagagg gcgcaactgc tcaagaacgt ctttaagaag aaccacgtga acttgtaccg   3600
ctctgaatcc ttgcaacaaa atctgctcca tgggtatgcg ttctctcaag atgaaaatgg   3660
aatcgtttca cagtctgaag tgataagagc atatgatacc acgaaacaga ggcccgacga   3720
atggtgatgg ggagagcctg aaaggcaggc tctgttacct ctctaaggag agctaccagg   3780
ttgtcaccgc agtctgctaa ccaattccag tctggtccat gaagaggaaa ggtagatctg   3840
agctcatctc gctgatggac attcagattc atgtatatta tagacataag cactgtgcaa   3900
ctgtactgta acaccatctc ttttggattt ttttaaggta tttgctaagt ctttgtaaac   3960
ggaaattgaa aatgacctgg tatcttgcca gagggctttc ttaaacggag aataagtcag   4020
tattcttatg ccattactgt ggggctgtaa ctgactgtca gtttattggc tgtaccacaa   4080
ggtaaccaac cattaaaaaa ctctaaatga tatttagtta aagggactct tggtatccag   4140
acttagattt caggatatgc tgaaacaaac cagcattctt aaggaactga ctcaccttcc   4200
tgagcaaaat ttctaaacaa gcatttgtgt ccaaaattgt cttgataaat gtttgccaaa   4260
gaggttcagt aagtgttttt ctagttcagt agtcatatgc ccagaaatgt aagagaaagt   4320
ttacttccag ttccgctgta agatctgcat gcctgacttt ccaaatgtaa gagtgattta   4380
caaaaatgaa tatttcaagg catttgctac taaaatcggt gatgttgcac ctttggcctt   4440
acaaatgctt ctttgttgtt tgtcgtgttt atttgttaga ggacacacgt gttaatgtga   4500
ctctgttgtt atgacactga tttttcaaac tatgtatgtt tcaggtattt ctgatgaagt   4560
ttcatcatca tttagatttt tctaaaaatc tggctaatgc agtagattga gtgatgtcat   4620
tttgtcttaa agtttttcct cttaagaaac atatgctacg tatttacgtg ggatttccaa   4680
agcttctgtt gcaatatttg gaataacatg tcagataaat gcatgggctt ttgtcctgtg   4740
ttccagttcc cactagagat gcctgtgtct tgtgtagcac acccagtgtt atggtgactg   4800
cccccctatac tgaagactga aaattatttc acagttcact catcaaatag ttcccaaaat   4860
tcgtcacatg ctgcttattg ggacaaatag gtagtacatt ttccccattt aaaaaatgcg   4920
gattttactc aggccggtaa ctttacagtc agaggacacg ttcatcatga gtagcttttg   4980
```

-continued

```
ttagtatgtt ttaaaatgta tcttcagttc aattattttc agcatttaca agacatctga   5040
aaatggctat tttgctacca acagtaaatg aaggggctgt ttaaaaacca caaccagttt   5100
tctacactat tttttaaata atactttcat ttgaaaaaaa ggaattagtt ttcagataca   5160
cttcagagat tgaagcaaac tatttgcctt ttactcaaaa gcctgcttgc ctttacatgg   5220
acttaccagc aaaataggta gaactttctc ttttaaaaaa agtcaactag aattgagaag   5280
aggtgatttt ttttcagatc gcttctcgag tttaatattt tcacattctt ttcacccttt   5340
ttctcaatct agatttaaaa ttaggatata tgtcatttcc ttgtctgtat ttgtagctcc   5400
ttagttacca gtatgcctct ccattttcta caaataagag gttataacac atatacataa   5460
ttctaacctt aagggaacac acgtttacat actttacttc ccaagccctt cctgtttggg   5520
gtacagattg agagagtcat gaatcaacac atctagcaag accacaggtg taagagtcta   5580
agatcgtctt caaaattctg aagtcccagt ctttacctgt ccagtgaatg aatattcaga   5640
gcagcttttc ctgggcttcc cagtggtgat agctgaggtc aaaccacaaa aaataagaaa   5700
gcaagagtga aatgcacccc tccagagaaa cactttgtag tgtttaattc tgttaataga   5760
gaagagctgc ttctgtttgc gctcacttca tcagtggcac ccttctgcag aattttaata   5820
taaaaacatt atggatataa tagaactgga ttttctgact taaaaatgta agttttattt   5880
taatcttgaa acgtggattg tttctgtgga gctcttaaac atgagaagaa tacttacggt   5940
tgataatgtg taacatgatc tgaaatgtga ctaatttgag cctctttgtc ccatcgtcct   6000
gtttttgaat tattgacatt gtcagtctct ttgcttcctg ggtgagactt ggggtttgag   6060
ggacagggaa tgaccttctt ggtgaaactt aaaatataac attgcaattg cagtgacttt   6120
acagtgttaa attagagaaa atagtctgat tttttaaacc ttccttaact ggaaaaaagt   6180
cacatggttt taccaggatt gaaataaaca gtcaatgtga cttttaacat gtgttttttt   6240
gaaataaagg gcacgtactc ttcaattaaa aagttcctta tagggactct ggcaaatgct   6300
aacacagttg ctttacaatg tttacaattc agacaatacg acttataata gaaaatcctc   6360
attcatttag cattgaaaag ctggaagttg cttctttaat gttgaatagt atacagtggt   6420
attgagcatg gactttctaa atgttttata tatacatata aaaatatatt ggtgtctcac   6480
acccagaaag atgttatatt gtagatatta ttaggaaaac agtgtttctc aggaacgttg   6540
taaattttaa atgatatatg tacttcccgt cctcccacct ccactctgtg ctctaatgtg   6600
agactgcttc agcagtgttg ctaagttaat ggaaaacttt ttctaatcaa gtcaggtgaa   6660
tgtgtattct gctaaataat gttagccatt tacatgaatt gtatggtcat taaatggaat   6720
cagtgattcc tctttaattt ccagagggga aatgaattat ggaaatcagt cagcattctg   6780
atcattaaat tttatacttt aattttgccg ttcagcattc taaatatcca atgtgaaagt   6840
cacatgataa tttgttttgc attgcgtgca ctgtacaaca cttacaactt gtcatttaaa   6900
atgttttctc gggaaatgaa tgctagtcag aaagtaatag attgtattat tcatagtttt   6960
aaaattatga caatgtcata attactacaa agctaaataa tcgtgtttat ttttgtgcag   7020
ttgccctttg atagttcctg gttttaaaac ctattaagtg tataatctta caaatagtca   7080
tctacaaaat ttatggagaa agtgcccagc ccattcacat cacatggacc aggaattctt   7140
ttgtaaatga cttaaggtaa catcatgcag ttcagtgcct aataaatgct ttttaatgat   7200
gaacatttct ataatgactc gtaagatacc atagtctgat tttctcaca ttaaaataac   7260
tgaagtcact tgtgtaacgt agttatactt tgctgcattt taattaacct tcaacagcta   7320
ttaaagtgga atgtaagtta aattttgaag gaaaggaaat aaatgttttc catatttcgt   7380
```

cttgatttac tttctgtatg agaacagctg tgtttttgat aggtttatgg tttgcatgag 7440
ttcatattta aagtgatcca ggccaatgca tggctattgc tgtaaatctt gatgtttatt 7500
tctgccttgt aaagttctat cacggcctac ctggaattta aaattcagta gacaaattaa 7560
ttggtcctct gcacaacttt tttaataagt agattatttt acaaagaaat ttgaacaaat 7620
ttaattgaat cttttgttta gcttgcctct aagaactttt cttaataaag ctcccaaaac 7680
ttctcagcaa ataaatctcc cttaagtagg aaagctagat ttcatatttg cttactttga 7740
attaacagca actttccaca ggtaaatctg ttcttgcaaa gatgtgagca gaatagttaa 7800
aaataatatt tttatgtttc atggttctaa atggaagcca taaatgcagt aaatactatc 7860
tgttgtttaa ctactttaat cgtcattttt tacattttca agtttattag gttaagaaaa 7920
acagggcagc cttggaaggc agctactaca gaaaactgca gttttgcgtt aaagataaag 7980
tagtattttc agctccctga aaaaccattc ctgctgaaac tgctgtagaa attgtgaagc 8040
tgcatgagtg gagagtattg aatctgtggt tatagtagtt ttctcaggtt tgtttatctt 8100
gatgtttgat gcactgtgtt ttatagttat taaaattgag taatattatt tctatgcagt 8160
gttatgtgtc attggccttt tgtgaatgtg catgttttaa actgcaaatt ttaaacattt 8220
tgtcctctaa ttgttattaa aaatgaaata aactttacca ttacttaaaa 8270

<210> SEQ ID NO 12
<211> LENGTH: 5434
<212> TYPE: DNA
<213> ORGANISM: Homo sapiens

<400> SEQUENCE: 12
ttttctgcac ccgccgcccg ggagagcggg agcctcggcc ctccgcgcgg ctgcagctac 60
ctaccctgcg cccggcccgg tccccgactt agggatggca aacttgcgcc ccgtggccgc 120
ccccgccagc gccggccccc gctcctgctg ctgacggcgc ccaggaaatc cacagcagtg 180
atacatgtga cgtccacact gacagtgccc tcctgtgggc atggctcagg ttgtgcgcag 240
ttcctggcac actggctgta actccgcccc tttctctccc tctcagtaaa gcaagattac 300
gcggtgacat gcctcacagc tgatcacgac acacggggat ggagagcaag agttatggag 360
aatacaggtt ggatgggcaa gggacatagg atgaccccag cctgtcccct cttactgtct 420
gtgattctgt ccctgcgcct ggccaccgcc ttcgaccccg cccccagtgc ctgctctgcc 480
ctggcctcgg gtgtgctcta cggggccttc tcgctgcagg acctctttcc taccatcgcc 540
tcgggctgct cctggaccct ggagaaccct gaccccacca agtactccct ctacctgcgc 600
ttcaaccgcc aggagcaggt gtgcgcacac tttgcccccc gcctgctgcc cctggaccac 660
tacctggtca actttacctg cctgcggcct agccccgagg aggcggtggc ccaggcggag 720
tcagaggtgg ggcggccaga agaggaggag gcagaggcgg cagcggggtt ggagctgtgc 780
agcggctcag gcccctttac cttcctgcac ttcgacaaga acttcgtgca gctgtgcctg 840
tcggctgagc cctccgaggc cccgcgcctg ctggcgcccg ctgccctagc cttccgcttt 900
gtcgaggtct tgctcatcaa caacaacaac tctagccaat tcacctgtgg tgtgctctgc 960
cgctggagtg aggagtgtgg ccgcgctgcc ggcagggcct gcggctttgc tcagccaggc 1020
tgcagctgcc ctggagaggc gggggccggc tccaccacca ccacatctcc aggccctcct 1080
gctgcccaca ccctgtccaa tgccctggtg cccgggggcc cagccccacc tgctgaggcc 1140
gatttgcact cggggagcag caatgatctg ttcacaaccg agatgagata tggtgaggag 1200
ccggaagagg aaccgaaagt gaaaacccag tggccgaggt ctgcagatga gcctgggcta 1260

-continued

```
tacatggcgc agacaggcga cccggcggct gaggagtggt ccccgtggag cgtgtgttcc   1320
ctgacgtgtg ggcagggtct gcaggtgcgg acccgctcct gtgtgtcctc cccctatggg   1380
accctgtgca gcgggcccct gcgggagacc aggccctgca acaattcagc cacctgccca   1440
gtgcacggcg tgtgggagga gtgggggtcc tggagcctgt gctcccgcag ctgcgggcgg   1500
gggtcccgga gccggatgcg gacctgcgtg cccccccagc acggcggcaa ggcctgcgag   1560
ggtcctgagc tgcagactaa gctctgcagt atggctgcct gcccggtgga aggccagtgg   1620
ttagaatggg gtccctgggg cccatgctcc acgtcctgtg ccaatgggac ccaacagcgc   1680
agccggaagt gcagcgtggc gggcccagcc tgggccacat gcacgggtgc cctcactgac   1740
acccgggagt gcagcaacct cgagtgcccg gccactgata gcaagtgggg gccatggaat   1800
gcgtggagcc tgtgctctaa gacgtgtgac acaggctggc agcgccgctt ccgcatgtgc   1860
caggccacgg gcacgcaggg ctacccctgc gagggcaccg gagaggaggt gaagccttgt   1920
agtgagaaga ggtgtccagc cttccatgag atgtgcaggg atgagtacgt gatgctgatg   1980
acgtggaaga aggcagctgc tggcgagatc atctacaaca agtgcccccc gaatgcctca   2040
gggtctgcca gccgccgctg tctcctcagt gcccaaggcg tggcgtactg gggctgccc    2100
agctttgctc gctgcatctc ccatgagtac cgctacctgt atctgtcact tagggagcac   2160
ctggccaagg ggcagcgcat gctggcaggc gagggcatgt cgcaggtggt gcgcagcctg   2220
caggagctac tggcccggcg cacctactat agtggggacc tgctcttctc tgtggacatt   2280
ctgaggaatg tcactgacac ctttaagagg gccacctacg tgccctcggc tgatgatgtg   2340
cagcgcttct tccaggtggt gagcttcatg gtggatgcgg aaaacaagga gaagtgggac   2400
gatgctcagc aggtgtcccc tggctctgtg cacctgctcc gtgtcgtgga ggacttcatt   2460
cacctggtgg gcgatgctct caaggccttc cagagctctc tgattgtcac agataatcta   2520
gtgatcagca ttcagcgaga gcccgtctca gctgtgtcca gtgacatcac gttccccatg   2580
cggggccgcc ggggcatgaa ggactgggtg cggcactcag aggaccgcct cttcctgccc   2640
aaggaggtgc tcagcctctc ctccccaggg aagccagcca catctggggc agcaggcagc   2700
cctggcaggg ggaggggccc aggaacggtg cctcctggcc caggccactc ccaccagcgc   2760
ctcctcccag cagaccctga tgagtcctcc tactttgtga tcggtgctgt actctaccgc   2820
acccttggcc tcatcctgcc gcctcccagg cccccgctgg ccgtcacatc ccgggtgatg   2880
acagtgactg tgcgcccccc tacccagcct ccagctgagc cctcatcac tgtggagctc    2940
tcctacatca tcaatgggac cacggatccc cattgcgcca gctgggacta ctccagagca   3000
gatgccagct caggagactg ggacactgaa aattgccaga ccctggagac ccaggcagct   3060
cacacccgct gccagtgcca gcacctgtcc acctttgctg tactagccca gccgcccaag   3120
gacctgaccc tggagctggc gggctccccc tcggtccccc tggtgatcgg ctgtgcagtg   3180
tcgtgcatgg cgctgctcac cctgctcgcc atctatgccg ccttttggag gttcataaaa   3240
tctgaacgct ccatcatctt gctgaacttc tgcctgtcca tcttggcatc caacatcctg   3300
atcctcgtgg gccagtcccg ggtgctgagc aagggcgtgt gcaccatgac ggctgccttc   3360
ctgcacttct tctttctctc ctccttttgc tgggtgctta ccgaggcctg gcagtcctac   3420
ctggctgtca ttgggcggat gcgcacccgc ctcgttcgca agcgcttcct ctgcctgggc   3480
tggggtctgc ctgccctggt ggtggccgtg tctgttggct ttacccgaac gaaaggatac   3540
ggtacatcca gctactgctg gctctccctg gagggcggcc tgctctacgc ctttgtgggc   3600
cctgcagccg tcattgtcct ggtgaacatg ctcatcggaa tcatcgtctt caacaagctc   3660
```

atggcacgtg atggcatctc cgacaaatcc aagaagcaga gggccgggtc ggagcggtgc 3720
ccctgggcca gcctgctcct cccctgctca gcgtgtggag cggtccccag ccccctgctc 3780
agctcagcct cggccaggaa cgccatggcc tcactctgga gctcctgcgt ggtgctgccc 3840
ctgctggcgc tcacctggat gtctgccgtc ctggctatga cagaccgccg ttccgtcctc 3900
ttccaggccc tctttgctgt cttcaactcc gcgcagggct ttgtcatcac tgctgtgcac 3960
tgcttcctgc gccgagaggt ccaggatgtg gtgaagtgcc agatgggggt gtgccgggct 4020
gatgagagcg aagactcccc tgactcgtgt aagaacgggc agctgcagat cctgtcagac 4080
tttgaaaagg atgtggatct ggcttgtcaa acagtgctgt tcaaggaggt caacacttgc 4140
aacccgtcca ccatcacggg cacactatcc cgcctgtccc tggatgagga tgaggagccc 4200
aagtcctgcc tcgtgggccc tgagggcagc ctcagcttct caccactgcc tgggaatatc 4260
ctggtgccca tggcagcctc accagggctg gggagcctc cgcccccaca ggaggccaac 4320
cctgtttaca tgtgtgggga gggtggcctg cggcagctgg acctcacatg gctgcggccc 4380
actgagccag gctctgaggg agactacatg gtgctgcccc ggcggacttt gagcctgcag 4440
cctggcggtg ggggtggagg tggtgaggat gcccccaggg cccggccgga ggggaccccc 4500
cggcgagctg ccaagacagt ggcccacact gaaggctacc ccagcttcct gtccgtggac 4560
cactcgggcc tggggctggg ccctgcctat ggatctctcc agaatcccta tggaatgacc 4620
ttccaaccgc caccgccgac acccagcgcc cgccaagtgc ccgagccagg ggagcgcagc 4680
cggaccatgc ctcgcaccgt gcccggctct accatgaaga tgggctccct ggagcgaaag 4740
aaattacggt attcagacct ggactttgag aaggtgatgc acacccggaa acggcattca 4800
gaactctacc acgagctcaa ccagaagttc cacactttcg accgctaccg cagccagtcc 4860
acggccaaga gggagaagcg gtggagtgtg tcctcgggtg gggcagccga gcggagcgtg 4920
tgcaccgata agcccagccc tggggagcgc cccagcttgt cccaacatcg gcgccatcag 4980
agctggagca ccttcaaatc tatgacactg ggctcgctgc cccccaagcc ccgagaacgg 5040
ctgactctgc accgggcagc agcctgggag cccacagaac caccggatgg tgacttccag 5100
acagaggtgt gagtgccacg ctggactgcc cactgcatat aaatatatat atctctctat 5160
tttcacactc cactttggaa ctacccagga gccagcgccc tctcccctct cccgagggct 5220
gggcagggag gcgccgtgga ctcagccagg ctgggggagc cggacatggc ttggcctggg 5280
gtcccagggc ccttccttgt ttctcagagg cccctcagcc actggaaccc catcttcagc 5340
ccagcctgtc cgtccctgtc ccgggctggg gaggggggag gggaactttg ttgggaataa 5400
acttcactct gtggaaaaaa aaaaaaaaaa aaaa 5434

<210> SEQ ID NO 13
<211> LENGTH: 2377
<212> TYPE: DNA
<213> ORGANISM: Homo sapiens

<400> SEQUENCE: 13
ctaaacccgg aagcgaggga ggaacttcgg agctgtcgcc cgggttaccg ggaggcggag 60
ccgccgagct cgctgtggcc cggatgttcg gtgcagctgc cagatccgct gatctagtgc 120
ttctcgaaaa aaaccttcag gcggcccatg gctgtcgata ttcaaccagc atgccttgga 180
ctttattgtg ggaagaccct attatttaaa aatggctcaa ctgaaatata tggagaatgt 240
ggggtatgcc caagaggaca gagaacgaat gcacagaaat attgtcagcc ttgcacagaa 300
tctcctgaac tttatgattg gctctatctt ggatttatgg caatgcttcc tctggtttta 360

-continued

```
cattggttct tcattgaatg gtactcgggg aaaaagagtt ccagcgcact tttccaacac    420

atcactgcat tatttgaatg cagcatggca gctattatca ccttacttgt gagtgatcca    480

gttggtgttc tttatattcg ttcatgtcga gtattgatgc tttctgactg gtacacgatg    540

ctttacaacc caagtccaga ttacgttacc acagtacact gtactcatga agccgtctac    600

ccactatata ccattgtatt tatctattac gcattctgct tggtattaat gatgctgctc    660

cgacctcttc tggtgaagaa gattgcatgt gggttaggga aatctgatcg atttaaaagt    720

atttatgctg cactttactt cttcccaatt ttaaccgtgc ttcaggcagt tggtggaggc    780

cttttatatt acgccttccc atacattata ttagtgttat ctttggttac tctggctgtg    840

tacatgtctg cttctgaaat agagaactgc tatgatcttc tggtcagaaa gaaaagactt    900

attgttctct tcagccactg gttacttcat gcctatggaa taatctccat ttccagagtg    960

gataaacttg agcaagattt gccccttttg gctttggtac ctacaccagc cctttttttac   1020

ttgttcactg caaaatttac cgaaccttca aggatactct cagaaggagc caatggacac   1080

tgagtgtaga catgtgaaat gccaaaaacc tgagaagtgc tcctaataaa aaagtaaatc   1140

aatcttaaca gtgtatgaga actattctat catatatggg aacaagattg tcagtatatc   1200

ttaatgtttg ggtttgtctt tgttttgttt atggttagac ttacagactt ggaaaatgca   1260

aaactctgta atactctgtt acacagggta atattatctg ctacactgga aggccgctag   1320

gaagcccttg cttctctcaa cagttcagct gttctttagg gcaaaatcat gtttctgtgt   1380

acctagcaat gtgttcccat tttattaaga aaagctttaa cacgtgtaat ctgcagtcct   1440

taacagtggc gtaattgtac gtacctgttg tgtttcagtt tgtttttcac ctataatgaa   1500

ttgtaaaaac aaacatactt gtggggtctg atagcaaaca tagaaatgat gtatattgtt   1560

ttttgttatc tatttatttt catcaataca gtattttgat gtattgcaaa aatagataat   1620

aatttatata acaggttttc tgtttataga ttggttcaag atttgtttgg attattgttc   1680

ctgtaaagaa aacaataata aaaagcttac ctacataaaa tttcaatgtt ttgacactta   1740

attgttgttt ggcacaatag tatggaagta attcaaactg gtaaatagtt tcctctcata   1800

tctcgggtat atatacatac catattttat tgatccagag atacttattt cactttgtga   1860

catctctgaa ttaggatgca tcttacaact gatggcttat tagatttaat gaaatacaga   1920

agatacacag aataaaaagg gttttcctgt ggttggtttg tggtttgtga taggtgttct   1980

gtgatgttta tgctttgaag gccttaagac tcatggttgc aaccatggaa gcaaaatgaa   2040

atttttagct cttaacctaa caacctgacc atgtttatcc atttttattg tttagaagtt   2100

tatttactga tacttggtgg aggttgtgtg aattagttaa attttaaatg tttaagactt   2160

ctattaacag ctgcaaaata tgaaagtaag tgcactcact tttcctgtag tagtctgtct   2220

tttgaattca cagcagttgt atccttgagt tactttgtta atgtattttt ctcagtacat   2280

ttaaccactg ggaaatgaac ccttgtacga atgtgtttct tcttctctgt aggaataaaa   2340

aataaatata aaaattttat ttgtattgca cacaaaa                             2377
```

<210> SEQ ID NO 14
<211> LENGTH: 3952
<212> TYPE: DNA
<213> ORGANISM: Homo sapiens

<400> SEQUENCE: 14

```
aacgacgctc ttgcgtaaag gcccggccca agggaacgtt cagggcgtct cggctttccc     60

cgctgctgct tctgctaggc ccagtgcgag accagagcac gagcgactcc cgtcgtcccc    120
```

-continued

```
ggccaggcag atgttggcct agtcctggcg cgaacgaagc gcgctatttc cctgcttcct    180
ctaggccaag cctgctttac ggcagggccc gcctcgggag cgagcacaga ccggggcagc    240
gaggccagcc aggcgccgac gaggtccccg aacgcgcacg cgctccgttc agctccgggt    300
ggcggccgcc ggagtagacg ttagccatgg aaaccgagag ctggcccggg cggggccgcg    360
gtgagctcgt tattcggccg ccgcagcttt tctgcctccg cattcgggca ctaaccaacc    420
tcccggcggg agcgcccagc ccgagtttac ctgcaaaaat gcggtccctg ggatgccttc    480
gcgtcttctc ttccctcggg tgacttgagg tttgtggtaa atatgccagc tctagaacac    540
atgaatcaga ttttacacat cttgtttgta tttttaccct ttctgtgggc acttgggact    600
ctgcccccac ccgatgcact tctcttatgg gcaatggagc aggttttaga gttcggcctt    660
ggaggctcat ctatgtcaac ccacttacgg ttattagtaa tgttcatcat gtctgctgga    720
acagctatag catcatattt cattccaagc actgttggtg tggttctttt catgactgga    780
tttggtttct tgctgagtct gaacttaagt gatatgggtc acaaaattgg aaccaaatct    840
aaggatttac ccagtggtcc ggaaaaacat ttttcatgga aggaatgcct tttctacatc    900
attatattag tcttggctct tttagaaact agcttgcttc atcactttgc tggcttctca    960
cagatttcta aaagcaattc ccaggctatt gtgggctatg gtttgatgat attacttata   1020
atactgtgga tacttagaga aattcaaagc gtatatatca ttggaatttt ccgaaatccc   1080
ttttatccga aggatgtgca aactgtgact gtattctttg agaagcaaac taggctcatg   1140
aagattggta ttgtcagacg gattttgcta actttagtat caccttttgc catgatagca   1200
tttctttcat tggacagttc cttacaaggg ctccactcag tgtctgtctg tattggattc   1260
acaagagcct ttagaatggt atggcagaat acagaaaatg ctttattgga gacagtcatt   1320
gtatcaacag tacacttgat ctccagtaca gacatatggt ggaacagaag cctggataca   1380
ggactcagac tcttactggt tggtatcata cgtgatcgtt tgattcagtt catctctaaa   1440
ttgcagtttg ccgtgactgt gcttttgaca tcatggacag agaaaaaaca acgtcgaaaa   1500
acaactgcca ctttatgtat actcaacatt gtcttttctc cattcgtgtt ggtcatcata   1560
gtttttttcta cactactctc ttctccctta ctccctcttt tcacccttcc tgtgttcttg   1620
gtggggtttc cccgacctat tcagagttgg ccaggagcag caggcaccac agcctgtgtg   1680
tgtgcagata cagtgtacta ctaccaaatg gtgcccaggt tgactgctgt actgcagact   1740
gcaatggcag ctggaagttt aggtctcctc ctacctggat ctcattactt gggccgtttt   1800
caggatcgtt taatgtggat aatgattctg gaatgtggct atacttactg ctctattaac   1860
attaaggggt tagaattgca ggaaacatcc tgtcatactg cagaagctcg cagagttgat   1920
gaagttttttg aagatgcttt tgagcaagaa tacacaagag tatgttccct taatgaacac   1980
tttggaaatg tcttgacacc ctgtactgtt ttgcctgtga aattgtattc tgatgccagg   2040
aatgttctat caggcataat tgattctcat gaaaacttaa aagaatttaa aggtgacctc   2100
attaaagtac ttgtgtggat acttgttcaa tactgctcca aaaggcctgg catgaaagag   2160
aatgttcaca acactgaaaa taaagggaaa gcacctctaa tgttgcctgc tttgaacact   2220
ttgccacctc ccaaatcccc agaagacata gacagtttaa attcagaaac ttttaatgac   2280
tggtctgatg ataatatttt tgatgatgag ccaactatca aaaaagtaat agaagaaaaa   2340
catcagttga aagatttgcc aggtacaaat ttgtttattc caggatcagt agaatcacag   2400
agggttggtg atcattctac aggcactgtt cctgaaaacg atctttacaa agcagttcta   2460
ttaggatacc ctgctgttga caaaggaaaa caagaggaca tgccatatat tcctctcatg   2520
```

```
gagttcagtt gttcacattc tcacttagta tgcttacccg cagagtggag gactagctgt   2580
atgcccagtt ccaaaatgaa ggagatgagc tcgttatttc cagaagactg gtaccaattt   2640
gttctaaggc agttggaatg ttatcattca gaagagaagg cctcaaatgt actggaagaa   2700
attgccaagg acaaagtttt aaaagacttt tatgttcata cagtaatgac ttgttatttt   2760
agtttatttg gaatagacaa tatggctcct agtcctggtc atatattgag agtttacggt   2820
ggtgttttgc cttggtctgt tgctttggac tggctcacag aaaagccaga actgtttcaa   2880
ctagcactga aagcattcag gtatactctg aaactaatga ttgataaagc aagtttaggt   2940
ccaatagaag actttagaga actgattaag taccttgaag aatatgaacg tgactggtac   3000
attggtttgg tatctgatga aaagtggaag gaagcaattt tacaagaaaa gccatacttg   3060
ttttctctgg ggtatgattc taatatggga atttacactg ggagagtgct tagccttcaa   3120
gaattattga tccaagtggg aaagttaaat cctgaagctg ttagaggtca gtgggccaat   3180
ctttcatggg aattacttta tgccacaaac gatgatgaag aacgttatag tatacaagct   3240
catccactac ttttaagaaa tcttacggta caagcagcag aacctcccct gggatatccg   3300
atttattctt caaaacctct ccacatacat ttgtattaga gctcattttg actgtaatgt   3360
catcaaatgc aatgttttta ttttttcatc ctaaaaaagt aactgtgatt cttgtaactt   3420
gaggacttct ccacaccccc attcagatgc ctgagaacag ctaagctccg taaagttggt   3480
tctcttagcc atcttaatgg ttctaaaaaa cagcaaaaac atctttatgt ctaagataaa   3540
agaactattt ggccaatatt tgtgccctct ggactttagt aggctttggt aaatgtgaga   3600
aaacttttgt agaattatca tataatgaat tttgtaatgc tttcttaaat gtgttatagg   3660
tgaattgcca tacaaagtta acagctatgt aatttttaca tacttaagag ataaacatat   3720
cagtgttcta agtagtgata atggatcctg ttgaaggtta acataatgtg tatatatttg   3780
tttgaaatat aatttatagt attttcaaat gtgctgattt attttgacat ctaatatctg   3840
aatgtttttg tatcaagtag tttgttttca tagacttcaa ttcataaact ttaaaaaact   3900
tttaataaaa tattttcctt ccttttcaaa taaaaaaaaa aaaaaaaaaa aa           3952
```

<210> SEQ ID NO 15
<211> LENGTH: 2695
<212> TYPE: DNA
<213> ORGANISM: Homo sapiens

<400> SEQUENCE: 15

```
acgcggccgg ctaccgagcc ctttgtgagg gctgtgagct gcgcctgacg gtggcaccat     60
gagcagctca ggtggggcgc ccggggcgtc cgccagctct gcgccgcccg cgcaggaaga    120
gggcatgacg tggtggtacc gctggctgtg tcgcctgtct ggggtgctgg gggcagtctc    180
ttgcgcgatc tctggcctct tcaactgcat caccatccac cctctgaaca tcgcggccgg    240
cgtgtggatg atcatgaatg ccttcatctt gttgctgtgt gaggcgccct tctgctgcca    300
gttcatcgag tttgcaaaca cagtggcgga gaaggtggac cggctgcgct cctggcagaa    360
ggctgtcttc tactgcggga tggcggtcgt tcccatcgtc atcagcctga ccctgaccac    420
gctgctgggc aacgccatcg cctttgctac gggggtgctg tacggactct ctgctctggg    480
caaaaagggc gatgcgatct cctatgccag gatccagcag cagaggcagc aggcggatga    540
ggagaagctc gcggagaccc tggaggggga gctgtgaagg gctgggcgcc cctccctccc    600
tgtcccctct tctggctctg tgtgggtcca agtgaggcct ggactgtcca cgctgaggca    660
cagcctggag aggggccttt gcacgtgtcc ctacacctgg agtcctctgc tcctttctcc    720
```

```
agactggctt aagccaggag ccactggctg ctggtgtgag ggtctgggct gctggacttg    780

aggcagagcc tgcagcagct gtgtggacac tacccagccc tactcctctg ctgggtgggt    840

ctgcagatct cacaccacag acagggctgc ctgtgacctg ctgtgacctg ggagcagctt    900

cccctggaga tgctggtcct ggcttgaggg gaggggcaag tgggaccctg ccacctgggc    960

actgagcaga gggacctccc ccagctctct tagcaggtgg agccccaggg cctgggacag   1020

cctgccgctg ccagcaacct cccactgctg cctagggtgc agcgcccact gtcaccctgc   1080

cttctgaaga agcccacagg gctcctaagg tgcaccccgg tacctggaac tgcagccttg   1140

gcagtgactg gacagctggg tgggggatgc tccctgctgg ccctgggaac cttggacagg   1200

ccacctcaag gcccctcggc tgcccctcct ccctgggcct gctggggccc ctaggttctg   1260

cccatcaccc cccgcccctg ctggccttgg tgctaaggaa gtggggagag caggctctcc   1320

ctggcaccga gggtgcccac cctctccctg gtgtggcccc gtcaacatca gccacagccc   1380

agccccatta gtgggttagc gggtctgacc tcagccccac tcaggtgctc ctgctggcct   1440

gcccaagccc tgccctcagg gagcttctgc cttttaagaa ctgggcagag gccacagtca   1500

cctccccaca cagagctgtc cccactgccc tgggtgccag gctgtccgga gccaggccta   1560

cccagggagg atgcagagag ctggtgccca ggatgtgcac ccccatattc cctctgccct   1620

gtggcctcag cccgctggcc tctctgaccg tgaggctggc tctcagccat cgggcaggtg   1680

cctggtcggg cctggcttag cccaggtggg gcttggcaga agcgggcggg tgtggaagat   1740

attccatctg gggccaaccc caggctgggc ctgcgctgag cttctggagc gcaggtactg   1800

ggtcttgcta agtgaactgt ttcccaggaa cacctctcgg gcccatctgc gtctgaggct   1860

gggagtggca tctgaggccg ggagtggcat ctgaggccag gagtggcagg ctggtgggct   1920

gggcgtgggg ttttctgggc cctgcccagt actgccctgg ggacttggtg ggctcctggg   1980

tcagcagcat cccacccctg ggagtctggc cagctgagcc ccagggtggc aggggcatta   2040

tagcctggtg gacatgtgcc ttcagggttc ctccggggcc accttcctca ggccagtgct   2100

gggttcaaag ggctgtgtgt gtgtgtgtgt gtgtgtgtgt atgtatatgt gtgtgggtgc   2160

acacatctgt cccatgtatg cagtgagacc tgtctacctc ccacaaggag caagggctct   2220

gcccgccctc tgctcattcc tacccaggta gtgggacccc gggccccctt ctgcctggct   2280

tgcctgcttc tgccctttcc agaggggtct cactgacagc cagagacagc aggagaaggg   2340

ttggctgtgg atcaaggaag gctgcccctg taccctgtgg ggaaatggtg ggtgcatggc   2400

tggatgcaga ggtggaaggc cctgggccac aggcgagagt gggcgtgtca cctgtcccag   2460

gttcccagca agtctgcagc tgtgcagtcc tggggtccct gaccctgtcg cccaggggc    2520

gtgctgtcca gcaggggccc tgccttgcaa ggaacgtctc ttccggcggc tgggccgctc   2580

ctgcctggtc tgggctgtgt gtggcgccct ttccttcttg tttgttcctc tgtgttctgt   2640

gtgcgtctta agcaataaag cgtggccgtg gctcgcgaaa aaaaaaaaaa aaaaa        2695
```

```
<210> SEQ ID NO 16
<211> LENGTH: 1646
<212> TYPE: DNA
<213> ORGANISM: Homo sapiens

<400> SEQUENCE: 16

ccctgcctta agtgcctact ggatcccggg agcctgggct ggggcctggg cactgcttcc     60

tccttggccc ctcaggccct tggaagcaga gagagaacct cttgcagatc ccaggctcgt    120

ccccagcaca gcagacacca ggaaggtggc cagagcctca ctgagccgaa ccgacggccg    180
```

-continued

```
cccacccacc caggctggag ccatggataa attccgcatg ctcttccagc acttccagtc    240

aagctcggag tcggtgatga atggcatctg cctgctgctg gctgcggtca ccgtcaagct    300

gtactcctcc tttgacttca actgtccctg cctggtgcac tacaatgcac tctacggcct    360

gggcctgctg ctgacgcccc cgctcgccct gtttctctgc ggcctcctcg ccaaccggca    420

gtctgtggtg atggtcgagg agtggcgccg gcccgcaggg caccggagga aggacccagg    480

catcatcagg tacatgtgct cctctgtgct gcagagggcg ctggccgccc ccctggtctg    540

gatcctgctg gccctccttg acgggaagtg cttcgtgtgt gccttcagca gctctgtgga    600

ccctgagaag tttctggact ttgccaacat gacccccagc caggtacagc tcttcctggc    660

caaggttccc tgcaaggagg atgagctggt cagggatagc cctgctcgga aggcagtgtc    720

tcgctacctg cggtgcctgt cacaggccat cggctggagc gtcaccctgc tgctgatcat    780

cgcggccttc ctggcccgct gcctgaggcc ctgcttcgac cagacagtct tcctgcagcg    840

cagatactgg agcaactacg tggacctgga gcagaagctc ttcgacgaga cctgctgtga    900

gcatgcgcgg gacttcgcgc accgctgcgt gctgcacttc tttgccagca tgcggagtga    960

gctgcaggcg cgggggctgc gccggggcaa tgcaggcagg agactcgagc tccccgcagt   1020

gcctgagccc ccagaaggcc tggatagtgg aagtgggaag gcccacctgc gcgcaatctc   1080

cagccgggag caggtggacc gcctcctaag cacgtggtac tccagcaagc cgccgctgga   1140

cctggctgca tcccccgggc tctgcggggg tggccttagc caccgcgccc ctaccttggc   1200

actgggcacg aggctgtcac aacacaccga cgtgtagggt cctggccagg cttgaagcgg   1260

cagtgttcgc aggtgaaatg ccgcgctgac aaagttctgg agtctttcca ggccgtgggg   1320

accccacggc aggcacccta agtcttgtta gcctcctttt taaagtagcc caatctctgc   1380

ctagtttctg ggtgtggcct ccagcgcgct tcacaaactt taatgtggac tcggttcacc   1440

gagggccttg ttaaatacag gttcagacag tgtagccagg accgagtctg agattctgca   1500

ttttaaacaa gctcctggag gctgatgtgc ttttggtcag tgaaccaaac tttgagtagc   1560

aagaatctaa gtaaatctgc catgggttct gggttctaga tgtcaattct aaataataat   1620

aatgacctta gtctgctgcc tcgata                                        1646
```

<210> SEQ ID NO 17
<211> LENGTH: 3099
<212> TYPE: DNA
<213> ORGANISM: Homo sapiens

<400> SEQUENCE: 17

```
ctctgctctg agctctgttg gtcccagcca ggagagcccg agtcatgagg tgggcaccca     60

gtgggcaggg tgggcagcag gggccctctt ggaggcagca gtgagttggg aagaggaggc    120

cgggccccac agcgggcatg atggacaagt tccggatgat cttccagttc ctgcagtcca    180

accaggagtc cttcatgaat ggcatctgtg gcatcatggc cctggccagt gcccagatgt    240

actcggcctt cgacttcaac tgcccctgcc tgccgggcta caatgcggcc tacagcgcgg    300

gcatcctgct ggcgccaccc ctggtgctct ttctgcttgg cctggtcatg aacaacaacg    360

tgtccatgct ggccgaagag tggaagcggc caccgggccg ccgggccaag gaccccgctg    420

tgttgcgcta catgttctgc tccatggccc agcgcgccct catcgcgcct gtcgtctggg    480

tggccgtcac gctactcgac ggcaaatgct tcctctgtgc cttctgcact gccgtgcccg    540

tgagcgcact gggcaacggc agcctggcac ccggccttcc tgcccccgag ctcgcccgcc    600

tgctggcccg ggtgccctgc cctgagatct acgatggcga ctggctgttg gcccgagagg    660
```

-continued

```
tggccgtgcg ttacctccgc tgcatctccc aggcgctggg ctggtccttc gtgctgctga    720
ccactctgct ggcattcgtg gtgcgctctg tgcggccctg cttcacgcag gccgccttcc    780
tcaagagcaa gtactggtcc cactatatcg acatcgagcg caagctcttc gacgagacgt    840
gcacggagca cgccaaagcc tttgccaagg tctgcatcca gcagttcttc gaggccatga    900
accatgacct ggagctgggt cacaccaacg ggacactggc cacggcccct gcttccgcag    960
ctgcccccac gacccccgat ggtgcggagg aggaaaggga gaagctgcgt ggcatcacgg   1020
atcaaggcac catgaacagg ctgctcacga gctggcacaa atgcaaaccg cctctgcggc   1080
tgggccagga ggagccaccg ctgatgggca acggctgggc tgggggtggg ccccggcctc   1140
cgcgtaagga ggtggccacc tacttcagca aagtgtgagg cgtggccagc tgaagaggca   1200
ggaacgggga tctgagccca cagcccctcc aacccccaaa ccaggtggaa aaaggaaggg   1260
tttcggtgct gggcagtact cccctaggca gatccacact ccgtagcact cgcctgccca   1320
ttggaggcag gaaatttgga gctggaaggg gatctgatgc cttcaggtgt gacactgccc   1380
tggatggccc tagggcagtg ggcccatgag cagtattagt ctaaaggggt cggaactgtc   1440
atggcaggta cagggaccaa tggctcccct ctgcccagcc cttcccaggc tgatgttcac   1500
tgtctcctcc caggttcaac agacatccct gcaccagggt ccaccctcgt ctgtggctgt   1560
tcagtacctc tcttccttta tgctccgggc tcggggagtg ggaatcatca ggcgtctcat   1620
gaagtgggag ccctctgatt tgggcaagcg tgtcgtaggt gagactgggt gtgccggggc   1680
aggtccataa ggacatgaca cacagcctac atggtgtgac acacctgggg tgacaggcga   1740
tgagacaaga tgtcagaagc taggttcaca tggaagaggt cagagtgtgt ggtcaccatg   1800
ggggtcatgt gacaattgtc caggtggact gcatgtttat ttagcacaaa ccaagcacaa   1860
aagtcctcct gtagaggggt ctttgaaaaa ccaccttaat acccacgtca catccaggtc   1920
tccaggggaa atcagaccat ccccaaggct tgagaagtta gacacagaag ctgaagtctc   1980
tccatttttc tcaaagaccc cacctcttgg ggatggagtt ctaagaggct aagaggagct   2040
ccaaggctct agcccaggtg ggatgagggt ggaggagagc agtgtaaaga gaaagcagct   2100
cagattccag agtgagacag aactgggtca aatggtgtct ctaccactca caaaccctgt   2160
ccctgggcca gctgcatcac tgcctgtgcc ttcgtttctt catctataca atgaggatga   2220
ggcccccccg gcccgccatc atggggttgc tgtgtgtaaa agcacatggc acatagtagg   2280
cacccagcac agggtggcta atgtatttgt tgatttctga acctaaggac ttccttcctc   2340
ctcccctggg cagggatgag acagcaacac aaacactcga gcttccatct tgttgaggag   2400
gaaacagagg tacagatagg tttctcagca ccgccctcag ctctgagaca taagtcccaa   2460
gcatctaagg attcatttg atcttggcat gattccatcc ttttttatcc atccttccct   2520
ctattcccac ttctggggtc cagtttccct cctcttaatt atttgggagg agttgctcag   2580
atctttgtgg gccaaggtgg gctgggaggg ctcttccagg aggtaggagt tggtatgggc   2640
cctgaagtca gggaggatta ggatgagcaa aaaacaaggt gtatgttggt gggtggcagc   2700
acttccagtg ggaagagaag gcccggaggt atcaggaggt acaaatgtga tgaagagcaa   2760
agctttgggt caggcacacc tgagttcaaa taccagcact gcaggacttg tggccagtca   2820
cccagccact ctaagcctca gtgtgtctgt ctataaaatg gatattagaa gacctgcttg   2880
gccaggcgga gtggctcatg cctgtaatcc cagcacttgg gaggccaagg agggaggatc   2940
acttgagcct gggagttgga gaccagcctg ggcaacatag caagactctg tctctgtaaa   3000
gtaataataa taataataag aagaagaaga agaataaaga gaagatttat aattttaaaa   3060
```

```
aaaaaaaaaa aaaaaaaaaa aagaaaaaaa aaaaaaaaa                        3099


<210> SEQ ID NO 18
<211> LENGTH: 2151
<212> TYPE: DNA
<213> ORGANISM: Homo sapiens

<400> SEQUENCE: 18

gatcgcggcg ccgccccaga ccgggggcgc agtcccactc gctccgagcc ccggtccccc     60

aagcctccct cccgggtacc tggggccgcg cccgccctgc gcccagctcc gccctccgtc    120

ggcccaggcc tgacagagcc cggcagccat gagtgccaac cccccggtggg acatcagcag    180

ggcgctgggg gtggccaagc tcttccacct ggtgtgcggg gtgcgggaag cctgcgtgac    240

cccgttcctg accctttacc tgaggcagct gggcttggcc gcgccctggg tgggcaccct    300

aatgggaacc aagcacctaa tcgctgcctt ctgggctccc gtctgtgcct tcctggccaa    360

aagctaccgg aaaaggagag cgcttctgat cggctccctg ctcggctcgg tgggggccag    420

cctgctgatg gtcctggtcc caccggtaga caaaaatcgg gtgcacttcc cttgtaatgg    480

aagcagcggc ctgaccagca cagacgcact cccgggggtc acgctacctg tgaacatcac    540

ctcggcccaa gagtctgcct ccagccaccc agccaagagg actgcagagg tggaaatgcc    600

tggcttcaga aacccacctg gtgaaagtga ccgagaaact ttccgtgatc tgcacgtcta    660

cttagcgccc tccgttgaag gagctaggac cacatcccaa gctctcctcc atcctgtcac    720

ttcggggctg aaagatcatc cctgggaagt tacttttgag gtggtcaaga cagccctccc    780

cttgcttact ggggggaaag ggcccgggaa tccagccaat ttgtcaggga ccaaggggaa    840

agcctgggct tttgacctgt ccttggaggc gttgcggcgg acttttatcc tctccttggg    900

gtccgtggcg ttctgggagc tgctgacagc gcctctggag caggtggcag atgacagcct    960

ttatgagttc ctggattttg tggatgccac tgaccgatac agaagcctgt gggtctggag   1020

gttgctgggc atgtcggcag gcgtgtgtgg catcacagcc ttggtggggc agctggactg   1080

cttcctgatg accagtggcc cccgaggtgt ggtccacttc tatgggtact cggtggtcag   1140

caccctggcc ttactggtga gcattgcctt tcccattccc atctgtcagc agtgggagcc   1200

cagctacaaa agggtcaaag cactgtccat tgtggggggt gacccccacc tcattctcct   1260

cgcctccacc actgttttgg taggagccat cgtcagtact gtccagaact ttctgttctg   1320

gcacatgaag gaccatggga gcggcgagct ggtcatgggt ttctcggtcg ccctcagctt   1380

gctgggggaa attctgcttc atccgttcaa agctacattg cttaggaaac tgtccaggac   1440

gggcctggtg gggctggggc tgagctgcct cgctgggcag ctgctgtact actctttcct   1500

ctggagctgg tggtccgtcc tccccattca gatcttgagt gccattagca acagagcttt   1560

gtggtgggct gtgggggcct cagtagagga cctggccact ccccgcatgg agagggctct   1620

gagtgccttg ttccgaggcc acttttacgg gagtggctgt agcctgggca gctttgtcgg   1680

gggcttcgtg gtgatgcgct tcagcctggc tgtgctctac caggcctgct gtgtggccct   1740

gttgctctgg ttggccttgc tcctgtccat acagcggagg ctgccccgag agcggaaaat   1800

caagtactcg aagctgctgt ccatggaggt gagtgacacc agtgactctg agcaggggac   1860

agaacaggac tggcttgtga aggccatgag ggaggaacac tcagactgaa agggctgaga   1920

aatccagagt gtgctgatcc agcaaggaac gaatggactg aacaaaactc agcctgctga   1980

ggacagaaac ctgccctgga ctgctgggag ccggggaaga gaggatgggt ctgtgctgaa   2040

ggcccaacag gatcatctca ttgcatgatt ttctttactt ttgaagtaaa aggagattta   2100
```

-continued

```
acttttaaaa aaaaaaaaaa aaaaaaaaaa aaaagaaaaa aaaaaaaaaa a          2151


<210> SEQ ID NO 19
<211> LENGTH: 4133
<212> TYPE: DNA
<213> ORGANISM: Homo sapiens

<400> SEQUENCE: 19

ctccctttca tctggtggcc ctagcgccac aagctgccgc ttaggaagtc cctgccggga     60

gcagaagtgg agacatcagc aggatggcat cggcaagtcg ctcccctccc gggcctcatc    120

tgccaaacga tcatctcctc ctccgaagtt gtatgcatga caggcgagtg gaaacttcac    180

taaaatgaag gcgattgaca caacagaagg aactccatcc tttcgggggc ttacgaaaat    240

aataagttta aaaaaaatag gaagggaatt ccctcgctcc atgatcactg agcgctctcc    300

taaggaaaag gaaatctccc ggggggtgcc gactacgggc ggcgggctta ggatgctccc    360

acgctccccg acccccaatc cccaggaccc gcaggacctc cggaggaacg cccgccagcc    420

cgcccggagc cacgcggcac aaggtgacac ggaccgcgcc gcgcgggccc ctcagccgcc    480

tgggcgaggc cgggagcagg gagaggggca tccgccggcc cgcggtacct tgtacttatc    540

aaagccagcc agctgctccg ggctcacgta ttcgtagcca gccatgacga cccgaaaact    600

gagcgcccac tcggcagcga ctcccggcta caaggctgtg acacacaagc accacaccgg    660

ctgggcaagg atggcaaaga ctgggctgcc cgagaaggga cagagtcagg ctggagggga    720

atctggatct gggcagctcc tggaccaaga gaatggagca ggggaatcag cgctggtctc    780

cgtctatgta catctggact ttccagataa gacctggccc cctgaactct ccaggacact    840

gactctccct gctgcctcag cttcctcttc cccaaggcct cttctcactg gcctcagact    900

cacaacaggt gagtacatga gctgcttcga ggcccagggc ttcaagtgga acctgtatga    960

ggtggtgagg gtgcccttga aggcgacaga tgtggctcga cttccatacc agctgtccat   1020

ctcctgtgcc acctcccctg gcttccagct gagctgctgc atccccagca caaacctggc   1080

ctacaccgcg gcctggagcc ctggagaggg cagcaaagct tcctccttca acgagtcagg   1140

ctctcagtgc tttgtgctgg ctgttcagcg ctgcccgatg gctgacacca cgtacgcttg   1200

tgacctgcag agcctgggcc tggctccact cagggtcccc atctccatca ccatcatcca   1260

ggatggagac atcacctgcc ctgaggacgc ctcggtgctc acctggaatg tcaccaaggc   1320

tggccacgtg gcacaggccc catgtcctga gagcaagagg ggcatagtga ggaggctctg   1380

tggggctgac ggagtctggg ggccggtcca cagcagctgc acagatgcga ggctcctggc   1440

cttgttcact agaaccaagc tgctgcaggc aggccagggc agtcctgctg aggaggtgcc   1500

acagatcctg gcacagctgc cagggcaggc ggcagaggca agttcaccct ccgacttact   1560

gaccctgctg agcaccatga aatacgtggc caaggtggtg gcagaggcca gaatacagct   1620

tgaccgcaga gccctgaaga atctcctgat tgccacagac aaggtcctag atatggacac   1680

caggtctctg tggaccctgg cccaagcccg gaagccctgg gcaggctcga ctctcctgct   1740

ggctgtggag accctggcat gcagcctgtg cccacaggac caccccttcg ccttcagctt   1800

acccaatgtg ctgctgcaga gccagctgtt tggacccacg tttcctgctg actacagcat   1860

ctccttccct actcggcccc cactgcaggc tcagattccc aggcactcac tggccccatt   1920

ggtccgtaat ggaactgaaa taagtattac tagcctggtg ctgcgaaaac tggaccacct   1980

tctgccctca aactatggac aagggctggg ggattccctc tatgccactc ctggcctggt   2040

ccttgtcatt tccatcatgg caggtgaccg ggccttcagc cagggagagg tcatcatgga   2100
```

-continued

```
ctttgggaac acagatggtt cccctcactg tgtcttctgg gatcacagtc tcttccaggg   2160

caggggggt tggtccaaag aagggtgcca ggcacaggtg gccagtgcca gccccactgc   2220

tcagtgcctc tgccagcacc tcactgcctt ctccgtcctc atgtccccac acactgttcc   2280

ggaagaaccc gctctggcgc tgctgactca agtgggcttg ggagcttcca tactggcgct   2340

gcttgtgtgc ctgggtgtgt actggctggt gtggagagtc gtggtgcgga acaagatctc   2400

ctatttccgc cacgccgccc tgctcaacat ggtgttctgc ttgctggccg cagacacttg   2460

cttcctgggc gccccattcc tctctccagg gccccgaagc ccgctctgcc ttgctgccgc   2520

cttcctctgt catttcctct acctggccac ctttttctgg atgctggcgc aggccctggt   2580

gttggcccac cagctgctct ttgtctttca ccagctggca aagcaccgag ttctccccct   2640

catggtgctc ctgggctacc tgtgcccact ggggttggca ggtgtcaccc tggggctcta   2700

cctacctcaa gggcaatacc tgagggaggg ggaatgctgg ttggatggga agggaggggc   2760

gttatacacc ttcgtggggc cagtgctggc catcataggc gtgaatgggc tggtactagc   2820

catggccatg ctgaagttgc tgagaccttc gctgtcagag ggacccccag cagagaagcg   2880

ccaagctctg ctgggggtga tcaaagccct gctcattctt acacccatct ttggcctcac   2940

ctgggggctg ggcctggcca ctctgttaga ggaagtctcc acggtccctc attacatctt   3000

caccattctc aacaccctcc agggcgtctt catcctattg tttggttgcc tcatggacag   3060

gaagatacaa gaagctttgc gcaaacgctt ctgccgcgcc caagccccca gctccaccat   3120

ctccctggcc acaaatgaag gctgcatctt ggaacacagc aaaggaggaa gcgacactgc   3180

caggaagaca gatgcttcag agtgaaccac acacggaccc atgttcctgc aagggagttg   3240

aggctgtgtg cttgaaccca ccagatgagc cctggcccaa tgctctgaac tcttcccgcc   3300

tcccggagct cagcccttga gaaaggcagg cttatatttc ccttagtgac actcatttat   3360

cttacagctc accccttctc atttctaaag tatccagcaa gaatagcagg aaaaattagc   3420

taaaggcacc taatgaataa gcctgccttt gctccagaaa taatcgacag atatcaaagt   3480

gcggaataat tacaagtaaa ctttctcaac cagtttttaa ctacaacaat acatgttgtg   3540

aatgaatata tttgataaaa atggttttaa ttgacctatt cagcgatttc tgattatttc   3600

tttttcaata gttatgaaga aaggatgact tacttgacag gaacctctga tctttcaaac   3660

attggagatg aagggcagaa tttggtttgt cttttcaagt ttaggaaaag gtgaagttaa   3720

ttggtccctc tttctttaac ctttaaaaaa tcaatataaa atgtaagttt cttaaccata   3780

tccatgtata gaggcattga ttgatatgag cacgttgtaa gaataggtta taaaaattta   3840

aagtttaata taaatttata tcaattaata aagtttaatt tatatttaaa aatgaatact   3900

agaagaaaat ctttttgaag acaccaagat atctatctgg ctgaattaac ttatggaatt   3960

cacaagagga agatgacagg attctgagaa atttttaaac tagatacgtg aaaaaagtct   4020

gatgaatcgg tctttgttaa ttatgcaatt catggatatt ttttataaaa tgggacgggg   4080

gcattttctg ttaaaataaa aatggttatg ctatcacgaa aaaaaaaaaa aaa          4133
```

<210> SEQ ID NO 20
<211> LENGTH: 7324
<212> TYPE: DNA
<213> ORGANISM: Homo sapiens

<400> SEQUENCE: 20

```
ctcgcggccg gcgaggggct gagctgacag ggccgcatcg gcttacccca ccttacttta     60

tcggaacgtg cctaagctgc tgcagctggc acccggttgc gctcggcgaa gagggctggg    120
```

-continued

```
ggcgggagat gacggtggtc ttctccctgc ttggcaccct gcgagcacca gctcccttct    180
cctcgccact ccaaggttgc agacgaagca gagatctggt tggagttgga gggtgagaga    240
aaatgaattc taatttacct gcagagaact taaccattgc agtcaatatg accaagactt    300
tgcctacagc agtaacgcat ggatttaatt ccactaatga cccaccttca atgtcaatta    360
caaggctttt tccagcctta ctggaatgct ttggcattgt cctttgtggc tacatagcag    420
gaagggccaa tgtcataaca tcaacccagg ccaaaggact aggaaatttt gtctccagat    480
ttgcacttcc agctttatta ttcaaaaaca tggttgtact taatttttcc aatgtggact    540
ggtccttcct atatagtatc ttaattgcca aagcttctgt atttttcatt gtatgtgtat    600
taaccttatt ggttgccagt cctgatagtc gatttagcaa agctggacta ttccctattt    660
ttgctacaca aagtaatgac tttgcattgg gataccctat agttgaagct ttatatcaaa    720
ctacataccc agaatatctc cagtacattt atttggtggc accaatatct cttatgatgt    780
taaaccctat agggtttatt ttctgtgaaa tccaaaagtg gaaagacact caaaatgctt    840
ctcaaaataa aataaaaatt gtgggactcg gactcctgcg tgtattacag aacccaatag    900
tatttatggt cttcattggc atcgccttca attttattct tgatcgaaag gtacctgtat    960
atgtcgaaaa ttttcttgat ggacttggaa attctttttc tggatcagcc ctattttatc   1020
ttggtctcac gatggtggga aaaataaaga gactgaagaa gtcggcattt gtagtactaa   1080
ttcttctcat cacagctaaa cttctggtgc tgccacttct gtgcagagaa atggtggaac   1140
tcttggacaa gggcgacagt gtggtgaacc atacaagttt atcaaattat gcatttctgt   1200
atggtgtatt tcctgtagca ccaggagtgg ctatctttgc aacacaattc aacatggaag   1260
tagaaattat aacctcaggg atggtgataa gcacatttgt gtctgctccc atcatgtacg   1320
tttctgcctg gttactgacc tttcccacta tggaccctaa gccattggca tatgccatcc   1380
agaatgttag ttttgatata agtattgtca gcctgatctc cttgatctgg tctctggcta   1440
ttcttctttt gagtaagaaa tataaacagc ttcctcatat gcttacaact aatttactca   1500
ttgctcagtc tattgtctgt gctggaatga tgatatggaa ttttgttaaa gaaaaaaatt   1560
ttgttggaca aattttggtg tttgttctat tgtacagctc cctctatagc acctacctgt   1620
ggacaggcct tctagcaatt tctttgtttc ttttgaaaaa gcgagagagg gtacaaattc   1680
ctgttggaat aatcataata tctggctggg gaattcctgc tctccttgtt ggtgttcttt   1740
tgataactgg aaaacacaat ggagatagca ttgactcagc cttcttttat ggaaaagaac   1800
agatgatcac cacagcagtc accctgttct gcagcatcct gatagctggc atatccctca   1860
tgtgcatgaa ccagactgcc caagcaggaa gctatgaagg tttcgatcag tctcagagcc   1920
acaaagtggt ggagcctgga aatactgctt ttgaggagag tccagcacca gtaaatgaac   1980
cagaactttt tacaagctct attccagaaa caagttgctg ctcctgctcc atgggaaatg   2040
gtgaattaca ctgcccatca atagagccaa tagcaaacac aagcaccagt gagcctgtga   2100
ttccttcgtt tgagaaaaac aatcattgtg tgagtcgctg taactcccag agctgcatat   2160
tagcccagga agaagaacag tatctacaga gtggagacca gcaactgacc cgacatgtgt   2220
tgctgtgttt acttctcatc attggcctgt tcgctaatct ttccagttgt ttatggtggc   2280
tattcaacca agagcctgga agactttatg ttgagttaca gtttttctgt gccgtgttta   2340
actttggtca gggatttatt tcctttggaa tctttggatt agataaacat ttaatcatcc   2400
tgcctttcaa aagaagactt gaattcctat ggaacaataa agacacagca gaaaacaggg   2460
attctcctgt ttcagaggaa ataaaaatga cctgtcaaca atttatccat tatcaccgtg   2520
```

-continued

```
acctctgtat ccgaaacatt gtcaaagaaa gaaggtgtgg tgcaaagact tctgctggaa   2580
ctttctgtgg ctgtgacctg gtgagctggc taattgaagt cggccttgcc tccgaccgtg   2640
gtgaagctgt gatatacgga gacaggctgg tacaaggggg agtcatccaa catattacca   2700
acgagtatga attccgggat gagtacttgt tttacagatt tcttcaaaag agtcctgaac   2760
agagtcctcc tgctattaat gcaaacactc tccaacagga aagatataaa gaaattgagc   2820
attcatcccc accctcacat tcccctaaga cctaaattat gcaggggaga accctacatg   2880
gaatcatatt ctagccgcgt attcattagt ttttagctgg gtgaccttgg gcaagttaac   2940
agaggcaacc tctctgagcc tcagttgtct cttctgtaaa atgtgaaaag atgtgctccc   3000
accacatgcg cagggtctgt gattttacat gtatgtaaaa cacataggaa gctgacttag   3060
gaaaaagaga aaaccaaatt aaagttctga taatgaatat aatatagtca tcctttagta   3120
tccaagggga ttggttccag gactcctgaa gatcccaaaa tctgaggata ctcaagtccc   3180
ttatataaaa tggtgtaggc cggcatggt ggctcacgcc tgtaatccca gtactttggg   3240
aggccgagtc aggtggatca cctgaggtca ggagttcaag accagcctgg ccaacatggc   3300
gaaaccccgt ctctactata aaatacaaaa aattagttgg gtgtggtggc gggtgcctgt   3360
aatcccagct actcaggagg ctgaggcagg agaatcgctt gaatctggga ggcagaggtt   3420
gctgtgagcc gagatcgtgc cactgcactc cagcctgagc aacagagcaa gactctatct   3480
caaaaataaa ataaaataaa ataaaataat taataaaatg gtgtagtatt tgcatataac   3540
ctatgcacat tctcccatat agtttaatca tctttagata cttataatgc ctaatacaat   3600
gtaaatgcta tgtaaatagt tgttgttata ctgtattgtt tagggaataa caataagaaa   3660
aacagtctgt acatgttcac tacagatgca accattgtta agcctgacta catcttttta   3720
tctgcggttg attgaatcta tggatgtgga acctgtgcat atggagggtc aactgtacta   3780
taaataatac gaatatgcca acattatata atcattgctt tctgcaactg tttactataa   3840
tttcaaaatt aatatcctat taactgttcc tataaattat caaatttggc aagtgtatta   3900
ctagcaggag atggacctta aattatgaca actttatatt ttttgatagc atctcttgaa   3960
aaagaatttt aatgattcta ataagaggtt ctttttcttt tttccatttc cttgacaaat   4020
agtactcatt taaaaactag agggctaggc ttagtggctc acgcctgtaa tctcagcact   4080
ttgggaggct gaggcgggca gatcgcttga ggtcaggagt tcaagaccag cccgggcaac   4140
gtggtgaaac ccggtctgta ctaaaaaaaa aaaaaaagaa aaagaaaaag aaaaaagaat   4200
acccaggtgt ggtagtgcat gcctgtagtc ccagctactt tggagactga ggtgggagta   4260
ccccttgagc ctgggaggcg caggttgcag tgaaccaaga tcacatcact gcacttcaac   4320
ctgggtgaca gagcaagacc ctgtctcaaa aacaaaaaac aagcaaaaaa aacctagagg   4380
cactattttt ttttaaagtt tgtcttttct tttctaccca aattactaat ctatgccatt   4440
aaggaaagga ataagaacct ccatatgtat tattatctcc acagtcctgc agaagtacaa   4500
tctgatcttt aactttcatg ctacaaataa taatttgagt agattaattt gaattttatc   4560
aacaaaatta ttgccatatg atgtatcatt tctgtgtttg aacaaagcat cgtaatgcag   4620
gataacttct actttattcc ctgtagttaa aaaaaaaaaa actatatagt tcaagccaat   4680
atttaaaaat tctaaaccta ggctgggcat ggtgactcat acctgtaatc ccagcacttt   4740
gggaggccga ggcaggtgaa ttgcttcagc ccaggagttc gagaccagcc tggccaatgt   4800
ggtgaaaccc catctctact aaaaaaaaaa aaaaaaaaaa aaattagcca ggtgtggtgg   4860
tgtgcacctg taatcccagc tacccaggag gctgaggcag gaaaattgct tgaaaccagg   4920
```

-continued

```
aggcagaggt tgcagtgagc tgagatcgtg ccactgcact ccagcctgag tgtcagagtg   4980
agactctgtc tcagaaaaaa aaaaaaaaat tctaaagatt acatttagaa tttagtcttt   5040
ttaaagtgtc catgtataaa aatatataat ttttaaaatt actaaatgtt gccttttctc   5100
ttagtctaat attttagcta ctaaaacaaa atataaactg gatagcttat aaacaacata   5160
aacttatttc tcacagtttt ggaggctgtg aagtccaaga ttaaggcact aacagatcta   5220
gtgtctggta aggcaaattt ctggctcata gatggtacct tcttgctgtg tccccacatg   5280
gtagatggga agaactggtc tcattggccc cttataagga cattaattcc actcaatagg   5340
ctccaccctc atgatctaat aacctctcaa aggccctacc tcctaatact aacacattga   5400
ggatgtgact tcaactttac atttctacag gcagagaagt ggggctgtgt aaattcttcc   5460
catcagtact tgaatgttca tttaacaaat aacttatcga gcatctagca tgttccagac   5520
acaatctgaa cactgagcac acaacagttg gaacaaatat gattcctatc ctcatggagc   5580
ttctattctc ctgtgaaaaa cagatgttaa acatgattga ggattaggtt tcaacataag   5640
aattctagga ggacacagac atttagacca tagcatcttc aggtaaactt tatcttcagt   5700
aaattaaaga gatctattta gatgaccttt gagcatctta attattagat gtcagtgcta   5760
gtttaactta ttttaaacgt ttcagatatt tatttaatta tactttaagt gtctcatgta   5820
aaaaagttat ttataaaata atttataggg ttagagtcat tgccctttta atgcaacaaa   5880
taaacagttt tttaaaaacc tgcatggggg ccaggcgcgg tggttcatac ctgcaatccc   5940
agcactttgg gaggtcgagg ctggcggatc acgaggtcag gagatcgaga ccaccctgat   6000
taatgcggtg aaatcccgtc tctactaaaa atacaaaaaa ttagccagac gtggtggtgg   6060
gcacctatag tcccagctac tcgggaggct gaggcaggag aatggcatga acccggaagg   6120
cggagcttgc agtgaaccaa gatcgcgcca ctgcactcca gcctgggcga cagagtgaga   6180
ctccatcgca aaaaaaaaaa aaaaaaaacc tgcatggaag cctagtatat ttattaataa   6240
caaataaatt atactttagt gtactattaa cctataccaa ttttaagttg tgattaggga   6300
atggggatgt ttttaagctg aattgtcttg ctgcggaact ttcctttttt aataagacca   6360
tattatgact ctgaatgctc aagggtaagt ctaaggcctc attgctgtta ccaggagatt   6420
tttctagtta cagtaataaa gatgttaatt cacatgcatg cagacaactg aaactcaagt   6480
ggagaatttg tttgtgaaca agtcatacta cttctgttat ttgcatgaat ggaatctgca   6540
atatcttttt ccatgggaga ccctaaaaga aaaccctgga tcagaatgat ctgcagtttc   6600
agataataaa ggcttttaag agacattttt agaattaaaa atatgctaat tttattaaat   6660
gaaaatattt gtaactgtta actttctcac tgacaaagca agtttctcaa taaaatacct   6720
atttaactt gcattactga catcttttct ttgagtaatc tgaataatgc agaagccatc   6780
atagaggtct tttctataca ttctcaatgt tttcttaaat gggtttcctg agttctgttc   6840
ttcatgactc tgggctctgc aaacagggtt tcccaattac gcattctata aacactttta   6900
tgaatgagtc aatatgacat tgagtccttt tcatacattt catcatttcc aatatgtaga   6960
gtgacagcta gaaaaatgat aaaattttga ttaaaaccta tctctttttc ttcagcatag   7020
tcaattgttt tcttaactct caatgagtaa ctccatgcct agcttgtgct tagctttcaa   7080
tattttaga ctaagacaaa gtgtatttgg cattttgaga acaacaatta atggtcagta   7140
aatttctaaa gcaagaaaaa tgtgaaacta gtgttttata tgtttgttac gcagcagaat   7200
gcggctctta gtgtttgccc cttcatatct catcatgtaa aatattaaat tactttaggc   7260
cactgcacat aggtagtcct gtcatgagtg atggctggag aaaagttcag gatcataaat   7320
```

```
gtta                                                               7324

<210> SEQ ID NO 21
<211> LENGTH: 1440
<212> TYPE: DNA
<213> ORGANISM: Homo sapiens

<400> SEQUENCE: 21

agttggtgtc atgcaagaat ctattcacac tgactaaaga tattggaaga gtgaagatca     60

gagaatttta agtctgaaat ttggcatcac tgccctgaac aatataacct tagttggcat    120

aaactactca tacagacaaa ggcattatcc atcacaataa gtaacttttt gtctttattt    180

caaccggaca atcgtgatta gaaaagctcc tgtgacaaaa ttcaagaaaa cctgacataa    240

atgaacaaca atacaacatg tattcaacca tctatgatct cttccatggc tttaccaatc    300

atttacatcc tcctttgtat tgttggtgtt tttggaaaca ctctctctca atggatattt    360

ttaacaaaaa taggtaaaaa aacatcaacg cacatctacc tgtcacacct tgtgactgca    420

aacttacttg tgtgcagtgc catgcctttc atgagtatct atttcctgaa aggtttccaa    480

tgggaatatc aatctgctca atgcagagtg gtcaattttc tgggaactct atccatgcat    540

gcaagtatgt ttgtcagtct cttaatttta agttggattg ccataagccg ctatgctacc    600

ttaatgcaaa aggattcctc gcaagagact acttcatgct atgagaaaat attttatggc    660

catttactga aaaaatttcg ccagcccaac tttgctagaa aactatgcat ttacatatgg    720

ggagttgtac tgggcataat cattccagtt accgtatact actcagtcat agaggctaca    780

gaaggagaag agagcctatg ctacaatcgg cagatggaac taggagccat gatctctcag    840

attgcaggtc tcattggaac cacatttatt ggattttcct ttttagtagt actaacatca    900

tactactctt ttgtaagcca tctgagaaaa ataagaacct gtacgtccat tatggagaaa    960

gatttgactt acagttctgt gaaaagacat cttttggtca tccagattct actaatagtt   1020

tgcttccttc cttatagtat ttttaaaccc attttttatg ttctacacca aagagataac   1080

tgtcagcaat tgaattattt aatagaaaca aaaaacattc tcacctgtct tgcttcggcc   1140

agaagtagca cagaccccat tatatttctt ttattagaca aaacattcaa gaagacacta   1200

tataatctct ttacaaagtc taattcagca catatgcaat catatggttg acttttgaat   1260

ggaaaacccc acaatattaa gaaaagcatt catgtgactt tattagggac actaaactac   1320

atcattaaca tgtcacagct tggttgacaa taatcaccaa gaaaatctct ttggttttta   1380

aaaataaata aacatatatt cataaaactc gaaaaaaaaa aaaaaaaaaa aaaaaaaaaa   1440

<210> SEQ ID NO 22
<211> LENGTH: 4965
<212> TYPE: DNA
<213> ORGANISM: Homo sapiens

<400> SEQUENCE: 22

aatctcacca cccagcaatg aggtatttta ctgctgtctc aagatcagat tattactgta     60

gagaagattt ttattttttg tttcattaac agattattat aaagcaaaaa gcatgcagaa    120

aaagaagcag acgttttaca ttgggaatta atgaaagcgt gtctgctagt tttgggtagg    180

agaactggga agttgttgct taaaatttta tatcacctcc acaaacaaaa ctcttcggaa    240

atggtaaaat aagaaaatgc atgattctag aggcattcct aagcacccac gtgtcaggct    300

ttgtggtgtc tgtggtatca tccgaccgtt tggactggtg gcttactgag agctccattt    360

ctggaaagcc ttacaagact gaggaatatc agactgcgaa tcaccgggaa cggttccttt    420
```

-continued

```
gcagcacaga agcaatctct ctccccatct tcgcatattc tgatggcaaa acaagtggaa    480
gaaaagagga agcatgactg cagatcagat cagttctctt tgtggattat attttcagta    540
aaatgtatgg atctatcttt tccttgttct tatatctaga tcatgagact tgactgaggc    600
tgtatcctta tcctccatcc atctatggcg aactatagcc atgcagctga caacattttg    660
caaaatctct cgcctctaac agcctttctg aaactgactt ccttgggttt cataatagga    720
gtcagcgtgg tgggcaacct cctgatctcc attttgctag tgaaagataa gaccttgcat    780
agagcacctt actacttcct gttggatctt tgctgttcag atatcctcag atctgcaatt    840
tgtttcccat ttgtgttcaa ctctgtcaaa aatggttcta cctggactta tgggactctg    900
acttgcaaag tgattgcctt tctgggggtt ttgtcctgtt tccacactgc tttcatgctc    960
ttctgcatca gtgtcaccag atacttagct atcgcccatc accgcttcta tacaaagagg   1020
ctgacctttt ggacgtgtct ggctgtgatc tgtatggtgt ggactctgtc tgtggccatg   1080
gcatttcccc cggttttaga cgtgggcact tactcattca ttagggagga agatcaatgc   1140
accttccaac accgctcctt cagggctaat gattccttag gatttatgct gcttcttgct   1200
ctcatcctcc tagccacaca gcttgtctac ctcaagctga tatttttcgt ccacgatcga   1260
agaaaaatga agccagtcca gtttgtagca gcagtcagcc agaactggac ttttcatggt   1320
cctggagcca gtggccaggc agctgccaat tggctagcag gatttggaag ggtcccacaa   1380
ccacccacct tgctgggcat caggcaaaat gcaaacacca caggcagaag aaggctattg   1440
gtcttagacg agttcaaaat ggagaaaaga atcagcagaa tgttctatat aatgactttt   1500
ctgtttctaa ccttgtgggg cccctacctg gtggcctgtt attggagagt tttgcaaga    1560
gggcctgtag taccaggggg atttctaaca gctgctgtct ggatgagttt tgcccaagca   1620
ggaatcaatc cttttgtctg cattttctca aacagggagc tgaggcgctg tttcagcaca   1680
acccttcttt actgcagaaa atccaggtta ccaagggaac cttactgtgt tatatgaggg   1740
agcatctgta aatctttagc cttgtgaaaa ctaaccttct ctgctgagca attgtggccc   1800
atagccatat tttgagaaga aattcaagaa tggaatcagc agttttaagg atttgggcaa   1860
cattctgcag tctttgcaat agttcaccta taatcctatt ttaaatctca gagtgatcct   1920
gctgactgcc agcaaaggtt tgtaattaag aagggactga accactgccc taagtttctt   1980
tatgtggtca aaaactagat aatgaaagta gcaggtgcta agtatcagtg ctaaatgctc   2040
tgtatgtcac tacatatgaa aaaacatcaa aaaacaatta gcattggaca tcttaataaa   2100
ttaagttgac atgaggtaaa tgtgttgata aaaactaatt ttagaagttt gaagacttta   2160
aaacatttca tactactatt gttttgcaaa gactaaaata tttggggact taaagtactg   2220
taatccacta aagacgtgcc aatgaattat tggaatatca cactttaaaa accgccttgt   2280
aagttctggg gagcattcca aagcagtata ttggttccaa ttagagttta cttttttttgt  2340
attaatacat tgctatttct aaataccact ttcctcatct actagtaaga ttgctagcat   2400
tgaactgtat tatgtggttt ttgttgattt ggtataaagt ttttccaatt catttatatt   2460
ttacaaatgc tagatattgg tctgggaggc aacattaatg gtaccagcct gtcacaactg   2520
agcagttcta ataatgcaga ataaatacat gttgccttaa agggttatct agtatccttc   2580
atcttattta gcactggagc aaatagccaa gggaaatcaa atcagtaact ggtcatggtc   2640
atgcatctaa aagtgcatgg aagatcattt attacttttt cctttttttct cacatggttt  2700
gaaacttaaa gtgcacatca ctgaaataat gagattttct tctacggtgt gctacccttt   2760
ctaaactgtt ctaagaagca ggcagttgat gtatgtttat attttaagtc agctgtcaag   2820
```

```
gggagaccac agccttagta tgacatcctg cacaatttgt gaagcattta ttctactgaa   2880
ggcacagtct tgtttatact ttctgcacat tcagtgtatt ggtaatttaa attatttcag   2940
ttttaacttg tgaaagctta tattatgatt tctggtattt tagaaataca ttagagtctg   3000
tgagtctcat tctttaagat acagatgtgt gaacttcaat ataaagttgc atttgccaaa   3060
atttacccgt gtagcctgtt aattttcttg aaataagttt tacatttttg gcacataaca   3120
actttttttt taatttggga ggcaagcaca aactaggaag actagcttta ttatggtttt   3180
gctttttgat tcttgtagct actacattcc agactggaaa tgtatgaatg ataatcaaca   3240
taatgctgat aaactgacat aatattatct gtaaaagcat tatttggtag tttattataa   3300
tcatccctct attattctta aatgccagta gtatttagag atgtgtacct gcttagttaa   3360
ttggctcaga attttaatat aaacatcaca ctttaatttg gagcatagta ccatagaaat   3420
ttggggttct aaatatacaa cttgtaagaa gaatggttta cactaacatt atgacaaaac   3480
tagaaaaagt tattattttt gtttgctttc tgttgttttg tttattggtt ggtttttgtg   3540
aagtttattt tttttggta tttgataatt aagattagga atctaataac acagaattcc   3600
atattgctat agtacttctg taaagagaat atcaatataa ataaggaaaa taaatcaatg   3660
aaatgtttca atgatatatg caactattca gttttgctct tataaggaca gctcaagcca   3720
tgaattagtg agcattctga cctcattttt actttacacc aaagttgatt agatctgaga   3780
caaaatttaa tgcacaacag tgagttggat ctagcaataa agtctccttg gtactgaaat   3840
cattatctaa aataaaggaa atgttatcaa aagatgttct gataacattg tgattgtaac   3900
tcaaaaaaat ttatagtaga aacgtaattg caatgatgat aataactaac tctgcttaga   3960
ggttcaaata tcaccagcaa tcagtaaaaa attcagcaat aatcttaagg ccagagagaa   4020
caggttcacc attgcataga caagaaaaca gatatgggtt aagagttggg gactgaggag   4080
tcaagagcaa cggccacgtg aagctgcctg actccaccta gctatttgga ataaccgatt   4140
cccacagttt tggtaagaaa ccagccccag taatcagtaa gtcaggctga actgcagtga   4200
cttttattta agcctactcc tgactaactt ggcatttgca ggtcaagcag gaagcagttg   4260
acaagacaca tcctcagtga atcaatgcca tttgtaactc aactggtaac agtagtaatc   4320
atacaaaata aaaacctgct tcagtgtctt aatgaccaaa tcacattatc tattttagca   4380
ctcattccaa aattcagtat ttaatgtaat taatctttaa tccataaaaa tacatcccca   4440
ctgtagcggg gcagggggtg tccaacttcc ctgtgagact gattatcaat aataatgtgt   4500
ctccctcttg gactgagcac acatctgagc tgaacggcct ttaaattgtt tttcataata   4560
gtggtgatat gtttgcgtgg atacgtctgt actatttcat ctggttcatt ttgcatgtaa   4620
tagatttatc tgtgagatgc ctggctgaag ctaggcattc agtctgtgac tgtggaatcc   4680
tatgcaggta ttaaccaagg cagaaagagg tgagtaactt gcccatttct ccacagagac   4740
cccatttaaa taacacaaaa ttgaccacag tgattagatg aaaaaattat ttgtagatag   4800
gataatctat tgactgaatt atcttttgca gatatcagct ggttggattt ctcaccagga   4860
ttgtctatag aagttaactg atttatgatt gttaacacat aaatatggcc acttatccat   4920
ttgcctcaac ttcaaaaaaa aaaaaaaaga aaaaaaaaaa aaaaa                  4965
```

<210> SEQ ID NO 23
<211> LENGTH: 3262
<212> TYPE: DNA
<213> ORGANISM: Homo sapiens

<400> SEQUENCE: 23

-continued

```
gcggcggggc tggcagcagt ggctgcccgc actgcgcccg ggcgctcgcc ttcgctgcag     60
ctcccggtgc cgccgctcgg gccggccccc cggcaggccc tcctcgttat ggccgcggcc    120
tcctccccgc ccagggccga gaggaagcgc tggggttggg gccgcctgcc aggcgcccgg    180
cggggcagcg cgggcctggc caagaagtgc cccttctcgc tggagctggc ggagggcggc    240
ccggcgggcg gcgcgctcta cgcgcccatc gcgcccggcg ccccaggtcc cgcgcccccct    300
gcgtccccgg ccgcgcccgc cgcgcccccca gttgcctccg accttggccc gcggccgccg    360
gtgagcctag acccgcgcgt ctccatctac agcacgcgcc gcccggtgtt ggcgcgcacc    420
cacgtccagg gccgcgtcta caacttcctc gagcgtccca ccggctggaa atgcttcgtt    480
taccacttcg ccgtcttcct catcgtcctg gtctgcctca tcttcagcgt gctgtccacc    540
atcgagcagt atgccgccct ggccacgggg actctcttct ggatggagat cgtgctggtg    600
gtgttcttcg ggacggagta cgtggtccgc ctctggtccg ccggctgccg cagcaagtac    660
gtgggcctct gggggcggct gcgctttgcc cggaagccca tttccatcat cgacctcatc    720
gtggtcgtgg cctccatggt ggtcctctgc gtgggctcca aggggcaggt gtttgccacg    780
tcggccatca ggggcatccg cttcctgcag atcctgagga tgctacacgt cgaccgccag    840
ggaggcacct ggaggctcct gggctccgtg gtcttcatcc accgccagga gctgataacc    900
accctgtaca tcggcttcct gggcctcatc ttctcctcgt actttgtgta cctggctgag    960
aaggacgcgg tgaacgagtc aggccgcgtg gagttcggca gctacgcaga tgcgctgtgg   1020
tggggggtgg tcacagtcac caccatcggc tatggggaca aggtgcccca gacgtgggtc   1080
gggaagacca tcgcctcctg cttctctgtc tttgccatct ccttctttgc gctcccagcg   1140
gggattcttg gctcggggtt tgccctgaag gtgcagcaga agcagaggca gaagcacttc   1200
aaccggcaga tcccggcggc agcctcactc attcagaccg catggaggtg ctatgctgcc   1260
gagaaccccg actcctccac ctggaagatc tacatccgga aggccccccg gagccacact   1320
ctgctgtcac ccagccccaa acccaagaag tctgtggtgg taaagaaaaa aaagttcaag   1380
ctggacaaag acaatggggt gactcctgga gagaagatgc tcacagtccc ccatatcacg   1440
tgcgaccccc cagaagagcg gcggctggac cacttctctg tcgacggcta tgacagttct   1500
gtaaggaaga gcccaacact gctggaagtg agcatgcccc atttcatgag aaccaacagc   1560
ttcgccgagg acctggacct ggaaggggag actctgctga cacccatcac ccacatctca   1620
cagctgcggg aacaccatcg ggccaccatt aaggtcattc gacgcatgca gtactttgtg   1680
gccaagaaga aattccagca agcgcggaag ccttacgatg tgcgggacgt cattgagcag   1740
tactcgcagg gccacctcaa cctcatggtg cgcatcaagg agctgcagag gaggctggac   1800
cagtccattg ggaagccctc actgttcatc tccgtctcag aaaagagcaa ggatcgcggc   1860
agcaacacga tcggcgcccg cctgaaccga gtagaagaca aggtgacgca gctggaccag   1920
aggctggcac tcatcaccga catgcttcac cagctgctct ccttgcacgg tggcagcacc   1980
cccggcagcg gcggcccccc cagagagggc ggggcccaca tcacccagcc ctgcggcagt   2040
ggcggctccg tcgaccctga gctcttcctg cccagcaaca ccctgcccac ctacgagcag   2100
ctgaccgtgc ccaggagggg ccccgatgag ggggtcctgag gaggggatgg ggctggggga   2160
tgggcctgag tgagagggga ggccaagagt ggccccacct ggccctctct gaaggaggcc   2220
acctcctaaa aggcccagag agaagagccc cactctcaga ggccccaata ccccatggac   2280
catgctgtct ggcacagcct gcacttgggg gctcagcaag gccacctctt cctggccggt   2340
gtgggggccc cgtctcaggt ctgagttgtt accccaagcg ccctggcccc cacatggtga   2400
```

```
tgttgacatc actggcatgg tggttgggac ccagtggcag ggcacagggc ctggcccatg   2460

tatggccagg aagtagcaca ggctgagtgc aggcccaccc tgcttggccc agggggcttc   2520

ctgaggggag acagagcaac ccctggaccc cagcctcaaa tccaggaccc tgccaggcac   2580

aggcagggca ggaccagccc acgctgacta cagggccgcc ggcaataaaa gcccaggagc   2640

ccatttggag ggcctgggcc tggctccctc actctcagga aatgctgacc catgggcagg   2700

agactgtgga gactgctcct gagcccccag cttccagcag gagggacagt ctcaccattt   2760

ccccagggca cgtggttgag tggggggaac gcccacttcc ctgggttaga ctgccagctc   2820

ttcctagctg gagaggagcc ctgcctctcc gcccctgagc ccactgtgcg tggggctccc   2880

gcctccaacc cctcgcccag tcccagcagc cagccaaaca cacagaaggg gactgccacc   2940

tcccccttgcc agctgctgag ccgcagagaa gtgacggttc ctacacagga caggggttcc   3000

ttctgggcat tacatcgcat agaaatcaat aatttgtggt gatttggatc tgtgttttaa   3060

tgagtttcac agtgtgattt tgattattaa ttgtgcaagc ttttcctaat aaacgtggag   3120

aatcacaggc tgggctgggc actgctctca ccttggttcc tggggcatcc atggggtctc   3180

tcacagacag gacccctgca gttcccctgg aagcagtgcc caggtggctg tggaatagga   3240

acgctaaaaa aaaaaaaaaa aa                                              3262
```

<210> SEQ ID NO 24
<211> LENGTH: 5909
<212> TYPE: DNA
<213> ORGANISM: Homo sapiens

<400> SEQUENCE: 24

```
ctttctttct ccctcctctc ctccatttgt tgtttgatgt ttcccactct ttgaggaagg     60

atggttgatt tggagagcga agtgccccct ctgcctccca ggtacaggtt tcgagatttg    120

ctgctagggg accaaggatg gcaaaacgac gacagggtac aagttgaatt ctatatgaat    180

gaaaatacat ttaaagaaag actaaaatta tttttcataa aaaaccagag atcaagtcta    240

aggatacgcc tgttcaattt ttctctcaaa ttactaagct gcttattata cataatccga    300

gtactactag aaaacccttc acaaggaaat gaatggtctc atatcttttg ggtgaacaga    360

agtctacctt tgtggggctt acaggtttca gtggcattga taagtctgtt tgaaacaata    420

ttacttggtt atcttagtta taagggaaac atctgggaac agattttacg aatacccttc    480

atcttggaaa taattaatgc agttcccttc attatctcaa tattctggcc ttccttaagg    540

aatctatttg tcccagtctt tctgaactgt tggcttgcca aacatgcctt ggaaaatatg    600

attaatgatc tacacagagc cattcagcgt acacagtctg caatgtttaa tcaagttttg    660

atttttaatat ctacattact atgccttatc ttcacctgca tttgtgggat ccaacatctg    720

gaacgaatag gaaagaagct gaatctcttt gactcccttt atttctgcat tgtgacgttt    780

tctactgtgg gcttcgggga tgtcactcct gaaacatggt cctccaagct tttgtagtt     840

gctatgattt gtgttgctct tgtggttcta cccatacagt ttgaacagct ggcttatttg    900

tggatggaga gacaaaagtc aggaggaaac tatagtcgac atagagctca aactgaaaag    960

catgtcgtcc tgtgtgtcag ctcactgaag attgatttac ttatggattt tttaaatgaa   1020

ttctatgctc atcctaggct ccaggattat tatgtggtga ttttgtgtcc tactgaaatg   1080

gatgtacagg ttcgaagggt actgcagatt ccaatgtggt cccaacgagt tatctacctt   1140

caaggttcag cccttaaaga tcaagaccta ttgagagcaa agatggatga cgctgaggcc   1200

tgttttattc tcagtagccg ttgtgaagtg gataggacat catctgatca ccaaacaatt   1260
```

-continued

```
ttgagagcat gggctgtgaa agattttgct ccaaattgtc ctttgtatgt ccagatatta   1320
aagcctgaaa ataaatttca catcaaattt gctgatcatg ttgtttgtga agaagagttt   1380
aaatacgcca tgttagcttt aaactgtata tgcccagcaa catctacact tattacacta   1440
ctggttcata cctctagagg gcaagaaggc cagcaatcgc cagaacaatg gcagaagatg   1500
tacggtagat gctccgggaa tgaagtctac cacattgttt tggaagaaag tacatttttt   1560
gctgaatatg aaggaaagag ttttacatat gcctctttcc atgcacacaa aaagtttggc   1620
gtctgcttga ttggtgttag gagggaggat aataaaaaca ttttgctgaa tccaggtcct   1680
cgatacatta tgaattctac agacatatgc ttttatatta atattaccaa agaagagaat   1740
tcagcattta aaaaccaaga ccagcagaga aaaagcaatg tgtccaggtc gttttatcat   1800
ggaccttcca gattacctgt acatagcata attgccagca tgggtactgt ggctatagac   1860
ttgcaagata caagctgtag atcagcaagt ggccctaccc tgtctcttcc tacagaggga   1920
agcaaagaaa taagaagacc tagcattgct cctgttttag aggttgcaga tacatcatcg   1980
attcaaacat gtgatcttct aagtgaccaa tcagaagatg aaactacacc agatgaagaa   2040
atgtcttcaa acttagagta tgctaaaggt tacccacctt attctccata tataggaagt   2100
tcacccactt tttgtcatct ccttcatgaa aaagtaccat tttgctgctt aagattagac   2160
aagagttgcc aacataacta ctatgaggat gcaaaagcct atggattcaa aaataaacta   2220
attatagttg cagctgaaac agctggaaat ggattatata actttattgt tcctctcagg   2280
gcatattata gaccaaagaa agaacttaat cccatagtac tgctattgga taacccgcca   2340
gatatgcatt ttctggatgc aatctgttgg tttccaatgg tttactacat ggtgggctct   2400
attgacaacc tagatgactt actcaggtgt ggagtgactt ttgctgctaa tatggtggtt   2460
gtggataaag agagcaccat gagtgccgag gaagactaca tggcagatgc caaaaccatt   2520
gtgaacgtgc agacactctt caggttgttt tccagtctca gtattatcac agagctaact   2580
caccccgcca acatgagatt catgcaattc agagccaaag actgttactc tcttgctctt   2640
tcaaaactgg aaaagaaaga acgggagaga ggctctaact tggcctttat gtttcgactg   2700
ccttttgctg ctgggagggt gtttagcatc agtatgttgg acactctgct gtatcagtca   2760
tttgtgaagg attatatgat ttctatcacg agacttctgt tgggactgga cactacacca   2820
ggatctgggt ttctttgttc tatgaaaatc actgcagatg acttatggat cagaacttat   2880
gccagacttt atcagaagtt gtgttcttct actggagatg ttcccattgg aatctacagg   2940
actgagtctc agaaacttac tacatctgag tctcaaatat ctatcagtgt agaagagtgg   3000
gaagacacca aagactccaa agaacaaggg caccaccgca gcaaccaccg caactcaaca   3060
tccagtgacc agtcggacca tcccttgctg cggagaaaaa gcatgcagtg ggcccgaaga   3120
ctgagcagaa aaggcccaaa acactctggt aaaacagctg aaaaaataac ccagcagcga   3180
ctgaacctct acaggaggtc agaaagacaa gagcttgctg aacttgtgaa aaatagaatg   3240
aaacacttgg gtctttctac agtgggatat gatgaaatga atgatcatca aagtaccctc   3300
tcctacatcc tgattaaccc atctccagat accagaatag agctgaatga tgttgtatac   3360
ttaattcgac cagatccact ggcctacctt ccaaacagtg agcccagtcg aagaaacagc   3420
atctgcaatg tcactggtca agattctcgg gaggaaactc aactttgata aaaataaaat   3480
gagaaacttt tttcctacaa agaccttgct tgaaaccaca aaagttttgc tggcacgaaa   3540
gaaactagat ggaaatatat gtaattctct catatttaaa aacgtaatct cttctcttag   3600
aagtatagat cattttgaaa cttaatgtac tacttactgg tactctccct attaatattt   3660
```

-continued

```
gaaggacctc aatggaataa atttgaaaag ctaaattaaa atacaaaaat ttaaatctga   3720
catttaattg ttttataata atccaaactc tatgaaagca attttaaaaa ttattaaggt   3780
tttatgaagt tgacaaaatc taactatatt tggtgcatca caatggacac agaatgctgc   3840
tgctcctctt aaaaattaaa tgtgtcatat tatattcttt aaacttactg ttttacaaaa   3900
ttgagctcat cgtaaatgtc tagtcttctc acatagagat taaccaacaa acttgtgtgg   3960
ctgacttttg tgtaagaatc atagtttgct ttagaataca aatctttaag tcattttaac   4020
tttttttttct gccttacgat ataaaaatat ttatcttaga atttgagatg ttcatagcat   4080
gttttattac attgaagaaa ctaaaacata aatgaaaaga aacactaggt tcctgcactt   4140
tttggtaact ttatgtctag caaatatttt atgccaagaa aagcatacta taaagcaaat   4200
atctattatt ctcctaaacg aatgcctagc atagagaaaa tacttaatac acatttgttg   4260
acttaaattt aattcaagga ttgaaaaatt aactggatat cttgaaatat acagtaatga   4320
ttgtccttag actcttgaac tttaccatct ttcctattca tatatctata tagtaaattt   4380
cactagaaaa attcttttaa aattgacaga agataattta taccttttat ggactctgaa   4440
gacacttcaa aacattaaaa gtccttatgt ctttggtaat gaaacaataa cactcaatga   4500
aggatgtatt aaaatttttg acttaatttt gaaatcgtat atatgagcta tactttaaca   4560
ttatgagaga aaagcataaa acaaaaatag gtagttcttg gcttttaaca ttaatgcaaa   4620
tcatgcagaa tttgagttat aaatttaaat ataaattgac cattgatgat atccagtttt   4680
tcattttttta cctgtattgc attttccccc tagagaaata gatcaaaaga gcacaagagt   4740
atgcgtacat agtttaccag gtagtagaag tgtgttaaaa tgttcctgta aaagaaacat   4800
tggtaaattt aaatacatac tgttctaatt ttgtattttt taatttttga atttgacatt   4860
gagtttaatt cagcaacaac aaaaaataca tataaaacta gaaagggact tttttttcctt   4920
tcttttcata atgaagcaga tcaacttaaa ggataataaa atttttaaag aaaagatatt   4980
ctaatgtact ctcaataatt ctacagaaat aaaactgtaa agtgcaatgt gaaatcaaag   5040
attatagtca ttgtataatt tggcttggag gctatgaaat gtcttttttt ctttttggta   5100
ttttacatta ttcacatttt agaataacaa gaacaccaag aattacccct aaaacagaga   5160
ccctgtattt aatctacttt gatcagagaa gtagaattta taacaggtta gctaaaattg   5220
ggagcatgcc ttaaaactta aagattgtat gcatatatgt gtatatgtta taaacgtgaa   5280
atatatttga cacacacatt cacatataaa ttgttaaaaa ctgaaggcag aatggaacta   5340
atatatgtaa cagagaaaaa caataaattt tatgaacttg ttttatattt gcatatcaag   5400
agtcaagtat gatgtttctt taagttgact ttttttactt cattattttt aggaataaat   5460
gtaagatttt acaaatcttt tatttcccca caagatctga agtttggtat ttttgcatta   5520
tgacagttgt tgagactagg attttaagct aggatatgat tatatttcct atataactaa   5580
aaattttgtt tcataaattt taaaataatt atttttgact atgaacatta gtccaaattt   5640
aatatttgac acagttcata ccagcttgct acaataatga taatttatta gtctttctgt   5700
tatttaaaga ataaaaacat gcttataaaa gacttttaat gaaatgttgc ctttttaaaa   5760
taattatact tgcacatgaa aataaaatat aaagtcaata atagtccttg tagcccaatg   5820
ggaattgatt ctgtttattg tctgtaccat tttgctacca gttacattga actgctttaa   5880
aataaataat aaaattattt ctaatgatg                                    5909
```

<210> SEQ ID NO 25
<211> LENGTH: 5472
<212> TYPE: DNA

<213> ORGANISM: Homo sapiens

<400> SEQUENCE: 25
ctgaacttta gctctctggc cggcgcctct gttgcccgga agggaggcaa gcccccttag 60
agttgccagt aacggacatg gctgcggccc ccggaggagg ggacgtgaag tgaggagggg 120
gttgggaggg gagaggacgc gggcgaggaa gaccagcccc ggggccccga tgttgtgact 180
gtgacagact cactggggtt tgtacatgct ggggaggagc cttcctttca ggggtgacca 240
cattcatctg ggcatgcctg cagtactctt ggcccatgga cctgaaggag aagcacctgg 300
gcgagcctcc ctcagccctg ggcctgtcca cgcggaaggc cctcagcgtc ctgaaggagc 360
agctggaggc agtgctggaa ggacatctca gggagcggaa gaagtgtctg acgtggaagg 420
aggtgtggag aagcagcttc ctccaccaca gtaaccgctg ctcctgcttc cactggccgg 480
gggcctcact catgctactg gccgtgctgc tgctgctggg ctgctgcggg ggacagccag 540
ccgggagccg tggggtgggg ctggtgaatg cctcggcctt gttcctgtta ctgcttctca 600
accttgtgct catcgggcgg caagaccggc tgaagcgtcg ggaggtagag cggaggctgc 660
gagggatcat tgaccaaatc caagatgccc tcagggatgg cagggagatc cagtggccca 720
gtgccatgta tccagacctc cacatgcctt ttgcgccatc ctggtccttg cactgggcct 780
acagagacgg acacctggtc aacctgccag tcagcctgct ggttgaagga gacatcatag 840
ctttgaggcc tggccaggaa tcgtttgctt ctctgagggg gatcaaggat gacgagcaca 900
tcgtcctgga gccgggagac ctcttccccc ccttctcccc tccaccctca ccccggggag 960
aagtggagag agggccacag agcccccagc agcaccggct tttccgtgtc cttgagaccc 1020
ctgtgattga caacatcaga tggtgcctgg acatggccct gtcccgacca gtcactgccc 1080
tggacaatga gcggttcaca gtgcagtcgg tgatgctaca ctatgctgtg cccgtggtcc 1140
tggccggctt cctcatcacc aatgccctgc gcttcatctt cagtgccccg ggggtcactt 1200
cctggcagta caccctcctc cagctccagg tgaatggcgt cctgcccatc ctcccccctgc 1260 tctttccagt cctctgggtt ctggcaactg cctgtggaga ggcccgtgtc ctggcccaga 1320
tgagcaaggc ctcacccagc tccctgctgg ctaagttctc agaggatact ctcagcagct 1380
atacggaggc tgtctcctct caggaaatgc tgcgctgcat ttggggccac ttcctgaggg 1440
tgctcggggg gacatcgcca acgctgagcc acagttccag cctgctgcac agcctgggct 1500
ctgtcacggt cctgtgctgt gtggacaaac aggggatcct gtcatggcca aatcccagcc 1560
cagagactgt actgttcttc agcgggaagg tggagccccc tcacagcagc catgaggacc 1620
tcaccgatgg cctatccacc cgctccttct gccatcccga gccccatgaa cgagacgccc 1680
tcctggctgg ctccctgaac aacaccctgc acctttccaa tgagcaggag cgtggcgact 1740
ggcctggcga ggctcccaag ccccccgagc cctattcaca ccacaaagcg catggccgca 1800
gcaaacaccc atctggctcc aacgtgagct tcagcaggga caccgagggt ggtgaagaag 1860
agcccagcaa gacccagcct gggatggaga gcgaccccta cgaagcagag gactttgtgt 1920
gtgactacca cctggagatg ctgagcctgt cccaggacca gcagaacccc tcctgcatcc 1980
agtttgatga ctccaactgg cagctgcacc tcacctccct caaacccctg ggcctcaatg 2040
tgctgctgaa cctgtgtgat gccagcgtca ccgagcgcct gtgccgattc tccgaccacc 2100
tgtgcaacat cgccctgcaa gagagccaca gcgccgtgct gcccgtccat gtgccctggg 2160
gcctctgcga gcttgcccgc ctcattggct tcactcctgg ggccaaggag cttttcaagc 2220
aggagaacca tctggcgctg taccgcctcc ccagtgccga gacaatgaag gagacatcgc 2280

-continued

```
tggggcggct ctcctgtgtc accaagcggc ggcctcccct cagccacatg atcagcctct   2340
tcattaaaga caccaccacc agcacagagc agatgctgtc ccatggcacc gctgatgtgg   2400
tcttagaggc ctgcacagac ttctgggacg gagctgacat ctaccctctc tcgggatctg   2460
acagaaagaa agtgctggac ttctaccagc gagcctgcct gtctgggtat tgctctgcct   2520
tcgcctacaa gcccatgaac tgcgccctgt cctctcagct caatggcaag tgcatcgagc   2580
tggtacaggt gcccggccaa agcagcatct tcaccatgtg cgagctgccc agcaccatcc   2640
ccatcaagca gaacgcccgc cgcagcagct ggagctctga cgaagggatc ggggaggtgc   2700
tggagaagga agactgcatg caggccctga gcggccagat cttcatgggc atggtgtcct   2760
cccagtacca ggcccggctg gacatcgtgc gcctcattga tgggcttgtc aacgcctgca   2820
tccgctttgt ctacttctct ttggaggatg agctcaaaag caaggtgttt gcagaaaaaa   2880
tgggcctgga gacaggctgg aactgccaca tctccctcac acccaatggt gacatgcctg   2940
gctccgagat cccccccctcc agccccagcc acgcaggctc cctgcatgat gacctgaatc   3000
aggtgtcccg agatgatgca gaagggctcc tcctcatgga ggaggagggc cactcggacc   3060
tcatcagctt ccagcctacg gacagcgaca tccccagctt cctggaggac tccaaccggg   3120
ccaagctgcc ccggggtatc caccaagtgc ggccccacct gcagaacatt gacaacgtgc   3180
ccctgctagt gccccttttc accgactgca ccccagagac catgtgtgag atgataaaga   3240
tcatgcaaga gtacggggag gtgacctgct gcctgggcag ctctgccaac ctgcggaaca   3300
gctgcctctt cctccagagc gacatcagca ttgccctgga tcccctgtac ccatcccgtt   3360
gctcctggga gacctttggc tacgccacca gcatcagcat ggcccaggcc tcggatggcc   3420
tttctcccct gcagctgtca gggcagctca acagcctgcc ctgttccctg acctttcgcc   3480
aggaggagac catcagcatc atccggctta tcgaacaggc tcggcatgcc acctatggca   3540
tccgtaagtg cttcctcttc ctgctgcagt gccagctgac tcttgtggtc atccagttcc   3600
tttcttgcct ggtccagctg ccgccactcc tgagtaccac cgacatcctg tggctgtcct   3660
gcttttgcta ccctctgctc agcatctctc tgctggggaa gcccccccat agctccatca   3720
tgtctatggc aacggggaaa aacctccagt ccattcccaa gaagacccag cactacttcc   3780
tgctctgctt cctgctcaag ttcagcctca ccatcagctc ctgcctcatc tgctttggct   3840
tcacactgca gagcttctgt gacagctccc gggaccgcaa cctcaccaac tgctcctccg   3900
tcatgctgcc cagcaacgac gacagggctc cagcctggtt tgaggacttt gccaatggac   3960
tgctgtcggc tcagaagctc acggccgccc tgattgtcct gcacactgtc ttcatttcca   4020
tcacccatgt gcatcgcacc aagcccctgt ggagaaagag ccccttgacc aacctctggt   4080
gggccgtgac agtgcctgtg gtgctgctgg gtcaggtggt ccagacggct gtggacctgc   4140
agctgtggac acacagggac agccacgtcc actttggcct ggaggacgtg cccctgctga   4200
catggctcct gggctgcctg tccctggtcc ttgtggtggt gaccaatgag atcgtgaagc   4260
tacatgagat tcgggtccga gtccgctacc agaagcgaca gaagctgcag tttgaaacta   4320
agctgggcat gaactctccc ttctgagcca ctggctgtgg tggctgtagt tgcccccgtc   4380
cctggggcta aagccagacc catttctgaa caggggagtt tgtatcatga atgtttccag   4440
gtttgctcct gcacccgtgg cactggaaac ccagctcccc gtgtcagacc ccgctgtctt   4500
cctgagccct ggggctcact gtggaggagc tgacggcctg ggcccttggc cagtcctggc   4560
tcttccctgg gcctcaccag ggacactctt gaatgtatgg cctcaggcgc tccctagagg   4620
ggccctaaac cccctcacct gtgagctacc ccctttaggg atcccttgcc cccttggaga   4680
```

```
tcccttgccc cccagtgcct ctgctcgtgg gtccctggac acggccttga agccaacctt   4740

ctttggagga gcaacagcag cagccttggc cgacgcgtcc aactcccaag gctgccgtgg   4800

agggcagggg ggtggtgctt gcctggatgt ggccccgagt gcctcccctc cctccctctg   4860

tgggggagtc tcccgcctga acctgaagat ggagcagggc ccccgcttcg ccctggagcc   4920

tcttcctgtg cctggctcaa gctggctgcc tgtcagtctt ggggaatctg gcccaggtct   4980

cctcagcctc tgccccagtt ctgggagaag tttctactgg tgtatatttt ttactggaaa   5040

tgagcctttt aggaatgaat gtagactggt ttgtattaaa atgtgtcaat tgctaagaaa   5100

tacctgtggc tggtctgtaa ggccactcca gggtctgccc acccccggcg gtggctggca   5160

aagggaggcc taaaccttcc tccatctacg cgggtgggtc cctcaggtct ggctcaggcg   5220

agacccctag ggtcaggggt ccccatgtca cagaggcaaa cacacagccc agtcacgtgg   5280

aatggtgttt tcattggtgt tagttggggg aagaggttaa tggttacaga gccagggcct   5340

gggccaatgg ggtcaggctc tccctgccct caggtgggca gtcggggctc ctgctgtggt   5400

ccgaagcccc tcccccattg tgtcctctca ggcagttgat agaataaatt ccatttaaaa   5460

tataaaaaaa aa                                                       5472
```

<210> SEQ ID NO 26
<211> LENGTH: 2880
<212> TYPE: DNA
<213> ORGANISM: Homo sapiens

<400> SEQUENCE: 26

```
tgctgctctc cgcccgcgtc cggctcgtgg ccccctactt cgggcaccat ggacacctcc     60

cggctcggtg tgctcctgtc cttgcctgtg ctgctgcagc tggcgaccgg gggcagctct    120

cccaggtctg gtgtgttgct gaggggctgc cccacacact gtcattgcga gcccgacggc    180

aggatgttgc tcagggtgga ctgctccgac ctggggctct cggagctgcc ttccaacctc    240

agcgtcttca cctcctacct agacctcagt atgaacaaca tcagtcagct gctcccgaat    300

cccctgccca gtctccgctt cctggaggag ttacgtcttg cgggaaacgc tctgacatac    360

attcccaagg gagcattcac tggcctttac agtcttaaag ttcttatgct gcagaataat    420

cagctaagac acgtacccac agaagctctg cagaatttgc gaagccttca atccctgcgt    480

ctggatgcta accacatcag ctatgtgccc ccaagctgtt tcagtggcct gcattccctg    540

aggcacctgt ggctggatga caatgcgtta acagaaatcc ccgtccaggc ttttagaagt    600

ttatcggcat tgcaagccat gaccttggcc ctgaacaaaa tacaccacat accagactat    660

gcctttggaa acctctccag cttggtagtt ctacatctcc ataacaatag aatccactcc    720

ctgggaaaga aatgctttga tgggctccac agcctagaga ctttagattt aaattacaat    780

aaccttgatg aattccccac tgcaattagg acactctcca accttaaaga actaggattt    840

catagcaaca atatcaggtc gatacctgag aaagcatttg taggcaaccc ttctcttatt    900

acaatacatt tctatgacaa tcccatccaa tttgttggga gatctgcttt tcaacattta    960

cctgaactaa gaacactgac tctgaatggt gcctcacaaa taactgaatt tcctgattta   1020

actggaactg caaacctgga gagtctgact ttaactggag cacagatctc atctcttcct   1080

caaaccgtct gcaatcagtt acctaatctc caagtgctag atctgtctta caacctatta   1140

gaagatttac ccagtttttc agtctgccaa aagcttcaga aaattgacct aagacataat   1200

gaaatctacg aaattaaagt tgacactttc cagcagttgc ttagcctccg atcgctgaat   1260

ttggcttgga acaaaattgc tattattcac cccaatgcat tttccacttt gccatcccta   1320
```

ataaagctgg acctatcgtc caacctcctg tcgtcttttc ctataactgg gttacatggt 1380
ttaactcact taaaattaac aggaaatcat gccttacaga gcttgatatc atctgaaaac 1440
tttccagaac tcaaggttat agaaatgcct tatgcttacc agtgctgtgc atttggagtg 1500
tgtgagaatg cctataagat ttctaatcaa tggaataaag gtgacaacag cagtatggac 1560
gaccttcata agaaagatgc tggaatgttt caggctcaag atgaacgtga ccttgaagat 1620
ttcctgcttg actttgagga agacctgaaa gcccttcatt cagtgcagtg ttcaccttcc 1680
ccaggcccct tcaaaccctg tgaacacctg cttgatggct ggctgatcag aattggagtg 1740
tggaccatag cagttctggc acttacttgt aatgctttgg tgacttcaac agttttcaga 1800
tcccctctgt acatttcccc cattaaactg ttaattgggg tcatcgcagc agtgaacatg 1860
ctcacgggag tctccagtgc cgtgctggct ggtgtggatg cgttcacttt tggcagcttt 1920
gcacgacatg gtgcctggtg ggagaatggg gttggttgcc atgtcattgg tttttttgtcc 1980 atttttgctt cagaatcatc tgttttcctg cttactctgg cagccctgga gcgtgggttc 2040
tctgtgaaat attctgcaaa atttgaaacg aaagctccat tttctagcct gaaagtaatc 2100
attttgctct gtgccctgct ggccttgacc atggccgcag ttcccctgct gggtggcagc 2160
aagtatggcg cctcccctct ctgcctgcct ttgccttttg gggagcccag caccatgggc 2220
tacatggtcg ctctcatctt gctcaattcc ctttgcttcc tcatgatgac cattgcctac 2280
accaagctct actgcaattt ggacaaggga gacctggaga atatttggga ctgctctatg 2340
gtaaaacaca ttgccctgtt gctcttcacc aactgcatcc taaactgccc tgtggctttc 2400
ttgtccttct cctctttaat aaaccttaca tttatcagtc ctgaagtaat taagtttatc 2460
cttctggtgg tagtcccact tcctgcatgt ctcaatcccc ttctctacat cttgttcaat 2520
cctcacttta aggaggatct ggtgagcctg agaaagcaaa cctacgtctg gacaagatca 2580
aaacacccaa gcttgatgtc aattaactct gatgatgtcg aaaaacagtc ctgtgactca 2640
actcaagcct tggtaacctt taccagctcc agcatcactt atgacctgcc tcccagttcc 2700
gtgccatcac cagcttatcc agtgactgag agctgccatc tttcctctgt ggcatttgtc 2760
ccatgtctct aattaatatg tgaaggaaaa tgttttcaaa ggttgagaac ctgaaaatgt 2820
gagattgagt atatcagagc agtaattaat aagaagagct gaggtgaaac tcggtttaaa 2880

<210> SEQ ID NO 27
<211> LENGTH: 3458
<212> TYPE: DNA
<213> ORGANISM: Homo sapiens

<400> SEQUENCE: 27
atgcccagcc cgccggggct ccgggcgcta tggctttgcg ccgcgctgtg cgcttcccgg 60
agggccggcg gcgcccccca gcccggcccg gggcccaccg cctgcccggc cccctgccac 120
tgccaggagg acggcatcat gctgtctgcc gactgctctg agctcgggct gtccgccgtt 180
ccgggggacc tggacccccct gacggcttac ctggacctca gcatgaacaa cctcacagag 240
cttcagcctg gcctcttcca ccacctgcgc ttcttggagg agctgcgtct ctctgggaac 300
catctctcac acatcccagg acaagcattc tctggtctct acagcctgaa aatcctgatg 360
ctgcagaaca atcagctggg aggaatcccc gcagaggcgc tgtgggagct gccgagcctg 420
cagtcgctgc gcctagatgc caacctcatc tccctggtcc cggagaggag ctttgagggg 480
ctgtcctccc tccgccacct ctggctggac gacaatgcac tcacggagat ccctgtcagg 540
gccctcaaca acctccctgc cctgcaggcc atgaccctgg ccctcaaccg catcagccac 600

-continued

```
atccccgact acgcgttcca gaatctcacc agccttgtgg tgctgcattt gcataacaac    660
cgcatccagc atctggggac ccacagcttc gaggggctgc acaatctgga gacactagac    720
ctgaattata acaagctgca ggagttccct gtggccatcc ggaccctggg cagactgcag    780
gaactggggt tccataacaa caacatcaag gccatcccag aaaaggcctt catggggaac    840
cctctgctac agacgataca cttttatgat aacccaatcc agtttgtggg aagatcggca    900
ttccagtacc tgcctaaact ccacacacta tctctgaatg gtgccatgga catccaggag    960
tttccagatc tcaaaggcac caccagcctg gagatcctga ccctgacccg cgcaggcatc   1020
cggctgctcc catcggggat gtgccaacag ctgcccaggc tccgagtcct ggaactgtct   1080
cacaatcaaa ttgaggagct gcccagcctg cacaggtgtc agaaattgga ggaaatcggc   1140
ctccaacaca accgcatctg ggaaattgga gctgacacct tcagccagct gagctccctg   1200
caagccctgg atcttagctg gaacgccatc cggtccatcc accccgaggc cttctccacc   1260
ctgcactccc tggtcaagct ggacctgaca gacaaccagc tgaccacact gcccctggct   1320
ggacttgggg gcttgatgca tctgaagctc aaagggaacc ttgctctctc ccaggccttc   1380
tccaaggaca gtttcccaaa actgaggatc ctggaggtgc cttatgccta ccagtgctgt   1440
ccctatggga tgtgtgccag cttcttcaag gcctctgggc agtgggaggc tgaagacctt   1500
caccttgatg atgaggagtc ttcaaaaagg cccctgggcc tccttgccag acaagcagag   1560
aaccactatg accaggacct ggatgagctc cagctggaga tggaggactc aaagccacac   1620
cccagtgtcc agtgtagccc tactccaggc cccttcaagc cctgtgagta cctctttgaa   1680
agctggggca tccgcctggc cgtgtgggcc atcgtgttgc tctccgtgct ctgcaatgga   1740
ctggtgctgc tgaccgtgtt cgctggcggg cctgtccccc tgcccccggt caagtttgtg   1800
gtaggtgcga ttgcaggcgc caacaccttg actggcattt cctgtggcct tctagcctca   1860
gtcgatgccc tgacctttgg tcagttctct gagtacggag cccgctggga gacggggcta   1920
ggctgccggg ccactggctt cctggcagta cttgggtcgg aggcatcggt gctgctgctc   1980
actctggccg cagtgcagtg cagcgtctcc gtctcctgtg tccgggccta tgggaagtcc   2040
ccctccctgg gcagcgttcg agcaggggtc ctaggctgcc tggcactggc agggctggcc   2100
gccgcgctgc ccctggcctc agtgggagaa tacggggcct ccccactctg cctgccctac   2160
gcgccacctg agggtcagcc agcagccctg ggcttcaccg tggccctggt gatgatgaac   2220
tccttctgtt tcctggtcgt ggccggtgcc tacatcaaac tgtactgtga cctgccgcgg   2280
ggcgactttg aggccgtgtg ggactgcgcc atggtgaggc acgtggcctg gctcatcttc   2340
gcagacgggc tcctctactg tcccgtggcc ttcctcagct ttgcctccat gctgggcctc   2400
ttccctgtca cgcccgaggc cgtcaagtct gtcctgctgg tggtgctgcc cctgcctgcc   2460
tgcctcaacc cactgctgta cctgctcttc aacccccact tccgggatga ccttcggcgg   2520
cttcggcccc gcgcagggga ctcagggccc ctagcctatg ctgcggccgg ggagctggag   2580
aagagctcct gtgattctac ccaggccctg gtagccttct ctgatgtgga tctcattctg   2640
gaagcttctg aagctgggcg gccccctggg ctggagacct atggcttccc ctcagtgacc   2700
ctcatctcct gtcagcagcc aggggccccc aggctggagg gcagccattg tgtagagcca   2760
gaggggaacc actttgggaa cccccaaccc tccatggatg gagaactgct gctgagggca   2820
gagggatcta cgccagcagg tggaggcttg tcagggggtg gcggctttca gccctctggc   2880
ttggcctttg cttcacacgt gtaaatatcc ctccccattc ttctcttccc ctctcttccc   2940
tttcctctct ccccctcggt gaatgatggc tgcttctaaa acaaatacaa ccaaaactca   3000
```

```
gcagtgtgat ctatagcagg atggcccagt ccctggctcc actgatcacc tctctcctgt   3060

gaccatcacc aacgggtgcc tcttggcctg gctttccctt ggccttcctc agcttcacct   3120

tgatactggg cctcttcctt gtcatgtctg aagctgtgga ccagagacct ggacttttgt   3180

ctgcttaagg gaaatgaggg aagtaaagac agtgaagggg tggagggttg atcagggcac   3240

agtggacagg gagacctcac agagaaaggc ctggaaggtg atttcccgtg tgactcatgg   3300

ataggataca aaatgtgttc catgtaccat taatcttgac atatgccatg cataaagact   3360

tcctattaaa ataagctttg gaagagatta cacatgatgt ctttttctta gagattcaca   3420

gtgcatgtta gtgtaataaa gagataagtc ctacagta                          3458


<210> SEQ ID NO 28
<211> LENGTH: 1600
<212> TYPE: DNA
<213> ORGANISM: Homo sapiens

<400> SEQUENCE: 28

acttcctgag ccgggctggc tgggtgggaa caggctcctt gccgcctccc cagcgctggc     60

cactaccaca ctgccgcccg cctgggcctc ctttcaacct cgtggtggag ccctgcggtt    120

tcccagcgga gccgggcccg gggctgctcc ctcgcgggcg aggctcacct gtcccggccc    180

ggccccctcc cgcgccccag gtggttcagg gcggggagga gccgcgcccc gccccgcgcg    240

gtagcagcca acgccggccc caggcgggtg cgctgggagc ctgggccggg agccgggtga    300

gggcgccgag aggctcggtg ggcgcgggcg gcgagatatg ccacacttct gcctgctgtt    360

ggcaaccctc ctggactagg ctgctcttgt taatcacatg gatgttgctg attactctga    420

gtgcaaacct tttcactgtt ccagagagga gcctgacaac cacattctcc ttctcaagat    480

ataagagttc ggaccgccca gcacacaagg tcagcatgct gctcctctgt cacgctctcg    540

ctatagctgt tgtccagatc gttatcttct cagaaagctg ggcatttgcc aagaacatca    600

acttctataa tgtgaggcct cctctcgacc ctacaccatt tccaaatagc ttcaagtgct    660

ttacttgtga aaacgcaggg gataattata actgcaatcg atgggcagaa gacaaatggt    720

gtccacaaaa tacacagtac tgtttgacag ttcatcactt caccagccac ggaagaagca    780

catccatcac caaaaagtgt gcctccagaa gtgaatgtca ttttgtcggt tgccaccaca    840

gccgagattc tgaacatacg gagtgtaggt cttgctgtga aggaatgatc tgcaatgtag    900

aattacccac caatcacact aatgcagtgt ttgccgtaat gcacgctcag agaacatctg    960

gcagcagtgc ccccacactc tacctaccag tgcttgcctg ggtctttgtg cttccattgc   1020

tgtgatgcca ccattcctag gagaggcaga gaccagcctc taaagcacaa gccaaaaact   1080

gtgtgaacgg tgaactttgg agtgaagatc aatcttgcac ttggtgaaga gtgcacattg   1140

gacctcaagg cgaaagccag tggtttgctt ggataaaatg ttcccgcatg aggccacagg   1200

actgaggatg ggaatttggc agggcctgag aagatggtct gacttccagg cttcctggtc   1260

aaagagagct acgtttgggc agttctgcag agaggatcct ggcaactagt cccacctgac   1320

taggccttta gctgaaagga tttcttgacc tccttgactg cctcagaggc tgccaggtca   1380

aaccctcttg tttatgtgat tagctcagag catctctatg aaatctaacc cttcccctca   1440

tgagaaagca gttttcccca ccaacagcat agtcaatgag aaaggcgact gtacgaagaa   1500

aacttccagt ggaactaata tgaaatctat ttgcaaatta tggggggaaa taaagctttt   1560

aaattataca atgaaaaaaa aaaaaaaaaa aaaaaaaaaa                        1600


<210> SEQ ID NO 29
```

<211> LENGTH: 3466
<212> TYPE: DNA
<213> ORGANISM: Homo sapiens

<400> SEQUENCE: 29

```
agttgctggg attcacaaca cactgacttc tggacgtggt cagggtggct ttctctggct     60

ggcatggact tgagcagaaa ctcattgccg gcttcctcct tgcacgagca ccaagtgatt    120

cccaggtccc ccatcctccc ctgggacatc gaggacacac aaaaaccttg ttcaccctcc    180

actgagagcg gggctagaga tggatgctga gtacaggaag ggtgtgtgag gattcctttg    240

gctccactct tgtttccaac tattgctggt cctaggcgcc cagtcctgag caaccatgac    300

gatggagact ctccccaagg ttctagaggt cgatgagaag tctccagaag ccaaggacct    360

gctgcccagc cagaccgcca gctccctgtg catcagctcc aggagcgagt ctgtctggac    420

caccaccccc aggagtaact gggaaatcta ccgcaagccc atcgttatca tgtcagtggg    480

cggtgccatc ctgcttttcg gcgtggtcat cacctgcttg gcctacacct tgaagctgag    540

tgacaagagt ctctccatcc tcaaaatggt agggcctggc ttcctgtccc tgggactcat    600

gatgctggtg tgcgggctgg tgtgggtgcc catcatcaaa aagaaacaga agcacagaca    660

gaagtcgaat ttcttacgca gcctcaagtc cttcttcctg actcgctgat ggtggtttcc    720

gcatctccct gccaccttga ctgggagaag atctgatgac caacatccga catccctgtc    780

tcctctgtgg ggtgccataa aactgatcca ggaaaatgct cttcctgacc ctgtggggaa    840

gatagagctt ggggctccac cctccatgca gccgggaatg ttgccagatg tatccacttg    900

atctctattc tgactgatgc ttccttggat cccggctgtg gccttccctt tggtcactct    960

aaccccctgc ccctgcatcc aggcatcatt catccaactc tctctgccaa gtgcaatgca   1020

tgctgggaaa ttcttcgaag gtgggctatg cccaagggag aacctcatgt ttacatatct   1080

gagtgccaga gctggattct tcatttgcat acttctggaa ccaaaactga cccacggagg   1140

tcctttacag aggagggagg gatggctgag ctctgaccca ttgggtttga cagccctagc   1200

tcccttagca gactttcaag atcacaagta tcaaacattc caaagactga acaatgaagg   1260

gaggcctggg aaaaatactc tccaagatgg cacgtgcccc tggacatgac aacatgactc   1320

taggggttag tcagctgaag aagtttagtt cctaattata taatatttac atcagaggca   1380

gtggggtagg ctaggggatg tcactgtttc cgcttgacct tatctttctc attgaccact   1440

gtcttctctg aacttgatca ttagccaagg acaaaatgca tgttgcccta atttctttcc   1500

taccccctgcc tctatctctg catctagaac agctaaatgg aaagatacag agggatcctg   1560

taaggttgtt ttccctttca cgtccatcaa gatcaaaatt gagagaatca agttccatat   1620

ctgaatgatc tgtaggtttc tagagatgga attcacgtca gaaaattcca acttctgtta   1680

tccctgcccc cacccaccaa aaaagccaac atttattaag tgtcgcattc tgggataagc   1740

cctggctggg ggcaagacac ggtccctgat gtcttcttgc ttcccgaggt gagagaggca   1800

gccaagccaa ctggcgaaat gtgggtgggt gtgggaacac aggcggtgtc taccctagac   1860

ttgatagagg acggagaaat tcctggaggc catgtcctcc aacccaaaaa caaaaggaaa   1920

gataagagtt accaaagagg ggaaagaatg gcattggaag cagcaggagc tgctatgcgt   1980

gtgcaggagt agcttgggga aggagaagca tgatggaatt aggaaactgc acggccattt   2040

gtctgacctc ccagatgttt ttacttcatc cctctctttc ccggcttccc acctcttcac   2100

caagtgccta gcgcagcttc tcctggaggc acattgaggg cctcctggtg tctatggtag   2160

agacgggaag tgggtttcca gagggcctgg caagcaaaga gtccctgaga agtgcttctg   2220
```

-continued

```
taactccctg tggcaaccaa gaggcccgta ggtgaaagaa cagaagcagt acctgtgagg   2280

gagccagcca cgctgcccta ggccaaagac ccctggagag catttggtaa tgaggtgtga   2340

gaggagagca tcctgcacca gaatcaccct tgtcttgagc taattctctt cactcctcag   2400

ccttgtggcc ttcccagtca ccatggccct ccagatatcc ccatcctgca tggcagttcc   2460

atatgcagag ccagaatcca tccttgttcc ttctgcattg tgagaaaatc catggaggaa   2520

agcacttgtg tcatggggac cacccctacc tgacccaccc acggagtcag agtttgggga   2580

actcatggcc gttgaggctc acccaggatg gccatagcct tcatggagac ccatgccagt   2640

gtggccatgt ctctagctca cctctagccc tgcacacagg tggtcaggac caatcttggg   2700

agtgttgcaa gtgctatgtc gttaattgta gttttagtgc ctcagtgaca aaccttgcag   2760

atcatttccc ttcttctgag atgaatgcag atttgatggc cctataatat tactcttgca   2820

ttcctcgatg cattcttaaa tgggagcaaa tgggatgggc cccagatcac tcactggaaa   2880

cccacactcc aggtgcctca tttcctctgc ccaggagatt gtagcctggg cacagctata   2940

tgaggagggc ccatttggat actgctatca tggatgtctt agtggaagga agtttaggga   3000

taaccacaac tctagaagtc caggttctgg actcactttg cagactctag cagtacctgc   3060

ctccattccc tgcccactca agctagtttc tcagcaaaga gaatatgagg aaatatcccc   3120

aaacatcgtc atccccactg ggatcctcca catgagtgtg ggctggaaag gttccagggt   3180

cacactgagg caggacattt tttgccaatg cctgttaccc catggaaggc tgaggtacgg   3240

atgcacctga tctggaaatg cagcccaggt cagactccac atttctgcaa caaagcatca   3300

cctgcaatga ctcttttcac gtcagtgggt caaaggacag aaccagcttc cgtgttttag   3360

gctcactaga ttgtctcatg ctccccatgg ctattctgtt tgggagaatt tgatctaacc   3420

cgaagcctaa aggaatcaat gtaatgttga attgtattct atgtaa                3466
```

<210> SEQ ID NO 30
<211> LENGTH: 3238
<212> TYPE: DNA
<213> ORGANISM: Homo sapiens

<400> SEQUENCE: 30

```
gaaaggagga gaggaagaga ggactaagag gggagcaagg cgaggaggcc gcggcgggcg     60

cagcgggcac ctgggccgtg ctgcccccgc gagcaaggcg ccgccattcc gctgctcggg    120

gcgccgccgc cgccgccacc gcgcccaggg gccatgctcc cgccgccccc gcgccagccg    180

ccgccccagg cgcgtgcggc ccgcggcgcg gtgcgcctgc agcggccctt cctgcgcagc    240

ccgctgggcg tgttgcggct gctgcagctg ctggccggcg ctgccttctg gatcactatc    300

gccaccagca agtaccaggg ccccgtgcac ttcgcgctct tcgtgtccgt gctcttctgg    360

ctgctcaccc tgggcctcta cttcctcacg ctgctgggca agcacgagct ggtccccgtg    420

ctgggctcgc gctggctcat ggtcaacgtg gcgcacgatg tgctggcggc cgcgctctac    480

ggcgccgcca ccggcatcat gagcgaccag atgcagcgcc acagctactg caacctcaag    540

gattacccgc tcccctgcgc ctaccacgcc ttcctggcgg ccgccgtctg cggcggcgtc    600

tgccacggcc tctacctgct ttcggcgctc tatggctgcg ggcgtcgctg ccagggcaag    660

caggaggtgg cgtgaggccg cccgcgcccg ccgcggcccc gatcggggcg ggggaatccc    720

cggagaccag cctccttaat cccttccccc gccgccgccc cgcgcgggtg cgccctggca    780

ccctctccct gccctccagc gtttccactg tcgcccgcgc ccgggaaccc tgacgctcag    840

ctcccgcccg acggcagcgc cgccgccgcc cagaatccca gcccagaatc ccgaccgccg    900
```

-continued

```
cgccggacgc gccgtctccc gggacaagcg caggctgcga tccgaggggc tgacacacac    960
tcgcagacga gccgccccga ggcgaaacct cgcggttcct cttcccttcc ctgctgagac   1020
taagacgtgg acaggggccg cgcagatccg ggggaggctc ccaaattgga accaggcttc   1080
tggctgcccc cttccctccc gccccgtggt cggaagagca ctcccttccc tggcccctca   1140
tccagcctcc ggtgctgtaa aacgcaggcg ctgggccgcg ggcggagctg aggacaggcc   1200
ttggctggtc ccaggatgag cgacgagttt ggttttagct ggggattgtg ctggcatcct   1260
gcgaagctcc tcccagccgg tctctctgtg ctcggttgtc ttggggtggg gcccatccgc   1320
cgaggtgggg accgatagga gaagccggtg ggttgtaccc ttacacttgt ggagtctcct   1380
cttgcctcta cctactccgc ctttgtcctt aaggtttttg caggccagtg ccaaacacac   1440
actaactgtc ctggcctctc cgtgacacaa gtctcttccc agccttcctc acaggcttct   1500
gccgcccccc tcatctccac cctcccccat atctgtttgc attaggagtt ccacgaccat   1560
ggtggaatgt taaggtgaac ccccacccct cttacagatg gggacccaga gcctgctctt   1620
gggaacagcc agagtaagat tggaacccag acttgcagtc cagcgctgtt tgcattaaaa   1680
gggtgggtga gtcaggaccc ctggctcagg agccgcctct cctaaaagag ggtttcaagg   1740
ccaaatgggt ttgtcaacgg tgctgtctcc ctttcttgga gatgctcatt agcttatcaa   1800
agactgagaa gtcccgctgt tacagaaata atttagtttg ctgtattaac tgctcctggg   1860
cctggagcag tattcccacc ttaagattcc cagcatccct gtgctgtccc ggctctcatt   1920
catgccgaag ggcccaaccc attggctgtg ttctgtttga agatttgggg ggcgccttct   1980
ctttcttccc cagggaattc tctagcagag ggaggggacc caccccagtg aggaagtaga   2040
ttgctgcctc tagccagaga cctgaactgg ggaatttgaa cattccttta cattgttgga   2100
gaaatgaagc caaagttatt cagatggttt tcccaggcta aaggaaagtc acctgcaaga   2160
gatcccggca ctgatctgga gcagctgaca gggtgggtct cccttaccaa agagaagaac   2220
cactctctgg cgctggggtg acctgctggc tgggcctgta aggtttccat gttgctgagg   2280
ccatggagat tcccagagct ggtcacaccg accgctctca gggcccgctg ccctgggctg   2340
gcaacaccat tctggccttg gcctgcagaa gctttcagag tcttcactgg cagtaggggg   2400
agatggggag aggaatgatc tctgcccagc cccttccttt ccaaaccatg caatggaaga   2460
gcccagatgg gtgaagattg attttgcctt aactcaagag aattcctgtt ctccttgtgc   2520
tatgatttgg acacaagatt ctggatacct ggaacttagc tgtgtactcc tgtaccctaa   2580
acagtggatt tgagttccag cgtttattct tttttccttt tttcagatca ccatctaagt   2640
tacatcttta gctcaggtcc atccttctca agatctcctt cttagccccc cagcccctgg   2700
tgctgtctgt ggtcaggtga ccttactcag gagcagatat ctccttggcc gccatggagc   2760
ctcatccatc cacacgtgcc tgtagcattc cagagctcac tgcccttcta gatgtgcctt   2820
cccgcttggc ttccagcggc ttgtgctcac tctgtctgcc aggtatgaga agaacacgta   2880
agaccgccac cacactcacc ctccctcaag gccctgtgcc ataggggtgg ccacccgacc   2940
tgcccccaga acttttggat actggaggca gttgcatagg tctccctctc tgggcaccag   3000
gactcagtcc agcccaagac tactctgggc agctcccatc ccagtctggg gccatttgca   3060
gactcaggaa aggatttcta cagtgttcta taaaagccaa aagagagagt gggtttggga   3120
agagtgaggg tggttgggga gaggggaccg atgtgcctca ttgtttagtg gtgattacaa   3180
atatgctttt ctggataaag tttggttgtt tgctcttaaa aaaaaaaaaa aaaaaaaa     3238
```

<210> SEQ ID NO 31

<211> LENGTH: 2337
<212> TYPE: DNA
<213> ORGANISM: Homo sapiens

<400> SEQUENCE: 31
atgctagaca gctgcaagct gaaaagtgcc tgcaatttgc catttatttg taataagaaa 60
ataataaaca ctgctggaac cagtaatgca gaagtcccct tggctgatcc cggaatgtac 120
cagctggaca ttacattaag aaggggtcaa agtttagctg ctcgagatcg aggagggacg 180
agtgatccat atgtgaagtt taaaatcgga ggaaaagaag tttttagaag taagataata 240
cacaagaacc tcaaccctgt gtgggaagaa aaagcttgta ttctggttga tcatcttagg 300
gagccattgt atataaaggt atttgactat gattttggac tacaggatga ctttatgggc 360
tcagcctttc tggatctgac acaattggag ttaaacaggc ccacagatgt gacccttact 420
ctgaaagatc ctcattatcc tgaccatgat cttggaatca ttttgctctc agtcatcctt 480
acccctaaag aaggagagtc cagggatgtg acaatgctaa tgaggaagag ttggaaaaga 540
tcaagtaagg aactttcaga aaatgaagtg gttggatctt atttctctgt gaagtctctc 600
ttttggagga cgtgcggcag gccagctctt cctgtcctgg gcttctgcag agcagagctt 660
cagaatcctt attgcaaaaa tgtacaattt cagacccaaa gtttacgcct atcagaccta 720
cacagaaaat cgcatctttg gagaggaata gtcagcatca ccttgattga agggagagac 780
ctcaaggcca tggattccaa cgggttgagc gatccctacg tgaagttccg gcttgggcat 840
cagaagtaca agagcaagat tatgccaaaa acgttgaatc ctcagtggag ggaacaattt 900
gattttcacc tttatgaaga aagaggagga gtcattgata tcactgcatg ggacaaagat 960
gctgggaaaa gggatgattt cattggcagg tgccaggtcg acctgtcagc cctcagtagg 1020
gaacagacgc acaagctgga gttgcagctg gaagagggtg agggacacct ggtgctgctg 1080
gtcactctga cagcatcagc cacagtcagc atctctgacc tgtctgtcaa ctccctggag 1140
gaccagaagg aacgagagga gatattaaag agatatagcc cattgaggat atttcacaac 1200
ctgaaagatg tgggatttct ccaggtgaaa gtcatcagag cggaagggtt aatggctgcc 1260
gacgtcactg gaaaaagtga cccattttgt gtggtagaac tgaacaacga tagactgcta 1320
acacatactg tctacaaaaa tctcaatcct gagtggaata aagtcttcac gttcaacatt 1380
aaagatatcc attcagttct tgaagtgaca gtttatgatg aagatcggga tcgaagtgct 1440
gactttctgg gcaaagttgc tataccattg ctgtctattc aaaatggtga acagaaagcc 1500
tacgtcttga aaaacaagca gctgacaggg ccaacaaagg gggtcatcta tcttgaaata 1560
gatgtgattt ttaatgctgt gaaagccagc ttacgaacat taatacccaa agaacagaag 1620
tacattgaag aggaaaacag actctctaaa cagctgctac taagaaactt tatcagaatg 1680
aaacgttgtg tcatggtgct ggtaaatgct gcatactacg ttaatagttg ctttgattgg 1740
gattcacccc caaggagtct cgctgctttt gtgctctttc tctttgttgt ctggaacttt 1800
gagctctaca tgataccact ggttttgttg ttactattga catggaacta cttcttgata 1860
atatcaggga aagataacag gcaacgtgat acagtagtgg aggacatgct agaggacgag 1920
gaagaagaag atgacaaaga tgacaaggac agtgaaaaaa agggatttat aaataaaatc 1980
tatgccatcc aggaggtatg tgtcagtgtc cagaacatcc tagatgaagt ggcttccttt 2040
ggcgaaagga ttaagaatac tttcaactgg actgtcccat tcttaagctg gctggccatt 2100
gtagccctct gtgtgttcac agccatcctg tactgcattc cgctgagata cattgtcctt 2160
gtctggggca tcaataaatt tacaaaaaag cttcggagtc catatgcaat tgataacaat 2220
gaactacttg acttcctttc cagagtccct tcagatgtac aagtggtgca ataccaagaa 2280
ctgaaaccag atccttctca tagcccatat aaaagaaaga aaaacaatct tggctag 2337

<210> SEQ ID NO 32
<211> LENGTH: 3343
<212> TYPE: DNA
<213> ORGANISM: Homo sapiens

<400> SEQUENCE: 32
gcagggacca gatccgcgag cccgtcagcc tgcgccatgg gctgcgacgg ccgcgtgtcg 60
gggctgctcc gccgcaacct gcagcccacg ctcacctact ggagcgtctt cttcagcttc 120
ggcctgtgca tcgccttcct ggggcccacg ctgctggacc tgcgctgtca gacgcacagc 180
tcgctgcccc agatctcctg ggtcttcttc tcgcagcagc tctgcctcct gctgggcagc 240
gccctcgggg gcgtcttcaa aaggaccctg gcccagtcac tatgggccct gttcacctcc 300
tctctggcca tctccctggt gtttgccgtc atccccttct gccgcgacgt gaaggtgctg 360
gcctcagtca tggcgctggc gggcttggcc atgggctgca tcgacaccgt ggccaacatg 420
cagctggtaa ggatgtacca gaaggactcg gccgtcttcc tccaggtgct ccatttcttc 480
gtgggctttg gtgctctgct gagccccctt attgctgacc ctttcctgtc tgaggccaac 540
tgcttgcctg ccaatagcac ggccaacacc acctcccgag gccacctgtt ccatgtctcc 600
agggtgctgg gccagcacca cgtagatgcc aagccttggt ccaaccagac gttcccaggg 660
ctgactccaa aggacggggc agggacccga gtgtcctatg ccttctggat catggccatc 720
atcaatcttc cagtgcccat ggctgtgctg atgctgctgt ccaaggagcg gctgctgacc 780
tgctgtcccc agaggaggcc cctgcttctg tctgctgatg agcttgcctt ggagacacag 840
cctcctgaga aggaagatgc ctcctcactg cccccaaagt ttcagtcaca cctagggcat 900
gaggacctgt tcagctgctg ccaaaggaag aacctcagag gagcccctta ttccttcttt 960
gccatccaca tcacggccgc cctggtcctg ttcatgacgg atgggttgac gggtgcctat 1020
tccgccttcg tgtacagcta tgctgtggag aagcccctgt ctgtgggaca caaggtggct 1080
ggctacctcc ccagcctctt ctggggcttc atcacactgg gccggctcct ctccattccc 1140
atatcctcaa gaatgaagcc ggccaccatg gttttcatca acgtggttgg cgtggtggtg 1200
acgttcctgg tgctgcttat ttctcctac aacgtcgtct tcctgttcgt ggggacggca 1260
agcctgggcc tgtttctcag cagcaccttt cccagcatgc tggcctacac ggaggactcg 1320
ctgcagtaca aggctgtgc aaccacagtg ctggtgacag gggcaggagt tggcgagatg 1380
gtgctgcaga tgctggttgg ttcgatattc caggctcagg gcagctatag tttcctggtc 1440
tgtggcgtga tctttggttg tctggctttt accttctata tcttgctcct gttttccac 1500 aggatgcacc ctggactccc atcagttcct acccaagaca gatcaattgg aatggaaaac 1560
tctgagtgct accagaggta aaactgggtg aagaaggcaa gagaagactt tcagcctctt 1620
gatcaccagc acgaccatac tgtttcagaa agctgggtgg tggtggaggc gctatctcaa 1680
tggctattca agtcttctcc actaaaactt ggttgggtag aggaaattaa attgagtcct 1740
ggtacctggt caaaatcatt agaagtttac ctggcttctc aagttatctt cttccctggt 1800
tcagactgtt ggtaagagct gtccagatac ccagatggga aggaaggaga cagccgcgcg 1860
cttcactcca tttgtcacct catgcatgga ccatactctg ggtttgagat cattcttcat 1920
tgaagtttgt aaaaataggt tgaaattgta aagctccatg atcattgcta tgtagatata 1980
tttcaattta agcaaaacaa gctgcaagtt attccctggc atgctcaaag gattttcgtg 2040

```
cttttcactt aatagtccaa agtctcttaa attcctgctg cagacatcaa tagcttatct   2100

atattctcaa acaccaaaag gaaaagttga atcttgctct ctttggtata ctaatgtagt   2160

ggtatgctaa gctggctcat accaacttag aaaagctgat tgtaaaattt tcattttgac   2220

agctggttat taaatgcagc cattattaaa aatcaaatca tacaaactta taattaaatc   2280

aattacattt aaaacaaagg taataaatat tcaaagcata tcacttccta atttgatctt   2340

gatgctcttg aggtaattta cgtccatggt acctgtgtgg tggaattact atatatgatg   2400

gtgtgctact gtgcaccttg tctcaactcc actcttcgtg atagcatgtt ggtagcttga   2460

aatcagcctg gtgggagtat taccatggac actggcaaaa gctacagatc ccggagagcc   2520

agtggttaaa catttaccag cataccactg ctagtaatca aggctaactg gtccagaaat   2580

cgcccaggag aatgaaatgg atgttccatt tttttctact gacattgact agcatataaa   2640

aggtatagaa acagcactaa gactttctga aaatacctaa tgaaaatttt acatcttttt   2700

ttgtttttgt ttttgttttt gagacagagt ctcactctgt tgccaggctg gaatgcagtg   2760

gcgtcatctc ggctcactgc aacctccgcc tcccagtttc aagcgattct cctgcctcag   2820

cctcccaagt agctgtgact acaggcgcat gccatcacgc acagctaatt ttttgtattt   2880

ttagtagaga cgggatttca ccgtgttagc caggatggtc ttgatctcct gacctcatga   2940

tctgcccgtc tcggcctccc aaagtgctgg gattacaggc gtgagccact gcacccagcc   3000

aaaaatttta catcttttat agagggaaaa aaactcttta taccatggca aggccttttc   3060

tttcacaaaa agctgggcct actgaacaat tcaagctgtg cagtagtaga ctgaaagcag   3120

gatttgttga ggagttacag ctcctgtcca gagcaaatcc tgtagtgata caaggagaat   3180

gtaaacttgc cagcttagac agggatcagt cctgagactg ctggcagtag caaatggcta   3240

ttagagtaac tgtataatgg ttttgcctgc actttctcta tgtatataca aatgtacatg   3300

tataaatata aaaattaagt gatcatgaaa gaaaaaaaaa aaa                    3343
```

<210> SEQ ID NO 33
<211> LENGTH: 1295
<212> TYPE: DNA
<213> ORGANISM: Homo sapiens

<400> SEQUENCE: 33

```
ccaaggtcct cccccgcacc cctgaggtcc tgcagacgac ggcgtcgtgg gtggtcaccg     60

ttatccctta ggtctggaga ggggacatcc gagcgagggc cacttgcggc caggcccgag    120

ctcgtccagc tccgggtgac cacagagtgc cgcgggcggg cagaggggcc ggaaacccag    180

gccgcttcgt ccctgtttcc ggcagcgccg cgctgctccg ggagccgctg tggcagcgta    240

tgctgccacg gggactgaag atggcgccgc gaggtgagat tccggaggta aacggttgtc    300

ctccaccccg ctggaaatcc tgttctttct gaacgggtgg tataatgcta cctatttcct    360

gctggaactt ttcatatttc tgtataaagg tgtcctgcta ccatatccaa cagctaacct    420

agtactggat gtggtgatgc tcctccttta tcttggaatt gaagtaattc gcctgttttt    480

tggtacaaag ggaaacctct gccagcgaaa gatgccgctc agtattagcg tggccttgac    540

cttcccatct gccatgatgg cctcctatta cctgctgctg cagacctacg tactccgcct    600

ggaagccatc atgaatggca tcttgctctt cttctgtggc tcagagcttt tacttgaggt    660

gctcaccttg gctgctttct ccagtatgga caggatttga agtacagaat ttcagccagc    720

agcccatcag gctgacacca cacatattgc ttctggtact ttagccacac cagtgagaat    780

tggtggggca agttgtcctg agaaaggctg tgtggctttt cttcagcaca gacatttggg    840
```

caagcaactc agcataaggc cagtgggtac catcttctaa accaggacca tcagcccaag 900
agactcttct acactccagt atagggaggg gcaaggttat tcccatcctg cccccttctca 960 gaaccagtcc cctgctgacc tcaagttctc ctccttgatc accgtggcca gagcatctcg 1020
tgtggaccat ctaggctcct tgggcttcaa gcaggacctg agccacatgc tccctgtacg 1080
agctgtgcta tacctgtccc acatgagcac ggagagcctc atgttggtgg gtttccagag 1140
tgatgtgaaa gcctctcacc ccaatcctcg gagactgagt tccacaactt ttttagtagc 1200
tcatagtgtt atttttctac tctcttcatg aaactaactt tattttataa taaatatgta 1260
ttttctgttg tggggaaaaa aaaaaaaaaa aaaaa 1295

<210> SEQ ID NO 34
<211> LENGTH: 1369
<212> TYPE: DNA
<213> ORGANISM: Homo sapiens

<400> SEQUENCE: 34
aaacaggaaa taaatacgaa tgaaactgag ctctaagcag catgtaacct ggcctgcatc 60
caggaaatag aggacttcgg atccttctaa ccctaccacc caactggccc cagtacattc 120
attctctcag gaaaaaaaac aaggtcccca cagcaaagaa aaggaatagg atcaagagat 180
acgtggctgc tggcagagca agcatgaatt cgatgacttc agcagttccg gtggccaatt 240
ctgtgttggt ggtggcaccc cacaatggtt atcctgtgac cccaggaatt atgtctcacg 300
tgcccctgta tccaaacagc cagccgcaag tccacctagt tcctgggaac ccacctagtt 360
tggtgtcgaa tgtgaatggg cagcctgtgc agaaagctct gaaagaaggc aaaaccttgg 420
gggccatcca gatcatcatt ggcctggctc acatcggcct cggctccatc atggcgacgg 480
ttctcgtagg ggaatacctg tctatttcat tctacggagg ctttcccttc tggggaggct 540
tgtggtttat catttcagga tctctctccg tggcagcaga aaatcagcca tattcttatt 600
gcctgctgtc tggcagtttg ggcttgaaca tcgtcagtgc aatctgctct gcagttggag 660
tcatactctt catcacagat ctaagtattc cccacccata tgcctacccc gactattatc 720
cttacgcctg ggtgtgaac cctggaatgg cgatttctgg cgtgctgctg gtcttctgcc 780
tcctggagtt tggcatcgca tgcgcatctt cccactttgg ctgccagttg gtctgctgtc 840
aatcaagcaa tgtgagtgtc atctatccaa acatctatgc agcaaaccca gtgatcaccc 900
cagaaccggt gacctcacca ccaagttatt ccagtgagat ccaagcaaat aagtaaggct 960
acagattctg gaagcatctt tcactgggac caaaagaagt cctcctccct ttctgggctt 1020
ccataaccca ggtcgttcct gttctgacag ctgaggaaac gtctctccca ctgtttgtac 1080
tctcaccttc attcttcaat tcagtctagg aaaccatgct gtttctctat caagaagaag 1140
acagagattt taaacagatg ttaaccaaga gggactccct agggcacatg catcagcaca 1200
tatgtgggca tccagcctct ggggccttgg cacacacaca ttcgtgtgct ctgctgcatg 1260
tgagcttgtg ggttagagga acaaatatct agacattcaa tcttcactct ttcaattgtg 1320
cattcattta ataaatagat actgagcatt caaaaaaaaa aaaaaaaaa 1369

<210> SEQ ID NO 35
<211> LENGTH: 1263
<212> TYPE: DNA
<213> ORGANISM: Homo sapiens

<400> SEQUENCE: 35
cacattaacc ggcaggatgt cggaggtgcg gctgccaccg ctacgcgccc tggacgactt 60
tgttctgggg tcggcgcgtc tggcggctcc ggatccatgc gacccgcagc gatggtgcca 120
ccgcgtcatc aacaacctcc tctactacca aaccaactac cttctctgct tcggcatcgg 180
cctcgctctc gccgggtacg tgcggccact tcatacgctc ctgagcgcgc tggtagtggc 240
ggtggccctc ggcgtgctgg tgtgggcagc tgagacccgc gcagctgtgc gccgctgccg 300
ccgcagccac cctgcagcct gcctggccgc agtgcttgcc gtcggcctcc tggtgctctg 360
ggtcgcgggc ggcgcttgca ccttcctgtt cagcatcgcc gggccggtgc ttctgatcct 420
ggtgcacgcc tcgttgcgcc tgcgcaacct taagaacaag attgagaaca agatcgagag 480
cattggtctc aagcggacgc caatgggcct gctactagag gcactgggac aagagcagga 540
ggctggatcc taggcccctg ggatctgtac ccaggacctg gagaatacca ccccaccccc 600
agcccataat tgggacccag agccctttcc cagcacttaa aacaggagcc tagagccccc 660
tgcccaaaca aaacaggaca tctgtgaccg ccctaccccc acgccagccc caaactaaga 720
tatccctcac acccagcccc cattacctag ggacaagagt cttccccagc cttgaaccta 780
ggaccaagag ccacctacat ccagccccaa aactggggct tcaggccaga gcatccatgg 840
ccaatttcaa attgtgaacc cagagacact cccatccacc cttctccatg ctcatcccca 900
aactggggcc tggagcaagg cactctcaaa tcttgaaccc tggaccaaag cttttccaga 960
ccccacccta ccttccaacc caggtcaaga cattgccaaa tcttgaactc agaacccaag 1020
tgttccatgc ccctgtgtgg atggagtcgg gtatcctgac tgttggaccc ctggtccagg 1080
tgatcccgac cctcaccagt cccatttgcc tccctccagc tctgcttagg cattttgccc 1140
ctcaccccaa tgttccacac catcgacaac caaggggtga ggtggggaca ggcctcagca 1200
gggaatgggg cgtatatgtt agtgttgctg caacaataaa gcctgttgca tctctcatgc 1260
caa 1263

<210> SEQ ID NO 36
<211> LENGTH: 2914
<212> TYPE: DNA
<213> ORGANISM: Homo sapiens

<400> SEQUENCE: 36
acatgctgcc caggctgcgc gggtgattgg cttggctgga cctgaatgat gcggctgtga 60
ttgctgaatt gtctgggcag gtttggagtc tctggcaagc tcccctgact gtgcatccct 120
ctggagacga agaggagggg gaggcctgtc ctctctggga tccattggtc acatccccct 180
gaggattccc gaatgcctac ctccagtgtc gtcaacatgg agttctgaag tccatgtggc 240
tcttcacagt gaatcaggtg ttaaggaaga tgcagagacg ccacagcagc aacacggata 300
acattccacc tgaaagaaac cgcagccagg cgctcagctc cgaggcgagt gtggatgaag 360
gtggcgtctt tgagagtctg aaggcagagg cagcctcccc accagcgctc ttctcgggct 420
tatcaggcag cctccccacc agctcgttcc cctccagcct ggtgctgggc tcctcggctg 480
gcggcgggga cgtgttcatc cagatgcccg cgtccaggga ggaaggaggg ggccggggcg 540
aggggggcgc ctaccaccac cgccagcccc accaccattt ccaccatggc ggccaccgcg 600
ggggctccct gctgcagcac gtgggtgggg accaccgggg gcactcggag gagggaggcg 660
acgagcagcc tgggacgccc gcccccgccc tgtccgagct gaaggctgtg atctgctggc 720
tccagaaagg actccccttc atcctgatcc tcctggccaa actgtgcttt cagcataagc 780
tcggcattgc tgtgtgcatc gggatggcca gcaccttcgc ctatgccaac tccacgcttc 840
gagaacaggt ctcactgaag gagaagaggt cagtgctggt catcttgtgg atcctggcct 900

-continued ttctggcggg gaacaccctc tatgtgcttt atacattcag ctcccagcag ctgtacaaca 960
gcctcatatt cctgaagccc aacctggaga tgctggactt ctttgacctg ctatggattg 1020
tggggatcgc agactttgtt ctgaagtaca tcaccatcgc cctcaagtgc ctcatcgtgg 1080
ccctgcccaa gatcatcctg gctgtcaagt ccaagggaaa gttctatctg gtcatcgagg 1140
agctgagcca gctgttccga tcccttgtcc ccatccagct gtggtacaaa tacatcatgg 1200
gtgacgactc ctccaacagc tacttcctgg gcggggtcct gatcgttctc tacagcctct 1260
gcaagtcctt cgacatctgt ggacgtgtgg gcggagttag gaaagccctg aagcttctct 1320
gtacctctca gaactatgga gtccgagcca ccgggcagca gtgcacagaa gctggtgaca 1380
tctgcgccat ctgtcaggcc gagttccgag agcctctgat tctcctgtgc cagcacgtgt 1440
tctgtgagga gtgcctctgc ctgtggctgg accgtgagcg cacctgcccg ctctgccgct 1500
cggtcgccgt ggacaccctg cgctgctgga aggacggcgc cacgtccgca cacttccagg 1560
tgtactagga ccgaacactg aggacaccca gaaggacgcc aaggattcag gacatttgcc 1620
cctgtgtgcc accaaaccag gactttcccc ttggcttggc atccctggct ctctcctggt 1680
acccagcaag acgtctgttc cagggcagtg tagcatcttt caagctccgt tactatggcg 1740
atggccatga tgttacaatc ccacttgcct gaataatcaa gtgggaaggg gaagcagagg 1800
gaaatggggc catgtgaatg cagctgctct gttctcccta ccctgaggaa aaaccaaagg 1860
gaagcaacag gaacttctgc aactggtttt tatcggaaag atcatcctgc ctgcagatgc 1920
tgttgaaggg gcacaagaaa ttggagctgg agaagattga tgaaagtgca ggtgtgtaag 1980
gaaatagaac agtctgctgg gagtcagacc tggaattctg attccaaact ctttattact 2040
ttgggaagtc actcagcctc cctgtagcca tctccagggt gacggaaccc agtgtattac 2100
ctgctggaac caaggaaact aacaatgtag gttactagtg aataccccaa tggtttctcc 2160
aattatgccc atgccaccaa aacaataaaa caaaattctc taacactgca aagagtgagc 2220
catgcctgtt aacactgtaa agaatgtaac atgtgggga cacacagggg cagatgggat 2280
ggtttagttt aggattttat tagtgcatgc cctaccctct gggggaacgt cccatctgag 2340
gttttcttct cggtgggggg atttaacttc tgtcctaggg aaaacagtgt ctgatgagga 2400
gtgtttccaa cacaggctac atgaattccc ctataccagt gcgaaagcag ccaggagtcc 2460
ccgttggaaa agaacaatgc cactctcttt tatgtatctt ggttctgcaa ctcatttgtt 2520
gtaagtaggg ttaatcgagt atcaggttca cagtatcctg cccttattat tttatgattc 2580
actgactcaa gttccacgaa gtccttagaa atggacctct tcatgtaaaa tatcttgaga 2640
ataataaatg tgagggaata agaaaggcaa gctttggaca cagatatgat aggtgcatca 2700
gcttcggaag agaagaatga tgtgcagagt gttaggaaga catccgggct gctgagactc 2760
gggattagaa gaaagagagg taaataaagt gggtcctgga atcttttagg acttctgctg 2820
taggacaaac agctgccttt ggtgttttaa tgtctcccaa agtacccttc agccaataaa 2880
taccatctgt tggtgcaaaa aaaaaaaaaa aaaa 2914

<210> SEQ ID NO 37
<211> LENGTH: 2286
<212> TYPE: DNA
<213> ORGANISM: Homo sapiens

<400> SEQUENCE: 37
agatccttga aagggttttg gttttgactg agcagaatgg tgccattgca gatcaacacg 60
cactttaaat aatcaaaacc cctatctttc ccctgggaag gaggaagccg aggaaggctg 120
tgtttctgac tcacacgggg gagtcggggg agtcgtaaac aaccctgaag agaacagcca 180
ggcctgttcc cgcaagccca gacaatgccg gtggaggaat ttgtggctgg ctggatctct 240
ggcgctctgg gcttggtcct gggacacccg tttgacactg taaaggtgag gctgcagacc 300
cagaccacct accggggcat cgttgattgc atggtcaaga tttaccgcca tgagtccctc 360
ctgggcttct tcaagggaat gagcttcccc attgccagca tagctgtggt caactctgtc 420
ctgtttgggg tctatagcaa caccctgctg gtgctcacgg ccacctccca ccaggagcgg 480
cgggcccagc cgcccagcta catgcacatc ttcctagcgg gctgcaccgg ggggttcctg 540
caggcctact gtctggctcc ttttgacctc atcaaagtcc ggctacaaaa ccagacagag 600
ccaagggccc agccagggag ccccccaccc cggtaccagg ggcccgtgca ctgtgcagcc 660
tccatcttcc gggaggaggg gccccggggg ctgttccgag gagcctgggc cctgacgctg 720
agggacaccc ccacggtggg gatctacttc atcacctatg aagggctctg tcgccagtac 780
acaccagaag gccagaatcc cagctcagcc acggtgctgg tggcaggggg ctttgcaggc 840
attgcttcct gggtggcagc cacgccctta gacatgatca agtcccggat gcagatggat 900
ggactgagac gcagagtgta ccaggggatg ctggactgca tggtgagcag catccggcag 960
gaaggactgg gagtcttctt ccggggggtc accatcaaca gtgcccgcgc ctttcccgtc 1020
aatgctgtca ccttcctcag ctacgaatat ctcctccgct ggtggggatg agccctgcgg 1080
caatgccagc agctccccat caggcccacg gcctggaggc cagtttgaga ttggaggcca 1140
ggttgaaagc ttgcaaatca gtgcaagagg ctcagccctt cctaaccaag gtgcctccca 1200
cccgcgcaga tctgggctgg gcagacacct gtgggagccg gaagccaggg ggcctgtgca 1260
gcctccctgt gtagctggcc ttgactcctt tgcctcccac atctgtgaaa cagggagcat 1320
gaggcacaag tgagctggca agtggtgctg gtgacatccc agctcctgtc ctgtgccttc 1380
acctcttttt tttttttttt tttttttga gatggagtct ttctctgtca cccaggctgg 1440
aatgcagtgg cgtgatctcg gctcactgca acctccgcct ttccaccttc cgggttcaag 1500
caactctcct gcctcagcct cccaagtagc tgggactata ggcgcccgcc accacaccca 1560
gctaaatttt tgtattttta gtagagacag ggtttcacca tgtcagccag gatggtcttg 1620
atctcctgac tttgtgatcc gcccgcgtcg gcctctcaaa gtgctgggat tacaggcgtg 1680
agccaccgcg cccggctgcc ttcacctctt aaggagctct gagactccac ttctgagagt 1740
ccctgcggcc tcccacctcc ctgcctttca aagctctctc ccccatgacc caggataacc 1800
ctatgtctcc tcccccagaa tccttcagtg gctctcatca ccttcaggaa aagcccaaac 1860
tccttccacc ctccaggttc ctccctcccc acgaggcttt gttctcctgg ggttgcttcc 1920
tggaccctga acaagttgtg ctctcattgg ccgggcctgg ccagcagtgc acagtgcctg 1980
gcaggttgac tctaccatcc ccggggctgg ccccgctctc ctccgagacc caggctgagc 2040
ccagtcccct cacccttcct tgacttacct ccccacctga ggctgacttt ggggttccca 2100
gacaccctac ccacacacat gccttgatca tagcacttgc ctgcgcttct tcagagtcat 2160
taatttgctt ctcggcttcc ccactggact gtgagctgcc tgaggtcagg gattgcgctt 2220
tggatggttt ccagcctgag cctggtgctt gaacagacgt gtgcaataaa tgctcgttaa 2280
atgatg 2286

<210> SEQ ID NO 38
<211> LENGTH: 1430
<212> TYPE: DNA
<213> ORGANISM: Homo sapiens

<400> SEQUENCE: 38
ggggcactga ggagcggcgc ccgcggggca gcgaggagcc cgatgcaggg ttctgcgcgt 60
catttccggt cccgcgggcg ccccgtgaag cccacctgga tccgccagcg ctgtgccact 120
ccccagtgcc gagctccgag ctgtctccgc ggcctcgcgc ccggcccctc caccgcgcac 180
ctcttaggcc ccgcccgcca gcgtcccttt gttgtgaagg cgccggggcc tagcgctatg 240
cctgcggcgg agactgcatc aggctctcgc gtctgcttct acgctttgcc tgggagaggc 300
cctggtggcc tcgttcctgg cgcccggagt ccctgctgcg gccccacccc cgggcggtca 360
cggtgaccca tgctgcccag cctggaggta aaatcgttcg tggctgtggc ttcagcatgt 420
cgtcctcggt gaaaacccca gcactggaag agctggttcc tggctccgaa gagaagccga 480
aaggcaggtc gcctctcagc tggggctctc tgtttggtca ccgaagtgag aagattgttt 540
ttgccaagag cgacggcggc acagatgaga acgtactgac cgtcaccatc acggagacca 600
cggtcatcga gtcagacttg ggtgtgtgga gctcgcgggc gctgctctac ctcacgctgt 660
ggttcttctt cagcttctgc acgctcttcc tcaacaagta catcctgtcc ctgctgggag 720
gcgagcccag catgctaggt gcggtgcaga tgctgtccac cacggttatc gggtgtgtga 780
aaaccctcgt tccttgctgt ttatatcagc acaaggcccg gctttcctac ccacccaact 840
tccttatgac gatgctgttt gtgggtctga tgaggtttgc aactgtggtt ttgggtttgg 900
tcagcctgaa aaatgtggcg gtttcgtttg ctgagacggt gaagagctcc gcccccatct 960
tcacggtgat catgtctcgg atgattctgg gggagtacac aggacgtccc agtgatcggg 1020
aggagcggga agagcttcag ctacaaccag gacgtggtgc tgctgcttct gacagacgga 1080
gtcctgttcc accttcagag cgtcacggcg tacgccctca tggggaaaat ctccccggtg 1140
actttcaggt cccgcaggcc ctgcaccgag tcgccttgtc catggcgctg ccctgcccca 1200
tgcttcctgc gtcctgagta ggaggtatct ccgagacagg aaaagtggcc gctctctctc 1260
actttttctg gaactcatgg tggtctcctg ggcttggtca ctgtctctca ccagcatgtt 1320
tctttgtgcg gtcaggaatt atttccaaat gctcctgaag cctagtgttt tagtgaacat 1380
tagtgattgt tagcagtggt tcaaaaaaaa aaaacttttt tttttttttt 1430

<210> SEQ ID NO 39
<211> LENGTH: 4303
<212> TYPE: DNA
<213> ORGANISM: Homo sapiens

<400> SEQUENCE: 39
cgccgcggcg gcagctgagt tgggctgagg tgtccctagc tggctctgcg gctcttccgg 60
gtctgggctc ggagattcac aggcggcccg cgaggccgag cgagggacgc atggccctga 120
ggcggccgca gggcttggcg gggtccggag gttgacctcg cccccgcagc cggccttcga 180
ggctgcctcc tccaggcagc ctctggggcc cgcgcccgcg cctgctcagg ctcccgtgtt 240
caggctgccc atcccctccc caccggcgtc ccggacgttg ggacctgtga ccgtggcctc 300
gggctgggct tccaaagccg gccgcagccc ggcgaccccc gaggcctctc gccccgggcc 360
cctagacctc tcactatgac cgcggccgcc gcctccaact gggggctgat cacgaacatc 420
gtgaacagca tcgtaggggt cagtgtcctc accatgccct tctgcttcaa acagtgcggc 480
atcgtcctgg gggcgctgct cttggtcttc tgctcatgga tgacgcacca gtcgtgcatg 540
ttcttggtga agtcggccag cctgagcaag cggaggacct acgccggcct ggcattccac 600
gcctacggga aggcaggcaa gatgctggtg gagaccagca tgatcgggct gatgctgggc 660

-continued

```
acctgcatcg ccttctacgt cgtgatcggc gacttggggt ccaacttctt tgcccggctg    720
ttcgggtttc aggtgggcgg caccttccgc atgttcctgc tgttcgccgt gtcgctgtgc    780
atcgtgctcc cgctcagcct gcagcggaac atgatggcct ccatccagtc cttcagcgcc    840
atggccctcc tcttctacac cgtgttcatg ttcgtgatcg tgctctcctc tctcaagcac    900
ggcctcttca gtgggcagtg gctgcggcgg gtcagctacg tccgctggga gggcgtcttc    960
cgctgcatcc ccatcttcgg catgtccttc gcctgccagt cccaggtgct gcccacctac   1020
gacagcctgg atgagccgtc agtgaaaacc atgagctcca tatttgcttc ctcccttaat   1080
gtggtcacca ccttctacgt catggtgggg tttttcggct acgtcagctt caccgaggcc   1140
acggccggca acgtgctcat gcactttccc tccaacctgg tgacggagat gctccgtgtg   1200
ggcttcatga tgtcagtggc tgtgggcttc cccatgatga tcctgccatg caggcaggcc   1260
ctgagcacgc tgctgtgtga gcagcagcaa aaagatggca cctttgcagc agggggctac   1320
atgcccccctc tccggtttaa agcacttacc ctctctgtgg tgtttggaac catggttggt   1380
ggcatcctta tccccaacgt ggagaccatc ctgggcctca caggagcgac catgggaagc   1440
ctcatctgct tcatctgccc ggcgctgatc tacaagaaaa tccacaagaa cgcactttcc   1500
tcccaggtgg tgctgtgggt cggcctgggc gtcctggtgg tgagcactgt caccacactg   1560
tctgtgagcg aggaggtccc cgaggacttg gcagaggaag cccctggcgg ccggcttgga   1620
gaggccgagg gtttgatgaa ggtggaggca gcgcggctct cagcccagga tccggttgtg   1680
gccgtggctg aggatggccg ggagaagccg aagctgccga aggagagaga ggagctggag   1740
caggcccaga tcaaggggcc cgtggatgtg cctggacggg aagatggcaa ggaggcaccg   1800
gaggaggcac agctcgatcg ccctgggcaa gggattgctg tgcctgtggg cgaggcccac   1860
cgccacgagc ctcctgttcc tcacgacaag gtggtggtag atgaaggcca agaccgagag   1920
gtgccagaag agaacaaacc tccatccaga cacgcgggcg gaaaggctcc aggggtccag   1980
ggccagatgg cgccgcctct gcccgactca gaaagagaga aacaagagcc ggagcaggga   2040
gaggttggga agaggcctgg acaggcccag gccttggagg aggcgggtga tcttcctgaa   2100
gatccccaga aagttccaga agcagatggt cagccagctg tccagcctgc aaaggaggac   2160
ctggggccag gagacagggg cctgcatcct cggccccagg cagtgctgtc tgagcagcag   2220
aacggcctgg cggtgggtgg aggggaaaag gccaaggggg gaccgccgcc aggcaacgcc   2280
gccggggaca cagggcagcc cgcagaggac agcgaccacg gtgggaagcc tcccctccca   2340
gcggagaagc cggctccagg gcctgggctg ccgcccgagc ctcgcgagca gagggacgtg   2400
gagcgagcgg gtggaaacca ggcggccagc cagctggagg aagctggcag ggcggagatg   2460
ctggaccacg ccgtcctgct tcaggtgatc aaagaacagc aggtgcagca aaagcgcttg   2520
ctggaccagc aggagaagct gctggcggtg atcgaggagc agcacaagga gatccaccag   2580
cagaggcagg aggacgagga ggataaaccc aggcaggtgg aggtgcatca agagcccggg   2640
gcagcggtgc ccagaggcca ggaggcccct gaaggcaagg ccagggagac ggtggagaat   2700
ctgcctcccc tgcctttgga ccctgtcctc agagctcctg gggccgccc tgctccatcc   2760
caggacctta accagcgctc cctggagcac tctgaggggc ctgtgggcag agaccctgct   2820
ggccctcctg acggcggccc tgacacagag cctcgggcag cccaggccaa gctgagagat   2880
ggccagaagg atgccgcccc cagggcagct ggcactgtga aggagctccc caagggcccg   2940
gagcaggtgc ccgtgccaga ccccgccagg gaagccgggg gcccagagga gcgcctcgca   3000
gaggaattcc ctgggcaaag tcaggacgtt actggcggtt cccaagacag gaaaaaacct   3060
```

-continued gggaaggagg tggcagccac tggcaccagc attctgaagg aagccaactg gctcgtggca 3120
gggccaggag cagagacggg ggaccctcgc atgaagccca agcaagtgag ccgagacctg 3180
ggccttgcag cggacctgcc cggtggggcg gaaggagcag ctgcacagcc ccaggctgtg 3240
ttacgccagc cggaactgcg ggtcatctct gatggcgagc agggtggaca gcagggccac 3300
cggctggacc atggcggtca cctggagatg agaaaggccc gcgggggga ccatgtgcct 3360 gtgtcccacg agcagccgag aggcggggag gacgctgctg tccaggagcc caggcagagg 3420
ccagagccag agctggggct caaacgagct gtcccggggg gccagaggcc ggacaatgcc 3480
aagcccaacc gggacctgaa actgcaggct ggctccgacc tccggaggcg acggcgggac 3540
cttggccctc atgcagaggg tcagctggcc ccgagggatg ggtcatcat tggccttaac 3600 cccctgcctg atgtccaggt gaacgacctc cgtggcgccc tggatgccca gctccgccag 3660
gctgcggggg gagctctgca ggtggtccac agccggcagc ttagacaggc gcctgggcct 3720
ccagaggagt cctagcacct gctggccatg agggccacgc cagccactgc cctcctcggc 3780
cagcagcagg tctgtctcag ccgcatccca gccaaactct ggaggtcaca ctcgcctctc 3840
cccagggttt catgtctgag gccctcacca agtgtgagtg acagtataaa agattcactg 3900
tggcatcgtt tccagaatgt tcttgctgtc gttctgttgc agctcttagt ctgaggtcct 3960
ctgacctcta gactctgagc tcactccagc ctgtgaggag aaacggcctc cgctgcgagc 4020
tggctggtgc actcccaggc tcaggctggg gagctgctgc gtctgtggtc aggcctcctg 4080
ctcctgccag ggagcacgcg tggtcttcgg gttgagctcg gccgtgcgtg gaggtgcgca 4140
tggctgctca tggtcccaac acaggctact gtgagagcca gcatccaacc ccacgcttgc 4200
agtgactcag aatgataatt attatgactg tttatcgatg cttcccacag tgtggtagaa 4260
agtcttgaat aaacactttt gccttcaccc agaaaaaaaa aaa 4303

<210> SEQ ID NO 40
<211> LENGTH: 1621
<212> TYPE: DNA
<213> ORGANISM: Homo sapiens

<400> SEQUENCE: 40
agaaacatcc tgcagcatct ccgtctccgg aggaaaaata catttgtctg ggcgaactcc 60
ggtggaaaag cgccccaggc tgccacagcc tagagatctt ggggctgcag ccctcgcggc 120
ctgccgaggg agcagggggc gcccgtggaa ctggctccct gcagctctgc ggctacacgc 180
ggacctcggc tgtgtgcgag gtggcggagg aggctggccg ggtgcgaatc cgtacccagc 240
cccagcatct tccacctgct gaggaccacc gctcagccat gggctaccag aggcaggagc 300
ctgtcatccc gccgcaggat tgccttattc aatgaagcaa gctgggtttc ctttgggaat 360
attgctttta ttctgggttt catatgttac agacttttcc cttgttttat tgataaaagg 420
aggggccctc tctggaacag atacctacca gtctttggtc aataaaactt tcggctttcc 480
agggtatctg ctcctctctg ttcttcagtt tttgtatcct tttatagttg atcctgaaaa 540
cgtgtttatc ggtcgccact tcattattgg actttccaca gttaccttta ctctgccttt 600
atccttgtac cgaaatatag caaagcttgg aaaggtctcc ctcatctcta caggtttaac 660
aactctgatt cttggaattg taatggcaag ggcaatttca ctgggtccac acataccaaa 720
aacagaagac gcttgggtat ttgcaaagcc caatgccatt caagcggtcg ggggttatgtc 780 ttttgcattt atttgccacc ataactcctt cttagtttac agttctctag aagaacccac 840
agtagctaag tggtcccgcc ttatccatat gtccatcgtg atttctgtat ttatctgtat 900
attctttgct acatgtggat acttgacatt tactggcttc acccaagggg acttatttga 960
aaattactgc agaaatgatg acctggtaac atttggaaga ttttgttatg gtgtcactgt 1020
cattttgaca taccctatgg aatgctttgt gacaagagag gtaattgcca atgtgttttt 1080
tggtgggaat ctttcatcgg ttttccacat tgttgtaaca gtgatggtca tcactgtagc 1140
cacgcttgtg tcattgctga ttgattgcct cgggatagtt ctagaactca atggtgtgct 1200
ctgtgcaact cccctcattt ttatcattcc atcagcctgt tatctgaaac tgtctgaaga 1260
accaaggaca cactccgata agattatgtc ttgtgtcatg cttcccattg gtgctgtggt 1320
gatggttttt ggattcgtca tggctattac aaatactcaa gactgcaccc atgggcagga 1380
aatgttctac tgctttcctg acaatttctc tctcacaaat acctcagagt ctcatgttca 1440
gcagacaaca caactttcta ctttaaatat tagtatcttt caatgagttg actgctttaa 1500
aaatatgtat gttttcatag actttaaaac acataacatt tacgcttgct ttagtctgta 1560
tttatgttat ataaaattat tattttggct tttatcaaga cttggctttt atgagtagtg 1620
c 1621

<210> SEQ ID NO 41
<211> LENGTH: 1805
<212> TYPE: DNA
<213> ORGANISM: Homo sapiens

<400> SEQUENCE: 41
cccgggcccc cggcggggct ctgcgctgcc ggagcttggg cgtctgctgc tgtcccggag 60
cgccaagtcg tccgaggtcc ggccgcccgg ccggggcggg gccagggagg cccggccttc 120
ccgcttcctg cctgagccgc aggcccgccc ctgcgtcctc cgcccgcctc tttcccgccg 180
ccgcctggga ggggacccgg gctgccaggc gcccagctgt gcccagatgg atgggacaga 240
gacccggcag cggaggctgg acagctgtgg caagccaggg gagctggggc ttcctcaccc 300
cctcagcaca ggaggactcc ctgtagcctc agaagatgga gctctcaggg cccctgagag 360
ccaaagcgtg acccccaagc cactggagac tgagcctagc agggagaccg cctggtccat 420
aggccttcag gtgaccgtgc ccttcatgtt tgcaggcctg ggactgtcct gggccggcat 480
gcttctggac tatttccagc actggcctgt gtttgtggag gtgaaagacc ttttgacatt 540
ggtgccgccc ctggtgggcc tgaaggggaa cctggagatg acactggcat ccagactctc 600
cacagctgcc aacactggac aaattgatga cccccaggag cagcacagag tcatcagcag 660
caacctggcc ctcatccagg tgcaggccac tgtcgtgggg ctcttggctg ctgtggctgc 720
gctgctgttg ggcgtggtgt ctcgagagga agtggatgtc gccaaggtgg agttgctgtg 780
tgccagcagt gtcctcactg ccttccttgc agcctttgcc ctgggggtgc tgatggtctg 840
tatagtgatt ggtgctcgaa agctcggggt caacccagac aacattgcca cgcccattgc 900
agccagcctg ggagacctca tcacactgtc cattctggct ttggttagca gcttcttcta 960
cagacacaaa gatagtcggt atctgacgcc gctggtctgc ctcagctttg cggctctgac 1020
cccagtgtgg gtcctcattg ccaagcagag cccacccatc gtgaagatcc tgaagtttgg 1080
ctggttccca atcatcctgg ccatggtcat cagcagtttc ggaggactca tcttgagcaa 1140
aaccgtttct aaacagcagt acaaaggcat ggcgatattt acccccgtca tatgtggtgt 1200
tggtggcaat ctggtggcca ttcagaccag ccgaatctca acctacctgc acatgtggag 1260
tgcacctggc gtcctgcccc tccagatgaa gaaattctgg cccaacccgt gttctacttt 1320
ctgcacgtca gaaatcaatt ccatgtcagc tcgagtcctg ctcttgctgg tggtcccagg 1380

```
ccatctgatt ttcttctaca tcatctacct ggtggagggt cagtcagtca taaacagcca   1440

gacctttgtg gtgctctacc tgctggcagg cctgatccag gtgacaatcc tgctgtacct   1500

cgcagaagtg atggttcggc tgacttggca ccaggccctg gatcctgaca accactgcat   1560

cccctacctt acagggctgg gggacctgct cggttcaagc tccgtgggcc acactgctgc   1620

tgtgccaaga aggtgtacag cctccccagg atggggcctc atacaaccct tcatctgcac   1680

tcaacattta atcgtgtcct tgctgtcttt ttattttcct ttttgtttgt tagcaaaaac   1740

ctctatttag atttcaataa tcagagaagt gtaaaataaa acagattata ttgtacttga   1800

aaaaa                                                               1805
```

```
<210> SEQ ID NO 42
<211> LENGTH: 2643
<212> TYPE: DNA
<213> ORGANISM: Homo sapiens

<400> SEQUENCE: 42

agggcggggc gggcagcagg tgagacgcca ggtctccagg gctccaatca ctccggagac     60

tgagccatgg ggggaaagca gcgggacgag gatgacgagg cctacgggaa gccagtcaaa    120

tacgacccct cctttcgagg ccccatcaag aacagaagct gcacagatgt catctgctgc    180

gtcctcttcc tgctcttcat tctaggttac atcgtggtgg ggattgtggc ctggttgtat    240

ggagaccccc ggcaagtcct ctaccccagg aactctactg ggcctactg tggcatgggg    300

gagaacaaag ataagccgta tctcctgtac ttcaacatct tcagctgcat cctgtccagc    360

aacatcatct cagttgctga gaacggccta cagtgcccca caccccaggt gtgtgtgtcc    420

tcctgcccgg aggacccatg gactgtggga aaaaacgagt tctcacagac tgttggggaa    480

gtcttctata caaaaaacag gaacttttgt ctgccagggg taccctggaa tatgacggtg    540

atcacaagcc tgcaacagga actctgcccc agtttcctcc tcccctctgc tccagctctg    600

gggcgctgct ttccatggac caacgttact ccaccggcgc tcccagggat caccaatgac    660

accaccatac agcaggggat cagcggtctt attgacagcc tcaatgcccg agacatcagt    720

gttaagatct ttgaagattt tgcccagtcc tggtattgga ttcttgttgc cctgggggtg    780

gctctggtct tgagcctact gtttatcttg cttctgcgcc tggtggctgg gcccctggtg    840

ctggtgctga tcctgggagt gctgggcgtg ctggcatacg gcatctacta ctgctgggag    900

gagtaccgag tgctgcggga caagggcgcc tccatctccc agctgggttt caccaccaac    960

ctcagtgcct accagagcgt gcaggagacc tggctggccg ccctgatcgt gttggcggtg   1020

cttgaagcca tcctgctgct gatgctcatc ttcctgcggc agcggattcg tattgccatc   1080

gccctcctga aggaggccag caaggctgtg ggacagatga tgtctaccat gttctaccca   1140

ctggtcacct ttgtcctcct cctcatctgc attgcctact gggccatgac tgctctgtac   1200

ctggctacat cggggcaacc ccagtatgtg ctctgggcat ccaacatcag ctcccccggc   1260

tgtgagaaag tgccaataaa tacatcatgc aaccccacgg cccaccttgt gaactcctcg   1320

tgcccagggc tgatgtgcgt cttccagggc tactcatcca aaggcctaat ccaacgttct   1380

gtcttcaatc tgcaaatcta tggggtcctg gggctcttct ggacccttaa ctgggtactg   1440

gccctgggcc aatgcgtcct cgctggagcc tttgcctcct tctactgggc cttccacaag   1500

ccccaggaca tccctacctt ccccttaatc tctgccttca tccgcacact ccgttaccac   1560

actgggtcat tggcatttgg agccctcatc ctgacccttg tgcagatagc ccgggtcatc   1620

ttggagtata ttgaccacaa gctcagagga gtgcagaacc ctgtagcccg ctgcatcatg   1680
```

-continued

```
tgctgtttca agtgctgcct ctggtgtctg gaaaaattta tcaagttcct aaaccgcaat   1740

gcatacatca tgatcgccat ctacgggaag aatttctgtg tctcagccaa aaatgcgttc   1800

atgctactca tgcgaaacat tgtcagggtg gtcgtcctgg acaaagtcac agacctgctg   1860

ctgttctttg ggaagctgct ggtggtcgga ggcgtggggg tcctgtcctt cttttttttc   1920

tccggtcgca tcccggggct gggtaaagac tttaagagcc cccacctcaa ctattactgg   1980

ctgcccatca tgacctccat cctgggggcc tatgtcatcg ccagcggctt cttcagcgtt   2040

ttcggcatgt gtgtggacac gctcttcctc tgcttcctgg aagacctgga gcggaacaac   2100

ggctccctgg accggcccta ctacatgtcc aagagccttc taaagattct gggcaagaag   2160

aacgaggcgc ccccggacaa caagaagagg aagaagtgac agctccggcc ctgatccagg   2220

actgcacccc acccccaccg tccagccatc caacctcact tcgccttaca ggtctccatt   2280

ttgtggtaaa aaaaggtttt aggccaggcg ccgtggctca cgcctgtaat ccaacacttt   2340

gagaggctga ggcgggcgga tcacctgagt caggagttcg agaccagcct ggccaacatg   2400

gtgaaacctc cgtctctatt aaaaatacaa aaattagccg agagtggtgg catgcacctg   2460

tcatcccagc tactcgggag gctgaggcag gagaatcgct tgaacccggg aggcagaggt   2520

tgcagtgagc cgagatcgcg ccactgcact ccaacctggg tgacagactc tgtctccaaa   2580

acaaaacaaa caaacaaaaa gattttatta aagatatttt gttaactcag taaaaaaaaa   2640

aaa                                                                 2643
```

<210> SEQ ID NO 43
<211> LENGTH: 11579
<212> TYPE: DNA
<213> ORGANISM: Homo sapiens

<400> SEQUENCE: 43

```
cggaccgtgc tttcgccgcc tgggagccgt ccggcgcagc agtttctagg tccccactgt     60

ccccgccgtc ccgccccttc gcgtcccggg aaccggctgg cttccgagcc gcactcgccg    120

atcctccagg catgccccgc tacgagctgg ctttaatcct gaaagccatg cagcggggtt    180

ggtacagtag gcttcactag acttagctgc aactcagaat ttctcctcca gcacctgagt    240

aaatgctgat ggtcttgtgg agagtggatt aagagtacga gctaagttct caatcccaat    300

taagaagcgg aaaatttaaa ctgtcttctt caaagtttat cacaaccacc accatcaaga    360

cagcaaacca aaggacaaag actttgaccc tgctgtgttg ctctgtgtag tccagttcac    420

gtatggttta cagacttggc tggggttact aaaaataaat aaaaagttgg acacttctgt    480

cattggagcg ctattattca caagttacca gaatgagagc tgtactggac acagcagaca    540

ttgccatagt ggccctgtat tttatcctgg tcatgtgcat tggtttttt gccatgtgga     600

aatctaatag aagcaccgtg agtggatact tcctggcggg gcgctctatg acctgggtaa    660

caattggtgc ctctctgttt gtgagcaata ttgggagtga gcacttcatt gggctggcag    720

gatctggagc tgcaagtgga tttgcagtgg gcgcatggga attcaatgcc ttactgcttt    780

tacaacttct gggatgggtt ttcatcccaa tttacatccg gtcaggggta tataccatgc    840

ctgaatactt gtccaagcga tttggtggcc ataggattca ggtctatttt gcagccttgt    900

ctctgattct ctatattttc accaagctct cggtggatct gtattcgggt gccctttta     960

tccaggagtc tttgggttgg aatctttatg tgtctgtcat cctgctcatt ggcatgactg   1020

ctttgctgac tgtcaccgga ggccttgttg cagtgatcta cacagacact ctgcaggctc   1080

tgctcatgat cattggggca cttacactta tgattattag cataatggag attggcgggt   1140
```

-continued

```
ttgaggaagt taagagaagg tacatgttgg cctcacccga tgtcacttcc atcttattga   1200
catacaacct ttccaacaca aattcttgta atgtctcccc taagaaagaa gccctgaaaa   1260
tgctgcggaa tccaacagat gaagatgttc cttggcctgg attcattctt gggcagaccc   1320
cagcttcagt atggtactgg tgtgctgacc aagtcatcgt gcagagggtc cttgcagcca   1380
aaaacattgc tcatgccaaa ggctctactc ttatggctgg cttcttaaag ctcctgccaa   1440
tgtttatcat agttgtccca ggaatgattt ccaggatact gtttactgat gatatagctt   1500
gcatcaaccc agagcactgc atgctggtgt gtggaagcag agctggttgc tccaatattg   1560
cttacccacg cctggtgatg aagctggttc ctgtgggcct tcggggttta atgatggcag   1620
tgatgattgc agctctgatg agtgacttag actctatctt taacagtgcc agtaccatat   1680
tcaccctcga tgtgtacaaa cttatccgca agagcgcaag ctcccgggag ttaatgattg   1740
tggggaggat atttgtggca tttatggtgg tgatcagcat agcatgggtg ccaatcatcg   1800
tggagatgca aggaggccag atgtaccttt acattcagga ggtagcagat tacctgacac   1860
ccccagtggc agccttgttc ctgctggcaa ttttctggaa gcgctgcaat gaacaagggg   1920
ctttctatgg tggaatggct ggctttgttc ttggagcagt ccgtttgata ctggcctttg   1980
cctaccgtgc cccagaatgt gaccaacctg ataataggcc gggcttcatc aaagacatcc   2040
attatatgta tgtggccaca ggattgtttt gggtcacggg actcattact gtaattgtga   2100
gccttctcac accacctccc acaaaggaac agattcgaac caccaccttt tggtctaaga   2160
agaacctggt ggtgaaggag aactgctccc caaaagagga accataccaa atgcaagaaa   2220
agagcattct gagatgcagt gagaataatg agaccatcaa ccacatcatt cccaacggga   2280
aatctgaaga cagcattaag ggccttcagc ctgaagatgt taatctgttg gtaacctgca   2340
gagaggaggg caacccagtg gcatccttag gtcattcaga ggcagaaaca ccagttgacg   2400
cttactccaa tgggcaagca gctctcatgg gtgagaaaga gagaaagaaa gaaacggatg   2460
atggaggtcg gtactggaag ttcatagact ggttttgtgg ctttaaaagt aagagcctca   2520
gcaagaggag tctcagagac ctgatggaag aggaggctgt ttgtttacag atgctagaag   2580
agactcggca agttaaagta atactaaata ttggactttt tgctgtgtgt tcacttggaa   2640
ttttcatgtt tgtttatttc tccttatgaa cttaaggata tggtgagaca ctaacttaag   2700
acaatactga ctggtctttg gggaaaaaag ttatgtaact gtgcatctct caggcattgt   2760
ttacgctgta ggttttagcc aaattttact tagcagaaaa tcatctaatt acaagacttt   2820
attttcccag agatggatta aagtaaatct tcaacttaag tgaagccaaa cctaacagac   2880
tgaattgtgc aaatgtggtt ttaaattttg cataccaaag taagaagaga ccaattattc   2940
tcacagagca cttagagcag aatatatgtt aagttaccat gaattaaggt atactgtctg   3000
cactgccaag tcttggcaga ccttaccctg aagtagaaga tttgctcatt tctaaagttt   3060
tttttctgtc tctgtaatcc ctcctaccat taagaaaaac ttatttctta gacattgtac   3120
aatcagttat gtactgaaaa tcgaatgtgc ttgtgtgata cttgtttcag gacaagttca   3180
tttgccaggt tcattttgtt agcatgagcc tacggattct gatttcccaa agaaagaatg   3240
ttttcctgta ggtatttttg taccaccagt atatggaatg ttagggaaaa actttgttcc   3300
agttcctttt tttttttctt tctactttca agtttaagtg aaccatactg aaatgaccaa   3360
caagtctgcc tgtaaagtta catgtcatga ttgtgttgtt aaatgattat gggggagaaa   3420
atgaagtaaa tgttgctgat gatccccata tttattgatc atattaaggt tgtttatata   3480
gtttggaaat gaccagcccc ctaagcagtg tttgattaac ttatgctaat cagatgatta   3540
```

-continued ctcatatatt ctgctaattt tctagcttta ttcttgttat ttggaaaaat tattagccaa 3600
atgccttcct aggtggatcc agttggaaga tatgtccaga aacctgaaga aaaattgacg 3660
ctgcctttgt gtgctggatt gctctacttg attagatcat gatatatcaa ggttgaattt 3720
ttagagggaa aatttaattc tgatatctta ttgcatcctt gataagtttt tccctgattt 3780
tttttttcct caaaagactt tccatctgta cacagcctct acatttttgt tgtagtgact 3840
tagagcataa ggatgtttca gtgcaaactg gccgtcggta acagaaaact cagtgcatac 3900
tttgctgttg ttaggttgtc aatatagtct ttctgtagga tggatagcat gtttgagagg 3960
tgccaaacaa gaacttttgg ggttagtagt gtgtcttgtg gagggtatta caggactgtg 4020
taattatagg actctaactt gacatggctt ggcacccact tgcagctagt gggtacaggg 4080
tacaaaagat gttagagaaa agctctacag attacgtact tctgtgtctt cgtatgctca 4140
acactgtcct ttgtcctcca tgaaagatga aggaagcaaa ttatgtatgt actttctttg 4200
accttcttta atctctgata ctttttagat tgcatgattt tactaggctt gtatttaggg 4260
aaattacttt cataaatact tttgtagatt ttgaatcaaa actcagtctt tttaattttt 4320
ttgtagtcta taaactagtt tcattatgat ggacttgatt agtccaaagt taattttaga 4380
aattgtcagg tagcatagtg tcttcccatg atcaggaggc tttctgaagg actgagtctg 4440
taaatgaaaa aataatttat gtatgaatag catgtatttc tgaagagctt agagtgcctt 4500
gtagaatttt tttctcaatt ttattcttga ggtttataat ttgggggcca aatagataga 4560
gctcatcatt ttcttgtttg gaagttgagg ctgcgacatg tccaaggtta tgaagtctct 4620
tttgggaaga acagaaacca ggtctccaaa tctggactca tggtttgttc agatgtgtct 4680
ggacaaatgg ttgtcaatgt tttgtcctgt tttttcaaag gaactgttct tcctttggga 4740 caacctttttg gtgtttggga aagtaataag atcttggatt tttcaaatta acattaagtt 4800
gtaagaacta aaattttctt tgaaccacat tactgtgtaa ttcactgata attgacatat 4860
tggctgggca gcctatctct tccatatcca gcgtaaatga ataggaggtg tttgtgattt 4920
tttttttctc cctttattta acattgagtc ctagtagttt ggagaattag ggtccctcta 4980
ccttctttct gctcttgtct tagtaagata cataaggtac atcatcttgt gtctgtgtgt 5040
atatagcagt aggtcaagtt tagagtacta aagtctgtaa ataaggaatg actattagca 5100
tattcattag aattgtttat tcttgccagt ataaacatca ttttatttag actaaagtcc 5160
ctgaagcttg tctttcttat tgcttcccag taatagataa tgtgctcgag taagtttgtg 5220
aattgctgat tgcaacttaa ttcagggacc agtcttcaat ctatatttca ttagaatgat 5280
tgttcctgga atgatcatac atggactgtc ttaagctagc aaaatgttca tactttacac 5340
tgactaaatg ggtcctaaat gatgacattg gtctttagac attaacatgt gtatattttt 5400
atattagctc aagctaaggt tcagaattga agcttgatat tgactagaat agctaaaagt 5460
caaaatgagg tgaggacact ggtcttggaa ggtagagaaa aataaatgtc ttaccaggtg 5520
ttaatggtat ccccagttct tagacttttg tcttctcagg caattttcat ctcaagatct 5580
gatgagaagg gcatattaca ttggtatgca ggatgattat tgcatatttt gtgggacctc 5640
taatttccct ggtcatcttt cagaatattc tgttctgcca cccccagaga gtaaacactt 5700
gagccgattt cttcttcccc agctattctt tcctggggggt aattatgctt tgtctttaga 5760
ttagagaagc atcaagcaat agcaatggtg ctgtgtcctt cggcctaaat tcaatagatc 5820
tcatctccta gggcttcctt ttcacttggc tcaaaggatc cattgtattt tggcacaaag 5880
agcctggcca gggtcatgta gccatagctc ttagggatga tacctcaaga aattagctgg 5940

```
gacccatcac tctgtgaaac ttcacatttt aagaactgag ttgagggggt tgttatgcac   6000
ttctgtaact tgaggctaag caaggggtta actcttgtga gagccaatag agtgtgtctg   6060
tattcgcagt ccatggctca ttttctttat agtaggcata tggatcttcc cctctgactt   6120
tgaatatcat ttggtgtggc ctgtgggtta ttttcattct ttaccaccaa ataaagcggc   6180
ttattagcta ctcagttact tgctactcaa aggttaggtc ttccctgttc ctgcttggca   6240
gtgttaaagc ttacagggtt aacttatgat gattctcctg gctcattttc atcagaggca   6300
tgatgactgg aaagggatca catgggtcgt tggtggtgac acctcactgt ttcctaggtt   6360
tggatagaga gatgtataca agacctttcc tgttaaatta cgtgactaca gagacttgcc   6420
aggacaaaat tttcctaaga aatcagaaaa atgattaagt gagataagta cctgggtgac   6480
acagatatta gcccgttggt aaaagacaac aaatattagc ttaaaatctg catatgtaga   6540
atcattttca ttagatttag agcttgaagc accttggctc tcagctactt taaactcctc   6600
cccatataaa tcagggcacc aataaataag tttcagcttt ttaaaccctg gtttgatgtt   6660
aagcattata aagtacgaag tttgttacca cagtagagat aatttagtag aaaaatgctt   6720
tgaggcttca gtatttgtaa gattttgcat tagccagatg ctaggttgtt gaaggcattt   6780
cagtgttgat aatagcctga gcagacttct ttacaaatgg gatctgtttc tatatgtgta   6840
tatgcccact taccattcag agagactggt ctttctcttt gtcttccttc acattgctgt   6900
gtcagttcta cacctagtct tttcagcact tagcaaattc aaattttgat ttttttgtca   6960
gcttagttca ctttaaggca tattggcatg gtgtgtgaaa gtgatgtttt gccccagtat   7020
tgaggacttt tagatccaaa taatgactca ttaaatataa ttatgtttta agtatactga   7080
atttctgtta gcttaaaatg ttaattctca ggaatgattt tctcacactt tgtgttggct   7140
aataataaaa gcactgtttt attctcaaaa ctccttttc aaaaattagg gagagagcag    7200
tagtgatcat ttatgtgagc ccctttgaaa tgatggtgtc agagtgcaga gaaacaatgg   7260
agttttgatg ccaaaaaggt ttttttgcag taaaagtaaa aatttggaat tagttggcat   7320
atagaggaac ccttttgtac tggaacgtat gaggctggat tgtgaaaagg taatctttcg   7380
attgctagac ttggttaact tagggctgca aatctttttc ttctgtcaag gtcacttaat   7440
atggaatgtt tttgtcagac tgtcctttgt tggaatactt tagctgttca gctactttga   7500
ctcctaggag agaatttagt taaggttcaa agtaattaac tggctttgcc agtggtgagt   7560
cccacaccat tattcactta gtagtcatat aaatgttttt atttaaactt ctctctcttc   7620
aatgctgaga ataaggcttt aaattactga ttcaccttta aaggaatgtt gtgagaattg   7680
atgtaatttc tgtttctgtt tccatctaaa cttctttata aaaagaggga ttagtttttt   7740
tgttttgggg taagcaccta atttatccag taaccaacaa ccctaaccat tggcatatat   7800
agtctttcac tcagaaataa acaaaaactg tttggtatat ctgtatcatt gctaatcttg   7860
tgcactttac tttttgggca gtaccataca tagtctgagg ctattgactt aaaccaataa   7920
ctgtacttta tgtaatgact cttaaatttg gttacctggg ttcacagctt gcttgaagag   7980
aaaggatgct agaataaagt aagcagctga agagcgagca aatcaagaca aaacacagtg   8040
gtctcagatt tttcgtagtg tgggaacagt ggttttgctc tataccactg aaaagcacta   8100
taacataatt gttgtccatg atactgaagc ttttcccctc acttctaggt tgtttacatt   8160
cagagctcta tcaataagag gaatacatat tacagtgaat tcgacaaccg cacaagttgg   8220
cagtaggtat ccccaaccta atttatcttg gtaaattcac cctgtttcct agtgctgctg   8280
gataaaagag tgtttacttt ttattgctct tagacagagt agtctagata agttttcaat   8340
```

-continued

```
ttatcaacat agcctagact tctgtaagtg gaatgttcat tagtaactca tctttttgtt   8400
gttataattg gaaacagaaa cgaggcttat tgctattgca gaaatcccaa actggcaaag   8460
gccagtatat atggtattcc ataatataac cagcttttga aatttatgtg tttggattag   8520
tgccttctgg ttaccagtat tgactctgct agtttgcacc tttccgttct taacagaaaa   8580
tttgtatttg ttattcctct taaattttgt cgtaactagt gaaggaagta aaaaaaaaaa   8640
aaaaacatgc attacattga catactttat gtgcagcctt tatttaggtt cagtgaaacc   8700
aggtagttct gtatttgtgt tgtagcctaa atgttgtttc ttttatatcc attaaaaact   8760
taaagttact tatgttctgt gatcttaatt ttgttgtgtt tccattgtag gttgataggt   8820
atatcgagaa caggtacgtg acaacagttt atattccatg atagaaagct aaagtccata   8880
gaaagcacaa aatcgtgttc acacattagt gtacccacac atagaaagca caagactaat   8940
agtattctct gtatcccaca agtgccagtc ataaaggcca ccaggtattt gtctcagagt   9000
tgctatgagc actacagtat tgataagccc aagacaatgc ggtatctaaa ctggtcctaa   9060
tggtaaggga cccaaaggaa taatctcaat aagtttgtac cacattgatg gagggagaga   9120
atataaatgt caagaatgcc aaaattatat ttgggggtta ctagctaaaa tggggtttga   9180
gggcttttta ctgcaacttg aaactggaga aatagggaca gatgtctagg tttttggtgg   9240
gtggaacagg tgacatattt ctgttttaag ctgtagtgtg attggggttt tttgtaaaaa   9300
atcttaaatc ttttaggaaa tattacctct taacagtgcc cccccaaaca tgcagaaagt   9360
catactttaa cagggcaaat actacttgtc tttgattttt tttgtgtacg tttgtatgtg   9420
agagatgaag ttacctttat ttttttccta tacttgactg tgcttcattt taataaagga   9480
taatttgatc tgagtgttct gagcatcaga ctaattctga agcatatttg ctagaggagc   9540
tactttgctt ttcacaatgg ggtggagagg attctttcac ttgtcccatt aaccctcttc   9600
tagtctagat gagatgaaat ctgttaatgt gtgtgtagaa gaaaacgtat gttcttctac   9660
tcagcattgc ccttttccac ctcctcactt cacctccgag tagcttgttt atcaagaatg   9720
aatgaatgtc tttgtcttaa attttgccca tgtgttaaaa gatgtaattc tcagaatggg   9780
agagaaatga ctacctttgt tcctactctt ttatataatt atccttttag ggaaagactt   9840
ggtcaactct aatatatcta gaaggaagac tatatctggt gtagactaat atgagatgtt   9900
ttagaagagt taacctgaac actttgaggg agagattatt cttgccagca aaaagctagc   9960
caggaatgag cctaccacat tatttgagaa tatcaaacct caggcctggg gggatgaggg  10020
gaagaagatt accagaagtg caggaaagag aagtttgagg aacacccttg gcttagcaac  10080
atgtgataat gcaaagctgt tataacctgt taatcctacg tactatgtgt tctgtacctt  10140
tacatgtttt taaatttaag atagtttgta agaactgtac aaaaaaatgc ttctggagat  10200
ttctttggca gaaatgcctt tcatctataa tttcatggag aactgcttta attagcctag  10260
gtgaaaagta gtcctagcag tgtaaatatg tataattaga gttttctaat ttcactgtga  10320
gatctctaac ttttgagtgg caaacagatc aagtcttttg ctcatagact tttctgtggg  10380
gttattaaaa tgcaaaagct ttattttttt taataatgcc atactccatt agtgtcagat  10440
gatggtatgg aatttgttcc cttgctttcc cccactgtta ctgcttcagt tttatagattg  10500
ccagcagagt tcagaaatag agcagggatt tacccgttct ttgcttggac atcccatttt  10560
cttttgtcca gacccatgtt ggcaatcatg tatgaactgt gttatacttc tcagtgcttt  10620
ctttttttctt tttgataaga tggatatcaa aaatagttgc tgtgcaaaag ttagtagtct  10680
tcttcaagaa gaaaaccaat tctttttcta ataatatcct gtgaaattgc ttcattcatt  10740
```

catttatttt taagccaaat gtcagcagag tgctgctgct tttatctagt aattttgata 10800
tgtaagtatt aatgcatttt taaaagatgt ctacattgaa acatgttctt cccagtgtcc 10860
tgcttatgat gctttgttca gatttttgt aagagaccag ttagtacact gggggtgtat 10920
attgtgtaca tgtgtcattt tagttaggca ttgtaggcca aatgtgatta taaatgaagt 10980
tgatgaacat taattttgtt attagtgagt tttttgaatt gtaaatggat ttccagttta 11040
ccttctgttg tctacagctt ttttaatttt aaggtttgac taattgtatc catctcattg 11100
tacagtgttt tagttgcaag cagaaagtag aatttggtat aaagcaggtt atttctatat 11160
tgaaaggagt acagttgaaa ttgtagattt aagattgtta aaatcatgac aattctaact 11220
tgtctattct aacctattgt gtacaatctg attttttaaa attgtaaaca tgtatgatct 11280
tggtttcatg tgtttttgaa agtgttattg tttaaaaaat gaaaaaagca tatctgctaa 11340
agagctgtca gttttcatta ctgactctgt aaaatacact gttctttgtg tactgtgtgt 11400
tattttgcca gctgctgcat tagccttcaa aagtatttgg aaacttaaga tgaactacat 11460
ttcttgcaaa gtacattcct ttctgtggta ttttgtcctg taactgaagt atagtaatta 11520
ttttatggaa atgttagcaa ttctgtacca actttgaata aaatgaaaaa tttataaaa 11579

<210> SEQ ID NO 44
<211> LENGTH: 6053
<212> TYPE: DNA
<213> ORGANISM: Homo sapiens

<400> SEQUENCE: 44
taggttgtga cagttggaag tgtcatgtac aacatgcggc gattaagtct ttcacccacc 60
ttttcaatgg gatttcatct gttagttact gtgagtctct tattttccca tgtggaccat 120
gtaattgctg agacagaaat ggaaggagaa ggaaatgaaa ctggtgaatg tactggatca 180
tattactgta agaaaggggt gattttgccc atttgggaac cccaagaccc ttcttttggg 240
gacaaaattg ctagagctac tgtgtatttt gtggccatgg tctacatgtt tcttggagtc 300
tctatcatag ctgatcggtt catgtcctct atagaagtca tcacatctca agaaaaagaa 360
ataaccataa agaaacccaa tggagagacc accaagacaa ctgtgaggat ctggaatgaa 420
acagtttcta acctgacctt gatggccctg ggatcttctg ctcctgagat tctcctttca 480
gtaattgaag tgtgtggcca taacttcact gcaggagacc tcggtcctag caccatcgtg 540
ggaagtgctg cattcaatat gttcatcatt attgcactct gtgtttatgt ggtgcctgac 600
ggagagacaa ggaagattaa gcatttgcgt gtcttctttg tgacagcagc ctggagcatc 660
tttgcctaca cctggcttta cattattttg tctgtcatat ctcctggtgt tgtggaggtc 720
tgggaaggtt tgcttacttt cttcttcttt cccatctgtg ttgtgttcgc ttgggtagcg 780
gataggagac ttctgtttta caagtatgtc tacaagaggt atcgagctgg caagcagagg 840
gggatgatta ttgaacatga aggagacagg ccatcttcta agactgaaat tgaaatggac 900
gggaaagtgg tcaattctca tgttgaaaat ttcttagatg gtgctctggt tctggaggtg 960
gatgagaggg accaagatga tgaagaagct aggcgagaaa tggctaggat tctgaaggaa 1020
cttaagcaga agcatccaga taaagaaata gagcaattaa tagaattagc taactaccaa 1080
gtcctaagtc agcagcaaaa aagtagagca ttttatcgca ttcaagctac tcgcctcatg 1140
actggagctg gcaacatttt aaagaggcat gcagctgacc aagcaaggaa ggctgtcagc 1200
atgcacgagg tcaacactga agtgactgaa aatgaccctg ttagtaagat cttctttgaa 1260
caagggacat atcagtgtct ggagaactgt ggtactgtgg cccttaccat tatccgcaga 1320

-continued

```
ggtggtgatt tgactaacac tgtgtttgtt gacttcagaa cagaggatgg cacagcaaat   1380
gctgggtctg attatgaatt tactgaagga actgtggtgt ttaagcctgg tgatacccag   1440
aaggaaatca gagtgggtat catagatgat gatatctttg aggaggatga aaatttcctt   1500
gtgcatctca gcaatgtcaa agtatcttct gaagcttcag aagatggcat actggaagcc   1560
aatcatgttt ctacacttgc ttgcctcgga tctccctcca ctgccactgt aactattttt   1620
gatgatgacc acgcaggcat ttttactttt gaggaacctg tgactcatgt gagtgagagc   1680
attggcatca tggaggtgaa agtattgaga acatctggag ctcgaggaaa tgttatcgtt   1740
ccatataaaa ccatcgaagg gactgccaga ggtggagggg aggattttga ggacacttgt   1800
ggagagctcg aattccagaa tgatgaaatt gtcaaaacaa tatcagtcaa ggtaattgat   1860
gatgaggagt atgagaaaaa caagaccttc ttccttgaga ttggagagcc ccgcctggtg   1920
gagatgagtg agaagaaagc cctgttattg aatgagcttg gtggcttcac aataacagga   1980
aaatacctgt ttggccaacc tgtcttcagg aaggttcatg ctagagaaca tccgattctc   2040
tctactgtaa tcaccattgc agacgaatat gatgacaagc agccactgac cagcaaagag   2100
gaagaggaga ggcgcattgc agaaatgggg cgccccatcc tgggagagca caccaagttg   2160
gaagtgatca ttgaagaatc ctatgaattc aagagtactg tggacaaact cattaagaag   2220
acaaacctgg cccttgtggt tgggactaac agctggagag aacagttcat tgaagctatc   2280
actgtcagtg ctggggaaga tgatgacgac gatgaatgtg gggaagagaa gctgccctcc   2340
tgtttcgatt acgtgatgca ctttctgact gtgttctgga aggtcctgtt tgccttcgtc   2400
ccccctactg aatactggaa tggctgggcg tgtttcattg tctccatcct catgattggc   2460
ctactgacag ctttcattgg agacctggct tcccactttg gctgcaccat tggcctgaaa   2520
gattctgtga ctgcagtcgt gttcgtcgca cttggaacat cagtgccaga cacatttgcc   2580
agcaaagtgg cagccaccca ggaccagtat gcagacgcct ccataggtaa cgtcacgggc   2640
agcaacgcgg tgaatgtctt cctgggaatc ggtgtggcct ggtccatcgc tgccatctac   2700
cacgcagcca atggggaaca gttcaaagtg tcccctggca cactagcttt ctctgtcact   2760
ctcttcacca tttttgcttt catcaatgtg gggtgctgc tgtatcggcg gaggccagaa   2820
atcggaggtg agctgggtgg gccccggact gccaagctcc tcacatcctg cctctttgtg   2880
ctcctatggc tcttgtacat tttcttctcc tccctggagg cctactgcca cataaaaggc   2940
ttctaaagga actatcagat atagtaaatt tatatatata catatatata cataaaaatt   3000
atgtataatg gacagaggaa actgacattt gtcatgttca cttacctgct gatggaatcc   3060
agcttcaaga gcatactctg tactagggcc gaagtaaaaa accatcacct cccattccca   3120
ggggcatcat catgttcaac aaggcatgga ggcagggcca tctttgcagc tcagtctaga   3180
agggctgcac tctctccagg ttgataaatc cttaaggctt tgatttgttt tgtttttggt   3240
tttgttttca gtggagctgg ggaggtagtt aatgtttggc tttatttttg ttattttgtt   3300
ttgttttgtt tttttgggag agtcagggtt gttgcttttc tttgtggaaa gtgaaaccat   3360
ccaaatgtaa atgggttttg gtaaaaattt aaatcattag tattccccct cacctccccc   3420
aatcacttta aaacttattt tggattaaga aaaaatctgg gcatggaaga agaaagaagc   3480
atgtcttcat cgtattacca aagttcatgc ttatctccgg aatgtgagtg gaggtgaagc   3540
tgcctccaag aagaagcata aaagtggaat ggagccagga aatccgatgg ttctagaaat   3600
agtctgatat ttaaacatgt gatacctggc agtctcgttt aacaggtaca aggaaaacgt   3660
gcctagattc ccaggaacgt gcaaaatcct ttctttctta tctctttagc tctggactgt   3720
```

-continued

```
gattggcaag gtccttcttc cagcattcag cccagctaag cccccaggtg ccccatccca   3780
accctgttcc tcctgtccac ctgccatccc ctatgcaaac agtaagaata accccattca   3840
aaaagcacat catcgttttc catttgcatt aacatgtgtc tcagtcccat gttgccgttg   3900
cttgggattg tctgtcagtt ttattttcaa aggcatccat ggcttgcaca atcctgttcc   3960
agtcatgact gaacatttgc tccttcttca tgtgccgttc ggaaatgttg ttgtgatacc   4020
tgttacacag tgcatggtga aaaacaaata aaacaaaaca aagagtatct gtatatagta   4080
gagtatagta catactgttc tcccatttgg caatgttgat tggacattga agacataagt   4140
gagttttctt ttcacctgag ttgttacttt tgtgctgtta ttgagtttga ttaattacta   4200
gggataaaag gagaaaatgg attattgttc acggttctgc acattcattt ctaagaagca   4260
ataactgtca tgtggggaga agttaaagct attgagagga tagcaggcaa actacaaaga   4320
tcttcatgga aaattagcca tgtggaacac atcagaggcc tctaaaaatc acccattaat   4380
tcaggaaggc caaggagaaa ggccttatag agacgttgat atgttggatg tgcctaggct   4440
ttcagagcca ccctttccac aacacccctc cctgcaaagt atttatttca catctgcact   4500
gtctggcaca gatggtagat agtgctggtt tgttcatttt attttttttac ttaaaaggct   4560
attttgagcc ctgtttcttt cactgtccag tctagtcctc tttgattata tcagtagttg   4620
ctgagtaaga aagaagccag ggtgaccaac gggcctttaa aagtgttgtc tcctctactt   4680
atgctgaaag agaaggcaat taaataagac tagtacctcc caggaggatt ggactgggat   4740
atttttaacc ctttaaaaag aatagctgtt tctatgttaa aataccaaag aacatggata   4800
aacccaacat tccaaagtag tgagtccact aatgagaaaa ataatagaat gactttggtc   4860
acctctcgga gacttctgtg tctataagga atcccaggct ggagacattc ctagccctct   4920
gtattgattc aaaaatactt aataaattaa agctgttgag acttattttt tcttctgtca   4980
ctcagtaacc atgatccttc ctcatttaat aaacatttgg tgactgaatg agtaattaaa   5040
tgctggttac ccacttaatg tgccaggtag tatgatactt tctggggact aagccatgaa   5100
caaaacagtc tagatccctg ccctcagaag ggttacagtt tatgtgatta ctattttcat   5160
gagtaaaagt gaagaaagcc atatggaaag atttttatct tgcaagaaaa aacaattatg   5220
aaactctttt aacataaaca cactgaaact gtatcaaagc aattgtccaa attgtattta   5280
tacccaagaa tttctttaac taagagagca taaggcatat gtttggaaaa ccacccctctt   5340
tatctttgac cgacttgcag ataaatatat ctctccattt taaaccaaga agggcaatca   5400
tgttggtgat ccagatcact gagaaagccc agtgtatccc atcttttatc tttgttggca   5460
atggaacttt tctatggccc acactttaca attctttgtc attctaaccc atccttccca   5520
tccttatttt tttttttttt gagaattgct aaatggaaag ctagcctaga agcaccaagt   5580
aaatatattc aaggaatata agttgtttaa acattagaaa aatttttgca ctcatttttt   5640
agctgtatta ggaatgtcaa taatcctgta gcaaattttc acagagaact ttaagaaatt   5700
cttgcattgg tcgatttcaa tttgaaagct ttttggtttg tttgcttttt aaattttcat   5760
gttctaggaa actatgattc tggttgttca ggattgttat tattatagtt gtgtaaaatt   5820
attttatttt gtgtgtattg tgcacagctt gggggggggg cgggaaatgc actaattgtg   5880
ctcttcctta taaatggtac atattactga cacagacaaa taaagtttct aattgtttct   5940
gatttaatca ctagtgatac agcatattct gtatgaaatg ttttctcctt tctcattgtc   6000
atctacttca tttttgttt tcatgttttg aagaaataaa aaccaaaatg gta           6053
```

<210> SEQ ID NO 45

<211> LENGTH: 5446
<212> TYPE: DNA
<213> ORGANISM: Homo sapiens

<400> SEQUENCE: 45

```
ccggtgccgc agcagcggcg ggtggctgtc gctgccctgc cctgcacggg gcagggcgga     60
gcgggctgag cagcccgggc gcgatgcgtt gagcgctcgg agggccaacc gccggtcccc    120
ttggcggcaa ccggcggcac ccatggaacc actgggcaac tggaggagcc tgcgggcgcc    180
actgcctccg atgctgttgc tgctgctcct gcaggtggcg gggcccgtgg gcgccctggc    240
ggagaccttg ctgaacgcgc cgagggccat gggcaccagt tccagcccgc ctagccctgc    300
gagcgtggtg gctcccggaa cgacgctgtt cgaggagagc cggctgcctg tgtttacgct    360
ggattacccc cacgtgcaga tcccccttcga gatcaccctt tggatcctgc tggcctccct    420
ggccaagatt ggcttccatc tgtatcacaa gttgcccaca atagtgcctg agagctgcct    480
tcttataatg gttggacttc tactaggtgg gattattttt ggtgttgatg agaagtctcc    540
ccctgcaatg aagactgatg tatttttctt gtacctcctc ccacccatcg tgctggatgc    600
cggctatttc atgcccactc gcccattctt tgagaacatt ggcacgattt tctggtatgc    660
tgtggtaggg acactttgga attccattgg cattggggtg tctttgtttg gtatctgcca    720
gatcgaagca ttcggcctca gcgacatcac tttgctccag aacctgctct ttggcagctt    780
aatctcagct gtcgatcctg tggctgtgct tgctgtcttt gagaacattc acgtcaatga    840
gcagctctac atcctggtct ttggagagtc cctgctgaat gatgcagtaa cagtggtcct    900
gtacaacttg ttcaagtcgt tttgccagat gaaaaccatt gagaccattg atgtgtttgc    960
aggaatcgcc aacttctttg ttgtgggaat cggtggggtg ctgattggca tcttcttggg   1020
ctttatagcg gcatttacta ctcgattcac ccataatatc cgagtgatcg agccactgtt   1080
tgttttcctg tacagttatt tgtcctacat cacagctgaa atgtttcacc tctcaggcat   1140
catggcaatc actgcttgtg caatgactat gaataagtac gtagaagaaa atgtatctca   1200
gaaatcctac acgaccatca agtacttcat gaagatgctg agcagtgtca gcgaaacctt   1260
gatcttcatc ttcatgggtg tgtctaccgt gggcaagaac cacgagtgga actgggcctt   1320
cgtctgcttc accctggcct tctgcctcat gtggcgagcc ctgggtgttt ttgtcctgac   1380
tcaggtcatt aataggttcc ggaccattcc cctgaccttt aaggaccagt tcatcattgc   1440
ctatggagga cttcgaggtg ccatctgttt tgcgttagtg tttctccttc ctgctgctgt   1500
gtttcctcgg aaaaaattgt ttattacggc tgccattgtt gtcatattct ttactgtctt   1560
cattctggga ataactattc gaccactggt ggagtttctt gatgtcaaga ggtccaataa   1620
gaaacaacaa gctgtcagtg aagaaatcta ttgtcggttg tttgatcatg tgaagactgg   1680
aattgaagat gtttgtggac attggggtca caacttttgg agagacaagt ttaagaagtt   1740
tgatgataaa tatctgcgga agcttttgat tcgggaaaac caaccaaagt caagtattgt   1800
atctttatat aaaaagcttg aaataaaaca tgccattgag atggcagaga ctgggatgat   1860
aagtactgtc cctacatttg catctctaaa tgattgtcgt gaagaaaaaa taaggaaggt   1920
cacgtccagt gaaactgatg aaattcgaga actcttatca agaaatctct atcaaatccg   1980
tcagcgaact ttatcctaca acagacacag tctgacagcc gacacaagtg agagacaagc   2040
caaggagatt ctgattcgcc ggcgacacag tttgcgagaa agcattagga aggacagcag   2100
cttgaatcga gaacacaggg cttccacttc aacctcccga tatttatcct tacctaaaaa   2160
tacgaagctt ccagaaaagc tacaaaagag gaggactatt tctattgcag atggcaatag   2220
```

-continued

```
cagcgactca gacgcagatg ccgggaccac cgtgctcaat ttgcagccca gagccaggcg   2280
cttcttgcca gaacagttct ccaagaaatc cccccagtcc tataaaatgg aatggaagaa   2340
tgaggtagat gttgattctg gccgagatat gcccagcacc cccccaacac cccacagcag   2400
agaaaagggc acccagacgt caggcttact acagcagccc cttctctcta aagaccagtc   2460
tggctcagag agggaagaca gtttgactga aggcatcccg cccaagccgc caccacggct   2520
ggtctggagg gcatcggaac ctggaagccg gaaagcccga tttgggagtg agaagcctta   2580
agagaagcag cgaaagcaga tctgagtgtc tgacccagga cagctgtggt ttgtcactct   2640
gaaacctgat gcaacagtgg aatccatgta aaactctctg tgcatctaaa tacttctgga   2700
gggcgacaga ttcatgccac ggataaatga ggcaaatccg aagaaaagga aaatcgaata   2760
aaaaatagtc ccacaaaata ccttttgtga ctaatgggta gcaatcgtat tatttgctgg   2820
cctgaagaga aaaaatggta atgtgtgcct ttattgaact tgaatgacag aacttgaaat   2880
ttttaacaca tccttcttgg tgaagatttt aatatattac ttatatgctt caaattttat   2940
ttatgaaaaa atatgtatat ctgtaatcag ttgttaagtg aatggcacta aaagtatcga   3000
gaacagcttt ctttcccagg ggtgaaggat ggcgctcggg ggtgactcct aagctcagcg   3060
tggaagcttt tccctgtcct gacccgatgg agcagccggt aagtgaagag cacagctgga   3120
agcagagaca ccttatgact caaactgggc aaacaatcgg aacgtcatgc agaaggaatg   3180
gcctgactcc tgcagtgcag attggaggcc ccagaactcc tatgaactac tgagagtcta   3240
ctggttttta acttgttcct ctgtctactg tgtgtttggg ggtgacatct aaattccatt   3300
tcttcttctt gtttaaatgg tgcagagaga aaggttgccc agacatccac cagcttactg   3360
tgttgacaga tttgggagca gcttttgatg aagttccacc catgagggtc catgtggcaa   3420
gtagggccac agggcagcac ctggttacaa cttgctggtg ggttttatgt tgtgcaatac   3480
taggaggagg aggcaggtga tctatgctga tctatgatca cctgcttcag tagaattttt   3540
ctgtagagtg ttgtttgaat tttgagcctc caggttagag gctccaagca gacaaagaag   3600
aaagtttgta gacacaatat tctaacattg cacaagttga tgagatatca agttttgaat   3660
attattcagg aagcactttg gagaatgtgg gagtcctact gttttgcact agtctgtaat   3720
ttgttacctc tccccattcg ataatatagt aactcagaat tttcatataa aattgaattc   3780
tactcattag agtacttttt aaaagtacag cagaaagaaa agaagtggaa cataagcatt   3840
caagattaat atttgattct ctatctctta actgtagatt ttattggcct gttttttttt   3900
tctaaataat tctttaaaac ttgactggaa catgcctctg catttctgag tgtagaaatt   3960
aaatgaagcc actcacagtc ctttgatttc ccactgaaga taccccaaag gatgcaagtg   4020
cctacagtat tatcaggagg agaacatgaa aatattaaga caaaaatcct cagcagttgt   4080
tctccacccc ttctccacct ccaccagcaa ggagaagtca atctacactt ttttctcatg   4140
ttctaaagtc ttagaatact gctggattgt tgagcatgag acagagcaaa ggttagatac   4200
acaaggtaca agttcatagg agcacaattc cttgattcag ggaaagtagc acagaatgca   4260
atttgaaaac tacaggctta ggactctgtg ccaaaaatct ctattttaaa tgaaaatatt   4320
tatataaaaa tacatttatt ctgcttaaca caaattaaaa ctgacataaa attttatgat   4380
aataacatga ttcaagaaat gtgatgtaga tttttgagaa tgccaaaaat caggtttcag   4440
aaaagctaca gtatgaaatc tgaaaagcaa cagaaattga aagtgacctt aaagaataaa   4500
tttcctaatt tttcccagtt tcctatgttt ataactatta taaagagttt aactttctgg   4560
aactgaagga gaaaacatga aaatgtttat attgcttctt gttaagcagg tagaccaaat   4620
```

tccgctttca gtaattcatc catacagaat ttggatgact atgtataaag gaaaacttaa 4680
atcttaatta ttatcagttt aaattttttt tgtttgttga atgacaaagg caataaaaat 4740
aaatttgact ttagcttttt ttctatactt tcctcttttt gtaattctta aattctagtc 4800
actagtcatt atgagagtat tgactaaata ttttcacaat ctaaatattg tcacaatcta 4860
aatttctgta gtacagagag ccgtagccct ttgtaaaggc tttcgttcgt ccaaacaaca 4920
cttgatccaa ccaaagttcc aatgtgactg tggatctttg ataggtcttt ggtgttggtt 4980
gtaacaaaat ttgatttgaa ctacctataa atgaaaagtc ggggtttatt actttatatg 5040
taatgctgag aggagactgt tgggaacagt tatgtcaatg agcaaactag aaattggctt 5100
caaagtctga tacttttaaa agcatgtgtt ttgtgtatat gctcacaaaa tgtctgtgaa 5160
gagatttctt tcagcttttg ctcagcttta tggtggggtg tactgtttta tctgggcggt 5220
gagggtattg atttacataa aaactgtaga caaacacagt acgagtctca gcacgttttg 5280
catttattgt actgcccaaa ttgtttttat gttaaaagtc acgtttcata atctgcaata 5340
tttttgtcaa agtgcacact gtactttctt cttaaaaacg tgattaaaga gatcactttg 5400
tccggatgaa gcagctgttg gcattatccg ctgaggcttg aaaaaa 5446

<210> SEQ ID NO 46
<211> LENGTH: 1440
<212> TYPE: DNA
<213> ORGANISM: Homo sapiens

<400> SEQUENCE: 46
ggggcggggc gcccagcggg atgcggtgaa gggcgagcgg cgcggcggct gcgatgagtg 60
cctctgcggc caccggggtc ttcgtgctgt ccctctcggc catcccggtc acctatgtct 120
tcaaccacct ggcggcccag catgattcct ggactattgt aggggttgct gccctcatcc 180
tgttcctggt agcactgctg gctcgtgtcc tcgtcaaaag aaaaccaccc cgggacccac 240
tgttctatgt gtatgcagtt tttggattta ccagcgtggt gaacctcatc ataggactgg 300
agcaagatgg aatcattgac gggttcatga cacactactt gagagagggt gaaccgtatc 360
tgaacaccgc atatgggcac atgatctgct actgggatgg ctctgctcat tatctgatgt 420
acctggtgat ggtggcagcc atagcatggg aggaaactta tagaaccatt ggcctatatt 480
gggttggatc tattattatg agtgttgttg tttttgtgcc aggaaacatt gtagggaagt 540
atggaacacg aatttgccct gctttttct taagcatacc atatacttgt cttcctgtct 600
gggctggttt cagaatctat aatcagccat cagaaaatta taattacccc tcaaaggtta 660
ttcaagaagc ccaagcgaaa gacctgctga gaagaccatt tgatttaatg ttggttgtgt 720
gtctcctcct ggcaactgga ttttgcctgt tcagaggttt gattgctttg gattgcccat 780
ctgagctctg ccgattatat acgcaatttc aagagcccta tctaaaggat cctgctgctt 840
atcctaaaat tcagatgctg gcatatatgt tctattctgt tccttacttt gtgactgcac 900
tgtatggctt agtggttcct ggatgttcct ggatgcctga catcacattg atacatgctg 960
gaggtctggc tcaggctcag ttttctcaca ttggtgcatc tcttcatgct agaactgctt 1020
atgtctacag agtccctgaa gaagcaaaaa tcctttttt agcattaaac atagtatatg 1080
gagttcttcc tcagctcttg gcctatcgtt gtatctacaa accagagttc ttcataaaaa 1140
caaaggcaga agaaaaagtg gaataaaaat attacttcat gttcctcctt tctaaattac 1200
taacttttgt tatactggta ctgatatttt gtcccatttc actctcttct catacgtgag 1260
tacttaagaa tatgtacatt cttgctctgc actgtatgtg tgagctatat ggtattgtgt 1320
aaattttttt tgaaggaaaa tggaaattct tgagaaacag tttgtttaaa gaaatatatt 1380
caaaatcatt tgtgaataaa cttgatcatc catctcaaaa aaaaaaaaaa aaaaaaaaaa 1440

<210> SEQ ID NO 47
<211> LENGTH: 2162
<212> TYPE: DNA
<213> ORGANISM: Homo sapiens

<400> SEQUENCE: 47
ggagggagcc ggagcgcttc tcccgagttg gtgatagatt ggtggtcatc caacatgcag 60
aaatgaatga gcagtgaaaa gcagcagagc cgatgggtca tgaggatgta agtgcgtttg 120
aaggcttcca caccctctac tccaggacag aatcatgaat aaactggagg ataagcagga 180
ccagatgata ccatgaagag aagtttacag gccctctatt gccaactgtt aagtttcctg 240
ctgatcttgg cactgaccga agcgctggca tttgccatcc aggaaccatc tcccagggaa 300
tctcttcagg tcctcccttc aggcactccc ccgggaacca tggtgacagc accccacagc 360
tctaccagac atacttctgt ggtgatgctg acccccaatc ccgatggacc cccctcacag 420
gctgcagctc ccatggcaac accgacaccc cgtgcagagg ggcaccctcc tacgcacacc 480
atctccacca tcgctgcgac agtaaccgcc ccccattctg aaagctccct gtccacaggg 540
cccgctccag cagccatggc aaccacatcc tccaagccag agggccgccc tcgagggcag 600
gctgccccca ccatcctgct gacaaagcca ccgggggcca ccagccgccc caccacagcg 660
cccccccgca ctaccacacg caggcccccc aggcccccag gctcttcccg aaaaggggct 720
ggtaattcat cacgccctgt cccgcctgca cctggtggcc actccaggag taaagaagga 780
cagcgaggac gaaatccaag ctccacacct ctggggcaga agcggcccct ggggaaaatc 840
tttcagatct acaagggcaa cttcacaggg tctgtggaac cggagccctc taccctcacc 900
cccaggaccc cactctgggg ctactcctct tcaccacagc cccagacagt ggctgcgacc 960
acagtgccca gcaatacctc atgggcaccc accaccacct ccctggggcc tgcaaaggac 1020
aagccaggcc ttcgcagagc agcccagggg ggtggttcta ccttcaccag ccaaggaggg 1080
acaccagatg ccacagcagc ctcaggtgcc cctgtcagtc cacaagctgc cccagtgcct 1140
tctcagcgcc cccaccacgg tgacccacag gatggcccca gccatagtga ctcttggctt 1200
actgttaccc ctggcaccag cagacctctg tctaccagct ctggggtctt cacggctgcc 1260
acggggccca ccccagctgc cttcgatacc agtgtctcag ccccttccca ggggattcct 1320
cagggagcat ccacaacccc acaagctcca acccatccct ccagggtctc agaaagcact 1380
atttctggag ccaaggagga gactgtggcc accctcacca tgaccgaccg ggtgcccagt 1440
cctctctcca cagtggtatc cacagccaca ggcaatttcc tcaaccgcct ggtccccgcc 1500
gggacctgga agcctgggac agcagggaac atctcccatg tggccgaggg ggacaaaccg 1560
cagcacagag ccaccatctg cctgagcaag atggatatcg cctgggtgat cctggccatc 1620
agcgtgccca tctcctcctg ctctgtcctg ctgacggtgt gctgcatgaa gaggaagaag 1680
aagaccgcca acccggagaa caacctgagc tactggaaca acaccatcac catggactac 1740
ttcaacaggc atgctgtgga gctgcccagg gagatccagt cccttgaaac ctctgaggac 1800
cagctctcag agccccgctc cccagccaat ggcgactata gagacactgg gatggtcctt 1860
gttaacccct tctgtcaaga aacactgttt gtgggaaacg atcaagtatc tgagatctaa 1920
ctacagcagg catcactttg ccattccgta tttttcgtct ctaaattata aatatacaaa 1980
tatatatatt ataaatataa cctttgtgta accctgactt aatgagaaac attttcagct 2040

```
tttttcccta tgaattgtca acatcttttt tacaagtgtg gtttaaaaaa aaaaaaactt   2100

tacagaatga tctgtggctt tataaaataa aggtatttct aagcaaaaaa aaaaaaaaaa   2160

aa                                                                  2162


<210> SEQ ID NO 48
<211> LENGTH: 1750
<212> TYPE: DNA
<213> ORGANISM: Homo sapiens

<400> SEQUENCE: 48

ccaagatgga ctcctcgcgg gcccggcagc agctccggcg gcgattcctc ctcctgccgg     60

acgccgaggc ccagctggac cgcgagggtg acgccgggcc gggtgaggcg cgcaccaagc    120

cgccccgagg ttctcagagg cgaggcgtcg gaaaacggcc ggcctccggc agccctggcc    180

cagtctggaa ggactgagtt tcggctttgc aagtcgaata tttaatgtca gggaagatcc    240

ttagaatcgc ggagtgctgt gcatcgtcat ttcagctgcg cttcagaatt ctctggagag    300

ctgatttgac acctatttgg aaatagcgat taaaattaaa aatacccacc agttttaagt    360

cttaaggatt taccagaaac atgcgtgtac cgcagtgtac aatgatgtgc gcagtgtttc    420

acttcaggat tgcttgtaat agcgaattac tagaaatatc tgccttgccc gtcagcagaa    480

agctgtttaa gtaaatttgg gtatatgtat acctgacaca tcaggtcgac tcgtatgtac    540

caatggggat gattttcaaa gggaagtgtg gaacactatg gtatgccgcc atttgggtac    600

aaaacagaaa cctccacagc tgttgagaaa aaggagaaac ctcttccaag acttaatatc    660

cattctggat tctggatttt ggcatccatt gttgtgacct attatgttga cttctttaaa    720

acccttaaag aaaacttcca cactagcagc tggtttctct gtggcagtgc cttgttgctt    780

gtcagtttat caattgcatt ttactgcata gtctacctgg aatggtattg tggaattgga    840

gaatatgatg tcaagtatcc agccttgata cccattacca ctgcctcctt tattgcagca    900

ggaatttgct tcaacattgc tttatggcat gtgtggtcgt tttcactcc attgttgttg     960

tttacccagt ttatgggggt tgtcatgttt atcacactcc ttggatgatt tccgaagaga   1020

cagggtcttc tatgttgccc aggctgtctt tgaactcctg ggatcaagtg atcctcctgc   1080

ctcagccttc gaagtagttg ggactacagg cccacgccac cgtgcctggc tggacatgta   1140

aatttgaagt gaatggttaa acatccagct agctgaaagc atggcagacc ctaacagaaa   1200

agctacagtg tgtttttgca gctatgaagt gaatggtttc ctggggaaaa ttgtgacttt   1260

gtataactgt tgttgaaacc agaataaatt atatttcact tgcatatgca taaattatta   1320

aaattttcag aagtcagtga tacagaagta ctattttgca atgttaatct gtttgagtct   1380

ttggagaaag tggtttcatt gtaggtacat agtgcactgt taatatttta aacaagtagt   1440

tcactcttcc atttaaggga tagcagttcc ttgtataaaa tgactggatg tgtataaagg   1500

aattatgttg tcatgtgcct ttaaccagct ttagtaatta ctataatctc atatttatga   1560

tagttttgtt aggtgacagg accaaatgaa aatattttat gttttctcat cactttagat   1620

tttatcatta tgtacattac tgggttttta gcatttccta atgtgaagtt ttaatcactt   1680

ttaagtatac atttttttct gtatcattta aataaaatat ttttataact ttaaaaaaaa   1740

aaaaaaaaaa                                                          1750


<210> SEQ ID NO 49
<211> LENGTH: 1678
<212> TYPE: DNA
<213> ORGANISM: Homo sapiens
```

<400> SEQUENCE: 49
gcatttctga ctcgagtccc cgccgcgctt gtcgtcgccg cagccgggat ccgcagcccc 60
gcgccatgga gccggccgcg ggcatccagc gccgcagctc ccaggggccc accgtcccgc 120
cgccgccccg gggccacgcg ccaccggctg ccgccccccgg cccggccccg ctgagctccc 180
cggtgcgcga gccgccccag ctggaggagg agcggcaggt gcggatcagc gagagcggcc 240
agttcagcga cgggctggag gaccgaggct tactagaaag cagcacccgc ctgaaacctc 300
acgaagccca gaactacagg aagaaggcat tgtgggtgtc ctggttctcc atcattgtca 360
ccctggccct cgcggtggct gcctttactg tctccgttat gaggtacagc gcctctgctt 420
ttgggtttgc atttgatgcc atcctggacg tcctgtcatc ggcgattgtc ctgtggcgtt 480
acagcaacgc ggccgctgtg cactctgccc atagggagta catagcctgt gtcatcttgg 540
gggtgatatt ccttctgtca tccatatgta tagtggtcaa agccatccat gacctctcaa 600
ctaggctgct cccagaagtg gacgatttcc tgttcagtgt ctccatttta agtgggattc 660
tttgcagcat cctggccgtg ttgaagttca tgctggggaa ggttctgacc agtagagcac 720
tcataacaga tgggtttaac tccctcgtgg gtggcgtgat gggcttctcc attcttctga 780
gcgcggaagt gttcaagcat gactcagcgg tctggtacct ggacggcagc ataggcgttc 840
tgatcggcct caccatattt gcctatgggg tcaaactcct catcgacatg gtgccgaggg 900
tgaggcagac acgtcactac gagatgtttg agtgaagggg gccagcatcc gcatgagacc 960
attgagatga ggagtttcca cataggcaaa gggtgccaat atttaactga acatctggtt 1020
tctttttgga agttttcttt cacatggttt gtcattacaa gacaaggtct gcccagccag 1080
gtggatctac cttgccccca tcacctgccg cccccatcaa acatgttggg acaatgccca 1140
taggaatgga cctccttccc cgtctccagc tgggactggt gttttttag tctctggagt 1200 atgatggttc tcatgggtag gatgagatct ttggcagaaa ggtcttcggt ggtgctctga 1260
gcctgcgctg cataggactg agcagaccca cctcctccag cttgggtggc cctgccactc 1320
ctggttccaa gtctctcctt tcctggcagg tcttaaggga agattgtacc cctcaccctt 1380
tacataccca gaatcatcag tatgtcactt cctaatttct atcagtgtat ctcattattt 1440
catactgttt tactaatcct aagtctaaac agatttgctc aaaaggagac cattctattt 1500
tttaaagtac ttagtgatac acgtataagc tttgcatgga cgaattaaat aagcacattg 1560
accttttctt gtacattcag aacctgaaca tccatgtgaa aactgggtcc atttttgaga 1620
gatgtgaaac tacagtttat ttgtaataaa taaatataat ctaaaaaaaa aaaaaaaa 1678

<210> SEQ ID NO 50
<211> LENGTH: 4128
<212> TYPE: DNA
<213> ORGANISM: Homo sapiens

<400> SEQUENCE: 50
aaagatagat cctgctccag gagccgggaa gccttgccct ggccagctgt gctgggcacc 60
tcccctgcct gcttcctggc ccacttgcag gcaaggtgag ggcatgcgaa tggctgccac 120
tgcctgggcg gggctccaag ggccacccct ccccaccctc tgtcccgcag tgaggacggg 180
actctactgc cgagaccagg ctcacgctga gaggtgggcc atgacctccg agacctcttc 240
cggaagccac tgtgccagga gcaggatgct gcggcgacgg gcccaggaag aggacagcac 300
cgtcctgatc gatgtgagcc cccctgaggc agagaagagg ggctcttacg ggagcacagc 360
ccacgcctcg gagccaggtg gacagcaagc ggccgcctgc agagctggga gtcctgccaa 420

-continued

```
gccccggatc gcagacttcg tcctcgtttg ggaggaggac ctgaagctag acaggcagca    480
ggacagtgcc gcccgggaca gaacagacat gcacaggacc tggcgggaga cttttctgga    540
taatcttcgt gcggctgggc tgtgtgtaga ccagcaggac gtccaggacg ggaacaccac    600
agtgcactac gccctcctca gcgcctcctg ggctgtgctc tgctactacg ccgaagacct    660
gcgcctgaag ctgcccttgc aggagttacc caaccaggcc tccaactggt cggccggcct    720
gctggcatgg ctgggcatcc ccaacgtcct gctggaggtt gtgccagacg tacccccccga    780
gtactactcc tgccggttca gagtgaacaa gctgccacgc ttcctcggga gtgacaacca    840
ggacaccttc ttcacaagca ccaagaggca ccaaattctg tttgagatcc tggccaagac    900
cccgtatggc cacgagaaga aaaacctgct tgggatccac cagctgctgg cagagggtgt    960
cctcagtgcc gccttccccc tgcatgacgg ccccttcaag acgcccccag agggcccgca   1020
ggctccacgc ctcaaccagc gccaagtcct tttccagcac tgggcgcgct ggggcaagtg   1080
gaacaagtac cagcccctgg accacgtgcg caggtacttc ggggagaagg tggccctcta   1140
cttcgcctgg ctcgggtttt acacaggctg gctcctgcca gcggcagtgg tgggcacact   1200
ggtgttcctg gtgggctgct tcctggtgtt ctcagacata cccacgcagg aactgtgtgg   1260
cagcaaggac agcttcgaga tgtgcccact ttgcctcgac tgccctttct ggctgctctc   1320
cagcgcctgt gccctggccc aggccggccg gctgttcgac cacggcggca ccgtgttctt   1380
cagcttgttc atggcactgt gggccgtgct gctgctggag tactggaagc ggaagagcgc   1440
cacgctggcc taccgctggg actgctctga ctacgaggac actgaggaga ggcctcggcc   1500
ccagtttgcc gcctcagccc ccatgacagc cccgaacccc atcacgggtg aggacgagcc   1560
ctacttccct gagaggagcc gcgcgcgccg catgctggcc ggctctgtgg tgatcgtggt   1620
gatggtggcc gtggtggtca tgtgcctcgt gtctatcatc ctgtaccgtg ccatcatggc   1680
catcgtggtg tccaggtcgg gcaacaccct tctcgcagcc tgggcctctc gcatcgccag   1740
cctcacgggg tctgtagtga acctcgtctt catcctcatc ctctccaaga tctatgtatc   1800
cctggcccac gtcctgacac gatgggaaat gcaccgcacc cagaccaagt tcgaggacgc   1860
cttcaccctc aaggtgttca tcttccagtt cgtcaacttc tactcctcac ccgtctacat   1920
tgccttcttc aagggcaggt ttgtgggata cccaggcaac taccacacct tgtttggagt   1980
ccgcaatgag gagtgcgcgg ctggaggctg cctgatcgag ctggcacagg agctcctggt   2040
catcatggtg ggcaagcagg tcatcaacaa catgcaggag gtcctcatcc cgaagctaaa   2100
gggctggtgg cagaagttcc ggcttcgctc caagaagagg aaggcgggag cttctgcagg   2160
ggctagccag gggccctggg aggacgacta tgagcttgtg ccctgtgagg gtctgtttga   2220
cgagtacctg gaaatggtgc tgcagttcgg cttcgtcacc atcttcgtgg ccgcctgtcc   2280
gctcgcgccg ctcttcgccc tgctcaacaa ctgggtggag atccgcttgg acgcgcgcaa   2340
gttcgtctgc gagtaccggc gcccggtggc cgagcgcgcc caggacatcg gcatctggtt   2400
ccacatcctg gcgggcctca cgcacctggc ggtcatcagc aacgccttcc tcctggcctt   2460
ctcgtccgac ttcctgccgc gcgcctacta ccggtggacc cgcgcccacg acctgcgcgg   2520
cttcctcaac ttcacgctgg cgcgagcccc gtcctccttc gccgccgcgc acaaccgcac   2580
gtgcaggtat cgggctttcc gggatgacga tggacattat tcccagacct actggaatct   2640
tcttgccatc cgcctggcct tcgtcattgt gtttgagcat gtggttttct ccgttggccg   2700
cctcctggac ctcctggtgc ctgacatccc agagtctgtg gagatcaaag tgaagcggga   2760
gtactacctg gctaagcagg cactggctga gaatgaggtt ctttttggaa cgaacggaac   2820
```

aaaggatgag cagcccgagg gctcagagct cagctcccac tggacaccct tcacggttcc 2880
caaggccagc cagctgcagc agtgacgcct ggaaggacat ctggtggtcc ttaggggagt 2940
ggcccctcct gagccctgcg agcagcgtcc ttttcctctt ccctcaggca gcggctgtgt 3000
gaaccgctgg ctgctgttgt gcctcatctc tgggcacatt gcctgcttcc ccccagcgcc 3060
ggcttctctc ctcagagcgc ctgtcactcc atccccggca gggagggacc gtcagctcac 3120
aaggccctct ttgtttcctg ctcccagaca taagcccaag gggcccctgc acccaaggga 3180
ccctgtccct cggtggcctc cccaggcccc tggacacgac agttctcctc aggcaggtgg 3240
gctttgtggt cctcgccgcc cctggccaca tcgccctctc ctcttacacc tggtgacctt 3300
cgaatgtttc agagcgcagg gccgttctcc ctcgtgtcct ctggacccac ccgccccttc 3360
ctgccctgtt tgcgcaggga catcacccac atgccccagc tctcggaccc tgcagctctg 3420
tgtcccaggc cacagcaaag gtctgttgaa cccctccctc cattcccagt tatctgggtc 3480
ctctggattc ttctgtttct tgaatcaggc tctgctttcc ccctagccac tacaggcagc 3540
ctctgacagt gccgctttac ttgcattctg cagcaattac atgtgtcctt ttgatccttg 3600
cccaacttcc ctccctctcc cagctcctgg cccctggccc agggcccctc ttgctgtttt 3660
tacctctgtt ccttggggcc tagtacccag caagcaccca aatgggggag gttttgggat 3720
gagaggagga aacgtgtata cctgtaacat ctggtggctc ttcccccaga agtttgtgtt 3780
catacataat tgttttccac gctggatcat aatgtgacgt gcagttctgc cctgtgctgg 3840
ggagccacat gaagcttccc ctggctaact tgctaccccg cagcaatccc agtgtggccg 3900
tctgcttgct aaaaaatgga tctgtgctca tctgtattga tgtccttgga gttctacaag 3960
tggaacttaa gtgtcaaaaa gaatatgtgg tttttagctg agcgtggtgg ctcacacctg 4020
taatcccagg actttgggag gctgaggcag gaggattaca aggtcaggag ttcgggacta 4080
gcctgtccaa catggtgaaa ccctgtcttt actaaaaatg caaaaatt 4128

<210> SEQ ID NO 51
<211> LENGTH: 1444
<212> TYPE: DNA
<213> ORGANISM: Homo sapiens

<400> SEQUENCE: 51
gctgaccatg ctggaactgc ggcgactaca gagcctgcgg gaacctcccc tttcgcccaa 60
gatctgctct gtccccctca tcctcctccc agggccctgg cgtctgggtc aagcagcgcc 120
ccacacctcg acccctcacc ccctcctccc gggctcttcc tgcggcctcc cctccacagt 180
ccgcaggctc tgggacagga ccgagtcctt ggctgcctgt ggagctcctg tgccagcagc 240
tgcgccccgg ctgcgctccg gatacccccca tccccgccac cgccgacctc ccgctccacc 300
gactgctgct cacgcccgac gggttcacgc cgcccctgcc ccgtgaagga ccgcgctgcg 360
gtgcggaggc aggatgacgc aaaacacggt gattgtgaat ggagttgcta tggcctctag 420
gccatcccag cccacccacg tcaacgtcca catccaccag gagtcagctt tgacacaact 480
gctgaaagct ggaggttctc tgaagaagtt tctttttcac cctggggaca ctgtgccttc 540
cacagccagg attggttatg agcagctggc tctaggggtg actcagatat tgctgggggt 600
tgtgagttgt gttcttggag tgtgtctcag cttggggccc tggactgtgc tgagtgcctc 660
aggctgtgcc ttctgggcgg ggtctgtggt gatcgcagca ggagctgggg ccattgtcca 720
tgagaagcac ccgggcaaac ttgctggcta tatatccagc ctgctcaccc tggcaggctt 780
tgctacagct atggctgctg ttgtcctctg cgtgaatagc ttcatctggc aaactgaacc 840

```
cttttatac atcgacactg tgtgtgatcg ctcagaccct gtcttcccta ccactgggta    900

cagatggatg cggcgaagtc aagagaacca atggcagaag gaggagtgta gagcttacat    960

gcagatgctg aggaagttgt tcacagcaat ccgtgccctg ttcctggctg tctgtgtctt   1020

gaaggtcatt gtgtccttgg tttccttggg agtaggtctt cgaaacttgt gtggccagag   1080

ctcccagccc ctgaatgagg aaggatcaga gaagaggcta ctgggggaga attcagtgcc   1140

cccttcgccc tctagggagc agacctccac tgccattgtc ctgtgagctg ccaaagaccc   1200

cacggggtgc ccgcatgtcc ctgtctaggg cagcccaggg cccccactcc tggctcctca   1260

cacttgcctc ccctatggcc gctctccaga ccctcctcct ttcttctccc cacatccgca   1320

cctgctgttc ccactctggg gttctcaagt ccatgaacag atattgttgc attttccaca   1380

atgctgatta aacataataa acaatccaga aaagcagttt tgcccagaaa aaaaaaaaaa   1440

aaaa                                                                1444
```

```
<210> SEQ ID NO 52
<211> LENGTH: 5397
<212> TYPE: DNA
<213> ORGANISM: Homo sapiens

<400> SEQUENCE: 52
```

```
cgcggaggcg gatgggcgcg gctccctccc ccactcaggc ctcttcacgg ggcggggggc     60

cgggtccccc agcccccacc cgcgccgtgt ccagctcctc gcgtgctcgc ggcggagccc    120

tgagcgcact gggtccgagt cctgcgcgcc ccctcaccac ctcccccgca cctgctcctc    180

ctcctcggtc ccgcccagcg cgccagcagc ccgatcccca gtgctgggag aagagagggg    240

gcgcaggcgg cgacacaaag ggtggagcgg cgggaccggg acccgggagg ctgcgcggca    300

tggacgccga gtaccctgcc tttgagcccc cgctctgcag cgagctcaag cacctgtgcc    360

ggcggctgcg ggaagcgtac cgcgagctca aggaggacct cacgcccttc aaggatgacc    420

gctactacag gctggcgccc atgcggctct acacgctctc caagcgccac tttgtcctcg    480

tgtttgtcgt cttcttcatc tgctttggcc tgaccatctt cgttgggatc agaggaccta    540

aagtgatcca gacttctgcg gctaattttt cactaaataa tagcaaaaag ctaaagccaa    600

ttcaaatact ttcaaatcca ctgtctacat acaatcagca actatggctg acatgtgttg    660

ttgagttgga tcaatcaaaa gaaacttcta ttaagacaag ctttcccatg actgttaaag    720

tcgatggtgt agctcaagat ggaaccacga tgtacattca taacaaagtt cacaaccgga    780

caaggaccct cacatgtgca gggaaatgtg cggagattat tgtggctcac cttggctacc    840

tgaactacac tcagtataca gtgatagtgg gatttgaaca cctgaagctc cccatcaagg    900

gaatgaactt cacatggaag acttataacc ctgccttctc ccggttggaa atctggttcc    960

ggtttttctt tgtggtgctc accttcatcg tcacttgcct gtttgcgcat tccctccgga   1020

aattttccat gagagactgg ggcatcgagc agaagtggat gtctgttctc ctgcctctgc   1080

tgctacttta caatgatccg ttcttccccc tctccttcct ggtcaacagc tggctcccag   1140

ggatgctgga tgacctcttt cagtccatgt tcctgtgcgc cctgctgctc ttctggctgt   1200

gcgtgtacca cgggattcgt gtccagggag aaagaaagtg tttaactttc tatttgccta   1260

aattcttcat tgttggacta ttgtggttgg cttctgttac gctaggaata tggcaaacag   1320

ttaacgaatt acatgatcca atgtaccagt atcgagttga taccggaaat tttcagggaa   1380

tgaaggtctt cttcatggtg gtggcagcgg tgtacattct gtacctcttg ttcttgatag   1440

tgcgggcgtg ttccgagcta cgtcacatgc cttatgtgga tctcaggttg aaatttttga   1500
```

-continued

```
ctgcattgac tttcgtagta cttgtcatta gcatcgccat cctttatttg agatttgggg   1560
cgcaagtact acaagacaat tttgtagcag agctgtcaac tcactaccag aattcagccg   1620
agttcttatc tttctatggc ctgttgaact tctatctcta caccttggcc tttgtatatt   1680
ctccatcgaa gaatgccctc tatgagtccc agctgaaaga caatcctgcc ttctccatgc   1740
tgaatgactc ggatgatgat gtgatttatg ggagtgacta tgaggaaatg ccgctgcaga   1800
acggccaggc catccgggcc aagtacaagg aggagtcaga tagtgactga gccccggcca   1860
gcccagcgag gcgacaagat gcctggatgc tttccccggt gaccgtctgc tgaccttccc   1920
ctgttatatt cagatttttc ttacaagcag agatttcctg ttcatttgtt tacatatttt   1980
tttaaaggaa aaccaaaact gagggtaaat ttaaatgttt agccaaattt attgtcatgg   2040
tggctacgag aagaggcatt gataacaagt ttcaacagcc aaatcctttt ttacagagat   2100
ttcagatgag cgtgttttca gtgatgagga aatttcacgt ttttagtaca gtgaattatg   2160
tacttttttt tcctgtaatc attcactgat tccaagttca cgggcagcct gtgactaggt   2220
cctcagcgtg acagcatcac cctctttctt ccccttttcca tggtactgtt ttgtgaccct   2280
ttaaactcaa agggaagcct tatctgtggc tgcttcaggg cagtccttcc tcgttgagtg   2340
gccagtgccc tgggtaacca ggtggctgaa gtgattggtc agttatgtgg actgcgtttt   2400
gtgcagtgtg tgagttatga ctcatcggga atgggagatg ctggggttcc aacccttcac   2460
gtcaccaaag gggaagtaat agtgtggagt tctgaggagg gtttgataag ttgaataagg   2520
aaaggctaag ataatttaca ggttaccaac tcatgtgggg aaggtcttac tgccatggtg   2580
cttttcaggg gcctgtgtgt acacacatga ttaaatggat ttgcctgtgg gaggtatggg   2640
caggagagga acccttacca ttccagtaaa tagcagtttc tgcaattctg ttgaatatga   2700
aatgccatag agctttattt atttatgtaa gtaaaagcta aatgaggggc caggtgcagt   2760
ggctcacatc tgtaatctca acactttggg aggccaaggt gggaggatca cttgagccca   2820
ggagtttgag accagcctgg gcaacacagg gagaccccgt ctctataaaa catttagaaa   2880
gttggctggg catgctgggg catgcccata gtcccagcta ctcaggaggc tgaggtggga   2940
ggattgcttg agccctggag gtcaaggctg cagtgagcca tgattgcacc actgcactcc   3000
agcctgggtg tcagagcgag aacccgtgtc ataaataaat aaagctacat gaaagattga   3060
tagaatattt tagattattt attggccaaa agtttttaaa actcatattt ggaagcaaaa   3120
tgaaaagcaa gtaaaatgtt ttaaatggtt catggaaaac gtatttgggt agaaggcaac   3180
tcgtgcttcc ggaaggggtt ccctgtcctc catgtgtcca catggcggtc aggtagggac   3240
gacctgttct gtaaagtcct tggcactgct gaatctgtgg catcatagaa ggccctggag   3300
cttccccgtt cctttcagtc agggactcca tatagagtct catgtggacg tctcccgtgc   3360
tttcctcttg acctctacag tcacacttct gttaacatct ggtaactgtg ggcaacctga   3420
ctgatgccgt cttggcaatt gaggtccaga agatgatagt tccgcaacgc aagcagtacc   3480
tacttttttt cttcatctat gcattgactc tcagattacc atgcagagct tcacgttatc   3540
atccacgtta agtagtgcta ggtaggacct tagagatgtt catgagaaac tatttgttat   3600
gactttcctt tgtatctttc cttttaattt aaactttaat gataatgtac ttttaatatg   3660
gattctattc acatttgttt taaaaacctt gtaaatatga atgtttaaga caacttactg   3720
caagggtaat tcaagtttac atgattttta aatttgcaat gatgtttttt ttattctgtg   3780
tattgaaaaa aattttctgt taccaaattt tacaacttct aataagacta ctataacttt   3840
atgtaaactg atgaagatgt gctgattaac atattctgtg atatggttta caacttttaa   3900
```

-continued tcataattgt ccatgatttt ggaatgctgt tatttatcag taaatgtaaa atatttgagg 3960
catttagcca tacacacact agaacttttt aaaactttgt cctatagtgt aattataaac 4020
tgatgactat tatcttcata cattgagtct tcatgcatca atgaaatgaa aaatatagga 4080
ttatttattt actttttgta actaagtggg aaataagaaa aaaagttaga aagtacttaa 4140
ggggaaaatc gttcttacta agtcatgtat tttcaacttg tcttccctgg tatatcataa 4200
ataccgacat attacatacc ccatgtaaaa ttttgcttaa actctctagc acttggcatg 4260
tagaatatgt accataggta tcaggttaaa acactaaagt ctgccagaaa cttttgacag 4320
tagcaagaaa attgttgaag aaaaaataaa ttatttactg agggtagtta tgttaaagtt 4380
ttgcgaactt aaagggctga ctttagttcc ttcatggtaa tggcttgagt aacatcatct 4440
ttgggatttt ttaaatactg gtccagtcta ggagaacctg gaagatgacc agaggtattt 4500
cagtttccct agggagagct tcgttatcca tgtggatgat aagtctgctt gatttattat 4560
taaatcatta tagcagtgaa gtggtgccat tttctctctc ttaagcccca tttgaaaggc 4620
tagagaaggg gatatatata ctatgttcaa ggtttgtaag gttgttaatg tacataattg 4680
cagattgcaa taaaagctta gatacatttt gtaaacccaa cccactaaat gagcaggtta 4740
caagacaaat gtcaccagcc tcaagtattt tatgaactat ttactgaggg tagttatgtt 4800
aaatagatta taatgtggta aattatttcc tgaatccttt atcacaggaa aaacacagac 4860
cctcataaaa gggataatta aaacggatgt gtctgaacat ttagtgaaga tgagacttaa 4920
aacatgaaag tgtatttgtg tattttgagg gttttagaaa ccggttgcct tagaggttag 4980
acttttgaag aaaaaaaaaa aaagatacag atcttttccc ctggccaaag ggaagttgta 5040
ttagtctgtg acatcttgtg atgctgttta tcttggtttg acattggaga tacgctagta 5100
actgtgatac catactataa aacagaagaa ttttctgcta ctaaaaactg ccttttttaca 5160 aaatgactgt aaatatttgt aaaataaaat aacactaaac tttaagccca aaaggagaga 5220
tagagccatg tgttcagttg tggacctgtc cgtggggcac agtgccaccc catcacagtg 5280
ttgctgtcat caggcaaaag tgaatgtttg tttatggcaa attcgtcttt tgcgaatggc 5340
ttaattctga cactaccttt ctgggaaatg ttaataaatt tttaatattc acttcta 5397

<210> SEQ ID NO 53
<211> LENGTH: 2358
<212> TYPE: DNA
<213> ORGANISM: Homo sapiens

<400> SEQUENCE: 53
cgcccgggag cgcgcccttc tctgcccgcg gtcggtgcgc tcggccggag gcgccgcggc 60
ggaacggaac ccagagaagg ggacgcgggg cggcggcgct cggggcttgc ccgcggcgag 120
ggaggctgcg cccaggtccc cggccccgcg ccgcgcgccc agccgcgcca tgggggaggc 180
gcccagcccc gcgcccgcgc tctgggactg ggactacctg gaccgctgct tcgcccgcca 240
ccgcgtctgc atctccttcg gcctgtggat ctgcgcctcc tcctgctgga tcgccgccca 300
cgcgctgctt ctctatctga gatgtgcaca gaaacccaga caggaccagt cggcactgtg 360
tgctgcgtgc tgcctcctga ccagtctgtg tgacaccgtc ggggctcttc tggccagaca 420
gctcacaatc caggttttca ctggtgccta cctagcagct attgacttag tgaactttat 480
gttcattctc ttcccagtct gtggatccaa attcaagtct aattcagatc gggaagcccg 540
agagaggaag aggaggcggc agctcagggc cagtgtgttt gccctggccc tgccgctgag 600
cctgggcccg tgctgggctc tgtgggttgc tgtcccgaag gcttcagcca ccatccgggg 660

```
gccacagcgg aggctgctag cgagcctgct gcaggaaaat actgagatcc tcggctacct    720
gctgggtagc gttgctgcct ttggctcctg ggcttctcgg atcccccctc tctccagaat    780
ttgccggggg aagacatttc cctccatcca cctgtggacc cggctcctgt cggccctggc    840
tggcctcctc tatgcctcgg ccattgtggc ccacgaccag caccctgagt acctgctgcg    900
ggccacaccc tggttcctga cctccctcgg ccgtgcggca ctggacctcg ctattatttt    960
cctttcgtgt gtgatgaaga gcaagatgag acaggcctta ggatttgcca aggaagccag   1020
agagagccct gacacccaag cccttttgac ctgtgcagag aaagaggaag aaaaccagga   1080
gaatttggat tgggtgcctc tcaccacact gtcacactgc aagtcactga ggacaatgac   1140
agcaatcagt cgctacatgg agctgaccat cgagcctgtg cagcaggcag gctgcagtgc   1200
caccaggctg ccaggtgacg ggcagacgag cgcccggagat gcgtccctgc aggacccccc   1260
gtcgtaccct cccgttcagg tcatccgggc ccgggtgtct tccggcagct cctctgaggt   1320
ctcctccatc aactccgacc tggagcagaa gtattgggag gccctaaact cggagcagtg   1380
ggaccctgaa gatgtgaacc tcgaaggcag caaagaaaat gtggagctac tgggatccca   1440
ggtgcaccag gactctgtga ggacagcaca cctgagtgat gatgattaac accttctgga   1500
gccagctcat cagctcagag cccagggtca ggagttcgtt cagtaacgca gcgggaatca   1560
atctgcactg acaccgcggc aggaactgaa gctgccctgg caagtgagga accaggagcc   1620
gtcactgagt gtggctgggc tacatcatag ctcatcacgg agctacgact ttgggtactg   1680
cggacagacc tggataggcc cagcattcgt tctgaagatc acagttcaca gaagcttttg   1740
cttcgtaaag ataatccaaa ggatctcaga cccgctcttc cttttccctt cattcccttg   1800
agagtcagcc atgaacggaa tacctgctag gttccaggaa tgagctcacc taacagatag   1860
caaatgtgtc tggttagatc tcagcagagc ccattctgca agacctggct gagccagatg   1920
agagggtggg ccctgtgctg gggggccttg ggtcacacac aggaaccgag acctggcttc   1980
caccccccag tcacccactt gggttatctg ctggaagtta tcgataggac tgtgtggcca   2040
accaagtgct tgtgagatca ctgacactgc aaaaacaaag caaactgctc cgggtaccag   2100
gacttcctcc aacctggcaa gggtgtgcgc tgaggcgggg cttgcaggtg agggggctgt   2160
atgcttcagg aactaactaa atgcatgcag aaggtaagag gcatgatggg aggtgttcaa   2220
gcacagcaat cccatttggg agttattttg atactgcgat gagtaagggt aagggcgcat   2280
ggaatggggc taaggtggga gtgaacactg ggtgaataa attttaaatc aattcaagta   2340
tctcaaaaaa aaaaaaaa                                                 2358
```

```
<210> SEQ ID NO 54
<211> LENGTH: 8821
<212> TYPE: DNA
<213> ORGANISM: Homo sapiens

<400> SEQUENCE: 54
```

```
agatagaaaa agtagtttgc ttggcatctc ccaaattatc ttgagcaaac aataaaataa     60
gaaatgtttc agaagacaat tcggctccca ggcccaaacc aaaactcgaa cctggtactt    120
tttgtaagtg cgggccaaga aaggggctgt aaagttaaag agccggtggc gcctctgaac    180
acacccgggc agggcgagca ggatgtcctt gtccagggag acccccttctc ctggctttga    240
ggaaggtgct ccctatcccc gcgggttcct ccgccaagcg ggacgccgcg ccgggcgggt    300
gagagaaagc ccgggcagga gagcacagag ccggcgactg gacgcgagcg cggggcgggt    360
ggagagcgtc tctccgggcg ccgctgctgt tgtcccgggt gctgaaaagc cgggaacttc    420
```

-continued

```
ccgggaagca gcggcacttt tctccctgga aggctaaaca tatttttgac tggtatgaac    480
ccattctact ttcatgcagt aaatataatt ttacactgct tagtgactct tgtgctgatg    540
tacacctgtg ataaaactgt cttcaagaat cgtggacttg cttttgtaac ggcattgctt    600
tttgctgtac atcctattca tactgaggcg gtggctggga tcgttggcag agcggacgtg    660
ttagcgtgtc tgctgtttct attggccttt ctctcgtaca acaggagtct ggatcagggc    720
tgtgttgggg gaagtttccc ttccacggtg tctcccttct tcttgctgct cagtttgttt    780
ctggggacct gtgcgatgct ggtgaaagag acaggcatca cggtgtttgg agtgtgcttg    840
gtttatgacc tcttttccct ttccaacaag caagacaagt cgagcaatgg ggccctctgt    900
ccacgcagcc cacagcagcc cgggagcccc cagccctcct cactgccagg ccatcctcac    960
cgggagaatg ggaagcagca gcggttccct cacaaaggag cttggggtgg ctgccactct   1020
ccactgccac cagaacccaa gagcagtgga ttcccagtgt ccccacgagc tgtgtggtcc   1080
atgatgagat tcctcaccta ttcctacctc ttggccttca atgtgtggct tctgcttgca   1140
cccgtgaccc tgtgctatga ctggcaggtc ggcagtattc ctctggtaga gaccatatgg   1200
gacatgcgga acttagccac catctttctg gcggttgtga tggccttatt gagcctgcac   1260
tgcttagcag cctttaagag actggagcac aaggaggttt tagtcggctt gttgttcctg   1320
gtgttcccgt tcattccagc cagcaacctc ttcttcaggg tgggttttgt ggtggcggag   1380
agagtccttt acatgcctag catgggctac tgcatccttt ttgtgcatgg actgagcaag   1440
ctctgcactt ggctgaatcg atgtggggcc accaccctga ttgtgtccac tgtgttgctg   1500
ctgttgcttt tctcttggaa aactgtgaaa cagaatgaaa tttggctgtc aagagagtcc   1560
ctattcaggt ctggagttca aactctgccc cacaatgcca aggttcacta caactatgcc   1620
aatttcctga aggaccaagg tcggaacaag gaagcgatct accactacag aacagctctc   1680
aagttgtatc cacgccatgc aagtgcgctc aacaaccttg gaacactgac gagagacaca   1740
gcagaggcaa agatgtacta tcagagggct ctccagctcc atccacagca taaccgggct   1800
cttttcaatc tggggaatct cctcaagtcc caggagaaaa aggaagaagc tatcacctta   1860
ctgaaggatt ccatcaaata tggtccagag tttgcagatg catattcaag cttagcttcg   1920
ttattggctg agcaggagcg gtttaaagaa gctgaagaaa tataccaaac tggaataaag   1980
aactgtccag acagctcaga tttacacaac aactatgggg ttttcttagt tgatactggc   2040
ttaccagaaa aggcagtggc ccattaccag caggccatca aacttagccc cagtcatcac   2100
gtggccatgg tgaacttggg aagactctac aggtcactgg gagagaacag catggctgaa   2160
gaatggtaca agcgcgccct gcaggtggca cacaaagctg agatattgtc acctttggga   2220
gcactgtatt acaacactgg ccgatacgaa gaggctttgc agatttacca ggaagctgca   2280
gcacttcagc cttctcagag ggagctccgc ttggcactgg ctcaggtttt ggccgtgatg   2340
ggtcagacaa aagaagctga aaagatgacc aatcacattg tgtcagagga gaccggatgc   2400
cttgaatgct atcgcctctt gtcagccatc tatagcaagc aggagaacca cgacaaggca   2460
cttgatgcta tagacaaggc tctccagctg aaaccaaagg acccaaaagt catttctgaa   2520
ctttttttca caaaaggaaa ccaattaaga gagcagaacc ttctcgacaa agcttttgag   2580
agctatagag tggctgtgca actaaaccca gaccaagcac aggcctggat gaacatgggt   2640
ggcatccaac acatcaaggg aaaatatgtg tctgcaagag cttattatga gagagcctta   2700
cagctggttc cagacagcaa actgctgaag gaaaatcttg ccaaattgga tcgcctagaa   2760
aaacgattac aagaagttcg agaaaaggat caaacatagc accaccgtct gacccaacct   2820
```

```
cataggataa tgtggtgcct ctgaaagggg agtgatggaa gccttgcttt cacatcagca   2880
ggggcacaac taatgagatt ttctctcatt ccgagttcag ggtgacacat tttgggacat   2940
ctgctggtag cccagtgctg aaggacttgc ttttccatga agaagacgaa aacagcaaac   3000
aagggcaaga aggtctgaga gggaaggaga atgacattta cacattttac agatttttgt   3060
ttggtttaac tccagatttc tcttgatata tctctgtgct tttgagacct ggagatctaa   3120
ttctgtttag acatttttg tcccagaaat acagaagctt gaaatgctat gaaggcagag   3180
cttctattct ttatgggatg aaatatttca aaagaggata aatcctctgt ggtaagccat   3240
ttggaaaatc ctaccaagaa ttggcttatt taattttcca gaaccaggaa tgagtatcta   3300
atagcttttg tagaaccttc cagaatatgt ggggaaaaag ggctattgct aagtgagctt   3360
tatctaatat cctcctaaga gttttactag tgcttttttg aggaattaca gggaagctcc   3420
tggaattgta catggatatc tttatcccta gggggaaatc aaggagctgg gcacccctaa   3480
ttctttatgg aagtgtttaa aactatttta attttattac aagtattact agagtggtgg   3540
ttctactcta agatttcaaa agtgcattta aaatcataca tgttcccgcc tgcaaatata   3600
ttgttatttt ggtggagaaa aaaatagtat attctacata aaaaattaaa gatattaact   3660
aagagaaatg tcctacttta ttatcttaat gttcagacat catgagattt attatttttt   3720
tgaaaaatat attgaaccat tgaggaacct ttatgatgta tcacagaaat cttcatagat   3780
tctaactaga tggaaaaaga gctctattta tttgtgttcc taggcttaat gagaattctg   3840
ggcttagaac atcaacgatt aatacccaga attctttgtt ttgagaatat tatggagaat   3900
gctctaaaaa tctagggtaa agatctaaat tcaaatttta aatatatatt tatatttaag   3960
aaataggaaa ggcaaagttg aactcacaat ttgacattta tttttagtgt tatttatttc   4020
ataacttata aaatatttaa tatatacata cacactcttc tttttctct gtacaaagtg    4080
gttttaatat cagctttcaa aactgatctt ataaaatgta aatctaaatt gtaaaatagt   4140
taagttttaa cagtccctcc caaactttgt gttgattatt cacttgctaa agagatgtga   4200
ggaatcagcc ttcagttttt tggcagtagt atattttgga agtgaagaaa ttggaacacc   4260
tgtttctaat ttggtcttca tcattagaga caaaaccaaa acactccagg cagtactgtt   4320
tatagtgctg agccaggtag cacacagaca tagtagccta aaggctcaca taattcgcat   4380
gctcaggcca gggcagggta aaaatagcct tctgcttctt tcaacccagt atcaggaagc   4440
actaccccag tgttattatt tgttttgtca aggtaagtct aaataaacaa gaaaaacttc   4500
ttcggaaggc atggcgaagg gagtatttta aatgaaaatg attacagaat ttgaattagc   4560
atgcatctct ttgtgtgcaa cagtaatcca agaatgtata tgttaccact acaaccattt   4620
gtttctaata gtttttcat gttatataac ataaatgtat ccacaacctt aattaagaac    4680
tattcttccc ccaaaatcat agtcctagtg tcaagaaaca tactccagtg tttattgtaa   4740
aataacaacc acaccctcaa attgaaaaaa gtgaatgtct aggactttat tacaactttt   4800
cagaataatc tgtaatgaaa actcatgctt aaaaatttaa tggaaaagac tgagccccaa   4860
attttgaata gtgattacgc cttacttgaa gtgctaataa aggtaggaga gtacatttgt   4920
tggaataaca gaaatggtga tttcagccta aaagtttctg agggtaaagg atcacatgac   4980
cttcaggaaa ctctctgcct cctgtaggtg ctttcctatc tcccccatcc ttccctaccc   5040
cttttccctt ttccttcctc tctttttctc tcactgtcac tctgtctaca cacactggca   5100
tcttttgaac actaaaagta agcactgttt tttaaaaaag taattatttg ttggatcaga   5160
tacttttatc ccaagtgaat accttcactg agatgtggcc aatgcaatag tttcacagta   5220
```

-continued

```
aaaacagtgc ctataagaaa atagatcaca tactattttt caatgatatt aagtgtattt   5280
tgtaactatt ttcatttggt ccttgtaaca tgaaataata catggaactt acctttataa   5340
taaaaatgga gtgccctggt tcatcataga ggtgcatcta gtttgccctt aatggaagta   5400
tacttgctgt gtggattgat agcaccttct tgaaatggag gagctcagct ggcctcatgg   5460
atgtgcaatt tttgcagtcc cacagggcct tgcatacaga agcaccccga gctcagttga   5520
atgtctgttt gatttttttct tatttatttt tttgagacac agttccactt tgtctttttg   5580
tcacccagga tggagttcag tggcacaaac atggctcact gtagcctcga cctccctggc   5640
tgaagggatc ctcccacctc agcctcccaa gtaaccgaga ctacaggcat atgccagcat   5700
gtccagctaa tttttgtatt ttttgtagag acagggtttc accatgttgc ccaggctggt   5760
ctcaaactcc tgggctcaag cgatctgccc acctctgcct cccaaagtgc tgggattaaa   5820
ggcataagcc accatgtcca actgaaattc ttaataatta ataatttttg agcaagaggt   5880
ccacactttc attttgcact gggttcccaa acaggtcctg ggtaggaagg atggctgagg   5940
ataaaacagg agttgctttg gcctggctga acatttgaac caatgatcag agtttcattt   6000
tatgattgtg ttactctgaa cagatttgct atttttttcc agctacattt agagttcctc   6060
atgtatatat cacccctctt tttccagtcc atctaacctc tcctttttttt tgtgcctaga   6120
atcagttctc cttgccttca aaatccctga taagtgtcca tttctttttg tatcctttga   6180
tgtagaagcc acaagaatgg ctttagcagc ttattttaat cttatgaatt attcattcag   6240
gattttttaa atgattcaga tgctttcaat ctgttaacag tatttataaa acatgtttca   6300
gtgatacaac ataggtgaac taaaccaaag atgcaaatgc cttggaggaa aagaaattgt   6360
attatagaga atcctgagat atatcctttt gggttgttta atttaaagcc tatcacaaaa   6420
caaagagaat tgtcgcactt taattccaac ctcctgcagt acttcacaac ccttagcata   6480
agattctgaa atttgtaata ggtggtacct agtttgatgc agggttttgc agcagttgtg   6540
cgaatgcctc tgcgcaacgg cctttcagtc agactaaatg agaaaatcca aactgtccta   6600
tcaaaactga cccacaataa ctgtactctg aggcgaaaca gagcaaatgt gggtttcctg   6660
ttttcattgt aaaacattcc aggttctcag attgaagagc tacattcagc tgatagttga   6720
catctgttcc ctcacacgta gtggctctca acacgggctg cactttggaa tcacctgagg   6780
acctttcgga atcttcggtt gaatcatcct ggctgtcctg gtgatgcttc ttatgtgcag   6840
ctaggctgga gaaccactac agggctgaca cctggaatgg gagcttgtaa cttttacaaa   6900
ataatagatg tttatcatct tttgcaattt ttacttttaa gtctatacta aaatgagcca   6960
aagaagtctt aacaatgatg tatggcacaa ttggttggtt gaggctatca ttccatgatt   7020
acaaataggt ggttatgtgg ggtggttttg cacttgtggc aattggactg caatttggcc   7080
ttaaaatgac acaattcctc gttctcagat ggagaggaat tgccttgaaa tttgcatgta   7140
ccagactaag tgccagtata tatatgactg atattttcgt gactcataga aggtgtccat   7200
ggtatagagt ttatgcctac atctctatct ttattttggg cacacatgag cttttgttaa   7260
ttatttcttt gtacttgtta gaatctgttt ttgaaaaaaa aaaaaaactt tgctttgatt   7320
tgtggtggat tcaccttctt aaaataataa atttagagga tattaggaat gacattcaaa   7380
acaaatatag tgagaggtga ttttttaaaa atttttgttc ctggtttcca aattatgttt   7440
actttgattt gattatatgt tggtatctcc caaatatagg ttaacttagc tatttaaatg   7500
gtatcttttg acatttaaaa agaattaagt acctgtcaaa tctagcattg aggttgcagt   7560
tgaataagat aaaagcttag gatgtcaaaa aataatatag agaaatatta taagatttta   7620
```

```
tgattattct tgacgttttt gatgcaaaag gaaaatatgc tgaatagttc ttccaaaaaa   7680
tattatttcc ctcaatattt tatttgtagc catgtaattt aaagagaaca gaaaataact   7740
gcaatcaaaa gtatggttta atatcaatca aagtggcaca acagaattga taagatcttt   7800
ataacaatca attggctgat attaaaatat tgattttaat tgatcttttc aattaaaatc   7860
tttagggcct gtaactcata aaatcagcat ccaccacaat atatggtcat tattggtttg   7920
taagcataga tcaccattga ctcctacctg gagagacatg tctatttcta aaaatccagt   7980
agtttctttg cattctcagt agtacacgtt gtatatatat atatgtaaca aatttggtag   8040
ttttcagtat gtgtgatgtc ctttgggggt tatttatctt gctggtccat aggaggggta   8100
cactacccca agaatcaaga catctgagtt ctagttctag ttctagctct gccactgaag   8160
agccacctta cctggggcaa gttagccatt gtctcccagt catgtttacc acccatgaaa   8220
ggactcgtcg gtttgatgtt tccattaagc tcaatgagta actctaatag ttactcttga   8280
atctggattg aaaaacacca tgcatctgat gagataattc ataaatgttg ccccttttt    8340
aaatgataca accctaaaag tgactgaatt gcccaagtgc ttgaacatgg cagaggtagt   8400
tactcctatt ttgcagtttg tgcacttaaa aattcctaca gtgattgtta ctttactggg   8460
gaaaaaagat gaggtgaaac ttcctcccaa ggaattaaaa tatctgtaga agccatggct   8520
tgcttttata atgtggaaat catttgattt gctgtaattc acgcagatcc ctccttttgt   8580
caggggggaaa tgatttgcat catgttcttt tttcataatg cttttacttc ctgtttggat  8640
cagttgtatg taaatgtaca tttttgttac tttggctgtg cccgttagaa tttatcttcc   8700
ataaagtatt tctcccattg agtctaatga tgtatacttt gcctaggtct ttccaaaatt   8760
aaatttatgt aaatgtctat tttatataaa atatgattaa aataagtatg tctggtttca   8820
a                                                                   8821

<210> SEQ ID NO 55
<211> LENGTH: 3771
<212> TYPE: DNA
<213> ORGANISM: Homo sapiens

<400> SEQUENCE: 55

gcgcggcggg cggcccctcc ccctgccagg tccgggcggg tgcctggagc cgccagagtt     60
tccgcacccg ggagggagat gcggccgggg ctcaggctcc ttgcagttgt aatttagatt    120
cgagaagtgg tttatccttt gactggaaaa gaaaagtagc tgcagtattc ccccagcact    180
tgctgagagc atgccgtatg ccaggctgtg aggctcgaga gacaagcagt ggaagagttg    240
cggcctgttt catctctgga ttgtaaatct gagcctcctt ctggcccctg gaaggggaca    300
gcatcaccat ggaatgattc ctaaccagca taatgctgga gccgggagcc accaacctgc    360
agttttcaga atggccgtgt tggacactga tttggatcac attcttccat cttctgttct    420
tcctccattc tgggctaagt tagtagtggg atcggttgcc attgtgtgtt ttgcacgcag    480
ctatgatgga gactttgtct ttgatgactc agaagctatt gttaacaata aggacctcca    540
agcagaaacg cccctggggg acctgtggca tcatgacttc tggggcagta gactgagcag    600
caacaccagc cacaagtcct accggcctct caccgtcctg actttcagga ttaactacta    660
cctctcggga ggcttccacc ccgtgggctt tcacgtggtc aacatcctcc tgcacagtgg    720
catctctgtc ctcatggtgg acgtcttctc ggttctgttt ggcggcctgc agtacaccag    780
taaaggccgg aggctgcacc tcgcccccag ggcgtccctg ctggccgcgc tgctgtttgc    840
tgtccatcct gtgcacaccg agtgtgttgc tggtgttgtc ggccgtgcag acctcctgtg    900
```

-continued

```
tgccctgttc ttcttgttat ctttccttgg ctactgtaaa gcatttagag aaagtaacaa    960
ggagggagcg cattcttcca ccttctgggt gctgctgagt atctttctgg gagcagtggc   1020
catgctgtgc aaagagcaag ggatcactgt gctgggttta aatgcggtat ttgacatctt   1080
ggtgataggc aaattcaatg ttctggaaat tgtccagaag gtactacata aggacaagtc   1140
attagagaat ctcggcatgc tcaggaacgg gggcctcctc ttcagaatga ccctgctcac   1200
ctctggaggg gctgggatgc tctacgtgcg ctggaggatc atgggcacgg gcccgccggc   1260
cttcaccgag gtggacaacc cggcctcctt tgctgacagc atgctggtga gggccgtaaa   1320
ctacaattac tactattcat tgaatgcctg gctgctgctg tgtccctggt ggctgtgttt   1380
tgattggtca atgggctgca tccccctcat taagtccatc agcgactgga gggtaattgc   1440
acttgcagca ctctggttct gcctaattgg cctgatatgc caagccctgt gctctgaaga   1500
cggccacaag agaaggatcc ttactctggg cctgggattt ctcgttatcc catttctccc   1560
cgcgagtaac ctgttcttcc gagtgggctt cgtggtcgca gagcgtgtcc tctacctccc   1620
cagcgttggg tactgtgtgc tgctgacttt tggattcgga gccctgagca aacataccaa   1680
gaaaaagaaa ctcattgccg ctgtcgtgct gggaatctta ttcatcaaca cgctgagatg   1740
tgtgctgcgc agcggcgagt ggcggagtga ggaacagctt ttcagaagtg ctctgtctgt   1800
gtgtcccctc aatgctaagg ttcactacaa cattggcaaa aacctggctg ataaaggcaa   1860
ccagacagct gccatcagat actaccggga agctgtaaga ttaaatccca agtatgttca   1920
tgccatgaat aatcttggaa atatcttaaa agaaaggaat gagctacagg aagctgagga   1980
gctgctgtct ttggctgttc aaatacagcc agactttgcc gctgcgtgga tgaatctagg   2040
catagtgcag aatagcctga aacggtttga agcagcagag caaagttacc ggacagcaat   2100
taaacacaga aggaaatacc cagactgtta ctacaacctc gggcgtctgt atgcagatct   2160
caatcgccac gtggatgcct tgaatgcgtg gagaaatgcc accgtgctga aaccagagca   2220
cagcctggcc tggaacaaca tgattatact cctcgacaat acaggtaatt tagcccaagc   2280
tgaagcagtt ggaagagagg cactggaatt aatacctaat gatcactctc tcatgttctc   2340
gttggcaaac gtgctgggga aatcccagaa atacaaggaa tctgaagctt tattcctcaa   2400
ggcaattaaa gcaaatccaa atgctgcaag ttaccatggt aatttggctg tgctttatca   2460
tcgttgggga catctagact tggccaagaa acactatgaa atctccttgc agcttgaccc   2520
cacggcatca ggaactaagg agaattacgg tctgctgaga agaaagctag aactaatgca   2580
aaagaaagct gtctgatcct gtttccttca tgttttgagt ttgagtgtgt gtgtgcatga   2640
ggcatatcat taatagtatg tggttacatt taaccattta aaagtcttag acatgttatt   2700
ttactgattt ttttctatga aaacaaagac atgcaaaaag attatagcac cagcaatata   2760
ctcttgaatg cgtgatatga tttttcattg aaattgtatt ttttcagaca actcaaatgt   2820
aattctaaaa ttccaaaaat gtcttttttta attaaacaga aaaagagaaa aaattatctt   2880
gagcaacttt tagtagaatt gagcttacat ttgggatctg agccttgtcg tgtatggact   2940
agcactatta aacttcaatt atgaccaaga aaggatacac tggcccctac aatttgtata   3000
aatattgaac atgtctatat attagcattt ttatttaatg acaaagcaaa ttaagttttt   3060
ttatctcttt tttttaaaac aacatactgt gaactttgta aggaaatatt tatttgtatt   3120
tttatgtttt gaatagggca aataatcgaa tgaggaatgg aagttttaac atagtatatc   3180
tatatgcttt tccccatagg aagaaattga ctcttgcagt ttttggatgc tctgacttgt   3240
gcaatttcaa tacacaggag attatgtaat gtaatatttt acataagcgg ttactatcaa   3300
```

-continued ttgaaagttc aagccatgct ttaggcaaga gcaggcagcc tcacatcttt atttttgtta 3360
catccaaggt gaagagggca acacatctgt gtaagctgct ttttagtgtg tttatctgaa 3420
ggccgttttc cattttgctt aatgtaacta cagacattat ccagaaaatg caaaattttc 3480
tatcaaatgg agccacattc ggggaattcg tggtattttt aagaattgag ttgttcctgc 3540
tgttttttat ttgatccaaa caatgttttg ttttgttctt ctctgtatgc tgttgaccta 3600
atgatttatg caatctctgt aatttcttat gcagtaaaat tactacacaa actagcatga 3660
aaatgtcata ttgccttctt aatcaattat tttcaagtag tgaactttgt atcctccttt 3720
accttaaaat gaaatcaaac tgaccaaatc atcaaaaaaa aaaaaaaaaa a 3771

<210> SEQ ID NO 56
<211> LENGTH: 4077
<212> TYPE: DNA
<213> ORGANISM: Homo sapiens

<400> SEQUENCE: 56
cgggcctcga gccgaggcag cagtgggaac gactcatcct ttttccagcc ctggggcgtg 60
gctggggtcg gggtcggggt cggggccggt gggggccccg cccccgtctc ctggcctgcc 120
cccttcatgg gccgcgatga tggcggccct gtacccgagc acggacctct cgggcgcctc 180
ctcctcctcc ctgccttcct ctccatcctc ttcctcgccg aacgaggtga tggcgctgaa 240
ggatgtgcgg gaggtgaagg aggagaatac gctgaatgag aagcttttct tgctggcgtg 300
cgacaagggt gactattata tggttaaaaa gattttggag gaaaacagtt caggtgactt 360
gaacataaat tgcgtagatg tgcttgggag aaatgctgtt accataacta ttgaaaacga 420
aaacttggat atactgcagc ttcttttgga ctacggttgt cagaaactaa tggaacgaat 480
tcagaatcct gagtattcaa caactatgga tgttgcacct gtcattttag ctgctcatcg 540
taacaactat gaaattctta caatgctctt aaaacaggat gtatctctac ccaagcccca 600
tgcagttggc tgtgaatgca cattgtgttc tgcaaaaaac aaaaaggata gcctccggca 660
ttccaggttt cgtcttgata tatatcgatg tttggccagt ccagctctaa taatgttaac 720
agaggaggat ccaattctga gagcatttga acttagtgct gatttaaaag aactaagtct 780
tgtggaggtg gaattcagga atgattatga ggaactagcc cggcaatgta aaatgtttgc 840
taaggattta cttgcacaag cccggaattc tcgtgaattg gaagttattc taaaccatac 900
gtctagtgac gagcctcttg acaaacgggg attattagaa gaaagaatga atttaagtcg 960
tctaaaactt gctatcaaat ataaccagaa agagtttgtc tcccagtcta actgccagca 1020
gttcctgaac actgtttggt ttggacagat gtcgggttac cgacgcaagc ccacctgtaa 1080
gaagataatg actgttttga cagtaggcat cttttggcca gttttgtcac tttgttattt 1140
gatagctccc aaatctcagt ttggcagaat cattcacaca ccttttatga aatttatcat 1200
tcatggagca tcatatttca catttctgct gttgcttaat ctatactctc ttgtctacaa 1260
tgaggataag aaaaacacaa tggggccagc ccttgaaaga atagactatc ttcttattct 1320
gtggattatt gggatgattt ggtcagacat taaaagactc tggtatgaag ggttggaaga 1380
ctttttagaa gaatctcgta atcaactcag ttttgtcatg aattctcttt atttggcaac 1440
ctttgccctc aaagtggttg ctcacaacaa gtttcatgat tttgctgatc ggaaggattg 1500
ggatgcattc catcctacac tggtggcaga agggcttttt gcatttgcaa atgttctaag 1560
ttatcttcgt ctcttttta tgtatacaac cagctctatc ttgggtccat tacagatttc 1620
aatgggacag atgttacaag attttggaaa atttcttggg atgtttcttc ttgttttgtt 1680

-continued

```
ttctttcaca attggactga cacaactgta tgataaagga tatacttcaa aggagcagaa   1740
ggactgtgta ggcatcttct gtgaacagca aagcaatgat accttccatt cgttcattgg   1800
cacctgcttt gctttgttct ggtatatttt ctccttagcg catgtggcaa tctttgtcac   1860
aagatttagc tatggagaag aactgcagtc ctttgtggga gctgtcattg ttggtacata   1920
caatgtcgtg gttgtgattg tgcttaccaa actgctggtg gcaatgcttc ataaaagctt   1980
tcagttgata gcaaatcatg aagacaaaga atggaagttt gctcgagcaa aattatggct   2040
tagctacttt gatgacaaat gtacgttacc tccacctttc aacatcattc cctcaccaaa   2100
gactatctgc tatatgatta gtagcctcag taagtggatt tgctctcata catcaaaagg   2160
caaggtcaaa cggcaaaaca gtttaaagga atggaggaat ttgaaacaga agagagatga   2220
aaactatcaa aaagtgatgt gctgcctagt gcatcgttac ttgacttcca tgagacagaa   2280
gatgcaaagt acagatcagg caactgtgga aaatctaaac gaactgcgcc aagatctgtc   2340
aaaattccga aatgaaataa gggatttact tggctttcgg acttctaaat atgctatgtt   2400
ttatccaaga aattaaccat tttctaaatc atggagcgaa taattttcaa taacagatcc   2460
aaaagactat attgcataac ttgcaatgaa attaatgaga tatatattga aataaagaat   2520
tatgtaaaag ccattcttta aaatatttat agcataaata tatgttatgt aaagtgtgta   2580
tatagaatta gtttttttaaa ccttctgtta gtggcttttt gcagaagcaa aacagattaa   2640
gtagatagat tttgttagca tgctgcttgg ttttcttact tagtgcttta aaatgttttt   2700
ttttatgttt aagaggggca gttataaatg gacacattgc ccagaatgtt ttgtaaaatg   2760
aagaccagca aatgtaggct gatctccttc acaggataca cttgaaatat agaagttatg   2820
ttttaaatat ctctgtttta ggagttcaca tatagttcag catttattgt ttaggagtat   2880
aattttattt tatctaaaat aatagtctat tttttctttt gtattttgtt ataatcttaa   2940
gcaacaaaga aaaaaccta atatttgaat ctatttatgt ctttcaattt aaattcactt   3000
cagtttttgt tattgtaata tatttacttt tacatggtta taatcacttt atatttttaa   3060
tgttttttc acttaatatt ttatatatac atttccatgt attgatgtag ttagtccaca   3120
tttaaatttt tatagaatta tatagttttt gaaaaataca gtcagtagat gttttatttt   3180
ttagctattc agttatgttt ataagtttgc atagctactt ctcgacattt ggtttgtttt   3240
aatttttttg tatcataata gtcctatttt tttttcaagt tggagtgaat gtttttagtt   3300
ttaagataga taggagacac ttttttatca catgtagtca caacctgttt tgtttttgta   3360
aaacatagga agtctcttta atgcaatgat ttgttttata tttggactaa ggttcttgag   3420
cttatctccc aaggtacttt ccataattta acacagcttc tataaaagtg acttcatgct   3480
tacttgtgga tcattcttgc tgcttaagat gaaaagcatt ggttttttaa aattagagaa   3540
taaaatatgt atttaaattt ttggtgtgtt cacataaagg gatgtagcta aaatgttttc   3600
ataggctatt atatattctc gcagcatttc cagttaagag gatattaggt atataattct   3660
cttcttaacc gaatgtcaga tggtcttacg ccacagggtg caggtaaccc ttggtctgta   3720
agcaccaccg atccagggat cattgtctaa ataggttact attgtttgtt tcatcttgct   3780
tttgcatttt tattttttaa tttccaaatt ttaagtgttc cctctttggg gcaaattctt   3840
ataaaaatgt ttattgtaaa gttatatatt ttgtctacga tgggattatg cacttcccaa   3900
ttgggatttt acatctggat ttttagtcat tctaaaaaac acctaattat taaaacattt   3960
atagagtgcc tactgtatgc atgagttgag ttgcttctga ggtacatttt gaatgacagc   4020
atattgtaag aaaaaaaaag gtgaataaaa tttgacatta gattataaaa aaaaaaa      4077
```

<210> SEQ ID NO 57
<211> LENGTH: 1297
<212> TYPE: DNA
<213> ORGANISM: Homo sapiens

<400> SEQUENCE: 57
gtgagagcca ggcgtccctc tgcctgccca ctcagtggca acacccggga gctgttttgt 60
cctttgtgga gcctcagcag ttccctcttt cagaactcac tgccaagagc cctgaacagg 120
agccaccatg cagtgcttca gcttcattaa gaccatgatg atcctcttca atttgctcat 180
ctttctgtgt ggtgcagccc tgttggcagt gggcatctgg gtgtcaatcg atggggcatc 240
ctttctgaag atcttcgggc cactgtcgtc cagtgccatg cagtttgtca acgtgggcta 300
cttcctcatc gcagccggcg ttgtggtctt tgctcttggt ttcctgggct gctatggtgc 360
taagactgag agcaagtgtg ccctcgtgac gttcttcttc atcctcctcc tcatcttcat 420
tgctgaggtt gcagctgctg tggtcgcctt ggtgtacacc acaatggctg agcacttcct 480
gacgttgctg gtagtgcctg ccatcaagaa agattatggt tcccaggaag acttcactca 540
agtgtggaac accaccatga aagggctcaa gtgctgtggc ttcaccaact atacggattt 600
tgaggactca ccctacttca aagagaacag tgcctttccc ccattctgtt gcaatgacaa 660
cgtcaccaac acagccaatg aaacctgcac caagcaaaag gctcacgacc aaaaagtaga 720
gggttgcttc aatcagcttt tgtatgacat ccgaactaat gcagtcaccg tgggtggtgt 780
ggcagctgga attgggggcc tcgagctggc tgccatgatt gtgtccatgt atctgtactg 840
caatctacaa taagtccact tctgcctctg ccactactgc tgccacatgg gaactgtgaa 900
gaggcaccct ggcaagcagc agtgattggg ggaggggaca ggatctaaca atgtcacttg 960
ggccagaatg gacctgccct ttctgctcca gacttggggc tagataggga ccactccttt 1020
taggcgatgc ctgactttcc ttccattggt gggtggatgg gtgggggggca ttccagagcc 1080 tctaaggtag ccagttctgt tgcccattcc cccagtctat taaacccttg atatgccccc 1140
taggcctagt ggtgatccca gtgctctact gggggatgag agaaaggcat tttatagcct 1200
gggcataagt gaaatcagca gagcctctgg gtggatgtgt agaaggcact tcaaaatgca 1260
taaacctgtt acaatgttaa aaaaaaaaaa aaaaaaa 1297

<210> SEQ ID NO 58
<211> LENGTH: 1480
<212> TYPE: DNA
<213> ORGANISM: Homo sapiens

<400> SEQUENCE: 58
agactgtccc gagcttcccc cgggcgggca gagggaagcc ggctggggat gaggagtgga 60
ggaggcagga atgcctggga cactcgcggg gcatgtgagc aggcccagaa gccatggccc 120
actataagac tgagcaggac gactggctga tcatctactt gaagtattta ctctttgtct 180
tcaacttctt cttctgggtc gggggagcag ccgtcctggc tgtgggcatc tggaccctgg 240
tggagaagag tggctacctc agcgtcctgg cctccagcac ctttgccgcc tccgcctaca 300
tcctcatctt tgcgggcgta cttgtcatgg tgaccggctt cctgggcttc ggtgccatcc 360
tctgggagcg gaagggctgc ctctccacgt atttctgcct gttgctcgtc atcttcctgg 420
ttgagctggt ggcgggagtc ctggcccatg tgtattacca gaggctgagt gatgaactga 480
agcagcactt gaaccggact ctggctgaga actacgggca gcccggagcc acgcagatca 540
ccgcctcagt ggaccgactc cagcaggatt tcaagtgctg tggaagcaac agctcagccg 600

-continued

```
actggcagca cagcacgtac atcctgttgc gggaggccga gggccgccag gtgcccgaca    660
gctgctgcaa gacagtggtg gtgcgctgcg gccagcgggc ccacccctcc aacatctata    720
aggtggaggg aggctgcctc accaagctgg agcagttcct ggccgaccac ctgctgctta    780
tgggggcagt gggcatcggg gtggcctgcc tgcagatctg cgggatggtt ctcacctgct    840
gcttgcacca gaggctccag cggcattttt actaatggcc aaccacctcc tcttccaact    900
gcccctcaag acaacatgtg gccacatgcc atctgcaagg cctgcagagt tagcaccagc    960
tccactaggg ccatagatgc cccctccttt gtgcctagct cctgcgaatc caccgagtgc   1020
ctgagaccat agcttctgtg cccacccagg cagagaccct cggccccctc tcctccattt   1080
ctgagccccc atggccagat cctgggcagg gaaatgatcc tttcaggaga caaccagagc   1140
ccctcaccag gaacgggggc acccgtggac tacgggaggg tggcggttgg gttctctgct   1200
ccctcccagc tcctgaacct ggaacaatcg gcagaaaacc caggaacccc ggcactcctg   1260
cattcagcac gggattcccc cacccatgcc cagaagccct gaccttgctg tttctggaaa   1320
aagcatgggg tggggcaggg agggctggca tttcccccag aagaccttgc cctttgacct   1380
gcccactctc cacactgcct cacctggaaa gccatgtcct gctggcctca ttccttcctg   1440
aagggcctag gagtggggag gcctgggtag ggcagccaca                         1480
```

<210> SEQ ID NO 59
<211> LENGTH: 2579
<212> TYPE: DNA
<213> ORGANISM: Homo sapiens

<400> SEQUENCE: 59

```
ggccctggct gccgccgctg cctcgtccgg actcggagag gacttgggag ggacagcggc     60
gctgggaggt ggcttagcag agactttcca gcaactgctg cccaggactt tttttttttt    120
ttttcttttt cccaggaggc ggcgacggcg gcggcggggg gagaggaaga gaaagaagcg    180
tctccagctg aagccaatgc agccctccgg ctctccgcga agaagttccc tgccccgatg    240
agcccccgcc gtgcgtcccc gactatcccc aggcgggcgt ggggcaccgg gcccagcgcc    300
gacgatcgct gccgttttgc ccttgggagt aggatgtggt gaaaggatgg ggcttctccc    360
ttacggggct cacaatggcc agagaagatt ccgtgaagtg tctgcgctgc ctgctctacg    420
ccctcaatct gctcttttgg ttaatgtcca tcagtgtgtt ggcagtttct gcttggatga    480
gggactacct aaataatgtt ctcactttaa ctgcagaaac gagggtagag gaagcagtca    540
ttttgactta ctttcctgtg gttcatccgg tcatgattgc tgtttgctgt ttccttatca    600
ttgtggggat gttaggatat tgtggaacgg tgaaaagaaa tctgttgctt cttgcatggt    660
actttggaag tttgcttgtc attttctgtg tagaactggc ttgtggcgtt tggacatatg    720
aacaggaact tatggttcca gtacaatggt cagatatggt cactttgaaa gccaggatga    780
caaattatgg attacctaga tatcggtggc ttactcatgc ttggaatttt tttcagagag    840
agtttaagtg ctgtggagta gtatatttca ctgactggtt ggaaatgaca gagatggact    900
ggcccccaga ttcctgctgt gttagagaat tcccaggatg ttccaaacag gcccaccagg    960
aagatctcag tgacctttat caagagggtt gtgggaagaa aatgtattcc tttttgagag   1020
gaaccaaaca actgcaggtg ctgaggtttc tgggaatctc cattggggtg acacaaatcc   1080
tggccatgat tctcaccatt actctgctct gggctctgta ttatgataga agggagccgg   1140
ggacagacca aatgatgtcc ttgaagaatg acaactctca gcacctgtca tgtccctcag   1200
tagaactgtt gaaaccaagc ctgtcaagaa tctttgaaca cacatccatg gcaaacagct   1260
```

```
ttaatacaca ctttgagatg gaggagttat aaaaagaaat gtcacagaag aaaaccacaa   1320

acttgtttta ctggacttgt gaatttttga gtacatacta tgtgtttcag aaatatgtag   1380

aaataaaaat gttgccataa aataacacct aagcatatac tattctatgc tttaaaatga   1440

ggatggaaaa gtttcatgtc ataagtcacc acctggacaa taattgatgc ccttaaaatg   1500

ctgaagacag atgtcatacc cactgtgtag cctgtgtatg acttttactg aacacagtta   1560

tgttttgagg cagcatggtt tgattagcat ttccgcatcc atgcaaacga gtcacatatg   1620

gtgggactgg agccatagta aaggttgatt tacttctacc aactagtata taaagtacta   1680

attaaatgct aacataggaa gttagaaaat actaataact tttattactc agcgatctat   1740

tcttctgatg ctaaataaat tatatatcag aaaactttca atattggtga ctacctaaat   1800

gtgatttttg ctggttacta aaatattctt accacttaaa agagcaagct aacacattgt   1860

cttaagctga tcagggattt tttgtatata agtctgtgtt aaatctgtat aattcagtcg   1920

atttcagttc tgataatgtt aagaataacc attatgaaaa ggaaaatttg tcctgtatag   1980

catcattatt tttagccttt cctgttaata aagctttact attctgtcct gggcttatat   2040

tacacatata actgttattt aaatacttaa ccactaattt tgaaaattac cagtgtgata   2100

cataggaatc attattcaga atgtagtctg gtctttagga agtattaata agaaaatttg   2160

cacataactt agttgattca gaaaggactt gtatgctgtt tttctcccaa atgaagactc   2220

tttttgacac taaacacttt ttaaaaagct tatctttgcc ttctccaaac aagaagcaat   2280

agtctccaag tcaatataaa ttctacagaa aatagtgttc tttttctcca gaaaaatgct   2340

tgtgagaatc attaaaacat gtgacaattt agagattctt tgttttattt cactgattaa   2400

tatactgtgg caaattacac agattattaa atttttttac aagagtatag tatatttatt   2460

tgaaatggga aaagtgcatt ttactgtatt ttgtgtattt tgtttatttc tcagaatatg   2520

gaaagaaaat taaaatgtgt caataaatat tttctagaga gtaaaaaaaa aaaaaaaaa    2579


<210> SEQ ID NO 60
<211> LENGTH: 2605
<212> TYPE: DNA
<213> ORGANISM: Homo sapiens

<400> SEQUENCE: 60

ggcggggccc ggtccagagg cggggacagc agggctccgg gcaaggaggt ctggatgctg     60

agggcggtcc ctgaggggcg ggcggggccc gaccggcgct ctgtgtggcc gaggccatga    120

agccgcagcc gcccggctag gccccgggcg gctctagccc agggcggccc gcggggcgct    180

gggcctggct cccggctccg gtttccgggc cggcgggtgg ccgctcacca tgcccggcaa    240

gcaccagcat ttccaggaac ctgaggtcgg ctgctgcggg aaatacttcc tgtttggctt    300

caacattgtc ttctgggtgc tgggagccct gttcctggct atcggcctct gggcctgggg    360

tgagaagggc gttctctcga acatctcagc gctgacagat ctgggaggcc ttgaccccgt    420

gtggctgttt gtggtagttg gaggcgtcat gtcggtgctg ggctttgctg gctgcattgg    480

ggccctccgg gagaacacct tcctgctcaa gtttttctcc gtgttcctcg gtctcatctt    540

cttcctggag ctggcaacag ggatcctggc ctttgtcttc aaggactgga ttcgagacca    600

gctcaacctc ttcatcaaca acaacgtcaa ggcctaccgg gacgacattg acctccagaa    660

cctcattgac tttgctcagg aatactggtc ttgctgcgga gcccgaggcc ccaatgactg    720

gaacctcaat atctacttca actgcactga cttgaacccc agccgggagc gctgcggggt    780

gcccttctcc tgctgcgtca gggaccctgc ggaggatgtc ctcaacaccc agtgtggcta    840
```

cgacgtccgg ctcaaactgg tgagagggga gctggagcag cagggcttca tccacaccaa 900
aggctgcgtg ggccagtttg agaagtggct gcaggacaac ctgattgtgg tggcgggagt 960
cttcatgggc atcgccctcc tccagatctt tggcatctgc ctggcccaga acctcgtgag 1020
tgacatcaag gcagtgaaag ccaactggag caaatggaat gatgactttg aaaaccactg 1080
gcttacgccc accatttccg aggtcctgtc cacggcgggg cctcagcaga actctctgac 1140
tggggcccct ggcccggccc cacccagccg acatgttttc tttggcctgg gtggtttata 1200
ccctgagcca acctttaaaa attggtagat ttcacataaa agtccagatc cacagcttct 1260
cttgaagaat gaccacctgg ctacgccggc tcttcggtgg caacactacc tgggacactg 1320
cctccccagt caccaagggc cccagctggc ccgttctact cacctaagtg ccgcctgacc 1380
cttgtacact aggagctggc ctcccacctc tgcagggtta ttccctgcac ctcgaggccg 1440
ctgcgggcca atctggagtg aaacacgggg acctgaagga tggagaggct ggaccccgct 1500
ttgaagaggg tgcagcctgg gaagggcggc cttgctgggg actgcggtgg gagtagagtg 1560
cccaggagag ggtctgaggg gtgggatggg ggtcaggaca attttgcaaa agaagtagct 1620
ggaagccatg ggactggcgg gagcctgttt gggggatctg gatggttgac tcctaggagt 1680
caagttcagc atcttcaccg tggctgcaga gctgcctgat gggcactaga gggcatgcca 1740
gccccacact ccctgggtct ggcttcctcc cgcaacctca ctctagtaga gcctgtgcct 1800
gcctactagc gctctggggt tcggagagtt tgggaatttc tcagagccaa ctggctcagg 1860
cttgggaagg ctggctgctg ccctcagctc cgcctcatca gctatgtgaa ggggtgtgtg 1920
tggagtgatc ctgccgcccc ctccctgggc tcgtccagag atctcaaact ccgatgcccc 1980
tggggccacg tatgttgtat aaatggatga aacaggccct tgagttggga gcctgcttca 2040
ctttgacttt cccactgttg ctggagacaa agacatcgtg atgagagaaa gttcgcacaa 2100
tctagtcggt aacagccact ttccttgaga ccaagagagt gcggtgggga tgggggggag 2160
agcacgggtc cccgtctgac agtggccgct gccatattca ggtgtagcta attgctctgg 2220
tgtgggaatg caggcctaat gacagaaatc tggagaagcc agaaatacag atttgtatgt 2280
gagatgtcct gattttttaa gttgttggca gaaattaatt cagaaatcaa atctgcaggc 2340
caaacaaggt gcaggaccca gctttggccc catgcccctg taggtccctc tgggacagtc 2400
accgctgggg tcctggctgc tctgtcattg agggatgctg ggcactgctg ccgggtggcc 2460
agggtatggg gcatgtgccc agcaatgtgg ctccttggcc ccgctggcca gtgtcctggg 2520
cccctgacag gcgctggctg tgagtggttt gtacatgcta caataaatgc agctggcagc 2580
attgtgcaaa aaaaaaaaaa aaaaa 2605

<210> SEQ ID NO 61
<211> LENGTH: 1159
<212> TYPE: DNA
<213> ORGANISM: Homo sapiens

<400> SEQUENCE: 61
agtgccccag gagctatgac aagcaaagga acatacttgc ctggagatag cctttgcgat 60
atttaaatgt ccgtggatac agaaatctct gcaggcaagt tgctccagag catattgcag 120
gacaagcctg taacgaatag ttaaattcac ggcatctgga ttcctaatcc ttttccgaaa 180
tggcaggtgt gagtgcctgt ataaaatatt ctatgtttac cttcaacttc ttgttctggc 240
tatgtggtat cttgatccta gcattagcaa tatgggtacg agtaagcaat gactctcaag 300
caatttttgg ttctgaagat gtaggctcta gctcctacgt tgctgtggac atattgattg 360

```
ctgtaggtgc catcatcatg attctgggct tcctgggatg ctgcggtgct ataaaagaaa    420

gtcgctgcat gcttctgttg tttttcatag gcttgcttct gatcctgctc ctgcaggtgg    480

cgacaggtat cctaggagct gttttcaaat ctaagtctga tcgcattgtg aatgaaactc    540

tctatgaaaa cacaaagctt ttgagcgcca caggggaaag tgaaaaacaa ttccaggaag    600

ccataattgt gtttcaagaa gagtttaaat gctgcggttt ggtcaatgga gctgctgatt    660

ggggaaataa ttttcaacac tatcctgaat tatgtgcctg tctagataag cagagaccat    720

gccaaagcta taatggaaaa caagtttaca aagagacctg tatttctttc ataaaagact    780

tcttggcaaa aaatttgatt atagttattg gaatatcatt tggactggca gttattgaga    840

tactgggttt ggtgttttct atggtcctgt attgccagat cgggaacaaa tgaatctgtg    900

gatgcatcaa cctatcgtca gtcaaacccc tttaaaatgt tgctttggct ttgtaaattt    960

aaatatgtaa gtgctatata agtcaggagc agctgtcttt ttaaaatgtc tcggctagct   1020

agaccacaga tatcttctag acatattgaa cacatttaag atttgaggga tataagggaa   1080

aatgatatga atgtgtattt ttactcaaaa taaaagtaac tgtttacgtt aaaaaaaaaa   1140

aaaaaaaaaa aaaaaaaaa                                                1159
```

<210> SEQ ID NO 62
<211> LENGTH: 2821
<212> TYPE: DNA
<213> ORGANISM: Homo sapiens

<400> SEQUENCE: 62

```
gaaggagtgg acccaacctg gccgcgccgc agaagtggct cccgaggaag ccggcgccgg     60

ggccgccgcc tcgtgtcccc tcggggcgca gtgctcgggg gtcggcgggc cagagccgag    120

gcgcggccgg ggagccgggg gctgcggggc cgagcgggca gccgcgcgag ggggcgggcg    180

ctcggcgacc cgggggccgg ccgggctgag ccccgcgccc cgggacgcgg gctggaagcg    240

acggaggagt gctgccgcgg gctgcggacc agcgccgtcc cctcacggag cggggattct    300

gctatgacag ttgggctccc cggagggtta acctgggtgt cctcggcaaa gttgtcgccg    360

agccgggagc ccgtgtaggg gccgcggcgc cgcggctcgg ggggcggccg ggcggccggc    420

ggcggtcgtg gctcggcggg gcccgcgcgg ccggggggct cctgggggtg tgcgccccca    480

gccggctgcc ctcgtggatg cctcccggcg gcggcgggcc catgaaagac tgcgagtaca    540

gccagatcag cacccacagc tcctccccca tggagtcgcc ccacaagaag aagaaaatcg    600

cggcccggag gaaatgggag gtgttcccgg gaagaaacaa gttcttctgt aacgggagga    660

tcatgatggc ccggcagacg ggcgtcttct acctgacgct cgtcctcatc ctggtcacta    720

gcggactctt cttcgccttc gactgtccgt acctggcggt gaaaatcacc cctgccatcc    780

ctgcagtcgc tggcatcctg ttcttctttg tgatggggac cctgctccgc accagcttca    840

gcgaccccgg agtcctccca cgagccacgc ctgatgaagc cgccgatctg gaaaggcaaa    900

tagatatcgc aaacggcacc agttcagggg ggtaccgccc gcctcccaga accaaagaag    960

tcatcatcaa tggccagacc gtgaaactta aatactgttt cacctgcaag attttccggc   1020

cccctcgcgc ctcccattgc agcctttgtg ataactgcgt agaacggttt gatcaccact   1080

gtccctgggt aggcaactgt gtggggaaaa gaaactacag atttttttat atgtttattt   1140

tatctctgtc ttttctgaca gtctttatat ttgcattcgt tatcacccac gtcattcttc   1200

gttcacagca aacaggattc ctaaatgccc ttaaggacag tcctgcaagc gtcctggagg   1260

ctgtggtgtg cttcttctct gtctggtcca tcgttggcct ctcaggattc cacacctact   1320
```

tgatcagctc caaccagaca acaaatgagg acattaaagg atcctggtca aataaaagag 1380
gtaaagaaaa ttacaatccc tacagctacg gaaatatctt taccaactgc tgtgttgccc 1440
tgtgtgggcc catctcacca agcctgatcg acagaagagg gtacatccag cccgacacgc 1500
cgcagccagc agcaccctcc aatggcatca ccatgtacgg ggccacgcag tcacagagtg 1560
acatgtgcga ccaagaccag tgcattcaga gcaccaaatt cgttttgcag gctgcagcca 1620
cgcccctgct gcagagcgag cccagcctca ccagcgacga gctgcacctg cccgggaagc 1680
ctggcctggg cacgccctgc gccagcctca cactgggccc gcccacaccg cccgcctcca 1740
tgcccaacct cgccgaggcc acgctcgcgg acgtgatgcc ccggaaagat gagcacatgg 1800
gccaccagtt cctgacgccc gatgaggcgc cctcgccccc caggctactg gcggcgggca 1860 gcccccctggc gcacagccgc accatgcacg tgctgggcct ggccagccag gactccctgc 1920
atgaggactc tgtgcgcggc ctggtgaagc tcagctccgt gtgacccaca tggccccagg 1980
ccgggggaca ccagaggctc ctccatgggc agcaggagtg agcggagggg tgtgtcccac 2040
agcgactttc ccagccaatg ccacggtgga gatgacagcc ccaggtctgg ggtacagaga 2100
ccacttagga tggcacaggg tggctggccc cggatgctga gagcttggtt tcatttgaat 2160
tttcttcccc aacctgagtg ctttgacaac aatggaaata gagaagtggc tgctttcttt 2220
tggtgaccct ccaggggtgg aatcggagtg tgtctgcccg cccttgtgac agacacacgg 2280
aaggcttctg acgcttgtgg ccagactgca attgcactta tgtgttatgc tactaatatt 2340
tgaaacagac ctgccattcc atttgttaat taaaaaaaaa aaaaatccta aagggaaaaa 2400
accgaccagg tgtggatctg catgccacgc tgccgtctgt gttacagtgg tgttgctatt 2460
tccaaggaag tgctgctttc tttttctttt tttaattttg tgaattttca agtgctgttt 2520
tgttggaaga cagtgcaacg aactgagact aatggacagt gtcatcactc agcttactgg 2580
gctgaggcgt ctgtggagag gtggcaccgg ggctgcagag ggcggctggg gttccgtcgt 2640
gtcgggtgtc acttcacctt ctgtttggcc gctcgatgag gtctcgtgtt gagatattgt 2700
gtgccacaac ccccacagtc ttcacctccg tgtgtgatga aacttcccgt ggacagccaa 2760
taaaatgacg tcctctgtta ttttggaaaa aaaaaaaaaa aaaaaaaaaa aaaaaaaaaa 2820
a 2821

<210> SEQ ID NO 63
<211> LENGTH: 5190
<212> TYPE: DNA
<213> ORGANISM: Homo sapiens

<400> SEQUENCE: 63
tctgggggct cggctttgcc gcgctcgctg cacttgggcg agagctggaa cgtggaccag 60
agctcggatc ccatcgcagc taccgcgatg agaggcgctc gcggcgcctg ggattttctc 120
tgcgttctgc tcctactgct tcgcgtccag acaggctctt ctcaaccatc tgtgagtcca 180
ggggaaccgt ctccaccatc catccatcca ggaaaatcag acttaatagt ccgcgtgggc 240
gacgagatta ggctgttatg cactgatccg ggctttgtca aatggacttt tgagatcctg 300
gatgaaacga atgagaataa gcagaatgaa tggatcacgg aaaaggcaga agccaccaac 360
accggcaaat acacgtgcac caacaaacac ggcttaagca attccattta tgtgtttgtt 420
agagatcctg ccaagctttt ccttgttgac cgctccttgt atgggaaaga agacaacgac 480
acgctggtcc gctgtcctct cacagaccca gaagtgacca attattccct caaggggtgc 540
caggggaagc ctcttcccaa ggacttgagg tttattcctg accccaaggc gggcatcatg 600

-continued

```
atcaaaagtg tgaaacgcgc ctaccatcgg ctctgtctgc attgttctgt ggaccaggag    660
ggcaagtcag tgctgtcgga aaaattcatc ctgaaagtga ggccagcctt caaagctgtg    720
cctgttgtgt ctgtgtccaa agcaagctat cttcttaggg aaggggaaga attcacagtg    780
acgtgcacaa taaaagatgt gtctagttct gtgtactcaa cgtggaaaag agaaaacagt    840
cagactaaac tacaggagaa atataatagc tggcatcacg gtgacttcaa ttatgaacgt    900
caggcaacgt tgactatcag ttcagcgaga gttaatgatt ctggagtgtt catgtgttat    960
gccaataata cttttggatc agcaaatgtc acaacaacct tggaagtagt agataaagga   1020
ttcattaata tcttccccat gataaacact acagtatttg taaacgatgg agaaaatgta   1080
gatttgattg ttgaatatga agcattcccc aaacctgaac accagcagtg gatctatatg   1140
aacagaacct tcactgataa atgggaagat tatcccaagt ctgagaatga aagtaatatc   1200
agatacgtaa gtgaacttca tctaacgaga ttaaaaggca ccgaaggagg cacttacaca   1260
ttcctagtgt ccaattctga cgtcaatgct gccatagcat ttaatgttta tgtgaataca   1320
aaaccagaaa tcctgactta cgacaggctc gtgaatggca tgctccaatg tgtggcagca   1380
ggattcccag agcccacaat agattggtat tttgtccag gaactgagca gagatgctct    1440
gcttctgtac tgccagtgga tgtgcagaca ctaaactcat ctgggccacc gtttggaaag   1500
ctagtggttc agagttctat agattctagt gcattcaagc acaatggcac ggttgaatgt   1560
aaggcttaca acgatgtggg caagacttct gcctatttta actttgcatt taaaggtaac   1620
aacaaagagc aaatccatcc ccacaccctg ttcactcctt tgctgattgg tttcgtaatc   1680
gtagctggca tgatgtgcat tattgtgatg attctgacct acaaatattt acagaaaccc   1740
atgtatgaag tacagtggaa ggttgttgag gagataaatg gaaacaatta tgtttacata   1800
gacccaacac aacttcctta tgatcacaaa tgggagtttc ccagaaacag gctgagtttt   1860
gggaaaaccc tgggtgctgg agctttcggg aaggttgttg aggcaactgc ttatggctta   1920
attaagtcag atgcggccat gactgtcgct gtaaagatgc tcaagccgag tgcccatttg   1980
acagaacggg aagccctcat gtctgaactc aaagtcctga gttaccttgg taatcacatg   2040
aatattgtga atctacttgg agcctgcacc attggagggc ccaccctggt cattacagaa   2100
tattgttgct atggtgatct tttgaatttt ttgagaagaa aacgtgattc atttatttgt   2160
tcaaagcagg aagatcatgc agaagctgca ctttataaga atcttctgca ttcaaaggag   2220
tcttcctgca gcgatagtac taatgagtac atggacatga aacctggagt ttcttatgtt   2280
gtcccaacca aggccgacaa aaggagatct gtgagaatag gctcatacat agaaagagat   2340
gtgactcccg ccatcatgga ggatgacgag ttggccctag acttagaaga cttgctgagc   2400
ttttcttacc aggtggcaaa gggcatggct ttcctcgcct ccaagaattg tattcacaga   2460
gacttggcag ccagaaatat cctccttact catggtcgga tcacaaagat ttgtgatttt   2520
ggtctagcca gagacatcaa gaatgattct aattatgtgg ttaaaggaaa cgctcgacta   2580
cctgtgaagt ggatggcacc tgaaagcatt ttcaactgtg tatacacgtt tgaaagtgac   2640
gtctggtcct atgggatttt tctttgggag ctgttctctt taggaagcag cccctatcct   2700
ggaatgccgg tcgattctaa gttctacaag atgatcaagg aaggcttccg gatgctcagc   2760
cctgaacacg cacctgctga aatgtatgac ataatgaaga cttgctggga tgcagatccc   2820
ctaaaaagac caacattcaa gcaaattgtt cagctaattg agaagcagat ttcagagagc   2880
accaatcata tttactccaa cttagcaaac tgcagcccca accgacagaa gcccgtggta   2940
gaccattctg tgcggatcaa ttctgtcggc agcaccgctt cctcctccca gcctctgctt   3000
```

```
gtgcacgacg atgtctgagc agaatcagtg tttgggtcac ccctccagga atgatctctt   3060

cttttggctt ccatgatggt tattttcttt tctttcaact tgcatccaac tccaggatag   3120

tgggcacccc actgcaatcc tgtctttctg agcacacttt agtggccgat gatttttgtc   3180

atcagccacc atcctattgc aaaggttcca actgtatata ttcccaatag caacgtagct   3240

tctaccatga acagaaaaca ttctgatttg gaaaaagaga gggaggtatg gactgggggc   3300

cagagtcctt tccaaggctt ctccaattct gcccaaaaat atggttgata gtttacctga   3360

ataaatggta gtaatcacag ttggccttca gaaccatcca tagtagtatg atgatacaag   3420

attagaagct gaaaacctaa gtcctttatg tggaaaacag aacatcatta gaacaaagga   3480

cagagtatga acacctgggc ttaagaaatc tagtatttca tgctgggaat gagacatagg   3540

ccatgaaaaa aatgatcccc aagtgtgaac aaaagatgct cttctgtgga ccactgcatg   3600

agcttttata ctaccgacct ggtttttaaa tagagtttgc tattagagca ttgaattgga   3660

gagaaggcct ccctagccag cacttgtata tacgcatcta taaattgtcc gtgttcatac   3720

atttgagggg aaaacaccat aaggtttcgt ttctgtatac aaccctggca ttatgtccac   3780

tgtgtataga agtagattaa gagccatata agtttgaagg aaacagttaa taccattttt   3840

taaggaaaca atataaccac aaagcacagt ttgaacaaaa tctcctcttt tagctgatga   3900

acttattctg tagattctgt ggaacaagcc tatcagcttc agaatggcat tgtactcaat   3960

ggatttgatg ctgtttgaca aagttactga ttcactgcat ggctcccaca ggagtgggaa   4020

aacactgcca tcttagtttg gattcttatg tagcaggaaa taaagtatag gtttagcctc   4080

cttcgcaggc atgtcctgga caccgggcca gtatctatat atgtgtatgt acgtttgtat   4140

gtgtgtagac aaatatttgg aggggtattt ttgccctgag tccaagaggg tcctttagta   4200

cctgaaaagt aacttggctt tcattattag tactgctctt gtttcttttc acatagctgt   4260

ctagagtagc ttaccagaag cttccatagt ggtgcagagg aagtggaagg catcagtccc   4320

tatgtatttg cagttcacct gcacttaagg cactctgtta tttagactca tcttactgta   4380

cctgttcctt agaccttcca taatgctact gtctcactga aacatttaaa ttttaccctt   4440

tagactgtag cctggatatt attcttgtag tttacctctt taaaaacaaa acaaaacaaa   4500

acaaaaaact cccctteetc actgcccaat ataaaaggca aatgtgtaca tggcagagtt   4560

tgtgtgttgt cttgaaagat tcaggtatgt tgcctttatg gtttccccct tctacatttc   4620

ttagactaca tttagagaac tgtggccgtt atctggaagt aaccatttgc actggagttc   4680

tatgctctcg cacctttcca aagttaacag attttggggt tgtgttgtca cccaagagat   4740

tgttgtttgc catactttgt ctgaaaaatt cctttgtgtt tctattgact tcaatgatag   4800

taagaaaagt ggttgttagt tatagatgtc taggtacttc aggggcactt cattgagagt   4860

tttgtcttgg atattcttga aagtttatat ttttataatt ttttcttaca tcagatgttt   4920

ctttgcagtg gcttaatgtt tgaaattatt ttgtggcttt ttttgtaaat attgaaatgt   4980

agcaataatg tcttttgaat attcccaagc ccatgagtcc ttgaaaatat tttttatata   5040

tacagtaact ttatgtgtaa atacataagc ggcgtaagtt taaaggatgt tggtgttcca   5100

cgtgttttat tcctgtatgt tgtccaattg ttgacagttc tgaagaattc taataaaatg   5160

tacatatata aatcaaaaaa aaaaaaaaaa                                    5190
```

<210> SEQ ID NO 64
<211> LENGTH: 1659
<212> TYPE: PRT
<213> ORGANISM: Homo sapiens

<400> SEQUENCE: 64

```
Ala Thr Gly Gly Cys Ala Gly Ala Thr Cys Cys Thr Gly Ala Gly Gly
1               5                   10                  15

Thr Ala Gly Thr Thr Gly Thr Gly Ala Gly Thr Ala Gly Cys Thr Gly
            20                  25                  30

Cys Ala Gly Cys Thr Cys Thr Cys Ala Thr Gly Ala Ala Gly Ala Gly
        35                  40                  45

Gly Ala Ala Ala Ala Thr Cys Gly Cys Thr Gly Cys Ala Ala Thr Thr
    50                  55                  60

Thr Thr Ala Ala Cys Cys Ala Gly Cys Ala Ala Ala Cys Ala Thr Cys
65                  70                  75                  80

Thr Cys Cys Ala Thr Cys Thr Gly Ala Gly Gly Ala Gly Cys Thr Thr
                85                  90                  95

Cys Thr Ala Thr Thr Ala Gly Ala Ala Gly Ala Cys Cys Ala Gly Ala
            100                 105                 110

Thr Gly Ala Gly Gly Cys Gly Ala Ala Ala Ala Cys Thr Cys Ala Ala
        115                 120                 125

Ala Thr Thr Thr Thr Thr Thr Thr Thr Cys Ala Thr Gly Ala Ala Thr
    130                 135                 140

Cys Cys Cys Thr Gly Thr Gly Ala Gly Ala Ala Gly Thr Thr Cys Thr
145                 150                 155                 160

Gly Gly Gly Cys Thr Cys Gly Ala Gly Gly Thr Ala Gly Ala Ala Ala
                165                 170                 175

Ala Cys Cys Ala Thr Gly Gly Ala Ala Ala Cys Thr Thr Gly Cys Cys
            180                 185                 190

Ala Thr Ala Cys Ala Ala Ala Thr Thr Cys Thr Ala Ala Ala Ala Ala
        195                 200                 205

Thr Thr Gly Cys Ala Ala Thr Gly Gly Thr Gly Ala Cys Thr Ala Thr
    210                 215                 220

Cys Cys Ala Gly Cys Thr Gly Gly Thr Cys Thr Thr Ala Thr Thr Thr
225                 230                 235                 240

Gly Gly Gly Cys Thr Ala Ala Gly Thr Ala Ala Cys Cys Ala Gly Ala
                245                 250                 255

Thr Gly Gly Thr Gly Gly Thr Ala Gly Cys Thr Thr Thr Cys Ala Ala
            260                 265                 270

Gly Gly Ala Ala Gly Ala Gly Ala Ala Thr Ala Cys Thr Ala Thr Ala
        275                 280                 285

Gly Cys Ala Thr Thr Cys Ala Ala Ala Cys Ala Cys Cys Thr Thr Thr
    290                 295                 300

Thr Cys Cys Thr Ala Ala Ala Ala Gly Gly Ala Thr Ala Thr Ala Thr
305                 310                 315                 320

Gly Gly Ala Cys Cys Gly Ala Ala Thr Gly Gly Ala Thr Gly Ala Cys
                325                 330                 335

Ala Cys Ala Thr Ala Thr Gly Cys Ala Gly Thr Gly Thr Ala Cys Ala
            340                 345                 350

Cys Ala Cys Ala Ala Ala Gly Thr Gly Ala Cys Gly Thr Gly Thr Ala
        355                 360                 365

Thr Gly Ala Thr Cys Ala Gly Thr Thr Ala Ala Thr Cys Thr Thr Cys
    370                 375                 380

Gly Cys Ala Gly Thr Ala Ala Ala Cys Cys Ala Gly Thr Ala Cys Thr
385                 390                 395                 400

Thr Gly Cys Ala Gly Cys Thr Ala Thr Ala Cys Ala Ala Thr Gly Thr
                405                 410                 415
```

```
Cys Thr Cys Cys Gly Thr Thr Gly Gly Gly Ala Ala Thr Cys Ala Thr
            420                 425                 430

Gly Cys Thr Thr Ala Thr Gly Ala Gly Ala Ala Cys Ala Ala Ala Gly
        435                 440                 445

Gly Thr Ala Cys Cys Ala Ala Gly Cys Ala Ala Thr Cys Thr Gly Cys
    450                 455                 460

Thr Ala Thr Gly Gly Cys Ala Ala Thr Cys Thr Gly Thr Cys Ala Gly
465                 470                 475                 480

Cys Ala Cys Thr Thr Cys Thr Ala Cys Ala Ala Gly Cys Gly Ala Gly
                485                 490                 495

Gly Ala Ala Ala Cys Ala Thr Cys Thr Ala Cys Cys Cys Thr Gly Gly
            500                 505                 510

Ala Ala Ala Thr Gly Ala Thr Ala Cys Cys Thr Thr Thr Gly Ala Cys
        515                 520                 525

Ala Thr Cys Gly Ala Thr Cys Cys Ala Gly Ala Ala Ala Thr Thr Gly
    530                 535                 540

Ala Ala Ala Cys Thr Gly Ala Gly Thr Gly Thr Thr Thr Cys Thr Thr
545                 550                 555                 560

Thr Gly Thr Gly Gly Ala Gly Cys Cys Ala Gly Ala Thr Gly Ala Ala
                565                 570                 575

Cys Cys Thr Thr Thr Thr Cys Ala Cys Ala Thr Thr Gly Gly Gly Ala
            580                 585                 590

Cys Ala Cys Cys Ala Gly Cys Ala Gly Ala Ala Ala Ala Thr Ala Ala
        595                 600                 605

Ala Cys Thr Gly Ala Ala Cys Thr Thr Ala Ala Cys Ala Cys Thr Gly
    610                 615                 620

Gly Ala Cys Thr Thr Cys Cys Ala Cys Ala Gly Ala Cys Thr Cys Cys
625                 630                 635                 640

Thr Ala Ala Cys Ala Gly Thr Gly Gly Ala Gly Cys Thr Thr Cys Ala
                645                 650                 655

Gly Thr Thr Thr Ala Ala Ala Cys Thr Gly Ala Ala Ala Gly Cys Cys
            660                 665                 670

Ala Thr Thr Ala Ala Thr Cys Thr Gly Cys Ala Gly Ala Cys Ala Gly
        675                 680                 685

Thr Thr Cys Gly Thr Cys Ala Thr Cys Ala Ala Gly Ala Ala Cys Thr
    690                 695                 700

Cys Cys Cys Thr Gly Ala Cys Thr Gly Thr Thr Ala Thr Gly Ala Cys
705                 710                 715                 720

Thr Thr Thr Ala Cys Thr Cys Thr Gly Ala Cys Thr Ala Thr Ala Ala
                725                 730                 735

Cys Ala Thr Thr Thr Gly Ala Cys Ala Ala Cys Ala Ala Gly Gly Cys
            740                 745                 750

Cys Cys Ala Thr Ala Gly Thr Gly Gly Ala Ala Gly Ala Ala Thr Thr
        755                 760                 765

Ala Ala Ala Ala Thr Ala Ala Gly Thr Thr Thr Ala Gly Ala Thr Ala
    770                 775                 780

Ala Thr Gly Ala Cys Ala Thr Thr Thr Cys Cys Ala Thr Cys Ala Gly
785                 790                 795                 800

Ala Gly Ala Ala Thr Gly Thr Ala Ala Ala Gly Ala Cys Thr Gly Gly
                805                 810                 815

Cys Ala Thr Gly Thr Ala Thr Cys Thr Gly Gly Ala Thr Cys Ala Ala
            820                 825                 830

Thr Thr Cys Ala Gly Ala Ala Gly Ala Ala Cys Ala Cys Thr Cys Ala
        835                 840                 845
```

-continued

```
Thr Thr Ala Cys Ala Thr Gly Ala Thr Gly Ala Thr Cys Thr Thr Thr
    850                 855                 860

Gly Ala Thr Gly Cys Cys Thr Thr Thr Gly Thr Cys Ala Thr Thr Cys
865                 870                 875                 880

Thr Gly Ala Cys Thr Thr Gly Cys Thr Thr Gly Gly Thr Thr Thr Cys
                885                 890                 895

Ala Thr Thr Ala Ala Thr Cys Cys Thr Cys Thr Gly Cys Ala Thr Thr
            900                 905                 910

Ala Gly Ala Thr Cys Thr Gly Thr Gly Ala Thr Thr Ala Gly Ala Gly
        915                 920                 925

Gly Ala Cys Thr Thr Cys Ala Gly Cys Thr Thr Cys Ala Gly Cys Ala
    930                 935                 940

Gly Gly Ala Gly Thr Thr Thr Gly Thr Cys Ala Ala Thr Thr Thr Thr
945                 950                 955                 960

Thr Thr Cys Cys Thr Cys Cys Thr Cys Cys Ala Thr Thr Ala Thr Ala
                965                 970                 975

Ala Gly Ala Ala Gly Gly Ala Ala Gly Thr Thr Thr Cys Thr Gly Thr
            980                 985                 990

Thr Thr Cys Thr Gly Ala Thr Cys  Ala Ala Ala Thr Gly  Gly Ala Ala
        995                 1000                 1005

Thr Thr  Thr Gly Thr Cys Ala  Ala Thr Gly Gly Ala  Thr Gly Gly
    1010                 1015                 1020

Thr Ala  Cys Ala Thr Thr Ala  Thr Gly Ala Thr Thr  Ala Thr Thr
    1025                 1030                 1035

Ala Thr  Thr Ala Gly Thr Gly  Ala Cys Ala Thr Ala  Thr Thr Gly
    1040                 1045                 1050

Ala Cys  Ala Ala Thr Cys Ala  Thr Thr Gly Gly Ala  Thr Cys Ala
    1055                 1060                 1065

Ala Thr  Thr Cys Thr Ala Ala  Ala Ala Ala Thr Gly  Gly Ala Ala
    1070                 1075                 1080

Ala Thr  Cys Cys Ala Ala Gly  Cys Thr Ala Ala Gly  Ala Gly Thr
    1085                 1090                 1095

Cys Thr  Ala Ala Cys Thr Ala  Gly Thr Thr Ala Thr  Gly Ala Thr
    1100                 1105                 1110

Gly Thr  Cys Thr Gly Thr Ala  Gly Cys Ala Thr Ala  Cys Thr Thr
    1115                 1120                 1125

Cys Thr  Thr Gly Gly Gly Ala  Cys Thr Thr Cys Thr  Ala Cys Cys
    1130                 1135                 1140

Ala Thr  Gly Cys Thr Cys Gly  Thr Gly Thr Gly Gly  Cys Thr Thr
    1145                 1150                 1155

Gly Gly  Ala Gly Thr Cys Ala  Thr Cys Cys Gly Ala  Thr Ala Cys
    1160                 1165                 1170

Cys Thr  Cys Gly Gly Thr Thr  Thr Cys Thr Thr Thr  Gly Cys Ala
    1175                 1180                 1185

Ala Ala  Gly Thr Ala Cys Ala  Ala Cys Cys Thr Cys  Cys Thr Cys
    1190                 1195                 1200

Ala Thr  Thr Thr Thr Gly Ala  Cys Cys Cys Thr Thr  Cys Ala Gly
    1205                 1210                 1215

Gly Cys  Ala Gly Cys Gly Cys  Thr Gly Cys Cys Cys  Ala Ala Thr
    1220                 1225                 1230

Gly Thr  Cys Ala Thr Cys Ala  Gly Gly Thr Thr Cys  Thr Gly Cys
    1235                 1240                 1245

Thr Gly  Cys Thr Gly Thr Gly  Cys Ala Gly Cys Thr  Ala Thr Gly
```

1250 1255 1260

Ala Thr Thr Thr Ala Cys Thr Thr Ala Gly Gly Thr Thr Ala Cys
1265 1270 1275

Thr Gly Cys Thr Thr Cys Thr Gly Thr Gly Gly Ala Thr Gly Gly
1280 1285 1290

Ala Thr Cys Gly Thr Gly Cys Thr Gly Gly Gly Gly Cys Cys Thr
1295 1300 1305

Thr Ala Cys Cys Ala Thr Gly Ala Cys Ala Ala Gly Thr Thr Thr
1310 1315 1320

Cys Gly Thr Thr Cys Thr Cys Thr Gly Ala Ala Cys Ala Thr Gly
1325 1330 1335

Gly Thr Cys Thr Cys Thr Gly Ala Gly Thr Gly Cys Cys Thr Thr
1340 1345 1350

Thr Thr Cys Thr Cys Thr Cys Thr Gly Ala Thr Ala Ala Ala Thr
1355 1360 1365

Gly Gly Ala Gly Ala Thr Gly Ala Thr Ala Thr Gly Thr Thr Thr
1370 1375 1380

Gly Cys Cys Ala Cys Gly Thr Thr Thr Gly Cys Ala Ala Ala Ala
1385 1390 1395

Ala Thr Gly Cys Ala Gly Cys Ala Ala Ala Ala Ala Ala Gly Thr
1400 1405 1410

Thr Ala Cys Thr Thr Ala Gly Thr Cys Thr Gly Gly Cys Thr Gly
1415 1420 1425

Thr Thr Thr Ala Gly Thr Ala Gly Ala Ala Thr Thr Thr Ala Cys
1430 1435 1440

Cys Thr Cys Thr Ala Cys Thr Cys Ala Thr Thr Cys Ala Thr Cys
1445 1450 1455

Ala Gly Cys Cys Thr Cys Thr Thr Thr Ala Thr Ala Thr Ala Thr
1460 1465 1470

Ala Thr Gly Ala Thr Thr Thr Thr Ala Ala Gly Thr Cys Thr Thr
1475 1480 1485

Thr Thr Cys Ala Thr Thr Gly Cys Ala Cys Thr Gly Ala Thr Cys
1490 1495 1500

Ala Cys Thr Gly Ala Thr Ala Cys Ala Thr Ala Cys Gly Ala Ala
1505 1510 1515

Ala Cys Ala Ala Thr Thr Ala Ala Gly Cys Ala Ala Thr Ala Cys
1520 1525 1530

Cys Ala Ala Cys Ala Ala Gly Ala Thr Gly Gly Cys Thr Thr Cys
1535 1540 1545

Cys Cys Ala Gly Ala Gly Ala Cys Thr Gly Ala Ala Cys Thr Thr
1550 1555 1560

Cys Gly Thr Ala Cys Ala Thr Thr Thr Ala Thr Ala Thr Cys Ala
1565 1570 1575

Gly Ala Ala Thr Gly Cys Ala Ala Ala Gly Ala Thr Cys Thr Ala
1580 1585 1590

Cys Cys Cys Ala Ala Cys Thr Cys Thr Gly Gly Ala Ala Ala Ala
1595 1600 1605

Thr Ala Cys Ala Gly Ala Thr Thr Ala Gly Ala Ala Gly Ala Thr
1610 1615 1620

Gly Ala Cys Cys Cys Thr Cys Cys Ala Gly Thr Ala Thr Cys Thr
1625 1630 1635

Thr Thr Ala Thr Thr Cys Thr Gly Cys Thr Gly Thr Thr Gly Thr
1640 1645 1650

```
Ala Ala  Ala Ala Ala Gly
    1655


<210> SEQ ID NO 65
<211> LENGTH: 553
<212> TYPE: PRT
<213> ORGANISM: Homo sapiens

<400> SEQUENCE: 65

Met Ala Asp Pro Glu Val Val Val Ser Ser Cys Ser Ser His Glu Glu
1               5                   10                  15

Glu Asn Arg Cys Asn Phe Asn Gln Gln Thr Ser Pro Ser Glu Glu Leu
            20                  25                  30

Leu Leu Glu Asp Gln Met Arg Arg Lys Leu Lys Phe Phe Phe Met Asn
        35                  40                  45

Pro Cys Glu Lys Phe Trp Ala Arg Gly Arg Lys Pro Trp Lys Leu Ala
    50                  55                  60

Ile Gln Ile Leu Lys Ile Ala Met Val Thr Ile Gln Leu Val Leu Phe
65                  70                  75                  80

Gly Leu Ser Asn Gln Met Val Val Ala Phe Lys Glu Glu Asn Thr Ile
                85                  90                  95

Ala Phe Lys His Leu Phe Leu Lys Gly Tyr Met Asp Arg Met Asp Asp
            100                 105                 110

Thr Tyr Ala Val Tyr Thr Gln Ser Asp Val Tyr Asp Gln Leu Ile Phe
        115                 120                 125

Ala Val Asn Gln Tyr Leu Gln Leu Tyr Asn Val Ser Val Gly Asn His
    130                 135                 140

Ala Tyr Glu Asn Lys Gly Thr Lys Gln Ser Ala Met Ala Ile Cys Gln
145                 150                 155                 160

His Phe Tyr Lys Arg Gly Asn Ile Tyr Pro Gly Asn Asp Thr Phe Asp
                165                 170                 175

Ile Asp Pro Glu Ile Glu Thr Glu Cys Phe Phe Val Glu Pro Asp Glu
            180                 185                 190

Pro Phe His Ile Gly Thr Pro Ala Glu Asn Lys Leu Asn Leu Thr Leu
        195                 200                 205

Asp Phe His Arg Leu Leu Thr Val Glu Leu Gln Phe Lys Leu Lys Ala
    210                 215                 220

Ile Asn Leu Gln Thr Val Arg His Gln Glu Leu Pro Asp Cys Tyr Asp
225                 230                 235                 240

Phe Thr Leu Thr Ile Thr Phe Asp Asn Lys Ala His Ser Gly Arg Ile
                245                 250                 255

Lys Ile Ser Leu Asp Asn Asp Ile Ser Ile Arg Glu Cys Lys Asp Trp
            260                 265                 270

His Val Ser Gly Ser Ile Gln Lys Asn Thr His Tyr Met Met Ile Phe
        275                 280                 285

Asp Ala Phe Val Ile Leu Thr Cys Leu Val Ser Leu Ile Leu Cys Ile
    290                 295                 300

Arg Ser Val Ile Arg Gly Leu Gln Leu Gln Gln Glu Phe Val Asn Phe
305                 310                 315                 320

Phe Leu Leu His Tyr Lys Lys Glu Val Ser Val Ser Asp Gln Met Glu
                325                 330                 335

Phe Val Asn Gly Trp Tyr Ile Met Ile Ile Ile Ser Asp Ile Leu Thr
            340                 345                 350

Ile Ile Gly Ser Ile Leu Lys Met Glu Ile Gln Ala Lys Ser Leu Thr
        355                 360                 365
```

```
Ser Tyr Asp Val Cys Ser Ile Leu Leu Gly Thr Ser Thr Met Leu Val
    370                 375                 380

Trp Leu Gly Val Ile Arg Tyr Leu Gly Phe Phe Ala Lys Tyr Asn Leu
385                 390                 395                 400

Leu Ile Leu Thr Leu Gln Ala Ala Leu Pro Asn Val Ile Arg Phe Cys
                405                 410                 415

Cys Cys Ala Ala Met Ile Tyr Leu Gly Tyr Cys Phe Cys Gly Trp Ile
            420                 425                 430

Val Leu Gly Pro Tyr His Asp Lys Phe Arg Ser Leu Asn Met Val Ser
        435                 440                 445

Glu Cys Leu Phe Ser Leu Ile Asn Gly Asp Asp Met Phe Ala Thr Phe
    450                 455                 460

Ala Lys Met Gln Gln Lys Ser Tyr Leu Val Trp Leu Phe Ser Arg Ile
465                 470                 475                 480

Tyr Leu Tyr Ser Phe Ile Ser Leu Phe Ile Tyr Met Ile Leu Ser Leu
                485                 490                 495

Phe Ile Ala Leu Ile Thr Asp Thr Tyr Glu Thr Ile Lys Gln Tyr Gln
            500                 505                 510

Gln Asp Gly Phe Pro Glu Thr Glu Leu Arg Thr Phe Ile Ser Glu Cys
        515                 520                 525

Lys Asp Leu Pro Asn Ser Gly Lys Tyr Arg Leu Glu Asp Asp Pro Pro
    530                 535                 540

Val Ser Leu Phe Cys Cys Cys Lys Lys
545                 550


<210> SEQ ID NO 66
<211> LENGTH: 1659
<212> TYPE: PRT
<213> ORGANISM: Homo sapiens

<400> SEQUENCE: 66

Ala Thr Gly Gly Cys Ala Gly Ala Thr Cys Cys Thr Gly Ala Gly Gly
1               5                   10                  15

Thr Ala Gly Thr Thr Gly Thr Gly Ala Gly Thr Ala Gly Cys Thr Gly
            20                  25                  30

Cys Ala Gly Cys Thr Cys Thr Cys Ala Thr Gly Ala Ala Gly Ala Gly
        35                  40                  45

Gly Ala Ala Ala Ala Thr Cys Gly Cys Thr Gly Cys Ala Ala Thr Thr
    50                  55                  60

Thr Thr Ala Ala Cys Cys Ala Gly Cys Ala Ala Ala Cys Ala Thr Cys
65                  70                  75                  80

Thr Cys Cys Ala Thr Cys Thr Gly Ala Gly Gly Ala Gly Cys Thr Thr
                85                  90                  95

Cys Thr Ala Thr Thr Ala Gly Ala Ala Gly Ala Cys Cys Ala Gly Ala
            100                 105                 110

Thr Gly Ala Gly Gly Cys Gly Ala Ala Ala Ala Cys Thr Cys Ala Ala
        115                 120                 125

Ala Thr Thr Thr Thr Thr Thr Thr Thr Cys Ala Thr Gly Ala Ala Thr
    130                 135                 140

Cys Cys Cys Thr Gly Thr Gly Ala Gly Ala Ala Gly Thr Thr Cys Thr
145                 150                 155                 160

Gly Gly Gly Cys Thr Cys Gly Ala Gly Gly Thr Ala Gly Ala Ala Ala
                165                 170                 175

Ala Cys Cys Ala Thr Gly Gly Ala Ala Ala Cys Thr Thr Gly Cys Cys
            180                 185                 190
```

```
Ala Thr Ala Cys Ala Ala Ala Thr Thr Cys Thr Ala Ala Ala Ala Ala
        195                 200                 205

Thr Thr Gly Cys Ala Ala Thr Gly Gly Thr Gly Ala Cys Thr Ala Thr
    210                 215                 220

Cys Cys Ala Gly Cys Thr Gly Gly Thr Cys Thr Thr Ala Thr Thr Thr
225                 230                 235                 240

Gly Gly Gly Cys Thr Ala Ala Gly Thr Ala Ala Cys Cys Ala Gly Ala
                245                 250                 255

Thr Gly Gly Thr Gly Gly Thr Ala Gly Cys Thr Thr Thr Cys Ala Ala
            260                 265                 270

Gly Gly Ala Ala Gly Ala Gly Ala Ala Thr Ala Cys Thr Ala Thr Ala
        275                 280                 285

Gly Cys Ala Thr Thr Cys Ala Ala Ala Cys Ala Cys Cys Thr Thr Thr
    290                 295                 300

Thr Cys Cys Thr Ala Ala Ala Ala Gly Gly Ala Thr Ala Thr Ala Thr
305                 310                 315                 320

Gly Gly Ala Cys Cys Gly Ala Ala Thr Gly Gly Ala Thr Gly Ala Cys
                325                 330                 335

Ala Cys Ala Thr Ala Thr Gly Cys Ala Gly Thr Gly Thr Ala Cys Ala
            340                 345                 350

Cys Ala Cys Ala Ala Ala Gly Thr Gly Ala Cys Gly Thr Gly Thr Ala
        355                 360                 365

Thr Gly Ala Thr Cys Ala Gly Thr Thr Ala Ala Thr Cys Thr Thr Cys
    370                 375                 380

Gly Cys Ala Gly Thr Ala Ala Ala Cys Cys Ala Gly Thr Ala Cys Thr
385                 390                 395                 400

Thr Gly Cys Ala Gly Cys Thr Ala Thr Ala Cys Ala Ala Thr Gly Thr
                405                 410                 415

Cys Thr Cys Cys Gly Thr Thr Gly Gly Gly Ala Ala Thr Cys Ala Thr
            420                 425                 430

Gly Cys Thr Thr Ala Thr Gly Ala Gly Ala Ala Cys Ala Ala Ala Gly
        435                 440                 445

Gly Thr Ala Cys Cys Ala Ala Gly Cys Ala Ala Thr Cys Thr Gly Cys
    450                 455                 460

Thr Ala Thr Gly Gly Cys Ala Ala Thr Cys Thr Gly Thr Cys Ala Gly
465                 470                 475                 480

Cys Ala Cys Thr Thr Cys Thr Ala Cys Ala Ala Gly Cys Gly Ala Gly
                485                 490                 495

Gly Ala Ala Ala Cys Ala Thr Cys Thr Ala Cys Cys Cys Thr Gly Gly
            500                 505                 510

Ala Ala Ala Thr Gly Ala Thr Ala Cys Cys Thr Thr Thr Gly Ala Cys
        515                 520                 525

Ala Thr Cys Gly Ala Thr Cys Cys Ala Gly Ala Ala Ala Thr Thr Gly
    530                 535                 540

Ala Ala Ala Cys Thr Gly Ala Gly Thr Gly Thr Thr Thr Cys Thr Thr
545                 550                 555                 560

Thr Gly Thr Gly Gly Ala Gly Cys Cys Ala Gly Ala Thr Gly Ala Ala
                565                 570                 575

Cys Cys Thr Thr Thr Thr Cys Ala Cys Ala Thr Thr Gly Gly Gly Ala
            580                 585                 590

Cys Ala Cys Cys Ala Gly Cys Ala Gly Ala Ala Ala Ala Thr Ala Ala
        595                 600                 605

Ala Cys Thr Gly Ala Ala Cys Thr Thr Ala Ala Cys Ala Cys Thr Gly
    610                 615                 620
```

Gly Ala Cys Thr Thr Cys Cys Ala Cys Ala Gly Ala Cys Thr Cys Cys
625 630 635 640

Thr Ala Ala Cys Ala Gly Thr Gly Gly Ala Gly Cys Thr Thr Cys Ala
645 650 655

Gly Thr Thr Thr Ala Ala Ala Cys Thr Gly Ala Ala Ala Gly Cys Cys
660 665 670

Ala Thr Thr Ala Ala Thr Cys Thr Gly Cys Ala Gly Ala Cys Ala Gly
675 680 685

Thr Thr Cys Gly Thr Cys Ala Thr Cys Ala Ala Gly Ala Ala Cys Thr
690 695 700

Cys Cys Cys Thr Gly Ala Cys Thr Gly Thr Thr Ala Thr Gly Ala Cys
705 710 715 720

Thr Thr Thr Ala Cys Thr Cys Thr Gly Ala Cys Thr Ala Thr Ala Ala
725 730 735

Cys Ala Thr Thr Thr Gly Ala Cys Ala Ala Cys Ala Ala Gly Gly Cys
740 745 750

Cys Cys Ala Thr Ala Gly Thr Gly Gly Ala Ala Gly Ala Ala Thr Thr
755 760 765

Ala Ala Ala Ala Thr Ala Ala Gly Thr Thr Thr Ala Gly Ala Thr Ala
770 775 780

Ala Thr Gly Ala Cys Ala Thr Thr Thr Cys Cys Ala Thr Cys Ala Gly
785 790 795 800

Ala Gly Ala Ala Thr Gly Thr Ala Ala Ala Gly Ala Cys Thr Gly Gly
805 810 815

Cys Ala Thr Gly Thr Ala Thr Cys Thr Gly Gly Ala Thr Cys Ala Ala
820 825 830

Thr Thr Cys Ala Gly Ala Ala Gly Ala Ala Cys Ala Cys Thr Cys Ala
835 840 845

Thr Thr Ala Cys Ala Thr Gly Ala Thr Gly Ala Thr Cys Thr Thr Thr
850 855 860

Gly Ala Thr Gly Cys Cys Thr Thr Thr Gly Thr Cys Ala Thr Thr Cys
865 870 875 880

Thr Gly Ala Cys Thr Thr Gly Cys Thr Thr Gly Gly Thr Thr Thr Cys
885 890 895

Ala Thr Thr Ala Ala Thr Cys Cys Thr Cys Thr Gly Cys Ala Thr Thr
900 905 910

Ala Gly Ala Thr Cys Thr Gly Thr Gly Ala Thr Thr Ala Gly Ala Gly
915 920 925

Gly Ala Cys Thr Thr Cys Ala Gly Cys Thr Thr Cys Ala Gly Cys Ala
930 935 940

Gly Gly Ala Gly Thr Thr Thr Gly Thr Cys Ala Ala Thr Thr Thr Thr
945 950 955 960

Thr Thr Cys Cys Thr Cys Cys Thr Cys Cys Ala Thr Thr Ala Thr Ala
965 970 975

Ala Gly Ala Ala Gly Gly Ala Ala Gly Thr Thr Thr Cys Thr Gly Thr
980 985 990

Thr Thr Cys Thr Gly Ala Thr Cys Ala Ala Ala Thr Gly Gly Ala Ala
995 1000 1005

Thr Thr Thr Gly Thr Cys Ala Ala Thr Gly Gly Ala Thr Gly Gly
1010 1015 1020

Thr Ala Cys Ala Thr Thr Ala Thr Gly Ala Thr Thr Ala Thr Thr
1025 1030 1035

Ala Thr Thr Ala Gly Thr Gly Ala Cys Ala Thr Ala Thr Thr Gly

```
    1040                1045                1050

Ala Cys  Ala Ala Thr Cys Ala  Thr Thr Gly Gly Ala  Thr Cys Ala
    1055                1060                1065

Ala Thr  Thr Cys Thr Ala Ala  Ala Ala Ala Thr Gly  Gly Ala Ala
    1070                1075                1080

Ala Thr  Cys Cys Ala Ala Gly  Cys Thr Ala Ala Gly  Ala Gly Thr
    1085                1090                1095

Cys Thr  Ala Ala Cys Thr Ala  Gly Thr Thr Ala Thr  Gly Ala Thr
    1100                1105                1110

Gly Thr  Cys Thr Gly Thr Ala  Gly Cys Ala Thr Ala  Cys Thr Thr
    1115                1120                1125

Cys Thr  Thr Gly Gly Gly Ala  Cys Thr Thr Cys Thr  Ala Cys Cys
    1130                1135                1140

Ala Thr  Gly Cys Thr Cys Gly  Thr Gly Thr Gly Gly  Cys Thr Thr
    1145                1150                1155

Gly Gly  Ala Gly Thr Cys Ala  Thr Cys Cys Gly Ala  Thr Ala Cys
    1160                1165                1170

Cys Thr  Cys Gly Gly Thr Thr  Thr Cys Thr Thr Thr  Gly Cys Ala
    1175                1180                1185

Ala Ala  Gly Thr Ala Cys Ala  Ala Cys Cys Thr Cys  Cys Thr Cys
    1190                1195                1200

Ala Thr  Thr Thr Thr Gly Ala  Cys Cys Cys Thr Thr  Cys Ala Gly
    1205                1210                1215

Gly Cys  Ala Gly Cys Gly Cys  Thr Gly Cys Cys Cys  Ala Ala Thr
    1220                1225                1230

Gly Thr  Cys Ala Thr Cys Ala  Gly Gly Thr Thr Cys  Thr Gly Cys
    1235                1240                1245

Thr Gly  Cys Thr Gly Thr Cys  Cys Ala Gly Cys Thr  Ala Thr Gly
    1250                1255                1260

Ala Thr  Thr Thr Ala Cys Thr  Thr Ala Gly Gly Thr  Thr Ala Cys
    1265                1270                1275

Thr Gly  Cys Thr Thr Cys Thr  Gly Thr Gly Gly Ala  Thr Gly Gly
    1280                1285                1290

Ala Thr  Cys Gly Thr Gly Cys  Thr Gly Gly Gly Gly  Cys Cys Thr
    1295                1300                1305

Thr Ala  Cys Cys Ala Thr Gly  Ala Cys Ala Ala Gly  Thr Thr Thr
    1310                1315                1320

Cys Gly  Thr Thr Cys Thr Cys  Thr Gly Ala Ala Cys  Ala Thr Gly
    1325                1330                1335

Gly Thr  Cys Thr Cys Thr Gly  Ala Gly Thr Gly Cys  Cys Thr Thr
    1340                1345                1350

Thr Thr  Cys Thr Cys Thr Cys  Thr Gly Ala Thr Ala  Ala Ala Thr
    1355                1360                1365

Gly Gly  Ala Gly Ala Thr Gly  Ala Thr Ala Thr Gly  Thr Thr Thr
    1370                1375                1380

Gly Cys  Cys Ala Cys Gly Thr  Thr Thr Gly Cys Ala  Ala Ala Ala
    1385                1390                1395

Ala Thr  Gly Cys Ala Gly Cys  Ala Ala Ala Ala Ala  Ala Gly Thr
    1400                1405                1410

Thr Ala  Cys Thr Thr Ala Gly  Thr Cys Thr Gly Gly  Cys Thr Gly
    1415                1420                1425

Thr Thr  Thr Ala Gly Thr Ala  Gly Ala Ala Thr Thr  Thr Ala Cys
    1430                1435                1440
```

Cys Thr Cys Thr Ala Cys Thr Cys Ala Thr Thr Cys Ala Thr Cys
1445 1450 1455

Ala Gly Cys Cys Thr Cys Thr Thr Thr Ala Thr Ala Thr Ala Thr
1460 1465 1470

Ala Thr Gly Ala Thr Thr Thr Thr Ala Ala Gly Thr Cys Thr Thr
1475 1480 1485

Thr Thr Cys Ala Thr Thr Gly Cys Ala Cys Thr Gly Ala Thr Cys
1490 1495 1500

Ala Cys Thr Gly Ala Thr Ala Cys Ala Thr Ala Cys Gly Ala Ala
1505 1510 1515

Ala Cys Ala Ala Thr Thr Ala Ala Gly Cys Ala Ala Thr Ala Cys
1520 1525 1530

Cys Ala Ala Cys Ala Ala Gly Ala Thr Gly Gly Cys Thr Thr Cys
1535 1540 1545

Cys Cys Ala Gly Ala Gly Ala Cys Thr Gly Ala Ala Cys Thr Thr
1550 1555 1560

Cys Gly Thr Ala Cys Ala Thr Thr Thr Ala Thr Ala Thr Cys Ala
1565 1570 1575

Gly Ala Ala Thr Gly Cys Ala Ala Ala Gly Ala Thr Cys Thr Ala
1580 1585 1590

Cys Cys Cys Ala Ala Cys Thr Cys Thr Gly Gly Ala Ala Ala Ala
1595 1600 1605

Thr Ala Cys Ala Gly Ala Thr Thr Ala Gly Ala Ala Gly Ala Thr
1610 1615 1620

Gly Ala Cys Cys Cys Thr Cys Cys Ala Gly Thr Ala Thr Cys Thr
1625 1630 1635

Thr Thr Ala Thr Thr Cys Thr Gly Cys Thr Gly Thr Thr Gly Thr
1640 1645 1650

Ala Ala Ala Ala Ala Gly
1655

<210> SEQ ID NO 67
<211> LENGTH: 553
<212> TYPE: PRT
<213> ORGANISM: Homo sapiens

<400> SEQUENCE: 67

Met Ala Asp Pro Glu Val Val Val Ser Ser Cys Ser Ser His Glu Glu
1 5 10 15

Glu Asn Arg Cys Asn Phe Asn Gln Gln Thr Ser Pro Ser Glu Glu Leu
20 25 30

Leu Leu Glu Asp Gln Met Arg Arg Lys Leu Lys Phe Phe Phe Met Asn
35 40 45

Pro Cys Glu Lys Phe Trp Ala Arg Gly Arg Lys Pro Trp Lys Leu Ala
50 55 60

Ile Gln Ile Leu Lys Ile Ala Met Val Thr Ile Gln Leu Val Leu Phe
65 70 75 80

Gly Leu Ser Asn Gln Met Val Val Ala Phe Lys Glu Glu Asn Thr Ile
85 90 95

Ala Phe Lys His Leu Phe Leu Lys Gly Tyr Met Asp Arg Met Asp Asp
100 105 110

Thr Tyr Ala Val Tyr Thr Gln Ser Asp Val Tyr Asp Gln Leu Ile Phe
115 120 125

Ala Val Asn Gln Tyr Leu Gln Leu Tyr Asn Val Ser Val Gly Asn His
130 135 140

```
Ala Tyr Glu Asn Lys Gly Thr Lys Gln Ser Ala Met Ala Ile Cys Gln
145                 150                 155                 160

His Phe Tyr Lys Arg Gly Asn Ile Tyr Pro Gly Asn Asp Thr Phe Asp
                165                 170                 175

Ile Asp Pro Glu Ile Glu Thr Glu Cys Phe Phe Val Glu Pro Asp Glu
            180                 185                 190

Pro Phe His Ile Gly Thr Pro Ala Glu Asn Lys Leu Asn Leu Thr Leu
        195                 200                 205

Asp Phe His Arg Leu Leu Thr Val Glu Leu Gln Phe Lys Leu Lys Ala
    210                 215                 220

Ile Asn Leu Gln Thr Val Arg His Gln Glu Leu Pro Asp Cys Tyr Asp
225                 230                 235                 240

Phe Thr Leu Thr Ile Thr Phe Asp Asn Lys Ala His Ser Gly Arg Ile
                245                 250                 255

Lys Ile Ser Leu Asp Asn Asp Ile Ser Ile Arg Glu Cys Lys Asp Trp
            260                 265                 270

His Val Ser Gly Ser Ile Gln Lys Asn Thr His Tyr Met Met Ile Phe
        275                 280                 285

Asp Ala Phe Val Ile Leu Thr Cys Leu Val Ser Leu Ile Leu Cys Ile
    290                 295                 300

Arg Ser Val Ile Arg Gly Leu Gln Leu Gln Gln Glu Phe Val Asn Phe
305                 310                 315                 320

Phe Leu Leu His Tyr Lys Lys Glu Val Ser Val Ser Asp Gln Met Glu
                325                 330                 335

Phe Val Asn Gly Trp Tyr Ile Met Ile Ile Ile Ser Asp Ile Leu Thr
            340                 345                 350

Ile Ile Gly Ser Ile Leu Lys Met Glu Ile Gln Ala Lys Ser Leu Thr
        355                 360                 365

Ser Tyr Asp Val Cys Ser Ile Leu Leu Gly Thr Ser Thr Met Leu Val
    370                 375                 380

Trp Leu Gly Val Ile Arg Tyr Leu Gly Phe Phe Ala Lys Tyr Asn Leu
385                 390                 395                 400

Leu Ile Leu Thr Leu Gln Ala Ala Leu Pro Asn Val Ile Arg Phe Cys
                405                 410                 415

Cys Cys Pro Ala Met Ile Tyr Leu Gly Tyr Cys Phe Cys Gly Trp Ile
            420                 425                 430

Val Leu Gly Pro Tyr His Asp Lys Phe Arg Ser Leu Asn Met Val Ser
        435                 440                 445

Glu Cys Leu Phe Ser Leu Ile Asn Gly Asp Asp Met Phe Ala Thr Phe
    450                 455                 460

Ala Lys Met Gln Gln Lys Ser Tyr Leu Val Trp Leu Phe Ser Arg Ile
465                 470                 475                 480

Tyr Leu Tyr Ser Phe Ile Ser Leu Phe Ile Tyr Met Ile Leu Ser Leu
                485                 490                 495

Phe Ile Ala Leu Ile Thr Asp Thr Tyr Glu Thr Ile Lys Gln Tyr Gln
            500                 505                 510

Gln Asp Gly Phe Pro Glu Thr Glu Leu Arg Thr Phe Ile Ser Glu Cys
        515                 520                 525

Lys Asp Leu Pro Asn Ser Gly Lys Tyr Arg Leu Glu Asp Asp Pro Pro
    530                 535                 540

Val Ser Leu Phe Cys Cys Cys Lys Lys
545                 550
```

<210> SEQ ID NO 68

<211> LENGTH: 1740
<212> TYPE: PRT
<213> ORGANISM: Homo sapiens

<400> SEQUENCE: 68

```
Ala Thr Gly Ala Cys Ala Gly Cys Cys Cys Cys Gly Gly Cys Gly Gly
1               5                   10                  15

Gly Thr Cys Cys Gly Cys Gly Cys Gly Gly Cys Thr Cys Ala Gly Ala
            20                  25                  30

Gly Ala Cys Cys Gly Ala Gly Cys Gly Gly Cys Thr Thr Cys Thr Gly
        35                  40                  45

Ala Cys Cys Cys Cys Cys Ala Ala Cys Cys Cys Cys Gly Gly Gly Thr
    50                  55                  60

Ala Thr Gly Gly Gly Ala Cys Cys Cys Ala Gly Gly Cys Gly Gly Gly
65                  70                  75                  80

Gly Cys Cys Thr Thr Cys Ala Cys Cys Gly Gly Cys Cys Cys Cys Thr
                85                  90                  95

Cys Cys Gly Ala Cys Ala Cys Cys Cys Cys Cys Ala Gly Ala Ala Gly
            100                 105                 110

Ala Gly Gly Ala Ala Gly Ala Cys Cys Thr Thr Cys Gly Cys Cys Gly
        115                 120                 125

Thr Cys Gly Thr Cys Thr Cys Ala Ala Ala Thr Ala Cys Thr Thr Thr
    130                 135                 140

Thr Thr Cys Ala Thr Gly Ala Gly Thr Cys Cys Cys Thr Gly Cys Gly
145                 150                 155                 160

Ala Cys Ala Ala Gly Thr Thr Thr Cys Gly Ala Gly Cys Cys Ala Ala
                165                 170                 175

Gly Gly Gly Cys Cys Gly Cys Ala Ala Gly Cys Cys Cys Thr Gly Cys
            180                 185                 190

Ala Ala Gly Cys Thr Gly Ala Thr Gly Cys Thr Gly Cys Ala Ala Gly
        195                 200                 205

Thr Gly Gly Thr Cys Ala Ala Gly Ala Thr Cys Cys Thr Gly Gly Thr
    210                 215                 220

Gly Gly Thr Cys Ala Cys Gly Gly Thr Gly Cys Ala Gly Cys Thr Cys
225                 230                 235                 240

Ala Thr Cys Cys Thr Gly Thr Thr Thr Gly Gly Gly Cys Thr Cys Ala
                245                 250                 255

Gly Thr Ala Ala Thr Cys Ala Gly Cys Thr Gly Gly Cys Thr Gly Thr
            260                 265                 270

Gly Ala Cys Ala Thr Thr Cys Cys Gly Gly Gly Ala Ala Gly Ala Gly
        275                 280                 285

Ala Ala Cys Ala Cys Cys Ala Thr Cys Gly Cys Cys Thr Thr Cys Cys
    290                 295                 300

Gly Ala Cys Ala Cys Cys Thr Cys Thr Thr Cys Cys Thr Gly Cys Thr
305                 310                 315                 320

Gly Gly Gly Cys Thr Ala Cys Thr Cys Gly Gly Ala Cys Gly Gly Ala
                325                 330                 335

Gly Cys Gly Gly Ala Thr Gly Ala Cys Ala Cys Cys Thr Thr Cys Gly
            340                 345                 350

Cys Ala Gly Cys Cys Thr Ala Cys Ala Cys Gly Cys Gly Gly Gly Ala
        355                 360                 365

Gly Cys Ala Gly Cys Thr Gly Thr Ala Cys Cys Ala Gly Gly Cys Cys
    370                 375                 380

Ala Thr Cys Thr Thr Cys Cys Ala Thr Gly Cys Thr Gly Thr Gly Gly
385                 390                 395                 400
```

```
Ala Cys Cys Ala Gly Thr Ala Cys Cys Thr Gly Gly Cys Gly Thr Thr
                405                 410                 415

Gly Cys Cys Thr Gly Ala Cys Gly Thr Gly Thr Cys Ala Cys Thr Gly
            420                 425                 430

Gly Gly Cys Cys Gly Gly Thr Ala Thr Gly Cys Gly Thr Ala Thr Gly
        435                 440                 445

Thr Cys Cys Gly Thr Gly Gly Thr Gly Gly Gly Gly Gly Thr Gly Ala
    450                 455                 460

Cys Cys Cys Thr Thr Gly Gly Ala Cys Cys Ala Ala Thr Gly Gly Cys
465                 470                 475                 480

Thr Cys Ala Gly Gly Gly Cys Thr Thr Gly Cys Thr Cys Thr Cys Thr
                485                 490                 495

Gly Cys Cys Ala Gly Cys Gly Gly Thr Ala Cys Thr Ala Cys Cys Ala
            500                 505                 510

Cys Cys Gly Ala Gly Gly Cys Cys Ala Cys Gly Thr Gly Gly Ala Cys
        515                 520                 525

Cys Cys Gly Gly Cys Cys Ala Ala Cys Gly Ala Cys Ala Cys Ala Thr
    530                 535                 540

Thr Thr Gly Ala Cys Ala Thr Thr Gly Ala Thr Cys Cys Gly Ala Thr
545                 550                 555                 560

Gly Gly Thr Gly Gly Thr Thr Ala Cys Thr Gly Ala Cys Thr Gly Cys
                565                 570                 575

Ala Thr Cys Cys Ala Gly Gly Thr Gly Gly Ala Thr Cys Cys Cys Cys
            580                 585                 590

Cys Cys Gly Ala Gly Cys Gly Gly Cys Cys Cys Cys Cys Thr Cys Cys
        595                 600                 605

Gly Cys Cys Cys Cys Cys Cys Ala Gly Cys Gly Ala Cys Gly Ala Thr
    610                 615                 620

Cys Thr Cys Ala Cys Cys Cys Thr Cys Thr Thr Gly Gly Ala Ala Ala
625                 630                 635                 640

Gly Cys Ala Gly Cys Thr Cys Cys Ala Gly Thr Thr Ala Cys Ala Ala
                645                 650                 655

Gly Ala Ala Cys Cys Thr Cys Ala Cys Gly Cys Thr Cys Ala Ala Ala
            660                 665                 670

Thr Thr Cys Cys Ala Cys Ala Ala Gly Cys Thr Gly Gly Thr Cys Ala
        675                 680                 685

Ala Thr Gly Thr Cys Ala Cys Cys Ala Thr Cys Cys Ala Cys Thr Thr
    690                 695                 700

Cys Cys Gly Gly Cys Thr Gly Ala Ala Gly Ala Cys Cys Ala Thr Thr
705                 710                 715                 720

Ala Ala Cys Cys Thr Cys Cys Ala Gly Ala Gly Cys Cys Thr Cys Ala
                725                 730                 735

Thr Cys Ala Ala Thr Ala Ala Thr Gly Ala Gly Ala Thr Cys Cys Cys
            740                 745                 750

Gly Gly Ala Cys Thr Gly Cys Thr Ala Thr Ala Cys Cys Thr Thr Cys
        755                 760                 765

Ala Gly Cys Gly Thr Cys Cys Thr Gly Ala Thr Cys Ala Cys Gly Thr
    770                 775                 780

Thr Thr Gly Ala Cys Ala Ala Cys Ala Ala Ala Gly Cys Ala Cys Ala
785                 790                 795                 800

Cys Ala Gly Thr Gly Gly Gly Cys Gly Gly Ala Thr Cys Cys Cys Cys
                805                 810                 815

Ala Thr Cys Ala Gly Cys Cys Thr Gly Gly Ala Gly Ala Cys Cys Cys
```

```
            820                 825                 830

Ala Gly Gly Cys Cys Cys Ala Cys Ala Thr Cys Cys Ala Gly Gly Ala
        835                 840                 845

Gly Thr Gly Thr Ala Ala Gly Cys Ala Cys Cys Cys Cys Ala Gly Thr
    850                 855                 860

Gly Thr Cys Thr Thr Cys Cys Ala Gly Cys Ala Cys Gly Gly Ala Gly
865                 870                 875                 880

Ala Cys Ala Ala Cys Ala Gly Cys Thr Thr Cys Cys Gly Gly Cys Thr
                885                 890                 895

Cys Cys Thr Gly Thr Thr Thr Gly Ala Cys Gly Thr Gly Gly Thr Gly
            900                 905                 910

Gly Thr Cys Ala Thr Cys Cys Thr Cys Ala Cys Cys Thr Gly Cys Thr
        915                 920                 925

Cys Cys Cys Thr Gly Thr Cys Cys Thr Thr Cys Cys Thr Cys Cys Thr
    930                 935                 940

Cys Thr Gly Cys Gly Cys Cys Cys Gly Cys Thr Cys Ala Cys Thr Cys
945                 950                 955                 960

Cys Thr Thr Cys Gly Ala Gly Gly Cys Thr Thr Cys Cys Thr Gly Cys
                965                 970                 975

Thr Gly Cys Ala Gly Ala Ala Cys Gly Ala Gly Thr Thr Thr Gly Thr
            980                 985                 990

Gly Gly Gly Gly Thr Thr Cys Ala  Thr Gly Thr Gly Gly  Cys Gly Gly
        995                 1000                1005

Cys Ala  Gly Cys Gly Gly Gly  Gly Ala Cys Gly Gly  Gly Thr Cys
    1010                1015                1020

Ala Thr  Cys Ala Gly Cys Cys  Thr Gly Thr Gly Gly  Gly Ala Gly
    1025                1030                1035

Cys Gly  Gly Cys Thr Gly Gly  Ala Ala Thr Thr Thr  Gly Thr Cys
    1040                1045                1050

Ala Ala  Thr Gly Gly Cys Thr  Gly Gly Thr Ala Cys  Ala Thr Cys
    1055                1060                1065

Cys Thr  Gly Cys Thr Cys Gly  Thr Cys Ala Cys Cys  Ala Gly Cys
    1070                1075                1080

Gly Ala  Thr Gly Thr Gly Cys  Thr Cys Ala Cys Cys  Ala Thr Cys
    1085                1090                1095

Thr Cys  Gly Gly Gly Cys Ala  Cys Cys Ala Thr Cys  Ala Thr Gly
    1100                1105                1110

Ala Ala  Gly Ala Thr Cys Gly  Gly Cys Ala Thr Cys  Gly Ala Gly
    1115                1120                1125

Gly Cys  Cys Ala Ala Gly Ala  Ala Cys Thr Thr Gly  Gly Cys Gly
    1130                1135                1140

Ala Gly  Cys Thr Ala Cys Gly  Ala Cys Gly Thr Cys  Thr Gly Cys
    1145                1150                1155

Ala Gly  Cys Ala Thr Cys Cys  Thr Cys Cys Thr Gly  Gly Gly Cys
    1160                1165                1170

Ala Cys  Cys Thr Cys Gly Ala  Cys Gly Cys Thr Gly  Cys Thr Gly
    1175                1180                1185

Gly Thr  Gly Thr Gly Gly Gly  Thr Gly Gly Gly Cys  Gly Thr Gly
    1190                1195                1200

Ala Thr  Cys Cys Gly Cys Thr  Ala Cys Cys Thr Gly  Ala Cys Cys
    1205                1210                1215

Thr Thr  Cys Thr Thr Cys Cys  Ala Cys Ala Ala Cys  Thr Ala Cys
    1220                1225                1230
```

Ala Ala Thr Ala Thr Cys Cys Thr Cys Ala Thr Cys Gly Cys Cys
1235 1240 1245

Ala Cys Ala Cys Thr Gly Cys Gly Gly Gly Thr Gly Gly Cys Cys
1250 1255 1260

Cys Thr Gly Cys Cys Cys Ala Gly Cys Gly Thr Cys Ala Thr Gly
1265 1270 1275

Cys Gly Cys Thr Thr Cys Thr Gly Cys Thr Gly Cys Thr Gly Cys
1280 1285 1290

Gly Thr Gly Gly Cys Thr Gly Thr Cys Ala Thr Cys Thr Ala Cys
1295 1300 1305

Cys Thr Gly Gly Gly Cys Thr Ala Cys Thr Gly Cys Thr Thr Cys
1310 1315 1320

Thr Gly Thr Gly Gly Cys Thr Gly Gly Ala Thr Cys Gly Thr Gly
1325 1330 1335

Cys Thr Gly Gly Gly Gly Cys Cys Cys Thr Ala Thr Cys Ala Thr
1340 1345 1350

Gly Thr Gly Ala Ala Gly Thr Thr Cys Cys Gly Cys Thr Cys Ala
1355 1360 1365

Cys Thr Cys Thr Cys Cys Ala Thr Gly Gly Thr Gly Thr Cys Thr
1370 1375 1380

Gly Ala Gly Thr Gly Cys Cys Thr Gly Thr Thr Cys Thr Cys Gly
1385 1390 1395

Cys Thr Cys Ala Thr Cys Ala Ala Thr Gly Gly Gly Gly Ala Cys
1400 1405 1410

Gly Ala Cys Ala Thr Gly Thr Thr Thr Gly Thr Gly Ala Cys Gly
1415 1420 1425

Thr Thr Cys Gly Cys Cys Gly Cys Cys Ala Thr Gly Cys Ala Gly
1430 1435 1440

Gly Cys Gly Cys Ala Gly Cys Ala Gly Gly Gly Cys Cys Gly Cys
1445 1450 1455

Ala Gly Cys Ala Gly Cys Cys Thr Gly Gly Thr Gly Thr Gly Gly
1460 1465 1470

Cys Thr Cys Thr Thr Cys Thr Cys Cys Cys Ala Gly Cys Thr Cys
1475 1480 1485

Thr Ala Cys Cys Thr Thr Thr Ala Cys Thr Cys Cys Thr Thr Cys
1490 1495 1500

Ala Thr Cys Ala Gly Cys Cys Thr Cys Thr Thr Cys Ala Thr Cys
1505 1510 1515

Thr Ala Cys Ala Thr Gly Gly Thr Gly Cys Thr Cys Ala Gly Cys
1520 1525 1530

Cys Thr Cys Thr Thr Cys Ala Thr Cys Gly Cys Gly Cys Thr Cys
1535 1540 1545

Ala Thr Cys Ala Cys Cys Gly Gly Cys Gly Cys Cys Thr Ala Cys
1550 1555 1560

Gly Ala Cys Ala Cys Cys Ala Thr Cys Ala Ala Gly Cys Ala Thr
1565 1570 1575

Cys Cys Cys Gly Gly Cys Gly Gly Cys Gly Cys Ala Gly Gly Cys
1580 1585 1590

Gly Cys Ala Gly Ala Gly Gly Ala Gly Ala Gly Cys Gly Ala Gly
1595 1600 1605

Cys Thr Gly Cys Ala Gly Gly Cys Cys Thr Ala Cys Ala Thr Cys
1610 1615 1620

Gly Cys Ala Cys Ala Gly Thr Gly Cys Cys Ala Gly Gly Ala Cys
1625 1630 1635

Ala Gly Cys Cys Cys Cys Ala Cys Cys Thr Cys Cys Gly Gly Cys
1640 1645 1650

Ala Ala Gly Thr Thr Cys Cys Gly Cys Cys Gly Cys Gly Gly Gly
1655 1660 1665

Ala Gly Cys Gly Gly Cys Thr Cys Gly Gly Cys Cys Thr Gly Cys
1670 1675 1680

Ala Gly Cys Cys Thr Thr Cys Thr Cys Thr Gly Cys Thr Gly Cys
1685 1690 1695

Thr Gly Cys Gly Gly Ala Ala Gly Gly Gly Ala Cys Cys Cys Cys
1700 1705 1710

Thr Cys Gly Gly Ala Gly Gly Ala Gly Cys Ala Thr Thr Cys Gly
1715 1720 1725

Cys Thr Gly Cys Thr Gly Gly Thr Gly Ala Ala Thr
1730 1735 1740

<210> SEQ ID NO 69
<211> LENGTH: 580
<212> TYPE: PRT
<213> ORGANISM: Homo sapiens

<400> SEQUENCE: 69

Met Thr Ala Pro Ala Gly Pro Arg Gly Ser Glu Thr Glu Arg Leu Leu
1 5 10 15

Thr Pro Asn Pro Gly Tyr Gly Thr Gln Ala Gly Pro Ser Pro Ala Pro
20 25 30

Pro Thr Pro Pro Glu Glu Glu Asp Leu Arg Arg Arg Leu Lys Tyr Phe
35 40 45

Phe Met Ser Pro Cys Asp Lys Phe Arg Ala Lys Gly Arg Lys Pro Cys
50 55 60

Lys Leu Met Leu Gln Val Val Lys Ile Leu Val Val Thr Val Gln Leu
65 70 75 80

Ile Leu Phe Gly Leu Ser Asn Gln Leu Ala Val Thr Phe Arg Glu Glu
85 90 95

Asn Thr Ile Ala Phe Arg His Leu Phe Leu Leu Gly Tyr Ser Asp Gly
100 105 110

Ala Asp Asp Thr Phe Ala Ala Tyr Thr Arg Glu Gln Leu Tyr Gln Ala
115 120 125

Ile Phe His Ala Val Asp Gln Tyr Leu Ala Leu Pro Asp Val Ser Leu
130 135 140

Gly Arg Tyr Ala Tyr Val Arg Gly Gly Gly Asp Pro Trp Thr Asn Gly
145 150 155 160

Ser Gly Leu Ala Leu Cys Gln Arg Tyr Tyr His Arg Gly His Val Asp
165 170 175

Pro Ala Asn Asp Thr Phe Asp Ile Asp Pro Met Val Val Thr Asp Cys
180 185 190

Ile Gln Val Asp Pro Pro Glu Arg Pro Pro Pro Pro Pro Ser Asp Asp
195 200 205

Leu Thr Leu Leu Glu Ser Ser Ser Ser Tyr Lys Asn Leu Thr Leu Lys
210 215 220

Phe His Lys Leu Val Asn Val Thr Ile His Phe Arg Leu Lys Thr Ile
225 230 235 240

Asn Leu Gln Ser Leu Ile Asn Asn Glu Ile Pro Asp Cys Tyr Thr Phe
245 250 255

Ser Val Leu Ile Thr Phe Asp Asn Lys Ala His Ser Gly Arg Ile Pro
260 265 270

```
Ile Ser Leu Glu Thr Gln Ala His Ile Gln Glu Cys Lys His Pro Ser
        275                 280                 285

Val Phe Gln His Gly Asp Asn Ser Phe Arg Leu Leu Phe Asp Val Val
    290                 295                 300

Val Ile Leu Thr Cys Ser Leu Ser Phe Leu Leu Cys Ala Arg Ser Leu
305                 310                 315                 320

Leu Arg Gly Phe Leu Leu Gln Asn Glu Phe Val Gly Phe Met Trp Arg
                325                 330                 335

Gln Arg Gly Arg Val Ile Ser Leu Trp Glu Arg Leu Glu Phe Val Asn
            340                 345                 350

Gly Trp Tyr Ile Leu Leu Val Thr Ser Asp Val Leu Thr Ile Ser Gly
        355                 360                 365

Thr Ile Met Lys Ile Gly Ile Glu Ala Lys Asn Leu Ala Ser Tyr Asp
    370                 375                 380

Val Cys Ser Ile Leu Leu Gly Thr Ser Thr Leu Leu Val Trp Val Gly
385                 390                 395                 400

Val Ile Arg Tyr Leu Thr Phe Phe His Asn Tyr Asn Ile Leu Ile Ala
                405                 410                 415

Thr Leu Arg Val Ala Leu Pro Ser Val Met Arg Phe Cys Cys Cys Val
            420                 425                 430

Ala Val Ile Tyr Leu Gly Tyr Cys Phe Cys Gly Trp Ile Val Leu Gly
        435                 440                 445

Pro Tyr His Val Lys Phe Arg Ser Leu Ser Met Val Ser Glu Cys Leu
    450                 455                 460

Phe Ser Leu Ile Asn Gly Asp Asp Met Phe Val Thr Phe Ala Ala Met
465                 470                 475                 480

Gln Ala Gln Gln Gly Arg Ser Ser Leu Val Trp Leu Phe Ser Gln Leu
                485                 490                 495

Tyr Leu Tyr Ser Phe Ile Ser Leu Phe Ile Tyr Met Val Leu Ser Leu
            500                 505                 510

Phe Ile Ala Leu Ile Thr Gly Ala Tyr Asp Thr Ile Lys His Pro Gly
        515                 520                 525

Gly Ala Gly Ala Glu Glu Ser Glu Leu Gln Ala Tyr Ile Ala Gln Cys
    530                 535                 540

Gln Asp Ser Pro Thr Ser Gly Lys Phe Arg Arg Gly Ser Gly Ser Ala
545                 550                 555                 560

Cys Ser Leu Leu Cys Cys Cys Gly Arg Asp Pro Ser Glu Glu His Ser
                565                 570                 575

Leu Leu Val Asn
            580


<210> SEQ ID NO 70
<211> LENGTH: 1698
<212> TYPE: PRT
<213> ORGANISM: Homo sapiens

<400> SEQUENCE: 70

Ala Thr Gly Gly Cys Cys Cys Gly Gly Cys Ala Gly Cys Cys Thr Thr
1               5                   10                  15

Ala Thr Cys Gly Thr Thr Thr Thr Cys Cys Cys Cys Ala Gly Gly Cys
            20                  25                  30

Ala Ala Gly Gly Ala Thr Thr Cys Cys Gly Gly Ala Gly Ala Gly Ala
        35                  40                  45

Gly Gly Ala Thr Cys Ala Gly Gly Thr Gly Thr Thr Thr Thr Cys Ala
    50                  55                  60
```

```
Gly Gly Thr Thr Ala Ala Cys Cys Gly Thr Cys Ala Gly Ala Ala Ala
65                  70                  75                  80

Cys Gly Cys Ala Ala Thr Gly Gly Cys Ala Cys Ala Thr Cys Gly Thr
                85                  90                  95

Gly Ala Thr Thr Cys Thr Gly Ala Gly Ala Thr Gly Ala Ala Ala Gly
            100                 105                 110

Ala Ala Gly Ala Ala Thr Gly Thr Cys Thr Ala Ala Gly Gly Gly Ala
        115                 120                 125

Ala Gly Ala Cys Cys Thr Gly Ala Ala Gly Thr Thr Thr Thr Ala Cys
    130                 135                 140

Thr Thr Cys Ala Thr Gly Ala Gly Cys Cys Cys Thr Thr Gly Thr Gly
145                 150                 155                 160

Ala Ala Ala Ala Ala Thr Ala Cys Cys Gly Ala Gly Cys Cys Ala Gly
                165                 170                 175

Ala Cys Gly Cys Cys Ala Gly Ala Thr Thr Cys Cys Gly Thr Gly Gly
            180                 185                 190

Ala Ala Ala Cys Thr Gly Gly Gly Thr Thr Thr Gly Cys Ala Gly Ala
        195                 200                 205

Thr Thr Thr Thr Gly Ala Ala Gly Ala Thr Ala Gly Thr Cys Ala Thr
    210                 215                 220

Gly Gly Thr Cys Ala Cys Cys Ala Cys Ala Cys Ala Gly Cys Thr Thr
225                 230                 235                 240

Gly Thr Thr Cys Gly Thr Thr Thr Thr Gly Gly Thr Thr Thr Ala Ala
                245                 250                 255

Gly Thr Ala Ala Cys Cys Ala Gly Cys Thr Gly Gly Thr Gly Gly Thr
            260                 265                 270

Thr Gly Cys Thr Thr Thr Cys Ala Ala Ala Gly Ala Ala Gly Ala Thr
        275                 280                 285

Ala Ala Cys Ala Cys Thr Gly Thr Thr Gly Cys Thr Thr Thr Thr Ala
    290                 295                 300

Ala Gly Cys Ala Cys Thr Thr Gly Thr Thr Thr Thr Thr Gly Ala Ala
305                 310                 315                 320

Ala Gly Gly Ala Thr Ala Thr Thr Cys Thr Gly Gly Thr Ala Cys Ala
                325                 330                 335

Gly Ala Thr Gly Ala Ala Gly Ala Thr Gly Ala Cys Thr Ala Cys Ala
            340                 345                 350

Gly Cys Thr Gly Cys Ala Gly Thr Gly Thr Ala Thr Ala Thr Ala Cys
        355                 360                 365

Thr Cys Ala Ala Gly Ala Gly Gly Ala Thr Gly Cys Cys Thr Ala Thr
    370                 375                 380

Gly Ala Gly Ala Gly Cys Ala Thr Cys Thr Thr Thr Thr Thr Thr Gly
385                 390                 395                 400

Cys Thr Ala Thr Thr Ala Ala Thr Cys Ala Gly Thr Ala Thr Cys Ala
                405                 410                 415

Thr Cys Ala Gly Cys Thr Ala Ala Ala Gly Gly Ala Cys Ala Thr Thr
            420                 425                 430

Ala Cys Cys Cys Thr Gly Gly Gly Gly Ala Cys Cys Cys Thr Thr Gly
        435                 440                 445

Gly Thr Thr Ala Thr Gly Gly Ala Gly Ala Ala Ala Ala Thr Gly Ala
    450                 455                 460

Ala Gly Ala Cys Ala Ala Thr Ala Gly Ala Ala Thr Thr Gly Gly Cys
465                 470                 475                 480

Thr Thr Ala Ala Ala Ala Gly Thr Cys Thr Gly Thr Ala Ala Gly Cys
```

-continued

```
                485                 490                 495

Ala Gly Cys Ala Thr Thr Ala Cys Ala Ala Gly Ala Ala Ala Gly Gly
            500                 505                 510

Gly Ala Cys Cys Ala Thr Gly Thr Thr Thr Cys Cys Thr Thr Cys Thr
        515                 520                 525

Ala Ala Thr Gly Ala Gly Ala Cys Ala Cys Thr Gly Ala Ala Thr Ala
    530                 535                 540

Thr Thr Gly Ala Cys Ala Ala Cys Gly Ala Cys Gly Thr Thr Gly Ala
545                 550                 555                 560

Gly Cys Thr Cys Gly Ala Thr Thr Gly Thr Gly Thr Thr Cys Ala Ala
                565                 570                 575

Thr Thr Ala Gly Ala Cys Cys Thr Thr Cys Ala Gly Gly Ala Cys Cys
            580                 585                 590

Thr Cys Thr Cys Cys Ala Ala Gly Ala Ala Gly Cys Cys Thr Cys Cys
        595                 600                 605

Gly Gly Ala Cys Thr Gly Gly Ala Ala Gly Ala Ala Cys Thr Cys Ala
    610                 615                 620

Thr Cys Ala Thr Thr Cys Thr Thr Cys Ala Gly Ala Cys Thr Gly Gly
625                 630                 635                 640

Ala Ala Thr Thr Thr Thr Ala Thr Cys Gly Gly Cys Thr Cys Thr Thr
                645                 650                 655

Ala Cys Ala Gly Gly Thr Thr Gly Ala Ala Ala Thr Cys Thr Cys Cys
            660                 665                 670

Thr Thr Thr Cys Ala Thr Cys Thr Thr Ala Ala Ala Gly Gly Cys Ala
        675                 680                 685

Thr Thr Gly Ala Cys Cys Thr Ala Cys Ala Gly Ala Cys Ala Ala Thr
    690                 695                 700

Thr Cys Ala Thr Thr Cys Cys Cys Gly Thr Gly Ala Gly Thr Thr Ala
705                 710                 715                 720

Cys Cys Ala Gly Ala Cys Thr Gly Thr Thr Ala Thr Gly Thr Cys Thr
                725                 730                 735

Thr Thr Cys Ala Gly Ala Ala Thr Ala Cys Gly Ala Thr Thr Ala Thr
            740                 745                 750

Cys Thr Thr Thr Gly Ala Cys Ala Ala Thr Ala Ala Ala Gly Cys Thr
        755                 760                 765

Cys Ala Cys Ala Gly Thr Gly Gly Cys Ala Ala Ala Ala Thr Cys Ala
    770                 775                 780

Ala Ala Ala Thr Cys Thr Ala Thr Thr Thr Thr Gly Ala Cys Ala Gly
785                 790                 795                 800

Thr Gly Ala Thr Gly Cys Cys Ala Ala Ala Ala Thr Thr Gly Ala Ala
                805                 810                 815

Gly Ala Ala Thr Gly Thr Ala Ala Ala Gly Ala Cys Thr Thr Gly Ala
            820                 825                 830

Ala Cys Ala Thr Ala Thr Thr Thr Gly Gly Ala Thr Cys Thr Ala Cys
        835                 840                 845

Thr Cys Ala Gly Ala Ala Ala Ala Ala Thr Gly Cys Thr Cys Ala Gly
    850                 855                 860

Thr Ala Thr Gly Thr Cys Cys Thr Gly Gly Thr Gly Thr Thr Thr Gly
865                 870                 875                 880

Ala Thr Gly Cys Ala Thr Thr Thr Gly Thr Cys Ala Thr Thr Gly Thr
                885                 890                 895

Gly Ala Thr Thr Thr Gly Cys Thr Thr Gly Gly Cys Ala Thr Cys Thr
            900                 905                 910
```

Cys Thr Thr Ala Thr Thr Cys Thr Gly Thr Gly Thr Ala Cys Ala Ala
915 920 925

Gly Ala Thr Cys Cys Ala Thr Thr Gly Thr Thr Cys Thr Thr Gly Cys
930 935 940

Thr Cys Thr Ala Ala Gly Gly Thr Thr Ala Cys Gly Gly Ala Ala Gly
945 950 955 960

Ala Gly Ala Thr Thr Thr Cys Thr Ala Ala Ala Thr Thr Thr Cys Thr
965 970 975

Thr Cys Cys Thr Gly Gly Ala Gly Ala Ala Gly Thr Ala Cys Ala Ala
980 985 990

Gly Cys Gly Gly Cys Cys Thr Gly Thr Gly Thr Gly Thr Gly Ala Cys
995 1000 1005

Ala Cys Cys Gly Ala Cys Cys Ala Gly Thr Gly Gly Gly Ala Gly
1010 1015 1020

Thr Thr Cys Ala Thr Cys Ala Ala Cys Gly Gly Cys Thr Gly Gly
1025 1030 1035

Thr Ala Thr Gly Thr Cys Cys Thr Gly Gly Thr Gly Ala Thr Thr
1040 1045 1050

Ala Thr Cys Ala Gly Cys Gly Ala Cys Cys Thr Ala Ala Thr Gly
1055 1060 1065

Ala Cys Ala Ala Thr Cys Ala Thr Thr Gly Gly Cys Thr Cys Cys
1070 1075 1080

Ala Thr Ala Thr Thr Ala Ala Ala Ala Ala Thr Gly Gly Ala Ala
1085 1090 1095

Ala Thr Cys Ala Ala Ala Gly Cys Ala Ala Ala Gly Ala Ala Thr
1100 1105 1110

Cys Thr Cys Ala Cys Ala Ala Ala Cys Thr Ala Thr Gly Ala Thr
1115 1120 1125

Cys Thr Cys Thr Gly Cys Ala Gly Cys Ala Thr Thr Thr Thr Thr
1130 1135 1140

Cys Thr Thr Gly Gly Ala Ala Cys Cys Thr Cys Thr Ala Cys Gly
1145 1150 1155

Cys Thr Cys Thr Thr Gly Gly Thr Thr Thr Gly Gly Gly Thr Thr
1160 1165 1170

Gly Gly Ala Gly Thr Cys Ala Thr Cys Ala Gly Ala Thr Ala Cys
1175 1180 1185

Cys Thr Gly Gly Gly Thr Thr Ala Thr Thr Thr Cys Cys Ala Gly
1190 1195 1200

Gly Cys Ala Thr Ala Thr Ala Ala Thr Gly Thr Gly Cys Thr Gly
1205 1210 1215

Ala Thr Thr Thr Thr Ala Ala Cys Ala Ala Thr Gly Cys Ala Gly
1220 1225 1230

Gly Cys Cys Thr Cys Ala Cys Thr Gly Cys Cys Ala Ala Ala Ala
1235 1240 1245

Gly Thr Thr Cys Thr Thr Cys Gly Gly Thr Thr Thr Thr Gly Thr
1250 1255 1260

Gly Cys Thr Thr Gly Thr Gly Cys Thr Gly Gly Thr Ala Thr Gly
1265 1270 1275

Ala Thr Thr Thr Ala Thr Cys Thr Gly Gly Gly Thr Thr Ala Cys
1280 1285 1290

Ala Cys Ala Thr Thr Cys Thr Gly Thr Gly Gly Cys Thr Gly Gly
1295 1300 1305

Ala Thr Thr Gly Thr Cys Thr Thr Ala Gly Gly Ala Cys Cys Ala
1310 1315 1320

```
Thr Ala  Cys Cys Ala Thr Gly  Ala Cys Ala Ala Gly  Thr Thr Thr
    1325                 1330                 1335

Gly Ala  Ala Ala Ala Thr Cys  Thr Gly Ala Ala Cys  Ala Cys Ala
    1340                 1345                 1350

Gly Thr  Thr Gly Cys Thr Gly  Ala Gly Thr Gly Thr  Cys Thr Gly
    1355                 1360                 1365

Thr Thr  Thr Thr Cys Thr Cys  Thr Gly Gly Thr Cys  Ala Ala Cys
    1370                 1375                 1380

Gly Gly  Thr Gly Ala Thr Gly  Ala Cys Ala Thr Gly  Thr Thr Thr
    1385                 1390                 1395

Gly Cys  Ala Ala Cys Cys Thr  Thr Thr Gly Cys Cys  Cys Ala Ala
    1400                 1405                 1410

Ala Thr  Cys Cys Ala Gly Cys  Ala Gly Ala Ala Gly  Ala Gly Cys
    1415                 1420                 1425

Ala Thr  Cys Thr Thr Gly Gly  Thr Gly Thr Gly Gly  Cys Thr Gly
    1430                 1435                 1440

Thr Thr  Cys Ala Gly Thr Cys  Gly Thr Cys Thr Gly  Thr Ala Thr
    1445                 1450                 1455

Thr Thr  Ala Thr Ala Thr Thr  Cys Cys Thr Thr Cys  Ala Thr Cys
    1460                 1465                 1470

Ala Gly  Cys Cys Thr Thr Thr  Thr Thr Ala Thr Ala  Thr Ala Thr
    1475                 1480                 1485

Ala Thr  Gly Ala Thr Thr Cys  Thr Cys Ala Gly Thr  Cys Thr Thr
    1490                 1495                 1500

Thr Thr  Thr Ala Thr Thr Gly  Cys Ala Cys Thr Thr  Ala Thr Thr
    1505                 1510                 1515

Ala Cys  Ala Gly Ala Thr Thr  Cys Thr Thr Ala Thr  Gly Ala Cys
    1520                 1525                 1530

Ala Cys  Cys Ala Thr Thr Ala  Ala Gly Ala Ala Ala  Thr Thr Cys
    1535                 1540                 1545

Cys Ala  Ala Cys Ala Gly Ala  Ala Thr Gly Gly Gly  Thr Thr Thr
    1550                 1555                 1560

Cys Cys  Thr Gly Ala Ala Ala  Cys Gly Gly Ala Thr  Thr Thr Gly
    1565                 1570                 1575

Cys Ala  Gly Gly Ala Ala Thr  Thr Cys Cys Thr Gly  Ala Ala Gly
    1580                 1585                 1590

Gly Ala  Ala Thr Gly Cys Ala  Gly Thr Ala Gly Cys  Ala Ala Ala
    1595                 1600                 1605

Gly Ala  Ala Gly Ala Gly Thr  Ala Thr Cys Ala Gly  Ala Ala Ala
    1610                 1615                 1620

Gly Ala  Gly Thr Cys Cys Thr  Cys Ala Gly Cys Cys  Thr Thr Cys
    1625                 1630                 1635

Cys Thr  Gly Thr Cys Cys Thr  Gly Cys Ala Thr Cys  Thr Gly Cys
    1640                 1645                 1650

Thr Gly  Thr Cys Gly Gly Ala  Gly Gly Ala Gly Gly  Ala Ala Ala
    1655                 1660                 1665

Ala Gly  Ala Ala Gly Thr Gly  Ala Thr Gly Ala Thr  Cys Ala Cys
    1670                 1675                 1680

Thr Thr  Gly Ala Thr Ala Cys  Cys Thr Ala Thr Thr  Ala Gly Cys
    1685                 1690                 1695
```

<210> SEQ ID NO 71
<211> LENGTH: 566
<212> TYPE: PRT

<213> ORGANISM: Homo sapiens

<400> SEQUENCE: 71

```
Met Ala Arg Gln Pro Tyr Arg Phe Pro Gln Ala Arg Ile Pro Glu Arg
1               5                   10                  15

Gly Ser Gly Val Phe Arg Leu Thr Val Arg Asn Ala Met Ala His Arg
            20                  25                  30

Asp Ser Glu Met Lys Glu Glu Cys Leu Arg Glu Asp Leu Lys Phe Tyr
        35                  40                  45

Phe Met Ser Pro Cys Glu Lys Tyr Arg Ala Arg Arg Gln Ile Pro Trp
    50                  55                  60

Lys Leu Gly Leu Gln Ile Leu Lys Ile Val Met Val Thr Thr Gln Leu
65                  70                  75                  80

Val Arg Phe Gly Leu Ser Asn Gln Leu Val Val Ala Phe Lys Glu Asp
                85                  90                  95

Asn Thr Val Ala Phe Lys His Leu Phe Leu Lys Gly Tyr Ser Gly Thr
            100                 105                 110

Asp Glu Asp Asp Tyr Ser Cys Ser Val Tyr Thr Gln Glu Asp Ala Tyr
        115                 120                 125

Glu Ser Ile Phe Phe Ala Ile Asn Gln Tyr His Gln Leu Lys Asp Ile
    130                 135                 140

Thr Leu Gly Thr Leu Gly Tyr Gly Glu Asn Glu Asp Asn Arg Ile Gly
145                 150                 155                 160

Leu Lys Val Cys Lys Gln His Tyr Lys Lys Gly Thr Met Phe Pro Ser
                165                 170                 175

Asn Glu Thr Leu Asn Ile Asp Asn Asp Val Glu Leu Asp Cys Val Gln
            180                 185                 190

Leu Asp Leu Gln Asp Leu Ser Lys Lys Pro Pro Asp Trp Lys Asn Ser
        195                 200                 205

Ser Phe Phe Arg Leu Glu Phe Tyr Arg Leu Leu Gln Val Glu Ile Ser
    210                 215                 220

Phe His Leu Lys Gly Ile Asp Leu Gln Thr Ile His Ser Arg Glu Leu
225                 230                 235                 240

Pro Asp Cys Tyr Val Phe Gln Asn Thr Ile Ile Phe Asp Asn Lys Ala
                245                 250                 255

His Ser Gly Lys Ile Lys Ile Tyr Phe Asp Ser Asp Ala Lys Ile Glu
            260                 265                 270

Glu Cys Lys Asp Leu Asn Ile Phe Gly Ser Thr Gln Lys Asn Ala Gln
        275                 280                 285

Tyr Val Leu Val Phe Asp Ala Phe Val Ile Val Ile Cys Leu Ala Ser
    290                 295                 300

Leu Ile Leu Cys Thr Arg Ser Ile Val Leu Ala Leu Arg Leu Arg Lys
305                 310                 315                 320

Arg Phe Leu Asn Phe Phe Leu Glu Lys Tyr Lys Arg Pro Val Cys Asp
                325                 330                 335

Thr Asp Gln Trp Glu Phe Ile Asn Gly Trp Tyr Val Leu Val Ile Ile
            340                 345                 350

Ser Asp Leu Met Thr Ile Ile Gly Ser Ile Leu Lys Met Glu Ile Lys
        355                 360                 365

Ala Lys Asn Leu Thr Asn Tyr Asp Leu Cys Ser Ile Phe Leu Gly Thr
    370                 375                 380

Ser Thr Leu Leu Val Trp Val Gly Val Ile Arg Tyr Leu Gly Tyr Phe
385                 390                 395                 400

Gln Ala Tyr Asn Val Leu Ile Leu Thr Met Gln Ala Ser Leu Pro Lys
```

-continued

```
                405                 410                 415

Val Leu Arg Phe Cys Ala Cys Ala Gly Met Ile Tyr Leu Gly Tyr Thr
            420                 425                 430

Phe Cys Gly Trp Ile Val Leu Gly Pro Tyr His Asp Lys Phe Glu Asn
        435                 440                 445

Leu Asn Thr Val Ala Glu Cys Leu Phe Ser Leu Val Asn Gly Asp Asp
    450                 455                 460

Met Phe Ala Thr Phe Ala Gln Ile Gln Gln Lys Ser Ile Leu Val Trp
465                 470                 475                 480

Leu Phe Ser Arg Leu Tyr Leu Tyr Ser Phe Ile Ser Leu Phe Ile Tyr
                485                 490                 495

Met Ile Leu Ser Leu Phe Ile Ala Leu Ile Thr Asp Ser Tyr Asp Thr
            500                 505                 510

Ile Lys Lys Phe Gln Gln Asn Gly Phe Pro Glu Thr Asp Leu Gln Glu
        515                 520                 525

Phe Leu Lys Glu Cys Ser Ser Lys Glu Glu Tyr Gln Lys Glu Ser Ser
    530                 535                 540

Ala Phe Leu Ser Cys Ile Cys Cys Arg Arg Arg Lys Arg Ser Asp Asp
545                 550                 555                 560

His Leu Ile Pro Ile Ser
                565


<210> SEQ ID NO 72
<211> LENGTH: 1659
<212> TYPE: PRT
<213> ORGANISM: Mus musculus

<400> SEQUENCE: 72

Ala Thr Gly Gly Cys Ala Ala Ala Thr Cys Cys Cys Gly Ala Gly Gly
1               5                   10                  15

Thr Gly Cys Thr Gly Gly Thr Thr Ala Gly Cys Ala Gly Cys Thr Gly
            20                  25                  30

Cys Ala Gly Ala Gly Cys Thr Cys Gly Cys Cys Ala Ala Gly Ala Thr
        35                  40                  45

Gly Ala Ala Ala Gly Cys Cys Cys Cys Thr Gly Cys Ala Cys Thr Thr
    50                  55                  60

Thr Cys Cys Ala Cys Cys Cys Gly Ala Gly Cys Thr Cys Gly Thr Cys
65                  70                  75                  80

Cys Cys Cys Gly Thr Cys Ala Gly Ala Gly Cys Ala Gly Cys Thr Thr
                85                  90                  95

Cys Thr Cys Thr Thr Ala Gly Ala Ala Gly Ala Cys Cys Ala Gly Ala
            100                 105                 110

Thr Gly Ala Gly Gly Cys Gly Gly Ala Ala Ala Cys Thr Cys Ala Ala
        115                 120                 125

Gly Thr Thr Cys Thr Thr Thr Thr Thr Thr Ala Thr Gly Ala Ala Thr
    130                 135                 140

Cys Cys Thr Thr Gly Thr Gly Ala Gly Ala Ala Gly Thr Thr Cys Thr
145                 150                 155                 160

Gly Gly Gly Cys Thr Cys Gly Gly Gly Gly Thr Ala Gly Gly Ala Ala
                165                 170                 175

Gly Cys Cys Ala Thr Gly Gly Ala Ala Ala Cys Thr Thr Gly Cys Cys
            180                 185                 190

Ala Thr Ala Cys Ala Gly Ala Thr Thr Cys Thr Gly Ala Ala Ala Ala
        195                 200                 205

Thr Cys Gly Cys Gly Ala Thr Gly Gly Thr Gly Ala Cys Thr Ala Thr
```

-continued

```
    210                 215                 220

Cys Cys Ala Gly Cys Thr Gly Gly Thr Thr Cys Thr Gly Thr Thr Thr
225                 230                 235                 240

Gly Gly Ala Cys Thr Ala Ala Gly Thr Ala Ala Cys Cys Ala Gly Ala
                245                 250                 255

Thr Gly Gly Thr Ala Gly Thr Ala Gly Cys Thr Thr Thr Cys Ala Ala
            260                 265                 270

Ala Gly Ala Gly Gly Ala Gly Ala Ala Cys Ala Cys Thr Ala Thr Ala
        275                 280                 285

Gly Cys Cys Thr Thr Cys Ala Ala Ala Cys Ala Cys Cys Thr Cys Thr
    290                 295                 300

Thr Cys Cys Thr Ala Ala Ala Gly Gly Gly Cys Thr Ala Cys Ala Thr
305                 310                 315                 320

Gly Gly Ala Thr Cys Gly Ala Ala Thr Gly Gly Ala Cys Gly Ala Cys
                325                 330                 335

Ala Cys Cys Thr Ala Thr Gly Cys Ala Gly Thr Gly Thr Ala Cys Ala
            340                 345                 350

Cys Thr Cys Ala Gly Ala Gly Thr Gly Ala Ala Gly Thr Gly Thr Ala
        355                 360                 365

Thr Gly Ala Cys Cys Ala Gly Ala Thr Cys Ala Thr Cys Thr Thr Thr
    370                 375                 380

Gly Cys Ala Gly Thr Gly Ala Cys Cys Cys Ala Gly Thr Ala Cys Thr
385                 390                 395                 400

Thr Gly Cys Ala Gly Cys Thr Thr Cys Ala Gly Ala Ala Cys Ala Thr
                405                 410                 415

Cys Thr Cys Cys Gly Thr Gly Gly Gly Cys Ala Ala Thr Cys Ala Cys
            420                 425                 430

Gly Cys Thr Thr Ala Thr Gly Ala Gly Ala Ala Cys Ala Ala Gly Gly
        435                 440                 445

Gly Gly Ala Cys Thr Ala Ala Gly Cys Ala Gly Thr Cys Gly Gly Cys
    450                 455                 460

Gly Ala Thr Gly Gly Cys Ala Ala Thr Cys Thr Gly Thr Cys Ala Gly
465                 470                 475                 480

Cys Ala Cys Thr Thr Cys Thr Ala Cys Ala Gly Gly Cys Ala Ala Gly
                485                 490                 495

Gly Ala Ala Cys Cys Ala Thr Cys Thr Gly Cys Cys Cys Cys Gly Gly
            500                 505                 510

Gly Ala Ala Cys Gly Ala Cys Ala Cys Cys Thr Thr Thr Gly Ala Cys
        515                 520                 525

Ala Thr Cys Gly Ala Thr Cys Cys Ala Gly Ala Ala Gly Thr Thr Gly
    530                 535                 540

Ala Ala Ala Cys Ala Gly Ala Ala Thr Gly Thr Thr Thr Cys Cys Thr
545                 550                 555                 560

Thr Gly Thr Ala Gly Ala Gly Cys Cys Ala Gly Ala Thr Gly Ala Ala
                565                 570                 575

Gly Cys Thr Thr Cys Cys Cys Ala Cys Cys Thr Thr Gly Gly Ala Ala
            580                 585                 590

Cys Gly Cys Cys Thr Gly Gly Ala Gly Ala Ala Ala Ala Thr Ala Ala
        595                 600                 605

Ala Cys Thr Cys Ala Ala Cys Cys Thr Gly Ala Gly Cys Cys Thr Gly
    610                 615                 620

Gly Ala Cys Thr Thr Cys Cys Ala Cys Ala Gly Ala Cys Thr Thr Cys
625                 630                 635                 640
```

-continued

Thr Gly Ala Cys Gly Gly Thr Gly Gly Ala Gly Cys Thr Cys Cys Ala
645 650 655

Gly Thr Thr Thr Ala Ala Gly Cys Thr Cys Ala Ala Ala Gly Cys Cys
660 665 670

Ala Thr Cys Ala Ala Thr Cys Thr Gly Cys Ala Gly Ala Cys Ala Gly
675 680 685

Thr Thr Cys Gly Ala Cys Ala Cys Cys Ala Gly Gly Ala Gly Cys Thr
690 695 700

Thr Cys Cys Thr Gly Ala Cys Thr Gly Thr Thr Ala Cys Gly Ala Cys
705 710 715 720

Thr Thr Thr Ala Cys Gly Cys Thr Gly Ala Cys Thr Ala Thr Ala Ala
725 730 735

Cys Ala Thr Thr Cys Gly Ala Cys Ala Ala Cys Ala Ala Gly Gly Cys
740 745 750

Thr Cys Ala Cys Ala Gly Thr Gly Gly Ala Ala Gly Ala Ala Thr Cys
755 760 765

Ala Ala Ala Ala Thr Ala Ala Gly Cys Thr Thr Ala Gly Ala Cys Ala
770 775 780

Ala Cys Gly Ala Cys Ala Thr Thr Thr Cys Thr Ala Thr Cys Ala Ala
785 790 795 800

Ala Gly Ala Ala Thr Gly Cys Ala Ala Ala Gly Ala Cys Thr Gly Gly
805 810 815

Cys Ala Thr Gly Thr Gly Thr Cys Thr Gly Gly Ala Thr Cys Ala Ala
820 825 830

Thr Thr Cys Ala Gly Ala Ala Gly Ala Ala Cys Ala Cys Ala Cys Ala
835 840 845

Cys Thr Ala Cys Ala Thr Gly Ala Thr Gly Ala Thr Cys Thr Thr Thr
850 855 860

Gly Ala Thr Gly Cys Cys Thr Thr Thr Gly Thr Cys Ala Thr Thr Cys
865 870 875 880

Thr Gly Ala Cys Cys Thr Gly Cys Thr Thr Gly Gly Cys Cys Thr Cys
885 890 895

Ala Cys Thr Gly Gly Thr Gly Cys Thr Gly Thr Gly Thr Gly Cys Cys
900 905 910

Ala Gly Gly Thr Cys Thr Gly Thr Gly Ala Thr Thr Ala Gly Gly Gly
915 920 925

Gly Thr Cys Thr Thr Cys Ala Gly Cys Thr Thr Cys Ala Gly Cys Ala
930 935 940

Gly Gly Ala Gly Thr Thr Thr Gly Thr Cys Ala Ala Cys Thr Thr Cys
945 950 955 960

Thr Thr Cys Cys Thr Thr Cys Thr Thr Cys Ala Cys Thr Ala Cys Ala
965 970 975

Ala Gly Ala Ala Gly Gly Ala Ala Gly Thr Thr Thr Cys Gly Gly Cys
980 985 990

Cys Thr Cys Thr Gly Ala Thr Cys Ala Gly Ala Thr Gly Gly Ala Gly
995 1000 1005

Thr Thr Cys Ala Thr Cys Ala Ala Cys Gly Gly Gly Thr Gly Gly
1010 1015 1020

Thr Ala Cys Ala Thr Thr Ala Thr Gly Ala Thr Cys Ala Thr Cys
1025 1030 1035

Ala Thr Thr Ala Gly Thr Gly Ala Cys Ala Thr Ala Thr Thr Gly
1040 1045 1050

Ala Cys Ala Ala Thr Cys Gly Thr Thr Gly Gly Ala Thr Cys Ala
1055 1060 1065

Gly Thr Thr Cys Thr Gly Ala Ala Ala Ala Thr Gly Gly Ala Ala
1070 1075 1080

Ala Thr Cys Cys Ala Ala Gly Cys Cys Ala Ala Gly Ala Gly Thr
1085 1090 1095

Cys Thr Cys Ala Cys Ala Ala Gly Cys Thr Ala Thr Gly Ala Thr
1100 1105 1110

Gly Thr Cys Thr Gly Cys Ala Gly Cys Ala Thr Ala Cys Thr Thr
1115 1120 1125

Cys Thr Cys Gly Gly Gly Ala Cys Gly Thr Cys Ala Ala Cys Thr
1130 1135 1140

Ala Thr Gly Cys Thr Cys Gly Thr Gly Thr Gly Gly Cys Thr Thr
1145 1150 1155

Gly Gly Ala Gly Thr Thr Ala Thr Cys Cys Gly Ala Thr Ala Cys
1160 1165 1170

Cys Thr Gly Gly Gly Thr Thr Thr Cys Thr Thr Thr Gly Cys Gly
1175 1180 1185

Ala Ala Gly Thr Ala Cys Ala Ala Thr Cys Thr Cys Cys Thr Thr
1190 1195 1200

Ala Thr Thr Cys Thr Gly Ala Cys Cys Cys Thr Cys Cys Ala Gly
1205 1210 1215

Gly Cys Ala Gly Cys Gly Cys Thr Gly Cys Cys Cys Ala Ala Cys
1220 1225 1230

Gly Thr Cys Ala Thr Gly Ala Gly Gly Thr Thr Cys Thr Gly Thr
1235 1240 1245

Thr Gly Cys Thr Gly Cys Gly Cys Thr Gly Cys Thr Ala Thr Gly
1250 1255 1260

Ala Thr Cys Thr Ala Thr Cys Thr Ala Gly Gly Cys Thr Ala Thr
1265 1270 1275

Thr Gly Cys Thr Thr Thr Thr Gly Cys Gly Gly Ala Thr Gly Gly
1280 1285 1290

Ala Thr Thr Gly Thr Gly Cys Thr Gly Gly Gly Cys Cys Cys Thr
1295 1300 1305

Thr Ala Cys Cys Ala Thr Gly Ala Gly Ala Ala Gly Thr Thr Cys
1310 1315 1320

Cys Gly Thr Thr Cys Cys Cys Thr Gly Ala Ala Cys Ala Gly Gly
1325 1330 1335

Gly Thr Cys Thr Cys Cys Gly Ala Gly Thr Gly Cys Cys Thr Gly
1340 1345 1350

Thr Thr Cys Thr Cys Gly Cys Thr Gly Ala Thr Ala Ala Ala Cys
1355 1360 1365

Gly Gly Ala Gly Ala Cys Gly Ala Thr Ala Thr Gly Thr Thr Thr
1370 1375 1380

Thr Cys Cys Ala Cys Ala Thr Thr Thr Gly Cys Gly Ala Ala Ala
1385 1390 1395

Ala Thr Gly Cys Ala Gly Cys Ala Gly Ala Ala Gly Ala Gly Thr
1400 1405 1410

Thr Ala Cys Cys Thr Gly Gly Thr Gly Thr Gly Gly Cys Thr Gly
1415 1420 1425

Thr Thr Cys Ala Gly Cys Cys Gly Ala Gly Thr Cys Thr Ala Cys
1430 1435 1440

Cys Thr Gly Thr Ala Cys Thr Cys Gly Thr Thr Cys Ala Thr Cys
1445 1450 1455

Ala Gly Cys Cys Thr Cys Thr Thr Cys Ala Thr Thr Thr Ala Cys

```
    1460                1465                1470

Ala Thr  Gly Ala Thr Thr Cys  Thr Gly Ala Gly Cys  Cys Thr Thr
    1475                1480                1485

Thr Thr  Cys Ala Thr Cys Gly  Cys Gly Cys Thr Cys  Ala Thr Cys
    1490                1495                1500

Ala Cys  Ala Gly Ala Cys Ala  Cys Ala Thr Ala Cys  Gly Ala Ala
    1505                1510                1515

Ala Cys  Ala Ala Thr Thr Ala  Ala Gly Cys Ala Cys  Thr Ala Cys
    1520                1525                1530

Cys Ala  Gly Cys Ala Ala Gly  Ala Thr Gly Gly Cys  Thr Thr Cys
    1535                1540                1545

Cys Cys  Ala Gly Ala Gly Ala  Cys Gly Gly Ala Ala  Cys Thr Thr
    1550                1555                1560

Cys Gly  Ala Ala Ala Gly Thr  Thr Thr Ala Thr Ala  Gly Cys Gly
    1565                1570                1575

Gly Ala  Ala Thr Gly Cys Ala  Ala Ala Gly Ala Cys  Cys Thr Cys
    1580                1585                1590

Cys Cys  Cys Ala Ala Cys Thr  Cys Cys Gly Gly Ala  Ala Ala Ala
    1595                1600                1605

Thr Ala  Cys Ala Gly Ala Thr  Thr Ala Gly Ala Ala  Gly Ala Thr
    1610                1615                1620

Gly Ala  Cys Cys Cys Thr Cys  Cys Gly Gly Gly Thr  Thr Cys Thr
    1625                1630                1635

Thr Thr  Ala Cys Thr Cys Thr  Gly Cys Thr Gly Cys  Thr Gly Cys
    1640                1645                1650

Ala Ala  Ala Ala Ala Gly
    1655


<210> SEQ ID NO 73
<211> LENGTH: 553
<212> TYPE: PRT
<213> ORGANISM: Mus musculus

<400> SEQUENCE: 73

Met Ala Asn Pro Glu Val Leu Val Ser Ser Cys Arg Ala Arg Gln Asp
1               5                   10                  15

Glu Ser Pro Cys Thr Phe His Pro Ser Ser Ser Pro Ser Glu Gln Leu
            20                  25                  30

Leu Leu Glu Asp Gln Met Arg Arg Lys Leu Lys Phe Phe Phe Met Asn
        35                  40                  45

Pro Cys Glu Lys Phe Trp Ala Arg Gly Arg Lys Pro Trp Lys Leu Ala
    50                  55                  60

Ile Gln Ile Leu Lys Ile Ala Met Val Thr Ile Gln Leu Val Leu Phe
65                  70                  75                  80

Gly Leu Ser Asn Gln Met Val Val Ala Phe Lys Glu Glu Asn Thr Ile
                85                  90                  95

Ala Phe Lys His Leu Phe Leu Lys Gly Tyr Met Asp Arg Met Asp Asp
            100                 105                 110

Thr Tyr Ala Val Tyr Thr Gln Ser Glu Val Tyr Asp Gln Ile Ile Phe
        115                 120                 125

Ala Val Thr Gln Tyr Leu Gln Leu Gln Asn Ile Ser Val Gly Asn His
    130                 135                 140

Ala Tyr Glu Asn Lys Gly Thr Lys Gln Ser Ala Met Ala Ile Cys Gln
145                 150                 155                 160

His Phe Tyr Arg Gln Gly Thr Ile Cys Pro Gly Asn Asp Thr Phe Asp
```

```
                165                 170                 175

Ile Asp Pro Glu Val Glu Thr Glu Cys Phe Leu Val Glu Pro Asp Glu
            180                 185                 190

Ala Ser His Leu Gly Thr Pro Gly Glu Asn Lys Leu Asn Leu Ser Leu
        195                 200                 205

Asp Phe His Arg Leu Leu Thr Val Glu Leu Gln Phe Lys Leu Lys Ala
    210                 215                 220

Ile Asn Leu Gln Thr Val Arg His Gln Glu Leu Pro Asp Cys Tyr Asp
225                 230                 235                 240

Phe Thr Leu Thr Ile Thr Phe Asp Asn Lys Ala His Ser Gly Arg Ile
                245                 250                 255

Lys Ile Ser Leu Asp Asn Asp Ile Ser Ile Lys Glu Cys Lys Asp Trp
            260                 265                 270

His Val Ser Gly Ser Ile Gln Lys Asn Thr His Tyr Met Met Ile Phe
        275                 280                 285

Asp Ala Phe Val Ile Leu Thr Cys Leu Ala Ser Leu Val Leu Cys Ala
    290                 295                 300

Arg Ser Val Ile Arg Gly Leu Gln Leu Gln Gln Glu Phe Val Asn Phe
305                 310                 315                 320

Phe Leu Leu His Tyr Lys Lys Glu Val Ser Ala Ser Asp Gln Met Glu
                325                 330                 335

Phe Ile Asn Gly Trp Tyr Ile Met Ile Ile Ile Ser Asp Ile Leu Thr
            340                 345                 350

Ile Val Gly Ser Val Leu Lys Met Glu Ile Gln Ala Lys Ser Leu Thr
        355                 360                 365

Ser Tyr Asp Val Cys Ser Ile Leu Leu Gly Thr Ser Thr Met Leu Val
    370                 375                 380

Trp Leu Gly Val Ile Arg Tyr Leu Gly Phe Phe Ala Lys Tyr Asn Leu
385                 390                 395                 400

Leu Ile Leu Thr Leu Gln Ala Ala Leu Pro Asn Val Met Arg Phe Cys
                405                 410                 415

Cys Cys Ala Ala Met Ile Tyr Leu Gly Tyr Cys Phe Cys Gly Trp Ile
            420                 425                 430

Val Leu Gly Pro Tyr His Glu Lys Phe Arg Ser Leu Asn Arg Val Ser
        435                 440                 445

Glu Cys Leu Phe Ser Leu Ile Asn Gly Asp Asp Met Phe Ser Thr Phe
    450                 455                 460

Ala Lys Met Gln Gln Lys Ser Tyr Leu Val Trp Leu Phe Ser Arg Val
465                 470                 475                 480

Tyr Leu Tyr Ser Phe Ile Ser Leu Phe Ile Tyr Met Ile Leu Ser Leu
                485                 490                 495

Phe Ile Ala Leu Ile Thr Asp Thr Tyr Glu Thr Ile Lys His Tyr Gln
            500                 505                 510

Gln Asp Gly Phe Pro Glu Thr Glu Leu Arg Lys Phe Ile Ala Glu Cys
        515                 520                 525

Lys Asp Leu Pro Asn Ser Gly Lys Tyr Arg Leu Glu Asp Asp Pro Pro
    530                 535                 540

Gly Ser Leu Leu Cys Cys Cys Lys Lys
545                 550
```

<210> SEQ ID NO 74
<211> LENGTH: 1773
<212> TYPE: PRT
<213> ORGANISM: Gallus gallus

<400> SEQUENCE: 74

Ala Thr Gly Ala Thr Cys Ala Cys Cys Cys Gly Thr Gly Gly Thr Thr
1               5                   10                  15

Thr Cys Cys Gly Thr Thr Cys Ala Gly Gly Cys Thr Thr Thr Thr Ala
            20                  25                  30

Cys Gly Gly Cys Thr Gly Thr Ala Gly Cys Ala Ala Thr Cys Gly Ala
        35                  40                  45

Thr Ala Thr Ala Gly Thr Gly Gly Thr Gly Cys Thr Ala Ala Gly Thr
    50                  55                  60

Gly Cys Cys Ala Gly Thr Thr Ala Gly Thr Thr Gly Cys Thr Cys Ala
65                  70                  75                  80

Gly Ala Cys Gly Thr Thr Thr Gly Thr Cys Ala Thr Thr Thr Cys Ala
                85                  90                  95

Gly Cys Ala Ala Thr Gly Gly Ala Gly Ala Cys Thr Cys Cys Thr Gly
            100                 105                 110

Ala Ala Gly Thr Gly Gly Cys Thr Gly Thr Ala Ala Gly Cys Ala Gly
        115                 120                 125

Cys Thr Gly Cys Ala Gly Thr Gly Cys Thr Cys Gly Gly Gly Ala Thr
    130                 135                 140

Gly Ala Cys Gly Ala Ala Gly Gly Gly Cys Thr Cys Thr Gly Cys Ala
145                 150                 155                 160

Gly Cys Thr Ala Cys Gly Gly Ala Cys Ala Ala Cys Ala Cys Cys Thr
                165                 170                 175

Ala Thr Thr Gly Cys Thr Gly Cys Cys Ala Cys Ala Ala Gly Ala Gly
            180                 185                 190

Cys Thr Gly Gly Thr Gly Gly Cys Gly Gly Ala Ala Gly Ala Cys Cys
        195                 200                 205

Ala Gly Cys Thr Gly Ala Gly Gly Ala Gly Gly Ala Ala Gly Cys Thr
    210                 215                 220

Gly Ala Ala Gly Thr Thr Cys Thr Thr Cys Thr Thr Cys Ala Thr Gly
225                 230                 235                 240

Ala Ala Cys Cys Cys Ala Thr Gly Thr Gly Ala Ala Ala Ala Ala Thr
                245                 250                 255

Thr Cys Thr Gly Gly Gly Cys Thr Cys Gly Gly Gly Gly Cys Ala Gly
            260                 265                 270

Ala Ala Ala Ala Cys Cys Thr Thr Gly Gly Ala Ala Ala Cys Thr Thr
        275                 280                 285

Gly Gly Gly Ala Thr Thr Cys Ala Gly Cys Thr Gly Cys Thr Cys Ala
    290                 295                 300

Ala Ala Ala Thr Ala Gly Cys Ala Ala Thr Gly Gly Thr Thr Ala Cys
305                 310                 315                 320

Cys Ala Thr Thr Cys Ala Gly Cys Thr Gly Gly Thr Gly Cys Thr Thr
                325                 330                 335

Thr Thr Thr Gly Gly Ala Thr Thr Gly Ala Gly Cys Ala Ala Thr Cys
            340                 345                 350

Ala Ala Ala Thr Gly Gly Thr Gly Gly Thr Thr Gly Cys Thr Thr Thr
        355                 360                 365

Cys Ala Ala Ala Gly Ala Ala Gly Ala Gly Ala Ala Cys Ala Cys Thr
    370                 375                 380

Ala Thr Thr Gly Cys Ala Thr Thr Cys Ala Ala Ala Cys Ala Thr Cys
385                 390                 395                 400

Thr Cys Thr Thr Cys Thr Thr Gly Ala Ala Ala Gly Gly Gly Thr Ala
                405                 410                 415

Cys Ala Thr Gly Gly Ala Cys Ala Gly Ala Ala Thr Gly Gly Ala Thr
420 425 430

Gly Ala Thr Ala Cys Cys Thr Ala Thr Gly Cys Gly Gly Thr Ala Thr
435 440 445

Ala Cys Ala Cys Ala Cys Ala Gly Ala Cys Ala Gly Ala Thr Gly Thr
450 455 460

Cys Thr Ala Thr Gly Ala Cys Cys Ala Ala Ala Thr Ala Thr Thr Cys
465 470 475 480

Thr Thr Thr Gly Cys Cys Ala Thr Cys Ala Ala Thr Cys Ala Gly Thr
485 490 495

Ala Cys Thr Thr Ala Cys Ala Gly Thr Thr Gly Cys Cys Cys Ala Ala
500 505 510

Cys Ala Thr Thr Thr Cys Thr Gly Thr Thr Gly Gly Ala Ala Ala Cys
515 520 525

Cys Ala Thr Gly Cys Thr Thr Ala Thr Gly Ala Gly Ala Ala Gly Ala
530 535 540

Ala Ala Gly Gly Ala Gly Cys Ala Gly Ala Ala Gly Ala Gly Ala Cys
545 550 555 560

Ala Gly Cys Thr Cys Thr Gly Gly Cys Thr Gly Thr Ala Thr Gly Thr
565 570 575

Cys Ala Ala Cys Ala Gly Thr Thr Cys Thr Ala Cys Ala Ala Gly Cys
580 585 590

Ala Ala Gly Gly Ala Ala Cys Cys Ala Thr Cys Thr Gly Thr Cys Cys
595 600 605

Thr Gly Gly Ala Ala Ala Thr Gly Ala Cys Ala Cys Cys Thr Thr Thr
610 615 620

Gly Ala Thr Ala Thr Ala Gly Ala Cys Cys Cys Ala Gly Ala Gly Ala
625 630 635 640

Thr Thr Gly Thr Gly Ala Cys Thr Gly Ala Cys Thr Gly Cys Thr Thr
645 650 655

Gly Thr Ala Cys Ala Thr Thr Gly Ala Gly Cys Cys Gly Ala Thr Gly
660 665 670

Ala Thr Gly Thr Cys Thr Thr Thr Ala Gly Ala Cys Ala Ala Cys Ala
675 680 685

Gly Ala Ala Cys Ala Gly Thr Gly Gly Gly Ala Ala Ala Gly Cys Ala
690 695 700

Cys Ala Ala Thr Thr Thr Gly Ala Ala Thr Thr Thr Cys Ala Cys Thr
705 710 715 720

Cys Thr Gly Gly Ala Thr Thr Thr Cys Cys Ala Cys Ala Gly Gly Cys
725 730 735

Thr Cys Gly Thr Gly Gly Cys Ala Gly Thr Gly Cys Ala Ala Cys Thr
740 745 750

Cys Ala Thr Gly Thr Thr Cys Ala Ala Thr Cys Thr Gly Ala Ala Gly
755 760 765

Gly Cys Ala Ala Thr Cys Ala Ala Cys Cys Thr Cys Cys Ala Gly Ala
770 775 780

Cys Cys Gly Thr Cys Cys Gly Thr Cys Ala Cys Cys Ala Cys Gly Ala
785 790 795 800

Gly Cys Thr Cys Cys Cys Thr Gly Ala Cys Thr Gly Thr Thr Ala Cys
805 810 815

Gly Ala Thr Thr Thr Cys Ala Cys Cys Cys Thr Gly Ala Cys Gly Ala
820 825 830

Thr Ala Gly Thr Gly Thr Thr Thr Gly Ala Thr Ala Ala Thr Ala Ala
835 840 845

```
Ala Gly Cys Cys Cys Ala Cys Ala Gly Thr Gly Gly Ala Ala Gly Ala
    850                 855                 860

Ala Thr Cys Ala Ala Ala Ala Thr Cys Ala Gly Thr Cys Thr Ala Gly
865                 870                 875                 880

Ala Cys Ala Ala Cys Gly Ala Cys Ala Thr Ala Gly Ala Gly Ala Thr
                885                 890                 895

Cys Ala Gly Gly Gly Ala Ala Thr Gly Thr Ala Ala Ala Gly Ala Cys
            900                 905                 910

Thr Gly Gly Cys Ala Cys Gly Thr Thr Thr Cys Thr Gly Gly Ala Thr
        915                 920                 925

Cys Ala Ala Thr Ala Cys Ala Gly Ala Ala Gly Ala Ala Thr Ala Cys
    930                 935                 940

Gly Cys Ala Thr Thr Ala Cys Ala Thr Gly Ala Thr Gly Ala Thr Cys
945                 950                 955                 960

Thr Thr Cys Gly Ala Thr Gly Cys Thr Thr Thr Thr Gly Thr Cys Ala
                965                 970                 975

Thr Ala Cys Thr Gly Ala Thr Cys Thr Gly Thr Cys Thr Gly Ala Gly
            980                 985                 990

Cys Thr Cys Ala Thr Thr Gly Ala  Thr Cys Cys Thr Thr  Thr Gly Cys
        995                  1000                1005

Ala Cys  Thr Cys Gly Ala Thr  Cys Ala Gly Thr Ala  Gly Thr Cys
    1010                 1015                 1020

Ala Ala  Ala Gly Gly Ala Ala  Thr Thr Cys Gly Gly  Cys Thr Cys
    1025                 1030                 1035

Cys Ala  Ala Ala Gly Ala Gly  Ala Ala Thr Thr Thr  Gly Thr Ala
    1040                 1045                 1050

Ala Gly  Thr Thr Thr Thr Thr  Thr Cys Cys Thr Ala  Thr Ala Thr
    1055                 1060                 1065

Thr Ala  Thr Thr Ala Cys Ala  Ala Gly Ala Ala Ala  Gly Ala Gly
    1070                 1075                 1080

Gly Thr  Ala Thr Cys Thr Thr  Ala Cys Ala Ala Thr  Gly Ala Thr
    1085                 1090                 1095

Cys Ala  Gly Ala Thr Gly Gly  Ala Ala Thr Thr Thr  Gly Thr Cys
    1100                 1105                 1110

Ala Ala  Thr Gly Gly Cys Thr  Gly Gly Thr Ala Thr  Ala Thr Cys
    1115                 1120                 1125

Cys Thr  Cys Ala Thr Thr Ala  Thr Gly Gly Thr Thr  Ala Gly Thr
    1130                 1135                 1140

Gly Ala  Thr Gly Thr Cys Cys  Thr Cys Ala Cys Thr  Ala Thr Cys
    1145                 1150                 1155

Gly Thr  Thr Gly Gly Ala Thr  Cys Ala Ala Cys Thr  Cys Thr Cys
    1160                 1165                 1170

Ala Ala  Ala Ala Thr Gly Gly  Ala Gly Ala Thr Ala  Cys Ala Gly
    1175                 1180                 1185

Gly Cys  Cys Ala Ala Gly Ala  Gly Thr Cys Thr Gly  Ala Cys Ala
    1190                 1195                 1200

Ala Gly  Thr Thr Ala Cys Gly  Ala Cys Gly Thr Cys  Thr Gly Thr
    1205                 1210                 1215

Ala Gly  Cys Ala Thr Ala Cys  Thr Cys Thr Thr Ala  Gly Gly Ala
    1220                 1225                 1230

Ala Cys  Ala Thr Cys Cys Ala  Cys Thr Ala Thr Gly  Cys Thr Gly
    1235                 1240                 1245

Gly Thr  Gly Thr Gly Gly Cys  Thr Thr Gly Gly Ala  Gly Thr Cys
```

1250 1255 1260

Ala Thr Thr Cys Gly Cys Thr Ala Cys Cys Thr Cys Gly Gly Thr
1265 1270 1275

Thr Thr Cys Thr Thr Thr Cys Ala Gly Ala Ala Gly Thr Ala Thr
1280 1285 1290

Ala Ala Thr Cys Thr Thr Cys Thr Cys Ala Thr Thr Cys Thr Ala
1295 1300 1305

Ala Cys Gly Cys Thr Gly Cys Gly Ala Gly Cys Ala Gly Cys Ala
1310 1315 1320

Cys Thr Ala Cys Cys Cys Ala Ala Cys Gly Thr Cys Ala Thr Gly
1325 1330 1335

Ala Gly Gly Thr Thr Cys Thr Gly Cys Thr Gly Thr Thr Gly Thr
1340 1345 1350

Gly Cys Thr Gly Cys Thr Ala Thr Gly Ala Thr Cys Thr Ala Thr
1355 1360 1365

Cys Thr Ala Gly Gly Thr Thr Ala Thr Thr Gly Thr Thr Thr Cys
1370 1375 1380

Thr Gly Cys Gly Gly Ala Thr Gly Gly Ala Thr Thr Gly Thr Ala
1385 1390 1395

Cys Thr Gly Gly Gly Gly Cys Cys Ala Thr Ala Cys Cys Ala Cys
1400 1405 1410

Gly Thr Gly Ala Ala Gly Thr Thr Cys Cys Gly Thr Thr Cys Thr
1415 1420 1425

Cys Thr Gly Ala Ala Thr Gly Thr Gly Gly Thr Thr Thr Cys Thr
1430 1435 1440

Gly Ala Ala Thr Gly Cys Cys Thr Cys Thr Thr Thr Thr Cys Ala
1445 1450 1455

Thr Thr Gly Ala Thr Ala Ala Ala Thr Gly Gly Ala Gly Ala Thr
1460 1465 1470

Gly Ala Cys Ala Thr Gly Thr Thr Thr Gly Cys Cys Ala Cys Thr
1475 1480 1485

Thr Thr Thr Gly Cys Ala Ala Ala Ala Ala Thr Gly Cys Ala Gly
1490 1495 1500

Cys Ala Gly Ala Ala Ala Ala Gly Thr Thr Ala Cys Thr Thr Gly
1505 1510 1515

Gly Thr Thr Thr Gly Gly Thr Thr Ala Thr Thr Cys Ala Gly Thr
1520 1525 1530

Ala Gly Ala Ala Thr Cys Thr Ala Cys Cys Thr Cys Thr Ala Cys
1535 1540 1545

Thr Cys Cys Thr Thr Cys Ala Thr Cys Ala Gly Cys Cys Thr Gly
1550 1555 1560

Thr Thr Cys Ala Thr Cys Thr Ala Cys Ala Thr Gly Gly Thr Gly
1565 1570 1575

Cys Thr Ala Ala Gly Thr Cys Thr Cys Thr Thr Cys Ala Thr Thr
1580 1585 1590

Gly Cys Ala Cys Thr Cys Ala Thr Thr Ala Cys Ala Gly Ala Thr
1595 1600 1605

Ala Cys Ala Thr Ala Thr Gly Ala Ala Ala Cys Thr Ala Thr Cys
1610 1615 1620

Ala Ala Gly Cys Ala Cys Thr Ala Cys Cys Ala Ala Cys Ala Ala
1625 1630 1635

Gly Ala Thr Gly Gly Cys Thr Thr Thr Cys Cys Ala Gly Ala Gly
1640 1645 1650

```
Ala Cys  Ala Gly Ala Ala Cys  Thr Thr Cys Ala Gly  Ala Gly Ala
    1655                1660                1665

Thr Thr  Thr Ala Thr Ala Thr  Cys Ala Cys Ala Gly  Thr Gly Cys
    1670                1675                1680

Ala Ala  Ala Gly Ala Cys Thr  Thr Ala Cys Cys Ala  Ala Ala Cys
    1685                1690                1695

Thr Cys  Thr Gly Gly Ala Ala  Gly Gly Thr Ala Cys  Ala Gly Ala
    1700                1705                1710

Thr Thr  Ala Gly Ala Ala Gly  Ala Gly Gly Ala Ala  Gly Gly Thr
    1715                1720                1725

Thr Cys  Thr Gly Thr Ala Thr  Cys Thr Cys Thr Cys  Thr Thr Cys
    1730                1735                1740

Thr Gly  Thr Thr Gly Thr Thr  Gly Cys Ala Gly Thr  Gly Gly Thr
    1745                1750                1755

Cys Cys  Thr Ala Gly Thr Gly  Ala Ala Cys Ala Thr  Ala Thr Cys
    1760                1765                1770


<210> SEQ ID NO 75
<211> LENGTH: 591
<212> TYPE: PRT
<213> ORGANISM: Gallus gallus

<400> SEQUENCE: 75

Met Ile Thr Arg Gly Phe Arg Ser Gly Phe Tyr Gly Cys Ser Asn Arg
1               5                   10                  15

Tyr Ser Gly Ala Lys Cys Gln Leu Val Ala Gln Thr Phe Val Ile Ser
            20                  25                  30

Ala Met Glu Thr Pro Glu Val Ala Val Ser Ser Cys Ser Ala Arg Asp
        35                  40                  45

Asp Glu Gly Leu Cys Ser Tyr Gly Gln His Leu Leu Leu Pro Gln Glu
    50                  55                  60

Leu Val Ala Glu Asp Gln Leu Arg Arg Lys Leu Lys Phe Phe Phe Met
65                  70                  75                  80

Asn Pro Cys Glu Lys Phe Trp Ala Arg Gly Arg Lys Pro Trp Lys Leu
                85                  90                  95

Gly Ile Gln Leu Leu Lys Ile Ala Met Val Thr Ile Gln Leu Val Leu
            100                 105                 110

Phe Gly Leu Ser Asn Gln Met Val Val Ala Phe Lys Glu Glu Asn Thr
        115                 120                 125

Ile Ala Phe Lys His Leu Phe Leu Lys Gly Tyr Met Asp Arg Met Asp
    130                 135                 140

Asp Thr Tyr Ala Val Tyr Thr Gln Thr Asp Val Tyr Asp Gln Ile Phe
145                 150                 155                 160

Phe Ala Ile Asn Gln Tyr Leu Gln Leu Pro Asn Ile Ser Val Gly Asn
                165                 170                 175

His Ala Tyr Glu Lys Lys Gly Ala Glu Glu Thr Ala Leu Ala Val Cys
            180                 185                 190

Gln Gln Phe Tyr Lys Gln Gly Thr Ile Cys Pro Gly Asn Asp Thr Phe
        195                 200                 205

Asp Ile Asp Pro Glu Ile Val Thr Asp Cys Leu Tyr Ile Glu Pro Met
    210                 215                 220

Met Ser Leu Asp Asn Arg Thr Val Gly Lys His Asn Leu Asn Phe Thr
225                 230                 235                 240

Leu Asp Phe His Arg Leu Val Ala Val Gln Leu Met Phe Asn Leu Lys
                245                 250                 255
```

```
Ala Ile Asn Leu Gln Thr Val Arg His His Glu Leu Pro Asp Cys Tyr
            260                 265                 270

Asp Phe Thr Leu Thr Ile Val Phe Asp Asn Lys Ala His Ser Gly Arg
        275                 280                 285

Ile Lys Ile Ser Leu Asp Asn Asp Ile Glu Ile Arg Glu Cys Lys Asp
    290                 295                 300

Trp His Val Ser Gly Ser Ile Gln Lys Asn Thr His Tyr Met Met Ile
305                 310                 315                 320

Phe Asp Ala Phe Val Ile Leu Ile Cys Leu Ser Ser Leu Ile Leu Cys
                325                 330                 335

Thr Arg Ser Val Val Lys Gly Ile Arg Leu Gln Arg Glu Phe Val Ser
            340                 345                 350

Phe Phe Leu Tyr Tyr Tyr Lys Lys Glu Val Ser Tyr Asn Asp Gln Met
        355                 360                 365

Glu Phe Val Asn Gly Trp Tyr Ile Leu Ile Met Val Ser Asp Val Leu
    370                 375                 380

Thr Ile Val Gly Ser Thr Leu Lys Met Glu Ile Gln Ala Lys Ser Leu
385                 390                 395                 400

Thr Ser Tyr Asp Val Cys Ser Ile Leu Leu Gly Thr Ser Thr Met Leu
                405                 410                 415

Val Trp Leu Gly Val Ile Arg Tyr Leu Gly Phe Phe Gln Lys Tyr Asn
            420                 425                 430

Leu Leu Ile Leu Thr Leu Arg Ala Ala Leu Pro Asn Val Met Arg Phe
        435                 440                 445

Cys Cys Cys Ala Ala Met Ile Tyr Leu Gly Tyr Cys Phe Cys Gly Trp
    450                 455                 460

Ile Val Leu Gly Pro Tyr His Val Lys Phe Arg Ser Leu Asn Val Val
465                 470                 475                 480

Ser Glu Cys Leu Phe Ser Leu Ile Asn Gly Asp Asp Met Phe Ala Thr
                485                 490                 495

Phe Ala Lys Met Gln Gln Lys Ser Tyr Leu Val Trp Leu Phe Ser Arg
            500                 505                 510

Ile Tyr Leu Tyr Ser Phe Ile Ser Leu Phe Ile Tyr Met Val Leu Ser
        515                 520                 525

Leu Phe Ile Ala Leu Ile Thr Asp Thr Tyr Glu Thr Ile Lys His Tyr
    530                 535                 540

Gln Gln Asp Gly Phe Pro Glu Thr Glu Leu Gln Arg Phe Ile Ser Gln
545                 550                 555                 560

Cys Lys Asp Leu Pro Asn Ser Gly Arg Tyr Arg Leu Glu Glu Glu Gly
                565                 570                 575

Ser Val Ser Leu Phe Cys Cys Cys Ser Gly Pro Ser Glu His Ile
            580                 585                 590


<210> SEQ ID NO 76
<211> LENGTH: 2424
<212> TYPE: PRT
<213> ORGANISM: Canis familiaris

<400> SEQUENCE: 76

Ala Thr Gly Ala Cys Cys Cys Cys Thr Thr Thr Thr Gly Gly Cys Ala
1               5                   10                  15

Gly Cys Thr Thr Gly Gly Cys Thr Thr Cys Thr Gly Cys Ala Ala Ala
            20                  25                  30

Gly Gly Cys Thr Thr Cys Ala Ala Ala Cys Thr Cys Ala Ala Gly Ala
        35                  40                  45
```

-continued

```
Gly Cys Thr Gly Cys Cys Thr Gly Gly Ala Ala Gly Ala Thr Thr Gly
    50                  55                  60

Thr Gly Gly Thr Gly Gly Ala Thr Thr Cys Ala Thr Thr Cys Ala Gly
65                  70                  75                  80

Cys Thr Cys Gly Cys Ala Gly Cys Ala Cys Ala Cys Gly Cys Cys Cys
                85                  90                  95

Cys Ala Gly Gly Thr Gly Gly Gly Cys Ala Cys Thr Gly Gly Thr Gly
            100                 105                 110

Gly Thr Cys Cys Cys Cys Ala Gly Gly Ala Ala Thr Cys Ala Gly Ala
        115                 120                 125

Cys Ala Ala Gly Gly Cys Cys Cys Thr Thr Ala Cys Cys Thr Thr Cys
    130                 135                 140

Gly Gly Ala Gly Ala Gly Thr Thr Ala Ala Cys Gly Thr Thr Cys Thr
145                 150                 155                 160

Cys Cys Cys Ala Cys Thr Cys Ala Thr Cys Thr Cys Cys Ala Thr Thr
                165                 170                 175

Cys Thr Thr Cys Ala Thr Cys Thr Gly Cys Gly Cys Cys Ala Gly Cys
            180                 185                 190

Cys Cys Thr Thr Cys Thr Cys Thr Cys Cys Cys Ala Cys Cys Gly Thr
        195                 200                 205

Thr Gly Cys Ala Cys Ala Gly Cys Ala Gly Thr Gly Gly Gly Cys Thr
    210                 215                 220

Ala Gly Ala Cys Gly Ala Thr Gly Ala Gly Cys Cys Ala Thr Ala Cys
225                 230                 235                 240

Thr Gly Cys Thr Gly Gly Ala Cys Ala Gly Gly Thr Thr Thr Thr Cys
                245                 250                 255

Ala Cys Thr Gly Cys Ala Thr Cys Ala Ala Gly Thr Ala Cys Cys Thr
            260                 265                 270

Cys Gly Cys Gly Gly Gly Cys Cys Cys Ala Gly Cys Gly Ala Gly Thr
        275                 280                 285

Gly Thr Cys Cys Cys Ala Ala Ala Cys Thr Cys Cys Cys Thr Thr Gly
    290                 295                 300

Ala Ala Ala Gly Ala Gly Gly Gly Ala Gly Thr Ala Ala Gly Ala Thr
305                 310                 315                 320

Ala Thr Thr Gly Gly Thr Thr Thr Cys Cys Cys Ala Ala Gly Cys Cys
                325                 330                 335

Thr Cys Cys Thr Thr Thr Cys Cys Cys Ala Thr Cys Cys Gly Gly Ala
            340                 345                 350

Cys Cys Thr Cys Cys Cys Cys Thr Thr Ala Cys Cys Thr Gly Ala Cys
        355                 360                 365

Ala Cys Thr Gly Cys Thr Ala Ala Gly Cys Cys Gly Ala Gly Gly Gly
    370                 375                 380

Gly Ala Ala Ala Ala Gly Ala Ala Gly Cys Cys Thr Cys Thr Cys Thr
385                 390                 395                 400

Gly Cys Ala Gly Thr Thr Cys Cys Gly Thr Gly Gly Ala Gly Ala Ala
                405                 410                 415

Ala Ala Gly Gly Cys Cys Thr Thr Thr Gly Gly Gly Gly Gly Thr Thr
            420                 425                 430

Thr Thr Gly Gly Ala Gly Ala Thr Gly Gly Gly Ala Ala Gly Thr Cys
        435                 440                 445

Thr Gly Ala Cys Thr Cys Thr Cys Cys Thr Cys Thr Cys Gly Gly Ala
    450                 455                 460

Ala Gly Ala Gly Cys Thr Cys Ala Ala Ala Cys Gly Gly Cys Ala Gly
465                 470                 475                 480
```

```
Cys Thr Cys Cys Cys Cys Gly Gly Cys Ala Cys Gly Cys Thr Gly Thr
                485                 490                 495

Thr Gly Cys Thr Ala Gly Gly Ala Cys Ala Ala Cys Cys Thr Cys Cys
            500                 505                 510

Gly Thr Thr Gly Cys Thr Ala Ala Gly Gly Gly Ala Ala Ala Gly Ala
        515                 520                 525

Gly Gly Cys Gly Gly Cys Thr Cys Cys Thr Cys Thr Gly Cys Thr Gly
    530                 535                 540

Ala Gly Ala Thr Thr Gly Ala Cys Ala Ala Gly Ala Cys Gly Cys Cys
545                 550                 555                 560

Gly Cys Thr Ala Cys Cys Ala Ala Thr Ala Gly Gly Gly Cys Gly Thr
                565                 570                 575

Cys Thr Ala Cys Thr Cys Thr Cys Cys Gly Gly Cys Cys Gly Cys Cys
            580                 585                 590

Thr Cys Thr Thr Cys Ala Ala Gly Gly Cys Cys Gly Cys Ala Cys Thr
        595                 600                 605

Thr Gly Thr Gly Ala Thr Thr Gly Gly Cys Thr Gly Cys Thr Gly Thr
    610                 615                 620

Cys Gly Thr Gly Cys Thr Gly Ala Cys Gly Thr Cys Ala Cys Gly Cys
625                 630                 635                 640

Ala Ala Cys Thr Cys Gly Ala Ala Cys Cys Gly Cys Cys Gly Ala Gly
                645                 650                 655

Ala Gly Ala Thr Cys Cys Thr Gly Gly Gly Thr Thr Thr Thr Cys Gly
            660                 665                 670

Cys Cys Cys Gly Cys Thr Cys Gly Gly Cys Ala Gly Gly Ala Gly Gly
        675                 680                 685

Thr Gly Thr Gly Cys Gly Gly Thr Thr Thr Gly Gly Gly Thr Thr Cys
    690                 695                 700

Cys Cys Gly Cys Gly Thr Gly Gly Ala Gly Gly Gly Thr Gly Cys Thr
705                 710                 715                 720

Gly Cys Thr Gly Gly Cys Thr Cys Gly Ala Ala Thr Gly Thr Ala Ala
                725                 730                 735

Ala Cys Ala Ala Thr Cys Thr Thr Thr Thr Thr Thr Thr Thr Thr Thr
            740                 745                 750

Thr Cys Thr Cys Cys Cys Cys Cys Thr Ala Gly Ala Gly Ala Thr Gly
        755                 760                 765

Gly Cys Ala Ala Ala Thr Cys Cys Thr Ala Cys Gly Gly Thr Thr Gly
    770                 775                 780

Thr Thr Ala Thr Ala Ala Gly Thr Ala Gly Cys Thr Gly Cys Ala Gly
785                 790                 795                 800

Cys Thr Cys Thr Cys Ala Thr Gly Ala Ala Gly Ala Gly Gly Ala Ala
                805                 810                 815

Ala Ala Thr Cys Gly Thr Thr Gly Cys Ala Cys Thr Thr Thr Thr Ala
            820                 825                 830

Gly Cys Cys Ala Gly Cys Ala Cys Ala Cys Ala Thr Cys Gly Cys Cys
        835                 840                 845

Cys Thr Cys Thr Gly Ala Gly Gly Ala Gly Cys Thr Thr Cys Thr Gly
    850                 855                 860

Thr Thr Ala Gly Ala Ala Gly Ala Cys Cys Ala Gly Ala Thr Ala Ala
865                 870                 875                 880

Gly Gly Cys Gly Ala Ala Ala Ala Cys Thr Cys Ala Ala Ala Thr Thr
                885                 890                 895

Thr Thr Thr Thr Thr Thr Cys Ala Thr Gly Ala Ala Thr Cys Cys Thr
```

-continued

```
            900                 905                 910

Thr Gly Thr Gly Ala Ala Ala Ala Gly Thr Thr Cys Thr Gly Gly Gly
        915                 920                 925

Cys Thr Cys Gly Ala Gly Gly Thr Ala Gly Ala Ala Ala Ala Cys Cys
    930                 935                 940

Ala Thr Gly Gly Ala Ala Gly Cys Thr Thr Gly Cys Cys Ala Thr Ala
945                 950                 955                 960

Cys Ala Ala Ala Thr Thr Cys Thr Ala Ala Ala Ala Ala Thr Thr Gly
                965                 970                 975

Cys Ala Ala Thr Gly Gly Thr Gly Ala Cys Thr Ala Thr Cys Cys Ala
            980                 985                 990

Gly Cys Thr Gly Gly Thr Cys Thr  Thr Thr Thr Thr Thr  Gly Gly Gly
        995                 1000                1005

Cys Thr  Ala Ala Gly Thr Ala  Ala Cys Cys Ala Gly  Ala Thr Gly
    1010                1015                1020

Gly Thr  Thr Gly Thr Ala Gly  Cys Thr Thr Thr Cys  Ala Ala Gly
    1025                1030                1035

Gly Ala  Ala Gly Ala Ala Ala  Ala Cys Ala Cys Thr  Ala Thr Ala
    1040                1045                1050

Gly Cys  Ala Thr Thr Cys Ala  Ala Ala Cys Ala Cys  Cys Thr Cys
    1055                1060                1065

Thr Thr  Cys Thr Thr Ala Ala  Ala Ala Gly Gly Ala  Thr Ala Thr
    1070                1075                1080

Ala Thr  Gly Gly Ala Cys Cys  Gly Ala Ala Thr Gly  Gly Ala Thr
    1085                1090                1095

Gly Ala  Cys Ala Cys Ala Thr  Ala Thr Gly Cys Ala  Gly Thr Gly
    1100                1105                1110

Thr Ala  Cys Ala Cys Ala Cys  Ala Ala Cys Gly Thr  Gly Ala Thr
    1115                1120                1125

Gly Thr  Ala Thr Ala Thr Gly  Ala Thr Cys Ala Gly  Ala Thr Cys
    1130                1135                1140

Ala Thr  Cys Thr Thr Thr Gly  Cys Ala Gly Thr Gly  Ala Ala Cys
    1145                1150                1155

Cys Ala  Gly Thr Ala Cys Thr  Thr Gly Cys Thr Thr  Cys Thr Ala
    1160                1165                1170

Cys Gly  Cys Ala Ala Thr Ala  Cys Cys Thr Cys Gly  Gly Thr Thr
    1175                1180                1185

Gly Gly  Gly Ala Ala Thr Cys  Ala Thr Gly Cys Thr  Thr Ala Thr
    1190                1195                1200

Gly Ala  Gly Ala Ala Cys Ala  Ala Gly Gly Gly Gly  Ala Cys Gly
    1205                1210                1215

Gly Ala  Ala Cys Ala Gly Thr  Cys Thr Gly Cys Thr  Ala Thr Gly
    1220                1225                1230

Gly Cys  Ala Ala Thr Cys Thr  Gly Thr Cys Ala Gly  Cys Ala Cys
    1235                1240                1245

Thr Thr  Cys Thr Ala Cys Ala  Ala Gly Cys Ala Gly  Gly Gly Ala
    1250                1255                1260

Ala Ala  Cys Ala Thr Cys Thr  Gly Thr Cys Cys Thr  Gly Gly Ala
    1265                1270                1275

Ala Ala  Thr Gly Ala Thr Ala  Cys Cys Thr Thr Cys  Gly Ala Cys
    1280                1285                1290

Ala Thr  Thr Gly Ala Thr Cys  Cys Ala Gly Ala Gly  Ala Thr Thr
    1295                1300                1305
```

-continued

```
Gly Ala  Ala Ala Cys Thr Gly  Ala Gly Thr Gly Thr  Thr Thr Cys
    1310                 1315                 1320

Thr Cys  Thr Gly Thr Ala Gly  Ala Gly Cys Cys Ala  Gly Cys Thr
    1325                 1330                 1335

Gly Ala  Gly Cys Cys Thr Thr  Thr Cys Cys Ala Cys  Gly Thr Cys
    1340                 1345                 1350

Gly Gly  Ala Ala Cys Ala Cys  Thr Gly Gly Ala Ala  Gly Ala Ala
    1355                 1360                 1365

Ala Ala  Thr Ala Ala Ala Cys  Thr Cys Ala Ala Cys  Thr Thr Ala
    1370                 1375                 1380

Ala Cys  Gly Cys Thr Gly Gly  Ala Cys Thr Thr Thr  Cys Ala Cys
    1385                 1390                 1395

Ala Gly  Ala Cys Thr Cys Cys  Thr Cys Ala Cys Gly  Gly Thr Gly
    1400                 1405                 1410

Gly Ala  Cys Cys Thr Gly Cys  Ala Gly Thr Thr Thr  Ala Ala Gly
    1415                 1420                 1425

Cys Thr  Gly Ala Ala Gly Gly  Cys Cys Ala Thr Thr  Ala Ala Thr
    1430                 1435                 1440

Cys Thr  Gly Cys Ala Gly Ala  Cys Cys Ala Thr Thr  Cys Gly Gly
    1445                 1450                 1455

Cys Ala  Thr Cys Ala Cys Gly  Ala Gly Cys Thr Cys  Cys Cys Thr
    1460                 1465                 1470

Gly Ala  Cys Thr Gly Thr Thr  Ala Thr Gly Ala Cys  Thr Thr Thr
    1475                 1480                 1485

Ala Cys  Thr Cys Thr Cys Ala  Cys Thr Ala Thr Ala  Ala Cys Ala
    1490                 1495                 1500

Thr Thr  Thr Gly Ala Cys Ala  Ala Thr Ala Ala Gly  Gly Cys Cys
    1505                 1510                 1515

Cys Ala  Thr Ala Gly Thr Gly  Gly Ala Ala Gly Ala  Ala Thr Thr
    1520                 1525                 1530

Ala Ala  Gly Ala Thr Ala Ala  Gly Thr Thr Thr Ala  Gly Ala Thr
    1535                 1540                 1545

Ala Ala  Thr Gly Ala Thr Ala  Thr Thr Thr Cys Cys  Ala Thr Cys
    1550                 1555                 1560

Ala Gly  Ala Gly Ala Ala Thr  Gly Thr Ala Ala Ala  Gly Ala Cys
    1565                 1570                 1575

Thr Gly  Gly Cys Ala Thr Gly  Thr Ala Thr Cys Gly  Gly Gly Ala
    1580                 1585                 1590

Thr Cys  Ala Ala Thr Thr Cys  Ala Gly Ala Ala Gly  Ala Ala Cys
    1595                 1600                 1605

Ala Cys  Thr Cys Ala Cys Thr  Ala Cys Ala Thr Gly  Ala Thr Gly
    1610                 1615                 1620

Ala Thr  Cys Thr Thr Thr Gly  Ala Thr Gly Cys Cys  Thr Thr Thr
    1625                 1630                 1635

Gly Thr  Thr Ala Thr Thr Cys  Thr Gly Ala Cys Ala  Thr Gly Cys
    1640                 1645                 1650

Thr Thr  Gly Gly Cys Thr Thr  Cys Ala Cys Thr Ala  Ala Cys Cys
    1655                 1660                 1665

Cys Thr  Gly Thr Gly Cys Cys  Thr Thr Cys Gly Ala  Thr Cys Thr
    1670                 1675                 1680

Gly Thr  Ala Ala Thr Thr Ala  Gly Ala Gly Gly Ala  Cys Thr Thr
    1685                 1690                 1695

Cys Ala  Gly Cys Thr Thr Cys  Ala Ala Cys Ala Gly  Gly Ala Ala
    1700                 1705                 1710
```

```
Thr Thr  Thr Gly Thr Cys Ala  Ala Thr Thr Thr Thr  Thr Thr Cys
    1715                 1720                 1725

Cys Thr  Cys Cys Thr Cys Cys  Ala Thr Thr Ala Thr  Ala Ala Gly
    1730                 1735                 1740

Ala Ala  Gly Gly Ala Ala Gly  Thr Thr Thr Cys Thr  Gly Thr Thr
    1745                 1750                 1755

Thr Cys  Thr Gly Ala Thr Cys  Gly Ala Ala Thr Gly  Gly Ala Ala
    1760                 1765                 1770

Thr Thr  Thr Gly Thr Cys Ala  Ala Thr Gly Gly Ala  Thr Gly Gly
    1775                 1780                 1785

Thr Ala  Cys Ala Thr Thr Ala  Thr Gly Ala Thr Thr  Ala Thr Thr
    1790                 1795                 1800

Ala Thr  Thr Ala Gly Thr Gly  Ala Cys Ala Thr Gly  Thr Thr Gly
    1805                 1810                 1815

Ala Cys  Ala Ala Thr Thr Ala  Thr Thr Gly Gly Ala  Thr Cys Ala
    1820                 1825                 1830

Ala Thr  Thr Cys Thr Gly Ala  Ala Ala Ala Thr Gly  Gly Ala Ala
    1835                 1840                 1845

Ala Thr  Thr Cys Ala Ala Gly  Cys Thr Ala Ala Gly  Ala Gly Thr
    1850                 1855                 1860

Cys Thr  Ala Ala Cys Ala Ala  Gly Thr Thr Ala Thr  Gly Ala Thr
    1865                 1870                 1875

Gly Thr  Thr Thr Gly Thr Ala  Gly Cys Ala Thr Ala  Cys Thr Thr
    1880                 1885                 1890

Cys Thr  Thr Gly Gly Gly Ala  Cys Thr Thr Cys Cys  Ala Cys Cys
    1895                 1900                 1905

Ala Thr  Gly Cys Thr Thr Gly  Thr Gly Thr Gly Gly  Cys Thr Thr
    1910                 1915                 1920

Gly Gly  Ala Gly Thr Thr Ala  Thr Thr Cys Gly Ala  Thr Ala Cys
    1925                 1930                 1935

Cys Thr  Cys Gly Gly Cys Thr  Thr Cys Thr Thr Thr  Cys Ala Gly
    1940                 1945                 1950

Ala Ala  Gly Thr Ala Cys Ala  Ala Thr Cys Thr Cys  Cys Thr Thr
    1955                 1960                 1965

Ala Thr  Thr Cys Thr Gly Ala  Cys Cys Cys Thr Gly  Cys Ala Gly
    1970                 1975                 1980

Gly Cys  Ala Gly Cys Ala Cys  Thr Gly Cys Cys Cys  Ala Gly Thr
    1985                 1990                 1995

Gly Thr  Cys Ala Thr Cys Ala  Gly Gly Thr Thr Cys  Thr Gly Thr
    2000                 2005                 2010

Thr Gly  Cys Thr Gly Thr Gly  Cys Cys Gly Cys Thr  Ala Thr Gly
    2015                 2020                 2025

Ala Thr  Thr Thr Ala Thr Thr  Thr Ala Gly Gly Cys  Thr Ala Thr
    2030                 2035                 2040

Thr Gly  Cys Thr Thr Cys Thr  Gly Thr Gly Gly Ala  Thr Gly Gly
    2045                 2050                 2055

Ala Thr  Thr Gly Thr Gly Cys  Thr Gly Gly Gly Gly  Cys Cys Gly
    2060                 2065                 2070

Thr Ala  Cys Cys Ala Thr Gly  Ala Thr Ala Ala Gly  Thr Thr Cys
    2075                 2080                 2085

Cys Gly  Thr Thr Cys Thr Cys  Thr Gly Ala Ala Cys  Ala Thr Gly
    2090                 2095                 2100

Gly Thr  Cys Thr Cys Thr Gly  Ala Gly Thr Gly Cys  Cys Thr Thr
```

2105 2110 2115

Thr Thr Cys Thr Cys Thr Cys Thr Gly Ala Thr Ala Ala Ala Thr
2120 2125 2130

Gly Gly Ala Gly Ala Thr Gly Ala Thr Ala Thr Gly Thr Thr Thr
2135 2140 2145

Gly Cys Cys Ala Cys Ala Thr Thr Thr Gly Cys Ala Ala Ala Ala
2150 2155 2160

Ala Thr Gly Cys Ala Ala Cys Ala Ala Ala Ala Ala Ala Gly Thr
2165 2170 2175

Thr Ala Cys Thr Thr Gly Gly Thr Cys Thr Gly Gly Cys Thr Gly
2180 2185 2190

Thr Thr Thr Ala Gly Cys Ala Gly Ala Ala Thr Thr Thr Ala Thr
2195 2200 2205

Cys Thr Cys Thr Ala Cys Thr Cys Ala Thr Thr Cys Ala Thr Cys
2210 2215 2220

Ala Gly Cys Cys Thr Cys Thr Thr Thr Ala Thr Ala Thr Ala Thr
2225 2230 2235

Ala Thr Gly Ala Thr Thr Thr Thr Ala Ala Gly Thr Cys Thr Thr
2240 2245 2250

Thr Thr Cys Ala Thr Cys Gly Cys Ala Cys Thr Gly Ala Thr Cys
2255 2260 2265

Ala Cys Thr Gly Ala Thr Ala Cys Gly Thr Ala Thr Gly Ala Ala
2270 2275 2280

Ala Cys Ala Ala Thr Thr Ala Ala Gly Cys Ala Thr Thr Ala Cys
2285 2290 2295

Cys Ala Ala Cys Ala Ala Gly Ala Thr Gly Gly Cys Thr Thr Thr
2300 2305 2310

Cys Cys Ala Gly Ala Gly Ala Cys Thr Gly Ala Ala Cys Thr Thr
2315 2320 2325

Cys Gly Thr Ala Cys Ala Thr Thr Thr Ala Thr Ala Thr Cys Ala
2330 2335 2340

Gly Ala Gly Thr Gly Cys Ala Ala Ala Gly Ala Thr Cys Thr Ala
2345 2350 2355

Cys Cys Cys Ala Ala Thr Thr Cys Thr Gly Gly Ala Ala Ala Ala
2360 2365 2370

Thr Ala Cys Ala Gly Ala Thr Thr Ala Gly Ala Ala Gly Ala Thr
2375 2380 2385

Gly Ala Cys Ala Cys Thr Cys Cys Ala Ala Thr Ala Thr Cys Thr
2390 2395 2400

Ala Thr Ala Thr Thr Cys Thr Gly Cys Thr Gly Thr Thr Gly Thr
2405 2410 2415

Ala Ala Ala Ala Ala Gly
2420

<210> SEQ ID NO 77
<211> LENGTH: 808
<212> TYPE: PRT
<213> ORGANISM: Canis familiaris

<400> SEQUENCE: 77

Met Thr Pro Phe Gly Ser Leu Ala Ser Ala Lys Ala Ser Asn Ser Arg
1 5 10 15

Ala Ala Trp Lys Ile Val Val Asp Ser Phe Ser Ser Gln His Thr Pro
20 25 30

Gln Val Gly Thr Gly Gly Pro Gln Glu Ser Asp Lys Ala Leu Thr Phe

-continued

```
        35                  40                  45

Gly Glu Leu Thr Phe Ser His Ser Ser Pro Phe Phe Ile Cys Ala Ser
    50                  55                  60

Pro Ser Leu Pro Pro Leu His Ser Ser Gly Leu Asp Asp Glu Pro Tyr
65                  70                  75                  80

Cys Trp Thr Gly Phe His Cys Ile Lys Tyr Leu Ala Gly Pro Ala Ser
                85                  90                  95

Val Pro Asn Ser Leu Glu Arg Gly Ser Lys Ile Leu Val Ser Gln Ala
            100                 105                 110

Ser Phe Pro Ile Arg Thr Ser Pro Tyr Leu Thr Leu Leu Ser Arg Gly
        115                 120                 125

Glu Lys Lys Pro Leu Cys Ser Ser Val Glu Lys Arg Pro Leu Gly Val
    130                 135                 140

Leu Glu Met Gly Ser Leu Thr Leu Leu Ser Glu Glu Leu Lys Arg Gln
145                 150                 155                 160

Leu Pro Gly Thr Leu Leu Leu Gly Gln Pro Pro Leu Leu Arg Glu Arg
                165                 170                 175

Gly Gly Ser Ser Ala Glu Ile Asp Lys Thr Pro Leu Pro Ile Gly Arg
            180                 185                 190

Leu Leu Ser Gly Arg Leu Phe Lys Ala Ala Leu Val Ile Gly Cys Cys
        195                 200                 205

Arg Ala Asp Val Thr Gln Leu Glu Pro Pro Arg Asp Pro Gly Phe Ser
    210                 215                 220

Pro Ala Arg Gln Glu Val Cys Gly Leu Gly Ser Arg Val Glu Gly Ala
225                 230                 235                 240

Ala Gly Ser Asn Val Asn Asn Leu Phe Phe Phe Leu Pro Leu Glu Met
                245                 250                 255

Ala Asn Pro Thr Val Val Ile Ser Ser Cys Ser Ser His Glu Glu Glu
            260                 265                 270

Asn Arg Cys Thr Phe Ser Gln His Thr Ser Pro Ser Glu Glu Leu Leu
        275                 280                 285

Leu Glu Asp Gln Ile Arg Arg Lys Leu Lys Phe Phe Phe Met Asn Pro
    290                 295                 300

Cys Glu Lys Phe Trp Ala Arg Gly Arg Lys Pro Trp Lys Leu Ala Ile
305                 310                 315                 320

Gln Ile Leu Lys Ile Ala Met Val Thr Ile Gln Leu Val Phe Phe Gly
                325                 330                 335

Leu Ser Asn Gln Met Val Val Ala Phe Lys Glu Glu Asn Thr Ile Ala
            340                 345                 350

Phe Lys His Leu Phe Leu Lys Gly Tyr Met Asp Arg Met Asp Asp Thr
        355                 360                 365

Tyr Ala Val Tyr Thr Gln Arg Asp Val Tyr Asp Gln Ile Ile Phe Ala
    370                 375                 380

Val Asn Gln Tyr Leu Leu Leu Arg Asn Thr Ser Val Gly Asn His Ala
385                 390                 395                 400

Tyr Glu Asn Lys Gly Thr Glu Gln Ser Ala Met Ala Ile Cys Gln His
                405                 410                 415

Phe Tyr Lys Gln Gly Asn Ile Cys Pro Gly Asn Asp Thr Phe Asp Ile
            420                 425                 430

Asp Pro Glu Ile Glu Thr Glu Cys Phe Ser Val Glu Pro Ala Glu Pro
        435                 440                 445

Phe His Val Gly Thr Leu Glu Glu Asn Lys Leu Asn Leu Thr Leu Asp
    450                 455                 460
```

Phe His Arg Leu Leu Thr Val Asp Leu Gln Phe Lys Leu Lys Ala Ile
465 470 475 480

Asn Leu Gln Thr Ile Arg His His Glu Leu Pro Asp Cys Tyr Asp Phe
485 490 495

Thr Leu Thr Ile Thr Phe Asp Asn Lys Ala His Ser Gly Arg Ile Lys
500 505 510

Ile Ser Leu Asp Asn Asp Ile Ser Ile Arg Glu Cys Lys Asp Trp His
515 520 525

Val Ser Gly Ser Ile Gln Lys Asn Thr His Tyr Met Met Ile Phe Asp
530 535 540

Ala Phe Val Ile Leu Thr Cys Leu Ala Ser Leu Thr Leu Cys Leu Arg
545 550 555 560

Ser Val Ile Arg Gly Leu Gln Leu Gln Gln Glu Phe Val Asn Phe Phe
565 570 575

Leu Leu His Tyr Lys Lys Glu Val Ser Val Ser Asp Arg Met Glu Phe
580 585 590

Val Asn Gly Trp Tyr Ile Met Ile Ile Ile Ser Asp Met Leu Thr Ile
595 600 605

Ile Gly Ser Ile Leu Lys Met Glu Ile Gln Ala Lys Ser Leu Thr Ser
610 615 620

Tyr Asp Val Cys Ser Ile Leu Leu Gly Thr Ser Thr Met Leu Val Trp
625 630 635 640

Leu Gly Val Ile Arg Tyr Leu Gly Phe Phe Gln Lys Tyr Asn Leu Leu
645 650 655

Ile Leu Thr Leu Gln Ala Ala Leu Pro Ser Val Ile Arg Phe Cys Cys
660 665 670

Cys Ala Ala Met Ile Tyr Leu Gly Tyr Cys Phe Cys Gly Trp Ile Val
675 680 685

Leu Gly Pro Tyr His Asp Lys Phe Arg Ser Leu Asn Met Val Ser Glu
690 695 700

Cys Leu Phe Ser Leu Ile Asn Gly Asp Asp Met Phe Ala Thr Phe Ala
705 710 715 720

Lys Met Gln Gln Lys Ser Tyr Leu Val Trp Leu Phe Ser Arg Ile Tyr
725 730 735

Leu Tyr Ser Phe Ile Ser Leu Phe Ile Tyr Met Ile Leu Ser Leu Phe
740 745 750

Ile Ala Leu Ile Thr Asp Thr Tyr Glu Thr Ile Lys His Tyr Gln Gln
755 760 765

Asp Gly Phe Pro Glu Thr Glu Leu Arg Thr Phe Ile Ser Glu Cys Lys
770 775 780

Asp Leu Pro Asn Ser Gly Lys Tyr Arg Leu Glu Asp Asp Thr Pro Ile
785 790 795 800

Ser Ile Phe Cys Cys Cys Lys Lys
805

<210> SEQ ID NO 78
<211> LENGTH: 1518
<212> TYPE: PRT
<213> ORGANISM: Danio rerio

<400> SEQUENCE: 78

Ala Thr Gly Thr Cys Thr Gly Ala Cys Cys Gly Ala Gly Cys Gly Thr
1 5 10 15

Cys Ala Cys Ala Cys Ala Cys Thr Cys Ala Thr Gly Ala Ala Ala Gly
20 25 30

```
Cys Gly Cys Ala Ala Cys Ala Cys Thr Thr Cys Thr Gly Gly Ala Cys
        35                  40                  45

Cys Cys Gly Gly Ala Gly Thr Gly Thr Gly Thr Gly Gly Ala Ala Ala
    50                  55                  60

Gly Cys Thr Thr Ala Ala Gly Gly Ala Gly Ala Ala Ala Ala Cys Thr
65                  70                  75                  80

Cys Ala Ala Gly Thr Ala Thr Thr Thr Cys Thr Thr Cys Ala Thr Gly
                85                  90                  95

Ala Gly Thr Cys Cys Gly Thr Gly Thr Cys Ala Gly Ala Ala Ala Thr
            100                 105                 110

Ala Cys Ala Gly Cys Ala Cys Thr Ala Gly Ala Gly Gly Ala Cys Gly
        115                 120                 125

Gly Ala Thr Ala Cys Cys Ala Thr Gly Gly Ala Ala Gly Ala Thr Gly
    130                 135                 140

Ala Thr Gly Cys Thr Thr Cys Ala Gly Ala Thr Ala Cys Thr Cys Ala
145                 150                 155                 160

Ala Gly Ala Thr Thr Thr Gly Thr Thr Thr Ala Gly Thr Ala Thr Thr
                165                 170                 175

Cys Ala Thr Cys Thr Ala Cys Cys Thr Gly Gly Thr Cys Thr Cys Thr
            180                 185                 190

Thr Thr Thr Gly Gly Ala Thr Thr Gly Ala Gly Cys Ala Ala Cys Gly
        195                 200                 205

Ala Gly Ala Thr Gly Ala Thr Gly Gly Thr Gly Ala Cys Gly Thr Thr
    210                 215                 220

Cys Ala Ala Ala Gly Ala Gly Gly Ala Ala Ala Ala Thr Cys Thr Cys
225                 230                 235                 240

Ala Thr Cys Gly Cys Cys Thr Thr Cys Ala Ala Gly Cys Ala Cys Thr
                245                 250                 255

Thr Cys Thr Thr Thr Cys Thr Gly Ala Ala Ala Ala Ala Cys Thr Ala
            260                 265                 270

Cys Ala Ala Gly Gly Ala Cys Ala Gly Cys Ala Ala Thr Ala Ala Ala
        275                 280                 285

Cys Ala Thr Thr Ala Cys Gly Cys Cys Thr Thr Gly Thr Ala Cys Ala
    290                 295                 300

Cys Ala Ala Ala Ala Cys Ala Thr Gly Ala Ala Gly Thr Thr Cys Ala
305                 310                 315                 320

Cys Gly Ala Cys Cys Ala Cys Ala Thr Cys Cys Thr Cys Thr Ala Cys
                325                 330                 335

Ala Cys Cys Ala Thr Cys Ala Gly Ala Cys Gly Gly Thr Ala Thr Cys
            340                 345                 350

Thr Ala Cys Ala Gly Cys Thr Ala Cys Ala Ala Ala Ala Cys Cys Thr
        355                 360                 365

Gly Ala Cys Gly Ala Thr Thr Gly Gly Cys Ala Ala Thr Cys Ala Ala
    370                 375                 380

Gly Cys Gly Cys Thr Gly Gly Ala Gly Ala Thr Gly Ala Thr Cys Gly
385                 390                 395                 400

Ala Thr Gly Gly Thr Cys Thr Gly Gly Cys Gly Ala Cys Thr Cys Cys
                405                 410                 415

Thr Cys Thr Gly Thr Cys Thr Cys Thr Cys Thr Gly Thr Cys Ala Gly
            420                 425                 430

Cys Ala Gly Thr Thr Gly Thr Ala Thr Cys Gly Ala Cys Ala Thr Gly
        435                 440                 445

Cys Gly Cys Gly Cys Gly Thr Cys Gly Thr Gly Cys Cys Gly Thr Cys
    450                 455                 460
```

-continued

```
Thr Ala Ala Thr Gly Ala Gly Ala Cys Gly Thr Thr Thr Gly Ala Ala
465                 470                 475                 480

Ala Thr Cys Gly Ala Thr Cys Cys Ala Cys Ala Thr Gly Thr Ala Gly
                485                 490                 495

Ala Gly Ala Cys Ala Gly Ala Gly Thr Gly Thr Gly Thr Thr Thr Cys
            500                 505                 510

Thr Gly Thr Gly Thr Ala Thr Cys Cys Cys Cys Thr Thr Thr Cys Thr
        515                 520                 525

Cys Cys Cys Ala Thr Cys Ala Cys Gly Ala Cys Thr Gly Ala Cys Ala
    530                 535                 540

Gly Thr Cys Thr Gly Gly Ala Ala Ala Ala Cys Thr Cys Cys Cys Thr
545                 550                 555                 560

Gly Ala Ala Cys Thr Thr Gly Ala Cys Thr Thr Thr Ala Gly Ala Thr
                565                 570                 575

Thr Thr Thr Cys Ala Ala Ala Gly Gly Thr Thr Gly Thr Thr Ala Gly
            580                 585                 590

Cys Gly Gly Thr Ala Ala Ala Cys Ala Thr Thr Thr Ala Thr Cys Thr
        595                 600                 605

Gly Ala Ala Gly Ala Thr Cys Ala Ala Gly Gly Cys Thr Ala Thr Cys
    610                 615                 620

Ala Ala Cys Ala Thr Thr Cys Ala Gly Ala Cys Gly Gly Thr Thr Cys
625                 630                 635                 640

Gly Cys Cys Ala Thr Cys Ala Ala Gly Ala Gly Thr Thr Ala Cys Cys
                645                 650                 655

Ala Gly Ala Cys Thr Gly Cys Thr Ala Cys Gly Ala Cys Thr Thr Cys
            660                 665                 670

Ala Gly Cys Ala Thr Thr Ala Ala Thr Ala Thr Cys Ala Thr Gly Thr
        675                 680                 685

Thr Thr Gly Ala Cys Ala Ala Thr Cys Gly Thr Gly Cys Ala Cys Ala
    690                 695                 700

Cys Ala Gly Cys Gly Gly Ala Cys Ala Gly Ala Thr Cys Ala Ala Gly
705                 710                 715                 720

Ala Thr Cys Thr Cys Thr Cys Thr Cys Ala Gly Cys Ala Gly Cys Gly
                725                 730                 735

Gly Cys Gly Thr Gly Cys Ala Gly Ala Thr Ala Ala Ala Cys Gly Thr
            740                 745                 750

Cys Thr Gly Thr Ala Ala Gly Gly Ala Cys Thr Gly Gly Ala Ala Cys
        755                 760                 765

Ala Thr Thr Thr Cys Thr Gly Gly Cys Thr Cys Ala Ala Gly Thr Ala
    770                 775                 780

Ala Gly Thr Thr Gly Ala Ala Cys Ala Gly Cys Cys Ala Cys Thr Thr
785                 790                 795                 800

Thr Gly Cys Gly Cys Thr Gly Ala Thr Thr Gly Thr Gly Gly Thr Gly
                805                 810                 815

Thr Thr Thr Gly Ala Cys Thr Gly Thr Thr Thr Gly Ala Thr Cys Ala
            820                 825                 830

Thr Cys Thr Gly Cys Thr Thr Cys Thr Gly Thr Cys Thr Gly Cys Thr
        835                 840                 845

Gly Thr Cys Ala Cys Thr Cys Ala Thr Cys Cys Thr Cys Thr Gly Cys
    850                 855                 860

Ala Cys Gly Cys Gly Cys Thr Cys Ala Gly Thr Cys Cys Ala Cys Ala
865                 870                 875                 880

Cys Ala Gly Gly Ala Thr Thr Thr Cys Thr Cys Cys Thr Ala Cys Ala
```

885 890 895

Gly Ala Cys Thr Gly Ala Ala Thr Ala Cys Ala Gly Ala Ala Gly Ala
900 905 910

Thr Thr Cys Ala Thr Gly Thr Cys Cys Ala Gly Thr Cys Ala Gly Cys
915 920 925

Ala Cys Ala Gly Thr Ala Ala Ala Ala Gly Cys Gly Thr Cys Thr Cys
930 935 940

Ala Thr Gly Gly Thr Cys Thr Gly Ala Gly Ala Gly Gly Cys Thr Gly
945 950 955 960

Gly Ala Gly Thr Thr Cys Ala Thr Cys Ala Ala Cys Gly Gly Cys Thr
965 970 975

Gly Gly Thr Ala Cys Ala Thr Cys Cys Thr Cys Ala Thr Cys Ala Thr
980 985 990

Cys Ala Thr Cys Ala Gly Cys Gly Ala Thr Gly Cys Gly Cys Thr Gly
995 1000 1005

Ala Cys Thr Ala Thr Thr Gly Cys Ala Gly Gly Cys Thr Cys Ala
1010 1015 1020

Ala Thr Cys Cys Thr Cys Ala Ala Ala Ala Thr Cys Thr Gly Cys
1025 1030 1035

Ala Thr Ala Cys Ala Gly Ala Gly Cys Ala Ala Ala Gly Ala Ala
1040 1045 1050

Cys Thr Gly Ala Cys Gly Ala Gly Cys Thr Ala Thr Gly Ala Cys
1055 1060 1065

Gly Thr Gly Thr Gly Cys Ala Gly Thr Ala Thr Thr Cys Thr Gly
1070 1075 1080

Cys Thr Gly Gly Gly Cys Ala Cys Thr Gly Cys Ala Ala Cys Ala
1085 1090 1095

Ala Thr Gly Cys Thr Gly Gly Thr Gly Thr Gly Gly Ala Thr Thr
1100 1105 1110

Gly Gly Ala Gly Thr Ala Ala Thr Gly Cys Gly Cys Thr Ala Cys
1115 1120 1125

Cys Thr Cys Ala Gly Thr Thr Thr Cys Thr Thr Cys Cys Ala Gly
1130 1135 1140

Ala Ala Ala Thr Ala Thr Thr Ala Thr Ala Thr Cys Cys Thr Cys
1145 1150 1155

Ala Thr Cys Cys Thr Cys Ala Cys Cys Cys Thr Gly Ala Ala Gly
1160 1165 1170

Gly Cys Thr Gly Cys Ala Cys Thr Thr Cys Cys Cys Ala Ala Thr
1175 1180 1185

Gly Thr Gly Ala Thr Thr Cys Gly Ala Thr Thr Cys Thr Cys Cys
1190 1195 1200

Ala Thr Cys Thr Gly Cys Gly Cys Thr Gly Thr Thr Ala Thr Gly
1205 1210 1215

Ala Thr Cys Thr Ala Cys Cys Thr Gly Ala Gly Thr Thr Ala Cys
1220 1225 1230

Thr Gly Cys Thr Thr Cys Thr Gly Cys Gly Gly Ala Thr Gly Gly
1235 1240 1245

Ala Thr Cys Gly Thr Thr Thr Thr Gly Gly Gly Gly Cys Cys Ala
1250 1255 1260

Cys Ala Cys Cys Ala Thr Gly Ala Ala Ala Ala Thr Thr Thr Thr
1265 1270 1275

Cys Gly Cys Ala Cys Ala Thr Thr Cys Ala Gly Thr Ala Gly Gly
1280 1285 1290

-continued

Gly Thr Thr Gly Cys Thr Gly Gly Cys Thr Gly Thr Cys Thr Thr
1295 1300 1305

Thr Thr Cys Thr Cys Cys Ala Thr Gly Ala Thr Thr Ala Ala Thr
1310 1315 1320

Gly Gly Gly Gly Ala Thr Gly Ala Ala Ala Thr Cys Thr Ala Cys
1325 1330 1335

Thr Cys Cys Ala Cys Gly Thr Thr Cys Ala Cys Cys Ala Ala Gly
1340 1345 1350

Cys Thr Cys Cys Gly Gly Gly Ala Ala Thr Ala Cys Ala Gly Cys
1355 1360 1365

Ala Cys Thr Cys Thr Gly Gly Thr Gly Thr Gly Gly Cys Thr Gly
1370 1375 1380

Thr Thr Cys Ala Gly Cys Ala Gly Ala Cys Thr Cys Thr Ala Cys
1385 1390 1395

Gly Thr Cys Thr Ala Cys Ala Gly Cys Thr Thr Cys Ala Thr Cys
1400 1405 1410

Cys Cys Gly Gly Thr Cys Thr Thr Cys Ala Cys Ala Thr Ala Cys
1415 1420 1425

Ala Thr Gly Gly Thr Thr Cys Thr Gly Ala Gly Thr Gly Thr Cys
1430 1435 1440

Thr Thr Cys Ala Thr Cys Gly Cys Cys Cys Thr Cys Ala Thr Cys
1445 1450 1455

Ala Cys Ala Gly Ala Cys Ala Cys Gly Thr Ala Thr Gly Ala Ala
1460 1465 1470

Ala Cys Cys Ala Thr Cys Ala Gly Gly Gly Thr Gly Ala Gly Thr
1475 1480 1485

Thr Ala Thr Thr Thr Cys Ala Gly Cys Thr Thr Cys Ala Gly Thr
1490 1495 1500

Gly Ala Gly Ala Gly Thr Ala Gly Cys Thr Gly Cys Ala Ala Ala
1505 1510 1515

<210> SEQ ID NO 79
<211> LENGTH: 506
<212> TYPE: PRT
<213> ORGANISM: Danio rerio

<400> SEQUENCE: 79

Met Ser Asp Arg Ala Ser His Thr His Glu Ser Ala Thr Leu Leu Asp
1 5 10 15

Pro Glu Cys Val Glu Ser Leu Arg Arg Lys Leu Lys Tyr Phe Phe Met
20 25 30

Ser Pro Cys Gln Lys Tyr Ser Thr Arg Gly Arg Ile Pro Trp Lys Met
35 40 45

Met Leu Gln Ile Leu Lys Ile Cys Leu Val Phe Ile Tyr Leu Val Ser
50 55 60

Phe Gly Leu Ser Asn Glu Met Met Val Thr Phe Lys Glu Glu Asn Leu
65 70 75 80

Ile Ala Phe Lys His Phe Phe Leu Lys Asn Tyr Lys Asp Ser Asn Lys
85 90 95

His Tyr Ala Leu Tyr Thr Lys His Glu Val His Asp His Ile Leu Tyr
100 105 110

Thr Ile Arg Arg Tyr Leu Gln Leu Gln Asn Leu Thr Ile Gly Asn Gln
115 120 125

Ala Leu Glu Met Ile Asp Gly Leu Ala Thr Pro Leu Ser Leu Cys Gln
130 135 140

```
Gln Leu Tyr Arg His Ala Arg Val Val Pro Ser Asn Glu Thr Phe Glu
145                 150                 155                 160

Ile Asp Pro His Val Glu Thr Glu Cys Val Ser Val Tyr Pro Leu Ser
                165                 170                 175

Pro Ile Thr Thr Asp Ser Leu Glu Asn Ser Leu Asn Leu Thr Leu Asp
            180                 185                 190

Phe Gln Arg Leu Leu Ala Val Asn Ile Tyr Leu Lys Ile Lys Ala Ile
        195                 200                 205

Asn Ile Gln Thr Val Arg His Gln Glu Leu Pro Asp Cys Tyr Asp Phe
    210                 215                 220

Ser Ile Asn Ile Met Phe Asp Asn Arg Ala His Ser Gly Gln Ile Lys
225                 230                 235                 240

Ile Ser Leu Ser Ser Gly Val Gln Ile Asn Val Cys Lys Asp Trp Asn
                245                 250                 255

Ile Ser Gly Ser Ser Lys Leu Asn Ser His Phe Ala Leu Ile Val Val
            260                 265                 270

Phe Asp Cys Leu Ile Ile Cys Phe Cys Leu Leu Ser Leu Ile Leu Cys
        275                 280                 285

Thr Arg Ser Val His Thr Gly Phe Leu Leu Gln Thr Glu Tyr Arg Arg
    290                 295                 300

Phe Met Ser Ser Gln His Ser Lys Ser Val Ser Trp Ser Glu Arg Leu
305                 310                 315                 320

Glu Phe Ile Asn Gly Trp Tyr Ile Leu Ile Ile Ile Ser Asp Ala Leu
                325                 330                 335

Thr Ile Ala Gly Ser Ile Leu Lys Ile Cys Ile Gln Ser Lys Glu Leu
            340                 345                 350

Thr Ser Tyr Asp Val Cys Ser Ile Leu Leu Gly Thr Ala Thr Met Leu
        355                 360                 365

Val Trp Ile Gly Val Met Arg Tyr Leu Ser Phe Phe Gln Lys Tyr Tyr
    370                 375                 380

Ile Leu Ile Leu Thr Leu Lys Ala Ala Leu Pro Asn Val Ile Arg Phe
385                 390                 395                 400

Ser Ile Cys Ala Val Met Ile Tyr Leu Ser Tyr Cys Phe Cys Gly Trp
                405                 410                 415

Ile Val Leu Gly Pro His His Glu Asn Phe Arg Thr Phe Ser Arg Val
            420                 425                 430

Ala Gly Cys Leu Phe Ser Met Ile Asn Gly Asp Glu Ile Tyr Ser Thr
        435                 440                 445

Phe Thr Lys Leu Arg Glu Tyr Ser Thr Leu Val Trp Leu Phe Ser Arg
    450                 455                 460

Leu Tyr Val Tyr Ser Phe Ile Pro Val Phe Thr Tyr Met Val Leu Ser
465                 470                 475                 480

Val Phe Ile Ala Leu Ile Thr Asp Thr Tyr Glu Thr Ile Arg Val Ser
                485                 490                 495

Tyr Phe Ser Phe Ser Glu Ser Ser Cys Lys
            500                 505


<210> SEQ ID NO 80
<211> LENGTH: 1659
<212> TYPE: PRT
<213> ORGANISM: Homo sapiens

<400> SEQUENCE: 80

Ala Thr Gly Gly Cys Cys Gly Ala Cys Cys Cys Thr Gly Ala Gly Gly
1               5                   10                  15
```

```
Thr Gly Gly Thr Gly Gly Thr Gly Thr Cys Cys Thr Cys Cys Thr Gly
            20                  25                  30

Cys Thr Cys Thr Ala Gly Cys Cys Ala Cys Gly Ala Gly Gly Ala Ala
        35                  40                  45

Gly Ala Gly Ala Ala Cys Cys Gly Gly Thr Gly Cys Ala Ala Cys Thr
    50                  55                  60

Thr Cys Ala Ala Cys Cys Ala Gly Cys Ala Gly Ala Cys Cys Ala Gly
65                  70                  75                  80

Cys Cys Cys Cys Ala Gly Cys Gly Ala Gly Gly Ala Ala Cys Thr Gly
                85                  90                  95

Cys Thr Gly Cys Thr Gly Gly Ala Ala Gly Ala Thr Cys Ala Gly Ala
            100                 105                 110

Thr Gly Cys Gly Gly Cys Gly Gly Ala Ala Gly Cys Thr Gly Ala Ala
        115                 120                 125

Gly Thr Thr Cys Thr Thr Cys Thr Thr Cys Ala Thr Gly Ala Ala Cys
    130                 135                 140

Cys Cys Cys Thr Gly Cys Gly Ala Gly Ala Ala Gly Thr Thr Cys Thr
145                 150                 155                 160

Gly Gly Gly Cys Cys Ala Gly Ala Gly Gly Cys Cys Gly Gly Ala Ala
                165                 170                 175

Gly Cys Cys Thr Thr Gly Gly Ala Ala Gly Cys Thr Gly Gly Cys Cys
            180                 185                 190

Ala Thr Cys Cys Ala Gly Ala Thr Cys Cys Thr Gly Ala Ala Gly Ala
        195                 200                 205

Thr Cys Gly Cys Cys Ala Thr Gly Gly Thr Gly Ala Cys Cys Ala Thr
    210                 215                 220

Cys Cys Ala Gly Cys Thr Gly Gly Thr Gly Cys Thr Gly Thr Thr Cys
225                 230                 235                 240

Gly Gly Cys Cys Thr Gly Ala Gly Cys Ala Ala Cys Cys Ala Gly Ala
                245                 250                 255

Thr Gly Gly Thr Gly Gly Thr Gly Gly Cys Cys Thr Thr Cys Ala Ala
            260                 265                 270

Ala Gly Ala Gly Gly Ala Ala Ala Ala Cys Ala Cys Ala Ala Thr Cys
        275                 280                 285

Gly Cys Cys Thr Thr Cys Ala Ala Gly Cys Ala Cys Cys Thr Gly Thr
    290                 295                 300

Thr Thr Cys Thr Gly Ala Ala Gly Gly Gly Cys Thr Ala Cys Ala Thr
305                 310                 315                 320

Gly Gly Ala Cys Cys Gly Gly Ala Thr Gly Gly Ala Cys Gly Ala Cys
                325                 330                 335

Ala Cys Cys Thr Ala Cys Gly Cys Cys Gly Thr Gly Thr Ala Cys Ala
            340                 345                 350

Cys Cys Cys Ala Gly Ala Gly Cys Gly Ala Cys Gly Thr Gly Thr Ala
        355                 360                 365

Cys Gly Ala Cys Cys Ala Gly Cys Thr Gly Ala Thr Cys Thr Thr Cys
    370                 375                 380

Gly Cys Cys Gly Thr Gly Ala Ala Cys Cys Ala Gly Thr Ala Cys Cys
385                 390                 395                 400

Thr Gly Cys Ala Gly Cys Thr Gly Thr Ala Cys Ala Ala Cys Gly Thr
                405                 410                 415

Gly Ala Gly Cys Gly Thr Gly Gly Gly Cys Ala Ala Cys Cys Ala Cys
            420                 425                 430

Gly Cys Cys Thr Ala Cys Gly Ala Gly Ala Ala Cys Ala Ala Gly Gly
        435                 440                 445
```

```
Gly Cys Ala Cys Cys Ala Ala Gly Cys Ala Gly Ala Gly Cys Gly Cys
    450                 455                 460

Cys Ala Thr Gly Gly Cys Cys Ala Thr Cys Thr Gly Cys Cys Ala Gly
465                 470                 475                 480

Cys Ala Cys Thr Thr Cys Thr Ala Cys Ala Ala Gly Cys Gly Gly Gly
                485                 490                 495

Gly Cys Ala Ala Cys Ala Thr Cys Thr Ala Cys Cys Cys Cys Gly Gly
            500                 505                 510

Cys Ala Ala Cys Gly Ala Cys Ala Cys Cys Thr Thr Cys Gly Ala Cys
        515                 520                 525

Ala Thr Cys Gly Ala Cys Cys Cys Cys Gly Ala Gly Ala Thr Cys Gly
    530                 535                 540

Ala Gly Ala Cys Ala Gly Ala Gly Thr Gly Cys Thr Thr Cys Thr Thr
545                 550                 555                 560

Cys Gly Thr Gly Gly Ala Gly Cys Cys Cys Gly Ala Cys Gly Ala Gly
                565                 570                 575

Cys Cys Thr Thr Thr Cys Cys Ala Cys Ala Thr Cys Gly Gly Cys Ala
            580                 585                 590

Cys Cys Cys Cys Thr Gly Cys Cys Gly Ala Gly Ala Ala Cys Ala Ala
        595                 600                 605

Gly Cys Thr Gly Ala Ala Cys Cys Thr Gly Ala Cys Cys Cys Thr Gly
    610                 615                 620

Gly Ala Cys Thr Thr Cys Cys Ala Cys Cys Gly Gly Cys Thr Gly Cys
625                 630                 635                 640

Thr Gly Ala Cys Cys Gly Thr Gly Gly Ala Gly Cys Thr Gly Cys Ala
                645                 650                 655

Gly Thr Thr Cys Ala Ala Gly Cys Thr Gly Ala Ala Gly Gly Cys Cys
            660                 665                 670

Ala Thr Cys Ala Ala Cys Cys Thr Gly Cys Ala Gly Ala Cys Cys Gly
        675                 680                 685

Thr Gly Cys Gly Gly Cys Ala Cys Cys Ala Gly Gly Ala Ala Cys Thr
    690                 695                 700

Gly Cys Cys Cys Gly Ala Cys Thr Gly Cys Thr Ala Cys Gly Ala Cys
705                 710                 715                 720

Thr Thr Cys Ala Cys Cys Cys Thr Gly Ala Cys Cys Ala Thr Cys Ala
                725                 730                 735

Cys Cys Thr Thr Cys Gly Ala Thr Ala Ala Cys Ala Ala Gly Gly Cys
            740                 745                 750

Cys Cys Ala Cys Ala Gly Cys Gly Gly Cys Cys Gly Gly Ala Thr Cys
        755                 760                 765

Ala Ala Gly Ala Thr Cys Ala Gly Cys Cys Thr Gly Gly Ala Cys Ala
    770                 775                 780

Ala Cys Gly Ala Cys Ala Thr Cys Ala Gly Cys Ala Thr Cys Cys Gly
785                 790                 795                 800

Gly Gly Ala Gly Thr Gly Cys Ala Ala Gly Gly Ala Cys Thr Gly Gly
                805                 810                 815

Cys Ala Cys Gly Thr Gly Ala Gly Cys Gly Gly Cys Ala Gly Cys Ala
            820                 825                 830

Thr Cys Cys Ala Gly Ala Ala Ala Ala Ala Cys Ala Cys Cys Cys Ala
        835                 840                 845

Cys Thr Ala Cys Ala Thr Gly Ala Thr Gly Ala Thr Cys Thr Thr Cys
    850                 855                 860

Gly Ala Cys Gly Cys Cys Thr Thr Cys Gly Thr Gly Ala Thr Cys Cys
```

```
865                 870                 875                 880

Thr Gly Ala Cys Cys Thr Gly Cys Cys Thr Gly Gly Thr Gly Thr Cys
                885                 890                 895

Cys Cys Thr Gly Ala Thr Cys Cys Thr Gly Thr Gly Cys Ala Thr Cys
            900                 905                 910

Ala Gly Ala Ala Gly Cys Gly Thr Cys Ala Thr Cys Ala Gly Gly Gly
        915                 920                 925

Gly Cys Cys Thr Gly Cys Ala Gly Cys Thr Cys Cys Ala Gly Cys Ala
    930                 935                 940

Gly Gly Ala Ala Thr Thr Cys Gly Thr Cys Ala Ala Cys Thr Thr Cys
945                 950                 955                 960

Thr Thr Cys Cys Thr Gly Cys Thr Gly Cys Ala Cys Thr Ala Cys Ala
                965                 970                 975

Ala Gly Ala Ala Ala Gly Ala Ala Gly Thr Gly Thr Cys Cys Gly Thr
            980                 985                 990

Cys Ala Gly Cys Gly Ala Cys Cys  Ala Gly Ala Thr Gly  Gly Ala Ala
        995                 1000                 1005

Thr Thr  Thr Gly Thr Gly Ala  Ala Cys Gly Gly Cys  Thr Gly Gly
    1010                 1015                 1020

Thr Ala  Cys Ala Thr Cys Ala  Thr Gly Ala Thr Cys  Ala Thr Cys
    1025                 1030                 1035

Ala Thr  Cys Ala Gly Cys Gly  Ala Cys Ala Thr Cys  Cys Thr Gly
    1040                 1045                 1050

Ala Cys  Ala Ala Thr Cys Ala  Thr Cys Gly Gly Cys  Ala Gly Cys
    1055                 1060                 1065

Ala Thr  Thr Cys Thr Gly Ala  Ala Gly Ala Thr Gly  Gly Ala Ala
    1070                 1075                 1080

Ala Thr  Cys Cys Ala Gly Gly  Cys Cys Ala Ala Gly  Ala Gly Cys
    1085                 1090                 1095

Cys Thr  Gly Ala Cys Cys Ala  Gly Cys Thr Ala Cys  Gly Ala Cys
    1100                 1105                 1110

Gly Thr  Gly Thr Gly Cys Ala  Gly Cys Ala Thr Thr  Cys Thr Gly
    1115                 1120                 1125

Cys Thr  Gly Gly Gly Ala Ala  Cys Cys Thr Cys Cys  Ala Cys Cys
    1130                 1135                 1140

Ala Thr  Gly Cys Thr Gly Gly  Thr Cys Thr Gly Gly  Cys Thr Cys
    1145                 1150                 1155

Gly Gly  Cys Gly Thr Gly Ala  Thr Cys Ala Gly Ala  Thr Ala Cys
    1160                 1165                 1170

Cys Thr  Gly Gly Gly Cys Thr  Thr Cys Thr Thr Cys  Gly Cys Cys
    1175                 1180                 1185

Ala Ala  Gly Thr Ala Cys Ala  Ala Cys Cys Thr Gly  Cys Thr Gly
    1190                 1195                 1200

Ala Thr  Thr Cys Thr Gly Ala  Cys Ala Cys Thr Gly  Cys Ala Gly
    1205                 1210                 1215

Gly Cys  Cys Gly Cys Cys Cys  Thr Gly Cys Cys Cys  Ala Ala Cys
    1220                 1225                 1230

Gly Thr  Gly Ala Thr Cys Cys  Gly Gly Thr Thr Cys  Thr Gly Cys
    1235                 1240                 1245

Thr Gly  Cys Thr Gly Cys Gly  Cys Cys Gly Cys Cys  Ala Thr Gly
    1250                 1255                 1260

Ala Thr  Cys Thr Ala Cys Cys  Thr Gly Gly Gly Cys  Thr Ala Cys
    1265                 1270                 1275
```

-continued

Thr Gly Cys Thr Thr Cys Thr Gly Cys Gly Gly Cys Thr Gly Gly
1280 1285 1290

Ala Thr Cys Gly Thr Gly Cys Thr Gly Gly Gly Cys Cys Cys Cys
1295 1300 1305

Thr Ala Cys Cys Ala Cys Gly Ala Cys Ala Ala Gly Thr Thr Cys
1310 1315 1320

Cys Gly Gly Thr Cys Cys Cys Thr Gly Ala Ala Cys Ala Thr Gly
1325 1330 1335

Gly Thr Gly Thr Cys Cys Gly Ala Gly Thr Gly Cys Cys Thr Gly
1340 1345 1350

Thr Thr Cys Ala Gly Cys Cys Thr Gly Ala Thr Cys Ala Ala Cys
1355 1360 1365

Gly Gly Cys Gly Ala Cys Gly Ala Cys Ala Thr Gly Thr Thr Cys
1370 1375 1380

Gly Cys Cys Ala Cys Cys Thr Thr Cys Gly Cys Cys Ala Ala Gly
1385 1390 1395

Ala Thr Gly Cys Ala Gly Cys Ala Gly Ala Ala Ala Ala Gly Cys
1400 1405 1410

Thr Ala Cys Cys Thr Gly Gly Thr Cys Thr Gly Gly Cys Thr Gly
1415 1420 1425

Thr Thr Cys Ala Gly Cys Cys Gly Gly Ala Thr Cys Thr Ala Cys
1430 1435 1440

Cys Thr Gly Thr Ala Cys Ala Gly Cys Thr Thr Cys Ala Thr Cys
1445 1450 1455

Ala Gly Cys Cys Thr Gly Thr Thr Cys Ala Thr Cys Thr Ala Cys
1460 1465 1470

Ala Thr Gly Ala Thr Cys Cys Thr Gly Ala Gly Cys Cys Thr Gly
1475 1480 1485

Thr Thr Thr Ala Thr Cys Gly Cys Cys Cys Thr Gly Ala Thr Cys
1490 1495 1500

Ala Cys Cys Gly Ala Thr Ala Cys Cys Thr Ala Cys Gly Ala Gly
1505 1510 1515

Ala Cys Ala Ala Thr Cys Ala Ala Gly Cys Ala Gly Thr Ala Cys
1520 1525 1530

Cys Ala Gly Cys Ala Gly Gly Ala Cys Gly Gly Cys Thr Thr Cys
1535 1540 1545

Cys Cys Cys Gly Ala Gly Ala Cys Ala Gly Ala Gly Cys Thr Gly
1550 1555 1560

Cys Gly Gly Ala Cys Cys Thr Thr Cys Ala Thr Cys Ala Gly Cys
1565 1570 1575

Gly Ala Gly Thr Gly Thr Ala Ala Gly Gly Ala Cys Cys Thr Gly
1580 1585 1590

Cys Cys Cys Ala Ala Cys Ala Gly Cys Gly Gly Cys Ala Ala Gly
1595 1600 1605

Thr Ala Cys Cys Gly Gly Cys Thr Gly Gly Ala Ala Gly Ala Thr
1610 1615 1620

Gly Ala Cys Cys Cys Cys Cys Cys Cys Gly Thr Gly Thr Cys Cys
1625 1630 1635

Cys Thr Gly Thr Thr Cys Thr Gly Cys Thr Gly Thr Thr Gly Cys
1640 1645 1650

Ala Ala Gly Ala Ala Gly
1655

<210> SEQ ID NO 81

<211> LENGTH: 1659
<212> TYPE: PRT
<213> ORGANISM: Homo sapiens

<400> SEQUENCE: 81

```
Ala Thr Gly Gly Cys Ala Gly Ala Thr Cys Cys Thr Gly Ala Gly Gly
1               5                   10                  15

Thr Ala Gly Thr Thr Gly Thr Gly Ala Gly Thr Ala Gly Cys Thr Gly
            20                  25                  30

Cys Ala Gly Cys Thr Cys Thr Cys Ala Thr Gly Ala Ala Gly Ala Gly
        35                  40                  45

Gly Ala Ala Ala Ala Thr Cys Gly Cys Thr Gly Cys Ala Ala Thr Thr
    50                  55                  60

Thr Thr Ala Ala Cys Cys Ala Gly Cys Ala Ala Ala Cys Ala Thr Cys
65                  70                  75                  80

Thr Cys Cys Ala Thr Cys Thr Gly Ala Gly Gly Ala Gly Cys Thr Thr
                85                  90                  95

Cys Thr Ala Thr Thr Ala Gly Ala Ala Gly Ala Cys Cys Ala Gly Ala
            100                 105                 110

Thr Gly Ala Gly Gly Cys Gly Ala Ala Ala Ala Cys Thr Cys Ala Ala
        115                 120                 125

Ala Thr Thr Thr Thr Thr Thr Thr Thr Cys Ala Thr Gly Ala Ala Thr
    130                 135                 140

Cys Cys Cys Thr Gly Thr Gly Ala Gly Ala Ala Gly Thr Thr Cys Thr
145                 150                 155                 160

Gly Gly Gly Cys Thr Cys Gly Ala Gly Gly Thr Ala Gly Ala Ala Ala
                165                 170                 175

Ala Cys Cys Ala Thr Gly Gly Ala Ala Ala Cys Thr Thr Gly Cys Cys
            180                 185                 190

Ala Thr Ala Cys Ala Ala Ala Thr Thr Cys Thr Ala Ala Ala Ala Ala
        195                 200                 205

Thr Thr Gly Cys Ala Ala Thr Gly Gly Thr Gly Ala Cys Thr Ala Thr
    210                 215                 220

Cys Cys Ala Gly Cys Thr Gly Gly Thr Cys Thr Thr Ala Thr Thr Thr
225                 230                 235                 240

Gly Gly Gly Cys Thr Ala Ala Gly Thr Ala Ala Cys Cys Ala Gly Ala
                245                 250                 255

Thr Gly Gly Thr Gly Gly Thr Ala Gly Cys Thr Thr Thr Cys Ala Ala
            260                 265                 270

Gly Gly Ala Ala Gly Ala Gly Ala Ala Thr Ala Cys Thr Ala Thr Ala
        275                 280                 285

Gly Cys Ala Thr Thr Cys Ala Ala Ala Cys Ala Cys Cys Thr Thr Thr
    290                 295                 300

Thr Cys Cys Thr Ala Ala Ala Ala Gly Gly Ala Thr Ala Thr Ala Thr
305                 310                 315                 320

Gly Gly Ala Cys Cys Gly Ala Ala Thr Gly Gly Ala Thr Gly Ala Cys
                325                 330                 335

Ala Cys Ala Thr Ala Thr Gly Cys Ala Gly Thr Gly Thr Ala Cys Ala
            340                 345                 350

Cys Ala Cys Ala Ala Ala Gly Thr Gly Ala Cys Gly Thr Gly Thr Ala
        355                 360                 365

Thr Gly Ala Thr Cys Ala Gly Thr Thr Ala Ala Thr Cys Thr Thr Cys
    370                 375                 380

Gly Cys Ala Gly Thr Ala Ala Ala Cys Cys Ala Gly Thr Ala Cys Thr
385                 390                 395                 400
```

```
Thr Gly Cys Ala Gly Cys Thr Ala Thr Ala Cys Ala Ala Thr Gly Thr
                405                 410                 415

Cys Thr Cys Cys Gly Thr Thr Gly Gly Gly Ala Ala Thr Cys Ala Thr
            420                 425                 430

Gly Cys Thr Thr Ala Thr Gly Ala Gly Ala Ala Cys Ala Ala Ala Gly
        435                 440                 445

Gly Thr Ala Cys Cys Ala Ala Gly Cys Ala Ala Thr Cys Thr Gly Cys
    450                 455                 460

Thr Ala Thr Gly Gly Cys Ala Ala Thr Cys Thr Gly Thr Cys Ala Gly
465                 470                 475                 480

Cys Ala Cys Thr Thr Cys Thr Ala Cys Ala Ala Gly Cys Gly Ala Gly
                485                 490                 495

Gly Ala Ala Ala Cys Ala Thr Cys Thr Ala Cys Cys Cys Thr Gly Gly
            500                 505                 510

Ala Ala Ala Thr Gly Ala Thr Ala Cys Cys Thr Thr Thr Gly Ala Cys
        515                 520                 525

Ala Thr Cys Gly Ala Thr Cys Cys Ala Gly Ala Ala Ala Thr Thr Gly
    530                 535                 540

Ala Ala Ala Cys Thr Gly Ala Gly Thr Gly Thr Thr Thr Cys Thr Thr
545                 550                 555                 560

Thr Gly Thr Gly Gly Ala Gly Cys Cys Ala Gly Ala Thr Gly Ala Ala
                565                 570                 575

Cys Cys Thr Thr Thr Thr Cys Ala Cys Ala Thr Thr Gly Gly Gly Ala
            580                 585                 590

Cys Ala Cys Cys Ala Gly Cys Ala Gly Ala Ala Ala Ala Thr Ala Ala
        595                 600                 605

Ala Cys Thr Gly Ala Ala Cys Thr Thr Ala Ala Cys Ala Cys Thr Gly
    610                 615                 620

Gly Ala Cys Thr Thr Cys Cys Ala Cys Ala Gly Ala Cys Thr Cys Cys
625                 630                 635                 640

Thr Ala Ala Cys Ala Gly Thr Gly Gly Ala Gly Cys Thr Thr Cys Ala
                645                 650                 655

Gly Thr Thr Thr Ala Ala Ala Cys Thr Gly Ala Ala Ala Gly Cys Cys
            660                 665                 670

Ala Thr Thr Ala Ala Thr Cys Thr Gly Cys Ala Gly Ala Cys Ala Gly
        675                 680                 685

Thr Thr Cys Gly Thr Cys Ala Thr Cys Ala Ala Gly Ala Ala Cys Thr
    690                 695                 700

Cys Cys Cys Thr Gly Ala Cys Thr Gly Thr Thr Ala Thr Gly Ala Cys
705                 710                 715                 720

Thr Thr Thr Ala Cys Thr Cys Thr Gly Ala Cys Thr Ala Thr Ala Ala
                725                 730                 735

Cys Ala Thr Thr Thr Gly Ala Cys Ala Ala Cys Ala Ala Gly Gly Cys
            740                 745                 750

Cys Cys Ala Thr Ala Gly Thr Gly Gly Ala Ala Gly Ala Ala Thr Thr
        755                 760                 765

Ala Ala Ala Ala Thr Ala Ala Gly Thr Thr Thr Ala Gly Ala Thr Ala
    770                 775                 780

Ala Thr Gly Ala Cys Ala Thr Thr Thr Cys Cys Ala Thr Cys Ala Gly
785                 790                 795                 800

Ala Gly Ala Ala Thr Gly Thr Ala Ala Ala Gly Ala Cys Thr Gly Gly
                805                 810                 815

Cys Ala Thr Gly Thr Ala Thr Cys Thr Gly Gly Ala Thr Cys Ala Ala
```

-continued

```
            820                 825                 830

Thr Thr Cys Ala Gly Ala Ala Gly Ala Ala Cys Ala Cys Thr Cys Ala
        835                 840                 845

Thr Thr Ala Cys Ala Thr Gly Ala Thr Gly Ala Thr Cys Thr Thr Thr
    850                 855                 860

Gly Ala Thr Gly Cys Cys Thr Thr Thr Gly Thr Cys Ala Thr Thr Cys
865                 870                 875                 880

Thr Gly Ala Cys Thr Thr Gly Cys Thr Thr Gly Gly Thr Thr Thr Cys
                885                 890                 895

Ala Thr Thr Ala Ala Thr Cys Cys Thr Cys Thr Gly Cys Ala Thr Thr
            900                 905                 910

Ala Gly Ala Thr Cys Thr Gly Thr Gly Ala Thr Thr Ala Gly Ala Gly
        915                 920                 925

Gly Ala Cys Thr Thr Cys Ala Gly Cys Thr Thr Cys Ala Gly Cys Ala
    930                 935                 940

Gly Gly Ala Gly Thr Thr Thr Gly Thr Cys Ala Ala Thr Thr Thr Thr
945                 950                 955                 960

Thr Thr Cys Cys Thr Cys Cys Thr Cys Cys Ala Thr Thr Ala Thr Ala
                965                 970                 975

Ala Gly Ala Ala Gly Gly Ala Ala Gly Thr Thr Thr Cys Thr Gly Thr
            980                 985                 990

Thr Thr Cys Thr Gly Ala Thr Cys  Ala Ala Ala Thr Gly  Gly Ala Ala
        995                 1000                1005

Thr Thr  Thr Gly Thr Cys Ala  Ala Thr Gly Gly Ala  Thr Gly Gly
    1010                 1015                 1020

Thr Ala  Cys Ala Thr Thr Ala  Thr Gly Ala Thr Thr  Ala Thr Thr
    1025                 1030                 1035

Ala Thr  Thr Ala Gly Thr Gly  Ala Cys Ala Thr Ala  Thr Thr Gly
    1040                 1045                 1050

Ala Cys  Ala Ala Thr Cys Ala  Thr Thr Gly Gly Ala  Thr Cys Ala
    1055                 1060                 1065

Ala Thr  Thr Cys Thr Ala Ala  Ala Ala Ala Thr Gly  Gly Ala Ala
    1070                 1075                 1080

Ala Thr  Cys Cys Ala Ala Gly  Cys Thr Ala Ala Gly  Ala Gly Thr
    1085                 1090                 1095

Cys Thr  Ala Ala Cys Thr Ala  Gly Thr Thr Ala Thr  Gly Ala Thr
    1100                 1105                 1110

Gly Thr  Cys Thr Gly Thr Ala  Gly Cys Ala Thr Ala  Cys Thr Thr
    1115                 1120                 1125

Cys Thr  Thr Gly Gly Gly Ala  Cys Thr Thr Cys Thr  Ala Cys Cys
    1130                 1135                 1140

Ala Thr  Gly Cys Thr Thr Gly  Thr Gly Thr Gly Gly  Cys Thr Thr
    1145                 1150                 1155

Gly Gly  Ala Gly Thr Cys Ala  Thr Cys Cys Gly Ala  Thr Ala Cys
    1160                 1165                 1170

Cys Thr  Cys Gly Gly Thr Thr  Thr Cys Thr Thr Thr  Gly Cys Ala
    1175                 1180                 1185

Ala Ala  Gly Thr Ala Cys Ala  Ala Cys Cys Thr Cys  Cys Thr Cys
    1190                 1195                 1200

Ala Thr  Thr Thr Thr Gly Ala  Cys Cys Cys Thr Thr  Cys Ala Gly
    1205                 1210                 1215

Gly Cys  Ala Gly Cys Gly Cys  Thr Gly Cys Cys Cys  Ala Ala Thr
    1220                 1225                 1230
```

-continued

```
Gly Thr  Cys Ala Thr Cys Ala  Gly Gly Thr Thr Cys  Thr Gly Cys
    1235                 1240                 1245

Thr Gly  Cys Thr Gly Thr Gly  Cys Ala Gly Cys Thr  Ala Thr Gly
    1250                 1255                 1260

Ala Thr  Thr Thr Ala Cys Thr  Thr Ala Gly Gly Thr  Thr Ala Cys
    1265                 1270                 1275

Thr Gly  Cys Thr Thr Cys Thr  Gly Thr Gly Gly Ala  Thr Gly Gly
    1280                 1285                 1290

Ala Thr  Cys Gly Thr Gly Cys  Thr Gly Gly Gly Gly  Cys Cys Thr
    1295                 1300                 1305

Thr Ala  Cys Cys Ala Thr Gly  Ala Cys Ala Ala Gly  Thr Thr Thr
    1310                 1315                 1320

Cys Gly  Thr Thr Cys Thr Cys  Thr Gly Ala Ala Cys  Ala Thr Gly
    1325                 1330                 1335

Gly Thr  Cys Thr Cys Thr Gly  Ala Gly Thr Gly Cys  Cys Thr Thr
    1340                 1345                 1350

Thr Thr  Cys Thr Cys Thr Cys  Thr Gly Ala Thr Ala  Ala Ala Thr
    1355                 1360                 1365

Gly Gly  Ala Gly Ala Thr Gly  Ala Thr Ala Thr Gly  Thr Thr Thr
    1370                 1375                 1380

Gly Cys  Cys Ala Cys Gly Thr  Thr Thr Gly Cys Ala  Ala Ala Ala
    1385                 1390                 1395

Ala Thr  Gly Cys Ala Gly Cys  Ala Ala Ala Ala Ala  Ala Gly Thr
    1400                 1405                 1410

Thr Ala  Cys Thr Thr Ala Gly  Thr Cys Thr Gly Gly  Cys Thr Gly
    1415                 1420                 1425

Thr Thr  Thr Ala Gly Thr Ala  Gly Ala Ala Thr Thr  Thr Ala Cys
    1430                 1435                 1440

Cys Thr  Cys Thr Ala Cys Thr  Cys Ala Thr Thr Cys  Ala Thr Cys
    1445                 1450                 1455

Ala Gly  Cys Cys Thr Cys Thr  Thr Thr Ala Thr Ala  Thr Ala Thr
    1460                 1465                 1470

Ala Thr  Gly Ala Thr Thr Thr  Thr Ala Ala Gly Thr  Cys Thr Thr
    1475                 1480                 1485

Thr Thr  Cys Ala Thr Thr Gly  Cys Ala Cys Thr Gly  Ala Thr Cys
    1490                 1495                 1500

Ala Cys  Thr Gly Ala Thr Ala  Cys Ala Thr Ala Cys  Gly Ala Ala
    1505                 1510                 1515

Ala Cys  Ala Ala Thr Thr Ala  Ala Gly Cys Ala Ala  Thr Ala Cys
    1520                 1525                 1530

Cys Ala  Ala Cys Ala Ala Gly  Ala Thr Gly Gly Cys  Thr Thr Cys
    1535                 1540                 1545

Cys Cys  Ala Gly Ala Gly Ala  Cys Thr Gly Ala Ala  Cys Thr Thr
    1550                 1555                 1560

Cys Gly  Thr Ala Cys Ala Thr  Thr Thr Ala Thr Ala  Thr Cys Ala
    1565                 1570                 1575

Gly Ala  Ala Thr Gly Cys Ala  Ala Ala Gly Ala Thr  Cys Thr Ala
    1580                 1585                 1590

Cys Cys  Cys Ala Ala Cys Thr  Cys Thr Gly Gly Ala  Ala Ala Ala
    1595                 1600                 1605

Thr Ala  Cys Ala Gly Ala Thr  Thr Ala Gly Ala Ala  Gly Ala Thr
    1610                 1615                 1620

Gly Ala  Cys Cys Cys Thr Cys  Cys Ala Gly Thr Ala  Thr Cys Thr
    1625                 1630                 1635
```

-continued

Thr Thr Ala Thr Thr Cys Thr Gly Cys Thr Gly Thr Thr Gly Thr
1640 1645 1650

Ala Ala Ala Ala Ala Gly
1655

<210> SEQ ID NO 82
<211> LENGTH: 2000
<212> TYPE: DNA
<213> ORGANISM: Rattus norvegicus

<400> SEQUENCE: 82
gttcgacaga agcttgtgat ttatggtcca aggaatccag tgtcagatca atagacaaaa 60
tgccccaggg aagttgtgtg tgcattctac tggacagatc agagactggt cagaacaggt 120
gcttggctgg cggtgcgtcc aaacctcaga gatggcaaat cctgaggtgg tggtaagcag 180
ctgcagttct caccaggatg aaagtccctg cactttctac ccgagctcat cccagtccga 240
gcagcttctc ttagaagatc agatgaggcg gaaactcaaa ttcttttttta tgaatccttg 300 cgagaagttc tgggctcggg gtaggaagcc atggaaactt gccatacaga ttctgaaaat 360
cgctatggtg actatccagc tggttctgtt tggactaagt aaccagatgg tagtagcttt 420
caaggaagag aacacgatag ccttcaaaca cctcttcctg aaaggctaca tggaccgaat 480
ggacgacacc tacgcggtgt acactcagaa tgatgtgtac gaccagatca tctttgcagt 540
gacccggtac ttgcaacttc gaaacatctc cgtcggcaac catgcttatg agaacaaggg 600
gactaagcag tcagcaatgg cagtctgtca gcacttctac aggcaaggca ccatctgccc 660
cgggaacgat accttcgaca tcgatccaga agtcgaaaca gactgtttcc ttatagagcc 720
agaggaagct ttccacatgg gaacacctgg agaaaacaaa ctcaacctga ccctggactt 780
ccacagactt ctgacagtgg agctccaatt taagctcaaa gccatcaacc tgcagacagt 840
tcgccaccag gagcttcctg actgttacga ctttaccctg actataacat tcgacaacaa 900
ggcacacagt ggaagaatca aaataagttt agacaacgac atttctatca gagaatgcaa 960
agattggcac gtgtctggat caattcagaa gaacacccac tacatgatga tcttcgatgc 1020
ctttgttatc ctgacctgct tgtcctcgct ggtgctctgc gccaggtctg tgattcgggg 1080
tcttcagctt cagcaggagt ttgtcaactt tttccttctt cactacaaga aggaagtttc 1140
ggcctctgat cagatggagt tcatcaacgg gtggtacatt atgatcatcg ttagtgacat 1200
actgacgatc gttggatcga ttctgaaaat ggaaatccaa gccaagagtc ttacaagcta 1260
cgatgtctgt agcatacttc ttgggacttc caccatgctc gtgtggcttg gcgttatccg 1320
atacctgggt ttctttgcga agtacaatct ccttatcctg accctccagg cagcgctgcc 1380
caatgtcatc aggttctgtt gctgtgcggc tatgatctat cttgggtatt gcttttgcgg 1440
atggattgtg ctgggccctt accatgagaa gttccgctct ctgaacaagg tctctgagtg 1500
cctattctca ctgataaatg gagacgacat gttttccacg ttcgcgaaaa tgcagcagaa 1560
aagttacctg gtgtggctgt tcagccgcgt ctacctgtac tcgttcatca gcctcttcat 1620
ctacatgatc ttgagccttt tcatcgcgct catcacagac acgtacgaaa ccattaagca 1680
ctaccagcaa gatggcttcc cagagacgga acttcgaaag tttatcgctg aatgcaaaga 1740
cctccccaac tctggaaaat acagattgga agatgaccct ccaggttctt tattctgctg 1800
ctgcaaaaag taactgtcgg gtttctctgt gcctgggagg aaaatacagt gtgtggatga 1860
gtcagagaca atatggatta ttggtaatca cgcaacagtg tgttcagata ctagtgttct 1920
gagttaactc acagctatga ctttgcgggg cctgttaaat atatttttaa atattaaaaa 1980

```
aaaaaaaaaa aaaaaaaaaa                                                 2000


<210> SEQ ID NO 83
<211> LENGTH: 553
<212> TYPE: PRT
<213> ORGANISM: Rattus norvegicus

<400> SEQUENCE: 83

Met Ala Asn Pro Glu Val Val Val Ser Ser Cys Ser Ser His Gln Asp
1               5                   10                  15

Glu Ser Pro Cys Thr Phe Tyr Pro Ser Ser Ser Gln Ser Glu Gln Leu
            20                  25                  30

Leu Leu Glu Asp Gln Met Arg Arg Lys Leu Lys Phe Phe Phe Met Asn
        35                  40                  45

Pro Cys Glu Lys Phe Trp Ala Arg Gly Arg Lys Pro Trp Lys Leu Ala
    50                  55                  60

Ile Gln Ile Leu Lys Ile Ala Met Val Thr Ile Gln Leu Val Leu Phe
65                  70                  75                  80

Gly Leu Ser Asn Gln Met Val Val Ala Phe Lys Glu Glu Asn Thr Ile
                85                  90                  95

Ala Phe Lys His Leu Phe Leu Lys Gly Tyr Met Asp Arg Met Asp Asp
            100                 105                 110

Thr Tyr Ala Val Tyr Thr Gln Asn Asp Val Tyr Asp Gln Ile Ile Phe
        115                 120                 125

Ala Val Thr Arg Tyr Leu Gln Leu Arg Asn Ile Ser Val Gly Asn His
    130                 135                 140

Ala Tyr Glu Asn Lys Gly Thr Lys Gln Ser Ala Met Ala Val Cys Gln
145                 150                 155                 160

His Phe Tyr Arg Gln Gly Thr Ile Cys Pro Gly Asn Asp Thr Phe Asp
                165                 170                 175

Ile Asp Pro Glu Val Glu Thr Asp Cys Phe Leu Ile Glu Pro Glu Glu
            180                 185                 190

Ala Phe His Met Gly Thr Pro Gly Glu Asn Lys Leu Asn Leu Thr Leu
        195                 200                 205

Asp Phe His Arg Leu Leu Thr Val Glu Leu Gln Phe Lys Leu Lys Ala
    210                 215                 220

Ile Asn Leu Gln Thr Val Arg His Gln Glu Leu Pro Asp Cys Tyr Asp
225                 230                 235                 240

Phe Thr Leu Thr Ile Thr Phe Asp Asn Lys Ala His Ser Gly Arg Ile
                245                 250                 255

Lys Ile Ser Leu Asp Asn Asp Ile Ser Ile Arg Glu Cys Lys Asp Trp
            260                 265                 270

His Val Ser Gly Ser Ile Gln Lys Asn Thr His Tyr Met Met Ile Phe
        275                 280                 285

Asp Ala Phe Val Ile Leu Thr Cys Leu Ser Ser Leu Val Leu Cys Ala
    290                 295                 300

Arg Ser Val Ile Arg Gly Leu Gln Leu Gln Gln Glu Phe Val Asn Phe
305                 310                 315                 320

Phe Leu Leu His Tyr Lys Lys Glu Val Ser Ala Ser Asp Gln Met Glu
                325                 330                 335

Phe Ile Asn Gly Trp Tyr Ile Met Ile Ile Val Ser Asp Ile Leu Thr
            340                 345                 350

Ile Val Gly Ser Ile Leu Lys Met Glu Ile Gln Ala Lys Ser Leu Thr
        355                 360                 365
```

-continued

```
Ser Tyr Asp Val Cys Ser Ile Leu Leu Gly Thr Ser Thr Met Leu Val
    370                 375                 380

Trp Leu Gly Val Ile Arg Tyr Leu Gly Phe Phe Ala Lys Tyr Asn Leu
385                 390                 395                 400

Leu Ile Leu Thr Leu Gln Ala Ala Leu Pro Asn Val Ile Arg Phe Cys
                405                 410                 415

Cys Cys Ala Ala Met Ile Tyr Leu Gly Tyr Cys Phe Cys Gly Trp Ile
            420                 425                 430

Val Leu Gly Pro Tyr His Glu Lys Phe Arg Ser Leu Asn Lys Val Ser
        435                 440                 445

Glu Cys Leu Phe Ser Leu Ile Asn Gly Asp Asp Met Phe Ser Thr Phe
    450                 455                 460

Ala Lys Met Gln Gln Lys Ser Tyr Leu Val Trp Leu Phe Ser Arg Val
465                 470                 475                 480

Tyr Leu Tyr Ser Phe Ile Ser Leu Phe Ile Tyr Met Ile Leu Ser Leu
                485                 490                 495

Phe Ile Ala Leu Ile Thr Asp Thr Tyr Glu Thr Ile Lys His Tyr Gln
            500                 505                 510

Gln Asp Gly Phe Pro Glu Thr Glu Leu Arg Lys Phe Ile Ala Glu Cys
        515                 520                 525

Lys Asp Leu Pro Asn Ser Gly Lys Tyr Arg Leu Glu Asp Asp Pro Pro
    530                 535                 540

Gly Ser Leu Phe Cys Cys Cys Lys Lys
545                 550
```

<210> SEQ ID NO 84
<211> LENGTH: 751
<212> TYPE: DNA
<213> ORGANISM: Sus scrofa

<400> SEQUENCE: 84

```
gtgaaatggc agatcctgag cctgtcataa gtagctgcag ctctcgtgaa gaggaaaatc      60

gctgcacttt taaccagcac acatgtccct ctgaggagcg tctattagaa gaccagatga     120

ggcgaaaact caaatttttt ttcatgactc cttgtgagaa gttctggact cgaggtcgaa     180

aaccatggaa acttgccatg caagttctaa aaattgcgat ggtgactatc cagctgatct     240

tttcgggct aagtaaccag atggtggtag ctttcaagga agagaacacg atagcattta      300

aacacctctt tctaaagggc tatgtggacc agatggatga cacatatgcc gtgtacaccc     360

aaagcgacgt atacgatcgg atcgtcttcg cagtgaacca gtacttgcag ctacgcagca     420

tctcggttgg gaaccacgct tacgagaaca agggcgcgga gcagtcggcc atggcgatct     480

gttggcactt ctacaagcaa ggaaacatct gtcctggaaa tgacaccttt gacgttgatc     540

cagaagtaaa aactgaatgt ttctttgttg agccggatga agctgttgac actggaacac     600

tggaggagaa taagctcaac ttaacccttg actttcacag actcctaacg gtggagctgc     660

agtttaaact caaggccatt aatctgcaga cgattcgcca tcacgaactc cctgactgtt     720

atgacttcac cctgaccata acatttgaca a                                    751
```

<210> SEQ ID NO 85
<211> LENGTH: 248
<212> TYPE: PRT
<213> ORGANISM: Sus scrofa

<400> SEQUENCE: 85

```
Met Ala Asp Pro Glu Pro Val Ile Ser Ser Cys Ser Ser Arg Glu Glu
1               5                   10                  15
```

```
Glu Asn Arg Cys Thr Phe Asn Gln His Thr Cys Pro Ser Glu Glu Arg
            20                  25                  30

Leu Leu Glu Asp Gln Met Arg Arg Lys Leu Lys Phe Phe Phe Met Thr
        35                  40                  45

Pro Cys Glu Lys Phe Trp Thr Arg Gly Arg Lys Pro Trp Lys Leu Ala
    50                  55                  60

Met Gln Val Leu Lys Ile Ala Met Val Thr Ile Gln Leu Ile Phe Phe
65                  70                  75                  80

Gly Leu Ser Asn Gln Met Val Val Ala Phe Lys Glu Glu Asn Thr Ile
                85                  90                  95

Ala Phe Lys His Leu Phe Leu Lys Gly Tyr Val Asp Gln Met Asp Asp
            100                 105                 110

Thr Tyr Ala Val Tyr Thr Gln Ser Asp Val Tyr Asp Arg Ile Val Phe
        115                 120                 125

Ala Val Asn Gln Tyr Leu Gln Leu Arg Ser Ile Ser Val Gly Asn His
    130                 135                 140

Ala Tyr Glu Asn Lys Gly Ala Glu Gln Ser Ala Met Ala Ile Cys Trp
145                 150                 155                 160

His Phe Tyr Lys Gln Gly Asn Ile Cys Pro Gly Asn Asp Thr Phe Asp
                165                 170                 175

Val Asp Pro Glu Val Lys Thr Glu Cys Phe Phe Val Glu Pro Asp Glu
            180                 185                 190

Ala Val Asp Thr Gly Thr Leu Glu Glu Asn Lys Leu Asn Leu Thr Leu
        195                 200                 205

Asp Phe His Arg Leu Leu Thr Val Glu Leu Gln Phe Lys Leu Lys Ala
    210                 215                 220

Ile Asn Leu Gln Thr Ile Arg His His Glu Leu Pro Asp Cys Tyr Asp
225                 230                 235                 240

Phe Thr Leu Thr Ile Thr Phe Asp
                245
```

<210> SEQ ID NO 86
<211> LENGTH: 2880
<212> TYPE: DNA
<213> ORGANISM: Pan troglodytes

<400> SEQUENCE: 86

```
cttactccaa tcaagcctct gcccgccagg aataggtaac ctgtgtgtgt ccgtttgctc      60

cttctaagag catgcctgat agatacttcg gtagcctctc cggatggccc cttcgtcggg     120

tagcctctcc tgatggggtc cttcgcccac cctgcctccc gcgccggcgc tccgggtgaa     180

tgtcaagggt ggctggctgc gaatacctcc ttcagctgct ggggttcccg acagtttgca     240

gtttttaaaa gtgcaccctc ggaagggctt ttcagactgg gtaaagctga cttttccaag     300

agatggcaga tcctgaggta gttgtgagta gctgcagctc tcatgaagag gaaaatcgct     360

gcaattttaa ccagcaaaca tctccatctg aggagcttct attagaagac cagatgaggc     420

gaaaactcaa atttttttc atgaatccct gtgagaagtt ctgggctcga ggtagaaaac     480

catggaaact tgccatacaa attctaaaaa ttgcaatggt gactatccag ctggtcttat     540

ttgggctaag taaccagatg gtggtagctt tcaaggaaga gaatactata gcattcaaac     600

accttttcct aaaaggatat atggaccgaa tggatgacac atatgcagtg tacacacaaa     660

gtgacgtgta tgatcagtta atcttcgcag taaaccagta cttgcagcta tacaatgtct     720

ccgttgggaa tcatgcttat gagaacaaag gtaccaagca atctgctatg gcaatctgtc     780
```

```
agcacttcta caagcgagga aacatctacc ctggaaatga tacctttgac atcgatccag    840
aaattgaaac tgagtgtttc tttgtggagc cagatgaacc ttttcacatt gggacaccag    900
cagaaaataa actgaactta acactggact tccacagact cctaacagtg gagcttcagt    960
ttaaactgaa agccattaat ctgcagacag ttcgtcatca agaactccct gactgttatg   1020
actttactct gactataaca tttgacaaca aggcccatag tggaagaatt aaaataagtt   1080
tagataatga catttccatc agagaatgta aagactggca tgtatctgga tcaattcaga   1140
agaacactca ttacatgatg atctttgatg cctttgtcat tctgacttgc ttggtttcat   1200
taatcctctg cattagatct gtgattagag gacttcagct tcagcaggta gggaacgttg   1260
ctttctagga atgctactga cattttgatt gacagagaca ttcactgtgc ctcccctctt   1320
ttccctaaag gagtttgtca atttttttcct cctccattat aagaagggag tttctgtttc   1380
tgatcaaatg gaatttgtca atggatggta cattatgatt attattagtg acatattgac   1440
aatcattgga tcaattctaa aaatggaaat ccaagctaag gtaatttttt tcctaatcat   1500
gctattgtta gtgtcagatt tgcactaatg gtaatgtatt tttccagaat gtaagaattt   1560
tcagaatgaa ttgtttcttc caaactgtat atcaagtaga cttgaaattg gtaatggtaa   1620
ttttcttaaa tctagtcagg aggtctctta ggcagagttt ttcaaagtgt gatccacaaa   1680
ccattgcatc agaatcattg ggtgcctggt aaagtgtacc atgttagacc tactgaattc   1740
agactcttcg gcggggcctg tgaattctta cacacaccaa aattcataca caaccaaggt   1800
aactaaggta agagtttttt ttttttttaa atcttacaag aaatgctcaa atctttaaca   1860
aaaatgagtg ggtctatagg ggaaagtgag gtcaaggcac tatggtgtgc atgcttgcat   1920
ttgtttcctc cgtccattca aagtgagaat gctcccattt tcttacttta ccattgatgt   1980
gctacaagct tatttatttt aagactaacc tagcctaaaa atcaactgtc cccacaaaat   2040
aaaaatcaca ttaaaaaaac taatagtgtt cagactaatc ttgctcaaac ttatgtttcc   2100
ctagtcttga tgcgactgat tgagtcacct ggggagttgg ttataaacct gggcagagac   2160
cccaaatgca atggctcaga gaagatagga gcttatttct gtcttatgca atagtcagaa   2220
tgggttttac agactggtga gtagctcaac atctcacagt cattcaggca cccatgttcc   2280
tcccatttttg tttctctgcc atcccttaag gacttgccct gactgcatga ttattgctgt   2340
gttgcctcaa acaggttgca gcttatggga agcaaaaaca cggtatggtg gaagctctcc   2400
catagactga tggcttggct caagagtggc cgactttatt tctgtacata tcccactgga   2460
tagaatttag tcaatcctaa ctgcagaggg agccagggaa cacagcccag gcatgtgcct   2520
aggaagggga gaatgggttt aggttgacac ttagcagctg ccactatatg tggctatagt   2580
atgtatcatt ggaatagatg tttaacttta gggacaaata aacaaaaaac caaaacaaaa   2640
aaaggagtaa ggggagagat ttgcagcaaa tctttatttt taccaacctc aactatcatt   2700
aatttcagtg aaccctaaat ggtgtccaac aaaatatctt tctagaccat tcaccgtctc   2760
tgcctcatag atgatcatat catgttttct tctcttctga aacctctaat acccttgtcc   2820
tatcctcatt ctaagctgat gaccttactt cctatttcac aaaaataata gaaaaaaaaa   2880
```

<210> SEQ ID NO 87
<211> LENGTH: 321
<212> TYPE: PRT
<213> ORGANISM: Pan troglodytes

<400> SEQUENCE: 87

```
Met Ala Asp Pro Glu Val Val Val Ser Ser Cys Ser Ser His Glu Glu
1               5                   10                  15
```

```
Glu Asn Arg Cys Asn Phe Asn Gln Gln Thr Ser Pro Ser Glu Glu Leu
            20                  25                  30

Leu Leu Glu Asp Gln Met Arg Arg Lys Leu Lys Phe Phe Phe Met Asn
        35                  40                  45

Pro Cys Glu Lys Phe Trp Ala Arg Gly Arg Lys Pro Trp Lys Leu Ala
    50                  55                  60

Ile Gln Ile Leu Lys Ile Ala Met Val Thr Ile Gln Leu Val Leu Phe
65                  70                  75                  80

Gly Leu Ser Asn Gln Met Val Val Ala Phe Lys Glu Glu Asn Thr Ile
                85                  90                  95

Ala Phe Lys His Leu Phe Leu Lys Gly Tyr Met Asp Arg Met Asp Asp
            100                 105                 110

Thr Tyr Ala Val Tyr Thr Gln Ser Asp Val Tyr Asp Gln Leu Ile Phe
        115                 120                 125

Ala Val Asn Gln Tyr Leu Gln Leu Tyr Asn Val Ser Val Gly Asn His
    130                 135                 140

Ala Tyr Glu Asn Lys Gly Thr Lys Gln Ser Ala Met Ala Ile Cys Gln
145                 150                 155                 160

His Phe Tyr Lys Arg Gly Asn Ile Tyr Pro Gly Asn Asp Thr Phe Asp
                165                 170                 175

Ile Asp Pro Glu Ile Glu Thr Glu Cys Phe Phe Val Glu Pro Asp Glu
            180                 185                 190

Pro Phe His Ile Gly Thr Pro Ala Glu Asn Lys Leu Asn Leu Thr Leu
        195                 200                 205

Asp Phe His Arg Leu Leu Thr Val Glu Leu Gln Phe Lys Leu Lys Ala
    210                 215                 220

Ile Asn Leu Gln Thr Val Arg His Gln Glu Leu Pro Asp Cys Tyr Asp
225                 230                 235                 240

Phe Thr Leu Thr Ile Thr Phe Asp Asn Lys Ala His Ser Gly Arg Ile
                245                 250                 255

Lys Ile Ser Leu Asp Asn Asp Ile Ser Ile Arg Glu Cys Lys Asp Trp
            260                 265                 270

His Val Ser Gly Ser Ile Gln Lys Asn Thr His Tyr Met Met Ile Phe
        275                 280                 285

Asp Ala Phe Val Ile Leu Thr Cys Leu Val Ser Leu Ile Leu Cys Ile
    290                 295                 300

Arg Ser Val Ile Arg Gly Leu Gln Leu Gln Gln Val Gly Asn Val Ala
305                 310                 315                 320

Phe
```

<210> SEQ ID NO 88
<211> LENGTH: 1868
<212> TYPE: DNA
<213> ORGANISM: Pan troglodytes

<400> SEQUENCE: 88

```
cctctagaga tggcagatcc tgaggtagtt gtgagtagct gcagctctca tgaagaggaa      60

aatcgctgca attttaacca gcaaacatct ccatctgagg agcttctatt agaagaccag     120

atgaggcgaa aactcaaatt ttttttcatg aatccctgtg agaagttctg ggctcgaggt     180

agaaaaccat ggaaacttgc catacaaatt ctaaaaattg caatggtgac tatccagctg     240

gtcttatttg ggctaagtaa ccagatggtg gtagctttca aggaagagaa tactatagca     300

ttcaaacacc ttttcctaaa aggatatatg gaccgaatgg atgacacata tgcagtgtac     360
```

-continued

```
acacaaagtg acgtgtatga tcagttaatc ttcgcagtaa accagtactt gcagctatac    420

aatgtctccg ttgggaatca tgcttatgag aacaaaggta ccaagcaatc tgctatggca    480

atctgtcagc acttctacaa gcgaggaaac atctaccctg gaaatgatac ctttgacatc    540

gatccagaaa ttgaaactga gtgtttcttt gtggagccag atgaaccttt tcacattggg    600

acaccagcag aaaataaact gaacttaaca ctggacttcc acagactcct aacagtggag    660

cttcagttta aactgaaagc cattaatctg cagacagttc gtcatcaaga actccctgac    720

tgttatgact ttactctgac tataacattt gacaacaagg cccatagtgg aagaattaaa    780

ataagtttag ataatgacat ttccatcaga gaatgtaaag actggcattc tccctccgtc    840

gcccagcctg gaaacactca ttacatgatg atctttgatg cctttgtcat tctgacttgc    900

ttggtttcat taatcctctg cattagatct gtgattagag gacttcagct tcagcaggag    960

tttgtcaatt ttttcctcct ccattataag aagggagttt ctgtttctga tcaaatggaa   1020

tttgtcaatg gatggtacat tatgattatt attagtgaca tattgacaat cattggatca   1080

attctaaaaa tggaaatcca agctaagagt ctaactagtt atgatgtctg tagcatactt   1140

cttgggactt ctaccatgct tgtgtggctt ggagtcatcc gatacctcgg tttctttgca   1200

aagtacaatc tcctcatttt gacccttcag gcagcactgc ccaatgtcat caggttctgc   1260

tgctgtgcag ctatgattta cttaggttac tgcttctgtg gatggatcgt gctggggcct   1320

taccatgaca agtttcgttc tctgaacatg gtctctgagt gcctttttctc tctgataaat   1380

ggagatgata tgtttgccac gtttgcaaaa atgcagcaaa aaagttactt agtctggctg   1440

tttagtagaa tttacctcta ctcattcatc agcctcttta tatatatgat tttaagtctt   1500

ttcattgcac tgatcactga tacatacgaa acaattaagc aataccaaca agatggcttc   1560

ccagagactg aacttcgtac atttatatca gaatgcaaag atctacccaa ctctggaaaa   1620

tacagattag aagatgaccc tccagtatct ttattctgct gttgtaaaaa gtagctatca   1680

ggtttatctg tactttagag gaaaatataa tgtgtagctg agttagaaca ctgtggatat   1740

tctgagatca gatgtagtat gtttgaagac tgttattttg agctaattga gacctataat   1800

tcaccaataa ctgtttatat ttttaaaagc aatatttaat gtctttgcag ctttatgctg   1860

ggcttgtt                                                             1868
```

<210> SEQ ID NO 89
<211> LENGTH: 554
<212> TYPE: PRT
<213> ORGANISM: Pan troglodytes

<400> SEQUENCE: 89

```
Met Ala Asp Pro Glu Val Val Val Ser Ser Cys Ser Ser His Glu Glu
1               5                   10                  15

Glu Asn Arg Cys Asn Phe Asn Gln Gln Thr Ser Pro Ser Glu Glu Leu
            20                  25                  30

Leu Leu Glu Asp Gln Met Arg Arg Lys Leu Lys Phe Phe Phe Met Asn
        35                  40                  45

Pro Cys Glu Lys Phe Trp Ala Arg Gly Arg Lys Pro Trp Lys Leu Ala
    50                  55                  60

Ile Gln Ile Leu Lys Ile Ala Met Val Thr Ile Gln Leu Val Leu Phe
65                  70                  75                  80

Gly Leu Ser Asn Gln Met Val Val Ala Phe Lys Glu Glu Asn Thr Ile
                85                  90                  95

Ala Phe Lys His Leu Phe Leu Lys Gly Tyr Met Asp Arg Met Asp Asp
            100                 105                 110
```

-continued

```
Thr Tyr Ala Val Tyr Thr Gln Ser Asp Val Tyr Asp Gln Leu Ile Phe
        115                 120                 125

Ala Val Asn Gln Tyr Leu Gln Leu Tyr Asn Val Ser Val Gly Asn His
    130                 135                 140

Ala Tyr Glu Asn Lys Gly Thr Lys Gln Ser Ala Met Ala Ile Cys Gln
145                 150                 155                 160

His Phe Tyr Lys Arg Gly Asn Ile Tyr Pro Gly Asn Asp Thr Phe Asp
                165                 170                 175

Ile Asp Pro Glu Ile Glu Thr Glu Cys Phe Phe Val Glu Pro Asp Glu
            180                 185                 190

Pro Phe His Ile Gly Thr Pro Ala Glu Asn Lys Leu Asn Leu Thr Leu
        195                 200                 205

Asp Phe His Arg Leu Leu Thr Val Glu Leu Gln Phe Lys Leu Lys Ala
    210                 215                 220

Ile Asn Leu Gln Thr Val Arg His Gln Glu Leu Pro Asp Cys Tyr Asp
225                 230                 235                 240

Phe Thr Leu Thr Ile Thr Phe Asp Asn Lys Ala His Ser Gly Arg Ile
                245                 250                 255

Lys Ile Ser Leu Asp Asn Asp Ile Ser Ile Arg Glu Cys Lys Asp Trp
            260                 265                 270

His Ser Pro Ser Val Ala Gln Pro Gly Asn Thr His Tyr Met Met Ile
        275                 280                 285

Phe Asp Ala Phe Val Ile Leu Thr Cys Leu Val Ser Leu Ile Leu Cys
    290                 295                 300

Ile Arg Ser Val Ile Arg Gly Leu Gln Leu Gln Gln Glu Phe Val Asn
305                 310                 315                 320

Phe Phe Leu Leu His Tyr Lys Lys Gly Val Ser Val Ser Asp Gln Met
                325                 330                 335

Glu Phe Val Asn Gly Trp Tyr Ile Met Ile Ile Ile Ser Asp Ile Leu
            340                 345                 350

Thr Ile Ile Gly Ser Ile Leu Lys Met Glu Ile Gln Ala Lys Ser Leu
        355                 360                 365

Thr Ser Tyr Asp Val Cys Ser Ile Leu Leu Gly Thr Ser Thr Met Leu
    370                 375                 380

Val Trp Leu Gly Val Ile Arg Tyr Leu Gly Phe Phe Ala Lys Tyr Asn
385                 390                 395                 400

Leu Leu Ile Leu Thr Leu Gln Ala Ala Leu Pro Asn Val Ile Arg Phe
                405                 410                 415

Cys Cys Cys Ala Ala Met Ile Tyr Leu Gly Tyr Cys Phe Cys Gly Trp
            420                 425                 430

Ile Val Leu Gly Pro Tyr His Asp Lys Phe Arg Ser Leu Asn Met Val
        435                 440                 445

Ser Glu Cys Leu Phe Ser Leu Ile Asn Gly Asp Asp Met Phe Ala Thr
    450                 455                 460

Phe Ala Lys Met Gln Gln Lys Ser Tyr Leu Val Trp Leu Phe Ser Arg
465                 470                 475                 480

Ile Tyr Leu Tyr Ser Phe Ile Ser Leu Phe Ile Tyr Met Ile Leu Ser
                485                 490                 495

Leu Phe Ile Ala Leu Ile Thr Asp Thr Tyr Glu Thr Ile Lys Gln Tyr
            500                 505                 510

Gln Gln Asp Gly Phe Pro Glu Thr Glu Leu Arg Thr Phe Ile Ser Glu
        515                 520                 525

Cys Lys Asp Leu Pro Asn Ser Gly Lys Tyr Arg Leu Glu Asp Asp Pro
```

530 535 540

Pro Val Ser Leu Phe Cys Cys Cys Lys Lys
545 550

<210> SEQ ID NO 90
<211> LENGTH: 2546
<212> TYPE: DNA
<213> ORGANISM: Pan troglodytes

<400> SEQUENCE: 90
tcctctagag atggcagatc ctgaggtagt tgtgagtagc tgcagctctc atgaagagga 60
aaatcgctgc aattttaacc agcaaacatc tccatctgag gagcttctat tagaagacca 120
gatgaggcga aaactcaaat ttttttcat gaatccctgt gagaagttct gggctcgagg 180
tagaaaacca tggaaacttg ccatacaaat tctaaaaatt gcaatggtga ctatccagta 240
cttgcagcta tacaatgtct ccgttgggaa tcatgcttat gagaacaaag gtaccaagca 300
atctgctatg gcaatctgtc agcacttcta caagcgagga aacatctacc ctggaaatga 360
tacctttgac atcgatccag aaattgaaac tgagtgtttc tttgtggagc cagatgaacc 420
ttttcacatt gggacaccag cagaaaataa actgaactta acactggact tccacagact 480
cctaacagtg gagcttcagt ttaaactgaa agccattaat ctgcagacag ttcgtcatca 540
agaactccct gactgttatg actttactct gactataaca tttgacaaca aggcccatag 600
tggaagaatt aaaataagtt tagataatga catttccatc agagaatgta aagactggca 660
tgtatctgga tcaattcaga agaacactca ttacatgatg atctttgatg cctttgtcat 720
tctgacttgc ttggtttcat taatcctctg cattagatct gtgattagag gacttcagct 780
tcagcaggag tttgtcaatt ttttcctcct ccattataag aagggagttt ctgtttctga 840
tcaaatggaa tttgtcaatg gatggtacat tatgattatt attagtgaca tattgacaat 900
cattggatca attctaaaaa tggaaatcca agctaagagt ctaactagtt atgatgtctg 960
tagcatactt cttgggactt ctaccatgct tgtgtggctt ggagtcatcc gatacctcgg 1020
tttctttgca aagtacaatc tcctcatttt gacccttcag gcagcactgc ccaatgtcat 1080
caggttctgc tgctgtgcag ctatgattta cttaggttac tgcttctgtg gatggatcgt 1140
gctggggcct taccatgaca agtttcgttc tctgaacatg gtctctgagt gccttttctc 1200
tctgataaat ggagatgata tgtttgccac gtttgcaaaa atgcagcaaa aaagttactt 1260
agtctggctg tttagtagaa tttacctcta ctcattcatc agcctcttta tatatatgat 1320
tttaagtctt ttcattgcac tgatcactga tacatacgaa acaattaagc aataccaaca 1380
agatggcttc ccagagactg aacttcgtac atttatatca gaatgcaaag atctacccaa 1440
ctctggaaaa tacagattag aagatgaccc tccagtatct ttattctgct gttgtaaaaa 1500
gtagctatca ggtttatctg tactttagag gaaaatataa tgtgtagctg agttagaaca 1560
ctgtggatat tctgagatca gatgtagtat gtttgaagac tgttattttg agctaattga 1620
gacctataat tcaccaataa ctgtttatat ttttaaaagc aatatttaat gtctttgcag 1680
ctttatgctg ggcttgtttt taaaacaact ttaatgagga aagctattgg attattatta 1740
tttcttgttt attttgccat ggctttagaa tgtattctgt atgcctctct tttgctctga 1800
tactcttgct tcctgctatt ctgattgtgc agactgtgta attagtggaa aacaatcctt 1860
ggtctgactg tgactttgga caactcagta accctggctt ggaccactct caggagtcca 1920
tccttgagag agtgggtgta gttaccattt atacagtaat cattgcattt taaaatctgc 1980
tcttgaaagg aagaataaga gtgcaccaga ataagagcgc accagaataa gagcgcacca 2040

```
gctaacaatg tgatacggcc atatgtcact taaggataga gatatgttct gagaaatgtg   2100

tcattaggcg attttgtcat taaacatcat agcatgtact tccacaaacc tagatggtat   2160

agcctactac acacctaggc tatttggtat agcctgttga tcctggggta caaatctgta   2220

caacatgtta ctgtattgaa tacagtaggc aattgtaaca caatggtaag tatctaaaca   2280

tagaaaaggg acagtaaaaa tatggtttta taatcttctg ggaccaccat tgtatatgcg   2340

gtacatcgtt gaccaaaaca tcgttatcca gcatatgact gtatttggtt atgaaagcca   2400

actgttactt gattctgctt ttagttctta agaggatcag gtttttaaat actcatttac   2460

aagttttcta tcctccttca gtgttaaagt agaaagtaaa aagagtatct tatacatgca   2520

tgaaattaaa gcatatacca aatgca                                        2546


<210> SEQ ID NO 91
<211> LENGTH: 497
<212> TYPE: PRT
<213> ORGANISM: Pan troglodytes

<400> SEQUENCE: 91

Met Ala Asp Pro Glu Val Val Val Ser Ser Cys Ser Ser His Glu Glu
1               5                   10                  15

Glu Asn Arg Cys Asn Phe Asn Gln Gln Thr Ser Pro Ser Glu Glu Leu
            20                  25                  30

Leu Leu Glu Asp Gln Met Arg Arg Lys Leu Lys Phe Phe Phe Met Asn
        35                  40                  45

Pro Cys Glu Lys Phe Trp Ala Arg Gly Arg Lys Pro Trp Lys Leu Ala
    50                  55                  60

Ile Gln Ile Leu Lys Ile Ala Met Val Thr Ile Gln Tyr Leu Gln Leu
65                  70                  75                  80

Tyr Asn Val Ser Val Gly Asn His Ala Tyr Glu Asn Lys Gly Thr Lys
                85                  90                  95

Gln Ser Ala Met Ala Ile Cys Gln His Phe Tyr Lys Arg Gly Asn Ile
            100                 105                 110

Tyr Pro Gly Asn Asp Thr Phe Asp Ile Asp Pro Glu Ile Glu Thr Glu
        115                 120                 125

Cys Phe Phe Val Glu Pro Asp Glu Pro Phe His Ile Gly Thr Pro Ala
    130                 135                 140

Glu Asn Lys Leu Asn Leu Thr Leu Asp Phe His Arg Leu Leu Thr Val
145                 150                 155                 160

Glu Leu Gln Phe Lys Leu Lys Ala Ile Asn Leu Gln Thr Val Arg His
                165                 170                 175

Gln Glu Leu Pro Asp Cys Tyr Asp Phe Thr Leu Thr Ile Thr Phe Asp
            180                 185                 190

Asn Lys Ala His Ser Gly Arg Ile Lys Ile Ser Leu Asp Asn Asp Ile
        195                 200                 205

Ser Ile Arg Glu Cys Lys Asp Trp His Val Ser Gly Ser Ile Gln Lys
    210                 215                 220

Asn Thr His Tyr Met Met Ile Phe Asp Ala Phe Val Ile Leu Thr Cys
225                 230                 235                 240

Leu Val Ser Leu Ile Leu Cys Ile Arg Ser Val Ile Arg Gly Leu Gln
                245                 250                 255

Leu Gln Gln Glu Phe Val Asn Phe Phe Leu Leu His Tyr Lys Lys Gly
            260                 265                 270

Val Ser Val Ser Asp Gln Met Glu Phe Val Asn Gly Trp Tyr Ile Met
        275                 280                 285
```

```
Ile Ile Ile Ser Asp Ile Leu Thr Ile Ile Gly Ser Ile Leu Lys Met
    290                 295                 300

Glu Ile Gln Ala Lys Ser Leu Thr Ser Tyr Asp Val Cys Ser Ile Leu
305                 310                 315                 320

Leu Gly Thr Ser Thr Met Leu Val Trp Leu Gly Val Ile Arg Tyr Leu
                325                 330                 335

Gly Phe Phe Ala Lys Tyr Asn Leu Leu Ile Leu Thr Leu Gln Ala Ala
            340                 345                 350

Leu Pro Asn Val Ile Arg Phe Cys Cys Cys Ala Ala Met Ile Tyr Leu
        355                 360                 365

Gly Tyr Cys Phe Cys Gly Trp Ile Val Leu Gly Pro Tyr His Asp Lys
    370                 375                 380

Phe Arg Ser Leu Asn Met Val Ser Glu Cys Leu Phe Ser Leu Ile Asn
385                 390                 395                 400

Gly Asp Asp Met Phe Ala Thr Phe Ala Lys Met Gln Gln Lys Ser Tyr
                405                 410                 415

Leu Val Trp Leu Phe Ser Arg Ile Tyr Leu Tyr Ser Phe Ile Ser Leu
            420                 425                 430

Phe Ile Tyr Met Ile Leu Ser Leu Phe Ile Ala Leu Ile Thr Asp Thr
        435                 440                 445

Tyr Glu Thr Ile Lys Gln Tyr Gln Gln Asp Gly Phe Pro Glu Thr Glu
    450                 455                 460

Leu Arg Thr Phe Ile Ser Glu Cys Lys Asp Leu Pro Asn Ser Gly Lys
465                 470                 475                 480

Tyr Arg Leu Glu Asp Asp Pro Pro Val Ser Leu Phe Cys Cys Cys Lys
                485                 490                 495

Lys


<210> SEQ ID NO 92
<211> LENGTH: 2714
<212> TYPE: DNA
<213> ORGANISM: Pan troglodytes

<400> SEQUENCE: 92

tcctctagag atggcagatc ctgaggtagt tgtgagtagc tgcagctctc atgaagagga      60

aaatcgctgc aattttaacc agcaaacatc tccatctgag gagcttctat tagaagacca     120

gatgaggcga aaactcaaat ttttttcat gaatccctgt gagaagttct gggctcgagg      180

tagaaaacca tggaaacttg ccatacaaat tctaaaaatt gcaatggtga ctatccagct     240

ggtcttattt gggctaagta accagatggt ggtagctttc aaggaagaga atactatagc     300

attcaaacac cttttcctaa aaggatatat ggaccgaatg gatgacacat atgcagtgta     360

cacacaaagt gacgtgtatg atcagttaat cttcgcagta aaccagtact tgcagctata     420

caatgtctcc gttgggaatc atgcttatga gaacaaaggt accaagcaat ctgctatggc     480

aatctgtcag cacttctaca agcgaggaaa catctaccct ggaaatgata cctttgacat     540

cgatccagaa attgaaactg agtgtttctt tgtggagcca gatgaacctt ttcacattgg     600

gacaccagca gaaaataaac tgaacttaac actggacttc cacagactcc taacagtgga     660

gcttcagttt aaactgaaag ccattaatct gcagacagtt cgtcatcaag aactccctga     720

ctgttatgac tttactctga ctataacatt tgacaacaag gcccatagtg gaagaattaa     780

aataagttta gataatgaca tttccatcag agaatgtaaa gactggcatg tatctggatc     840

aattcagaag aacactcatt acatgatgat ctttgatgcc tttgtcattc tgacttgctt     900
```

-continued

```
ggtttcatta atcctctgca ttagatctgt gattagagga cttcagcttc agcaggagtt    960

tgtcaatttt ttcctcctcc attataagaa gggagtttct gtttctgatc aaatggaatt   1020

tgtcaatgga tggtacatta tgattattat tagtgacata ttgacaatca ttggatcaat   1080

tctaaaaatg gaaatccaag ctaagagtct aactagttat gatgtctgta gcatacttct   1140

tgggacttct accatgcttg tgtggcttgg agtcatccga tacctcggtt tctttgcaaa   1200

gtacaatctc ctcattttga cccttcaggc agcactgccc aatgtcatca ggttctgctg   1260

ctgtgcagct atgatttact taggttactg cttctgtgga tggatcgtgc tggggcctta   1320

ccatgacaag tttcgttctc tgaacatggt ctctgagtgc cttttctctc tgataaatgg   1380

agatgatatg tttgccacgt ttgcaaaaat gcagcaaaaa agttacttag tctggctgtt   1440

tagtagaatt tacctctact cattcatcag cctctttata tatatgattt taagtctttt   1500

cattgcactg atcactgata catacgaaac aattaagcaa taccaacaag atggcttccc   1560

agagactgaa cttcgtacat ttatatcaga atgcaaagat ctacccaact ctggaaaata   1620

cagattagaa gatgaccctc cagtatcttt attctgctgt tgtaaaaagt agctatcagg   1680

tttatctgta ctttagagga aaatataatg tgtagctgag ttagaacact gtggatattc   1740

tgagatcaga tgtagtatgt ttgaagactg ttattttgag ctaattgaga cctataattc   1800

accaataact gtttatattt ttaaaagcaa tatttaatgt ctttgcagct ttatgctggg   1860

cttgttttta aaacaacttt aatgaggaaa gctattggat tattattatt tcttgtttat   1920

tttgccatgg ctttagaatg tattctgtat gcctctcttt tgctctgata ctcttgcttc   1980

ctgctattct gattgtgcag actgtgtaat tagtggaaaa caatccttgg tctgactgtg   2040

actttggaca actcagtaac cctggcttgg accactctca ggagtccatc cttgagagag   2100

tgggtgtagt taccatttat acagtaatca ttgcatttta aaatctgctc ttgaaaggaa   2160

gaataagagt gcaccagaat aagagcgcac cagaataaga gcgcaccagc taacaatgtg   2220

atacggccat atgtcactta aggatagaga tatgttctga gaaatgtgtc attaggcgat   2280

tttgtcatta aacatcatag catgtacttc cacaaaccta gatggtatag cctactacac   2340

acctaggcta tttggtatag cctgttgatc ctggggtaca aatctgtaca acatgttact   2400

gtattgaata cagtaggcaa ttgtaacaca atggtaagta tctaaacata gaaaagggac   2460

agtaaaaata tggttttata atcttctggg accaccattg tatatgcggt acatcgttga   2520

ccaaaacatc gttatccagc atatgactgt atttggttat gaaagccaac tgttacttga   2580

ttctgctttt agttcttaag aggatcaggt ttttaaatac tcatttacaa gttttctatc   2640

ctccttcagt gttaaagtag aaagtaaaaa gagtatctta tacatgcatg aaattaaagc   2700

atataccaaa tgca                                                      2714
```

<210> SEQ ID NO 93
<211> LENGTH: 553
<212> TYPE: PRT
<213> ORGANISM: Pan troglodytes

<400> SEQUENCE: 93

```
Met Ala Asp Pro Glu Val Val Val Ser Ser Cys Ser Ser His Glu Glu
1               5                   10                  15

Glu Asn Arg Cys Asn Phe Asn Gln Gln Thr Ser Pro Ser Glu Glu Leu
            20                  25                  30

Leu Leu Glu Asp Gln Met Arg Arg Lys Leu Lys Phe Phe Phe Met Asn
        35                  40                  45

Pro Cys Glu Lys Phe Trp Ala Arg Gly Arg Lys Pro Trp Lys Leu Ala
```

-continued

```
    50                  55                  60

Ile Gln Ile Leu Lys Ile Ala Met Val Thr Ile Gln Leu Val Leu Phe
65                  70                  75                  80

Gly Leu Ser Asn Gln Met Val Val Ala Phe Lys Glu Glu Asn Thr Ile
                85                  90                  95

Ala Phe Lys His Leu Phe Leu Lys Gly Tyr Met Asp Arg Met Asp Asp
            100                 105                 110

Thr Tyr Ala Val Tyr Thr Gln Ser Asp Val Tyr Asp Gln Leu Ile Phe
        115                 120                 125

Ala Val Asn Gln Tyr Leu Gln Leu Tyr Asn Val Ser Val Gly Asn His
    130                 135                 140

Ala Tyr Glu Asn Lys Gly Thr Lys Gln Ser Ala Met Ala Ile Cys Gln
145                 150                 155                 160

His Phe Tyr Lys Arg Gly Asn Ile Tyr Pro Gly Asn Asp Thr Phe Asp
                165                 170                 175

Ile Asp Pro Glu Ile Glu Thr Glu Cys Phe Phe Val Glu Pro Asp Glu
            180                 185                 190

Pro Phe His Ile Gly Thr Pro Ala Glu Asn Lys Leu Asn Leu Thr Leu
        195                 200                 205

Asp Phe His Arg Leu Leu Thr Val Glu Leu Gln Phe Lys Leu Lys Ala
    210                 215                 220

Ile Asn Leu Gln Thr Val Arg His Gln Glu Leu Pro Asp Cys Tyr Asp
225                 230                 235                 240

Phe Thr Leu Thr Ile Thr Phe Asp Asn Lys Ala His Ser Gly Arg Ile
                245                 250                 255

Lys Ile Ser Leu Asp Asn Asp Ile Ser Ile Arg Glu Cys Lys Asp Trp
            260                 265                 270

His Val Ser Gly Ser Ile Gln Lys Asn Thr His Tyr Met Met Ile Phe
        275                 280                 285

Asp Ala Phe Val Ile Leu Thr Cys Leu Val Ser Leu Ile Leu Cys Ile
    290                 295                 300

Arg Ser Val Ile Arg Gly Leu Gln Leu Gln Gln Glu Phe Val Asn Phe
305                 310                 315                 320

Phe Leu Leu His Tyr Lys Lys Gly Val Ser Val Ser Asp Gln Met Glu
                325                 330                 335

Phe Val Asn Gly Trp Tyr Ile Met Ile Ile Ile Ser Asp Ile Leu Thr
            340                 345                 350

Ile Ile Gly Ser Ile Leu Lys Met Glu Ile Gln Ala Lys Ser Leu Thr
        355                 360                 365

Ser Tyr Asp Val Cys Ser Ile Leu Leu Gly Thr Ser Thr Met Leu Val
    370                 375                 380

Trp Leu Gly Val Ile Arg Tyr Leu Gly Phe Phe Ala Lys Tyr Asn Leu
385                 390                 395                 400

Leu Ile Leu Thr Leu Gln Ala Ala Leu Pro Asn Val Ile Arg Phe Cys
                405                 410                 415

Cys Cys Ala Ala Met Ile Tyr Leu Gly Tyr Cys Phe Cys Gly Trp Ile
            420                 425                 430

Val Leu Gly Pro Tyr His Asp Lys Phe Arg Ser Leu Asn Met Val Ser
        435                 440                 445

Glu Cys Leu Phe Ser Leu Ile Asn Gly Asp Asp Met Phe Ala Thr Phe
    450                 455                 460

Ala Lys Met Gln Gln Lys Ser Tyr Leu Val Trp Leu Phe Ser Arg Ile
465                 470                 475                 480
```

-continued

```
Tyr Leu Tyr Ser Phe Ile Ser Leu Phe Ile Tyr Met Ile Leu Ser Leu
                485                 490                 495

Phe Ile Ala Leu Ile Thr Asp Thr Tyr Glu Thr Ile Lys Gln Tyr Gln
            500                 505                 510

Gln Asp Gly Phe Pro Glu Thr Glu Leu Arg Thr Phe Ile Ser Glu Cys
        515                 520                 525

Lys Asp Leu Pro Asn Ser Gly Lys Tyr Arg Leu Glu Asp Asp Pro Pro
    530                 535                 540

Val Ser Leu Phe Cys Cys Cys Lys Lys
545                 550


<210> SEQ ID NO 94
<211> LENGTH: 1896
<212> TYPE: DNA
<213> ORGANISM: Silurana tropicalis

<400> SEQUENCE: 94

ttgcaactag gtctgacagt aggacaatgt ggcaggtcac gtgacagcag tgctgatggt     60

agagatgcgc cagcattcag gtctgagagc agaaagaaaa gctggccaaa acaaaggaca    120

ttctctttgc tgcttcgcta gctgagacgc tgctatagta tagcagacat ggaaaaccca    180

gagctaataa agacatgcaa ctctttggat gaacatgatg gtccctactg ctgcaagcag    240

tgccctatga ctgatgagct acttatggaa gaccagctac gaaggaaact taaattcttt    300

ttcatgaacc catgtgagaa gttccgtgcc cgtggacgaa agccttggaa gctttgtatt    360

caaattttaa aaattgcaat ggtgacaatc caattagttt tatttggact cagtaatgaa    420

atggtagtca cctttaaaga ggagaacact gtagctttta agcatctgtt tttgaaagga    480

tataaggatg gacatgatga cacatatgct atctacagtc aagaagatgt tcatgctcat    540

ataaacttta caattaaaag gtacctagag ctacaaaaca tatctgttgg aaatcatgca    600

tatgaaagta atggtaaagg tcaaactgga atgtcattat gtcaacatta ctataaacaa    660

gggagtatct ttcctggaaa tgaaacattt gaaattgacc cacaaataga tactgaatgt    720

ttccatattg atccatcaac tctgtgttct aatgacacac ctgcagaata ctactggtct    780

aatatgacac tagacttcta tagacttgtt tcagttgaaa ttatgtttaa gcttaaagca    840

attaatcttc aaaccattcg tcatcatgaa cttccagact gctatgactt catggttata    900

ataacatttg ataataaggc acacagtgga aggataaaaa tcagcttaga taatgatgtt    960

ggaatccagg aatgcaaaga ctggcatgtg tctggatcta ttcaaaaaaa tactcattac   1020

atgatgattt ttgatgctgc tgttattttg gtctgcttat cttccataac actctgcatt   1080

cgctccgtgg ttaaaggaat tcacctacaa aaagaatatg taaacttttt ccagcatcgt   1140

tttgcaagga ctgtgtcctc agctgatcgc atggaatttg tcaatggctg gtacattatg   1200

ataatcatca gtgatgtttt gtcaattatt ggctcaatct tgaagatgga gatccaagca   1260

aagagcctca ccagttatga tgtctgcagt attctcttgg gaacatccac cttattagtg   1320

tggcttggag ttattcgcta cttgggattt tttaagaaat acaatcttct gatcctgaca   1380

cttagggcag ccttacctaa tgtgatacga ttctgctgtt gtgctgctat gatctacctg   1440

ggctactgct tctgtggctg gattgttctg ggccttaccc atgtaaagtt caggtccctg   1500

aacatggttt cagagtgcct gttctccctt attaatggag acgatatgtt tacaacgttt   1560

tcaatcatgc aggagaagag ctacttggtt tggctgttta gtcgcattta tttgtattcc   1620

tttataagtc tcttcatata catggttctg agtctcttca ttgcacttat tactgacaca   1680

tacgatacaa tcaagaatta ccagatcgat ggctttccag aatcagaact tcacacattt   1740
```

```
gtatccgagt gcaaagattt gccaacctct ggtcgatata gggaacaaga cgagacctcc   1800

tgtttgtcta tgctgtgttg taatcggtaa aaaagaatcc cagaagaagc actttatcca   1860

tggcctttaa aaatctgcaa aaaaaaaaaa aaaaaa                             1896


<210> SEQ ID NO 95
<211> LENGTH: 553
<212> TYPE: PRT
<213> ORGANISM: Silurana tropicalis

<400> SEQUENCE: 95

Met Glu Asn Pro Glu Leu Ile Lys Thr Cys Asn Ser Leu Asp Glu His
1               5                   10                  15

Asp Gly Pro Tyr Cys Cys Lys Gln Cys Pro Met Thr Asp Glu Leu Leu
            20                  25                  30

Met Glu Asp Gln Leu Arg Arg Lys Leu Lys Phe Phe Phe Met Asn Pro
        35                  40                  45

Cys Glu Lys Phe Arg Ala Arg Gly Arg Lys Pro Trp Lys Leu Cys Ile
    50                  55                  60

Gln Ile Leu Lys Ile Ala Met Val Thr Ile Gln Leu Val Leu Phe Gly
65                  70                  75                  80

Leu Ser Asn Glu Met Val Val Thr Phe Lys Glu Glu Asn Thr Val Ala
                85                  90                  95

Phe Lys His Leu Phe Leu Lys Gly Tyr Lys Asp Gly His Asp Asp Thr
            100                 105                 110

Tyr Ala Ile Tyr Ser Gln Glu Asp Val His Ala His Ile Asn Phe Thr
        115                 120                 125

Ile Lys Arg Tyr Leu Glu Leu Gln Asn Ile Ser Val Gly Asn His Ala
    130                 135                 140

Tyr Glu Ser Asn Gly Lys Gly Gln Thr Gly Met Ser Leu Cys Gln His
145                 150                 155                 160

Tyr Tyr Lys Gln Gly Ser Ile Phe Pro Gly Asn Glu Thr Phe Glu Ile
                165                 170                 175

Asp Pro Gln Ile Asp Thr Glu Cys Phe His Ile Asp Pro Ser Thr Leu
            180                 185                 190

Cys Ser Asn Asp Thr Pro Ala Glu Tyr Tyr Trp Ser Asn Met Thr Leu
        195                 200                 205

Asp Phe Tyr Arg Leu Val Ser Val Glu Ile Met Phe Lys Leu Lys Ala
    210                 215                 220

Ile Asn Leu Gln Thr Ile Arg His His Glu Leu Pro Asp Cys Tyr Asp
225                 230                 235                 240

Phe Met Val Ile Ile Thr Phe Asp Asn Lys Ala His Ser Gly Arg Ile
                245                 250                 255

Lys Ile Ser Leu Asp Asn Asp Val Gly Ile Gln Glu Cys Lys Asp Trp
            260                 265                 270

His Val Ser Gly Ser Ile Gln Lys Asn Thr His Tyr Met Met Ile Phe
        275                 280                 285

Asp Ala Ala Val Ile Leu Val Cys Leu Ser Ser Ile Thr Leu Cys Ile
    290                 295                 300

Arg Ser Val Val Lys Gly Ile His Leu Gln Lys Glu Tyr Val Asn Phe
305                 310                 315                 320

Phe Gln His Arg Phe Ala Arg Thr Val Ser Ser Ala Asp Arg Met Glu
                325                 330                 335

Phe Val Asn Gly Trp Tyr Ile Met Ile Ile Ile Ser Asp Val Leu Ser
            340                 345                 350
```

```
Ile Ile Gly Ser Ile Leu Lys Met Glu Ile Gln Ala Lys Ser Leu Thr
        355                 360                 365

Ser Tyr Asp Val Cys Ser Ile Leu Leu Gly Thr Ser Thr Leu Leu Val
    370                 375                 380

Trp Leu Gly Val Ile Arg Tyr Leu Gly Phe Phe Lys Lys Tyr Asn Leu
385                 390                 395                 400

Leu Ile Leu Thr Leu Arg Ala Ala Leu Pro Asn Val Ile Arg Phe Cys
                405                 410                 415

Cys Cys Ala Ala Met Ile Tyr Leu Gly Tyr Cys Phe Cys Gly Trp Ile
            420                 425                 430

Val Leu Gly Pro Tyr His Val Lys Phe Arg Ser Leu Asn Met Val Ser
        435                 440                 445

Glu Cys Leu Phe Ser Leu Ile Asn Gly Asp Asp Met Phe Thr Thr Phe
    450                 455                 460

Ser Ile Met Gln Glu Lys Ser Tyr Leu Val Trp Leu Phe Ser Arg Ile
465                 470                 475                 480

Tyr Leu Tyr Ser Phe Ile Ser Leu Phe Ile Tyr Met Val Leu Ser Leu
                485                 490                 495

Phe Ile Ala Leu Ile Thr Asp Thr Tyr Asp Thr Ile Lys Asn Tyr Gln
            500                 505                 510

Ile Asp Gly Phe Pro Glu Ser Glu Leu His Thr Phe Val Ser Glu Cys
        515                 520                 525

Lys Asp Leu Pro Thr Ser Gly Arg Tyr Arg Glu Gln Asp Glu Thr Ser
    530                 535                 540

Cys Leu Ser Met Leu Cys Cys Asn Arg
545                 550


<210> SEQ ID NO 96
<211> LENGTH: 1896
<212> TYPE: DNA
<213> ORGANISM: Silurana tropicalis

<400> SEQUENCE: 96

ttgcaactag gtctgacagt aggacaatgt ggcaggtcac gtgacagcag tgctgatggt      60

agagatgcgc cagcattcag gtctgagagc agaaagaaaa gctggccaaa acaaaggaca     120

ttctctttgc tgcttcgcta gctgagacgc tgctatagta tagcagacat ggaaaaccca     180

gagctaataa agacatgcaa ctctttggat gaacatgatg gtccctactg ctgcaagcag     240

tgccctatga ctgatgagct acttatggaa gaccagctac gaaggaaact taaattcttt     300

ttcatgaacc catgtgagaa gttccgtgcc cgtggacgaa agccttggaa gctttgtatt     360

caaattttaa aaattgcaat ggtgacaatc caattagttt tatttggact cagtaatgaa     420

atggtagtca cctttaaaga ggagaacact gtagctttta agcatctgtt tttgaaagga     480

tataaggatg gacatgatga cacatatgct atctacagtc aagaagatgt tcatgctcat     540

ataaacttta caattaaaag gtacctagag ctacaaaaca tatctgttgg aaatcatgca     600

tatgaaagta atggtaaagg tcaaactgga atgtcattat gtcaacatta ctataaacaa     660

gggagtatct ttcctggaaa tgaaacattt gaaattgacc cacaaataga tactgaatgt     720

ttccatattg atccatcaac tctgtgttct aatgacacac ctgcagaata ctactggtct     780

aatatgacac tagacttcta tagacttgtt tcagttgaaa ttatgtttaa gcttaaagca     840

attaatcttc aaaccattcg tcatcatgaa cttccagact gctatgactt catggttata     900

ataacatttg ataataaggc acacagtgga aggataaaaa tcagcttaga taatgatgtt     960
```

ggaatccagg aatgcaaaga ctggcatgtg tctggatcta ttcaaaaaaa tactcattac 1020
atgatgattt ttgatgctgc tgttattttg gtctgcttat cttccataac actctgcatt 1080
cgctccgtgg ttaaaggaat tcacctacaa aaagaatatg taaacttttt ccagcatcgt 1140
tttgcaagga ctgtgtcctc agctgatcgc atggaatttg tcaatggctg gtacattatg 1200
ataatcatca gtgatgtttt gtcaattatt ggctcaatct tgaagatgga gatccaagca 1260
aagagcctca ccagttatga tgtctgcagt attctcttgg gaacatccac cttattagtg 1320
tggcttggag ttattcgcta cttgggattt tttaagaaat acaatcttct gatcctgaca 1380
cttagggcag ccttacctaa tgtgatacga ttctgctgtt gtgctgctat gatctacctg 1440
ggctactgct tctgtggctg gattgttctg gggccttacc atgtaaagtt caggtccctg 1500
aacatggttt cagagtgcct gttctccctt attaatggag acgatatgtt tacaacgttt 1560
tcaatcatgc aggagaagag ctacttggtt tggctgttta gtcgcattta tttgtattcc 1620
tttataagtc tcttcatata catggttctg agtctcttca ttgcacttat tactgacaca 1680
tacgatacaa tcaagaatta ccagatcgat ggctttccag aatcagaact tcacacattt 1740
gtatccgagt gcaaagattt gccaacctct ggtcgatata gggaacaaga cgagacctcc 1800
tgtttgtcta tgctgtgttg taatcggtaa aaaagaatcc cagaagaagc actttatcca 1860
tggcctttaa aaatctgcaa aaaaaaaaaa aaaaaa 1896

<210> SEQ ID NO 97
<211> LENGTH: 553
<212> TYPE: PRT
<213> ORGANISM: Silurana tropicalis

<400> SEQUENCE: 97

Met Glu Asn Pro Glu Leu Ile Lys Thr Cys Asn Ser Leu Asp Glu His
1 5 10 15

Asp Gly Pro Tyr Cys Cys Lys Gln Cys Pro Met Thr Asp Glu Leu Leu
20 25 30

Met Glu Asp Gln Leu Arg Arg Lys Leu Lys Phe Phe Phe Met Asn Pro
35 40 45

Cys Glu Lys Phe Arg Ala Arg Gly Arg Lys Pro Trp Lys Leu Cys Ile
50 55 60

Gln Ile Leu Lys Ile Ala Met Val Thr Ile Gln Leu Val Leu Phe Gly
65 70 75 80

Leu Ser Asn Glu Met Val Val Thr Phe Lys Glu Glu Asn Thr Val Ala
85 90 95

Phe Lys His Leu Phe Leu Lys Gly Tyr Lys Asp Gly His Asp Asp Thr
100 105 110

Tyr Ala Ile Tyr Ser Gln Glu Asp Val His Ala His Ile Asn Phe Thr
115 120 125

Ile Lys Arg Tyr Leu Glu Leu Gln Asn Ile Ser Val Gly Asn His Ala
130 135 140

Tyr Glu Ser Asn Gly Lys Gly Gln Thr Gly Met Ser Leu Cys Gln His
145 150 155 160

Tyr Tyr Lys Gln Gly Ser Ile Phe Pro Gly Asn Glu Thr Phe Glu Ile
165 170 175

Asp Pro Gln Ile Asp Thr Glu Cys Phe His Ile Asp Pro Ser Thr Leu
180 185 190

Cys Ser Asn Asp Thr Pro Ala Glu Tyr Tyr Trp Ser Asn Met Thr Leu
195 200 205

Asp Phe Tyr Arg Leu Val Ser Val Glu Ile Met Phe Lys Leu Lys Ala

-continued

```
    210                 215                 220

Ile Asn Leu Gln Thr Ile Arg His His Glu Leu Pro Asp Cys Tyr Asp
225                 230                 235                 240

Phe Met Val Ile Ile Thr Phe Asp Asn Lys Ala His Ser Gly Arg Ile
                245                 250                 255

Lys Ile Ser Leu Asp Asn Asp Val Gly Ile Gln Glu Cys Lys Asp Trp
            260                 265                 270

His Val Ser Gly Ser Ile Gln Lys Asn Thr His Tyr Met Met Ile Phe
        275                 280                 285

Asp Ala Ala Val Ile Leu Val Cys Leu Ser Ser Ile Thr Leu Cys Ile
    290                 295                 300

Arg Ser Val Val Lys Gly Ile His Leu Gln Lys Glu Tyr Val Asn Phe
305                 310                 315                 320

Phe Gln His Arg Phe Ala Arg Thr Val Ser Ser Ala Asp Arg Met Glu
                325                 330                 335

Phe Val Asn Gly Trp Tyr Ile Met Ile Ile Ile Ser Asp Val Leu Ser
            340                 345                 350

Ile Ile Gly Ser Ile Leu Lys Met Glu Ile Gln Ala Lys Ser Leu Thr
        355                 360                 365

Ser Tyr Asp Val Cys Ser Ile Leu Leu Gly Thr Ser Thr Leu Leu Val
    370                 375                 380

Trp Leu Gly Val Ile Arg Tyr Leu Gly Phe Phe Lys Lys Tyr Asn Leu
385                 390                 395                 400

Leu Ile Leu Thr Leu Arg Ala Ala Leu Pro Asn Val Ile Arg Phe Cys
                405                 410                 415

Cys Cys Ala Ala Met Ile Tyr Leu Gly Tyr Cys Phe Cys Gly Trp Ile
            420                 425                 430

Val Leu Gly Pro Tyr His Val Lys Phe Arg Ser Leu Asn Met Val Ser
        435                 440                 445

Glu Cys Leu Phe Ser Leu Ile Asn Gly Asp Asp Met Phe Thr Thr Phe
    450                 455                 460

Ser Ile Met Gln Glu Lys Ser Tyr Leu Val Trp Leu Phe Ser Arg Ile
465                 470                 475                 480

Tyr Leu Tyr Ser Phe Ile Ser Leu Phe Ile Tyr Met Val Leu Ser Leu
                485                 490                 495

Phe Ile Ala Leu Ile Thr Asp Thr Tyr Asp Thr Ile Lys Asn Tyr Gln
            500                 505                 510

Ile Asp Gly Phe Pro Glu Ser Glu Leu His Thr Phe Val Ser Glu Cys
        515                 520                 525

Lys Asp Leu Pro Thr Ser Gly Arg Tyr Arg Glu Gln Asp Glu Thr Ser
    530                 535                 540

Cys Leu Ser Met Leu Cys Cys Asn Arg
545                 550
```

<210> SEQ ID NO 98
<211> LENGTH: 6923
<212> TYPE: DNA
<213> ORGANISM: Homo sapiens

<400> SEQUENCE: 98

```
cgcgctgcct gagctgagcc gccgtaggtg aggggcccgc gtccccgccc gccctgggcg      60

ccgcgcctgg cactgatcct gccggtcgcc cactgtcgcc gccgccgccg cccgcgggca     120

ccatgacagc tctgagcgct ggggttacag actgtggttt tgtgcttgct caccaaagct     180

aacctcagca tgctcaaaag gaagcagagt tccagggtgg aagcccagcc agtcactgac     240
```

-continued

```
tttggtcctg atgagtctct gtcggataat gctgacatcc tctggattaa caaaccatgg    300
gttcactctt tgctgcgcat ctgtgccatc atcagcgtca tttctgtttg tatgaatacg    360
ccaatgacct tcgagcacta tcctccactt cagtatgtga ccttcacttt ggatacatta    420
ttgatgtttc tctacacggc agagatgata gcaaaaatgc acatccgggg cattgtcaag    480
ggggatagtt cctatgtgaa agatcgctgg tgtgtttttg atggatttat ggtctttttgc   540
ctttgggttt ctttggtgct acaggtgttt gaaattgctg atatagttga tcagatgtca    600
ccttggggca tgttgcggat tccacggcca ctgattatga tccgagcatt ccggatttat    660
ttccgatttg aactgccaag gaccagaatt acaaatattt taaagcgatc gggagaacaa    720
atatggagtg tttccatttt tctacttttc tttctacttc tttatggaat tttaggagtt    780
cagatgtttg gaacatttac ttatcactgt gttgtaaatg acacaaagcc agggaatgta    840
acctggaata gtttagctat tccagacaca cactgctcac cagagctaga agaaggctac    900
cagtgcccac ctggatttaa atgcatggac cttgaagatc tgggacttag caggcaagag    960
ctgggctaca gtggctttaa tgagatagga actagtatat tcaccgtcta tgaggccgcc   1020
tcacaggaag gctgggtgtt cctcatgtac agagcaattg acagctttcc ccgttggcgt   1080
tcctacttct atttcatcac tctcattttc ttcctcgcct ggcttgtgaa gaacgtgttt   1140
attgctgtta tcattgaaac atttgcagaa atcagagtac agtttcaaca aatgtgggga   1200
tcgagaagca gcactacctc aacagccacc acccagatgt ttcatgaaga tgctgctgga   1260
ggttggcagc tggtagctgt ggatgtcaac aagccccagg gacgcgcccc agcctgcctc   1320
cagaaaatga tgcggtcatc cgttttccac atgttcatcc tgagcatggt gaccgtggac   1380
gtgatcgtgg cggctagcaa ctactacaaa ggagaaaact tcaggaggca gtacgacgag   1440
ttctacctgg cggaggtggc ttttacagta ctttttgatt tggaagcact tctgaagata   1500
tggtgtttgg gatttactgg atatattagc tcatctctcc acaaattcga actactactc   1560
gtaattggaa ctactcttca tgtataccca gatctttatc attcacaatt cacgtacttt   1620
caggttctcc gagtagttcg gctgattaag atttcacctg cattagaaga ctttgtgtac   1680
aagatatttg gtcctggaaa aaagcttggg agtttggttg tatttactgc cagcctcttg   1740
attgttatgt cagcaattag tttgcagatg ttctgctttg tcgaagaact ggacagattt   1800
actacgtttc cgagggcatt tatgtccatg ttccagatcc tcacccagga aggatgggtg   1860
gacgtaatgg accaaactct aaatgctgtg ggacatatgt gggcacccgt ggttgccatc   1920
tatttcattc tctatcatct tttgccact ctgatcctcc tgagtttgtt tgttgctgtt   1980
attttggaca acttagaact tgatgaagac ctaaagaagc ttaaacaatt aaagcaaagt   2040
gaagcaaatg cggacaccaa agaaaagctc cctttacgcc tgcgaatctt tgaaaaattt   2100
ccaaacagac ctcaaatggt gaaaatctca aagcttcctt cagattttac agttcctaaa   2160
atcagggaga gttttatgaa gcagtttatt gaccgccagc aacaggacac atgttgcctc   2220
ctgagaagcc tcccgaccac ctcttcctcc tcctgcgacc actccaaacg ctcagcaatt   2280
gaggacaaca aatacatcga ccaaaaactt cgcaagtctg ttttcagcat cagggcaagg   2340
aaccttctgg aaaaggagac cgcagtcact aaaatcttaa gagcttgcac ccgacagcgc   2400
atgctgagcg gatcatttga ggggcagccc gcaaaggaga ggtcaatcct cagcgtgcag   2460
catcatatcc gccaagagcg caggtcacta agacatggat caaacagcca gaggatcagc   2520
aggggaaaat ctcttgaaac tttgactcaa gatcattcca atacagtgag atatagaaat   2580
gcacaaagag aagacagtga aataaagatg attcaggaaa aaaaggagca agcagagatg   2640
```

```
aaaaggaaag tgcaagaaga ggaactcaga gagaaccacc catacttcga taagccactg   2700
ttcattgtcg ggcgagaaca caggttcaga aacttttgcc gggtggtggt ccgagcacgc   2760
ttcaacgcat ctaaaacaga ccctgtcaca ggagctgtga aaaatacaaa gtaccatcaa   2820
ctttatgatt tgctgggatt ggtcacttac ctggactggg tcatgatcat cgtaaccatc   2880
tgctcttgca tttccatgat gtttgagtcc ccgtttcgaa gagtcatgca tgcacctact   2940
ttgcagattg ctgagtatgt gtttgtgata ttcatgagca ttgagcttaa tctgaagatt   3000
atggcagatg gcttattttt cactccaact gctgtcatca gggacttcgg tggagtaatg   3060
gacatattta tatatcttgt gagcttgata tttctttgtt ggatgcctca aaatgtacct   3120
gctgaatcgg gagctcagct tctaatggtc cttcggtgcc tgagacctct gcgcatattc   3180
aaactggtgc cccagatgag gaaagttgtt cgagaacttt tcagcggctt caaggaaatt   3240
tttttggtct ccattctttt gctgacatta atgctcgttt ttgcaagctt tggagttcag   3300
ctttttgctg gaaaactggc caagtgcaat gatcccaaca ttattagaag ggaagattgc   3360
aatggcatat tcagaattaa tgtcagtgtg tcaaagaact taaatttaaa attgaggcct   3420
ggagagaaaa aacctggatt ttgggtgccc cgtgtttggg cgaatcctcg gaactttaat   3480
ttcgacaatg tgggaaacgc tatgctggcg ttgtttgaag ttctctcctt gaaaggctgg   3540
gtggaagtga gagatgttat tattcatcgt gtggggccga tccatggaat ctatattcat   3600
gtttttgtat tcctgggttg catgattgga ctgacccttt ttgttggagt agttattgct   3660
aatttcaatg aaaacaaggg gacggctttg ctgaccgtcg atcagagaag atgggaagac   3720
ctgaagagcc gactgaagat cgcacagcct cttcatcttc cgcctcgccc ggataatgat   3780
ggttttagag ctaaaatgta tgacataacc cagcatccat tttttaagag gacaatcgca   3840
ttactcgtcc tggcccagtc ggtgttgctc tctgtcaagt gggacgtcga ggacccggtg   3900
accgtacctt tggcaacaat gtcagttgtt ttcaccttca tctttgttct ggaggttacc   3960
atgaagatca tagcaatgtc gcctgctggc ttctggcaaa gcagaagaaa ccgatacgat   4020
ctcctggtga cgtcgcttgg cgttgtatgg gtggtgcttc actttgccct cctgaatgca   4080
tatacttaca tgatgggcgc ttgtgtgatt gtatttaggt ttttctccat ctgtggaaaa   4140
catgtaacgc taaagatgct cctcttgaca gtggtcgtca gcatgtacaa gagcttcttt   4200
atcatagtag gcatgtttct cttgctgctg tgttacgctt ttgctggagt tgttttattt   4260
ggtactgtga aatatgggga gaatattaac aggcatgcaa atttttcttc ggctggaaaa   4320
gctattaccg tactgttccg aattgtcaca ggtgaagact ggaacaagat tatgcatgac   4380
tgtatggttc agcctccgtt ttgtactcca gatgaattta catactgggc aacagactgt   4440
ggaaattatg ctggggcact tatgtatttc tgttcatttt atgtcatcat tgcctacatc   4500
atgctaaatc tgcttgtagc cataattgtg gagaatttct ccttgtttta ttccactgag   4560
gaggaccagc ttttaagtta caatgatctt cgccactttc aaataatatg gaacatggtg   4620
gatgataaaa gagagggggt gatccccacg ttccgcgtca agttcctgct gcggctactg   4680
cgtgggaggc tggaggtgga cctggacaag gacaagctcc tgtttaagca catgtgctac   4740
gaaatggaga ggctccacaa tggcggcgac gtcaccttcc atgatgtcct gagcatgctt   4800
tcataccggt ccgtggacat ccggaagagc ttgcagctgg aggaactcct ggcgagggag   4860
cagctggagt acaccataga ggaggaggtg gccaagcaga ccatccgcat gtggctcaag   4920
aagtgcctga agcgcatcag agctaaacag cagcagtcgt gcagtatcat ccacagcctg   4980
agagagagtc agcagcaaga gctgagccgg tttctgaacc cgcccagcat cgagaccacc   5040
```

-continued cagcccagtg aggacacgaa tgccaacagt caggacaaca gcatgcaacc tgagacaagc 5100
agccagcagc agctcctgag ccccacgctg tcggatcgag gaggaagtcg gcaagatgca 5160
gccgacgcag ggaaacccca gaggaaattt gggcagtggc gtctgccctc agccccaaaa 5220
ccaataagcc attcagtgtc ctcagtcaac ttacggtttg gaggaaggac aaccatgaaa 5280
tctgtcgtgt gcaaaatgaa ccccatgact gacgcggctt cctgcggttc tgaagttaag 5340
aagtggtgga cccggcagct gactgtggag agcgacgaaa gtggggatga ccttctggat 5400
atttaggtgg atgtcaatgt agatgaattt ctagtggtgg aaaccgtttt ctaataatgt 5460
ccttgattgt ccagtgagca atctgtaatt gatctataac tgaattccag cttgtcacaa 5520
gatgtttata aattgatttt catcctgcca cagaaaggca taagctgcat gtatgatggg 5580
ttactatcaa tcattgctca aaaaaatttt tgtataatga cagtactgat aatattagaa 5640
atgataccgc aagcaaatgt atatcactta aaaatgtcat atattctgtc tgcgtaaact 5700
aaggtatata ttcatatgtg ctctaatgca gtattatcac cgccccgcaa aagagtgcta 5760
agcccaaagt ggctgatatt tagggtacag gggttatagc tttagttcac atctttccca 5820
tttccactag aaatatttct cttgagagaa tttattattt atgattgatc tgaaaaggtc 5880
agcactgaac ttatgctaaa atgatagtag ttttacaaac tacagattct gaattttaaa 5940
aagtatcttc tttttctcgt gttatatttt taaatataca caagacattt ggtgaccaga 6000
acaagttgat ttctgtcctc agttatgtta atgaaactgt tgcctccttc taagaaaatt 6060
gtgtgtgcaa gcaccaggca aagaaatgga ctcaggatgc ttagcggttt aaaacaaacc 6120
tgtagataaa tcacttgagt gacatagttg cgcaaagatg ttaagtttct taagaaacct 6180
tttaataact gagtttagca aaaagaataa aactatatag ctcaatttat ttaaaaaaat 6240
ctttgcatgt gtgatgttat cattggcttc atttcttacc caaggtatgt ctgttttgcc 6300
ataaatcagc agagtcattt cattctgggt gatcctaaca caccattgct acgttagatt 6360
tgaaatgaca tctctgttaa aagaatcttc tatggaaata atggtgccct gcaaaatctt 6420
cctttgaact cacaggttag ggatcacaca acttacttaa tcgtttttttg tttttgtttt 6480 ttttccttat atgtcaatgg cccatgtcct ccgggaaaat tagaaaagca aaatgattac 6540
aaagtgctgt tagatttctt gtgctgggcc agccaagtag aagtggactt gacttggacc 6600
tttaactatt ttattacaga ttggacattt gctgttcaga tgttttttaa cagagggatt 6660
atctcagaat cctgtgacct ccaggttgtt ttataatcta tttttctcta tttaacattc 6720
ctcagataga taggcaaata ggacattcct tctgtgtcac agaagtatcg tggtagtggc 6780
agtctacagt ttatatgatt cattgtaact atgagataaa gaacaaccag tcatgtggcc 6840
aaaaggatta gatttgattt gatgttcact tggagtttac tttttgtaca tacaagataa 6900
aataaatatt ggatttgtaa aat 6923

<210> SEQ ID NO 99
<211> LENGTH: 1738
<212> TYPE: PRT
<213> ORGANISM: Homo sapiens

<400> SEQUENCE: 99

Met Leu Lys Arg Lys Gln Ser Ser Arg Val Glu Ala Gln Pro Val Thr
1               5                   10                  15

Asp Phe Gly Pro Asp Glu Ser Leu Ser Asp Asn Ala Asp Ile Leu Trp
            20                  25                  30

Ile Asn Lys Pro Trp Val His Ser Leu Leu Arg Ile Cys Ala Ile Ile

-continued

```
        35                  40                  45

Ser Val Ile Ser Val Cys Met Asn Thr Pro Met Thr Phe Glu His Tyr
    50                  55                  60

Pro Pro Leu Gln Tyr Val Thr Phe Thr Leu Asp Thr Leu Leu Met Phe
65                  70                  75                  80

Leu Tyr Thr Ala Glu Met Ile Ala Lys Met His Ile Arg Gly Ile Val
                85                  90                  95

Lys Gly Asp Ser Ser Tyr Val Lys Asp Arg Trp Cys Val Phe Asp Gly
            100                 105                 110

Phe Met Val Phe Cys Leu Trp Val Ser Leu Val Leu Gln Val Phe Glu
        115                 120                 125

Ile Ala Asp Ile Val Asp Gln Met Ser Pro Trp Gly Met Leu Arg Ile
    130                 135                 140

Pro Arg Pro Leu Ile Met Ile Arg Ala Phe Arg Ile Tyr Phe Arg Phe
145                 150                 155                 160

Glu Leu Pro Arg Thr Arg Ile Thr Asn Ile Leu Lys Arg Ser Gly Glu
                165                 170                 175

Gln Ile Trp Ser Val Ser Ile Phe Leu Leu Phe Phe Leu Leu Leu Tyr
            180                 185                 190

Gly Ile Leu Gly Val Gln Met Phe Gly Thr Phe Thr Tyr His Cys Val
        195                 200                 205

Val Asn Asp Thr Lys Pro Gly Asn Val Thr Trp Asn Ser Leu Ala Ile
    210                 215                 220

Pro Asp Thr His Cys Ser Pro Glu Leu Glu Glu Gly Tyr Gln Cys Pro
225                 230                 235                 240

Pro Gly Phe Lys Cys Met Asp Leu Glu Asp Leu Gly Leu Ser Arg Gln
                245                 250                 255

Glu Leu Gly Tyr Ser Gly Phe Asn Glu Ile Gly Thr Ser Ile Phe Thr
            260                 265                 270

Val Tyr Glu Ala Ala Ser Gln Glu Gly Trp Val Phe Leu Met Tyr Arg
        275                 280                 285

Ala Ile Asp Ser Phe Pro Arg Trp Arg Ser Tyr Phe Tyr Phe Ile Thr
    290                 295                 300

Leu Ile Phe Phe Leu Ala Trp Leu Val Lys Asn Val Phe Ile Ala Val
305                 310                 315                 320

Ile Ile Glu Thr Phe Ala Glu Ile Arg Val Gln Phe Gln Gln Met Trp
                325                 330                 335

Gly Ser Arg Ser Ser Thr Thr Ser Thr Ala Thr Thr Gln Met Phe His
            340                 345                 350

Glu Asp Ala Ala Gly Gly Trp Gln Leu Val Ala Val Asp Val Asn Lys
        355                 360                 365

Pro Gln Gly Arg Ala Pro Ala Cys Leu Gln Lys Met Met Arg Ser Ser
    370                 375                 380

Val Phe His Met Phe Ile Leu Ser Met Val Thr Val Asp Val Ile Val
385                 390                 395                 400

Ala Ala Ser Asn Tyr Tyr Lys Gly Glu Asn Phe Arg Arg Gln Tyr Asp
                405                 410                 415

Glu Phe Tyr Leu Ala Glu Val Ala Phe Thr Val Leu Phe Asp Leu Glu
            420                 425                 430

Ala Leu Leu Lys Ile Trp Cys Leu Gly Phe Thr Gly Tyr Ile Ser Ser
        435                 440                 445

Ser Leu His Lys Phe Glu Leu Leu Leu Val Ile Gly Thr Thr Leu His
    450                 455                 460
```

-continued

```
Val Tyr Pro Asp Leu Tyr His Ser Gln Phe Thr Tyr Phe Gln Val Leu
465                 470                 475                 480

Arg Val Val Arg Leu Ile Lys Ile Ser Pro Ala Leu Glu Asp Phe Val
                485                 490                 495

Tyr Lys Ile Phe Gly Pro Gly Lys Lys Leu Gly Ser Leu Val Val Phe
            500                 505                 510

Thr Ala Ser Leu Leu Ile Val Met Ser Ala Ile Ser Leu Gln Met Phe
        515                 520                 525

Cys Phe Val Glu Glu Leu Asp Arg Phe Thr Thr Phe Pro Arg Ala Phe
    530                 535                 540

Met Ser Met Phe Gln Ile Leu Thr Gln Glu Gly Trp Val Asp Val Met
545                 550                 555                 560

Asp Gln Thr Leu Asn Ala Val Gly His Met Trp Ala Pro Val Val Ala
                565                 570                 575

Ile Tyr Phe Ile Leu Tyr His Leu Phe Ala Thr Leu Ile Leu Leu Ser
            580                 585                 590

Leu Phe Val Ala Val Ile Leu Asp Asn Leu Glu Leu Asp Glu Asp Leu
        595                 600                 605

Lys Lys Leu Lys Gln Leu Lys Gln Ser Glu Ala Asn Ala Asp Thr Lys
    610                 615                 620

Glu Lys Leu Pro Leu Arg Leu Arg Ile Phe Glu Lys Phe Pro Asn Arg
625                 630                 635                 640

Pro Gln Met Val Lys Ile Ser Lys Leu Pro Ser Asp Phe Thr Val Pro
                645                 650                 655

Lys Ile Arg Glu Ser Phe Met Lys Gln Phe Ile Asp Arg Gln Gln Gln
            660                 665                 670

Asp Thr Cys Cys Leu Leu Arg Ser Leu Pro Thr Thr Ser Ser Ser Ser
        675                 680                 685

Cys Asp His Ser Lys Arg Ser Ala Ile Glu Asp Asn Lys Tyr Ile Asp
    690                 695                 700

Gln Lys Leu Arg Lys Ser Val Phe Ser Ile Arg Ala Arg Asn Leu Leu
705                 710                 715                 720

Glu Lys Glu Thr Ala Val Thr Lys Ile Leu Arg Ala Cys Thr Arg Gln
                725                 730                 735

Arg Met Leu Ser Gly Ser Phe Glu Gly Gln Pro Ala Lys Glu Arg Ser
            740                 745                 750

Ile Leu Ser Val Gln His His Ile Arg Gln Glu Arg Arg Ser Leu Arg
        755                 760                 765

His Gly Ser Asn Ser Gln Arg Ile Ser Arg Gly Lys Ser Leu Glu Thr
    770                 775                 780

Leu Thr Gln Asp His Ser Asn Thr Val Arg Tyr Arg Asn Ala Gln Arg
785                 790                 795                 800

Glu Asp Ser Glu Ile Lys Met Ile Gln Glu Lys Lys Glu Gln Ala Glu
                805                 810                 815

Met Lys Arg Lys Val Gln Glu Glu Glu Leu Arg Glu Asn His Pro Tyr
            820                 825                 830

Phe Asp Lys Pro Leu Phe Ile Val Gly Arg Glu His Arg Phe Arg Asn
        835                 840                 845

Phe Cys Arg Val Val Val Arg Ala Arg Phe Asn Ala Ser Lys Thr Asp
    850                 855                 860

Pro Val Thr Gly Ala Val Lys Asn Thr Lys Tyr His Gln Leu Tyr Asp
865                 870                 875                 880

Leu Leu Gly Leu Val Thr Tyr Leu Asp Trp Val Met Ile Ile Val Thr
                885                 890                 895
```

-continued

```
Ile Cys Ser Cys Ile Ser Met Met Phe Glu Ser Pro Phe Arg Arg Val
            900                 905                 910

Met His Ala Pro Thr Leu Gln Ile Ala Glu Tyr Val Phe Val Ile Phe
        915                 920                 925

Met Ser Ile Glu Leu Asn Leu Lys Ile Met Ala Asp Gly Leu Phe Phe
    930                 935                 940

Thr Pro Thr Ala Val Ile Arg Asp Phe Gly Gly Val Met Asp Ile Phe
945                 950                 955                 960

Ile Tyr Leu Val Ser Leu Ile Phe Leu Cys Trp Met Pro Gln Asn Val
                965                 970                 975

Pro Ala Glu Ser Gly Ala Gln Leu Leu Met Val Leu Arg Cys Leu Arg
            980                 985                 990

Pro Leu Arg Ile Phe Lys Leu Val  Pro Gln Met Arg Lys  Val Val Arg
        995                 1000                1005

Glu Leu  Phe Ser Gly Phe Lys  Glu Ile Phe Leu Val  Ser Ile Leu
    1010                 1015                1020

Leu Leu  Thr Leu Met Leu Val  Phe Ala Ser Phe Gly  Val Gln Leu
    1025                 1030                1035

Phe Ala  Gly Lys Leu Ala Lys  Cys Asn Asp Pro Asn  Ile Ile Arg
    1040                 1045                1050

Arg Glu  Asp Cys Asn Gly Ile  Phe Arg Ile Asn Val  Ser Val Ser
    1055                 1060                1065

Lys Asn  Leu Asn Leu Lys Leu  Arg Pro Gly Glu Lys  Lys Pro Gly
    1070                 1075                1080

Phe Trp  Val Pro Arg Val Trp  Ala Asn Pro Arg Asn  Phe Asn Phe
    1085                 1090                1095

Asp Asn  Val Gly Asn Ala Met  Leu Ala Leu Phe Glu  Val Leu Ser
    1100                 1105                1110

Leu Lys  Gly Trp Val Glu Val  Arg Asp Val Ile Ile  His Arg Val
    1115                 1120                1125

Gly Pro  Ile His Gly Ile Tyr  Ile His Val Phe Val  Phe Leu Gly
    1130                 1135                1140

Cys Met  Ile Gly Leu Thr Leu  Phe Val Gly Val Val  Ile Ala Asn
    1145                 1150                1155

Phe Asn  Glu Asn Lys Gly Thr  Ala Leu Leu Thr Val  Asp Gln Arg
    1160                 1165                1170

Arg Trp  Glu Asp Leu Lys Ser  Arg Leu Lys Ile Ala  Gln Pro Leu
    1175                 1180                1185

His Leu  Pro Pro Arg Pro Asp  Asn Asp Gly Phe Arg  Ala Lys Met
    1190                 1195                1200

Tyr Asp  Ile Thr Gln His Pro  Phe Phe Lys Arg Thr  Ile Ala Leu
    1205                 1210                1215

Leu Val  Leu Ala Gln Ser Val  Leu Leu Ser Val Lys  Trp Asp Val
    1220                 1225                1230

Glu Asp  Pro Val Thr Val Pro  Leu Ala Thr Met Ser  Val Val Phe
    1235                 1240                1245

Thr Phe  Ile Phe Val Leu Glu  Val Thr Met Lys Ile  Ile Ala Met
    1250                 1255                1260

Ser Pro  Ala Gly Phe Trp Gln  Ser Arg Arg Asn Arg  Tyr Asp Leu
    1265                 1270                1275

Leu Val  Thr Ser Leu Gly Val  Val Trp Val Val Leu  His Phe Ala
    1280                 1285                1290

Leu Leu  Asn Ala Tyr Thr Tyr  Met Met Gly Ala Cys  Val Ile Val
```

-continued

```
    1295                1300                1305

Phe Arg Phe Phe Ser Ile Cys Gly Lys His Val Thr Leu Lys Met
    1310                1315                1320

Leu Leu Leu Thr Val Val Val Ser Met Tyr Lys Ser Phe Phe Ile
    1325                1330                1335

Ile Val Gly Met Phe Leu Leu Leu Leu Cys Tyr Ala Phe Ala Gly
    1340                1345                1350

Val Val Leu Phe Gly Thr Val Lys Tyr Gly Glu Asn Ile Asn Arg
    1355                1360                1365

His Ala Asn Phe Ser Ser Ala Gly Lys Ala Ile Thr Val Leu Phe
    1370                1375                1380

Arg Ile Val Thr Gly Glu Asp Trp Asn Lys Ile Met His Asp Cys
    1385                1390                1395

Met Val Gln Pro Pro Phe Cys Thr Pro Asp Glu Phe Thr Tyr Trp
    1400                1405                1410

Ala Thr Asp Cys Gly Asn Tyr Ala Gly Ala Leu Met Tyr Phe Cys
    1415                1420                1425

Ser Phe Tyr Val Ile Ile Ala Tyr Ile Met Leu Asn Leu Leu Val
    1430                1435                1440

Ala Ile Ile Val Glu Asn Phe Ser Leu Phe Tyr Ser Thr Glu Glu
    1445                1450                1455

Asp Gln Leu Leu Ser Tyr Asn Asp Leu Arg His Phe Gln Ile Ile
    1460                1465                1470

Trp Asn Met Val Asp Asp Lys Arg Glu Gly Val Ile Pro Thr Phe
    1475                1480                1485

Arg Val Lys Phe Leu Leu Arg Leu Leu Arg Gly Arg Leu Glu Val
    1490                1495                1500

Asp Leu Asp Lys Asp Lys Leu Leu Phe Lys His Met Cys Tyr Glu
    1505                1510                1515

Met Glu Arg Leu His Asn Gly Gly Asp Val Thr Phe His Asp Val
    1520                1525                1530

Leu Ser Met Leu Ser Tyr Arg Ser Val Asp Ile Arg Lys Ser Leu
    1535                1540                1545

Gln Leu Glu Glu Leu Leu Ala Arg Glu Gln Leu Glu Tyr Thr Ile
    1550                1555                1560

Glu Glu Glu Val Ala Lys Gln Thr Ile Arg Met Trp Leu Lys Lys
    1565                1570                1575

Cys Leu Lys Arg Ile Arg Ala Lys Gln Gln Gln Ser Cys Ser Ile
    1580                1585                1590

Ile His Ser Leu Arg Glu Ser Gln Gln Gln Glu Leu Ser Arg Phe
    1595                1600                1605

Leu Asn Pro Pro Ser Ile Glu Thr Thr Gln Pro Ser Glu Asp Thr
    1610                1615                1620

Asn Ala Asn Ser Gln Asp Asn Ser Met Gln Pro Glu Thr Ser Ser
    1625                1630                1635

Gln Gln Gln Leu Leu Ser Pro Thr Leu Ser Asp Arg Gly Gly Ser
    1640                1645                1650

Arg Gln Asp Ala Ala Asp Ala Gly Lys Pro Gln Arg Lys Phe Gly
    1655                1660                1665

Gln Trp Arg Leu Pro Ser Ala Pro Lys Pro Ile Ser His Ser Val
    1670                1675                1680

Ser Ser Val Asn Leu Arg Phe Gly Gly Arg Thr Thr Met Lys Ser
    1685                1690                1695
```

-continued

```
Val Val  Cys Lys Met Asn Pro  Met Thr Asp Ala Ala  Ser Cys Gly
    1700                1705                1710

Ser Glu  Val Lys Lys Trp Trp  Thr Arg Gln Leu Thr  Val Glu Ser
    1715                1720                1725

Asp Glu  Ser Gly Asp Asp Leu  Leu Asp Ile
    1730                1735
```

```
<210> SEQ ID NO 100
<211> LENGTH: 1566
<212> TYPE: DNA
<213> ORGANISM: Homo sapiens

<400> SEQUENCE: 100

agccgcgagc ggcggccgcg gggccgagga gcctgggccg ggccgggcgg ggactactcc     60

ggagtcagga ggcagcagcg gcggaggacg aggatctctg gcagtcagcg ccgctcggac    120

gccgccggca ccatgggctg ctgcaccgga cgctgctcgc tcatctgcct ctgcgcgctg    180

cagttggtct cagcattaga gaggcagatc tttgacttcc ttggtttcca gtgggcgcct    240

attcttggaa attttctaca cataatagtt gtcatattgg gtttgtttgg gaccattcag    300

tacagacctc gatacataat ggtgtataca gtgtggactg ccctctgggt cacctggaat    360

gtgttcatta tctgctttta tttggaagta ggtggactct caaaggacac cgatctaatg    420

acattcaata tctctgtaca tcggtcatgg tggagagaac atgggcctgg ttgtgtcaga    480

agagtgctgc ctccctcagc ccatggcatg atggacgatt acacgtacgt ctctgtcaca    540

ggctgcatcg ttgacttcca gtacctggag gtcatccaca gtgctgtcca aatactactc    600

tctttggtgg gttttgtgta tgcctgttat gtgatcagta tttccatgga agaagaagac    660

acatattcat gtgatctgca agtatgcaaa catcttttta tccagatgct gcaaattatt    720

gaataagcaa gaattagtaa gatattatca ccaaattgtc acatcagtca agcctcatgt    780

gcttcctaag aactgaggtg atgcattatt ttagagtgtc attctaaacc ccagattcaa    840

catcttccta atctttctag tgcagtctaa tatataaatt ttatgaaaag cataggtttt    900

tttttaacca gcagtgctct ttgagaattt acattgattc ctaaagattg ccattgcttt    960

gtataaaatg ttataaatta tcttagcatc ttacctggaa tttccactaa attcaccaat   1020

ttatgatttg tgaaatctga ttttactttt tgaaaatttt catgtgaatt tcccattttc   1080

agtgttgtag cacctctctc ttcctctaag atcctccaag ctcatcaaaa gccatgatct   1140

tattatacca gcagttttat ttattcaatc tttcaacaag tagttattga acttctataa   1200

tgtgccaggc tctggagctc gccttacacc aaacagacac aatcgatcca ttcgaagtgt   1260

cgtaattaca cattgaggga ccaactagac cttttctcat tgtaaacttg gagcaaaagt   1320

aaattcatta aaataaattt acattatagt gccacaaaaa aatgaacaga accagaaagc   1380

attttttaca aaaattaaca gaacagtgtg atagagggga aaaggatgtg agatcatggt   1440

gccctacctt caatagggtg gccagaaaac acctctctga agaagcagca tttgagctga   1500

gacctgaaga acgaggagtc agtgatgcag agaacctcag gagatgcctt ccaatctgag   1560

aaaaga                                                              1566
```

```
<210> SEQ ID NO 101
<211> LENGTH: 197
<212> TYPE: PRT
<213> ORGANISM: Homo sapiens

<400> SEQUENCE: 101

Met Gly Cys Cys Thr Gly Arg Cys Ser Leu Ile Cys Leu Cys Ala Leu
```

-continued

```
1               5                   10                  15

Gln Leu Val Ser Ala Leu Glu Arg Gln Ile Phe Asp Phe Leu Gly Phe
            20                  25                  30

Gln Trp Ala Pro Ile Leu Gly Asn Phe Leu His Ile Ile Val Val Ile
        35                  40                  45

Leu Gly Leu Phe Gly Thr Ile Gln Tyr Arg Pro Arg Tyr Ile Met Val
    50                  55                  60

Tyr Thr Val Trp Thr Ala Leu Trp Val Thr Trp Asn Val Phe Ile Ile
65                  70                  75                  80

Cys Phe Tyr Leu Glu Val Gly Gly Leu Ser Lys Asp Thr Asp Leu Met
                85                  90                  95

Thr Phe Asn Ile Ser Val His Arg Ser Trp Trp Arg Glu His Gly Pro
            100                 105                 110

Gly Cys Val Arg Arg Val Leu Pro Pro Ser Ala His Gly Met Met Asp
        115                 120                 125

Asp Tyr Thr Tyr Val Ser Val Thr Gly Cys Ile Val Asp Phe Gln Tyr
    130                 135                 140

Leu Glu Val Ile His Ser Ala Val Gln Ile Leu Leu Ser Leu Val Gly
145                 150                 155                 160

Phe Val Tyr Ala Cys Tyr Val Ile Ser Ile Ser Met Glu Glu Glu Asp
                165                 170                 175

Thr Tyr Ser Cys Asp Leu Gln Val Cys Lys His Leu Phe Ile Gln Met
            180                 185                 190

Leu Gln Ile Ile Glu
        195


<210> SEQ ID NO 102
<211> LENGTH: 2958
<212> TYPE: DNA
<213> ORGANISM: Homo sapiens

<400> SEQUENCE: 102

tggagtcgct cgctgactcg ccctgcgccc tcgccgcgga caccggagct gcggccgctc     60

cccgctgtcc cccagcttac tccaatcaag cctctgcccg ccaggaacag gtaacctgtg    120

tgtgtccgtt tgctccttct aagagcatgc ctgatagata cttcggtagc ctctccggat    180

ggccccttcg tcgggtagcc tctcctgatg gggtccttcg cccaccctgc ctcccgcgcc    240

ggcgctccgg gtgaatgtca agggtggctg gctgcgaata cctccttcag ctgctggggt    300

tcccgacagt ttgcagtttt taaaagtgca ccctcggaag ggcttttcag actgggtaaa    360

cctgactttt ccaagagatg gcagatcctg aggtagttgt gagtagctgc agctctcatg    420

aagaggaaaa tcgctgcaat tttaaccagc aaacatctcc atctgaggag cttctattag    480

aagaccagat gaggcgaaaa ctcaaatttt ttttcatgaa tccctgtgag aagttctggg    540

ctcgaggtag aaaaccatgg aaacttgcca tacaaattct aaaaattgca atggtgacta    600

tccagctggt cttatttggg ctaagtaacc agatggtggt agctttcaag gaagagaata    660

ctatagcatt caaacacctt ttcctaaaag gatatatgga ccgaatggat gacacatatg    720

cagtgtacac acaaagtgac gtgtatgatc agttaatctt cgcagtaaac cagtacttgc    780

agctatacaa tgtctccgtt gggaatcatg cttatgagaa caaaggtacc aagcaatctg    840

ctatggcaat ctgtcagcac ttatacaagc gaggaaacat ctaccctgga aatgatacct    900

ttgacatcga tccagaaatt gaaactgagt gtttctttgt ggagccagat gaaccttttc    960

acattgggac accagcagaa aataaactga acttaacact ggacttccac agactcctaa   1020
```

-continued

```
cagtggagct tcagtttaaa ctgaaagcca ttaatctgca gacagttcgt catcaagaac   1080

tccctgactg ttatgacttt actctgacta taacatttga caacaaggcc catagtggaa   1140

gaattaaaat aagtttagat aatgacattt ccatcagaga atgtaaagac tggcatgtat   1200

ctggatcaat tcagaagaac actcattaca tgatgatctt tgatgccttt gtcattctga   1260

cttgcttggt ttcattaatc ctctgcatta gatctgtgat tagaggactt cagcttcagc   1320

aggtagggaa cgttgctttc taggaatgct actgacattt tgattgacag agacattcac   1380

tgtgcctccc ctcttttccc taaaggagtt tgtcaatttt ttcctcctcc attataagaa   1440

ggaagtttct gtttctgatc aaatggaatt tgtcaatgga tggtacatta tgattattat   1500

tagtgacata ttgacaatca ttggatcaat tctaaaaatg gaaatccaag ctaaggtaat   1560

tttttcccta atcatgctat tgttagtgtc agatttgcac taatggtaat gtatttttcc   1620

agaatgtaag aattttcaga atgaattgtt tcttccaaac tgtatatcaa gtagacttga   1680

aattggtaat ggtaattttc ttaaatctag tcaggaggtc tcttaggcag agtttttcaa   1740

agtgtgatcc acaaaccatt gcatcagaat cattgggtgc ctggtaaagt gtaccatgtt   1800

agacctactg aattcagact cttcggcggg gcctgtgaat tcttacacac accaaaattc   1860

atacacaacc aaggtaacta aggtaagagt tttttttttt ttttaatctt acaagaaatg   1920

ctcgaatctt taacaaaaat gagtggggct ataggggaaa gtgaggtcaa ggcactatgg   1980

tgtgcatgct tgcatttgtt tcctccgtcc attcaaagtg agaatgctcc catttttctta   2040

ctttaccatt gatgtgctac aagcttattt attttaagac taacctagcc taaaaatcaa   2100

ctgtccccac aaaataaaaa tcacattaaa aaaactaata gtgttcagac taatcttgct   2160

caaacttatg tttccctagt cttgatgcaa ctgattgagt cacctgggga gttggttata   2220

aacctgggca gagaccccaa atgcaatggc tcagagaaga taggagctta tttctgtctt   2280

atgcaatagt cagaatgggt tttacagact ggtgagtagc tcaacatctc acagtcattc   2340

aggcacccat gttcctccca ttttgtttct ctgccacccc ttaaggactt gccctgactg   2400

catgattatt gccgtgttgc ctcaaacagg ttgcagctta tgggaagcaa aaacacggta   2460

tggtagaagc tctcccatag actgatggct tggctcaaga gtggccgact ttatttctgt   2520

acatatccca ctggatagaa tttagtcaat cctaactgca gagggagcca gggaacacag   2580

cccaggcatg tgcctaggaa ggggagaatg ggtttaggtt gacacttagc agctgccact   2640

atatgtggct atagtatgta tcattggaat agatgtttaa ctttagggac aaataaaaaa   2700

ccaaaacaaa aaaaggagta aggggagaga tttgcagcaa atctttattt ttaccaacct   2760

caactatcat taatttcagt gaaccctaaa tggtatccaa caaaatatct ttctagacca   2820

ttcaccgtct ctgcctcata gatgatcata tcatgttttc ttctcttctg aaacctctaa   2880

tacccttgtc ctatcctcat tctaagctga tgaccttact tcctatttca caaaaataat   2940

agaaaaaaaa aaaaaaaa                                                2958
```

<210> SEQ ID NO 103
<211> LENGTH: 2727
<212> TYPE: DNA
<213> ORGANISM: Homo sapiens

<400> SEQUENCE: 103

```
atagcctttc aaatttcggt taatggtaac tctcatcagt tactcaagcc aaaaatcttg     60

gattcatcac agactcctct ctttcactaa tctcttcttc cccacatcta atccaagagg    120

aaatcctatt gttctacctt cattggccag gcactgtgac tcatataatc ccagcacatt    180
```

-continued

```
gggaggctga ggcgggagga tggcttgagc ccaggagttc cagaccagcc tgggaaacat    240
agtgaggccc catctctaca aaaaattaaa aaaattagca gtcaaggtgg catgtgtctg    300
taatccaagc tacttggggg gctgaggtgg gaggatttct tgagcccggg aagtcgaggc    360
tgcattgagc cacggttgtg ccacggcact ccagcctggg tgacagagtg agacccctgt    420
ttccaaaaaa aaaaaaaaaa aaaaagaata aaaatcacct ggtcaactcc actattacca    480
gcctggtcca agctactatc tctcatttat attattgcaa tagcctcctc actcctccaa    540
caacctgctg tcaaccacag cagccaacat ctgatcatat cacttctgtt tgtggttctc    600
aaatctcccc aattgagtta cagtaaaaga caaacttggt gagtgccacc ttatctctat    660
aactgtatac cctttctatt gctcactcca gccagatgca atatccttgc caagcaccct    720
cctgtctcag ggcctttgca cttgccagtc cctgtgcctg gaaggcttct cccctagatt    780
tttgcatgac ttctccctcc ctcccttcag atctttgctc aaatgccttc tttttagtgt    840
atgtaaaatg acaaacccat acccattcct tatcccctcc tctgaatttt ctcttcagca    900
attatcagca gcaagtgtcc caaagtttct attaacttat ttctgttgtc tctttcttcc    960
ctccactaga atgtaagctt tatgagagca gagacttttg tttgttcact gctttatcct   1020
tagcacctaa aacagtgcct tactcatagt tacctcaata tttattgcca aatgaatttc   1080
tgctttataa tctgattata tttttccact ctctcttaga gtctaactag ttatgatgtc   1140
tgtagcatac ttcttgggac ttctaccatg cttgtgtggc ttggagtcat ccgatacctc   1200
ggtttctttg caaagtacaa cctcctcatt ttgacccttc aggcagcgct gcccaatgtc   1260
atcaggttct gctgctgtgc agctatgatt tacttaggtt actgcttctg tggatggatc   1320
gtgctggggc cttaccatga caagtttcgt tctctgaaca tggtctctga gtgccttttc   1380
tctctgataa atggagatga tatgtttgcc acgtttgcaa aaatgcagca aaaaagttac   1440
ttagtctggc tgtttagtag aatttacctc tactcattca tcagcctctt tatatatatg   1500
attttaagtc ttttcattgc actgatcact gatacatacg aaacaattaa gcaataccaa   1560
caagatggct tcccagagac tgaacttcgt acatttatat cagaatgcaa agatctaccc   1620
aactctggaa aatacagatt agaagatgac cctccagtaa ctttattctg ctgttgtaaa   1680
aagtagctat caggtttatc tgtactttag aggaaaatat aatgtgtagc tgagttggaa   1740
cactgtggat attctgagat cagatgtagt atgtttgaag actgttattt tgagctaatt   1800
gagacctata attcaccaat aactgtttat atttttaaaa gcaatattta atgtctttgc   1860
aactttatgc tgggattgtt tttaaaaaaa actttaatga ggaaagctat tggattatta   1920
ttatttcttg tttattttgc catggcttta gaatgtattc tgtatgcctc tcttttgctc   1980
tgatactgtt gctcctgcta ttctgattgt gcagactgta taattagtgg aaaacaatcc   2040
ttggtctgac tgtgactttg gacaactcag taaccctggc ttggaccact ctcaggagtc   2100
catccttgag agagtgggtg tagttaccat ttatacagta atcattgcat tttaaaatct   2160
tctcttgaaa ggaagaataa gagtgcacca gaataagagc gcaccagaat aagagcacac   2220
cagctaacaa tgtgatacgg ccatatgtca cttaaggatg gagatatgtt ctgagaaatg   2280
tgtcattagg cgattttgtc attaaacatc atagcatgta cttccacaaa cctagatggt   2340
atagcctact acacacctag gctatttggt atagcctgtt ggtcctgggg tacaaatctg   2400
tacaacatgt tactgtattg aatacagtag gcaattgtaa ctcaatggta agtatctaaa   2460
catagaaaag ggacagtaaa aatatggttt tataatcttc tgggaccacc attgtatatg   2520
cggtacatca ttgaccaaaa catcgttatc cagcatatga ctgtatttgg ttatgaaagc   2580
```

-continued

```
caactgttac ttgattctgc ttttagttct taagaggatc aggcttttaa atactcattt   2640

acaagctttc tatcctcctt cagtgttaaa gtagaaagta aaaagagtat cttatacatg   2700

catgaaatta aagcatatac caaatgc                                        2727


<210> SEQ ID NO 104
<211> LENGTH: 172
<212> TYPE: PRT
<213> ORGANISM: Homo sapiens

<400> SEQUENCE: 104

Met Leu Val Trp Leu Gly Val Ile Arg Tyr Leu Gly Phe Phe Ala Lys
1               5                   10                  15

Tyr Asn Leu Leu Ile Leu Thr Leu Gln Ala Ala Leu Pro Asn Val Ile
            20                  25                  30

Arg Phe Cys Cys Cys Ala Ala Met Ile Tyr Leu Gly Tyr Cys Phe Cys
        35                  40                  45

Gly Trp Ile Val Leu Gly Pro Tyr His Asp Lys Phe Arg Ser Leu Asn
    50                  55                  60

Met Val Ser Glu Cys Leu Phe Ser Leu Ile Asn Gly Asp Asp Met Phe
65                  70                  75                  80

Ala Thr Phe Ala Lys Met Gln Gln Lys Ser Tyr Leu Val Trp Leu Phe
                85                  90                  95

Ser Arg Ile Tyr Leu Tyr Ser Phe Ile Ser Leu Phe Ile Tyr Met Ile
            100                 105                 110

Leu Ser Leu Phe Ile Ala Leu Ile Thr Asp Thr Tyr Glu Thr Ile Lys
        115                 120                 125

Gln Tyr Gln Gln Asp Gly Phe Pro Glu Thr Glu Leu Arg Thr Phe Ile
    130                 135                 140

Ser Glu Cys Lys Asp Leu Pro Asn Ser Gly Lys Tyr Arg Leu Glu Asp
145                 150                 155                 160

Asp Pro Pro Val Thr Leu Phe Cys Cys Cys Lys Lys
                165                 170


<210> SEQ ID NO 105
<211> LENGTH: 321
<212> TYPE: PRT
<213> ORGANISM: Homo sapiens

<400> SEQUENCE: 105

Met Ala Asp Pro Glu Val Val Val Ser Ser Cys Ser Ser His Glu Glu
1               5                   10                  15

Glu Asn Arg Cys Asn Phe Asn Gln Gln Thr Ser Pro Ser Glu Glu Leu
            20                  25                  30

Leu Leu Glu Asp Gln Met Arg Arg Lys Leu Lys Phe Phe Phe Met Asn
        35                  40                  45

Pro Cys Glu Lys Phe Trp Ala Arg Gly Arg Lys Pro Trp Lys Leu Ala
    50                  55                  60

Ile Gln Ile Leu Lys Ile Ala Met Val Thr Ile Gln Leu Val Leu Phe
65                  70                  75                  80

Gly Leu Ser Asn Gln Met Val Val Ala Phe Lys Glu Glu Asn Thr Ile
                85                  90                  95

Ala Phe Lys His Leu Phe Leu Lys Gly Tyr Met Asp Arg Met Asp Asp
            100                 105                 110

Thr Tyr Ala Val Tyr Thr Gln Ser Asp Val Tyr Asp Gln Leu Ile Phe
        115                 120                 125

Ala Val Asn Gln Tyr Leu Gln Leu Tyr Asn Val Ser Val Gly Asn His
```

-continued

```
    130                 135                 140

Ala Tyr Glu Asn Lys Gly Thr Lys Gln Ser Ala Met Ala Ile Cys Gln
145                 150                 155                 160

His Leu Tyr Lys Arg Gly Asn Ile Tyr Pro Gly Asn Asp Thr Phe Asp
                165                 170                 175

Ile Asp Pro Glu Ile Glu Thr Glu Cys Phe Phe Val Glu Pro Asp Glu
            180                 185                 190

Pro Phe His Ile Gly Thr Pro Ala Glu Asn Lys Leu Asn Leu Thr Leu
        195                 200                 205

Asp Phe His Arg Leu Leu Thr Val Glu Leu Gln Phe Lys Leu Lys Ala
    210                 215                 220

Ile Asn Leu Gln Thr Val Arg His Gln Glu Leu Pro Asp Cys Tyr Asp
225                 230                 235                 240

Phe Thr Leu Thr Ile Thr Phe Asp Asn Lys Ala His Ser Gly Arg Ile
                245                 250                 255

Lys Ile Ser Leu Asp Asn Asp Ile Ser Ile Arg Glu Cys Lys Asp Trp
            260                 265                 270

His Val Ser Gly Ser Ile Gln Lys Asn Thr His Tyr Met Met Ile Phe
        275                 280                 285

Asp Ala Phe Val Ile Leu Thr Cys Leu Val Ser Leu Ile Leu Cys Ile
    290                 295                 300

Arg Ser Val Ile Arg Gly Leu Gln Leu Gln Gln Val Gly Asn Val Ala
305                 310                 315                 320

Phe
```

RATIONALE, METHODS, AND ASSAYS FOR IDENTIFYING HUMAN AND NON-HUMAN PRIMATE TASTE SPECIFIC GENES AND USE THEREOF IN TASTE MODULATOR AND THERAPEUTIC SCREENING ASSAYS

RELATED AND PRIORITY PATENT APPLICATIONS

This application is a divisional of U.S. application Ser. No. 12/134,302 filed Jun. 6, 2008 (now U.S. Pat. No. 7,932,058, and claims priority to earlier filed provisional applications by the present Assignee Senomyx Inc relating to a novel rationale for identifying primate taste specific genes and in particular for identification of the primate salt receptor gene or genes. These provisional applications are U.S. Application Ser. No. 60/929,017, filed Jun. 8, 2007; U.S. Application Ser. No. 60/929,007, filed Jun. 8, 2007; U.S. Application Ser. No. 60/947,052, filed Jun. 29, 2007; U.S. Application Ser. No. 60/935,297; filed Aug. 3, 2007; U.S. Application Ser. No. 60/987,611, filed Nov. 13, 2007; U.S. Application Ser. No. 60/988,938, filed Nov. 19, 2007; U.S. Application Ser. No. 60/991,274, filed Nov. 30, 2007; U.S. Application Ser. No. 60/991,289, filed Nov. 30, 2007; U.S. Application Ser. No. 60/992,502, filed Dec. 5, 2007; U.S. Application Ser. No. 60/992,517, filed Dec. 5, 2007; U.S. Application Ser. No. 61/017,244, filed Dec. 28, 2007, US. Application Ser. No. 61/021,437, filed Jan. 16, 2008, US. Application Ser. No. 61/043,257, filed Apr. 8, 2008, U.S. Application Ser. No. 61/053,310, filed May 10, 2008. In addition, this application relates to, and claims priority to U.S. Ser. No. 11/808,356, filed on Jun. 8, 2007 and U.S. Ser. No. 12/134,390 filed on Jun. 6, 2008 and claiming priority to the same applications as this application. All of the afore-mentioned provisional and non-provisional applications are incorporated by reference in their entireties herein.

FIELD OF THE INVENTION

This application generally relates to novel protocols for identifying and functionalizing taste specific genes, especially taste specific genes of primates and non-human primates, which based on their structure, tissue specific expression, cells, where they are expressed in specific tissues and cells therein, and level of expression are predicted to elicit or be involved in one or more taste cell specific functions. As described and shown infra these methods have identified taste specific GPCRs, ion channels, and other transmembrane proteins likely to regulate taste specific cellular activities. In fact, as disclosed in a related application filed on even date claiming benefit of priority to the same provisional and utility applications as the subject application, these methods have already successfully identified a gene which encodes a salty taste receptor in primates including humans, rodents, and likely other vertebrates.

More specifically, the invention relates to novel rationales for identifying and functionalizing human and primate taste specific genes, the taste specific genes identified using these rationale, and specific novel taste cell subsets which express these taste specific genes and the functional characterization of these genes, gene products and novel taste cell subsets and their use as potential taste receptor or therapeutic targets, e.g., salt receptor targets. The genes and gene products identified using these protocols are useful targets in high-throughput screening efforts to identify human salty taste enhancers. These targets are initially identified using a combination of two different techniques, gene chips and a polymerase chain reaction (PCR) screen, resulting in a set of genes which are taste specific and potential taste, e.g., salt or fat taste receptor target genes. First, Affymetrix gene chips containing most all known macaque genes are used to determine which genes are specifically expressed in primate circumvallate at the back of the tongue and fungiform papilla taste cells at the front of the tongue and not lingual epithelial cells isolated by laser capture microdissection. Second, PCR is used to determine which ion channels, from channels we have cataloged in the human/macaque genomes, are specifically expressed in macaque fungiform and/or circumvallate (CV) papilla taste cells but not lingual epithelial cells isolated by laser capture microdissection. Taste-specific expression of genes identified by either approach, are confirmed using an independent histological method such as in situ hybridization or immunohistochemistry, to determine which genes are expressed in taste cells. Using double labeling histological methods, it is determined what novel taste-specific genes are expressed in sweet, bitter, and umami cells that express the taste-specific ion channel TRPM5, sour cells that express the taste-specific ion channel PKD2L1/PKD1L3, or a unique cell type that does not express TRPM5 or PKD2L1/PKD1L3. A taste-specific gene, preferably an ion channel, that is conductive or activated by sodium and is expressed in a TRPM5- and PKD2L1/PKD1L3-negative cell population is a probable candidate for screening efforts to identify the gene(s) that encode mammalian salty taste receptors, as well as specific cell types wherein these salty taste receptor genes are expressed such as in the oral cavity and urinary tract, and also for use in high throughput assays designed to identify enhancers of saltiness in humans. The invention further provides infra in vitro and in vivo strategies for functionalizing the identified taste specific genes, especially those genes identified in unique taste cell subsets also described infra. As described infra and in more detail in the related application cited above, these strategies have already successfully identified a human and non-human primate salty taste receptor and therefore should be effective for functionalizing other taste specific genes such as fat and metallic taste receptors or other taste specific genes involved in ancillary taste cell functions enumerated infra.

In addition, as further described infra, improvements of these methods are also provided which use the combination of real time polymerase chain reaction detection of gene expression and immunochemical assays using taste buds from human post-mortem samples and other methods have been utilized to successfully isolate and identify other unique human taste cell subsets and lineages which in all likelihood are involved in detecting other taste modalities or other taste cell functions.

More specifically, the improved method identifies human taste specific genes by quantitative polymerase chain reaction (PCR). Particularly, the inventors demonstrate taste specific gene expression in humans and primates and have validated the observed specificity of expression by a quantitative method (qPCR or "TaqMan") The identified human taste specific genes (Table 8 infra) (most of which have known primate and other species counterparts) encode multi-span transmembrane proteins and therefore are predicted to include receptors involved in different taste modalities and other functions. (One of the identified human ion channels genes disclosed therein has been confirmed to encode a salty taste receptor.)

Also, in a related aspect this application identifies taste specific genes expressed in humans based on the identification of their counterparts (orthologs) in non-human primates using the disclosed rationales. The inventors predicted that as primates and humans are closely evolutionarily related that gene expression patterns seen in primate taste tissues would correlate to those observed for these genes in human taste tissues. Based on this assumption, taste specific genes shown to be taste specific in primates (including those recited in Tables 1-5 infra) were selected to be validated in human taste buds using non-microarray analysis (TaqMan qPCR).

In another related aspect the invention detects human taste specific genes in human LCM cDNA using LCM from post-mortem LC human tissues and a single cDNA amplification step, establishing that human postmortem LCM human tissue can be used to quantify the expression of taste specific genes sung qPCR.

In yet another related aspect the invention establishes that human taste specific genes can be measured by quantitative qPCR (taqMan) and that gene expression profiles of human taste specific genes can be directly measured by TaqMan and the results used to validate previous gene expression data obtained from microarrays and/or in situ hybridization (ISH) from non-human, e.g., macaque taste cell samples.

In an additional aspect the invention provides an improved method for the identification of a set of human and non-human primate taste specific genes which should identify all potential taste receptor and taste modulator genes based on a selection protocol which compares the expression of taste specific genes in cells in the top versus the bottom of the taste bud.

In another related aspect the invention identifies novel human taste-bud specific genes using the successive approaches of gene expression via microarray in primate LCM tongue tissue; top specific gene expression within the taste bud (akin to known taste receptors) and TaqMan quantification of gene expression in human postmortem tissues and have identified new human taste specific genes not described previously as being taste specific.

In another related aspect the invention identifies human taste specific genes expressed in human post-mortem tissues and provides methods for the functionalization of these genes and cells which express these genes or a combination thereof.

In another related aspect the invention provides a method for identifying and categorizing human taste specific genes which are involved in different functions of the taste buds based on measuring their expression by quantitative qPCR or based on where they are expressed in human taste buds.

In another related aspect the invention provides the specific primate and human taste specific genes identified using these methods which are involved in different taste cell functions including taste sensation, taste bud growth and development, control of the lifespan of mature taste bud cells, and the maintenance differentiation and proliferation of taste-bud committed taste stem cells.

Also, the invention provides the specific primate and human taste specific genes identified using these methods and the corresponding gene products as biomarkers of taste-bud committed stem cells.

Also, the invention provides the specific primate and human taste specific genes identified using these methods and the corresponding gene products as biomarkers of different mature taste cell subsets.

Also, the invention provides the specific primate and human taste specific genes identified using these methods and the corresponding gene products in methods which purify, enrich or ablate specific taste cell subsets and taste-bud committed stem cells.

More specifically, this application identifies novel categories of taste specific genes which are tabulated and enumerated infra derived from primates and human taste cell specific sources (See tables 1-8). These genes are expressed in chemosensory or taste cells, e.g. human and non-human primate fungiform or circumvallate macaque taste cells, and taste (e.g., fungiform, circumvallate, foliate, or palate) cells derived from other mammals such as other non-human primates. These genes are referred to by the inventors as "taste-specific" genes because they are strongly expressed in taste cells. These taste-specific genes include genes which are directly or indirectly involved in taste detection and modulation, e.g., salty, umami, sweet, sour, fatty, metallic, or bitter taste transduction as well as including genes which are involved in biological functions not directly related to taste detection such as the modulation of digestion, taste cell turnover, regulation of the immune system, particularly of the oral cavity, and the regulation of metabolism e.g., carbohydrate metabolism, diabetes, obesity, cachexia, detection of food during digestion, et al.

Relating to the foregoing the present invention provides novel sets of genes that are expressed specifically in human and non-human primate (macaque) chemosensory, e.g., macaque fungiform or circumvallate papilla taste cells that are not expressed or are expressed at significantly lower levels in lingual epithelial cells that are useful in screening assays, preferably high throughput screening assays, for identifying compounds that directly or indirectly modulate different taste modalities, e.g., salty, sweet, umami, bitter, sour, fatty, or metallic.

While the identified taste-specific genes include genes which are directly or indirectly involved in taste detection and modulation, e.g., salty, umami, sweet, sour, fatty, metallic, or bitter taste transduction they also include genes which are involved in biological functions not directly related to taste detection such as the modulation of digestion, taste cell turnover, regulation of the immune system, particularly of the oral cavity, and the regulation of metabolism e.g., carbohydrate metabolism, diabetes, obesity, cachexia, detection of food during digestion, et al.

With particular respect to fat or lipid taste detection the present invention further identifies a subgenus of taste specific genes which are predicted to be involved in detecting fats or lipids based on the presence of characteristic lipid or fat binding motifs or based on the classification of these genes. These genes potentially may be used to screen for compounds that enhance or mimic or block fatty taste detection by the taste buds and potentially detection, binding or absorption by gastrointestinal tissues since it is likely that taste receptors which sense fats or lipids may be expressed in the gastrointestinal tissues as has been observed with other types of taste receptors (sweet, umami and bitter). These genes are referred to herein as "fat taste-specific" genes because they are expressed specifically in taste cells and because based on their structure or prior fictionalization as binding to fatty acids or lipids they are predicted to be involved in fat taste detection in human and non-human primates and likely other mammals. Also, these putative fat taste-specific genes include genes that may also play an ancillary role in other taste modalities and the detection or isolation of taste cells involved in other taste modalities such as, e.g., salty, umami, sweet, sour, metallic, or bitter taste transduction. In addition based on their structural characteristics such as characteristic motifs or prior functional characterization as fatty acid or lipid receptors these genes are predicted to possess other non-taste biological functions involving lipid transport and fat metabolism such as gastric motility and gastric peptide secretion.

Further relating to the foregoing the present invention identifies taste specific human and non-human primate (macaque) genes and the corresponding gene products or cells that express same that are useful in screening assays, preferably high throughput screening assays, for identifying compounds that are useful e.g., as therapeutics in the treatment of digestive system disorders such as cancers and autoimmune disorders, for modulating taste cell apoptosis or taste cell turnover, for inducing taste cell regeneration, for affecting the regulation of immunity in the oral cavity, and the regulation of metabolism, e.g., in the treatment of diabetes, obesity, eating disorders, and other metabolic disorders.

Also relating to the foregoing the invention provides a novel set of human and primate (macaque) and human genes which are useful in the identification and/or isolation and/or enrichment of specific types or lineages of taste or chemosensory cells, e.g., taste or chemosensory cells that are involved in specific taste modalities, immune system regulation in the oral cavity, taste cell apoptosis or taste cell turnover, taste cell regeneration, digestive system regulation, and the regulation of metabolism such as cells that aid in food detection, the secretion of hormones or enzymes involved in hunger and digestion, and the like.

Further, the invention relates to the use of these isolated chemosensory or taste cells in screening assays for identifying compounds that modulate taste, as well as in the identification of therapeutics for modulating the immune system, particularly the regulation of the immune homeostasis in the oral cavity, regulation of taste cell apoptosis, turnover or taste cell regeneration and proliferation, regulation of hormones or enzymes involved in digestion and other taste cell functions, treatment of digestive system disorders such as oral or digestive system cancers, autoimmune or inflammatory digestive disorders, treatment of diabetes, obesity, eating disorders, or other metabolic disorders, and the like.

Further relating to the foregoing the present invention provides a novel set of human and primate (macaque) genes and the corresponding gene products or cells that express same that are useful in screening assays, preferably high throughput screening assays, for identifying compounds that are useful e.g., as therapeutics in the treatment or prevention of digestive system disorders involving aberrant lipid and fat metabolism and the co morbidities associated with aberrant fat and lipid intake and metabolism such as obesity, hepatic steatosis, liver cirrhosis, atherosclerosis, hyperglycemia, insulin resistance and hepatic insulin resistance, type 1 and type 2 diabetes, abdominal obesity, cancers that are obesity or diet related, and the like.

Also, the invention relates to the use of such putative taste receptor genes and the corresponding polypeptides and cells which express same such as cancers and autoimmune disorders, in identifying compounds for modulating taste cell apoptosis or taste cell turnover, particularly compounds that modulate or inhibit fat taste cell regeneration and adipocyte differentiation, e.g., for affecting the regulation of metabolism, e.g., in the treatment of diabetes, obesity, fat accumulation, eating disorders, and other metabolic disorders.

Also relating to the foregoing the invention provides a novel set of human and primate (macaque) genes which are useful in identifying, isolating and/or enriching fat taste receptor expressing cells or cell lineages that upon maturation give rise to fat taste receptor cells using the subject genes or probes specific thereto such as nucleic acids or antibodies.

Also, the invention relates to the use of isolated chemosensory, e.g., taste or gastrointestinal, e.g., enteroendocrine cells which express one or more of the genes reported herein the identification and/or isolation and/or enrichment or ablation of specific types or lineages of taste or chemosensory cells, e.g., taste or chemosensory cells that are involved in specific taste modalities, immune system regulation in the oral cavity, taste cell apoptosis or taste cell turnover, taste cell regeneration, digestive system regulation, and the regulation of metabolism such as cells that aid in food detection, the secretion of hormones or enzymes involved in hunger and digestion, and the like.

Further, the invention relates to the use of these isolated chemosensory or taste cells in screening assays for identifying compounds that modulate taste, as well as in the identification of therapeutics for modulating the immune system, regulation of taste cell apoptosis, turnover or taste cell regeneration and proliferation, regulation of hormones or enzymes involved in digestion and other taste cell functions, treatment of digestive system disorders such as digestive system cancers, of diabetes, obesity, eating disorders, or other metabolic disorders, and the like.

The present invention further provides methods of isolating, purifying and marking desired taste cell types and taste cell lineages including e.g., umami, sweet, salty, bitter, fat, sour, metallic as well as taste stem cells and other immature and mature taste cell lineages including cells that differentiate into taste bud cells, taste cell neurons, taste immune cells et al. based on the expression or absence of expression of one or more of the taste specific genes provided herein. These isolation and purification methods include both positive and negative cell separation methods. For example desired taste cell lineages or types may be isolated by positive cell selection methods e.g., by the use of fluorescence activated cell sorting (FACS), magnetic bead cell selection e.g., by visual identification of desired cells such as individual transfected cells by electrophysiology using antibody coated beads. Alternatively, desired taste cell lineages or types may be recovered or purified by negative cell purification and isolation methods wherein the desired cell types are enriched or purified from a mixed cell population by the removal of one or several undesired cell lineages e.g., by contacting a mixed cell suspension containing the desired taste cells and undesired cells e.g., derived from the tongue, oral cavity or gastrointestinal tract and associated organs with cytotoxic antibodies specific to a target gene or genes expressed on the undesired taste cell type(s) which are to be removed.

Also the invention relates to the use of markers e.g., antibodies or oligonucleotides, that are specific to one or more of the subject taste specific genes provided herein in mapping regions of the tongue and oral cavity which are involved in specific taste and non-taste specific functions, mapping of cell comprised on specific regions of the gastrointestinal tract and associated organs such as the intestinal epithelium or urinary tract that express specific taste specific genes and which therefore are involved in one or more of the taste cell specific functions disclosed herein, and/or the use of the subject genes and markers specific thereto in taste cell differentiation studies, e.g. for identifying compounds that induce the differentiation or dedifferentiation of taste cells e.g., adult or embryonic stem cells and other pluripotent or immature cell types into desired taste cell lineages and taste cell types.

In yet another aspect, this invention relates to assays for identifying a compound having potential in vivo application for modulating human salty or other specific taste. This method comprises the steps of (i) contacting a cell that expresses a gene encoding an ion channel, receptor or transporter identified as a putative salty taste affecting gene according to any one of the methods above, or a gene encoding a polypeptide possessing at least 90% sequence identity to the polypeptide encoded thereby, with at least one putative enhancer compound; (ii) assaying sodium conductance, receptor activity or sodium transport in the presence and absence of said putative enhancer; and (iii) identifying the compound as a potential salty taste enhancer based on whether it increases sodium conductance, the activity of said receptor or sodium transport. In various embodiments, the gene encodes an ion channel or the gene encodes a GPCR. Preferably, the gene is a human gene. More preferably, the method further includes testing the effect of the compound or a derivative thereof in a human taste test. Preferably, the selected compound promotes sodium ion transport into taste bud cells. The putative salty taste affecting gene may be expressed in an amphibian oocyte, or in a mammalian cell, preferably a *Xenopus oocyte* or a mammalian cell selected from the group consisting of a HEK293, HEK293T, Swiss3T3, CHO, BHK, NIH3T3, monkey L cell, African green monkey kidney cell, Ltk-cell and COS cell. Preferably, the putative salty taste affecting gene is expressed under the control of a regulatable promoter. The putative salty taste affecting gene may be expressed stably or transiently. In a preferred mode, the putative salty taste affecting gene is selected from tables 1-8

In a preferred mode, the assay of step (ii) is an electrophysiological assay which uses a sodium sensitive dye, and preferred dyes include membrane potential dyes selected from the group consisting of Molecular Devices Membrane Potential Kit (Cat#R8034), Di-4-ANEPPS (pyridinium, 4-(2-(6-(dibutylamino)-2-naphthalen-yl)ethenyl)-1-(3-sulfopropyl) hydroxide, inner salt, DiSBACC4(2) (bis-(1,2-dibabituric acid)-triethine oxanol), Cc-2-DMPE (Pacific Blue 1,2-dietradecanoyl-sn-glycerol-3phosphoethanolamine, triethylammonium salt) and SBFI-AM (1,3-benzenedicrboxylic acid, 4,4-[1,4,10-trioxa-7,13-diazacylopentadecane-7,13-diylbis(5-methoxy-6,1,2-benzofurandiyl)}bis-tetrakis {(acetyloxy)methyl}ester (Molecular Probes), more preferably, the sodium sensitive dye is sodium green tetraacetate (Molecular Probes) or Na-sensitive Dye Kit (Molecular Devices). In another preferred mode, the assay of step (ii) is a two electrode voltage clamping assay in *Xenopus oocytes*, or the assay is a patch clamp assay in mammalian cells. Preferably, the assay measures activity by an ion flux assay, including using atomic absorption spectroscopy to detect ion flux.

Alternatively, the assay may use a fluorescence plate reader (FLIPR), or a voltage imaging plate reader (VIPR), which is used to increase ion channel-dependent sodium or fluid absorption. In a preferred embodiment of this method, the activity of the putative salty taste affecting gene is assayed in a frog oocyte electrophysiologically by patch clamping or two electrode voltage clamping, preferably using an automatic imaging instrument, which may be a fluorescence plate reader (FLIPR) or a voltage imaging plate reader (VIPR).

In yet another mode, this invention relates to assays for identifying a compound having potential in vivo application for modulating human sweet, bitter, umami, or sour taste. This method comprises the steps of (i) contacting a cell that expresses a gene in Tables 1-8 with at least one putative enhancer or blocker compound; (ii) assaying sodium conductance, receptor activity or taste gene product function in the presence and absence of said putative enhancer or blocker; and (iii) identifying the compound as a potential enhancer or blocker for sweet, bitter or umami taste based on whether it modulates sodium conductance, the activity of said receptor or taste gene product function.

In a more specific embodiment the present invention relates to assays that screen for activators of TRPM5 or umami (T1R1/T1R3) and/or sweet (T1R2/T1R3) taste receptors preferably those which modulate insulin metabolism and/or the release of a satiety peptide such as GLP-1 (glucagon-like peptide 1), which may be used in treating or preventing metabolic and eating disorders such as in the treatment of one of obesity, diabetes, weight management, fat metabolism, glucose metabolism, insulin metabolism, satiety or other conditions wherein the release of satiety peptides or insulin metabolism is desirably controlled or reduced.

In another specific embodiment the present invention relates to assays using endogenous taste cells, e.g., gastrointestinal cells such as gastro-endocrine or gastro-epithelial cells or cells on the tongue or oral cavity, that screen for compounds which act as activators of TRPM5 or umami (T1R1/T1R3) and/or sweet (T1R2/T1R3) taste receptors, preferably those which modulate insulin metabolism and/or the release of a satiety peptide such as GLP-1 (glucagon-like peptide 1), which activators may be used in treating or preventing metabolic and eating disorders such as in the treatment of one of obesity, diabetes, weight management, fat metabolism, glucose metabolism, insulin metabolism, satiety or other conditions wherein the release of satiety peptides such as GLP-1 (glucagon-like peptide 1) is desirably controlled or reduced.

This invention in a more specific embodiment relates to specific taste specific genes identified infra, e.g., FAM26A, GPR113, MCTP1, TMEM16G, TMEM30B, TMEM44, and TUSC3 that are expressed in chemosensory or more specifically taste cells, e.g., human and primate fungiform or circumvallate macaque taste cells, and taste (e.g., fungiform, circumvallate, foliate, or palate) cells derived from other mammals such as humans and non-human primates. and isolated taste cells expressing including cells wherein these genes are expressed as novel taste cells (do not correspond to prior taste modality) and that do not express TRPM5 or PKD2L1/PKD1L3.

Also, the invention relates to enriched, isolated or purified taste cell subsets which expresses at least one of FAM26A, MCTP1, TMEM30B, and/or TUSC3 and which further express at least one T1R or T2R or TRPM5 gene and/or which express T1R2/T1R3 or T1R1/T1R3 or T1R3 only. Particularly, the invention provides isolated taste cells that express GPR113 and/or TMEM16G and which isolated taste cells which further expresses at least one of T1R2/T1R3, T1R1/T1R3, T1R3 only, a T2R gene and/or TRPM5.

Also, the invention relates specifically to a method of using a probe specific to a gene or gene product corresponding to the genes to identify and/or isolate and or enrich taste specific cells from non-taste cells in a sample. For example, these methods include a method herein the gene is FAM26A, MCTP1, TMEM30B, and/or TUSC3 and the identified, isolated or enriched cell further expresses T1R1/T1R3, T1R2/T1R3, T1R3 only, a T2R, and/or TRPM5. Also, the invention includes methods wherein the gene is GPR113 and/or TMEM16G and the isolated, identified or enriched cell further expresses at least one of T1R2/T1R3, T1R1/T1R3, T1R3 only, a T2R or TRPM5 and/or wherein said taste cells are human or macaque taste cells. and wherein said isolated taste cells do not express PKD2L1, PKD1L3, or TRPM5 and/or wherein said cells do not express a T1R or a T2R and/or said taste cells express transducin or gustducin.

Also, the invention relates to the use of these identified taste specific genes or an ortholog or variant thereof encoding a protein at least 90% identical thereto in a cell isolation, purification, enrichment, or marking technique that isolates, purifies, enriches and/or marks at least one desired taste cell subtype or lineage contained in a mixed cell population or cell suspension comprising a desired taste cell type or lineage based on the expression or absence of expression of at least one gene contained in Tables 1-8 or an ortholog thereof, or a gene encoding a protein that is at least 90% identical to said gene or an ortholog thereof. Particularly, the invention includes methods wherein the taste cell subtype or taste cell lineage is isolated, purified, enriched, or marked by a method that includes the use of a fluorescence activated cell sorter (FACS) or by the use of labeled magnetic beads and wherein the cell suspension containing the cells may be produced by enzymatic digestion and/or tissue disaggregation of tissues containing taste cells. and methods wherein the desired taste cell subtype or taste cell lineage is isolated, purified, enriched or marked by a method that includes a negative cell selection technique that eliminates at least one non-target taste cell subtype or lineage based on the expression or absence of expression of at least one other taste cell specific gene identified herein. These methods may e.g., use cytotoxic antibodies to specifically kill at least one non-target cell type or lineage. These isolation methods may e.g., result in isolates containing sweet taste cells, umami taste cells, sour, salty, or fat taste cell subtype or lineages, taste stem cells taste cell neurons, or taste immune cells.

Also, the invention relates to methods of using a cell isolated, purified, enriched or marked according to these methods in screens for taste modulatory compounds, or in a method that screens for compounds that induce the differentiation of said enriched, isolated, purified or marked taste stem cells into one or more taste cell lineages or subtypes or taste buds or in a method wherein said taste cell lineages or subtypes are identified based on the expression or absence of expression of at least one the identified taste specific gene identified above. These cells may be used to screen for compounds that modulate at least one of sweet, umami, bitter, sour, fat, salty or metallic taste wherein the gene is GPR113 or TMEM16G or TMEM44 or to screen for compounds that modulate taste cell differentiation or turnover.

Also, the invention relates to these cells or the gene or gene product encoded thereby in assays that screen for compounds that modulate or treat the diseases and conditions involving taste cells previously identified. This in particular relates to GPR113 or the corresponding gene product or cells which express same or an ortholog or variant thereof in assays to identify compounds that modulate taste cell differentiation or taste cell turnover.

Also, the invention relates to isolated immature taste cells and/or taste stem cells that express TMEM44 or GPR113 and the use in an assay for identifying taste modulators, in particular which screens for sweet, umami, bitter, fat, salty, metallic and/or astringent taste modulators. Also, the invention relates to a recombinant cell engineered to co-express T1R3 and GPR113 and optionally TRPM5. Also, the invention embraces an assay for identifying compounds which modulate taste cell differentiation and/or maturation based on whether said compound specifically binds and/or modulates the activity of GPR113.

Also, the invention relates to the use of these cells in assays that screen for compounds that modulate the differentiation and/or maturation of sweet or umami taste cells. Also, the invention provides a method of using GPR113 as a marker to identify, enrich and/or isolate or ablate unique taste cells which express GPR113, TRPM5 and T1R3 wherein said taste cells do not express T1R1, T1R2 and/or a T2R or are immature, e.g., by FACS or magnetic bead cell separation or by use of cytotoxins.

In addition the invention relates to the discovery that TMEM44 and MFSD4 are expressed in unique taste cell type and that these gene are expressed in sensory taste cells that are not sweet, bitter, umami, or sour cells which further expresses another taste-specific gene disclosed herein. Also, the present invention relates to the discovery that expression of TMEM44 and MFSD4 are markers for a unique taste cell type that may correspond to a fat receptor. Further, the invention relates to the discovery that ATP8A1, FAM26B and SLC4A11 are expressed in many TRPM5 cells, suggesting that these genes are expressed in sweet, umami, and bitter taste cells, since TRPM5 is a marker of sweet, bitter, and umami taste cells.

This invention in a more specific embodiment identifies genes infra, e.g., FAM26A, GPR113, MCTP1, TMEM16G, TMEM30B, TMEM44, and TUSC3 that are expressed in chemosensory or more specifically taste cells, e.g., human or primate fungiform or circumvallate macaque taste cells, and taste (e.g., fungiform, circumvallate, foliate, or palate) cells derived from other mammals such as humans and non-human primates. and isolated taste cells expressing including cells wherein these genes are expressed as novel taste cells (do not correspond to prior taste modality) and that do not express TRPM5 or PKD2L1/PKD1L3.

Also, the present invention relates to the discovery that MFSD4 is expressed in cells that do not express TRPM5 (bitter, sweet, umami) indicating that the expression of this gene is a marker for a unique taste cell type that could correspond to salt, fat, or another taste modality, and, furthermore, that this gene may encode the primary salt or fat receptor.

Also, the invention reveals that the expression pattern of MFSD4 is very similar to TMEM44, indicating that both genes are expressed in the same taste cell type and may be comprised in a heteromeric taste receptor.

Also, the invention relates to the discovery that ATP8A1, FAM26B, and SLC4A11 can be used as markers for sweet, bitter, and umami taste cells or cells expressing TRPM5.

Also, the invention relates to the discovery that ATP8A1, FAM26B, and SLC4A11 and compounds that enhance or inhibit these gene products can selectively modulate taste cell function and responses to tastants including sweet, bitter, and umami.

Also, the invention relates to the discovery based on in situ hybridization results that that TUSC3, ASCL1, FAM26A, FAM26C, IKBKAP, LOC285965, SCNN1D, SLC4A11, SLC26A7, and TMEM30B all are expressed by unique taste cell subsets comprised in primate taste buds and therefore can be used as biomarkers to isolate, enrich, mark or ablate these cells and thereby determine the taste related function of these taste bud cells.

Also, the present invention relates to the discovery that MFSD4 can be used as a marker for a unique, novel taste cell type that does not correspond to sweet, bitter, and umami taste cells. Moreover, the invention relates to the discovery that MFSD4 and compounds that enhance or inhibit this gene product can selectively modulate taste cell function and responses to tastants other than sweet, bitter, and umami, which include salt, fat, and other tastants. Based on the foregoing, the invention relates to the discovery that MFSD4 may correspond to the salt receptor or fat receptor. Also, MFSD4 may be a marker of immature taste cells or developing taste cells.

Related thereto, the present invention also relates to the discovery that MFSD4 and compounds that enhance or inhibit this gene product can selectively modulate taste cell development and/or differentiation of specific taste cell types (i.e. bitter taste cells).

Also, the present invention relates to the discovery that MFSD4 and TMEM44 are expressed in the same unique taste cell type. Also, the present invention relates to the discovery that MFSD4 and TMEM44 may form a complex (heterodimer) to generate a taste receptor for a different taste than sweet, umami, sour or bitter, likely salt or fat. and may be used in screening assays.

Also, the present invention relates to the discovery that ATP8A1, FAM26B, and SLC4A11 are expressed in many TRPM5 cells, suggesting that these genes are expressed in sweet, umami, and bitter taste cells, since TRPM5 is a marker of sweet, bitter, and umami taste cells. and may regulate taste perception or other taste cell function. Moreover, the present invention reveals that ATP8A1, FAM26B, and SLC4A11 are expressed in many TRPM5 cells, suggesting that these genes are expressed in sweet, umami, and bitter taste cells, since TRPM5 is a marker of sweet, bitter, and umami taste cells.

In another embodiment the invention relates to the discovery that ASCL1 also known as MASH is a transcription factor that defines and is a useful marker of sour taste cells as it is selectively expressed in sour taste cells that express PKD1L3 but not in other taste cell types, i.e., it is not expressed in sweet, bitter, or umami cells which express TRPM5. Therefore, the ASCL1 transcription factor may bind to promoter elements in genes involved in sour taste perception. Thus, the invention provides the use thereof in screening the genome for ASCL1 motifs to identify genes in sour cells, including sour receptor genes such as PKD2L1, PKD1L3, or additional genes that may form a complex with PKD2L1/PKD1L3 to generate a sour receptor.

In another embodiment the invention establishes ASCL1 to be a marker of type III taste cells. Type III taste are defined by morphological criteria which include: staining with an intermediate density by electron microscopy and making synaptic contacts with nerve fibers. Thus, the invention reveals that type III taste cells, a cell type previously defined by morphological criteria, correspond to sour taste receptor cells defined by gene expression criteria.

In another embodiment the invention relates to the discovery that other taste receptor cells for sweet, bitter, umami, and salt are likely to express specific transcription factors related thereto that define those cell types. Therefore, the invention provides assays detecting the expression of all transcription factors in the genome in taste cells by PCR and/or histology to determine which taste cell types express which transcription factors.

In another embodiment the invention relaters to the discovery that the ASCL1 transcription factor binds to promoter elements in genes involved in sour taste perception. Thus, the invention encompasses such sequences found in the genome that comprise ASCL1 motifs and the use thereof to identify genes in sour cells, including sour receptor genes such as PKD2L1, PKD1L3, or additional genes that may form a complex with PKD2L1/PKD1L3 to generate a sour receptor.

In another embodiment the invention relates to the discovery that ASCL1 (aka MASH1) is a marker useful for identifying, purifying, and/or isolating or ablating sour taste cells in a mixed cell sample, e.g., derived from the tongue or gastrointestinal or urinary tract.

In a related embodiment the invention provides the use of ASCL1 as a marker of Type III taste cells that correspond to sour taste receptor cells In another embodiment the invention establishes that because ASCL1 defines the sour taste cell lineage it may also control sour taste cell development.

In another embodiment the invention provides the use of ASCL1 transcription factor DNA binding sequences as a probe to identify sour cell genes and sour taste receptor genes that possess related structure such as ASCL1 motifs.

Also, the invention provides the use of these and other taste cell specific transcription factors to define, mark, and/or label taste cell types because each taste cell will express one or more transcription factors that define that taste modality.

The invention further provides the use of these transcription factors that define taste modalities in cell ablation studies to specifically eliminate a specific taste cell or taste modality.

Also, the invention provides ASCL1 or other taste transcriptional gene knockouts which result in transgenic animals possessing altered taste perception and other phenotypic effects, e.g., elimination of sour taste perception or altered urinary or digestive function since ASCL1 may be involved in the metabolic response to pH changes such as excess acidity.

Also, the invention provides the use of these transcription factors that define new taste cell types which can be used in cell ablation studies and in vitro assays to determine what taste modality is lacking as a result of this ablation (i.e. what taste modality is eliminated).

In another embodiment this invention identifies taste-specific genes NALCN, TRPML3 and NKAIN3 which when expressed separately or in combination are predicted to comprise a taste receptor, putatively a salty taste receptor, as these 3 genes are expressed in primate taste cells, are enriched in the top fraction of taste bud cells, and are known to encode sodium channels. In addition the invention relates to the discovery that NALCN is expressed in a unique taste cell subset and is predicted to encode a taste related function. (As noted, TRPML3 has been shown to encode a salty taste receptor).

In a related embodiment the present invention relates to the use of these taste specific ion channel genes as markers which can be used to enrich, identify or isolate salt receptor expressing cells.

In another embodiment the invention relates to assays that identify compounds that modulate the function of the use of NALCN, TRPML3 and/or NKAIN3 and the use of the identified compounds to modulate salty taste perception.

In another embodiment the invention relates to other taste specific genes, i.e., KIT, IKBKAP, LOC285965, and SV2B that are expressed in specific subsets of taste specific cells.

In another embodiment, this invention relates to the discovery that KIT is specifically expressed in TRPM5 and T1R3 taste cells and T1R1 taste cells indicating that the gene can be used as a marker to identify umami taste cells in a mixed cell population and/or may modulate the expression and activity of the umami taste receptor.

In another embodiment, this invention relates to the discovery that IKBKAP and SV2B are specifically expressed in PKD1L3 sour taste receptor cells indicating that these genes can be used as markers to identify sour taste cells and/or modulate taste, especially sour taste.

Also, in another embodiment this invention relates to the discovery that LOC285965 is specifically expressed in TRPM5 and T1R3 taste cell subsets and T1R3 cells lacking T1R1 and T1R2 suggesting that this gene can be used as a marker of these taste cell subsets and/or may associate with or modulate the T1R3 gene and/or encode a taste receptor distant from T1R1/T1R3 or T1R2/T1R3.

Further, in another embodiment the invention relates to the discovery that SV2B is specifically expressed in PKD1L3 cells indicating that this gene can be used as a marker of these specific cell subsets and/or may encode a polypeptide that modulates the activity or expression of the PKD1L3 sour taste receptor.

In addition, in another embodiment the invention relates to the discovery that MFSD4 is expressed in sensory taste cells that are not sweet, bitter, umami, or sour cells and that this gene is expressed in a similar taste cell population as TMEM44.

Also, in another embodiment the invention relates to primate taste specific genes identified in Table 4 found by gene chip analysis which encode transmembrane proteins for ion channels that can conduct sodium, ion transporters, G-protein coupled receptors, or may encode novel multi-transmembrane proteins with no known function which are candidate salty taste receptors.

In another embodiment, the invention relates to the use of compounds that enhance or inhibit IKBKAP and SV2B gene products to selectively modulate taste cell function and responses to sour tastants as well as other functions of the PKD1L3 taste cell population.

In another embodiment, since IKBKAP is mutated in the human disease familial dysautonomia, where taste buds are absent or atrophic and individuals exhibit deficiencies in detection of sweet, bitter, sour, and salty tastants (hypogeusia) the invention related to the discovery that IKBKAP expression in PKD1L3 cells may be important for taste cell development and/or maintenance.

In another embodiment since Botulinum neurotoxin (BoTox) enters neuronal-type cells by interacting with SV2B; the invention relates to the use of BoTox and derivatives to selectively modulate sour taste as well as other functions of the PKD1L3 taste cell population.

In another embodiment since KIT is expressed in umami taste cells the invention relates to the use thereof as a marker of this taste cell type.

In another embodiment the invention relates to the use of KIT and compounds that enhance or inhibit this gene product to selectively modulate taste cell function and responses to umami tastants.

In another embodiment the invention relates to the use of Gleevec (Imatinib), an inhibitor of the KIT tyrosine kinase activity, and other KIT tyrosine kinase inhibitors for selectively inhibiting umami taste.

In another embodiment the invention relates to the discovery that individuals with gain of function mutations in KIT, for example in gastrointestinal stromal tumors (GIST), may have altered umami taste perception.

In another embodiment since LOC285965 is expressed in T1R3 only taste cells similar to GPR113 the invention relates to the use as a marker for a unique, novel taste cell type (T1R3 only cells) that does not correspond to sweet, bitter, and umami taste cells.

In another embodiment the invention relates to the discovery that LOC285965 may correspond to the salt receptor or fat receptor or a receptor for astringency or metallic taste by itself or in combination with GPR113, which is also expressed in T1R3 only cells.

In another embodiment the invention relates to the discovery that LOC285965 may be a coreceptor with T1R3 for specific sweet or umami tastants or other novel tastants such as astringent and metallic tastants.

In another aspect the invention relates to the discovery that compounds that enhance or inhibit LOC285965 can selectively modulate taste function and responses to tastants.

In another embodiment the invention relates to the discovery that LOC285965 may correspond to a marker of immature taste cells that are differentiating into sweet or umami cells.

In another embodiment the invention relates to the discovery that LOC285965 and compounds that enhance or inhibit this gene product can selectively modulate taste cell development and/or differentiation of specific taste cell types (i.e. sweet or umami taste cells).

In another embodiment the invention relates to the discovery that MFSD4 and compounds that enhance or inhibit this gene product can selectively modulate taste cell function and responses to tastants other than sweet, bitter, umami, and sour which include salt, fat, and other tastants.

In another embodiment the invention relates to the discovery that MFSD4 may correspond to the salt receptor or fat receptor.

In another embodiment the invention relates to the discovery that MFSD4 may correspond to a marker of immature taste cells or developing taste cells or support cells.

In another embodiment the invention relates to the use of MFSD4 and compounds that enhance or inhibit this gene product to selectively modulate taste cell development and/or differentiation of specific taste cell types (i.e. bitter taste cells).

In another embodiment the invention relates to the discovery that MFSD4 and TMEM44 are expressed in the same unique taste cell population.

In another embodiment the invention relates to the discovery that MFSD4 and TMEM44 may form a complex (heterodimer) to generate a taste receptor for salt or fat.

In another embodiment the invention relates to the use of the genes listed in Tables 1-8 in assays for candidate salt or fat taste receptors.

BACKGROUND OF THE INVENTION

This invention and the specific rationales for identifying and functionalizing taste specific genes were developed with their initial objective being the identification and functionalization of a gene encoding a salty taste receptor. With respect thereto, epithelial sodium channels (ENaC) are members of the ENaC/degenerin family of ion channels that includes acid-sensing ion channels (ASIC) in mammals, mechanosensitive degenerin channels in worms, and FMRF-amide peptide-gated channels in mollusks (Kellenger, S, and Schild, L. (2002) Physiol. Rev. 82:735-767). ENaC mediates amiloride-sensitive apical membrane $Na^+$ transport across high resistance epithelia in numerous tissues including kidney, colon, and lung and have been well studied and predicted to be involved in salty taste in primates and other species.

ENaC is known to be a heterotrimeric channel comprised of alpha, beta, and gamma subunits or delta, beta, and gamma subunits. Particularly, this heterotrimeric channel has been hypothesized to be involved in human salty taste perception. Previously, assays have been developed by the present assignee using ENaC sequences to identify compounds that modulate the delta beta gamma and alpha beta gamma human ENaC to examine if these compounds will potentially modulate human salty taste perception. Also, these compounds potentially may be used to treat human pathologies involving aberrant ENaC function.

Unlike other mammals, amiloride only slightly reduces the intensity of sodium chloride taste, i.e., by about 15-20% when used at concentrations that specifically modulate ENaC function (Halpern, B. P. (1998) Neuroscience and Behavioral Reviews. 23: 5-47). Experiments conducted by the inventors have shown that amiloride, or the more potent amiloride derivative phenamil did not elicit a significant effect on perceived human salt intensity when tested at levels 300-fold (for amiloride) and 3000-fold (for benzamil) above IC50 values for alpha beta gamma ENaC (equivalent to 10-fold for amiloride and 100-fold for benzamil over IC50 values for delta beta gamma ENaC). Thus, additional non-ENaC genes are likely involved in human salty taste.

In addition, it has been recently reported that taste receptors may be expressed in non-oral tissues, e.g., in the digestive system and potentially other organs such as the kidney. Particularly it has been reported that sweet, umami and bitter taste receptors are expressed in cells other than in the oral cavity such as gastrointestinal cells. (See, e.g., Stermini et al., Amer J Physiol. Gastrointestinal and Liver Physiology, 292: G457-G461, 2007; Mace, O. J. et al, J. Physiology. 10.1113/jphysiol.2007.130906. Published online May 10, 2007). Also, it has been reported by various groups (Margolskee et al., Bezencon et al., Rozengurt et al, and Stermini et al. (2007) (Id)) that bitter and umami taste receptors and other taste signaling molecules such as TRPM5 and gustducin are expressed in specialized cells in the gastrointestinal tract. (See e.g., Margolskee et al., Genes Brain Behavior 2007 (epub March 21); Rozengurt et al., Amer. J. Physiol. Gastroent. Liver Physiol. 291(2):G171-7 (2006); Bezencon et al., Chem Senses 32(1):41-47 (2007)). Margolskee et al. (Id) further reports that the loss of T1R3 or gustducin in rodents resulted in changes in insulin metabolism and the release of satiety peptides such as GLP-1 (glucagon-like peptide 1).

Based on the foregoing, it has been suggested that salty receptors may be expressed in the urinary tract. Taste receptors are purported to be involved in functions not directly related to taste such as digestive functions such as gastric motility, absorption, food detection, metabolism, and immune regulation of the oral or digestive tract and may also affect functions relating to sodium absorption, excretion and transport such as blood pressure and fluid retention.

Therefore, the identification of taste cell specific genes and identifying what specific cells these genes are specifically expressed (including unique taste cell subsets) should facilitate a better understanding of taste and non-taste functions of these taste receptors and should also facilitate the use of these genes, gene products and cells which express same in assays for identifying novel taste modulators and therapeutics, e.g., for treating digestive diseases such as autoimmune, inflammatory and cancers, metabolism, diabetes, eating disorders, obesity, taste cell turnover, hypertension, fluid retention, and immune regulation of the digestive system.

BRIEF DESCRIPTION AND OBJECTS OF THE INVENTION

The invention obviates the problems of the prior art in that it provides novel rationales for identifying and functionalizing primate and human taste specific genes and unique taste cell subsets and further provides novel uses of these taste specific genes, gene products, and modulators of these taste specific genes and cells containing.

This invention in one embodiment relates to the identification of genes that are expressed specifically in chemosensory or taste cells, particularly human and non-human primate (macaque) fungiform or circumvallate papilla cells, and in taste cells (fungiform, circumvallate, foliate, and palate) of other mammals such as humans and other non-human primates. These genes include genes which are directly or indirectly involved in detecting specific taste modalities such as salty, sweet, bitter, umami, sour, fatty and metallic taste and/or in modulating taste intensity and duration.

This invention in another embodiment relates to the identification of genes that are expressed specifically in chemosensory or taste cells, particularly primate (macaque) circumvallate cells and likely in other chemosensory or taste cells and similar cells derived from other mammals such as humans and non-human primates that are involved in other taste cell functions including by way of example taste cell apoptosis or taste cell turnover, taste cell regeneration, digestion, regulation of the immune system in the oral cavity, regulation of carbohydrate or other metabolic functions relating to digestion, food detection, taste cell trafficking, and the like.

The invention in another embodiment further relates to the identification of specific genes or gene products expressed specifically in human and primate (macaque) or other mammalian taste cells that can be used as markers for the identification, isolation, or enrichment of specific taste cell subtypes or taste cell lineages including by way of example sweet, umami, sour, bitter, salty, fatty and metallic taste cells and for isolating taste cells that are involved in non-taste functions such as regulation of immunity, e.g., in the oral cavity, regulation of digestion or metabolism, regulation of taste cell apoptosis, turnover, or taste cell differentiation and proliferation, and regulation of sodium excretion, transport and absorption.

The invention in another embodiment further relates to the use of these taste cell specific genes or gene products or said isolated or enriched taste cell lineages or taste cell types expressing said taste cell specific genes for use in screening assays, e.g. for identifying compounds that elicit of modulate sweet, sour, umami, salty, bitter, fatty or metallic taste as well as the use of these genes, gene products, or isolated or enriched taste cells for the identification of potential therapeutic compounds, e.g., therapeutics for treatment of various digestive system disorders such as ulcerative colitis, Cohn's disease, celiac disease, dyspepsia, cancers of the digestive system, compounds for modulating taste cell turnover or apoptosis or for regulating taste cell differentiation and regeneration e.g., in geriatric subjects or individuals with cancer, or undergoing chemotherapy, or radiation, compounds for modulating or enhancing the immune system of the oral cavity, compounds for the regulation of digestion and metabolism, e.g., compounds that affect the production of digestive fluids, hormones or enzymes such as saliva, stomach and intestinal fluids, GLP-1 (glucagon-like peptide 1), GIP (glucose-dependent insulinotrophic polypeptide), secretin, amylase et al., compounds that affect digestive motility, compounds for treating diabetes, for modulating food detection, and compounds for treating obesity or eating disorders, cachexia, and the like.

This invention in its more specific embodiments relates to novel rationales and methods, and results to date using these rationale and methods for identification and characterization of novel taste-specific genes that based on various parameters constitute salt or other taste modality receptor targets. The targets using these protocols are useful targets in high-throughput screening efforts to identify human salty taste enhancers. These targets are initially identified using two different techniques, gene chips and a polymerase chain reaction (PCR) screen, to identify novel salt receptor target genes. First, Affymetrix gene chips containing most all known macaque genes are used to determine which genes are specifically expressed in primate circumvallate at the back of the tongue and fungiform papilla taste cells at the front of the tongue and not lingual epithelial cells isolated by laser capture microdissection. Second, PCR is used to determine which ion channels, from channels we have cataloged in the human/macaque genomes, are specifically expressed in macaque fungiform and/or circumvallate (CV) papilla taste cells but not lingual epithelial cells isolated by laser capture microdissection. Taste-specific expression of genes identified by either approach, are confirmed using an independent histological method such as in situ hybridization or immunohistochemistry, to determine which genes are expressed in taste cells. Using double labeling histological methods, it is determined what novel taste-specific genes are expressed in sweet, bitter, and umami cells that express the taste-specific ion channel TRPM5, sour cells that express the taste-specific ion channel PKD2L1/PKD1L3, or a unique cell type that does not express TRPM5 or PKD2L1/PKD1L3. A taste-specific gene, preferably an ion channel, that is conductive or activated by sodium and is expressed in a TRPM5- and PKD2L1/PKD1L3-negative cell population is a probable candidate for screening efforts to identify the gene(s) that encode mammalian salty taste receptors, as well as specific cell types wherein these salty taste receptor genes are expressed such as in the oral cavity and urinary tract, and also for use in high throughput assays designed to identify enhancers of saltiness in humans.

In another aspect we describe an improvement of the afore-described methods in the subject application by a method wherein genes expressed in primate taste buds are identified and functionalized using a specific protocol which hinges on where they are expressed and their level of expression in the taste bud. The inventors have developed a rationale wherein they are able to assign gene expression patterns within the primate taste bud (and likely human taste specific genes given the conservation of structure between primate (macaque) and human genes) for all taste bud-specific genes. Specifically, using a comparison of gene expression between the top and bottom sections of the primate taste bud, the inventors have found that they are able to classify genes into one of several functional classes that include taste receptor genes. A subset of genes in this classification is likely to encode taste receptors that include those for salty taste and other yet to be defined taste specificities.

The rationale for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively (see FIG. 38 and examples infra).

In a related embodiment the invention relates to these categorized taste specific genes. As disclosed infra, gene expression data obtained was queried to obtain three sets of genes. (Appendices 1-3 of this patent application). The first and second sets are genes that are expressed at a higher level in the top or bottom of the primate taste bud relative to the bottom or top respectively. Top-specific genes are listed in Appendix 1 and bottom specific genes are listed in Appendix 2. The third set of genes is expressed at a higher level in the top of the primate taste bud relative to surrounding lingual epithelium samples. These additional taste bud-specific genes are listed in Appendix 3.

Also, in another embodiment this invention describes rationales which are useful for and which have successfully identified human genes which are taste specific and which are predicted to be involved in one or more of the afore-described taste bud related functions. Specifically, these methods include methods which identify human taste specific genes by quantitative polymerase chain reaction (PCR) using taste buds from human postmortem samples. It is an improvement over the primate gene assays since this method provides direct results concerning human taste specific genes which may be functionalized using the described methods.

Also, in another embodiment this invention identifies taste specific genes which should be involved in specific taste cell functions based on where the gene is expressed and levels of expression in the taste bud. These methods are able to classify genes into one of several functional classes that include taste receptor genes. It is an improvement since it provides accurate predictions regarding the taste specific genes which may be functionalized using the described methods.

In another embodiment the invention provides the use of the afore-mentioned improved rationale to demonstrate taste specific gene expression in humans (in addition to primate) and validates the specificity of expression by a quantitative method (qPCR or "TaqMan"). These methods identify the genes contained in the Table 8 infra which all encode multi-span transmembrane proteins, and are predicted to include yet unidentified taste receptors as well as other genes involved in taste modulation including the fat and salt receptor and genes involved in ancillary functions afore-mentioned.

Also, in yet another embodiment the invention identifies unique taste cell subsets which themselves can be used in screens for taste modulatory and therapeutic compounds as described infra, and also further exploits the elucidation of these unique taste cell populations as part of its strategies for identifying salty and other types of taste sensing cells such as fat, metallic, astringent, CO2, et al.

In another embodiment the invention relates to the use of these identified taste specific genes in assays designed to identify therapeutics for the treatment of digestive system disorders such as digestive cancers, autoimmune and inflammatory digestive disorders such as ulcerative colitis, dyspepsia, Cohn's disease, celiac disease, inflammatory bowel syndrome, diverticulitis, et al., for regulating taste cell apoptosis or taste cell turnover, for inducing taste cell regeneration e.g. in geriatrics, cancer patients or individuals undergoing chemotherapy or radiation, for modulating the immune system of the oral cavity, for regulation of digestive mucous and fluids, enzymes or hormones such as GLP-1 (glucagon-like peptide 1), GIP (glucose-dependent insulinotrophic polypeptide), amylase, saliva, stomach acids, intestinal fluids, pepsin, secretin, and the like; for treatment of diabetes, eating disorders, cachexia, and other metabolic disorders involving these genes and/or isolated or enriched taste cells.

In another embodiment the invention relates to the use taste-associated genes and polypeptides in assays to ascertain their role in taste cell development and apoptosis, taste cell regeneration, modulation of transcription factors that modulate taste cell receptor expression, e.g., bitter taste receptors, taste receptor trafficking to and from the apical membrane/taste pore region, regulation of taste cell action potential firing frequency/membrane potential to control the intensity of and/or to modulate specific tastes, neurotransmitter release to afferent nerves that regulate taste intensity or specific tastes, and taste cell signaling to nerve fibers.

In another embodiment the invention relates to the use of these taste-associated genes and polypeptides in assays to ascertain their role in and to identify compounds that specifically bind to or which modulate the activity of these genes which compounds may be used to treat or prevent pathological conditions involving digestive function. These conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract.

In another embodiment the invention relates to the use of these taste-associated genes and polypeptides in assays to ascertain their role in and to identify compounds that may be used to treat or prevent pathological conditions involving gastrointestinal fluids, mucous, enzymes or hormones involved with digestion or hunger such as gastrin, secretin, pepsin, cholecystokinin, glucose-dependent insulinotrophic polypeptide (GIP), glucagon-like peptide 1 (GLP-1), amylase, ghrelin, leptin and the like. Also these compounds may enhance the production of saliva or other digestive mucous secretions and fluids. These compounds potentially may be used to suppress or induce hunger and/or to modulate digestion in subjects in need thereof.

In another embodiment the invention relates to the use of these taste-associated genes and polypeptides in assays to ascertain their role in and to the use of these genes, gene products, or cells that express same such as but not restricted to taste cells, e.g., gastrointestinal or oral cavity derived cells, in screening assays to identify compounds that bind to or modulate the activity or amount of these genes or gene products compounds which potentially may be used to treat or prevent pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system.

In another embodiment the invention relates to the use of these taste-associated genes and polypeptides in assays to ascertain their role in and in screening assays to identify compounds that bind to or modulate the activity of these genes or gene products which compounds potentially may be used to modulate gastric reflux and diseases or conditions associated therewith such as gastroesophageal reflux disease, heartburn, Barrett's esophagus, and esophagitis.

In another embodiment the invention relates to the use of these taste-associated genes and polypeptides in assays to ascertain their role in and in screening assays to identify compounds that bind to or which modulate the activity of these genes or gene products and which therefore potentially may be used to treat or prevent cancers or malignancies associated with the digestive system such as by way of example cancers of the tongue, and oral cavity such as cancers of the taste buds and salivary gland cancers, stomach, esophagus, small or large intestine, anus or rectum, pancreas, gall bladder, liver, colorectal or colon.

In another embodiment the invention relates to the use of these taste-associated genes and polypeptides in assays to ascertain their role in and in screening assays to identify compounds that bind to or which modulate the activity of genes or gene products which compounds potentially my be use to treat or prevent appetite dysfunction and conditions associated therewith such as obesity, anorexia, bulimia, and cachexia associated therewith.

In another embodiment the invention relates to the use of these taste-associated genes and polypeptides for the isolation or enrichment of specific taste cell lineages or subtypes particularly taste cells derived e.g., from the tongue, oral cavity, or gastrointestinal system, which express one or several of these taste-cell associated genes.

In another embodiment the invention relates to the use of these taste-associated genes and polypeptides in assays to ascertain their role in and in assays to identify compounds that bind to or which modulate the activity of these genes or gene products which may be used to treat or prevent pathological conditions involving digestive function. These conditions include by way of example functional dyspepsia (bad digestion) and other dyspepsias which may or may not be ulcer derived or related and may involve different areas of the digestive tract such as the upper abdominal tract, the mid-abdominal tract or the lower abdominal tract.

In another embodiment the invention relates to the use of these taste-associated genes and polypeptides in assays to ascertain their role in and in screening assays to identify compounds that may be used to treat or prevent pathological conditions involving gastrointestinal hormones, enzymes or fluids involved with digestion or hunger such as saliva, digestive fluids, gastrin, secretin, cholecystokinin, glucose-dependent insulinotrophic polypeptide, glucagon-like peptide 1, amylase, or ghrelin, leptin and the like. These compounds potentially may be used to suppress or induce hunger or to modulate digestion in subjects in need thereof.

In another embodiment the invention relates to the use of these taste-associated genes and polypeptides in assays to ascertain their role in and in screening assays to identify compounds that bind to or modulate the activity of these genes or gene products which compounds potentially may be used to treat or prevent pathological or chronic inflammatory or autoimmune gastrointestinal conditions such as Crohn's disease, inflammatory bowel syndrome (IBD), celiac disease, ulcerative colitis, diverticulitis, gastritis, reflux esophagitis, and the like. These compounds potentially may be used to treat or prevent autoimmune or inflammatory diseases affecting the digestive system.

In another embodiment the invention relates to the use of these taste-associated genes and polypeptides in assays to ascertain their role in and in screening assays to identify compounds that bind to or modulate the activity of these genes which compounds that potentially may be used to modulate gastric reflux and diseases or conditions associated therewith such as gastroesophageal reflux disease, heartburn, Barrett's esophagus, and esophagitis.

In another embodiment the invention relates to the use of these taste-associated genes and polypeptides in assays to ascertain their role in and in screening assays to identify compounds that bind to or which modulate the activity of these genes and which compounds therefore potentially may be used to treat or prevent cancers or malignancies associated with the digestive system such as by way of example cancers of the salivary glands and taste buds, tongue, oral cavity, stomach, esophagus, small or large intestine, anus, pancreas, gall bladder, liver, colorectal, or colon.

In another embodiment the invention relates to the use of these taste-associated genes and polypeptides in assays to ascertain their role in and in screening assays for identifying compounds that regulate ion transport or ion flux, particularly sodium ions in order to identify therapeutic compounds that may be e.g., used to modulate blood pressure and fluid retention and conditions and diseases involving aberrant sodium absorption, excretion and transport.

In another embodiment the invention relates to the use of these taste-associated genes and polypeptides in assays to ascertain their role in and in screening assays for identifying compounds that regulate selective apoptosis of taste cells, modulation of transcription factors that control taste receptor expression, autocrine/paracrine modulation of taste cell development, taste bud lifetime, screens using genes that result in supertaster phenotypes, compounds that activate taste stem cells, compounds that affect trafficking of taste cell receptors e.g., from the apical membrane/taste pore region, compounds that affect taste intensity by modulating regulation of taste cell action via potential firing frequency/membrane potential, compounds that regulate neurotransmitter release to afferent nerves that control general or specific taste intensity, and autocrine/paracrine modulation of taste receptor function.

In another embodiment the invention relates to the use of these taste-associated genes and polypeptides in assays to ascertain their role in and in screening assays for identifying compounds that affect regeneration of taste cells or taste buds, e.g., in diseased or geriatric individuals or after injury or surgery, subjects undergoing chemotherapy or after injury, compounds for modulating drug-induced dysgeusia, ageusia, taste bud loss, dry mouth or xerostomia as for example found in Sjogren's syndrome, compounds that are useful in maintaining oral hygiene, treating or preventing halitosis, noxious oral microbia such as viruses and bacteria, and the like.

In another embodiment the invention relates to the use of these taste-associated genes and polypeptides in methods of isolating, purifying and marking desired taste cell types and taste cell lineages including e.g., umami, sweet, salty, bitter, fat, sour, metallic as well as taste stem cells and other immature and mature taste cell lineages including cells that differentiate into taste bud cells, taste cell neurons, taste immune cells et al. based on the expression or absence of expression of one or more of the taste specific genes provided herein. These isolation and purification methods include both positive and negative cell separation methods. For example, desired taste cell lineages or types may be isolated by positive cell selection methods e.g., by the use of fluorescence activated cell sorting (FACS), magnetic bead cell selection e.g., by visual identification of desired cells such as individual transfected cells by electrophysiology using antibody coated beads. Alternatively, desired taste cell lineages or types may be recovered or purified by negative cell purification and isolation methods wherein the desired cell types are enriched or purified from a mixed cell population by the removal of one or several undesired cell lineages e.g., by contacting a mixed cell suspension containing the desired taste cells and undesired cells e.g., derived from the tongue, oral cavity or gastrointestinal tract and associated organs with cytotoxic antibodies specific to a target gene or genes expressed on the undesired taste cell type(s) which are to be removed.

In another embodiment the invention relates to the use of these taste-associated genes and polypeptides in assays to ascertain their role in and in screening assays to in taste cell differentiation studies, e.g. for identifying compounds that induce the differentiation or dedifferentiation of taste cells e.g., adult or embryonic stem cells and other pluripotent or immature cell types into desired taste cell lineages and taste cell types.

In another embodiment the invention relates to, as described in detail infra, a rationale and criteria for a candidate salty taste gene, preferably an ion channel which are:

a) Specific expression in primate (macaque) taste cells, particularly fungiform and/or circumvallate papilla derived taste cells, but also foliate and palate taste cells, and not lingual epithelial cells OR expression at higher levels in taste cells than lingual cells b) Expression in a taste cell by histological methods. Specifically, expression in a unique taste cell type that does not express the sweet, bitter, and umami cell marker TRPM5 or the sour cell marker PKD2L1/PKD1L3. This unique cell type could be a dedicated salt sensing cell.

c) Functional expression as a sodium channel or a sodium-activated receptor with basal, constitutive function (i.e. a fraction of the channel population is open and passing sodium at rest) in heterologous expression systems (such as *Xenopus* oocytes and mammalian cells) or primary neurons (such as dorsal root ganglia neurons).

Genes fulfilling these criteria will be advanced into high-throughput screening efforts to identify compounds that enhance human salt perception. In addition the taste-specific genes reported herein, e.g., in Tables 1, 2, and 3 supra will be useful in the therapeutic screening assays as afore-mentioned.

Therefore in this patent application we describe screening assays to identify genes putatively involved in salty taste perception as well as taste and other taste-cell mediated activities in general.

In another embodiment the invention relates to a specific rationale that identifies taste-specific genes encoding membrane proteins expressed specifically in taste cells and not lingual cells at higher levels in taste cells than lingual epithelial cells using gene chip and/or PCR methodologies and use same as salt receptor targets in assays to identify salty taste modulators as well as compounds that affect other taste modalities and taste perception and taste-cell related biological and cellular functions and taste cell related phenotypes in general.

In another embodiment the invention relates to a rationale that determines which taste-specific genes are expressed in taste cells and especially in sweet, bitter, and/or umami cells (TRPM5 positive), sour cells (PKD2L1/PKD1L3 positive) or a unique cell type (TRPM5 negative). These unique cell types will likely comprise cells dedicated to salty taste perception.

In another embodiment the invention relates to the use of these taste-associated genes and polypeptides in assays to identify modulators (enhancers) of taste-specific ion channels or taste-specific genes as these compounds may modulate human salty taste perception.

In another embodiment the invention relates to a rationale wherein the inventors describe and are able to assign herein gene expression patterns within the primate taste bud for all taste bud-specific genes. Specifically, using a comparison of gene expression between the top and bottom sections of the primate taste bud, this invention classifies genes into one of several functional classes that include taste receptor genes. A subset of genes in this classification is likely to encode taste receptors that include those for salty taste and other yet to be defined taste specificities. (The rational for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively.)

In another embodiment the invention relates to novel methods for functional characterization of taste bud specific genes based on certain expression criteria. The invention provides three sets of genes which are contained in the Appendices 1-3 to this application identified using this rationale. The first and second sets are genes that are expressed at a higher level in the top or bottom of the primate taste bud relative to the bottom or top respectively. Top-specific genes are listed in Appendix 1 and bottom specific genes are listed in Appendix 2. (Accordingly, these lists contain top enriched and bottom enriched mRNAs). The third set of genes was identified as expressed at a higher level in the top of the primate taste bud relative to surrounding lingual epithelium. This set of taste bud-specific genes was obtained by the identification of taste bud-specific genes by comparing gene expression between whole (top+bottom) taste bud and lingual epithelium LCM samples. These additional taste bud-specific genes are listed in Appendix 3.

In another embodiment the invention relates to the discovery that taste-associated genes and polypeptides are expressed predominantly at the top of the taste buds. In contrast to prior knowledge, our new data clearly indicate that known taste receptor genes are expressed at a higher level in the top fraction of taste buds. It is reasonable to expect other yet to be identified taste receptor genes to be represented in the top-enriched gene list.

In another embodiment the invention relates to the functional characterization of particular "target" taste bud specific genes based on where they are expressed in the taste bud cells. The inventors have discovered based on gene expression profiles of the top and bottom fractions of the taste bud suggest that there are distinct functions for cells in each compartment. Functional classes of genes expressed in the top cells indicate these are mature sensory cells whereas those expressed in the bottom cells indicate these are immature progenitor cells associated with a basement membrane containing cellular environment. Examples of top-specific functional classes include taste receptors, taste-specific signal transduction components and receptors. Examples of bottom-specific functional classes include extracellular matrix components, growth factors and cell cycle-associated proteins.

In another embodiment the invention relates to a comprehensive listing of taste specific genes in the Tables and Appendices of this application. By fractionating the taste bud into top and bottom compartments the inventors have increased the sensitivity of mRNA detection in each compartment by a factor of approximately two and has identified virtually all taste bud specific genes.

In another embodiment the invention relates to a method for identifying genes involved in different functions of the taste bud based on measuring their expression in the top versus bottom of the taste bud.

In another embodiment the invention relates to the use of these taste-associated genes and polypeptides in assays to ascertain their role in and in screening assays to genes identified using the above method where genes involved in taste sensation would be over-expressed in the top part of the taste bud.

In another embodiment the invention relates to the set of genes identified using the above method where genes involved in modulation of taste sensation would be over-expressed in the top part of the taste bud.

In another embodiment the invention relates to a set of genes identified using the above method where genes involves in taste bud growth and development are over-expressed in the bottom part of the taste bud.

In another embodiment the invention relates to the genes identified using the above methods where the genes are involved in control of the lifespan of mature taste bud cells are over-expressed in the top part of the taste bud.

In another embodiment the invention relates to the genes identified using the above methods where genes involved in the maintenance, differentiation and proliferation of taste-bud committed stem cells will be over-expressed at the bottom of the taste bud.

In another embodiment the invention relates to the genes identified using the methods, where the genes represent biomarkers of taste-bud committed stem cells will be over-expressed at the bottom of the taste bud.

In another embodiment the invention relates to the genes identified using the above methods where genes representing biomarkers of different mature taste cell subsets will be over-expressed in the top of the taste bud.

In another embodiment the invention provides a set of genes identified as described above and the use thereof in order to purify, enrich, isolate or label specific taste cell subsets.

In another embodiment the invention provides electrophysiological assays that measure conductance of putative taste ion channels identified herein in the presence and absence of putative enhancers.

In another embodiment the invention identifies enhancers of the subject putative salty taste related ion channels and other taste affecting genes in an oocyte expression system.

In another embodiment the invention relates to the use of these taste-associated genes and polypeptides in patch clamping or two electrode voltage clamping assays using oocytes that express a putative salty taste receptor ion channel for identifying compounds that modulate the activity of this channel and therefore modulate salty taste. These and other objects of the present invention are met by one or more of the embodiments described below.

In another embodiment the invention relates to methods of isolating, purifying and marking desired taste cell types and taste cell lineages including e.g., umami, sweet, salty, bitter, fat, sour, metallic as well as taste stem cells and other immature and mature taste cell lineages including cells that differentiate into taste bud cells, taste cell neurons, taste immune cells et al. based on the expression or absence of expression of one or more of the taste specific genes provided herein. These isolation and purification methods include both positive and negative cell separation methods. For example desired taste cell lineages or types may be isolated by positive cell selection methods e.g., by the use of fluorescence activated cell sorting (FACS), magnetic bead cell selection e.g., by visual identification of desired cells such as individual transfected cells by electrophysiology using antibody coated beads. Alternatively, desired taste cell lineages or types may be recovered or purified by negative cell purification and isolation methods wherein the desired cell types are enriched or purified from a mixed cell population by the removal of one or several undesired cell lineages e.g., by contacting a mixed cell suspension containing the desired taste cells and undesired cells e.g., derived from the tongue, oral cavity or gastrointestinal tract and associated organs with cytotoxic antibodies specific to a target gene or genes expressed on the undesired taste cell type(s) which are to be removed.

In another embodiment the invention relates to the use of these taste-associated genes and polypeptides in assays to ascertain their role in and in screening assays to methods of using these genes and gene products as markers e.g., using probes specific thereto such as antibodies or oligonucleotides, i.e., that are specific to one or more of the subject taste specific genes provided herein in mapping regions of the tongue and oral cavity which are involved in specific taste and non-taste specific functions, mapping of cell comprised on specific regions of the gastrointestinal tract and associated organs such as the intestinal epithelium or urinary tract that express specific taste specific genes and which therefore are involved in one or more of the taste cell specific functions disclosed herein, and/or the use of the subject genes and markers specific thereto in taste cell differentiation studies, e.g. for identifying compounds that induce the differentiation or dedifferentiation of taste cells e.g., adult or embryonic stem cells and other pluripotent or immature cell types into desired taste cell lineages and taste cell types.

In another specific embodiment the present invention relates to assays using endogenous taste cells, e.g., gastrointestinal cells such as gastro-endocrine or gastro-epithelial cells or cells on the tongue or oral cavity, that screen for compounds which act as activators of TRPM5 or umami (T1R1/T1R3) and/or sweet (T1R2/T1R3) taste receptors, preferably those which modulate insulin metabolism and/or the release of a satiety peptide such as GLP-1 (glucagon-like peptide 1), which activators may be used in treating or preventing metabolic and eating disorders such as in the treatment of one of obesity, diabetes, weight management, fat metabolism, glucose metabolism, insulin metabolism, satiety or other conditions wherein the release of satiety peptides such as GLP-1 (glucagon-like peptide 1) is desirably controlled or reduced.

This invention in a more specific embodiment relates to specific taste specific genes identified infra, e.g., FAM26A, GPR113, MCTP1, TMEM16G, TMEM30B, TMEM44, and TUSC3 that are expressed in chemosensory or more specifically taste cells, e.g., human and primate fungiform or circumvallate macaque taste cells, and taste (e.g., fungiform, circumvallate, foliate, or palate) cells derived from other mammals such as humans and non-human primates. and isolated taste cells expressing including cells wherein these genes are expressed as novel taste cells (do not correspond to prior taste modality) and that do not express TRPM5 or PKD2L1/PKD1L3.

Also, the invention in another embodiment relates to enriched, isolated or purified taste cell subsets which expresses at least one of FAM26A, MCTP1, TMEM30B, and/or TUSC3 and which further express at least one T1R or T2R or TRPM5 gene and/or which express T1R2/T1R3 or T1R1/T1R3 or T1R3 only. Particularly, the invention provides isolated taste cells that express GPR113 and/or TMEM16G and which isolated taste cells which further expresses at least one of T1R2/T1R3, T1R1/T1R3, T1R3 only, a T2R gene and/or TRPM5.

Also, the invention in another embodiment relates specifically to a method of using a probe specific to a gene or gene product corresponding to the genes to identify and/or isolate and or enrich taste specific cells from non-taste cells in a sample. For example, these methods include a method herein the gene is FAM26A, MCTP1, TMEM30B, and/or TUSC3 and the identified, isolated or enriched cell further expresses T1R1/T1R3, T1R2/T1R3, T1R3 only, a T2R, and/or TRPM5. Also, the invention includes methods wherein the gene is GPR113 and/or TMEM16G and the isolated, identified or enriched cell further expresses at least one of T1R2/T1R3, T1R1/T1R3, T1R3 only, a T2R or TRPM5 and/or wherein said taste cells are human or macaque taste cells. and wherein said isolated taste cells do not express PKD2L1, PKD1L3, or TRPM5 and/or wherein said cells do not express a T1R or a T2R and/or said taste cells express transducin or gustducin.

Also, the invention relates to the use of TUSC3, ASCL1, FAM26A, FAM26C, IKBKAP, LOC285965, SCNN1D, SLC4A11, SLC26A7, and TMEM30B as a biomarker of specific taste cells and the isolated cells which express same as all of these genes are expressed by unique taste cell subsets comprised in primate taste buds and therefore can be used as biomarkers to isolate, enrich, mark or ablate these cells and thereby determine the taste related function of these taste bud cells.

Also, the invention in another embodiment relates to the use of these identified taste specific genes or an ortholog or variant thereof encoding a protein at least 90% identical thereto in a cell isolation, purification, enrichment, or marking technique that isolates, purifies, enriches and/or marks at least one desired taste cell subtype or lineage contained in a mixed cell population or cell suspension comprising a desired taste cell type or lineage based on the expression or absence of expression of at least one gene contained in Tables 1-8 or an ortholog thereof, or a gene encoding a protein that is at least 90% identical to said gene or an ortholog thereof. Particularly, the invention includes methods wherein the taste cell subtype or taste cell lineage is isolated, purified, enriched, or marked by a method that includes the use of a fluorescence activated cell sorter (FACS) or by the use of labeled magnetic beads and wherein the cell suspension containing the cells may be produced by enzymatic digestion and/or tissue disaggregation of tissues containing taste cells. and methods wherein the desired taste cell subtype or taste cell lineage is isolated, purified, enriched or marked by a method that includes a negative cell selection technique that eliminates at least one non-target taste cell subtype or lineage based on the expression or absence of expression of at least one other taste cell specific gene identified herein. These methods may e.g., use cytotoxic antibodies to specifically kill at least one non-target cell type or lineage. These isolation methods may e.g., result in isolates containing sweet taste cells, umami taste cells, sour, salty, or fat taste cell subtype or lineages, taste stem cells taste cell neurons, or taste immune cells.

Also, the invention in another embodiment relates to methods of using a cell isolated, purified, enriched or marked according to these methods in screens for taste modulatory compounds, or in a method that screens for compounds that induce the differentiation of said enriched, isolated, purified or marked taste stem cells into one or more taste cell lineages or subtypes or taste buds or in a method wherein said taste cell lineages or subtypes are identified based on the expression or absence of expression of at least one the identified taste specific gene identified above. These cells may be used to screen for compounds that modulate at least one of sweet, umami, bitter, sour, fat, salty or metallic taste wherein the gene is GPR113 or TMEM16G or TMEM44 or to screen for compounds that modulate taste cell differentiation or turnover.

Also, the invention in another embodiment relates to these cells or the gene or gene product encoded thereby in assays that screen for compounds that modulate or treat the diseases and conditions involving taste cells previously identified. This in particular relates to GPR113 or the corresponding gene product or cells which express same or an ortholog or variant thereof in assays to identify compounds that modulate taste cell differentiation or taste cell turnover.

Also, the invention in another embodiment relates to isolated immature taste cells and/or taste stem cells that express TMEM44 or GPR113 and the use in an assay for identifying taste modulators, in particular which screens for sweet, umami, bitter, fat, salty, metallic and/or astringent taste modulators. Also, the invention relates to a recombinant cell engineered to co-express T1R3 and GPR113 and optionally TRPM5. Also, the invention embraces an assay for identifying compounds which modulate taste cell differentiation and/or maturation based on whether said compound specifically binds and/or modulates the activity of GPR113.

Also, the invention in another embodiment relates to the use of these cells in assays that screen for compounds that modulate the differentiation and/or maturation of sweet or umami taste cells. Also, the invention provides a method of using GPR113 as a marker to identify, enrich and/or isolate or ablate unique taste cells which express GPR113, TRPM5 and T1R3 wherein said taste cells do not express T1R1, T1R2 and/or a T2R or are immature, e.g., by FACS or magnetic bead cell separation or by use of cytotoxins.

In addition the invention in another embodiment relates to the discovery that TMEM44 and MFSD4 are expressed in unique taste cell type and that these gene are expressed in sensory taste cells that are not sweet, bitter, umami, or sour cells which further expresses another taste-specific gene disclosed herein. Also, the present invention relates to the discovery that expression of TMEM44 and MFSD4 are markers for a unique taste cell type that may correspond to a fat receptor. Further, the invention relates to the discovery that ATP8A1, FAM26B and SLC4A11 are expressed in many TRPM5 cells, suggesting that these genes are expressed in sweet, umami, and bitter taste cells, since TRPM5 is a marker of sweet, bitter, and umami taste cells.

This invention in a more specific embodiment identifies genes infra, e.g., FAM26A, GPR113, MCTP1, TMEM16G, TMEM30B, TMEM44, and TUSC3 that are expressed in chemosensory or more specifically taste cells, e.g., human or primate fungiform or circumvallate macaque taste cells, and taste (e.g., fungiform, circumvallate, foliate, or palate) cells derived from other mammals such as humans and non-human primates. and isolated taste cells expressing including cells wherein these genes are expressed as novel taste cells (do not correspond to prior taste modality) and that do not express TRPM5 or PKD2L1/PKD1L3.

Also, the present invention in another embodiment relates to the discovery that MFSD4 is expressed in cells that do not express TRPM5 (bitter, sweet, umami) indicating that the expression of this gene is a marker for a unique taste cell type e.g., a salt, fat, or another taste modality, and, furthermore, that this gene may encode the primary salt or fat receptor.

Also, the invention in another embodiment reveals that the expression pattern of MFSD4 is very similar to TMEM44, indicating that both genes are expressed in the same taste cell type and may be comprised in a heteromeric taste receptor.

Also, the invention in another embodiment relates to the discovery that ATP8A1, FAM26B, and SLC4A11 can be used as markers for sweet, bitter, and umami taste cells or cells expressing TRPM5.

Also, the invention in another embodiment relates to the discovery that ATP8A1, FAM26B, and SLC4A11 and compounds that enhance or inhibit these gene products can selectively modulate taste cell function and responses to tastants including sweet, bitter, and umami.

Also, the present invention in another embodiment relates to the discovery that MFSD4 can be used as a marker for a unique, novel taste cell type that does not correspond to sweet, bitter, and umami taste cells. Moreover, the invention relates to the discovery that MFSD4 and compounds that enhance or inhibit this gene product can selectively modulate taste cell function and responses to tastants other than sweet, bitter, and umami, which include salt, fat, and other tastants. Based on the foregoing, the invention relates to the discovery that MFSD4 may correspond to the salt receptor or fat receptor. Also, MFSD4 may be a marker of immature taste cells or developing taste cells.

Related thereto, in another embodiment the present invention also relates to the discovery that MFSD4 and compounds that enhance or inhibit this gene product can selectively modulate taste cell development and/or differentiation of specific taste cell types (i.e. bitter taste cells).

Also, the present invention in another embodiment relates to the discovery that MFSD4 and TMEM44 are expressed in the same unique taste cell type. Also, the present invention relates to the discovery that MFSD4 and TMEM44 may form a complex (heterodimer) to generate a taste receptor for a different taste than sweet, umami, sour or bitter, likely salt or fat. and may be used in screening assays.

Also, in another embodiment the present invention relates to the discovery that ATP8A1, FAM26B, and SLC4A11 are expressed in many TRPM5 cells, suggesting that these genes are expressed in sweet, umami, and bitter taste cells, since TRPM5 is a marker of sweet, bitter, and umami taste cells. and may regulate taste perception or other taste cell function. Moreover, the present invention reveals that ATP8A1, FAM26B, and SLC4A11 are expressed in many TRPM5 cells, suggesting that these genes are expressed in sweet, umami, and bitter taste cells, since TRPM5 is a marker of sweet, bitter, and umami taste cells.

In another embodiment the invention relates to the discovery that ASCL1 also known as MASH is a transcription factor that defines and is a useful marker of sour taste cells as it is selectively expressed in sour taste cells that express PKD1L3 but not in other taste cell types, i.e., it is not expressed in sweet, bitter, or umami cells which express TRPM5. Therefore, the ASCL1 transcription factor may bind to promoter elements in genes involved in sour taste perception. Thus, the invention provides the use thereof in screening the genome for ASCL1 motifs to identify genes in sour cells, including sour receptor genes such as PKD2L1, PKD1L3, or additional genes that may form a complex with PKD2L1/PKD1L3 to generate a sour receptor.

In another embodiment the invention establishes ASCL1 to be a marker of type III taste cells. Type III taste are defined by morphological criteria which include: staining with an intermediate density by electron microscopy and making synaptic contacts with nerve fibers. Thus, the invention reveals that type III taste cells, a cell type previously defined by morphological criteria, correspond to sour taste receptor cells defined by gene expression criteria.

In another embodiment the invention relates to the discovery that other taste receptor cells for sweet, bitter, umami, and salt are likely to express specific transcription factors related thereto that define those cell types. Therefore, the invention provides assays detecting the expression of all transcription factors in the genome in taste cells by PCR and/or histology to determine which taste cell types express which transcription factors.

In another embodiment the invention relaters to the discovery that the ASCL1 transcription factor binds to promoter elements in genes involved in sour taste perception. Thus, the invention encompasses such sequences found in the genome that comprise ASCL1 motifs and the use thereof to identify genes in sour cells, including sour receptor genes such as PKD2L1, PKD1L3, or additional genes that may form a complex with PKD2L1/PKD1L3 to generate a sour receptor.

In another embodiment the invention relates to the discovery that ASCL1 (aka MASH1) is a marker useful for identifying, purifying, and/or isolating or ablating sour taste cells in a mixed cell sample, e.g., derived from the tongue or gastrointestinal or urinary tract.

In a related embodiment the invention provides the use of ASCL1 as a marker of Type III taste cells that correspond to sour taste receptor cells In another embodiment the invention establishes that because ASCL1 defines the sour taste cell lineage it may also control sour taste cell development.

In another embodiment the invention provides the use of ASCL1 transcription factor DNA binding sequences as a probe to identify sour cell genes and sour taste receptor genes that possess related structure such as ASCL1 motifs.

Also, in another embodiment the invention provides the use of these and other taste cell specific transcription factors to define, mark, and/or label taste cell types because each taste cell will express one or more transcription factors that define that taste modality.

The invention further provides in another embodiment the use of these transcription factors that define taste modalities in cell ablation studies to specifically eliminate a specific taste cell or taste modality.

Also, in another embodiment the invention provides ASCL1 or other taste transcriptional gene knockouts which result in transgenic animals possessing altered taste perception and other phenotypic effects, e.g., elimination of sour taste perception or altered urinary or digestive function since ASCL1 may be involved in the metabolic response to pH changes such as excess acidity.

Also, t in another embodiment he invention provides the use of these transcription factors that define new taste cell types which can be used in cell ablation studies and in vitro assays to determine what taste modality is lacking as a result of this ablation (i.e. what taste modality is eliminated).

In another embodiment this invention identifies taste-specific genes NALCN, TRPML3 and NKAIN3 which when expressed separately or in combination are predicted to comprise a taste receptor, putatively a salty taste receptor, as these 3 genes are expressed in primate taste cells, are enriched in the top fraction of taste bud cells, and are known to encode sodium channels. In addition the invention relates to the discovery that NALCN is expressed in a unique taste cell subset and is predicted to encode a taste related function. (As noted, TRPML3 has been shown to encode a salty taste receptor).

In a related embodiment the present invention relates to the use of these taste specific ion channel genes as markers which can be used to enrich, identify or isolate salt receptor expressing cells.

In another embodiment the invention relates to assays that identify compounds that modulate the function of the use of NALCN, TRPML3 and/or NKAIN3 and the use of the identified compounds to modulate salty taste perception.

In another embodiment the invention relates to other taste specific genes, i.e., KIT, IKBKAP, LOC285965, and SV2B that are expressed in specific subsets of taste specific cells.

In another embodiment, this invention relates to the discovery that KIT is specifically expressed in TRPM5 and T1R3 taste cells and T1R1 taste cells indicating that the gene can be used as a marker to identify umami taste cells in a mixed cell population and/or may modulate the expression and activity of the umami taste receptor.

In another embodiment, this invention relates to the discovery that IKBKAP and SV2B are specifically expressed in PKD1L3 sour taste receptor cells indicating that these genes can be used as markers to identify sour taste cells and/or modulate taste, especially sour taste.

Also, in another embodiment this invention relates to the discovery that LOC285965 is specifically expressed in TRPM5 and T1R3 taste cell subsets and T1R3 cells lacking T1R1 and T1R2 suggesting that this gene can be used as a marker of these taste cell subsets and/or may associate with or modulate the T1R3 gene and/or encode a taste receptor distant from T1R1/T1R3 or T1R2/T1R3.

Further, in another embodiment the invention relates to the discovery that SV2B is specifically expressed in PKD1L3 cells indicating that this gene can be used as a marker of these specific cell subsets and/or may encode a polypeptide that modulates the activity or expression of the PKD1L3 sour taste receptor.

In addition, in another embodiment the invention relates to the discovery that MFSD4 is expressed in sensory taste cells that are not sweet, bitter, umami, or sour cells and that this gene is expressed in a similar taste cell population as TMEM44.

In another embodiment, the invention relates to the use of compounds that enhance or inhibit IKBKAP and SV2B gene products to selectively modulate taste cell function and responses to sour tastants as well as other functions of the PKD1L3 taste cell population.

In another embodiment, since IKBKAP is mutated in the human disease familial dysautonomia, where taste buds are absent or atrophic and individuals exhibit deficiencies in detection of sweet, bitter, sour, and salty tastants (hypogeusia) the invention relates to the discovery that IKBKAP expression in PKD1L3 cells may be important for taste cell development and/or maintenance.

In another embodiment since Botulinum neurotoxin (BoTox) enters neuronal-type cells by interacting with SV2B; the invention in another embodiment relates to the use of BoTox and derivatives to selectively modulate sour taste as well as other functions of the PKD1L3 taste cell population.

In another embodiment since KIT is expressed in umami taste cells the invention relates to the use thereof as a marker of this taste cell type.

In another embodiment the invention relates to the use of KIT and compounds that enhance or inhibit this gene product to selectively modulate taste cell function and responses to umami tastants.

In another embodiment the invention relates to the use of Gleevec (Imatinib), an inhibitor of the KIT tyrosine kinase activity, and other KIT tyrosine kinase inhibitors for selectively inhibiting umami taste.

In another embodiment the invention relates to the discovery that individuals with gain of function mutations in KIT, for example in gastrointestinal stromal tumors (GIST), may have altered umami taste perception.

In another embodiment since LOC285965 is expressed in T1R3 only taste cells similar to GPR113 the invention relates to the use as a marker for a unique, novel taste cell type (T1R3 only cells) that does not correspond to sweet, bitter, and umami taste cells.

In another embodiment the invention relates to the discovery that LOC285965 may correspond to the salt receptor or fat receptor or a receptor for astringency or metallic taste by itself or in combination with GPR113, which is also expressed in T1R3 only cells.

Also, the invention relates to the discovery that TUSC3, ASCL1, FAM26A, FAM26C, IKBKAP, LOC285965, SCNN1D, SLC4A11, SLC26A7, and TMEM30B may be used as biomarkers of specific taste cells and the isolated cells which express same as all of these genes are expressed by unique taste cell subsets comprised in primate taste buds and therefore can be used as biomarkers to isolate, enrich, mark or ablate these cells and thereby determine the taste related function of these taste bud cells.

In another embodiment the invention relates to the discovery that LOC285965 may be a coreceptor with T1R3 for specific sweet or umami tastants or other novel tastants such as astringent and metallic tastants.

In another aspect the invention relates to the discovery that compounds that enhance or inhibit LOC285965 can selectively modulate taste function and responses to tastants.

In another embodiment the invention relates to the discovery that LOC285965 may correspond to a marker of immature taste cells that are differentiating into sweet or umami cells.

In another embodiment the invention relates to the discovery that LOC285965 and compounds that enhance or inhibit this gene product can selectively modulate taste cell development and/or differentiation of specific taste cell types (i.e. sweet or umami taste cells).

Moreover, in a related embodiment this invention identifies a novel set of genes, i.e., FAM26A, GPR113, MCTP1, TMEM16G, TMEM30B, TMEM44, TUSC3, P8A1, FAM26B, SLC4A11, ASCL1 and MFSD4 and the aforementioned genes that are expressed in chemosensory or more specifically taste cells, e.g., primate fungiform or circumvallate macaque taste cells, and taste (e.g., fungiform, circumvallate, foliate, or palate) cells derived from other mammals such as humans and non-human primates. In some embodiments these genes are expressed in novel taste cells that do not express TRPM5 or PKD2L1/PKD1L3. These genes are referred to herein as "taste-specific" genes because they are strongly expressed in taste cells, preferably a previously unidentified taste cell type that may be involved in fat or salty taste perception. These taste-specific genes include genes which are directly or indirectly involved in taste detection and modulation, e.g., salty, umami, sweet, sour, fatty, metallic, or bitter taste transduction as well as including genes which are involved in biological functions not directly related to taste detection such as the modulation of digestion, taste cell turnover, regulation of the immune system, particularly of the oral cavity, and the regulation of metabolism e.g., carbohydrate metabolism, diabetes, obesity, cachexia, detection of food during digestion, et al.

In another embodiment the invention relates to the discovery that taste cells in the bottom half of the taste bud are immature.

In another embodiment the invention reveals that taste cells in the top half of the taste bud are mature and express genes for sweet, bitter, umami, and sour taste receptors.

In another embodiment the invention reveals SHH to be a marker of immature and developing taste cells at the bottom of the taste bud.

In another embodiment the invention reveals TMEM44 and MFSD4 to be markers of immature and developing taste cells at the bottom of the taste bud.

In another embodiment the invention reveals a subpopulation of TMEM44 cells may be mature salty taste cells.

In another embodiment the invention suggests that a salt receptor will be expressed in the top taste bud cells, since all other known taste receptors are expressed in the top taste bud cells.

In a related embodiment the invention suggests that a salty taste cell will be present in the top half of the taste bud since all other known professional, mature taste cells are expressed in the top of the taste bud.

In a specific embodiment this invention reveals TMEM44 cells, which comprise about 40% of the taste bud cell population and are located towards the bottom of the taste bud, and have identified that other genes are expressed by these cells or in the bottom of the taste bud including MFSD4 and Sonic Hedgehog (SHH) (a cytokine involved in immature cell differentiation). Based thereon, this invention predicts that cells expressing TMEM44 represent an immature taste cell population that includes stem cells that replenish the taste bud cells every 2-3 weeks in the human and while immature, they may comprise a subset of mature cells that may be responsible for salt sensation.

Also in a specific embodiment this invention reveals that GPR113 cells which represent about 10% of the taste bud cell population, are distinct from sweet, bitter, and umami taste cells, are located in the top of the taste bud, and express T1R3 and TRPM5 but not the G protein alpha subunit gustducin (GNAT3), suggesting that these cells represent a novel taste cell population that detects a novel taste modality such as fat.

Also in a specific embodiment this invention reveals the existence of another cell subset which express TRPM5 and T1R3 and which include sweet cells (which also express TIR2) as well as umami cells (which also express T1R1).

Also in a specific embodiment this invention reveals that bitter (T2R expressing taste cells) express TRPM5 but not T1R3.

Also in a specific embodiment this invention reveals that sweet, bitter, and umami cells express GNAT3 indicating that this gene can be used as a marker of these types of taste cells.

Also in a specific embodiment this invention reveals that PKD2L1 and PKD1L3 cells: (which cells have been previously described to be responsible for sour taste sensation) comprise about 10% of the taste bud cell population located in the top of the taste bud, and are heterogeneous, i.e. there are distinct PKD2L1 and PKD1L3 'single positive' cell populations in addition to a PKD2L1 and PKD1L3 'double positive' cell population suggesting that one of these subsets may represent a salt sensing cell.

Also in a specific embodiment this invention reveals the existence of another subset of taste cells (~8% of the taste bud cell population) that does not express any of the following markers: TMEM44, TRPM5, PKD2L1 or PKD1L3 which in addition or alternatively may represent a salt sensing cells.

More specifically, in a specific embodiment this invention provides a TMEM44 cell ablated non-human animal, e.g., a rodent.

Also, in a specific embodiment the invention provides taste cell suspensions consisting essentially of TMEM44 expressing taste cells.

Also, in a specific embodiment this invention provides a method of using the TMEM44 taste cell ablated animal (rodent) or the TMEM cell suspension for identifying the function of TMEM expressing cells in a taste modality, preferably salt or fat.

Also, in a specific embodiment the invention provides a GPR113 taste cell ablated animal, e.g., a rodent.

Also in a specific embodiment the invention provides taste cell suspensions consisting essentially of GPR113 expressing taste cells.

Also in a specific embodiment the invention provides a method of using the GPR113 taste cell ablated rodent or the GPR113 cell suspension for identifying the function of GPR113 expressing cells in a taste modality, preferably salt or fat.

Also, in a specific embodiment, the invention provides for PKD2L1 and/or PKD1L3 taste cell ablated animals, e.g., rodents.

Also, in a specific embodiment, the invention provides for taste cell suspensions consisting essentially of PKD2L1 and/or PKD1L3 expressing cells.

Also in a specific embodiment the invention reveals that the cells in the bottom half of taste buds are immature whereas taste cells in the top half of the taste bud are mature and express taste receptor genes. Cells in the bottom half of the taste bud express the gene sonic hedgehog (SHH), which is a marker of developing cells. TMEM44 taste cells are localized in the bottom half of the taste bud and the expression pattern of TMEM44 is similar to that of SHH. Thus, TMEM44 cells (which also express MFSD4) are immature and comprise, in part, developing taste cells. Supporting this finding, a small fraction of taste cells expressing TMEM44 also express either TRPM5 (a marker of mature sweet, bitter, and umami cells) or PKD1L3 (a marker of mature sour cells). Cells expressing both TMEM44 and TRPM5 (or PKD1L3) are, therefore, maturing into professional taste cells. By contrast, cells in the top half of the taste bud are mature taste cells, do not express SHH, and express taste receptor genes for the sweet, bitter, umami, and sour taste receptors. Since all mature, professional taste cells and taste receptors are localized to the top half of the taste bud, the salty taste cell and the salty taste receptor should also be present in the top half of the taste bud. Therefore, the invention demonstrates that taste cells in the bottom half of the taste bud are immature.

Also in a specific embodiment the invention demonstrates that taste cells in the top half of the taste bud are mature and express genes for sweet, bitter, umami, and sour taste receptors.

Also in a specific embodiment the invention demonstrates TMEM44 and MFSD4 are markers of immature and developing taste cells at the bottom of the taste bud.

Also the invention reveals a subpopulation of TMEM44 cells may comprise a mature salty taste cell.

SUMMARY OF THE INVENTION

This invention relates in general to novel and improved rationales for identifying (systematically and comprehensively) sets of primate genes which should encompass virtually all primate and human taste specific genes. Thereby, the invention provides a library of genes which will contain all primate and human taste receptors as well as taste specific genes involved in ancillary functions such as those relating to digestion, excretion and sodium ion related functions. These genes and gene products and cells expressing same are useful in screening assays for identifying taste modulators and therapeutics. A further advantage of the invention is that the invention provides methods for categorizing these genes into specific categories which should correlate to function thereby facilitating the number of genes to be functionalized by methods also provided in this application. More specifically, the invention has identified a subgenus of human and primate genes which will contain all taste receptors and taste modulators including those not yet identified. For example, this subgenus contained the salty taste receptor and in all likelihood other taste receptors involved in fat, metallic, CO2, astringent and the like.

Therefore, this invention in its more broad embodiments identifies genes that are expressed in chemosensory, e.g., human and non-human primate (macaque) fungiform and/or circumvallate papilla taste cells, and taste (e.g., fungiform, circumvallate, foliate, or palate) cells derived from other mammals such as humans and non-human primates ("taste specific"). These genes include genes which are directly or indirectly involved in taste detection and taste modulation, e.g., salty, umami, sweet, sour, fatty, metallic, or bitter taste transduction as well as functions not directly related to taste detection and taste modulation such as genes that are involved in the modulation of digestion and the production and composition of digestive fluids, mucous, enzymes and hormones such as saliva, stomach and intestinal fluids, GLP-1 (glucagon-like peptide 1), GIP (glucose-dependent insulinotrophic polypeptide), secretin, pepsin, and the like; genes that are involved in regulation of blood pressure and fluid retention, genes that are involved in taste receptor trafficking, taste cell turnover and taste cell regeneration, genes that are involved in the regulation of the immune system of the oral cavity and gastrointestinal system, genes that are involved in the prevention or onset of gastrointestinal related diseases such as cancers, inflammatory and autoimmune diseases affecting the oral cavity and digestive system, genes that are involved in the regulation of metabolism e.g., carbohydrate metabolism, obesity, eating disorders, genes that are involved in the detection of food during digestion, et al.

Relating to the foregoing the present invention provides genes that are expressed in human and non-human primate (macaque) chemosensory, e.g., primate (macaque) circumvallate and/or fungiform papilla taste cells that are not expressed or are expressed at significantly lower levels in lingual epithelial cells that are useful in screening assays, preferably high throughput screening assays, for identifying compounds that directly or indirectly modulate different taste modalities, e.g., salty, sweet, umami, bitter, sour, fatty, or metallic.

Further relating to the foregoing the present invention provides genes that are useful in screening assays, preferably high throughput screening assays for identifying compounds that are useful as therapeutics in the treatment of digestive system disorders, for modulating taste cell apoptosis or taste cell turnover, for inducing taste cell regeneration, for effecting the regulation of immunity in the oral cavity or digestive system, and the treatment of diabetes, obesity, eating disorders, and other metabolic disorders.

Also relating to the foregoing the invention provides a novel set of genes which are useful in the identification and/or isolation and/or enrichment of specific types or lineages of taste or chemosensory cells, e.g., taste or chemosensory cells that are involved in specific taste modalities, immune system regulation in the oral cavity, taste cell apoptosis or taste cell turnover, taste cell regeneration, digestive system regulation, and the regulation of metabolism such as by aiding in food detection, the secretion of hormones or enzymes involved in hunger and digestion, and the like.

Further, the invention relates to the use of the isolated chemosensory or taste cells in screening assays for identifying compounds that modulate taste, as well as in the identification of therapeutics for modulating the immune system regulation of the oral cavity, taste cell apoptosis turnover, taste cell regeneration, regulation of hormones or enzymes or fluids and mucous involved in digestion and other taste cell functions, treatment of digestive system disorders, treatment of diabetes, obesity, eating disorders, or other metabolic disorders, and the like.

This invention more specifically relates to novel rationale, methods, and assays including electrophysiological assays that identify and characterize novel taste-specific genes, including those that function as salty taste receptors.

It was hypothesized by the inventors (in part based on properties of known taste receptors) that human salty taste may be mediated, in part, by a sodium or other ion channels as well as transporters and GPCRs expressed specifically in taste-cells. Based on this assumption and other criteria provided infra, the invention provides methods for identifying taste-specific genes, including genes that may regulate salty taste, as well as other taste modalities taste cell mediated functions and phenotypes using gene chip and PCR methodologies. The compounds identified and their derivatives that modulate the activity of these target genes potentially can be used as modulators of human salty taste in foods, beverages and medicinals for human consumption. Also, such compounds and their derivatives potentially may be used to treat diseases involving aberrant ion channel function. Further the compounds identified using the genes identified herein and cells which express same are useful in therapeutic screening assays as discussed herein for identifying potential therapeutics that modulate other taste-cell related functions and phenotypes.

In one mode this invention identifies genes expressed in primate taste cells and use of these genes for screening for taste modulators and for identifying and isolating specific taste cell lineages and subtypes. These genes are identified based on their selective expression in primate fungiform papilla taste cells found at the front of the tongue and circumvallate papilla taste cells found at the back of the tongue using gene-chips microarrays from taste receptor cells as compared to non-taste lingual epithelial cells isolated by laser capture microdissection (LCM). Since salt perception is most prevalent at the front of the tongue, a salt receptor gene is likely contained within this set of identified genes.

In another mode, this invention provides a method for identifying a gene encoding a polypeptide involved in taste, preferably salty taste in a mammal. One embodiment of this method comprises the steps of (i) identifying a set of genes including genes which are expressed in macaque taste (fungiform and circumvallate papilla taste cells) but which are not expressed in lingual epithelial cells and/or genes which are expressed in taste cells at substantially higher levels than in lingual cells; (ii) identifying a subset of genes within the set of genes identified in (i) which are selected based on criteria which suggest that they are likely salt receptor candidates, i.e., putative ion channels and/or encode multidomain transmembrane proteins. These genes are then examined to determine whether these genes are expressed or not expressed in taste cells which express umami, sweet or bitter taste receptors (T1Rs or T2Rs) or sour taste receptors (PKD2L1/PKD1L3); and (iii) functionally expressing one or more genes in the subset identified according to (ii) and determining which of these genes function as a sodium responsive ion channel or sodium responsive receptor or transporter and thereby identifying this gene or genes as a putative gene that modulates salty taste. Typically, the taste tissues for this method are derived from human, primate, or rodent sources. In one preferred embodiment of the method, the genes in step (iii) function as sodium responsive ion channels, and more preferably, when the genes are expressed, a fraction of the channel population is open and passing sodium at rest.

In a preferred embodiment, step (i) comprises the use of laser capture microdissection (LCM) to dissect and purify taste tissues from non-taste tissues. In one mode of this embodiment, step (i) comprises RNA amplification of genes from taste cells and lingual cells and the amplified genes are screened against a gene chip containing a sample of genes specific to the particular mammal from which the taste and lingual tissues are obtained, and preferably, the gene chips include a set of annotated human genes. In an alternative mode of this embodiment, step (i) comprises high throughput PCR using primers for each ion channel in a mammalian genome.

In another preferred embodiment, step (ii) is effected by in situ hybridization using antisense RNA probes specific for the set of genes identified in step (i) to determine level of expression in taste versus lingual cells. In an alternative preferred embodiment, step (ii) is effected by use of immunochemical detection using a labeled antibody specific to the protein encoded by gene or genes identified in step (i).

In another embodiment of the method for identifying a gene encoding a polypeptide involved in salty taste perception in a mammal, the method of this invention comprises the steps of (i) identifying a set of macaque genes including genes which are expressed in taste cells but which are not expressed in lingual cells and/or genes which are expressed in taste cells at substantially higher levels than in macaque lingual cells; (ii) identifying a subset of genes within the set of genes identified in (i) which are not expressed in taste cells which express umami, sweet or bitter taste receptors (T1Rs or T2Rs) or sour taste receptors (PKD2L1/PKD1L3); and (iii) determining, in a primary neuron which expresses one or more genes in the subset identified according to (ii), which of said genes functions as a sodium responsive ion channel or sodium responsive receptor or transporter and thereby identifying this gene or genes as a putative gene that modulates salty taste. In one mode of this embodiment, step (iii) comprises contacting the neuron with an antibody which specifically binds the gene and inhibits its function.

Genes identified according to either of the methods described above may be characteristic of cells which do not express TRPM5 and PKD2L1/PKD1L3. In another mode, this invention provides a method to assist in selecting cells which do not express TRPM5 and PKD2L1/PKD1L3 by determining whether a cell expresses a gene identified according to the methods above. Preferably, the gene used in the method of this paragraph is one of the genes listed in Tables 1-3, listing taste-specific genes encoding transmembrane proteins in taste cells. Efforts were focused on transmembrane genes since all known taste receptor genes for sweet, bitter, umami, and sour taste encode transmembrane proteins.

In another aspect this application provides an improvement of the afore-described methods in which genes expressed in primate taste buds are identified and functionalized using the disclosed methods. The inventors have developed a rationale wherein they are able to assign gene expression patterns within the primate taste bud for all taste bud-specific genes. Specifically, using a comparison of gene expression between the top and bottom sections of the primate taste bud, the inventors have found that they are able to classify genes into one of several functional classes that include taste receptor genes. A subset of genes in this classification is likely to encode taste receptors that include those for salty taste and other yet to be defined taste specificities.

The rationale for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively, see FIG. 38.

In order to get more information on gene expression in both the top and bottom fractions of the taste bud the inventors isolate the corresponding fractions of primate taste buds using laser capture microdissection (LCM). This technique is described supra and briefly involves excision of specific groups of cells from tissue sections based on morphological distinctions. In the case of taste buds, the inventors are able to readily identify these structures in sections of primate tongue. As exemplified in the supporting experimental example infra, tissue collection was limited to taste buds in circumvallate papillae and then to only taste buds that were sectioned sagittally and at the taste pore. The inventors reasoned that only this type of section would reliably isolate top and bottom fractions. An example of sections used in sample collection is shown in FIG. 39.

The gene expression data obtained was queried to obtain three sets of genes. The first and second sets are genes that are expressed at a higher level in the top or bottom of the primate taste bud relative to the bottom or top respectively. Top-specific genes are listed in Appendix 1 and bottom specific genes are listed in Appendix 2. Accordingly, these lists contain top enriched and bottom enriched mRNAs. The third set of genes was identified as expressed at a higher level in the top of the primate taste bud relative to surrounding lingual epithelium. This set of taste bud-specific genes applications describing the identification of taste bud-specific genes by comparing gene expression between whole (top+bottom) taste bud and lingual epithelium LCM samples. These additional taste bud-specific genes are listed in Appendix 3.

This methodology achieves various advantages and makes certain discoveries including the following:

First, the inventors have found that taste receptor genes are expressed predominantly at the top of the taste bud. In contrast to prior knowledge, the data obtained using these methods clearly indicate that known taste receptor genes are expressed at a higher level in the top fraction of taste buds. It is reasonable to expect yet to be identified taste receptor genes are represented in the genes which are enriched at the top of the taste bud.

Second, the inventive top-versus-bottom gene classification methods allow for the functional classification of genes based on their expression in the cells in the top versus the bottom of the taste bud. Gene expression profiles at the top and bottom fractions of the taste bud suggest distinct functions for cell in each compartment. Functional classes of genes expressed in the top cells indicate that these are mature sensory cells whereas those expressed in the bottom cells indicate that these are immature progenitor cells associated with a basement membrane containing cellular environment. Examples of top-specific functional clauses include taste receptors, taste-specific signal transduction components and receptors. Examples of bottom-specific functional classes include matrix components, growth factors, and cell-cycle-associated proteins.

Third, this methodology allows for the identification of additional taste bud-specific genes. It has been found that by fractionating the taste bud into top and bottom compartments that the inventors have increased the sensitivity of mRNA detection in each compartment by a factor of about 2. This facilitates the identification of other taste specific genes not identified by the prior-described methods. These genes are contained in the Appendices to this patent application.

Therefore, these methods can be used to identify genes involved in different functions of the taste bud based on measuring their expression in the top versus bottom of the taste bud, e.g., where genes over-expressed in the top part of the taste bud. are predicted to be involved in one or more taste sensation, modulation of taste sensation, control of the lifespan of mature taste bud cells or they may be used as biomarkers of different mature taste cell subsets.

By contrast using the inventive rationale genes over-expressed at the bottom of the taste bud are predicted e.g., to be involved in one or more of the maintenance, differentiation and proliferation of taste-bud committed stem cells; or they will represent biomarkers of taste-bud committed stem cells.

In addition, genes expressed specifically in the top or bottom can be using to purify these functionally distinct taste bud cell subsets.

Also, in another aspect this invention describes rationales which are useful and have successfully identified human genes which are taste specific and which are predicted to be involved in one or more of the afore-described taste bud related functions. Specifically, these methods identify human taste specific genes by quantitative polymerase chain reaction (PCR). This also is an improvement of the afore-described methods for identifying taste specific genes, i.e., taste genes expressed in primate taste buds. and more optimally the previous described methods wherein the inventors assign gene expression patterns within the primate taste bud for all taste bud-specific genes; specifically, using a comparison of gene expression between the top and bottom sections of the primate taste bud. and thereby are e able to classify genes into one of several functional classes that include taste receptor genes.

By contrast, the third method demonstrates taste specific gene expression in humans (in addition to primate) and validates the specificity of expression by a quantitative method (qPCR or “TaqMan”). These methods have been used to identify genes contained in the Table 8 infra which all encode multi-span transmembrane proteins, and are predicted to include yet unidentified receptors and other genes involved in taste modulation including the fat and salt receptor and other taste receptors whose function has yet to be defined.

The previous methods which identify primate taste specific genes are useful as primates and humans are closely evolutionary related it is likely that gene expression pattern will also be closely related. Based on this reasonable assumption, taste specific genes identified by these methods (See Tables 1-4) were selected by the subject improved method to be validated in human taste buds using a technology distinct from microarray analysis—TaqMan qPCR.

As disclosed infra, these methods require a source of human taste buds. Human taste buds can be isolated by laser capture microdissection (LCM). This technique has been described supra and involves the excision and isolation of selected cells or groups of cells from tissue sections based on morphological distinctions. In the case of taste buds, these structures can be readily identified in sections of human tongue. In an exemplary embodiment (example 46 infra) tissue collection was limited to taste buds (TB) in circumvallate papillae and, as a control, cells from the adjacent lingual epithelium (LE). FIG. 47 which shows an example of sections used in sample collection, described in more detail in example 46). Essentially, multiple LCM preparations from different human donors are pooled (~4500 cells per sample), RNA extracted and amplified (e.g., by WT-Ovation Pico RNA Amplification System) (NuGEN Technologies, Inc) and analyzed using TaqMan technology to determine specific levels of gene expression in the TB and LE pools.

Thereafter, the expression of the taste-specific genes is quantified by TaqMan in LCM derived cDNA from both LE and TB from the same donors. Exemplary results using this methodology are contained in Table 8 infra. More specifically, gene expression is measured in TaqMan as a CT (cycle threshold) value. Briefly the CT value for a given sample is determined by the PCR cycle at which the amount of gene-specific PCR product (as measured by fluorescence) reaches a set value. For highly expressed genes, the threshold will be reached early in the PCR run and the CT value will be relatively low (<35) while genes with very low or no expression will not reach the threshold before cycle 35. Expression of genes with CT values >40 are defined as not detectable.

As can be seen from the data in Table 8, for the majority of genes which were identified as being human taste specific genes when assayed using this methodology, expression was not detected in LE samples (CT>40) but was readily detectable in TB samples (CT<35). This is significant outcome as this group of human taste specific genes has not been described before as taste-specific in human tissue.

In contrast to the afore described gene chip and microarray methods, this technique provides yet additional benefits. and discoveries including the following:

Firstly, these methods allow for human taste specific genes to be detected in human LCM cDNA which were not previously known to be taste specific. Particularly, this approach that uses LCM from post-mortem human tissue samples and a single cDNA amplification step, the data obtained to date clearly indicate that postmortem LCM human tissue can be used to quantify the expression of taste specific genes using qPCR.

Secondly, this methodology allows for the expression of human taste specific genes to be reliably and accurately measured by quantitative PCR (TaqMan) providing for the gene expression profiles of taste specific genes as measured by TaqMan. This methodology further validated gene expression data obtained from the previously described methods which used microarrays and/or in situ hybridization (ISH).

Thirdly, these methods have shown to indeed identify human taste bud specific genes which are functional. Particularly, by using the successive approaches of gene expression via microarray in primate LCM tongue tissue; Top-specific gene expression within the taste bud (akin to known taste receptors) and now TaqMan quantification of gene expression in human postmortem tastes tissues, the inventors we identified new human taste specific genes that had not been described previously. (Table 8)

Therefore, these methods allow for identification of human taste specific genes in postmortem tissues, and the identifying of human genes involved in different functions of the taste bud based on measuring their expression by quantitative PCR.

It is anticipated that these human taste specific genes, based on the manner that they were identified, expressed, and categorized are involved in one or more of (i) taste sensation, modulation of taste sensation, regulation of taste bud growth and development, control of the lifespan of mature taste bud cells, and/or are involved in the maintenance, differentiation and proliferation of taste-bud committed stem cells. In addition, genes identified using these methods are biomarkers of taste-bud committed stem cells. or represent biomarkers of different mature taste cell subsets. Therefore, these genes and gene products can be used as a basis in methods which enrich or purify these cell subsets.

In addition, as well as its more generic embodiments this invention further describes certain information and characterization of taste specific genes identified by the rationales described in detail infra. These discoveries are enumerated as follows:

Particularly, the invention describes with respect to the genes infra which are expressed in primate and human taste cell subsets and also describe specific uses of these genes, cells and gene products in taste biology. These genes which are selectively expressed in primate fungiform papilla taste cells at the front of the tongue and circumvallate papilla taste cells at the back of the tongue were identified were identified using the afore-described gene chips/microarray methods by comparing expression in taste receptor cells compared to non-taste lingual epithelial cells isolated by laser capture micro-dissection (LCM). Since salty taste perception is most prevalent at the front of the tongue, taste receptor genes including the salty taste and other taste receptor should be present within this gene set. The genes in Table 6 are expressed in different subsets of primate taste cells and were identified by gene chip analysis and shown to be expressed in subsets of taste cells by in situ hybridization analysis.

The results obtained contained in the examples reveal that FAM26A, MCTP1, TMEM30B, and TUSC3 are expressed in many TRPM5 cells, suggesting that these genes are expressed in sweet, umami, and bitter taste cells, since TRPM5 is a marker of sweet, bitter, and umami taste cells. Also, the results show that GPR113 and TMEM16G are expressed in a subset of TRPM5 cells, suggesting that these genes could be selectively expressed in sweet, umami, or bitter taste cells (or a combination thereof).

Also, these results show that TMEM44 is expressed in cells that do not express TRPM5 (bitter, sweet, umami) or PKD1L3 (sour), indicating that the expression of this gene is a marker for a unique taste cell type that could correspond to salt, fat, or another taste modality, and, furthermore, that this gene may encode the primary salt or fat receptor.

Based on the foregoing, the application teaches that FAM26A, MCTP1, TMEM30B, and TUSC3 can be used as markers for sweet, bitter, and umami taste cells or cells expressing TRPM5. In addition, FAM26A, MCTP1, TMEM30B, and TUSC3 and compounds that enhance or inhibit these gene products can selectively modulate taste cell function and responses to tastants including sweet, bitter, and umami.

In addition, these results indicate that GPR113 and TMEM16G can be used as a marker for sweet, bitter, or umami taste cells or subsets of TRPM5 cells. Also, the results indicate that GPR113 and TMEM16G and compounds that enhance or inhibit these gene products can selectively modulate taste cell function and responses to tastants including sweet, bitter, or umami.

Still further and based thereon this application teaches the use of these that TMEM44 can be used as a marker for a unique, novel taste cell type that does not correspond to sweet, bitter, and umami taste cells and that TMEM44 and compounds that enhance or inhibit this gene product can selectively modulate taste cell function and responses to tastants other than sweet, bitter, and umami, which include salt, fat, and other tastants.

Still further and based thereon this application teaches the use of these that TMEM44 may correspond to a salt receptor or fat receptor, or a marker of immature taste cells or stem cells. Also, TMEM44 and compounds that enhance or inhibit this gene product can selectively modulate taste cell development and/or differentiation of specific taste cell types (i.e. bitter taste cells).

Still further and based thereon this application teaches the use of these gene products and compounds that enhance or inhibit gene products can affect: selective apoptosis of taste cells responding to aversive taste modalities such as bitter and sour cells; modulation of transcription factors that control taste receptor expression; modulation of specific bitter receptor expression to minimize off-tastes of vegetables, children's medicine, and coffee; autocrine/paracrine modulation of taste cell development; prolongation of taste bud lifetime; development of supertasters (rodent model systems) to screen for chemical and biological toxins (terrorism), rancid/spoiled/contaminated food and beverage products; and activation of stem cells to differentiate into defined taste cell types.

Still further this application teaches the use of these gene products as ancillary taste receptors or primary taste receptors including receptors for salt, fat, and other taste modalities including metallic.

Still further this application teaches the use of these gene products and compounds that enhance or inhibit gene products, can modulate the function of any cell expressing a taste receptor, including but not limited to cells in the gastrointestinal tract such as enteroendocrine cells that regulate gastric motility and peptide secretion (e.g. GLP-1: glucagon-like peptide 1; GIP: gastric inhibitory peptide) as well as the other therapeutic applications of taste specific genes and modulators afore-mentioned. These applications include trafficking of taste receptors to and from the apical membrane/taste pore region to enhance or repress general or specific tastes; regulation of taste cell action potential firing frequency/membrane potential to control the intensity of general or specific tastes; regulation of neurotransmitter release to afferent nerve to control the intensity of general or specific tastes; and autocrine/paracrine modulation of taste receptor function; regeneration of taste cells as well as prophylaxis/prevention of taste cell loss following injury, chemotherapy for cancer, radiation therapy for cancer, drug-induced dysgeusia, ageusia, and taste bud loss in the geriatric population; oral hygiene, halitosis, detoxification of noxious substances in oral cavity, and neutralization/elimination of bacteria, viruses, and other immunogens in the saliva/mouth; saliva composition and treatment of dry mouth in conditions of xerostomia and autoimmune disease (Sjogren's syndrome).

Also, this application teaches using double label in situ hybridization histology what specific TRPM5 cell type that GPR113 is expressed in. As disclosed infra in the examples and supporting figure we identify that GPR113 is not expressed in T1R1 umami cells, T1R2 sweet cells, or T2R bitter cells. GPR113 is expressed in a subset of T1R3 cells that do not express T1R1 or T1R2. Thus, GPR113 cells define a new taste cell type of T1R3 only cells.

Therefore, this application teaches the use of GPR113 as a marker for this unique taste cell type that because it is in a unique cell population, is a GPCR (many taste receptors are known to be GPCRs) likely corresponds to a specific taste modality or modulates a specific taste modality such as CO2 sensation, salt, fat, metallic or astringent. Also, GPR113 may associate with T1R3 to form a novel taste receptor for sweet, umami, or other tastants.

Further based on the foregoing, this application teaches the use of GPR113 as a marker to identify and isolate this unique, novel taste cell type (T1R3 only cells) that does not correspond to sweet, bitter, and umami taste cells. and used to identify taste modulators and the aforementioned therapeutic applications of compounds modulating taste specific genes.

Also, the inseminators further identified using the same rationales (gene chip, in situ hybridization analysis) that the genes KIT, IKBKAP, LOC285965, and SV2B are taste specific taste cells and are expressed in the specific primate taste cell subsets (see Table 7 infra). In addition, we show infra that another gene, MFDS4, is expressed in sensory taste cells that are not sweet, umami, bitter or sour cells, suggesting that this gene is expressed in a similar taste cell subset as TMEM44.

Also, in Table 4 the application provides a listing of other primate taste-specific genes also identified by the same rationales. This listing of genes include genes encoding transmembrane proteins such as ion channels (sodium), GPCRs, ion transporters, as well as multi-transmembrane proteins with no function yet assigned. These genes and gene products are also useful in the same therapeutic and taste modulatory screening assays.

Based on the foregoing observations and the information in Table 7, the invention further teaches that since IKBKAP and SV2B are expressed in many PKD1L3 cells, that these genes are likely expressed in sour taste cells, since PKD1L3 is a marker of sour taste cells.

Also, based on the finding that KIT is expressed in cells that express the umami taste receptor component T1R1, the application teaches that KIT is likely expressed in cells responsible for umami taste perception.

Also, based on the finding (as determined by in situ hybridization of primate taste bud cells) that all of TUSC3, ASCL1, FAM26A, FAM26C, IKBKAP, LOC285965, SCNN1D, SLC4A11, SLC26A7, and TMEM30B are expressed by specific taste cell subsets that these genes may be used as biomarkers and that the genes and gene products may be used isolate, mark or ablate these cells and thereby determine the taste related function of these taste bud cells. Based on this same finding the invention further relates to these isolated cells and assays using these cells and genes to identify taste modulators.

Also, based on the finding that LOC285965 is expressed in cells that express TRPM5 and T1R3 but not in cells that express the umami taste receptor component T1R1, or the sweet taste receptor component T1R2; the application teaches that LOC285965 is expressed in the 'T1R3 only' population of taste cells (similar to GPR113).

Also, based on the experimental findings that IKBKAP and SV2B are expressed in PKD1L3 sour taste cells the application teaches that they can be used as markers of this taste cell population.

Also, based on these same experimental findings, the application further teaches that that IKBKAP and SV2B and compounds that enhance or inhibit these gene products can selectively modulate taste cell function and responses to sour tastants as well as other functions of the PKD1L3 taste cell population.

Also, based on these same findings and the fact that IKBKAP is mutated in the human disease familial dysautonomia, where taste buds are absent or atrophic and individuals exhibit deficiencies in detection of sweet, bitter, sour, and salty tastants (hypogeusia), this application teaches that IKBKAP expression in PKD1L3 cells may be important for taste cell development and/or maintenance.

Also, based on these same findings and the fact that Botulinum neurotoxin (BoTox) enters neuronal-type cells by interacting with SV2B; the application also teaches that BoTox may selectively modulate sour taste as well as other functions of the PKD1L3 taste cell population.

Also, based on the findings that KIT is expressed in umami taste cells, this application teaches its use as a marker of this taste cell type.

Also, based on these same findings, the application teaches that KIT and compounds that enhance or inhibit this gene product can selectively modulate taste cell function and responses to umami tastants.

Also, based on these findings and the fact that Gleevec (Imatinib), is an inhibitor of the KIT tyrosine kinase activity, this application teaches that this and other KIT tyrosine kinase inhibitors may selectively inhibit umami taste. Also, these findings suggest that individuals with gain of function mutations in KIT, for example in gastrointestinal stromal tumors (GIST), may have altered umami taste perception.

Also, based on the findings that LOC285965 is expressed in T1R3 only taste cells similar to GPR113, this application teaches that this gene can be used as a marker for a unique, novel taste cell type (T1R3 only cells) that does not correspond to sweet, bitter, and umami taste cells.

Also, based on these findings, the application also teaches that LOC285965 may correspond to the salt receptor or fat receptor or a receptor for astringency or metallic taste by itself or in combination with GPR113.

Also, based on these findings the application teaches that LOC285965 may be a coreceptor with T1R3 for specific sweet or umami tastants or other novel tastants such as astringent and metallic tastants.

Still further, based on these findings the application teaches that compounds that enhance or inhibit LOC285965 can selectively modulate taste function and responses to tastants.

Also, based on these findings the application teaches that LOC285965 may correspond to a marker of immature taste cells that are differentiating into sweet or umami cells.

Also, based on these findings the application teaches that LOC285965 and compounds that enhance or inhibit this gene product can selectively modulate taste cell development and/or differentiation of specific taste cell types (i.e. sweet or umami taste cells).

Also, based on experimental findings the application teaches suggest that MFSD4 and compounds that enhance or inhibit this gene product can selectively modulate taste cell function and responses to tastants other than sweet, bitter, umami, and sour which include salt, fat, and other tastants.

Also, based on experimental findings this application teaches that MFSD4 may correspond to the salt receptor or fat receptor. or may be used as a marker of immature taste cells or developing taste cells or support cells. Still further, these findings suggest that MFSD4 and compounds that enhance or inhibit this gene product can selectively modulate taste cell development and/or differentiation of specific taste cell types (i.e. bitter taste cells).

Also, based on experimental findings that reveal that MFSD4 and TMEM44 are expressed in the same taste cell population the application teaches that this cell may respond to specific tastants and also that MFSD4 and TMEM44 may form a complex (heterodimer) to generate a taste receptor (such as fat, CO2, salt, metallic, or other taste modality).

Also, we describe experimental findings have demonstrated (see results infra in the examples) that the ASCL1 (aka MASH1) transcription factor defines sour taste cells. ASCL1 is expressed in sour taste cells expressing the sour taste receptor gene PKD1L3; ASCL1 is not expressed in sweet, bitter, and umami taste cells expressing TRPM5. ASCL1 was previously reported to be a marker of type III taste cells. Type III taste are defined by morphological criteria which include: staining with an intermediate density by electron microscopy and making synaptic contacts with nerve fibers. Thus, these results demonstrate that type III taste cells, a cell type previously defined by morphological criteria, correspond to sour taste receptor cells defined by gene expression criteria.

This application describes that an application of this finding is that the ASCL1 transcription factor may bind to promoter elements in genes involved in sour taste perception. Thus, the genome could be screened for ASCL1 motifs to identify genes in sour cells, including sour receptor genes such as PKD2L1, PKD1L3, or additional genes that may form a complex with PKD2L1/PKD1L3 to generate a sour receptor.

Analogously, other taste receptor cells for sweet, bitter, umami, and salt are likely to express specific transcription factors that define those cell types. Therefore, this application teaches that the expression of all transcription factors in the genome can be analyzed in taste cells by PCR and/or histology to determine which taste cell types express which transcription factors.

The application further describes various other practical applications of these discoveries. For example, the ASCL1 (aka MASH1) can be used as a marker of sour taste cells and further identify and allow for the isolation of Type III taste cells which correspond to sour taste receptor cells.

Moreover, it has been determined that ASCL1 defines the sour taste cell lineage and may control sour taste cell development. Therefore, the invention teaches that ASCL1 transcription factor DNA binding sequences can be used to identify sour cell genes and sour taste receptor genes. Also, such transcription factors can be used to define, mark, and/or label taste cell types. With respect thereto, each taste cell will express one or more transcription factors that define that taste modality.

Also, the application teaches the use of the identified transcription factors that define taste modalities such as ASCL1 in cell ablation studies to specifically eliminate a specific taste. Moreover, the application teaches the use of transcription factors that define new taste cell types in cell studies to determine what taste modality is lacking (i.e. what taste can an animal no longer perceive).

Also, as described and supported by data infra, the invention has determined that taste cells expressing the PKD2L1 and PKD1L3 genes, previously implicated in sour taste are heterogeneous and comprise multiple cell populations. In the front of the tongue, in fungiform (FG) papilla there are cells expressing PKD2L1 only, PKD1L3 only, and both PKD2L1 plus PKD1L3. In the back of the tongue, in circumvallate papilla (CV), most cells coexpress PKD2L1 plus PKD1L3, but i addition to this population there is a distinct group of taste cells that express PKD1L3 only and a smaller set of cells that express PKD2L1 only. Previous literature has suggested that cells expressing PKD2L1 (encompassing PKD2L1 and cells coexpresing PKD2L1 plus PKD1L3) responded to sour taste (Huang et al, Nature 2006 Aug. 24; 442(7105):934-8. However, PKD1L3 cells were not previously known and no function has yet been ascribed. Based thereon, the application teaches the use of PKD1L3 cells as candidate basic or salty taste responding cells and that PKD1L3 is involved in a different taste modality, e.g., basic taste perception since the related sour receptor, PKD2L1, responds to acidic taste.

In addition the invention provides experimental findings that the FAM26C gene is expressed in TRPM5 cells (see results infra) and teaches its use as a marker of sweet bitter and umami cells.

Also, based on the experimental findings herein the application teaches that PKD1L3 only taste cells are candidate taste cells, e.g., which modulate basic taste sensation or other taste modalities, and that PKD1L3 is a candidate taste receptor, e.g., basic taste sensation. Also, the application teaches that PKD1L3 may complex with one of the gene products identified herein to form a taste receptor.

Also, based on the experimental findings that FAM26C is expressed in TRPM5 cells, including sweet, bitter, and umami taste cells, the application describes its use as a marker of this taste cell population and FAM26C and use of compounds that enhance or inhibit FAM26C to selectively modulate taste cell function and responses to sweet, bitter, and umami tastants as well as other functions of the TRPM5 taste cell population, including functions of the GPR113 expressing taste cells that are candidate salty taste cells and that coexpress T1R3.

Also, This application provides data shown infra, indicating that taste cells in the bottom of the taste buds are immature whereas cells in the top half are mature and express taste receptor genes. Cells in the bottom half of the taste bud express the gene sonic hedgehog (SHH), which is a marker of developing cells. TMEM44 taste cells are localized in the bottom half of the taste bud and the expression pattern of TMEM44 is similar to SHH. Therefore, this application teaches that TMEM44 cells, (which also express MFSD4) are immature and comprise, in part, developing taste cells. Further supportive of this finding, a small fraction of taste cells expressing TMEM44 also express either TRPM5 (a marker of mature sweet, bitter and umami cells) or PKD1L3 (a marker of mature sour cells). Cells expressing both TMEM44 and TRPM5 (or PKD1L3) are Therefore maturing into professional taste cells. By contrast, cells in the top half of the taste bud are mature taste cells, do not express SHH, and express taste receptor genes for the sweet, bitter, umami, and sour taste receptors. Since all mature, professional taste cells and taste receptors are localized to the top half of the taste bud, the salty taste cell and the salty taste receptor should be found in the top half of the taste bud as well.

Also, this application teaches methods for identifying and assaying the expression of taste specific genes and identifying specific taste receptors and taste cell subsets which have shown that the taste cells in the bottom half of the taste bud are immature, that the taste cells in the top half of the taste bud are mature and express genes for sweet, bitter, umami, and sour taste receptors, that SHH is a marker of immature and developing taste cells at the bottom of the taste bud. and that TMEM44 and MFSD4 are markers of immature and developing taste cells at the bottom of the taste bud.

The application predicts based on these results that a subpopulation of TMEM44 cells may be mature salty taste cells. and that a salt receptor and a salty taste cell will be expressed or comprised in the top taste bud cells, since all other known taste receptors are expressed in the top taste bud cells. This is a reasonable assumption based on the results obtained by the inventors herein, especially since all other known professional, mature taste cells are expressed in the top of the taste bud.

Also, based on experimental findings herein, and further relating to the foregoing, the inventors have gleaned the following information relating to several subsets of taste bud cells we have identified discussed above, including:

With respect to TMEM44 cells, they have found that these cells comprise about 40% of the taste bud cell population and are located towards the bottom of the taste bud. Also, we have identified other genes expressed by these cells or in the bottom of the taste bud including MFSD4 and Sonic Hedgehog (SHH). The latter is a cytokine involved in immature cell differentiation. For this reason, they predict that TMEM44 represents an immature taste cell population that includes stem cells that replenish the taste bud cells every 2-3 weeks in the human. While these cells are immature, they may still contain a subset of mature cells that may be responsible for taste such as salt sensation.

Also, with respect to GPR113 cells, they have discovered that these cells represent about 10° A of the taste bud cell population, and are distinct from sweet, bitter, and umami taste cells, and are located in the top of the taste bud. They express T1R3 and TRPM5 but not the G protein alpha subunit gustudin (GNAT3), suggesting that they represent a novel taste cell population that detects a new taste modality such as fat. Other cells that express TRPM5 and T1R3 include sweet cells (also express TIR2) as well as umami cells (also express T1R1). Bitter cells (also express T2Rs) express TRPM5 but not T1R3. In contrast to GPR113 cells, sweet, bitter, and umami cells all express GNAT3.

Also, with respect to PKD2L1 and PKD1L3 cells, reportedly responsible for sour taste sensation, they are found to constitute about 10% of the taste bud cell population and are located in the top of the taste bud. As discussed below, we have observed that these cells are heterogeneous and that there are distinct PKD2L1 and PKD1L3 'single positive' cell populations in addition to a PKD2L1 and PKD1L3 'double positive' cell population. This heterogeneity suggests that one of these subsets could represent a salt sensing cell.

Also, the experimental findings herein suggest that there is another subset of taste cells (~8% of the taste bud cell population) that does not express any of the following markers: TMEM44, TRPM5, PKD2L1 or PKD1L3, which may represent another taste e.g., CO2 or salt sensing cells. As disclosed a primary focus of this invention was the elucidation of the salty taste receptor. These results were successful as TRPML3 gene has been shown to be a salty taste receptor.

The invention further exploits the elucidation of these unique taste cell populations as part of its strategies for identifying salty and other types of taste sensing cells such as fat, metallic, astringent, CO2, et al.

The application provides different methods. For example, one way to identify the salt cell or other taste cell modality population is to use cell ablation. This technique employs diphtheria toxin under the control of a promoter of a gene expressed in one of the taste cell subsets described above to selectively eliminate this taste cell population, while leaving all other taste cell populations intact. Cell ablation has been used successfully in other laboratories to selectively eliminate sweet (T1R2) and sour (PKD2L1) taste cell populations (work of Charles Zuker). Therefore, ablation of the afore-identified taste cell subsets described above and then use nerve recoding and licking/behavior tests will enable evaluating whether the resulting mice still sense a particular type of tastant, e.g., salt, sour, basic, metallic et al. Based thereon, the inventors have made various predictions which will be confirmed or ruled out by the subject functional assays enumerated below:

(1) Assuming that TMEM44 ablated mice do not sense salt but still sense sweet, bitter, umami, and sour, this result would point this population, or a subset of cells within this population, as the salt sensing cell. Alternatively, the resulting mice may lack taste buds and the ability to detect all 5 taste qualities because TMEM44 is expressed in immature cells or may elicit no effect.

(2) Assuming that GPR113 ablated mice cannot sense salt but still sense sweet, bitter, umami, and sour, this result would point to GPR113 expressing cells as the salt sensing cells. (As noted TRPML3 cells have been shown to sense salt, therefore this outcome is not probable. More likely, another taste modality would be affected.)

(3) Assuming that PKD2L1 ablated mice cannot sense salt but still sense sweet, bitter, umami, and sour, this result would point to PKD2L1 expressing cells as the salt sensing cells. (Again, as TRPML3 cells have been shown to sense salt, this outcome is not probable. More likely, another taste modality would potentially be affected.)

(4) Assuming that PKD1L3 ablated mice cannot sense salt but still sense sweet, bitter, umami, and sour. This result would point to PKD1L3 expressing cells as the salt sensing cells. (Again, as TRPML3 cells have been shown to sense salt, this outcome is not probable. More likely, another taste modality would potentially be affected.)

(5) If none of these mice are deficient in salt perception, this suggests that the putative population of taste cells (8%) that do not express any of the aforementioned markers could be the salt sensing cell, or that all or multiple mature taste cell populations are capable of sensing salt.

Another means taught herein in order to identify the salt sensing cell involves generating a single cell suspension from taste buds and then performing single cell analyses with electrophysiology (patch clamping) or calcium imaging coupled with single cell PCR to identify which population(s) responds to sodium.

With respect to the foregoing assays, there are two main models to account for salt sensation in taste buds:

The first model is the labeled line model. In this model, a single cell type is responsible for sensing a given taste quality. This is true for sweet, bitter, umami and sour. In this model, there is a dedicated cell type responsible for salt sensation. As discussed above, and in the related utility application filed on even date, the inventors have narrowed down the list of candidate salt sensing cells and described techniques that have identified TRPML3 as a salt receptor and that TRPML3 expressing cells sense salty taste.

The second model is the across fibre model where there is not a single cell type responsible for salt sensation. Instead, all or multiple cell types sense salt. In this model, a cell surface molecule, such as a receptor or ion channel, expressed in all or multiple mature taste cells would constitute the salt sensor.

The way to distinguish between these two models is to perform cell ablation experiments such as are described above. Ablation experiments in Varitint mice depleted of TRPML3 taste cells indicate that these mice are deficient in their ability to taste salt. These results suggest TRPML3 expressing cells as being responsible for salty taste.

In yet another related aspect of the invention, the inventors teach three primate taste specific genes, TRPML3, NKAIN3 and NALCN, expressed in primate taste cells that were identified as taste specific genes by gene chip analysis, and shown to function as sodium channels in the literature. These genes were identified as being enriched in the top fraction of taste buds along with all other known taste receptor genes. Therefore, these genes were identified as probable candidates for encoding a salty taste receptor. As described in detail, and substantiated by extensive functional data in a related patent application filed on even date as this application, one of these genes, TRPML3 has been shown in functional assays and transgenic animals to be necessary for salty taste perception and to correspond to a salty taste receptor. These ion channel genes, are expressed as follows in the top versus the bottom of taste buds and in taste versus lingual epithelium tissues: NALCN, (aka VGCNL1), top vs. bottom ratio of 7.2, and TB vs. LE ratio of 11.2; TRPML3 (aka MCOLN3) top vs. bottom ratio of 1.6, and TB vs. LE ratio of 10.2; and NKAIN3 (aka FAM77D) which has a top vs. bottom ratio of 1.5, and TB vs. LE ratio of 3.3.

As reported in Cell. 2007 Apr. 20; 129(2):371-83, the neuronal channel NALCN contributes resting sodium permeability and is required for normal respiratory rhythm. Also, Lu et al. describe that NALCN as a sodium leak channel. Further, with respect to TRPML3, J. Biol. Chem. 2007 Oct. 25; [Epub ahead of print] teach that a gain-of-function mutation in TRPML3 causes the mouse varitint-waddler phenotype. Also, Kim et al., describes TRPML3 as a channel permeable to sodium after exposure of the channel to no/low sodium (as in saliva), consistent with a salt receptor. Also, with respect to the NKAIN 3 gene, in Gorokhova et al., Human Mol. Genet. 2007 Oct. 15; 16(20):3394-410. Epub 2007 Jul. 2, this gene is reported as a member of a novel family of transmembrane proteins interacting with {beta} subunits of the Na,K-ATPase. Also, Gorokhova et al., describes a *Drosophila* homologue of NKAIN3 as an amiloride-insensitive sodium channel, consistent with a salt receptor. Again, the TRPML3 gene and its functional properties and that it encodes a salty taste receptor and its therapeutic applications are discussed extensively in the utility and PCT patent applications filed on the same date as this application, incorporated by reference in their entireties herein Based on these observations and the experimental data therein and in this application, it was predicted and later confirmed that these 3 genes would include an ion channel that is involved in salty taste (TRPML3) Also, based thereon, this application teaches that NALCN, and NKAIN3 may constitute other salty taste receptors expressed in taste bud cells or may modulate the function of TRPML3 and/or may associate with TRPML3 to produce a functional taste receptor. Based on the foregoing, the application teaches the use of NALCN, and NKAIN3 as markers to identify salty taste receptor cells.

In addition, the application provides additional information in the examples concerning the NALCN taste-specific gene. Particularly, as described in the examples infra, the inventors demonstrated that NALCN is a taste-specific gene by end-point PCR using purified taste buds and lingual epithelial cells isolated by laser capture microdissection. They also found that NALCN is expressed in a novel, unique taste cell type distinct from sweet, bitter, umami, and sour taste cells by immunohistochemistry with a NALCN antibody.

Therefore, since NALCN is a taste-specific gene, is expressed in a novel taste cell type, and has been reported to function as a sodium-channel, the application teaches that NALCN is a candidate salty taste receptor and/or a marker of the salty taste cell population. Since NALCN and TRPML3 are both expressed in novel taste cell types, the application teaches that NALCN and TRPML3 may be co expressed in the same taste cell population. Accordingly, NALCN and TRPML3 may function together in a complex; or NALCN may function independently of TRPML3 as another salty taste receptor. For example, the application teaches that NALCN may function downstream of TRPML3 akin to how TRPM5 functions downstream of sweet, bitter, and umami receptors. In this manner, NALCN would be involved in the signal transduction pathway for salty taste but not constitute the primary salty taste sensory receptor.

This can be determined in mice. Rodents have 3 distinct taste cell types:

Type III cells correspond to sour cells (PKD2L1 positive, SNAP-25 positive);

Type II cells correspond to sweet, bitter, and umami cells (TRPM5-positive, IP3R3 positive); and Type I cells have no defined function.

As shown in the examples infra, the inventors have demonstrated that NALCN is not expressed in IP3R3 cells (Type II) or SNAP-25 cells (Type III) in rodent. Thus, NALCN expression is implicated in Type I cells, and Type I cells are candidate salty taste cells.

However, alternatively, the application teaches that Type I cells may correspond to immature taste cells and if so, would likely be coexpressed with TMEM44/MFSD4 in an immature taste cell population.

Based on the foregoing discoveries, the invention further teaches NALCN as an additional salty (or other taste such as metallic or fat) taste receptor candidate gene or accessory molecule and based thereon the use thereof as a marker to identify these taste cells.

In addition, since NALCN is a sodium ion channel, and is expressed in the top half of taste buds in cells that have an indeterminate taste function, the application teaches that NALCN may control the resting membrane potential and excitability of the taste cells it is expressed in. Related thereto, compounds that enhance or inhibit function of the NALCN channel may regulate the excitability of salty taste cells, i.e., TRPML3 cells.

Based on this modulatory property, the application teaches that compounds that enhance or inhibit function of the NALCN channel may increase and decrease salt perception respectively, e.g., alone or in combination with TRPML3.

In addition, this application teaches that NALCN may associate with TRPML3 to form a salty taste receptor. (Again, as shown in the related applications filed on even date the ablation of TRPML3 expressing taste cells in Varitint mice results in inhibition of salty taste perception in these rodents and in vitro electrophysiological assays using this ion channel have confirmed that it is a functional sodium channels and may be used to identify TRPML3 blockers and enhancers which should modulate salty taste).

Moreover, based on the experimental findings the application teaches that NALCN can be used as a marker of type I taste cells, which likely include salty taste cells. Alternatively, as type I taste cells may function as precursor cells for sweet, bitter, umami and sour taste cells, modulation of NALCN function may control taste cell differentiation and development into mature taste cell types.

In addition, because the application teaches that TMEM44 and MFSD4 are markers of immature taste cells, the application also teaches that NALCN may be expressed in the subset of immature taste cells expressing TMEM44/MFSD4.

Further, because type I taste cells may also function as glial (support) cells, the application teaches that modulation of NALCN function may indirectly control the activity of sweet, bitter, umami, and sour cells and, as a result, sweet, bitter, umami, and sour taste.

Also, the application teaches based on the experimental findings that compounds that enhance or inhibit function of NALCN may increase and decrease salt perception respectively.

In yet another aspect, this invention describes an assay for identifying a compound having potential in vivo application for modulating human salty taste. This method comprises the steps of (i) contacting a cell that expresses a gene encoding an ion channel, receptor or transporter identified as a putative salty taste affecting gene according to any one of the methods above, or a gene encoding a polypeptide possessing at least 90% sequence identity to the polypeptide encoded thereby, with at least one putative enhancer compound; (ii) assaying sodium conductance, receptor activity or sodium transport in the presence and absence of said putative enhancer; and (iii) identifying the compound as a potential salty taste enhancer based on whether it increases sodium conductance, the activity of said receptor or sodium transport. In various embodiments, the gene encodes an ion channel or the gene encodes a GPCR. Preferably, the gene is a human gene. More preferably, the method further includes testing the effect of the compound or a derivative thereof in a human taste test. Preferably, the selected compound promotes sodium ion transport into taste bud cells. The putative salty taste affecting gene may be expressed in an amphibian oocyte, or in a mammalian cell, preferably a *Xenopus oocyte* or a mammalian cell selected from the group consisting of a HEK293, HEK293T, Swiss3T3, CHO, BHK, NIH3T3, monkey L cell, African green monkey kidney cell, Ltk-cell and COS cell. Preferably, the putative salty taste affecting gene is expressed under the control of a regulatable promoter. The putative salty taste affecting gene may be expressed stably or transiently. In a preferred mode, the putative salty taste affecting gene is selected from tables 1-8.

In a preferred mode, the assay of step (ii) is an electrophysiological assay which uses a sodium sensitive dye, and preferred dyes include membrane potential dyes selected from the group consisting of Molecular Devices Membrane Potential Kit (Cat #R8034), Di-4-ANEPPS (pyridinium, 4-(2-(6-(dibutylamino)-2-naphthalen-yl)ethenyl)-1-(3-sulfopropyl) hydroxide, inner salt, DiSBACC4(2) (bis-(1,2-dibabituric acid)-triethine oxanol), Cc-2-DMPE (Pacific Blue 1,2-di-etradecanoyl-sn-glycerol-3phosphoethanolamine, triethylammonium salt) and SBFI-AM (1,3-benzenedicrboxylic acid, 4,4-[1,4,10-trioxa-7,13-diazacylopentadecane-7,13-diylbis(5-methoxy-6,1,2-benzofurandiyl)}bis-tetrakis {(acetyloxy)methyl}ester (Molecular Probes), more preferably, the sodium sensitive dye is sodium green tetraacetate (Molecular Probes) or Na-sensitive Dye Kit (Molecular Devices). In another preferred mode, the assay of step (ii) is a two electrode voltage clamping assay in *Xenopus oocytes*, or the assay is a patch clamp assay in mammalian cells. Preferably, the assay measures activity by an ion flux assay, including using atomic absorption spectroscopy to detect ion flux.

Alternatively, the assay may use a fluorescence plate reader (FLIPR), or a voltage imaging plate reader (VIPR), which is used to increase ion channel-dependent sodium or fluid absorption. In a preferred embodiment of this method, the activity of the putative salty taste affecting gene is assayed in a frog oocyte electrophysiologically by patch clamping or two electrode voltage clamping, preferably using an automatic imaging instrument, which may be a fluorescence plate reader (FLIPR) or a voltage imaging plate reader (VIPR).

In yet another mode, this invention describes an assay for identifying a compound having potential in vivo application for modulating human sweet, bitter, umami, or sour taste. This method comprises the steps of (i) contacting a cell that expresses a gene in Tables 1-8 with at least one putative enhancer or blocker compound; (ii) assaying sodium conductance, receptor activity or taste gene product function in the presence and absence of said putative enhancer or blocker; and (iii) identifying the compound as a potential enhancer or blocker for sweet, bitter or umami taste based on whether it modulates sodium conductance, the activity of said receptor or taste gene product function.

In yet another mode, this invention describes an assay for identifying a compound having potential in vivo application for as a potential therapeutic. This method comprises the steps of (i) contacting a cell that expresses a gene in Tables 1-3 with at least one putative enhancer or blocker compound; (ii) assaying sodium conductance, receptor activity or taste gene product function in the presence and absence of said putative enhancer or blocker; and (iii) identifying the compound as a potential therapeutic that may be used to modulate a taste cell related function or phenotype that does not directly involve taste such a digestive disorder or disease, taste cell or taste bud turnover or regeneration, immune regulation of the oral or digestive system, or treatment of a metabolic disorder such as diabetes, obesity, eating disorder et al., based on whether it modulates sodium conductance, the activity of said receptor or taste gene product function.

In yet another mode the present invention describes using the genes identified herein as markers to identify and/or purify specific taste cells including sweet, bitter, umami, sour, and other cells including stem cells. These methods include positive and negative cell isolation and selection methods and selection and are based on the expression or absence of expression of one or several of the genes contained in Tables 1-3, or an allelic variant or ortholog or gene that hybridizes thereto under stringent hybridization conditions and/or a gene encoding a polypeptide that is at least 80% identical to the polypeptides or orthologs thereof encoded by the genes contained in Table 1-3, moiré preferably at least 90% identical and still more preferably at least 95% identical. In one embodiment, antibodies directed against the proteins encoded by these genes produced by methods well known to those skilled in the art can be used to label cells in a suspension of taste bud cells produced by enzymatic digestion and tissue disaggregation (Herness, M. An exemplary dissociation procedure for mammalian taste buds. is reported in Neuroscience Letters. 106: 60-64, 1989). The separation can be achieved by using a fluorescence activated cell sorter (See e.g., Beavis, A. J. and K. J. Pennline. Biotechniques. 21: 498-503, 1996) or by magnetic beads (See e.g., Jurman, M. E., L. M. Boland, Y. Liu, and G. Yellen. Visual identification of individual transfected cells for electrophysiology using antibody coated beads. Biotechniques. 17: 876-881, 1994). Alternatively, cells belonging to a specific subset can also be purified by negative selection methods, e.g., by eliminating taste bud cells representing other subsets using cytotoxic antibodies against their specific markers produced using methods well known to those skilled in the art) from a cell suspension of taste bud cells.

Figure 17:
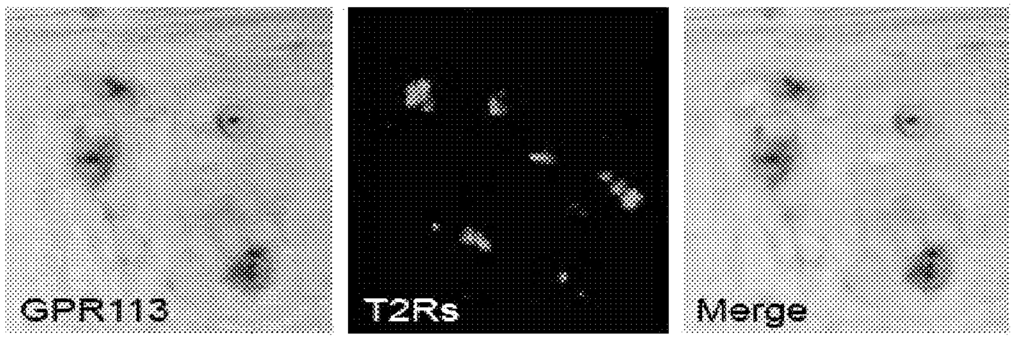

FIG. 17 shows that GPR113 is not expressed in T2R bitter cells. Double label in situ hybridization of primate circumvallate papilla showing that GPR113 (purple color; left image) does not colocalize with T2R (red; middle image). Note that GPR113 and T2R, a marker of bitter cells, are in different taste cells (merged image on the right).

Figure 18:
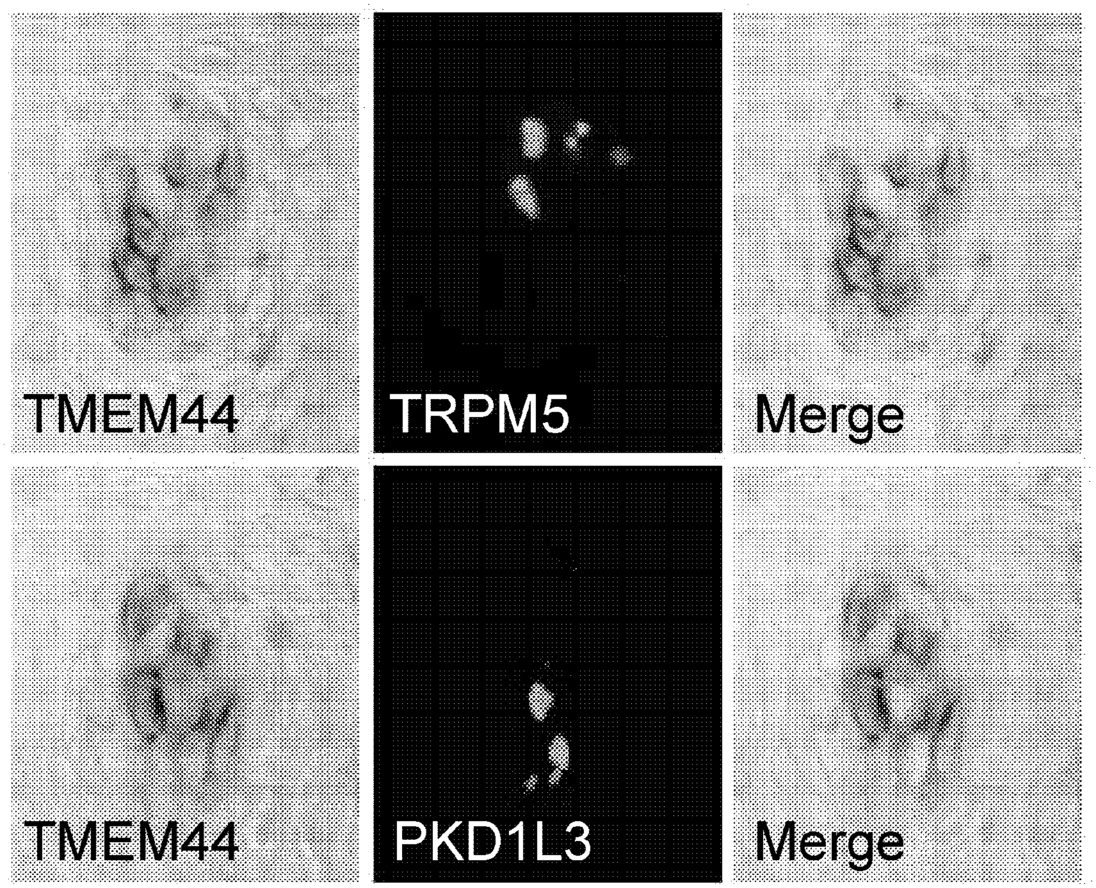

FIG. 18 shows that TMEM44 is not expressed in TRPM5 or PKD1L3 cells in fungiform taste buds. Double label in situ hybridization of primate fungiform papilla from the front of the tongue showing that TMEM44 (blue/purple color; left images) does not colocalize with TRPM5 (red; middle top image) or PKD1L3 (red; middle bottom image). Note that TMEM44 cells do not express TRPM5, a marker of sweet, umami, and bitter taste cells, or PKD1L3, a marker of sour cells, in the merged images on the right.

Figure 19:
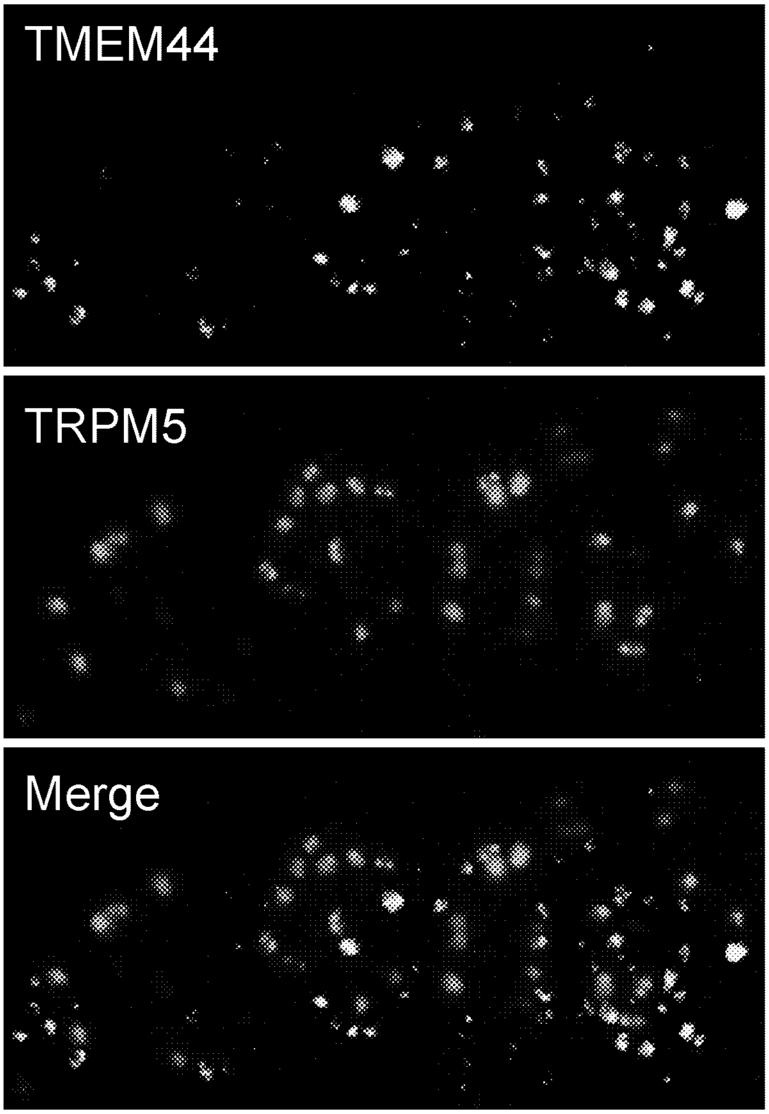

FIG. 19 shows that TMEM44 is not expressed in TRPM5 cells in circumvallate papilla. Double fluorescent label in situ hybridization of primate circumvallate papilla at the back of the tongue showing that TMEM44 (green cells; top image) does not colocalize with TRPM5 (red cells; middle image). Note that TMEM44 cells do not express TRPM5, a marker of sweet, umami, and bitter taste cells (merged image on the bottom).

Figure 20:
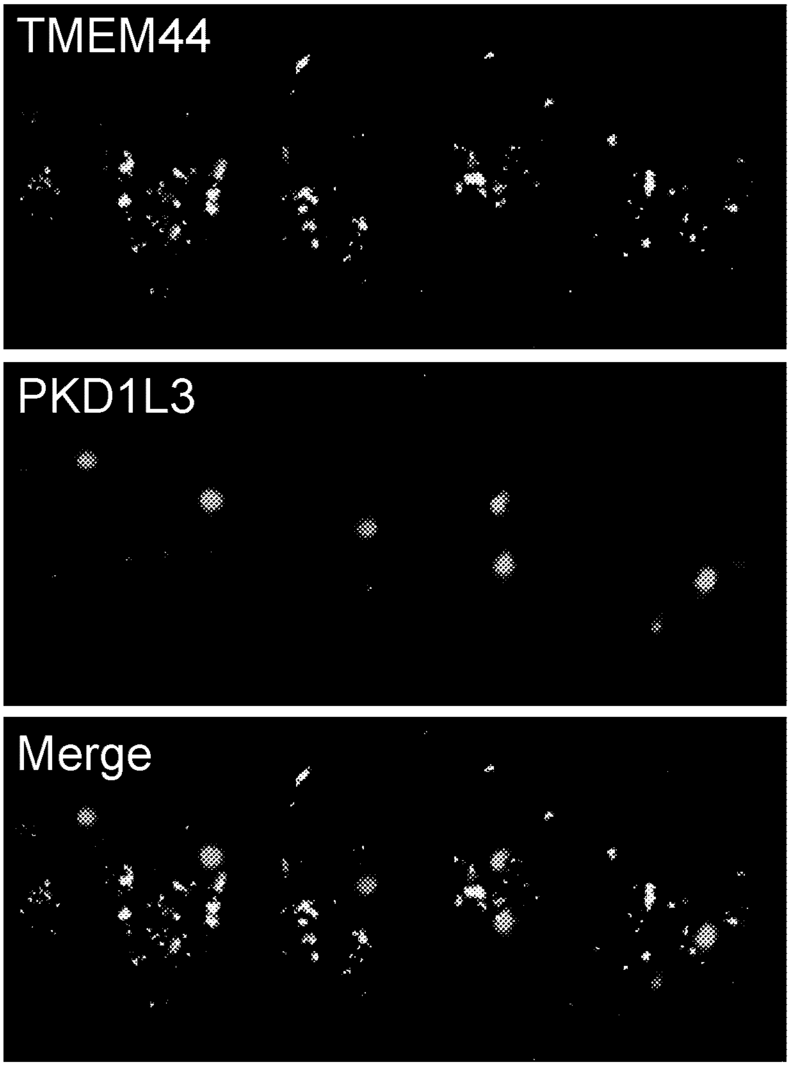

FIG. 20 shows that TMEM44 is not expressed in PKD1L3 cells in circumvallate papilla. Double fluorescent label in situ hybridization of primate circumvallate papilla at the back of the tongue showing that TMEM44 (green cells; top image) does not colocalize with PKD1L3 (red cells; middle image). Note that TMEM44 cells do not express PKD1L3, a marker of sour taste cells (merged image on the bottom).

Figure 21:
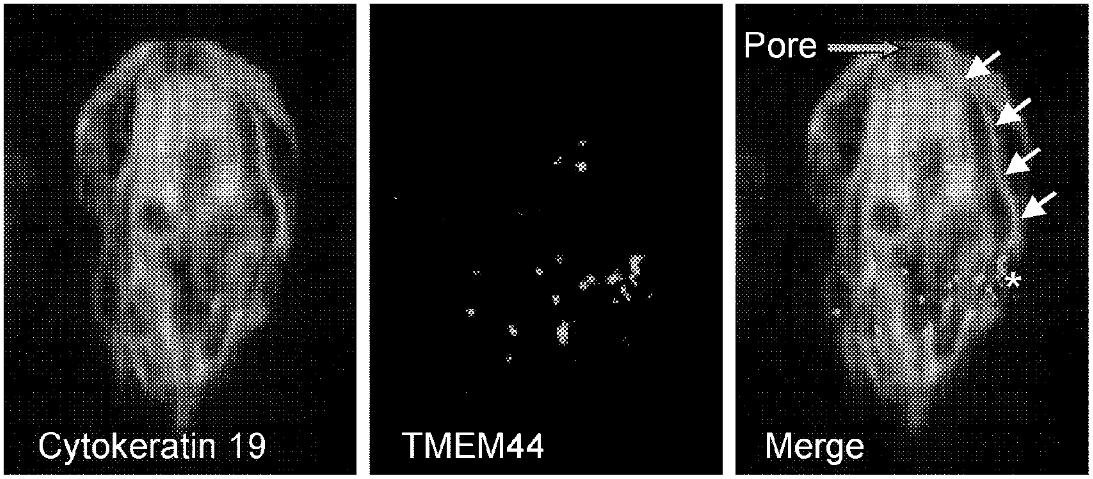

FIG. 21 shows that TMEM44 cells extend processes to the taste pore. Double label histology experiment of primate circumvallate papilla at the back of the tongue. Cytokeratin 19 protein (green; left image) is present in cells expressing TMEM44 RNA (red; middle image). Note that TMEM44 cells extend processes to the taste pore facing the saliva. Asterisk denotes a TMEM44 cell nucleus and white arrows denote the apical process of this same cell extending to the taste pore (merged image on the right). Thus, TMEM44 cells are sensory taste cells that can sample the saliva for tastants. Cytokeratin 19 is a marker of all taste cells.

Figure 22:
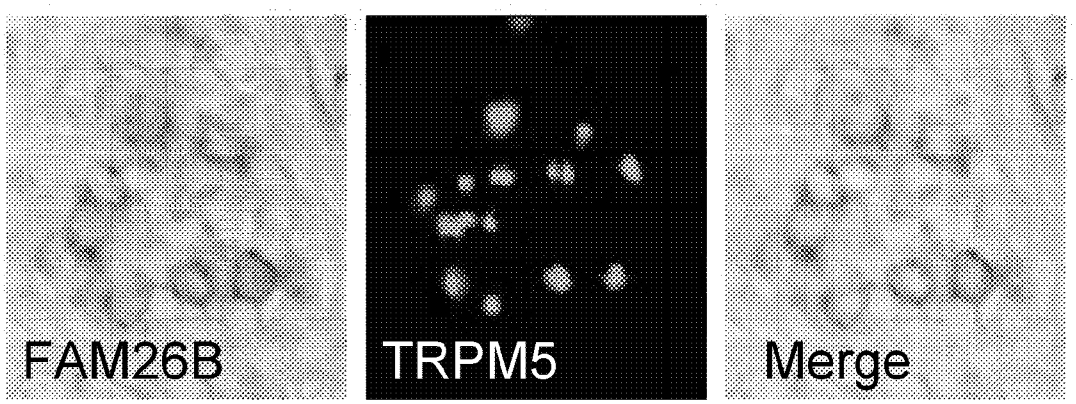

FIG. 22 shows that FAM26B is expressed in TRPM5 cells Double label in situ hybridization of primate circumvallate papilla showing that FAM26B (blue/purple color; left image) colocalizes with TRPM5 (red; middle image). Note that FAM26B cells express TRPM5, a marker of sweet, umami, and bitter taste cells (merged image on the right).

Figure 23:
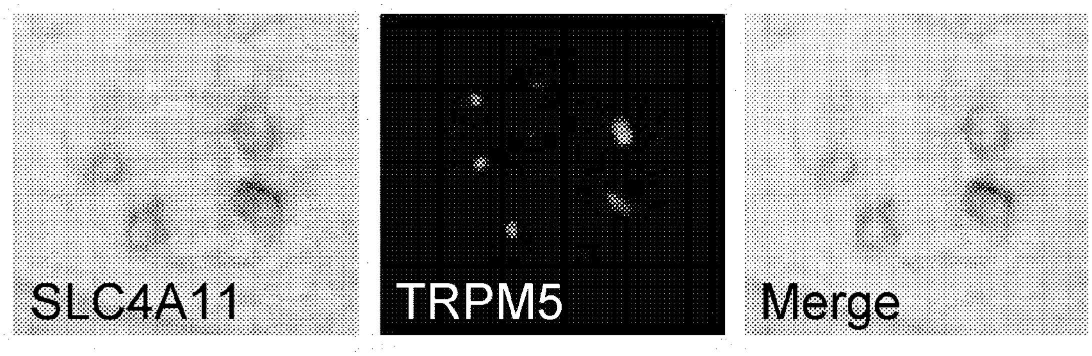

FIG. 23 shows that SLC4A11 is expressed in TRPM5 cells. Double label in situ hybridization of primate circumvallate papilla showing that SLC4A11 (blue/purple color; left image) colocalizes with TRPM5 (red; middle image). Note that SLC4A11 cells express TRPM5, a marker of sweet, umami, and bitter taste cells (merged image on the right).

Figure 24:
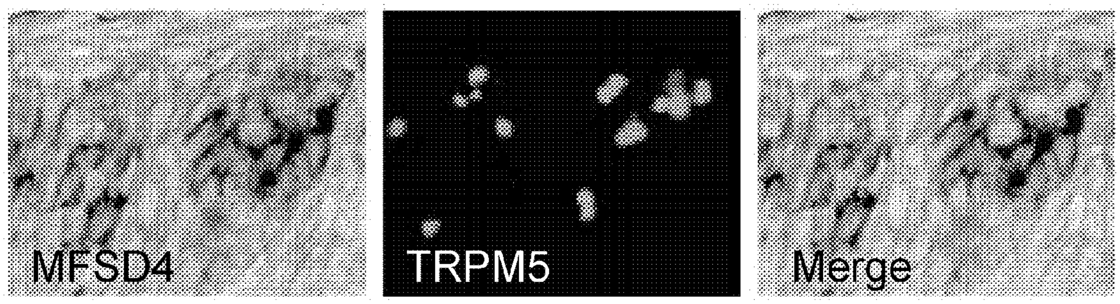

FIG. 24 reveals that MFSD4 is not expressed in TRPM5 cells. Double label in situ hybridization of primate circumvallate papilla showing that MFSD4 (blue/purple color; left image) does not colocalize with TRPM5 (red; middle image). Note that MFSD4 cells do not express TRPM5, a marker of sweet, umami, and bitter taste cells (merged image on the right). Two taste buds are shown.

Figure 25:
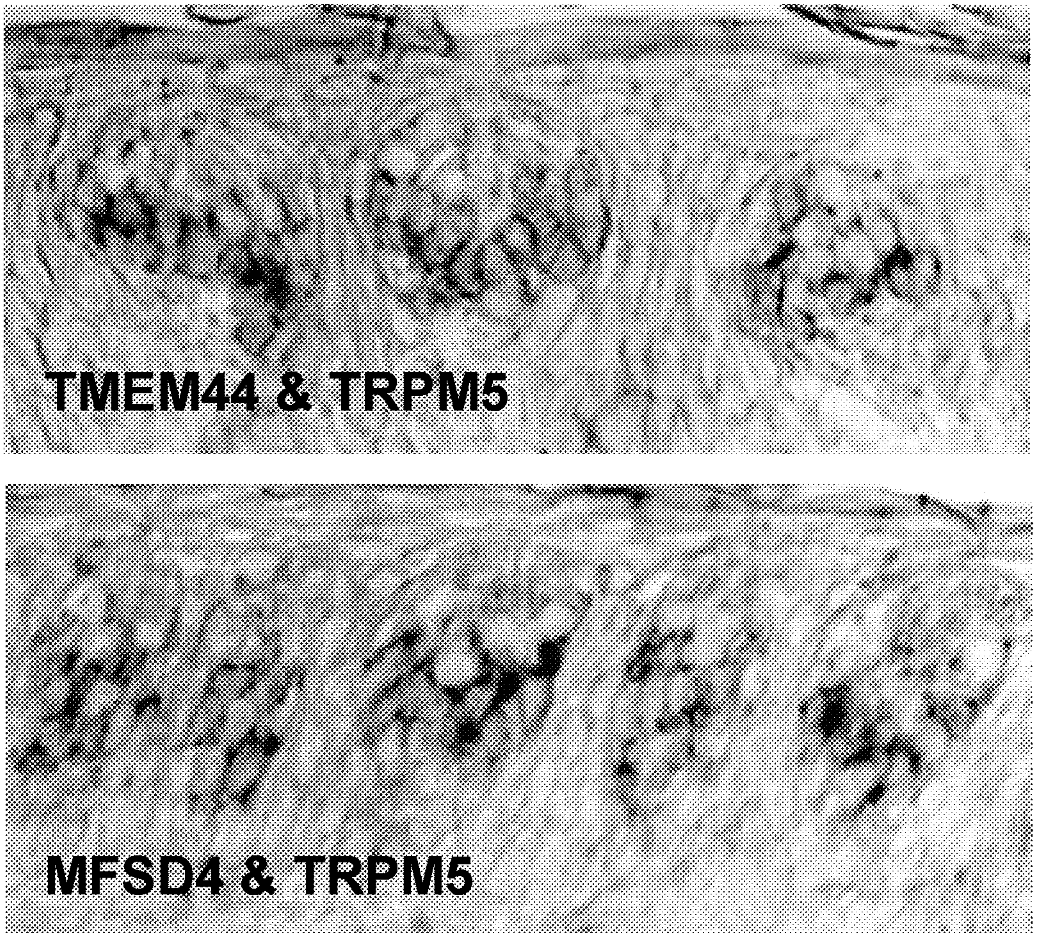

FIG. 25 shows that MFSD4 and TMEM44 are expressed in the same taste cells. Double label in situ hybridization of primate circumvallate papilla showing that MFSD4 and TMEM44 are expressed in the same taste cell population. TMEM44 (top blue/purple color) and MFSD4 (bottom blue/purple color) do not colocalize with TRPM5 (red color top and bottom images) and are expressed in taste cells in the bottom halves of taste buds. The equivalent localization, abundance, and morphology of TMEM44 and MFSD4 taste cells indicates that these cells are identical and that both TMEM44 and MFSD4 genes are expressed in the same taste cell type.

Figure 26:
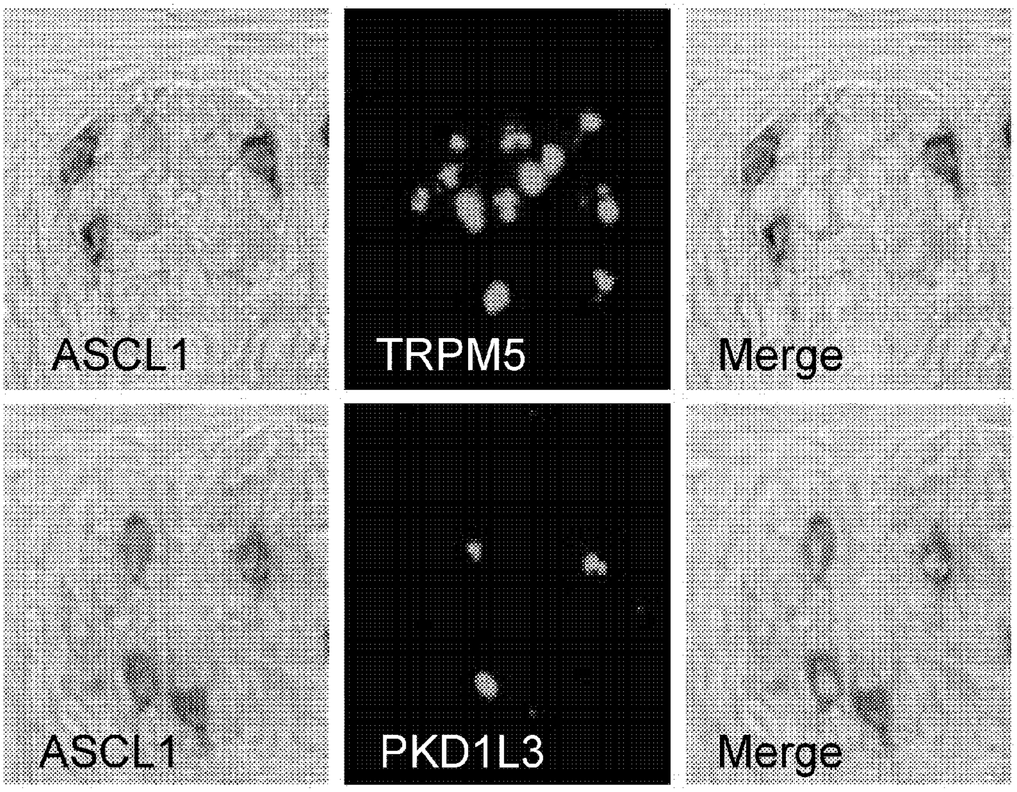

FIG. 26 shows that ASCL1 is expressed in sour taste cells but not sweet, bitter or umami taste cells. Double label in situ hybridization of primate circumvallate papilla from the back of the tongue showing that ASCL1 (blue/purple color; left images) does not colocalize with TRPM5 (red; middle top image) but does colocalize with PKD1L3 (red; middle bottom image). Note that ASCL1 cells do not express TRPM5, a marker of sweet, umami, and bitter taste cells, but do express PKD1L3, a marker of sour cells, in the merged images on the right.

Figure 27:
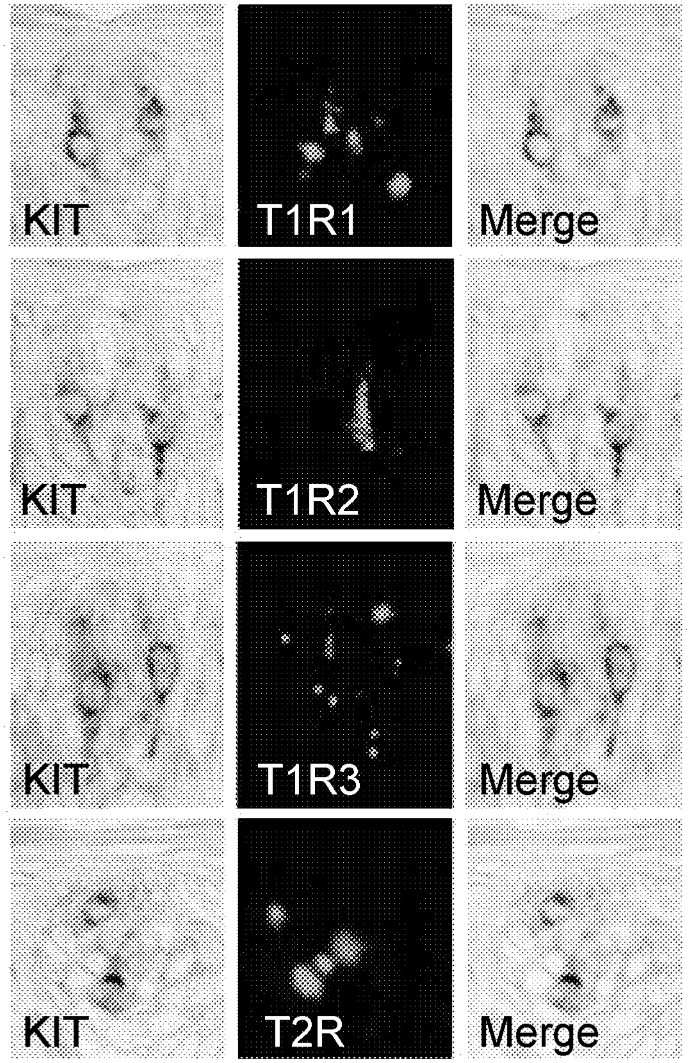

FIG. 27 shows that KIT is expressed in T1R1 umami taste cells. Double label in situ hybridization of primate circumvallate papilla from the back of the tongue showing that KIT (blue/purple color; left images) colocalizes with T1R1 (red; middle image top row), does not colocalize with T1R2 (red; middle image $2^{nd}$ row), does colocalize with T1R3 (red; middle image $3^{rd}$ row), and does not colocalize with T2Rs (red; middle image bottom row). Note that KIT cells express T1R1 and T1R3, markers of umami taste cells, but not T1R2 or T2Rs, markers of sweet and bitter cells respectively, in the merged images on the right.

Figure 28:
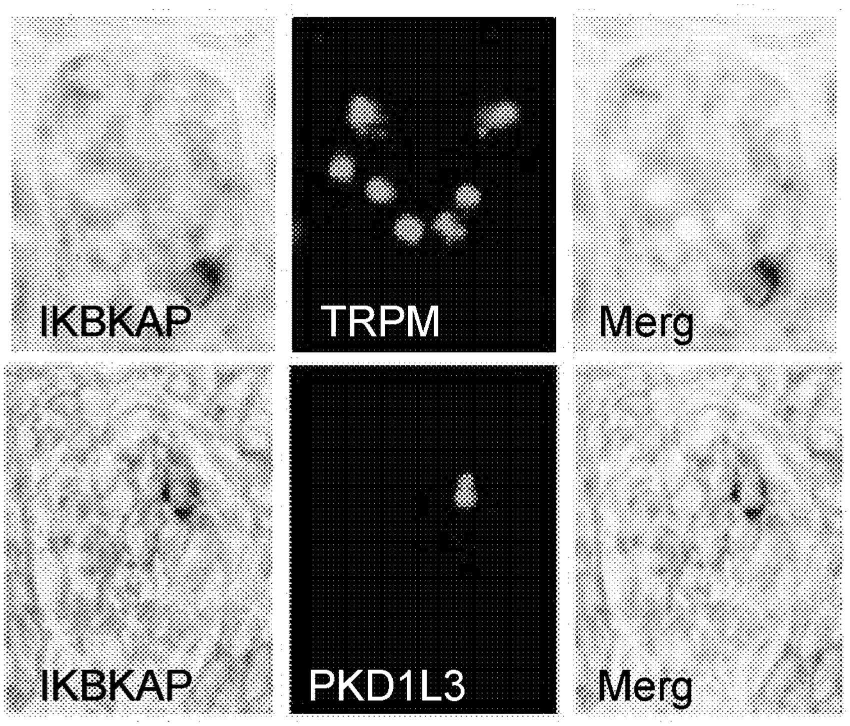

FIG. 28 shows that IKBKAP is expressed in PKD1L3 sour taste cells. Double fluorescent label in situ hybridization of primate circumvallate papilla at the back of the tongue showing that IKBKAP (blue/purple color; left images) does not colocalize with TRPM5 (red; middle image top) but does colocalize with PKD1L3 (red; middle image bottom). Note that IKBKAP cells express PKD1L3, a marker of sour taste cells (merge image bottom) but do not express TRPM5, a marker of sweet, umami, and bitter taste cells (merged image top).

Figure 29:
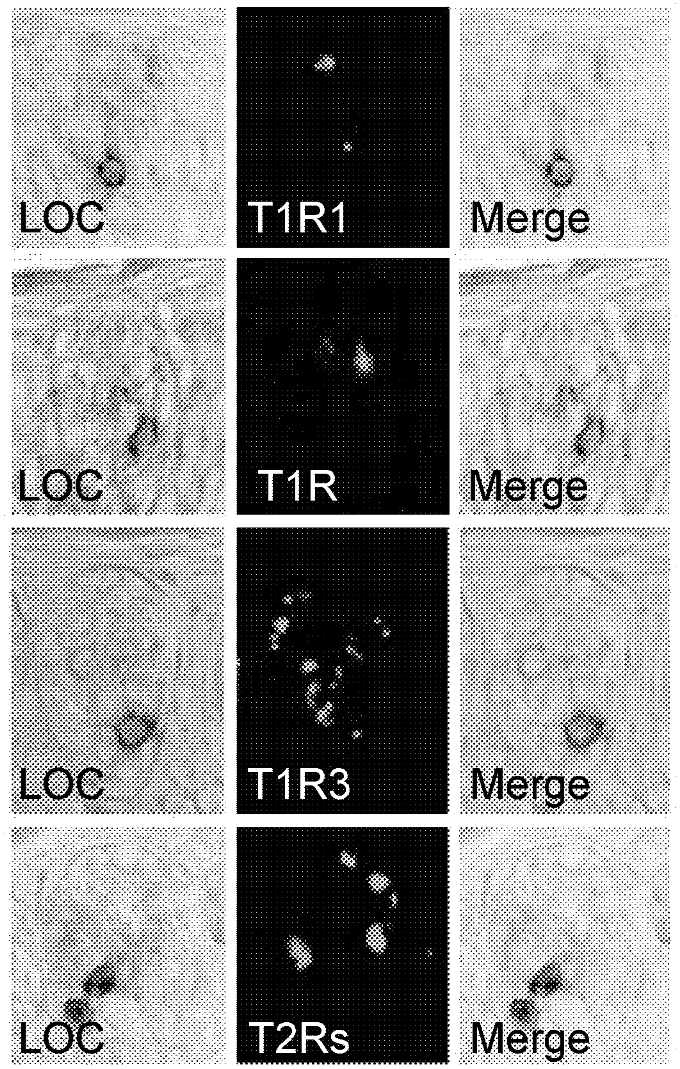

FIG. 29 shows that LOC285965 is expressed in T1R3 only taste cells. Double label in situ hybridization of primate circumvallate papilla from the back of the tongue showing that LOC285965 (blue/purple color; left images) does not colocalize with T1R1 (red; middle image top row), does not colocalize with T1R2 (red; middle image $2^{nd}$ row), does colocalize with T1R3 (red; middle image $3^{rd}$ row), and does not colocalize with T2Rs (red; middle image bottom row). Note that LOC285965 cells express T1R3, but not T1R1, T1R2 or T2Rs, markers of umami, sweet and bitter cells respectively, in the merged images on the right.

Figure 30:
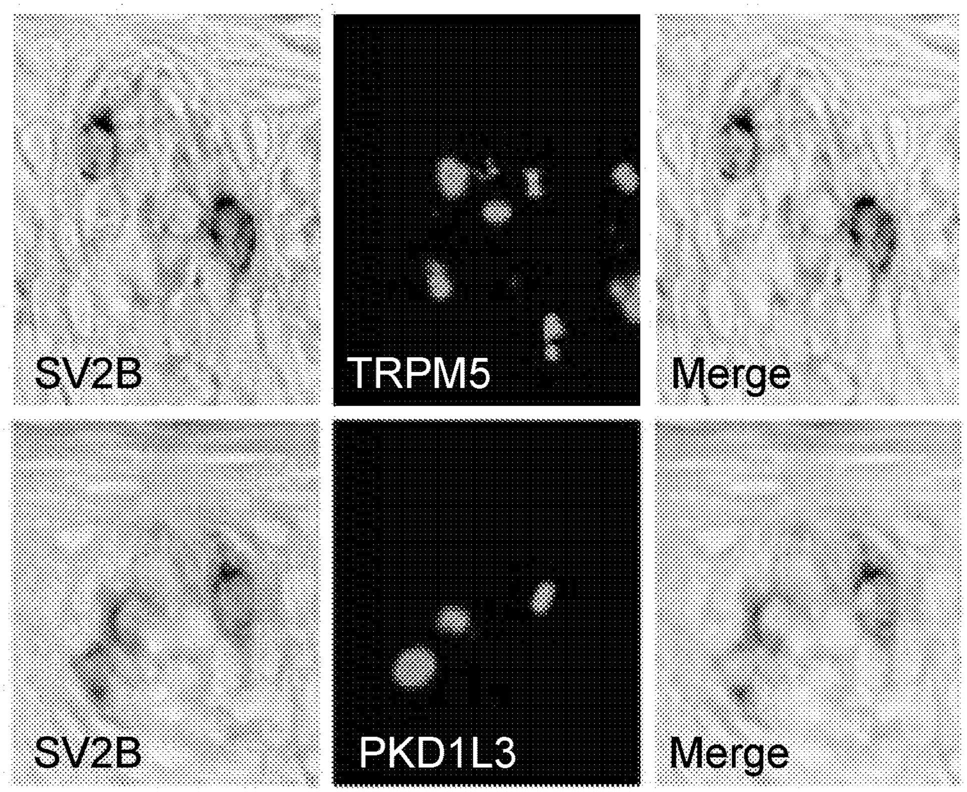

FIG. 30 shows that SV2B is expressed in PKD1L3 sour taste cells. Double fluorescent label in situ hybridization of primate circumvallate papilla at the back of the tongue showing that SV2B (blue/purple color; left images) does not colocalize with TRPM5 (red; middle image top) but does colocalize with PKD1L3 (red; middle image bottom). Note that SV2B cells express PKD1L3, a marker of sour taste cells (merge image bottom) but do not express TRPM5, a marker of sweet, umami, and bitter taste cells (merged image top).

Figure 31:
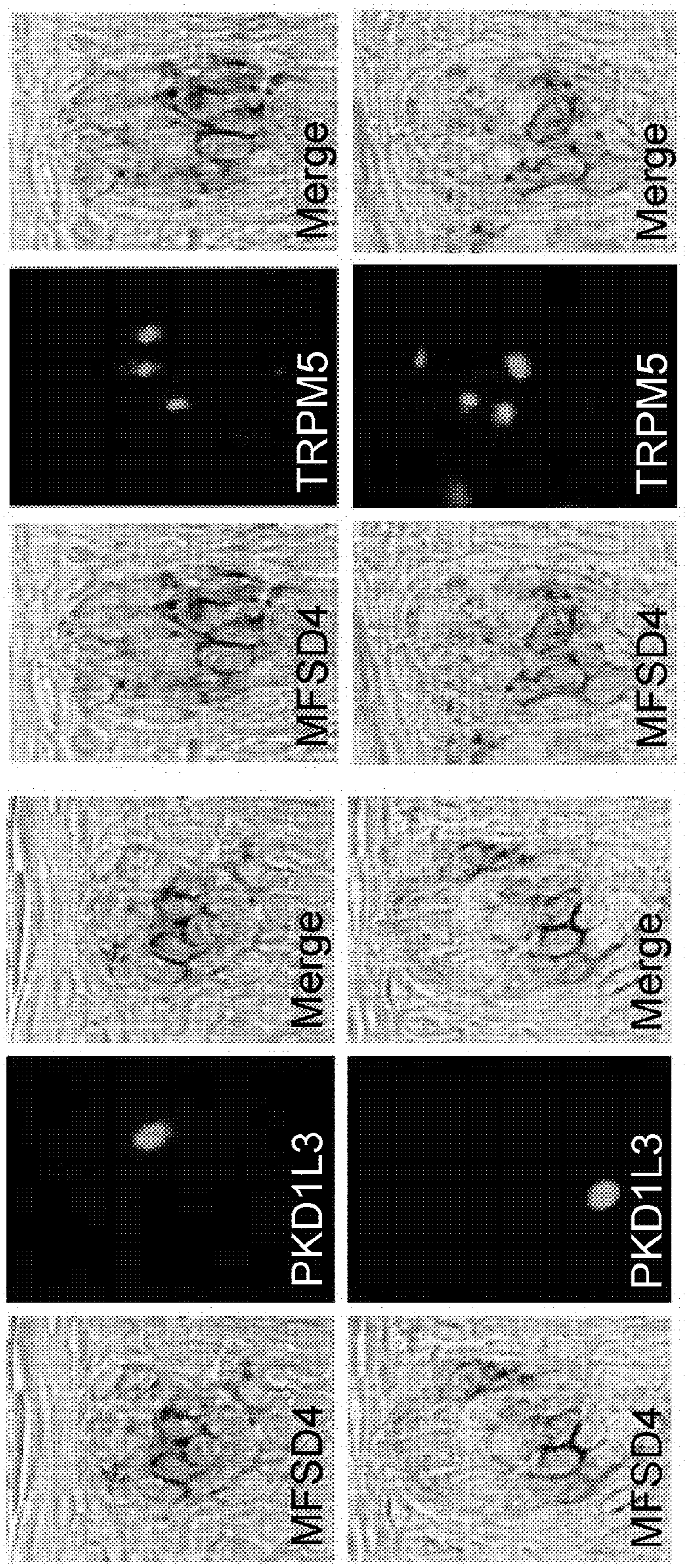

FIG. 31 shows that MFSD4 is expressed in a unique taste cell type. Double label in situ hybridization of primate circumvallate papilla showing that MFSD4 (blue/purple color; left image) does not colocalize with PKD1L3 or TRPM5 (red; middle images) but is expressed in a unique taste cell type. Note that MFSD4 cells do not express PKD1L3, a marker of sour taste cells or TRPM5, a marker of sweet, umami, and bitter taste cells (merged images on the right). Two taste buds each are shown for PKD1L3 & TRPM5 double labels.

Figure 32:
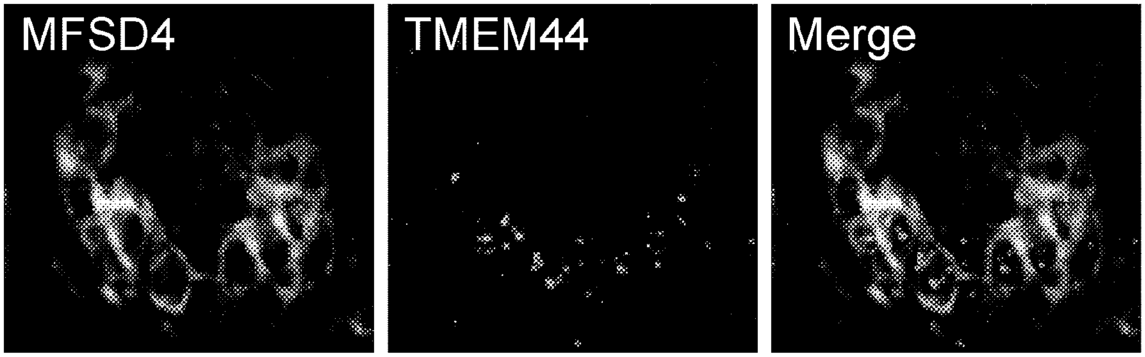

FIG. 32 shows that MFSD4 and TMEM44 are expressed in the same taste cell population. Double label in situ hybridization of primate circumvallate papilla showing that MFSD4 and TMEM44 are expressed in the same taste cell population. MFSD4 (left; green) and TMEM44 (middle; red) signals are present in the same taste cells (right; merged image).

Figure 33:
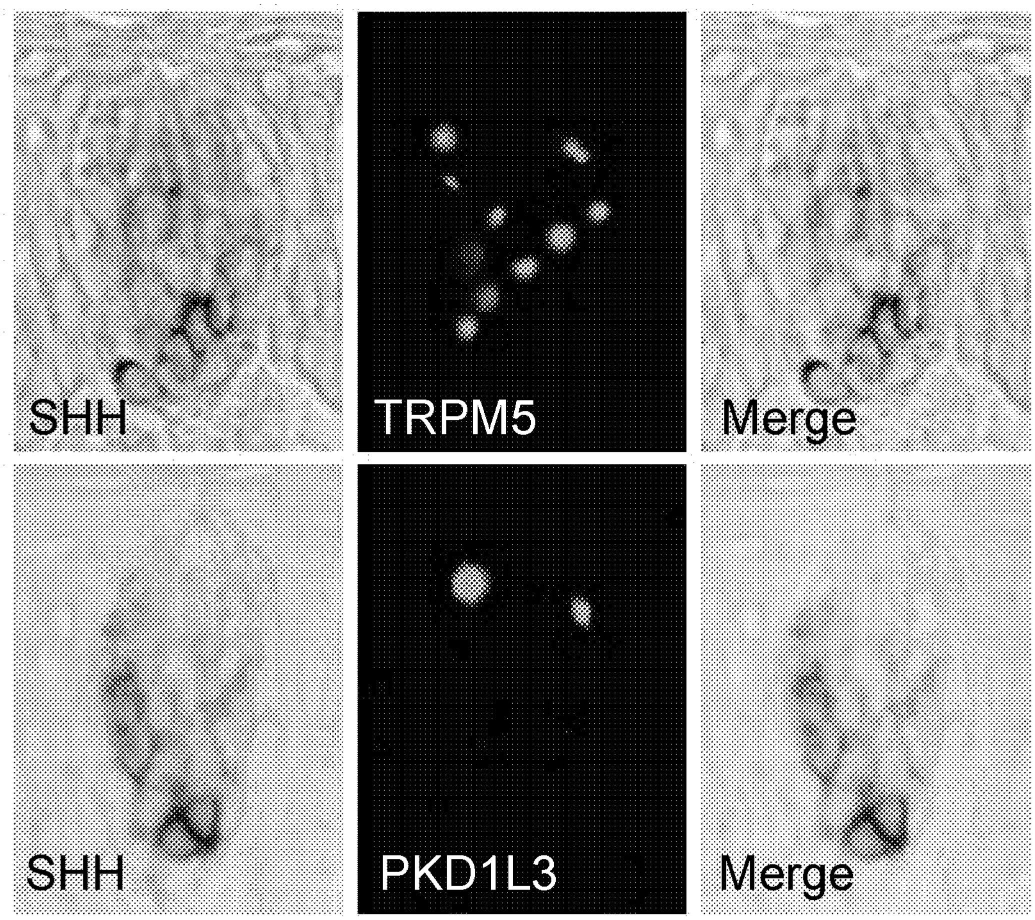

FIG. 33 contains an experiment showing that SHH is expressed in immature taste cells in the bottom of the taste bud. Double in situ hybridization of primate circumvallate papilla at the back of the tongue showing that SHH (blue/purple color; left images) does not colocalize with TRPM5 (red; middle image top) or PKD1L3 (red; middle image bottom). Note that SHH cells do not express TRPM5, a marker of sweet, bitter, and umami taste cells (merge; right image top) or PKD1L3 (merge; right image bottom). Both TRPM5 and PKD1L3 genes are expressed in professional taste cells.

Figure 34:
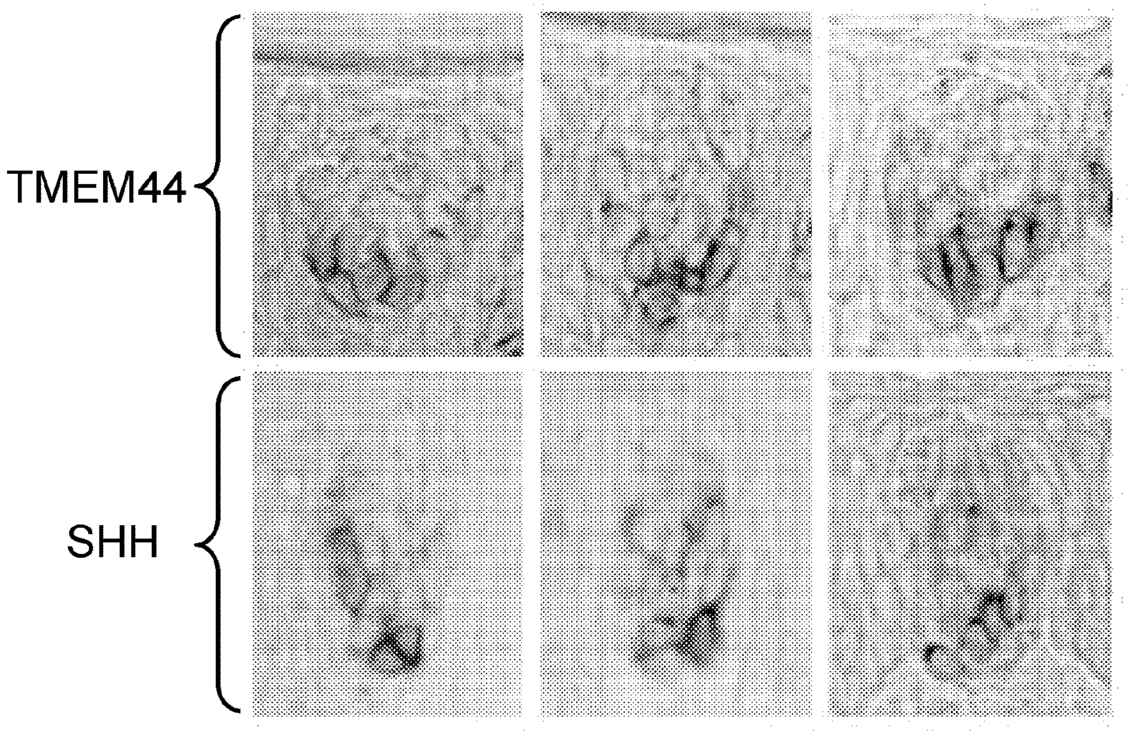

FIG. 34 contains an experiment showing that TMEM44 and SHH are expressed in immature taste cells at the bottom of the taste bud. In situ hybridization of primate circumvallate papilla at the back of the tongue showing that TMEM44 (blue/purple color; top 3 images) is expressed in cells towards the base of the taste bud. A similar expression pattern was observed with SHH (blue/purple color; bottom 3 images). Since SHH is marker of immature, developing taste cells, these data indicate that TMEM44 is expressed in and is a marker of immature taste cells FIG. 35 contains a schematic model of taste cell development. In situ hybridization of primate circumvallate papilla at the back of the tongue showing SHH (blue/purple color) expression at the base of the taste bud and PKD1L3 (red color) expression towards the top of the taste bud. This model indicates a gradient of SHH expression from high levels at the base of the taste bud (immature cells) to low levels at the top of the taste bud (mature cells). As SHH expression levels decrease, expression of taste receptor genes such as TRPM5 and PKD1L3 increase. Thus, an opposite gradient of taste cell maturation exists where taste cells progressively mature and express taste receptor genes as they differentiate from the bottom to the top of the taste bud.

Figure 36:
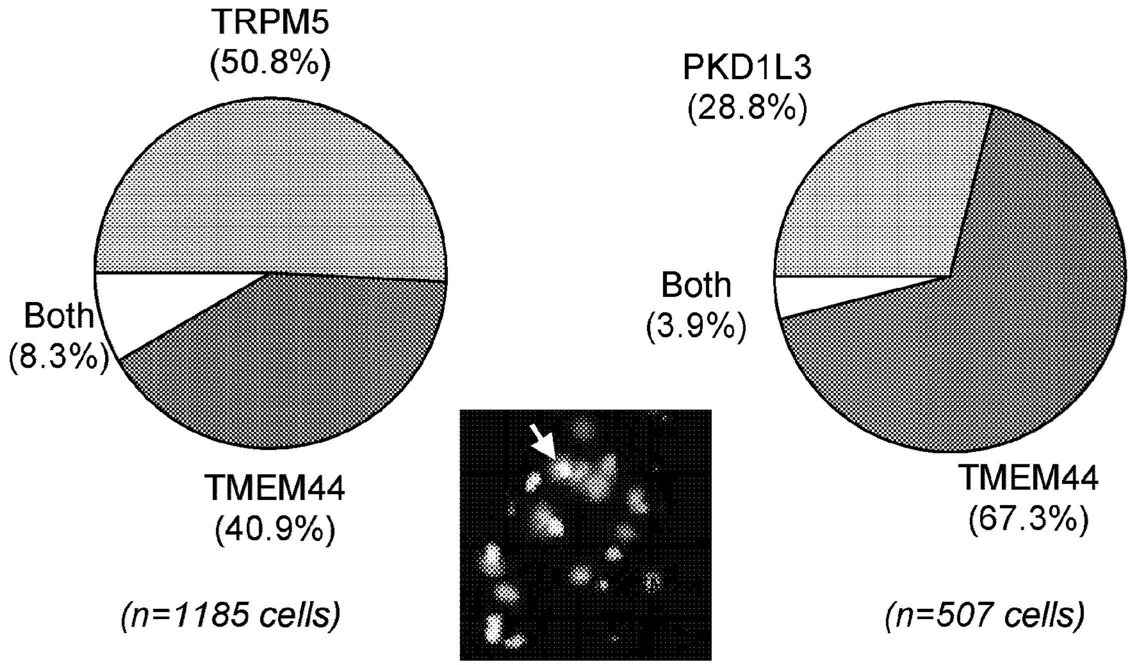

FIG. 36 shows that a small fraction of TMEM44 cells express TRPM5 or PKD1L3 as they differentiate into mature taste cells. Double label in situ hybridization of primate circumvallate papilla was performed using TRPM5 and TMEM44 riboprobes (left pie chart) or PKD1L3 and TMEM44 riboprobes (right pie chart). Taste cells expressing TRPM5 (blue graph region; left pie chart), TMEM44 (magenta graph region; left pie chart), or TRPM5 plus TMEM44 (labeled 'both' and yellow graph region; left pie chart) genes were counted and graphed in pie charts. Taste cells expressing PKD1L3 (blue graph region; right pie chart), TMEM44 (magenta graph region; right pie chart), or TRPM5 plus TMEM44 (labeled 'both' and yellow graph region; right pie chart) genes were counted and graphed in pie charts. Total number of counted cells is listed below each pie chart in parentheses. A small fraction of TMEM44 cells also express TRPM5 or PKD1L3, indicating that these cells are differentiating from an immature state (TMEM44 only) to a mature state (TRPM5 or PKD1L3 only). Inset shows example of CV taste bud labeled with TMEM44 (green) and TRPM5 (red). Note cell indicated with arrow that coexpresses both TMEM44 and TRPM5 (yellow).

Figure 37:
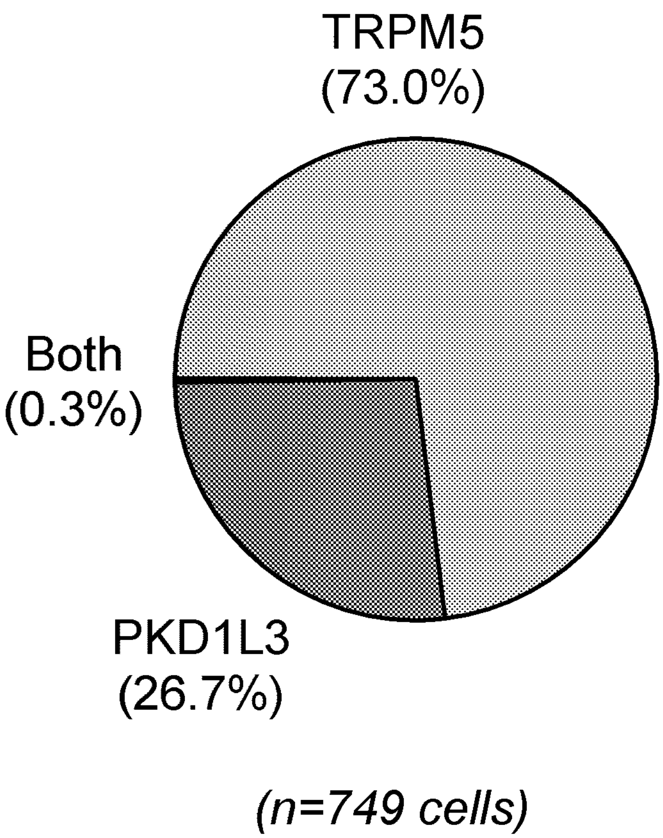

FIG. 37 contains an experiment showing that mature taste cells do not coexpress markers for distinct taste modalities. Double label in situ hybridization of primate circumvallate papilla was performed using TRPM5 and PKD1L3. Taste cells expressing TRPM5 (blue graph region), PKD1L3 (magenta graph region), or TRPM5 plus PKD1L3 (labeled 'both' and yellow graph region which is too small to see any yellow segment due to the near absence of cells within this category) genes were counted and graphed in the pie chart. Total number of counted cells is listed below the pie chart in parentheses.

Figure 38:
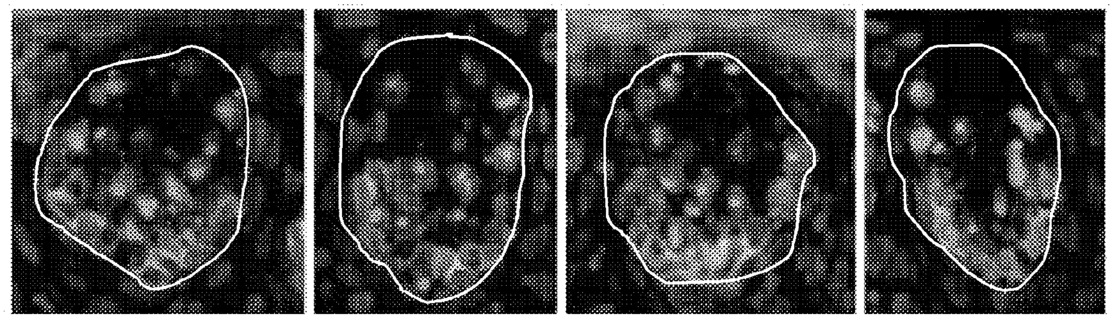

FIG. 38 contains an experiment showing that levels of gene expression define two compartments in primate taste buds. To create this overlay image sagittal sections of primate taste buds were initially stained with DAPI (4',6-diamidino-2-phenylindole) to visualize cell nuclei; blue color. Double label in situ hybridization images of the same sections for TMEM44; green color and TRPM5+PKD1L3; pink color were then added. The overlay image shows that TMEM44 expression is restricted to the bottom third of each of the four taste buds shown and that TRPM5+PKD1L3 expression occurs predominantly in the upper regions of each of the taste buds.

Figure 39:
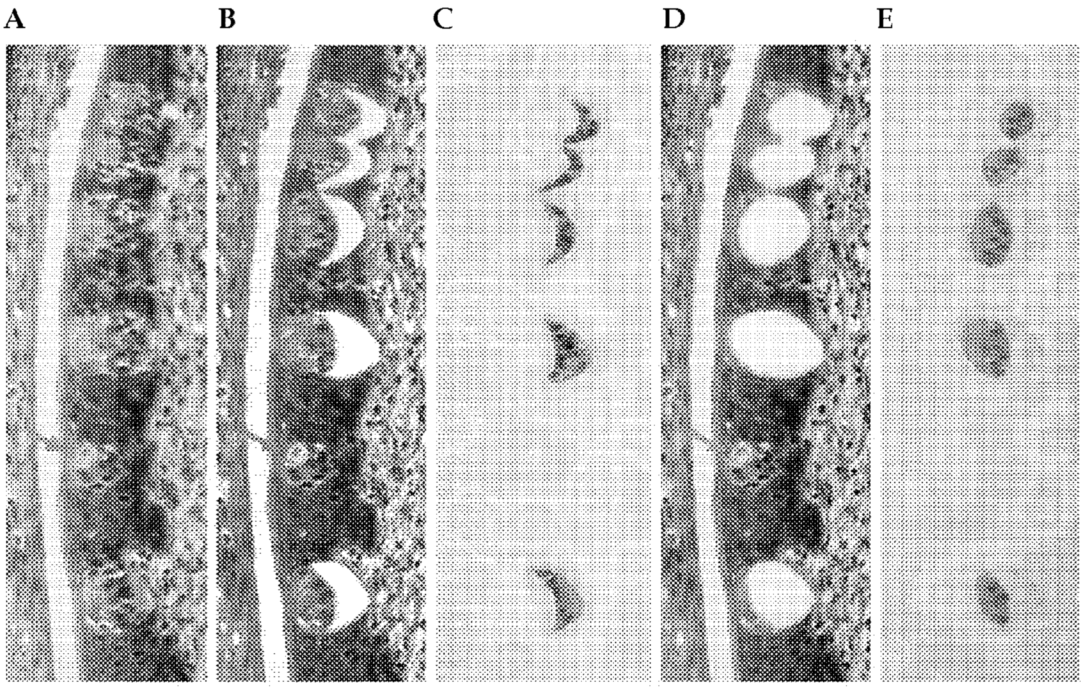

FIG. 39 shows an exemplary experiment showing laser capture microdissection of top and bottom regions of primate taste buds. Panel) contains a methyl blue stained section A of macaque circumvallate taste buds. Panel B shows Section A following excision of bottom fraction of taste buds. Panel C contains the bottom fraction of taste buds. Panel D shows Section A following excision of bottom and top fractions of taste buds. Panel E shows the Top fraction of taste buds. Note, top and bottom fractions were only collected from taste buds exhibiting optimal morphology in section. In the example shown, the taste bud labeled with an arrow was excluded due to suboptimum sectioning or morphology.

Figure 40:
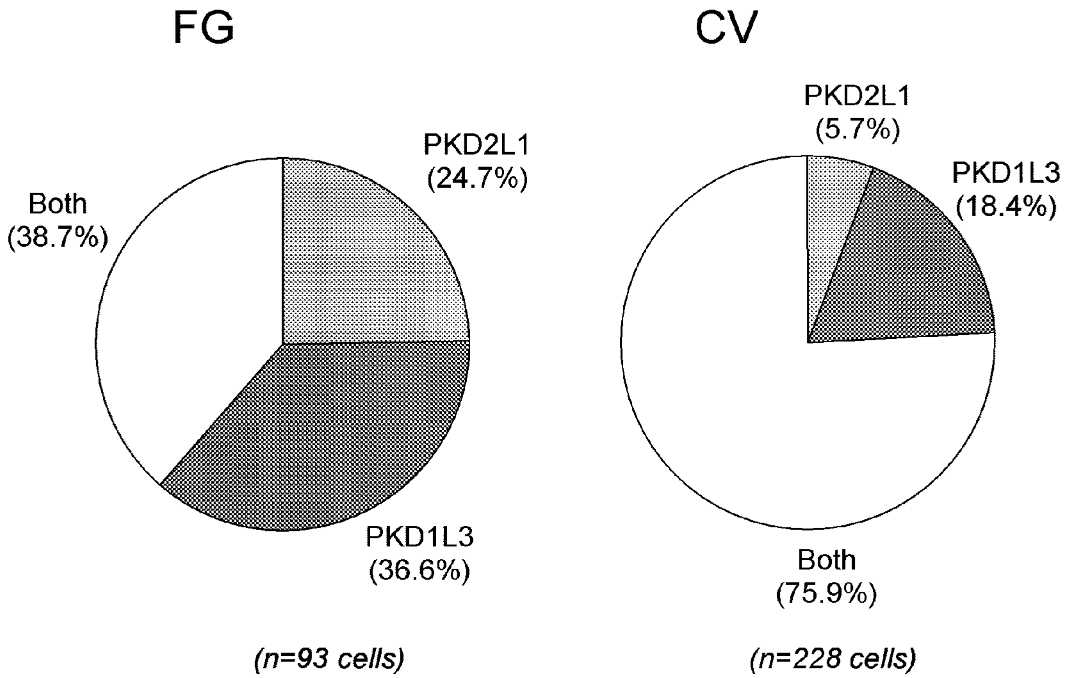

FIG. 40 contains the results of an experiment establishing that distinct cell populations PKD2L1, PKD1L3 and PKD2L1 plus PKD1L3. Double label in situ hybridization of primate fungiform (FG; left) and circumvallate (CV; right) was performed using PKD2L1 and PKD1L3 riboprobes. Taste cells expressing PKD2L1 (blue graph regions), PKD1L3 (magenta graph regions), or PKD2L1 plus PKD1L3 (labeled 'both' and yellow graph regions) genes were counted and graphed in pie charts. Total number of counted cells is listed below each pie chart in parentheses.

Figure 41:
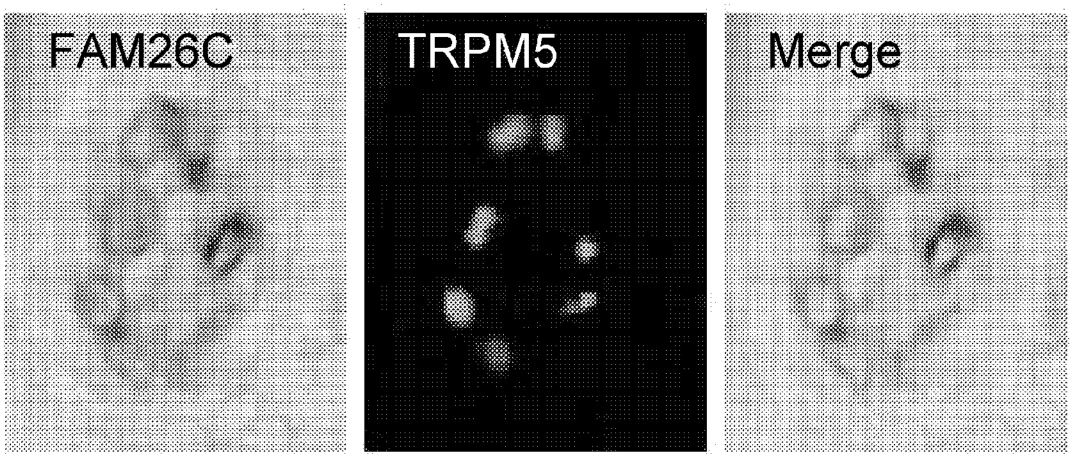

FIG. 41 The experiment in FIG. 41 shows that FAM26C is expressed in TRPM5 taste cells. Therein double in situ hybridization of primate circumvallate papilla at the back of the tongue showing that FAM26C (blue/purple color; left image) colocalizes with TRPM5 (red; middle image). Note that FAM26C cells express TRPM5, a marker of sweet, bitter, and umami taste cells (merge; right image).

Figure 42:
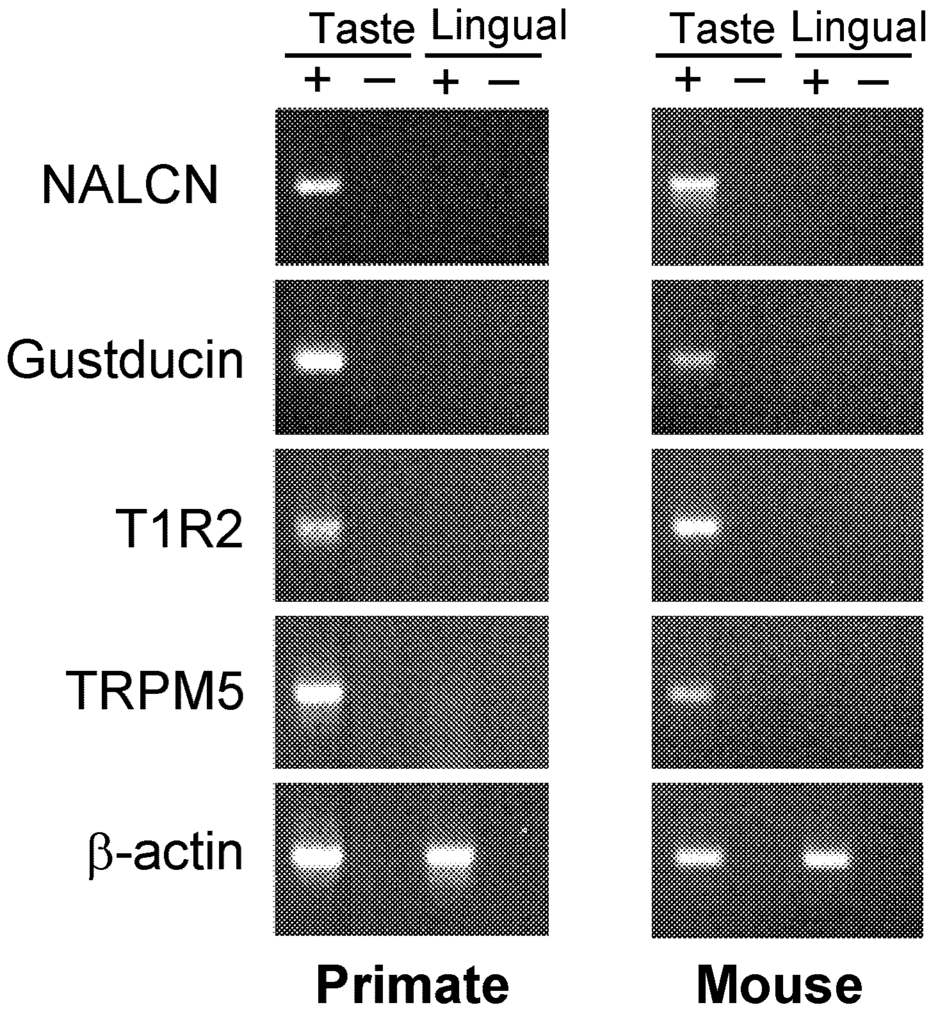

FIG. 42 The experiment in FIG. 42 shows that NALCN is a taste-specific gene. The figure shows end-point PCR experiments on circumvallate taste buds (taste) and lingual epithelial cells (lingual) of non-human primate (left) and mouse (right) isolated by laser-capture microdissection demonstrating that NALCN is a taste-specific gene. NALCN is only expressed in taste cells and is not detectable in lingual cells, similar to the known taste-specific genes gustducin, T1R2, and TRPM5. □-actin is detectable in both taste and lingual samples, indicating that high-quality RNA was present in both samples. '+' indicates that reverse transcription was performed and '−' indicates that no reverse transcription was performed. PCR bands were only observed with reverse transcriptase indicating that PCR products are derived from mRNA and not genomic DNA. PCR products were cloned and sequenced to verify that the bands corresponded to the expected gene products.

Figure 43:
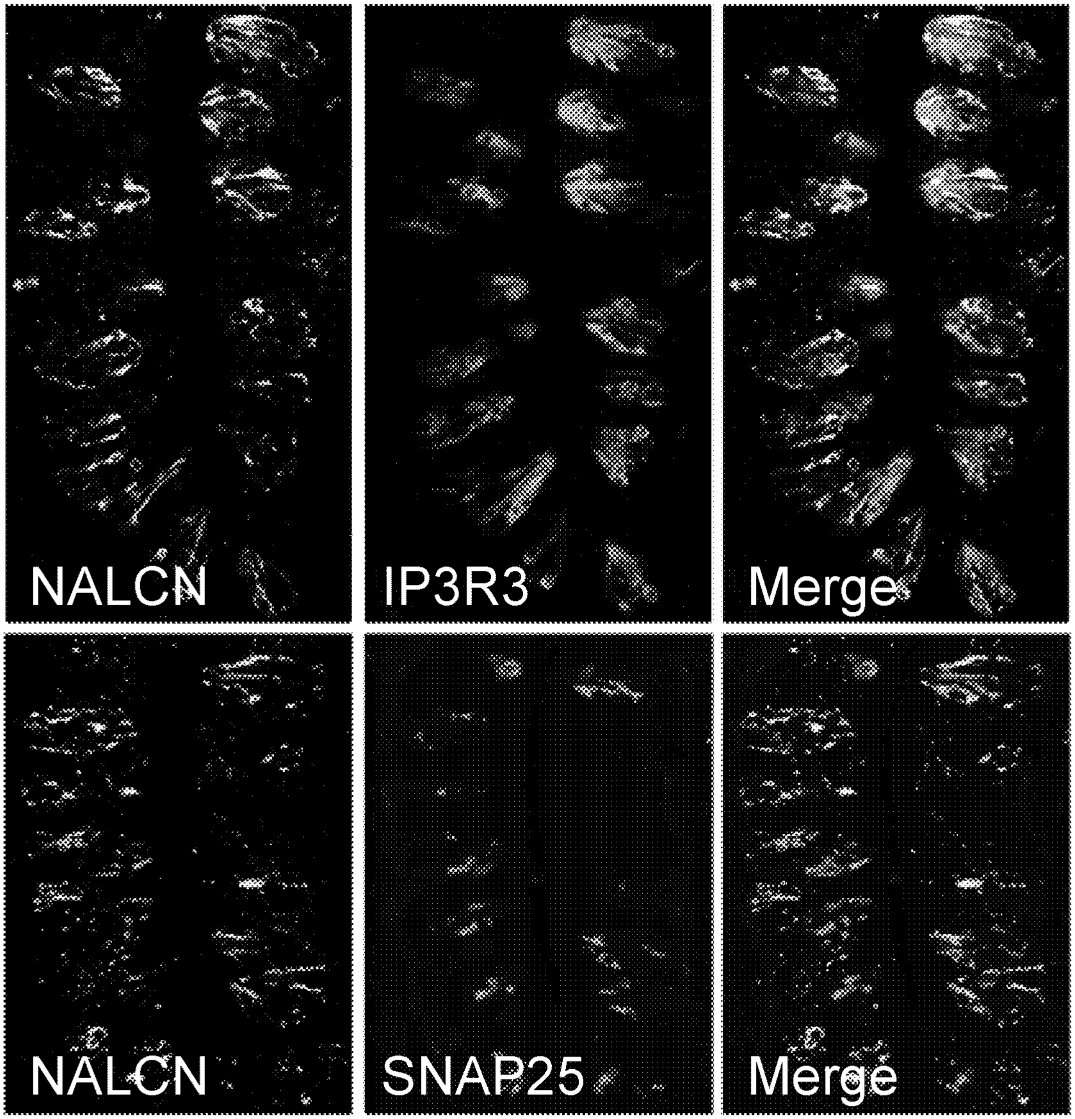

FIG. 43 The experiment in FIG. 43 shows that NALCN is expressed in a unique taste cell type effected at low magnification. Therein is shown a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel taste cell population. Numerous taste buds are shown.

Figure 44:
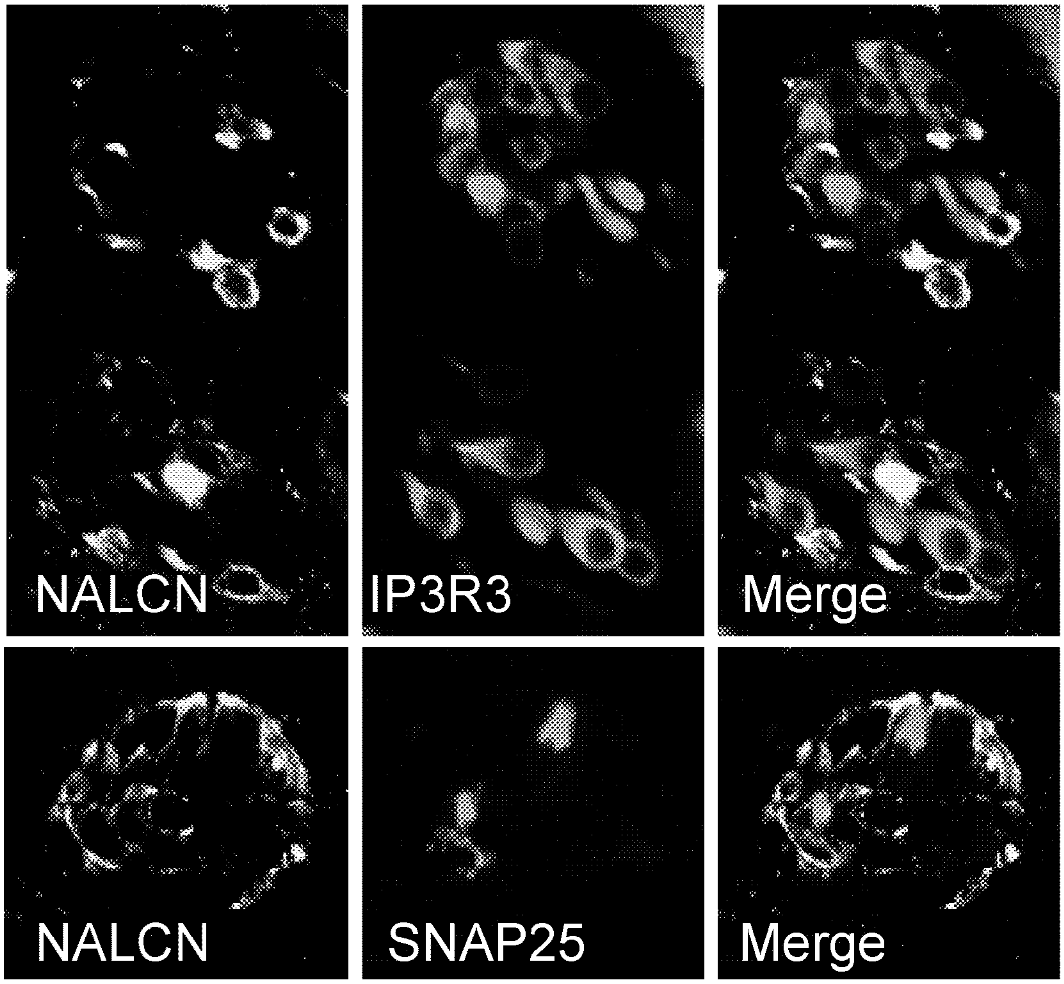

FIG. 44 The experiment in FIG. 44 also shows that NALCN is expressed in a unique taste cell type but at high magnification. Therein is contained a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel taste cell population. One to two taste buds are shown.

Figure 45:
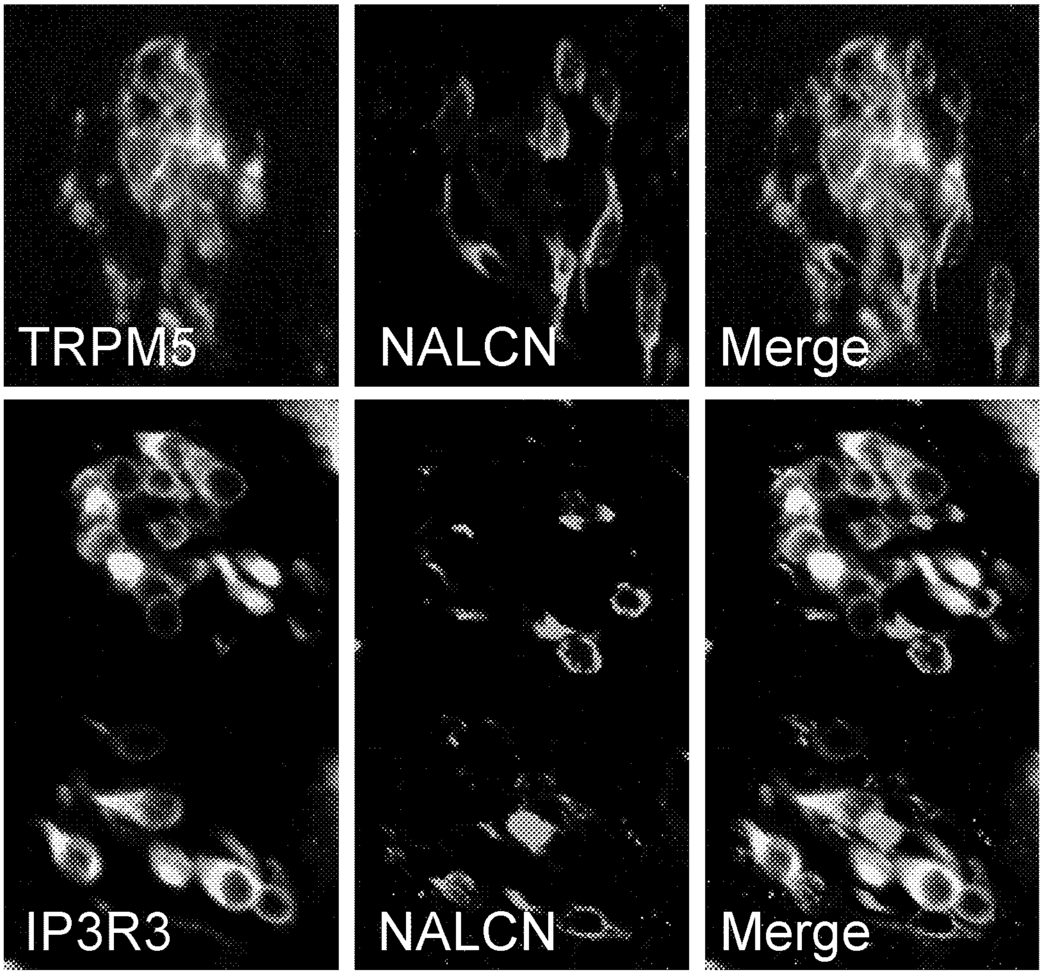

FIG. 45 The experiment in FIG. 45 shows that NALCN is not expressed in TRPM5 cells. The figure contains a double label immunochemistry of circumvallate papilla from the back of the tongue showing that NALCN (red color, middle images( ) does not colocalize with TRPM5 in non-human primate (green, left image top row) or IP3R3 in rat (green; left image bottom row). Note that red and green stains localize to different cell types in the merged images on the right. Since TRPM5 and IP3R3 mark sweet, bitter, and umami cells, equivalent to type II cells, NALCN is not expressed in type II cells in non-human primate and rat.

Figure 46:
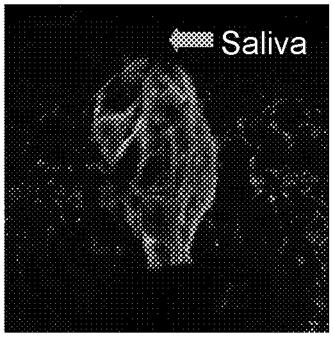

FIG. 46 The experiment in FIG. 46 shows that NALCN is expressed in a subset of fungiform taste cells. Therein single label immunochemistry of fungiform papilla from the front of the tongue of non-human primate showing that NALCN (red color) is expressed in a subset of taste cells. Top of the taste bud, facing saliva, if oriented towards the top in the image is shown (see arrow). unique taste cell type but at high magnification. Therein is contained a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel. taste cell population. One to two taste buds are shown.

Figure 47:
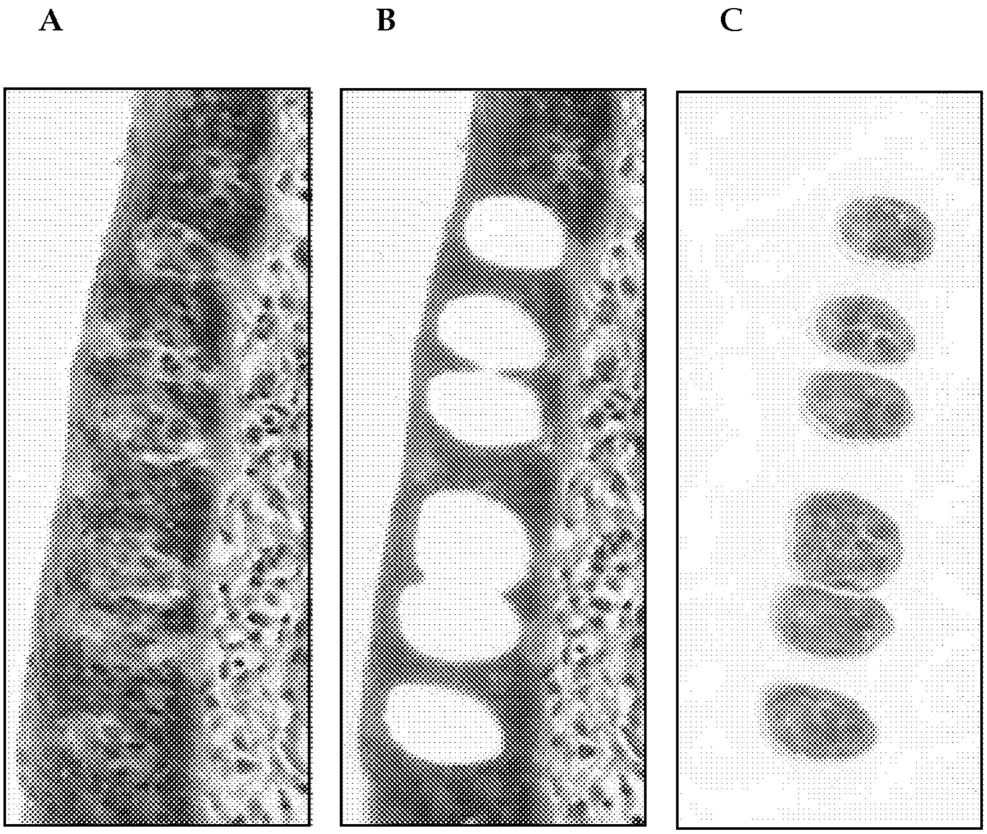

FIG. 47 shows the laser capture microdissection of human taste buds. Panel A shows methyl blue stained section of human circumvallate human taste buds. Panel B shows Section A following excision of taste buds. Panel C contains the captured taste buds.

DETAILS OF THE INVENTION

The invention relates to the identification of genes expressed in taste tissues of human and macaque, particularly fungiform and/or circumvallate papilla derived taste cells which are putatively involved in salty taste or other taste modalities or taste in general; or which are involved in taste cell related functions and phenotypes that do not directly involve taste such as taste cell or taste bud regeneration and turnover, immunoregulation of the oral cavity or digestive system, regulation of digestion or metabolism, onset or prevention of digestive system disorders such a cancers, autoimmune diseases, and inflammatory conditions such as IBD, ulcerative colitis, Sjogren's syndrome, celiac disease, Crohn's disease, and the like and the use thereof in screening assays to identify compounds that modulate salty taste perception or other taste modalities or taste in general or for identifying potential therapeutics for use in humans. In particular the invention includes use of the following methodologies, to identify novel taste-specific genes:

1) Laser Capture Microdissection (LCM) and RNA Amplification:

In laser capture microdissection, a fine laser beam is used to dissect and purify taste cells from histological sections. This method isolates taste cells, devoid of contaminating lingual epithelial cells and connective tissue, and allows one to perform molecular biology experiments on a highly enriched taste cell population. In parallel, lingual epithelial cells are isolated by LCM and used as a negative control devoid of taste cells. LCM is advantageous to manual or enzymatic dissection of taste papilla because these crude techniques yield a heterogeneous mixture of taste and lingual cells in which taste cells comprise 1-20% of collected material. RNA amplification amplifies total RNAs from taste cells and lingual cells isolated by LCM up to 1 million-fold in a non-biased fashion to generate sufficient genetic material to perform molecular biology studies (gene chips or PCR). We have found that 5,000 taste cells are sufficient for gene chip experiments with macaque taste tissue and greater than 10,000 taste cells are sufficient for PCR experiments with macaque taste tissue.

2) Gene Chips:

Gene chips contain most all annotated genes on a small chip. Hybridizing RNA, isolated and amplified from taste and lingual cells, to gene chips can be used to determine which specific genes are expressed in taste cells and not lingual cells and which specific genes are expressed at higher levels in taste cells compared to lingual cells. Gene chips experiments were conducted using paired macaque fungiform (FG) and circumvallate (CV) taste and lingual samples using Affymetrix rhesus macaque genome arrays and analyzed using GeneSpring GX v7.3 software (Agilent Technologies). 5000 fungiform and CV taste and lingual cells were separately isolated by LCM and total RNA was purified for each sample. RNA was then amplified and hybridized to gene chips. Data analyses are performed using two separate algorithms: Affymetrix Microarray Suite 5 (MAS5) which takes into account both perfect match and mismatch probes on gene chips, and robust multi-chip algorithm (RMA) which only takes into account perfect match probes on gene chips. Taste-specific genes encoding transmembrane proteins are identified in this analysis.

3) PCR:

High-throughput PCR is performed in 96 well plates using primers specific for ion channels in the human/macaque genome and amplified RNA from human/macaque taste and lingual cells isolated by LCM. Detection of products of the appropriate size in taste cells but not lingual cells and DNA sequencing of PCR products (to confirm gene identity) indicates the ion channel of interest is a taste-specific gene. Prior to high-throughput PCR using primers against ion channels identified in the macaque genome, quality-control PCR reactions are first performed on up to 4 known taste-specific genes and 2 housekeeping genes to ensure that taste and lingual RNAs are of high quality. Four taste-specific genes which may be examined are the G alpha protein gustducin (GNAT3), the sweet receptor components, the ion channel TRPM5 and the enzyme phospholipase beta 2; the two housekeeping genes examined are beta-actin and GAPDH. Specific expression of the taste genes by taste cells but not lingual cells plus expression of the ubiquitous housekeeping genes by both taste and lingual cells indicates high quality RNA material.

PCR products are analyzed on agarose gels to determine if bands of the appropriate size are present in taste cells but not lingual cells. Genes with this expression pattern are putative taste-specific genes. All taste-specific genes were cloned and sequenced to confirm the gene identities.

4) In Situ Hybridization:

Antisense RNA probes specific for an individual gene(s) (identified by gene chips or PCR) are hybridized to tissue sections containing taste cells to determine if the mRNA transcript for the gene of interest is expressed in taste cells, specifically in sour, sweet, bitter, and/or umami cells or in a unique cell type that may be involved in salty taste detection. In double labeling in situ hybridization, two different RNA probes are generated to label two different genes, specifically two different taste-specific genes identified by gene chip and/or PCR approaches. Alternatively, one probe can be generated to label a single gene to determine if the gene is expressed in taste cells. For double labeling studies, the first gene is labeled with a FITC probe that generates one color in a fluorescent microscope while the second gene is labeled with a digoxygenin (DIG) probe that generates a different color in a fluorescent microscope. Superimposition of probe 1 and probe 2 reveals if genes are expressed in the same or in different cell types. For example, if a unique ion channel identified by gene chip or PCR approaches colocalizes to cells expressing TRPM5, that unique ion channel is expressed in cells responsible for sweet, bitter, and/or umami taste. By contrast, if a unique ion channel identified by gene chip or PCR approaches does not colocalize to cells expressing TRPM5, that unique ion channel is expressed in a different cell type that may be responsible for salty taste (or another taste modality) and that unique ion channel may be directly involved in sodium detection.

5) Immunohistochemistry:

Antibodies specific for an individual protein (whose gene was identified by gene chips or PCR) are applied to tissue sections containing taste cells to determine if the protein of interest is expressed in taste cells, specifically in sour, sweet, bitter, and/or umami cells or in a unique cell type that may be involved in salty taste detection. In double labeling immunohistochemistry, two different antibody probes are used to label two different proteins, specifically two different taste-specific proteins whose genes were identified by gene chip and/or PCR approaches. Alternatively, one antibody probe can be used to label a single protein to determine if the protein is expressed in taste cells. For double labeling studies, the first protein is labeled with an antibody at a very dilute concentration that can only be detected with a sensitive detection method termed tyramide signal amplification (TSA). The second protein is then labeled with another antibody and detected using a non-TSA method. The dilute first antibody cannot be detected by the standard non-TSA method; therefore, two different antibodies from the same species (e.g. rabbit polyclonal antibodies) will not cross-react and, therefore, can be used in double labeling experiments. Superimposition of protein label 1 and protein label 2 reveals if proteins are expressed in the same or in different cell types. For example, if a unique ion channel identified by gene chip or PCR approaches colocalizes to cells expressing TRPM5, that unique ion channel is expressed in cells responsible for sweet, bitter, and/or umami taste. By contrast, if a unique ion channel identified by gene chip or PCR approaches does not colocalize to cells expressing TRPM5, that unique ion channel is expressed in a different cell type that may be responsible for salty taste (or another taste modality) and that unique ion channel may be directly involved in sodium detection.

In particular the present invention preferably uses the following rationale to select potential salty taste receptor or ion channel candidates. It is again emphasized that while this rationale is focused on isolating and functionalizing salty taste receptors because of its inclusive criteria discussed below it likely will identify non-salty taste receptors as well such as fat or metallic taste receptors and genes that encode other functions of taste cells such as discussed above.

First taste buds are isolated using LCM as described above from human or macaque (*Macaca fascicularis*). Macaque genes are on average 90-95% identical to human genes and the macaque is an excellent experimental model for study of human biology including taste. Thus taste genes identified in the macaque will be highly similar to their human orthologs and carry out similar functions to those seen in humans. Using LCM a fine laser beam is used to dissect and purify taste cells from histological sections. This method isolates taste cells devoid of contaminating lingual epithelial cells and connective tissue and allows molecular biology experiments to be effected on a highly enriched taste cell population. In parallel, lingual epithelial cells are isolated by LCM and used as a negative control devoid of taste cells. LCM is advantageous to manual or enzymatic dissection of taste papilla because these crude techniques tend to yield a heterogeneous mixture of taste and lingual cells in which taste cells only comprise about 1-20% of the collected material.

Secondly, RNA isolated from taste and non-taste cells is analyzed using gene chips/microarrays. Gene chips contain most all annotated genes on a small chip. Hybridizing RNA, isolated from taste and lingual cells, to gene chips can be used to determine which specific genes are expressed in taste cells and not lingual cells as well as which specific genes are expressed at higher levels in taste cells compared to lingual cells. In order to identify genes for which probe sets are not functional on gene chips, gene chips were performed on 21 macaque non-taste tissues. Probe sets for genes not yielding data above background levels include both probe sets that do not hybridize efficiently to gene targets as well as probe sets not represented within the panel of 21 macaque tissues. These genes, representing genes not covered by the gene chip approach, are analyzed separately by PCR and/or histology to identify genes, specifically genes encoding transmembrane proteins, which are expressed in taste cells and not lingual cells as well as genes expressed at higher levels in taste cells compared to lingual cells isolated by LCM.

Third, taste-specific genes identified by gene chips and/or PCR are examined by histology using double labeling approaches, With in situ hybridization antisense probes specific for individual genes are hybridized to tissue sections containing taste cells to determine if the mRNA transcript for the gene of interest is expressed in taste cells, specifically in sweet bitter, sour and/or umami taste cells or in a unique cell type that may be involved in salt or other taste modality, e.g., fat taste detection. Using immunohistochemistry antibodies specific for an individual protein (which gene was identified by gene chips) these antibodies are applied to tissue sections containing taste cells to determine if the protein of interest is expressed in taste cells, specifically in sweet, bitter, sour and/or umami cells or in a unique cell type that may be involved in salt or fat taste detection. Genes expressed in taste cells expressing TRPM5, a marker for sweet, bitter, and umami cells, would encode proteins that may modulate sweet, bitter and/or umami taste. Genes expressed in taste cells expressing PKD2L1 or PKD1L3, markers for sour cells, would encode proteins that may modulate sour taste. Genes expressed in taste cells expressing neither TRPM5 nor PKD2L1 or PKD1L3 would encode proteins expressed in a unique cell type that may correspond to a salt or fat cell. Therefore, genes expressed in a unique taste cell type may correspond to a salty taste receptor or a fat taste receptor and may modulate salty or fat taste detection.

Fourth, taste-specific genes expressed in a unique cell type are analyzed by use of functional assays including electrophysiology to determine of gene products expressed in heterologous systems such as HEK293 cells or *Xenopus* oocytes generate sodium-responsive receptors or sodium-conducting ion channels. A salt receptor target should respond to sodium ions at concentrations relevant for human taste (between 20-140 mM sodium).

Fifthly, to ultimately validate the role of a gene as a salt receptor, genes meeting the criteria set forth above are advanced into high-throughput screens to identify enhancers and blockers and these compounds are tested in salty taste tests to determine if they augment or repress salty taste perception. In parallel, mouse knockouts are generated lacking the gene of interest and physiological (nerve recordings) and behavioral (2-bottle preference tests and gustometer tests) experiments are performed to determine if the animals are deficient in or lack salty taste perception.

Therefore, salt receptor candidates will comprise the following criteria: 1) Genes expressed specifically in taste cells or at higher levels in taste cells than lingual cells in gene chip and/or PCR experiments (these are defined as taste-specific genes); 2) Genes expressed in a unique cell type, that does not correspond to sweet, bitter, sour, and/or umami cells by histology; 3) Gene products that generate sodium responsive receptors or sodium channels in electrophysiology or functional experiments; and 4) Enhancers or blockers of gene products modulate salty taste perception and/or mouse knockouts of genes of interest are deficient in or lack salty taste responsiveness.

In a preferred embodiment, step (i) comprises the use of laser capture microdissection (LCM) to dissect and purify taste tissues from non-taste tissues. In one mode of this embodiment, step (i) comprises RNA amplification of genes from taste cells and lingual cells and the amplified genes are screened against a gene chip containing a sample of genes specific to the particular mammal from which the taste and lingual tissues are obtained, and preferably, the gene chips include a set of annotated human genes. In an alternative mode of this embodiment, step (i) comprises high throughput PCR using primers for each ion channel in a mammalian genome.

In another preferred embodiment, step (ii) is effected by in situ hybridization using antisense RNA probes specific for the set of genes identified in step (i) to determine level of expression in taste versus lingual cells. In an alternative preferred embodiment, step (ii) is effected by use of immunochemical detection using a labeled antibody specific to the protein encoded by gene or genes identified in step (i).

In another embodiment of the method for identifying a gene encoding a polypeptide involved in salty taste perception in a mammal, the method of this invention comprises the steps of (i) identifying a set of macaque genes including genes which are expressed in taste cells but which are not expressed in lingual cells and/or genes which are expressed in taste cells at substantially higher levels than in macaque lingual cells; (ii) identifying a subset of genes within the set of genes identified in (i) which are not expressed in taste cells which express umami, sweet or bitter taste receptors (T1Rs or T2Rs) or sour taste receptors (PKD2L1/PKD1L3); and (iii) determining, in a primary neuron which expresses one or more genes in the subset identified according to (ii), which of said genes functions as a sodium responsive ion channel or sodium responsive receptor or transporter and thereby identifying this gene or genes as a putative gene that modulates salty taste. In one mode of this embodiment, step (iii) comprises contacting the neuron with an antibody which specifically binds the gene and inhibits its function.

Genes identified according to either of the methods described above may be characteristic of cells which do not express TRPM5 and PKD2L1/PKD1L3. In another mode, this invention provides a method to assist in selecting cells which do not express TRPM5 and PKD2L1/PKD1L3 by determining whether a cell expresses a gene identified according to the methods above. Preferably, the gene used in the method of this paragraph is one of the genes listed in Tables 1-3, listing taste-specific genes encoding transmembrane proteins in taste cells. Efforts were focused on transmembrane genes since all known taste receptor genes for sweet, bitter, umami, and sour taste encode transmembrane proteins.

In another aspect this application provides an improvement of the afore-described methods in which genes expressed in primate (e.g., macaque) taste buds are identified and functionalized using the disclosed methods. The inventors have developed a rationale wherein they are able to assign gene expression patterns within the primate taste bud for all taste bud-specific genes. Specifically, using a comparison of gene expression between the top and bottom sections of the human or primate taste bud, the inventors have found that they are able to classify genes into one of several functional classes that include taste receptor genes. A subset of genes in this classification is likely to encode all taste receptors and should include those for salty taste and other yet to be defined taste specificities.

The rationale for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively, see FIG. 38, described in the examples infra.

In order to get more information on gene expression in both the top and bottom fractions of the taste bud the inventors isolate the corresponding fractions of primate taste buds using laser capture microdissection (LCM). This technique is described supra and briefly involves excision of specific groups of cells from tissue sections based on morphological distinctions. In the case of taste buds, the inventors are able to readily identify these structures in sections of primate tongue. As exemplified in the supporting experimental example infra, tissue collection was limited to taste buds in circumvallate papillae and then to only taste buds that were sectioned sagittally and at the taste pore. The inventors reasoned that only this type of section would reliably isolate top and bottom fractions. An example of sections used in sample collection is shown in FIG. 39.

The gene expression data obtained is then queried to obtain three sets of genes. The first and second sets are genes that are expressed at a higher level in the top or bottom of the primate taste bud relative to the bottom or top respectively. A third set of genes is identified by comparing gene expression between whole (top+bottom) taste bud and lingual epithelium LCM samples.

This methodology achieves various advantages including the following:

Firstly, the inventors have found that taste receptor genes are expressed predominantly at the top of the taste bud. In contrast to prior knowledge, the data obtained using these methods clearly indicate that known taste receptor genes are expressed at a higher level in the top fraction of taste buds. It is reasonable to expect yet to be identified taste receptor genes are represented in the genes which are enriched at the top of the taste bud.

Secondly, the inventive top-versus-bottom gene classification methods allow for the functional classification of genes based on their expression in the cells in the top versus the bottom of the taste bud. Gene expression profiles at the top and bottom fractions of the taste bud suggest distinct functions for cell in each compartment. Functional classes of genes expressed in the top cells indicate that these are mature sensory cells whereas those expressed in the bottom cells indicate that these are immature progenitor cells associated with a basement membrane containing cellular environment. Examples of top-specific functional clauses include taste receptors, taste-specific signal transduction components and receptors. Examples of bottom-specific functional classes include matrix components, growth factors, and cell-cycle-associated proteins.

Thirdly, this methodology allows for the identification of additional taste bud-specific genes. It has been found that by fractionating the taste bud into top and bottom compartments that the inventors have increased the sensitivity of mRNA detection in each compartment by a factor of about 2. This facilitates the identification of other taste specific genes not identified by the prior-described methods.

Therefore, these methods can be used to identify genes involved in different functions of the taste bud based on measuring their expression in the top versus bottom of the taste bud, e.g., where genes over-expressed in the top part of the taste bud. are predicted to be involved in one or more taste sensation, modulation of taste sensation, control of the lifespan of mature taste bud cells or they may be used as biomarkers of different mature taste cell subsets.

By contrast using the inventive rationale genes over-expressed at the bottom of the taste bud are predicted e.g., to be involved in one or more of the maintenance, differentiation and proliferation of taste-bud committed stem cells; or they will represent biomarkers of taste-bud committed stem cells. n addition, genes expressed specifically in the top or bottom can be using to purify these functionally distinct taste bud cell subsets.

Also, in another aspect this invention describes rationales which are useful and have successfully identified human genes which are taste specific and which are predicted to be involved in one or more of the afore-described taste bud related functions. Specifically, these methods identify human taste specific genes (also identified by the afore-described macaque taste gene selection method) by quantitative polymerase chain reaction (PCR). This is an improvement of the afore-described methods for identifying primate taste specific genes, i.e., taste genes specifically expressed in primate taste buds and may be combined with these method and the previous described method wherein the inventors assign gene expression patterns for genes expressed within the primate taste bud for all taste bud-specific genes; specifically, by comparing taste specific gene expression between the top and bottom sections of the primate taste bud and thereby are able to classify genes into one of several functional classes that include taste receptor genes.

This third method is advantageous as it validates the results of the prior methods (since the identified human taste specific genes are present in those identified as taste specific in the macaque) and also demonstrates similar pattern of taste specific gene expression in humans (in addition to primate) and validates the specificity of expression by a quantitative method (qPCR or "TaqMan").

However, it should be emphasized that the subject methods which identify primate taste specific genes are still very predictive as primates and humans are closely evolutionary related. Therefore, gene expression patterns should also be closely related. Based on this reasonable assumption, taste specific genes identified in the macaque are selected to be validated as being taste specific by assaying the expression thereof in human taste buds using a technology distinct from microarray analysis—TaqMan qPCR.

These methods similarly require a source of isolated (human) taste buds. Human taste buds can be isolated by laser capture microdissection (LCM). This technique has been described supra and involves the excision and isolation of selected cells or groups of cells from tissue sections based on morphological distinctions. In the case of human taste buds, these structures similarly can be readily identified in sections of human tongue. Essentially, multiple LCM preparations from different human donors are pooled (~4500 cells per sample), RNA extracted and amplified (e.g., by WT-Ovation Pico RNA Amplification System) (NuGEN Technologies, Inc) and analyzed using TaqMan technology to determine specific levels of gene expression in the TB and LE pools.

Thereafter, the expression of the taste-specific genes is quantified by TaqMan in LCM derived cDNA from both LE and TB from the same donors. More specifically, gene expression is measured in TaqMan as a CT (cycle threshold) value. Briefly the CT value for a given sample is determined by the PCR cycle at which the amount of gene-specific PCR product (as measured by fluorescence) reaches a set value. For highly expressed genes, the threshold will be reached early in the PCR run and the CT value will be relatively low (<35) while genes with very low or no expression will not reach the threshold before cycle 35. Expression of genes with CT values >40 are defined as not detectable.

For the majority of genes which are identified as being human taste specific genes when assayed using this methodology, expression is not detected in LE samples (CT>40) but is readily detectable in TB samples (CT<35). This is significant outcome as this group of human taste specific genes has not been described before as taste-specific in human tissue.

In contrast to the afore described gene chip and microarray methods, this technique provides yet additional benefits. and discoveries including the following:

Firstly, these methods allow for human taste specific genes to be detected in human LCM cDNA which were not previously known to be taste specific. Particularly, this approach that uses LCM from post-mortem human tissue samples and a single cDNA amplification step, the data obtained to date clearly indicate that postmortem LCM human tissue can be used to quantify the expression of taste specific genes using qPCR.

Secondly, this methodology allows for the expression of human taste specific genes to be reliably and accurately measured by quantitative PCR (TaqMan) providing for the gene expression profiles of taste specific genes as measured by TaqMan. This methodology further validates gene expression data obtained from the previously described methods which used microarrays and/or in situ hybridization (ISH).

Thirdly, these methods have shown to indeed identify human taste bud specific genes which are functional. Particularly, by using the successive approaches of gene expression via microarray in primate LCM tongue tissue; Top-specific gene expression within the taste bud (akin to known taste receptors) and now TaqMan quantification of gene expression in human postmortem tastes tissues, the techniques identify human taste specific genes that had not been described previously.

Therefore, these methods allow for identification of human taste specific genes in postmortem tissues, and the identifying of human genes involved in different functions of the taste bud based on measuring their expression by quantitative PCR.

It is anticipated that these human taste specific genes, based on the manner that they were identified, expressed, and categorized are involved in one or more of (i) taste sensation, modulation of taste sensation, regulation of taste bud growth and development, control of the lifespan of mature taste bud cells, and/or are involved in the maintenance, differentiation and proliferation of taste-bud committed stem cells. In addition, genes identified using these methods are biomarkers of taste-bud committed stem cells. or represent biomarkers of different mature taste cell subsets. Therefore, these genes and gene products can be used as a basis in methods which enrich or purify these cell subsets.

Using these rationales, or a combination thereof, the genes contained in Tables 1-8 infra were identified. These Tables are briefly described as follows.

Table 1:

This table summarizes primate taste-bud expressed genes that were identified as multi plasma membrane proteins with little or no functional characterization. The set is consistent with this gene set including taste receptors and more particularly including salty taste receptors as the identified genes includes genes identified as sodium channels. This Table comprises the most probable candidates for salty receptor genes and genes responsible for other characterized and uncharacterized taste receptors and polypeptides that modulate taste intensity as well as genes encoding transmembrane proteins involved in other taste cell functions.

Table 2:

This table summarizes primate taste-bud expressed genes that were identified as multi plasma membrane proteins with have been functionally characterized but which are potential candidates for salty taste and other taste receptors. In addition this gene set includes genes encoding transmembrane polypeptides involved in other taste cell related functions.

Table 3:

This Table contains other fungiform expressed genes and potential taste receptor candidates. This Table of genes was derived after compiling a list of ion channel genes permeable to sodium that were systematically tested for expression in laser capture micro-dissected primate tongue tissue from lingual epithelium and taste buds by end point PCR. Genes that were expressed in fungiform taste buds but not circumvallate taste buds or lingual epithelium were included in this list. Moreover, this list of genes includes other genes which were selected that are likely to encode multi-domain transmembrane proteins included on the macaque oligo array that did not satisfy the inclusion criteria of the systematic array and are not included in the Gene Lists contained in Tables 1 and 2.

Table 4:

This table contains additional new taste-specific genes identified in macaque fungiform and/or circumvallate taste-buds by gene chip analysis. These genes all encode transmembrane proteins with no described function or that function as ion channels, ion transporters, or G-protein coupled receptors. Accession numbers, ratios of gene expression in taste cells (TB) to non-taste lingual epithelial cells (LE), and the p values calculated using a two-tailed Student's t-test are listed.

Table 5:

This table contains additional primate genes previously described as fatty acid receptors or which contain amino acid motifs that are associated with lipid binding. This list of genes includes genes that do not encode multi-transmembrane proteins but which are reported to participate in lipid transport or binding at close to the plasma membrane.

Table 6:

This table contains 11 taste-specific genes shown to be expressed in different subsets of primate taste cells. These genes were identified as taste-specific genes by gene chip analysis and shown to be expressed in subsets of taste cells by in situ hybridization analysis as described in the experimental examples and Figures.

Table 7:

This table lists 4 other primate taste specific genes identified by the inventive rationales and provides information as to the specific cell types in which these genes are expressed.

Table 8:

This table contains a listing of the human taste-specific genes which were quantified by TaqMan in LCM derived cDNA from both LE and TB from the same donors. As noted in Example 46, gene expression was measured in TaqMan as a CT (cycle threshold) value. Briefly the CT value for a given sample was determined by the PCR cycle at which the amount of gene-specific PCR product (as measured by fluorescence) reaches a set value. For highly expressed genes, the threshold is reached early in the PCR run and the CT value is relatively low (<35) while genes with very low or no expression do not reach the threshold before cycle 35. Expression of genes with CT values >40 are defined as not detectable. For the majority of genes listed in Table 8 expression was not detected in LE samples (CT>40) but was readily detectable in TB samples (CT<35).

Therefore, based on the foregoing, the subject invention provides methods for identifying human and other primate taste specific genes, including genes involved in salty taste perception or other taste perception modalities or modulation of taste modalities such as fat, metallic, CO2, sweet, bitter, sour, etc. and the use in screening assays for identifying human salty or other taste enhancers and other taste modulatory compounds and for identifying potential therapeutics that modulate other taste cell related functions and phenotypes including diseases and conditions not directly related to taste transduction.

Particularly, the present invention includes the use of cell-based assays to identify salty taste modulators (enhancers). These compounds have potential application in modulating human salty taste perception. Compounds identified for example in electrophysiological assays and their biologically acceptable derivatives are to be tested in human taste tests using human volunteers to confirm their effect on human salty taste perception. In addition compounds identified as potential therapeutics will be evaluated in appropriate in vitro and in vivo models depending on the nature of the intended application. For example compounds identified as potential therapeutics for diabetes may be evaluated in well known diabetic animal models such the NOD mouse model or BB rat model. Similarly, compounds identified as potential therapeutics for IBD or Crohn's disease may be tested in rodent animal models for IBD or Crohn's disease.

As discussed further infra, the cell-based assays used to identify taste, e.g., salty taste modulatory or therapeutic compounds will preferably comprise high throughput screening platforms to identify compounds that modulate (enhance) the activity of genes involved in salty taste perception using cells that express the genes disclosed herein or combinations thereof. Additionally, these sequences may be modified to introduce silent mutations or mutations having a functional effect such as defined mutations that affect ion (sodium) influx. As noted above, the assays will preferably comprise electrophysiological assays effected in amphibian oocytes or assays using mammalian cells that express a an ion channel according to the invention using fluorescent ion sensitive dyes or membrane potential dyes, e.g., sodium-sensitive dyes. Preferably, compounds that modulate such ion channels are identified by screening using electrophysiological assays effected with oocytes that express an ion channel identified herein (e.g., patch clamping or two electrode voltage clamping).

Still alternatively, compounds that modulate the subject ion channels putatively involved in salty taste may be detected by ion flux assays, e.g., radiolabeled-ion flux assays or atomic absorption spectroscopic coupled ion flux assays. As disclosed supra, these compounds have potential application in modulating human salty taste perception or for modulating other biological processes involving aberrant or normal ion channel function.

The subject cell-based assays use mutant nucleic acid sequences which are expressed in desired cells, preferably oocytes or human cells such as HEK-293 cells, or other human or mammalian cells conventionally used in screens for identifying ion channel or GPCR modulatory compounds. These cells may further be engineered to express other sequences, e.g., other taste GPCRs, i.e., T1Rs or T2Rs such as are described in other patent applications by the present Assignee Senomyx as well as appropriate G proteins. The oocyte system is advantageous as it allows for direct injection of multiple mRNA species, provides for high protein expression and can accommodate the deleterious effects inherent in the overexpression of ion channels. The drawbacks are however that electrophysiological screening using amphibian oocytes is not as amenable to high throughput screening of large numbers of compounds and is not a mammalian system. As noted, the present invention embraces assays using mammalian cells, preferably high throughput assays.

Some ion channels putatively involved in salty taste (ENaC) proteins are known to form heteromeric channels comprised of three subunits, an alpha, beta, and a gamma or delta subunit. The sequences of these respective ENaC subunits are disclosed in an earlier patent application by the present Assignee, U.S. Ser. No. 10/133,573 which is incorporated by reference in its entirety herein. Upon co-expression in a suitable cell these subunits result in a heterotrimeric channel having cation ion channel activity; in particular it responds to sodium and should similarly respond to lithium ions in cell-based assays such as those which are disclosed herein and in Senomyx's prior application referenced above.

The Senomyx application incorporated by reference provides high throughput screening assays using mammalian cells transfected or seeded into wells or culture plates wherein functional expression in the presence of test compounds is allowed to proceed.

The invention specifically provides methods of screening for modulators, e.g., activators, inhibitors, stimulators, enhancers, etc., of human salty taste or other taste modalities and potential therapeutics that target other taste cell functions or phenotypes using the nucleic acids and proteins, sequences provided herein. Such modulators can affect salty taste or other taste modalities or taste cell related functions and phenotypes, e.g., by modulating transcription, translation, mRNA or protein stability; by altering the interaction of the ion channel with the plasma membrane, or other molecules; or by affecting ion channel protein activity. Compounds are screened, e.g., using high throughput screening (HTS), to identify those compounds that can bind to and/or modulate the activity of a taste receptor or taste ion channel polypeptide or transporter or fragment thereof. In the present invention, proteins are recombinantly expressed in cells, e.g., human cells, or frog oocytes and the modulation of activity is assayed by using any measure of ion channel, receptor or transporter function, such as measurement of the membrane potential, or measures of changes in intracellular sodium or lithium levels. Methods of assaying ion, e.g., cation, channel function include, for example, patch clamp techniques, two electrode voltage clamping, measurement of whole cell currents, and fluorescent imaging techniques that use ion sensitive fluorescent dyes and ion flux assays, e.g., radiolabeled-ion flux assays or ion flux assays.

An enhancer of a gene identified as set forth in the current application can be used for a number of different purposes. For example, it can be included as a flavoring agent to modulate the salty taste of foods, beverages, soups, medicines, and other products for human consumption. Additionally, the invention provides kits for carrying out the herein-disclosed assays.

DEFINITIONS

"Putative taste receptor or ion channel gene" refers to a gene expressed in taste cells that is not expressed in lingual cells or is expressed substantially less in lingual cells that moreover preferably is not expressed in taste cells that express a T1R, T2R, TRPM5, or PKD2L1/PKD1L3 gene.

"Putative salty taste receptor or ion channel gene" refers to a gene specifically expressed in taste cells that is not expressed in lingual cells or is expressed substantially less in lingual cells that moreover preferably is not expressed in taste cells that express a T1R or T2R gene. Preferably this gene will also be an ion channel or a G protein coupled receptor.

"Putative fat or lipid taste receptor or ion channel gene" refers to a gene specifically expressed in taste cells that is not expressed in lingual cells or is expressed substantially less in lingual cells that moreover preferably is not expressed in taste cells that express a T1R or T2R gene. Preferably this gene will also comprise specific motifs characteristic of fatty acid or lipid binding or be predicted to be a fat or lipid associated taste receptor based on its prior identification as encoding a fatty acid binding protein or to possess a structure or homology to another fatty acid binding protein.

"Taste Cell" refers to a cell that when mature expresses at least one receptor, transporter, or ion channel that directly or indirectly regulates or modulates a specific taste modality such as sweet, sour, umami, salty, bitter, fatty, metallic or other taste perception or general taste perception such as taste intensity or the duration of a taste response. Taste cells express mRNA and/or a protein for the gene C6orf15 (chromosome reading frame 15)—also known as STG. This gene has been described as a taste-specific gene (M. Neira et al. Mammalian Genome 12: 60-66, 2001) and is among the macaque taste specific genes reported herein. In addition a mature taste receptor cell typically will express mRNA and/or protein for alpha ENaC. We have data (not shown herein) that reveals that alpha ENaC is expressed in at least sweet, bitter, umami, sour and most likely salty taste cells. Further, a mature taste receptor cell will typically express mRNA and/or protein for cytokeratin 19. This protein is only expressed in mature taste cells and is not found in basal or stem cells. (L. Wong et al. Chemical Senses 19(3): 251-264, 1994). Furthermore, taste cells can be identified by those skilled in the art base on their characteristic morphology. In particular mature taste receptor taste cells are elongated and spindle-shaped. Also, a mature taste receptor cell has the apex of the cell (apical membrane) penetrating into the taste pore thereby gaining access or exposure to saliva. By contrast, an immature taste cell, e.g., a basal cell or stem cell is rounded and is not exposed to the taste pore and saliva. Also, unlike mature taste cells, basal and stem cells tend to be localized towards the base of taste buds.

"Chemosensory cells" are cells that are involved in sensing of chemical stimulants such as tastants and other chemical sensory stimuli such as odorants. Chemosensory cells herein include in particular taste receptor cells and cells comprised in the digestive or urinary tract or other organs that when mature express one or more taste receptors. For example, gastrointestinal chemosensory cells are known which express T1Rs or T2Rs and which cells are likely involved in food sensing, metabolism, digestion, diabetes, food absorption, gastric motility, et al. In addition, cells found in the urinary tract likely express salty taste receptors and are involved in sodium transport, excretion and functions associated therewith such as blood pressure and fluid retention. Further, in the digestive system chemosensory cells that express taste receptors may also express chromogranin A, which is a marker of secretory granules. (C. Stermini, "Taste Receptors in the Gastrointestinal Tract. IV. Functional Implications of Bitter Taste Receptors in Gastrointestinal Chemosensing". American Journal of Physiology, Gastrointestinal and Liver Physiology.", 292:G457-G461, 2007).

"Taste-cell associated gene" or "taste specific gene" herein refers to a gene expressed by a taste cell that is not expressed by lingual cell that is involved in a taste or non-taste related taste cell function or phenotype. Taste cells include cells in the oral cavity that express taste receptors such as the tongue and taste cells in other areas of the body that express taste receptors such as the digestive system and urinary tract. Such genes are contained in Tables 1, 2, 3, 4, 5, 6, 7, and 8. With respect to putative taste receptor or taste modulatory genes, preferably, these genes are expressed more in cells comprised in the top half relative to the bottom half of the taste bud. These genes include genes involved in taste and non-taste related functions such a taste cell turnover, diseases affecting the digestive system or oral cavity, immunoregulation of the oral cavity and/or digestive system, digestive and metabolic functions involving taste cells such a diabetes, obesity, blood pressure, fluid retention et al. In referring to the particular taste specific genes identified herein these genes include the nucleic acid sequences corresponding the Accession Numbers contained in Tables 1, 2, 3, 4, 5, 6, 7, and 8 and contained in the Sequence Listing preceding the claims as well as orthologs thereof and chimeras and variants including allelic variants thereof. In particular such variants include sequences encoding polypeptides that are at least 80% identical, more preferably at least 90% or 95, 96, 97, 98 or 99% identical to the polypeptides encoded by the genes corresponding to the recited Accession numbers or to orthologs thereof, especially human and non-human primate orthologs. In addition, the genes include nucleic acid sequences that hybridize under stringent hybridization conditions to a nucleic acid sequence corresponding to one of the gene sequences corresponding to the gene Accession numbers recited in the Tables and sequence listing herein.

"Cation channels" are a diverse group of proteins that regulate the flow of cations across cellular membranes. The ability of a specific cation channel to transport particular cations typically varies with the valency of the cations, as well as the specificity of the given channel for a particular cation.

"Homomeric channel" refers to a cation channel composed of identical alpha subunits, whereas "heteromeric channel" refers to a cation channel composed of two or more different types of alpha subunits. Both homomeric and heteromeric channels can include auxiliary beta subunits.

A "beta subunit" is a polypeptide monomer that is an auxiliary subunit of a cation channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits.

The term "authentic" or wild-type" or "native" nucleic acid sequences refer to the wild-type nucleic acid sequences contained in the Tables and sequence listing herein as well as splice variants and other nucleic acid sequences generally known in the art.

The term "authentic" or "wild-type" or "native" polypeptides refers to the polypeptide encoded by the genes and nucleic acid sequence contained in the Tables and Sequence Listing.

The term "modified enhance receptor nuclear acid sequence" or "optimized nucleic acid sequence" refers to a nucleic acid sequence which contains one or more mutations, particularly those that affect (inhibit or enhance) gene activity in recombinant host cells, and most especially oocytes or human cells such as HEK-293 cells. Particularly, these mutations include those that affect gating by the resultant ion channel containing the mutated subunit sequence. The ion channel may comprise such mutations in one or several of the three subunits that constitute the particular ion channel. The modified nucleic acid sequence for example may contain substitution mutations in one subunit that affect (impair) gating function or defective surface expression. The invention embraces the use of other mutated gene sequences, i.e., splice variants, those containing deletions or additions, chimeras of the subject sequences and the like. Further, the invention may use sequences which may be modified to introduce host cell preferred codons, particularly amphibian or human host cell preferred codons.

The term receptor or ion channel protein or transporter or fragment thereof, or a nucleic acid encoding a particular taste receptor or ion channel or transporter or a fragment thereof according to the invention refers to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to an amino acid sequence encoded by the wild-type nucleic acid or amino acid sequence of the taste protein, e.g., proteins encoded by the gene nucleic acid sequences contained in the Tables and Sequence Listing herein as well as fragments thereof, and conservatively modified variants thereof; (3) polypeptides encoded by nucleic acid sequences which specifically hybridize under stringent hybridization conditions to an anti-sense strand corresponding to a nucleic acid sequence encoding a gene encoded by one of said genes, and conservatively modified variants thereof; (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to a nucleic acid, e.g., those disclosed herein.

A putative salty or other taste specific gene or polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Typically these genes will encode proteins that have ion channel activity, i.e., they are permeable to sodium or lithium.

By "determining the functional effect" or "determining the effect on the cell" is meant assaying the effect of a compound that increases or decreases a parameter that is indirectly or directly under the influence of a taste gene, preferably salty taste gene identified herein e.g., functional, physical, phenotypic, and chemical effects. Such functional effects include, but are not limited to, changes in ion flux, membrane potential, current amplitude, and voltage gating, a as well as other biological effects such as changes in gene expression of any marker genes, and the like. The ion flux can include any ion that passes through the channel, e.g., sodium or lithium, and analogs thereof such as radioisotopes. Such functional effects can be measured by any means known to those skilled in the art, e.g., patch clamping, using voltage-sensitive dyes, or by measuring changes in parameters such as spectroscopic characteristics (e.g., fluorescence, absorbance, refractive index), hydrodynamic (e.g., shape), chromatographic, or solubility properties.

"Inhibitors," "activators," and "modulators" of the subject taste cell expressed polynucleotide and polypeptide sequences are used to refer to activating, inhibitory, or modulating molecules identified using in vitro and in vivo assays of these polynucleotide and polypeptide sequences. Inhibitors are compounds that, e.g., bind to, partially or totally block activity, decrease, prevent, delay activation, inactivate, desensitize, or down regulate the activity or expression of these taste specific proteins, e.g., antagonists. "Activators" are compounds that increase, open, activate, facilitate, enhance activation, sensitize, agonize, or up regulate protein activity. Inhibitors, activators, or modulators also include genetically modified versions of the subject taste cell specific proteins, e.g., versions with altered activity, as well as naturally occurring and synthetic ligands, antagonists, agonists, peptides, cyclic peptides, nucleic acids, antibodies, antisense molecules, siRNA, ribozymes, small organic molecules and the like. Such assays for inhibitors and activators include, e.g., expressing the subject taste cell specific protein in vitro, in cells, cell extracts, or cell membranes, applying putative modulator compounds, and then determining the functional effects on activity, as described above.

Samples or assays comprising the proteins encoded by genes identified herein that are treated with a potential activator, inhibitor, or modulator are compared to control samples without the inhibitor, activator, or modulator to examine the extent of activation or migration modulation. Control samples (untreated with inhibitors) are assigned a relative protein activity value of 100%. Inhibition of an ion channel is achieved when the activity value relative to the control is about 80%, preferably 50%, more preferably 25-0%. Activation of an ion channel is achieved when the activity value relative to the control (untreated with activators) is 110%, more preferably 150%, more preferably 200-500% (i.e., two to five fold higher relative to the control), more preferably 1000-3000% or higher.

The term "test compound" or "drug candidate" or "modulator" or grammatical equivalents as used herein describes any molecule, either naturally occurring or synthetic compound, preferably a small molecule, or a protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, siRNA, oligonucleotide, ribozyme, etc., to be tested for the capacity to modulate cold sensation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., a gene or sequence contained in the Tables and Sequence Listing herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nucl. Acids Res. 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci., USA 89:10915 (1989)) alignments (B) of 50, expectation (E) of 10, M=5, =−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., J. Biol. Chem. 273(52):35095-35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (1); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell ($_{3rd}$ ed., 1994) and Cantor and Schimmel, Biophysical Chemistry Part I: The Conformation of Biological Macromolecules (1980). "Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include extracellular domains, transmembrane domains, and cytoplasmic domains. Typical domains are made up of sections of lesser organization such as stretches of .beta.-sheet and .alpha.-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, chemical, or other physical means. For example, useful labels include $^{32P}$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical.

This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1.xSSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and Current Protocols in Molecular Biology, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR Protocols, A Guide to Methods and Applications, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

The term antibody, as used herein, also includes antibody fragments either produced by the modification of whole antibodies, or those synthesized de novo using recombinant DNA methodologies (e.g., single chain Fv), chimeric, humanized or those identified using phage display libraries (see, e.g., McCafferty et al., Nature 348:552-554 (1990)) For preparation of antibodies, e.g., recombinant, monoclonal, or polyclonal antibodies, many technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988) and Harlow & Lane, Using Antibodies, A Laboratory Manual (1999); and Goding, Monoclonal Antibodies: Principles and Practice (2d ed. 1986)).

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a protein, polymorphic variants, alleles, orthologs, and conservatively modified variants, or splice variants, or portions thereof, can be selected to obtain only those polyclonal antibodies that are specifically immunoreactive with proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); and Pickar, Dosage Calculations (1999).

Therefore, based on the foregoing, this invention provides in its generic embodiments methods for identifying taste specific genes which may be functionalized using the methods disclosed herein. These techniques have identified all of the genes contained in Tables 1-8 too be taste specific. In addition, as disclosed in the experimental examples this invention further provides specific information and characterization of certain human and primate taste specific genes identified by the rationales described in detail infra and further practical applications of these genes, gene products, and cells which express same as well as modulators of these genes. The more specific aspects of the invention are described as follows and in the examples.

Particularly, the inventors provide lists of genes in Table 6 and 7 infra which are expressed in primate taste cell subsets and describe uses of these genes in taste biology. These genes which are selectively expressed in primate fungiform papilla taste cells at the front of the tongue and circumvallate papilla taste cells at the back of the tongue were identified were identified using the afore-described gene chips/microarray methods by comparing expression in taste receptor cells compared to non-taste lingual epithelial cells isolated by laser capture micro-dissection (LCM). Since salty taste perception is most prevalent at the front of the tongue, taste receptor genes potentially including the salty taste and other taste receptor could be present within this gene set. The genes in Table 6 and Table 7 as reported therein are expressed in different subsets of primate taste cells and were identified by gene chip analysis and shown to be expressed in subsets of taste cells by in situ hybridization analysis.

For example, results contained in the experimental examples and figures referred to therein reveal that FAM26A, MCTP1, TMEM30B, and TUSC3 are expressed in many TRPM5 cells, suggesting that these genes are expressed in sweet, umami, and bitter taste cells, since TRPM5 is a marker of sweet, bitter, and umami taste cells. Also, the results show that GPR113 and TMEM16G are expressed in a subset of TRPM5 cells, suggesting that these genes could be selectively expressed in sweet, umami, or bitter taste cells (or a combination thereof).

Also, the results contained in the experimental examples and figures referred to therein show that TMEM44 is expressed in cells that do not express TRPM5 (bitter, sweet, umami) or PKD1L3 (sour), indicating that the expression of this gene is a marker for a unique taste cell type that could correspond to salt, fat, or another taste modality, and, furthermore, that this gene may encode the primary salt or fat receptor.

Based on the foregoing, this invention contemplates the use of FAM26A, MCTP1, TMEM30B, and TUSC3 as markers alone or in combination with other taste specific genes contained herein for marking, isolating, enriching or ablating sweet, bitter, and umami taste cells or cells expressing TRPM5. In addition, this invention includes the use FAM26A, MCTP1, TMEM30B, and TUSC3 and compounds that enhance or inhibit these gene products in order to selectively modulate taste cell function and responses to tastants including sweet, bitter, and umami.

In addition, the results contained in the experimental examples and figures referred to therein indicate that GPR113 and TMEM16G can be used as a marker for sweet, bitter, or umami taste cells or subsets of TRPM5 cells. Therefore, the invention further describes the use of the use of GPR113 and TMEM16G as markers alone or in combination with other taste specific genes contained herein for marking, isolating, enriching or ablating sweet, bitter, and umami taste cells or cells expressing TRPM5.

In addition, the results contained in the experimental examples and figures referred to therein indicate that GPR113 and TMEM16G and compounds that enhance or inhibit these gene products can selectively modulate taste cell function and responses to tastants including sweet, bitter, or umami. Therefore, the invention further embraces the use of these genes and corresponding polypeptides in assays for identifying sweet, bitter or umami taste modulators.

In addition, based on the finding (as determined by in situ hybridization of primate taste bud cells) that all of TUSC3, ASCL1, FAM26A, FAM26C, IKBKAP, LOC285965, SCNN1D, SLC4A11, SLC26A7, and TMEM30B are expressed by specific taste cell subsets that these genes may be used as biomarkers and that the genes and gene products may be used isolate, mark or ablate these cells and thereby determine the taste related function of these taste bud cells. Based on this same finding the invention further relates to these isolated cells and assays using these cells and genes to identify taste modulators Still further, the results contained in the experimental examples and figures referred to therein indicate that TMEM44 can be used as a marker for a unique, novel taste cell type that does not correspond to sweet, bitter, and umami taste cells and that TMEM44 and compounds that enhance or inhibit this gene product can selectively modulate taste cell function and responses to tastants other than sweet, bitter, and umami, which include salt, fat, and other tastants. Therefore, the invention further includes the use of these genes and their corresponding polypeptides in screening assays for identifying taste modulators.

Still further, the results contained in the experimental examples and figures referred to therein indicate that TMEM44 may correspond to a salt receptor or fat receptor, or a marker of immature taste cells or stem cells. Also, this suggests that TMEM44 and compounds that enhance or inhibit this gene product can selectively modulate taste cell development and/or differentiation of specific taste cell types (i.e. bitter taste cells). Accordingly, the invention embraces the use of these genes and polypeptides in screening assays for identifying compounds that selectively modulate taste cell development and/or differentiation of specific taste cell types (i.e. bitter taste cells).

Still further, based on the experimental data, the invention embraces the use of these gene products and compounds that enhance or inhibit gene products can affect: selective apoptosis of taste cells responding to aversive taste modalities such as bitter and sour cells; modulation of transcription factors that control taste receptor expression; modulation of specific bitter receptor expression to minimize off-tastes of vegetables, children's medicine, and coffee; autocrine/paracrine modulation of taste cell development; prolongation of taste bud lifetime; development of supertasters (rodent model systems) to screen for chemical and biological toxins (terrorism), rancid/spoiled/contaminated food and beverage products; and activation of stem cells to differentiate into defined taste cell types.

In addition, the invention further encompasses the possibility that these gene products can also be ancillary taste receptors or primary taste receptors including receptors for salt, fat, and other taste modalities including metallic. This can be determined by the inventive methods.

Also, based on the experimental results, the invention includes the use of these gene products and compounds that enhance or inhibit gene products to modulate the function of any cell expressing a taste receptor, including but not limited to cells in the gastrointestinal tract such as enteroendocrine cells that regulate gastric motility and peptide secretion (e.g. GLP-1: glucagon-like peptide 1; GIP: gastric inhibitory peptide) as well as the other therapeutic applications of taste specific genes and modulators afore-mentioned. These applications include trafficking of taste receptors to and from the apical membrane/taste pore region to enhance or repress general or specific tastes; regulation of taste cell action potential firing frequency/membrane potential to control the intensity of general or specific tastes; regulation of neurotransmitter release to afferent nerve to control the intensity of general or specific tastes; and autocrine/paracrine modulation of taste receptor function; regeneration of taste cells as well as prophylaxis/prevention of taste cell loss following injury, chemotherapy for cancer, radiation therapy for cancer, drug-induced dysgeusia, ageusia, and taste bud loss in the geriatric population; oral hygiene, halitosis, detoxification of noxious substances in oral cavity, and neutralization/elimination of bacteria, viruses, and other immunogens in the saliva/mouth; saliva composition and treatment of dry mouth in conditions of xerostomia and autoimmune disease (Sjogren's syndrome).

Still further, the results contained in the experimental examples and figures referred to therein indicate by use of double label in situ hybridization histology what specific TRPM5 cell type that GPR113 is expressed in. As disclosed infra we identify that GPR113 is not expressed in T1R1 umami cells, T1R2 sweet cells, or T2R bitter cells. Also, it was found that GPR113 is expressed in a subset of T1R3 cells that do not express T1R1 or T1R2. Thus, GPR113 cells define a new taste cell type of T1R3 only cells. Accordingly, this invention embraces the use of this gene to mark, enrich, isolate or ablate these cells.

Also, based on this discovery the invention provides for the use of GPR113 as a marker for this unique taste cell type that because it is in a unique cell population, is a GPCR (many taste receptors are already known to be GPCRs) and therefore this cell likely corresponds to a specific taste modality for which taste cells have not yet been characterized or modulates a specific taste modality such as CO2 sensation, salt, fat, metallic or astringent. Also, the invention provides for the further possibility that GPR113 may associate with T1R3 to form a novel taste receptor for sweet, umami, or other tastants.

Further, based on the foregoing experimental evidence, this invention provides for the use of GPR113 or the corresponding polypeptide as a marker to identify and isolate this unique, novel taste cell type (T1R3 only cells) that does not correspond to sweet, bitter, and umami taste cells and its use to identify taste modulators as well as the aforementioned therapeutic applications of compounds modulating taste specific polypeptides.

Still further, the results contained in the experimental examples and figures referred to therein indicate that the genes KIT, IKBKAP, LOC285965, and SV2B are taste specific taste genes and are expressed in the specific primate taste cell subsets (see Table 7 infra). In addition, the results contained in the experimental examples and figures referred to therein indicate that another gene, MFDS4 is expressed in sensory taste cells that are not sweet, umami, bitter or sour cells, suggesting that this gene is expressed in a similar taste cell subset as TMEM44. Therefore, the invention includes the use of these genes and corresponding polypeptides in screening assays for taste modulators and therapeutics and as biomarkers of specific, unique taste cell subsets.

Still further, in Tables 1-5 of this application the inventors provide a listing of primate taste-specific genes also identified by the inventive rationales that have been demonstrated to reliably include functional taste specific genes already known. These listing of genes include genes encoding transmembrane proteins such as ion channels (sodium), GPCRs, ion transporters, as well as multi-transmembrane proteins with no function yet assigned. Therefore, the invention further includes functionalizing these genes and assessing their function in taste detection or modulation or ancillary taste cell functions.

Still further, the results contained in the experimental examples and figures referred to therein indicate that IKBKAP and SV2B are expressed in many PKD1L3 cells, and that these genes are likely expressed in sour taste cells, since PKD1L3 is a marker of sour taste cells. Therefore, the invention embraces screening assays to assess the effect of modulators on specific taste modalities including sour, or basic taste or other tastes.

Still further, the results contained in the experimental examples and figures referred to therein indicate that KIT is expressed in cells that express the umami taste receptor component T1R1. This is predicted by the inventors to support a view that KIT is expressed in cells responsible for umami taste perception. Accordingly, KIT may modulate umami taste perception.

Still further, the results contained in the experimental examples and figures referred to therein indicate that LOC285965 is expressed in cells that express TRPM5 and T1R3 but not in cells that express the umami taste receptor component T1R1, or the sweet taste receptor component T1R2. These results suggest that LOC285965 is expressed in the 'T1R3 only' population of taste cells (similar to GPR113).

Still further, the results contained in the experimental examples and figures referred to therein indicate that IKBKAP and SV2B are expressed in PKD1L3 sour taste cells and indicate that they can be used as markers of this taste cell population. Therefore, the invention includes the use thereof to mark, enrich, isolate or ablate these taste cells so that their effect can be assessed in vitro or in vivo.

Still further, the results contained in the experimental examples and figures referred to therein indicate that IKBKAP and SV2B and compounds that enhance or inhibit these gene products can selectively modulate taste cell function and responses to sour tastants as well as other functions of the PKD1L3 taste cell population. Accordingly, this invention includes the use of these genes and gene products in sour taste modulatory or other taste assays.

Still further, the results contained in the experimental examples and figures referred to therein indicate further that since IKBKAP is mutated in the human disease familial dysautonomia, where taste buds are absent or atrophic and individuals exhibit deficiencies in detection of sweet, bitter, sour, and salty tastants (hypogeusia) that IKBKAP expression in PKD1L3 cells may be important for taste cell development and/or maintenance. Accordingly, the invention embraces the use of this gene and gene product in assays to identify compounds that modulate taste cell development and/or maintenance.

Also, these same findings that and the fact that Botulinum neurotoxin (BoTox) enters neuronal-type cells by interacting with SV2B; indicate that BoTox may selectively modulate sour taste as well as other functions of the PKD1L3 taste cell population. Therefore, SV2B modulators identified by the inventive methods may elicit neuronal effects and may be useful in cosmetic applications.

Also, the same aforementioned findings that KIT is expressed in umami taste cells indicate that it can be used as a marker of this taste cell type. Therefore, the invention embraces the use of KIT as a marker of umami cells. Also, because these findings that indicate that KIT and compounds that enhance or inhibit this gene product can selectively modulate taste cell function and responses to umami tastants the invention further embraces the compounds identified and their use in modulating umami gene functions including taste and food sensing.

Also, these same findings and the fact that Gleevec (Imatinib), is an inhibitor of the KIT tyrosine kinase activity, indicate that this and other KIT tyrosine kinase inhibitors may selectively inhibit umami taste. Also, these findings suggest that individuals with gain of function mutations in KIT, for example in gastrointestinal stromal tumors (GIST), may have altered umami taste perception. Therefore, the invention further embraces the use of KIT modulators in treating gastrointestinal cancers and for detecting these conditions.

Still further, the results contained in the experimental examples and figures referred to therein indicate that LOC285965 is expressed in T1R3 only taste cells similar to GPR113 and indicate that this gene is useful as a marker for a unique, novel taste cell type (T1R3 only cells) that does not correspond to sweet, bitter, and umami taste cells.

Still further, the results contained in the experimental examples and figures referred to therein indicate that LOC285965 may correspond to a salt receptor or fat receptor or a receptor for astringency or metallic taste by itself or in combination with GPR113. Therefore, the invention further provides for this possibility.

Still further, the results contained in the experimental examples and figures referred to therein indicate that LOC285965 may be a coreceptor with T1R3 for specific sweet or umami tastants or other novel tastants such as astringent and metallic tastants.

Still further, these same findings suggest that compounds that enhance or inhibit LOC285965 can selectively modulate taste function and responses to tastants. Accordingly, the invention embraces the use of this gene and gene products in screening assays for taste modulators.

Also, these same findings suggest that LOC285965 may correspond to a marker of immature taste cells that are differentiating into sweet or umami cells. Therefore, the invention embraces the use of this gene or polypeptide as a marker of immature taste cells and/or to isolate, enrich or deplete these cells.

Also, these same findings suggest that LOC285965 and compounds that enhance or inhibit this gene product can selectively modulate taste cell development and/or differentiation of specific taste cell types (i.e. sweet or umami taste cells). Therefore, the invention embraces the use of these compounds as sweet or umami or other taste modulators.

Still further, the results contained in the experimental examples and figures referred to therein indicate that MFSD4 and compounds that enhance or inhibit this gene product can selectively modulate taste cell function and responses to tastants other than sweet, bitter, umami, and sour which include salt, fat, and other tastants. Therefore, the invention includes the use of MFSD4 modulators to modulate taste.

Also, these same findings suggest that MFSD4 may correspond to the salt receptor or fat receptor or may be used as a marker of immature taste cells or developing taste cells or support cells. The invention Therefore includes the use of this gene in such usages.

Still further, these findings suggest that MFSD4 and compounds that enhance or inhibit this gene product can selectively modulate taste cell development and/or differentiation of specific taste cell types (i.e. bitter taste cells). Accordingly, the invention embraces the use of modulators of this gene for modulating taste cell development or differentiation.

Also, the data infra reveal that MFSD4 and TMEM44 are expressed in the same taste cell population which may respond to specific tastants. Therefore, the invention includes assays which coexpress these genes in order to identify taste modulators.

Also, the invention embraces the resultant taste receptor wherein MFSD4 and TMEM44 form a complex (heterodimer) to generate a taste receptor (such as fat, CO2, salt, metallic, or other taste modality).

Still further, the results contained in the experimental examples and figures referred to therein indicate that the ASCL1 (aka MASH1) transcription factor defines sour taste cells. ASCL1 is expressed in sour taste cells expressing the sour taste receptor gene PKD1L3; ASCL1 is not expressed in sweet, bitter, and umami taste cells expressing TRPM5. ASCL1 was previously reported to be a marker of type III taste cells. Type III taste are defined by morphological criteria which include: staining with an intermediate density by electron microscopy and making synaptic contacts with nerve fibers. Thus, our results demonstrate that type III taste cells, a cell type previously defined by morphological criteria, correspond to sour taste receptor cells defined by gene expression criteria.

Therefore, an application of this finding is that the ASCL1 transcription factor may bind to promoter elements in genes involved in sour taste perception. Thus, the genome could be screened for ASCL1 motifs to identify genes in sour cells, including sour receptor genes such as PKD2L1, PKD1L3, or additional genes that may form a complex with PKD2L1/PKD1L3 to generate a sour receptor.

Analogously, other taste receptor cells for sweet, bitter, umami, and salt are likely to express specific transcription factors that define those cell types. Therefore, the invention further embraces methods wherein the expression of all transcription factors in the genome is analyzed in taste cells by PCR and/or histology to determine which taste cell types express which transcription factors.

These finding further support other applications of this gene. For example, the invention includes the use of ASCL1 (aka MASH1) as a marker of sour taste cells and further for the isolation of Type III taste cells which correspond to sour taste receptor cells.

Moreover, because it has been determined that ASCL1 defines the sour taste cell lineage and may control sour taste cell development, the invention further provides for ASCL1 transcription factor DNA binding sequences to be used to identify sour cell genes and sour taste receptor genes. Also, the invention includes the use of such transcription factors can be used to define, mark, and/or label taste cell types. With respect thereto, each taste cell will express one or more transcription factors that define that taste modality.

Also, the invention further encompasses the use of the identified transcription factors to define taste modalities and in cell ablation studies to specifically eliminate a specific taste. Moreover, the invention includes the use of these identified transcription factors that define new taste cell types in cell studies to determine what taste modality is lacking (i.e. what taste can an animal no longer perceive).

Also, as described and supported by data infra, this invention also shows that taste cells expressing the PKD2L1 and PKD1L3 genes, previously implicated in sour taste are heterogeneous and comprise multiple cell populations. In the front of the tongue, in fungiform (FG) papilla there are cells expressing PKD2L1 only, PKD1L3 only, and both PKD2L1 plus PKD1L3. By contrast, in the back of the tongue, in circumvallate papilla (CV), most cells coexpress PKD2L1 plus PKD1L3.

Also, the invention reveals that in addition thereto there is a distinct group of taste cells that express PKD1L3 only and a smaller set of cells that express PKD2L1 only. Previous literature has suggested that cells expressing PKD2L1 (encompassing PKD2L1 and cells coexpresing PKD2L1 plus PKD1L3) respond to sour taste (Huang et al, Nature 2006 Aug. 24; 442(7105):934-8.) However, PKD1L3 cells were not previously known and no function has yet been ascribed.

Therefore, the invention further contemplates the use of PKD1L3 cells as candidate basic or salt responding cells and that PKD1L3 is involved in a different (other than sour) taste modality, e.g., basic taste perception since the related sour receptor, PKD2L1, responds to acidic taste.

Still further, the results contained in the experimental examples and figures referred to therein indicate that the FAM26C gene is expressed in TRPM5 cells (see results infra) and therefore can be used as a marker of sweet, bitter and umami cells. Therefore, the invention further includes the use of FAM26C as a marker or to isolate, enrich or purify or ablate specific taste cells including sweet, bitter and umami cells.

Also, based on these same findings the invention includes the possibility that PKD1L3 only taste cells are candidate taste cells, e.g., which modulate basic taste sensation or other taste modalities, and that PKD1L3 is a candidate taste receptor, e.g., basic taste sensation. Also, the invention provides for an embodiment wherein PKD1L3 may complex with one of the gene products identified herein to form a taste receptor.

Also, based on the findings that FAM26C is expressed in TRPM5 cells, including sweet, bitter, and umami taste cells, it can be used as a marker of this taste cell population and FAM26C and compounds that enhance or inhibit FAM26C can selectively modulate taste cell function and responses to sweet, bitter, and umami tastants as well as other functions of the TRPM5 taste cell population, including functions of the TRPM5 taste cells that are candidate salty taste cells and that coexpress T1R3.

Also, as shown infra, this invention reveals that taste cells in the bottom of the taste buds are immature whereas cells in the top half are mature and express taste receptor genes. Cells in the bottom half of the taste bud express the gene sonic hedgehog (SHH), which is a marker of developing cells. TMEM44 taste cells are localized in the bottom half of the taste bud and the expression pattern of TMEM44 is similar to SHH. Therefore, we have predicted that TMEM44 cells, (which also express MFSD4) are immature and comprise, in part, developing taste cells. Supportive of this finding, a small fraction of taste cells expressing TMEM44 also express either TRPM5 (a marker of mature sweet, bitter and umami cells) or PKD1L3 (a marker of mature sour cells). Cells expressing both TMEM44 and TRPM5 (or PKD1L3) are therefore maturing into professional taste cells. By contrast, cells s in the top half of the taste bud are mature taste cells, do not express SHH, and express taste receptor genes for the sweet, bitter, umami, and sour taste receptors. Since all mature, professional taste cells and taste receptors are localized to the top half of the taste bud, the invention further includes methods for recovery of a fraction of taste bud cells that should include virtually all the functional taste cells including the salty taste cells. Particularly, recovery of the cells in the top half of the taste buds should include cells expressing the salty taste receptor.

Therefore, the invention and methods for assaying taste specific genes and identifying specific taste receptors and taste cell subsets have shown that the taste cells in the bottom half of the taste bud are immature, that the taste cells in the top half of the taste bud are mature and express genes for sweet, bitter, umami, and sour taste receptors, and further that SHH can be used as a marker of immature and developing taste cells at the bottom of the taste bud and that TMEM44 and MFSD4 are markers of immature and developing taste cells at the bottom of the taste bud.

It is predicted based on these results that a subpopulation of TMEM44 cells may be mature taste cells corresponding to a yet unidentified taste cell, e.g., metallic, fat, astringent, CO2, and the like and that a corresponding taste receptor and taste cell will be expressed or comprised in the top taste bud cells, since all other known taste receptors are expressed in the top taste bud cells. This is a reasonable assumption based on the results obtained by the inventors herein, especially since all other known professional, mature taste cells are expressed in the top of the taste bud.

More specifically, and further relating to the foregoing, and the results and data in the experimental examples and supporting figures, the inventors have gleaned the following information relating to several subsets of taste bud cells we have identified discussed above, including:

(i) with particular respect to TMEM44 cells, the inventors have found that these cells comprise about 40% of the taste bud cell population and are located towards the bottom of the taste bud. Also, we have identified other genes expressed by these cells or in the bottom of the taste bud including MFSD4 and Sonic Hedgehog (SHH). The latter is a cytokine involved in immature cell differentiation. For this reason, we predict that TMEM44 represents an immature taste cell population that includes stem cells that replenish the taste bud cells every 2-3 weeks in the human. While these cells are immature, they may still contain a subset of mature cells that may be responsible for taste such as salt sensation.

(ii) with particular respect to GPR113 cells, the inventors have discovered that these cells represent about 10% of the taste bud cell population, and are distinct from sweet, bitter, and umami taste cells, and are located in the top of the taste bud. They express T1R3 and TRPM5 but not the G protein alpha subunit gustudin (GNAT3), suggesting that they represent a novel taste cell population that detects a new taste modality such as fat. Other cells that express TRPM5 and T1R3 include sweet cells (also express TIR2) as well as umami cells (also express T1R1). Bitter cells (also express T2Rs) express TRPM5 but not T1R3. In contrast to GPR113 cells, sweet, bitter, and umami cells all express GNAT3.

(iii) with particular respect to PKD2L1 and PKD1L3 cells, reportedly responsible for sour taste sensation, the inventors have found that they comprise about 10% of the taste bud cell population and are located in the top of the taste bud. Also, they have observed that these cells are heterogeneous and that there are distinct PKD2L1 and PKD1L3 'single positive' cell populations in addition to a PKD2L1 and PKD1L3 'double positive' cell population. This heterogeneity suggests that one of these subsets could represent a salt or another type of taste sensing cell.

(iv) with particular respect to other markers, the inventors' results suggest that there is another subset of taste cells (~8% of the taste bud cell population) that does not express any of the following markers: TMEM44, TRPM5, PKD2L1 or PKD1L3, which may represent another taste e.g., CO2 or salt sensing cells. As disclosed while a primary focus of this invention was the elucidation of the salty taste receptor and that these efforts have been successful as the TRPML3 gene has been shown to be a salty taste receptor there may be other salty taste receptors.

The invention further includes the use of these unique taste cell populations as part of its strategies for identifying salty and other types of taste sensing cells such as fat, metallic, astringent, CO2, et al.

Also, the invention further encompasses the use of the genes reported herein as a specific means for confirming the identity of salt and other types of taste cells. In particular, the invention includes the use of the specific taste genes reported herein in methods of cell ablation as a means to identify the specific effect of the selective removal of distinct cell subsets on taste and other ancillary taste related functions already mentioned.

One way to identify the salt cell or other taste cell modality population is to use cell ablation. This technique employs diphtheria toxin under the control of a promoter of a gene expressed in one of the taste cell subsets described above to selectively eliminate this taste cell population, while leaving all other taste cell populations intact. Cell ablation has been used successfully in other laboratories to selectively eliminate sweet (T1R2) and sour (PKD2L1) taste cell populations (work of Charles Zuker). Therefore, ablation of the afore-identified taste cell subsets described herein and others and these of the resultant ablated animals in assays of function (such as nerve recoding and licking/behavior tests will enable evaluating whether the resulting mice still sense a particular type of tastant, e.g., salt, sour, basic, metallic et al or possess an ancillary taste cell function such as taste cell differentiation, proliferation, et al.

For example, in the case of TMEM44, assuming that TMEM44 ablated mice do not sense salt but still sense sweet, bitter, umami, and sour, this result would point this population, or a subset of cells within this population, as the salt sensing cell. Alternatively, if the resulting mice lack taste buds this would suggest that the mice lose the ability to detect all 5 taste qualities because TMEM44 is expressed in immature cells or cell ablation may elicit no effect.

Alternatively, in the case of GPR113, assuming that GPR113 ablated mice cannot sense salt but still sense sweet, bitter, umami, and sour, this result would point to GPR113 expressing cells as the salt sensing cells. (As noted TRPML3 cells have been shown to sense salt, therefore this outcome is not probable. More likely, another taste modality would be affected.)

Alternatively, in the case of PKD2L1 assuming that PKD2L1 ablated mice cannot sense salt but still sense sweet, bitter, umami, and sour, this result would point to PKD2L1 expressing cells as the salt sensing cells. (Again, as TRPML3 cells have been shown to sense salt, this outcome is not probable. More likely, another taste modality would potentially be affected.)

Still alternatively in the case of PKD1L3, assuming that PKD1L3 ablated mice cannot sense salt but still sense sweet, bitter, umami, and sour, this result would point to PKD1L3 expressing cells as the salt sensing cells. (Again, as TRPML3 cells have been shown to sense salt, this outcome is not probable. More likely, another taste modality would potentially be affected.)

Yet alternatively, if none of these mice are deficient in salt or another taste perception, this suggests that the putative population of taste cells (8%) that do not express any of the aforementioned markers could be the salt or another desired taste cell subset, e.g., a fat or metallic taste sensing cell, or that all or multiple mature taste cell populations are capable of sensing salt.

Another means encompassed by the invention for the use in identifying salt or other types of taste cells and further based on the information provided herein relating to taste specific genes and the identified unique taste cell subsets, and the various genes they express or do not express involves generating a single cell suspension from taste buds and then performing single cell analyses with electrophysiology (patch clamping) or calcium imaging coupled with single cell PCR to identify which population(s) responds to sodium or other ions or molecules.

With respect to the foregoing, there are two main models to account for salt sensation in taste buds:

The first model is the labeled line model. In this model, a single cell type is responsible for sensing a given taste quality. This is true for sweet, bitter, umami and sour. In this model, there is a dedicated cell type responsible for salt sensation. As discussed above, we have narrowed down the list of candidate salt sensing cells and described techniques we would use to identify the salt cell.

The second model is the across fibre model where there is not a single cell type responsible for salt sensation. Instead, all or multiple cell types sense salt. In this model, a cell surface molecule, such as a receptor or ion channel, expressed in all or multiple mature taste cells would constitute the salt sensor.

The way to distinguish between these two models and to determine which is valid is to perform ell ablation experiments such as are described above.

In yet another aspect of the invention, this invention provides three primate taste specific genes expressed specifically in primate taste cells that were identified as taste specific genes by gene chip analysis, and shown to function as sodium channels in the literature. These genes, NALCN, NKAIN3 and TRPML3 were identified as being enriched in the top fraction of taste buds along with all other known taste receptor genes. Therefore, these genes are probable candidates for encoding a salty taste receptor. As described in detail, and substantiated by extensive functional data in a related patent application filed on even date as this application, cells expressing one of these genes, TRPML3 has been shown in functional assays and transgenic animals to be necessary for salty taste perception and to correspond to a salty taste receptor.

These ion channels were selected as probable candidates for the salty taste receptor based on a compilation of the rationales provide herein including the primate microarray/gene chip methods, the top versus bottom gene selection technique (these ion channels are all expressed in the top half of taste buds) and that they are identified in the qPCR methods as being expressed by isolated human taste bud cells. In addition all of these genes were selected as they correspond to previously reported putative sodium channels (but not known to be expressed specifically in taste cells much less to be expressed specifically in the top portion of the taste bud where a salty taste cell would be predicted to be present. The gene expression profiles for these 3 ion channels detected according to the inventive method is as follows:

NALCN, (aka VGCNL1), top vs. bottom ratio of 7.2, and TB vs. LE ratio of 11.2; TRPML3 (aka MCOLN3) top vs. bottom ratio of 1.6, and vs. LE ratio of 10.2; and NKAIN3 (aka FAM7D) which has a top vs. bottom ratio of 1.5, and TB vs. LE ratio of 3.3.

There has been information reported about all of these ion channels in the literature. For example, in Cell. 2007 Apr. 20; 129(2):371-83, the neuronal channel NALCN reportedly contributes resting sodium permeability and is required for normal respiratory rhythm. Also, Lu et al., describe that NALCN as a sodium leak channel. Further, in Kim et al., J. Biol. Chem. 2007 Oct. 25; [Epub ahead of print] the authors teach that a gain-of-function mutation in TRPML3 causes the mouse varitint-waddler phenotype. Also, Kim et al., (Id.) describes TRPML3 as a channel permeable to sodium after exposure of the channel to no/low sodium (consistent with saliva), and which was deemed by the inventors to potentially correlate with a putative salt receptor. Also, with respect to the NKAIN 3 gene, in Gorokhova et al., Human Mol. Genet. 2007 Oct. 15; 16(20):3394-410. Epub 2007 Jul. 2, this gene is reported as a member of a novel family of transmembrane proteins interacting with {beta} subunits of the Na,K-ATPase. Also, Gorokhova et al., (Id.) describe a *Drosophila* homologue of NKAIN3 as an amiloride-insensitive sodium channel, which the inventors also concluded would potentially be consistent with a putative salt receptor.

The identification of TRPML3 gene as encoding a polypeptide that is involved in salty taste and evidence that it functions as a salty taste receptor and the therapeutic applications of this gene are discussed extensively in the utility and PCT patent applications filed on the same date as this application, incorporated by reference in their entireties herein, and therefore is not discussed herein. However, this information is relevant as it substantiates the validity of the subject rationales for identifying and functionalizing the identified primate and human taste specific genes.

However, based thereon, NALCN, and NKAIN3 may still constitute other salty taste receptors expressed in taste bud cells and/or may modulate the function of TRPML3 and/or may associate with TRPML3 to produce a functional taste receptor. Based on the foregoing, NALCN, and NKAIN3 may constitute markers to identify salty taste receptor cells.

In addition, the inventors have obtained additional information concerning NALCN taste-specific gene identified by gene chip analysis and which gene was further found to be enriched in the top fraction of taste bud cells (along with all other known taste receptor genes).

Particularly, as described in the examples infra, it was demonstrated that NALCN is a taste-specific gene by endpoint PCR using purified taste buds and lingual epithelial cells isolated by laser capture microdissection. It was found that NALCN is expressed in a novel, unique taste cell type distinct from sweet, bitter, umami, and sour taste cells by immunohistochemistry with a NALCN antibody.

Therefore, since NALCN is a taste-specific gene, is expressed in a novel taste cell type, (and has been reported to function as a sodium-channel), NALCN is a candidate salty taste receptor and/or a marker of the salty taste cell population. Since NALCN and TRPML3 are both expressed in novel taste cell types, NALCN and TRPML3 may be coexpressed in the same taste cell population. Accordingly, NALCN and TRPML3 may function together in a complex; or NALCN may function independently of TRPML3 as another salty taste receptor. For example, NALCN may function downstream of TRPML3 akin to how TRPM5 functions downstream of sweet, bitter, and umami receptors. In this manner, NALCN would be involved in the signal transduction pathway for salty taste but not constitute the primary salty taste sensory receptor.

This can be determined in mice. Rodents have 3 distinct taste cell types:

Type III cells correspond to sour cells (PKD2L1 positive, SNAP-25 positive);

Type II cells correspond to sweet, bitter, and umami cells (TRPM5-positive, IP3R3 positive); and Type I cells have no defined function.

As shown in the examples infra, the inventors have demonstrated that NALCN is not expressed in IP3R3 cells (Type II) or SNAP-25 cells (Type III) in rodent. Thus, NALCN expression is implicated in Type I cells, and Type I cells are candidate salty taste cells.

However, alternatively, Type I cells may correspond to immature taste cells and if so, would likely be coexpressed with TMEM44/MFSD4 in an immature taste cell population.

Therefore, based on the foregoing information, the invention further encompasses NALCN as an additional salty (or other taste such as metallic or fat) taste receptor candidate gene and based thereon the use thereof as a marker to identify these taste cells.

In addition, since NALCN is a sodium ion channel, and is expressed in the top half of taste buds in cells that have an indeterminate taste function NALCN may control the resting membrane potential and excitability of the taste cells it is expressed in. Related thereto, compounds that enhance or inhibit function of the NALCN channel may regulate the excitability of salty taste cells, i.e., TRPML3 cells.

Based on this modulatory property, compounds that enhance or inhibit function of the NALCN channel may increase and decrease salt perception respectively, e.g., alone or in combination with TRPML3.

Also, NALCN may associate with TRPML3 to form a salty taste receptor. (As shown in the related application ablation of TRPML3 expressing taste cells in Varitint mice results in inhibition of salty taste perception in these rodents and in vitro electrophysiological assays using this ion channel have confirmed that it is a functional sodium channels and may be used to identify TRPML3 blockers and enhancers which should modulate salty taste).

Moreover, NALCN can be used as a marker of type I taste cells, which likely include salty taste cells. Alternatively, as type I taste cells may function as precursor cells for sweet, bitter, umami and sour taste cells, modulation of NALCN function may control taste cell differentiation and development into mature taste cell types.

In addition, because TMEM44 and MFSD4 are markers of immature taste cells, NALCN may be expressed in the subset of immature taste cells expressing TMEM44/MFSD4.

Further, because type I taste cells may also function as glial (support) cells, modulation of NALCN function may indirectly control the activity of sweet, bitter, umami, and sour cells and, as a result, sweet, bitter, umami, and sour taste.

Also, compounds that enhance or inhibit function of NALCN may increase and decrease salt perception respectively.

In yet another aspect, this invention provides specific assays for identifying a compound having potential in vivo application for modulating human salty taste. One method comprises the steps of (i) contacting a cell that expresses a gene encoding an ion channel, receptor or transporter identified as a putative salty taste affecting gene according to any one of the methods above, or a gene encoding a polypeptide possessing at least 90% sequence identity to the polypeptide encoded thereby, with at least one putative enhancer compound; (ii) assaying sodium conductance, receptor activity or sodium transport in the presence and absence of said putative enhancer; and (iii) identifying the compound as a potential salty taste enhancer based on whether it increases sodium conductance, the activity of said receptor or sodium transport. In various embodiments, the gene encodes an ion channel or the gene encodes a GPCR. Preferably, the gene is a human gene. More preferably, the method further includes testing the effect of the compound or a derivative thereof in a human taste test. Preferably, the selected compound promotes sodium ion transport into taste bud cells. The putative salty taste affecting gene may be expressed in an amphibian oocyte, or in a mammalian cell, preferably a *Xenopus oocyte* or a mammalian cell selected from the group consisting of a HEK293, HEK293T, Swiss3T3, CHO, BHK, NIH3T3, monkey L cell, African green monkey kidney cell, Ltk-cell and COS cell. Preferably, the putative salty taste affecting gene is expressed under the control of a regulatable promoter. The putative salty taste affecting gene may be expressed stably or transiently. In a preferred mode, the putative salty taste affecting gene is selected from tables 1-8 and in the Sequence Listing.

Recombinant Expression of Taste (Salty) Gene Identified Herein

To obtain high level expression of a cloned gene, such as those cDNAs encoding the subject genes, one typically subclones the gene into an expression vector that contains a strong promoter to direct transcription, a transcription/translation terminator, and if for a nucleic acid encoding a protein, a ribosome binding site for translational initiation. Suitable eukaryotic and prokaryotic promoters are well known in the art and described, e.g., in Sambrook et al., and Ausubel et al., supra. For example, bacterial expression systems for expressing the taste specific protein are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available. For example, retroviral expression systems may be used in the present invention. As described infra, the subject putative salty taste affecting genes are preferably expressed in human cells such as HEK-293 cells which are widely used for high throughput screening.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the identified gene and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

The vectors used in the invention may include a regulatable promoter, e.g., tet-regulated systems and the RU-486 system (see, e.g., Gossen & Bujard, Proc. Nat'l Acad. Sci. USA 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a gene sequence under the direction of the polyhedrin promoter or other strong baculovirus promoters.

The elements that are typically included in expression vectors also include a replicon that functions in the particular host cell. In the case of *E. coli*, the vector may contain a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods may be used to produce bacterial, mammalian, yeast or insect cell lines that express large quantities of the desired taste specific protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983). Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the gene.

After the expression vector is introduced into the cells, the transfected cells are cultured under conditions favoring expression of the gene. In some instances, such polypeptides may be recovered from the culture using standard techniques identified below.

Assays for Modulators of Putative Taste Cell Specific Gene Products Identified Herein Modulation of a putative taste cell specific protein, can be assessed using a variety of in vitro and in vivo assays, including cell-based models as described above. Such assays can be used to test for inhibitors and activators of the protein or fragments thereof, and, consequently, inhibitors and activators thereof. Such modulators are potentially useful in medications or as flavorings to modulate salty or other taste modalities or taste in general or for usage as potential therapeutics for modulating a taste cell related function or phenotype involving one or several of the identified taste cell specific genes reported herein.

Assays using cells expressing the subject taste specific proteins, either recombinant or naturally occurring, can be performed using a variety of assays, in vitro, in vivo, and ex vivo, as described herein. To identify molecules capable of modulating activity thereof, assays are performed to detect the effect of various candidate modulators on activity preferably expressed in a cell.

The channel activity of ion channel proteins in particular can be assayed using a variety of assays to measure changes in ion fluxes including patch clamp techniques, measurement of whole cell currents, radiolabeled ion flux assays or a flux assay coupled to atomic absorption spectroscopy, and fluorescence assays using voltage-sensitive dyes or lithium or sodium sensitive dyes (see, e.g., Vestergarrd-Bogind et al., J. Membrane Biol. 88:67-75 (1988); Daniel et al., J. Pharmacol. Meth. 25:185-193 (1991); Hoevinsky et al., J. Membrane Biol. 137:59-70 (1994)). For example, a nucleic acid encoding a protein or homolog thereof can be injected into *Xenopus oocytes* or transfected into mammalian cells, preferably human cells such as HEK-293 cells. Channel activity can then be assessed by measuring changes in membrane polarization, i.e., changes in membrane potential.

A preferred means to obtain electrophysiological measurements is by measuring currents using patch clamp techniques, e.g., the "cell-attached" mode, the "inside-out" mode, and the "whole cell" mode (see, e.g., Ackerman et al., New Engl. J. Med. 336:1575-1595, 1997). Whole cell currents can be determined using standard methodology such as that described by Hamil et al., Pflugers. Archiv. 391:185 (1981).

Channel activity is also conveniently assessed by measuring changes in intracellular ion levels, i.e., sodium or lithium. Such methods are exemplified herein. For example, sodium flux can be measured by assessment of the uptake of radiolabeled sodium or by using suitable fluorescent dyes. In a typical microfluorimetry assay, a dye which undergoes a change in fluorescence upon binding a single sodium ion, is loaded into the cytosol of taste cell specific ion channel-expressing cells. Upon exposure to an agonist, an increase in cytosolic sodium is reflected by a change in fluorescence that occurs when sodium is bound.

The activity of the subject taste cell specific polypeptides can in addition to these preferred methods also be assessed using a variety of other in vitro and in vivo assays to determine functional, chemical, and physical effects, e.g., measuring the binding thereof to other molecules, including peptides, small organic molecules, and lipids; measuring protein and/or RNA levels, or measuring other aspects of the subject polypeptides, e.g., transcription levels, or physiological changes that affects the taste cell specific protein's activity. When the functional consequences are determined using intact cells or animals, one can also measure a variety of effects such as changes in cell growth or pH changes or changes in intracellular second messengers such as IP3, cGMP, or cAMP, or components or regulators of the phospholipase C signaling pathway. Such assays can be used to test for both activators and inhibitors of KCNB proteins. Modulators thus identified are useful for, e.g., many diagnostic and therapeutic applications.

In Vitro Assays

Assays to identify compounds with modulating activity on the subject genes are preferably performed in vitro. The assays herein preferably use full length protein according to the invention or a variant thereof. This protein can optionally be fused to a heterologous protein to form a chimera. In the assays exemplified herein, cells which express the full-length polypeptide are preferably used in high throughput assays are used to identify compounds that modulate gene function. Alternatively, purified recombinant or naturally occurring protein can be used in the in vitro methods of the invention. In addition to purified protein or fragment thereof, the recombinant or naturally occurring taste cell protein can be part of a cellular lysate or a cell membrane. As described below, the binding assay can be either solid state or soluble. Preferably, the protein, fragment thereof or membrane is bound to a solid support, either covalently or non-covalently. Often, the in vitro assays of the invention are ligand binding or ligand affinity assays, either non-competitive or competitive (with known extracellular ligands such as menthol). These in vitro assays include measuring changes in spectroscopic (e.g., fluorescence, absorbance, refractive index), hydrodynamic (e.g., shape), chromatographic, or solubility properties for the protein.

Preferably, a high throughput binding assay is performed in which the protein is contacted with a potential modulator and incubated for a suitable amount of time. A wide variety of modulators can be used, as described below, including small organic molecules, peptides, antibodies, and ligand analogs. A wide variety of assays can be used to identify modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. In such assays the known ligand is bound first, and then the desired compound i.e., putative enhancer is added. After the particular protein is washed, interference with binding, either of the potential modulator or of the known ligand, is determined. Often, either the potential modulator or the known ligand is labeled.

In addition, high throughput functional genomics assays can also be used to identify modulators of cold sensation by identifying compounds that disrupt protein interactions between the taste specific polypeptide and other proteins to which it binds. Such assays can, e.g., monitor changes in cell surface marker expression, changes in intracellular calcium, or changes in membrane currents using either cell lines or primary cells. Typically, the cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the phenotype of the cells is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the protein encoded by a cDNA according to the invention can be isolated using a yeast two-hybrid system, mammalian two hybrid system, or phage display screen, etc. Targets so identified can be further used as bait in these assays to identify additional components that may interact with the particular ion channel, receptor or transporter protein which members are also targets for drug development (see, e.g., Fields et al., Nature 340:245 (1989); Vasavada et al., Proc. Nat'l Acad. Sci. USA 88:10686 (1991); Fearon et al., Proc. Nat'l Acad. Sci. USA 89:7958 (1992); Dang et al., Mol. Cell. Biol. 11:954 (1991); Chien et al., Proc. Nat'l Acad. Sci. USA 9578 (1991); and U.S. Pat. Nos. 5,283,173, 5,667,973, 5,468,614, 5,525,490, and 5,637,463).

Cell-Based In Vivo Assays

In preferred embodiments, wild-type and mutant taste cell specific proteins are expressed in a cell, and functional, e.g., physical and chemical or phenotypic, changes are assayed to identify modulators that modulate function or which restore the function of mutant genes, e.g., those having impaired gating function. Cells expressing proteins can also be used in binding assays. Any suitable functional effect can be measured, as described herein. For example, changes in membrane potential, changes in intracellular lithium or sodium levels, and ligand binding are all suitable assays to identify potential modulators using a cell based system. Suitable cells for such cell based assays include both primary cells and recombinant cell lines engineered to express a protein. The subject taste cell specific proteins therefore can be naturally occurring or recombinant. Also, as described above, fragments of these proteins or chimeras with ion channel activity can be used in cell based assays. For example, a transmembrane domain of a ion channel or GPCR or transporter gene according to the invention can be fused to a cytoplasmic domain of a heterologous protein, preferably a heterologous ion channel protein. Such a chimeric protein would have ion channel activity and could be used in cell based assays of the invention. In another embodiment, a domain of the taste cell specific protein, such as the extracellular or cytoplasmic domain, is used in the cell-based assays of the invention.

In another embodiment, cellular polypeptide levels of the particular target taste polypeptide can be determined by measuring the level of protein or mRNA. The level of protein or proteins related to ion channel activation are measured using immunoassays such as western blotting, ELISA and the like with an antibody that selectively binds to the polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatic ally labeled antibodies, and the like, as described herein.

Alternatively, protein expression can be measured using a reporter gene system. Such a system can be devised using a promoter of the target gene operably linked to a reporter gene such as chloramphenicol acetyltransferase, firefly luciferase, bacterial luciferase, beta-galactosidase and alkaline phosphatase. Furthermore, the protein of interest can be used as an indirect reporter via attachment to a second reporter such as red or green fluorescent protein (see, e.g., Mistili & Spector, Nature Biotechnology 15:961-964 (1997)). The reporter construct is typically transfected into a cell. After treatment with a potential modulator, the amount of reporter gene transcription, translation, or activity is measured according to standard techniques known to those of skill in the art.

In another embodiment, a functional effect related to signal transduction can be measured. An activated or inhibited ion channel or GPCR or transporter will potentially alter the properties of target enzymes, second messengers, channels, and other effector proteins. The examples include the activation of phospholipase C and other signaling systems. Downstream consequences can also be examined such as generation of diacyl glycerol and IP3 by phospholipase C.

Assays for ion channel activity include cells that are loaded with ion or voltage sensitive dyes to report activity, e.g., by observing sodium influx or intracellular sodium release. Assays for determining activity of such receptors can also use known agonists and antagonists for these receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. Radiolabeled ion flux assays or a flux assay coupled to atomic absorption spectroscopy can also be used.

Animal Models

Animal models also find potential use in screening for modulators of gene activity. Transgenic animal technology results in gene overexpression, whereas siRNA and gene knockout technology results in absent or reduced gene expression following homologous recombination with an appropriate gene targeting vector. The same technology can also be applied to make knock-out cells. When desired, tissue-specific expression or knockout of the target gene may be necessary. Transgenic animals generated by such methods find use as animal models of responses related to the gene target. For example such animals expressing a gene or genes according to the invention may be used to derive supertaster phenotypes such as for use in screening of chemical and biological toxins, rancid/spoiled/contaminated foods, and beverages or for screening for therapeutic compounds that modulate taste stem cell differentiation.

Knock-out cells and transgenic mice can be made by insertion of a marker gene or other heterologous gene into an endogenous gene site in the mouse genome via homologous recombination. Such mice can also be made by substituting an endogenous gene with a mutated version of the target gene, or by mutating an endogenous gene, e.g., by exposure to known mutagens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., Science 244:1288 (1989)). Chimeric targeted mice can be derived according to Hogan et al., Manipulating the Mouse Embryo: A Laboratory Manual (1988) and Teratocarcinomas and Embryonic Stem Cells: A Practical Approach (Robertson, ed., 1987).

Candidate Modulators

The compounds tested as modulators of the putative taste related proteins or other non-taste related functions and phenotypes involving taste cells can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of a protein. Typically, test compounds will be small organic molecules, peptides, lipids, and lipid analogs. In one embodiment, the compound is a menthol analog, either naturally occurring or synthetic.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md.). C. Solid State and Soluble High Throughput Assays.

Additionally soluble assays can be effected using a target taste specific protein, or a cell or tissue expressing a target taste protein disclosed herein, either naturally occurring or recombinant. Still alternatively, solid phase based in vitro assays in a high throughput format can be effected, where the protein or fragment thereof, such as the cytoplasmic domain, is attached to a solid phase substrate. Any one of the assays described herein can be adapted for high throughput screening, e.g., ligand binding, calcium flux, change in membrane potential, etc.

In the high throughput assays of the invention, either soluble or solid state, it is possible to screen several thousand different modulators or ligands in a single day. This methodology can be used for assaying proteins in vitro, or for cell-based or membrane-based assays comprising an protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, The Adhesion Molecule Facts Book I (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, J. Am. Chem. Soc. 85:2149-2154 (1963) (describing solid phase synthesis of e.g., peptides); Geysen et al., J. Immunol. Meth. 102:259-274 (1987) (describing synthesis of solid phase components on pins); Frank & Doring, Tetrahedron 44:6031-6040 (1988) (describing synthesis of various peptide sequences on cellulose disks); Fodor et al., Science, 251:767-777 (1991); Sheldon et al., Clinical Chemistry 39(4):718-719 (1993); and Kozal et al., Nature Medicine 2(7):753-759 (1996) (all describing arrays of biopolymers fixed to solid substrates). Non-chemical approaches for fixing tag binders to substrates include other common methods, such as heat, cross-linking by UV radiation, and the like.

Having described the invention supra, the examples provided infra further illustrate some preferred embodiments of the invention. These examples are provided only for purposes of illustration and should not be construed as limiting the subject invention.

Practical Applications of the Invention

Compounds which modulate, preferably enhance the activity of genes identified herein in the Tables have important implications in modulation of human salty taste and potentially other taste modalities or taste in general. In addition these compounds are potentially useful in therapeutic applications involving other taste cell related functions and phenotypes such as taste cell turnover, digestive diseases, digestive function, regulation of metabolism, regulation of immunity in the oral cavity and/or digestive system and the like.

Compounds which activate taste ion channels in taste papillae on the tongue can be used to enhance salt sensation by promoting $Na^+$ transport into taste bud cells. This has obvious consumer applications in improving the taste and palatability of low salt foods and beverages.

In addition the genes and gene products herein can be used as markers for identifying, isolating or enriching specific taste cell types or lineages including sweet, bitter, umami, sour, salt, fat, metallic et al.

Further the genes and gene products specific to taste cells identified herein can be used to identify compounds that modulate apoptosis of taste cells, modulate transcription factors that control taste receptor expression, modulate bitter receptor expression e.g., to alleviate the off-taste of some vegetables, medicines, coffee, and the like; modulate autocrine/paracrine modulation of taste cell development, prolong taste bud lifetime, yield supertaster animal phenotypes for use in screening such as for bioterrorism or animals for use in screening for compounds that induce the activation and differentiation of stem cells into taste cells in vivo.

In addition the subject genes and gene products and cells which express may be used to identify ancillary taste receptors or primary taste receptors such as fat or metallic taste cells.

Also the subject genes, gene products and cells which express same can be used in screens to identify compounds that affect digestive function such s gastric motility, food detection, food absorption or the production of digestive fluids, peptides, hormones or enzymes such as Glucagon Like Peptide-1, Glucose Dependent Insulinotropic polypeptide, pepsin, secretin, amylase, saliva, et al.

Also the subject genes, gene products and cells which express same may be used to screen for compounds that affect trafficking of taste receptors to and from the apical membrane/taste pore region to enhance or repress general or specific tastes, regulation of taste cell action potential firing frequency/membrane potential to control the intensity of general or specific tastes, regulation of neurotransmitter release to afferent nerve to control the intensity of general or specific taste, and autocrine/paracrine modulation of taste receptor function.

Further the subject genes, gene products and cells which express same can be used to identify compounds that regenerate taste cells such as in geriatric individuals or patients with cancer, chemotherapy radiation, injury or surgery affecting taste, drug-induced dysgeusia, ageusia, and for alleviating taste bud loss.

Still further the subject genes and gene products and cells which express same can be used to screen for compounds that affect oral hygiene, halitosis, detoxification of noxious substances in the oral cavity, and neutralization/elimination of bacteria, viruses, and other immunogens in the saliva/mouth or digestive tract.

Yet additionally the subject genes, gene products and cells which express same can be used in screens to identify compounds that affect saliva production and composition and treatment of dry mouth in conditions such as xerostomia and Sjogren's disease, in autoimmune or inflammatory gastrointestinal diseases, IBD, ulcerative colitis, and diverticulitis and cancers affecting the oral cavity and digestive tract.

The following examples were effected using the materials and methods described supra. These examples are put forth so as to provide those of ordinary skill in the art with a complete disclosure and description of how to make and use the subject invention, and are not intended to limit the scope of what is regarded as the invention.

EXAMPLES

Example 1

Figure 1:
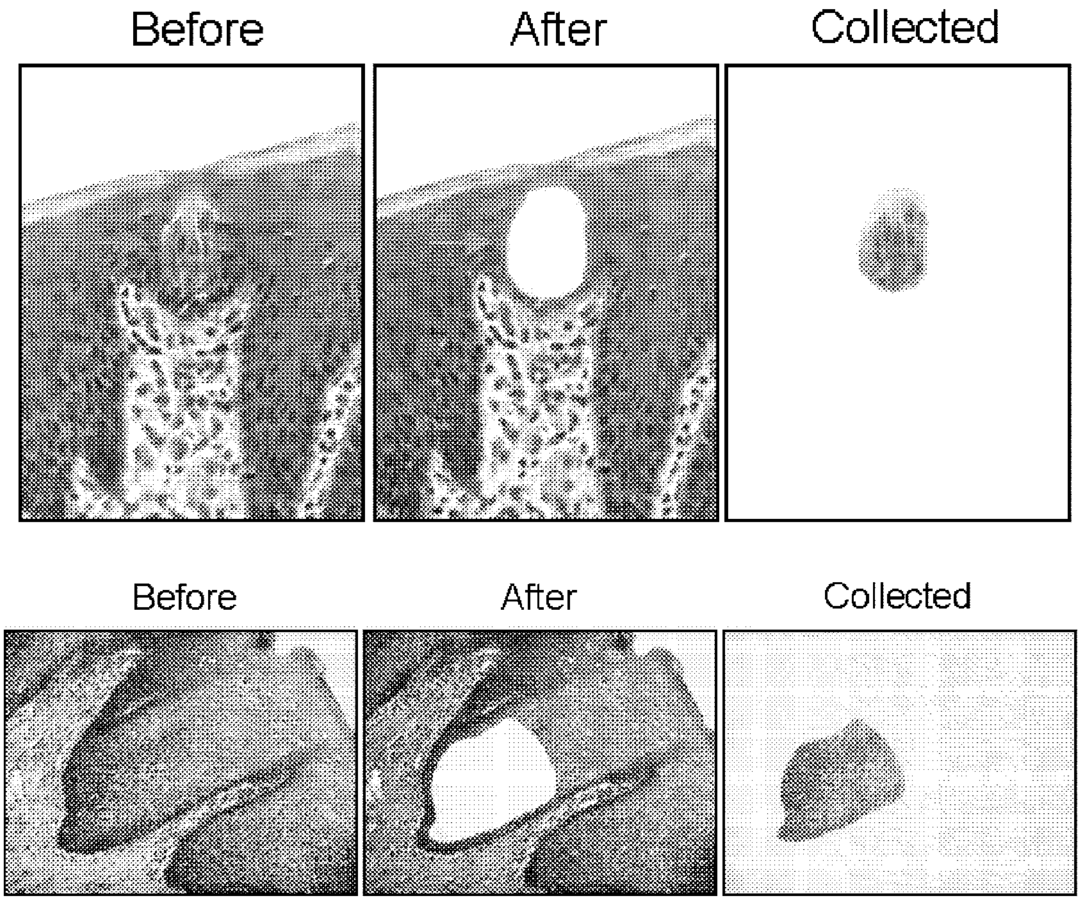
FIG. 1 contains an example of laser capture microdissection (LCM) on primate fungiform (FG) taste tissue (top row) and lingual epithelium (LE) non-taste tissue (bottom row) Top row: Left image shows FG tissue before LCM with a single FG taste bud. Middle image shows FG tissue after LCM where single FG taste bud has been removed. Right image shows collected and isolated FG taste bud used for molecular biology experiments to discover taste-specific genes. Bottom row: Left image shows tissue before LCM with LE from anterior tongue surface. Middle image shows tissue after LCM where a region of LE has been removed. Right image shows collected and isolated LE region used for molecular biology experiments to discover taste-specific genes.

This experimental example the results of which are contained in FIG. 1 is exemplary of the results obtained with laser capture microdissection (LCM) on primate fungiform (FG) taste tissue (top row) and lingual epithelium (LE) non-taste tissue (bottom row). Shown in the top row, in the left image is FG tissue before LCM with a single FG taste bud. The middle image in FIG. 1 shows FG tissue after LCM where single FG taste bud has been removed. The right image in FIG. 1 shows collected and isolated FG taste bud used for molecular biology experiments to discover taste-specific genes. Shown in the bottom row, in the left image is tissue before LCM with LE from anterior tongue surface. The middle image in the same Figure shows tissue after LCM where a region of LE has been removed. Shown in the right image is the collected and isolated LE region used for molecular biology experiments to discover taste-specific genes.

Example 2

Figure 2:
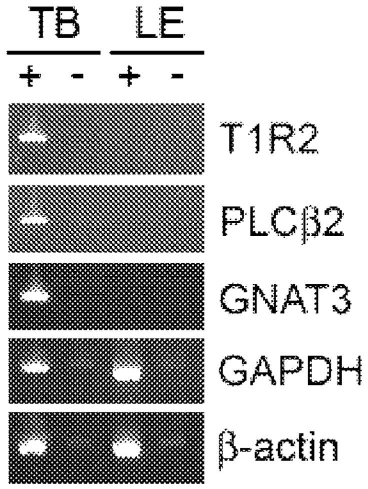
FIG. 2 contains an example of PCR quality control of primate taste and lingual cells collected by LCM. Taste bud cells (TB), but not lingual epithelial cells (LE), specifically express the known taste-specific genes T1R2 (a component of the sweet receptor), PLCbeta2 (an enzyme involved in sweet, bitter, and umami taste detection), and GNAT3 (i.e. gustducin, a G-protein alpha subunit involved in sweet, bitter, and umami taste detection). By contrast, both taste and lingual cells express the ubiquitous housekeeping genes GAPDH and beta-actin, indicating that taste and lingual cell RNA is intact and of high quality. '+' indicates reverse transcription and '−' indicates no reverse transcription was performed.

This experimental example the results of which are contained in FIG. 2 is exemplary of PCR quality control of primate taste and lingual cells collected by LCM. It can be seen therefrom that taste bud cells (TB), but not lingual epithelial cells (LE), specifically express the known taste-specific genes T1R2 (a component of the sweet receptor), PLCbeta2 (an enzyme involved in sweet, bitter, and umami taste detection), and GNAT3 (i.e. gustducin, a G-protein alpha subunit involved in sweet, bitter, and umami taste detection). By contrast, it can be seen that both taste and lingual cells express the ubiquitous housekeeping genes GAPDH and beta-actin, indicating that taste and lingual cell RNA is intact and of high quality. '+' indicates reverse transcription and '−' indicates no reverse transcription was performed.

Example 3

Figure 3:
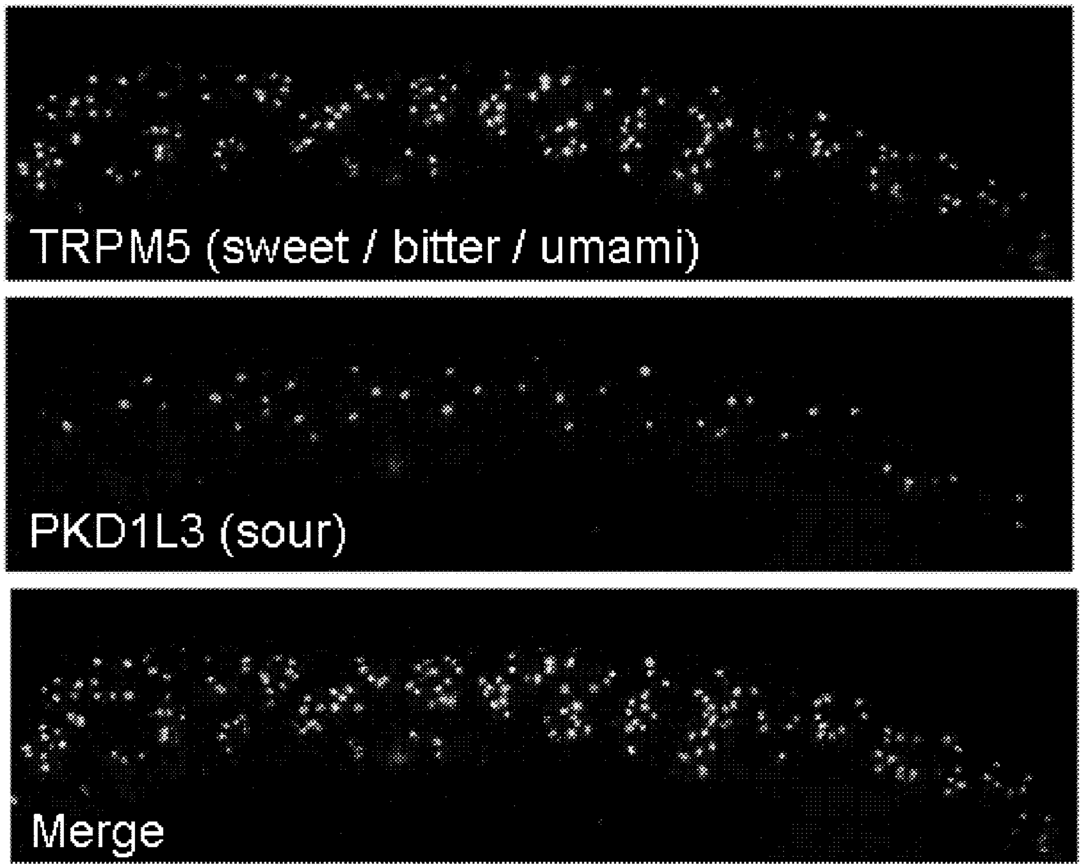
FIG. 3 contains an example of double labeling in situ hybridization illustrating expression of TRPM5 and PKD1L3 in different taste cells in primate circumvallate (CV) taste tissue. TRPM5 (top; green) is not detectable in cells expressing PKD1L3 (middle; red). Overlay of TRPM5 and PKD1L3 signals is depicted in the bottom image. Note that TRPM5 and PKD1L3 signals are present in different taste cells. TRPM5 is expressed in cells responsible for sweet, bitter, and umami taste, whereas PKD1L3 is expressed in cells responsible for sour taste.

This example relates to the experiment contained in FIG. 3. Shown therein is an example of double labeling in situ hybridization illustrating expression of TRPM5 and PKD1L3 in different taste cells in primate circumvallate (CV) taste tissue. It can be seen that TRPM5 (top; green) is not detectable in cells expressing PKD1L3 (middle; red). The overlay of TRPM5 and PKD1L3 signals is depicted in the bottom image. It can further be seen that TRPM5 and PKD1L3 signals are present in different taste cells. Particularly, TRPM5 is expressed in cells responsible for sweet, bitter, and umami taste, whereas PKD1L3 is expressed in cells responsible for sour taste.

Example 4

Figure 4:
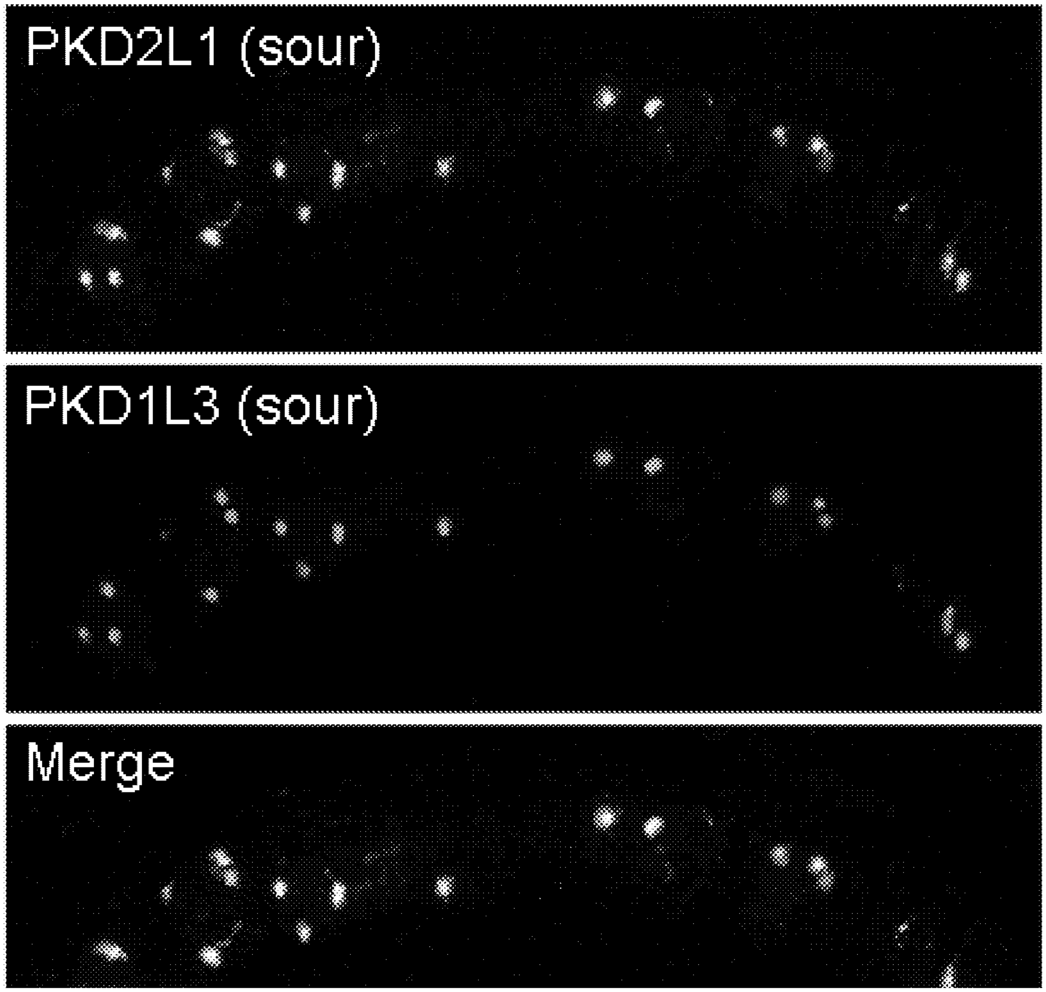
FIG. 4 contains an example of double labeling in situ hybridization illustrating coexpression of PKD2L1 and PKD1L3 in the same taste cells in primate circumvallate (CV) taste tissue. PKD2L1 (top; green) is coexpressed in cells expressing PKD1L3 (middle; red). Overlay of PKD2L1 and PKD1L3 signals is depicted in the bottom image in yellow. Note that both PKD2L1 and PKD1L3 signals are present in the same taste cells. Both PKD2L1 and PKD1L3 are expressed in cells responsible for sour taste.

This example which is contained in FIG. 4 shows a double labeling in situ hybridization illustrating coexpression of PKD2L1 and PKD1L3 in the same taste cells in primate circumvallate (CV) taste tissue. It can be seen therein that PKD2L1 (top; green) is coexpressed in cells expressing PKD1L3 (middle; red). The overlay of PKD2L1 and PKD1L3 signals is depicted in the bottom image in yellow. It can further be seen that both PKD2L1 and PKD1L3 signals are present in the same taste cells. Both PKD2L1 and PKD1L3 are expressed in cells responsible for sour taste.

Example 5

Figure 5:
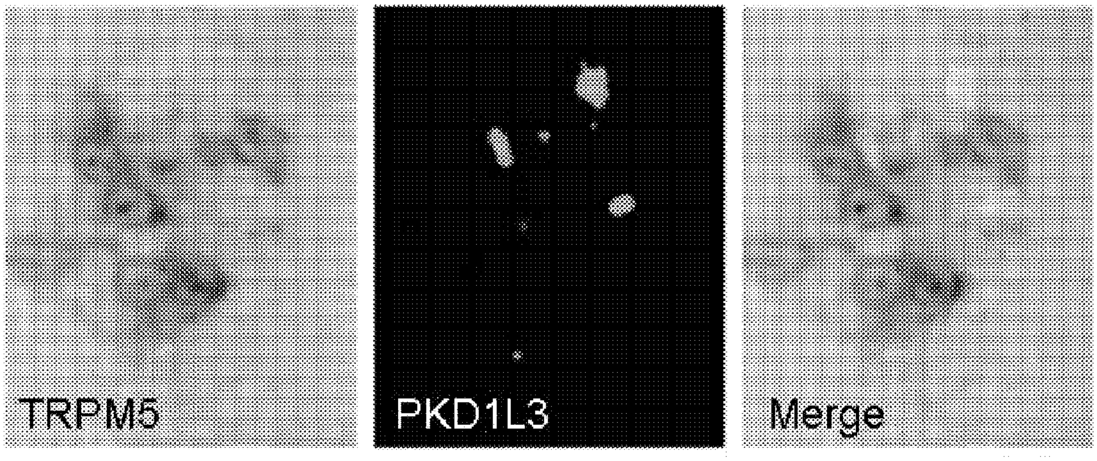
FIG. 5 contains an example of double labeling in situ hybridization illustrating expression of TRPM5 and PKD1L3 in different taste cells in primate fungiform (FG) taste tissue. TRPM5 (left; purple stain) is not detectable in cells expressing PKD1L3 (middle; red). Overlay of TRPM5 and PKD1L3 signals is depicted in the left image. Note that TRPM5 and PKD1L3 signals are present in different taste cells. TRPM5 is expressed in cells responsible for sweet, bitter, and umami taste, whereas PKD1L3 is expressed in cells responsible for sour taste tissue.

This example relates to the experiments contained in FIG. 5. This experiment is an example of double labeling in situ hybridization illustrating expression of TRPM5 and PKD1L3 in different taste cells in primate fungiform (FG) taste tissue. It can be seen therein that TRPM5 (left; purple stain) is not detectable in cells expressing PKD1L3 (middle; red). The overlay of TRPM5 and PKD1L3 signals is depicted in the left image. It can further be seen therein that TRPM5 and PKD1L3 signals are present in different taste cells. Particularly, the Figure shows that TRPM5 is expressed in cells responsible for sweet, bitter, and umami taste, whereas PKD1L3 is expressed in cells responsible for sour taste.

Example 6

Figure 6:
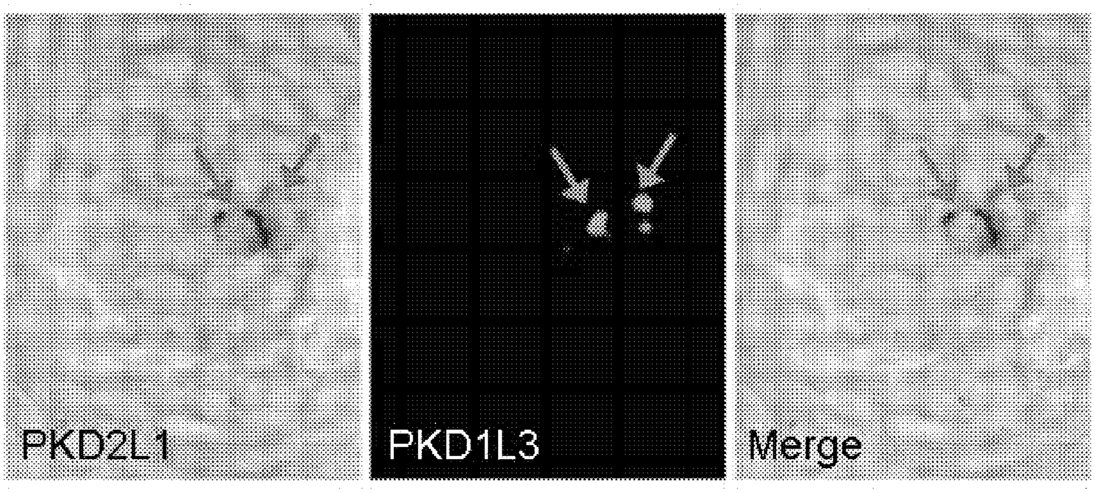
FIG. 6 contains an example of double labeling in situ hybridization illustrating coexpression of PKD2L1 and PKD1L3 in the same taste cells in primate fungiform (FG) taste tissue. PKD2L1 (left; purple stain) is coexpressed in cells expressing PKD1L3 (middle; red). Overlay of PKD2L1 and PKD1L3 signals is depicted in the right image. Note that both PKD2L1 and PKD1L3 signals are present in the same taste cells. Both PKD2L1 and PKD1L3 are expressed in cells responsible for sour taste.

This example relates to the results of a double labeling in situ hybridization experiment contained in FIG. 6. The Figure illustrates the coexpression of PKD2L1 and PKD1L3 in the same taste cells in primate fungiform (FG) taste tissue. It can further be seen that PKD2L1 (left; purple stain) is coexpressed in cells expressing PKD1L3 (middle; red). The overlay of PKD2L1 and PKD1L3 signals is depicted in the right image. The Figure further reveals that that both PKD2L1 and PKD1L3 signals are present in the same taste cells. Both PKD2L1 and PKD1L3 are expressed in cells responsible for sour taste.

Example 7

Figure 7:
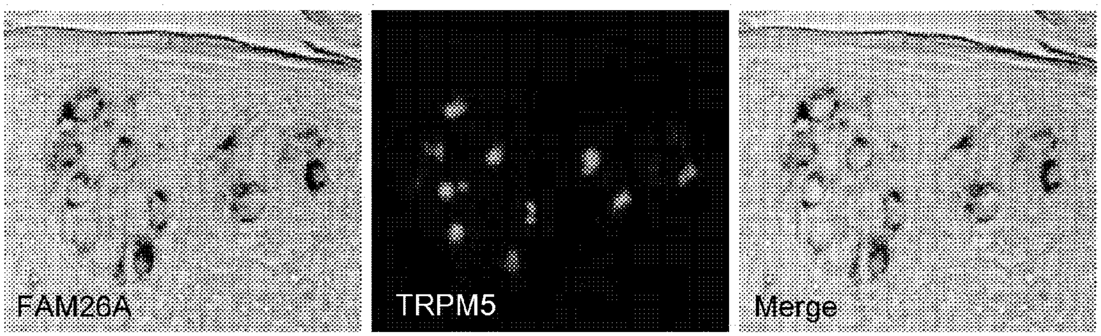
FIG. 7 contains an example of a double labeling hybridization experiment using primate circumvallate papilla. The results in FIG. 7 reveal that FAM26A (purple color; left image) colocalizes with TRPM5 (red; middle image). The results contained in the figure also show that FAM26A cells express TRPM5, a marker of sweet, umami, and bitter taste cells (merged image on the right).

This example relates to the double labeling hybridization experiment contained in FIG. 7. This experiment which again involved double label in situ hybridization of primate circumvallate papilla revealed that FAM26A (purple color; left image) colocalizes with TRPM5 (red; middle image). The results contained in the figure also show that FAM26A cells express TRPM5, a marker of sweet, umami, and bitter taste cells (merged image on the right).

Example 8

Figure 8:
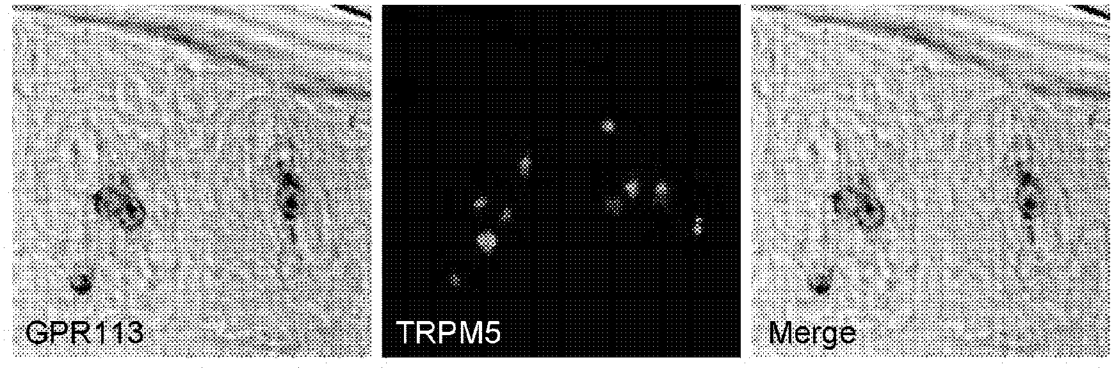
FIG. 8 contains another double label in situ hybridization experiment. This hybridization experiment which again used primate circumvallate papilla revealed that the taste cell specific gene GPR113 (purple color; left image) colocalizes with a subset of TRPM5 cells (red; middle image). It can be seen from the figure that that only a fraction of cells expressing TRPM5, a marker of sweet, umami, and bitter taste cells, also express GPR113 (merged image on the right), but that all GPR113 cells express TRPM5. Two taste buds are shown.

This example relates to the double label in situ hybridization experiment contained in FIG. 8. This hybridization experiment which again used primate circumvallate papilla revealed that the taste cell specific gene GPR113 (purple color; left image) colocalizes with a subset of TRPM5 cells (red; middle image). It can be seen from the figure that that only a fraction of cells expressing TRPM5, a marker of sweet, umami, and bitter taste cells, also express GPR113 (merged image on the right), but that all GPR113 cells express TRPM5. Two taste buds are shown.

Example 9

Figure 9:
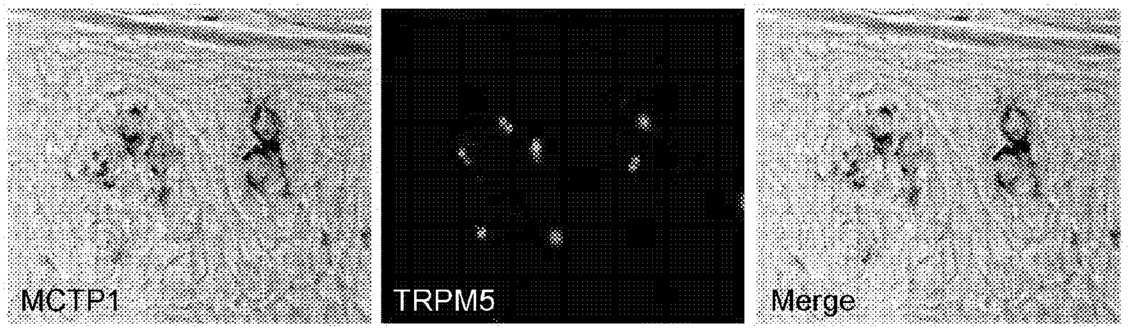
FIG. 9 contains another double hybridization experiment using primate circumvallate papilla cells. The results contained in the Figure reveal that MCTP1 (purple color; left image), a taste cell specific gene, colocalizes with TRPM5 (red; middle image). It can be further seen that MCTP1 cells express TRPM5, a marker of sweet, umami, and bitter taste cells (merged image on the right). Two taste buds are shown in the Figure.

The experiment contained in FIG. 9 is another double hybridization experiment using primate circumvallate papilla cells. The results contained in the Figure reveal that MCTP1 (purple color; left image), a taste cell specific gene, colocalizes with TRPM5 (red; middle image). It can be seen that MCTP1 cells express TRPM5, a marker of sweet, umami, and bitter taste cells (merged image on the right). Two taste buds are shown in the Figure.

Example 10

Figure 10:
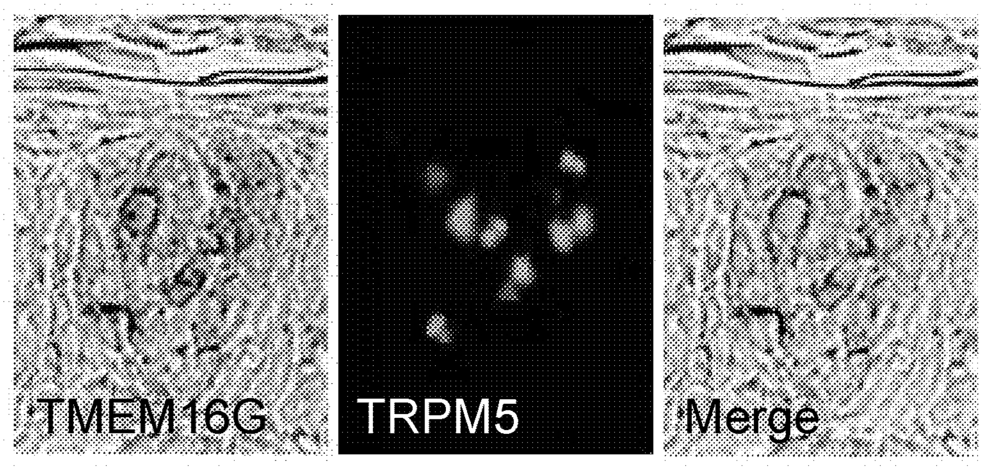
FIG. 10 contains another double label in situ hybridization experiment using primate circumvallate papilla cells. The results in FIG. 10 show that TMEM16G (purple color; left image) colocalizes with a subset of TRPM5 cells (red; middle image). It can also be seen that only a fraction of cells expressing TRPM5, a marker of sweet, umami, and bitter taste cells, also express TMEM16G (merged image on the right), but that all TMEM16G cells express TRPM5.

This example relates to another double label in situ hybridization of primate circumvallate papilla cells. The results in FIG. 10 show that TMEM16G (purple color; left image) colocalizes with a subset of TRPM5 cells (red; middle image). It can also be seen that only a fraction of cells expressing TRPM5, a marker of sweet, umami, and bitter taste cells, also express TMEM16G (merged image on the right), but that all TMEM16G cells express TRPM5.

Example 11

Figure 11:
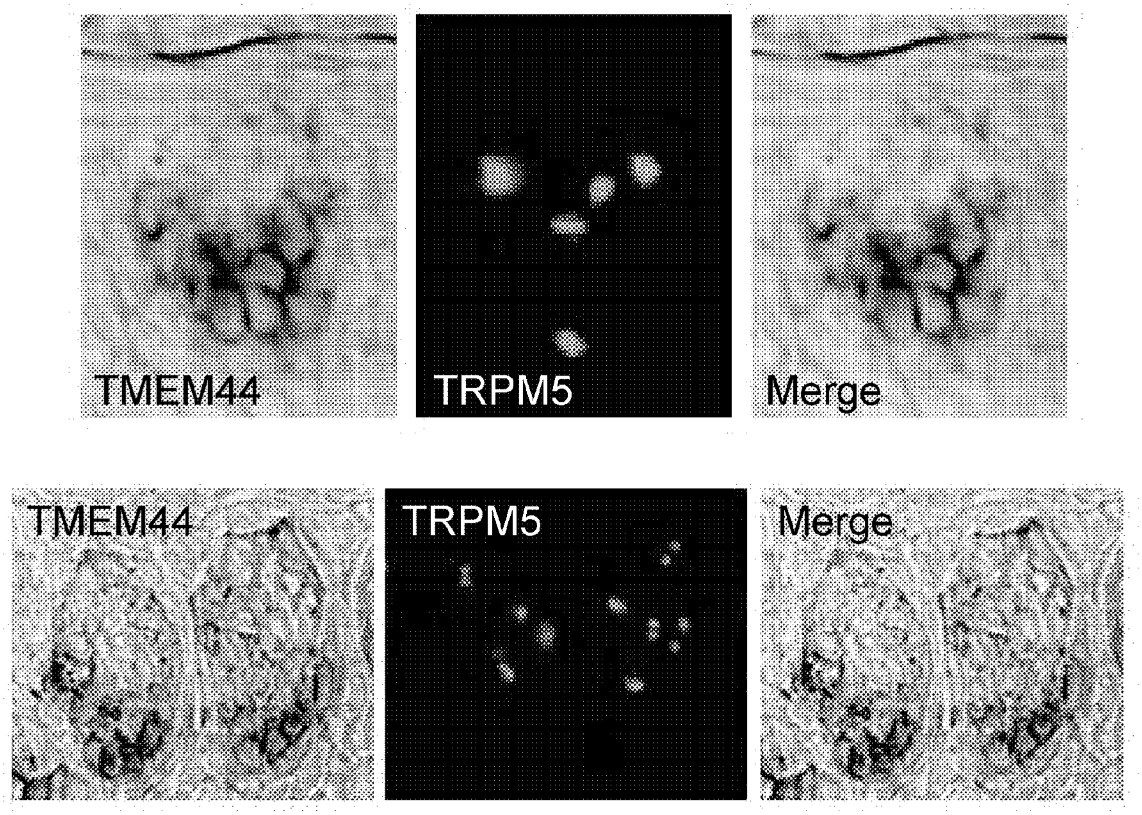
FIG. 11 contains another double label in situ hybridization experiment using primate circumvallate papilla cells. The results contained in FIG. 11 show that TMEM44 (purple color; left image), a taste cell specific gene, does not colocalize with TRPM5 (red; middle image). It can be seen from the results in the figure that TMEM44 cells do not express TRPM5, a marker of sweet, umami, and bitter taste cells (merged image on the right). Two taste buds are shown in the figure.

This example relates to another double label in situ hybridization of primate circumvallate papilla cells. The results contained in FIG. 11 show that TMEM44 (purple color; left image), a taste cell specific gene, does not colocalize with TRPM5 (red; middle image). It can be seen from the results in the figure that TMEM44 cells do not express TRPM5, a marker of sweet, umami, and bitter taste cells (merged image on the right). Two taste buds are shown in the figure.

Example 12

Figure 12:
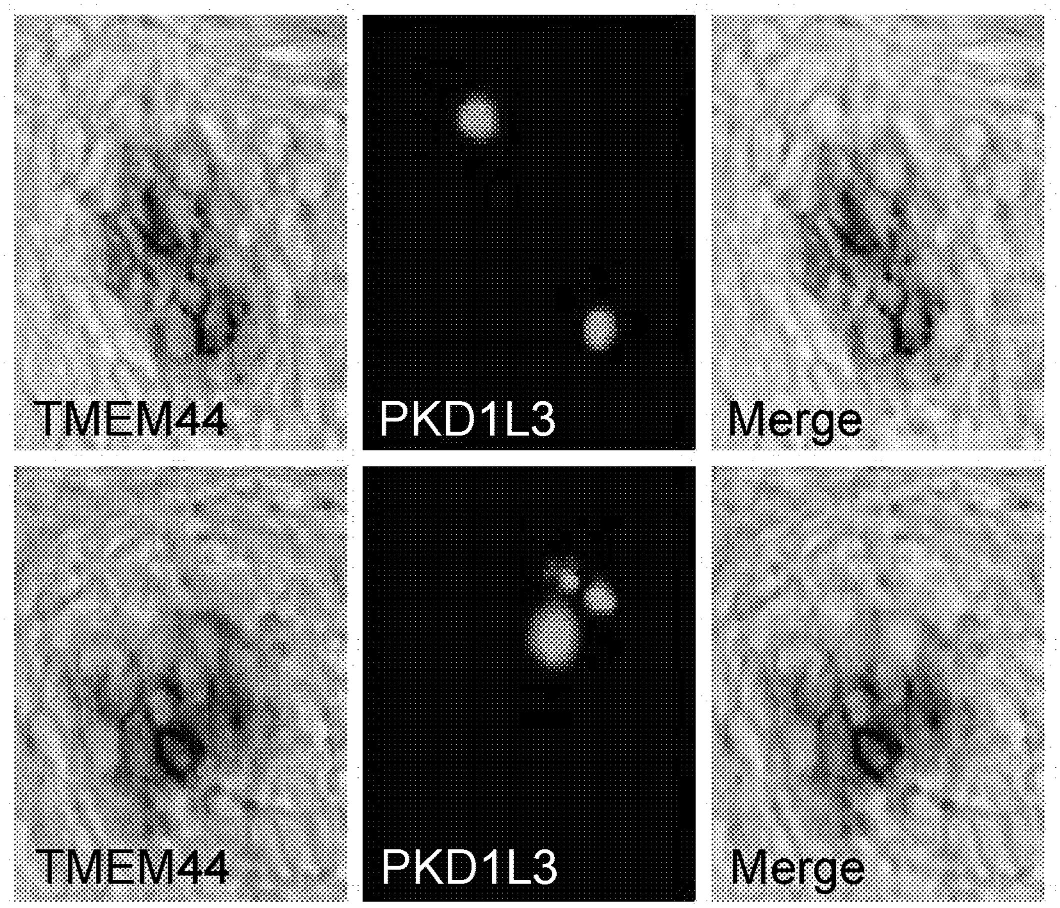
FIG. 12 contains another double label in situ hybridization experiment of primate circumvallate papilla cells. The results contained therein reveal that TMEM44 (purple color; left image) does not colocalize with PKD1L3 (red; middle image). It can also be seen therein that TMEM44 cells do not express PKD1L3, a marker of sour taste cells (merged image on the right). Two taste buds are shown.

This example relates to the double label in situ hybridization of primate circumvallate papilla cells contained in FIG. 12. The results contained therein reveal that TMEM44 (purple color; left image) does not colocalize with PKD1L3 (red; middle image). It can also be seen that TMEM44 cells do not express PKD1L3, a marker of sour taste cells (merged image on the right). Two taste buds are shown.

Example 13

Figure 13:
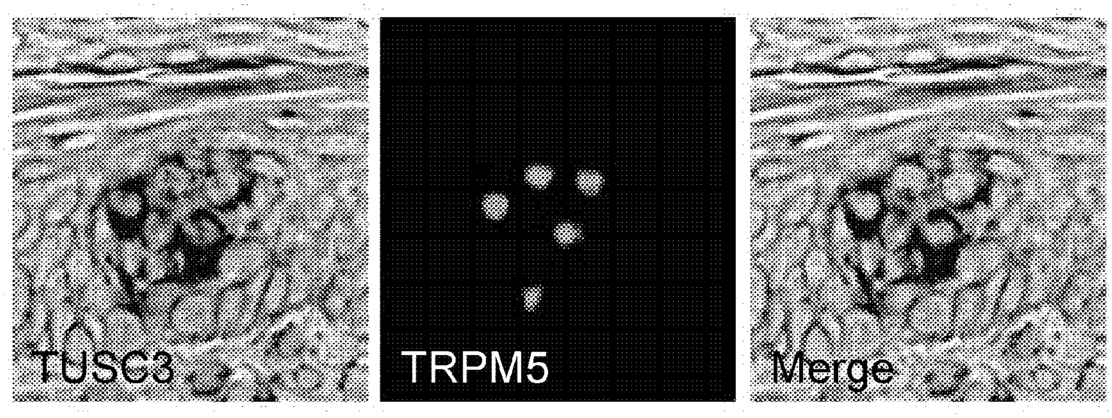
FIG. 13 contains another double label in situ hybridization experiment using primate circumvallate papilla cells. The results which are contained in FIG. 13 show that TUSC3 (purple color; left image), a taste cell specific gene, colocalizes with TRPM5 (red; middle image). It can also be seen that TUSC3 cells express TRPM5, a marker of sweet, umami, and bitter taste cells (merged image on the right).
Figure 14:
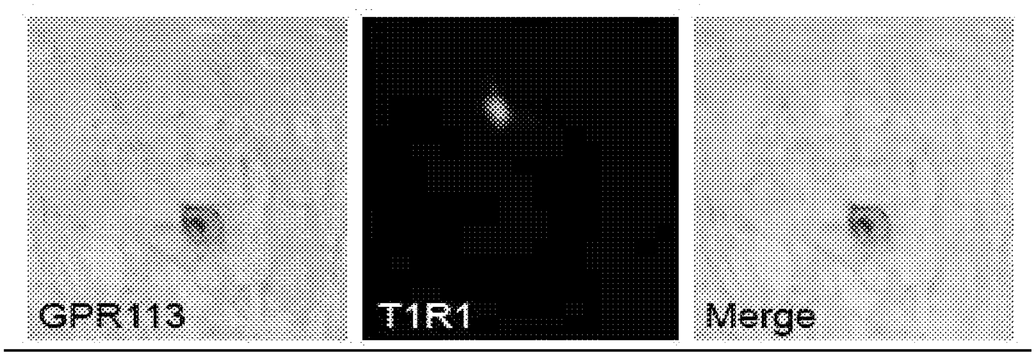
FIG. 14 shows that GPR113 is not expressed in T1R1 umami cells. Double label in situ hybridization of primate circumvallate papilla showing that GPR113 (purple color; left image) does not colocalize with T1R1 (red; middle image). Note that GPR113 and T1R1, a marker of umami cells, are in different taste cells (merged image on the right).
Figure 15:
FIG. 15 shows that GPR113 is not expressed in T1R2 sweet cells. Double label in situ hybridization of primate circumvallate papilla showing that GPR113 (purple color; left image) does not colocalize with T1R2 (red; middle image). Note that GPR113 and T1R2, a marker of sweet cells, are in different taste cells (merged image on the right).
Figure 16:
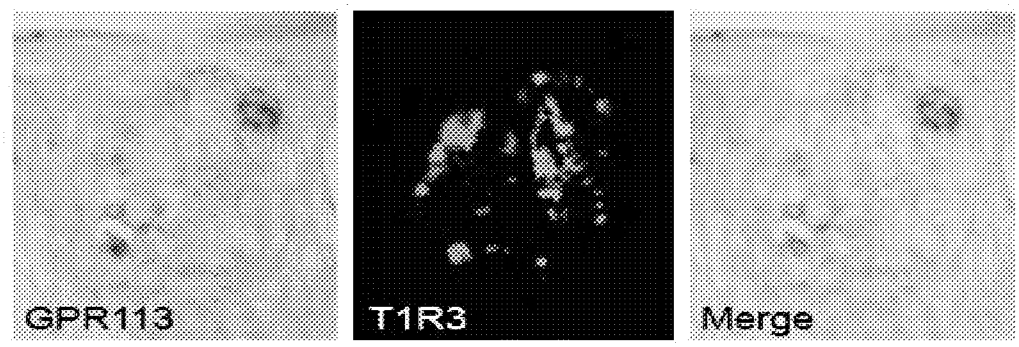
FIG. 16 shows that GPR113 is expressed in a subset of T1R3 cells. Double label in situ hybridization of primate circumvallate papilla showing that GPR113 (purple color; left image) does colocalize with a subset of T1R3 cells (red; middle image). Note that GPR113 is always expressed in cells with T1R3, but that there are T1R3 cells that do not express GPR113 (merged image on the right). These T1R3 cells that do not express GPR113 likely coexpress either T1R1 or T1R2. The T1R3 only cells are a new population of taste cells that coexpress GPR113.

This example relates to another double label in situ hybridization of primate circumvallate papilla cells. The results which are contained in FIG. 13 show that TUSC3 (purple color; left image), a taste cell specific gene, colocalizes with TRPM5 (red; middle image). It can also be seen that TUSC3 cells express TRPM5, a marker of sweet, umami, and bitter taste cells (merged image on the right).

Example 14

This example shows that GPR113 is not expressed in T1R1 umami cells. Double label in situ hybridization of primate circumvallate papilla showing that GPR113 (purple color; left image) does not colocalize with T1R1 (red; middle image). Note that GPR113 and T1R1, a marker of umami cells, are in different taste cells (merged image on the right)

Example 15

This example shows that GPR113 is not expressed in T1R2 sweet cells. Double label in situ hybridization of primate circumvallate papilla showing that GPR113 (purple color; left image) does not colocalize with T1R2 (red; middle image). Note that GPR113 and T1R2, a marker of sweet cells, are in different taste cells (merged image on the right).

Example 16

This example shows that GPR113 is expressed in a subset of T1R3 cells. Double label in situ hybridization of primate circumvallate papilla showing that GPR113 (purple color; left image) does colocalize with a subset of T1R3 cells (red; middle image). Note that GPR113 is always expressed in cells with T1R3, but that there are T1R3 cells that do not express GPR113 (merged image on the right). These T1R3 cells that do not express GPR113 likely coexpress either T1R1 or T1R2. The T1R3 only cells are a new population of taste cells that coexpress GPR113.

Example 17

This example shows that GPR113 is not expressed in T2R bitter cells. Double label in situ hybridization of primate circumvallate papilla showing that GPR113 (purple color; left image) does not colocalize with T2R (red; middle image). Note that GPR113 and T2R, a marker of bitter cells, are in different taste cells (merged image on the right).

Example 18

This example contains an experiment that shows that TMEM44 is not expressed in TRPM5 or PKD1L3 cells in fungiform taste buds. Double label in situ hybridization experiments were conducted using primate fungiform papilla from the front of the tongue showing that TMEM44 (blue/purple color; left images) does not colocalize with TRPM5 (red; middle top image) or PKD1L3 (red; middle bottom image). Note that TMEM44 cells do not express TRPM5, a marker of sweet, umami, and bitter taste cells, or PKD1L3, a marker of sour cells, in the merged images on the right.

Example 19

This example contains an experiment that shows that TMEM44 is not expressed in TRPM5 cells in circumvallate papilla. Double fluorescent label in situ hybridization of primate circumvallate papilla at the back of the tongue showing that TMEM44 (green cells; top image) does not colocalize with TRPM5 (red cells; middle image). Note that TMEM44 cells do not express TRPM5, a marker of sweet, umami, and bitter taste cells (merged image on the bottom).

Example 20

This example contains experiments that show that TMEM44 is not expressed in PKD1L3 cells in circumvallate papilla. Double fluorescent label in situ hybridization of primate circumvallate papilla at the back of the tongue showing that TMEM44 (green cells; top image) does not colocalize with PKD1L3 (red cells; middle image). Note that TMEM44 cells do not express PKD1L3, a marker of sour taste cells (merged image on the bottom).

Example 21

This example contains experiments that reveal that TMEM44 cells extend processes to the taste pore. Double label histology experiment of primate circumvallate papilla at the back of the tongue. Cytokeratin 19 protein (green; left image) is present in cells expressing TMEM44 RNA (red; middle image). Note that TMEM44 cells extend processes to the taste pore facing the saliva. Asterisk denotes a TMEM44 cell nucleus and white arrows denote the apical process of this same cell extending to the taste pore (merged image on the right). Thus, TMEM44 cells are sensory taste cells that can sample the saliva for tastants. Cytokeratin 19 is a marker of all taste cells.

Example 22

This example shows that FAM26B is expressed in TRPM5 cells. Double label in situ hybridization of primate circumvallate papilla showing that FAM26B (blue/purple color; left image) colocalizes with TRPM5 (red; middle image). Note that FAM26B cells express TRPM5, a marker of sweet, umami, and bitter taste cells (merged image on the right).

Example 23

This example shows that SLC4A11 is expressed in TRPM5 cells. Double label in situ hybridization of primate circumvallate papilla showing that SLC4A11 (blue/purple color; left image) colocalizes with TRPM5 (red; middle image). Note that SLC4A11 cells express TRPM5, a marker of sweet, umami, and bitter taste cells (merged image on the right).

Example 24

This example shows that MFSD4 is not expressed in TRPM5 cells. Double label in situ hybridization of primate circumvallate papilla showing that MFSD4 (blue/purple color; left image) does not colocalize with TRPM5 (red; middle image). Note that MFSD4 cells do not express TRPM5, a marker of sweet, umami, and bitter taste cells (merged image on the right). Two taste buds are shown.

Example 25

This example shows that MFSD4 and TMEM44 are expressed in the same taste cells. Double label in situ hybridization of primate circumvallate papilla showing that MFSD4 and TMEM44 are expressed in the same taste cell population. TMEM44 (top blue/purple color) and MFSD4 (bottom blue/purple color) do not colocalize with TRPM5 (red color top and bottom images) and are expressed in taste cells in the bottom halves of taste buds. The equivalent localization, abundance, and morphology of TMEM44 and MFSD4 taste cells indicates that these cells are identical and that both TMEM44 and MFSD4 genes are expressed in the same taste cell type FIG. 26 shows that ASCL1 is expressed in sour taste cells but not sweet, bitter, or umami taste cells. Double label in situ hybridization of primate circumvallate papilla from the back of the tongue showing that ASCL1 (blue/purple color; left images) does not colocalize with TRPM5 (red; middle top image) but does colocalize with PKD1L3 (red; middle bottom image). Note that ASCL1 cells do not express TRPM5, a marker of sweet, umami, and bitter taste cells, but do express PKD1L3, a marker of sour cells, in the merged images on the right.

Example 26

Example 26 shows that ASCL1 is expressed in sour taste cells but not sweet, bitter, or umami taste cells. Double label in situ hybridization of primate circumvallate papilla from the back of the tongue showing that ASCL1 (blue/purple color; left images) does not colocalize with TRPM5 (red; middle top image) but does colocalize with PKD1L3 (red; middle bottom image). Note that ASCL1 cells do not express TRPM5, a marker of sweet, umami, and bitter taste cells, but do express PKD1L3, a marker of sour cells, in the merged images on the right.

Example 27

KIT is expressed in T1R1 umami taste cells. Double label in situ hybridization of primate circumvallate papilla from the back of the tongue showing that KIT (blue/purple color; left images) colocalizes with T1R1 (red; middle image top row), does not colocalize with T1R2 (red; middle image 2$^{nd}$ row), does colocalize with T1R3 (red; middle image 3$^{rd}$ row), and does not colocalize with T2Rs (red; middle image bottom row). Note that KIT cells express T1R1 and T1R3, markers of umami taste cells, but not T1R2 or T2Rs, markers of sweet and bitter cells respectively, in the merged images on the right.

Example 28

IKBKAP is expressed in PKD1L3 sour taste cells. Double fluorescent label in situ hybridization of primate circumvallate papilla at the back of the tongue showing that IKBKAP (blue/purple color; left images) does not colocalize with TRPM5 (red; middle image top) but does colocalize with PKD1L3 (red; middle image bottom). Note that IKBKAP cells express PKD1L3, a marker of sour taste cells (merge image bottom) but do not express TRPM5, a marker of sweet, umami, and bitter taste cells (merged image top).

Example 29

This experiment revealed that the taste specific gene LOC285965 is expressed in T1R3 only taste cells. Double label in situ hybridization of primate circumvallate papilla from the back of the tongue showing that LOC285965 (blue/purple color; left images) does not colocalize with T1R1 (red; middle image top row), does not colocalize with T1R2 (red; middle image 2$^{nd}$ row), does colocalize with T1R3 (red; middle image 3$^{rd}$ row), and does not colocalize with T2Rs (red; middle image bottom row). Note that LOC285965 cells express T1R3, but not T1R1, T1R2 or T2Rs, markers of umami, sweet and bitter cells respectively, in the merged images on the right.

Example 30

This experiment revealed that the taste specific gene SV2B is expressed in PKD1L3 sour taste cells. Double fluorescent label in situ hybridization of primate circumvallate papilla at the back of the tongue showing that SV2B (blue/purple color; left images) does not colocalize with TRPM5 (red; middle image top) but does colocalize with PKD1L3 (red; middle image bottom). Note that SV2B cells express PKD1L3, a marker of sour taste cells (merge image bottom) but do not express TRPM5, a marker of sweet, umami, and bitter taste cells (merged image top).

Example 31

This experiment revealed that the taste specific gene MFSD4 is expressed in a unique taste cell type. Double label in situ hybridization of primate circumvallate papilla showing that MFSD4 (blue/purple color; left image) does not colocalize with PKD1L3 or TRPM5 (red; middle images) but is expressed in a unique taste cell type. Note that MFSD4 cells do not express PKD1L3, a marker of sour taste cells or TRPM5, a marker of sweet, umami, and bitter taste cells (merged images on the right). Two taste buds each are shown for PKD1L3 & TRPM5 double labels.

Example 32

This experiment revealed that the taste specific genes MFSD4 and TMEM44 are expressed in the same taste cell population. Double label in situ hybridization of primate circumvallate papilla showing that MFSD4 and TMEM44 are expressed in the same taste cell population. MFSD4 (left; green) and TMEM44 (middle; red) signals are present in the same taste cells (right; merged image).

Example 33

This experiment the results of which are contained in FIG. 33 revealed that SHH is expressed in immature taste cells in the bottom of the taste bud. Double in situ hybridization of primate circumvallate papilla at the back of the tongue showing that SHH (blue/purple color; left images) does not colocalize with TRPM5 (red; middle image top) or PKD1L3 (red; middle image bottom). Note that SHH cells do not express TRPM5, a marker of sweet, bitter, and umami taste cells (merge; right image top) or PKD1L3 (merge; right image bottom). Both TRPM5 and PKD1L3 genes are expressed in professional taste cells.

Example 34

This experiment the results of which are contained in FIG. 34 show that the taste specific genes TMEM44 and SHH are expressed in immature taste cells at the bottom of the taste bud. In situ hybridization of primate circumvallate papilla at the back of the tongue showing that TMEM44 (blue/purple color; top 3 images) is expressed in cells towards the base of the taste bud. A similar expression pattern was observed with SHH (blue/purple color; bottom 3 images). Since SHH is marker of immature, developing taste cells, these data indicate that TMEM44 is expressed in and is a marker of immature taste cells.

Example 35

Figure 35:
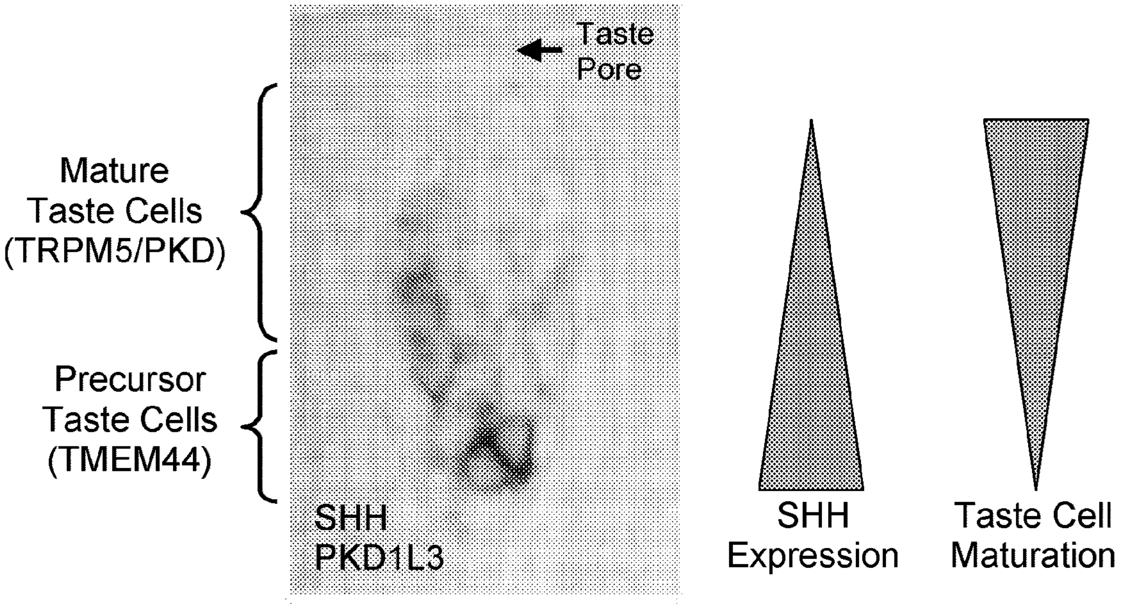

This experiment relates to the experiment in FIG. 35. In situ hybridization of primate circumvallate papilla at the back of the tongue showing SHH (blue/purple color) expression at the base of the taste bud and PKD1L3 (red color) expression towards the top of the taste bud. This figure contains a schematic model of taste cell development which indicates that there is a gradient of SHH expression from high levels at the base of the taste bud (immature cells) to low levels at the top of the taste bud (mature cells). As SHH expression levels decrease, expression of taste receptor genes such as TRPM5 and PKD1L3 increase. Thus, an opposite gradient of taste cell maturation exists where taste cells progressively mature and express taste receptor genes as they differentiate from the bottom to the top of the taste bud.

Example 36

This experiment the results of which are contained in FIG. 36 show that a small fraction of TMEM44 cells express TRPM5 or PKD1L3 as they differentiate into mature taste cells. Double label in situ hybridization of primate circumvallate papilla was performed using TRPM5 and TMEM44 riboprobes (left pie chart) or PKD1L3 and TMEM44 riboprobes (right pie chart). Taste cells expressing TRPM5 (blue graph region; left pie chart), TMEM44 (magenta graph region; left pie chart), or TRPM5 plus TMEM44 (labeled 'both' and yellow graph region; left pie chart) genes were counted and graphed in pie charts. Taste cells expressing PKD1L3 (blue graph region; right pie chart), TMEM44 (magenta graph region; right pie chart), or TRPM5 plus TMEM44 (labeled 'both' and yellow graph region; right pie chart) genes were counted and graphed in pie charts. Total number of counted cells is listed below each pie chart in parentheses. A small fraction of TMEM44 cells also express TRPM5 or PKD1L3, indicating that these cells are differentiating from an immature state (TMEM44 only) to a mature state (TRPM5 or PKD1L3 only). Inset shows example of CV taste bud labeled with TMEM44 (green) and TRPM5 (red). Note cell indicated with arrow that coexpresses both TMEM44 and TRPM5 (yellow).

Example 37

This experiment the results of which are contained in FIG. 37 reveals that mature taste cells do not coexpress markers for distinct taste modalities. Double label in situ hybridization of primate circumvallate papilla was performed using TRPM5 and PKD1L3. Taste cells expressing TRPM5 (blue graph region), PKD1L3 (magenta graph region), or TRPM5 plus PKD1L3 (labeled 'both' and yellow graph region which is too small to see any yellow segment due to the near absence of cells within this category) genes were counted and graphed in the pie chart. Total number of counted cells is listed below the pie chart in parentheses.

Example 38

Top Versus Bottom Gene Expression in the Taste Buds

The experiments and results herein relate to a systematic method for assigning gene expression patterns within the primate taste bud for taste bud-specific genes. Specifically, using a comparison of gene expression between the top and bottom sections of the primate taste bud, the inventors were able to classify genes into one of several functional classes that include taste receptor genes. A subset of genes in this classification is likely to encode taste receptors that include those for salty taste and other yet to be defined taste specificities.

As explained previously, the rationale for comparing gene expression between the top and bottom of the primate taste bud arose from the histological localization of mRNAs for a number of candidate taste receptor genes. Expression of a subset of these genes appeared to be localized at the bottom portion of the taste bud while other genes were predominantly expressed at the top of the taste bud. These patterns of expression are exemplified by the TMEM44 and TRPM5 genes which are expressed at the bottom and top of the taste bud respectively, see FIG. 38.

In order to get more information on gene expression in both the top and bottom fractions of the taste bud we undertook an experiment to isolate the corresponding fractions of primate taste buds using laser capture microdissection (LCM). As described previously, LCM involves the excision and isolation of selected cells or groups of cells from tissue sections based on morphological distinctions. In the case of taste buds, we can readily identify these structures in sections of primate tongue. In this specific example tissue collection was limited to taste buds in circumvallate papillae and then to only taste buds that were sectioned sagittally and at the taste pore. We reasoned it was only from this type of section would we be able to reliably isolate top and bottom fractions. An example of sections used in sample collection is shown in FIG. 39.

Multiple LCM preparations from each of 4 animals were pooled (4 top samples, 4 bottom samples, ~5000 cells per sample) RNA extracted and analyzed using Affymetrix whole genome macaque Gene Chips to obtain global mRNA expression profiles for the top and bottom fractions.

The gene expression data was queried to obtain three sets of genes. The first and second sets are genes that are expressed at a higher level in the top or bottom of the primate taste bud relative to the bottom or top respectively. Top-specific genes were listed in one group of genes, and bottom specific genes are listed in a second group. Accordingly, these lists contain top enriched and bottom enriched mRNAs. The third set of genes was also identified as being expressed at a higher level in the top of the primate taste bud relative to surrounding lingual epithelium.

An exemplary experiment validating this methodology is contained in FIG. 38. This experiment contains an experiment showing that levels of gene expression define two compartments in primate taste buds. To create this overlay image sagittal sections of primate taste buds were initially stained with DAPI (4',6-diamidino-2-phenylindole) to visualize cell nuclei; blue color. Double label in situ hybridization images of the same sections for TMEM44; green color and TRPM5+PKD1L3; pink color were then added. The overlay image shows that TMEM44 expression is restricted to the bottom third of each of the four taste buds shown and that TRPM5+PKD1L3 expression occurs predominantly in the upper regions of each of the taste buds.

FIG. 39 shows an exemplary experiment showing laser capture microdissection of top and bottom regions of primate taste buds. Panel) contains a methyl blue stained section A of macaque circumvallate taste buds. Panel B shows Section A following excision of bottom fraction of taste buds. Panel C contains the bottom fraction of taste buds. Panel D shows Section A following excision of bottom and top fractions of taste buds. Panel E shows the Top fraction of taste buds. Note, top and bottom fractions were only collected from taste buds exhibiting optimal morphology in section. In the example shown, the taste bud labeled with an arrow was excluded due to suboptimum sectioning or morphology.

The results obtained by the inventors revealed that taste receptor genes are expressed predominantly at the top of the taste bud. In contrast to what has been reported, the data of the inventors suggests that known taste receptor genes are expressed at higher level in the top fraction of the taste buds.

Therefore, this technique should allow for other yet to be identified taste receptor genes to be represented in the top-enriched set of genes.

In addition, there is an apparent functional classification that can be made based on top versus bottom taste bud cells. The gene expression profiles of the top and bottom fractions of the taste bud suggest distinct functions for cells in each compartment. Functional classes of genes represented in the top cells indicate that these are mature sensory cells whereas those expressed in the bottom cells indicate these are immature progenitor cells associated with a basement membrane containing cellular environment. Examples of top specific functional classes include taste receptors, taste-specific signal transduction components and receptors. Examples of bottom-specific functional classes include extracellular metric components, growth factors and cell-cycle associated proteins.

Also, based thereon, these techniques allow for the identification of additional taste bud-specific genes. By fractionating the taste buds into top and bottom compartments the inventors were able to increase the sensitivity of mRNA detection in each compartment by a factor of approximately two. This enables us to identify another set of taste bud specific genes Example 39

This experiment the results of which are contained in FIG. 40 establish that distinct cell populations PKD2L1, PKD1L3 and PKD2L1 plus PKD1L3. Double label in situ hybridization of primate fungiform (FG; left) and circumvallate (CV; right) was performed using PKD2L1 and PKD1L3 riboprobes. Taste cells expressing PKD2L1 (blue graph regions), PKD1L3 (magenta graph regions), or PKD2L1 plus PKD1L3 (labeled 'both' and yellow graph regions) genes were counted and graphed in pie charts. Total number of counted cells is listed below each pie chart in parentheses.

Example 40

This experiment the results of which are contained in FIG. 41 shows that FAM26C is expressed in TRPM5 taste cells. Therein double in situ hybridization of primate circumvallate papilla at the back of the tongue showing that FAM26C (blue/purple color; left image) colocalizes with TRPM5 (red; middle image). Note that FAM26C cells express TRPM5, a marker of sweet, bitter, and umami taste cells (merge; right image).

Example 41

This experiment the results of which are contained in FIG. 42 shows that NALCN is a taste-specific gene. The figure shows end-point PCR experiments on circumvallate taste buds (taste) and lingual epithelial cells (lingual) of non-human primate (left) and mouse (right) isolated by laser-capture microdissection demonstrating that NALCN is a taste-specific gene. NALCN is only expressed in taste cells and is not detectable in lingual cells, similar to the known taste-specific genes gustducin, T1R2, and TRPM5. β-actin is detectable in both taste and lingual samples, indicating that high-quality RNA was present in both samples. '+' indicates that reverse transcription was performed and '−' indicates that no reverse transcription was performed. PCR bands were only observed with reverse transcriptase indicating that PCR products are derived from mRNA and not genomic DNA. PCR products were cloned and sequenced to verify that the bands corresponded to the expected gene products.

Example 42

This experiment the results of which are contained in FIG. 43 shows that NALCN is expressed in a unique taste cell type effected at low magnification. Therein is shown a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel taste cell population. Numerous taste buds are shown.

Example 43

This experiment the results of which are contained in FIG. 44 also shows that NALCN is expressed in a unique taste cell type but at high magnification. Therein is contained a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel taste cell population. One to two taste buds are shown.

Example 44

This experiment the results of which are contained in FIG. 45 shows that NALCN is not expressed in TRPM5 cells. The figure contains a double label immunochemistry of circumvallate papilla from the back of the tongue showing that NALCN (red color, middle images( ) does not colocalize with TRPM5 in non-human primate (green, left image top row) or IP3R3 in rat (green; left image bottom row). Note that red and green stains localize to different cell types in the merged images on the right. Since TRPM5 and IP3R3 mark sweet, bitter, and umami cells, equivalent to type II cells, NALCN is not expressed in type II cells in non-human primate and rat.

Example 45

The experiment in FIG. 46 shows that NALCN is expressed in a subset of fungiform taste cells. Therein single label immunochemistry of fungiform papilla from the front of the tongue of non-human primate showing that NALCN (red color) is expressed in a subset of taste cells. Top of the taste bud, facing saliva, if oriented towards the top in the image is shown (see arrow). unique taste cell type but at high magnification. Therein is contained a double label immunohistochemistry of rat circumvallate papilla from the back of the tongue showing that NALCN (green color; left images) does not colocalize with IP3R3 (red; middle image top row) or SNAP-25 (red; middle image bottom row). Note that red and green stains localize to different cell types in the merged images on the right. Since IP3R3 is a marker of sweet, bitter, and umami cells whereas SNAP-25 is a marker of sour cells, NALCN is not expressed in sweet, bitter, umami, or sour cells but in a unique and novel. taste cell population. One to two taste buds are shown Example 46

Identification of Human Taste Specific Genes by Quantitative PCR

Experiments enabling the identification of human taste specific genes by quantitative polymerase chain reaction (PCR) were also effected. In the previous examples we described genes expressed in primate taste buds and we assigned gene expression patterns within the primate taste bud for all taste bud-specific genes; specifically, using a comparison of gene expression between the top and bottom sections of the primate taste bud. By these methods the inventors were able to classify genes into one of several functional classes that include taste receptor genes. In this example we demonstrate taste specific gene expression in humans (in addition to primate) and have validated the specificity of expression by a quantitative method (qPCR or "TaqMan"). The genes described in Table below, identified by these methods all encode multi-span transmembrane proteins, and it is likely that they include the salt receptor and others taste receptors whose function has yet to be defined.

In these experiments the inventors used human taste bud samples. In order to isolate human taste buds we performed laser capture microdissection (LCM). This technique has been described in detail in the provisional patent applications and incorporated by reference and supra. Briefly, it involves the excision and isolation of selected cells or groups of cells from tissue sections based on morphological distinctions. In the case of taste buds, we can readily identify these structures in sections of human tongue. In this specific example tissue collection was limited to taste buds (TB) in circumvallate papillae and, as a control, cells from the adjacent lingual epithelium (LE). An example of sections used in sample collection is shown in FIG. 47. Multiple LCM preparations from each of 3 human donors were pooled (~4500 cells per sample), RNA extracted and amplified by WT-Ovation Pico RNA Amplification System (NuGEN Technologies, Inc) and analyzed using TaqMan technology to determine specific levels of gene expression in the TB and LE pools.

The expression of the taste-specific genes was quantified by TaqMan in LCM derived cDNA from both LE and TB from the same donors. FIG. 47 shows the laser capture microdissection of human taste buds. Panel A shows methyl blue stained section of human circumvallate human taste buds. Panel B shows Section A following excision of taste buds. Panel C contains the captured taste buds.

A list of the analyzed human genes expressed are contained in Table 8 infra. Gene expression is measured in TaqMan as a CT (cycle threshold) value. Briefly the CT value for a given sample is determined by the PCR cycle at which the amount of gene-specific PCR product (as measured by fluorescence) reaches a set value. For highly expressed genes, the threshold will be reached early in the PCR run and the CT value will be relatively low (<35) while genes with very low or no expression will not reach the threshold before cycle 35. Expression of genes with CT values >40 are defined as not detectable. For the majority of genes listed in the Table, expression was not detected in LE samples (CT>40) but was readily detectable in TB samples (CT<35).

The group of human taste specific genes contained in Table 8 has not been described before as taste-specific in human tissue.

Therefore, these results show that by using this approach that uses LCM from post-mortem human tissue samples and a single cDNA amplification step, our data clearly indicate that postmortem LCM human tissue can be used to quantify the expression of taste specific genes using qPCR. and that human taste specific genes can be measured by quantitative PCR (TaqMan). Particularly, gene expression profiles of taste specific genes can be measured by TaqMan. This methodology validated gene expression data obtained from microarrays and/or in situ hybridization (ISH). Therefore, by using the successive approaches of gene expression via microarray in primate LCM tongue tissue; top-specific gene expression within the taste bud (akin to known taste receptors) and TaqMan quantification of gene expression in human postmortem tastes tissues, new human taste specific genes that had not been described previously were identified as contained in Table 8.

Additional Results and Tables Listing Taste Specific Genes (Human and Macaque)

The primate taste bud-specific gene list which resulted in the taste-specific genes contained in Tables 1-5 below were generated by the use of specific inclusion criteria. These inclusion criteria used Affymetrix MAS5 normalized data as follows:

Inclusion Criteria

Using Affymetrix MASS normalized data

FG taste bud mean expression value ≥50

FG versus LE expression ratio ≥2-fold up

FG versus LE expression ratio p value ≤0.05

[01] 424 probe sets

[02] Using Affymetrix GC-RMA normalized data

FG taste bud mean expression value ≥20

FG versus LE expression ratio ≥2-fold up

FG versus LE expression ratio p value ≤0.05

[03] 504 probe sets

[04] PLUS 3211 probe sets isolated from both data sets

[05] [TOTAL Number of Primate Taste Bud Specific probe Sets Equals 4139}

[06] TOTAL Number of Primate Taste Bud Specific Genes Equals 3455

TABLE 1

This table summarizes primate taste-bud expressed genes that were identified as multi-plasma membrane proteins with little or no functional characterization. The set is consistent with this gene set including taste receptors and more particularly including salty taste receptors as the identified genes includes genes identified as sodium channels. This Table comprises the most probable candidates for salty receptor genes and genes responsible for other characterized and uncharacterized taste receptors and polypeptides that modulate taste intensity as well as genes encoding transmembrane proteins involved in other taste cell functions. Representative accession numbers are from primate (i.e. *Macaca mulatta* abbreviated *Mm*) or humans (i.e. *Homo sapiens* abbreviated *Hs*).

| Representative Public ID | Representative Public ID: Species | MAS5 LE mean | MAS5 TB mean | MAS5 fold change | MAS5 p value |
|---|---|---|---|---|---|
| XM_001085855 | *Mm* | 168.1 | 825.8 | 4.9 | 0.0007 |
| XM_001106014 | *Mm* | 50.9 | 113.9 | 2.2 | 0.0386 |
| XM_001084081 | *Mm* | 17.1 | 174.9 | 10.2 | 0.0066 |
| XM_001099138 | *Mm* | 126.8 | 547.4 | 4.3 | 0.0244 |
| XM_001101439 | *Mm* | 30.3 | 102.6 | 3.4 | 0.0250 |
| XM_001113252 | *Mm* | 5.0 | 702.3 | 139.3 | 0.0006 |
| XM_001107314 | *Mm* | 12.3 | 74.2 | 6.0 | 0.0001 |
| XR_014466 | *Mm* | 185.9 | 584.9 | 3.1 | 0.0056 |
| XR_013101 | *Mm* | 63.8 | 405.3 | 6.4 | 0.0103 |
| XM_001083619 | *Mm* | 16.5 | 155.4 | 9.4 | 0.0496 |
| XM_001088479 | *Mm* | 344.9 | 1388.2 | 4.0 | 0.0043 |
| XM_001088853 | *Mm* | 44.9 | 102.2 | 2.3 | 0.1992 |

TABLE 1-continued

This table summarizes primate taste-bud expressed genes that were identified as multi-plasma membrane proteins with little or no functional characterization. The set is consistent with this gene set including taste receptors and more particularly including salty taste receptors as the identified genes includes genes identified as sodium channels. This Table comprises the most probable candidates for salty receptor genes and genes responsible for other characterized and uncharacterized taste receptors and polypeptides that modulate taste intensity as well as genes encoding transmembrane proteins involved in other taste cell functions. Representative accession numbers are from primate (i.e. *Macaca mulatta* abbreviated *Mm*) or humans (i.e. *Homo sapiens* abbreviated *Hs*).

| Representative Public ID | Representative Public ID: Species | MAS5 LE mean | MAS5 TB mean | MAS5 fold change | MAS5 p value |
|---|---|---|---|---|---|
| XM_001085289 | *Mm* | 416.8 | 2226.5 | 5.3 | 0.0001 |
| XM_001086036 | *Mm* | 34.3 | 88.7 | 2.6 | 0.0421 |
| XM_001114058 | *Mm* | 404.5 | 3269.5 | 8.1 | 0.0007 |
| XM_001112907 | *Mm* | 81.7 | 715.0 | 8.8 | 0.0223 |
| BV165948 | *Mm* | 35.9 | 111.9 | 3.1 | 0.0172 |
| BV166168 | *Mm* | 11.1 | 93.6 | 8.5 | 0.0026 |
| BV166439 | *Mm* | 11.0 | 75.4 | 6.9 | 0.0016 |
| BV209038 | *Mm* | 35.5 | 154.1 | 4.3 | 0.0139 |
| BV209579 | *Mm* | 22.4 | 51.7 | 2.3 | 0.0393 |
| BV209589 | *Mm* | 18.5 | 109.8 | 5.9 | 0.0340 |
| BV209803 | *Mm* | 31.9 | 97.2 | 3.0 | 0.0775 |
| BV209934 | *Mm* | 40.2 | 104.0 | 2.6 | 0.0606 |
| BV210562 | *Mm* | 626.9 | 1473.7 | 2.4 | 0.0003 |
| BV211039 | *Mm* | 164.1 | 439.3 | 2.7 | 0.0026 |
| BV445286 | *Mm* | 51.7 | 493.2 | 9.5 | 0.0039 |
| BV447952 | *Mm* | 36.9 | 454.5 | 12.3 | 0.0001 |
| BV447979 | *Mm* | 22.4 | 123.1 | 5.5 | 0.0001 |
| BV448453 | *Mm* | 36.7 | 184.8 | 5.0 | 0.0333 |
| BV448619 | *Mm* | 32.7 | 90.3 | 2.8 | 0.0288 |
| BV448731 | *Mm* | 374.3 | 769.4 | 2.1 | 0.0179 |
| BV448735 | *Mm* | 20.6 | 1485.7 | 72.2 | 0.0010 |
| BV448827 | *Mm* | 44.4 | 110.9 | 2.5 | 0.0441 |
| AL833583 | *Hs* | 31.4 | 267.0 | 8.5 | 0.1140 |
| CB550378 | *Mm* | 16.2 | 136.4 | 8.4 | 0.0164 |
| CN804030 | *Mm* | 431.4 | 1060.7 | 2.5 | 0.0387 |
| CO774248 | *Mm* | 22.4 | 70.6 | 3.1 | 0.0233 |
| NM_000166 | *Hs* | 19.1 | 64.4 | 3.4 | 0.0466 |
| NM_000335 | *Hs* | 4.5 | 381.4 | 85.4 | 0.0003 |
| NM_001001666 | *Hs* | 13.0 | 139.7 | 10.7 | 0.0009 |
| NM_001001994 | *Hs* | 40.0 | 1037.3 | 25.9 | 0.0003 |
| NM_001002796 | *Hs* | 3.7 | 2066.5 | 558.9 | 0.0046 |
| NM_001004746 | *Hs* | 35.3 | 102.1 | 2.9 | 0.0148 |
| NM_001010898 | *Hs* | 26.8 | 106.7 | 4.0 | 0.0016 |
| NM_001011655 | *Hs* | 8.2 | 1258.5 | 154.2 | 0.0035 |
| NM_001012302 | *Hs* | 28.9 | 64.8 | 2.2 | 0.0090 |
| NM_001017970 | *Hs* | 348.7 | 1779.2 | 5.1 | 0.0000 |
| NM_001025356 | *Hs* | 43.1 | 175.0 | 4.1 | 0.0071 |
| NM_001033026 | *Hs* | 90.2 | 180.8 | 2.0 | 0.0091 |
| NM_001037984 | *Hs* | 134.6 | 263.8 | 2.0 | 0.0032 |
| NM_001040456 | *Hs* | 46.2 | 155.1 | 3.4 | 0.0019 |
| NM_001042680 | *Hs* | 28.4 | 59.3 | 2.1 | 0.0495 |
| NM_001046 | *Hs* | 41.8 | 182.3 | 4.4 | 0.0002 |
| NM_001076674 | *Hs* | 174.4 | 351.5 | 2.0 | 0.0666 |
| NM_001077241 | *Hs* | 52.8 | 129.7 | 2.5 | 0.0175 |
| NM_001079669 | *Hs* | 245.7 | 3971.8 | 16.2 | 0.0000 |
| NM_001425 | *Hs* | 29.3 | 60.9 | 2.1 | 0.1000 |
| NM_001606 | *Hs* | 700.5 | 3503.3 | 5.0 | 0.0000 |
| NM_002211 | *Hs* | 7.1 | 42.6 | 6.0 | 0.0249 |
| NM_003615 | *Hs* | 8.4 | 413.3 | 48.9 | 0.0034 |
| NM_004099 | *Hs* | 66.5 | 174.0 | 2.6 | 0.0010 |
| NM_005502 | *Hs* | 223.5 | 611.5 | 2.7 | 0.0264 |
| NM_005724 | *Hs* | 321.1 | 666.4 | 2.1 | 0.0048 |
| NM_007213 | *Hs* | 23.6 | 78.8 | 3.3 | 0.0336 |
| NM_012329 | *Hs* | 43.0 | 209.1 | 4.9 | 0.0577 |
| NM_014399 | *Hs* | 2718.3 | 5413.0 | 2.0 | 0.0013 |
| NM_014858 | *Hs* | 62.8 | 176.7 | 2.8 | 0.0597 |
| NM_014982 | *Hs* | 18.0 | 86.9 | 4.8 | 0.0493 |
| NM_015205 | *Hs* | 177.2 | 389.7 | 2.2 | 0.0234 |
| NM_015257 | *Hs* | 38.7 | 134.4 | 3.5 | 0.0269 |
| NM_015292 | *Hs* | 986.6 | 2513.0 | 2.5 | 0.0004 |
| NM_015916 | *Hs* | 5.2 | 152.3 | 29.5 | 0.0057 |
| NM_016127 | *Hs* | 1915.3 | 3775.3 | 2.0 | 0.0003 |
| NM_016235 | *Hs* | 27.7 | 584.2 | 21.1 | 0.0007 |
| NM_016475 | *Hs* | 49.3 | 143.6 | 2.9 | 0.0400 |
| NM_017586 | *Hs* | 266.0 | 1076.2 | 4.0 | 0.0140 |
| NM_017672 | *Hs* | 68.9 | 231.9 | 3.4 | 0.0074 |
| NM_017744 | *Hs* | 81.3 | 202.7 | 2.5 | 0.0061 |
| NM_017799 | *Hs* | 42.0 | 191.1 | 4.6 | 0.0047 |
| NM_017801 | *Hs* | 78.5 | 154.7 | 2.0 | 0.0110 |
| NM_017814 | *Hs* | 33.0 | 100.7 | 3.1 | 0.0049 |
| NM_017849 | *Hs* | 43.5 | 109.5 | 2.5 | 0.0092 |
| NM_017905 | *Hs* | 32.5 | 91.7 | 2.8 | 0.0382 |
| NM_017918 | *Hs* | 48.9 | 232.0 | 4.7 | 0.0012 |
| NM_018056 | *Hs* | 25.7 | 63.3 | 2.5 | 0.0298 |
| NM_018452 | *Hs* | 48.4 | 146.0 | 3.0 | 0.0090 |
| NM_018487 | *Hs* | 8.9 | 924.9 | 103.6 | 0.0004 |
| NM_018502 | *Hs* | 14.0 | 47.3 | 3.4 | 0.0234 |
| NM_019118 | *Hs* | 37.5 | 451.0 | 12.0 | 0.0000 |
| NM_020215 | *Hs* | 12.9 | 108.0 | 8.4 | 0.0112 |
| NM_020448 | *Hs* | 34.7 | 93.3 | 2.7 | 0.0445 |
| NM_020925 | *Hs* | 27.9 | 480.2 | 17.2 | 0.0069 |
| NM_021194 | *Hs* | 132.0 | 329.5 | 2.5 | 0.0493 |
| NM_021259 | *Hs* | 20.1 | 115.0 | 5.7 | 0.0178 |
| NM_021637 | *Hs* | 6.9 | 64.5 | 9.3 | 0.0032 |
| NM_021727 | *Hs* | 46.6 | 106.0 | 2.3 | 0.0132 |
| NM_022369 | *Hs* | 8.6 | 131.0 | 15.3 | 0.0940 |
| NM_022458 | *Hs* | 32.9 | 145.1 | 4.4 | 0.0203 |
| NM_022495 | *Hs* | 33.1 | 154.8 | 4.7 | 0.0239 |
| NM_023003 | *Hs* | 16.0 | 157.6 | 9.9 | 0.0175 |
| NM_023943 | *Hs* | 7.7 | 57.2 | 7.4 | 0.0375 |
| NM_024628 | *Hs* | 47.5 | 710.7 | 15.0 | 0.0018 |
| NM_024630 | *Hs* | 71.6 | 386.9 | 5.4 | 0.0159 |
| NM_024956 | *Hs* | 64.7 | 129.7 | 2.0 | 0.0211 |
| NM_025257 | *Hs* | 9.7 | 275.1 | 28.2 | 0.0024 |
| NM_030651 | *Hs* | 7.1 | 183.8 | 25.9 | 0.0053 |
| NM_030923 | *Hs* | 6.5 | 1801.8 | 276.3 | 0.0004 |
| NM_031442 | *Hs* | 8.7 | 73.8 | 8.5 | 0.0415 |
| NM_031484 | *Hs* | 88.3 | 881.7 | 10.0 | 0.0001 |
| NM_032012 | *Hs* | 390.0 | 1480.2 | 3.8 | 0.0006 |
| NM_032016 | *Hs* | 135.4 | 961.3 | 7.1 | 0.0023 |
| NM_032295 | *Hs* | 112.6 | 267.8 | 2.4 | 0.0152 |
| NM_032483 | *Hs* | 87.0 | 224.8 | 2.6 | 0.0200 |
| NM_032824 | *Hs* | 90.1 | 335.9 | 3.7 | 0.0563 |
| NM_032826 | *Hs* | 17.5 | 62.2 | 3.6 | 0.0084 |
| NM_032890 | *Hs* | 93.4 | 987.6 | 10.6 | 0.0000 |
| NM_033102 | *Hs* | 7.8 | 125.6 | 16.1 | 0.0202 |
| NM_138346 | *Hs* | 573.4 | 2006.8 | 3.5 | 0.0001 |
| NM_139075 | *Hs* | 48.1 | 138.1 | 2.9 | 0.0046 |
| NM_144638 | *Hs* | 19.8 | 92.2 | 4.6 | 0.0170 |
| NM_144649 | *Hs* | 21.9 | 52.6 | 2.4 | 0.1617 |
| NM_144686 | *Hs* | 18.0 | 406.4 | 22.6 | 0.0034 |
| NM_145290 | *Hs* | 44.9 | 192.8 | 4.3 | 0.1919 |
| NM_152288 | *Hs* | 353.5 | 1590.1 | 4.5 | 0.0006 |
| NM_152522 | *Hs* | 357.2 | 514.3 | 1.4 | 0.0595 |
| NM_152588 | *Hs* | 182.1 | 560.3 | 3.1 | 0.0148 |
| NM_152778 | *Hs* | 43.7 | 208.5 | 4.8 | 0.0139 |
| NM_153354 | *Hs* | 38.2 | 118.1 | 3.1 | 0.0523 |
| NM_153365 | *Hs* | 600.9 | 1850.8 | 3.1 | 0.0027 |
| NM_153704 | *Hs* | 8.9 | 46.9 | 5.3 | 0.0288 |
| NM_153811 | *Hs* | 105.8 | 303.3 | 2.9 | 0.0433 |
| NM_173512 | *Hs* | 10.3 | 77.0 | 7.5 | 0.0169 |
| NM_173653 | *Hs* | 159.5 | 357.2 | 2.2 | 0.0187 |
| NM_174926 | *Hs* | 8.2 | 211.1 | 25.9 | 0.0246 |
| NM_175861 | *Hs* | 15.1 | 74.4 | 4.9 | 0.0146 |
| NM_177964 | *Hs* | 27.7 | 267.4 | 9.7 | 0.0016 |
| NM_178818 | *Hs* | 54.5 | 167.8 | 3.1 | 0.0145 |

TABLE 1-continued

This table summarizes primate taste-bud expressed genes that were identified as multi-plasma membrane proteins with little or no functional characterization. The set is consistent with this gene set including taste receptors and more particularly including salty taste receptors as the identified genes includes genes identified as sodium channels. This Table comprises the most probable candidates for salty receptor genes and genes responsible for other characterized and uncharacterized taste receptors and polypeptides that modulate taste intensity as well as genes encoding transmembrane proteins involved in other taste cell functions. Representative accession numbers are from primate (i.e. *Macaca mulatta* abbreviated *Mm*) or humans (i.e. *Homo sapiens* abbreviated *Hs*).

| Representative Public ID | Representative Public ID: Species | MAS5 LE mean | MAS5 TB mean | MAS5 fold change | MAS5 p value |
|---|---|---|---|---|---|
| NM_181644 | *Hs* | 63.9 | 520.8 | 8.2 | 0.0095 |
| NM_181787 | *Hs* | 52.3 | 246.1 | 4.7 | 0.0109 |
| NM_182494 | *Hs* | 5.4 | 1159.4 | 215.5 | 0.0010 |
| NM_182504 | *Hs* | 8.4 | 53.3 | 6.4 | 0.0151 |
| NM_182532 | *Hs* | 4.8 | 74.8 | 15.5 | 0.0180 |
| NM_182547 | *Hs* | 1722.3 | 3135.0 | 1.8 | 0.0023 |
| NM_198276 | *Hs* | 35.7 | 127.6 | 3.6 | 0.0226 |
| NM_207351 | *Hs* | 116.0 | 890.6 | 7.7 | 0.0035 |
| XM_001128552 | *Hs* | 4.7 | 292.8 | 62.8 | 0.0505 |
| XM_370997 | *Hs* | 6.3 | 70.5 | 11.2 | 0.0057 |
| XM_927351 | *Hs* | 5.3 | 1085.9 | 204.3 | 0.0027 |

TABLE 2

Table 2 below summarizes primate taste-bud expressed genes that were identified as multitransmembrane domain proteins that have been functionally characterized and which are potential candidates for salty taste and other taste receptors. In addition this gene set includes genes encoding transmembrane polypeptides involved in other taste cell related functions. Representative accession numbers are from primate (i.e. *Macaca mulatta* abbreviated *Mm*) or humans (i.e. *Homo sapiens* abbreviated *Hs*).

| Representative Public ID | Representative Public ID: Species | MAS5 LE mean | MAS5 TB mean | MAS5 fold change | MAS5 p value |
|---|---|---|---|---|---|
| XR_011926 | *Mm* | 11.4 | 213.4 | 18.7 | 0.0231 |
| XM_001099450 | *Mm* | 10.2 | 57.8 | 5.7 | 0.0126 |
| XM_001098390 | *Mm* | 12.8 | 93.4 | 7.3 | 0.0196 |
| XM_001086764 | *Mm* | 12.5 | 58.0 | 4.6 | 0.0870 |
| XM_001114476 | *Mm* | 5.3 | 122.9 | 23.1 | 0.0047 |
| XM_001110867 | *Mm* | 16.0 | 245.0 | 15.3 | 0.0015 |
| R58928 | *Mm* | 5.6 | 50.6 | 9.0 | 0.0126 |
| XM_001093116 | *Mm* | 8.8 | 121.0 | 13.7 | 0.0095 |
| XM_001099593 | *Mm* | 9.4 | 126.9 | 13.6 | 0.0008 |
| XR_010972 | *Mm* | 9.2 | 547.5 | 59.6 | 0.0005 |
| XM_001084620 | *Mm* | 4.4 | 1917.8 | 433.3 | 0.0001 |
| XM_001090982 | *Mm* | 34.3 | 229.2 | 6.7 | 0.0060 |
| XM_001098500 | *Mm* | 20.0 | 1366.9 | 68.2 | 0.0022 |
| XM_001088661 | *Mm* | 12.7 | 70.0 | 5.5 | 0.0327 |
| XM_001097918 | *Mm* | 367.0 | 1244.3 | 3.4 | 0.0059 |
| XM_001089122 | *Mm* | 9.9 | 176.2 | 17.8 | 0.0307 |
| XM_001106548 | *Mm* | 16.7 | 854.3 | 51.2 | 0.0001 |
| BV166050 | *Mm* | 12.1 | 108.1 | 8.9 | 0.0043 |
| BV166421 | *Mm* | 10.3 | 2141.3 | 207.1 | 0.0001 |
| BV166428 | *Mm* | 90.1 | 1287.4 | 14.3 | 0.0010 |
| BV166437 | *Mm* | 13.5 | 253.1 | 18.7 | 0.0871 |
| BV166724 | *Mm* | 9.6 | 59.6 | 6.2 | 0.0304 |
| BV166739 | *Mm* | 150.9 | 719.0 | 4.8 | 0.0002 |
| BV166741 | *Mm* | 159.5 | 303.8 | 1.9 | 0.0297 |
| BV166749 | *Mm* | 56.6 | 156.9 | 2.8 | 0.0055 |
| BV166757 | *Mm* | 212.7 | 1221.6 | 5.7 | 0.0011 |
| BV166818 | *Mm* | 23.3 | 157.6 | 6.8 | 0.0822 |
| BV208636 | *Mm* | 25.4 | 584.3 | 23.0 | 0.0013 |
| BV208853 | *Mm* | 23.0 | 225.5 | 9.8 | 0.0043 |
| BV209086 | *Mm* | 22.9 | 85.6 | 3.7 | 0.0012 |
| BV209237 | *Mm* | 26.3 | 1562.2 | 59.5 | 0.0000 |
| BV209238 | *Mm* | 302.6 | 964.7 | 3.2 | 0.0073 |
| BV209550 | *Mm* | 5.3 | 2121.2 | 398.1 | 0.0000 |

TABLE 2-continued

Table 2 below summarizes primate taste-bud expressed genes that were identified as multitransmembrane domain proteins that have been functionally characterized and which are potential candidates for salty taste and other taste receptors. In addition this gene set includes genes encoding transmembrane polypeptides involved in other taste cell related functions. Representative accession numbers are from primate (i.e. *Macaca mulatta* abbreviated *Mm*) or humans (i.e. *Homo sapiens* abbreviated *Hs*).

| Representative Public ID | Representative Public ID: Species | MAS5 LE mean | MAS5 TB mean | MAS5 fold change | MAS5 p value |
|---|---|---|---|---|---|
| BV209574 | *Mm* | 20.8 | 111.0 | 5.3 | 0.0154 |
| BV210515 | *Mm* | 100.4 | 202.2 | 2.0 | 0.0022 |
| BV210859 | *Mm* | 46.9 | 140.8 | 3.0 | 0.0156 |
| BV210983 | *Mm* | 181.8 | 563.9 | 3.1 | 0.0031 |
| BV447592 | *Mm* | 12.8 | 1670.7 | 130.7 | 0.0003 |
| BV447751 | *Mm* | 4.4 | 406.5 | 91.5 | 0.0010 |
| BV448581 | *Mm* | 50.3 | 159.8 | 3.2 | 0.0422 |
| BV448600 | *Mm* | 6.9 | 179.2 | 26.1 | 0.0071 |
| AK057677 | *Hs* | 17.8 | 616.2 | 34.6 | 0.0017 |
| AK095199 | *Hs* | 6.0 | 189.4 | 31.8 | 0.0313 |
| NM_000068 | *Hs* | 20.9 | 379.4 | 18.1 | 0.0007 |
| NM_000112 | *Hs* | 21.3 | 337.8 | 15.9 | 0.0182 |
| NM_000238 | *Hs* | 8.8 | 427.4 | 48.5 | 0.0019 |
| NM_000617 | *Hs* | 72.1 | 238.1 | 3.3 | 0.0359 |
| NM_001001396 | *Hs* | 18.4 | 116.6 | 6.3 | 0.0081 |
| NM_001001787 | *Hs* | 414.9 | 2580.5 | 6.2 | 0.0006 |
| NM_001008783 | *Hs* | 1.0 | 114.5 | 117.2 | 0.0196 |
| NM_001017403 | *Hs* | 4.6 | 265.1 | 57.2 | 0.0086 |
| NM_001020818 | *Hs* | 484.8 | 1455.0 | 3.0 | 0.0006 |
| NM_001023587 | *Hs* | 163.3 | 1680.5 | 10.3 | 0.0042 |
| NM_001024938 | *Hs* | 35.3 | 114.7 | 3.2 | 0.0255 |
| NM_001029858 | *Hs* | 4.3 | 2244.2 | 523.9 | 0.0033 |
| NM_001076785 | *Hs* | 6.7 | 128.0 | 19.0 | 0.0178 |
| NM_001106 | *Hs* | 12.5 | 65.6 | 5.2 | 0.0223 |
| NM_002241 | *Hs* | 3.2 | 132.8 | 42.1 | 0.0018 |
| NM_002980 | *Hs* | 35.9 | 156.4 | 4.4 | 0.0119 |
| NM_003043 | *Hs* | 213.6 | 900.2 | 4.2 | 0.0147 |
| NM_003304 | *Hs* | 144.8 | 663.9 | 4.6 | 0.0007 |
| NM_003641 | *Hs* | 33.5 | 327.9 | 9.8 | 0.0086 |
| NM_004616 | *Hs* | 13.2 | 795.8 | 60.4 | 0.0022 |
| NM_004733 | *Hs* | 314.5 | 810.9 | 2.6 | 0.0187 |
| NM_004770 | *Hs* | 1.8 | 305.6 | 173.7 | 0.0098 |
| NM_004974 | *Hs* | 1.9 | 125.3 | 65.7 | 0.0017 |
| NM_004996 | *Hs* | 923.5 | 4019.0 | 4.4 | 0.0000 |
| NM_005173 | *Hs* | 29.8 | 3560.0 | 119.4 | 0.0000 |
| NM_005415 | *Hs* | 468.3 | 1315.2 | 2.8 | 0.0035 |
| NM_005669 | *Hs* | 2293.8 | 4587.3 | 2.0 | 0.0009 |
| NM_006054 | *Hs* | 681.2 | 1701.5 | 2.5 | 0.0035 |
| NM_006435 | *Hs* | 1431.8 | 4294.5 | 3.0 | 0.0198 |
| NM_006598 | *Hs* | 71.4 | 673.6 | 9.4 | 0.0021 |
| NM_006608 | *Hs* | 66.8 | 172.7 | 2.6 | 0.1044 |
| NM_007001 | *Hs* | 10.3 | 80.3 | 7.8 | 0.0472 |
| NM_012129 | *Hs* | 303.5 | 542.9 | 1.8 | 0.0154 |
| NM_014220 | *Hs* | 81.6 | 306.2 | 3.8 | 0.0029 |
| NM_015236 | *Hs* | 6.2 | 407.8 | 66.3 | 0.0041 |
| NM_016395 | *Hs* | 25.6 | 100.9 | 3.9 | 0.0407 |
| NM_018144 | *Hs* | 75.3 | 214.4 | 2.8 | 0.1049 |
| NM_018155 | *Hs* | 84.9 | 411.3 | 4.8 | 0.0005 |
| NM_020724 | *Hs* | 5.7 | 44.6 | 7.8 | 0.0120 |
| NM_021095 | *Hs* | 41.5 | 203.3 | 4.9 | 0.0262 |
| NM_022109 | *Hs* | 763.0 | 1828.3 | 2.4 | 0.0046 |
| NM_022154 | *Hs* | 20.8 | 552.8 | 26.5 | 0.0087 |
| NM_022754 | *Hs* | 65.5 | 213.6 | 3.3 | 0.1189 |
| NM_024534 | *Hs* | 27.0 | 549.1 | 20.3 | 0.1113 |
| NM_030571 | *Hs* | 373.9 | 735.4 | 2.0 | 0.0062 |
| NM_031462 | *Hs* | 6.1 | 51.5 | 8.5 | 0.0173 |
| NM_033272 | *Hs* | 7.0 | 677.5 | 97.3 | 0.0185 |
| NM_052885 | *Hs* | 13.8 | 64.7 | 4.7 | 0.0270 |
| NM_133329 | *Hs* | 7.6 | 160.7 | 21.3 | 0.0078 |
| NM_138694 | *Hs* | 11.9 | 227.0 | 19.0 | 0.0066 |
| NM_144673 | *Hs* | 19.6 | 288.7 | 14.7 | 0.0004 |
| NM_152264 | *Hs* | 19.3 | 87.7 | 4.5 | 0.0088 |
| NM_152686 | *Hs* | 17.7 | 392.4 | 22.2 | 0.0099 |
| NM_153357 | *Hs* | 9.7 | 84.5 | 8.7 | 0.0578 |
| NM_178276 | *Hs* | 1442.4 | 2921.0 | 2.0 | 0.0028 |
| NM_178568 | *Hs* | 9.5 | 48.1 | 5.0 | 0.0462 |
| XM_370711 | *Hs* | 17.4 | 91.9 | 5.3 | 0.0236 |

TABLE 2-continued

Table 2 below summarizes primate taste-bud expressed genes that were identified as multitransmembrane domain proteins that have been functionally characterized and which are potential candidates for salty taste and other taste receptors. In addition this gene set includes genes encoding transmembrane polypeptides involved in other taste cell related functions. Representative accession numbers are from primate (i.e. *Macaca mulatta* abbreviated *Mm*) or humans (i.e. *Homo sapiens* abbreviated *Hs*).

| Representative Public ID | Representative Public ID: Species | MAS5 LE mean | MAS5 TB mean | MAS5 fold change | MAS5 p value |
|---|---|---|---|---|---|
| XM_931948 | *Hs* | 256.3 | 1010.3 | 3.9 | 0.0000 |
| XM_001084141 | *Mm* | 65.3 | 229.1 | 3.5 | 0.0024 |
| XM_001108664 | *Mm* | 21.1 | 79.8 | 3.8 | 0.0184 |
| XM_001103706 | *Mm* | 82.6 | 232.7 | 2.8 | 0.0027 |
| NM_207627 | *Hs* | 8.1 | 181.4 | 22.3 | 0.0499 |
| XM_001083115 | *Mm* | 228.6 | 705.3 | 3.1 | 0.0040 |
| XM_001103565 | *Mm* | 328.5 | 797.1 | 2.4 | 0.0015 |
| BV166047 | *Mm* | 10.0 | 98.9 | 9.9 | 0.0445 |
| BV166216 | *Mm* | 5.9 | 218.2 | 37.0 | 0.0000 |
| BV166400 | *Mm* | 160.3 | 1036.6 | 6.5 | 0.0001 |
| BV166539 | *Mm* | 111.9 | 1279.1 | 11.4 | 0.0036 |
| BV166725 | *Mm* | 6.7 | 78.5 | 11.6 | 0.0192 |
| BV208837 | *Mm* | 41.7 | 209.0 | 5.0 | 0.0010 |
| BV209241 | *Mm* | 230.8 | 515.4 | 2.2 | 0.0041 |
| BV209592 | *Mm* | 42.0 | 303.8 | 7.2 | 0.0004 |
| BV445228 | *Mm* | 42.3 | 136.5 | 3.2 | 0.0530 |
| BV447852 | *Mm* | 4.0 | 120.0 | 30.2 | 0.0205 |
| NM_018398 | *Hs* | 5.8 | 273.7 | 46.9 | 0.0294 |
| NM_001035 | *Hs* | 18.1 | 59.4 | 3.3 | 0.0342 |
| NM_001736 | *Hs* | 168.9 | 1036.9 | 6.1 | 0.0013 |
| NM_001992 | *Hs* | 7.0 | 73.7 | 10.6 | 0.0081 |
| NM_004700 | *Hs* | 5.2 | 114.1 | 22.1 | 0.0005 |
| NM_005845 | *Hs* | 35.4 | 616.0 | 17.4 | 0.0007 |
| NM_006218 | *Hs* | 46.6 | 186.2 | 4.0 | 0.0460 |
| NM_012072 | *Hs* | 12.7 | 110.8 | 8.7 | 0.0448 |
| NM_012319 | *Hs* | 16.7 | 165.4 | 9.9 | 0.0586 |
| NM_013384 | *Hs* | 19.1 | 187.2 | 9.8 | 0.0010 |
| NM_013388 | *Hs* | 40.4 | 79.5 | 2.0 | 0.0281 |
| NM_014331 | *Hs* | 90.2 | 544.5 | 6.0 | 0.0006 |
| NM_015444 | *Hs* | 38.1 | 134.1 | 3.5 | 0.1685 |
| NM_017746 | *Hs* | 24.5 | 54.3 | 2.2 | 0.0858 |
| NM_017839 | *Hs* | 21.9 | 139.0 | 6.3 | 0.0280 |
| NM_021814 | *Hs* | 126.4 | 686.9 | 5.4 | 0.0006 |
| NM_022374 | *Hs* | 777.3 | 1714.3 | 2.2 | 0.0027 |
| NM_022768 | *Hs* | 10.2 | 95.9 | 9.4 | 0.0320 |
| NM_024809 | *Hs* | 40.6 | 87.9 | 2.2 | 0.0498 |
| NM_025141 | *Hs* | 685.7 | 1708.0 | 2.5 | 0.0006 |
| NM_025154 | *Hs* | 267.0 | 1000.7 | 3.7 | 0.0000 |
| NM_031301 | *Hs* | 22.8 | 185.8 | 8.1 | 0.0629 |
| NM_032027 | *Hs* | 288.0 | 667.2 | 2.3 | 0.0548 |
| NM_144991 | *Hs* | 13.5 | 40.9 | 3.0 | 0.0153 |
| NM_152261 | *Hs* | 38.0 | 262.7 | 6.9 | 0.0025 |
| NM_152621 | *Hs* | 54.5 | 367.4 | 6.7 | 0.0128 |
| NM_182589 | *Hs* | 6.2 | 214.2 | 34.5 | 0.0258 |
| XM_290972 | *Hs* | 44.3 | 225.5 | 5.1 | 0.0000 |

TABLE 3

Fungiform Specific Genes and Other Potential Tate Receptor Candidates This Table of genes was derived after compiling a list of ion channel genes permeable to sodium that were systematically tested for expression in laser capture microdissected primate tongue tissue from lingual epithelium and taste buds by end point PCR. Genes that were expressed in fungiform taste buds but not circumvallate taste buds or lingual epithelium were included in this list. Moreover, this list of genes includes other genes which were selected that are likely to encode multidomain transmembrane proteins included on the macaque oligo array that did not satisfy the inclusion criteria of the systematic array and are not included in the Gene Lists contained in Tables 1 and 2 supra.

| RefSeq Transcript ID |
|---|
| NM_178826 |
| NM_021625 |

TABLE 3-continued

Fungiform Specific Genes and Other Potential Tate Receptor Candidates This Table of genes was derived after compiling a list of ion channel genes permeable to sodium that were systematically tested for expression in laser capture microdissected primate tongue tissue from lingual epithelium and taste buds by end point PCR. Genes that were expressed in fungiform taste buds but not circumvallate taste buds or lingual epithelium were included in this list. Moreover, this list of genes includes other genes which were selected that are likely to encode multidomain transmembrane proteins included on the macaque oligo array that did not satisfy the inclusion criteria of the systematic array and are not included in the Gene Lists contained in Tables 1 and 2 supra.

| RefSeq Transcript ID |
|---|
| NM_020199 |
| NM_014386 |
| NM_006765 |
| NM_016113 |
| NM_003305 |
| NM_007369 |
| NM_018202 |
| NM_005725 |
| NM_000334 |
| NM_002976 |
| NM_002977 |
| NM_030782 |
| CK232413 |
| NM_005669 |
| NM_001001188 |
| XR_018915 |
| NM_145239 |
| NM_012264 |
| NM_001040151 |
| NM_005727 |
| NM_004621 |
| NM_002420 |
| NM_019841 |
| NM_153835 |
| NM_018653 |
| NM_152487 |
| NM_018022 |
| NM_001040142 |
| NM_000297 |
| NM_001040107 |
| NM_032824 |
| NM_031457 |
| NM_018298 |
| BV445354 |
| XM_001111007 |
| BV444941 |
| AANU01224075; AANU01224076 |

[014] (CLASS 2 Genes) Putative Fatty Taste Gene Receptors

TABLE 4

Additional new taste-specific genes identified in macaque fungiform and/or circumvallate taste-buds by gene chip analysis. These genes all encode transmembrane proteins with no described function or that function as ion channels, ion transporters, or G-protein coupled receptors. Accession numbers, ratios of gene expression in taste cells (TB) to non-taste lingual epithelial cells (LE), and the p values calculated using a two-tailed Student's t-test are listed.

| Accession number or Unigene cluster | TB vs. LE ratio | TB vs. LE p value |
|---|---|---|
| BC017041 | 4.93 | 0.3961 |
| XM_001094702 | 4.36 | 0.0817 |
| XM_001093133 | 6.08 | 0.3922 |
| NM_020141 | 5.00 | 0.1647 |
| XM_001101699 | 5.16 | 0.0204 |
| XM_001084342 | 11.25 | 0.0894 |
| XM_001097482 | 6.19 | 0.0498 |
| *Hs*.98728 | 8.99 | 0.0141 |
| *Mm*u.5446 | 16.62 | 0.1980 |
| XM_001113863 | 18.35 | 0.1654 |

TABLE 4-continued

Additional new taste-specific genes identified in macaque fungiform and/or circumvallate taste-buds by gene chip analysis. These genes all encode transmembrane proteins with no described function or that function as ion channels, ion transporters, or G-protein coupled receptors. Accession numbers, ratios of gene expression in taste cells (TB) to non-taste lingual epithelial cells (LE), and the p values calculated using a two-tailed Student's t-test are listed.

| Accession number or Unigene cluster | TB vs. LE ratio | TB vs. LE p value |
|---|---|---|
| *Hs*.568078 | 13.28 | 0.3665 |
| *Hs*.136017 | 4.93 | 0.0575 |
| XM 001086597 | 6.50 | 0.0156 |
| XM_001103527 | 15.02 | 0.3411 |
| *Hs*.127196 | 10.66 | 0.2504 |
| *Hs*.21606 | 11.47 | 0.3328 |
| XM_001083605 | 13.09 | 0.1231 |
| XM_001083934 | 25.63 | 0.3774 |
| XM_001085321 | 5.89 | 0.2483 |
| *Hs*.88972 | 5.01 | 0.1045 |
| *Hs*.47068 | 14.48 | 0.0790 |
| XR_010355 | 6.71 | 0.1362 |
| XM_001088824 | 9.47 | 0.0968 |
| NM_198503 | 56.03 | 0.0551 |
| *Hs*.292453 | 5.45 | 0.2891 |
| XM_001082226 | 1.33 | 0.2803 |
| XM_001115408 | 5.84 | 0.2666 |
| *Hs*.285976.2.S1 | 6.57 | 0.0156 |
| *Hs*.306723 | 4.72 | 0.0762 |
| XM_001117492 | 55.50 | 0.0903 |
| XM_001114070 | 4.99 | 0.3147 |
| XM_001083482 | 8.39 | 0.1759 |
| XM_001085289 | 6.53 | 0.0358 |
| XM_001090289 | 5.70 | 0.2157 |
| XM_001099752 | 4.72 | 0.0333 |
| XM_001103706 | 1.53 | 0.6021 |
| XM_001108095 | 10.17 | 0.2344 |
| XM_001099350 | 1.50 | 0.7839 |
| XM_001092868 | 11.47 | 0.0594 |
| XM_001082482 | 5.76 | 0.0990 |
| XM_001087669 | 5.40 | 0.2955 |
| XM_001085445 | 322.37 | 0.1177 |
| XM_001095050 | 23.94 | 0.3918 |
| XM_001090844 | 5.21 | 0.0776 |
| XM_001118514 | 5.56 | 0.0704 |
| XR_011068 | 11.49 | 0.3387 |
| XM_001099407 | 10.13 | 0.1970 |
| XM _001098987 | 226.16 | 0.0153 |
| XR_012702 | 9.67 | 0.3743 |
| XM_001090295 | 10.66 | 0.3814 |
| XM_001101662 | 9.51 | 0.1324 |
| XM_001113146 | 5.38 | 0.2783 |
| XM_001103667 | 5.24 | 0.2633 |
| XM_001106443 | 5.16 | 0.0742 |
| XM_001103701 | 5.23 | 0.0055 |
| *Hs*.76722 | 7.66 | 0.3632 |
| NM_052832 | 199.81 | 0.0108 |
| XM_001114769 | 13.77 | 0.0748 |
| *Mm*u.9408 | 5.68 | 0.1025 |
| NM_001032861 | 7.74 | 0.0691 |
| *Hs*.199243 | 8.99 | 0.3158 |
| XM_001111927 | 2.33 | 0.0255 |
| *Hs*.255056 | 10.46 | 0.3185 |
| XM_001084483 | 1.78 | 0.3006 |
| XM_001108758 | 0.45 | 0.0553 |
| XM_001084211 | 77.55 | 0.0168 |
| *Hs*.8116 | 24.11 | 0.2107 |
| *Hs*.18653 | 21.23 | 0.2566 |
| *Hs*.35861 | 1.07 | 0.6589 |
| XM_001118212 | 5.53 | 0.1690 |
| XM_001090523 | 29.84 | 0.0230 |
| XM_001099752 | 16.53 | 0.0181 |
| XM_001108428 | 14.42 | 0.0212 |
| XM_001103909 | 22.02 | 0.0309 |
| *Hs*.211167 | 7.44 | 0.4008 |
| XM_001083172 | 57.01 | 0.1186 |
| XM_001112011 | 5.33 | 0.0137 |
| *Hs*.166845 | 9.46 | 0.2667 |
| XM_001111915 | 34.66 | 0.3156 |

TABLE 4-continued

Additional new taste-specific genes identified in macaque fungiform and/or circumvallate taste-buds by gene chip analysis. These genes all encode transmembrane proteins with no described function or that function as ion channels, ion transporters, or G-protein coupled receptors. Accession numbers, ratios of gene expression in taste cells (TB) to non-taste lingual epithelial cells (LE), and the p values calculated using a two-tailed Student's t-test are listed.

| Accession number or Unigene cluster | TB vs. LE ratio | TB vs. LE p value |
|---|---|---|
| XM_001117478 | 112.45 | 0.0068 |
| *Hs*.45080 | 11.18 | 0.0012 |

TABLE 5

Table 5 below contains primate genes previously described as fatty acid receptors or which contain amino acid motifs that are associated with lipid binding. This list of genes includes genes that do not encode multi-transmembrane proteins but which are reported to participate in lipid transport or binding at close to the plasma membrane.

| Public Transcript ID | Public Transcript ID: Species | MAS5 LE mean | MAS5 TB mean | MAS5 fold change | MAS5 p value |
|---|---|---|---|---|---|
| CO583226 | *Mm* | 8.5 | 48.0 | 5.7 | 0.0226 |
| CB309123 | *Mm* | 17.1 | 130.1 | 7.6 | 0.0367 |
| NM_001647 | *Hs* | 21.9 | 119.7 | 5.5 | 0.0235 |
| NM_016619 | *Hs* | 22.1 | 1139.3 | 51.6 | 0.0018 |
| NM_207352 | *Hs* | 91.3 | 405.4 | 4.4 | 0.0245 |
| NM_000229 | *Hs* | 13.4 | 77.3 | 5.8 | 0.0036 |
| NM_021105 | *Hs* | 20.6 | 203.8 | 9.9 | 0.0000 |
| NM_004915 | *Hs* | 17.5 | 139.7 | 8.0 | 0.0811 |
| NM_001017403 | *Hs* | 4.6 | 265.1 | 57.2 | 0.0086 |
| NM_002899 | *Hs* | 631.1 | 3718.0 | 5.9 | 0.0001 |
| NM_001153 | *Hs* | 1778.3 | 3990.5 | 2.2 | 0.0000 |
| NM_017784 | *Hs* | 144.0 | 348.8 | 2.4 | 0.0002 |
| NM_001077400 | *Hs* | 16.4 | 197.3 | 12.0 | 0.0050 |
| NM_000253 | *Hs* | 7.1 | 493.9 | 69.4 | 0.0018 |
| NM_002336 | *Hs* | 111.3 | 1452.8 | 13.0 | 0.0000 |
| NM_032360 | *Hs* | 32.8 | 168.5 | 5.1 | 0.0180 |
| NM_001004746 | *Hs* | 35.3 | 102.1 | 2.9 | 0.0148 |
| NM_006551 | *Hs* | 10.0 | 78.1 | 7.8 | 0.0191 |
| AB220498 | *Mm* | 81.7 | 715.0 | 8.8 | 0.0223 |
| XM_001086422 | *Mm* | 48.4 | 262.8 | 5.4 | 0.0345 |
| NM_014349 | *Hs* | 24.4 | 98.5 | 4.0 | 0.0054 |
| XM_001100224 | *Mm* | 173.6 | 525.8 | 3.0 | 0.0411 |
| NM_006684 | *Hs* | 7.5 | 107.1 | 14.4 | 0.0465 |
| NM_006377 | *Hs* | 405.4 | 2498.0 | 6.2 | 0.0000 |
| CO583346 | *Mm* | 160.3 | 1036.6 | 6.5 | 0.0001 |

TABLE 6

The 11 taste-specific genes contained in Table 6 were shown to be expressed in different subsets of primate taste cells. These genes were identified as taste-specific genes by gene chip analysis and shown to be expressed in subsets of taste cells by in situ hybridization analysis as described in the experimental examples and Figures.

| Gene Name | Cell type gene expressed in |
|---|---|
| FAM26A | Many TRPM5 cells |
| GPR113 | Subset TRPM5 cells |
| MCTP1 | Many TRPM5 cells |
| TMEM16G | Subset TRPM5 cells |
| TMEM30B | Many TRPM5 cells |
| TMEM44 | Many non-TRPM5 and non-PKD1L3 cells |
| TUSC3 | Many TRPM5 cells |
| FAM26C | MANY TRPM5 CELLS |
| FAM26B | Many TRPM5 cells |
| MFSD4 | Many Non-TRPM5 cells |
| ATP8A1 | Many TRPM5 and some non-TRPM5 cells |

TABLE 6-continued

The 11 taste-specific genes contained in Table 6 were shown to be expressed in different subsets of primate taste cells. These genes were identified as taste-specific genes by gene chip analysis and shown to be expressed in subsets of taste cells by in situ hybridization analysis as described in the experimental examples and Figures.

| Gene Name | Cell type gene expressed in |
|---|---|
| SLC4A11 | Many TRPM5 cells |
| SLC4A7 | Subset TRPM5 cells |

Table 7 below lists 4 other primate taste specific genes identified by the inventive rationales and provides information as to the specific cell types in which these genes are expressed.

TABLE 7

| Gene Name | Cell type gene expressed in |
|---|---|
| KIT | TRPM5 & T1R3 subset; T1R1 umami taste receptor cells |
| IKBKAP | PKD1L3 sour taste receptor cells |
| LOC285965 | TRPM5 & T1R3 subset; T1R3 only cells lacking T1R1 (umami) and T1R2 (sweet) |
| SV2B | PKD1L3 sour taste receptor cells |

TABLE 8

Table 8 contains a listing of the human taste-specific genes which were quantified by TaqMan in LCM derived cDNA from both LE and TB from the same donors. As noted in Example 46, gene expression was measured in TaqMan as a CT (cycle threshold) value. Briefly the CT value for a given sample was determined by the PCR cycle at which the amount of gene-specific PCR product (as measured by fluorescence) reaches a set value. For highly expressed genes, the threshold is reached early in the PCR run and the CT value is relatively low (<35) while genes with very low or no expression do not reach the threshold before cycle 35. Expression of genes with CT values > 40 are defined as not detectable. For the majority of genes listed in Table 8 below, expression was not detected in LE samples (CT > 40) but was readily detectable in TB samples (CT < 35).

| Gene Title | Gene Symbol | TB CT value | LE CT value* |
|---|---|---|---|
| solute carrier family 9 (sodium/hydrogen exchanger), member 2 | SLC9A2 | 24.63 | No Ct |
| solute carrier family 44, member 4 | SLC44A4 | 25.2 | No Ct |
| membrane-spanning 4-domains, subfamily A, member 8B | MS4A8B | 25.2 | No Ct |
| tetraspanin 2 | TSPAN2 | 25.79 | No Ct |
| transmembrane protein 38B | TMEM38B | 26.44 | No Ct |
| family with sequence similarity 26, member C | FAM26C | 26.93 | No Ct |
| LR8 protein | LR8 | 28.01 | No Ct |
| leucine-rich repeat-containing G protein-coupled receptor 6 | LGR6 | 28.01 | No Ct |
| G protein-coupled receptor, family C, group 5, member B | GPRC5B | 28.51 | 38.69 |
| solute carrier family 35, member E2 | SLC35E2 | 28.58 | 39.46 |
| G protein-coupled receptor 155 | GPR155 | 28.64 | No Ct |
| LAG1 longevity assurance homolog 2 (*S. cerevisiae*) | LASS2 | 29.12 | No Ct |
| major facilitator superfamily domain containing 4 | MFSD4 | 29.23 | No Ct |
| transmembrane protein 108 | TMEM108 | 29.28 | No Ct |
| tetraspanin 17 | TSPAN17 | 29.37 | No Ct |
| G protein-coupled receptor 113 | GPR113 | 29.44 | No Ct |
| transmembrane protein 163 | TMEM163 | 29.61 | No Ct |
| Hypothetical protein LOC644139 | LOC644139 | 29.93 | No Ct |
| transmembrane protein 16G | TMEM16G | 30 | No Ct |
| transient receptor potential cation channel, subfamily C, member 1 | TRPC1 | 30.11 | No Ct |
| transmembrane 6 superfamily member 1 | TM6SF1 | 30.13 | 36.8 |
| leucine-rich repeat-containing G protein-coupled receptor 5 | LGR5 | 30.15 | No Ct |
| transmembrane protein 44 | TMEM44 | 30.26 | No Ct |
| family with sequence similarity 26, member A | FAM26A | 30.39 | No Ct |
| Transmembrane protein 118 | TMEM118 | 30.91 | No Ct |
| chromosome 14 open reading frame 135 | C14orf135 | 32.17 | 38.68 |
| solute carrier family 8 (sodium/calcium exchanger), member 1 | SLC8A1 | 32.72 | No Ct |
| brain-specific angiogenesis inhibitor 2 | BAI2 | 32.97 | No Ct |
| hypothetical protein LOC130576 | LOC130576 | 34.03 | No Ct |
| potassium voltage-gated channel, KQT-like subfamily, member 1 | KCNQ1 | 34.26 | No Ct |
| ATPase, Class VI, type 11A | ATP11A | 34.33 | No Ct |
| ATPase, aminophospholipid transporter (APLT), Class I, type 8A, member 1 | ATP8A1 | 34.54 | No Ct |
| chromosome 14 open reading frame 101 | C14orf101 | 35.44 | 38.27 |
| potassium channel, subfamily T, member 2 | KCNT2 | 35.62 | No Ct |
| synaptic vesicle glycoprotein 2B | SV2B | 35.95 | No Ct |

*No Ct = CT value > 40, or, not detectable. See text.

[025] As afore mentioned the taste cell specific genes identified herein and the corresponding gene products and cells which express same e.g., endogenous taste or chemosensory cells and recombinant cells including the taste specific genes recited in Tables 1, 2, 3, 4, 5, 6, 7, and 8 and their orthologs, allelic variants, variants possessing at least 90% sequence identity thereto and/or genes which specifically hybridize thereto under hybridization conditions denied supra may be used in assays to identify taste modulatory compounds as well as in therapeutic screening assays.

[026] For example these taste specific genes, polypeptides and cells expressing same can be used to screen for compounds for treatment of digestive system disorders. These disorders include by way of example conditions affecting digestion such as dyspepsia, autoimmune and inflammatory diseases affecting the digestive system such as ulcerative colitis, inflammatory bowel syndrome, Crohn's syndrome, celiac disease, and precancers and cancers that affect the digestive system such as cancers affecting the salivary glands, taste buds, stomach, pancreas, gall bladder, esophagus, small or large intestine, anus or colon.

[027] Also these taste specific genes may be used in screening assays to identify compounds that affect taste cell turnover. It is known that taste cells turnover rapidly (about every couple of weeks). Moreover, many conditions including chemotherapy or radiation treatment, as well as old age may negatively affect the ability of taste cells to develop. The result is a diminished sense of taste which may result in a decreased quality of life in cancer patients or the elderly. This is particularly pronounced in patients with head and neck cancer, esophageal, stomach, lung, or pancreatic cancers. Additionally, this may evolve along with another condition, cachexia or wasting syndrome that combines to reduce the desire to eat. Lack of proper nutrition is a serious cause of morbidity and mortality in cancer patients. The subject taste specific genes contain genes expressed in stem cells suggesting that they are markers of stem cells that are the precursors of and which evolve into taste cells. These genes or cells which express same can be used to identify signals that accelerate taste cell development. These signals which likely comprise cytokine-like receptors present on taste cells likely mediate taste cell development and can be used in screens to identify compounds that induce taste cell differentiation or proliferation. The ligands therefore potentially may be isolated from saliva and may account for the ability of saliva to influence taste function. For example, patients with Sjogren's syndrome (an autoimmune disease that attacks the salivary glands) exhibit altered taste functions. The subject genes and the study of gene expression in the salivary glands by use of gene arrays will facilitate an understanding of these differentiation mechanisms.

[028] The subject taste cell specific genes and corresponding gene products and cells which express these genes may also be used in order to identify potential therapeutics for modulating the immune system of the oral cavity. The oral cavity is populated by normal flora as is the digestive tract. Alterations in normal flora may give rise to conditions such as gingivitis, halitosis, gastric problems and other infections that may result in tooth decay or tooth loss. Included within the taste cell specific genes identified herein are a number of immune system genes. These genes and the corresponding polypeptides or cells which express same can be used to identify therapeutics for maintaining immune homeostasis in the oral cavity, preventing overgrowth of pathogenic microbia, and for identification of the cell types in the oral cavity that are the key players in maintaining proper oral cavity immunity.

[029] Moreover, the subject taste cell specific genes and the corresponding gene products or cells which express same are useful in screening assays for identifying compounds for treatment of diabetes, eating disorders such as obesity, anorexia, bulimia, and other metabolic disorders. The expression of taste receptors in the digestive system likely represents a comprehensive system that detects food and different types at different places during digestion. Therefore, "sensing" the presence of food or specific types such as carbohydrates, fats, umami foods, salts, should trigger various signals that may regulate the production of molecules that participate in the regulation of digestion such as GIP (glucose-dependent insulinotrophic polypeptide) and GLP-1 (glucagon-like peptide 1) produced by the enteroendocrine cells in the intestine. It is likely that taste receptors on these cells regulate the production of other molecular signals in other cells of the digestive system when triggered. These phenomena may be studied by determining which cells express different receptors and then using gene arrays to study the molecules that these cells produce when activated.

[030] References

[031] All the references cited in this application are incorporated by reference in their entirety herein.

[032] SEQUENCE LISTING

>gi|89886487|ref|NM_014848.3|*Homo sapiens* synaptic vesicle glycoprotein 2B (SV2B) (SEQ ID NO:1)

| Probe Set ID | Gene Title | Gene Symbol | Ratio Top verus Bottom | p value Top versus Bottom |
|---|---|---|---|---|
| MmugDNA.12222.1.S1_at | chloride channel, calcium activated, family member 1 | CLCA1 | 28.26 | 0.0794 |
| MmugDNA.18105.1.S1_at | ST8 alpha-N-acetyl-neuraminide alpha-2,8-sialyltransferase 1 | ST8SIA1 | 25.30 | 0.0112 |
| MmugDNA.11091. .S1_at | — | — | 14.48 | 0.0463 |
| MmugDNA.15011. 1.S1_at | toll-like receptor 10 precursor | LOC697980 | 14.47 | 0.0262 |
| MmugDNA.41559.1 .S1_at | taste receptor, type 2, member 16 | TAS2R16 | 13.96 | 0.0356 |
| MmugDNA.24584. 1.S1_at | hypothetical protein LOC703243 | LOC703243 | 13.55 | 0.0725 |
| MmugDNA.15361. 1.S1_at | phosphatidylinositol glycan, class N | LOC699219 | 12.99 | 0.0249 |
| Mmu.10677.1.S1_t | matrix metalloproteinase 7 | MMP7 | 11.87 | 0.0181 |
| MmuSTS.783.1.S1_at | taste receptor T2R7 | LOC717909 | 11.70 | 0.0671 |
| MmugDNA.25181. 1.S1_at | 3-hydroxysteroid epimerase | LOC713549 | 11.52 | 0.0396 |
| MmugDNA.9747.1. S1_at | — | — | 11.31 | 0.0934 |
| MmugDNA.10468. 1.S1_at | hypothetical protein LOC709833 | LOC709833 | 11.21 | 0.0379 |

-continued

| Probe Set ID | Gene Title | Gene Symbol | Ratio Top verus Bottom | p value Top versus Bottom |
|---|---|---|---|---|
| MmugDNA.7746.1.S1_at | Protein FAM3B precursor (Cytokine-like protein 2-21) | LOC722516 | 11.10 | 0.0882 |
| MmugDNA.11368.1.S1_at | proprotein convertase subtilisin/kexin type 2 | PCSK2 | 10.97 | 0.0486 |
| MmugDNA.26966.1.S1_at | — | — | 10.92 | 0.0376 |
| MmugDNA.15380.1.S1_at | taste receptor T2R13 | LOC718046 | 10.82 | 0.0924 |
| MmugDNA.32635.1.S1_at | — | — | 10.78 | 0.0891 |
| MmugDNA.37045.1.S1_at | — | — | 10.61 | 0.0029 |
| MmugDNA.36075.1.S1_at | potassium voltage-gated channel, shaker-related subfamily, member 2 | KCNA2 | 10.45 | 0.0060 |
| MmugDNA.35060.1.S1_at | kinesin-like motor protein C20orf23 | LOC695167 | 10.35 | 0.0420 |
| MmugDNA.13207.1.S1_at | — | — | 10.20 | 0.0665 |
| MmunewRS.875.1 S1_at | neuroligin 4 | NLGN4X | 10.13 | 0.0053 |
| MmugDNA.35863. 1.S1_at | zinc finger protein 533 | LOC704204 | 10.10 | 0.0657 |
| MmugDNA.121.1.S1_at | golgi SNAP receptor complex member 2 isoform A | LOC716841 | 10.09 | 0.0493 |
| MmugDNA.38131.1.S1_at | kelch-like 8 | LOC700864 | 9.90 | 0.0023 |
| MmugDNA.41159.1.S1_at | interleukin 17B receptor | IL17RB | 9.77 | 0.0005 |
| MmugDNA.11591.1.S1_s_at | dipeptidase 2 | LOC701570 | 9.73 | 0.0020 |
| MmugDNA.5167.1.S1_at | male sterility domain containing 1 | LOC710740 | 9.37 | 0.0930 |
| MmugDNA.656.1.S1_at | — | — | 9.25 | 0.0001 |
| MmugDNA.7006.1.S1_at | sialyltransferase 7E | LOC705908 | 9.24 | 0.0467 |
| MmugDNA.3684.1.S1_at | G protein-coupled receptor 85 | GPR85 | 9.18 | 0.0664 |
| MmugDNA.1571.1.S1_at | — | — | 9.09 | 0.0263 |
| MmugDNA.24639.1.S1_at | — | — | 9.04 | 0.0042 |
| MmuSTS.906.1.S1_at | taste receptor, type 2, member 14 | LOC718111 | 9.00 | 0.0288 |
| MmugDNA.30874.1.S1_at | transmembrane protein 45B | LOC718735 | 9.00 | 0.0000 |
| MmugDNA.34847.1.S1_at | apoptosis inhibitor 5 | API5 | 8.45 | 0.0755 |
| MmuSTS.778.1.S1_at | Taste receptor type 2 member 49 (T2R49) (T2R56) | TAS2R49 | 8.44 | 0.0007 |
| MmuSTS.2869.1.S1_at | tachykinin 1 isoform alpha precursor | TAC1 | 8.44 | 0.0726 |
| MmugDNA.30525.1.S1_at | FCH and double SH3 domains 1 | — | 8.37 | 0.0258 |
| MmugDNA.42433.1.S1_at | — | — | 8.36 | 0.0058 |
| MmugDNA.10579.1.S1_at | dopamine receptor interacting protein | — | 8.30 | 0.0060 |
| MmugDNA.16546.1.S1_at | CMP-N-acetylneuraminic acid hydroxylase | LOC574186 | 8.25 | 0.0649 |
| MmugDNA.29722.1.S1_at | — | — | 8.18 | 0.0717 |
| MmuSTS.4056.1.S1_at | Cornifin B (Small proline-rich protein IB) (SPR-IB) (14.9 kDa pancornulin) | LOC717850 | 7.96 | 0.0689 |
| MmugDNA.30502.1.S1_at | NIPA-like domain containing 2 | LOC703585 | 7.94 | 0.0421 |
| MmugDNA.6642.1.S1_at | leprecan-like 1 | LOC704118 | 7.86 | 0.0183 |
| MmugDNA.23279.1.S1_at | transmembrane protein 46 | LOC702501 | 7.85 | 0.0427 |
| MmugDNA.3909.1.S1_at | CG2698-PA | LOC710299 | 7.80 | 0.0116 |
| MmugDNA.39327.1.S1_at | — | — | 7.78 | 0.0960 |
| MmugDNA.3544.1.S1_at | solute carrier family 22 (organic cation transporter), member 15 | LOC710102 | 7.72 | 0.0869 |
| MmugDNA.39807.1.S1_at | protocadherin beta 13 precursor | LOC700999 | 7.71 | 0.0311 |
| MmugDNA.17676.1.S1_at | PXR2b protein | PEX5L | 7.65 | 0.0969 |
| MmugDNA.30327.1.S1_at | — | — | 7.62 | 0.0341 |
| MmugDNA.6455.1.S1_at | F11 receptor | F11R | 7.58 | 0.0487 |
| MmugDNA.3223.1.S1_at | — | — | 7.57 | 0.0247 |
| MmugDNA.11678.1.S1_at | 3(2),5-bisphosphate nucleotidase 1 (Bisphosphate 3-nucleotidase 1) (PAP-inositol-1,4-phosphatase) (PIP) | — | 7.57 | 0.0034 |
| MmugDNA.7247.1.S1_at | nemo-like kinase | NLK | 7.56 | 0.0087 |
| MmugDNA.10209.1.S1_at | PHD finger protein 14 | PHF14 | 7.51 | 0.0000 |
| MmuSTS.3737.1.S1_at | protein tyrosine phosphatase, receptor type, C isoform 1 precursor | LOC712657 | 7.42 | 0.0139 |
| MmuSTS.1381.1.S1_at | basic helix-loop-helix domain containing, class B, 5 | LOC701485 | 7.39 | 0.0378 |
| MmugDNA.20444.1.S1_at | formin 2 | LOC708376 | 7.38 | 0.0999 |
| MmuSTS.1175.1.S1_at | Taste receptor type 2 member 10 (T2R10) (Taste receptor family B member 2) (TRB2) | TAS2R10 | 7.36 | 0.0445 |
| MmuSTS.2644.1.S1_s_at | taste receptor T2R55 | LOC695053 | 7.36 | 0.0182 |
| MmuSTS.3441.1.S1_at | annexin A9 | ANXA9 | 7.32 | 0.0133 |
| MmugDNA.9493.1.S1_at | — | — | 7.30 | 0.0007 |
| MmugDNA.4334.1.S1_at | tyrosine aminotransferase | TAT | 7.18 | 0.0194 |
| MmuSTS.1040.1.S1_at | ST8 alpha-N-acetyl-neuraminide alpha-2, 8-sialyltransferase 5 | ST8SIA5 | 7.18 | 0.0759 |
| MmugDNA.25088.1.S1_at | GTP-binding protein Rit2 (Ras-like protein expressed in neurons) (Ras-like without CAAX protein 2) | RIT2 | 7.14 | 0.0292 |
| MmugDNA.689.1.S1_at | hypothetical protein LOC707842 | LOC707842 | 7.11 | 0.0615 |
| MmugDNA.4223.1.S1_at | echinoderm microtubule associated protein like 5 | LOC718818 | 7.08 | 0.0053 |
| MmugDNA.29749.1.S1_at | — | — | 7.02 | 0.0598 |
| MmugDNA.1798.1.S1_at | doublecortin and CaM kinase-like 3 | LOC699654 | 6.99 | 0.0589 |
| MmuSTS.1232.1.S1_at | copine IV | LOC717868 /// LOC719231 | 6.98 | 0.0579 |
| MmuSTS.784.1.S1_at | taste receptor, type 2, member 8 | LOC717924 | 6.95 | 0.0189 |
| MmugDNA.26125.1.S1_at | — | — | 6.94 | 0.0509 |
| MmuSTS.2013.1.S1_at | protocadherin beta 10 | PCDHB10 | 6.92 | 0.0000 |
| MmugDNA.19056.1.S1_at | somatostatin receptor 1 | SSTR1 | 6.90 | 0.0040 |
| MmugDNA.43165.1.S1_at | — | — | 6.88 | 0.0378 |
| MmugDNA.34029.1.S1_at | secernin 1 | SCRN1 | 6.83 | 0.0410 |

-continued

| Probe Set ID | Gene Title | Gene Symbol | Ratio Top verus Bottom | p value Top versus Bottom |
|---|---|---|---|---|
| MmugDNA.40941.1.S1_at | — | — | 6.81 | 0.0380 |
| MmugDNA.21034.1.S1_at | — | — | 6.68 | 0.0782 |
| MmugDNA.31223.1.S1_at | protocadherin beta 3 | PCDHB3 | 6.68 | 0.0261 |
| MmugDNA.10620.1.S1_at | Rho GTPase activating protein 18 | LOC711107 | 6.67 | 0.0000 |
| MmugDNA.35495.1.S1_at | — | — | 6.67 | 0.0569 |
| MmugDNA.23300.1.S1_at | KIAA0828 protein | KIAA0828 | 6.65 | 0.0692 |
| MmugDNA.20297.1.S1_at | hypothetical protein LOC705695 | LOC705695 | 6.64 | 0.0273 |
| MmugDNA.43474.1.S1_at | protection of telomeres 1 | POT1 | 6.62 | 0.0587 |
| MmuSTS.1939.1.S1_at | Fibroblast growth factor 11 (FGF-11) (Fibroblast growth factor homologous factor 3) (FHF-3) | FGF11 | 6.61 | 0.0983 |
| MmugDNA.26964.1.S1_at | calponin like transmembrane domain protein | LOC709910 | 6.59 | 0.0179 |
| MmugDNA.33339.1.S1_at | — | — | 6.58 | 0.0179 |
| MmugDNA.32991.1.S1_at | ectonucleotide pyrophosphatase/phosphodiesterase 6 | LOC693950 | 6.54 | 0.0834 |
| MmugDNA.34284.1.S1_at | Sodium channel beta-3 subunit precursor | LOC714673 | 6.52 | 0.0945 |
| MmugDNA.20971.1.S1_at | — | — | 6.49 | 0.0462 |
| MmugDNA.9521.1.S1_at | glutaminyl-peptide cyclotransferase | QPCT | 6.49 | 0.0528 |
| MmuSTS.1179.1.S1_s_at | taste receptor, type 2, member 43 | LOC694161 | 6.47 | 0.0060 |
| MmugDNA.25858.1.S1_at | — | — | 6.47 | 0.0087 |
| MmugDNA.38257.1.S1_at | hypothetical protein LOC701675 | LOC701675 | 6.46 | 0.0506 |
| MmugDNA.41639.1.S1_at | phosphodiesterase 1 C, calmodulin-dependent 70 kDa | PDE1 C | 6.44 | 0.0007 |
| MmugDNA.33151.1.S1_at | — | — | 6.42 | 0.0253 |
| MmugDNA.1887.1.S1_at | zinc finger protein 395 | LOC698947 | 6.41 | 0.0237 |
| MmuSTS.1713.1.S1_at | WNT1 inducible signaling pathway protein 3 | WISPS | 6.37 | 0.0601 |
| MmugDNA.8585.1.S1_at | — | — | 6.34 | 0.0451 |
| MmugDNA.17339.1.S1_s_at | leucine rich repeat neuronal 3 | LOC701932 | 6.31 | 0.0171 |
| MmuSTS.527.1.S1_at | platelet-derived growth factor C precursor | — | 6.30 | 0.0362 |
| MmugDNA.15109.1.S1_s_at | — | — | 6.29 | 0.0096 |
| MmugDNA.2733.1.S1_s_at | Fatty acid-binding protein, epidermal (E-FABP) (Psoriasis-associated fatty acid-binding protein homolog) (PA-FABP) | — | 6.23 | 0.0651 |
| MmugDNA.35813.1.S1_at | — | — | 6.23 | 0.0411 |
| MmugDNA.20157.1.S1_at | nel-like 1 precursor | LOC701438 | 6.21 | 0.0389 |
| MmugDNA.39143.1.S1_at | — | — | 6.20 | 0.0333 |
| MmuSTS.2452.1.S1_at | McLeod syndrome-associated, Kell blood group protein | LOC696407 | 6.20 | 0.0099 |
| MmugDNA.33888.1.S1_at | egl nine homolog 1 | LOC713410 | 6.18 | 0.0609 |
| MmugDNA.7614.1.S1_at | ADP-ribosylation factor-like 6 | LOC696616 | 6.17 | 0.0002 |
| MmuSTS.1330.1.S1_at | dual-specificity tyrosine-(Y)-phosphorylation regulated kinase 2 | DYRK2 | 6.16 | 0.0203 |
| MmuSTS.3090.1.S1_at | latrophilin 3 | LPHN3 | 6.16 | 0.0063 |
| MmugDNA.23556.1.S1_at | — | — | 6.14 | 0.0144 |
| MmuSTS.1177.1.S1_at | taste receptor, type 2, member 39 | TAS2R39 | 6.10 | 0.0094 |
| MmugDNA.14803.1.S1_s_at | Fibroblast growth factor 12 (FGF-12) (Fibroblast growth factor homologous factor 1) (FHF-1) | LOC705813 | 6.05 | 0.0344 |
| Mmu.3466.1.S1_at | — | — | 6.03 | 0.0171 |
| MmugDNA.35142.1.S1_at | — | — | 6.01 | 0.0002 |
| MmuSTS.3438.1.S1_at | ankyrin 2 | ANK2 | 6.01 | 0.0264 |
| MmugDNA.16713.1.S1_at | potassium channel tetramerisation domain containing 4 | LOC701916 | 6.00 | 0.0289 |
| MmugDNA.23811. .S1_at | sel-1 suppressor of lin-12-like | LOC708651 | 5.97 | 0.0664 |
| MmunewRS.311.1.S1_at | — | — | 5.95 | 0.0419 |
| MmugDNA.2511.1.S1_at | — | — | 5.93 | 0.0561 |
| MmugDNA.5134.1.S1_at | thrombospondin 4 | THBS4 | 5.90 | 0.0003 |
| MmugDNA.27291. .S1_at | — | — | 5.90 | 0.0192 |
| MmugDNA.35237.1.S1_at | — | — | 5.89 | 0.0799 |
| MmugDNA.29494.1.S1_at | coagulation factor II receptor | F2R | 5.86 | 0.0249 |
| MmugDNA.41193.1.S1_at | phosducin-like 3 | — | 5.86 | 0.0302 |
| MmugDNA.27343.1.S1_s_at | DnaJ (Hsp40) homolog, subfamily C, member 3 | LOC695757 | 5.83 | 0.0649 |
| MmugDNA.8284.1.S1_at | — | — | 5.77 | 0.0007 |
| MmuSTS.909.1.S1_at | taste receptor, type 2, member 50 | LOC693513 | 5.76 | 0.0712 |
| MmuSTS.2673.1.S1_at | calmegin | CLGN | 5.76 | 0.0576 |
| MmugDNA.37138.1.S1_at | Discs large homolog 2 (Postynaptic density protein PSD-93) (Channel-associated protein of synapse-110) (Chapsyn-110) | LOC704826 | 5.76 | 0.0582 |
| MmugDNA.15905.1.S1_at | — | — | 5.68 | 0.0480 |
| MmugDNA.32064.1.S1_at | butyrophilin-like 8 | BTNL8 | 5.67 | 0.0176 |
| MmugDNA.34572.1.S1_at | decay accelerating factor for complement | LOC714370 | 5.65 | 0.0083 |
| MmugDNA.22059.1.S1_at | integrin alpha 2 | ITGA2 | 5.64 | 0.0227 |
| MmuSTS.861.1.S1_at | CG7231-PB, isoform B | LOC715256 | 5.62 | 0.0968 |
| MmugDNA.29329.1.S1_at | — | — | 5.61 | 0.0108 |
| MmugDNA.14073.1.S1_at | microtubule-associated protein 6 isoform 2 | LOC696223 | 5.60 | 0.0103 |
| MmugDNA.27825.1.S1_at | alpha 4 type IV collagen | COL4A4 | 5.59 | 0.0662 |
| MmugDNA.34698.1.S1_at | ankyrin repeat domain 43 | LOC708755 | 5.57 | 0.0236 |
| MmuSTS.2650.1.S1_at | adenylate kinase 5 isoform 1 | LOC706248 | 5.57 | 0.0477 |
| MmugDNA.21615.1.S1_at | — | — | 5.56 | 0.0504 |
| MmugDNA.18178.1.S1_at | autotaxin | ENPP2 | 5.56 | 0.0036 |
| MmuSTS.1143.1.S1_at | Beta-synuclein | SNCB | 5.53 | 0.0727 |
| MmugDNA.40607.1.S1_at | hypothetical protein LOC717552 | LOC717552 | 5.53 | 0.0701 |

-continued

| Probe Set ID | Gene Title | Gene Symbol | Ratio Top verus Bottom | p value Top versus Bottom |
|---|---|---|---|---|
| MmugDNA.18538.1.S1_s_at | serine (or cysteine) proteinase inhibitor, clade I (neuroserpin), member 1 | SERPINI1 | 5.53 | 0.0790 |
| MmugDNA.5368.1.S1_at | — | — | 5.50 | 0.0256 |
| MmugDNA.30317.1.S1_at | Baculoviral IAP repeat-containing protein 4 (Inhibitor of apoptosis protein 3) (X-linked inhibitor of apoptosis protein) (X-linked IAP) (IAP-like protein) (HILP) | LOC698057 | 5.49 | 0.0475 |
| MmugDNA.35810.1.S1_at | adenosine A2b receptor | ADORA2B | 5.48 | 0.0099 |
| MmugDNA.22262.1.S1_at | neurotrypsin precursor | LOC704461 | 5.46 | 0.0150 |
| Mmu.9266.1.S1_x_at | alpha-defensin 3 precursor | LOC574310 | 5.46 | 0.0796 |
| MmugDNA.1819.1.S1_at | chromodomain helicase DNA binding protein 5 | — | 5.44 | 0.0524 |
| MmugDNA.37049.1.S1_at | Dipeptidyl aminopeptidase-like protein 6 (Dipeptidylpeptidase VI) (Dipeptidylpeptidase 6) (Dipeptidylpeptidase IV-like protein) (Dipeptidyl aminopeptidase-related protein) (DPPX) | LOC718148 | 5.42 | 0.0278 |
| MmugDNA.26844.1.S1_at | hypothetical protein LOC716906 | LOC716906 | 5.40 | 0.0620 |
| MmugDNA.40160.1.S1_at | — | — | 5.34 | 0.0828 |
| MmugDNA.13497.1.S1_at | runt-related transcription factor 2 isoform b | LOC703331 | 5.33 | 0.0463 |
| MmugDNA.35702.1.S1_at | ADAMTS-like 1 | ADAMTSL1 | 5.33 | 0.0106 |
| Mmu.335.1.S1_at | carboxypeptidase E | CPE | 5.30 | 0.0493 |
| MmugDNA.13656.1.S1_at | — | — | 5.30 | 0.0030 |
| MmugDNA.22297.1.S1_at | lysozyme | LOC718361 | 5.29 | 0.0804 |
| MmugDNA.28583.1.S1_at | — | — | 5.25 | 0.0006 |
| MmugDNA.18724.1.S1_s_at | UDP-Gal:betaGIcNAc beta 1,4- galactosyltransferase 6 | B4GALT6 | 5.25 | 0.0461 |
| MmugDNA.38162.1.S1_at | — | — | 5.24 | 0.0001 |
| MmugDNA.27108.1.S1_at | matrix metalloproteinase 19 | MMP19 | 5.21 | 0.0313 |
| MmugDNA.24659.1.S1_at | mesothelin isoform 1 preproprotein | LOC698095 | 5.19 | 0.0431 |
| Mmu.11741.1.S1_at | N-ethylmaleimide-sensitive factor | LOC715297 | 5.19 | 0.0035 |
| MmugDNA.1267.1.S1_s_at | cytochrome P450 3A64 /// Cytochrome P450 3A7 (CYPIIIA7) (P450-HFLA) | CYP3A64 /// LOC718917 | 5.18 | 0.0847 |
| MmuSTS.3164.1.S1_at | cathepsin C | CTSC | 5.16 | 0.0003 |
| MmugDNA.2042.1.S1_at | dual specificity phosphatase 10 | DUSP10 | 5.16 | 0.0148 |
| MmuSTS.4822.1.S1_at | GATA binding protein 6 | LOC699591 | 5.15 | 0.0204 |
| MmugDNA.28021.1.S1_at | zinc finger and BTB domain containing 10 | LOC704721 | 5.15 | 0.0905 |
| MmugDNA.32990.1.S1_at | protocadherin beta 5 | PCDHB5 | 5.14 | 0.0458 |
| MmugDNA.27188.1.S1_at | hypothetical protein LOC694387 | LOC694387 | 5.11 | 0.0446 |
| MmugDNA.18606.1.S1_at | — | — | 5.10 | 0.0278 |
| MmugDNA.36968.1.S1_at | microsomal triglyceride transfer protein large subunit | MTTP | 5.07 | 0.0525 |
| MmugDNA.12625.1.S1_at | Ras protein-specific guanine nucleotide-releasing factor 2 | LOC711350 | 5.07 | 0.0298 |
| MmuSTS.597.1.S1_s_at | Hypoxanthine-guanine phosphoribosyltransferase (HGPRT) (HGPRTase) | LOC709186 | 5.07 | 0.0051 |
| MmugDNA.8387.1.S1_at | S-acyl fatty acid synthase thioesterase, medium chain (Thioesterase II) (Thioesterase domain-containing protein 1) | THEDC1 | 5.06 | 0.0290 |
| MmugDNA.19071.1.S1_at | — | — | 5.06 | 0.0453 |
| MmugDNA.1497.1.S1_at | vacuolar protein sorting 13A isoform A | LOC705323 | 5.04 | 0.0367 |
| MmugDNA.26354.1.S1_at | GEM 1 protein | GEM 1 | 5.04 | 0.0011 |
| MmunewRS.58.1.S1_at | — | — | 5.04 | 0.0241 |
| MmuSTS.531.1.S1_at | UDP-GIcNAc:betaGal beta-1,3-N-acetylglucosaminyltransferase 1 | LOC693396 | 5.04 | 0.0968 |
| MmugDNA.38025.1.S1_at | glycoprotein M6B | GPM6B | 5.03 | 0.0248 |
| MmuSTS.1448.1.S1_at | v-yes-1 Yamaguchi sarcoma viral related oncogene homolog | LYN | 5.03 | 0.0807 |
| MmugDNA.1649.1.S1_at | DHHC-containing protein 20 | LOC705802 | 5.02 | 0.0886 |
| MmugDNA.38429.1.S1_at | hypothetical protein LOC698744 | LOC698744 | 5.00 | 0.0001 |
| MmugDNA.3432.1.S1_at | plexin C1 | LOC711320 | 4.99 | 0.0000 |
| MmugDNA.30924.1.S1_at | mothers against decapentaplegic homolog 4 | SMAD4 | 4.97 | 0.0151 |
| MmugDNA.43332.1.S1_at | — | — | 4.96 | 0.0931 |
| MmuSTS.4050.1.S1_at | diacylglycerol kinase, beta | DGKB | 4.95 | 0.0176 |
| MmugDNA.31803.1.S1_at | calcium binding protein 39-like | CAB39L | 4.88 | 0.0227 |
| MmugDNA.42361.1.S1_at | — | — | 4.87 | 0.0521 |
| MmugDNA.36141.1.S1_at | — | — | 4.87 | 0.0504 |
| MmuSTS.2022.1.S1_at | Glutathione-requiring prostaglandin D synthase (Glutathione-dependent PGD synthetase) (Prostaglandin-H2D-isomerase) (Hematopoietic prostaglandin D synthase) (H-PGDS) | PGDS | 4.87 | 0.0504 |
| MmugDNA.20560.1.S1_at | tripartite motif protein 9 | TRIM9 | 4.86 | 0.0363 |
| MmuSTS.1776.1.S1_at | SATB family member 2 | SATB2 | 4.86 | 0.0000 |
| MmugDNA.17660.1.S1_s_at | ectonucleotide pyrophosphatase/ phosphodiesterase 4 (putative function) | LOC703680 | 4.83 | 0.0657 |
| MmugDNA.8441.1.S1_s_at | GalNAc-4-sulfotransferase 2 | LOC703877 | 4.83 | 0.0984 |
| MmugDNA.10568.1.S1_at | — | — | 4.81 | 0.0080 |
| MmugDNA.5130.1.S1_at | neuropilin- and tolloid-like protein 2 precursor | LOC716468 | 4.81 | 0.0436 |
| MmugDNA.10470.1.S1_at | cyclic nucleotide gated channel beta 1 | LOC708851 | 4.80 | 0.0916 |
| MmugDNA.25697.1.S1_at | — | — | 4.80 | 0.0646 |
| MmugDNA.2214.1.S1_at | protocadherin beta 14 | PCDHB14 | 4.79 | 0.0153 |
| MmuSTS.1120.1.S1_s_at | protocadherin alpha 9 | PCDHA9 | 4.78 | 0.0373 |
| MmugDNA.33308.1.S1_at | tetratricopeptide repeat domain 7 B | LOC696029 | 4.76 | 0.0022 |

-continued

| Probe Set ID | Gene Title | Gene Symbol | Ratio Top verus Bottom | p value Top versus Bottom |
|---|---|---|---|---|
| MmugDNA.9526.1.S1_at | Kelch repeat and BTB domain-containing protein 11 (Kelch domain-containing protein 7B) | KBTBD11 | 4.75 | 0.0031 |
| MmugDNA.42933.1.S1_at | hypothetical protein LOC712344 | LOC712344 | 4.74 | 0.0099 |
| MmugDNA.28339.1.S1_at | c-myc promoter binding protein | LOC709675 | 4.74 | 0.0345 |
| MmugDNA.16977.1.S1_at | — | — | 4.73 | 0.0001 |
| MmugDNA.9216.1.S1_s_at | tripartite motif protein 31 isoform alpha | — | 4.71 | 0.0045 |
| MmugDNA.29917.1.S1_at | — | — | 4.69 | 0.0000 |
| MmugDNA.8704.1.S1_at | stanniocalcin 2 precursor | LOC703900 | 4.69 | 0.0960 |
| MmugDNA.11746.1.S1_at | hypothetical protein LOC716531 | LOC716531 | 4.64 | 0.0001 |
| MmugDNA.7242.1.S1_at | ring finger protein 183 | LOC705679 | 4.63 | 0.0183 |
| MmugDNA.34448.1.S1_at | — | — | 4.62 | 0.0856 |
| MmugDNA.12226.1.S1_at | KIAA1946 | LOC712442 | 4.61 | 0.0021 |
| MmugDNA.16242.1.S1_at | — | — | 4.61 | 0.0284 |
| MmugDNA.42287.1.S1_at | Beta crystallin A2 (Beta-A2-crystallin) | LOC701178 | 4.59 | 0.0674 |
| MmugDNA.13689.1.S1_at | acyl-Coenzyme A oxidase 3, pristanoyl | ACOX3 | 4.58 | 0.0836 |
| MmugDNA.35429.1.S1_at | — | — | 4.58 | 0.0297 |
| MmugDNA.42474.1.S1_at | neural cell adhesion molecule 1 | NCAM1 | 4.58 | 0.0986 |
| MmugDNA.42278.1.S1_at | — | — | 4.58 | 0.0006 |
| MmugDNA.15856.1.S1_at | — | — | 4.57 | 0.0006 |
| MmugDNA.26231.1.S1_at | protein phosphatase 1, regulatory (inhibitor) subunit 14B | — | 4.56 | 0.0040 |
| MmuSTS.1471.1.S1_at | guanylate cyclase activator 1A (retina) | LOC695552 | 4.56 | 0.0712 |
| MmugDNA.38210.1.S1_at | — | — | 4.56 | 0.0013 |
| MmugDNA.8341.1.S1_at | potassium voltage-gated channel, subfamily H, member 7 isoform 2 | LOC702259 | 4.55 | 0.0691 |
| MmugDNA.40476.1.S1_at | CG17660-PA | LOC698581 | 4.55 | 0.0164 |
| MmugDNA.21371.1.S1_at | L1 cell adhesion molecule | L1 CAM | 4.54 | 0.0016 |
| MmugDNA.10362.1.S1_at | — | — | 4.54 | 0.0247 |
| MmugDNA.34200.1.S1_at | solute carrier family 16, member 10 | LOC696132 | 4.54 | 0.0008 |
| MmugDNA.10673.1.S1_at | — | — | 4.53 | 0.0098 |
| MmugDNA.34348.1.S1 at | — | — | 4.51 | 0.0776 |
| MmugDNA.14801.1.S1_at | — | — | 4.51 | 0.0800 |
| MmugDNA.16806.1.S1_at | — | — | 4.51 | 0.0104 |
| MmugDNA.26715.1.S1_at | hypothetical protein LOC705319 | LOC705319 | 4.50 | 0.0377 |
| MmugDNA.29516.1.S1_at | Transcribed locus | — | 4.50 | 0.0131 |
| MmugDNA.35871.1.S1_at | alpha-fetoprotein | AFP | 4.49 | 0.0827 |
| MmuSTS.3720.1.S1_at | prostaglandin-endoperoxide synthase 1 | PTGS1 | 4.49 | 0.0550 |
| MmugDNA.13337.1.S1_at | — | — | 4.48 | 0.0825 |
| MmugDNA.42244.1.S1_at | — | — | 4.48 | 0.0930 |
| MmugDNA.21236.1.S1_at | arginine/serine-rich coiled-coil 1 | LOC704232 | 4.47 | 0.0144 |
| MmugDNA.36820.1.S1_at | 1-acylglycerol-3-phosphate O-acyltransferase 5 | AGPAT5 | 4.47 | 0.0076 |
| MmugDNA.37762.1.S1_at | methylenetetrahydrofolate dehydrogenase (NADP + dependent) 1-like | LOC705222 | 4.47 | 0.0074 |
| MmugDNA.3018.1.S1_at | Corticotropin-lipotropin precursor (Pro-opiomelanocortin) (POMC) | POMC | 4.46 | 0.0858 |
| MmugDNA.30526.1.S1_at | breast cancer membrane protein 11 | LOC714517 | 4.46 | 0.0302 |
| MmuSTS.2215.1.S1_at | carbohydrate (N-acetylglucosamine-6-O) sulfotransferase 2 | LOC713994 | 4.45 | 0.0820 |
| MmuSTS.1144.1.S1_at | Jun dimerization protein p21 SNFT | LOC710551 | 4.45 | 0.0023 |
| MmugDNA.33092.1.S1_s_at | alpha-2-glycoprotein 1, zinc | LOC710136 | 4.44 | 0.0971 |
| MmugDNA.34402.1.S1_at | taste receptor, type 1, member 2 | LOC714666 | 4.44 | 0.0587 |
| MmugDNA.583.1.S1_at | phosphatidylinositol transfer protein, cytoplasmic 1 isoform a | LOC718773 | 4.43 | 0.0076 |
| MmugDNA.10551.1.S1_at | Alpha-1,6-mannosyl-glycoprotein 2-beta-N-acetylglucosaminyltransferase (Mannoside acetylglucosaminyltransferase 2) (N-glycosyl-oligosaccharide-glycoprotein N-acetylglucosaminyltransferase II) (Beta-1,2-N-acetylglucosaminyltransferase II). . . | MGAT2 | 4.42 | 0.0455 |
| MmugDNA.10172.1.S1_at | — | — | 4.42 | 0.0763 |
| MmugDNA.7644.1.S1_at | amyloid beta (A4) precursor-like protein 2 | APLP2 | 4.42 | 0.0771 |
| MmuSTS.4251.1.S1_at | DnaJ (Hsp40) homolog, subfamily B, member 9 | LOC701094 | 4.42 | 0.0012 |
| MmugDNA.30872.1.S1_at | Tescalcin (TSC) | TESC | 4.41 | 0.0018 |
| MmugDNA.16779.1.S1_at | solute carrier organic anion transporter family member 4A1 | SLCO4A1 | 4.41 | 0.0008 |
| MmugDNA.36628.1.S1_at | — | — | 4.39 | 0.0293 |
| MmugDNA.39982.1.S1_at | hydrogen voltage-gated channel 1 | LOC709745 | 4.39 | 0.0378 |
| MmugDNA.12304.1.S1_at | — | — | 4.39 | 0.0926 |
| MmugDNA.22401.1.S1_at | goosecoid | LOC702308 | 4.39 | 0.0452 |
| MmugDNA.3017.1.S1_at | — | — | 4.39 | 0.0176 |
| MmugDNA.40588.1.S1_at | — | — | 4.38 | 0.0736 |
| MmugDNA.9680.1.S1_at | — | — | 4.38 | 0.0521 |
| MmugDNA.27684.1.S1_at | guanine nucleotide binding protein (G protein), alpha 14 | LOC705448 | 4.38 | 0.0003 |
| MmugDNA.24197.1.S1_at | — | — | 4.37 | 0.0840 |
| MmugDNA.28806.1.S1_at | — | — | 4.37 | 0.0872 |
| MmugDNA.21653.1.S1_at | Y17G7B.10b | LOC704285 | 4.37 | 0.0535 |
| MmugDNA.26796.1.S1_at | beta-galactoside alpha-2,6-sialyltransferase II | LOC713552 | 4.37 | 0.0025 |
| MmugDNA.41976.1.S1_s_at | probable nucleolar complex protein 14 | LOC720068 | 4.37 | 0.0973 |
| MmuSTS.63.1.S1_at | hemochromatosis protein | HFE | 4.37 | 0.0581 |
| MmugDNA.17587.1.S1_at | molybdenum cofactor synthesis 3 | MOCS3 | 4.36 | 0.0773 |

-continued

| Probe Set ID | Gene Title | Gene Symbol | Ratio Top verus Bottom | p value Top versus Bottom |
|---|---|---|---|---|
| MmugDNA.22799.1.S1_at | — | — | 4.35 | 0.0910 |
| MmugDNA.43244.1.S1_at | — | — | 4.35 | 0.0287 |
| MmugDNA.4726.1.S1_at | — | — | 4.35 | 0.0236 |
| MmugDNA.27474.1.S1_at | NIF3 NGG1 interacting factor 3-like 1 | — | 4.34 | 0.0009 |
| MmuSTS.113.1.S1_at | monogenic, audiogenic seizure susceptibility 1 | LOC697794 | 4.34 | 0.0120 |
| MmugDNA.13225.1.S1_at | — | — | 4.34 | 0.0230 |
| MmugDNA.40434.1.S1_at | ataxin-1 ubiquitin-like interacting protein | LOC714928 | 4.34 | 0.0944 |
| MmuSTS.3087.1.S1_at | RAD50 homolog isoform 1 | LOC710718 | 4.33 | 0.0858 |
| MmugDNA.2856.1.S1_at | — | — | 4.32 | 0.0586 |
| MmugDNA.24690.1.S1_at | — | — | 4.32 | 0.0188 |
| MmugDNA.17638.1.S1_at | — | — | 4.32 | 0.0420 |
| Mmu.4140.1.S1_at | peptidylglycine alpha-amidating monooxygenase isoform b, preproprotein | LOC707733 | 4.31 | 0.0208 |
| MmuSTS.1399.1.S1_at | complement factor B | CFB | 4.31 | 0.0450 |
| MmugDNA.28599.1.S1_at | dedicator of cytokinesis 10 | DOCK10 | 4.30 | 0.0532 |
| MmugDNA.5642.1.S1_at | — | — | 4.28 | 0.0091 |
| MmugDNA.33945.1.S1_at | — | — | 4.28 | 0.0090 |
| MmugDNA.845.1.S1_at | N(4)-(beta-N-acetylglucosaminyl)-L-asparaginase precursor (Glycosylasparaginase) (Aspartylglucosaminidase) (N4-(N-acetyl-beta-glucosaminyl)-L-asparagine amidase) (AGA) | AGA | 4.28 | 0.0049 |
| MmugDNA.14017.1.S1_at | dedicator of cytokinesis 9 | DOCK9 | 4.28 | 0.0381 |
| MmugDNA.1746.1.S1_at | — | — | 4.27 | 0.0148 |
| MmugDNA.7878.1.S1_at | — | — | 4.27 | 0.0396 |
| MmugDNA.42983.1.S1_s_at | tripeptidyl-peptidase I precursor | LOC709838 | 4.27 | 0.0116 |
| MmugDNA.17468.1.S1_at | protocadherin beta 6 | PCDHB6 | 4.27 | 0.0080 |
| MmugDNA.27490.1.S1_at | — | — | 4.26 | 0.0588 |
| MmugDNA.25045.1.S1_at | — | — | 4.26 | 0.0872 |
| MmugDNA.21311.1.S1_at | ankyrin repeat and SOCS box-containing protein 4 | ASB4 | 4.26 | 0.0713 |
| MmugDNA.12780.1.S1 at | BMX non-receptor tyrosine kinase | BMX | 4.26 | 0.0018 |
| MmugDNA.39574.1.S1_at | RWD domain containing 2 | RWDD2 | 4.25 | 0.0242 |
| MmugDNA.23856.1.S1_at | — | — | 4.24 | 0.0588 |
| MmugDNA.10231.1.S1_at | mannosidase, endo-alpha | LOC716710 | 4.24 | 0.0469 |
| MmugDNA.38293.1.S1_at | quiescin Q6 isoform a | LOC718589 | 4.23 | 0.0244 |
| MmugDNA.32049.1.S1_at | transmembrane protein 64 | LOC695826 | 4.23 | 0.0216 |
| MmugDNA.10078.1.S1_at | allantoicase | ALLC | 4.22 | 0.0463 |
| MmugDNA.34409.1.S1_at | — | — | 4.22 | 0.0589 |
| MmugDNA.3676.1.S1_at | — | — | 4.22 | 0.0067 |
| MmugDNA.27799.1.S1_at | hypothetical protein LOC703244 | LOC703244 | 4.20 | 0.0047 |
| MmugDNA.35140.1.S1_at | UDP-glucuronate decarboxylase 1 | LOC718456 | 4.20 | 0.0026 |
| MmugDNA.12308.1.S1_at | — | — | 4.20 | 0.0676 |
| MmugDNA.29177.1.S1_at | DNA polymerase zeta catalytic subunit (Seizure-relatedprotein 4) | LOC703920 | 4.19 | 0.0016 |
| MmugDNA.366.1.S1_at | fucosyltransferase 11 (alpha (1,3) fucosyltransferase) | LOC706552 | 4.19 | 0.0249 |
| MmugDNA.31712.1.S1_at | polypeptide N-acetylgalactosaminyltransferase 6 | GALNT6 | 4.18 | 0.0496 |
| MmuSTS.649.1.S1_at | interleukin 25 isoform 1 precursor | LOC713943 | 4.18 | 0.0789 |
| MmugDNA.41214.1.S1_at | — | — | 4.16 | 0.0827 |
| MmugDNA.28831.1.S1_at | G protein-regulated inducer of neurite outgrowth 1 | LOC697365 | 4.16 | 0.0458 |
| MmugDNA.8787.1.S1_at | Protein C10orf70 | — | 4.15 | 0.0040 |
| MmuSTS.3573.1.S1_at | protocadherin 8 | PCDH8 | 4.15 | 0.0273 |
| MmugDNA.13403.1.S1_at | complement component 5 receptor 1 (C5a ligand) | C5AR1 | 4.14 | 0.0245 |
| MmugDNA.21971.1.S1_at | N-acylsphingosine amidohydrolase (acid ceramidase) 1 preproprotein isoform a | LOC703699 | 4.13 | 0.0000 |
| MmugDNA.17057.1.S1_at | RECK protein precursor | — | 4.13 | 0.0061 |
| MmugDNA.22311.1.S1_at | — | — | 4.12 | 0.0879 |
| MmugDNA.8200.1.S1_at | transglutaminase 7 | LOC712676 | 4.12 | 0.0472 |
| MmugDNA.42341.1.S1 at | rabconnectin-3 beta isoform 2 | LOC695302 | 4.11 | 0.0175 |
| MmugDNA.601.1.S1_at | SPRY domain-containing SOCS box protein SSB-4 | LOC715278 | 4.10 | 0.0041 |
| MmugDNA.27605.1.S1_at | Spir-1 protein isoform 1 | LOC722155 | 4.09 | 0.0878 |
| MmugDNA.17977.1.S1_at | neurexin 1 | NRXN1 | 4.09 | 0.0029 |
| MmugDNA.9585.1.S1_at | histone deacetylase 9 isoform 3 | LOC708314 | 4.08 | 0.0429 |
| MmugDNA.43369.1.S1_at | T-cell immunomodulatory protein | LOC716435 | 4.08 | 0.0209 |
| MmuSTS.2480.1.S1_at | zinc finger protein 287 | LOC695524 | 4.08 | 0.0212 |
| MmugDNA.37092.1.S1_at | down-regulator of transcription 1 (predicted) | DR1 | 4.08 | 0.0606 |
| MmugDNA.30978.1.S1_at | desmoglein 2 | DSG2 | 4.06 | 0.0049 |
| MmuSTS.3837.1.S1_at | solute carrier organic anion transporter family, member 2A1 | SLCO2A1 | 4.05 | 0.0641 |
| MmugDNA.26101.1.S1_at | — | — | 4.04 | 0.0842 |
| MmugDNA.25428.1.S1_at | zinc finger protein 382 | LOC713048 | 4.04 | 0.0143 |
| MmugDNA.4774.1.S1_at | — | — | 4.04 | 0.0319 |
| MmugDNA.30877.1.S1_at | zyg-11 homolog B (C. elegans)-like | LOC715671 | 4.04 | 0.0081 |
| MmugDNA.24520.1.S1_at | synapsin II isoform IIa | LOC695412 | 4.04 | 0.0046 |
| MmugDNA.11034.1.S1_at | — | — | 4.04 | 0.0031 |
| MmugDNA.21096.1.S1_at | zinc finger protein 275 | ZNF275 | 4.03 | 0.0093 |
| MmugDNA.43413.1.S1_at | immunoglobin superfamily, member 21 | LOC701539 | 4.03 | 0.0227 |
| MmugDNA.42897.1.S1_at | hypothetical protein LOC701560 | LOC701560 | 4.03 | 0.0379 |
| MmugDNA.19620.1.S1_at | — | — | 4.02 | 0.0364 |
| MmugDNA.15063.1.S1_s_at | phosphatidate cytidylyltransferase 1 | LOC706649 | 4.02 | 0.0319 |

-continued

| Probe Set ID | Gene Title | Gene Symbol | Ratio Top verus Bottom | p value Top versus Bottom |
|---|---|---|---|---|
| MmugDNA.21133.1.S1_at | — | — | 4.01 | 0.0911 |
| MmugDNA.12118.1.S1_at | — | — | 4.00 | 0.0007 |
| MmugDNA.20406.1.S1_at | GLE1-like, RNA export mediator isoform 1 | LOC717474 | 4.00 | 0.0184 |
| MmugDNA.34611.1.S1_at | — | — | 4.00 | 0.0155 |
| MmugDNA.19800.1.S1_at | vang-like 1 | LOC709730 | 3.99 | 0.0971 |
| MmugDNA.6828.1.S1_at | zinc finger protein 233 | LOC713398 | 3.99 | 0.0396 |
| MmugDNA.32366.1.S1_at | — | — | 3.99 | 0.0269 |
| MmugDNA.13572.1.S1_at | — | — | 3.99 | 0.0080 |
| MmugDNA.23433.1.S1 at | — | — | 3.98 | 0.0701 |
| MmugDNA.22715.1.S1_s_at | — | — | 3.98 | 0.0039 |
| MmugDNA.334.1.S1_at | serine (or cysteine) proteinase inhibitor, clade B (ovalbumin), member 2 | SERPINB2 | 3.96 | 0.0921 |
| MmuSTS.1861.1.S1_at | cholinergic receptor, nicotinic, alpha polypeptide 10 | LOC718133 | 3.96 | 0.0531 |
| MmugDNA.28216.1.S1_at | CDC42-binding protein kinase alpha isoform B | LOC697811 | 3.95 | 0.0269 |
| MmugDNA.33930.1.S1_at | LIN-7 homolog A (LIN-7A) (mLin-7) (Mammalian LIN-seven protein 1) (MALS-1) (Vertebrate LIN 7 homolog 1) (Veli-1protein) | LOC697557 | 3.95 | 0.0069 |
| MmugDNA.2196.1.S1_at | — | — | 3.94 | 0.0044 |
| MmuSTS.1116.1.S1_at | — | — | 3.94 | 0.0137 |
| MmugDNA.29351. .S1_at | alpha-synuclein isoform NACP140 | LOC706985 | 3.94 | 0.0198 |
| MmugDNA.12808. .S1_at | hypothetical protein LOC694824 | LOC694824 | 3.94 | 0.0695 |
| MmugDNA.9043.1 S1_at | ADP-ribosylation factor-like 6 interacting protein 2 | LOC710647 | 3.94 | 0.0582 |
| Mmu.937.1.S1_at | hypothetical protein LOC710176 | LOC710176 | 3.94 | 0.0314 |
| MmugDNA.13793. .S1_at | — | — | 3.93 | 0.0047 |
| MmugDNA.22471. .S1_at | — | — | 3.93 | 0.0011 |
| MmugDNA.13861. .S1_at | fatty acid 2-hydroxylase | LOC710403 | 3.92 | 0.0262 |
| MmugDNA.31129.1.S1_at | G protein-coupled receptor, family C, group 5, member B | GPRC5B | 3.92 | 0.0025 |
| MmugDNA.41489.1.S1_at | — | — | 3.91 | 0.0302 |
| MmugDNA.12173.1.S1_at | hypothetical protein LOC695417 | LOC695417 | 3.91 | 0.0320 |
| MmugDNA.37274.1.S1_s_at | secretin receptor | SCTR | 3.91 | 0.0497 |
| MmugDNA.10795.1.S1_at | SVH protein | LOC695210 | 3.90 | 0.0590 |
| MmugDNA.24744.1.S1_at | homeodomain leucine zipper protein | LOC713087 | 3.90 | 0.0347 |
| MmugDNA.39071.1.S1_at | — | — | 3.89 | 0.0087 |
| MmugDNA.818.1.S1_at | — | — | 3.89 | 0.0375 |
| MmugDNA.4556.1.S1_at | Sorting nexin-5 | — | 3.89 | 0.0175 |
| MmugDNA.13966.1.S1_s_at | regulator of G-protein signalling 8 | RGS8 | 3.89 | 0.0312 |
| MmunewRS.597.1.S1_at | Ral GEF with PH domain and SH3 binding motif 2 isoform 2 | LOC717165 | 3.89 | 0.0520 |
| MmuSTS.4601.1.S1_at | interleukin 19 isoform 1 precursor | LOC694806 | 3.89 | 0.0032 |
| MmugDNA.13652.1.S1_at | — | — | 3.87 | 0.0550 |
| MmugDNA.7329.1.S1_s_at | — | — | 3.86 | 0.0750 |
| MmugDNA.40738.1.S1_at | — | — | 3.86 | 0.0007 |
| MmugDNA.2633.1.S1_at | small nuclear RNA activating complex, polypeptide 1, 43 kDa | LOC704797 | 3.86 | 0.0327 |
| MmugDNA.7168.1.S1_at | — | — | 3.86 | 0.0832 |
| MmugDNA.36780.1.S1_at | — | — | 3.85 | 0.0778 |
| Mmu.14893.1.S1_x_at | cytochrome P450 3A64 | CYP3A64 | 3.84 | 0.0771 |
| MmugDNA.19443.1.S1_at | ataxin 2-binding protein 1 isoform 1 | LOC713147 | 3.84 | 0.0099 |
| MmugDNA.30992.1.S1_at | SH3 and multiple ankyrin repeat domains 2 isoform 1 | LOC708192 | 3.84 | 0.0487 |
| MmugDNA.33696.1.S1_at | hyaluronan binding protein 4 | LOC710213 | 3.82 | 0.0699 |
| MmugDNA.20527.1.S1_at | — | — | 3.82 | 0.0945 |
| MmugDNA.9900.1.S1_at | nuclear factor of activated T-cells, cytoplasmic, calcineurin-dependent 2 isoform C | LOC710601 | 3.82 | 0.0643 |
| MmuSTS.3411.1.S1_at | Ribose-phosphate pyrophosphokinase I (Phosphoribosyl pyrophosphate synthetase I) (PRS-I) | LOC702529 | 3.82 | 0.0608 |
| MmugDNA.4816.1.S1_at | hypothetical protein LOC719170 | LOC719170 | 3.81 | 0.0018 |
| MmugDNA.35136.1.S1_at | transmembrane protein 35 | LOC702205 | 3.81 | 0.0773 |
| MmugDNA.25086.1.S1_at | glucosidase, alpha; neutral C | GANC | 3.80 | 0.0077 |
| MmugDNA.1845.1.S1_at | — | — | 3.80 | 0.0967 |
| MmugDNA.29812.1.S1_at | adaptor-related protein complex 3, beta 2 subunit | AP3B2 | 3.79 | 0.0056 |
| MmuSTS.4436.1.S1_at | — | — | 3.79 | 0.0006 |
| MmuSTS.782.1.S1_at | potassium voltage-gated channel, Shab-related subfamily, member 2 | KCNB2 | 3.79 | 0.0129 |
| MmugDNA.3088.1.S1_at | WNK lysine deficient protein kinase 3 | WNK3 | 3.79 | 0.0093 |
| MmuSTS.3509.1.S1_at | Complement component 6 | C6 | 3.78 | 0.0826 |
| MmugDNA.41339.1.S1_at | GTP cyclohydrolase I (GTP-CH-I) | GCH1 | 3.78 | 0.0160 |
| MmugDNA.14784.1.S1_at | — | — | 3.77 | 0.0005 |
| MmugDNA.9742.1.S1_at | — | — | 3.77 | 0.0120 |
| MmugDNA.5664.1.S1_at | — | — | 3.76 | 0.0445 |
| MmugDNA.480.1.S1_at | — | — | 3.75 | 0.0159 |
| MmugDNA.34213.1.S1_at | cDNA sequence BCO21395 | LOC709217 | 3.74 | 0.0930 |
| MmugDNA.16508.1.S1_at | — | — | 3.73 | 0.0079 |
| MmugDNA.17649.1.S1_at | Sp3 transcription factor | SP3 | 3.73 | 0.0274 |
| MmugDNA.41644.1.S1_at | spermatogenesis associated 5-like 1 | LOC713376 | 3.72 | 0.0074 |
| MmugDNA.9202.1.S1_at | — | — | 3.72 | 0.0472 |
| MmugDNA.17057.1.S1_s_at | tumor suppressor candidate 3 isoform a | LOC701123 | 3.72 | 0.0011 |
| MmuSTS.56.1.S1_at | hypothetical protein LOC715723 | LOC715723 | 3.72 | 0.0043 |
| MmugDNA.39898.1.S1_at | — | — | 3.71 | 0.0068 |

-continued

| Probe Set ID | Gene Title | Gene Symbol | Ratio Top verus Bottom | p value Top versus Bottom |
|---|---|---|---|---|
| MmugDNA.40119.1.S1_s_at | HIV-1 Tat interactive protein 2, 30 kDa | LOC701908 | 3.71 | 0.0078 |
| MmugDNA.27371.1.S1_at | hypothetical protein LOC697751 | LOC697751 | 3.71 | 0.0857 |
| MmugDNA.16327.1.S1_at | pad-1-like | DOPEY2 | 3.70 | 0.0023 |
| MmuSTS.3363.1.S1_at | phosphodiesterase 2A, cGMP-stimulated | PDE2A | 3.70 | 0.0029 |
| MmugDNA.14309.1.S1_at | activated leukocyte cell adhesion molecule | LOC703777 | 3.70 | 0.0030 |
| MmugDNA.24681.1.S1_at | CTAGE family, member 5 | — | 3.70 | 0.0392 |
| MmuSTS.101.1.S1_at | acyl-Coenzyme A oxidase isoform b | LOC705197 | 3.69 | 0.0138 |
| MmugDNA.27013.1.S1_at | — | — | 3.69 | 0.0484 |
| MmugDNA.29538.1.S1_at | — | — | 3.69 | 0.0315 |
| MmugDNA.43028.1.S1_at | — | — | 3.68 | 0.0468 |
| MmugDNA.34314.1.S1_at | synovial sarcoma, X breakpoint 2 interacting protein | SSX2IP | 3.67 | 0.0570 |
| MmugDNA.33133.1.S1_at | hypothetical protein LOC711218 | LOC711218 | 3.67 | 0.0227 |
| MmugDNA.11493.1.S1_at | — | — | 3.67 | 0.0378 |
| MmugDNA.16985.1.S1_at | ets variant gene 1 | ETV1 | 3.67 | 0.0532 |
| MmuSTS.1797.1.S1_at | — | — | 3.67 | 0.0668 |
| MmuSTS.2054.1.S1_at | protein (peptidyl-prolyl cis/trans isomerase) NIMA-interacting, 4 (parvulin) | LOC699273 | 3.67 | 0.0431 |
| MmugDNA.18533.1.S1_at | phospholipase D family, member 5 | LOC706256 | 3.66 | 0.0682 |
| MmuSTS.1511.1.S1_at | RNA binding motif protein 15 B | LOC700716 | 3.66 | 0.0181 |
| MmugDNA.15936.1.S1_at | — | — | 3.66 | 0.0183 |
| MmugDNA.29618.1.S1_at | K09A9.6 | LOC712623 | 3.65 | 0.0282 |
| MmugDNA.831.1.S1_at | — | — | 3.65 | 0.0675 |
| MmugDNA.22531.1.S1_s_at | — | — | 3.65 | 0.0988 |
| MmugDNA.6653.1.S1_at | tudor repeat associator with PCTAIRE 2 | PCTAIRE2BP | 3.65 | 0.0018 |
| MmugDNA.25839.1.S1_at | RAD1 homolog isoform 1 | LOC703720 | 3.64 | 0.0444 |
| MmugDNA.6534.1.S1_at | hypothetical protein LOC701296 | LOC701296 | 3.64 | 0.0007 |
| MmugDNA.30983.1.S1_at | — | — | 3.64 | 0.0165 |
| MmugDNA.18313.1.S1_at | arrestin beta 1 isoform A | LOC695250 | 3.64 | 0.0141 |
| MmugDNA.25553.1.S1_at | retinitis pigmentosa GTPase regulator interacting protein 1 | LOC697345 | 3.63 | 0.0105 |
| MmugDNA.31716.1.S1_s_at | molybdenum cofactor sulfurase | LOC715633 | 3.62 | 0.0761 |
| MmugDNA.41201.1.S1_at | — | — | 3.62 | 0.0012 |
| MmugDNA.7740.1.S1_at | — | — | 3.61 | 0.0206 |
| MmugDNA.1555.1.S1_at | C29E4.8 | LOC714698 | 3.61 | 0.0795 |
| MmugDNA.27957.1.S1_at | ganglioside induced differentiation associated protein 2 | LOC714615 | 3.59 | 0.0280 |
| MmugDNA.2255.1.S1_at | phosphatidylinositol-4-phosphate 5-kinase, type I, beta isoform 2 | LOC700538 | 3.59 | 0.0003 |
| MmugDNA.23037.1.S1_at | Ephrin type-B receptor 2 precursor (Tyrosine-protein kinase receptor EPH-3) (Neural kinase) (Nuk receptor tyrosine kinase) (SEK-3) | LOC720107 | 3.59 | 0.0647 |
| MmugDNA.41938.1.S1_at | proline-rich protein PRP2 | LOC702863 | 3.59 | 0.0012 |
| MmugDNA.7947.1.S1_at | — | — | 3.59 | 0.0538 |
| MmugDNA.4820.1.S1_at | Rho GTPase activating protein 6 | ARHGAP6 | 3.59 | 0.0726 |
| MmugDNA.31476.1.S1_at | Ras-related protein Rab-28 (Rab-26) | LOC694111 | 3.58 | 0.0643 |
| MmugDNA.16749.1.S1_at | — | — | 3.58 | 0.0095 |
| MmugDNA.39259.1.S1_at | — | — | 3.57 | 0.0161 |
| MmugDNA.3689.1.S1_at | nuclear factor of kappa light polypeptide gene enhancer in B-cells inhibitor, beta isoform a | LOC694844 | 3.57 | 0.0001 |
| MmugDNA.17315.1.S1_at | — | — | 3.57 | 0.0712 |
| MmugDNA.23019.1.S1_at | — | — | 3.56 | 0.0014 |
| MmugDNA.37589.1.S1_at | Ubiquitin-conjugating enzyme E2S (Ubiquitin-conjugating enzyme E2-24 kDa) (Ubiquitin-protein ligase) (Ubiquitin carrier protein) (E2-EPF5) | — | 3.55 | 0.0112 |
| MmugDNA.17498.1.S1_at | — | — | 3.55 | 0.0024 |
| MmugDNA.13233.1.S1_at | brain expressed X-linked 2 | LOC696048 | 3.55 | 0.0065 |
| MmugDNA.22053.1.S1_at | gamma-glutamyl carboxylase | GGCX | 3.55 | 0.0254 |
| MmugDNA.35529.1.S1_at | PARK2 co-regulated | PACRG | 3.55 | 0.0412 |
| MmugDNA.40108.1.S1_at | hypothetical protein LOC698322 | LOC698322 | 3.54 | 0.0882 |
| Mmu.1639.1.S1_at | solute carrier family 15 (H+30/peptide transporter), member 2 | SLC15A2 | 3.54 | 0.0400 |
| MmugDNA.19566.1.S1_at | Type I iodothyronine deiodinase (Type-1 5deiodinase) (DI01) (Type 1 DI) (5DI) | D101 | 3.54 | 0.0037 |
| MmuSTS.106.1.S1_at | Elongation factor 1-delta (EF-1-delta) (Antigen NY-CO-4) | — | 3.54 | 0.0407 |
| MmugDNA.41451.1.S1_s_at | F33H2.6 | LOC710209 | 3.52 | 0.0008 |
| MmugDNA.39857.1.S1_at | hypothetical protein LOC703607 | LOC703607 | 3.52 | 0.0070 |
| MmuSTS.3342.1.S1_at | SET and MYND domain containing 3 | SMYD3 | 3.52 | 0.0919 |
| MmugDNA.31877.1.S1_at | calreticulin 3 | LOC719532 | 3.52 | 0.0899 |
| MmugDNA.13028.1.S1_at | periaxin | LOC707626 | 3.52 | 0.0013 |
| MmugDNA.29176.1.S1_at | MEGF11 protein | LOC714198 | 3.51 | 0.0977 |
| MmuSTS.4142.1.S1_at | — | — | 3.51 | 0.0060 |
| MmugDNA.17878.1.S1_at | CG5359-PA | LOC711098 | 3.51 | 0.0020 |
| MmugDNA.41017.1.S1_at | — | — | 3.50 | 0.0855 |
| MmugDNA.12740.1.S1_at | — | — | 3.49 | 0.0567 |
| MmugDNA.2965.1.S1_at | butyrate-induced transcript 1 | LOC709590 | 3.49 | 0.0306 |
| MmuSTS.4796.1.S1_at | flavin containing monooxygenase 4 | FMO4 | 3.49 | 0.0927 |
| MmuSTS.4569.1.S1_at | MAD, mothers against decapentaplegic homolog 9 | SMAD9 | 3.48 | 0.0297 |
| MmuSTS.3579.1.S1_at | — | — | 3.48 | 0.0321 |
| MmugDNA.29168.1.S1_at | Collagen alpha-1(111) chain precursor | LOC719369 | 3.47 | 0.0245 |

-continued

| Probe Set ID | Gene Title | Gene Symbol | Ratio Top verus Bottom | p value Top versus Bottom |
|---|---|---|---|---|
| MmugDNA.24379.1.S1_at | tissue factor pathway inhibitor | TFPI | 3.47 | 0.0251 |
| MmugDNA.6495.1.S1_at | hypothetical protein LOC701956 | LOC701956 | 3.47 | 0.0063 |
| MmugDNA.31684. .S1_at | Protein C6orf78 homolog | LOC714815 | 3.47 | 0.0341 |
| MmugDNA.8650.1.S1_at | solute carrier family 6, member 17 | LOC701162 | 3.47 | 0.0032 |
| MmuSTS.2222.1.S _at | synaptic vesicle protein 2B homolog | LOC710980 | 3.46 | 0.0052 |
| MmuSTS.2708.1.S _at | ADAM metallopeptidase domain 10 | ADAM10 | 3.46 | 0.0615 |
| MmugDNA.4023.1.S1_at | — | — | 3.46 | 0.0005 |
| MmugDNA.3743.1.S1_at | transmembrane and coiled-coil domains 3 | LOC716185 | 3.46 | 0.0184 |
| MmuSTS.3521.1.S _at | arginyltransferase 1 | ATE1 | 3.45 | 0.0116 |
| MmugDNA.35799. .S1_at | — | — | 3.45 | 0.0060 |
| MmugDNA.3417.1.S1_at | — | — | 3.45 | 0.0480 |
| MmugDNA.14546.1.S1_at | testis specific, 10 interacting protein | LOC715217 | 3.45 | 0.0517 |
| MmugDNA.41404.1.S1_at | cytoplasmic polyadenylation element binding protein 3 | LOC698133 | 3.45 | 0.0022 |
| MmugDNA.40609.1.S1_at | — | — | 3.45 | 0.0449 |
| MmugDNA.15703.1.S1_at | putative homeodomain transcription factor 1 | PHTF1 | 3.44 | 0.0091 |
| MmugDNA.6582.1.S1_at | hypothetical protein LOC701911 | LOC701911 | 3.44 | 0.0206 |
| MmugDNA.28101.1.S1_at | ST3 beta-galactoside alpha-2,3-sialyltransferase 5 | ST3GAL5 | 3.44 | 0.0116 |
| MmugDNA.41240.1.S1_at | — | — | 3.44 | 0.0124 |
| MmugDNA.8735.1.S1_at | — | — | 3.44 | 0.0204 |
| MmugDNA.14126.1.S1_at | hypothetical protein LOC694536 | LOC694536 | 3.44 | 0.0688 |
| MmugDNA.31606.1.S1_at | — | — | 3.43 | 0.0033 |
| MmugDNA.34884.1.S1_at | CUB and zona pellucida-like domains 1 | LOC706861 | 3.43 | 0.0890 |
| MmugDNA.23074.1.S1_at | plexin A2 | LOC713800 | 3.43 | 0.0004 |
| MmuSTS.1012.1.S1_at | USP6 N-terminal like | USP6NL | 3.43 | 0.0199 |
| MmugDNA.40409.1.S1_at | Y55F3AM.9 | LOC703159 | 3.42 | 0.0256 |
| MmuSTS.3876.1.S1_at | solute carrier family 6 (amino acid transporter), member 14 | SLC6A14 | 3.42 | 0.0305 |
| MmugDNA.38177.1.S1_at | F-box only protein 21 isoform 2 | LOC693647 | 3.41 | 0.0637 |
| MmugDNA.35235.1.S1_at | hypothetical protein LOC710443 | LOC710443 | 3.41 | 0.0899 |
| MmugDNA.19514.1.S1_at | — | — | 3.41 | 0.0487 |
| MmugDNA.25771.1.S1_at | Protein C20orf22 homolog | LOC706758 | 3.41 | 0.0889 |
| MmugDNA.3375.1.S1_at | ankyrin repeat domain 28 | LOC696592 | 3.41 | 0.0355 |
| MmunewRS.255.1.S1_at | — | — | 3.41 | 0.0055 |
| MmugDNA.38350.1.S1_s_at | Potassium channel, subfamily K, member 5 | — | 3.41 | 0.0273 |
| MmugDNA.29156.1.S1_at | cyclin T2 isoform b | LOC708813 | 3.40 | 0.0315 |
| MmugDNA.1804.1.S1_at | — | — | 3.40 | 0.0046 |
| MmugDNA.13727.1.S1_at | beta-site APP-cleaving enzyme 1 | BACE1 | 3.40 | 0.0104 |
| MmugDNA.36294.1.S1_at | dopa decarboxylase (aromatic L-amino acid decarboxylase) | DDC | 3.40 | 0.0052 |
| MmugDNA.18015.1.S1_at | HLA class II histocompatibility antigen, DM beta chain precursor (MHC class II antigen DMB) | LOC717870 | 3.40 | 0.0951 |
| MmugDNA.10946.1.S1_at | — | — | 3.40 | 0.0129 |
| MmugDNA.35307.1.S1_at | IQ motif containing G | LOC714807 | 3.39 | 0.0051 |
| MmugDNA.40386.1.S1_at | hypothetical protein LOC718008 | LOC718008 | 3.39 | 0.0568 |
| MmuSTS.1442.1.S1_at | — | — | 3.39 | 0.0810 |
| MmugDNA.30491.1.S1_at | neurexin 3 | LOC678699 | 3.39 | 0.0046 |
| MmugDNA.40498.1.S1_at | — | — | 3.38 | 0.0141 |
| MmuSTS.3629.1.S1_at | EMI domain containing 1 | LOC717414 | 3.38 | 0.0283 |
| MmugDNA.42049.1.S1_at | synaptotagmin-like 5 | LOC697915 | 3.38 | 0.0543 |
| MmugDNA.33991.1.S1_at | ELOVL family member 6, elongation of long chain fatty acids (FEN1/E1o2, SUR4/E1o3-like, yeast) | LOC698870 | 3.37 | 0.0453 |
| MmugDNA.30419.1.S1_at | — | — | 3.37 | 0.0108 |
| MmugDNA.38819.1.S1_at | hypothetical protein LOC716712 | LOC716712 | 3.37 | 0.0815 |
| MmugDNA.11736.1.S1_at | — | — | 3.37 | 0.0918 |
| MmugDNA.8760.1.S1_at | — | — | 3.37 | 0.0545 |
| MmugDNA.21748.1.S1_at | FXYD domain containing ion transport regulator 4 | LOC717636 | 3.37 | 0.0147 |
| MmugDNA.40624.1.S1_at | — | — | 3.37 | 0.0144 |
| MmugDNA.34981.1.S1_at | CG17687-PA | LOC716031 | 3.36 | 0.0598 |
| MmugDNA.21769.1.S1_at | transmembrane protein 141 | LOC721687 | 3.36 | 0.0278 |
| MmugDNA.12396.1.S1_at | zinc finger protein 621 | LOC717189 | 3.36 | 0.0150 |
| MmugDNA.35827.1.S1_s_at | glucosaminyl (N-acetyl) transferase 2, 1-branching enzyme isoform B | LOC697468 | 3.35 | 0.0492 |
| MmugDNA.31910.1.S1_at | — | — | 3.35 | 0.0987 |
| MmugDNA.39573.1.S1_s_at | — | — | 3.35 | 0.0001 |
| MmugDNA.27074.1.S1_at | hypothetical protein LOC707868 | LOC707868 | 3.35 | 0.0014 |
| MmugDNA.4152.1.S1_at | esophageal cancer related gene 4 protein | LOC713611 | 3.34 | 0.0126 |
| MmugDNA.28574.1.S1_at | zinc finger protein 483 | ZNF483 | 3.34 | 0.0050 |
| MmugDNA.14788.1.S1_at | CG14868-PA | LOC715968 | 3.34 | 0.0385 |
| Mmu.2046.1.S1_at | Hypothetical protein LOC693623 | — | 3.34 | 0.0130 |
| MmugDNA.38470.1.S1_at | hypothetical protein LOC704380 | LOC704380 | 3.33 | 0.0041 |
| MmugDNA.43475.1.S1_at | inositol polyphosphate-4-phosphatase, type 1 | INPP4A | 3.33 | 0.0395 |
| MmugDNA.11863.1.S1_at | receptor expression enhancing protein 1 | LOC697390 | 3.32 | 0.0807 |
| MmugDNA.12356.1.S1_at | peroxinl | LOC702392 | 3.32 | 0.0067 |
| MmugDNA.34502.1.S1_at | bactericidal/permeability-increasing protein-like 2 | LOC717287 | 3.32 | 0.0813 |
| MmugDNA.28096.1.S1_at | KIAA1799 protein | LOC696830 | 3.32 | 0.0034 |
| MmugDNA.19117.1.S1_at | — | — | 3.32 | 0.0948 |
| MmugDNA.22544.1.S1_at | lysosomal-associated membrane protein 2 | LAMP2 | 3.32 | 0.0120 |
| MmugDNA.2026.1.S1_at | neuraminidase | NEU1 | 3.32 | 0.0176 |

-continued

| Probe Set ID | Gene Title | Gene Symbol | Ratio Top verus Bottom | p value Top versus Bottom |
|---|---|---|---|---|
| MmuSTS.2482.1.S1_at | zinc finger protein 3 isoform 2 | LOC719069 | 3.31 | 0.0772 |
| MmugDNA.8202.1.S1_at | — | — | 3.31 | 0.0236 |
| MmugDNA.12374.1.S1_at | 5-nucleotidase, cytosolic III isoform 1 | LOC708743 | 3.31 | 0.0020 |
| MmugDNA.18151.1.S1_at | — | — | 3.31 | 0.0350 |
| MmugDNA.40189.1.S1_at | 3-hydroxy-3-methylglutaryl-Coenzyme A reductase | HMGCR | 3.31 | 0.0110 |
| MmugDNA.43623.1.S1_s_at | disabled homolog 2 | DAB2 | 3.31 | 0.0650 |
| MmugDNA.22195.1.S1_at | prospero-related homeobox 1 | LOC709465 | 3.31 | 0.0373 |
| MmugDNA.12057.1.S1_at | hypothetical protein LOC708157 | LOC708157 | 3.31 | 0.0963 |
| MmugDNA.29604.1.S1_at | — | — | 3.30 | 0.0482 |
| MmugDNA.36778.1.S1_at | ADAMTS-like 3 | LOC712844 | 3.30 | 0.0777 |
| MmugDNA.43352.1.S1_at | chromobox homolog 2 isoform 1 | LOC717462 | 3.30 | 0.0674 |
| MmugDNA.41900.1.S1_at | nudix-type motif 10 | LOC695921 | 3.30 | 0.0511 |
| MmugDNA.5215.1.S1_at | — | — | 3.30 | 0.0039 |
| MmugDNA.3581.1.S1_at | — | — | 3.29 | 0.0050 |
| MmugDNA.42978.1.S1_at | — | — | 3.29 | 0.0052 |
| MmugDNA.11001.1.S1_at | transcription factor-like nuclear regulator | — | 3.29 | 0.0396 |
| MmugDNA.32117.1.S1_at | — | — | 3.28 | 0.0977 |
| MmugDNA.4792.1.S1_at | — | — | 3.28 | 0.0123 |
| MmugDNA.14682.1.S1_at | — | — | 3.28 | 0.0017 |
| MmuSTS.1437.1.S1_at | L-plastin | LCP1 | 3.27 | 0.0624 |
| Mmu.1276.1.S1_at | serine protease inhibitor, Kunitz type, 2 | LOC714755 | 3.27 | 0.0799 |
| MmugDNA.29558.1.S1_at | leucine rich repeat containing 7 | LOC702347 | 3.27 | 0.0047 |
| MmugDNA.36803.1.S1_at | — | — | 3.26 | 0.0986 |
| MmugDNA.37994.1.S1_at | — | — | 3.26 | 0.0694 |
| MmugDNA.37151.1.S1_at | — | — | 3.26 | 0.0730 |
| MmuSTS.2193.1.S1_at | acid sphingomyelinase-like phosphodiesterase 3A | LOC713696 | 3.25 | 0.0359 |
| MmugDNA.15609.1.S1_at | — | — | 3.25 | 0.0134 |
| MmugDNA.34021.1.S1_at | ARP3 actin-related protein 3 homolog | ACTR3 | 3.25 | 0.0910 |
| MmugDNA.13552.1.S1_at | — | — | 3.25 | 0.0538 |
| MmugDNA.14095.1.S1_at | calpain 9 | CAPN9 | 3.25 | 0.0723 |
| MmugDNA.20778.1.S1_at | transcriptional regulator ATRX isoform 2 | LOC705735 | 3.24 | 0.0808 |
| MmuSTS.3264.1.S1_at | norrin | LOC702203 | 3.24 | 0.0996 |
| MmugDNA.21014.1.S1_at | — | — | 3.24 | 0.0033 |
| MmugDNA.26007.1.S1_at | — | — | 3.24 | 0.0467 |
| Mmu.14792.1.S1_at | solute carrier family 40 (iron-regulated transporter), member 1 | SLC40A1 | 3.24 | 0.0230 |
| MmugDNA.14237.1.S1_at | Dynein heavy chain at 16F CG7092-PA | LOC694115 | 3.24 | 0.0962 |
| MmuSTS.4208.1.S1_at | glucosaminyl (N-acetyl) transferase 3, mucin type | LOC702754 | 3.22 | 0.0016 |
| MmugDNA.19093.1.S1_at | — | — | 3.22 | 0.0397 |
| MmugDNA.8868.1.S1_at | hypothetical protein LOC710705 | LOC710705 | 3.21 | 0.0002 |
| MmugDNA.16163.1.S1_at | — | — | 3.21 | 0.0003 |
| MmugDNA.30042.1.S1_at | CG1 protein (F18) | LOC703003 | 3.21 | 0.0622 |
| MmugDNA.100.1.S1_at | — | — | 3.20 | 0.0940 |
| MmugDNA.10033.1.S1_at | poliovirus receptor | LOC714190 | 3.20 | 0.0577 |
| MmugDNA.26257.1.S1_at | echinoderm microtubule associated protein like 1 isoform b | LOC705977 | 3.20 | 0.0866 |
| MmugDNA.37272.1.S1_at | zinc finger protein 467 | LOC712106 | 3.20 | 0.0577 |
| MmugDNA.30904.1.S1_at | — | — | 3.19 | 0.0072 |
| MmuSTS.772.1.S1_at | cytosolic sialic acid 9-0-acetylesterase homolog | LOC711816 | 3.19 | 0.0375 |
| MmugDNA.1780.1.S1_at | — | — | 3.19 | 0.0140 |
| MmuSTS.1855.1.S1_at | cadherin 2, type 1 preproprotein | LOC711526 | 3.19 | 0.0108 |
| MmugDNA.36726.1.S1_at | NG22 protein | SLC44A4 | 3.18 | 0.0184 |
| MmugDNA.28522.1.S1_at | — | — | 3.18 | 0.0106 |
| MmugDNA.40772.1.S1_at | — | — | 3.18 | 0.0538 |
| MmugDNA.40592.1.S1_at | reticulon 4 receptor-like 1 | LOC720246 | 3.18 | 0.0448 |
| MmugDNA.41621.1.S1_at | F54C1.5a | LOC702261 | 3.18 | 0.0527 |
| MmugDNA.20138.1.S1_at | CXXC finger 6 | LOC707759 | 3.17 | 0.0697 |
| MmugDNA.30196.1.S1_at | — | — | 3.17 | 0.0365 |
| Mmu.16247.1.S1_at | EF hand domain family, member Al | LOC706065 | 3.17 | 0.0044 |
| MmugDNA.24683.1.S1_at | — | — | 3.17 | 0.0121 |
| MmugDNA.21254.1.S1_at | hypothetical protein LOC695666 | LOC695666 | 3.16 | 0.0344 |
| MmugDNA.30331.1.S1_at | multiple C2-domains with two transmembrane regions 1 isoform S | LOC697733 | 3.16 | 0.0017 |
| MmugDNA.14053.1.S1_at | — | — | 3.16 | 0.0862 |
| MmuSTS.72.1.S1_at | hephaestin isoform a | LOC709879 | 3.15 | 0.0624 |
| Mmu.12852.1.S1_ t | Nedd4 family interacting protein 1 | LOC705716 | 3.15 | 0.0181 |
| MmugDNA.21162. .Sl_at | 1D-myo-inositol-trisphosphate 3-kinase B | LOC698185 | 3.15 | 0.0210 |
| MmugDNA.2522.1.S1_at | gamma-aminobutyric acid (GABA) A receptor, beta 3 isoform 2 precursor | GABRB3 | 3.15 | 0.0383 |
| MmugDNA.1070.1.S1_at | — | — | 3.15 | 0.0660 |
| MmugDNA.11921.1.S1_at | CG7071-PA, isoform A | LOC708298 | 3.15 | 0.0754 |
| MmuSTS.2765.1.S1_at | class III alcohol dehydrogenase 5 chi subunit | ADH5 | 3.14 | 0.0011 |
| MmugDNA.40331. .Sl_at | — | — | 3.14 | 0.0007 |
| MmugDNA.25139.1.S1_at | carboxypeptidase D precursor | LOC712407 | 3.14 | 0.0055 |
| MmugDNA.12314.1.S1_at | — | — | 3.14 | 0.0034 |
| MmugDNA.32572.1.S1_at | Fibroblast growth factor 14 (FGF-14) (Fibroblast growth factor homologous factor 4) (FHF-4) | FGF14 | 3.14 | 0.0082 |

-continued

| Probe Set ID | Gene Title | Gene Symbol | Ratio Top verus Bottom | p value Top versus Bottom |
|---|---|---|---|---|
| MmugDNA.3590.1.S1_at | — | — | 3.13 | 0.0150 |
| MmugDNA.13879.1.S1_at | mannosidase, alpha, class 2A, member 1 | LOC705480 | 3.13 | 0.0429 |
| MmugDNA.3209.1.S1_at | microfibrillar-associated protein 3-like | MFAP3L | 3.12 | 0.0120 |
| MmugDNA.7233.1.S1_at | — | — | 3.12 | 0.0851 |
| MmugDNA.15955.1.S1_at | TAO kinase 2 | TAOK2 | 3.12 | 0.0021 |
| MmugDNA.38589.1.S1_at | lethal (2) k00619 CG4775-PA | LOC715015 | 3.12 | 0.0309 |
| MmugDNA.546.1.S1_at | alpha glucosidase II alpha subunit isoform 2 | LOC718672 | 3.12 | 0.0262 |
| MmugDNA.41951.1.S1_at | LPS-responsive vesicle trafficking, beach and anchor containing | LOC693823 | 3.12 | 0.0005 |
| MmugDNA.1873.1.S1_at | — | — | 3.11 | 0.0183 |
| MmugDNA.18551.1.S1_at | inositol polyphosphate-5-phosphatase, 75 kDa | INPP5B | 3.11 | 0.0058 |
| MmugDNA.15348.1.S1_at | ERO1-like | ERO1L | 3.10 | 0.0079 |
| MmugDNA.20795.1.S1_at | slit homolog 1 | LOC697716 | 3.10 | 0.0012 |
| MmugDNA.28842.1.S1_at | CKLF-like MARVEL transmembrane domain containing 7 isoform b | LOC704329 | 3.10 | 0.0648 |
| MmugDNA.10278.1.S1_at | slit and trk like 3 protein | LOC700660 | 3.10 | 0.0457 |
| MmugDNA.41181.1.S1_at | — | — | 3.09 | 0.0747 |
| MmugDNA.42278.1.S1_s_at | — | — | 3.09 | 0.0003 |
| Mmu.12401.1.S1_at | SECIS binding protein 2 | LOC697442 | 3.09 | 0.0551 |
| MmugDNA.7049.1.S1_at | — | — | 3.09 | 0.0652 |
| MmugDNA.11735.1.S1_at | — | — | 3.08 | 0.0835 |
| MmugDNA.42396.1.S1_at | germ cell-less | LOC701545 | 3.08 | 0.0538 |
| MmugDNA.26488.1.S1_at | — | — | 3.08 | 0.0363 |
| MmugDNA.2284.1.S1_at | notch 2 preproprotein | LOC713798 | 3.08 | 0.0619 |
| MmugDNA.28250.1.S1_at | — | — | 3.08 | 0.0459 |
| MmugDNA.17056.1.S1_s_at | reticulon 4 receptor precursor | LOC694382 | 3.08 | 0.0373 |
| MmunewRS.972.1.S1_at | glutamate decarboxylase-like 1 | LOC706457 | 3.08 | 0.0098 |
| MmugDNA.11045.1.S1_s_at | microtubule-associated protein 7 | LOC705355 | 3.07 | 0.0015 |
| MmuSTS.1473.1.S1_at | mitogen-activated protein kinase 9 isoform 1 | LOC699736 | 3.07 | 0.0243 |
| MmugDNA.31498.1.S1_at | — | — | 3.07 | 0.0225 |
| MmuSTS.4269.1.S1_at | glutamate receptor, metabotropic 8 | GRM8 | 3.07 | 0.0386 |
| MmugDNA.18449.1.S1_s_at | zinc finger, ZZ type with EF hand domain 1 | — | 3.06 | 0.0534 |
| MmugDNA.11192.1.S1_at | CG8312-PA, isoform A | LOC705659 | 3.06 | 0.0538 |
| MmugDNA.1116.1.S1_at | — | — | 3.06 | 0.0407 |
| MmugDNA.30277.1.S1_at | — | — | 3.06 | 0.0039 |
| MmugDNA.14729.1.S1_at | CD82 antigen isoform 2 | CD82 | 3.06 | 0.0323 |
| MmugDNA.27419.1.S1_at | actin-related protein 3-beta isoform 1 | LOC715965 | 3.06 | 0.0384 |
| MmuSTS.3981.1.S1_at | SH3-domain GRB2-like 2 | SH3GL2 | 3.05 | 0.0871 |
| MmugDNA.37217.1.S1_at | — | — | 3.05 | 0.0935 |
| MmugDNA.15075.1.S1_at | hypothetical protein LOC716982 | LOC716982 | 3.05 | 0.0080 |
| MmugDNA.16118.1.S1_at | hect domain and RLD 3 | HERC3 | 3.05 | 0.0004 |
| MmunewRS.326.1.S1_at | hypothetical protein LOC717316 | LOC717316 | 3.05 | 0.0589 |
| MmugDNA.9126.1.S1_at | lin-7 homolog C | LIN7C | 3.05 | 0.0998 |
| MmugDNA.10794.1.S1_at | — | — | 3.04 | 0.0857 |
| MmugDNA.32230.1.S1_at | nucleolar protein 1, 120 kDa | — | 3.04 | 0.0954 |
| MmugDNA.37502.1.S1_at | — | — | 3.04 | 0.0417 |
| MmugDNA.17117.1.S1_at | hypothetical protein LOC700172 | LOC700172 | 3.04 | 0.0173 |
| MmugDNA.9078.1.S1_at | zinc finger protein 141 (clone pHZ-44) | ZNF141 | 3.03 | 0.0537 |
| MmugDNA.9853.1.S1_at | arachidonate 5-lipoxygenase | ALOX5 | 3.03 | 0.0808 |
| MmugDNA.22211.1.S1_at | PET112-like | LOC694983 | 3.03 | 0.0437 |
| MmugDNA.26554.1.S1_at | UDP glycosyltransferase 3 family, polypeptide Al | LOC700115 | 3.03 | 0.0736 |
| MmugDNA.3964.1.S1_at | chromosome 2 open reading frame 30 | LOC716460 | 3.03 | 0.0238 |
| MmugDNA.36028.1.S1_at | — | — | 3.03 | 0.0039 |
| MmugDNA.19859.1.S1_at | hypothetical protein LOC700866 | LOC700866 | 3.03 | 0.0654 |
| MmugDNA.15510.1.S1_s_at | beta-amyloid binding protein precursor | LOC694282 | 3.02 | 0.0002 |
| MmugDNA.16151.1.S1_at | zinc finger protein 567 | LOC713173 | 3.02 | 0.0327 |
| MmugDNA.43512.1.S1_at | Transcribed locus | — | 3.02 | 0.0112 |
| MmuSTS.1643.1.S1 _at | transient receptor potential cation channel, subfamily M, member 5 | LOC705070 | 3.02 | 0.0082 |
| MmugDNA.24619.1.S1_at | WD repeat domain 56 | LOC705146 | 3.01 | 0.0331 |
| MmuSTS.3607.1.S1_at | cadherin 11, type 2 preproprotein | LOC708826 | 3.01 | 0.0107 |
| MmugDNA.29541.1.S1_at | — | — | 3.00 | 0.0050 |
| MmugDNA.36083.1.S1_s_at | — | — | 3.00 | 0.0042 |
| MmugDNA.15113.1.S1_at | endoplasmic reticulum oxidoreductin 1-Lbeta | LOC710912 | 3.00 | 0.0927 |
| MmuSTS.2617.1.S1_at | — | — | 3.00 | 0.0676 |
| Mmu.380.1.S1_at | tetratricopeptide repeat domain 27 | LOC707021 | 3.00 | 0.0738 |
| MmuSTS.898.1.S1_at | engulfment and cell motility 1 isoform 1 /// hypothetical protein LOC713462 | LOC705818 /// LOC713462 | 3.00 | 0.0255 |
| MmugDNA.21372.1.S1_at | formin binding protein 3 | PRPF40A | 3.00 | 0.0062 |
| MmugDNA.6394.1.S1_at | microtubule-associated protein tau | MAPT | 3.00 | 0.0052 |
| MmugDNA.10807.1.S1_at | HESB like domain containing 1 | — | 2.99 | 0.0965 |
| MmugDNA.34681.1.S1_at | sortilin-related receptor containing LDLR class A repeats preproprotein | LOC713011 | 2.99 | 0.0129 |
| MmugDNA.6380.1.S1_at | ankylosis, progressive homolog | LOC717689 | 2.99 | 0.0159 |
| MmugDNA.4142.1.S1_at | RAB3B, member RAS oncogene family | LOC712683 | 2.99 | 0.0030 |
| MmugDNA.20373.1.S1_at | galactosylceramidase | GALC | 2.98 | 0.0973 |

-continued

| Probe Set ID | Gene Title | Gene Symbol | Ratio Top verus Bottom | p value Top versus Bottom |
|---|---|---|---|---|
| MmugDNA.29366.1.S1_at | Transitional endoplasmic reticulum ATPase (TER ATPase) (15S Mg(2 + 30)-ATPase p97 subunit) (Valosin-containing protein) (VCP) | LOC698707 | 2.98 | 0.0020 |
| MmugDNA.33876.1.S1_s_at | olfactomedin 2 | LOC711336 | 2.98 | 0.0088 |
| MmugDNA.7330.1.S1_at | mannosidase, alpha, class 1C, member 1 | MANI C1 | 2.98 | 0.0027 |
| MmuSTS.2879.1.S1_at | transforming growth factor, beta receptor Ill (betaglycan, 300 kDa) | LOC705053 | 2.98 | 0.0240 |
| MmugDNA.39004.1.S1_at | sweet taste receptor T1r isoform b | LOC720987 | 2.98 | 0.0973 |
| MmugDNA.32903.1.S1_at | Protein C9orf116 (Pierce 1) | LOC720855 | 2.97 | 0.0828 |
| MmugDNA.23567.1.S1_at | HMT1 hnRNP methyltransferase-like 6 | PRMT6 | 2.97 | 0.0334 |
| MmugDNA.24770.1.S1_at | hypothetical protein LOC696555 | LOC696555 | 2.97 | 0.0271 |
| MmugDNA.39298.1.S1_at | EGF-like-domain, multiple 5 | MEGF9 | 2.97 | 0.0006 |
| MmugDNA.39357.1.S1_at | — | — | 2.97 | 0.0237 |
| MmugDNA.6683.1.S1_at | — | — | 2.96 | 0.0069 |
| MmugDNA.17131.1.S1_at | — | — | 2.96 | 0.0290 |
| MmuSTS.2496.1.S1_at | zinc finger protein 618 | LOC708866 | 2.95 | 0.0450 |
| MmugDNA.17574.1.S1_at | polycystic kidney disease 2-like 1 | PKD2L1 | 2.95 | 0.0062 |
| MmuSTS.4419.1.S1_at | FXYD domain-containing ion transport regulator 6 | LOC698456 | 2.95 | 0.0109 |
| MmuSTS.546.1.S1_at | membrane associated guanylate kinase, WW and PDZ domain containing 1 isoform a | LOC698092 | 2.95 | 0.0917 |
| MmugDNA.5553.1.S1_at | hypothetical protein LOC695259 | LOC695259 | 2.95 | 0.0337 |
| MmugDNA.1170.1.S1_at | — | — | 2.94 | 0.0216 |
| MmugDNA.39293.1.S1_at | — | — | 2.94 | 0.0220 |
| MmugDNA.36751. .S1_at | — | — | 2.94 | 0.0034 |
| MmugDNA.2580.1.S1_at | adaptor-related protein complex 3, beta 1 subunit | AP3B1 | 2.94 | 0.0353 |
| MmugDNA.42089. .S1_at | ectonucleoside triphosphate diphosphohydrolase 3 | ENTPD3 | 2.94 | 0.0140 |
| MmugDNA.5339.1.S1_at | transportin 1 | LOC707195 | 2.94 | 0.0080 |
| MmugDNA.37020.1.S1_at | dedicator of cytokinesis 1 | DOCK1 | 2.94 | 0.0400 |
| MmuSTS.2157.1.S1_at | Scm-like with four mbt domains 1 | LOC694961 | 2.93 | 0.0548 |
| MmuSTS.2057.1.S1_at | phosphoinositide-specific phospholipase C beta 1 isoform a | LOC718387 | 2.93 | 0.0630 |
| MmugDNA.32391.1.S1_at | hepatocellular carcinoma-associated antigen 112 | LOC713786 | 2.93 | 0.0012 |
| MmugDNA.15308.1.S1_s_at | — | — | 2.93 | 0.0128 |
| MmuSTS.1570.1.S1_at | neurobeachin | NBEA | 2.93 | 0.0050 |
| MmugDNA.22319.1.S1_at | histidine triad nucleotide binding protein 3 | LOC712779 | 2.93 | 0.0091 |
| MmugDNA.32797.1.S1_at | CTAGE family, member 5 isoform 1 | LOC699511 | 2.93 | 0.0027 |
| MmugDNA.9436.1.S1_at | — | — | 2.92 | 0.0507 |
| MmugDNA.28664.1.S1_at | guanine nucleotide binding protein, alpha stimulating activity polypeptide 1 isoform c | LOC694289 | 2.92 | 0.0333 |
| MmugDNA.21110.1.S1_at | zinc finger protein 398 isoform 1 | LOC710358 | 2.92 | 0.0141 |
| MmugDNA.5715.1.S1_at | tissue inhibitor of matrix metalloproteinase-1 | TIMP-1 | 2.92 | 0.0113 |
| MmugDNA.13442.1.S1_at | ATPase, aminophospholipid transporter (APLT), class I, type 8A, member 1 | LOC702630 | 2.92 | 0.0030 |
| Mmu.3604.1.S1_s_at | synaptotagmin binding, cytoplasmic RNA interacting protein | LOC700732 | 2.92 | 0.0255 |
| MmugDNA.35867.1.S1_at | fibronectin leucine rich transmembrane protein 3 | FLRT3 | 2.92 | 0.0081 |
| MmugDNA.27436.1.S1_at | — | — | 2.92 | 0.0200 |
| MmugDNA.9183.1.S1_at | Protein NipSnap3B (SNAP1) | NIPSNAP3B | 2.91 | 0.0192 |
| MmugDNA.39239.1.S1_at | TMEM9 domain family, member B /// hypothetical protein LOC719509 | LOC694700 /// LOC708447 /// LOC719509 | 2.91 | 0.0009 |
| MmugDNA.9888.1.S1_at | Tetratricopeptide repeat protein 9 (TPR repeat protein 9) | LOC693495 | 2.91 | 0.0121 |
| MmugDNA.29679.1.S1_at | — | — | 2.91 | 0.0380 |
| MmugDNA.36914.1.S1_at | — | — | 2.90 | 0.0254 |
| MmugDNA.38533.1.S1_at | — | — | 2.90 | 0.0802 |
| MmugDNA.6837.1.S1_at | sorting nexin 13 | SNX13 | 2.89 | 0.0060 |
| MmugDNA.3572.1.S1_at | — | — | 2.89 | 0.0038 |
| MmugDNA.27179.1.S1_at | synapse-associated protein 102 | LOC697179 | 2.89 | 0.0797 |
| MmugDNA.37780.1.S1_at | — | — | 2.89 | 0.0748 |
| MmugDNA.31668.1.S1_at | — | — | 2.89 | 0.0279 |
| MmuSTS.4659.1.S1_at | tumor necrosis factor, alpha-induced protein 3 | TNFAIP3 | 2.89 | 0.0946 |
| MmugDNA.25426.1.S1_at | — | — | 2.89 | 0.0361 |
| MmugDNA.24776.1.S1_at | protein phosphatase 1, regulatory subunit 7 | LOC700574 | 2.89 | 0.0728 |
| MmugDNA.5386.1.S1_at | zinc finger protein 354B | LOC712885 | 2.89 | 0.0369 |
| MmugDNA.21944. .S1_s_at | holocytochrome c synthase (cytochrome c heme-lyase) | HCCS | 2.89 | 0.0331 |
| MmugDNA.2867.1.S1_at | — | — | 2.88 | 0.0624 |
| MmugDNA.21421. .S1_at | RAB3A interacting protein isoform alpha 2 | LOC717215 | 2.88 | 0.0107 |
| MmugDNA.3747.1.S1_at | Transmembrane protein 51 | LOC693771 | 2.88 | 0.0127 |
| MmugDNA.26393. .S1_at | MOCO sulphurase C-terminal domain containing 2 | LOC705543 | 2.88 | 0.0080 |
| MmugDNA.22547. .S1_at | transcriptional adaptor 2-like | TADA2L | 2.87 | 0.0311 |
| MmugDNA.7154.1.S1_at | kelch repeat and BTB (POZ) domain containing 2 | KBTBD2 | 2.87 | 0.0286 |
| MmugDNA.14782.1.S1_at | CG15120-PA | LOC715522 | 2.87 | 0.0118 |
| MmuSTS.3706.1.S1_at | presenilin 2 | PSEN2 | 2.87 | 0.0715 |
| MmugDNA.15936.1.S1_s_at | — | — | 2.87 | 0.0067 |
| MmugDNA.39373.1.S1_at | putative aminopeptidase Fxna | LOC717415 | 2.87 | 0.0888 |
| MmugDNA.34782.1.S1_at | Keratin, type II cytoskeletal 8 (Cytokeratin-8) (CK-8) (Keratin-8) (K8) | — | 2.87 | 0.0613 |
| MmugDNA.8649.1.S1_at | p300/CBP-associated factor | LOC698283 | 2.87 | 0.0028 |

-continued

| Probe Set ID | Gene Title | Gene Symbol | Ratio Top verus Bottom | p value Top versus Bottom |
|---|---|---|---|---|
| MmugDNA.29427.1.S1_at | hypothetical protein LOC702110 | LOC702110 | 2.86 | 0.0045 |
| MmugDNA.26314.1.S1_at | basigin isoform 1 | LOC721068 | 2.86 | 0.0328 |
| MmugDNA.2721.1.S1_s_at | — | — | 2.86 | 0.0111 |
| MmugDNA.27358.1.S1_at | — | — | 2.86 | 0.0056 |
| MmugDNA.15702.1.S1_at | — | — | 2.86 | 0.0184 |
| MmugDNA.43128.1.S1_at | choline kinase alpha isoform a | LOC710564 | 2.86 | 0.0726 |
| MmuSTS.3669.1.S1_at | eyes absent 1 isoform b | LOC694364 | 2.86 | 0.0024 |
| MmugDNA.31695.1.S1_at | Alpha-parvin (Calponin-like integrin-linked kinase-binding protein) (CH-ILKBP) | LOC703481 | 2.85 | 0.0278 |
| MmugDNA.6693.1.S1_at | CG3304-PA, isoform A | LOC708497 | 2.85 | 0.0432 |
| Mmu.3814.1.S1_at | MGC15407-like | LOC677698 | 2.85 | 0.0073 |
| MmugDNA.8146.1.S1_at | ELOVL family member 7, elongation of long chain fatty acids | LOC709866 | 2.85 | 0.0008 |
| MmugDNA.17821.1.S1_at | Protein KIAA1434 | LOC719117 | 2.85 | 0.0623 |
| MmugDNA.34061.1.S1_s_at | glycosyltransferase 28 domain containing 1 | LOC706863 | 2.85 | 0.0030 |
| MmugDNA.43525.1.S1_at | — | — | 2.85 | 0.0870 |
| MmugDNA.11817.1.S1_at | — | — | 2.84 | 0.0015 |
| MmugDNA.10536.1.S1_at | — | — | 2.84 | 0.0255 |
| MmugDNA.20224.1.S1_at | cullin 4B | CUL4B | 2.84 | 0.0531 |
| MmugDNA.21065.1.S1_at | — | — | 2.84 | 0.0726 |
| MmugDNA.11873.1.S1_s_at | NEDD4 family-interacting protein 2 (NEDD4 WW domain-binding protein 5A) (Putative MAPK-activating protein PM04/PM05/PM06/PM07) (Putative NF-kappa-B-activating protein 413) | NDFIP2 | 2.84 | 0.0019 |
| MmugDNA.30250.1.S1_at | multiple coiled-coil GABABR1-binding protein | LOC722750 | 2.84 | 0.0046 |
| MmugDNA.3547.1.S1_at | nuclear receptor binding factor 2 | LOC697756 | 2.84 | 0.0023 |
| MmugDNA.39661.1.S1_at | heparan sulfate 2-0-sulfotransferase 1 | HS2ST1 | 2.84 | 0.0407 |
| MmugDNA.23891.1.S1_at | Derlin-3 (Degradation in endoplasmic reticulum protein 3) (Der1-like protein 3) (DERtrin-3) | DERL3 | 2.84 | 0.0321 |
| MmugDNA.35787.1.S1_at | — | — | 2.83 | 0.0922 |
| MmugDNA.15859.1.S1_at | hypothetical protein LOC709702 | LOC709702 | 2.83 | 0.0784 |
| MmugDNA.906.1.S1_at | tRNA nucleotidyl transferase, CCA-adding, 1 | TRNT1 | 2.83 | 0.0724 |
| MmugDNA.39895.1.S1_at | — | — | 2.83 | 0.0492 |
| MmugDNA.12342.1.S1_at | — | — | 2.83 | 0.0679 |
| MmugDNA.41431. .S1_at | — | — | 2.83 | 0.0252 |
| MmugDNA.24761. .S1_at | — | — | 2.82 | 0.0013 |
| MmugDNA.8211.1.S1_at | — | — | 2.82 | 0.0781 |
| MmugDNA.40614. .S1_at | — | — | 2.82 | 0.0136 |
| MmugDNA.9573.1.S1_at | — | — | 2.82 | 0.0541 |
| MmugDNA.36144.1.S1_at | G-protein coupled receptor 113 | LOC696215 | 2.82 | 0.0137 |
| MmugDNA.5429.1.S1_at | RNA pseudouridylate synthase domain containing 4 | LOC714162 | 2.82 | 0.0238 |
| MmugDNA.390.1.S1_at | — | — | 2.82 | 0.0224 |
| MmuSTS.1860.1.S1_at | Homeobox protein CDX-1 (Caudal-type homeobox protein 1) | CDX1 | 2.82 | 0.0302 |
| MmugDNA.15649.1.S1_at | — | — | 2.81 | 0.0524 |
| MmugDNA.41609.1.S1_at | golgi apparatus protein 1 | LOC710037 | 2.81 | 0.0682 |
| MmugDNA.39981.1.S1_at | microtubule associated monoxygenase, calponin and LIM domain containing 2 | MICAL2 | 2.81 | 0.0354 |
| MmugDNA.41888.1.S1_at | UDP glycosyltransferase 8 (UDP-galactose ceramide galactosyltransferase) | UGT8 | 2.81 | 0.0002 |
| Mmu.1028.1.S1_at | Tetraspanin-8 (Tspan-8) (Transmembrane 4 superfamily member 3) (Tumor-associated antigen CO-029) | TSPAN8 | 2.80 | 0.0037 |
| MmugDNA.40411.1.S1_at | — | — | 2.80 | 0.0431 |
| MmugDNA.6270.1.S1_at | — | — | 2.80 | 0.0207 |
| MmugDNA.3465.1.S1 at | — | — | 2.80 | 0.0758 |
| MmugDNA.28869.1.S1_s_at | follicular lymphoma variant translocation 1 | LOC700476 | 2.80 | 0.0299 |
| MmugDNA.17877.1.S1_at | — | — | 2.80 | 0.0198 |
| MmugDNA.43133.1.S1_at | Nucleoside diphosphate kinase homolog 5 (NDK-H 5) (NDP kinase homolog 5) (nm23-H5) (Testis-specific nm23 homolog) (Inhibitor of p53-induced apoptosis-beta) (IPIA-beta) | LOC713837 | 2.80 | 0.0119 |
| MmugDNA.38316.1.S1_at | family with sequence similarity 20, member A | LOC718937 | 2.80 | 0.0064 |
| MmugDNA.28033.1.S1_at | SID1 transmembrane family, member 1 | SIDT1 | 2.80 | 0.0014 |
| MmugDNA.29959.1.S1_at | transducin-like enhancer protein 4 | TLE4 | 2.80 | 0.0125 |
| MmugDNA.11210.1.S1_s_at | protocadherin gamma subfamily A, 12 isoform 2 precursor | LOC702071 | 2.79 | 0.0187 |
| MmuSTS.1312.1.S1_at | DnaJ (Hsp 40) homolog, subfamily C, member 6 | LOC698682 | 2.79 | 0.0716 |
| MmugDNA.19131.1.S1_at | BTB (POZ) domain containing 4 | BTBD4 | 2.79 | 0.0448 |
| MmugDNA.26541.1.S1_at | fibronectin type III domain containing 4 | LOC702098 | 2.79 | 0.0462 |
| MmugDNA.11140.1.S1_at | notch homolog 5 | LOC694004 | 2.79 | 0.0549 |
| MmugDNA.20304.1.S1_at | modulator of apoptosis 1 | LOC707922 /// LOC708231 | 2.79 | 0.0003 |
| MmugDNA.8309.1.S1_at | — | — | 2.79 | 0.0744 |
| MmugDNA.35571.1.S1_at | transposon-derived Buster3 transposase-like | LOC695905 | 2.79 | 0.0239 |
| MmuSTS.3190.1.S1_at | — | — | 2.78 | 0.0062 |
| MmugDNA.31552.1.S1_at | CG18769-PB, isoform B | LOC698670 | 2.78 | 0.0044 |
| MmugDNA.11968.1.S1_at | — | — | 2.78 | 0.0831 |

-continued

| Probe Set ID | Gene Title | Gene Symbol | Ratio Top verus Bottom | p value Top versus Bottom |
|---|---|---|---|---|
| MmugDNA.31850.1.S1_at | START domain containing 4, sterol regulated | LOC706654 | 2.78 | 0.0281 |
| MmugDNA.26580.1.S1_at | TGF beta receptor associated protein -1 | LOC713102 | 2.78 | 0.0062 |
| MmugDNA.39053.1.S1_at | — | — | 2.78 | 0.0250 |
| MmugDNA.13898.1.S1_at | — | — | 2.78 | 0.0892 |
| Mmu.15592.2.S1_at | phosphatidylinositol glycan, class F isoform 1 | LOC714844 | 2.78 | 0.0019 |
| MmugDNA.29438.1.S1_at | — | — | 2.78 | 0.0522 |
| MmugDNA.13438.1.S1_at | CG11670-PA | LOC701685 | 2.77 | 0.0273 |
| MmugDNA.33828.1.S1_at | hypothetical protein LOC693883 | LOC693883 | 2.77 | 0.0613 |
| MmugDNA.12035.1.S1_at | — | — | 2.77 | 0.0187 |
| MmugDNA.28591.1.S1_s_at | taspase 1 | TASP1 | 2.77 | 0.0529 |
| MmugDNA.29219.1.S1_at | — | — | 2.77 | 0.0025 |
| MmugDNA.17221.1.S1_at | hypothetical protein LOC719100 | LOC719100 | 2.77 | 0.0461 |
| Mmu.2523.1.S1_at | legumain | LGMN | 2.76 | 0.0855 |
| MmugDNA.14436.1.S1_at | — | — | 2.76 | 0.0851 |
| MmugDNA.12446.1.S1_at | — | — | 2.76 | 0.0162 |
| MmugDNA.24601.1.S1_at | — | — | 2.76 | 0.0027 |
| MmugDNA.7915.1.S1_at | — | — | 2.76 | 0.0117 |
| MmugDNA.35603.1.S1_at | Sortilin precursor (Neurotensin receptor 3) (NTR3) (NT3) (Glycoprotein 95) (Gp95) (100 kDa NT receptor) | SORT1 | 2.75 | 0.0309 |
| MmugDNA.36573.1.S1_at | CTCL tumor antigen se57-1 | LOC694841 | 2.75 | 0.0207 |
| MmuSTS.2972.1.S1_at | lipase A precursor | LOC695240 | 2.75 | 0.0071 |
| MmuSTS.3122.1.S1_at | myosin VIIA and Rab interacting protein | LOC717173 | 2.74 | 0.0042 |
| MmugDNA.26602.1.S1_at | nuclear factor of activated T-cells, cytosolic component 1 isoform C | LOC698089 | 2.74 | 0.0049 |
| MmuSTS.1119.1.S1_at | secreted modular calcium-binding protein 2 | LOC703155 | 2.74 | 0.0582 |
| MmugDNA.38654.1.S1_at | — | — | 2.74 | 0.0116 |
| MmugDNA.24367.1.S1_at | islet cell autoantigen 1 | LOC695889 | 2.74 | 0.0417 |
| MmugDNA.7470.1.S1_at | — | — | 2.74 | 0.0823 |
| MmugDNA.21317.1.S1_at | spermatid perinuclear RNA-binding protein | LOC695402 | 2.74 | 0.0240 |
| MmugDNA.36894.1.S1_at | dehydrogenase/reductase (SDR family) member 7 | DHRS7 | 2.74 | 0.0004 |
| MmuSTS.3892.1.S1_at | sphingomyelin phosphodiesterase 1, acid lysosomal | SMPD1 | 2.73 | 0.0291 |
| MmuSTS.3004.1.S1_at | mutS homolog 3 | MSH3 | 2.73 | 0.0912 |
| MmugDNA.18199.1.S1_at | unc-13 homolog D | LOC704431 | 2.73 | 0.0133 |
| MmugDNA.32264.1.S1_at | G protein-coupled receptor 126 alpha 2 | LOC706017 | 2.73 | 0.0429 |
| MmuSTS.2507.1.S1_at | GTP binding protein 1 | GTPBP1 | 2.73 | 0.0496 |
| MmugDNA.22747.1.S1_at | tripartite motif-containing 2 | LOC696517 | 2.73 | 0.0162 |
| MmuSTS.1188.1.S1_at | phospholipid scramblase 1 | LOC713232 | 2.73 | 0.0006 |
| MmugDNA.2003.1.S1_at | — | — | 2.73 | 0.0904 |
| MmugDNA.6213.1.S1_at | — | — | 2.73 | 0.0031 |
| MmugDNA.27564.1.S1_at | Guanine nucleotide-binding protein G(t), alpha-3 subunit (Gustducin alpha-3 chain) | LOC708828 | 2.73 | 0.0162 |
| MmugDNA.33552.1.S1_at | — | — | 2.73 | 0.0364 |
| MmuSTS.2414.1.S1_at | Guanine nucleotide-binding protein alpha-12 subunit (G alpha-12) | LOC699857 | 2.72 | 0.0319 |
| MmugDNA.37242.1.S1_at | serine/threonine kinase 32A | LOC708524 | 2.72 | 0.0499 |
| MmuSTS.2307.1.S1_at | beta isoform of regulatory subunit B55, protein phosphatase 2 | PPP2R2B | 2.72 | 0.0797 |
| MmugDNA.35445.1.S1_at | PHD finger protein 7 isoform 1 | LOC697103 | 2.72 | 0.0380 |
| MmugDNA.31310.1.S1_at | CG13902-PA | LOC699197 | 2.72 | 0.0796 |
| Mmu.13628.1.S1_x_at | FGFR1 oncogene partner 2 | LOC708905 | 2.72 | 0.0287 |
| MmugDNA.34470.1.S1_s_at | hypothetical protein LOC708552 | LOC708552 | 2.71 | 0.0083 |
| MmugDNA.27420.1.S1_at | — | — | 2.71 | 0.0567 |
| MmugDNA.15282.1.S1_at | hypothetical protein LOC711477 | LOC711477 | 2.71 | 0.0018 |
| MmugDNA.12849.1.S1_at | Eukaryotic translation initiation factor 6 (eIF-6) (B4 integrin interactor) (CAB) (p27(BBP)) (B(2)GCN homolog) | ITGB4BP | 2.71 | 0.0280 |
| MmugDNA.14244.1.S1_at | — | — | 2.71 | 0.0049 |
| MmugDNA.25223.1.S1_at | CG31803-PA | LOC701263 | 2.71 | 0.0197 |
| MmugDNA.22504.1.S1_at | — | — | 2.71 | 0.0906 |
| MmuSTS.3220.1.S1_at | v-myb myeloblastosis viral oncogene homolog (avian)-like 1 | MYBL1 | 2.71 | 0.0824 |
| MmugDNA.13093.1.S1_at | hypothetical protein LOC708259 | LOC708259 | 2.71 | 0.0701 |
| MmugDNA.13057.1.S1_at | protease, serine, 36 | LOC714626 | 2.70 | 0.0599 |
| MmugDNA.9375.1.S1_at | — | — | 2.70 | 0.0479 |
| MmuSTS.1294.1.S1_at | RAP1, GTPase activating protein 1 | RAP1GAP | 2.70 | 0.0278 |
| MmugDNA.11685.1.S1_at | poly (ADP-ribose) polymerase family, member 8 | LOC702637 | 2.70 | 0.0995 |
| Mmu.14396.1.S1_at | Glutathione S-transferase Al (GTH1) (HA subunit 1) (GST-epsilon) (GSTA1-1) (GST class-alpha) | — | 2.70 | 0.0140 |
| MmugDNA.20427.1.S1_at | inosine monophosphate dehydrogenase 1 isoform b | LOC701039 | 2.70 | 0.0686 |
| MmugDNA.26008.1.S1_at | — | — | 2.70 | 0.0015 |
| MmugDNA.24890.1.S1_at | CG4341-PA | LOC698022 | 2.70 | 0.0249 |
| MmuSTS.1767.1.S1_at | N-myc downstream regulated gene 3 | LOC702452 | 2.70 | 0.0887 |
| MmugDNA.28653.1.S1_at | — | — | 2.70 | 0.0331 |
| MmugDNA.11814.1.S1_at | zinc finger protein 322A | LOC701098 | 2.70 | 0.0466 |
| MmugDNA.25299.1.S1_at | Small nuclear ribonucleoprotein Sm D1 (snRNP core protein D1) (Sm-D1) (Sm-D autoantigen) | LOC698965 | 2.70 | 0.0816 |
| MmugDNA.41883.1.S1_at | — | — | 2.70 | 0.0762 |

-continued

| Probe Set ID | Gene Title | Gene Symbol | Ratio Top verus Bottom | p value Top versus Bottom |
|---|---|---|---|---|
| MmugDNA.31230.1.S1_at | Fibronectin type-III domain-containing protein 3a | LOC705570 | 2.69 | 0.0370 |
| MmugDNA.42805.1.S1_at | Kinesin-like protein KIF2 | LOC696561 | 2.69 | 0.0624 |
| MmugDNA.26243.1.S1_at | — | — | 2.69 | 0.0404 |
| MmugDNA.27058.1.S1_at | phosphoribosyl pyrophosphate amidotransferase proprotein | LOC694868 | 2.69 | 0.0094 |
| MmugDNA.41943.1.S1_at | — | — | 2.69 | 0.0346 |
| MmugDNA.9762.1.S1_at | — | — | 2.69 | 0.0721 |
| MmugDNA.22290.1.S1_at | brefeldin A-inhibited guanine nucleotide-exchange protein 1 | LOC704359 | 2.69 | 0.0717 |
| MmugDNA.41355.1.S1_at | — | — | 2.68 | 0.0676 |
| MmugDNA.37885.1.S1_at | homer 1 | HOMER1 | 2.68 | 0.0925 |
| MmugDNA.38723.1.S1_at | a disintegrin and metalloprotease domain 28 isoform 1 | LOC710953 | 2.68 | 0.0741 |
| MmugDNA.12874.1.S1_at | — | — | 2.68 | 0.0745 |
| MmugDNA.38436.1.S1_at | hypothetical protein LOC695519 | LOC695519 | 2.68 | 0.0060 |
| MmugDNA.23725.1.S1_at | stress 70 protein chaperone, microsome-associated, 60 kDa | STCH | 2.67 | 0.0479 |
| MmugDNA.18237.1.S1_at | peroxisomal short-chain alcohol dehydrogenase | — | 2.67 | 0.0492 |
| Mmu.7752.1.S1_at | hypothetical protein LOC704532 | LOC704532 | 2.67 | 0.0265 |
| Mmu.7453.1.S1_at | rabaptin, RAB GTPase binding effector protein 1 | LOC711646 | 2.67 | 0.0190 |
| MmugDNA.13154.1.S1_at | — | — | 2.67 | 0.0955 |
| MmugDNA.12949.1.S1_at | — | — | 2.67 | 0.0394 |
| MmuSTS.2807.1.S1_at | solute carrier family 38, member 1 | LOC702135 | 2.67 | 0.0217 |
| MmugDNA.28465.1.S1_at | Transgelin-3 (Neuronal protein NP25) (Neuronal protein 22) (NP22) | TAGLN3 | 2.67 | 0.0651 |
| MmugDNA.29560.1.S1_at | hypothetical protein LOC710681 | LOC710681 | 2.67 | 0.0154 |
| MmugDNA.16975.1.S1_at | — | — | 2.67 | 0.0968 |
| MmugDNA.30208.1.S1_at | — | — | 2.66 | 0.0462 |
| MmugDNA.33379.1.S1_at | — | — | 2.66 | 0.0063 |
| MmugDNA.29425.1.S1_at | B0507.2 | LOC704194 | 2.66 | 0.0105 |
| MmugDNA.28288.1.S1_at | Dual specificity protein phosphatase 3 (Dual specificity protein phosphatase VHR) | DUSP3 | 2.66 | 0.0224 |
| MmugDNA.15303.1.S1_s_at | ninein isoform 5 | LOC709532 | 2.65 | 0.0437 |
| MmugDNA.29050.1.S1_at | — | — | 2.65 | 0.0291 |
| MmunewRS.265.1.S1_at | kin of IRRE like 3 | LOC714534 | 2.65 | 0.0267 |
| MmugDNA.24675.1.S1_at | — | — | 2.65 | 0.0414 |
| MmugDNA.8597.1.S1_at | — | — | 2.65 | 0.0379 |
| MmugDNA.10005.1.S1_at | pre-B-cell leukemia transcription factor interacting protein 1 | LOC717036 | 2.65 | 0.0501 |
| MmugDNA.951.1.S1_at | — | — | 2.65 | 0.0297 |
| MmugDNA.35108.1.S1_at | secretory carrier membrane protein 5 | LOC710454 | 2.64 | 0.0103 |
| MmugDNA.13757.1.S1_at | Placenta-specific gene 8 protein (C15 protein) | PLAC8 | 2.64 | 0.0186 |
| MmugDNA.30027.1.S1_at | hypothetical protein LOC695033 | LOC695033 | 2.64 | 0.0128 |
| MmugDNA.7760.1.S1_at | — | — | 2.64 | 0.0072 |
| MmugDNA.21589.1.S1_at | protocadherin beta 4 | PCDHB4 | 2.64 | 0.0703 |
| Mmu.9306.1.S1_at | growth factor receptor-bound protein 2 isoform 2 | LOC702041 | 2.63 | 0.0360 |
| MmugDNA.11105.1.S1_at | centaurin, gamma 2 isoform 2 | LOC693652 | 2.63 | 0.0244 |
| MmugDNA.26258.1.S1_at | — | — | 2.63 | 0.0637 |
| Mmu.14771.1.S1_at | calcipressin 1 isoform c | LOC697108 | 2.63 | 0.0245 |
| MmugDNA.30706.1.S1_at | — | — | 2.63 | 0.0016 |
| MmugDNA.37595.1.S1_s_at | mortality factor 4 like 1 isoform b | LOC711357 | 2.63 | 0.0734 |
| MmugDNA.42160.1.S1_at | — | — | 2.63 | 0.0710 |
| MmugDNA.34056.1.S1_at | RAP1 interacting factor 1 | LOC694817 | 2.63 | 0.0344 |
| MmugDNA.40644.1.S1_at | solute carrier family 41 member 1 | LOC696944 | 2.62 | 0.0135 |
| MmugDNA.43211.1.S1_at | IBR domain containing 1 | LOC716647 | 2.62 | 0.0077 |
| MmugDNA.32694.1.S1_at | tumor necrosis factor, alpha-induced protein 8 | LOC700778 | 2.62 | 0.0399 |
| MmugDNA.22014.1.S1_at | golgi autoantigen, golgin subfamily a, 7 | LOC709911 | 2.62 | 0.0044 |
| MmugDNA.32609.1.S1_at | — | — | 2.61 | 0.0756 |
| MmugDNA.28006.1.S1_at | minichromosome maintenance protein domain containing 1 | LOC714711 | 2.61 | 0.0293 |
| MmugDNA.21156.1.S1_at | — | — | 2.61 | 0.0666 |
| MmuSTS.2808.1.S1_s_at | chromobox homolog 3 | — | 2.61 | 0.0714 |
| MmugDNA.14756.1.S1_at | hypothetical protein LOC694136 | LOC694136 | 2.61 | 0.0658 |
| MmuSTS.4364.1.S1 at | sterol 0-acyltransferase (acyl-Coenzyme A: cholesterol acyltransferase) 1 | SOAT1 | 2.61 | 0.0632 |
| MmugDNA.34121.1.S1_at | pappalysin 2 | PAPPA2 | 2.60 | 0.0655 |
| MmugDNA.3334.1.S1_at | sidekick homolog 1 | LOC719431 | 2.60 | 0.0565 |
| MmugDNA.14892.1.S1_at | iduronate-2-sulfatase | IDS | 2.60 | 0.0535 |
| MmugDNA.39834.1.S1_s_at | — | — | 2.60 | 0.0269 |
| MmugDNA.16052.1.S1_at | SEC10 protein | EX005 | 2.60 | 0.0882 |
| MmugDNA.10569.1.S1_at | Golgin subfamily A member 1 (Golgin-97) | LOC693285 | 2.60 | 0.0126 |
| MmugDNA.10679.1.S1_at | vacuolar H+ATPase G1 | LOC699522 | 2.60 | 0.0027 |
| MmugDNA.1854.1.S1_at | ankyrin repeat domain 20 family, member A2 | LOC707318 | 2.60 | 0.0773 |
| MmugDNA.23815.1.S1_at | — | — | 2.59 | 0.0204 |
| Mmu.7599.1.S1_at | smooth muscle cell associated protein 5 | LOC706656 | 2.59 | 0.0065 |
| MmugDNA.14931.1.S1_at | syntaxin 7 | LOC701269 | 2.59 | 0.0544 |
| MmugDNA.13732.1.S1_at | — | — | 2.59 | 0.0529 |
| MmugDNA.4660.1.S1_at | — | — | 2.59 | 0.0470 |
| MmugDNA.23822.1.S1_s_at | cell adhesion molecule 1 | CADM1 | 2.59 | 0.0163 |
| MmugDNA.37623.1.S1_at | protein tyrosine phosphatase, receptor type, G precursor | LOC703937 | 2.59 | 0.0246 |
| MmugDNA.32519.1.S1_at | — | — | 2.58 | 0.0279 |
| MmugDNA.13687.1.S1_at | — | — | 2.58 | 0.0779 |

-continued

| Probe Set ID | Gene Title | Gene Symbol | Ratio Top verus Bottom | p value Top versus Bottom |
|---|---|---|---|---|
| MmuSTS.4721.1.S1_at | thyroid hormone receptor interactor 11 | LOC697489 | 2.58 | 0.0012 |
| MmugDNA.21480.1.S1_at | — | — | 2.58 | 0.0742 |
| MmugDNA.13466.1.S1_at | activating transcription factor 6 | LOC720056 | 2.58 | 0.0029 |
| MmuSTS.3905.1.S1_at | recoverin | LOC717807 | 2.57 | 0.0728 |
| MmuSTS.1760.1.S1_at | alpha-N-acetylgalactosaminidase | NAGA | 2.57 | 0.0040 |
| MmugDNA.9095.1.S1_at | — | — | 2.57 | 0.0102 |
| MmugDNA.535.1.S1_at | — | — | 2.57 | 0.0131 |
| MmugDNA.22662.1.S1_at | — | — | 2.57 | 0.0151 |
| MmugDNA.42675.1.S1_at | transforming growth factor, beta 2 | LOC707540 | 2.57 | 0.0522 |
| MmugDNA.6958.1.S1_at | — | — | 2.57 | 0.0725 |
| MmugDNA.2631.1.S1_at | Tetraspanin-6 (Tspan-6) (Transmembrane 4 superfamily member 6) (T245 protein) (Tetraspanin TM4-D) (A15 homolog) | LOC703166 | 2.57 | 0.0170 |
| MmugDNA.13189.1.S1_at | CG10233-PA, isoform A | LOC706860 | 2.57 | 0.0238 |
| Mmu.14100.1.S1_at | hypothetical protein LOC716612 | LOC716612 | 2.56 | 0.0589 |
| MmugDNA.37486.1.S1_at | — | — | 2.56 | 0.0030 |
| MmugDNA.6803.1.S1_at | — | — | 2.56 | 0.0676 |
| MmugDNA.20096.1.S1_at | tropomodulin 3 (ubiquitous) | TMOD3 | 2.56 | 0.0158 |
| MmugDNA.4732.1.S1_at | — | — | 2.56 | 0.0239 |
| MmugDNA.3551.1.S1_at | Y73F8A.5 | LOC697670 | 2.56 | 0.0018 |
| MmugDNA.11777.1.S1_at | — | — | 2.56 | 0.0022 |
| MmugDNA.6129.1.S1_at | solute carrier family 25, member 35 | LOC721965 | 2.56 | 0.0343 |
| MmuSTS.1392.1.S1_at | — | — | 2.55 | 0.0039 |
| MmugDNA.33992.1.S1_at | PTPRF interacting protein alpha 1 | PPFIA1 | 2.55 | 0.0925 |
| MmuSTS.1581.1.S1_at | IQ motif containing GTPase activating protein 2 | IQGAP2 | 2.55 | 0.0393 |
| MmugDNA.32972.1.S1_at | — | — | 2.55 | 0.0061 |
| MmuSTS.1848.1.S1_at | resistance to inhibitors of cholinesterase 8B isoform 2 | LOC703061 | 2.55 | 0.0576 |
| MmugDNA.12186.1.S1_at | protein tyrosine phosphatase-like (proline instead of catalytic arginine), member b | — | 2.55 | 0.0353 |
| MmugDNA.10635.1.S1_at | Hypothetical protein LOC717382 | — | 2.54 | 0.0303 |
| MmugDNA.7743.1.S1_at | hypothetical protein LOC694489 | LOC694489 | 2.54 | 0.0909 |
| MmugDNA.22818.1.S1_at | L0057821 | LOC700803 | 2.54 | 0.0571 |
| MmugDNA.28543.1.S1_at | ubiquitin specific protease 46 | LOC698618 | 2.54 | 0.0001 |
| MmugDNA.7920.1.S1_at | synaptosomal-associated protein 29 | LOC696708 | 2.53 | 0.0316 |
| MmugDNA.41817.1.S1_at | — | — | 2.53 | 0.0047 |
| MmugDNA.33998.1.S1_at | CG9240-PA /// hypothetical protein LOC718215 | LOC696105 /// LOC718215 | 2.53 | 0.0613 |
| MmuSTS.4005.1.S1_at | thrombospondin 2 precursor | LOC708165 | 2.53 | 0.0700 |
| MmugDNA.7442.1.S1_at | NAD(P) dependent steroid dehydrogenase-like | LOC714229 | 2.53 | 0.0286 |
| MmugDNA.37241.1.S1_at | hypothetical protein LOC704834 | LOC704834 | 2.53 | 0.0785 |
| MmugDNA.18544.1.S1_at | MAPK/MAK/MRK overlapping kinase | RAGE | 2.52 | 0.0619 |
| MmugDNA.14567.1.S1_at | CGI-01 protein isoform 1 | LOC704943 | 2.52 | 0.0722 |
| MmugDNA.39392.1.S1_at | Tumor necrosis factor receptor superfamily member 19L precursor (Receptor expressed in lymphoid tissues) | LOC718143 | 2.52 | 0.0339 |
| MmugDNA.36135.1.S1_at | — | — | 2.52 | 0.0009 |
| MmugDNA.38008.1.S1_at | asparaginase-like 1 protein | LOC718871 | 2.52 | 0.0079 |
| MmugDNA.894.1.S1_at | — | — | 2.52 | 0.0553 |
| MmugDNA.9940.1.S1_s_at | — | — | 2.52 | 0.0117 |
| MmugDNA.30902.1.S1_at | zinc finger protein 452 | LOC708122 | 2.52 | 0.0174 |
| MmunewRS.671.1.S1_at | — | — | 2.51 | 0.0611 |
| MmugDNA.29345.1.S1_at | Golgi-localized syntaphilin-related protein isoform C | LOC699436 | 2.51 | 0.0454 |
| MmuSTS.1714.1.S1_s_at | muscle-type acylphosphatase 2 | LOC716728 | 2.51 | 0.0007 |
| MmugDNA.17463.1.S1_at | hypothetical protein LOC696917 | LOC696917 | 2.51 | 0.0447 |
| MmuSTS.4655.1.S1_at | 2',5'-oligoadenylate synthetase 1 | OAS1 | 2.51 | 0.0103 |
| MmugDNA.2445.1.S1_at | — | — | 2.51 | 0.0229 |
| MmuSTS.2654.1.S1_at | ATP-binding cassette, sub-family A member 3 | LOC696496 | 2.51 | 0.0198 |
| MmugDNA.10791.1.S1_at | Coiled-coil domain-containing protein 11 | LOC700084 | 2.50 | 0.0645 |
| MmugDNA.30349.1.S1_at | Transmembrane protein 33 (DB83 protein) | TMEM33 | 2.50 | 0.0047 |
| MmugDNA.8272.1.S1_at | — | — | 2.50 | 0.0928 |
| MmuSTS.3815.1.S1_at | ATPase, H+ transporting, lysosomal accessory protein 1 | ATP6AP1 | 2.50 | 0.0128 |
| MmugDNA.16292.1.S1_at | transmembrane protein 56 | LOC709729 | 2.50 | 0.0116 |
| MmugDNA.33608.1.S1_at | jumonji domain containing 1B | LOC716648 | 2.50 | 0.0832 |
| MmugDNA.20325.1.S1_s_at | Kruppel-like factor 3 (basic) | KLF3 | 2.50 | 0.0533 |
| MmugDNA.36544.1.S1_at | — | — | 2.50 | 0.0239 |
| MmugDNA.18568.1.S1_s_at | coiled-coil domain containing 64 | LOC698147 | 2.50 | 0.0156 |
| MmuSTS.1282.1.S1_at | retinoic acid induced 2 | LOC693329 | 2.50 | 0.0020 |
| MmugDNA.16604.1.S1_at | — | — | 2.50 | 0.0753 |
| MmugDNA.2019.1.S1_at | — | — | 2.50 | 0.0009 |
| MmugDNA.15319.1.S1_at | EH-domain containing 3 | LOC705316 | 2.49 | 0.0546 |
| MmuSTS.3025.1.S1_at | — | — | 2.49 | 0.0259 |
| MmugDNA.4609.1.S1_at | sparc/osteonectin, cwcv and kazal-like domains proteoglycan 1 | SPOCK1 | 2.49 | 0.0876 |
| MmugDNA.26967. .S1_at | ROD1 regulator of differentiation 1 | LOC711210 | 2.49 | 0.0050 |
| MmugDNA.37971. .S1_at | heat shock 70 kDa protein 4 isoform a | LOC709585 | 2.49 | 0.0242 |
| MmuSTS.3404.1.S_at | — | — | 2.49 | 0.0276 |
| MmugDNA.2456.1.S1_at | CG14185-PA | LOC698952 | 2.49 | 0.0639 |

-continued

| Probe Set ID | Gene Title | Gene Symbol | Ratio Top verus Bottom | p value Top versus Bottom |
|---|---|---|---|---|
| Mmu.4703.1.S1_at | — | — | 2.49 | 0.0143 |
| MmugDNA.16581. .S1_at | calponin 3 | LOC709538 | 2.49 | 0.0128 |
| MmugDNA.6.1.S1_at | secretogranin Ill | LOC694089 | 2.49 | 0.0059 |
| MmuSTS.1273.1.S1_at | doublecortin and CaM kinase-like 1 | LOC722071 | 2.49 | 0.0570 |
| MmugDNA.39606.1.S1_at | DNAJ domain-containing | LOC700339 | 2.48 | 0.0702 |
| MmugDNA.32745.1.S1_at | — | — | 2.48 | 0.0016 |
| MmugDNA.5221.1.S1_at | — | — | 2.48 | 0.0528 |
| MmugDNA.13152.1.S1_at | — | — | 2.48 | 0.0168 |
| MmugDNA.27246.1.S1_s_at | leucine rich repeat containing 16 | LOC694909 | 2.48 | 0.0648 |
| MmuSTS.3254.1.S1_at | semaphorin 3A | LOC708263 | 2.47 | 0.0730 |
| MmugDNA.12122.1.S1_s_at | — | — | 2.47 | 0.0389 |
| MmugDNA.29872.1.S1 at | GTPase activating Rap/RanGAP domain-like 1 isoform 1 | LOC695674 | 2.47 | 0.0024 |
| MmugDNA.34800.1.S1_at | — | — | 2.47 | 0.0944 |
| MmugDNA.25958.1.S1_at | DEAH (Asp-Glu-Ala-Asp/His) box polypeptide 57 | LOC713523 | 2.47 | 0.0649 |
| MmugDNA.32735.1.S1_at | hypothetical protein LOC702345 | LOC702345 | 2.47 | 0.0058 |
| MmugDNA.17104.1.S1_at | — | — | 2.47 | 0.0822 |
| MmugDNA.15497.1.S1_at | Hypothetical protein LOC708044 | — | 2.47 | 0.0563 |
| MmugDNA.13708.1.S1_at | — | — | 2.47 | 0.0398 |
| MmugDNA.35844.1.S1_at | Protein C10orf57 homolog | LOC701130 | 2.47 | 0.0547 |
| MmugDNA.3000.1.S1_at | signal sequence receptor gamma subunit | LOC706518 | 2.47 | 0.0144 |
| MmugDNA.18159.1.S1_at | bone morphogenetic protein receptor type II | BMPR2 | 2.47 | 0.0575 |
| Mmu.10229.1.S1_at | CD46 molecule, complement regulatory protein | CD46 | 2.47 | 0.0654 |
| MmugDNA.13343.1.S1_at | erythrocyte protein band 4.1-like 1 isoform L | LOC710697 | 2.47 | 0.0020 |
| MmugDNA.32527.1.S1_at | mitogen-activated protein kinase kinase kinase 7 interacting protein 2 | LOC696875 | 2.46 | 0.0710 |
| MmugDNA.8354.1.S1_at | HGFL protein | LOC716694 | 2.46 | 0.0605 |
| MmugDNA.32803.1.S1_at | hypothetical protein LOC717255 | LOC717255 | 2.46 | 0.0654 |
| MmugDNA.25652.1.S1_at | netrin-G1 ligand | LOC698610 | 2.46 | 0.0244 |
| MmugDNA.39872.1.S1_at | parathyroid hormone-responsive B1 isoform 2 | LOC708412 | 2.46 | 0.0721 |
| MmugDNA.13779.1.S1_at | protein kinase C and casein kinase substrate in neurons 3 | LOC713919 | 2.46 | 0.0997 |
| MmugDNA.11262.1.S1_at | — | — | 2.46 | 0.0172 |
| MmugDNA.11097.1.S1_at | Ribonuclease K6 precursor (RNase K6) | — | 2.46 | 0.0658 |
| MmugDNA.13830.1.S1_at | — | — | 2.45 | 0.0381 |
| MmugDNA.20861.1.S1_at | spermatogenesis associated 13 | LOC721468 | 2.45 | 0.0640 |
| MmuSTS.2607.1.S1_at | citrate synthase precursor, isoform a | — | 2.45 | 0.0385 |
| MmugDNA.15111.1.S1_at | — | — | 2.45 | 0.0528 |
| MmuSTS.2246.1.S1_at | phospholipase C, gamma 2 (phosphatidylinositol-specific) | PLCG2 | 2.45 | 0.0006 |
| MmugDNA.17805.1.S1_at | solute carrier family 9 (sodium/hydrogen exchanger), isoform 2 | LOC712199 | 2.45 | 0.0407 |
| MmugDNA.19536.1.S1_at | — | — | 2.45 | 0.0378 |
| MmugDNA.17107.1.S1_at | mitogen-activated protein kinase 1 | MAPK1 | 2.44 | 0.0344 |
| MmugDNA.24092.1.S1_at | hypothetical protein LOC708570 | LOC708570 | 2.44 | 0.0745 |
| MmugDNA.14738.1.S1_at | TRAF2 and NCK interacting kinase | TNIK | 2.44 | 0.0358 |
| MmugDNA.5147.1.S1_s_at | Kelch repeat and BTB domain-containing protein 4 (BTB and kelch domain-containing protein 4) | LOC711452 | 2.44 | 0.0121 |
| MmugDNA.6438.1.S1_at | nudix (nucleoside diphosphate linked moiety X)-type motif 21 | LOC707828 | 2.44 | 0.0458 |
| MmugDNA.17791.1.S1_at | — | — | 2.44 | 0.0445 |
| MmugDNA.19209.1.S1_s_at | Neutrophil gelatinase-associated lipocalin precursor (NGAL) (p25) (25 kDa alpha-2-microglobulin-related subunit of MMP-9) (Lipocalin-2) (Oncogene 24p3) | LOC697208 | 2.44 | 0.0703 |
| MmugDNA.20574.1.S1_at | v-kit Hardy-Zuckerman 4 feline sarcoma viral oncogene homolog | KIT | 2.44 | 0.0258 |
| MmugDNA.35313.1.S1_at | hypothetical protein LOC704554 /// adenylate cyclase 9 | ADCY9 /// LOC704554 | 2.44 | 0.0330 |
| MmugDNA.20823.1.S1_at | — | — | 2.43 | 0.0067 |
| MmugDNA.42796.1.S1_at | inositol 1,3,4,5,6-pentakisphosphate 2-kinase | LOC705937 | 2.43 | 0.0129 |
| MmugDNA.17764.1.S1_at | CG6678-PA | LOC715524 | 2.43 | 0.0114 |
| MmugDNA.43422.1.S1_at | postsynaptic protein CRIPT | LOC714949 | 2.43 | 0.0240 |
| MmugDNA.34136.1.S1_at | Normal mucosa of esophagus-specific gene 1 protein | LOC713440 | 2.43 | 0.0780 |
| MmugDNA.30592.1.S1_at | transmembrane 9 superfamily member 2 | TM9SF2 | 2.43 | 0.0017 |
| MmugDNA.27400.1.S1 at | mannosyl (alpha-1,3-)-glycoprotein beta-1, 4-N-acetylglucosaminyltransferase, isoenzyme A | LOC708094 | 2.43 | 0.0393 |
| MmuSTS.4839.1.S1_at | golgi phosphoprotein 2 | LOC715029 | 2.43 | 0.0064 |
| Mmu.8934.1.S1_at | Alpha- and gamma-adaptin-binding protein p34 | LOC711436 | 2.43 | 0.0144 |
| MmugDNA.2329.1.S1_at | — | — | 2.43 | 0.0587 |
| MmugDNA.17344.1.S1_at | neurotrophin 3 | NTF3 | 2.42 | 0.0822 |
| MmugDNA.36340.1.S1_at | — | — | 2.42 | 0.0398 |
| MmugDNA.21012.1.S1_at | rabphilin 3A-like (without C2 domains) | — | 2.42 | 0.0932 |
| MmugDNA.17438.1.S1_at | — | — | 2.42 | 0.0767 |
| MmuSTS.1305.1.S1_at | disrupted in renal carcinoma 2 | LOC715135 | 2.42 | 0.0004 |
| MmuSTS.664.1.S1_at | caspase 7 isoform delta | LOC697633 | 2.42 | 0.0130 |
| MmugDNA.26043.1.S1_at | Ataxin-7-like protein 1 | LOC698666 | 2.41 | 0.0286 |
| MmugDNA.33509.1.S1_at | CG11178-PB, isoform B | LOC693868 | 2.41 | 0.0659 |
| MmugDNA.6922.1.S1_at | — | — | 2.41 | 0.0385 |
| MmugDNA.31513.1.S1_at | ubiquitin specific protease 38 | LOC700235 | 2.41 | 0.0544 |

-continued

| Probe Set ID | Gene Title | Gene Symbol | Ratio Top verus Bottom | p value Top versus Bottom |
|---|---|---|---|---|
| MmuSTS.1706.1.S1_at | ATP binding cassette, sub-family A (ABC1), member 13LOC695208 | 2.41 | 0.0215 | |
| MmuSTS.415.1.S1_at | — | — | 2.41 | 0.0183 |
| MmugDNA.5945.1.S1_at | CG6729-PA | LOC711172 | 2.41 | 0.0529 |
| MmugDNA.16172. .S1_at | transmembrane protein 5 | TMEM5 | 2.41 | 0.0000 |
| MmugDNA.7215.1.S1_at | uronyl-2-sulfotransferase | LOC697355 | 2.41 | 0.0823 |
| MmugDNA.20155. .S1_at | — | — | 2.41 | 0.0172 |
| MmugDNA.39588. .S1_at | — | — | 2.41 | 0.0526 |
| MmugDNA.1883.1.S1_at | EGFR-coamplified and overexpressed protein | LOC716151 | 2.41 | 0.0004 |
| MmugDNA.2888.1.S1_at | HMT1 hnRNP methyltransferase-like 1 | PRMT2 | 2.41 | 0.0030 |
| MmugDNA.36209. .S1_at | — | — | 2.40 | 0.0506 |
| MmugDNA.5649.1.S1_at | autocrine motility factor receptor | LOC699972 | 2.40 | 0.0223 |
| MmugDNA.33055.1.S1_at | hypothetical protein LOC696384 | LOC696384 | 2.40 | 0.0752 |
| MmuSTS.2026.1.S1_at | cAMP-dependent protein kinase inhibitor gamma | LOC712474 | 2.40 | 0.0094 |
| MmugDNA.14045.1.S1_at | advillin | LOC712581 | 2.40 | 0.0001 |
| MmugDNA.35277.1.S1_s_at | actin related protein 2/3 complex, subunit 5 | LOC699657 | 2.40 | 0.0138 |
| MmugDNA.30729.1.S1_s_at | golgi reassembly stacking protein 2 | LOC694170 | 2.40 | 0.0106 |
| MmugDNA.36130.1.S1_at | attractin | ATRN | 2.40 | 0.0097 |
| MmugDNA.7819.1.S1_at | mitogen-activated protein kinase 8 isoform 1 | LOC711115 | 2.39 | 0.0438 |
| MmugDNA.43615.1.S1_at | — | — | 2.39 | 0.0695 |
| MmugDNA.25611.1.S1_at | phosphodiesterase 6D, cGMP-specific, rod, delta | LOC712629 | 2.39 | 0.0100 |
| MmugDNA.27560.1.S1_at | Hypothetical protein LOC709178 | — | 2.39 | 0.0044 |
| MmugDNA.13637.1.S1_at | zinc finger protein 135 (clone pHZ-17) | LOC706617 | 2.39 | 0.0734 |
| MmugDNA.103.1.S1_at | PDZ and LIM domain 7 isoform 2 | LOC706581 | 2.39 | 0.0805 |
| MmugDNA.41605.1.S1_s_at | casein kinase II, alpha 1 polypeptide | LOC714841 | 2.39 | 0.0647 |
| MmuSTS.3945.1.S1_at | synaptotagmin I | SYT1 | 2.39 | 0.0424 |
| MmugDNA.5481.1.S1_at | — | — | 2.39 | 0.0011 |
| MmugDNA.10940.1.S1_at | — | — | 2.39 | 0.0516 |
| MmugDNA.9600.1.S1_at | regulating synaptic membrane exocytosis 2 isoform 1 | LOC694366 | 2.39 | 0.0629 |
| MmuSTS.2040.1.S1_at | hypothetical protein LOC716045 | LOC716045 | 2.38 | 0.0203 |
| MmugDNA.5934.1.S1_at | — | — | 2.38 | 0.0282 |
| MmugDNA.7962.1.S1 at | syntaphilin | SNPH | 2.38 | 0.0359 |
| MmugDNA.13339.1.S1_at | G protein-coupled receptor 178 | LOC705039 | 2.38 | 0.0053 |
| MmuSTS.1208.1.S1_at | trimethyllysine hydroxylase, epsilon | TMLHE | 2.38 | 0.0921 |
| MmugDNA.31636.1.S1_at | HMT1 hnRNP methyltransferase-like 3 | LOC701789 | 2.38 | 0.0213 |
| MmugDNA.3222.1.S1_at | — | — | 2.38 | 0.0317 |
| MmugDNA.38925.1.S1_at | CG15021-PA | LOC699097 | 2.38 | 0.0200 |
| MmugDNA.8848.1.S1_at | transmembrane protein 37 | LOC695060 | 2.38 | 0.0843 |
| MmuSTS.168.1.S1_x_at | isopentenyl-diphosphate delta isomerase | LOC710052 | 2.38 | 0.0011 |
| MmugDNA.10165.1.S1_at | Hematological and neurological expressed 1 | — | 2.38 | 0.0381 |
| MmugDNA.14296.1.S1_at | — | — | 2.37 | 0.0118 |
| MmugDNA.26530.1.S1_at | hypothetical protein LOC721032 | LOC721032 | 2.37 | 0.0873 |
| MmugDNA.42344.1.S1_at | ADP-ribosylarginine hydrolase | ADPRH | 2.37 | 0.0911 |
| MmugDNA.31196.1.S1_at | — | — | 2.37 | 0.0106 |
| MmugDNA.6107.1.S1_at | Juxtaposed with another zinc finger protein 1 | LOC697973 | 2.37 | 0.0564 |
| MmugDNA.12227. .S1_at | — | — | 2.37 | 0.0092 |
| MmugDNA.6506.1.S1_at | — | — | 2.37 | 0.0548 |
| MmugDNA.33621. .S1_at | zinc finger protein 528 | LOC720193 | 2.37 | 0.0807 |
| MmugDNA.5483.1.S1_at | cell death inducing protein | LOC705579 | 2.37 | 0.0183 |
| MmugDNA.4206.1.S1_at | calcium-activated potassium channel beta 4 subunit | LOC717360 | 2.37 | 0.0762 |
| MmugDNA.27722.1.S1_at | — | — | 2.37 | 0.0449 |
| MmugDNA.37306.1.S1_at | melanoma antigen family E, 1 | LOC705379 | 2.36 | 0.0431 |
| MmugDNA.38283.1.S1_at | NADPH cytochrome B5 oxidoreductase | LOC695553 | 2.36 | 0.0419 |
| MmugDNA.9872.1.S1_at | lysosomal-associated membrane protein 1 | LAMP1 | 2.36 | 0.0380 |
| MmugDNA.39305.1.S1_at | Fc fragment of IgG binding protein | LOC700539 | 2.36 | 0.0153 |
| MmugDNA.19557.1.S1_at | filamin-binding LIM protein-1 isoform a | LOC695727 | 2.36 | 0.0284 |
| Mmu.4737.1.S1_at | riboflavin kinase | LOC704540 | 2.36 | 0.0146 |
| MmugDNA.3346.1.S1_at | makorin, ring finger protein, 2 | LOC697649 | 2.36 | 0.0193 |
| MmuSTS.3988.1.S1_at | Cathepsin S precursor | LOC708080 | 2.36 | 0.0054 |
| MmugDNA.38289.1.S1_at | WD repeat domain 27 | LOC695097 | 2.36 | 0.0583 |
| MmugDNA.684.1.S1_at | alpha 2 type IX collagen | LOC694248 | 2.36 | 0.0316 |
| MmugDNA.41344.1.S1_at | solute carrier family 4 member 11 | LOC718393 | 2.36 | 0.0120 |
| MmugDNA.8324.1.S1_at | — | — | 2.35 | 0.0096 |
| MmugDNA.12588.1.S1_at | — | — | 2.35 | 0.0199 |
| MmugDNA.36202.1.S1_at | — | — | 2.35 | 0.0482 |
| MmugDNA.23185.1.S1_at | TATA element modulatory factor 1 | LOC696619 | 2.35 | 0.0108 |
| MmugDNA.12313.1.S1_at | CG2943-PA | LOC702573 | 2.35 | 0.0270 |
| MmugDNA.15670.1.S1_s_at | insulysin | IDE | 2.35 | 0.0735 |
| MmugDNA.30396.1.S1_at | Corneodesmosin precursor (S protein) | LOC714553 | 2.35 | 0.0729 |
| MmugDNA.12626.1.S1_s_at | SWI/SNF-related matrix-associated actin-dependent regulator of chromatin a4 | SMARCA4 | 2.35 | 0.0853 |
| MmugDNA.20551.1.S1_at | discoidin, CUB and LCCL domain containing 1 | DCBLD1 | 2.35 | 0.0001 |
| MmugDNA.19751.1.S1_at | ADP-ribosylhydrolase like 1 isoform 1 | LOC697842 | 2.34 | 0.0761 |
| MmugDNA.5198.1.S1_at | uncharacterized protein family UPF0227 member RGD1359682 | LOC717757 | 2.34 | 0.0500 |
| MmugDNA.28177.1.S1_s_at | hypothetical protein LOC712492 | LOC712492 | 2.34 | 0.0330 |

-continued

| Probe Set ID | Gene Title | Gene Symbol | Ratio Top verus Bottom | p value Top versus Bottom |
|---|---|---|---|---|
| MmugDNA.14571.1.S1_s_at | phosphatidylinositol glycan, class T precursor | LOC710556 | 2.34 | 0.0061 |
| Mmu.15853.1.S1_x_at | ADP-ribosylation-like factor 6 interacting protein 5LOC696360 | 2.34 | 0.0344 | |
| MmuSTS.255.1.S1_at | non-imprinted in Prader-Willi/Angelman syndrome 1 | LOC710236 | 2.34 | 0.0619 |
| MmugDNA.10012.1.S1_at | transmembrane protein 16D | LOC695973 | 2.34 | 0.0997 |
| MmugDNA.19562.1.S1_at | zinc finger protein 406 isoform ZFAT-1 | LOC698512 | 2.34 | 0.0839 |
| MmugDNA.22652.1.S1_s_at | — | — | 2.34 | 0.0641 |
| MmugDNA.29515.1.S1_at | splicing factor, arginine/serine-rich 14 | LOC719666 | 2.34 | 0.0382 |
| MmugDNA.17884.1.S1_at | Nuclear respiratory factor 1 (NRF-1) (Alpha palindromic-binding protein) (Alpha-pal) | LOC701933 | 2.34 | 0.0353 |
| MmugDNA.32746.1.S1_at | — | — | 2.34 | 0.0282 |
| MmuSTS.1396.1.S1_s_at | zinc finger, MYND domain containing 11 | ZMYND11 | 2.34 | 0.0128 |
| MmugDNA.18506.1.S1_at | basic beta 1 syntrophin | LOC703245 | 2.33 | 0.0093 |
| MmugDNA.26826.1.S1_s_at | solute carrier family 11 (proton-coupled divalent metal ion transporters), member 1 | SLC11A1 | 2.33 | 0.0675 |
| MmugDNA.38731.1.S1_at | steroid 5 alpha-reductase 2-like | LOC696381 | 2.33 | 0.0646 |
| MmugDNA.27590.1.S1_at | — | — | 2.33 | 0.0789 |
| MmugDNA.17575.1.S1_at | — | — | 2.33 | 0.0623 |
| MmugDNA.17935.1.S1_at | — | — | 2.33 | 0.0075 |
| MmugDNA.22419.1.S1 at | — | — | 2.33 | 0.0972 |
| MmugDNA.23057.1.S1_at | — | — | 2.33 | 0.0060 |
| MmugDNA.41434.1.S1_at | gamma-glutamyl hydrolase precursor | LOC700747 | 2.33 | 0.0384 |
| MmugDNA.17895.1.S1_at | — | — | 2.33 | 0.0135 |
| MmugDNA.23827.1.S1_at | hypothetical protein LOC699699 | LOC699699 | 2.33 | 0.0944 |
| MmugDNA.10050.1.S1_at | — | — | 2.33 | 0.0710 |
| Mmu.2224.1.A1_at | — | — | 2.32 | 0.0001 |
| Mmu.12870.1.S1_at | thymic dendritic cell-derived factor 1 | TMEM59 | 2.32 | 0.0246 |
| MmugDNA.19523.1.S1_at | CD164 antigen, sialomucin | CD164 | 2.32 | 0.0019 |
| MmugDNA.22579.1.S1_at | Growth-arrest-specific protein 7 (GAS-7) | LOC717827 | 2.32 | 0.0431 |
| MmuSTS.2905.1.S1_at | Pre-B lymphocyte protein 3 precursor (VpreB3 protein) (N27C7-2) | VPREB3 | 2.32 | 0.0105 |
| MmugDNA.41669.1.S1_at | apolipoprotein B mRNA editing enzyme, catalytic polypeptide-like 4 (putative) | LOC714993 | 2.32 | 0.0081 |
| MmugDNA.11443.1.S1_at | — | — | 2.32 | 0.0432 |
| MmugDNA.18263.1.S1_at | zinc finger, DHHC domain containing 9 | ZDHHC9 | 2.32 | 0.0271 |
| MmuAffx.1008.1.S1_at | Glutathione peroxidase 3 precursor (GSHPx-3) (GPx-3) (Plasma glutathione peroxidase) (GSHPx-P) (Extracellular glutathione peroxidase) (GPx-P) | LOC713057 | 2.32 | 0.0926 |
| MmugDNA.22975.1.S1_at | hydroxysteroid dehydrogenase like 1 | LOC714962 | 2.31 | 0.0247 |
| MmugDNA.35709.1.S1_at | calsyntenin 2 | LOC715514 | 2.31 | 0.0056 |
| MmugDNA.14527.1.S1_at | F-box only protein 2 | LOC722738 | 2.31 | 0.0601 |
| MmugDNA.35626.1.S1_s_at | Ras association (RaIGDS/AF-6) domain family 6 isoform a | LOC704459 | 2.31 | 0.0137 |
| MmuSTS.2492.1.S1_at | zinc finger protein 509 | LOC712422 | 2.31 | 0.0239 |
| MmuSTS.3145.1.S1_at | nodal modulator 2 isoform 2 | LOC714226 | 2.31 | 0.0001 |
| MmuSTS.3540.1.S1_at | p21-activated kinase 3 | PAK3 | 2.31 | 0.0898 |
| MmugDNA.15593.1.S1_at | lysosomal acid phosphatase 2 | ACP2 | 2.31 | 0.0605 |
| MmugDNA.18121.1.S1_at | — | — | 2.31 | 0.0029 |
| MmugDNA.39434.1.S1_at | — | — | 2.31 | 0.0976 |
| MmugDNA.25583.1.S1_at | PDZ domain containing 8 | LOC709084 | 2.31 | 0.0851 |
| MmugDNA.38757.1.S1_at | — | — | 2.31 | 0.0970 |
| MmugDNA.10667.1.S1_at | ribophorin II precursor | LOC708971 | 2.30 | 0.0244 |
| MmugDNA.22894.1.S1_at | cellular modulator of immune recognition | LOC708030 | 2.30 | 0.0097 |
| MmuSTS.4136.1.S1_at | enolase 2 | ENO2 | 2.30 | 0.0000 |
| MmunewRS.108.1.S1_at | RNA binding motif protein 18 | LOC698457 | 2.30 | 0.0318 |
| MmugDNA.13579.1.S1_at | — | — | 2.30 | 0.0823 |
| MmugDNA.13215.1.S1_at | myosin VB | MYO5B | 2.30 | 0.0008 |
| MmuSTS.3395.1.S1_at | T16G12.5 | LOC704499 | 2.30 | 0.0158 |
| MmugDNA.3907.1.S1_at | — | — | 2.30 | 0.0862 |
| MmugDNA.26180.1.S1_at | — | — | 2.29 | 0.0769 |
| MmugDNA.37638.1.S1_at | Hypothetical protein LOC721042 | — | 2.29 | 0.0189 |
| MmuSTS.4204.1.S1_at | growth arrest-specific 8 | GAS8 | 2.29 | 0.0119 |
| MmuSTS.1320.1.S1_at | Calcipressin-2 (Thyroid hormone-responsive protein ZAKI-4) (Down syndrome candidate region 1-like 1) (Myocyte-enriched calcineurin-interacting protein 2) (MCIP2) | DSCR1 L1 | 2.29 | 0.0211 |
| MmuSTS.1142.1.S1_at | pleiomorphic adenoma gene-like 1 isoform 2 | LOC699985 | 2.29 | 0.0086 |
| MmuSTS.1514.1.S1_at | — | — | 2.29 | 0.0218 |
| MmuSTS.629.1.S1_at | insulin-like growth factor 2 receptor | IGF2R | 2.29 | 0.0358 |
| MmugDNA.34704.1.S1_at | pecanex homolog | LOC694094 | 2.29 | 0.0679 |
| MmuSTS.2468.1.S1_at | DHHC1 protein | ZDHHC3 | 2.29 | 0.0010 |
| MmugDNA.39065.1.S1_at | elongation factor Tu GTP binding domain containing 1 | — | 2.29 | 0.0258 |
| MmugDNA.43592.1.S1_at | — | — | 2.29 | 0.0291 |
| MmugDNA.18594.1.S1_at | DNA-directed RNA polymerases I, II, and III 7.0 kDa polypeptide (ABC10-alpha) (RPB7.0) (RPB10alpha) (RPABC4) | POLR2K | 2.29 | 0.0182 |
| MmugDNA.22717.1.S1_at | — | — | 2.29 | 0.0484 |
| MmugDNA.11519.1.S1_at | breakpoint cluster region isoform 1 | LOC709258 | 2.28 | 0.0734 |
| MmugDNA.14224.1.S1_at | hypothetical protein LOC715184 | LOC715184 | 2.28 | 0.0889 |

-continued

| Probe Set ID | Gene Title | Gene Symbol | Ratio Top verus Bottom | p value Top versus Bottom |
|---|---|---|---|---|
| MmugDNA.2963.1.S1_at | KIAA1900 | LOC709276 | 2.28 | 0.0527 |
| MmugDNA.41313.1.S1_at | Oxytocin-neurophysin 1 precursor (OT-NPI) | OXT | 2.28 | 0.0512 |
| MmugDNA.23270.1.S1_at | archaemetzincins-2 isoform 1 | LOC718462 | 2.28 | 0.0394 |
| MmugDNA.7783.1.S1_at | solute carrier organic anion transporter family, member 3A1 | SLCO3A1 | 2.28 | 0.0616 |
| MmugDNA.40350.1.S1_s_at | glutamate dehydrogenase 1 | GLUD1 | 2.28 | 0.0037 |
| MmugDNA.9234.1.S1_at | tau tubulin kinase 2 | LOC712249 | 2.27 | 0.0807 |
| MmugDNA.21304.1.S1_s_at | MAX protein isoform c | LOC708228 | 2.27 | 0.0165 |
| MmuSTS.3238.1.S1_at | raft-linking protein | RAFTLIN | 2.27 | 0.0108 |
| MmuSTS.1238.1.S1_at | serine/threonine protein phosphatase with EF-hand motifs 1 | PPEF1 | 2.27 | 0.0956 |
| MmugDNA.39116.1.S1_at | CDW92 antigen isoform 2 | LOC715816 | 2.27 | 0.0566 |
| Mmu.924.1.S1_at | anaphase promoting complex subunit 13 | LOC717294 | 2.27 | 0.0128 |
| MmugDNA.33266.1.S1_at | — | — | 2.27 | 0.0418 |
| MmuSTS.1309.1.S1_at | Doublesex- and mab-3-related transcription factor 2 (Doublesex-like 2 protein) (DSXL-2) | DMRT2 | 2.27 | 0.0682 |
| MmugDNA.34994.1.S1_s_at | — | — | 2.27 | 0.0940 |
| MmugDNA.42427.1.S1_at | — | — | 2.27 | 0.0034 |
| MmugDNA.16606.1.S1_s_at | synapse-associated protein 97 | DLG1 | 2.27 | 0.0636 |
| MmugDNA.16402.1.S1_at | cyclin M4 | LOC710164 | 2.27 | 0.0425 |
| MmugDNA.42754.1.S1_at | — | — | 2.27 | 0.0453 |
| MmugDNA.29639.1.S1_at | — | — | 2.27 | 0.0957 |
| MmugDNA.4933.1.S1_at | — | — | 2.27 | 0.0759 |
| MmugDNA.30201.1.S1_at | Transcription factor Ovo-like 2 (hOvo2) (Zinc finger protein 339) | LOC719066 | 2.27 | 0.0162 |
| MmugDNA.13664.1.S1_at | — | — | 2.26 | 0.0969 |
| MmugDNA.11714.1.S1_at | transmembrane 6 superfamily member 1 | LOC700147 | 2.26 | 0.0935 |
| MmuSTS.160.1.S1_at | cancer susceptibility candidate 1 | LOC707753 | 2.26 | 0.0756 |
| MmugDNA.32421.1.S1_at | Mediator complex subunit 4 (Mediator of RNA polymerase II transcription subunit 4) (Vitamin D3 receptor-interacting protein complex 36 kDa component) (DRIP36) (Activator-recruited cofactor 36 kDa component) (ARC36) (TRAP/SMCC/PC2 subunit... | LOC704644 | 2.26 | 0.0005 |
| MmugDNA.617.1.S1_at | pleckstrin homology domain containing, family H (with MyTH4 domain) member 1 | LOC713855 | 2.26 | 0.0144 |
| MmugDNA.29286.1.S1_at | hypothetical protein LOC708459 | LOC708459 | 2.26 | 0.0585 |
| MmugDNA.26513.1.S1_at | — | — | 2.26 | 0.0079 |
| MmugDNA.4207.1.S1_at | hypothetical protein LOC695219 | LOC695219 | 2.25 | 0.0404 |
| Mmu.11792.1.S1_at | syntaxin 12 | LOC716455 | 2.25 | 0.0076 |
| MmugDNA.3187.1.S1_at | midline 1 | LOC713037 | 2.25 | 0.0123 |
| MmuSTS.2358.1.S1_at | Reticulon-2 (Neuroendocrine-specific protein-like 1) (NSP-like protein 1) (NSPLI) | RTN2 | 2.25 | 0.0554 |
| MmugDNA.13865.1.S1_at | — | — | 2.25 | 0.0808 |
| MmuSTS.1169.1.S1_at | carbohydrate (chondroitin 4) sulfotransferase 12 | CHST12 | 2.25 | 0.0631 |
| MmugDNA.7568.1.S1_at | myotubularin related protein 6 | MTMR6 | 2.25 | 0.0109 |
| MmugDNA.42542.1.S1_at | — | — | 2.25 | 0.0141 |
| MmuSTS.2722.1.S1_at | homer 2 | HOMER2 | 2.25 | 0.0035 |
| MmugDNA.10742.1.S1_at | farnesyl-diphosphate farnesyltransferase 1 | FDFT1 | 2.25 | 0.0008 |
| MmugDNA.42437.1.S1_at | N-ethylmaleimide-sensitive factor attachment protein, alpha | LOC717355 | 2.25 | 0.0490 |
| MmugDNA.23264.1.S1_at | — | — | 2.25 | 0.0558 |
| MmugDNA.33445.1.S1_at | ring finger protein 180 | LOC698166 | 2.25 | 0.0840 |
| MmugDNA.31781.1.S1_at | vacuolar protein sorting 37C | LOC694898 | 2.25 | 0.0416 |
| MmugDNA.15898.1.S1_s_at | ATPase, H+transporting, lysosomal 70kD, V1 subunit A, isoform 1 | LOC696878 /// LOC709958 | 2.25 | 0.0009 |
| MmugDNA.29220.1.S1_at | mitogen-activated protein kinase kinase kinase 13 | LOC701085 | 2.25 | 0.0665 |
| MmugDNA.18194.1.S1_at | mitogen-activated protein kinase kinase 6 | LOC693914 | 2.25 | 0.0209 |
| Mmu.10240.1.S1_at | ubiquitin C-terminal hydrolase UCH37 | LOC712473 | 2.25 | 0.0146 |
| MmugDNA.2778.1.S1_at | WW, C2 and coiled-coil domain containing 1 | LOC720812 | 2.25 | 0.0619 |
| MmugDNA.14327.1.S1_at | lactamase, beta isoform a | LOC705365 | 2.24 | 0.0027 |
| MmugDNA.6356.1.S1_at | CG14980-PB | LOC718128 | 2.24 | 0.0083 |
| MmugDNA.41963.1.S1_s_at | calcium binding atopy-related autoantigen 1 | LOC701131 /// LOC708654 | 2.24 | 0.0120 |
| MmuSTS.357.1.S1_s_at | matin | LOC704451 | 2.24 | 0.0520 |
| MmugDNA.12984.1.S1_at | influenza virus NS1A binding protein isoform a | LOC714152 | 2.24 | 0.0122 |
| MmugDNA.36042.1.S1_at | myotubularin-related protein 2 | MTMR2 | 2.24 | 0.0122 |
| MmugDNA.32344.1.S1_at | phosphatidylinositol glycan, class K | PIGK | 2.24 | 0.0015 |
| MmuSTS.1829.1.S1_at | shroom | LOC699613 | 2.24 | 0.0312 |
| Mmu.14177.1.S1_at | unc-50 homolog | UNC50 | 2.24 | 0.0511 |
| MmugDNA.17303.1.S1_at | — | — | 2.24 | 0.0816 |
| MmuSTS.4053.1.S1_at | diacylglycerol kinase, iota | DGKI | 2.24 | 0.0540 |
| MmugDNA.31861.1.S1_at | ADP-ribosylation factor interacting protein 1 isoform 2 | LOC697533 | 2.24 | 0.0738 |
| MmugDNA.32277.1.S1_at | DNA methyltransferase 2 | DNMT2 | 2.24 | 0.0117 |
| MmugDNA.7347.1.S1_at | — | — | 2.23 | 0.0783 |
| MmuSTS.242.1.S1_x_at | hypothetical protein LOC710534 | LOC710534 | 2.23 | 0.0769 |
| MmugDNA.29827.1.S1_at | — | — | 2.23 | 0.0209 |
| MmuSTS.2213.1.S1_at | TO3G11.3 | — | 2.23 | 0.0690 |
| MmugDNA.37378.1.S1_at | — | — | 2.23 | 0.0285 |
| MmuSTS.3577.1.S1_at | protocadherin beta 15 | PCDHB15 | 2.23 | 0.0039 |

-continued

| Probe Set ID | Gene Title | Gene Symbol | Ratio Top verus Bottom | p value Top versus Bottom |
|---|---|---|---|---|
| MmugDNA.39878.1.S1_at | CG15528-PA | LOC716271 | 2.23 | 0.0314 |
| MmugDNA.21179.1.S1_at | SEC22 vesicle trafficking protein homolog C isoform b | LOC716351 | 2.23 | 0.0145 |
| MmuSTS.3806.1.S1_at | ADP-ribosylation factor GTPase activating protein 3 | LOC711160 | 2.23 | 0.0530 |
| MmugDNA.31478.1.S1_at | Ras-related protein Rab-33A (Small GTP-binding protein S10) | RAB33A | 2.23 | 0.0714 |
| MmugDNA.9384.1.S1_at | — | — | 2.23 | 0.0215 |
| MmuSTS.3704.1.S1_at | protein kinase, X-linked | PRKX | 2.23 | 0.0502 |
| MmugDNA.1624.1.S1_at | F-box only protein 3 isoform 2 | LOC693281 | 2.22 | 0.0611 |
| MmugDNA.732.1.S1_at | hexosaminidase B | HEXB | 2.22 | 0.0224 |
| MmugDNA.12951.1.S1_at | zinc finger protein 77 | LOC712142 | 2.22 | 0.0290 |
| MmugDNA.24637.1.S1_at | zinc finger protein HIT-39 | LOC710861 | 2.22 | 0.0274 |
| MmuSTS.1852.1.S1_at | cell division cycle 25A isoform a | LOC710858 | 2.22 | 0.0331 |
| MmugDNA.34293.1.S1_at | UDP-Gal:betaGlcNAc beta 1,4- galactosyltransferase 5 | B4GALT5 | 2.22 | 0.0063 |
| MmuSTS.4187.1.S1_at | NAD(P)H:quinone oxidoreductase type 3, polypeptide A2 | LOC704519 | 2.22 | 0.0262 |
| MmugDNA.42423.1.S1_at | — | — | 2.22 | 0.0136 |
| MmugDNA.34057.1.S1_at | Protein C9orf46 | LOC693286 | 2.22 | 0.0134 |
| MmugDNA.35491.1.S1_at | CG13624-PC, isoform C | LOC703459 | 2.22 | 0.0168 |
| MmugDNA.22976.1.S1_s_at | CG2747-PB, isoform B | — | 2.22 | 0.0105 |
| MmuSTS.1422.1.S1_at | hypothetical protein LOC721211 | LOC721211 | 2.22 | 0.0334 |
| MmugDNA.22793.1.S1_at | tribbles homolog 2 | LOC710966 | 2.22 | 0.0901 |
| MmugDNA.40572.1.S1_at | fucosidase, alpha-L- 1, tissue | FUCA1 | 2.22 | 0.0228 |
| MmugDNA.817.1.S1_at | proteasome (prosome, macropain) 26S subunit, ATPase 2 | LOC722117 | 2.21 | 0.0637 |
| MmugDNA.38292.1.S1_at | SORCS receptor 1 isoform b | LOC693969 | 2.21 | 0.0537 |
| MmugDNA.35537.1.S1_at | cathepsin L | CTSL | 2.21 | 0.0957 |
| MmugDNA.8681.1.S1_at | CG14967-PA | LOC709307 | 2.21 | 0.0675 |
| MmuSTS.3280.1.S1_at | calcium channel, voltage-dependent, alpha 2/delta subunit 2 isoform b | LOC702429 | 2.21 | 0.0789 |
| MmugDNA.38348.1.S1_at | adducin 1 (alpha) | ADD1 | 2.21 | 0.0553 |
| MmugDNA.8155.1.S1_at | — | — | 2.21 | 0.0001 |
| Mmu.394.1.S1_at | — | — | 2.21 | 0.0019 |
| Mmu.14589.1.A1_at | Secretory carrier membrane protein 1 | — | 2.21 | 0.0253 |
| MmugDNA.15428.1.S1_at | acetoacetyl-CoA synthetase | LOC707015 | 2.21 | 0.0296 |
| MmugDNA.2672.1.S1_at | — | — | 2.21 | 0.0718 |
| Mmu.7319.1.S1_at | hypothetical protein LOC698039 | LOC698039 | 2.21 | 0.0978 |
| Mmu.14167.1.S1_at | DNA topoisomerase I | LOC697300 | 2.21 | 0.0879 |
| MmugDNA.26813.1.S1_at | — | — | 2.20 | 0.0739 |
| MmugDNA.18358.1.S1_at | jumonji domain containing 2B | JMJD2B | 2.20 | 0.0264 |
| MmugDNA.30037.1.S1_at | hypothetical protein LOC700951 | LOC700951 | 2.20 | 0.0539 |
| MmugDNA.40481.1.S1_at | dynamin binding protein | LOC709334 | 2.20 | 0.0109 |
| MmugDNA.25680.1.S1_at | hypothetical protein LOC702485 | LOC702485 | 2.20 | 0.0848 |
| MmugDNA.20470.1.S1_at | — | — | 2.20 | 0.0464 |
| MmugDNA.7063.1.S1_at | — | — | 2.20 | 0.0848 |
| MmugDNA.37434.1.S1_at | karyopherin alpha 1 | KPNA1 | 2.20 | 0.0119 |
| MmuSTS.2333.1.S1_at | Peroxisome assembly factor 1 (PAF-1) (Peroxin-2) (Peroxisomal membrane protein 3) (35 kDa peroxisomal membrane protein) (RING finger protein 72) | LOC701636 | 2.20 | 0.0939 |
| MmugDNA.17606.1.S1_at | BTB (POZ) domain containing 11 isoform 3 /// hypothetical protein LOC705027 | LOC704916 /// LOC705027 | 2.20 | 0.0238 |
| MmugDNA.32862.1.S1_at | zinc finger protein 174 | ZNF174 | 2.20 | 0.0684 |
| MmugDNA.2565.1.S1_at | — | — | 2.20 | 0.0079 |
| MmugDNA.35698.1.S1_at | — | — | 2.20 | 0.0366 |
| MmugDNA.23911.1.S1_at | — | — | 2.19 | 0.0292 |
| MmugDNA.21753.1.S1_at | — | — | 2.19 | 0.0073 |
| MmugDNA.8775.1.S1_at | — | — | 2.19 | 0.0057 |
| MmugDNA.22114.1.S1_at | 5'-methylthioadenosine phosphorylase | MTAP | 2.19 | 0.0179 |
| MmuSTS.3163.1.S1_at | regulator of G-protein signalling 7 | RGS7 | 2.19 | 0.0763 |
| MmugDNA.10574.1.S1_at | amyloid beta A4 precursor protein-binding, family B, member 1 isoform delta E9 | LOC712585 | 2.19 | 0.0110 |
| MmugDNA.11741.1.S1_at | hypothetical protein LOC694910 | LOC694910 | 2.19 | 0.0055 |
| MmugDNA.25725.1.S1_at | Potassium voltage-gated channel subfamily E member 1 (IKs producing slow voltage-gated potassium channel beta subunit Mink) (Minimal potassium channel) (Delayed rectifier potassium channel subunit IsK) | KCNE1 | 2.19 | 0.0377 |
| MmugDNA.39110.1.S1_at | membrane component chromosome 11 surface marker 1 isoform 1 | LOC717473 | 2.19 | 0.0812 |
| MmugDNA.2250.1.S1_at | hypothetical protein LOC716978 | LOC716978 | 2.19 | 0.0969 |
| MmugDNA.17877.1.S1_s_at | — | — | 2.19 | 0.0717 |
| MmugDNA.24132.1.S1_at | F16A11.1 | LOC703783 | 2.19 | 0.0504 |
| MmugDNA.34793.1.S1_at | — | — | 2.19 | 0.0542 |
| MmugDNA.7971.1.S1_at | hypothetical protein LOC719652 | LOC719652 | 2.19 | 0.0475 |
| MmugDNA.96.1.S1_at | — | — | 2.18 | 0.0813 |
| MmuSTS.2238.1.S1_at | collapsin response mediator protein 1 | CRMP1 | 2.18 | 0.0048 |
| MmugDNA.17576.1.S1_at | p21-activated kinase 1 | LOC698585 | 2.18 | 0.0691 |
| MmugDNA.42599.1.S1_at | acyl-CoA synthetase long-chain family member 5 isoform a | LOC696404 | 2.18 | 0.0180 |
| MmuSTS.4809.1.S1_at | fucosyltransferase 8 | FUT8 | 2.18 | 0.0898 |
| MmugDNA.33186.1.S1_at | kelch-like 20 | LOC708546 | 2.18 | 0.0022 |

-continued

| Probe Set ID | Gene Title | Gene Symbol | Ratio Top verus Bottom | p value Top versus Bottom |
|---|---|---|---|---|
| MmugDNA.39650.1.S1_at | multiple coagulation factor deficiency 2 | LOC717900 | 2.18 | 0.0365 |
| MmugDNA.12193.1.S1_at | beta chimerin | CHN2 | 2.18 | 0.0041 |
| MmugDNA.35302.1.S1_at | sterol regulatory element-binding transcription factor 2 | LOC712307 | 2.18 | 0.0113 |
| MmugDNA.327.1.S1_at | — | — | 2.18 | 0.0722 |
| MmugDNA.38687.1.S1_at | hypothetical protein LOC698137 | LOC698137 | 2.18 | 0.0558 |
| MmugDNA.7208.1.S1_at | seizure related 6 homolog (mouse)-like 2 isoform 2 | LOC707244 | 2.18 | 0.0767 |
| MmugDNA.16529.1.S1_at | twisted gastrulation | LOC705804 | 2.18 | 0.0004 |
| Mmu.1309.1.S1_at | BCL2-associated transcription factor 1 | BCLAF1 | 2.18 | 0.0898 |
| MmugDNA.42025.1.S1_at | — | — | 2.17 | 0.0333 |
| MmugDNA.20036.1.S1_at | — | — | 2.17 | 0.0261 |
| MmugDNA.36083.1.S1_at | — | — | 2.17 | 0.0019 |
| MmuSTS.4278.1.S1_at | secretagogin precursor | LOC694072 | 2.17 | 0.0504 |
| MmuSTS.4293.1.S1_at | CEGP1 protein | LOC708152 | 2.17 | 0.0095 |
| Mmu.12751.1.S1_at | Grancalcin | GCA | 2.17 | 0.0079 |
| MmuSTS.4137.1.S1_at | ectonucleoside triphosphate diphosphohydrolase 6 | ENTPD6 | 2.17 | 0.0582 |
| MmugDNA.36157.1.S1_at | — | — | 2.17 | 0.0466 |
| MmugDNA.40937.1.S1_at | hypothetical protein LOC699965 | LOC699965 | 2.17 | 0.0264 |
| MmugDNA.41687.1.S1_at | — | — | 2.17 | 0.0243 |
| MmugDNA.32233.1.S1_s_at | Transmembrane protein 50B (HCV p7-transregulated protein 3) | TMEM5OB | 2.17 | 0.0009 |
| MmugDNA.38432.1.S1_at | WD repeat and FYVE domain containing 3 isoform 1 | LOC706535 | 2.17 | 0.0583 |
| MmuSTS.2292.1.S1_at | protein phosphatase 1, regulatory (inhibitor) subunit 3F | LOC715950 | 2.17 | 0.0293 |
| MmugDNA.28838.1.S1_at | tumor necrosis factor receptor superfamily, member 25 | TNFRSF25 | 2.17 | 0.0954 |
| MmugDNA.43442.1.S1_at | — | — | 2.17 | 0.0092 |
| MmugDNA.40985.1.S1_at | — | — | 2.17 | 0.0995 |
| MmugDNA.1900.1 Si_s_at | — | — | 2.16 | 0.0135 |
| Mmu.11367.1.S1_ t | developmentally regulated protein TPO1 | LOC710413 | 2.16 | 0.0661 |
| MmugDNA.11644. .S1_at | CG5022-PA | LOC711670 | 2.16 | 0.0671 |
| MmugDNA.5070.1 S1_at | hypothetical protein LOC709015 | LOC709015 | 2.16 | 0.0456 |
| MmugDNA.34622. .S1_at | B aggressive lymphoma gene | PARP9 | 2.16 | 0.0894 |
| MmugDNA.28503. .S1_at | — | — | 2.16 | 0.0168 |
| MmugDNA.14771. .S1_s_at | — | — | 2.16 | 0.0146 |
| MmugDNA.4305.1 S1_at | — | — | 2.16 | 0.0396 |
| MmugDNA.42501. .S1_at | Dmx-like 2 | LOC693954 | 2.16 | 0.0536 |
| Mmu.828.1.S1_at | leucine rich repeat containing 40 | LOC702565 | 2.16 | 0.0103 |
| MmugDNA.26452.1.S1_at | TRIO and F-actin-binding protein (Protein Tara) (Trio-associated repeat on actin) | LOC701241 | 2.16 | 0.0659 |
| MmugDNA.14006.1.S1_at | methyltransferase 5 domain containing 1 | LOC698208 | 2.16 | 0.0220 |
| MmugDNA.16489.1.S1_at | — | — | 2.16 | 0.0929 |
| MmugDNA.33403.1.S1_at | WD repeat and SOCS box-containing protein 2 (WSB-2) (CS box-containing WD protein) | LOC695359 | 2.16 | 0.0010 |
| MmuSTS.3848.1.S1_at | Surfeit locus protein 5 | LOC714097 | 2.16 | 0.0346 |
| MmugDNA.28161.1.S1_at | AMIGO protein | AMIGO1 | 2.16 | 0.0117 |
| Mmu.1020.1.S1_s_at | cysteine-rich with EGF-like domains 1 isoform 2 | LOC699345 | 2.15 | 0.0581 |
| MmugDNA.23895.1.S1_at | — | — | 2.15 | 0.0568 |
| MmugDNA.34300.1.S1_at | — | — | 2.15 | 0.0476 |
| MmugDNA.25815.1.S1_at | — | — | 2.15 | 0.0128 |
| MmuSTS.2538.1.S1_at | Interleukin-13 receptor alpha-1 chain precursor (IL-13R-alpha-1) (IL-13RA-1) (CD213a1 antigen) | LOC710986 | 2.15 | 0.0172 |
| MmugDNA.31245.1.S1_at | butyrophilin, subfamily 2, member A2 isoform a | LOC699861 | 2.15 | 0.0979 |
| MmugDNA.36602.1.S1_at | transducin-like enhancer protein 1 | LOC707336 | 2.15 | 0.0343 |
| MmugDNA.21781.1.S1_at | Testis-specific Y-encoded-like protein 3 (TSPY-like 3) | LOC712128 | 2.15 | 0.0723 |
| Mmu.2576.1.S1_at | RING1 and YY1 binding protein | LOC694390 | 2.15 | 0.0893 |
| MmugDNA.9098.1.S1_at | SWI/SNF related, matrix associated, actin dependent regulator of chromatin, subfamily a, member 1 | SMARCA1 | 2.15 | 0.0737 |
| MmugDNA.14464.1.S1_at | ornithine decarboxylase antizyme inhibitor | LOC693581 | 2.15 | 0.0021 |
| MmugDNA.6468.1.S1_at | WD repeat domain 48 | LOC695026 | 2.15 | 0.0807 |
| MmugDNA.12543.1.S1_at | R13A5.9 | LOC710476 | 2.14 | 0.0209 |
| MmugDNA.35647.1.S1_at | BTB and kelch domain containing 3 | LOC706382 | 2.14 | 0.0185 |
| MmugDNA.18973.1.S1_at | nucleobindin 1 | LOC718380 | 2.14 | 0.0548 |
| MmugDNA.7913.1.S1_at | — | — | 2.14 | 0.0589 |
| MmugDNA.9254.1.S1_at | solute carrier family 35, member C1 | SLC35C1 | 2.14 | 0.0474 |
| MmuSTS.702.1.S1_at | inhibin, beta B (activin AB beta polypeptide) | INHBB | 2.14 | 0.0076 |
| MmugDNA.1591.1.S1_at | — | — | 2.14 | 0.0915 |
| Mmu.8048.1.S1_at | protein phosphatase 3 (formerly 2B), catalytic subunit, alpha isoform (calcineurin A alpha) | PPP3CA | 2.13 | 0.0704 |
| MmugDNA.19851.1.S1_at | — | — | 2.13 | 0.0874 |
| MmugDNA.5616.1.S1_at | serine/threonine kinase 38 | STK38 | 2.13 | 0.0148 |
| MmugDNA.4789.1.S1_at | TP53-regulating kinase (p53-related protein kinase) (Nori-2) | LOC716636 | 2.13 | 0.0179 |
| MmugDNA.38238.1.S1_at | stearoyl-CoA desaturase (delta-9-desaturase) | LOC694079 | 2.13 | 0.0088 |
| MmugDNA.14345.1.S1_s_at | — | — | 2.13 | 0.0164 |
| MmugDNA.17444.1.S1_at | nucleoplasmin 2 | LOC715448 | 2.13 | 0.0571 |
| MmuSTS.4377.1.S1_at | — | — | 2.13 | 0.0948 |
| MmugDNA.26500.1.S1_at | KIAA0564 protein | KIAA0564 | 2.13 | 0.0336 |
| MmugDNA.4249.1.S1_at | — | — | 2.13 | 0.0344 |
| MmuSTS.935.1.S1_at | talin 2 | LOC705008 | 2.13 | 0.0652 |

-continued

| Probe Set ID | Gene Title | Gene Symbol | Ratio Top verus Bottom | p value Top versus Bottom |
|---|---|---|---|---|
| MmugDNA.33197.1.S1_at | — | — | 2.13 | 0.0665 |
| MmugDNA.39459.1.S1_at | Sec23 (S. cerevisiae) homolog B | LOC698440 | 2.13 | 0.0020 |
| MmuSTS.3997.1.S1_at | — | — | 2.12 | 0.0188 |
| Mmu.9557.1.S1_at | OTU domain containing 4 protein isoform 1 | LOC701837 | 2.12 | 0.0798 |
| MmugDNA.14887.1.S1_at | Protein NipSnap1 | LOC717745 | 2.12 | 0.0225 |
| MmugDNA.25767.1.S1_at | like-glycosyltransferase | LOC717403 | 2.12 | 0.0858 |
| MmugDNA.30227.1.S1_at | nitric oxide synthase trafficking isoform 1 | LOC705063 | 2.12 | 0.0210 |
| MmugDNA.29197.1.S1_at | hypothetical protein LOC698413 | LOC698413 | 2.12 | 0.0069 |
| MmugDNA.35367.1.S1_at | — | — | 2.12 | 0.0045 |
| MmuSTS.1000.1.S1_at | myoneurin | LOC698094 | 2.12 | 0.0044 |
| MmugDNA.27645.1.S1_at | hypothetical protein LOC710801 | LOC710801 | 2.12 | 0.0193 |
| MmugDNA.32669.1.S1_at | Sur-8 CG5407-PA, isoform A | — | 2.12 | 0.0319 |
| MmugDNA.43367.1.S1_at | genetic suppressor element 1 | LOC693298 | 2.12 | 0.0210 |
| MmugDNA.41452.1.S1_at | sperm protein 17 | L00574157 | 2.12 | 0.0436 |
| MmugDNA.37832.1.S1_at | — | — | 2.12 | 0.0135 |
| MmugDNA.33994.1.S1_at | unc-5 homolog B | LOC715786 | 2.12 | 0.0074 |
| MmugDNA.31700.1.S1_at | stromal membrane-associated protein 1-like | LOC694502 | 2.12 | 0.0138 |
| MmugDNA.12779.1.S1_at | remodeling and spacing factor 1 | LOC699078 | 2.12 | 0.0480 |
| MmugDNA.20356.1.S1_at | platelet-activating factor acetylhydrolase 2 | LOC719750 | 2.11 | 0.0689 |
| MmuSTS.1250.1.S1_at | cAMP responsive element binding protein-like 2 | LOC696952 | 2.11 | 0.0786 |
| MmugDNA.1301.1.S1_at | InaD-like protein isoform 1 | LOC694408 | 2.11 | 0.0733 |
| MmugDNA.38366.1.S1_at | Eukaryotic translation initiation factor 3 subunit 1 (eIF-3alpha) | LOC712295 | 2.11 | 0.0343 |
| MmugDNA.15094.1.S1_at | hypothetical protein LOC699533 | LOC699533 | 2.11 | 0.0073 |
| MmugDNA.24933.1.S1_at | hypothetical protein LOC701291 | LOC701291 | 2.11 | 0.0405 |
| MmugDNA.18451.1.S1_at | Peroxiredoxin-4 (Prx-IV) (Thioredoxin peroxidase A0372) (Thioredoxin-dependent peroxide reductase A0372) (Antioxidant enzyme A0E372) (A0E37-2) | LOC697635 | 2.11 | 0.0133 |
| MmugDNA.30695.1.S1_at | — | — | 2.11 | 0.0121 |
| MmugDNA.21266.1.S1_s_at | sorcin isoform b | LOC705215 | 2.11 | 0.0255 |
| MmugDNA.41706.1.S1_at | — | — | 2.11 | 0.0059 |
| MmuSTS.2300.1.S1_at | — | — | 2.11 | 0.0732 |
| MmuSTS.2136.1.S1_at | AXIN1 up-regulated 1 | LOC694328 | 2.10 | 0.0010 |
| MmugDNA.34250.1.S1_at | hypothetical protein LOC697587 | LOC697587 | 2.10 | 0.0430 |
| MmugDNA.30761.1.S1_at | abhydrolase domain containing 10 | — | 2.10 | 0.0313 |
| MmugDNA.25568.1.S1_at | ligase III, DNA, ATP-dependent | LIG3 | 2.10 | 0.0203 |
| MmugDNA.41814.1.S1_at | Meis1 homolog | MEIS1 | 2.10 | 0.0730 |
| MmugDNA.23946.1.S1_at | — | — | 2.10 | 0.0824 |
| MmugDNA.15939.1.S1_at | — | — | 2.10 | 0.0599 |
| MmuSTS.3941.1.S1_at | cell cycle progression 1 isoform 2 | LOC698918 | 2.09 | 0.0097 |
| MmugDNA.31766.1.S1_at | — | — | 2.09 | 0.0173 |
| MmugDNA.34607.1.S1_at | THAP domain containing 7 | LOC693821 | 2.09 | 0.0838 |
| Mmu.10002.1.S1_at | methionine adenosyltransferase II, alpha | MAT2A | 2.09 | 0.0100 |
| MmugDNA.8056.1.S1_at | Uteroglobin precursor (Secretoglobin family 1A member 1) (Clara cell phospholipid-binding protein) (CCPBP) (Clara cells 10 kDa secretory protein) (CC10) (Urinary protein 1) (Urine protein 1) (UP1) | LOC718857 | 2.09 | 0.0677 |
| MmugDNA.8398.1.S1_at | odd Oz/ten-m homolog 3 | LOC700867 | 2.09 | 0.0151 |
| MmugDNA.41504.1.S1_at | SUM01/sentrin/SMT3 specific protease 2 | SENP2 | 2.09 | 0.0168 |
| MmugDNA.25057.1.S1_s_at | VW/ domain containing E3 ubiquitin protein ligase 2 | VVVVP2 | 2.09 | 0.0899 |
| MmugDNA.30167.1.S1_at | tumor rejection antigen (gp96) 1 | HSP90B1 | 2.09 | 0.0317 |
| MmugDNA.23937.1.S1_at | — | — | 2.09 | 0.0679 |
| MmunewRS.900.1.S1_at | — | — | 2.08 | 0.0913 |
| Mmu.13707.1.S1_at | Transcribed locus, moderately XP_001163736.1 prostaglandin-D synthase +Pan troglodytes+ | — | 2.08 | 0.0995 |
| MmugDNA.42106.1.S1_at | — | — | 2.08 | 0.0031 |
| MmugDNA.25377.1.S1_at | — | — | 2.08 | 0.0867 |
| MmugDNA.33263.1.S1_at | amine oxidase, copper containing 2 isoform b | LOC711900 | 2.08 | 0.0495 |
| Mmu.10780.1.S1_at | ATP-binding cassette, sub-family D, member 3 | ABCD3 | 2.08 | 0.0668 |
| MmugDNA.23614.1.S1_at | DDHD domain containing 1 | LOC694361 | 2.08 | 0.0695 |
| MmugDNA.28356.1.S1_at | hypothetical protein LOC715793 | LOC715793 | 2.08 | 0.0799 |
| MmugDNA.39375.1.S1_at | oligonucleotide/oligosaccharide-binding fold containing 1 | LOC714968 | 2.08 | 0.0397 |
| MmugDNA.17230.1.S1_at | ets homologous factor | LOC717350 | 2.08 | 0.0092 |
| MmugDNA.43483.1.S1_at | ubiquitin specific protease 47 | USP47 | 2.07 | 0.0354 |
| MmuSTS.4574.1.S1_at | Alpha-mannosidase IIx (Mannosyl-oligosaccharide 1,3-1,6-alpha-mannosidase) (MAN 11x) (Mannosidase alpha class 2A member 2) | MAN2A2 | 2.07 | 0.0066 |
| MmugDNA.42098.1.S1_at | AP-1 complex subunit sigma-2 (Adapter-related protein complex 1 sigma-1 B subunit) (Sigma-adaptin 1 B) (Adaptor protein complex AP-1 sigma-1 B subunit) (Golgi adaptor HA1 /AP1 adaptin sigma-1B subunit) (Clathrin assembly protein complex 1 si... | LOC713244 | 2.07 | 0.0007 |
| MmugDNA.21632.1.S1_at | KIAA0368 protein | KIAA0368 | 2.07 | 0.0077 |
| MmugDNA.8695.1.S1_at | — | — | 2.07 | 0.0027 |
| MmugDNA.3713.1.S1_at | CG14535-PA | LOC712374 | 2.07 | 0.0672 |
| MmugDNA.32882.1.S1_at | Hypothetical protein LOC718964 | — | 2.07 | 0.0156 |

-continued

| Probe Set ID | Gene Title | Gene Symbol | Ratio Top verus Bottom | p value Top versus Bottom |
|---|---|---|---|---|
| MmugDNA.39148.1.S1_at | — | — | 2.07 | 0.0379 |
| MmuSTS.2882.1.51_at | TCDD-inducible poly(ADP-ribose) polymerase | LOC706180 | 2.07 | 0.0051 |
| MmugDNA.6389.1.S1_at | — | — | 2.07 | 0.0452 |
| MmugDNA.25050.1.S1_at | restin | RSN | 2.07 | 0.0543 |
| MmugDNA.28737.1.S1_at | CG2843-PA | LOC695474 | 2.07 | 0.0871 |
| MmugDNA.39973.1.S1_at | Jade1 protein long isoform | LOC693690 | 2.06 | 0.0012 |
| Mmu.14041.1.S1_at | ubiquitin specific protease 15 | USP15 | 2.06 | 0.0149 |
| MmugDNA.30790.1.S1_at | chromobox homolog 7 | CBX7 | 2.06 | 0.0331 |
| MmugDNA.35116.1.51_at | kelch-like 12 | LOC694420 /// LOC694548 /// LOC705991 | 2.06 | 0.0120 |
| MmugDNA.9677.1.S1_at | — | — | 2.06 | 0.0871 |
| MmugDNA.16866.1.S1_at | Rho guanine nucleotide exchange factor (GEF) 10-like isoform 2 | LOC701164 | 2.06 | 0.0444 |
| MmugDNA.12243.1.S1_at | — | — | 2.06 | 0.0214 |
| MmuSTS.1567.1.S1_at | diphosphomevalonate decarboxylase | MVD | 2.06 | 0.0860 |
| MmuSTS.4422.1.S1_at | tripartite motif-containing 36 | TRIM36 | 2.06 | 0.0017 |
| MmuSTS.3089.1.S1_at | latrophilin 1 | LPHN1 | 2.06 | 0.0754 |
| MmugDNA.3623.1.S1_at | CG30497-PA, isoform A | LOC714457 | 2.06 | 0.0085 |
| MmuSTS.633.1.S1_at | apical protein of Xenopus-like | APXL | 2.06 | 0.0169 |
| MmuSTS.3572.1.S1_at | coronin, actin binding protein, 2B | CORO2B | 2.06 | 0.0096 |
| MmugDNA.8806.1.S1_at | — | — | 2.06 | 0.0017 |
| MmugDNA.15578.1.S1_at | — | — | 2.06 | 0.0364 |
| MmugDNA.25084.1.51_at | baculoviral IAP repeat-containing 6 | BIRC6 | 2.05 | 0.0157 |
| MmugDNA.1057.1.S1_at | DnaJ (Hsp40) homolog, subfamily A, member 1 | DNAJA1 | 2.05 | 0.0253 |
| MmugDNA.28429.1.S1_at | hypothetical protein LOC716268 | LOC716268 | 2.05 | 0.0256 |
| MmugDNA.25034.1.51_at | regulator of G-protein signalling 11 isoform 1 | LOC694588 | 2.05 | 0.0266 |
| MmugDNA.42945.1.S1_at | — | — | 2.05 | 0.0548 |
| MmugDNA.26306.1.51_at | — | — | 2.05 | 0.0580 |
| MmugDNA.17707.1.S1_at | — | — | 2.05 | 0.0141 |
| MmugDNA.1190.1.S1_at | dpy-19-like 1, like | LOC699789 /// LOC707898 /// LOC709323 | 2.05 | 0.0511 |
| MmugDNA.32656.1.S1_at | axonemal dynein light chain 1 | LOC697410 | 2.05 | 0.0635 |
| MmugDNA.20986.1.S1_s_at | cytochrome P450, family 39, subfamily A, polypeptide 1 | LOC704242 | 2.05 | 0.0860 |
| MmugDNA.19048.1.S1_at | SDA1 domain containing 1 | LOC700863 | 2.05 | 0.0742 |
| MmugDNA.39253.1.S1_at | CDC42 effector protein 5 | LOC718922 | 2.05 | 0.0045 |
| MmugDNA.14544.1.S1_at | — | — | 2.05 | 0.0125 |
| MmugDNA.4740.1.S1_at | chromosome 2 open reading frame 7 | LOC706052 | 2.04 | 0.0714 |
| MmugDNA.5141.1.S1_at | hypothetical protein LOC715248 | LOC715248 | 2.04 | 0.0755 |
| MmugDNA.19626.1.S1_at | tripartite motif protein 32 (predicted) | LOC705563 | 2.04 | 0.0199 |
| Mmu.2091.3.S1_x_at | HLA class I histocompatibility antigen, A-74 alpha chain precursor (MHC class I antigen A*74) (Aw-74) (Aw-19) /// HLA class I histocompatibility antigen, B-38 alpha chain precursor (MHC class I antigen B*38) (Bw-4) /// major histocom | LOC699243 /// LOC699987/// LOC715737 /// LOC721022 /// LOC723284 /// LOC723552 /// MAMU-A | 2.04 | 0.0896 |
| MmugDNA.40849.1.S1_at | 7-dehydrocholesterol reductase | DHCR7 | 2.04 | 0.0437 |
| MmugDNA.2414.1.S1_at | plastin 1 | PLS1 | 2.04 | 0.0023 |
| MmugDNA.19830.1.S1_at | glycoprotein hormone alpha 2 | LOC717261 | 2.04 | 0.0977 |
| MmugDNA.27493.1.S1_at | Rho-guanine nucleotide exchange factor (Rho-interacting protein 2) (RhoGEF) (RIP2) | LOC703897 | 2.04 | 0.0532 |
| Mmu.1943.1.S1_at | Taxi (human T-cell leukemia virus type I) binding protein 1 | LOC698103 | 2.04 | 0.0133 |
| MmunewRS.977.1.S1_s_at | hypothetical protein LOC719873 | LOC719873 | 2.04 | 0.0805 |
| MmugDNA.28230.1.S1_at | intersex-like | LOC698032 | 2.04 | 0.0031 |
| MmugDNA.14009.1.S1_s_at | 5T4 oncofetal trophoblast glycoprotein | LOC693944 | 2.04 | 0.0005 |
| MmugDNA.3795.1.S1_at | dynactin 4 (p62) | DCTN4 | 2.04 | 0.0039 |
| MmugDNA.24691.1.S1_at | selenoprotein I | SELI | 2.04 | 0.0078 |
| MmugDNA.5288.1.S1_at | pyridoxine 5'-phosphate oxidase | PNPO | 2.04 | 0.0025 |
| MmuSTS.2059.1.S1_at | phospholipase C beta 4 isoform a | LOC718418 | 2.04 | 0.0043 |
| MmugDNA.10284.1.S1_at | MORC family CW-type zinc finger 2 | MORC2 | 2.04 | 0.0531 |
| MmugDNA.22142.1.S1_at | — | — | 2.04 | 0.0858 |
| MmuSTS.3730.1.S1_at | SLIT-ROBO Rho GTPase activating protein 2 | SRGAP2 | 2.04 | 0.0146 |
| MmugDNA.21501.1.S1_at | — | — | 2.03 | 0.0030 |
| MmuSTS.4228.1.S1_at | dehydrogenase/reductase (SDR family) member 8 | DHRS8 | 2.03 | 0.0360 |
| MmugDNA.14076.1.S1_s_at | tripartite motif-containing 59 | LOC704829 | 2.03 | 0.0593 |
| MmuSTS.4498.1.S1_at | LGP1 homolog | LOC709656 | 2.03 | 0.0795 |
| MmugDNA.37577.1.S1_at | MAM domain containing glycosylphosphatidylinositol anchor 1 | LOC719423 | 2.03 | 0.0884 |
| MmugDNA.3734.1.S1_at | eukaryotic translation initiation factor 5A2 | LOC695647 | 2.03 | 0.0565 |
| MmugDNA.1893.1.S1_at | RNA guanylyltransferase and 5-phosphatase | LOC721442 | 2.03 | 0.0469 |
| MmugDNA.2395.1.S1_at | — | — | 2.03 | 0.0090 |
| MmugDNA.8455.1.S1_at | tigger transposable element derived 2 | LOC706461 | 2.03 | 0.0283 |
| MmugDNA.20114.1.S1_at | translocating chain-associating membrane protein | TRAM1 | 2.03 | 0.0380 |
| MmugDNA.442.1.S1_at | UDP-Gal:betaGlcNAc beta 1,3-galactosyltransferase 4 | B3GALT4 | 2.03 | 0.0668 |

-continued

| Probe Set ID | Gene Title | Gene Symbol | Ratio Top verus Bottom | p value Top versus Bottom |
|---|---|---|---|---|
| MmugDNA.476.1.S1_s_at | programmed cell death 6 interacting protein | LOC706636 | 2.03 | 0.0387 |
| MmugDNA.39070.1.S1_at | androgen-induced 1 | LOC700988 | 2.03 | 0.0113 |
| MmugDNA.38882.1.S1_at | hypothetical protein LOC712812 | LOC712812 | 2.03 | 0.0123 |
| Mmu.6318.1.S1_at | family with sequence similarity 18, member B /// Protein FAM18B | FAM18B /// LOC719298 /// LOC723697 | 2.03 | 0.0170 |
| Mmu.2050.1.S1_s_at | HIG1 domain family member 1A (Hypoxia-inducible gene 1 protein) | HIGD1A | 2.03 | 0.0066 |
| MmugDNA.8048.1.S1_at | calcium/calmodulin-dependent protein kinase II inhibitor 1 | LOC705302 | 2.02 | 0.0005 |
| MmugDNA.10177.1.S1_at | TNF receptor-associated factor 3 | TRAF3 | 2.02 | 0.0434 |
| MmuSTS.735.1.S1_at | — | — | 2.02 | 0.0009 |
| MmugDNA.1551.1.S1_s_at | chloride channel 3 isoform c | LOC694472 | 2.02 | 0.0414 |
| Mmu.7639.1.S1_at | signal transducer and activator of transcription 1 | STAT1 | 2.02 | 0.0894 |
| MmuSTS.2418.1.S1_at | — | — | 2.02 | 0.0452 |
| MmuSTS.88.1.S1_at | — | — | 2.02 | 0.0434 |
| MmugDNA.29466.1.S1_at | phosphorylase kinase, beta | PHKB | 2.02 | 0.0634 |
| MmugDNA.21556.1.S1_at | DNA primase large subunit, 58 kDa | LOC712921 | 2.02 | 0.0187 |
| Mmu.4348.1.S1_at | membrane interacting protein of RGS16 | LOC694849 | 2.02 | 0.0243 |
| MmugDNA.2374.1.S1_at | — | — | 2.02 | 0.0321 |
| MmugDNA.20015.1.Sl_at | — | — | 2.02 | 0.0683 |
| MmuSTS.1350.1.S1_at | — | — | 2.02 | 0.0712 |
| MmugDNA.15232.1.S1_at | — | — | 2.02 | 0.0376 |
| MmugDNA.7589.1.S1_at | F-box only protein 24 isoform 1 | LOC719216 | 2.02 | 0.0212 |
| MmugDNA.12745. .Sl_at | integrin, alpha 8 | ITGA8 | 2.02 | 0.0990 |
| MmugDNA.20321. .Sl_at | HIR (histone cell cycle regulation defective, S. cerevisiae) homolog A | LOC719142 | 2.02 | 0.0441 |
| MmuSTS.2829.1.S_at | — | — | 2.02 | 0.0906 |
| MmugDNA.12571. .Sl_at | Ras-associated protein Rapt | LOC694037 | 2.02 | 0.0243 |
| MmugDNA.34707. .Sl_at | slit and trk like 6 | LOC699338 | 2.02 | 0.0231 |
| MmugDNA.19770. .Sl_at | tumor differentially expressed 2-like | SERINC2 | 2.01 | 0.0493 |
| MmugDNA.18541. .Sl_at | RAB guanine nucleotide exchange factor (GEF) 1 | LOC695887 | 2.01 | 0.0739 |
| MmugDNA.8837.1.S1_at | karyopherin alpha 4 | KPNA4 | 2.01 | 0.0619 |
| MmugDNA.22626. .Sl_at | dihydrolipoamide S-acetyltransferase (E2 component of pyruvate dehydrogenase complex) | — | 2.01 | 0.0061 |
| MmugDNA.6899.1.S1_at | — | — | 2.01 | 0.0370 |
| MmugDNA.40422.1.S1_at | — | — | 2.01 | 0.0545 |
| MmugDNA.12060.1.S1_at | UDP-glucose:glycoprotein glucosyltransferase 2 | LOC697784 | 2.01 | 0.0461 |
| MmugDNA.23452.1.S1_at | valosin containing protein (p97)/p47 complex interacting protein 1 | LOC703582 | 2.01 | 0.0501 |
| MmugDNA.6995.1.S1_at | — | — | 2.01 | 0.0671 |
| MmugDNA.599.1.S1_at | dpy-19-like 3 | LOC700921 | 2.01 | 0.0681 |
| Mmu.2601.1.S1_at | transmembrane emp24 protein transport domain containing 4 | LOC699105 | 2.01 | 0.0032 |
| MmuSTS.4174.1.S1_at | Cathepsin F precursor (CATSF) | LOC713743 | 2.01 | 0.0025 |
| MmugDNA.26527.1.S1_at | zinc finger protein 697 | LOC715582 | 2.01 | 0.0171 |
| MmunewRS.902.1.S1_at | embigin homolog | LOC702068 | 2.01 | 0.0964 |
| MmugDNA.10114.1.S1_at | odd Oz/ten-m homolog 4 | LOC701138 | 2.01 | 0.0938 |
| MmugDNA.37121.1.S1_at | dishevelled-associated activator of morphogenesis 1 | LOC701706 | 2.01 | 0.0282 |
| MmugDNA.34099.1.S1_at | — | — | 2.00 | 0.0953 |
| MmugDNA.25664.1.S1_at | zinc finger protein 710 | LOC701358 | 2.00 | 0.0791 |
| MmugDNA.33143.1.S1_at | nuclear factor, interleukin 3 regulated | LOC704757 | 2.00 | 0.0359 |
| MmugDNA.4085.1.S1_at | cyclin El isoform 1 | LOC700589 | 2.00 | 0.0203 |
| MmuSTS.749.1.S1_at | LysM, putative peptidoglycan-binding, domain containing 1 | LOC709539 | 2.00 | 0.0752 |
| MmugDNA.24820.1.S1_at | casein kinase 1, gamma 3 | CSNK1G3 | 2.00 | 0.0461 |
| MmugDNA.29470.1.S1_at | — | — | 2.00 | 0.0098 |
| MmugDNA.19512.1.S1_at | tenascin C (hexabrachion) | TNC | 92.06 | 0.0005 |
| MmugDNA.6877.1.S1_at | ankyrin repeat and sterile alpha motif domain containing 1B | LOC694033 | 37.28 | 0.0256 |
| MmuSTS.2164.1.S1_s_at | BUB1 budding uninhibited by benzimidazoles 1 homolog | LOC696598 | 30.10 | 0.0998 |
| MmuSTS.355.1.S1_at | podoplanin | PDPN | 29.70 | 0.0578 |
| MmugDNA.23448.1.S1_at | Keratin, type I cytoskeletal 14 (Cytokeratin-14) (CK-14) (Keratin-14) (K14) | LOC703932 | 26.57 | 0.0038 |
| MmugDNA.1670.1.S1_at | cysteine and tyrosine-rich 1 protein precursor | LOC708008 | 25.38 | 0.0325 |
| MmuSTS.4685.1.S1_at | thymidylate synthetase | TYMS | 24.58 | 0.0475 |
| MmugDNA.2975.1.S1_at | DNA polymerase epsilon subunit 2 | LOC707526 | 24.10 | 0.0653 |
| MmugDNA.32729.1.S1_at | antigen identified by monoclonal antibody Ki-67 | MKI67 | 22.59 | 0.0758 |
| MmugDNA.33387.1.S1_at | T-LAK cell-originated protein kinase | PBK | 19.75 | 0.0623 |
| MmuSTS.3275.1.S1_at | Probable dimethyladenosine transferase (S-adenosylmethionine-6-N,N-adenosyl(rRNA) dimethyltransferase) (18S rRNA dimethylase) | — | 19.29 | 0.0213 |
| MmugDNA.13802.1.S1_at | decorin | DCN | 17.00 | 0.0183 |
| MmuSTS.4094.1.S1_at | endothelin receptor type B | EDNRB | 16.58 | 0.0867 |
| MmugDNA.17329.1.S1_at | cell division cycle associated 7 | LOC696474 | 16.22 | 0.0389 |
| MmugDNA.38956.1.S1_at | nucleolar and spindle associated protein 1 | NUSAP1 | 15.82 | 0.0583 |
| MmugDNA.24653.1.S1_at | hyaluronan-mediated motility receptor | HMMR | 14.87 | 0.0507 |
| MmugDNA.12273.1.S1_at | DNA topoisomerase II, alpha isozyme | TOP2A | 14.45 | 0.0012 |
| MmugDNA.17571.1.S1_at | Repetin | LOC712894 | 14.37 | 0.0893 |

-continued

| Probe Set ID | Gene Title | Gene Symbol | Ratio Top verus Bottom | p value Top versus Bottom |
|---|---|---|---|---|
| MmugDNA.40742.1.S1_at | cyclin B2 | LOC702184 | 14.17 | 0.0157 |
| MmugDNA.36470.1.S1_at | kinetochore associated 2 | LOC696232 | 13.85 | 0.0725 |
| MmugDNA.19272.1.S1_s_at | sperm associated antigen 5 | SPAG5 | 13.79 | 0.0181 |
| MmuSTS.844.1.S1_at | lymphocyte-specific protein 1 isoform 1 | LOC721048 | 13.75 | 0.0307 |
| MmugDNA.25384.1.S1_at | Ubiquitin-conjugating enzyme E2 C (Ubiquitin-protein ligase C) (Ubiquitin carrier protein C) (UbcH10) | UBE2C | 13.38 | 0.0002 |
| MmuSTS.2303.1.S1_s_at | discs large homolog 7 | LOC696772 | 13.04 | 0.0536 |
| MmuSTS.1203.1.S1_at | alpha 1 type XV collagen | COL15A1 | 12.52 | 0.0022 |
| MmugDNA.11364.1.S1_at | forkhead box M1 isoform 3 | LOC708805 | 12.31 | 0.0691 |
| MmugDNA.18486.1.S1_s_at | serine protease inhibitor, Kazal type 2 (acrosin-trypsin inhibitor) | LOC693946 | 12.30 | 0.0374 |
| MmuSTS.2672.1.S1_at | centromere protein F (350/400kD) | LOC709000 | 12.11 | 0.0860 |
| MmugDNA.41909.1.S1_at | endomucin | LOC709580 | 12.02 | 0.0215 |
| MmugDNA.24707.1.S1_at | Fibroblast growth factor 19 precursor (FGF-19) | FGF19 | 11.99 | 0.0680 |
| MmugDNA.19464.1.S1_at | ubiquitin-like, containing PHD and RING finger domains, 1 | LOC695531 | 11.73 | 0.0111 |
| MmugDNA.28534.1.S1_at | interleukin 1 receptor, type II | IL1 R2 | 11.11 | 0.0247 |
| MmuSTS.3846.1.S1_at | sulfotransferase, estrogen-preferring | SULT1E1 | 11.06 | 0.0880 |
| MmuSTS.1223.1.S1_at | periostin, osteoblast specific factor | POSTN | 10.97 | 0.0077 |
| MmugDNA.10977.1.S1_at | DAZ interacting protein 1 isoform 2 | LOC695529 | 10.94 | 0.0839 |
| MmugDNA.33823.1.S1_s_at | KIAA0101 | KIAA0101 | 10.89 | 0.0363 |
| MmugDNA.35172.1.S1_at | hypothetical protein LOC701037 | LOC701037 | 10.86 | 0.0896 |
| MmuSTS.1955.1.S1_at | baculoviral IAP repeat-containing protein 5 isoform 1 | LOC709565 | 10.69 | 0.0838 |
| MmugDNA.40509.1.S1_at | basonuclin 2 | BNC2 | 10.50 | 0.0020 |
| MmugDNA.33427.1.S1_at | — | — | 10.41 | 0.0428 |
| MmuSTS.3136.1.S1_at | Regulator of G-protein signaling 5 | RGS5 | 10.29 | 0.0555 |
| MmugDNA.4481.1.S1_at | EGF-containing fibulin-like extracellular matrix protein 1 precursor | LOC718984 | 10.22 | 0.0021 |
| MmuSTS.2035.1.S1_at | platelet-derived growth factor receptor alpha | PDGFRA | 10.01 | 0.0496 |
| MmuSTS.3987.1.S1_at | — | SLC27A3 | 9.99 | 0.0105 |
| MmugDNA.8100.1.S1_at | polymerase (DNA directed), epsilon | POLE | 9.87 | 0.0244 |
| MmugDNA.9037.1.S1_at | Nasopharyngeal carcinoma-associated antigen NPC-A-5 | — | 9.87 | 0.0936 |
| MmugDNA.33356.1.S1_at | development and differentiation enhancing factor 1 | LOC695681 | 9.84 | 0.0572 |
| MmugDNA.33929.1.S1_at | trophinin associated protein (tastin) | LOC709931 | 9.71 | 0.0772 |
| MmuSTS.4310.1.S1_at | histone 1, H2ai (predicted) | LOC695891 | 9.64 | 0.0566 |
| MmuSTS.2700.1.S1_at | E2F transcription factor 7 | LOC694423 | 9.61 | 0.0927 |
| MmugDNA.9851.1.S1_at | arachidonate 15-lipoxygenase | ALOX15 | 9.59 | 0.0773 |
| MmugDNA.4983.1.S1_at | collagen, type XXVII, alpha 1 | LOC708451 | 9.38 | 0.0390 |
| MmuSTS.2858.1.S1_at | SRY (sex determining region Y)-box 15 | SOX15 | 9.38 | 0.0147 |
| MmunewRS.17.1.S1_at | aurora kinase B | AURKB | 9.35 | 0.0340 |
| MmuSTS.1534.1.S1_at | — | KIF20A | 9.26 | 0.0827 |
| MmugDNA.34877.1.S1_at | melanoma-associated chondroitin sulfate proteoglycan 4 | LOC713086 | 9.25 | 0.0703 |
| MmuSTS.1125.1.S1_at | snail 2 | SNAI2 | 9.21 | 0.0089 |
| MmugDNA.37680.1.S1_at | WD repeat and HMG-box DNA binding protein 1 | WDHD1 | 9.11 | 0.0234 |
| MmugDNA.5089.1.S1_at | growth factor receptor-bound protein 10 isoform a | LOC694786 | 9.10 | 0.0634 |
| MmugDNA.40702.1.S1_at | enolase superfamily member 1 | ENOSF1 | 9.03 | 0.0552 |
| Mmu.11047.2.S1_s_at | Ig gamma-1 chain C region | LOC711303 | 8.99 | 0.0572 |
| MmuSTS.4834.1.S1_at | glioma-associated oncogene homolog 1 | GLI1 | 8.98 | 0.0230 |
| MmugDNA.32726.1.S1_at | Antigen KI-67 | LOC705021 | 8.97 | 0.0000 |
| MmugDNA.25678.1.S1_at | EGF-like-domain, multiple 9 | LOC700106 | 8.94 | 0.0026 |
| MmuSTS.3919.1.S1_s_at | regulator of G-protein signaling 10 isoform a | LOC703125 | 8.93 | 0.0254 |
| MmugDNA.23023.1.S1_at | hypothetical protein LOC702839 | LOC702839 | 8.93 | 0.0988 |
| MmugDNA.13565.1.S1_at | kinesin family member 11 | KIF11 | 8.83 | 0.0906 |
| MmuSTS.1877.1.S1_at | collagen, type XVIII, alpha 1 | COL18A1 | 8.81 | 0.0147 |
| MmugDNA.34601.1.S1_at | Ribosomal protein S6 | RPS6 | 8.79 | 0.0857 |
| MmugDNA.33493.1.S1_at | tumor protein p73-like | LOC703997 | 8.70 | 0.0516 |
| MmugDNA.13626.1.S1_at | prostaglandin 12 (prostacyclin) synthase /// prostaglandin 12 (prostacyclin) synthase | PTGIS | 8.67 | 0.0049 |
| MmugDNA.15250.1.S1_at | centromere protein A, 17 kDa | CENPA | 8.66 | 0.0498 |
| MmugDNA.32562.1.S1_s_at | Hemoglobin theta-1 subunit (Hemoglobin theta-1 chain) (Theta-1-globin) /// alpha 2 globin | HBQ1 /// LOC701930 | 8.53 | 0.0646 |
| MmugDNA.31059.1.S1_at | Securin (Pituitary tumor-transforming protein 1) (Tumor transforming protein 1) (Esp1-associated protein) (hPTTG) | PTTG1 | 8.52 | 0.0329 |
| MmugDNA.24523.1.S1_at | cell division cycle associated 2 | LOC711581 | 8.46 | 0.0921 |
| MmugDNA.33436.1.S1_at | thymosin-like 8 | LOC693501 | 8.40 | 0.0296 |
| MmugDNA.978.1.S1_at | CDNA FLJ41452 fis, clone BRSTN2010363 | — | 8.22 | 0.0795 |
| MmugDNA.21584.1.S1_s_at | — | — | 8.21 | 0.0000 |
| MmuSTS.2916.1.S1_at | iroquois homeobox protein 2 | IRX2 | 8.18 | 0.0698 |
| MmugDNA.7359.1.S1_s_at | TYRO protein tyrosine kinase binding protein | TYROBP | 8.15 | 0.0468 |
| MmugDNA.33098.1.S1_at | homeobox A3 isoform a | LOC699979 | 8.11 | 0.0577 |
| MmugDNA.18373.1.S1_at | hypothetical protein LOC697150 | LOC697150 | 8.11 | 0.0360 |
| MmugDNA.8851.1.S1_at | E2F transcription factor 2 | E2F2 | 8.10 | 0.0630 |
| MmugDNA.21962.1.S1_at | inhibin beta A | INHBA | 8.09 | 0.0493 |
| MmuSTS.1592.1.S1_at | neuritin | LOC722968 | 8.08 | 0.0300 |
| MmuSTS.4722.1.S1_at | thyroid hormone receptor interactor 13 | LOC709328 | 7.99 | 0.0914 |
| MmugDNA.16663.1.S1_at | alpha 1 type VII collagen | COL7A1 | 7.91 | 0.0603 |
| MmugDNA.5836.1.S1_at | pregnancy-associated plasma protein A, pappalysin 1 | PAPPA | 7.58 | 0.0602 |

-continued

| Probe Set ID | Gene Title | Gene Symbol | Ratio Top verus Bottom | p value Top versus Bottom |
|---|---|---|---|---|
| MmuSTS.2073.1.S1_at | peripheral myelin protein 22 | LOC693527 | 7.57 | 0.0237 |
| MmugDNA.29315.1.S1_at | DEP domain containing 1a | LOC701888 | 7.46 | 0.0609 |
| MmuSTS.4833.1.S1_at | gap junction protein, beta 5 (connexin 31.1) | LOC711078 | 7.46 | 0.0501 |
| MmugDNA.36119.1.S1_at | hypothetical protein FLJ10357 | FLJ10357 | 7.46 | 0.0549 |
| MmuSTS.4814.1.S1_at | gamma-aminobutyric acid (GABA) A receptor, epsilon | GABRE | 7.35 | 0.0325 |
| MmugDNA.29829.1.S1_at | hypothetical protein LOC718022 | LOC718022 | 7.26 | 0.0181 |
| MmugDNA.10011.1.S1_at | establishment of cohesion 1 homolog 2 | LOC713186 | 7.23 | 0.0759 |
| MmugDNA.15721.1.S1_at | DNA polymerase theta | POLO | 7.21 | 0.0495 |
| MmugDNA.23132.1.S1_s_at | muscleblind-like 1 | LOC708735 | 7.18 | 0.0870 |
| MmugDNA.16746.1.S1_at | Transcribed locus | — | 7.13 | 0.0397 |
| MmugDNA.9813.1.S1_at | steroid-sensitive protein 1 | LOC708504 | 7.09 | 0.0041 |
| MmugDNA.42865.1.S1_at | cell division cycle 2 protein | CDC2 | 7.09 | 0.0944 |
| MmuSTS.673.1.S1_s_at | chromatin assembly factor 1, subunit A (p150) | LOC721861 | 7.08 | 0.0407 |
| MmugDNA.42327.1.S1_at | fibulin 1 | FBLN1 | 7.05 | 0.0157 |
| MmuSTS.3146.1.S1_s_at | minichromosome maintenance deficient protein 5 | MCM5 | 7.02 | 0.0229 |
| MmugDNA.9770.1.S1_at | G-2 and S-phase expressed 1 | LOC714207 | 7.02 | 0.0673 |
| MmuSTS.4144.1.S1_at | glutathione transferase A5 | — | 7.01 | 0.0016 |
| MmugDNA.1499.1.S1_at | Pigment epithelium-derived factor precursor (PEDF) (EPC-1) | LOC721262 | 6.99 | 0.0750 |
| MmuSTS.1535.1.S1_at | kinesin family member 2C | KIF2C | 6.86 | 0.0738 |
| MmuSTS.3642.1.S1_at | fibroblast growth factor receptor 2 | FGFR2 | 6.84 | 0.0157 |
| MmugDNA.3959.1.S1_at | hypothetical protein LOC701440 | LOC701440 | 6.74 | 0.0674 |
| MmugDNA.22744.1.S1_s_at | — | — | 6.73 | 0.0581 |
| MmugDNA.10643.1.S1_s_at | Apolipoprotein D precursor (Apo-D) (ApoD) | LOC709223 | 6.71 | 0.0197 |
| MmugDNA.41251.1.S1_at | hypothetical protein LOC712701 | LOC712701 | 6.69 | 0.0805 |
| MmugDNA.25121.1.S1_at | pancreatic ribonuclease | RNASE1 | 6.65 | 0.0350 |
| MmugDNA.18755.1.S1_at | hypothetical protein LOC200030 | LOC200030 | 6.64 | 0.0332 |
| MmuSTS.644.1.S1_at | citron | LOC695846 | 6.63 | 0.0190 |
| MmugDNA.35559.1.S1_at | Histone H1.2 (H1 d) | LOC698238 | 6.62 | 0.0050 |
| MmugDNA.37528.1.S1_at | — | — | 6.57 | 0.0211 |
| MmugDNA.41268.1.S1_at | cyclin B1 | CCNB1 | 6.55 | 0.0927 |
| MmugDNA.40366.1.S1_at | solute carrier family 24, member 5 | SLC24A5 | 6.55 | 0.0000 |
| Mmu.5727.1.S1_at | G1/S-specific cyclin-D2 | CCND2 | 6.53 | 0.0003 |
| MmugDNA.9497.1.S1_at | kinesin family member C1 | KIFC1 | 6.44 | 0.0172 |
| MmuSTS.1904.1.S1_at | dicer1 | LOC702516 | 6.43 | 0.0387 |
| MmugDNA.25436.1.S1_at | minichromosome maintenance protein 3 | MCM3 | 6.40 | 0.0000 |
| MmuSTS.1881.1.S1_at | alpha 3 type VI collagen isoform 5 precursor | LOC694701 | 6.38 | 0.0086 |
| MmuSTS.4021.1.S1_at | cytochrome P450, family 4, subfamily B, polypeptide 1 | LOC709290 | 6.35 | 0.0285 |
| MmugDNA.35290.1.S1_at | hypothetical protein LOC696863 | LOC696863 | 6.33 | 0.0371 |
| MmugDNA.32826.1.S1_at | kallikrein 8 isoform 2 | — | 6.32 | 0.0948 |
| MmugDNA.36260.1.S1_at | EGF, latrophilin and seven transmembrane domain containing 1 | ELTD1 | 6.31 | 0.0018 |
| MmuSTS.4328.1.S1_at | plasminogen activator inhibitor type 1, member 2 | SERPINE2 | 6.28 | 0.0044 |
| MmugDNA.41228.1.S1_at | NADP-dependent leukotriene B4 12-hydroxydehydrogenase /// NADP-dependent leukotriene B4 12-hydroxydehydrogenase (15-oxoprostaglandin 13-reductase) | LTB4DH | 6.27 | 0.0527 |
| MmugDNA.31506.1.S1_at | 3-hydroxy-3-methylglutaryl-Coenzyme A synthase 2 (mitochondrial) | HMGCS2 | 6.25 | 0.0306 |
| MmuSTS.3741.1.S1_at | tyrosine phosphatase, receptor-type, Z polypeptide 1 | PTPRZ1 | 6.23 | 0.0829 |
| MmugDNA.20272.1.S1_at | cysteine-rich, angiogenic inducer, 61 | CYR61 | 6.21 | 0.0552 |
| MmugDNA.14075.1.S1_at | Restin | — | 6.21 | 0.0576 |
| MmugDNA.35622.1.S1_at | Kinesin family member 14 | KIF14 | 6.21 | 0.0036 |
| MmugDNA.19983.1.S1_s_at | testis derived transcript | CAV1 | 6.20 | 0.0330 |
| MmuSTS.1023.1.S1_at | — | SCN4B | 6.19 | 0.0994 |
| MmugDNA.42793.1.S1_at | calcium/calmodulin-dependent protein kinase kinase 1, alpha | CAMKK1 | 6.18 | 0.0467 |
| MmugDNA.23406.1.S1_at | SH3 domain containing ring finger 2 | SH3RF2 | 6.17 | 0.0135 |
| MmugDNA.19771.1.S1_at | Transcribed locus | — | 6.16 | 0.0821 |
| MmuSTS.1779.1.S1_at | NIMA (never in mitosis gene a)-related kinase 2 | NEK2 | 6.16 | 0.0886 |
| MmugDNA.7491.1.S1_at | Biliverdin reductase A | — | 6.13 | 0.0066 |
| MmugDNA.30433.1.S1_at | SHC SH2-domain binding protein 1 | LOC716009 | 6.05 | 0.0001 |
| MmugDNA.13151.1.S1_at | Probable G-protein coupled receptor 92 | GPR92 | 6.04 | 0.0268 |
| MmugDNA.39863.1.S1_at | chromosome 18 open reading frame 24 | C18orf24 | 5.99 | 0.0496 |
| MmugDNA.34856.1.S1_at | RNA binding motif protein 6 | RBM6 | 5.96 | 0.0446 |
| Mmu.16175.1.S1_at | CK230007 | — | 5.95 | 0.0684 |
| Mmu.11188.1.S1_at | caldesmon 1 isoform 4 | LOC707050 | 5.93 | 0.0513 |
| MmuSTS.2639.1.S1_at | FAT tumor suppressor 2 precursor | LOC713698 | 5.91 | 0.0047 |
| MmugDNA.22443.1.S1_at | nuclear factor I/B | NFIB | 5.88 | 0.0187 |
| MmugDNA.19397.1.S1_at | Chromosome 2 open reading frame 17 | C2orf17 | 5.88 | 0.0483 |
| MmugDNA.26212.1.S1_at | ephrin-B1 | EFNB1 | 5.88 | 0.0634 |
| MmugDNA.27687.1.S1_s_at | guanine nucleotide binding protein gamma 11 | LOC700606 | 5.87 | 0.0207 |
| MmugDNA.42502.1.S1_at | Activity-dependent neuroprotector | ADNP | 5.86 | 0.0016 |
| MmugDNA.35031.1.S1_at | Transcription factor COE1 (OE-1) (0/E-1) (Early B-cell factor) (Olfactory neuronal transcription factor) (01f-1) | LOC694086 | 5.82 | 0.0007 |
| Mmu.1262.1.A1_at | — | MEF2C | 5.82 | 0.0164 |
| | MADS box transcription enhancer factor 2, polypeptide C | | | |

-continued

| Probe Set ID | Gene Title | Gene Symbol | Ratio Top verus Bottom | p value Top versus Bottom |
|---|---|---|---|---|
| MmuSTS.2987.1.S1_at | (myocyte enhancer factor 2C) | LOC694992 | 5.77 | 0.0370 |
| MmugDNA.24078.1.S1_at | hypothetical protein LOC699417 | LOC699417 | 5.76 | 0.0711 |
| MmugDNA.40153.1.S1_at | olfactomedin-like 2A | OLFML2A | 5.74 | 0.0254 |
| MmugDNA.37742.1.S1_at | oncostatin M receptor | LOC693569 | 5.74 | 0.0716 |
| MmugDNA.8988.1.S1_at | hypothetical protein LOCI 43381 | LOCI 43381 | 5.70 | 0.0738 |
| MmugDNA.18189.1.S1_at | Insulin-like growth factor-binding protein 4 precursor (IGFBP-4) (IBP-4) (IGF-binding protein 4) | LOC700963 | 5.69 | 0.0440 |
| MmugDNA.8529.1.S1_at | Secretory granule proteoglycan core protein precursor (Platelet proteoglycan core protein) (P.PG) (Hematopoetic proteoglycan core protein) (Serglycin) | PRG1 | 5.63 | 0.0001 |
| MmugDNA.23178.1.S1_at | Chromobox homolog 5 (HP1 alpha homolog, Drosophila) | CBX5 | 5.59 | 0.0958 |
| MmugDNA.36354.1.S1_at | fibroblast growth factor receptor 3 | FGFR3 | 5.59 | 0.0298 |
| MmugDNA.39673.1.S1_at | SRY (sex determining region Y)-box 6 | SOX6 | 5.57 | 0.0064 |
| MmuSTS.4420.1.S1_at | TPX2, microtubule-associated protein homolog | TPX2 | 5.54 | 0.0556 |
| MmugDNA.12787.1.S1_at | tensin /// tensin | TNS | 5.54 | 0.0009 |
| MmugDNA.35052.1.S1_at | Dermatopontin precursor (Tyrosine-rich acidic matrix protein) (TRAMP) | LOC700181 | 5.51 | 0.0038 |
| MmugDNA.27071.1.S1_at | retinoic acid receptor responder (tazarotene induced) 2 | LOC704993 | 5.50 | 0.0557 |
| MmugDNA.21100.1.S1_at | laminin alpha 3 subunit isoform 1 | LOC701313 | 5.49 | 0.0087 |
| MmugDNA.37305.1.S1_at | FRA1OAC1 protein | LOC700389 | 5.48 | 0.0630 |
| MmugDNA.17614.1.S1_at | T-box 5 | TBX5 | 5.48 | 0.0963 |
| MmugDNA.23701.1.S1_at | — | — | 5.46 | 0.0105 |
| MmugDNA.6672.1.S1_at | dystonin | DST | 5.46 | 0.0844 |
| MmugDNA.40463.1.S1_at | MRNA; cDNA DKFZp68680610 (from clone DKFZp68680610) | — | 5.44 | 0.0808 |
| MmuSTS.2214.1.S1_at | six transmembrane epithelial antigen of the prostate | STEAP1 | 5.44 | 0.0063 |
| MmuSTS.1928.1.S1_at | myeloblastosis proto-oncogene product isoform 2 | LOC712321 | 5.41 | 0.0003 |
| MmugDNA.35645.1.S1_s_at | Rho GTPase activating protein 9 | ARHGAP9 | 5.40 | 0.0030 |
| MmugDNA.14897.1.S1_at | AXL receptor tyrosine kinase isoform 2 | LOC706123 | 5.35 | 0.0181 |
| MmugDNA.1117.1.S1_at | Friend leukemia virus integration 1 | FLI1 | 5.35 | 0.0975 |
| MmuSTS.4424.1.S1_at | frizzled 7 | LOC703064 | 5.31 | 0.0161 |
| MmugDNA.25887.1.S1_s_at | filamin 1 (actin-binding protein-280) | FLNA | 5.29 | 0.0256 |
| MmugDNA.40242.1.S1_at | LOC441301 | — | 5.27 | 0.0914 |
| MmugDNA.21548.1.S1_s_at | anthrax toxin receptor 2 | LOC696513 | 5.26 | 0.0654 |
| MmugDNA.36182.1.S1_at | aquaporin 1 | AQP1 | 5.26 | 0.0435 |
| MmugDNA.14767.1.S1_at | FRAS1 related extracellular matrix protein 2 | FREM2 | 5.25 | 0.0835 |
| MmugDNA.33751.1.S1_at | Dexamethasone-induced Ras-related protein 1 (Activator of G-protein signaling 1) | RASD1 | 5.25 | 0.0984 |
| MmugDNA.25691.1.S1_at | solute carrier family 16 (monocarboxylic acid transporters), member 6 | SLC16A6 | 5.25 | 0.0466 |
| MmuSTS.1922.1.S1_at | v-ets erythroblastosis virus E26 oncogene homolog 1 | ETS1 | 5.23 | 0.0322 |
| MmugDNA.3558.1.S1_at | serine/threonine protein kinase 6 | AURKA | 5.22 | 0.0358 |
| MmugDNA.4124.1.S1_at | cell division cycle associated 5 | LOC721995 | 5.21 | 0.0575 |
| MmugDNA.2333.1.S1_at | synaptopodin | SYNPO | 5.21 | 0.0006 |
| MmuSTS.2701.1.S1_at | epidermal growth factor-like protein 6 precursor | LOC711280 | 5.20 | 0.0491 |
| MmugDNA.40392.1.S1_at | lumican | LUM | 5.19 | 0.0120 |
| MmugDNA.21491.1.S1_at | CDNA clone IMAGE:6043059, partial cds | — | 5.19 | 0.0980 |
| MmugDNA.22192.1.S1_at | vitamin K-dependent protein S precursor | LOC694845 | 5.18 | 0.0750 |
| MmugDNA.28039.1.S1_at | Chromosome 10 open reading frame 18 | C10orf18 | 5.17 | 0.0535 |
| MmugDNA.23945.1.S1_at | mitochondrial ribosomal protein L54 | LOC713878 | 5.16 | 0.0885 |
| MmugDNA.28350.1.S1_at | Heparin-binding growth factor 1 precursor (HBGF-1) (Acidic fibroblast growth factor) (aFGF) (Beta-endothelial cell growth factor) (ECGF-beta) | FGF1 | 5.16 | 0.0183 |
| MmugDNA.4851.1.S1_at | angiotensin II receptor, type 1 | LOC712773 | 5.15 | 0.0653 |
| MmugDNA.34285.1.S1_at | nitric oxide synthase trafficking isoform 1 | — | 5.14 | 0.0724 |
| MmugDNA.19357.1.S1_at | Transcribed locus, strongly similar to XP_496055.1 similar to p40 sapiens+ | — | 5.13 | 0.0676 |
| Mmu.14966.1.S1_at | EH domain binding protein 1 | LOC693902 | 5.12 | 0.0757 |
| MmugDNA.42808.1.S1_at | transcription factor 8 (represses interleukin 2 expression) | TCF8 | 5.11 | 0.0254 |
| MmugDNA.30007.1.S1_at | coiled-coil domain containing 102A | LOC704988 | 5.10 | 0.0846 |
| MmugDNA.5184.1.S1_s_at | beta globin | LOC715559 | 5.10 | 0.0122 |
| MmuSTS.2069.1.S1_at | Rac GTPase activating protein 1 | LOC711887 | 5.06 | 0.0587 |
| MmugDNA.15651.1.S1_at | steroid sulfatase (microsomal), arylsulfatase C, isozyme S | STS | 5.04 | 0.0307 |
| MmugDNA.19465.1.S1_at | Transcribed locus, weakly similar to NP_060190.1 signal-transducing adaptor protein-2 sapiens+ | — | 5.03 | 0.0125 |
| MmugDNA.27239.1.S1_s_at | retinol-binding protein 4, plasma precursor | LOC701270 | 5.03 | 0.0423 |
| MmugDNA.43409.1.S1_at | solute carrier family 27 member 3 | LOC718424 | 5.02 | 0.0762 |
| MmugDNA.13155.1.S1_at | chondroitin sulfate proteoglycan 2 (versican) | LOC712365 | 5.00 | 0.0576 |
| MmugDNA.18099.1.S1_at | complement component 3 | C3 | 4.97 | 0.0146 |
| MmuSTS.2151.1.S1_at | branched chain aminotransferase 1, cytosolic | LOC707321 | 4.96 | 0.0031 |
| MmunewRS.412.1.S1_s_at | solute carrier family 9 (sodiumhydrogen exchanger), isoform 4 (SLC9A4), mRNA | SLC9A4 | 4.95 | 0.0130 |
| MmugDNA.9733.1.S1_at | Muscleblind-like (Drosophila) | MBNL1 | 4.95 | 0.0396 |
| MmugDNA.20784.1.S1_at | quaking homolog, KH domain RNA binding (mouse) | QKI | 4.95 | 0.0001 |
| MmuSTS.2287.1.S1_at | peroxisome proliferator-activated receptor gamma 1-b | PPARGAMMA | 4.93 | 0.0218 |
| MmuSTS.1783.1.S1_at | nuclear factor I/A | LOC694022 | 4.92 | 0.0568 |

-continued

| Probe Set ID | Gene Title | Gene Symbol | Ratio Top verus Bottom | p value Top versus Bottom |
|---|---|---|---|---|
| MmugDNA.5690.1.S1_at | septin 4 isoform 3 | LOC714724 | 4.92 | 0.0427 |
| MmugDNA.23105.1.S1_s_at | Ig lambda chain V-II region BUR /// Ig lambda chain V-II region MGC /// Immunoglobulin lambda-like polypeptide 1 precursor (Immunoglobulin-related protein 14.1) (Immunoglobulin omega polypeptide) (Ig lambda-5) (CD179b antigen) /// Ig lambda chain V-II region NIG-84 | LOC706778 /// LOC707940 /// LOC708547 /// LOC720711 | 4.91 | 0.0034 |
| MmugDNA.39956.1.S1_at | Hairless homolog (mouse) | HR | 4.90 | 0.0242 |
| MmuSTS.2029.1.S1_at | polo-like kinase | PLK1 | 4.88 | 0.0403 |
| MmuSTS.154.1.S1_x_at | — | BTN3A2 | 4.87 | 0.0977 |
| MmugDNA.35115.1.S1_at | heparan sulfate proteoglycan 2 | HSPG2 | 4.85 | 0.0002 |
| MmugDNA.964.1.S1_at | SH3-domain binding protein 1 | SH3BP1 | 4.83 | 0.0803 |
| MmugDNA.9449.1.S1_at | WD repeat domain 76 | LOC711191 | 4.83 | 0.0376 |
| MmuSTS.165.1.S1_at | inhibitor of DNA binding 3 | LOC710290 | 4.82 | 0.0001 |
| MmugDNA.43567.1.S1_at | Homo sapiens, Similar to hypothetical protein FLJ21936, clone IMAGE:4044084, mRNA | — | 4.82 | 0.0615 |
| MmugDNA.40816.1.S1_at | tumor necrosis factor, alpha-induced protein 9 | TNFAIP9 | 4.82 | 0.0196 |
| MmugDNA.23454.1.S1_at | 15-hydroxyprostaglandin dehydrogenase +NAD (Prostaglandin dehydrogenase 1) | HPGD | 4.82 | 0.0099 |
| MmugDNA.38346.1.S1_at | phosphoserine aminotransferase isoform 1 | LOC706387 | 4.81 | 0.0646 |
| MmugDNA.28728.1.S1_at | KIAA0485 protein | KIAA0485 | 4.80 | 0.0069 |
| MmuSTS.4004.1.S1_at | thrombospondin 1 precursor | LOC705413 | 4.78 | 0.0185 |
| MmugDNA.23996.1.S1_at | alpha 2 type I collagen | LOC700359 | 4.75 | 0.0161 |
| MmugDNA.18235.1.S1_at | TGFB-induced factor 2 (TALE family homeobox) | TGIF2 | 4.72 | 0.0241 |
| MmugDNA.30842.1.S1_s_at | Transgelin (Smooth muscle protein 22-alpha) (SM22-alpha) (WS3-10) (22 kDa actin-binding protein) | TAGLN | 4.71 | 0.0509 |
| MmugDNA.822.1.S1_at | Transcribed locus, moderately similar to XP_517655.1 similar to KIAA0825 protein +Pan troglodytes+ | — | 4.71 | 0.0218 |
| MmugDNA.19564.1.S1_s_at | melanoma cell adhesion molecule | LOC708449 | 4.71 | 0.0221 |
| MmugDNA.26005.1.S1_at | thyroglobulin | TG | 4.71 | 0.0150 |
| MmugDNA.9817.1.S1_at | Likely ortholog of mouse TORC2-specific protein AVO3 (S. cerevisiae) | AVO3 | 4.70 | 0.0316 |
| MmugDNA.12099.1.S1_at | transducer of ERBB2, 1 | TOB1 | 4.70 | 0.0197 |
| MmugDNA.20357.1.S1_at | interleukin 1 receptor, type I | IL1 R1 | 4.69 | 0.0159 |
| MmugDNA.38818.1.S1_at | adipocyte enhancer binding protein 1 precursor | LOC699977 | 4.67 | 0.0329 |
| MmugDNA.34995.1.S1_s_at | collagen, type I, alpha 1 | COL1A1 | 4.66 | 0.0032 |
| MmugDNA.4218.1.S1_at | four and a half LIM domains 1 | FHL1 | 4.65 | 0.0322 |
| MmuSTS.869.1.S1_at | dysferlin | DYSF | 4.64 | 0.0604 |
| MmugDNA.31007.1.S1_s_at | fibronectin 1 | FN1 | 4.63 | 0.0000 |
| MmugDNA.21203.1.S1_x_at | amyloid beta (A4) precursor protein-binding, family B, member 1 interacting protein | LOC707383 | 4.61 | 0.0921 |
| MmugDNA.16224.1.S1_s_at | hypothetical protein LOC704308 | LOC704308 | 4.60 | 0.0117 |
| MmugDNA.22096.1.S1_at | Galectin-1 (Lectin galactoside-binding soluble 1) (Beta-galactoside-binding lectin L-14-I) (Lactose-binding lectin 1) (S-Lac lectin 1) (Galaptin) (14 kDa lectin) (HPL) (HBL) (Putative MAPK-activating protein MP12) | LGALS1 | 4.59 | 0.0571 |
| MmugDNA.26778.1.S1_at | Hypothetical protein similar to KIAA0187 gene product | LOC96610 | 4.58 | 0.0395 |
| MmugDNA.16831.1.S1_s_at | synuclein, gamma (breast cancer-specific protein 1) | LOC696535 | 4.58 | 0.0058 |
| MmugDNA.35261.1.S1_at | Fc fragment of IgG, low affinity IIa, receptor (CD32) | FCGR2A | 4.58 | 0.0713 |
| MmugDNA.31316.1.S1_at | hypothetical protein LOC702054 /// hypothetical protein LOC702584 | LOC702054 /// LOC702584 | 4.57 | 0.0204 |
| MmugDNA.30287.1.S1_at | GTPase, IMAP family member 6 isoform 1 | LOC713565 | 4.57 | 0.0897 |
| MmugDNA.5299.1.S1_at | Rho-related BTB domain containing 1 | RHOBTB1 | 4.56 | 0.0702 |
| MmugDNA.30627. .S1_s_at | jub, ajuba homolog isoform 1 | LOC712865 | 4.55 | 0.0343 |
| MmuSTS.220.1.S1_at | SCL/TAL1 interrupting locus | LOC710099 | 4.54 | 0.0619 |
| MmugDNA.33541. .S1_at | calpain small subunit 2 | LOC698721 | 4.54 | 0.0190 |
| MmugDNA.10511. .S1_at | mucin 15 | LOC700194 | 4.53 | 0.0419 |
| MmuSTS.90.1.S1_at | high mobility group AT-hook 2 | HMGA2 | 4.53 | 0.0315 |
| MmugDNA.22320. .S1_s_at | pregnancy specific beta-1-glycoprotein 4 | PSG4 | 4.52 | 0.0011 |
| MmugDNA.6347.1.S1_at | runt-related transcription factor 3 | RUNX3 | 4.51 | 0.0494 |
| MmugDNA.21974.1.S1_at | keratin 5 | KRT3 | 4.50 | 0.0002 |
| MmugDNA.21584.1.S1_at | — | — | 4.49 | 0.0045 |
| MmugDNA.19709.1.S1_x_at | growth hormone 1 | GH1 | 4.48 | 0.0372 |
| MmuSTS.4832.1.S1_at | connexin 31 | LOC710834 | 4.48 | 0.0144 |
| MmugDNA.24059.1.S1_at | Transcribed locus | — | 4.47 | 0.0651 |
| MmugDNA.32484.1.S1_s_at | tissue inhibitor of metalloproteinase 3 (Sorsby fundus dystrophy, pseudoinflammatory) | TIMP3 | 4.47 | 0.0150 |
| MmugDNA.35122.1.S1_at | Discoidin domain receptor family, member 2 | DDR2 | 4.47 | 0.0050 |
| MmugDNA.18271.1.S1_at | CDNA FLJ44429 fis, clone UTERU2015653 | — | 4.46 | 0.0001 |
| MmuSTS.2362.1.S1_at | S100-B (S100 calcium-binding protein B) (S-100 protein beta subunit) (S-100 protein beta chain) | S100B | 4.45 | 0.0185 |
| MmugDNA.41157.1.S1_at | matrix Gla protein | MGP | 4.44 | 0.0252 |
| MmuSTS.934.1.S1_at | four jointed box 1 | LOC717833 | 4.44 | 0.0328 |
| MmugDNA.30788.1.S1_at | COBL-like 1 | LOC702934 | 4.41 | 0.0521 |
| MmugDNA.1969.1.S1_at | hypothetical protein LOC714686 | LOC714686 | 4.40 | 0.0385 |
| MmuSTS.112.1.S1_at | Asporin precursor (Periodontal ligament-associated protein 1) (PLAP-1) | LOC718125 | 4.40 | 0.0318 |

-continued

| Probe Set ID | Gene Title | Gene Symbol | Ratio Top verus Bottom | p value Top versus Bottom |
|---|---|---|---|---|
| MmugDNA.13768.1.S1_at | CDNA: FLJ22256 fis, clone HRCO2860 | — | 4.39 | 0.0198 |
| MmugDNA.28759.1.S1_at | — | — | 4.39 | 0.0482 |
| MmugDNA.15862.1.S1_at | CDC28 protein kinase 2 | LOC697324 | 4.39 | 0.0028 |
| MmugDNA.22453.1.S1_at | keratin 13 isoform b | LOC706830 | 4.38 | 0.0080 |
| MmugDNA.34784.1.S1_at | CDNA FLJ12091 fis, clone HEMBB1002582 | — | 4.38 | 0.0522 |
| MmugDNA.41887.1.S1_at | MYB-related protein B | MYBL2 | 4.36 | 0.0821 |
| MmugDNA.17000.1.S1_at | Activating transcription factor 7 | ATF7 | 4.36 | 0.0972 |
| MmugDNA.29263.1.S1_at | Glycoprotein hormones alpha chain precursor (Anterior pituitary glycoprotein hormones common alpha subunit) (Follitropin alpha chain) (Follicle-stimulating hormone alpha chain) (FSH-alpha) (Lutropin alpha chain) (Luteinizing hormone alph... | LOC697859 | 4.34 | 0.0348 |
| MmugDNA.21650.1.S1_at | Epidermal growth factor receptor (erythroblastic leukemia viral (v-erb-b) oncogene homolog, avian) | EGFR | 4.33 | 0.0164 |
| MmugDNA.24420.1.S1_at | kidney predominant protein NCU-G1 | LOC719468 | 4.33 | 0.0291 |
| MmugDNA.26915.1.S1_at | follistatin | FST | 4.32 | 0.0314 |
| MmugDNA.35764.1.S1_s_at | High affinity immunoglobulin epsilon receptor gamma-subunit precursor (FceRl gamma) (IgE Fc receptor gamma-subunit) (Fc-epsilon RI-gamma) | LOC720291 | 4.32 | 0.0456 |
| MmugDNA.23015.1.S1_at | Y43E12A.2 | LOC702083 | 4.32 | 0.0536 |
| MmuSTS.3532.1.S1_at | CD53 antigen | LOC702350 | 4.31 | 0.0013 |
| MmuSTS.1975.1.S1_at | nuclear receptor subfamily 3, group C, member 1 | NR3C1 | 4.31 | 0.0356 |
| MmugDNA.30097.1.S1_at | coronin, actin binding protein, 1C | CORO1C | 4.30 | 0.0925 |
| MmugDNA.16359.1.S1_at | deleted in liver cancer 1 | DLC1 | 4.30 | 0.0527 |
| MmugDNA.23180.1.S1_at | cartilage associated protein | CRTAP | 4.29 | 0.0637 |
| MmugDNA.11572.1.S1_at | chemokine (C-X-C motif) ligand 12 (stromal cell-derived factor 1) | CXCL12 | 4.28 | 0.0367 |
| MmuSTS.3488.1.S1_at | CD48 antigen precursor (B-lymphocyte activation marker BLAST-1) (BCM1 surface antigen) (Leucocyte antigen MEM-102) (TCT.1) | CD48 | 4.28 | 0.0930 |
| Mmu.9771.1.S1_at | osteomodulin | OMD | 4.28 | 0.0946 |
| MmugDNA.34344.1.S1_at | Neuron navigator 1 | NAV1 | 4.27 | 0.0395 |
| MmugDNA.37179.1.S1_at | CG10889-PA | LOC714837 | 4.27 | 0.0079 |
| MmugDNA.985.1.S1_at | pyruvate dehydrogenase kinase 4 | PDK4 | 4.25 | 0.0509 |
| MmugDNA.19882.1.S1_at | potassium channel tetramerisation domain containing 15 | LOC704761 | 4.25 | 0.0224 |
| MmuSTS.3690.1.S1_at | collagen, type VI, alpha 1 | COL6A1 | 4.23 | 0.0002 |
| MmuSTS.3265.1.S1_at | RGM domain family, member A | LOC712949 | 4.23 | 0.0001 |
| MmugDNA.7509.1.S1_at | hypothetical protein LOC710962 | LOC710962 | 4.22 | 0.0691 |
| MmugDNA.15267.1.S1_at | RNA binding protein with multiple splicing 2 | LOC712536 | 4.22 | 0.0002 |
| MmugDNA.15951.1.S1_at | reticulon 4 | RTN4 | 4.21 | 0.0366 |
| MmugDNA.13995.1.S1_at | — | — | 4.21 | 0.0348 |
| MmugDNA.19825.1.S1_s_at | phosducin-like 3 | LOC696369 | 4.21 | 0.0667 |
| MmugDNA.3461.1.S1_at | similar to RIKEN cDNA 1200014N16 gene | MGC14289 | 4.19 | 0.0308 |
| MmugDNA.23968.1.S1_s_at | ubiquitin specific protease 32 | LOC716857 | 4.19 | 0.0249 |
| MmuSTS.3891.1.S1_at | smoothened | LOC701334 | 4.19 | 0.0433 |
| MmuSTS.3429.1.S1_at | Collagen alpha-1(XII) chain precursor | LOC717820 | 4.19 | 0.0386 |
| MmuSTS.1967.1.S1_at | FYN binding protein (FYB-120/130) isoform 1 | LOC693951 | 4.18 | 0.0997 |
| MmugDNA.27563.1.S1_at | hypothetical protein FLJ13910 /// hypothetical protein LOC285074 | FLJ13910 /// LOC285074 | 4.16 | 0.0252 |
| MmugDNA.15700.1.S1_s_at | phosphoglycerate dehydrogenase | PHGDH | 4.15 | 0.0032 |
| MmuSTS.3850.1.S1_at | ABI gene family, member 3 (NESH) binding protein | LOC701192 | 4.14 | 0.0817 |
| MmugDNA.1158.1.S1_at | CD36 antigen (collagen type I receptor, thrombospondin receptor) | CD36 | 4.14 | 0.0397 |
| MmugDNA.34925.1.S1_at | secreted protein, acidic, cysteine-rich (osteonectin) | SPARC | 4.09 | 0.0078 |
| MmugDNA.31894.1.S1_at | thioredoxin interacting protein | LOC698683 | 4.09 | 0.0028 |
| MmugDNA.18794.1.S1_at | cell division cycle 20 | CDC20 | 4.09 | 0.0481 |
| MmuSTS.1308.1.S1_at | dystrophin (muscular dystrophy, Duchenne and Becker types) | DMD | 4.09 | 0.0098 |
| MmugDNA.27355.1.S1_at | low density lipoprotein-related protein 1 | LRP1 | 4.08 | 0.0607 |
| MmugDNA.7866.1.S1_at | DNA replication factor | LOC711530 | 4.07 | 0.0109 |
| MmugDNA.31873.1.S1_at | Fatty acid-binding protein, adipocyte (AFABP) (Adipocyte lipid-binding protein) (ALBP) (A-FABP) | FABP4 | 4.07 | 0.0130 |
| MmugDNA.36912.1.S1_at | complement factor D preproprotein | LOC721138 | 4.07 | 0.0237 |
| MmugDNA.10186.1.S1_at | AF15q14 protein | AF15Q14 | 4.06 | 0.0211 |
| MmugDNA.6192.1.S1_at | Baculoviral IAP repeat-containing 6 (apollon) | BIRC6 | 4.06 | 0.0861 |
| MmugDNA.26073.1.S1_at | RAB30, member RAS oncogene family | LOC701550 | 4.03 | 0.0735 |
| MmugDNA.21516.1.S1_at | phospholipid transfer protein | PLTP | 4.03 | 0.0251 |
| MmugDNA.36883.1.S1_at | PDZ domain containing 3 | PDZK3 | 4.02 | 0.0007 |
| MmugDNA.16991.1.S1_at | integrin alpha 7 precursor | LOC707279 | 4.02 | 0.0319 |
| MmugDNA.3447.1.S1_at | diacylglycerol 0-acyltransferase homolog 2 | LOC696549 | 4.02 | 0.0054 |
| MmugDNA.17919.1.S1_at | arachidonate 15-lipoxygenase, second type | ALOX15B | 4.01 | 0.0499 |
| MmugDNA.35103.1.S1_at | actin, alpha 2, smooth muscle, aorta | ACTA2 | 4.01 | 0.0296 |
| Mmu.16433.2.S1_at | collagen, type III, alpha 1 (Ehlers-Danlos syndrome type IV, autosomal dominant) | COL3A1 | 3.99 | 0.0332 |
| MmugDNA.24230.1.S1_s_at | chemokine-like factor superfamily 3 isoform a | LOC695592 | 3.99 | 0.0604 |
| MmugDNA.16772.1.S1_at | immunoglobulin J chain | LOC706650 | 3.98 | 0.0350 |

-continued

| Probe Set ID | Gene Title | Gene Symbol | Ratio Top verus Bottom | p value Top versus Bottom |
|---|---|---|---|---|
| MmugDNA.34863.1.S1_at | hypothetical protein LOC283445 | LOC283445 | 3.98 | 0.0580 |
| MmunewRS.431.1.S1_at | tyrosine phosphatase, receptor type, S | — | 3.97 | 0.0140 |
| MmuSTS.61.1.S1_at | helicase, lymphoid-specific | LOC701598 | 3.97 | 0.0034 |
| MmugDNA.34155.1.S1_at | nidogen (enactin) | NID1 | 3.95 | 0.0965 |
| MmugDNA.9153.1.S1_s_at | angiopoietin 1 | ANGPT1 | 3.94 | 0.0482 |
| MmugDNA.36429.1.S1_at | Phosphoglycerate dehydrogenase like 1 | PHGDHL1 | 3.93 | 0.0965 |
| MmugDNA.26560.1.S1_at | Transcribed locus | — | 3.93 | 0.0251 |
| MmugDNA.36525.1.S1_at | junctional adhesion molecule 2 | JAM2 | 3.91 | 0.0727 |
| MmugDNA.43116.1.S1_at | glycoprotein (transmembrane) nmb isoform b precursor | LOC704990 | 3.91 | 0.0020 |
| MmugDNA.14973.1.S1_at | CDC45-like | LOC711800 | 3.90 | 0.0056 |
| MmuSTS.1523.1.S1_at | mannose receptor C type 1 | MRC1 | 3.90 | 0.0326 |
| MmugDNA.39378.1.S1_at | ribonuclease HI, large subunit | RNASEH2A | 3.90 | 0.0623 |
| MmugDNA.27459.1.S1_at | Transcribed locus | — | 3.89 | 0.0217 |
| MmugDNA.17136.1.S1_at | Sorbin and SH3 domain containing 1 | SORBS1 | 3.89 | 0.0146 |
| MmugDNA.15966.1.S1_at | Bromodomain adjacent to zinc finger domain, 2A | BAZ2A | 3.88 | 0.0740 |
| MmugDNA.20219.1.S1_at | myc target 1 | LOC711296 | 3.88 | 0.0363 |
| MmugDNA.43499.1.S1_at | — | — | 3.88 | 0.0557 |
| MmugDNA.10801.1.S1_s_at | — | — | 3.86 | 0.0121 |
| Mmu.6201.1.S1_at | Glycogen phosphorylase, liver | PYGL | 3.86 | 0.0383 |
| MmuSTS.4157.1.S1_at | Mitotic spindle assembly checkpoint protein MAD2A (MAD2-like 1) (HsMAD2) | LOC708574 | 3.85 | 0.0975 |
| MmugDNA.37083.1.S1_at | pleckstrin homology-like domain, family B, member 2 | LOC709353 | 3.84 | 0.0493 |
| MmugDNA.2976.1.S1_at | hypothetical protein LOC718180 | LOC718180 | 3.83 | 0.0297 |
| MmugDNA.34946.1.S1_at | — | — | 3.82 | 0.0871 |
| MmugDNA.2272.1.S1_at | CDNA FLJ34664 fis, clone LIVER2000592 | — | 3.82 | 0.0256 |
| MmugDNA.27284.1.S1_at | endothelial differentiation, lysophosphatidic acid G-protein-coupled receptor, 2 | LOC709208 | 3.81 | 0.0286 |
| MmugDNA.29523.1.S1_at | hypothetical protein LOC700994 | LOC700994 | 3.81 | 0.0180 |
| MmugDNA.33148.1.S1_at | mitochondrial glycerol 3-phosphate acyltransferase | GPAM | 3.79 | 0.0111 |
| MmugDNA.12151.1.S1_at | chromosome 18 open reading frame 54 | LOC694192 | 3.79 | 0.0342 |
| MmugDNA.11637.1.S1_s_at | nestin | LOC718562 | 3.79 | 0.0391 |
| Mmu.15601.1.S2_s_at | Intestinal alkaline phosphatase | — | 3.79 | 0.0175 |
| MmugDNA.27885.1.S1_at | excision repair cross-complementing rodent repair deficiency complementation group 6 - like | LOC699138 | 3.78 | 0.0396 |
| MmugDNA.33913.1.S1_at | Calmodulin-like 4 | CALML4 | 3.77 | 0.0635 |
| MmugDNA.42756.1.S1_at | — | — | 3.77 | 0.0776 |
| MmugDNA.33637.1.S1_s_at | melanoma antigen family D, 4 isoform 1 | LOC697293 | 3.76 | 0.0236 |
| MmugDNA.32538.1.S1_at | ecotropic viral integration site 2B | LOC712972 | 3.76 | 0.0866 |
| MmugDNA.7512.1.S1_at | mediator of RNA polymerase II transcription, subunit 13 homolog | THRAP1 | 3.76 | 0.0009 |
| MmuSTS.4815.1.S1_at | gamma-aminobutyric acid (GABA) A receptor, pi | GABRP | 3.76 | 0.0213 |
| MmugDNA.42949.1.S1_at | Kinectin 1 (kinesin receptor) | KTN1 | 3.75 | 0.0642 |
| MmugDNA.9357.1.S1_at | Similar to ribosomal protein S12 | — | 3.75 | 0.0693 |
| MmuSTS.1780.1.S1_at | hypothetical protein LOC710960 | LOC710960 | 3.75 | 0.0391 |
| MmugDNA.40177.1.S1_at | HRAS-like suppressor 5 (H-rev107-like protein 5) | LOC718317 | 3.75 | 0.0439 |
| MmugDNA.41855.1.S1_at | chloride intracellular channel 4 | CLIC4 | 3.75 | 0.0477 |
| MmugDNA.39310.1.S1_at | homeo box C4 | HOXC4 | 3.75 | 0.0753 |
| MmugDNA.33364.1.S1_at | lysosomal-associated membrane protein 1 | LAMP1 | 3.75 | 0.0891 |
| MmuSTS.2956.1.S1_at | Lysosomal-associated multispanning membrane protein-5 | LAPTM5 | 3.74 | 0.0769 |
| MmugDNA.15666.1.S1_at | prostatic secretory protein (PSP-94) | MSMB | 3.74 | 0.0536 |
| MmugDNA.37771.1.S1_at | Ring finger protein 12 | RNF12 | 3.73 | 0.0118 |
| MmugDNA.25197.1.S1_at | asp (abnormal spindle)-like, microcephaly associated | LOC711153 | 3.73 | 0.0360 |
| MmugDNA.35955.1.S1_at | Ubiquitin-conjugating enzyme E2D 3 (UBC4/5 homolog, yeast) | UBE2D3 | 3.73 | 0.0666 |
| MmugDNA.39545.1.S1_at | sialyltransferase 7 | ST6GALNAC2 | 3.73 | 0.0048 |
| MmugDNA.24940.1.S1_at | SERTA domain containing 4 | SERTAD4 | 3.73 | 0.0064 |
| MmuSTS.2245.1.S1_at | phospholipase C, delta 1 | PLCD1 | 3.72 | 0.0012 |
| MmugDNA.4054.1.S1_at | solute carrier family 25 (mitochondrial carrier; Graves disease autoantigen), member 16 | SLC25A16 | 3.72 | 0.0026 |
| MmugDNA.38062.1.S1_at | Very hypothetical protein | — | 3.71 | 0.0666 |
| MmuSTS.1539.1.S1_at | lamin B1 | LMNB1 | 3.70 | 0.0425 |
| MmugDNA.29710.1.S1_at | mitogen-activated protein kinase kinase kinase 6 | LOC715911 | 3.70 | 0.0525 |
| MmugDNA.3079.1.S1_at | START domain containing 7 | STARD7 | 3.70 | 0.0054 |
| MmuSTS.3358.1.S1_at | Hematopoietic progenitor cell antigen CD34 precursor | LOC713858 | 3.70 | 0.0201 |
| MmugDNA.23709.1.S1_at | Ras-related protein Rab-13 | LOC695135 | 3.69 | 0.0042 |
| MmugDNA.13640.1.S1_at | Plunc precursor (Palate lung and nasal epithelium clone protein) (Lung-specific protein X) (Nasopharyngeal carcinoma-related protein) (Tracheal epithelium-enriched protein) (Secretory protein in upper respiratory tracts) (Von Ebn... | PLUNC | 3.68 | 0.0341 |
| MmugDNA.19840.1.S1_at | Flavin containing monooxygenase 2 | FMO2 | 3.67 | 0.0200 |
| MmugDNA.12797.1.S1_at | early B-cell factor 3 | LOC713536 | 3.67 | 0.0679 |
| MmugDNA.43327.1.S1_at | Alpha crystallin B chain (Alpha(B)-crystallin) (Rosenthal fiber component) (Heat-shock protein beta-5) (HspB5) (NY-REN-27 antigen) | CRYAB | 3.66 | 0.0179 |
| MmugDNA.26357.1.S1_at | CG14299-PA, isoform A | LOC700766 | 3.65 | 0.0974 |

-continued

| Probe Set ID | Gene Title | Gene Symbol | Ratio Top verus Bottom | p value Top versus Bottom |
|---|---|---|---|---|
| Mmu.16242.1.S1_at | Pallidin (Pallid protein homolog) (Syntaxin 13-interacting protein) | PLDN | 3.65 | 0.0676 |
| MmugDNA.3343.1.S1_at | suppressor of cytokine signaling 3 | SOCS3 | 3.65 | 0.0146 |
| MmunewRS.372.1.S1_at | gi:39645656 Homo sapiens similar to Serinethreonine-protein kinase Nek1 (NimA-related protein kinase 1), mRNA (cDNA clone MGC:75495 IMAGE:30383658), complete cds | MGC75495 | 3.64 | 0.0005 |
| MmugDNA.4113.1.S1_at | heat shock 22 kDa protein 8 | HSPB8 | 3.64 | 0.0306 |
| MmugDNA.42494.1.S1_at | Transcribed locus | — | 3.64 | 0.0679 |
| MmuSTS.4058.1.S1_at | sushi-repeat-containing protein, X-linked | SRPX | 3.63 | 0.0619 |
| MmugDNA.17872.1.S1_at | Putative serum amyloid A-3 protein | SAA3P | 3.63 | 0.0242 |
| MmugDNA.34659.1.S1_s_at | hypothetical protein LOC705662 | LOC705662 | 3.63 | 0.0100 |
| MmugDNA.34077.1.S1_at | WD repeat and FYVE domain containing 2 | WDFY2 | 3.63 | 0.0201 |
| MmugDNA.3557.1.S1_at | WD40 repeat protein Interacting with phospholnositides of 49 kDa | W1P149 | 3.62 | 0.0905 |
| MmugDNA.5835.1.S1_at | hypothetical protein LOC700615 | LOC700615 | 3.62 | 0.0021 |
| MmunewRS.1055.1.S1_at | Myosin regulatory light chain 2, smooth muscle isoform (Myosin RLC) (LC20) (Myosin regulatory light chain 9) | LOC709784 | 3.61 | 0.0184 |
| MmuSTS.4533.1.S1_at | breast cancer 1, early onset isoform 1 | LOC712634 | 3.61 | 0.0225 |
| MmugDNA.37529.1.S1_at | pleckstrin homology domain containing, family H (with MyTH4 domain) member 2 | LOC713488 | 3.61 | 0.0629 |
| MmugDNA.36745.1.S1_at | tubulin, beta 8 | — | 3.61 | 0.0229 |
| MmugDNA.21536.1.S1_at | proline arginine-rich end leucine-rich repeat protein | PRELP | 3.61 | 0.0589 |
| MmugDNA.29432.1.S1_at | CDNA FLJ12246 fis, clone MAMMA1001343 | — | 3.61 | 0.0308 |
| MmuSTS.911.1.S1_at | enhancer of zeste 2 | EZH2 | 3.60 | 0.0107 |
| MmugDNA.17513.1.S1_at | LIM and cysteine-rich domains 1 | LMCD1 | 3.59 | 0.0642 |
| MmunewRS.170.1.S1_at | gi:34535503 Homo sapiens cDNA FLJ46364 fis, clone TESTI4051015, weakly similar to Aquaporin 7 | — | 3.59 | 0.0005 |
| MmugDNA.37690.1.S1_at | zinc finger protein 208 | ZNF208 | 3.59 | 0.0722 |
| MmugDNA.14830.1.S1_at | thyroid hormone responsive (SPOT14 homolog, rat) | THRSP | 3.58 | 0.0198 |
| MmugDNA.38914.1.S1_at | Rap guanine nucleotide exchange factor (GEF)-like 1 | LOC699843 | 3.57 | 0.0737 |
| MmugDNA.15276.1.S1_at | sushi, von Willebrand factor type A, EGF and pentraxin domain containing 1 | LOC709478 | 3.57 | 0.0542 |
| MmugDNA.9453.1.S1_at | lysyl oxidase preproprotein | LOC699997 | 3.57 | 0.0512 |
| MmuSTS.417.1.S1_at | alpha-2A-adrenergic receptor | ADRA2A | 3.56 | 0.0301 |
| MmugDNA.328.1.S1_at | Nuclear protein 1 (Protein p8) (Candidate of metastasis 1) | P8 | 3.56 | 0.0178 |
| MmugDNA.34766.1.S1_at | Corticoliberin precursor (Corticotropin-releasing factor) (CRF) (Corticotropin-releasing hormone) | LOC702877 | 3.55 | 0.0843 |
| MmugDNA.7723.1.S1_at | male-specific lethal 3-like 1 (Drosophila) | MSL3L1 | 3.55 | 0.0630 |
| MmugDNA.25407.1.S1_at | carboxypeptidase M | CPM | 3.54 | 0.0593 |
| MmuSTS.1530.1.S1_at | Kv channel interacting protein 2 isoform 6 | LOC712434 | 3.54 | 0.0273 |
| MmugDNA.12610.1.S1_at | OX-2 membrane glycoprotein precursor (MRC OX-2 antigen) (CD200 antigen) | CD200 | 3.54 | 0.0915 |
| MmuSTS.835.1.S1_at | downregulated in ovarian cancer 1 isoform 2 | LOC699594 | 3.54 | 0.0876 |
| MmugDNA.21403.1.S1_at | trigger of mitotic entry 1 | LOC722088 | 3.53 | 0.0250 |
| MmugDNA.2694.1.S1_at | ZW10 interactor (ZW10-interacting protein 1) (Zwint-1) | LOC702198 | 3.52 | 0.0095 |
| MmugDNA.32957.1.S1_at | CG15105-PA, isoform A | LOC696852 | 3.51 | 0.0745 |
| MmunewRS.730.1.S1_at | cadherin 13 | CDH13 | 3.50 | 0.0291 |
| MmugDNA.28367.1.S1_at | SPARC-like 1 | SPARCL1 | 3.49 | 0.0017 |
| MmugDNA.28270.1.S1_at | Early B-cell factor | EBF | 3.48 | 0.0343 |
| MmugDNA.30316.1.S1_at | Protein inhibitor of activated STAT, 1 | PIAS1 | 3.48 | 0.0646 |
| MmuSTS.1363.1.S1_at | annexin A8 | ANXA8 | 3.48 | 0.0190 |
| MmugDNA.6544.1.S1_at | Triosephosphate isomerase (TIM) (Triose-phosphate isomerase) | TPI1 | 3.48 | 0.0290 |
| MmugDNA.15422.1.S1_at | absent in melanoma 1 | LOC697117 | 3.47 | 0.0217 |
| MmugDNA.37873.1.S1_at | kinase related protein, telokin | MYLK | 3.44 | 0.0740 |
| MmugDNA.22106.1.S1_at | sterile alpha motif domain containing 4 | SAMD4 | 3.44 | 0.0269 |
| MmugDNA.25115.1.S1_at | delta-like 1 homolog isoform 1 | LOC707595 | 3.43 | 0.0452 |
| MmugDNA.25541.1.S1_at | hypothetical protein LOC705360 | LOC705360 | 3.43 | 0.0002 |
| MmuSTS.3320.1.S1_at | cyclin E2 isoform 1 | LOC700382 | 3.43 | 0.0417 |
| MmuSTS.4488.1.S1_at | spectrin, beta, non-erythrocytic 1 | SPTBN1 | 3.43 | 0.0416 |
| MmugDNA.13714.1.S1_at | kallikrein 11 isoform 2 precursor | — | 3.43 | 0.0019 |
| MmugDNA.14368.1.S1_at | lipidosin | LOC709676 | 3.41 | 0.0245 |
| MmugDNA.7128.1.S1_at | triggering receptor expressed on myeloid cells 4 | TREM4 | 3.41 | 0.0097 |
| MmugDNA.15051.1.S1_at | A kinase (PRKA) anchor protein 2 | AKAP2 | 3.41 | 0.0145 |
| MmugDNA.39271.1.S1_at | Transcribed locus | — | 3.41 | 0.0712 |
| MmugDNA.38296.1.S1_at | KIAA1102 protein | KIAA1102 | 3.40 | 0.0636 |
| MmugDNA.12755.1.S1_s_at | bone morphogenetic protein 1 | BMP1 | 3.39 | 0.0254 |
| MmugDNA.35196.1.S1_at | Transcribed locus | — | 3.39 | 0.0878 |
| MmugDNA.7507.1.S1_at | ATP-binding cassette, sub-family A, member 9 | LOC693411 | 3.39 | 0.0736 |
| Mmu.15849.1.S1_at | transcription elongation regulator 1 isoform 1 | LOC707912 | 3.38 | 0.0370 |
| MmugDNA.25155.1.S1_at | Nuclear ubiquitous casein and cyclin-dependent kinases substrate (P1) | NUCKS1 | 3.38 | 0.0007 |
| MmuSTS.2361.1.S1_at | S100-A2 (S100 calcium-binding protein A2) (Protein S-100L) (CAN19) | LOC715264 | 3.37 | 0.0014 |
| MmuAffx.23.12.S1_at | Transcribed locus, strongly XP_001153513.1 hypothetical protein [Pan troglodytes] | — | 3.36 | 0.0459 |

-continued

| Probe Set ID | Gene Title | Gene Symbol | Ratio Top verus Bottom | p value Top versus Bottom |
|---|---|---|---|---|
| MmugDNA.13395.1.S1_at | interferon, gamma-inducible protein 16 | LOC719253 | 3.34 | 0.0180 |
| MmugDNA.34006.1.S1_at | leucine rich repeat and death domain containing protein isoform 1 | LOC700580 | 3.34 | 0.0246 |
| MmugDNA.13401.1.S1_s_at | metastasis associated lung adenocarcinoma transcript 1 (non-coding RNA) | MALAT1 | 3.34 | 0.0765 |
| MmuSTS.2405.1.S1_at | growth differentiation factor 11 | GDF11 | 3.34 | 0.0680 |
| MmugDNA.22100.1.S1_at | Baculoviral IAP repeat-containing protein 5 (Apoptosis inhibitor survivin) (Apoptosis inhibitor 4) | BIRC5 | 3.34 | 0.0120 |
| MmuSTS.2514.1.S1_at | hematopoietically expressed homeobox | LOC699012 | 3.33 | 0.0592 |
| MmugDNA.29693.1.S1_at | hypothetical protein FLJ21742 | FLJ21742 | 3.33 | 0.0066 |
| MmuSTS.1347.1.S1_at | high-mobility group box 2 | LOC697057 | 3.32 | 0.0266 |
| MmuSTS.1397.1.S1_at | Complement C1q subcomponent subunit B precursor | LOC718307 | 3.31 | 0.0198 |
| MmugDNA.42305.1.S1_at | A kinase (PRKA) anchor protein 13 | AKAP13 | 3.31 | 0.0571 |
| MmugDNA.19389.1.S1_at | Chromosome 21 open reading frame 34 | C21orf34 | 3.30 | 0.0456 |
| MmugDNA.12452.1.S1_at | hypothetical protein LOC699186 | LOC699186 | 3.30 | 0.0179 |
| MmugDNA.26596.1.S1_at | methyltransferase like 4 | LOC696353 | 3.30 | 0.0082 |
| MmuSTS.4306.1.S1_at | glycogenin 2 | LOC703955 | 3.30 | 0.0119 |
| MmuSTS.1398.1.S1_at | complement component 1, s subcomponent | C1S | 3.29 | 0.0531 |
| MmugDNA.37738.1.S1_at | GRAM domain containing 3 | LOC697870 | 3.29 | 0.0849 |
| MmugDNA.36423.1.S1_at | angiomotin like 1 | LOC698211 | 3.29 | 0.0435 |
| MmugDNA.38698.1.S1_at | complement component 1, q subcomponent, receptor 1 | C1QR1 | 3.28 | 0.0036 |
| MmugDNA.21696.1.S1_at | hypothetical protein BC007901 | LOC91461 | 3.28 | 0.0816 |
| MmugDNA.20213.1.S1_at | meningioma expressed antigen 5 (hyaluronidase) | MGEA5 | 3.27 | 0.0067 |
| MmugDNA.19007.1.S1_at | catalase | CAT | 3.26 | 0.0419 |
| MmugDNA.20699.1.S1_at | hypothetical protein LOC694371 | LOC694371 | 3.26 | 0.0587 |
| MmugDNA.6381.1.S1_at | cystatin F | LOC704850 | 3.26 | 0.0825 |
| MmugDNA.13610.1.S1_at | Full length insert cDNA clone YT94E02 | — | 3.25 | 0.0318 |
| MmuSTS.159.1.S1_at | microfibrillar-associated protein 4 | LOC709521 | 3.25 | 0.0567 |
| MmugDNA.3114.1.S1_at | Wee1-like protein kinase (WEE1hu) | WEE1 | 3.25 | 0.0474 |
| MmuSTS.2860.1.S1_at | Neuroligin 4 | — | 3.24 | 0.0013 |
| MmuSTS.3636.1.S1_at | Ets2 repressor factor | ERF | 3.24 | 0.0422 |
| MmugDNA.24307.1.S1_s_at | Sarcospan (K-ras oncogene-associated protein) (Kirsten-ras-associated protein) | SSPN | 3.24 | 0.0853 |
| MmugDNA.18122.1.S1_at | RAP2B, member of RAS oncogene family | RAP2B | 3.24 | 0.0026 |
| MmugDNA.13964.1.S1_at | trophoblast-derived noncoding RNA | TncRNA | 3.23 | 0.0115 |
| MmugDNA.7717.1.S1_at | MCM10 minichromosome maintenance deficient 10 (S. cerevisiae) | MCM10 | 3.23 | 0.0644 |
| MmugDNA.10682.1.S1_at | aquaporin 7 | AQP7 | 3.22 | 0.0409 |
| MmugDNA.9561.1.S1_at | tissue inhibitor of matrix metalloproteinase-2 | TIMP-2 | 3.22 | 0.0005 |
| MmugDNA.9052.1.S1_at | MAM domain containing 2 | LOC700333 | 3.21 | 0.0581 |
| MmugDNA.23764.1.S1_at | cyclin A | CCNA2 | 3.21 | 0.0284 |
| MmugDNA.962.1.S1_at | platelet-derived growth factor receptor beta /// hypothetical LOC711667 /// protein LOC711667 | PDGFRB | 3.20 | 0.0641 |
| MmugDNA.30376.1.S1_at | minichromosome maintenance protein 7 | MCM7 | 3.20 | 0.0000 |
| MmugDNA.40338.1.S1_s_at | Collagen alpha-1(V) chain precursor | LOC722009 | 3.20 | 0.0018 |
| MmugDNA.43126.1.S1_at | KIAA1909 protein | KIAA1909 | 3.19 | 0.0678 |
| MmugDNA.12886.1.S1_at | hypothetical protein LOC283755 /// D15F37 (pseudogene)/// MGC57820 protein | LOC283755 /// MN7 /// MGC57820 | 3.19 | 0.0143 |
| MmugDNA.33174.1.S1_at | T-cell receptor beta chain V region C5 precursor | — | 3.18 | 0.0008 |
| MmugDNA.20801.1.S1_at | Transcribed locus, moderately similar to XP_515629.1 similar to U5 snRNP-specific protein, 200 kDa; U5 snRNP-specific protein, 200 kDa (DEXH RNA helicase family) [Pan troglodytes] | — | 3.16 | 0.0121 |
| MmuSTS.249.1.S1_at | integrin, beta 2 | ITGB2 | 3.16 | 0.0580 |
| MmugDNA.18032.1.S1_at | desmoglein 3 (pemphigus vulgaris antigen) | DSG3 | 3.16 | 0.0084 |
| MmugDNA.32328.1.S1_at | lipoma HMGIC fusion partner | LOC696978 | 3.16 | 0.0243 |
| MmugDNA.3768.1.S1_at | Kruppel-like factor 8 | KLF8 | 3.16 | 0.0772 |
| MmugDNA.34645.1.S1_s_at | hypothetical protein LOC714309 | LOC714309 | 3.15 | 0.0439 |
| MmugDNA.19768.1.S1 at | proliferation associated nuclear element 1 isoform a | LOC709006 | 3.15 | 0.0103 |
| MmugDNA.19278.1.S1_at | phosphatase and actin regulator 2 | PHACTR2 | 3.15 | 0.0524 |
| MmugDNA.26562.1.S1_s_at | growth arrest-specific 5 | GASS | 3.14 | 0.0006 |
| MmugDNA.15046.1.S1_at | hemicentin 1 | LOC714026 | 3.14 | 0.0142 |
| MmugDNA.32563.1.S1_at | methionine sulfoxide reductase B3 isoform 2 | LOC717617 | 3.13 | 0.0827 |
| MmugDNA.3350.1.S1_at | L-3-hydroxyacyl-Coenzyme A dehydrogenase | HADHSC | 3.13 | 0.0983 |
| MmugDNA.27093.1.S1_at | alpha-2-macroglobulin | A2M | 3.13 | 0.0027 |
| MmugDNA.28905.1.S1_at | testis/prostate/placenta-expressed protein, isoform 2 isoform 1 | LOC706183 | 3.12 | 0.0596 |
| MmunewRS.723.1.S1_at | serine (or cysteine) proteinase inhibitor, Glade H, member 1 | SERPINH1 | 3.12 | 0.0967 |
| MmugDNA.39240.1.S1_at | acyl-CoA synthetase long-chain family member 1 | LOC694871 | 3.12 | 0.0034 |
| MmugDNA.36848.1.S1_at | Tissue factor pathway inhibitor 2 precursor (TFPI-2) (Placental protein 5) (PP5) | TFPI2 | 3.11 | 0.0431 |
| MmugDNA.5658.1.S1_at | Bcl-2-related protein Al (BFL-1 protein) (Hemopoietic-specific early response protein) (GRS protein) | BCL2A1 | 3.11 | 0.0888 |
| MmugDNA.25040.1.S1_at | clusterin | CLU | 3.11 | 0.0568 |

-continued

| Probe Set ID | Gene Title | Gene Symbol | Ratio Top verus Bottom | p value Top versus Bottom |
|---|---|---|---|---|
| MmugDNA.15918.1.S1_at | monocyte to macrophage differentiation-associated precursor | LOC706723 | 3.10 | 0.0191 |
| MmugDNA.5064.1.S1_at | transforming growth factor, beta-induced, 68 kDa | TGFBI | 3.10 | 0.0079 |
| MmuSTS.4112.1.S1_at | early growth response 1 | EGR1 | 3.10 | 0.0015 |
| MmugDNA.37314.1.S1_at | Zinc finger, CCHC domain containing 6 | ZCCHC6 | 3.09 | 0.0274 |
| MmugDNA.16942.1.S1_at | CDNA FLJ34374 fis, clone FEBRA2017502 | — | 3.09 | 0.0999 |
| MmugDNA.24636.1.S1_at | RAB, member of RAS oncogene family-like 2B | RABL2B | 3.09 | 0.0696 |
| MmugDNA.24841.1.S1_at | hypothetical protein LOC709979 | LOC709979 | 3.08 | 0.0018 |
| MmuSTS.4753.1.S1_at | Wnt inhibitory factor 1 | WIF1 | 3.08 | 0.0124 |
| MmugDNA.30671.1.S1_at | DEAD (Asp-Glu-Ala-Asp) box polypeptide 39 | LOC718822 | 3.08 | 0.0898 |
| MmugDNA.2069.1.S1_at | Isocitrate dehydrogenase 1 (NADP+30), soluble | IDH1 | 3.08 | 0.0678 |
| MmugDNA.37149.1.S1_at | oxysterol binding protein-like 6 | OSBPL6 | 3.08 | 0.0801 |
| MmugDNA.1095.1.S1_at | Mediator of RNA polymerase II transcription, subunit 28 homolog (yeast) | MED28 | 3.07 | 0.0008 |
| MmugDNA.41794.1.S1_at | moesin | MSN | 3.07 | 0.0208 |
| MmugDNA.1253.1.S1_at | — | — | 3.07 | 0.0105 |
| MmugDNA.17781.1.S1_at | neuroepithelial cell transforming gene 1 | NET1 | 3.07 | 0.0094 |
| MmugDNA.18663.1.S1_at | Slit homolog 2 (Drosophila) | SLIT2 | 3.07 | 0.0607 |
| MmugDNA.25811.1.S1_at | Transcribed locus | — | 3.07 | 0.0033 |
| MmugDNA.18485.1.S1_at | GC-rich sequence DNA-binding factor candidate | LOC700489 | 3.07 | 0.0819 |
| MmugDNA.10654.1.S1_at | X-ray repair complementing defective repair in Chinese hamster cells 5 (double-strand-break rejoining; Ku autoantigen, 80 kDa) | XRCC5 | 3.06 | 0.0952 |
| MmugDNA.42236.1.S1_at | Ribosomal protein Ll Oa | RPL10A | 3.05 | 0.0207 |
| MmugDNA.35088.1.S1_at | Fibroblast growth factor receptor 1 (fms-related tyrosine kinase 2, Pfeiffer syndrome) | FGFR1 | 3.05 | 0.0419 |
| MmugDNA.18922.1.S1_at | Hypothetical protein AY099107 | LOCI 52185 | 3.05 | 0.0748 |
| MmugDNA.31239.1.S1_at | Forkhead box 03A | FOXO3A | 3.03 | 0.0108 |
| MmugDNA.5694.1.S1_at | ADAM metallopeptidase with thrombospondin type 1 motif, 5 | ADAMTS5 | 3.03 | 0.0946 |
| MmugDNA.39840.1.S1_at | coactosin-like 1 | LOC715376 | 3.03 | 0.0023 |
| MmuSTS.2604.1.S1_at | zinc finger homeobox 1 b | ZFHX1 B | 3.02 | 0.0942 |
| MmugDNA.21087.1.S1_at | integrin, alpha 5 (fibronectin receptor, alpha polypeptide) | ITGA5 | 3.02 | 0.0160 |
| MmuSTS.3523.1.S1_at | B-cell CLL/lymphoma 11B isoform 1 | LOC705238 | 3.02 | 0.0082 |
| Mmu.7842.1.S1_at | alpha 1 type IV collagen | COL4A1 | 3.02 | 0.0409 |
| MmugDNA.8730.1.S1_at | Homo sapiens, clone IMAGE:4778480, mRNA | — | 3.02 | 0.0632 |
| MmuSTS.4829.1.S1_at | growth hormone receptor | GHR | 3.02 | 0.0012 |
| MmugDNA.14593.1.S1_at | frizzled 4 | LOC704754 | 3.01 | 0.0106 |
| MmugDNA.42280.1.S1_at | — | — | 3.01 | 0.0740 |
| MmugDNA.34063.1.S1_at | lysophosphatidylglycerol acyltransferase 1 | LPGAT1 | 3.01 | 0.0644 |
| MmuSTS.124.1.S1_at | Homeobox protein Hox-Al 0 (Hox-1 H) (Hox-1.8) (PL) | LOC704713 | 3.01 | 0.0416 |
| MmuSTS.24.1.S1_at | Glycoprotein Xg precursor (Protein PBDX) | XG | 3.01 | 0.0839 |
| MmugDNA.10983.1.S1_at | septin 10 | 10-Sep | 2.99 | 0.0257 |
| MmugDNA.10337.1.S1_at | CG9047-PA, isoform A | LOC704595 | 2.99 | 0.0300 |
| MmugDNA.15798.1.S1_s_at | HLA class II histocompatibility antigen, DQ(2) alpha chain precursor | LOC717623 | 2.99 | 0.0862 |
| MmugDNA.8592.1.S1_at | fatty acid binding protein 3, muscle and heart (mammary-derived growth inhibitor) | FABP3 | 2.99 | 0.0766 |
| MmugDNA.31542.1.S1_at | colon carcinoma related protein | LOC719328 | 2.98 | 0.0021 |
| MmuSTS.1998.1.S1_at | estrogen receptor 1 | ESR1 | 2.98 | 0.0868 |
| MmugDNA.22982.1.S1_at | hypothetical protein LOC708514 | LOC708514 | 2.98 | 0.0729 |
| MmugDNA.25545.1.S1_at | Full length insert cDNA clone ZD69D05 | — | 2.98 | 0.0295 |
| MmugDNA.8954.1.S1_at | glycerol-3-phosphate dehydrogenase 1 (soluble) | GPD1 | 2.97 | 0.0050 |
| MmuSTS.1138.1.S1_at | Phospholipase A2, membrane associated precursor (Phosphatidylcholine 2-acylhydrolase) (Group IIA phospholipase A2) (GIIC sPLA2) (Non-pancreatic secretory phospholipase A2) (NPS-PLA2) | PLA2G2A | 2.97 | 0.0880 |
| MmugDNA.10778.1.S1_at | cyclin-dependent kinase inhibitor 3 | LOC694877 | 2.97 | 0.0442 |
| MmugDNA.10040.1.S1_at | p53-regulated DDA3 isoform a | LOC698060 | 2.96 | 0.0854 |
| Mmu.2305.1.S1_at | bluestreak CG6451-PA | — | 2.96 | 0.0295 |
| MmuSTS.2278.1.51_at | peroxidasin | LOC721654 | 2.95 | 0.0127 |
| MmugDNA.1496.1.S1_at | fatty acid desaturase 3 | LOC722337 | 2.95 | 0.0442 |
| MmugDNA.29758.1.S1_at | proline-rich cyclin Al -interacting protein | LOC709846 | 2.94 | 0.0143 |
| MmuSTS.3401.1.Sl_s_at | CCAAT/enhancer-binding protein alpha (C/EBP alpha) | LOC717153 | 2.94 | 0.0015 |
| MmugDNA.2393.1.Sl_at | perilipin | PLIN | 2.93 | 0.0008 |
| MmugDNA.393.1.Sl_at | CDNA FLJ26120 fis, clone SYN00419 | — | 2.93 | 0.0092 |
| MmugDNA.30771.1.Sl_at | spermatogenesis associated factor SPAF | LOC708640 | 2.93 | 0.0712 |
| MmugDNA.15387.1.Sl_at | NEDD8 ultimate buster-1 | NYREN18 | 2.92 | 0.0520 |
| MmugDNA.5488.1.Sl_at | dehydrogenase/reductase (SDR family) member 3 | LOC715548 | 2.92 | 0.0258 |
| MmugDNA.35654.1.Sl_at | minichromosome maintenance protein 6 | MCM6 | 2.92 | 0.0680 |
| MmugDNA.30962.1.Sl_at | advanced glycosylation end product-specific receptor isoform 1 precursor | LOC717296 | 2.92 | 0.0097 |
| MmugDNA.36279.1.Sl_at | P3ECSL | LOC705660 | 2.91 | 0.0626 |
| MmugDNA.30623.1.Sl_at | ephrin receptor EphAl | EPHA1 | 2.91 | 0.0185 |
| MmugDNA.42862.1.Sl_s_at | Fasciculation and elongation protein zeta 2 (Zygin-2) (Zygin II) (Zygin-related protein types I/II) | LOC708288 | 2.91 | 0.0388 |

-continued

| Probe Set ID | Gene Title | Gene Symbol | Ratio Top verus Bottom | p value Top versus Bottom |
|---|---|---|---|---|
| MmuSTS.2298.1.Sl_at | deafness, autosomal dominant 5 protein | DFNA5 | 2.91 | 0.0812 |
| MmugDNA.18093.1.Sl_at | FERM domain containing 6 | LOC707266 | 2.91 | 0.0939 |
| MmugDNA.34261.1.Sl_at | PI-3-kinase-related kinase SMG-1 | LOC693542 | 2.90 | 0.0022 |
| MmugDNA.39398.1.Sl_at | hypothetical protein LOC699173 | LOC699173 | 2.89 | 0.0182 |
| MmugDNA.6471.1.Sl_at | Cerebellar degeneration-related antigen 1 (CDR34) | LOC698431 | 2.89 | 0.0015 |
| MmugDNA.38313.1.Sl_at | Serum amyloid A protein precursor (SAA) /// serum amyloid A1 isoform 2 | LOC694944 /// SAA1 | 2.89 | 0.0137 |
| MmugDNA.4080.1.Sl_at | peptidylprolyl isomerase F (cyclophilin F) | PPIF | 2.88 | 0.0024 |
| MmugDNA.26182.1.Sl_at | heterogeneous nuclear ribonucleoprotein Al | HNRPA1 | 2.87 | 0.0025 |
| MmugDNA.27473.1.Sl_at | CASP8 and FADD-like apoptosis regulator | CFLAR | 2.87 | 0.0203 |
| MmugDNA.35112.1.Sl_at | kleisin beta isoform 2 | LOC716120 | 2.87 | 0.0321 |
| MmugDNA.22473.1.Sl_at | PP2135 protein | PP2135 | 2.86 | 0.0928 |
| MmugDNA.37882.1.Sl_at | hypothetical protein LOC703464 /// hypothetical protein LOC705990 | LOC703464 /// LOC705990 | 2.86 | 0.0211 |
| MmuAffx.52.1.Al_at | chemokine (C-C motif) ligand 4 | CCL4 | 2.84 | 0.0361 |
| MmugDNA.31283.1.Sl_at | hypothetical protein LOC693798 | LOC693798 | 2.84 | 0.0659 |
| MmuSTS.2520.1.Sl_at | heterogeneous nuclear ribonucleoprotein H2 | HNRPH2 | 2.84 | 0.0827 |
| MmugDNA.28432.1.Sl_at | adipocyte-specific adhesion molecule | LOC708098 | 2.84 | 0.0517 |
| MmugDNA.13083.1.Sl_at | activating transcription factor 7 interacting protein | LOC698815 | 2.84 | 0.0965 |
| MmugDNA.8865.1.Sl_at | Visinin-like protein 1 (VILIP) (Neural visinin-like protein 1) (NVL-1) (NVP-1) (21 kDa CABP) | LOC699459 | 2.83 | 0.0285 |
| MmuSTS.2601.1.Sl_at | embryonal Fyn-associated substrate isoform 2 | LOC713838 | 2.83 | 0.0000 |
| MmugDNA.38045.1.Sl_at | Transcribed locus | — | 2.82 | 0.0094 |
| MmugDNA.9654.1.Sl_at | Heterogeneous nuclear ribonucleoprotein D (AU-rich element RNA binding protein 1, 37 kDa) | HNRPD | 2.82 | 0.0440 |
| MmugDNA.38313.1.Sl_s_at | serum amyloid Al isoform 2 | LOC694944 | 2.81 | 0.0253 |
| MmugDNA.24597.1.Sl_at | carbonyl reductase 3 | LOC695769 | 2.81 | 0.0598 |
| MmugDNA.36863.1.Sl_at | vang-like 1 | LOC709730 | 2.80 | 0.0744 |
| MmugDNA.15427.1.Sl_at | sterile alpha motif and leucine zipper containing kinase | AZKZAK | 2.80 | 0.0920 |
| MmugDNA.19311.1.S1_at | laminin, beta 2 | LAMB2 | 2.80 | 0.0012 |
| MmugDNA.22113.1.Sl_at | Transcribed locus, strongly similar to XP_510155.1 similar to PAPOLA protein [Pan troglodytes] | — | 2.80 | 0.0719 |
| MmuSTS.3531.1.Sl_s_at | — | CCL4L | 2.80 | 0.0516 |
| MmugDNA.21105.1.S1_at | DNA ligase I | LIG1 | 2.80 | 0.0904 |
| MmugDNA.15362.1.S1_at | HEG homolog | HEG | 2.77 | 0.0055 |
| MmugDNA.6611.1.Sl_at | hypothetical protein LOC701646 | LOC701646 | 2.77 | 0.0623 |
| MmugDNA.10320.1.S1_at | nicotinamide nucleotide adenylyltransferase 3 | NMNAT3 | 2.77 | 0.0937 |
| MmugDNA.5714.1.S1_at | timeless homolog | LOC712835 | 2.77 | 0.0737 |
| MmugDNA.6879.1.S1_at | SNF1-like kinase 2 | LOC711453 | 2.77 | 0.0878 |
| MmugDNA.40900.1.S1_at | Host cell factor-binding transcription factor Zhangfei (HCF-binding transcription factor Zhangfei) (Tyrosine kinase-associated leucine zipper protein LAZip) | LOC702942 | 2.76 | 0.0186 |
| MmugDNA.5326.1.S1_at | cyclin-dependent kinase 3 | CDK3 | 2.76 | 0.0203 |
| MmugDNA.42369.1.S1_s_at | Josephin domain containing 3 | LOC696602 | 2.76 | 0.0792 |
| MmuSTS.607.1.S1_at | Heat-shock protein beta-7 (HspB7) (Cardiovascular heat shock protein) (cvHsp) | LOC696704 | 2.75 | 0.0029 |
| MmugDNA.39315.1.S1_at | Leukemia inhibitory factor receptor | LIFR | 2.75 | 0.0588 |
| MmuSTS.631.1.S1_at | angiomotin like 2 | LOC718868 | 2.74 | 0.0095 |
| MmuSTS.2866.1.S1_at | Stathmin (Phosphoprotein p19) (pp19) (Oncoprotein 18) (0p18) (Leukemia-associated phosphoprotein p18) (pp17) (Prosolin) (Metablastin) (Protein Pr22) | LOC719733 | 2.74 | 0.0870 |
| MmugDNA.41518.1.S1_s_at | vimentin | VIM | 2.74 | 0.0725 |
| MmugDNA.5148.1.S1_at | Notchless gene homolog | NLE1 | 2.74 | 0.0939 |
| MmugDNA.34796.1.S1_at | chromosome 10 open reading frame 99 | C10orf99 | 2.73 | 0.0070 |
| MmugDNA.27576.1.S1_at | — | — | 2.73 | 0.0033 |
| MmuSTS.2115.1.S1_at | — | ARHGEF6 | 2.72 | 0.0401 |
| MmugDNA.27574.1.S1_at | membrane-spanning 4-domains, subfamily A, member 6A isoform 2 | LOC697689 | 2.72 | 0.0785 |
| MmugDNA.12560.1.S1_at | enoyl Coenzyme A hydratase domain containing 3 | LOC693583 | 2.72 | 0.0499 |
| MmugDNA.35275.1.S1_at | transmembrane protease, serine 8 (intestinal) | LOC697965 | 2.72 | 0.0064 |
| MmugDNA.43094.1.S1_at | procollagen C-endopeptidase enhancer 2 | PCOLCE2 | 2.72 | 0.0769 |
| Mmu.3054.2.S1_at | upstream of NRAS | CSDE1 | 2.72 | 0.0039 |
| MmuSTS.2641.1.S1_at | ATP synthase, H+transporting, mitochondrial F1 complex, alpha subunit | — | 2.72 | 0.0461 |
| MmugDNA.18980.1.S1_at | neuromedin B | NMB | 2.71 | 0.0546 |
| MmugDNA.23958.1.S1_at | G protein-coupled receptor 37 | GPR37 | 2.71 | 0.0888 |
| MmugDNA.43305.1.S1_at | — | — | 2.71 | 0.0499 |
| MmugDNA.31834.1.S1_at | Fanconi anemia group A protein (Protein FACA) | LOC714932 | 2.71 | 0.0205 |
| MmugDNA.36837.1.S1_at | poly(rC) binding protein 2 (predicted) /// poly(rC) binding protein 2 | LOC694744 /// LOC703175 | 2.70 | 0.0636 |
| MmugDNA.11099.1.S1_at | Catenin (cadherin-associated protein), beta 1, 88 kDa | CTNNB1 | 2.70 | 0.0381 |
| MmugDNA.37576.1.S1_at | PHD finger protein 20-like 1 isoform 1 | LOC701406 | 2.70 | 0.0015 |
| MmuSTS.541.1.S1_at | oxysterol-binding protein-like protein 8 isoform a DKFZP761 NO | LOC693338 | 2.69 | 0.0396 |
| MmugDNA.16521.1.S1_at | hypothetical protein DKFZp761N09121 | 9121 | 2.69 | 0.0319 |

-continued

| Probe Set ID | Gene Title | Gene Symbol | Ratio Top verus Bottom | p value Top versus Bottom |
|---|---|---|---|---|
| MmugDNA.9406.1.S1_at | Ubiquitin-conjugating enzyme E2H (UBC8 homolog, yeast) | UBE2H | 2.69 | 0.0368 |
| MmuSTS.3625.1.S1_at | polycystin 2 | LOC702179 | 2.68 | 0.0079 |
| MmugDNA.41756.1.S1_at | membrane protein, palmitoylated 3 (MAGUK p55 subfamily member 3) | MPP3 | 2.68 | 0.0063 |
| MmugDNA.7204.1.S1_at | serum/glucocorticoid regulated kinase | LOC713082 | 2.67 | 0.0050 |
| MmugDNA.19300.1.S1_at | Endothelial protein C receptor precursor (Endothelial cell protein C receptor) (Activated protein C receptor) (APC receptor) (CD201 antigen) | LOC706040 | 2.67 | 0.0858 |
| MmugDNA.7974.1.S1_at | TRAF interacting protein | TRAIP | 2.67 | 0.0891 |
| MmugDNA.14150.1.S1_at | CG8745-PA | LOC702302 | 2.67 | 0.0453 |
| MmugDNA.24498.1.S1_at | replication factor C (activator 1) 4, 37 kDa | RFC4 | 2.67 | 0.0043 |
| MmugDNA.31559.1.S1_at | CTD small phosphatase-like protein (CTDSP-like) (Small C-terminal domain phosphatase 3) (Small CTD phosphatase 3) (SCP3) (Nuclear LIM interactor-interacting factor 1) (NLI-interacting factor 1) (NIF-like protein) (RBSP3) (YA22 protein) (... | LOC697898 | 2.67 | 0.0039 |
| MmugDNA.27755.1.S1_at | Similar to KIAA0393 protein | MGC57820 | 2.67 | 0.0755 |
| MmuSTS.825.1.S1_x_at | degenerative spermatocyte homolog 1, lipid desaturase | LOC702128 | 2.67 | 0.0943 |
| MmugDNA.32190.1.S1_at | HRAS-like suppressor 3 | HRASLS3 | 2.66 | 0.0205 |
| MmugDNA.378.1.S1_at | Syntaxin 7 | STX7 | 2.66 | 0.0271 |
| MmugDNA.7129.1.S1_at | UDP-N-acetyl-alpha-D-galactosamine:polypeptide N-acetylgalactosaminyltransferase-like 4 | LOC701790 | 2.66 | 0.0855 |
| MmugDNA.37173.1.S1_at | methyltransferase like 7A | LOC693894 | 2.66 | 0.0812 |
| MmugDNA.15924.1.S1_at | Eukaryotic translation initiation factor 4E member 2 | EIF4E2 | 2.66 | 0.0777 |
| MmugDNA.18344.1.S1_at | Jagged 1 (Alagille syndrome) | JAG1 | 2.66 | 0.0523 |
| MmugDNA.18912.1.S1_at | inter-alpha trypsin inhibitor heavy chain precursor 5 isoform 2 | LOC722614 | 2.65 | 0.0437 |
| MmugDNA.38963.1.S1_at | inhibitor of DNA binding 1 isoform b | LOC713160 | 2.65 | 0.0167 |
| MmugDNA.38359.1.S1_at | H2A histone family, member Y | H2AFY | 2.65 | 0.0069 |
| MmuSTS.1880.1.S1_at | collagen, type IV, alpha 2 | COL4A2 | 2.65 | 0.0233 |
| MmuSTS.999.1.S1_at | myc proto-oncogene protein | MYC | 2.65 | 0.0644 |
| MmugDNA.27587.1.S1_at | Homo sapiens, clone IMAGE:5170410, mRNA | — | 2.65 | 0.0784 |
| MmugDNA.20660.1.S1_at | tripartite motif-containing 33 protein | TRIM33 | 2.64 | 0.0247 |
| MmugDNA.7029.1.S1_at | Receptor activity-modifying protein 3 precursor (CRLR activity-modifying protein 3) (Calcitonin-receptor-like receptor activity-modifying protein 3) | LOC697349 | 2.64 | 0.0289 |
| MmuSTS.3328.1.S1_at | origin recognition complex, subunit 1 | LOC713271 | 2.63 | 0.0374 |
| MmugDNA.38420.1.S1_s_at | Transmembrane BAX inhibitor motif-containing protein 4 (Z-protein) (S1 R protein) | TMBIM4 | 2.63 | 0.0011 |
| MmugDNA.32616.1.S1_at | XIAP associated factor-1 isoform 1 | LOC713425 | 2.63 | 0.0099 |
| MmugDNA.2794.1.S1_at | Epithelial membrane protein 1 (EMP-1) (Tumor-associated membrane protein) (CL-20) (B4B protein) | EMP1 | 2.63 | 0.0386 |
| MmugDNA.28550.1.S1_at | heat shock protein, alpha-crystallin-related, B6 | LOC710760 | 2.62 | 0.0083 |
| MmugDNA.19535.1.S1_at | desmocollin 3 | DSC3 | 2.62 | 0.0261 |
| MmugDNA.14923.1.S1_at | Adenomatosis polyposis coli 2 | APC2 | 2.62 | 0.0847 |
| MmugDNA.10555.1.S1_at | CDNA FLJ36553 fis, clone TRACH2008478 | — | 2.61 | 0.0113 |
| MmugDNA.35200.1.S1_at | hypothetical protein FLJ13305 | FLJ13305 | 2.61 | 0.0709 |
| MmugDNA.10323.1.S1_s_at | RNA binding motif protein 25 | LOC695911 | 2.60 | 0.0340 |
| MmugDNA.25448.1.S1_at | CG13745-PA | LOC699878 | 2.60 | 0.0499 |
| MmugDNA.40326.1.S1_at | MRNA; cDNA DKFZp686F1318 (from clone DKFZp686F1318) | — | 2.60 | 0.0643 |
| MmugDNA.11833.1.S1_at | Homo sapiens, clone IMAGE:5278284, mRNA | — | 2.60 | 0.0515 |
| MmugDNA.31867.1.S1_at | golgi associated, gamma adaptin ear containing, ARF binding protein 2 | GGA2 | 2.59 | 0.0586 |
| MmugDNA.33539.1.S1_at | Ankyrin 3, node of Ranvier (ankyrin G) | ANK3 | 2.59 | 0.0204 |
| MmugDNA.37283.1.S1_at | Polypyrimidine tract binding protein 2 | PTBP2 | 2.57 | 0.0946 |
| MmugDNA.40388.1.S1_at | lactotransferrin | LOC713115 | 2.57 | 0.0012 |
| MmunewRS.711.1.S1_at | corticotropin releasing hormone binding protein | LOC707589 | 2.56 | 0.0397 |
| MmugDNA.20034.1.S1_at | Full length insert cDNA clone ZD69D05 | — | 2.55 | 0.0473 |
| MmugDNA.40606.1.S1_at | Activin A receptor type II-like 1 | ACVRL1 | 2.55 | 0.0529 |
| MmugDNA.42565.1.S1_at | H+transporting F1 ATP synthase epsilon subunit | — | 2.55 | 0.0439 |
| MmugDNA.16683.1.S1_at | solute carrier family 24 (sodium/potassium/calcium exchanger), member 3 | SLC24A3 | 2.54 | 0.0562 |
| MmugDNA.864.1.S1_at | Chromosome 16 open reading frame 28 | C16orf28 | 2.54 | 0.0225 |
| MmugDNA.41780.1.S1_at | interleukin 6 signal transducer receptor | IL-6 | 2.53 | 0.0980 |
| MmugDNA.37515.1.S1_at | Hypothetical protein FLJ13941 | FLJ13941 | 2.53 | 0.0038 |
| MmugDNA.25797.1.S1_at | Hypothetical protein MGC10067 | MGC10067 | 2.53 | 0.0315 |
| MmugDNA.27004.1.S1_at | follistatin-like 1 | FSTL1 | 2.52 | 0.0172 |
| MmugDNA.1644.1.S1_at | eukaryotic translation initiation factor 5B | EIF5B | 2.52 | 0.0295 |
| MmugDNA.23477.1.S1_at | RAS and EF hand domain containing | RASEF | 2.52 | 0.0477 |
| MmugDNA.40191.1.S1_at | Ubiquinol-cytochrome c reductase complex 14 kDa protein (Complex III subunit VI) (QP-C) | UQCRB | 2.52 | 0.0061 |
| MmugDNA.5276.1.S1_at | two AAA domain containing protein | LOC704478 | 2.51 | 0.0788 |
| MmugDNA.9275.1.S1_at | Acetyl-Coenzyme A synthetase 2 (ADP forming) | ACAS2 | 2.51 | 0.0312 |
| MmugDNA.23637.1.S1_at | Rho GTPase activating protein 23 | ARHGAP23 | 2.51 | 0.0377 |

-continued

| Probe Set ID | Gene Title | Gene Symbol | Ratio Top verus Bottom | p value Top versus Bottom |
|---|---|---|---|---|
| MmugDNA.31862.1.S1_at | Transcribed locus, moderately similar to XP_524454.1 LOC469069 [Pan troglodytes] | — | 2.51 | 0.0338 |
| MmugDNA.39520.1.S1_at | Rho GDP-dissociation inhibitor 2 (Rho GDI 2) (Rho-GDI beta) (Ly-GDI) | ARHGDIB | 2.50 | 0.0744 |
| MmugDNA.22495.1.S1_at | choline phosphotransferase 1 | LOC696056 | 2.50 | 0.0276 |
| MmugDNA.40534.1.S1_s_at | S-phase kinase-associated protein 2 isoform 1 | LOC700617 | 2.49 | 0.0640 |
| MmugDNA.25179.1.S1_s_at | hypothetical protein LOC707276 /// Acidic leucine-rich nuclear phosphoprotein 32 family member B (PHAPI2 protein) (Silver-stainable protein SSP29) (Acidic protein rich ANP32B /// in leucines) | LOC707276 | 2.49 | 0.0301 |
| MmugDNA.20756.1.S1_at | methionine aminopeptidase 1D | MAP1 D | 2.49 | 0.0157 |
| MmugDNA.10451.1.S1_at | lipoprotein lipase | LPL | 2.48 | 0.0793 |
| MmugDNA.37784.1.S1_at | Microfibrillar-associated protein 5 precursor (MFAP-5) (Microfibril-associated glycoprotein 2) (MAGP-2) (MP25) | MFAP5 | 2.48 | 0.0288 |
| MmugDNA.11410.1.S1_at | WW domain-containing adapter with a coiled-coil region isoform 1 | LOC715828 | 2.48 | 0.0246 |
| MmugDNA.16003.1.S1_at | hypothetical protein LOC713457 | LOC713457 | 2.48 | 0.0832 |
| MmugDNA.7480.1.S1_at | Glutaredoxin-1 (Thioltransferase-1) (TTase-1) | GLRX | 2.48 | 0.0177 |
| MmugDNA.41094.1.S1_at | cytochrome P450, family 2, subfamily E, polypeptide 2 homolog | LOC718303 | 2.47 | 0.0545 |
| MmuSTS.2498.1.S1_at | zinc finger protein 8 | ZNF8 | 2.47 | 0.0011 |
| MmuSTS.3305.1.S1_at | Oxysterols receptor LXR-alpha (Liver X receptor alpha) (Nuclear orphan receptor LXR-alpha) | NR1H3 | 2.47 | 0.0882 |
| MmugDNA.22116.1.S1_at | Neurotensin/neuromedin N precursor | NTS | 2.47 | 0.0663 |
| MmuSTS.1525.1.S1_at | mitochondrial ribosomal protein L35 | MRPL35 | 2.47 | 0.0431 |
| MmugDNA.14539.1.S1_at | KIAA1450 protein | KIAA1450 | 2.46 | 0.0140 |
| MmugDNA.2162.1.S1_at | C20orf111 | LOC693890 | 2.46 | 0.0194 |
| MmugDNA.14181.1.S1_at | CDNA: FLJ23006 fis, clone LNG00414 | — | 2.46 | 0.0527 |
| MmugDNA.38899.1.S1_at | alpha 2 type VI collagen isoform 2C2 precursor | LOC709493 | 2.46 | 0.0950 |
| MmugDNA.12419.1.S1_at | sno, strawberry notch homolog 1 | LOC709260 | 2.46 | 0.0741 |
| Mmu.13956.1.S1_at | mitochondrial aldehyde dehydrogenase 2 | ALDH2 | 2.46 | 0.0559 |
| MmugDNA.27955.1.S1_at | thrombospondin 3 | THBS3 | 2.45 | 0.0003 |
| Mmu.12740.1.S1_at | activating transcription factor 2 | LOC699072 | 2.45 | 0.0690 |
| MmugDNA.2942.1.S1_at | Ras-related protein Rab-15 | LOC708330 | 2.44 | 0.0561 |
| MmugDNA.42705.1.S1_at | SH3 multiple domains 1 | LOC714868 | 2.44 | 0.0830 |
| MmugDNA.2199.1.S1_at | hypothetical protein LOC706003 | LOC706003 | 2.44 | 0.0707 |
| MmugDNA.31469.1.S1_at | Mitochondrial 28S ribosomal protein S25 (S25mt) (MRP-S25) | LOC703261 | 2.44 | 0.0413 |
| MmugDNA.32362.1.S1_at | v-maf musculoaponeurotic fibrosarcoma oncogene homolog B (avian) | MAFB | 2.43 | 0.0446 |
| MmugDNA.37182.1.S1_at | C17G10.1 | LOC700219 | 2.43 | 0.0349 |
| MmugDNA.3948.1.S1_at | B-cell lymphoma 6 protein | LOC708736 | 2.43 | 0.0461 |
| MmugDNA.29568.1.S1_at | Hypothetical gene supported by BX640700 | — | 2.43 | 0.0882 |
| MmugDNA.22001.1.S1_at | mucin 7, salivary | LOC707153 | 2.43 | 0.0161 |
| MmugDNA.24814.1.S1_at | RAS protein activator like 2 | RASAL2 | 2.43 | 0.0553 |
| MmugDNA.23518.1.S1_at | Muscleblind-like 2 (Drosophila) | MBNL2 | 2.42 | 0.0661 |
| MmugDNA.10700.1.S1_at | opioid growth factor receptor-like 1 | LOC715189 | 2.42 | 0.0889 |
| MmugDNA.13067.1.S1_at | serine/threonine kinase 4 | STK4 | 2.42 | 0.0978 |
| MmugDNA.40225.1.S1_at | LIM domain containing preferred translocation partner in lipoma | LPP | 2.42 | 0.0289 |
| MmugDNA.31182.1.S1_at | centrosome spindle pole associated protein | LOC704476 | 2.42 | 0.0587 |
| MmugDNA.19553.1.S1_at | damage-specific DNA binding protein 2 (48kD) | DDB2 | 2.41 | 0.0098 |
| MmugDNA.2267.1.S1_at | Transcribed locus | — | 2.41 | 0.0491 |
| MmugDNA.2874.1.S1_at | DNA polymerase gamma subunit 2, mitochondrial precursor (Mitochondrial DNA polymerase accessory subunit) (PoIG-beta) (MtPolB) (DNA polymerase gamma accessory 55 kDa subunit) (p55) | LOC720356 | 2.41 | 0.0413 |
| Mmu.11306.1.S1_at | MYC binding protein 2 | MYCBP2 | 2.41 | 0.0484 |
| MmugDNA.27252.1.S1_at | Transcribed locus | — | 2.41 | 0.0826 |
| MmugDNA.4547.1.S1_at | aarF domain containing kinase 5 | ADCK5 | 2.41 | 0.0068 |
| MmugDNA.29817.1.S1_at | Ubiquitin-conjugating enzyme E2E 2 (UBC4/5 homolog, yeast) | UBE2E2 | 2.41 | 0.0791 |
| MmugDNA.22188.1.S1_at | Rho guanine nucleotide exchange factor (GEF) 10 | ARHGEF10 | 2.40 | 0.0882 |
| MmugDNA.3376.1.S1_at | caspase recruitment domain family, member 8 | CARD8 | 2.40 | 0.0302 |
| MmugDNA.43065.1.S1_at | pregnancy-induced growth inhibitor isoform 1 | LOC714549 | 2.40 | 0.0211 |
| MmugDNA.40500.1.S1_at | hypothetical protein LOC694075 | LOC694075 | 2.40 | 0.0409 |
| MmugDNA.11419.1.S1_at | molecule interacting with Rab13 | MICAL-L1 | 2.39 | 0.0963 |
| MmugDNA.1847.1.S1_at | tissue inhibitor of metalloproteinase 2 | TIMP2 | 2.39 | 0.0030 |
| MmugDNA.11882.1.S1_at | hypothetical protein LOC721782 | LOC721782 | 2.39 | 0.0452 |
| MmuSTS.1231.1.S1_at | copine II | LOC703557 | 2.39 | 0.0061 |
| MmugDNA.22620.1.S1_at | Galectin-7 (Gal-7) (HKL-14) (P17) (p53-induced protein 1) | LGALS7 | 2.38 | 0.0861 |
| Mmu.15973.14.S1_at | growth hormone variant /// growth hormone 1 isoform 1 /// | CSH-3 /// CSH-4 /// GH1 | 2.38 | 0.0038 |

-continued

| Probe Set ID | Gene Title | Gene Symbol | Ratio Top verus Bottom | p value Top versus Bottom |
|---|---|---|---|---|
| | chorionic somatommamotropin hormone 3 /// growth hormone 1 /// chorionic somatommamotropin hormone 4 | /// LOC700885 /// LOC718116 /// LOC718474 | | |
| MmugDNA.40962.1.S1_at | Patched homolog (Drosophila) | PTCH | 2.37 | 0.0228 |
| MmugDNA.11810.1.S1_at | chromatin-specific transcription elongation factor large subunit | LOC708066 | 2.37 | 0.0275 |
| MmuSTS.2967.1.S1_at | alcohol dehydrogenase, iron containing, 1 | LOC703118 | 2.37 | 0.0768 |
| MmugDNA.3168.1.S1_at | CDNA clone IMAGE:5294683, partial cds | — | 2.37 | 0.0307 |
| MmugDNA.4900.1.S1_s_at | amylase, alpha 2A; pancreatic | AMY2A | 2.37 | 0.0873 |
| MmuSTS.1626.1.S1_at | thyroid hormone receptor interactor 10 | LOC703934 | 2.36 | 0.0148 |
| MmuSTS.3226.1.S1_at | myosin IXA | LOC701520 | 2.36 | 0.0256 |
| MmugDNA.23835.1.S1_at | RNA binding motif protein 5 | RBM5 | 2.35 | 0.0695 |
| MmuSTS.1925.1.S1_at | Tissue factor precursor (TF) (Coagulation factor III) (Thromboplastin) (CD142 antigen) | F3 | 2.35 | 0.0169 |
| MmugDNA.23256.1.S1_at | guanylate cyclase 1, soluble, alpha 3 | LOC699365 | 2.35 | 0.0208 |
| MmunewRS.334.1.S1_at | gi:42657654 | — | 2.35 | 0.0278 |
| MmugDNA.524.1.S1_at | Full length insert cDNA clone YX74D05 | — | 2.34 | 0.0963 |
| MmuSTS.891.1.S1_at | Microfibrillar-associated protein 2 precursor (MFAP-2) (Microfibril-associated glycoprotein) (MAGP) (MAGP-1) | MFAP2 | 2.34 | 0.0609 |
| MmuSTS.4399.1.S1_at | cell division cycle associated 8 | LOC719808 | 2.34 | 0.0254 |
| MmugDNA.36.1.S1_at | Sorting nexin-10 | SNX10 | 2.33 | 0.0528 |
| MmugDNA.24165.1.S1_at | ATP synthase lipid-binding protein, mitochondrial precursor (ATP synthase proteolipid P1) (ATPase protein 9) (ATPase subunit C) | — | 2.33 | 0.0024 |
| MmugDNA.38800.1.S1_at | connexin 43 | GJA1 | 2.33 | 0.0658 |
| MmugDNA.2930.1.S1_at | Full length insert cDNA clone ZEO3F06 | — | 2.33 | 0.0266 |
| MmugDNA.42198.1.S1_at | glycosyltransferase-like 1B | LOC714846 | 2.33 | 0.0727 |
| MmugDNA.782.1.S1_s_at | adenine phosphoribosyltransferase isoform b | APRT | 2.33 | 0.0978 |
| MmugDNA.40585.1.31_at | — | — | 2.32 | 0.0884 |
| Mmu.13676.1.31_s_at | Transcribed locus | — | 2.32 | 0.0702 |
| MmugDNA.38278.1.31_at | Solute carrier family 1 (glutamate/neutral amino acid transporter), member 4 | SLC1A4 | 2.32 | 0.0846 |
| MmugDNA.37513.1.31_at | Y-box-binding protein 2 (Germ cell-specific Y-box-binding protein) (FRGY2 homolog) | LOC714750 | 2.32 | 0.0853 |
| MmuSTS.699.1.31_at | calcium activated chloride channel 2 | LOC711959 | 2.32 | 0.0311 |
| MmugDNA.35545.1.31_at | DEAD (Asp-Glu-Ala-Asp) box polypeptide 17 | DDX17 | 2.32 | 0.0193 |
| MmuSTS.4279.1.31_at | ephrin A4 isoform b | LOC717315 | 2.31 | 0.0921 |
| MmuSTS.4415.1.31_at | nuclear matrix protein p84 | THOC1 | 2.31 | 0.0067 |
| MmugDNA.20377.1.31_at | growth arrest-specific 6 | LOC716066 | 2.31 | 0.0374 |
| MmugDNA.9919.1.S1_at | solute carrier family 25, member 36 | LOC715375 | 2.30 | 0.0365 |
| MmugDNA.41865.1.31_at | procollagen C-endopeptidase enhancer | PCOLCE | 2.30 | 0.0277 |
| Mmu.2142.1.31_at | tripartite motif-containing 22 | TRIM22 | 2.30 | 0.0336 |
| MmugDNA.21471.1.31_at | butyrophilin-like 9 | BTNL9 | 2.30 | 0.0203 |
| MmugDNA.33142.1.31_at | Thyroid hormone receptor associated protein 2 | THRAP2 | 2.30 | 0.0902 |
| MmugDNA.911.1.31_at | tRNA splicing endonuclease 54 homolog (SEN54, S. cerevisiae) | LOC702604 | 2.29 | 0.0159 |
| MmugDNA.462.1.31_at | Chromobox homolog 3 (HP1 gamma homolog, Drosophila) | CBX3 | 2.29 | 0.0325 |
| MmugDNA.16130.1.31_at | hypothetical protein LOC90393 | LOC90393 | 2.29 | 0.0237 |
| MmugDNA.32185.1.31_s_at | Troponin T, fast skeletal muscle (TnTf) (Fast skeletal muscle troponin T) (fTnT) (Beta TnTF) | LOC704095 | 2.29 | 0.0954 |
| MmuSTS.268.1.S1_at | U2-associated SR140 protein | LOC716408 | 2.29 | 0.0066 |
| MmugDNA.39036.1.31_at | Coatomer subunit zeta-2 (Zeta-2 coat protein) (Zeta-2 COP) | COPZ2 | 2.28 | 0.0507 |
| MmugDNA.21025.1.31_at | cold inducible RNA binding protein | LOC706175 | 2.28 | 0.0249 |
| MmugDNA.40486.1.31_s_at | Immortalization-up-regulated protein (Hepatocyte growth factor activator inhibitor type 2-related small pprotein) (HAI-2-related small protein) (H2RSP) | LOC714854 | 2.28 | 0.0153 |
| MmugDNA.26396.1.31_at | proline rich 6 | LOC700414 | 2.28 | 0.0073 |
| MmuSTS.2009.1.31_at | protocadherin 18 precursor | LOC698420 | 2.27 | 0.0824 |
| MmugDNA.9315.1.31_at | kinesin light chain 3 | LOC714331 | 2.27 | 0.0027 |
| MmugDNA.31698.1.31_at | chromosome 10 open reading frame 86 | LOC705375 | 2.27 | 0.0652 |
| MmugDNA.30174.1.31_at | v-ets erythroblastosis virus E26 oncogene like | ERG | 2.27 | 0.0267 |
| MmuSTS.7.1.31_at | GULP, engulfment adaptor PTB domain containing 1 | LOC708601 | 2.27 | 0.0459 |
| MmuSTS.4265.1.31_at | glypican 4 | LOC706665 | 2.26 | 0.0874 |
| MmugDNA.14551.1. S1 _at | cat eye syndrome critical region protein 1 isoform a precursor | LOC709295 | 2.26 | 0.0215 |
| MmugDNA.28933.1.31_at | septin 11 | 11-Sep | 2.26 | 0.0320 |
| MmugDNA.24711.1.31_at | rhomboid family 1 | LOC693423 | 2.26 | 0.0985 |
| MmugDNA.22992.1.31_at | zinc finger protein (C2H2 type) 277 | ZNF277 | 2.26 | 0.0065 |
| MmugDNA.24410.1.31_at | melanoma associated antigen (mutated) 1 | MUM1 | 2.26 | 0.0947 |
| MmugDNA.9906.1.S1_at | Histone H1.5 (Histone H1 a) | LOC705100 | 2.26 | 0.0128 |
| MmuSTS.3965.1.31_at | colony stimulating factor 1 receptor precursor | LOC711512 | 2.26 | 0.0542 |
| MmugDNA.1769.1.S1_at | CG4699-PA, isoform A | LOC713138 | 2.25 | 0.0713 |
| MmugDNA.43306.1.31_at | cyclin I | — | 2.25 | 0.0498 |
| MmugDNA.42603.1.31_at | ankyrin repeat domain 28 | LOC696592 | 2.25 | 0.0775 |
| MmugDNA.37006.1.31_at | B-cell translocation gene 1, anti-proliferative | LOC710112 | 2.25 | 0.0352 |
| MmugDNA.7428.1.31_at | Wolf-Hirschhorn syndrome candidate 1 protein isoform 1 | LOC712618 | 2.25 | 0.0954 |

-continued

| Probe Set ID | Gene Title | Gene Symbol | Ratio Top verus Bottom | p value Top versus Bottom |
|---|---|---|---|---|
| MmugDNA.37011.1.31_at | CXXC finger 6 | LOC694137 | 2.25 | 0.0304 |
| MmugDNA.35449.1.31_at | Sialyltransferase 7 ((alpha-N-acetylneuraminy1-2,3-beta-galactosy1-1,3)-N-acetyl galactosaminide alpha-2,6-sialyltransferase) B /// CDNA clone IMAGE:3831740, partial cds | SIAT7B | 2.24 | 0.0030 |
| MmuSTS.1106.1.S1_at | platelet/endothelial cell adhesion molecule (CD31 antigen) | LOC718302 | 2.24 | 0.0231 |
| MmugDNA.12061.1.S1_at | — | — | 2.24 | 0.0089 |
| MmuSTS.4678.1.S1_at | three prime repair exonuclease 1 isoform d | LOC710035 | 2.24 | 0.0664 |
| Mmu.4786.2.S1_at | pyrophosphatase 1 | LOC716720 | 2.24 | 0.0781 |
| MmugDNA.38317.1.S1_at | Transcribed locus | — | 2.23 | 0.0610 |
| MmugDNA.26830.1.S1_at | polymerase (DNA directed), eta | LOC700772 | 2.23 | 0.0463 |
| MmugDNA.18586.1.S1_at | structural maintenance of chromosomes 2-like 1 | SMC2L1 | 2.23 | 0.0554 |
| MmugDNA.11249.1.S1_at | potassium channel tetramerisation domain containing 12 | LOC695756 | 2.23 | 0.0517 |
| MmugDNA.8879.1.S1_at | sestrin 3 | SESN3 | 2.23 | 0.0195 |
| MmugDNA.24687.1.S1_at | SLIT-ROBO Rho GTPase activating protein 1 | SRGAP1 | 2.22 | 0.0821 |
| MmugDNA.37739.1.S1_at | serine/threonine kinase 24 (STE20 homolog, yeast) | STK24 | 2.22 | 0.0258 |
| MmuSTS.1280.1.S1_at | RAB39 | LOC709951 | 2.21 | 0.0169 |
| MmugDNA.24944.1.S1_at | Cytochrome P450, family 4, subfamily F, polypeptide 3 | — | 2.21 | 0.0677 |
| MmunewRS.254.1.S1_at | putative ISG12(c) protein | IF127 | 2.21 | 0.0683 |
| MmugDNA.34004.1.S1_s_at | secretory carrier membrane protein 2 | SCAM P2 | 2.21 | 0.0608 |
| MmugDNA.12030.1.S1_at | SEC8 protein | — | 2.20 | 0.0199 |
| MmugDNA.21255.1.S1_at | neutrophil cytosolic factor 1 | NCF1 | 2.20 | 0.0161 |
| MmugDNA.43588.1.S1_at | hypothetical protein LOC712570 | LOC712570 | 2.20 | 0.0824 |
| MmugDNA.23296.1.S1_s_at | thyroid receptor-interacting protein 6 | TRIP6 | 2.20 | 0.0513 |
| MmugDNA.14929.1.S1_at | insulin-like growth factor 2 mRNA binding protein 2 isoform b | LOC701536 | 2.20 | 0.0109 |
| MmugDNA.39168.1.S1_at | platelet-derived growth factor C precursor | LOC700236 | 2.19 | 0.0284 |
| MmuSTS.1102.1.S1_at | poly(rC) binding protein 4 isoform b | PCBP4 | 2.19 | 0.0477 |
| MmugDNA.41718.1.S1_at | CG12134-PA, isoform A | LOC706314 | 2.19 | 0.0509 |
| MmugDNA.36456.1.S1_at | Cl q and tumor necrosis factor related protein 2 | LOC695783 | 2.18 | 0.0650 |
| MmuSTS.4542.1.S1_at | Glycophorin C (PAS-2) (Glycoprotein beta) (GLPC) (Glycoconnectin) (Sialoglycoprotein D) (Glycophorin D) (GPD) (CD236 antigen) | LOC712092 | 2.18 | 0.0118 |
| MmugDNA.10214.1.S1_at | KIAA0792 gene product | KIAA0792 | 2.18 | 0.0596 |
| MmugDNA.7604.1.S1_at | THO complex 2 | THOC2 | 2.18 | 0.0947 |
| MmugDNA.4607.1.S1_at | zinc finger protein 326 isoform 2 | LOC696575 | 2.18 | 0.0302 |
| MmugDNA.26241.1.S1_at | cytochrome b5 reductase | LOC714058 | 2.18 | 0.0499 |
| MmugDNA.24148.1.S1_at | trafficking protein, kinesin binding 2 | LOC701779 | 2.17 | 0.0404 |
| MmugDNA.15712.1.S1_x_at | Cathepsin B | CTSB | 2.17 | 0.0099 |
| MmugDNA.34134.1.S1_at | quaking homolog, KH domain RNA binding isoform HQK-5 | LOC712600 | 2.17 | 0.0569 |
| MmugDNA.20961.1.S1_at | abhydrolase domain containing 1 (predicted) | LOC711493 | 2.17 | 0.0641 |
| MmugDNA.11400.1.S1_at | Homo sapiens, clone IMAGE:6152133, mRNA | — | 2.17 | 0.0985 |
| MmugDNA.32260.1.S1_at | — | — | 2.17 | 0.0854 |
| MmugDNA.3224.1.S1_at | beta adrenergic receptor kinase 2 | LOC714510 | 2.17 | 0.0824 |
| MmuSTS.144.1.S1_at | minichromosome maintenance protein 2 | LOC710888 | 2.16 | 0.0450 |
| MmugDNA.8814.1.S1_at | TBC1 domain family, member 4 | LOC696915 | 2.15 | 0.0771 |
| MmugDNA.31838.1.S1_s_at | histamine N-methyltransferase | HNMT | 2.15 | 0.0984 |
| MmuSTS.224.1.S1_at | solute carrier family 25, member 27 | SLC25A27 | 2.15 | 0.0161 |
| MmugDNA.24609.1.S1_at | hypothetical protein LOC707415 | LOC707415 | 2.14 | 0.0692 |
| MmugDNA.9218.1.S1_at | RNA binding motif protein 30 | RBM30 | 2.14 | 0.0450 |
| MmugDNA.1986.1.S1_at | type 1 tumor necrosis factor receptor shedding aminopeptidase regulator | ARTS-1 | 2.14 | 0.0959 |
| MmugDNA.21483.1.S1_at | zinc finger protein 579 | LOC701452 | 2.14 | 0.0953 |
| MmugDNA.16054.1.S1_at | TWIST neighbor | LOC707781 | 2.14 | 0.0733 |
| MmugDNA.7039.1.S1_at | — | — | 2.14 | 0.0038 |
| MmuSTS.3729.1.S1_at | fibromodulin precursor | LOC703048 | 2.14 | 0.0183 |
| MmugDNA.10834.1.S1_at | allograft inflammatory factor 1 | AIF1 | 2.14 | 0.0300 |
| MmugDNA.32311.1.S1_at | hormone-sensitive lipase | LOC707997 | 2.14 | 0.0209 |
| MmugDNA.12478.1.S1_at | pleckstrin homology domain containing, family C (with FERM domain) member 1 | LOC693958 | 2.14 | 0.0232 |
| MmugDNA.37583.1.S1_at | Protein tyrosine phosphatase, receptor type, S | PTPRS | 2.13 | 0.0946 |
| MmugDNA.19987.1.S1_s_at | hypothetical protein LOC284454 | LOC284454 | 2.13 | 0.0374 |
| MmugDNA.7038.1.S1_at | Fc fragment of IgG, low affinity 111b, receptor (CD16b) | FCGR3B | 2.13 | 0.0550 |
| MmugDNA.32358.1.S1_at | lamin A/C | LMNA | 2.13 | 0.0347 |
| MmugDNA.16962.1.S1_at | establishment of cohesion 1 homolog 1 | LOC698845 | 2.13 | 0.0556 |
| MmugDNA.23571.1.S1_at | Epithelial stromal interaction 1 (breast) | EPSTI1 | 2.13 | 0.0778 |
| MmuSTS.2627.1.S1_at | exostoses (multiple)-like 1 | EXTL1 | 2.13 | 0.0154 |
| MmuSTS.1193.1.S1_at | phorbol-12-myristate-13-acetate-induced protein 1 | LOC702789 | 2.13 | 0.0133 |
| MmugDNA.20278.1.S1_at | Insulin-like growth factor-binding protein 7 precursor (IGFBP-7) (IBP-7) (IGF-binding protein 7) (MAC25 protein) (Prostacyclin-stimulating factor) (PGI2-stimulating factor) (IGFBP-rP1) | LOC693564 | 2.12 | 0.0219 |
| MmugDNA.22598.1.S1_at | poliovirus receptor-related 1 (herpesvirus entry mediator C; nectin) | PVRL1 | 2.12 | 0.0579 |
| MmugDNA.3092.1.S1_at | Heterogeneous nuclear ribonucleoproteins A2/B1 (hnRNP A2 / hnRNP B1) | HNRPA2B1 | 2.12 | 0.0077 |

-continued

| Probe Set ID | Gene Title | Gene Symbol | Ratio Top verus Bottom | p value Top versus Bottom |
|---|---|---|---|---|
| MmuSTS.8.1.S1_at | Histone H2A.x (H2a/x) | LOC703073 | 2.12 | 0.0010 |
| MmuSTS.2363.1.S1_at | squamous cell carcinoma antigen recognized by T cells 2 | LOC716054 | 2.12 | 0.0083 |
| MmuSTS.3798.1.S1_at | scavenger receptor class A, member 3 isoform 1 | LOC718263 | 2.12 | 0.0501 |
| MmugDNA.22785.1.S1_at | — | — | 2.11 | 0.0320 |
| MmugDNA.38565.1.S1_at | v-fos FBJ murine osteosarcoma viral oncogene homolog | FOS | 2.11 | 0.0239 |
| MmugDNA.20885.1.S1_at | chromosome 10 open reading frame 6 | LOC710786 | 2.11 | 0.0526 |
| MmugDNA.11836.1.S1_at | — | — | 2.11 | 0.0069 |
| MmugDNA.16849.1.S1_at | NAD-dependent deacetylase sirtuin-4 (SIR2-like protein 4) | LOC720498 | 2.11 | 0.0416 |
| MmuSTS.4531.1.S1_at | ankyrin repeat and SOCS box-containing protein 1 | ASB1 | 2.11 | 0.0647 |
| MmugDNA.607.1.S1_at | ras-like protein TC10 | LOC717769 | 2.11 | 0.0443 |
| MmugDNA.33195.1.S1_at | hypothetical protein LOC704974 /// G-protein coupled purinergic receptor P2Y5 | LOC704974 /// LOC705081 | 2.11 | 0.0049 |
| MmugDNA.40999.1.S1_at | DAB2 interacting protein | DAB2IP | 2.10 | 0.0008 |
| MmugDNA.9833.1.S1_at | v-maf musculoaponeurotic fibrosarcoma oncogene homolog (avian) | MAF | 2.10 | 0.0082 |
| MmugDNA.21011.1.S1_at | hypothetical protein FLJ90396 | FLJ90396 | 2.10 | 0.0507 |
| MmugDNA.2101.1.S1_at | stearoyl-CoA desaturase (delta-9-desaturase) | SCD | 2.10 | 0.0023 |
| MmuSTS.822.1.S1_at | drebrin 1 | DBN1 | 2.10 | 0.0386 |
| MmugDNA.41100.1.S1_at | GPI-anchored metastasis-associated protein homolog | LOC718197 | 2.10 | 0.0588 |
| MmugDNA.38957.1.S1_at | Cleavage stimulation factor, 3' pre-RNA, subunit 2, 64 kDa, tau variant | CSTF2T | 2.10 | 0.0646 |
| MmugDNA.34474.1.S1_at | cysteine sulfinic acid decarboxylase-related protein 2 | LOC701290 | 2.08 | 0.0698 |
| MmugDNA.9802.1.S1_at | aldehyde dehydrogenase 3 family, member Al | ALDH3A1 | 2.08 | 0.0132 |
| MmugDNA.43169.1.S1_at | CD109 antigen (Gov platelet alloantigens) | CD109 | 2.08 | 0.0492 |
| MmuSTS.698.1.S1_at | CKLF-like MARVEL transmembrane domain-containing protein 6 (Chemokine-like factor superfamily member 6) | CMTM6 | 2.08 | 0.0065 |
| MmugDNA.34248.1.S1_at | splicing factor, arginine/serine-rich 15 | LOC701931 | 2.08 | 0.0239 |
| MmugDNA.33686.1.S1_s_at | hypothetical protein LOC722265 | LOC722265 | 2.08 | 0.0776 |
| MmugDNA.33032.1.S1_at | K06A9.1b | LOC710668 | 2.07 | 0.0082 |
| MmugDNA.14765.1.S1_at | polymerase I and transcript release factor | PTRF | 2.07 | 0.0288 |
| MmugDNA.32283.1.S1_at | ladinin 1 | LOC707971 | 2.07 | 0.0106 |
| MmuSTS.2113.1.S1_at | — | ARHGEF19 | 2.07 | 0.0016 |
| MmugDNA.11281.1.S1_at | proline-, glutamic acid-, leucine-rich protein 1 | LOC709306 | 2.07 | 0.0128 |
| MmugDNA.21716.1.S1_at | CDNA FLJ36544 fis, clone TRACH2006378 | — | 2.07 | 0.0908 |
| MmugDNA.33042.1.S1_at | latent transforming growth factor beta binding protein 2 | LOC699435 | 2.07 | 0.0762 |
| MmugDNA.9373.1.S1_at | metastasis-associated protein 2 | — | 2.06 | 0.0100 |
| Mmu.13445.1.S1_at | calumenin precursor | LOC699730 | 2.06 | 0.0342 |
| MmuSTS.4590.1.S1_at | transglutaminase 2 | TGM2 | 2.06 | 0.0817 |
| MmugDNA.19480.1.S1_at | KIAA1219 protein | KIAA1219 | 2.06 | 0.0781 |
| MmugDNA.10100.1.S1_at | hypothetical protein LOC722637 | LOC722637 | 2.06 | 0.0099 |
| MmugDNA.16322.1.S1_at | Transcribed locus, weakly similar to NP_055301.1 neuronal thread protein AD7c-NTP[Homo sapiens] | — | 2.06 | 0.0989 |
| MmugDNA.4438.1.S1_at | transmembrane protein 39B | LOC706700 | 2.06 | 0.0916 |
| MmugDNA.35973.1.S1_at | agrin | LOC693314 | 2.06 | 0.0197 |
| MmugDNA.36549.1.S1_at | Hypothetical protein FLJ14888 | FLJ14888 | 2.06 | 0.0846 |
| MmugDNA.15963.1.S1_at | PABP1-dependent poly A-specific ribonuclease subunit PAN3 | PAN3 | 2.05 | 0.0740 |
| MmugDNA.18234.1.S1_at | runt-related transcription factor 2 isoform b | LOC703331 | 2.05 | 0.0228 |
| MmugDNA.32119.1.S1_at | cytosolic malic enzyme 1 | ME1 | 2.05 | 0.0425 |
| MmugDNA.18163.1.S1_at | gamma-aminobutyric acid (GABA) B receptor 1 isoform a precursor | LOC708987 | 2.05 | 0.0129 |
| MmugDNA.18569.1.S1_at | phospholipase A2, group IVB | LOC707262 | 2.04 | 0.0116 |
| MmugDNA.23773.1.S1_at | alpha 1 type XVIII collagen isoform 1 precursor | LOC721919 | 2.04 | 0.0444 |
| Mmu.16285.1.A1_at | — | ANP32A | 2.04 | 0.0274 |
| MmuSTS.2061.1.S1_at | phospholipase C gamma 1 isoform a | LOC697069 | 2.04 | 0.0259 |
| MmugDNA.25737.1.S1_at | Abl-interactor 1 | ABM | 2.04 | 0.0333 |
| MmugDNA.37418.1.S1_at | NMD3 homolog | LOC701677 | 2.04 | 0.0354 |
| MmugDNA.29644.1.S1_at | RAN binding protein 2-like 1 | RANBP2L1 | 2.04 | 0.0405 |
| MmugDNA.22841.1.S1_at | Karyopherin alpha 5 (importin alpha 6) | KPNA5 | 2.04 | 0.0159 |
| MmugDNA.40840.1.S1_at | ring finger and KH domain containing 2 | LOC719403 | 2.03 | 0.0970 |
| MmugDNA.39873.1.S1_s_at | solute carrier family 38, member 2 | LOC702253 | 2.03 | 0.0018 |
| MmugDNA.29688.1.S1_at | G-protein coupled receptor 116 | LOC704887 | 2.03 | 0.0715 |
| MmugDNA.2555.1.S1_at | CDNA FLJ37816 fis, clone BRSSN2003093 | — | 2.03 | 0.0765 |
| MmugDNA.27712.1.S1_at | golgi SNAP receptor complex member 1 | GOSR1 | 2.03 | 0.0166 |
| MmuSTS.3453.1.S1_at | PYD and CARD domain containing isoform b | LOC713563 | 2.03 | 0.0818 |
| MmugDNA.38737.1.S1_s_at | transcription factor B1, mitochondrial | LOC701830 | 2.03 | 0.0574 |
| MmugDNA.371.1.S1_at | — | — | 2.03 | 0.0252 |
| MmuSTS.2285.1.S1_at | POU domain, class 5, transcription factor 1 | POU5F1 | 2.02 | 0.0989 |
| MmugDNA.11375.1.S1_at | spartin | LOC693663 | 2.02 | 0.0884 |
| MmuSTS.3541.1.S1_at | NOD2 protein | LOC695542 | 2.02 | 0.0867 |
| MmunewRS.886.1.S1_at | gi:51465519 | — | 2.02 | 0.0891 |
| MmugDNA.33688.1.S1_at | ribosomal protein L17 | RPL17 | 2.02 | 0.0384 |
| MmugDNA.31199.1.S1_at | ADP-ribosylation factor-like protein 4C (ADP-ribosylation factor-like 7) | ARL4C | 2.02 | 0.0154 |

-continued

| Probe Set ID | Gene Title | Gene Symbol | Ratio Top verus Bottom | p value Top versus Bottom |
|---|---|---|---|---|
| MmugDNA.32540.1.S1_at | centaurin-alpha 2 protein | CENTA2 | 2.02 | 0.0939 |
| MmugDNA.19746.1.S1_at | solute carrier family 2 (facilitated glucose transporter), member 3 | SLC2A3 | 2.02 | 0.0013 |
| MmugDNA.30247.1.S1_at | RNA-binding region containing protein 2 isoform b | LOC704198 | 2.01 | 0.0297 |
| MmugDNA.35944.1.S1_at | CDNA FLJ13136 fis, clone NT2RP3003139 | — | 2.01 | 0.0963 |
| MmugDNA.29822.1.S1_at | carbonic anhydrase IV | CA4 | 2.01 | 0.0637 |
| MmugDNA.15283.1.S1_at | Transcribed locus | — | 2.01 | 0.0424 |
| MmuSTS.1380.1.S1_at | basic helix-loop-helix domain containing, class B, 3 | BHLHB3 | 2.01 | 0.0588 |
| MmugDNA.19213.1.S1_at | unconventional myosin class XV CG2174-PA | LOC711013 | 2.01 | 0.0214 |
| Mmu.2043.1.S1_at | axonal transport of synaptic vesicles | LOC722674 | 2.01 | 0.0295 |
| MmugDNA.18297.1.S1_at | COP9 (constitutive photomorphogenic) homolog, subunit 2 | LOC714814 | 2.00 | 0.0897 |
| MmuSTS.263.1.S1_at | sprouty homolog 1, antagonist of FGF signaling | LOC708752 | 2.00 | 0.0535 |
| MmuSTS.542.1.S1_at | osteopetrosis associated transmembrane protein 1 | LOC701341 | 2.00 | 0.0249 |
| MmugDNA.39776.1.S1_at | hypothetical protein LOC696417 | LOC696417 | 2.00 | 0.0224 |
| MmuSTS.4423.1.S1_at | frizzled homolog 2 | FZD2 | 2.00 | 0.0679 |
| MmugDNA.40363.1.S1_at | Hypothetical protein FLJ10948 | FLJ10948 | 2.00 | 0.0540 |
| Mmu.3412.1.A1_at | Transcribed locus | — | 2.00 | 0.0909 |
| MmugDNA.31062.1.S1_at | CDC42 binding protein kinase gamma (DMPK-like) | CDC42BPG | 2.00 | 0.0044 |
| MmugDNA.36785.1.S1_a_at | hypothetical protein MGC2780 | MGC2780 | 107.99 | 0.2056 |
| MmugDNA.11034.1.S1_at | MRNA full length insert cDNA clone EUROIMAGE 994183 | — | 66.61 | 0.0016 |
| MmugDNA.15521.1.S1_at | helicase with zinc finger /// ovostatin 2 /// cDNA sequence BC048546 | HELZ /// OVOS2 /// LOC440080 | 38.75 | 0.0810 |
| MmugDNA.6868.1.S1_at | adenosine deaminase-like | ADAL | 29.88 | 0.0860 |
| MmugDNA.3759.1.S1_at | zinc finger protein 208 | ZNF208 | 27.54 | 0.1523 |
| MmugDNA.19225.1.S1_at | hemochromatosis type 2 (juvenile) | HFE2 | 27.11 | 0.1919 |
| MmugDNA.19620.1.S1_at | Transcribed locus | — | 26.88 | 0.0322 |
| MmunewRS.411.1.S1_at | T-cell lymphoma breakpoint-associated target 1 | TCBA1 | 23.70 | 0.0159 |
| MmugDNA.5507.1.S1_at | — | — | 23.68 | 0.0045 |
| MmuSTS.2342.1.S1_at | receptor (calcitonin) activity modifying protein 2 | RAMP2 | 22.81 | 0.0433 |
| MmuSTS.4185.1.S1_at | nidogen 2 | NID2 | 22.41 | 0.0046 |
| Mmu.12045.1.S1_at | phosphatidylinositol glycan, class K | PIGK | 21.51 | 0.0191 |
| Mmu.2196.1.A1 _at | APP-70 mRNA fragment for amyloid precursor protein protease inhibitor domain. | X15985 | 21.32 | 0.0840 |
| MmuSTS.1412.1.S1_at | potassium intermediate/small conductance calcium-activated chann, subfamily N, member 3 | KCNN3 | 20.30 | 0.0082 |
| MmugDNA.21052.1.S1_at | Transcribed locus | — | 19.79 | 0.0089 |
| MmugDNA.5232.1.S1_at | CDNA clone IMAGE:4811759 | — | 16.97 | 0.0006 |
| MmugDNA.13275.1.S1_at | solute carrier family 34 (sodium phosphate), member 2 | LOC694217 | 16.22 | 0.1746 |
| MmugDNA.33984.1.S1_at | CDNA clone IMAGE:4814828 | — | 16.07 | 0.1046 |
| MmugDNA.31271.1.S1_at | Replication protein A3, 14 kDa | RPA3 | 15.96 | 0.0083 |
| MmugDNA.19644.1.S1_at | anterior pharynx defective 1 homolog B (C. elegans) /// anterior pharynx defective 1 homolog B (C. elegans) | APH1 B | 15.89 | 0.0141 |
| MmuSTS.4301.1.S1_at | sema domain, seven thrombospondin repeats (type 1 and type 1-lik, , transmembrane domain (TM) and short cytoplasmic domain, (semaphorin) 5A | SEMA5A | 15.83 | 0.0613 |
| MmugDNA.39574.1.S1_at | RWD domain containing 2 | RWDD2 | 15.13 | 0.0179 |
| MmuSTS.4181.1.S1_at | cullin 2 | CUL2 | 15.12 | 0.0079 |
| MmugDNA.30525.1.S1_at | Transcribed locus, weakly XP_489263.1 RIKEN cDNA 9130004002 gene [Mus musculus] | 230450_at | 15.07 | 0.0170 |
| MmuSTS.2619.1.S1_at | erythroblast membrane-associated protein (Scianna blood group) | ERMAP | 14.89 | 0.1814 |
| MmugDNA.18007.1.S1_s_at | family with sequence similarity 102, member B | FAM102B | 14.49 | 0.1119 |
| MmuSTS.4534.1.S1_at | Bruton agammaglobulinemia tyrosine kinase | BTK | 13.98 | 0.0369 |
| MmuSTS.898.1.S1_at | Engulfment and cell motility 1 | ELMO1 | 13.94 | 0.0068 |
| MmugDNA.1875.1.S1_at | aldehyde dehydrogenase 1 family, member B1 | ALDH1 B1 | 13.77 | 0.1752 |
| MmugDNA.8764.1.S1_at | — | — | 13.77 | 0.0751 |
| MmuSTS.2829.1.S1_at | solute carrier family 7 (cationic amino acid transporter, y + sys, m), member 6 | SLC7A6 | 13.70 | 0.0036 |
| MmugDNA.12524.1.S1_at | response gene to complement 32 | RGC32 | 13.37 | 0.0077 |
| MmugDNA.24601.1.S1_at | Chromosome 18 open reading frame 17 | C18orf17 | 13.37 | 0.0025 |
| MmugDNA.9600.1.S1_at | regulating synaptic membrane exocytosis 2 | RIMS2 | 13.30 | 0.0310 |
| MmugDNA.14408.1.S1_at | chromosome 12 open reading frame 24 | C12orf24 | 12.75 | 0.1070 |
| MmugDNA.37885.1.S1_at | homer homolog 1 (Drosophila) | HOMER1 | 12.68 | 0.0144 |
| MmugDNA.15936.1.S1_s_at | CDNA: FLJ21874 fis, clone HEP02488 | — | 12.38 | 0.0063 |
| MmuSTS.3629.1.S1_at | EMI domain containing 1 | EMID1 | 12.26 | 0.0380 |
| MmugDNA.10412.1.S1_x_at | Hypothetical protein KIAA0187 gene product /// Immunoglobulin lambda locus | LOC96610 /// IGL@ | 12.20 | 0.2034 |
| MmugDNA.21132.1.S1_at | hypothetical locus FLJ30594 | FLJ30594 | 12.08 | 0.1018 |
| MmugDNA.16717.1.S1_s_at | seizure related 6 homolog (mouse)-like 2 /// seizure related 6 homolog (mouse)-like 2 isoform 1 | SEZ6L2 /// LOC652900 | 11.95 | 0.0313 |
| MmuSTS.721.1.S1_at | N-acetylneuraminate pyruvate lyase (dihydrodipicolinate synthase | NPL | 11.73 | 0.0624 |
| MmugDNA.23998.1.S1_at | DKFZP43480335 protein | DKFZP434B0335 | 11.67 | 0.0140 |
| Mmu.10472.1.S1_at | acid sphingomyelinase-like phosphodiesterase 3A | LOC713696 | 11.58 | 0.0004 |

-continued

| Probe Set ID | Gene Title | Gene Symbol | Ratio Top verus Bottom | p value Top versus Bottom |
|---|---|---|---|---|
| MmugDNA.34582.1.S1_at | limbic system-associated membrane protein | LSAMP | 11.56 | 0.1465 |
| MmugDNA.27799.1.S1_at | chromosome 8 open reading frame 47 | C8orf47 | 11.54 | 0.0051 |
| MmugDNA.35367.1.S1_at | transmembrane emp24 protein transport domain containing 8 | TMED8 | 11.54 | 0.0000 |
| MmuSTS.4580.1.S1_at | heparan sulfate (glucosamine) 3-0-sulfotransferase 5 | HS3ST5 | 11.36 | 0.0340 |
| MmugDNA.14099.1.S1_at | protein disulfide isomerase family A, member 5 | PDIA5 | 11.07 | 0.0354 |
| MmunewRS.286.1.S1_at | cDNA FLJ46082 fis, clone TESTI2005153. | gi:34536371 | 10.92 | 0.1933 |
| MmugDNA.13637.1.S1_at | hypothetical protein LOCI 69834 | LOCI 69834 | 10.91 | 0.0446 |
| MmugDNA.21508.1.S1_at | CDNA FLJ37235 fis, clone BRAMY2002525 | — | 10.58 | 0.2144 |
| MmugDNA.26503.1.S1_at | polyhomeotic-like 2 (Drosophila) | PHC2 | 10.50 | 0.0002 |
| MmugDNA.9977.1.S1_at | ethanolamine kinase 1 | ETNK1 | 10.43 | 0.0022 |
| MmuSTS.629.1.S1_at | insulin-like growth factor 2 receptor | IGF2R | 10.32 | 0.0115 |
| MmugDNA.42459.1.S1_at | nucleotide binding protein 1 (MinD homolog, E. coli) | NUBP1 | 10.13 | 0.0076 |
| MmugDNA.16304.1.S1_at | paraoxonase 2 | PON2 | 10.03 | 0.2019 |
| MmugDNA.27226.1.S1_at | chromosome 10 open reading frame 49 | C10orf49 | 10.03 | 0.1874 |
| MmugDNA.27601.1.S1_at | — | — | 10.01 | 0.0801 |
| MmugDNA.19069.1.S1_at | transient receptor potential cation channel, subfamily M, member 7 | TRPM7 | 9.84 | 0.0026 |
| MmugDNA.12483.1.S1_at | HLA complex group 27 | HCG27 | 9.82 | 0.1032 |
| MmugDNA.15012.1.S1_at | Arylformamidase | AFMID | 9.78 | 0.0546 |
| MmugDNA.689.1.S1_at | hypothetical protein LOC707842 | LOC707842 | 9.65 | 0.1426 |
| MmugDNA.1511.1.S1_at | Transcribed locus | — | 9.54 | 0.1466 |
| MmugDNA.6078.1.S1_at | Sp2 transcription factor | SP2 | 9.47 | 0.1325 |
| MmugDNA.34436.1.S1_at | Hypothetical protein LOCI 52485 | LOCI 52485 | 9.36 | 0.0053 |
| Mmu.15003.1.S1_x_at | activating signal cointegrator 1 complex subunit 3-like 1 | LOC705184 | 9.28 | 0.0157 |
| MmugDNA.24349.1.S1_at | Transcribed locus | — | 9.26 | 0.0882 |
| MmugDNA.21279.1.S1_at | Leucine-rich repeat protein SHOC-2 (Ras-binding protein Sur-8) | RP11-139H14.4 | 9.21 | 0.0670 |
| MmugDNA.13732.1.S1_at | PHD finger protein 20-like 1 | PHF20L1 | 9.20 | 0.0626 |
| MmugDNA.28092.1.S1_at | breakpoint cluster region isoform 1 | LOC644165 | 9.11 | 0.2063 |
| MmugDNA.4326.1.S1_at | Transcribed locus | — | 8.93 | 0.0080 |
| Mmu.15748.1.S1_s_at | Transcribed locus, weakly XP_933032.2 hypothetical protein [Homo sapiens] | — | 8.88 | 0.0874 |
| MmugDNA.17676.1.S1_at | peroxisomal biogenesis factor 5-like | PEX5L | 8.86 | 0.0737 |
| MmugDNA.38590.1.S1_at | ligand-gated ion channel, zinc activated 1 | LGICZ1 | 8.81 | 0.0142 |
| MmugDNA.33781.1.S1_at | dynein, axonemal, heavy polypeptide 10 | DNAH10 | 8.80 | 0.1157 |
| MmugDNA.43623.1.S1_s_at | disabled homolog 2, mitogen-responsive phosphoprotein (Drosophila) | DAB2 | 8.75 | 0.0103 |
| MmugDNA.20593.1.S1_at | tripeptidyl peptidase II | TPP2 | 8.68 | 0.2180 |
| MmugDNA.24454.1.S1_at | phosphatidic acid phosphatase type 2C | PPAP2C | 8.68 | 0.1046 |
| MmugDNA.4150.1.S1_at | hypothetical protein FLJ40298 | FLJ40298 | 8.67 | 0.1356 |
| MmugDNA.22927.1.S1_at | — | — | 8.66 | 0.1089 |
| MmugDNA.39321.1.S1_at | CDNA FLJ41751 fis, clone HSYRA2008154 | — | 8.65 | 0.0090 |
| MmugDNA.38636.1.S1_at | hypothetical protein FLJ39653 | FLJ39653 | 8.61 | 0.0384 |
| MmugDNA.8681.1.S1_at | KIAA0100 /// hypothetical protein FLJ22349 | KIAA0100 /// FLJ22349 | 8.61 | 0.0075 |
| MmugDNA.27488.1.S1_at | suppression of tumorigenicity 14 (colon carcinoma) | ST14 | 8.58 | 0.0576 |
| MmugDNA.29768.1.S1_at | melanocortin 2 receptor accessory protein | MRAP | 8.56 | 0.0423 |
| MmugDNA.42270.1.S1_at | gremlin 1, cysteine knot superfamily, homolog (Xenopus laevis) | GREM1 | 8.53 | 0.1415 |
| MmugDNA.30894.1.S1_at | Transcribed locus, strongly NP_067647.1 leucine-rich repeat-containing G protein-coupled receptor 7 [Homo sapiens] | — | 8.44 | 0.1092 |
| MmugDNA.37925.1.S1_at | plasma glutamate carboxypeptidase | PGCP | 8.43 | 0.0055 |
| MmugDNA.7703.1.S1_s_at | pyrroline-5-carboxylate reductase family, member 2 | PYCR2 | 8.42 | 0.0481 |
| MmugDNA.29962.1.S1_at | procollagen-proline, 2-oxoglutarate 4-dioxygenase (proline 4-hydroxylase), alpha polypeptide III | P4HA3 | 8.41 | 0.0311 |
| MmugDNA.29322.1.S1_at | chromosome 6 open reading frame 159 | C6orf159 | 8.37 | 0.1465 |
| MmugDNA.32728.1.S1_at | GLIS family zinc finger 2 | LOC708454 | 8.33 | 0.0118 |
| MmugDNA.39848.1.S1_at | DIP2 disco-interacting protein 2 homolog C (Drosophila) | DIP2C | 8.32 | 0.0054 |
| MmugDNA.9959.1.S1_at | — | — | 8.31 | 0.2016 |
| MmuSTS.2576.1.S1_at | DnaJ (Hsp40) homolog, subfamily B, member 12 | DNAJB12 | 8.25 | 0.0207 |
| MmugDNA.3860.1.S1_at | — | — | 8.16 | 0.0618 |
| Mmu.4703.1.S1_at | — | C0774986 | 8.16 | 0.0134 |
| MmugDNA.33155.1.S1_at | likely ortholog of MEF2-activating SAP | FLJ36070 | 8.15 | 0.0863 |
| MmugDNA.20631.1.S1_at | transcriptional regulator Transcribed locus, strongly XP_513258.1 LOC456687 [Pan troglodytes] | 230613_at | 8.08 | 0.2120 |
| MmugDNA.39834.1.S1_s_at | fragile histidine triad gene | FHIT | 8.00 | 0.0019 |
| MmugDNA.26008.1.S1_at | musashi homolog 2 (Drosophila) | MSI2 | 7.97 | 0.0002 |
| MmugDNA.36272.1.S1_s_at | dCMP deaminase | DCTD | 7.87 | 0.0027 |
| MmugDNA.21159.1.S1_at | hypothetical protein FLJ31846 | FLJ31846 | 7.84 | 0.1945 |
| MmugDNA.7644.1.S1_at | amyloid beta (A4) precursor-like protein 2 | APLP2 | 7.82 | 0.0540 |
| MmugDNA.26889.1.S1_at | Transcribed locus | — | 7.82 | 0.1703 |
| MmugDNA.35633.1.S1_at | Transcribed locus, strongly NP_659486.1 hypothetical protein MGC10067 [Homo sapiens] | — | 7.80 | 0.0389 |
| MmugDNA.11626.1.S1_at | dynein, cytoplasmic 2, heavy chain 1 | DYNC2H1 | 7.80 | 0.0014 |
| MmugDNA.18533.1.S1_at | phospholipase D family, member 5 | PLD5 | 7.80 | 0.0512 |

-continued

| Probe Set ID | Gene Title | Gene Symbol | Ratio Top verus Bottom | p value Top versus Bottom |
|---|---|---|---|---|
| MmugDNA.36604.1.S1_at | Transcribed locus | — | 7.77 | 0.0005 |
| MmugDNA.12098.1.S1_at | Transcribed locus | — | 7.76 | 0.0954 |
| MmugDNA.8791.1.S1_at | KIAA0586 | KIAA0586 | 7.72 | 0.0606 |
| MmugDNA.25037.1.S1_at | CDNA FLJ30090 fis, clone BNGH41000015 | — | 7.68 | 0.0828 |
| MmugDNA.30003.1.S1_at | BTB (POZ) domain containing 16 | BTBD16 | 7.66 | 0.0893 |
| MmugDNA.29464.1.S1_at | inositol monophosphatase domain containing 1 | IMPAD1 | 7.65 | 0.0204 |
| MmugDNA.29130.1.S1_at | adenylate cyclase 1 (brain) | ADCY1 | 7.64 | 0.0222 |
| MmugDNA.42065.1.S1_at | distal-less homeobox 6 | DLX6 | 7.64 | 0.2136 |
| MmugDNA.3371.1.S1_at | reticulon 1 | RTN1 | 7.63 | 0.0730 |
| MmugDNA.23995.1.S1_at | zinc finger protein 501 | ZNF501 | 7.62 | 0.1374 |
| MmugDNA.5842.1.S1_at | — | — | 7.59 | 0.1545 |
| MmugDNA.21402.1.S1_at | R3H domain and coiled-coil containing 1 | R3HCC1 | 7.58 | 0.0122 |
| MmugDNA.11091.1.S1_at | Nuclear factor I/A | NFIA | 7.58 | 0.0395 |
| MmuSTS.383.1.S1_at | lipase, gastric | LIPF | 7.56 | 0.1613 |
| MmugDNA.26814.1.S1_at | chromosome 3 open reading frame 19 | C3orf19 | 7.55 | 0.0189 |
| MmugDNA.38434.1.S1_at | WD repeat domain 5B | WDR5B | 7.50 | 0.1039 |
| MmugDNA.5186.1.S1_at | RNA binding motif protein 23 | RBM23 | 7.45 | 0.0136 |
| MmugDNA.22050.1.S1_at | EID-2-like inhibitor of differentiation-3 | EID-3 | 7.45 | 0.0340 |
| MmugDNA.40688.1.S1_at | zinc finger protein 235 | ZNF235 | 7.43 | 0.0135 |
| MmugDNA.30778.1.S1_at | growth factor, augmenter of liver regeneration (ERV1 homolog, S. cerevisiae) | GFER | 7.42 | 0.0002 |
| MmuSTS.2673.1.S1_at | calmegin | CLGN | 7.41 | 0.0581 |
| MmugDNA.9553.1.S1_at | Mannosidase, alpha, class 1A, member 1 | MAN1A1 | 7.38 | 0.0114 |
| MmugDNA.16242.1.S1_at | — | — | 7.37 | 0.0006 |
| MmugDNA.23074.1.S1_at | plexin A2 | PLXNA2 | 7.36 | 0.0096 |
| MmugDNA.31786.1.S1_at | hypothetical protein LOCI 58402 | LOCI 58402 | 7.36 | 0.0327 |
| MmugDNA.9822.1.S1_at | immunoglobulin superfamily containing leucine-rich repeat 2 | ISLR2 | 7.34 | 0.1736 |
| MmugDNA.5439.1.S1_at | catechol-O-methyltransferase | COMT | 7.32 | 0.0094 |
| MmugDNA.23942.1.S1_at | — | — | 7.26 | 0.0768 |
| MmugDNA.37455.1.S1_at | Transcribed locus | — | 7.25 | 0.0155 |
| MmugDNA.34284.1.S1_at | sodium channel, voltage-gated, type III, beta | SCN3B | 7.25 | 0.0578 |
| MmugDNA.19576.1.S1_at | zinc finger protein 547 | ZNF547 | 7.24 | 0.0782 |
| MmugDNA.34395.1.S1_at | zinc finger protein 230 | ZNF230 | 7.23 | 0.0152 |
| MmugDNA.6131.1.S1_at | chromosome 16 open reading frame 35 | C16orf35 | 7.20 | 0.1537 |
| MmugDNA.6727.1.S1_at | — | — | 7.20 | 0.0804 |
| MmugDNA.24272.1.S1_at | KIAA1922 protein | KIAA1922 | 7.19 | 0.1247 |
| MmugDNA.6286.1.S1_at | zinc finger protein 599 | ZNF599 | 7.14 | 0.0790 |
| MmuSTS.3570.1.S1_at | collagen, type IV, alpha 4 | COL4A4 | 7.14 | 0.0006 |
| MmugDNA.39056.1.S1_at | chromodomain helicase DNA binding protein 4 | CHD4 | 7.13 | 0.0047 |
| MmugDNA.34250.1.S1_at | hypothetical protein LOC645644 | FLJ42627 | 7.13 | 0.0043 |
| MmuSTS.1813.1.S1_at | sterol 0-acyltransferase 2 | SOAT2 | 7.11 | 0.0279 |
| MmugDNA.24694.1.S1_at | Retinoblastoma binding protein 4 | RBBP4 | 7.10 | 0.0185 |
| MmugDNA.24480.1.S1_at | splicing factor proline/glutamine-rich (polypyrimidine tract binding protein associated) | SFPQ | 7.09 | 0.0095 |
| MmugDNA.33264.1.S1_at | TIP41, TOR signalling pathway regulator-like (S. cerevisiae) | TIPRL | 7.08 | 0.1207 |
| MmugDNA.31611.1.S1_at | PRotein Associated with TIr4 | MGC40499 | 7.01 | 0.0583 |
| MmugDNA.26071.1.S1_s_at | RAB30, member RAS oncogene family | RAB30 | 6.97 | 0.0043 |
| MmugDNA.11685.1.S1_at | poly (ADP-ribose) polymerase family, member 8 | PARP8 | 6.94 | 0.0303 |
| MmugDNA.38371.1.S1_at | hexosaminidase A (alpha polypeptide) | HEXA | 6.94 | 0.0512 |
| MmugDNA.5558.1.S1_at | tRNA phosphotransferase 1 | TRPT1 | 6.93 | 0.0013 |
| MmugDNA.34597.1.S1_at | tetraspanin 1 | TSPAN1 | 6.86 | 0.0007 |
| MmugDNA.18788.1.S1_at | Capping protein (actin filament) muscle Z-line, alpha 2 | CAPZA2 | 6.85 | 0.0915 |
| MmugDNA.28272.1.S1_at | molybdenum cofactor synthesis 1 | MOCS1 | 6.83 | 0.0681 |
| MmugDNA.14078.1.S1_at | EBNA1 binding protein 2 | EBNA1BP2 | 6.82 | 0.0463 |
| MmuSTS.2123.1.S1_at | retinal outer segment membrane protein 1 | ROM1 | 6.81 | 0.0210 |
| MmugDNA.9513.1.S1_at | exostoses (multiple)-like 2 | EXTL2 | 6.79 | 0.0112 |
| Mmu.7528.1.S1_at | Zygin 1 | ZYG1 | 6.76 | 0.0713 |
| MmugDNA.12416.1.S1_at | coiled-coil domain containing 51 | CCDC51 | 6.76 | 0.0052 |
| MmuSTS.3946.1.S1_at | T-cell activation kelch repeat protein | TA-KRP | 6.76 | 0.0172 |
| MmugDNA.12522.1.S1_at | Pyrophosphatase (inorganic) 2 | PPA2 | 6.74 | 0.0061 |
| MmugDNA.39796.1.S1_at | DIRAS family, GTP-binding RAS-like 3 | DIRAS3 | 6.72 | 0.0734 |
| MmugDNA.1685.1.S1_at | zinc finger protein 682 | ZNF682 | 6.72 | 0.0142 |
| MmuSTS.2157.1.S1_at | Scm-like with four mbt domains 1 | SFMBT1 | 6.71 | 0.0051 |
| MmugDNA.2165.1.S1_at | small nuclear ribonucleoprotein polypeptide E | SNRPE | 6.70 | 0.0389 |
| MmugDNA.2643.1.S1_at | chromosome 11 open reading frame 59 | C11orf59 | 6.69 | 0.0306 |
| MmugDNA.13192.1.S1_s_at | peptidylprolyl isomerase E (cyclophilin E) | PPIE | 6.67 | 0.0336 |
| MmugDNA.13901.1.S1_at | KIAA0194 protein | KIAA0194 | 6.65 | 0.0029 |
| MmugDNA.9677.1.S1_at | hypothetical protein MGC39606 /// hypothetical protein LOC644596 | MGC39606 /// LOC644596 | 6.64<br>6.64 | 0.0636<br>0.0539 |
| MmugDNA.21296.1.S1_at | CDNA FLJ14188 fis, clone NT2RP2005980 | — | | |
| MmugDNA.36977.1.S1_at | transmembrane protein 107 | TMEM107 | 6.62 | 0.0537 |
| MmuSTS.3859.1.S1_at | solute carrier family 26, member 9 | SLC26A9 | 6.62 | 0.0483 |
| MmuSTS.514.1.S1_at | ATPase, Class VI, type 11 C | ATP11C | 6.62 | 0.0004 |
| MmugDNA.18137.1.S1_at | — | — | 6.60 | 0.0451 |
| MmugDNA.36662.1.S1_at | STAM binding protein-like 1 | STAMBPL1 | 6.60 | 0.0041 |

-continued

| Probe Set ID | Gene Title | Gene Symbol | Ratio Top verus Bottom | p value Top versus Bottom |
|---|---|---|---|---|
| MmugDNA.13357.1.S1_at | KDEL (Lys-Asp-Glu-Leu) endoplasmic reticulum protein retention receptor 1 | KDELR1 | 6.58 | 0.0618 |
| MmugDNA.34884.1.S1_at | CUB and zona pellucida-like domains 1 | CUZD1 | 6.58 | 0.0561 |
| MmugDNA.10426.1.S1_at | neuron navigator 3 | NAV3 | 6.56 | 0.0493 |
| MmunewRS.777.1.S1_at | This record was removed as a result of standard genome annotation processing. | | 6.54 | 0.0904 |
| MmugDNA.32277.1.S1_at | DNA (cytosine-5-)-methyltransferase 2 | DNMT2 | 6.51 | 0.0001 |
| MmunewRS.654.1.S1_at | taste receptor, type 2, member 44 | TAS2R44 | 6.51 | 0.1568 |
| MmuSTS.3981.1.S1_at | SH3-domain GRB2-like 2 | SH3GL2 | 6.48 | 0.0289 |
| MmugDNA.23979.1.S1_at | tetratricopeptide repeat domain 8 | TTC8 | 6.47 | 0.0227 |
| MmugDNA.9202.1.S1_at | PRO0633 | — | 6.45 | 0.0369 |
| MmugDNA.19839.1.S1_at | metallothionein 1G | MT1G | 6.44 | 0.0115 |
| MmugDNA.11505.1.S1_at | RNA (guanine-9-) methyltransferase domain containing 3 RG9MTD3 | | 6.44 | 0.0224 |
| MmugDNA.37839.1.S1_s_at | Full length insert cDNA clone ZD82B02 | — | 6.41 | 0.0024 |
| MmugDNA.26070.1.S1_at | putatative 28 kDa protein | L0056902 | 6.39 | 0.0219 |
| MmugDNA.4320.1.S1_at | chromosome 14 open reading frame 93 | C14orf93 | 6.39 | 0.0814 |
| MmugDNA.42430.1.S1_at | chromosome 5 open reading frame 28 | C5orf28 | 6.39 | 0.0427 |
| MmugDNA.13752.1.S1_at | spermatogenesis associated 7 | SPATA7 | 6.37 | 0.0117 |
| MmugDNA.39646.1.S1_s_at | chromosome 19 open reading frame 10 | C19orf10 | 6.36 | 0.1162 |
| MmugDNA.4241.1.S1_at | FRAS1 related extracellular matrix 3 | FREM3 | 6.34 | 0.0744 |
| MmugDNA.5102.1.S1_at | — | — | 6.33 | 0.0111 |
| MmugDNA.23567.1.S1_at | protein arginine methyltransferase 6 | PRMT6 | 6.33 | 0.0382 |
| MmugDNA.42806.1.S1_at | — | — | 6.33 | 0.0980 |
| MmugDNA.35790.1.S1_at | solute carrier family 7 (cationic amino acid transporter, y + system), member 3 | SLC7A3 | 6.31 | 0.1159 |
| MmugDNA.11215.1.S1_at | — | — | 6.30 | 0.0526 |
| MmugDNA.9057.1.S1_at | transmembrane protein 107 /// transmembrane protein 107 | TMEM107 | 6.28 | 0.0390 |
| MmugDNA.37336.1.S1_at | stathmin-like 2 | STMN2 | 6.27 | 0.1549 |
| MmugDNA.117.1.S1_at | DPH5 homolog (S. cerevisiae) | DPH5 | 6.27 | 0.0417 |
| Mmu.15115.1.S1_at | Ribonuclease UK114 (14.5 kDa translational inhibitor protein) (p14.5) (UK114 antigen homolog) | LOC705533 | 6.25 | 0.0280 |
| MmugDNA.21121.1.S1_at | Insulin-like growth factor 1 receptor | IGF1 R | 6.25 | 0.0700 |
| MmugDNA.13304.1.S1_at | Fukuyama type congenital muscular dystrophy (fukutin) | FCMD | 6.24 | 0.0342 |
| MmugDNA.40836.1.S1_at | chromosome 6 open reading frame 168 | C6orf168 | 6.23 | 0.0000 |
| MmugDNA.23421.1.S1_at | FLJ16124 protein | FLJ16124 | 6.23 | 0.1070 |
| MmugDNA.29466.1.S1_at | Transcribed locus | — | 6.22 | 0.0243 |
| MmugDNA.41017.1.S1_at | CDNA clone IMAGE:4791585 | — | 6.20 | 0.0430 |
| MmugDNA.18662.1.S1_at | parathyroid hormone receptor 2 | PTHR2 | 6.19 | 0.1555 |
| MmugDNA.27914.1.S1_at | family with sequence similarity 55, member D | FAM55D | 6.19 | 0.1240 |
| MmugDNA.39981.1.S1_at | microtubule associated monoxygenase, calponin and LIM domain containing 2 | MICAL2 | 6.17 | 0.0214 |
| MmugDNA.33630.1.S1_at | apolipoprotein B mRNA editing enzyme, catalytic polypeptide-like 3G | APOBEC3G | 6.13 | 0.0918 |
| MmugDNA.41272.1.S1_at | KIAA0174 | KIAA0174 | 6.12 | 0.0498 |
| MmugDNA.4554.1.S1_at | membrane-associated ring finger (C3HC4) 9 | 9-Mar | 6.12 | 0.0006 |
| MmuSTS.4598.1.S1_at | hypoxia up-regulated 1 | HYOU1 | 6.11 | 0.0224 |
| MmugDNA.40815.1.S1_at | Family with sequence similarity 77, member D | FAM77D | 6.11 | 0.0370 |
| MmugDNA.10816.1.S1_at | CDNA FLJ90571 fis, clone OVARC1001725, highly Homo sapiens patched related protein TRC8 (TRC8) gene | — | 6.09 | 0.0585 |
| Mmu.15827.1.S1_at | tafazzin | TAZ | 6.09 | 0.0279 |
| MmugDNA.18337.1.S1_at | neurofilament, heavy polypeptide 200 kDa | NEFH | 6.08 | 0.0788 |
| MmuSTS.3411.1.S1_at | phosphoribosyl pyrophosphate synthetase 1 | PRPS1 | 6.08 | 0.0271 |
| MmugDNA.4215.1.S1_at | matrix-remodelling associated 8 | MXRA8 | 6.07 | 0.0277 |
| MmugDNA.2493.1.S1_at | Full-length cDNA clone CSODI054YK19 of Placenta Cot 25-normalized of Homo sapiens (human) | — | 6.07 | 0.0954 |
| MmugDNA.29221.1.S1_at | mannosidase, alpha, class 2A, member 1 | MAN2A1 | 6.06 | 0.0356 |
| MmuSTS.2268.1.S1_at | polymerase (RNA) II (DNA directed) polypeptide C, 33 kDa | POLR2C | 6.06 | 0.0054 |
| MmugDNA.16039.1.S1_at | Transcribed locus | — | 6.05 | 0.1426 |
| MmugDNA.23370.1.S1_at | SH3 and PX domains 2A | SH3PXD2A | 6.02 | 0.1440 |
| Mmu.5073.1.S1_at | histone deacetylase 1 | LOC708441 | 6.01 | 0.0636 |
| MmugDNA.18754.1.S1_at | hypothetical protein LOC134466 | LOC134466 | 6.00 | 0.0506 |
| MmugDNA.34454.1.S1_at | — | — | 5.97 | 0.0048 |
| MmugDNA.23057.1.S1_at | hypothetical gene supported by AK125122 | FLJ13137 | 5.97 | 0.0012 |
| MmugDNA.27855.1.S1_at | — | — | 5.97 | 0.0167 |
| MmuSTS.3142.1.S1_at | methyl-CpG binding domain protein 5 | MBD5 | 5.95 | 0.0115 |
| MmugDNA.23903.1.S1_at | Protein inhibitor of activated STAT, 2 | PIAS2 | 5.94 | 0.0193 |
| MmugDNA.7631.1.S1_at | CDNA FLJ11682 fis, clone HEMBA1004880 | — | 5.94 | 0.1697 |
| MmugDNA.20356.1.S1_at | platelet-activating factor acetylhydrolase 2, 40 kDa | PAFAH2 | 5.94 | 0.0009 |
| MmugDNA.2708.1.S1_at | Son of sevenless homolog 1 (Drosophila) | SOS1 | 5.91 | 0.0461 |
| MmugDNA.10905.1.S1_at | tectonic | FLJ21127 | 5.89 | 0.0025 |
| MmugDNA.28625.1.S1_at | without children CG5965-PA | LOC707028 | 5.89 | 0.0638 |
| MmugDNA.11493.1.S1_at | eukaryotic translation initiation factor 4A, isoform 2 | EIF4A2 | 5.87 | 0.0421 |
| MmugDNA.23572.1.S1_s_at | glutamate-cysteine ligase, modifier subunit | GCLM | 5.86 | 0.0027 |
| MmuSTS.2280.1.S1_at | Dapper, antagonist of beta-catenin, homolog 1 (Xenopus laevis) | DACT1 | 5.86 | 0.0752 |

-continued

| Probe Set ID | Gene Title | Gene Symbol | Ratio Top verus Bottom | p value Top versus Bottom |
|---|---|---|---|---|
| MmugDNA.25697.1.S1_at | Ubiquitin-conjugating enzyme E2W (putative) | UBE2W | 5.85 | 0.0579 |
| MmugDNA.24422.1.S1_at | glucosidase, beta, acid 3 (cytosolic) | GBA3 | 5.84 | 0.1210 |
| MmugDNA.26055.1.S1_at | THAP domain containing 5 | THAP5 | 5.82 | 0.1799 |
| MmuSTS.1960.1.S1_at | forkhead box D1 | FOXD1 | 5.81 | 0.0736 |
| MmugDNA.35294.1.S1_at | protein tyrosine phosphatase-like A domain containing 1 | PTPLAD1 | 5.80 | 0.0213 |
| MmugDNA.15150.1.S1_at | histone deacetylase 8 | HDAC8 | 5.77 | 0.0384 |
| MmugDNA.32612.1.S1_s_at | prostaglandin D2 synthase 21 kDa (brain) /// prostaglandin D2 synthase 21 kDa (brain) | PTGDS | 5.77 | 0.1930 |
| MmuSTS.1829.1.S1_at | Shroom-related protein | ShrmL | 5.77 | 0.0060 |
| MmuSTS.3849.1.S1_at | Spectrin repeat containing, nuclear envelope 2 | SYNE2 | 5.74 | 0.0000 |
| Mmu.13961.1.S1_at | Protein NipSnap3A (NipSnap4) (Target for Salmonella secreted protein C) (TassC) | LOC716188 | 5.72 | 0.0252 |
| MmugDNA.29451.1.S1_at | Transcribed locus | 241668_s_at | 5.71 | 0.1366 |
| MmugDNA.39448.1.S1_at | Interferon regulatory factor 2 | IRF2 | 5.71 | 0.0394 |
| MmugDNA.13520.1.S1_at | cytoplasmic linker associated protein 2 | CLASP2 | 5.70 | 0.0457 |
| MmugDNA.35274.1.S1_at | Hypothetical protein FLJ30707 | FLJ30707 | 5.69 | 0.0422 |
| MmugDNA.1285.1.S1_at | zinc finger protein-like 1 | ZFPL1 | 5.67 | 0.1329 |
| MmugDNA.31491.1.S1_at | KIAA1333 | KIAA1333 | 5.66 | 0.1185 |
| MmuSTS.1032.1.S1_at | nucleoporin 133 kDa | NUP133 | 5.65 | 0.1949 |
| MmugDNA.28191.1.S1_at | Pleiotropic regulator 1 (PRL1 homolog, Arabidopsis) | PLRG1 | 5.64 | 0.0702 |
| MmugDNA.42978.1.S1_at | Transcribed locus, weakly XP_530800.1 PREDICTED: hypothetical protein XP_530800 +Pan troglodytes+ | — | 5.64 | 0.0280 |
| MmugDNA.11439.1.S1_at | 5'-nucleotidase domain containing 1 | NT5DC1 | 5.64 | 0.0577 |
| MmuSTS.706.1.S1_at | interleukin-1 receptor-associated kinase 4 | IRAK4 | 5.64 | 0.0778 |
| MmugDNA.37826.1.S1_at | Hypothetical protein LOC285346 | LOC285346 | 5.63 | 0.0874 |
| MmuSTS.4259.1.S1_at | dual specificity phosphatase 4 | DUSP4 | 5.63 | 0.1028 |
| MmunewRS.954.1.S1_at | zinc finger protein 484 isoform a | ZNF484 | 5.63 | 0.1344 |
| MmugDNA.24846.1.S1_at | vacuolar protein sorting 26 homolog B (S. cerevisiae) | VPS26B | 5.61 | 0.0039 |
| MmugDNA.36142.1.S1_at | chromosome 9 open reading frame 117 | C9orf117 | 5.58 | 0.0052 |
| MmugDNA.3197.1.S1_at | RNA binding motif protein 25 | RBM25 | 5.58 | 0.2066 |
| MmugDNA.30489.1.S1_at | neurolysin (metallopeptidase M3 family) | NLN | 5.56 | 0.0281 |
| MmugDNA.15190.1.S1_at | chromosome 1 open reading frame 151 | C1orf151 | 5.55 | 0.0874 |
| MmugDNA.21034.1.S1_at | UDP-N-acetyl-alpha-D-galactosamine:polypeptide N-acetylgalactosaminyltransferase 1 (GaINAc-T1) | GALNT1 | 5.54 | 0.0402 |
| MmugDNA.14671.1.S1_at | dynein, cytoplasmic 2, light intermediate chain 1 | DYNC2LI1 | 5.52 | 0.0052 |
| MmugDNA.21379.1.S1_at | SNF1-like kinase 2 | SNF1LK2 | 5.52 | 0.0281 |
| MmugDNA.5564.1.S1_at | zinc finger protein 3 | ZNF3 | 5.51 | 0.0061 |
| MmugDNA.30983.1.S1_at | Metallophosphoesterase 1 | MPPE1 | 5.50 | 0.0158 |
| MmuSTS.2242.1.S1_at | TH1-like (Drosophila) | TH1 L | 5.49 | 0.0001 |
| MmugDNA.7470.1.S1_at | hypothetical LOC400523 | LOC400523 | 5.49 | 0.0366 |
| MmugDNA.34874.1.S1_at | casein kinase 2, alpha prime polypeptide | CSNK2A2 | 5.47 | 0.0014 |
| MmugDNA.43133.1.S1_at | non-metastatic cells 5, protein expressed in (nucleoside-diphosphate kinase) | NME5 | 5.45 | 0.0009 |
| MmuSTS.3223.1.S1_at | phospholipase D3, phophatidylcholine-specific | PLD3 | 5.44 | 0.0358 |
| Mmu.10002.1.S1_s_at | methionine adenosyltransferase II, alpha | MAT2A | 5.44 | 0.0000 |
| MmugDNA.32811.1.S1_at | Transcribed locus | — | 5.44 | 0.0954 |
| MmugDNA.284.1.S1_at | hypothetical LOCI 49643 | LOCI 49643 | 5.43 | 0.0564 |
| MmuSTS.2289.1.S1_at | protein phosphatase 1, regulatory subunit 10 | PPP1 R10 | 5.43 | 0.0004 |
| MmugDNA.7541.1.S1_at | coiled-coil domain containing 88 | CCDC88 | 5.41 | 0.0296 |
| MmugDNA.1662.1.S1_at | PRP38 pre-mRNA processing factor 38 (yeast) domain containing A | PRPF38A | 5.39 | 0.0054 |
| MmuSTS.4599.1.S1_at | huntingtin interacting protein B | HYPB | 5.38 | 0.0000 |
| MmugDNA.5606.1.S1_at | 5'-nucleotidase, cytosolic III-like | NT5C3L | 5.38 | 0.0235 |
| MmugDNA.12250.1.S1_at | CDNA clone IMAGE: 3928921 | — | 5.37 | 0.0135 |
| MmugDNA.25740.1.S1_at | coenzyme Q9 homolog (S. cerevisiae) | COQ9 | 5.37 | 0.0000 |
| MmugDNA.34111. .S1_s_at | heat shock 105 kDa/110 kDa protein 1 | HSPH1 | 5.37 | 0.0000 |
| MmugDNA.21848. .S1_at | TSPY-like 1 | TSPYL1 | 5.37 | 0.0105 |
| MmugDNA.9756.1.S1_at | HERPUD family member 2 | HERPUD2 | 5.36 | 0.0453 |
| Mmu.3466.1.S1_at | — | CN648872 | 5.36 | 0.0770 |
| MmugDNA.23725.1.S1_at | stress 70 protein chaperone, microsome-associated, 60 kDa | STCH | 5.34 | 0.0144 |
| MmugDNA.38793.1.S1_at | cholecystokinin | CCK | 5.33 | 0.2072 |
| MmugDNA.41164.1.S1_at | phosphonoformate immuno-associated protein 5 | PFAAP5 | 5.32 | 0.0567 |
| MmugDNA.35343.1.S1_s_at | CDNA FLJ41946 fis, clone PLACE6019701 | — | 5.31 | 0.0490 |
| MmugDNA.26593.1.S1_at | armadillo repeat containing, X-linked 5 | ARMCX5 | 5.31 | 0.0081 |
| MmugDNA.14053.1.S1_at | — | — | 5.29 | 0.0696 |
| MmugDNA.9095.1.S1_at | zinc finger protein 396 | ZNF396 | 5.27 | 0.0141 |
| MmugDNA.25958.1.S1_at | DEAH (Asp-Glu-Ala-Asp/His) box polypeptide 57 | DHX57 | 5.27 | 0.0389 |
| MmugDNA.21062.1.S1_at | suppression of tumorigenicity 7 | ST7 | 5.27 | 0.0326 |
| MmugDNA.12969.1.S1_at | ribonuclease H2, subunit C | RNASEH2C | 5.27 | 0.0527 |
| MmugDNA.39661.1.S1_at | heparan sulfate 2-O-sulfotransferase 1 | HS2ST1 | 5.26 | 0.0062 |
| MmugDNA.26250.1.S1_at | zinc finger protein 111 | LOC388565 | 5.25 | 0.0232 |
| MmugDNA.39242.1.S1_at | melanoma inhibitory activity family, member 3 | MIA3 | 5.25 | 0.0014 |
| MmugDNA.35720.1.S1_at | zinc finger protein 306 /// zinc finger protein 306 | ZNF306 | 5.25 | 0.0552 |
| MmuSTS.4680.1.S1_at | thymic stromal lymphopoietin | TSLP | 5.25 | 0.0113 |
| MmugDNA.35830.1.S1_at | — | — | 5.24 | 0.0523 |
| MmuSTS.2253.1.S1_at | polymerase (DNA directed), iota | POLI | 5.23 | 0.0000 |

-continued

| Probe Set ID | Gene Title | Gene Symbol | Ratio Top verus Bottom | p value Top versus Bottom |
|---|---|---|---|---|
| MmugDNA.41690.1.S1_at | Fibronectin type III domain containing 3 | FNDC3 | 5.23 | 0.0908 |
| MmugDNA.16026.1.S1_at | — | — | 5.22 | 0.0871 |
| MmugDNA.12860.1.S1_at | hypothetical protein 284297 | FLJ35258 | 5.21 | 0.0605 |
| Mmu.6352.1.S1_at | F 1 6A11.1 | LOC703783 | 5.21 | 0.0698 |
| MmugDNA.28831.1.S1_at | G protein-regulated inducer of neurite outgrowth 1 | KIAA1893 | 5.21 | 0.0138 |
| MmuSTS.4601.1.S1_at | interleukin 19 | IL19 | 5.20 | 0.0401 |
| MmugDNA.25269.1.S1_at | chitinase domain containing 1 | CHID1 | 5.20 | 0.0280 |
| MmuAffx.956.1.S1_at | dolichyl-diphosphooligosaccharide-protein glycosyltransferase | — | 5.20 | 0.0203 |
| MmugDNA.10359.1.S1_at | DEAH (Asp-Glu-Ala-His) box polypeptide 30 | DHX30 | 5.20 | 0.0654 |
| MmugDNA.32727.1.S1_at | — | — | 5.19 | 0.0109 |
| MmugDNA.37069.1.S1_at | dihydropyrimidinase | DPYS | 5.19 | 0.0266 |
| MmugDNA.30075.1.S1_at | chromosome 6 open reading frame 162 | C6orf162 | 5.18 | 0.0316 |
| MmugDNA.9073.1.S1_at | — | — | 5.18 | 0.0376 |
| MmugDNA.12316.1.S1_at | KIAA0090 | KIAA0090 | 5.18 | 0.0905 |
| MmugDNA.39259.1.S1_at | MRNA; cDNA DKFZp564E202 (from clone DKFZp564E202)/// CDNA FLJ44257 fis, clone TKIDN2015263 | — | 5.17 | 0.0284 |
| MmugDNA.38606.1.S1_at | chromosome 9 open reading frame 89 | C9orf89 | 5.16 | 0.0215 |
| MmugDNA.3686.1.S1_at | intraflagellar transport 57 homolog (Chlamydomonas) | IFT57 | 5.14 | 0.0000 |
| MmugDNA.29286.1.S1_at | zinc finger protein 320 /// hypothetical protein FLJ38482 | ZNF320 /// FLJ38482 | 5.14 | 0.0252 |
| MmugDNA.31720.1.S1_at | CUE domain containing 1 | CUEDC1 | 5.14 | 0.0362 |
| MmugDNA.22403.1.S1_at | receptor accessory protein 5 | REEP5 | 5.14 | 0.0303 |
| MmugDNA.1116.1.S1_at | Transcribed locus | — | 5.12 | 0.0056 |
| MmugDNA.8918.1.S1_at | WNT1 inducible signaling pathway protein 2 | WISP2 | 5.12 | 0.1048 |
| MmugDNA.17764.1.S1_at | RCC1 domain containing 1 | RCCD1 | 5.11 | 0.0040 |
| MmugDNA.31260.1.S1_at | chromosome 11 open reading frame 63 | C11orf63 | 5.11 | 0.0246 |
| Mmu.6716.1.S1_at | Cathepsin S precursor | LOC708080 | 5.09 | 0.0754 |
| MmuSTS.299.1.S1_at | potassium intermediate/small conductance calcium-activated chann, subfamily N, member 2 | KCNN2 | 5.09 | 0.0055 |
| MmugDNA.31161.1.S1_at | Homo sapiens, clone IMAGE:4095671, mRNA | — | 5.09 | 0.0722 |
| MmugDNA.34930.1.S1_at | — | — | 5.08 | 0.1327 |
| MmugDNA.19331.1.S1_at | Full-length cDNA clone CSODK012YA15 of HeLa cells Cot 25-normalized of Homo sapiens (human) | — | 5.07 | 0.0161 |
| MmugDNA.36727.1.S1_at | zinc finger, MYM-type 4 | ZMYM4 | 5.07 | 0.0456 |
| MmugDNA.42518.1.S1_at | nudE nuclear distribution gene E homolog like 1 (A. nidulans) | NDEL1 | 5.05 | 0.0746 |
| MmugDNA.14355.1.S1_at | chromosome 21 open reading frame 6 | C21orf6 | 5.05 | 0.0047 |
| MmugDNA.4328.1.S1_at | zinc finger protein 480 | ZNF480 | 5.03 | 0.0101 |
| MmuSTS.2927.1.S1_at | potassium voltage-gated channel, subfamily H (eag-related), memb, 3 | KCNH3 | 5.00 | 0.0509 |
| MmuSTS.4230.1.S1_at | discs, large (Drosophila) homolog-associated protein 4 | DLGAP 4 | 5.00 | 0.0584 |
| MmugDNA.27648.1.S1_at | — | — | 4.98 | 0.0573 |
| MmugDNA.41452.1.S1_at | sperm autoantigenic protein 17 | SPA17 | 4.98 | 0.0031 |
| MmuSTS.3254.1.S1_at | sema domain, immunoglobulin domain (Ig), short basic domain, sec, ted, (semaphorin) 3A | SEMA3A | 4.98 | 0.0854 |
| MmugDNA.3708.1.S1_at | Full length insert cDNA clone YX81 F03 | — | 4.97 | 0.0024 |
| MmugDNA.3643.1.S1_at | hypothetical protein LOC643749 | LOC643749 | 4.97 | 0.0165 |
| MmugDNA.7067.1.S1_at | RNA binding motif protein 18 | LOC698457 | 4.97 | 0.0025 |
| MmugDNA.10033.1.S1_at | poliovirus receptor | PVR | 4.96 | 0.0778 |
| MmugDNA.16402.1.S1_at | cyclin M4 | CNNM4 | 4.96 | 0.0001 |
| MmugDNA.42450.1.S1_at | — | — | 4.96 | 0.1236 |
| MmugDNA.7713.1.S1_at | chromosome 4 open reading frame 17 | C4orf17 | 4.96 | 0.0059 |
| MmugDNA.11708.1.S1_at | chloride channel CLIC-like 1 | CLCC1 | 4.95 | 0.0038 |
| MmugDNA.19659.1.S1_at | Interleukin 17 receptor D | IL17RD | 4.95 | 0.0034 |
| MmugDNA.11406.1.S1_at | protein tyrosine phosphatase, receptor type, G | PTPRG | 4.95 | 0.0002 |
| MmugDNA.3737.1.S1_at | chromosome 13 open reading frame 23 | C13orf23 | 4.95 | 0.0133 |
| MmugDNA.1748.1.S1_at | transmembrane protein 27 | TMEM27 | 4.94 | 0.0726 |
| MmugDNA.30715.1.S1_at | armadillo repeat containing 8 | ARMC8 | 4.94 | 0.0096 |
| MmugDNA.31956.1.S1_at | Transcribed locus | — | 4.94 | 0.0633 |
| MmugDNA.2511.1.S1_at | CDNA FLJ40061 fis, clone TESOP2000083 | — | 4.94 | 0.1619 |
| MmugDNA.20090.1.S1_at | TDP-glucose 4,6-dehydratase | TGDS | 4.93 | 0.0336 |
| MmugDNA.17318.1.S1_at | Transcribed locus | — | 4.91 | 0.1084 |
| MmugDNA.22124.1.S1_at | transmembrane protein 138 | TMEM138 | 4.90 | 0.1081 |
| Mmu.6994.1.S1_at | basic fibroblast growth factor mRNA, partial cds. | AF251270 | 4.89 | 0.0539 |
| MmugDNA.25717.1.S1_s_at | retinoblastoma-like 2 (p130) | RBL2 | 4.89 | 0.1029 |
| MmugDNA.32584.1.S1_at | zinc finger protein 571 | ZNF571 | 4.88 | 0.0004 |
| MmuSTS.32.1.S1_at | zinc finger protein 32 | ZNF32 | 4.87 | 0.0000 |
| MmugDNA.30643.1.S1_at | B9 protein | EPPB9 | 4.86 | 0.1011 |
| MmugDNA.14909.1.S1_at | N-acetyltransferase 1 (arylamine N-acetyltransferase) | NAT1 | 4.86 | 0.0099 |
| MmuSTS.2239.1.S1_at | testis expressed sequence 264 | TEX264 | 4.85 | 0.0109 |
| MmugDNA.28738.1.S1_at | zinc finger protein 354C | LOC713468 | 4.85 | 0.0244 |
| MmuSTS.773.1.S1_at | core 1 UDP-galactose:N-acetylgalactosamine-alpha-R beta 1,3-gala, osyltransferase 2 | C1GALT2 | 4.85 | 0.0022 |
| MmugDNA.7405.1.S1_at | multiple substrate lipid kinase | MULK | 4.84 | 0.0000 |

-continued

| Probe Set ID | Gene Title | Gene Symbol | Ratio Top verus Bottom | p value Top versus Bottom |
|---|---|---|---|---|
| MmugDNA.8329.1.S1_at | chromosome 10 open reading frame 72 | C10orf72 | 4.83 | 0.1341 |
| MmugDNA.33312.1.S1_at | zinc finger, CCHC domain containing 9 | ZCCHC9 | 4.83 | 0.0024 |
| Mmu.11141.1.S1_at | catenin (cadherin-associated protein), alpha 1, 102 kDa | CTNNA1 | 4.83 | 0.0647 |
| MmugDNA.3844.1.S1_at | — | — | 4.82 | 0.0000 |
| MmuSTS.1873.1.S1_at | cornichon homolog | CNIH | 4.82 | 0.0001 |
| Mmu.1020.1.S1_s_at | cysteine-rich with EGF-like domains 1 isoform 2 | LOC699345 | 4.82 | 0.0586 |
| MmugDNA.24075.1.S1_at | CG15828-PA | 244889 at_ | 4.81 | 0.0948 |
| MmugDNA.30042.1.S1_at | chromosome X open reading frame 6 | CXorf6 | 4.81 | 0.0517 |
| MmuSTS.351.1.S1_at | synaptophysin | SYP | 4.81 | 0.0485 |
| MmugDNA.38488.1.S1_s_at | LSM10, U7 small nuclear RNA associated | LSM10 | 4.80 | 0.0004 |
| MmugDNA.1625.1.S1_at | protein kinase, AMP-activated, alpha 1 catalytic subunit | PRKAA1 | 4.80 | 0.0425 |
| MmugDNA.25564.1.S1_at | MRNA; cDNA DKFZp564G1162 (from clone DKFZp564G1162) | — | 4.79 | 0.0079 |
| MmugDNA.29139.1.S1_at | chromosome 14 open reading frame 50 | C14o rf50 | 4.79 | 0.1206 |
| MmuSTS.1491.1.S1_at | zinc finger protein 281 | ZNF281 | 4.78 | 0.0190 |
| MmugDNA.5201.1.S1_at | chromosome 14 open reading frame 130 | C14orf130 | 4.78 | 0.0074 |
| MmunewRS.875.1.S1_at | neuroligin 4, Y-linked | NLGN4Y | 4.78 | 0.0000 |
| MmugDNA.6389.1.S1_at | zinc finger, CCHC domain containing 12 | ZCCHC12 | 4.76 | 0.0124 |
| MmugDNA.12224.1.S1_at | CDNA clone IMAGE:4821804 | — | 4.76 | 0.0779 |
| MmunewRS.335.1.S1_at | full length insert cDNA clone YZ18805. | gi:3483412 | 4.75 | 0.0715 |
| MmugDNA.21758.1.S1_at | DNA cross-link repair 1C (PSO2 homolog, S. cerevisiae) | DCLRE1 C | 4.75 | 0.1520 |
| MmugDNA.4778.1.S1_at | KIAA1505 protein | KIAA1505 | 4.75 | 0.1070 |
| MmugDNA.133.1.S1_at | zinc finger protein 223 | LOC711740 | 4.74 | 0.1432 |
| MmugDNA.7270.1.S1_at | zinc finger protein 641 | ZNF641 | 4.74 | 0.0002 |
| MmugDNA.20328.1.S1_s_at | N-acetylglucosamine-1-phosphate transferase, gamma subunit | GNPTG | 4.74 | 0.0000 |
| MmugDNA.40786.1.S1_at | arylsulfatase family, member K | ARSK | 4.74 | 0.0631 |
| Mmu.11997.1.S1_at | calmodulin 1 | LOC698552 | 4.73 | 0.0030 |
| MmugDNA.1667.1.S1_at | immunoglobulin superfamily, member 4D | IGSF4D | 4.73 | 0.1791 |
| MmugDNA.20342.1.S1_at | spindlin family, member 2 /// spindlin family, member 2 /// spindlin-like protein 2 /// spindlin-like protein 2 | SPIN2 /// SPIN-2 | 4.72 | 0.0223 |
| MmugDNA.3891.1.S1_at | chromosome 2 open reading frame 15 | C2orf15 | 4.72 | 0.0163 |
| MmugDNA.32461. .S1_at | — | — | 4.72 | 0.0094 |
| MmugDNA.14567. .S1_at | KIAA0859 | KIAA0859 | 4.72 | 0.1058 |
| MmugDNA.43246. .S1_at | neutral sphingomyelinase (N-SMase) activation associated factor | NSMAF | 4.72 | 0.0053 |
| MmugDNA.2324.1.S1_at | KIAA0895 protein | KIAA0895 | 4.71 | 0.0648 |
| MmugDNA.1640.1.S1_at | Transcribed locus | — | 4.71 | 0.1101 |
| MmugDNA.42549. .S1_at | galanin | GAL | 4.71 | 0.0951 |
| MmugDNA.3017.1.S1_at | LQK1 hypothetical protein short isoform | LQK1 | 4.70 | 0.0226 |
| MmugDNA.28661. .S1_at | coiled-coil domain containing 28B | CCDC28B | 4.69 | 0.1325 |
| MmuSTS.4364.1.S _at | sterol 0-acyltransferase 1 | SOAT1 | 4.69 | 0.0729 |
| MmugDNA.2668.1.S1_at | mannose receptor-like | LOC709768 | 4.69 | 0.0118 |
| MmugDNA.8460.1.S1_at | LAG1 longevity assurance homolog 6 (S. cerevisiae) | LASS6 | 4.68 | 0.0041 |
| MmugDNA.30211. .S1_at | ATPase, Ca+30+transporting, type 2C, member 1 | ATP2C1 | 4.67 | 0.0624 |
| MmugDNA.22541. .S1_at | chromosome 1 open reading frame 89 /// chromosome 1 open reading frame 89 | C1orf89 | 4.66 | 0.0231 |
| MmugDNA.23541. .S1_at | coiled-coil domain containing 50 | CCDC50 | 4.65 | 0.0487 |
| MmugDNA.38008.1.S1_at | asparaginase-like 1 protein | LOC718871 | 4.65 | 0.0005 |
| MmugDNA.34690.1.S1_at | MAWD binding protein | MAWBP | 4.65 | 0.0787 |
| MmugDNA.31478.1.S1_at | RAB33A, member RAS oncogene family | RAB33A | 4.64 | 0.0430 |
| MmugDNA.28356.1.S1_at | hypothetical protein LOC715793 | LOC715793 | 4.64 | 0.1301 |
| MmugDNA.35760.1.S1_at | receptor transporter protein 4 | RTP4 | 4.63 | 0.1847 |
| MmugDNA.1257.1.S1_at | peptidylprolyl isomerase (cyclophilin)-like 1 | PPIL1 | 4.63 | 0.0032 |
| MmugDNA.38638.1.S1_at | inhibitor of kappa light polypeptide gene enhancer in B-cells, kinase beta Ill nicastrin | IKBKB /// NCSTN | 4.61 | 0.0019 |
| MmugDNA.31887.1.S1_at | hypothetical LOC402617 | LOC402617 | 4.60 | 0.1114 |
| MmugDNA.18767.1.S1_at | MRNA full length insert cDNA clone EUROIMAGE 110216 | — | 4.57 | 0.1233 |
| MmugDNA.40451.1.S1_at | polycomb group ring finger 1 | PCGF1 | 4.56 | 0.0175 |
| MmugDNA.18456.1.S1_at | CDNA FLJ33400 fis, clone BRACE2009828 | — | 4.55 | 0.1261 |
| MmugDNA.31245.1.S1_at | butyrophilin, subfamily 2, member A2 | BTN2A2 | 4.55 | 0.0552 |
| MmugDNA.43078.1.S1_at | KIAA1838 | KIAA1838 | 4.55 | 0.0050 |
| MmugDNA.39763.1.S1_at | ubiquitin specific peptidase 36 | USP36 | 4.54 | 0.0836 |
| MmugDNA.12921.1.S1_at | hypothetical protein FLJ36208 | FLJ36208 | 4.54 | 0.1669 |
| MmugDNA.3000.1.S1_at | signal sequence receptor, gamma (translocon-associated protein gamma) | SSR3 | 4.54 | 0.0185 |
| MmugDNA.31177.1.S1_at | zinc finger protein 582 | ZNF582 | 4.54 | 0.0129 |
| MmuSTS.2548.1.S1_at | thioredoxin domain containing 12 (endoplasmic reticulum) | TXNDC12 | 4.54 | 0.0231 |
| MmugDNA.32746.1.S1_at | inositol 1,4,5-triphosphate receptor, type 2 | ITPR2 | 4.54 | 0.0394 |
| MmugDNA.14882.1.S1_s_at | Huntingtin interacting protein K | HYPK | 4.53 | 0.0411 |
| MmugDNA.2875.1.S1_at | protein-O-mannosyltransferase 1 | POMT1 | 4.53 | 0.0018 |
| MmugDNA.13007.1.S1_at | hypothetical protein LOC284669 | LOC284669 | 4.52 | 0.0142 |
| Mmu.3693.1.S1_at | splicing factor p54 | LOC702698 | 4.52 | 0.0572 |
| MmugDNA.20453.1.S1_at | heterogeneous nuclear ribonucleoprotein L | HNRPL | 4.51 | 0.0000 |
| MmugDNA.14296.1.S1_at | hypothetical protein FLJ37201 | FLJ37201 | 4.51 | 0.0035 |
| MmugDNA.9174.1.S1_at | coiled-coil domain containing 129 | CCDC129 | 4.51 | 0.0743 |

-continued

| Probe Set ID | Gene Title | Gene Symbol | Ratio Top verus Bottom | p value Top versus Bottom |
|---|---|---|---|---|
| MmugDNA.17031.1.S1_at | DTW domain containing 1 | DTWD1 | 4.50 | 0.0000 |
| MmugDNA.10168.1.S1_at | trafficking protein particle complex 4 | TRAPPC4 | 4.50 | 0.0069 |
| MmugDNA.33621.1.S1_at | zinc finger-like | LOC400713 | 4.49 | 0.0368 |
| MmugDNA.28329.1.S1_at | Zinc finger protein 250 | ZNF250 | 4.49 | 0.0001 |
| MmugDNA.3693.1.S1_at | DEAD (Asp-Glu-Ala-Asp) box polypeptide 17 | DDX17 | 4.49 | 0.0217 |
| MmugDNA.5788.1.S1_s_at | transmembrane 4 L six family member 5 | TM4SF5 | 4.48 | 0.1028 |
| MmugDNA.3666.1.S1_at | glucose 6 phosphatase, catalytic, 3 | G6PC3 | 4.47 | 0.0353 |
| MmugDNA.4300.1.S1_at | CDNA clone IMAGE:4812643 | — | 4.47 | 0.0315 |
| MmugDNA.13717.1.S1_at | Type 1 tumor necrosis factor receptor shedding aminopeptidase regulator | ARTS-1 | 4.46 | 0.0839 |
| MmugDNA.31311. .S1_at | methyltransferase like 5 | METTL5 | 4.46 | 0.0001 |
| MmugDNA.19122.1.S1_at | N-deacetylase/N-sulfotransferase (heparan glucosaminyl) 2 | NDST2 | 4.46 | 0.1122 |
| MmugDNA.17470.1.S1_at | translocase of inner mitochondrial membrane 9 homolog (yeast) | TIMM9 | 4.45 | 0.0749 |
| MmugDNA.36689.1.S1_at | dihydroxyacetone kinase 2 homolog (S. cerevisiae) | DAK | 4.45 | 0.2128 |
| MmugDNA.32341. .S1_at | UDP-N-acetyl-alpha-D-galactosamine:polypeptide N-acetylgalactosaminyltransferase 5 (GaINAc-T5) | GALNT5 | 4.45 | 0.0515 |
| MmugDNA.29495. .S1_at | ankyrin and armadillo repeat containing | ANKAR | 4.45 | 0.0616 |
| MmugDNA.9999.1.S1_at | cytochrome b5 domain containing 2 | CYB5D2 | 4.45 | 0.0104 |
| MmugDNA.28421. .S1_at | Discs, large (Drosophila) homolog-associated protein 1 | DLGAP1 | 4.45 | 0.0793 |
| MmugDNA.38681. .S1_at | — | — | 4.44 | 0.1501 |
| MmugDNA.28495. .S1_at | integrin beta 1 binding protein 1 | ITGB1 BP1 | 4.44 | 0.0060 |
| MmugDNA.42735. .S1_at | hypothetical protein LOC144874 | LOC144874 | 4.44 | 0.1195 |
| MmugDNA.6818.1.S1_at | armadillo repeat containing 2 | ARMC2 | 4.43 | 0.0802 |
| MmugDNA.40576. .S1_at | — | — | 4.43 | 0.1762 |
| MmugDNA.8518.1.S1_at | Hypothetical protein LOC645323 | LOC645323 | 4.42 | 0.1298 |
| MmugDNA.16049.1.S1_at | Ubiquitin specific peptidase 30 | USP30 | 4.42 | 0.0000 |
| MmuSTS.4469.1.S1_s_at | vasodilator-stimulated phosphoprotein | VASP | 4.42 | 0.0468 |
| MmugDNA.38086.1.S1_at | chromosome 10 open reading frame 137 | C10orf137 | 4.41 | 0.0223 |
| MmugDNA.31273.1.S1_at | bobby sox homolog (Drosophila) | BBX | 4.41 | 0.0269 |
| MmugDNA.39436.1.S1_at | Transcribed locus | — | 4.41 | 0.0107 |
| MmuSTS.2675.1.S1_s_at | ATP-binding cassette, sub-family B (MDR/TAP), member 10 | ABCB10 | 4.41 | 0.0156 |
| Mmu.2243.1.S1_at | eukaryotic translation initiation factor 3, subunit 2 beta, 36 kDa | EIF3S2 | 4.40 | 0.0204 |
| MmugDNA.14154.1.S1_at | ceroid-lipofuscinosis, neuronal 5 | CLN5 | 4.40 | 0.0271 |
| MmugDNA.8714.1.S1_s_at | inosine triphosphatase (nucleoside triphosphate pyrophosphatase) | ITPA | 4.40 | 0.0380 |
| Mmu.15592.2.S1_at | phosphatidylinositol glycan, class F isoform 1 | LOC714844 | 4.39 | 0.0098 |
| MmugDNA.19980.1.S1_at | tripartite motif-containing 5 | TRIMS | 4.39 | 0.1642 |
| MmugDNA.3645.1.S1_at | serine/threonine kinase receptor associated protein | STRAP | 4.39 | 0.0135 |
| MmugDNA.29562.1.S1_at | prohibitin | PHB | 4.37 | 0.0035 |
| MmugDNA.2122.1.S1_at | stomatin | STOM | 4.37 | 0.0263 |
| MmugDNA.20601.1.S1_s_at | prolyl endopeptidase-like | PREPL | 4.37 | 0.0512 |
| MmugDNA.26227.1.S1_at | RFT1 homolog (S. cerevisiae) | RFT1 | 4.37 | 0.1974 |
| MmugDNA.119.1.S1_at | zinc finger protein 542 | ZNF542 | 4.36 | 0.1250 |
| MmugDNA.38257.1.S1_at | chromosome 3 open reading frame 18 | C3orf18 | 4.36 | 0.0391 |
| MmugDNA.38303.1.S1_at | TAF4b RNA polymerase II, TATA box binding protein (TBP)-associated factor, 105 kDa | TAF4B | 4.35 | 0.0954 |
| Mmu.13799.1.S1_at | hypothetical protein LOC696762 | LOC696762 | 4.35 | 0.0294 |
| MmugDNA.24015.1.S1_at | LanC !antibiotic synthetase component C-like 2 (bacterial) | LANCL2 | 4.35 | 0.0403 |
| MmugDNA.38882.1.S1_at | zinc finger protein 775 | ZNF775 | 4.35 | 0.0238 |
| MmugDNA.11471.1.S1_at | ATPase family, AAA domain containing 1 | ATAD1 | 4.35 | 0.0077 |
| MmugDNA.6735.1.S1_at | zinc finger protein 642 | ZNF642 | 4.33 | 0.0727 |
| MmugDNA.18469.1.S1_at | zinc finger protein 588 | ZNF588 | 4.33 | 0.1354 |
| MmugDNA.11216.1.S1_at | cancer susceptibility candidate 4 | CASC4 | 4.33 | 0.0008 |
| MmugDNA.28842.1.S1_at | CKLF-like MARVEL transmembrane domain containing 7 | CMTM7 | 4.32 | 0.0168 |
| MmugDNA.19883.1.S1_at | SECIS binding protein 2 | SECISBP2 | 4.32 | 0.0191 |
| MmugDNA.18544.1.S1_at | renal tumor antigen | RAGE | 4.32 | 0.0365 |
| MmugDNA.31414.1.S1_at | SMT3 suppressor of mif two 3 homolog 1 (S. cerevisiae) | SUMO1 | 4.32 | 0.0298 |
| MmugDNA.30985.1.S1_at | glucosidase, beta (bile acid) 2 | GBA2 | 4.32 | 0.0080 |
| MmugDNA.33696.1.S1_at | hyaluronan binding protein 4 | HABP4 | 4.32 | 0.0433 |
| MmugDNA.24247.1.S1_at | chromosome 10 open reading frame 11 | Cl Oorfl 1 | 4.31 | 0.1241 |
| Mmu.11729.1.S1_s_at | Translocon-associated protein beta subunit precursor (TRAP-beta) (Signal sequence receptor beta subunit) (SSR-beta) | LOC719383 | 4.31 | 0.0536 |
| MmugDNA.33158.1.S1_at | coiled-coil domain containing 22 | CCDC22 | 4.30 | 0.0689 |
| MmugDNA.10111.1.S1 _at | chromosome 1 open reading frame 131 | Cl orfl 31 | 4.29 | 0.0196 |
| MmugDNA.43034.1.S1_at | HLA-B associated transcript 5 | BATS | 4.29 | 0.0313 |
| MmugDNA.10771.1.S1_at | ligase IV, DNA, ATP-dependent | LIG4 | 4.29 | 0.0048 |
| MmugDNA.39663.1.S1_at | Bernardinelli-Seip congenital lipodystrophy 2 (seipin) /// BSCL2 /// heterogeneous nuclear ribonucleoprotein U-like 2 | HNRPUL2 | 4.28 | 0.0093 |
| MmugDNA.36927.1.S1_at | DNA (cytosine-5-)-methyltransferase 3 alpha | DNMT3A | 4.28 | 0.0096 |
| MmugDNA.24861.1.S1_s_at | neuroguidin, EIF4E binding protein | NGDN | 4.27 | 0.0007 |
| MmugDNA.24533.1.S1_at | cathepsin S | CTSS | 4.27 | 0.0031 |
| MmuSTS.1546.1.S1_at | musashi homolog 2 | MSI2 | 4.27 | 0.0014 |

-continued

| Probe Set ID | Gene Title | Gene Symbol | Ratio Top verus Bottom | p value Top versus Bottom |
|---|---|---|---|---|
| MmugDNA.831.1.S1_at | Chromosome 14 open reading frame 161 | Cl 4orfl 61 | 4.26 | 0.0165 |
| MmugDNA.10644.1.S1_at | Muscleblind-like 2 (Drosophila) | MBNL2 | 4.25 | 0.0000 |
| MmugDNA.33695.1.S1_at | zinc finger protein 34 | ZNF34 | 4.25 | 0.0030 |
| MmugDNA.23792.1.S1_at | thrombospondin, type I, domain containing 3 | THSD3 | 4.24 | 0.1178 |
| MmugDNA.12396.1.S1_at | chromosome 3 open reading frame 41 | C3orf41 | 4.24 | 0.0202 |
| MmugDNA.21184.1.S1_at | hypoxia inducible factor 3, alpha subunit | HIF3A | 4.24 | 0.1766 |
| MmugDNA.6866.1.S1_at | STEAP family member 3 | STEAP3 | 4.24 | 0.1494 |
| MmugDNA.15710.1.S1_at | vacuolar protein sorting 39 (yeast) | VPS39 | 4.23 | 0.0007 |
| Mmu.586.1.S1_at | Protein KIAA0143 | LOC696036 | 4.23 | 0.0432 |
| MmuSTS.2503.1.S1_at | zinc finger, SWIM domain containing 5 | ZSWIMS | 4.23 | 0.0370 |
| MmugDNA.21399.1.S1_at | Transcribed locus | — | 4.22 | 0.0664 |
| MmuSTS.2401.1.S1_s_at | replication protein A1, 70 kDa | RPA1 | 4.22 | 0.0162 |
| Mmu.5491.1.S1_at | prosaposin | LOC709510 | 4.22 | 0.1033 |
| MmugDNA.15874.1.S1_at | Mitochondrial fission regulator 1 | MTFR1 | 4.21 | 0.0570 |
| MmugDNA.32637.1.S1_at | nucleosomal binding protein 1 | NSBP1 | 4.21 | 0.0038 |
| MmugDNA.10551.1.Sl_at | mannosyl (alpha-1,6-)-glycoprotein beta-1,2-N-acetylglucosaminyltransferase /// mannosyl (alpha-1,6-)-glycoprotein beta-1,2-N-acetylglucosaminyltransferase | MGAT2 | 4.21 | 0.0530 |
| MmugDNA.41398.1.S1_at | chromosome 3 open reading frame 31 | C3orf31 | 4.21 | 0.0943 |
| MmugDNA.17617.1.S1_s_at | trophinin /// trophinin | TRO | 4.21 | 0.0108 |
| MmugDNA.39122.1.S1_at | chromosome 3 open reading frame 1 | C3orf1 | 4.21 | 0.0262 |
| MmugDNA.18454.1.S1_at | Transcribed locus | — | 4.20 | 0.0989 |
| MmugDNA.39611.1.S1_at | Dedicator of cytokinesis 2 | DOCK2 | 4.19 | 0.1153 |
| MmuSTS.2075.1.S1_at | POU domain, class 2, transcription factor 3 | POU2F3 | 4.19 | 0.0002 |
| MmugDNA.28348.1.S1_s_at | chaperonin containing TCP1, subunit 2 (beta) | CCT2 | 4.18 | 0.0291 |
| MmugDNA.26826.1.S1_s_at | solute carrier family 11 (proton-coupled divalent metal ion transporters), member 1 | SLC11A1 | 4.17 | 0.0308 |
| Mmu.9862.2.S1_at | F-box only protein 4 isoform 2 | LOC697007 | 4.17 | 0.2109 |
| Mmu.303.1.S1_at | crystallin, zeta | LOC704403 | 4.17 | 0.0292 |
| MmugDNA.19380.1.S1_at | chromosome 1 open reading frame 19 | Cl orf19 | 4.16 | 0.0000 |
| MmugDNA.11030.1.S1_s_at | chromosome 3 open reading frame 15 | C3orfl 5 | 4.16 | 0.0146 |
| MmugDNA.732.1.S1_at | hexosaminidase B (beta polypeptide) | HEXB | 4.16 | 0.0013 |
| MmugDNA.43014.1.S1 _at | hypothetical LOC389172 | LOC389172 | 4.16 | 0.0052 |
| MmugDNA.14429.1.S1_at | chromosome X open reading frame 58 | CXorf58 | 4.15 | 0.0672 |
| MmugDNA.33820.1.S1_at | KIAA0100 | KIAA0100 | 4.15 | 0.0184 |
| MmugDNA.1154.1.S1_at | SNF1-like kinase /// SNF1-like kinase | SNF1 LK | 4.15 | 0.0142 |
| MmugDNA.9493.1.S1_at | phosphodiesterase 4D, cAMP-specific (phosphodiesterase E3 dunce homolog, Drosophila) | PDE4D | 4.15 | 0.0016 |
| MmugDNA.38138.1.S1_at | zinc finger protein 267 | ZNF267 | 4.14 | 0.0014 |
| MmugDNA.37212.1.S1_at | zinc finger, ZZ-type containing 3 | ZZZ3 | 4.14 | 0.0098 |
| MmugDNA.41461.1.S1_at | zinc finger protein 333 | ZNF333 | 4.14 | 0.1972 |
| MmugDNA.19606.1.S1_at | pseudouridylate synthase 7 homolog (S. cerevisiae)-like /// pseudouridylate synthase 7 homolog (S. cerevisiae)-like | PUS7L | 4.13 | 0.0653 |
| MmugDNA.11456.1.S1_at | ligatin | LGTN | 4.13 | 0.0557 |
| MmugDNA.36143.1.S1_s_at | choline dehydrogenase | CHDH | 4.13 | 0.2015 |
| MmugDNA.7248.1.S1_s_at | CCR4-NOT transcription complex, subunit 2 | CNOT2 | 4.13 | 0.0005 |
| MmugDNA.5833.1.S1_at | phosphoinositide-3-kinase, regulatory subunit 4, p150 | PIK3R4 | 4.13 | 0.0029 |
| MmugDNA.39422.1.S1_at | UDP-GIcNAc:betaGal beta-1,3-N-acetylglucosaminyltransferase 1 | B3GNT1 | 4.12 | 0.0370 |
| MmugDNA.1591.1.S1_at | Homo sapiens, clone IMAGE:3352913, mRNA | — | 4.12 | 0.0569 |
| MmugDNA.34328. .Sl_at | dyslexia susceptibility 1 candidate 1 | DYX1C1 | 4.12 | 0.0834 |
| MmugDNA.111.1.S1_at | zinc finger protein 180 | ZNF180 | 4.11 | 0.1267 |
| MmugDNA.5762.1.S1_at | vacuolar protein sorting 25 homolog (S. cerevisiae) | VPS25 | 4.10 | 0.0377 |
| MmugDNA.16868. .Sl_at | hypothetical protein FLJ36665 | FLJ36665 | 4.09 | 0.1171 |
| MmugDNA.6114.1.S1_s_at | DEAD (Asp-Glu-Ala-Asp) box polypeptide 18 | DDX18 | 4.09 | 0.0159 |
| MmugDNA.33106.1.S1_at | — | — | 4.09 | 0.0272 |
| MmugDNA.24857.1.S1_at | RAP2A, member of RAS oncogene family /// RAP2B, member of RAS oncogene family RAP2A /// | RAP2B | 4.07 | 0.1231 |
| MmunewRS.1035.1.S1_s_at | cDNA FLJ31653 fis, clone NT2RI2004190. | gi:16551556 | 4.06 | 0.0241 |
| MmugDNA.6270.1.S1_at | synaptogyrin 1 | SYNGR1 | 4.06 | 0.0066 |
| MmugDNA.42267.1.S1_at | Transcribed locus | — | 4.06 | 0.1725 |
| MmugDNA.1721.1.S1_at | zinc finger protein 442 /// zinc finger protein 442 | ZNF442 | 4.06 | 0.0870 |
| MmugDNA.1190.1.S1_at | dpy-19-like 2 (C. elegans) | DPY19L2 | 4.06 | 0.0340 |
| MmugDNA.10350.1.S1_at | DEAH (Asp-Glu-Ala-His) box polypeptide 16 | DHX16 | 4.05 | 0.0105 |
| MmuSTS.2597.1.S1_at | eukaryotic translation elongation factor 1 epsilon 1 | EEF1 E1 | 4.05 | 0.0005 |
| MmugDNA.13760.1.S1_at | AHA1 , activator of heat shock 90 kDa protein ATPase homolog 1 (yeast) | AHSA1 | 4.05 | 0.0000 |
| MmugDNA.27617.1.S1_at | tektin 2 (testicular) | TEKT2 | 4.04 | 0.0469 |
| MmugDNA.29808.1.S1_at | mannosidase, alpha, class 2C, member 1 | MAN2C1 | 4.04 | 0.0015 |
| MmugDNA.29621.1.S1_at | bone morphogenetic protein 6 | BMP6 | 4.04 | 0.0815 |
| MmugDNA.26069.1.S1_at | — | — | 4.04 | 0.0531 |
| MmuSTS.3237.1.S1_at | RAD54 homolog B (S. cerevisiae) | RAD54B | 4.04 | 0.0748 |
| Mmu.9266.1.S1_x_at | alpha-defensin 4 precursor, mRNA, complete cds. | AY859406 | 4.02 | 0.0972 |
| MmugDNA.35254.1.S1_at | nudix (nucleoside diphosphate linked moiety X)-type motif 16 pseudogene | NUDT16P | 4.01 | 0.1650 |

-continued

| Probe Set ID | Gene Title | Gene Symbol | Ratio Top verus Bottom | p value Top versus Bottom |
|---|---|---|---|---|
| MmugDNA.40333.1.S1_at | low density lipoprotein receptor-related protein associated protein 1 | LRPAP1 | 4.01 | 0.0177 |
| Mmu.4677.1.S1_s_at | rabconnectin-3 beta isoform 2 | LOC695302 | 4.01 | 0.0167 |
| MmugDNA.15059.1.S1_at | zinc finger protein 780B | ZNF780B | 4.01 | 0.1768 |
| MmugDNA.2321.1.S1_at | ELL associated factor 2 | EAF2 | 4.00 | 0.0663 |
| Mmu.14167.1.S1_at | DNA topoisomerase I | LOC697300 | 4.00 | 0.1952 |
| MmugDNA.3213.1.S1_at | single stranded DNA binding protein 4 | SSBP4 | 4.00 | 0.0429 |
| MmugDNA.42484.1.S1_at | ARP6 actin-related protein 6 homolog (yeast) | ACTR6 | 4.00 | 0.0252 |
| MmugDNA.7865.1.S1_at | PPAR binding protein | PPARBP | 4.00 | 0.0589 |
| MmugDNA.18301. .Sl_at | chromosome 18 open reading frame 10 | Cl 8orf10 | 4.00 | 0.0013 |
| MmugDNA.40541. .Sl_at | zinc finger protein 555 | ZNF555 | 4.00 | 0.0028 |
| MmugDNA.6772.1.S1_at | ER degradation enhancer, mannosidase alpha-like 2 | EDEM2 | 3.99 | 0.0411 |
| MmugDNA.24353. .Sl_at | retinoic acid receptor responder (tazarotene induced) 1 | RARRES1 | 3.99 | 0.1529 |
| MmugDNA.34452. .Sl_s_at | — | — | 3.98 | 0.0067 |
| MmugDNA.9814.1.S1_at | Transcribed locus | — | 3.98 | 0.0111 |
| MmugDNA.27740.1.S1_at | U2-associated SR140 protein | SR140 | 3.98 | 0.0286 |
| MmuSTS.3952.1.S1_at | SEC22 vesicle trafficking protein homolog C (S. cerevisiae) | SEC22C | 3.98 | 0.0001 |
| MmugDNA.36936.1.S1_at | deoxyguanosine kinase | DGUOK | 3.97 | 0.0061 |
| MmugDNA.16551.1.S1_at | hypothetical protein FLJ25770 | FLJ25770 | 3.97 | 0.0789 |
| MmugDNA.32988.1.S1_at | ring finger protein 123 | RNF123 | 3.97 | 0.0078 |
| MmugDNA.40932.1.S1_at | zinc finger protein 691 | ZNF691 | 3.97 | 0.0191 |
| MmugDNA.42528.1.S1_at | cytochrome P450, family 4, subfamily F, polypeptide 2 | CYP4F2 | 3.96 | 0.1843 |
| MmugDNA.38754.1.S1_at | Galactokinase 2 | GALK2 | 3.96 | 0.0572 |
| MmuSTS.2536.1.S1_at | Interferon tau-1 | IFNT1 | 3.96 | 0.1884 |
| MmugDNA.21837.1.S1_at | CDNA FLJ40810 fis, clone TRACH2009743 | — | 3.95 | 0.0554 |
| Mmu.10030.1.S1_at | syntenin isoform 3 | LOC698381 | 3.95 | 0.0001 |
| Mmu.5329.1.S1_at | Phospholipid hydroperoxide glutathione peroxidase, mitochondrial precursor (PHGPx) (GPX-4) | GPX4 | 3.95 | 0.1220 |
| MmugDNA.36752.1.S1_at | lymphocyte antigen 6 complex, locus G5C | LY6G5C | 3.93 | 0.1998 |
| MmuSTS.897.1.S1_at | sema domain, seven thrombospondin repeats (type 1 and type 1-lik, , transmembrane domain (TM) and short cytoplasmic domain, (semaphorin) 5B | SEMASB | 3.93 | 0.0637 |
| MmugDNA.40072.1.S1_at | hypothetical protein DKFZp313A2432 | DKFZp313A2432 | 3.93 | 0.1059 |
| MmugDNA.19577.1.S1_at | phosphatidylinositol glycan anchor biosynthesis, class M | PIGM | 3.93 | 0.2113 |
| MmugDNA.11968.1.S1_at | UBX domain containing 7 | UBXD7 | 3.93 | 0.0163 |
| MmugDNA.19665.1.S1_at | hypothetical protein LOC196394 | LOC196394 | 3.93 | 0.0165 |
| MmugDNA.23833.1.S1_at | chromosome 21 open reading frame 58 | C2lorf58 | 3.93 | 0.1718 |
| MmugDNA.27456.1.S1_at | polymerase (RNA) I polypeptide D, 16 kDa | POLR1D | 3.92 | 0.0000 |
| MmugDNA.30349.1.S1_at | Transcribed locus | — | 3.92 | 0.0066 |
| MmugDNA.7253.1.S1_at | — | — | 3.92 | 0.1111 |
| MmugDNA.14931.1.S1_at | t-SNARE domain containing 1 | TSNARE1 | 3.91 | 0.0947 |
| MmugDNA.30795.1.S1_at | chromosome 10 open reading frame 81 | ClOorf81 | 3.91 | 0.0955 |
| MmugDNA.17018.1.S1_s_at | butyrophilin, subfamily 2, member Al | BTN2A1 | 3.91 | 0.0004 |
| MmugDNA.26488.1.S1_at | nischarin | NISCH | 3.90 | 0.0435 |
| MmugDNA.1076.1.S1_at | WD repeat domain 61 | WDR61 | 3.89 | 0.0001 |
| MmugDNA.19511.1.S1_at | death inducer-obliterator 1 | DIDO1 | 3.89 | 0.0638 |
| MmugDNA.5147.1.S1_s_at | kelch repeat and BTB (POZ) domain containing 4 | KBTBD4 | 3.89 | 0.0043 |
| MmugDNA.26429.1.S1_at | AP2 associated kinase 1 | AAK1 | 3.89 | 0.1855 |
| MmugDNA.36463.1.S1_s_at | tyrosine kinase, non-receptor, 1 | TNK1 | 3.89 | 0.0001 |
| MmuSTS.1060.1.S1_at | Solute carrier family 25, member 29 | SLC25A29 | 3.89 | 0.0804 |
| MmugDNA.12692.1.S1_at | quinolinate phosphoribosyltransferase (nicotinate-nucleotide pyrophosphorylase (carboxylating)) | QPRT | 3.88 | 0.0444 |
| MmugDNA.19435.1.S1_s_at | DnaJ (Hsp40) homolog, subfamily A, member 1 | DNAJA1 | 3.88 | 0.0014 |
| MmugDNA.1963.1.S1_at | CDNA clone IMAGE:5278089 | — | 3.88 | 0.1079 |
| MmugDNA.40985.1.S1_at | CDNA clone IMAGE:4825288 | — | 3.88 | 0.0338 |
| MmuSTS.3495.1.S1_at | A kinase (PRKA) anchor protein 3 | AKAP3 | 3.87 | 0.0508 |
| MmuSTS.3737.1.S1_at | protein tyrosine phosphatase, receptor type, C | PTPRC | 3.87 | 0.0186 |
| MmugDNA.31476.1.S1_at | RAB28, member RAS oncogene family | RAB28 | 3.87 | 0.0939 |
| MmugDNA.30719.1.S1_at | dom-3 homolog Z (C. elegans) | DOM3Z | 3.87 | 0.0007 |
| MmugDNA.3113.1.S1_at | transient receptor potential cation channel, subfamily C, member 2 | TRPC2 | 3.87 | 0.0121 |
| MmuSTS.4117.1.S1_at | transmembrane protein 15 | TMEM15 | 3.87 | 0.0145 |
| MmugDNA.41463.1.S1_at | Vac14 homolog (S. cerevisiae) | VAC14 | 3.86 | 0.0546 |
| MmugDNA.26499.1.S1_at | leupaxin | LPXN | 3.86 | 0.0090 |
| MmugDNA.37595.1.S1_at | mortality factor 4 like 1 | MORF4L1 | 3.85 | 0.0059 |
| MmugDNA.22504.1.S1_at | — | — | 3.84 | 0.0508 |
| MmugDNA.20249.1.S1_at | RNA binding motif protein 26 | RBM26 | 3.84 | 0.0198 |
| MmugDNA.13483.1.S1_at | — | — | 3.84 | 0.0604 |
| MmugDNA.16424.1.S1_at | gelsolin (amyloidosis, Finnish type) | GSN | 3.84 | 0.0118 |
| MmugDNA.16896.1.S1_at | stromal antigen 3 | STAGS | 3.82 | 0.0959 |
| MmuSTS.2334.1.S1_at | peroxisomal membrane protein 4, 24 kDa | PXMP4 | 3.81 | 0.0013 |
| MmugDNA.28442.1.S1_s_at | chromosome 20 open reading frame 74 | C20orf74 | 3.81 | 0.0043 |
| MmugDNA.6811.1.S1_at | smu-1 suppressor of mec-8 and unc-52 homolog (C. elegans) | SMU1 | 3.80 | 0.0001 |

-continued

| Probe Set ID | Gene Title | Gene Symbol | Ratio Top verus Bottom | p value Top versus Bottom |
|---|---|---|---|---|
| MmugDNA.13860.1.S1_at | — | — | 3.79 | 0.0387 |
| MmugDNA.13463.1.S1_at | COP9 constitutive photomorphogenic homolog subunit 6 (Arabidopsis) | COPS6 | 3.79 | 0.0192 |
| MmugDNA.4402.1.S1_s_at | mago-nashi homolog | FLJ10292 | 3.78 | 0.0492 |
| MmugDNA.18844.1.S1_at | cholinergic receptor, nicotinic, alpha 1 (muscle) | CHRNA1 | 3.77 | 0.1879 |
| MmugDNA.40143.1.S1_at | transmembrane protein 67 | TMEM67 | 3.77 | 0.0848 |
| MmuSTS.2481.1.S1_at | zinc finger protein 294 | ZNF294 | 3.77 | 0.0304 |
| MmugDNA.30140.1.S1_at | thioredoxin-like 4B | TXNL4B | 3.77 | 0.0239 |
| MmugDNA.38654.1.S1_at | MORN repeat containing 2 | MORN2 | 3.77 | 0.0047 |
| MmuSTS.2773.1.S1_at | solute carrier family 1 (neutral amino acid transporter), member | SLC1A5 | 3.76 | 0.0113 |
| MmugDNA.31203.1.S1_at | THAP domain containing, apoptosis associated protein 2 | THAP2 | 3.76 | 0.0136 |
| MmugDNA.13298.1.S1_at | zinc finger protein 473 | ZNF473 | 3.76 | 0.0210 |
| MmugDNA.19431.1.S1_at | ZXD family zinc finger C | ZXDC | 3.76 | 0.1070 |
| MmugDNA.33573.1.S1_s_at | serine/threonine kinase 16 | STK16 | 3.76 | 0.0507 |
| MmugDNA.24286.1.S1_at | coagulation factor II (thrombin) receptor-like 1 | F2RL1 | 3.76 | 0.0055 |
| MmugDNA.41306.1.S1_at | zinc finger protein 650 | ZNF650 | 3.76 | 0.0002 |
| MmugDNA.8919.1.S1_at | Transcribed locus | — | 3.75 | 0.0786 |
| MmugDNA.4185.1.S1_at | nicolin 1 | NICN1 | 3.75 | 0.1272 |
| MmugDNA.21236.1.S1_at | arginine/serine-rich coiled-coil 1 | LOC704232 | 3.75 | 0.0445 |
| MmugDNA.32661.1.S1_at | dihydropyrimidine dehydrogenase | DPYD | 3.75 | 0.0062 |
| MmugDNA.20872.1.S1_at | docking protein 1, 62 kDa (downstream of tyrosine kinase 1) | DOK1 | 3.75 | 0.0846 |
| MmugDNA.34300.1.S1_at | nicotinamide nucleotide adenylyltransferase 1 | NMNAT1 | 3.75 | 0.0851 |
| MmuSTS.3697.1.S1_at | COP9 constitutive photomorphogenic homolog subunit 4 | COPS4 | 3.74 | 0.0000 |
| MmuSTS.3649.1.S1_at | chloride channel 4 | CLCN4 | 3.74 | 0.1113 |
| MmugDNA.40690.1.S1_at | zinc finger protein 197 | ZNF197 | 3.74 | 0.0025 |
| MmugDNA.41072.1.S1_at | chromosome X and Y open reading frame 10 | CXYorf10 | 3.73 | 0.0146 |
| MmugDNA.26793.1.S1_at | hypothetical protein MGC40579 | MGC40579 | 3.73 | 0.0030 |
| MmugDNA.7453.1.S1_at | integrator complex subunit 9 | RC74 | 3.73 | 0.0020 |
| MmugDNA.41810.1.S1_at | KIAA1429 | KIAA1429 | 3.72 | 0.0204 |
| MmugDNA.42873.1.S1_at | nuclear transcription factor, X-box binding 1 | NFX1 | 3.72 | 0.1160 |
| MmugDNA.13884.1.S1_at | TNFAIP3 interacting protein 2 | TNIP2 | 3.72 | 0.0166 |
| MmugDNA.6002.1.S1_at | apolipoprotein A-I binding protein | APOA1 BP | 3.72 | 0.0046 |
| MmugDNA.28839.1.S1_at | Hypothetical protein LOCI 50384 | LOC150384 | 3.72 | 0.0243 |
| MmugDNA.11009.1.S1_at | elongation factor Tu GTP binding domain containing 1 | EFTUD1 | 3.72 | 0.0006 |
| MmuSTS.2811.1.S1_s_at | solute carrier family 39 (zinc transporter), member 7 | SLC39A7 | 3.72 | 0.1074 |
| MmugDNA.11298.1.S1_at | RNA binding motif protein 12B | RBM12B | 3.72 | 0.1376 |
| MmugDNA.38831.1.S1_at | transient receptor potential cation channel, subfamily C, member 4 associated protein | TRPC4AP | 3.71 | 0.0751 |
| MmuSTS.1121.1.S1_at | single-strand-selective monofunctional uracil-DNA glycosylase 1 | SMUG1 | 3.71 | 0.1049 |
| MmugDNA.23627.1.S1_at | caspase 2, apoptosis-related cysteine peptidase (neural precursor cell expressed, developmentally down-regulated 2) | CASP2 | 3.71 | 0.1012 |
| Mmu.14962.1.S1_at | glycosyltransferase 8 domain containing 1 | LOC695999 | 3.71 | 0.0060 |
| MmugDNA.13631.1.S1_s_at | CD320 molecule | CD320 | 3.71 | 0.0663 |
| MmugDNA.23982.1.S1_at | phosphoprotein associated with glycosphingolipid microdomains 1 /// phosphoprotein associated with glycosphingolipid microdomains 1 | PAG1 /// LOC653745 | 3.71 | 0.0018 |
| MmuSTS.2557.1.S1_at | tumor necrosis factor (ligand) superfamily, member 19 | TNFSF4 | 3.70 | 0.0375 |
| MmugDNA.9215.1.S1_s_at | REX2, RNA exonuclease 2 homolog (S. cerevisiae) | REXO2 | 3.70 | 0.0235 |
| MmugDNA.14634.1.S1_at | alcohol dehydrogenase IB (class!), beta polypeptide | ADH1 B | 3.70 | 0.2072 |
| MmuSTS.2989.1.S1_at | met proto-oncogene | MET | 3.69 | 0.0006 |
| MmugDNA.6796.1.S1_at | F-box and WD-40 domain protein 8 | FBXW8 | 3.69 | 0.0022 |
| MmugDNA.35611.1.S1_at | — | — | 3.69 | 0.0476 |
| MmunewRS.1092.1.S1_at | F-box and WD-40 domain protein 12 | FBXW12 | 3.69 | 0.1972 |
| MmugDNA.37110.1.S1_at | chromosome 1 open reading frame 34 | C1orf34 | 3.69 | 0.0005 |
| MmugDNA.8905.1.S1_at | Transcribed locus, strongly XP_376888.2 PREDICTED: Laminin receptor 1[Homo sapiens] | — | 3.69 | 0.0321 |
| MmugDNA.24188.1.S1_s_at | deleted in a mouse model of primary ciliary dyskinesia | RP11-529I10.4 | 3.68 | 0.0323 |
| MmugDNA.36794.1.S1_at | zinc finger protein 593 | ZNF593 | 3.68 | 0.0540 |
| MmuSTS.4394.1.S1_at | DENN/MADD domain containing 4A | DENND4A | 3.67 | 0.0345 |
| MmugDNA.4893.1.S1_at | hypothetical protein MGC16385 | MGC16385 | 3.67 | 0.0054 |
| MmunewRS.474.1.S1_at | ras homolog gene family, member C | RHOC | 3.67 | 0.1242 |
| MmugDNA.29861. .S1_at | carbonic anhydrase XI | CA11 | 3.67 | 0.0227 |
| MmugDNA.3791.1.S1_at | sphingosine-1-phosphate phosphatase 1 | SGPP1 | 3.67 | 0.0007 |
| MmugDNA.10595. .S1_at | — | — | 3.67 | 0.1276 |
| MmugDNA.34611. .S1_at | Hypothetical protein LOC643011 | LOC643011 | 3.67 | 0.0005 |
| MmugDNA.38962.1.S1_at | acid phosphatase 6, lysophosphatidic | ACP6 | 3.66 | 0.0113 |
| MmugDNA.3351.1.S1_at | DNA segment on chromosome 4 (unique) 234 expressed sequence | D4S234E | 3.66 | 0.0658 |
| MmugDNA.2806.1.S1_s_at | mitogen-activated protein kinase kinase kinase kinase 1 | MAP4K1 | 3.66 | 0.0540 |
| MmugDNA.1419.1.S1_at | CDNA: FLJ23065 fis, clone LNG04894 | — | 3.65 | 0.1255 |
| MmugDNA.24776.1.S1_at | protein phosphatase 1, regulatory subunit 7 | PPP1 R7 | 3.65 | 0.0367 |
| MmugDNA.35069.1.S1_at | RAB6B, member RAS oncogene family | RAB6B | 3.65 | 0.0351 |
| MmugDNA.29893.1.S1_at | ankyrin repeat domain 28 | ANKRD28 | 3.64 | 0.0027 |

-continued

| Probe Set ID | Gene Title | Gene Symbol | Ratio Top verus Bottom | p value Top versus Bottom |
|---|---|---|---|---|
| MmugDNA.2018.1.S1_at | RNA binding protein 51, serine-rich domain /// RNA binding protein S1, serine-rich domain | RNPS1 | 3.64 | 0.0026 |
| MmugDNA.31080. .S1_at | phosphatidylinositol glycan anchor biosynthesis, class | OPIGO | 3.64 | 0.0464 |
| MmugDNA.24890. .S1_at | transmembrane and tetratricopeptide repeat containing 2 | TMTC2 | 3.64 | 0.0230 |
| MmugDNA.5735.1.S1_at | — | — | 3.64 | 0.0557 |
| MmugDNA.26841. .S1_at | estrogen-related receptor alpha | ESRRA | 3.63 | 0.0274 |
| MmugDNA.27441. .S1_at | protein phosphatase 2 (formerly 2A), regulatory subunit A (PR 65), beta isoform | PPP2R1 B | 3.63 | 0.0345 |
| MmuSTS.1040.1.S _at | ST8 alpha-N-acetyl-neuraminide alpha-2,8-sialyltransferase 5 | ST8SIA5 | 3.63 | 0.0623 |
| MmugDNA.7493.1.S1_at | intraflagellar transport 122 homolog (Chlamydomonas) | IFT122 | 3.63 | 0.0020 |
| MmuSTS.3957.1.S1_at | splicing factor, arginine/serine-rich 6 | SFRS6 | 3.62 | 0.0000 |
| MmugDNA.29820.1.S1_at | calcium and integrin binding 1 (calmyrin) | CIB1 | 3.62 | 0.0323 |
| MmugDNA.16149.1.S1_at | Full-length cDNA clone CSODCO25YPO3 of Neuroblastoma Cot 25-normalized of Homo sapiens (human) | — | 3.62 | 0.0491 |
| MmugDNA.6842.1.S1_at | proteasome maturation protein | POMP | 3.62 | 0.0204 |
| MmuSTS.1527.1.S1_at | mitochondrial ribosomal protein L49 | MRPL49 | 3.62 | 0.0034 |
| MmugDNA.19557.1.S1_at | filamin binding LIM protein 1 | FBLIM1 | 3.61 | 0.0016 |
| MmugDNA.32221.1.S1_at | family with sequence similarity 3, member C | FAM3C | 3.61 | 0.0022 |
| MmuSTS.1501.1.S1_at | membrane cofactor protein | MCP | 3.60 | 0.0015 |
| MmugDNA.38325.1.S1_s_at | chromosome 15 open reading frame 17 | C15orf17 | 3.60 | 0.0580 |
| MmugDNA.3200.1.S1_at | Homo sapiens, clone IMAGE:5768746, mRNA | — | 3.60 | 0.1685 |
| MmugDNA.2659.1.S1_at | coiled-coil domain containing 32 | CCDC32 | 3.60 | 0.0505 |
| MmugDNA.19268.1.S1_at | mitochondrial ribosomal protein L2 | MRPL2 | 3.60 | 0.0018 |
| MmugDNA.24173.1.S1_at | Mastermind-like 2 (Drosophila) | MAML2 | 3.59 | 0.0493 |
| MmugDNA.24843.1.S1_at | zinc finger protein 226 | ZNF226 | 3.59 | 0.0000 |
| MmugDNA.35062.1.S1_s_at | aconitase 2, mitochondrial | ACO2 | 3.59 | 0.0031 |
| MmugDNA.17481.1.S1_at | tripartite motif-containing 36 | TRIM36 | 3.58 | 0.0010 |
| MmugDNA.3106.1.S1_at | protective protein for beta-galactosidase (galactosialidosis) | PPGB | 3.58 | 0.0000 |
| MmugDNA.38210.1.S1_at | Full-length cDNA clone CSODF025YA01 of Fetal brain of Homo sapiens (human) | — | 3.58 | 0.0127 |
| MmugDNA.15726.1.S1_at | corin, serine peptidase | CORIN | 3.58 | 0.2106 |
| MmugDNA.24500.1.S1_at | CGI-09 protein | CGI-09 | 3.57 | 0.0000 |
| MmugDNA.16131.1.S1_at | penta-EF-hand domain containing 1 | PEF1 | 3.57 | 0.0794 |
| MmugDNA.9872.1.S1_at | lysosomal-associated membrane protein 1 | LAMP1 | 3.56 | 0.0236 |
| Mmu.4348.1.S1_at | membrane interacting protein of RGS16 | LOC694849 | 3.56 | 0.0006 |
| MmugDNA.5941.1.S1_at | BTB (POZ) domain containing 9 | BTBD9 | 3.56 | 0.1375 |
| MmugDNA.10425.1.S1_at | chondroitin polymerizing factor | CHPF | 3.56 | 0.0133 |
| MmugDNA.845.1.S1_at | aspartylglucosaminidase | AGA | 3.56 | 0.0019 |
| MmugDNA.3137.1.S1_at | protein phosphatase 1G (formerly 2C), magnesium-dependent, gamma isoform | PPM1 G | 3.56 | 0.0107 |
| MmugDNA.35064. .S1_at | acyl-Coenzyme A oxidase 2, branched chain | ACOX2 | 3.55 | 0.0374 |
| MmugDNA.33241. .S1_at | Impact homolog (mouse) | IMPACT | 3.55 | 0.0052 |
| MmugDNA.18757. .S1_at | chromosome 3 open reading frame 39 | C3orf39 | 3.55 | 0.0763 |
| MmugDNA.4130.1.S1_at | mitochondrial ribosomal protein L14 | MRPL14 | 3.55 | 0.0210 |
| MmugDNA.7996.1.S1_at | zinc finger protein 536 | ZNF536 | 3.55 | 0.1304 |
| MmugDNA.34470. .S1_s_at | Hypothetical protein FLJ20309 | FLJ20309 | 3.55 | 0.0078 |
| MmugDNA.722.1.S1_at | — | — | 3.54 | 0.0027 |
| MmugDNA.26101. .S1_at | chromosome 10 open reading frame 25 | C10orf25 | 3.54 | 0.1140 |
| MmugDNA.10676. .S1_s_at | Dmx-like 1 | DMXL1 | 3.54 | 0.0303 |
| MmugDNA.16755. .S1_at | ureidopropionase, beta | UPB1 | 3.54 | 0.1655 |
| MmugDNA.22341. .S1_at | CDNA FLJ31513 fis, clone NT2RI1000127 | — | 3.54 | 0.0101 |
| MmuSTS.4756.1.S1_at | Fanconi anemia, complementation group A | FANCA | 3.54 | 0.0421 |
| MmuSTS.149.1.S1_at | MAM domain containing glycosylphosphatidylinositol anchor 1 | MDGA1 | 3.54 | 0.0991 |
| Mmu.9020.1.S1_at | — | CN802973 | 3.53 | 0.0706 |
| MmugDNA.14464.1.S1_at | antizyme inhibitor 1 | AZIN1 | 3.53 | 0.0000 |
| MmugDNA.3591.1.S1_at | hematopoietic signal peptide-containing | LOC284361 | 3.52 | 0.0013 |
| MmugDNA.2520.1.S1_at | gamma-aminobutyric acid (GABA) A receptor, beta 3 | GABRB3 | 3.52 | 0.1177 |
| MmugDNA.9838.1.S1_x_at | protein disulfide isomerase family A, member 4 /// protein disulfide isomerase family A, member 4 | PDIA4 | 3.52 | 0.0436 |
| MmugDNA.961.1.S1_at | hypothetical protein BC009862 | LOC90113 | 3.52 | 0.0115 |
| MmugDNA.11411.1.S1_at | — | — | 3.52 | 0.0264 |
| MmuSTS.3925.1.S1_at | sal-like 2 (Drosophila) | SALL2 | 3.51 | 0.0042 |
| MmugDNA.32205.1.S1_s_at | cytochrome b5 type A (microsomal) | CYB5A | 3.51 | 0.0112 |
| MmugDNA.32647.1.S1_at | KIAA0409 | KIAA0409 | 3.51 | 0.0080 |
| MmugDNA.11293.1.S1_at | F-box protein 4 | FBXO4 | 3.51 | 0.0376 |
| MmugDNA.4391.1.S1_at | secernin 2 | SCRN2 | 3.51 | 0.0570 |
| MmugDNA.15005.1.S1_at | glutaminase | GLS | 3.50 | 0.1533 |
| MmugDNA.28947.1.S1_at | lactamase, beta 2 | LACTB2 | 3.50 | 0.0364 |
| MmugDNA.16632.1.S1_at | Coenzyme Q10 homolog B (S. cerevisiae) | COQ10B | 3.50 | 0.0485 |
| MmugDNA.8992.1.S1_at | cytoplasmic beta-actin | LOC709469 | 3.50 | 0.1131 |
| MmugDNA.36746.1.S1_at | FYVE, RhoGEF and PH domain containing 6 | FGD6 | 3.50 | 0.0657 |
| MmugDNA.24282.1.S1_at | RIKEN cDNA 4921524J17 | LOC388272 | 3.50 | 0.0156 |
| MmugDNA.6398.1.S1_at | 1-acylglycerol-3-phosphate 0-acyltransferase 7 (lysophosphatidic acid acyltransferase, eta) | AGPAT7 | 3.50 | 0.0454 |

-continued

| Probe Set ID | Gene Title | Gene Symbol | Ratio Top verus Bottom | p value Top versus Bottom |
|---|---|---|---|---|
| MmugDNA.8757.1.S1_at | chromosome 21 open reading frame 108 | C21orf108 | 3.49 | 0.0797 |
| MmugDNA.26500.1.S1_at | KIAA0564 protein | RP11-125A7.3 | 3.49 | 0.0000 |
| MmugDNA.34273.1.S1_at | Mitochondrial transcription termination factor | MTERF | 3.49 | 0.0856 |
| MmuSTS.2708.1.S1_at | a disintegrin and metalloproteinase domain 10 | ADAM10 | 3.49 | 0.0131 |
| MmugDNA.41055.1.S1_at | chromosome 3 open reading frame 62 | C3orf62 | 3.49 | 0.0726 |
| MmugDNA.29251.1.S1_at | guanine nucleotide binding protein (G protein), alpha transducing activity polypeptide 2 | GNAT2 | 3.49 | 0.0400 |
| MmugDNA.26180.1.S1_at | Chromosome 9 open reading frame 42 | C9orf42 | 3.49 | 0.0292 |
| MmuSTS.1660.1.S1_at | leucyl-tRNA synthetase 2, mitochondrial | LARS2 | 3.49 | 0.0460 |
| MmugDNA.43332.1.S1_at | Transcribed locus | — | 3.49 | 0.0334 |
| MmugDNA.20126.1.S1_at | 5,10-methenyltetrahydrofolate synthetase (5-formyltetrahydrofolate cyclo-ligase) | MTHFS | 3.48 | 0.0071 |
| MmuSTS.1987.1.S1_at | death-associated protein | DAP | 3.48 | 0.0005 |
| MmugDNA.40683.1.S1_at | heterogeneous nuclear ribonucleoprotein K | HNRPK | 3.48 | 0.0301 |
| MmugDNA.22114.1.S1_at | methylthioadenosine phosphorylase | MTAP | 3.47 | 0.0264 |
| MmugDNA.40281.1.S1_at | Transcribed locus | 237420 at_ | 3.47 | 0.0200 |
| MmugDNA.9668.1.S1_at | PWP1 homolog (S. cerevisiae) | PWP1 | 3.47 | 0.0124 |
| MmugDNA.3432.1.S1_at | plexin C1 | PLXNC1 | 3.47 | 0.0162 |
| MmugDNA.11221.1.S1_s_at | catenin (cadherin-associated protein), beta 1, 88 kDa | CTNNB1 | 3.47 | 0.0447 |
| MmugDNA.32959.1.S1_at | CDNA FLJ38419 fis, clone FEBRA2009846 | — | 3.47 | 0.1735 |
| MmugDNA.19660.1.S1_s_at | epoxide hydrolase 1, microsomal (xenobiotic) | EPHX1 | 3.46 | 0.0000 |
| MmuSTS.4149.1.S1_at | lipoic acid synthetase | LIAS | 3.45 | 0.0166 |
| MmugDNA.27400.1.S1_at | mannosyl (alpha-1,3-)-glycoprotein beta-1,4-N-acetylglucosaminyltransferase, isozyme A | MGAT4A | 3.45 | 0.0004 |
| MmugDNA.3969.1.S1_at | Transcribed locus, strongly XP_372416.1 PREDICTED: leucine rich repeat containing 10 [Homo sapiens] | — | 3.45 | 0.1619 |
| MmunewRS.977.1.S1_s_at | chromosome 10 open reading frame 125 | C10orf125 | 3.45 | 0.0268 |
| MmugDNA.336.1.S1_s_at | SH3 and multiple ankyrin repeat domains 2 | SHANK2 | 3.44 | 0.0424 |
| MmugDNA.10656.1.S1_at | GPI-anchored membrane protein 1 | GPIAP1 | 3.44 | 0.0012 |
| MmugDNA.38403.1.S1_at | — | — | 3.44 | 0.0927 |
| MmugDNA.28792.1.S1_at | metallo-beta-lactamase superfamily protein | LOCI 53364 | 3.43 | 0.0467 |
| MmugDNA.15913.1.S1_at | NudC domain containing 2 | NUDCD2 | 3.43 | 0.0000 |
| MmugDNA.10398.1.S1_s_at | G protein-coupled receptor 172A | GPR172A | 3.43 | 0.0559 |
| MmugDNA.15.1.S1_at | Hypothetical protein FLJ30655 | FLJ30655 | 3.43 | 0.0037 |
| MmugDNA.39070.1.S1_at | androgen-induced 1 | AIG1 | 3.43 | 0.0025 |
| MmugDNA.2721.1.S1_s_at | Transcribed locus, weakly XP_864747.1 PREDICTED: hypothetical protein XP_859654 [Canis familiaris] | — | 3.43 | 0.0094 |
| Mmu.12027.3.S1_at | heterogeneous nuclear ribonucleoprotein K isoform a | LOC709112 | 3.43 | 0.0681 |
| MmugDNA.38984.1.S1_at | uracil-DNA glycosylase 2 | UNG2 | 3.43 | 0.0995 |
| MmuSTS.4179.1.S1_at | cathepsin O | CTSO | 3.43 | 0.0144 |
| MmugDNA.26924.1.S1_at | hypothetical protein LOC720691 | LOC720691 | 3.42 | 0.1571 |
| Mmu.1137.1.S1_at | clone 2.32 T-cell receptor gamma chain mRNA, complete cds. | AY190025 | 3.42 | 0.0301 |
| MmuSTS.3149.1.S1_at | nuclear receptor subfamily 2, group F, member 6 | NR2F6 | 3.42 | 0.0585 |
| MmugDNA.3922.1.S1_at | CDNA clone IMAGE:5266242 | — | 3.42 | 0.0051 |
| MmugDNA.8473.1.S1_at | KIAA1875 | KIAA1875 | 3.42 | 0.0943 |
| MmugDNA.38687.1.S1_at | family with sequence similarity 121 B /// NODAL modulator 3 | FAM121B /// NOMO3 | 3.42 | 0.1139 |
| MmugDNA.21376.1.S1_s_at | SMAD, mothers against DPP homolog 3 (Drosophila) /// uroporphyrinogen decarboxylase | SMAD3 /// UROD | 3.42 | 0.0101 |
| MmugDNA.17400.1.S1_at | UDP-N-acetyl-alpha-D-galactosamine:polypeptide N-acetylgalactosaminyltransferase 7 (GaINAc-T7) | GALNT7 | 3.42 | 0.0000 |
| Mmu.4958.1.S1_at | Rhesus monkey apolipoprotein(a) mRNA, 3 end. | J04635 | 3.42 | 0.0785 |
| MmugDNA.9546.1.S1_s_at | succinate dehydrogenase complex, subunit B, iron sulfur (Ip) | SDHB | 3.41 | 0.0242 |
| MmugDNA.8291.1.S1_at | spectrin, beta, erythrocytic (includes spherocytosis, clinical type I) /// spectrin, beta, erythrocytic (includes spherocytosis, clinical type I) | SPTB /// LOC653716 | 3.41 | 0.1210 |
| MmugDNA.5881.1.S1_at | IQ motif containing C | IQCC | 3.40 | 0.0207 |
| MmugDNA.2675.1.S1_at | trimethyllysine hydroxylase, epsilon | TMLHE | 3.40 | 0.1204 |
| MmugDNA.36751. .S1_at | ret finger protein 2 | RFP2 | 3.40 | 0.0005 |
| MmugDNA.32977.1.S1_at | osmosis responsive factor | OSRF | 3.40 | 0.0100 |
| MmugDNA.20463.1.S1_at | EST from clone 27306, 5' end | — | 3.40 | 0.0005 |
| MmugDNA.14340.1.S1_s_at | SEH1-like (S. cerevisiae) | SEH1L | 3.39 | 0.0258 |
| MmugDNA.34005.1.S1_at | CG8580-PA, isoform A | LOC718520 | 3.39 | 0.0005 |
| MmugDNA.767.1.S1_at | hypothetical protein BC015395 | LOCI 30940 | 3.39 | 0.1357 |
| MmugDNA.10620.1.S1_at | Rho GTPase activating protein 18 | ARHGAP18 | 3.39 | 0.0000 |
| Mmu.11667.1.S1_at | Calcyclin-binding protein (CacyBP) (hCacyBP) (Siah-interacting protein) (S100A6-binding protein) | CACYBP /// LOC709343 | 3.39 | 0.0000 |
| MmugDNA.8892.1.S1_at | hypothetical protein LOC646482 | LOC646482 | 3.38 | 0.1081 |
| MmugDNA.26367.1.S1_at | acyl-CoA synthetase short-chain family member 1 | ACSS1 | 3.38 | 0.0380 |
| MmugDNA.2176.1.S1_at | interferon stimulated exonuclease gene 20 kDa | ISG20 | 3.38 | 0.0000 |
| MmugDNA.29483.1.S1_at | UDP-N-acetyl-alpha-D-galactosamine:polypeptide N-acetylgalactosaminyltransferase 13 (GaINAc-T13) | GALNT13 | 3.38 | 0.0534 |
| MmuSTS.3944.1.S1_at | succinate-CoA ligase, GDP-forming, beta subunit | SUCLG2 | 3.37 | 0.0043 |
| MmugDNA.2878.1.S1_at | IQ motif containing E | IQCE | 3.37 | 0.0575 |

-continued

| Probe Set ID | Gene Title | Gene Symbol | Ratio Top verus Bottom | p value Top versus Bottom |
|---|---|---|---|---|
| MmugDNA.24079.1.S1_s_at | coiled-coil domain containing 115 | CCDC115 | 3.37 | 0.0018 |
| MmugDNA.646.1.S1_at | zinc finger protein 420 | ZNF420 | 3.37 | 0.0215 |
| MmuSTS.2567.1.S1_s_at | Ubiquitin-like 4 | UBL4 | 3.37 | 0.0006 |
| MmunewRS.414.1.S1_at | transcription elongation factor A (SID-like 1 | TCEAL1 | 3.37 | 0.0002 |
| MmugDNA.18382.1.S1_at | potassium channel tetramerisation domain containing 18 | KCTD18 | 3.37 | 0.0036 |
| MmugDNA.36367.1.S1_at | replication factor C (activator 1) 1, 145 kDa | RFC1 | 3.36 | 0.0093 |
| MmuSTS.2408.1.S1_s_at | splicing factor, arginine/serine-rich 15 | SFRS15 | 3.36 | 0.0084 |
| MmugDNA.38549.1.S1_at | elongation protein 4 homolog (S. cerevisiae) | ELP4 | 3.36 | 0.0279 |
| MmugDNA.27232.1.S1_at | RNA binding motif and ELMO/CED-12 domain 1 | RBED1 | 3.36 | 0.0628 |
| MmugDNA.30570.1.S1_at | flightless I homolog (Drosophila) | FLII | 3.36 | 0.0522 |
| MmugDNA.22711.1.S1_at | arginyl-tRNA synthetase-like | RARSL | 3.36 | 0.0078 |
| MmugDNA.40118.1.S1_at | vitelliform macular dystrophy 2-like 2 | VMD2L2 | 3.35 | 0.0953 |
| MmuSTS.3727.1.S1_at | protein tyrosine phosphatase, non-receptor type substrate 1 | PTPNS1 | 3.35 | 0.0115 |
| MmugDNA.16151.1.S1_at | zinc finger protein 567 | ZNF567 | 3.35 | 0.0104 |
| MmugDNA.34207.1.S1_at | Transcribed locus | — | 3.35 | 0.1488 |
| MmugDNA.3005.1.S1_at | polymerase (RNA) II (DNA directed) polypeptide B, 140 kDa | POLR2B | 3.34 | 0.0033 |
| MmugDNA.26951.1.S1_at | zinc finger protein 174 | ZNF174 | 3.34 | 0.0446 |
| MmugDNA.25836.1.S1_at | SWI/SNF related, matrix associated, actin dependent regulator of chromatin, subfamily a, member 4 | SMARCA4 | 3.34 | 0.0394 |
| MmugDNA.40790.1.S1_at | matrin 3 | MATR3 | 3.34 | 0.0880 |
| MmugDNA.15859.1.S1_s_at | FAST kinase domains 2 | FASTKD2 | 3.33 | 0.0003 |
| MmugDNA.26707.1.S1_at | aarF domain containing kinase 4 | ADCK4 | 3.33 | 0.0000 |
| MmuSTS.1553.1.S1_at | Mitogen-activated protein kinase kinase kinase 7 interacting protein 1 | MAP3K7IP1 | 3.33 | 0.0067 |
| MmugDNA.27387.1.S1_s_at | mannosidase, alpha, class 2B, member 1 | MAN2B1 | 3.32 | 0.0175 |
| MmugDNA.23626.1.S1_at | — | — | 3.32 | 0.0842 |
| MmugDNA.27590.1.S1_at | — | — | 3.32 | 0.1370 |
| MmugDNA.13842.1.S1_at | ADP-ribosylation-like factor 6 interacting protein 4 | ARL6IP4 | 3.31 | 0.0687 |
| MmugDNA.36711. .S1_at | bolA-like 1 (E. coli) | BOLA1 | 3.31 | 0.0000 |
| MmugDNA.35351. .S1_at | round spermatid basic protein 1 | RSBN1 | 3.31 | 0.0414 |
| MmunewRS.884.1.S1_at | zinc finger protein 29 | MGC75360 | 3.31 | 0.1372 |
| MmugDNA.21146. .S1_at | STT3, subunit of the oligosaccharyltransferase complex, homolog A (S. cerevisiae) | STT3A | 3.29 | 0.0106 |
| MmugDNA.14126. .S1_at | chromosome 1 open reading frame 176 | C1orf176 | 3.29 | 0.0492 |
| MmugDNA.3522.1.S1_at | KRIT1, ankyrin repeat containing | KRIT1 | 3.29 | 0.0900 |
| MmugDNA.1835.1.S1_at | zinc finger protein 786 | ZNF786 | 3.29 | 0.0065 |
| MmugDNA.30488.1.S1_at | isocitrate dehydrogenase 2 (NADP+), mitochondrial | IDH2 | 3.29 | 0.0771 |
| MmugDNA.35876.1.S1_at | ST8 alpha-N-acetyl-neuraminide alpha-2,8-sialyltransferase 2 | ST8SIA2 | 3.28 | 0.0593 |
| MmugDNA.29769.1.S1_at | Proteasome (prosome, macropain) subunit, beta type, 7 | PSMB7 | 3.28 | 0.1130 |
| MmuSTS.3141.1.S1_at | methionine adenosyltransferase I, alpha | MAT1A | 3.28 | 0.0685 |
| MmugDNA.28691.1.S1_at | chromosome 4 open reading frame 30 | C4orf30 | 3.28 | 0.0289 |
| MmugDNA.27041.1.S1_at | solute carrier family 25 (mitochondrial carrier; phosphate carrier), member 23 | SLC25A23 | 3.27 | 0.0245 |
| MmugDNA.1453.1.S1_at | dysbindin (dystrobrevin binding protein 1) domain containing 2 | DBNDD2 | 3.27 | 0.0046 |
| MmuSTS.2928.1.S1_at | potassium voltage-gated channel, subfamily H (eag-related), memb, 7 | KCNH7 | 3.27 | 0.1254 |
| Mmu.1184.1.S1_at | endomembrane protein emp70 precursor isolog | TM9SF3 | 3.27 | 0.1019 |
| MmugDNA.17590.1.S1_at | hypothetical gene supported by BC036588 | LOC400657 | 3.27 | 0.0882 |
| MmugDNA.4941.1.S1_at | ring finger protein 14 | RNF14 | 3.27 | 0.1095 |
| MmugDNA.15613.1.S1_at | glucosamine (N-acetyl)-6-sulfatase (Sanfilippo disease IIID) | GNS | 3.27 | 0.0730 |
| MmugDNA.15594.1.S1_at | gonadotropin-releasing hormone 2 | GNRH2 | 3.27 | 0.0389 |
| MmuSTS.1234.1.S1_at | carnitine palmitoyltransferase II | CPT2 | 3.26 | 0.0017 |
| MmugDNA.1780.1.S1_at | — | — | 3.26 | 0.0226 |
| MmugDNA.36001.1.S1_at | septin 3 | 3-Sep | 3.26 | 0.1383 |
| MmugDNA.18459.1.S1_at | protease, serine, 15 | PRSS15 | 3.26 | 0.1011 |
| MmugDNA.31437.1.S1_at | Glycosylphosphatidylinositol specific phospholipase D1 | GPLD1 | 3.26 | 0.0097 |
| MmugDNA.736.1.S1_at | Full-length cDNA clone CSODJ002YF02 of T cells (Jurkat cell line) Cot 10-normalized of Homo sapiens (human) | — | 3.25 | 0.0015 |
| MmugDNA.27420.1.S1_at | — | — | 3.25 | 0.0258 |
| MmugDNA.16170.1.S1_s_at | transmembrane protein 4 | TMEM4 | 3.25 | 0.0005 |
| MmugDNA.37197.1.S1_at | cytochrome b5 domain containing 1 | CYB5D1 | 3.25 | 0.0905 |
| MmugDNA.3346.1.S1_at | makorin, ring finger protein, 2 | MKRN2 | 3.25 | 0.0000 |
| MmugDNA.8231.1.S1_at | triple functional domain (PTPRF interacting) | TRIO | 3.25 | 0.2126 |
| MmugDNA.32917.1.S1_at | G protein-coupled receptor 56 | GPR56 | 3.24 | 0.0001 |
| MmugDNA.34839.1.S1_at | unc-5 homolog A (C. elegans) | UNC5A | 3.24 | 0.0215 |
| MmugDNA.35448.1.S1_at | phosphohistidine phosphatase 1 | PHPT1 | 3.24 | 0.0749 |
| MmugDNA.8574.1.S1_at | tetraspanin 32 | TSPAN32 | 3.24 | 0.0871 |
| MmugDNA.33908.1.S1_at | KIAA0141 | KIAA0141 | 3.24 | 0.0050 |
| MmuSTS.4810.1.S1_at | follicular lymphoma variant translocation 1 | FVT1 | 3.23 | 0.0006 |
| MmugDNA.17221.1.S1_at | chromosome 11 open reading frame 11 | C11orf11 | 3.23 | 0.0529 |
| MmugDNA.15445.1.S1_at | chromosome 14 open reading frame 132 | C14orf132 | 3.23 | 0.0629 |
| MmugDNA.37901.1.S1_at | COX4 neighbor | COX4NB | 3.23 | 0.0005 |
| MmugDNA.9762.1.S1_at | Hypothetical protein LOC643382 | LOC643382 | 3.23 | 0.0376 |

-continued

| Probe Set ID | Gene Title | Gene Symbol | Ratio Top verus Bottom | p value Top versus Bottom |
|---|---|---|---|---|
| MmuSTS.2544.1.S1_at | translocase of inner mitochondrial membrane 23 homolog (yeast) | TIMM23 | 3.22 | 0.0000 |
| MmuSTS.3926.1.S1_at | tetraspanin 31 | TSPAN31 | 3.22 | 0.0303 |
| MmugDNA.23914.1.S1_at | hypothetical gene supported by AF064843; AK025716 /// hypothetical protein LOC642361 /// hypothetical protein LOC646509 | LOC439994 /// LOC642361 /// LOC646509 | 3.21 | 0.1319 |
| MmugDNA.25504.1.S1_at | tubulin, gamma complex associated protein 5 | TUBGCP5 | 3.21 | 0.0027 |
| MmugDNA.19562.1.S1_at | ZNF406 /// zinc finger protein 406 /// Zinc finger protein 406 | LOC654252 | 3.21 | 0.0468 |
| MmugDNA.11799.1.S1_at | CAS1 domain containing 1 | CASD1 | 3.21 | 0.0679 |
| MmugDNA.22745.1.S1_at | oxidoreductase NAD-binding domain containing 1 | OXNAD1 | 3.21 | 0.0025 |
| MmugDNA.29698.1.S1_at | transmembrane protein 128 | TMEM128 | 3.21 | 0.0063 |
| MmugDNA.21404.1.S1_at | high-mobility group 20B | HMG20B | 3.20 | 0.0295 |
| MmugDNA.37311.1.S1_at | F-box and leucine-rich repeat protein 20 | FBXL20 | 3.20 | 0.1599 |
| MmugDNA.26098.1.S1_at | Yip1 domain family, member 4 | YIPF4 | 3.20 | 0.0937 |
| MmunewRS.416.1.S1_at | ATPase, H+transporting, lysosomal 5658 kDa, V1 subunit B, isoform 1 (Renal tubular acidosis with deafness), mRNA (cDNA clone MGC:74733 IMAGE:5208385), complete cds./ GEN = ATP6V1 B1 /PROD = ATPase, H+ transporting, lysosomal 5658kD, V1subunit B, isoform 1 | gi:39645818 | 3.20 | 0.0716 |
| MmugDNA.24420.1.S1_s_at | Chromosome 1 open reading frame 85 | C1orf85 | 3.19 | 0.0399 |
| MmugDNA.1438.1.S1_at | mitochondrial ribosomal protein 63 | MRP63 | 3.19 | 0.0838 |
| MmugDNA.25245.1.S1_at | cSH-PTP2 | LOC441868 | 3.18 | 0.0771 |
| MmugDNA.20570.1.S1_at | WW domain binding protein 1 | WBP1 | 3.18 | 0.0001 |
| MmugDNA.37020.1.S1_at | dedicator of cytokinesis 1 | DOCK1 | 3.18 | 0.0728 |
| MmuSTS.1407.1.S1_at | potassium channel, subfamily K, member 3 | KCNK3 | 3.18 | 0.0806 |
| MmugDNA.11054.1.S1_at | transmembrane protein 53 | TMEM53 | 3.18 | 0.1004 |
| MmugDNA.25885.1.S1_at | ATP/GTP binding protein-like 3 | AGBL3 | 3.18 | 0.0755 |
| MmugDNA.38701.1.S1_at | glucosidase, alpha; acid (Pompe disease, glycogen storage disease type II) | GAA | 3.18 | 0.0184 |
| MmugDNA.43423.1.S1_s_at | Nuclear respiratory factor 1 | NRF1 | 3.18 | 0.0933 |
| MmugDNA.3251.1.S1_at | KIAA1183 protein | KIAA1183 | 3.18 | 0.2092 |
| MmugDNA.30199.1.S1_at | transmembrane protein 70 | TMEM70 | 3.18 | 0.0021 |
| MmugDNA.15760.1.S1_at | peroxiredoxin 5 | PRDX5 | 3.17 | 0.1334 |
| MmugDNA.30636.1.S1_at | eukaryotic translation initiation factor 2-alpha kinase 3 | EIF2AK3 | 3.17 | 0.0171 |
| MmugDNA.36645.1.S1_at | isochorismatase domain containing 1 | ISOC1 | 3.17 | 0.0099 |
| Mmu.3814.1.S1_at | MGC15407-like | LOC677698 | 3.17 | 0.0744 |
| MmugDNA.16486.1.S1_at | coiled-coil domain containing 66 | CCDC66 | 3.16 | 0.0054 |
| MmugDNA.12087.1.S1_at | peptidyl-tRNA hydrolase 1 homolog (S. cerevisiae) | PTRH1 | 3.16 | 0.0024 |
| MmugDNA.33464.1.S1_at | PHD finger protein 6 /// PHD finger protein 6 | PHF6 | 3.16 | 0.0667 |
| MmuSTS.238.1.S1_at | 3-hydroxymethyl-3-methylglutaryl-Coenzyme A lyase (hydroxymethyl, utaricaciduria) | HMGCL | 3.16 | 0.0027 |
| MmunewRS.64.1.S1_at | mitochondrial ribosomal protein L13 | MRPL13 | 3.16 | 0.0003 |
| MmugDNA.15050.1.S1_x_at | chromosome 5 open reading frame 31 | C5orf31 | 3.16 | 0.0390 |
| Mmu.3280.1.S1_at | retinoblastoma-associated protein 140 | LOC722528 | 3.16 | 0.0136 |
| MmugDNA.28942.1.S1_at | — | — | 3.16 | 0.0067 |
| MmugDNA.43211.1.S1_at | IBR domain containing 1 | IBRDC1 | 3.15 | 0.0006 |
| MmuSTS.1528.1.S1_at | mitochondrial ribosomal protein L50 | MRPL50 | 3.15 | 0.0206 |
| MmuSTS.3308.1.S1_at | SATB family member 1 | SATB1 | 3.15 | 0.0007 |
| MmugDNA.8392.1.S1_s_at | SWI/SNF related, matrix associated, actin dependent regulator of chromatin, subfamily a, member 5 | SMARCA5 | 3.15 | 0.0053 |
| MmugDNA.11966.1.S1_at | ribonuclease T2 | RNASET2 | 3.15 | 0.0025 |
| MmugDNA.19079.1.S1_s_at | karyopherin alpha 1 (importin alpha 5) | KPNA1 | 3.14 | 0.0136 |
| MmuSTS.2957.1.S1_at | LIM domain binding 1 | LDB1 | 3.14 | 0.0697 |
| MmuSTS.1291.1.S1_at | de-etiolated 1 | DET1 | 3.14 | 0.0395 |
| MmugDNA.9689.1.S1_at | chromosome 20 open reading frame 82 | C20orf82 | 3.14 | 0.0503 |
| MmugDNA.4538.1.S1_at | dynein, light chain, roadblock-type 2 | DYNLRB2 | 3.14 | 0.0037 |
| MmugDNA.10006.1.S1_at | activating signal cointegrator 1 complex subunit 3-like 1 /// activating signal cointegrator 1 complex subunit 3-like 1 | ASCC3L1 | 3.14 | 0.0043 |
| MmugDNA.35020.1.S1_at | PHD finger protein 20 | PHF20 | 3.14 | 0.0000 |
| MmugDNA.18760.1.S1_at | integrin alpha FG-GAP repeat containing 3 | ITFG3 | 3.14 | 0.0000 |
| MmuSTS.4243.1.S1_s_at | protein phosphatase 1F (PP2C domain containing) | PPM1 F | 3.14 | 0.0303 |
| MmugDNA.21710.1.S1_at | CDNA FLJ38498 fis, clone FELNG2000241 | — | 3.14 | 0.0038 |
| MmugDNA.18438.1.S1_at | Rho guanine nucleotide exchange factor (GEF) 12 | ARHGEF12 | 3.13 | 0.1368 |
| MmugDNA.27794.1.S1_at | Transcribed locus, strongly NP_079090.1 Cas-Br-M (murine) ecotropic retroviral transforming sequence-like 1; E-cadherin binding protein E7 [Homo sapiens] | — | 3.13 | 0.0004 |
| MmugDNA.36386.1.S1_at | hypothetical protein LOC283680 | LOC283680 | 3.13 | 0.0048 |
| MmugDNA.13015.1.S1_at | echinoderm microtubule associated protein like 4 | EML4 | 3.13 | 0.0093 |
| MmugDNA.7282.1.S1_at | hypothetical protein MGC5242 | MGC5242 | 3.13 | 0.0008 |
| MmugDNA.36432.1.S1_at | smoothelin | SMTN | 3.13 | 0.0273 |
| MmugDNA.21419.1.S1_at | hypothetical protein LOC644096 | LOC644096 | 3.13 | 0.0006 |
| Mmu.2231.1.S1_at | F-actin capping protein alpha-1 subunit | CAPZA1 | 3.13 | 0.1124 |
| MmugDNA.30086.1.S1_at | CG13876-PA | LOC693668 | 3.13 | 0.0672 |
| MmugDNA.8672.1.S1_at | syndecan 3 (N-syndecan) | SDC3 | 3.13 | 0.0201 |
| MmugDNA.1837.1.S1_at | radial spokehead-like 1 /// radial spokehead-like 1 | RSHL1 | 3.13 | 0.2159 |

-continued

| Probe Set ID | Gene Title | Gene Symbol | Ratio Top verus Bottom | p value Top versus Bottom |
|---|---|---|---|---|
| MmugDNA.40109.1.S1_at | ubiquitin-like 7 (bone marrow stromal cell-derived) | UBL7 | 3.13 | 0.0040 |
| MmuSTS.3145.1.S1_at | NODAL modulator 1 | NOMO1 | 3.12 | 0.0003 |
| MmugDNA.1608.1.S1_at | F-box and leucine-rich repeat protein 2 | FBXL2 | 3.12 | 0.0301 |
| MmugDNA.7343.1.S1_at | CDNA clone IMAGE:4797878 | — | 3.12 | 0.1962 |
| MmugDNA.20535.1.S1_at | chromosome 1 open reading frame 50 | C1orf50 | 3.12 | 0.0081 |
| MmuSTS.2562.1.S1_s_at | tumor suppressing subtransferable candidate 1 | TSSC1 | 3.12 | 0.0010 |
| MmugDNA.19650.1.S1_at | deoxyhypusine hydroxylase/monooxygenase /// deoxyhypusine hydroxylase/monooxygenase | DOHH | 3.12 | 0.0831 |
| MmugDNA.3700.1.S1_at | transmembrane protein 39A | TMEM39A | 3.12 | 0.0384 |
| MmugDNA.41216.1.S1_at | AF034176 Human mRNA (Tripodis and Ragoussis) Homo sapiens cDNA clone ntcon5 contig | — | 3.11 | 0.1344 |
| MmugDNA.24685.1.S1_at | retinitis pigmentosa 2 (X-linked recessive) | RP2 | 3.11 | 0.0605 |
| MmuSTS.507.1.S1_s_at | N-acylsphingosine amidohydrolase 3-like | ASAH3L | 3.11 | 0.0119 |
| MmugDNA.988.1.S1_at | 3-phosphoinositide dependent protein kinase-1 | PDPK1 | 3.11 | 0.0509 |
| MmugDNA.3400.1.S1_at | Doublecortin domain-containing protein 2 | LOC642926 | 3.11 | 0.0189 |
| MmugDNA.15806. .S1_at | CDNA clone IMAGE:4813920 | — | 3.11 | 0.1892 |
| MmugDNA.41923. .S1_at | eukaryotic translation initiation factor 2 alpha kinase 4 | EIF2AK4 | 3.11 | 0.0696 |
| MmugDNA.7995.1.S1_at | cysteine-rich PAK1inhibitor | CRIPAK | 3.11 | 0.1785 |
| MmugDNA.5163.1.S1_at | Transcribed locus | — | 3.10 | 0.0566 |
| MmugDNA.23909. .S1_at | acyl-Coenzyme A dehydrogenase family, member 8 | ACAD8 | 3.10 | 0.1817 |
| MmugDNA.28412. .S1_at | KIAA1370 | KIAA1370 | 3.10 | 0.0000 |
| MmugDNA.11861. .S1_at | salvador homolog 1 (Drosophila) | SAV1 | 3.10 | 0.0059 |
| MmugDNA.7288.1.S1_s_at | KIAA0280 | KIAA0280 | 3.09 | 0.0105 |
| MmugDNA.15715. .S1_at | HCLS1 associated protein X-1 | HAX1 | 3.09 | 0.0106 |
| MmugDNA.38581. .S1_at | excision repair cross-complementing rodent repair deficiency, complementation group 1 (includes overlapping antisense sequence) | ERCC1 | 3.09 | 0.0102 |
| MmugDNA.9603.1.S1_at | KIAA0753 | KIAA0753 | 3.09 | 0.0595 |
| MmugDNA.22362.1.S1_at | proteasome (prosome, macropain) subunit, beta type, 1 | PSMB1 | 3.09 | 0.0108 |
| MmugDNA.6764.1.S1_at | ATPase type 13A1 | ATP13A1 | 3.08 | 0.0244 |
| MmunewRS.184.1.S1_at | hypothetical protein LOC701867 | LOC701867 | 3.08 | 0.1983 |
| MmugDNA.23270.1.S1_at | hypothetical protein FLJ32065 | FLJ32065 | 3.08 | 0.0304 |
| MmugDNA.41792.1.S1_at | keratinocyte associated protein 3 | KRTCAP3 | 3.08 | 0.0277 |
| MmugDNA.28683.1.S1_at | chromosome 9 open reading frame 39 | C9orf39 | 3.08 | 0.0154 |
| MmuSTS.4748.1.S1_at | ubiquitin specific protease 18 | USP18 | 3.08 | 0.1155 |
| MmugDNA.13548.1.S1_at | cytochrome c oxidase subunit Va | COX5A | 3.07 | 0.0790 |
| MmugDNA.30189.1.S1_at | hypothetical protein LOC283481 | LOC283481 | 3.07 | 0.2062 |
| MmugDNA.35491.1.S1_at | adult retina protein | LOC153222 | 3.07 | 0.0001 |
| MmugDNA.37253.1.S1_s_at | heterogeneous nuclear ribonucleoprotein D-like | HNRPDL | 3.07 | 0.0577 |
| MmugDNA.31553.1.S1_at | cofactor of BRCA1 | COBRA1 | 3.07 | 0.0232 |
| MmugDNA.25401.1.S1_at | abhydrolase domain containing 14B | ABHD14B | 3.07 | 0.0170 |
| MmuSTS.4318.1.S1_at | solute carrier family 36 (proton/amino acid symporter), member 4 | SLC36A4 | 3.07 | 0.1274 |
| MmuSTS.4037.1.S1_at | solute carrier family 41, member 2 | SLC41A2 | 3.07 | 0.1483 |
| MmugDNA.41507.1.S1_at | ATP-binding cassette, sub-family B (MDR/TAP), member 6 | ABCB6 | 3.06 | 0.0126 |
| MmugDNA.14233.1.S1_at | sperm specific antigen 2 | SSFA2 | 3.06 | 0.0120 |
| MmugDNA.34695.1.S1_at | Leucine rich repeat neuronal 6C | LRRN6C | 3.06 | 0.1945 |
| MmugDNA.39744.1.S1_at | zinc finger protein 609 | ZNF609 | 3.06 | 0.0160 |
| MmugDNA.4156.1.S1_at | ATPase, H+ transporting VO subunit E2-like (rat) | ATP6VOE2L | 3.06 | 0.0340 |
| MmugDNA.29456.1.S1_at | Breakpoint cluster region protein, uterine leiomyoma, 2 | WDR22 | 3.06 | 0.0131 |
| MmugDNA.4944.1.S1_at | tau tubulin kinase 1 | TTBK1 | 3.05 | 0.0548 |
| MmugDNA.22968.1.S1_at | — | — | 3.05 | 0.0531 |
| MmugDNA.42434.1.S1_at | N-acetylglucosaminidase, alpha- (Sanfilippo disease IIIB) | NAGLU | 3.05 | 0.0982 |
| MmugDNA.42291.1.S1_at | G protein-coupled receptor kinase 6 | GRK6 | 3.05 | 0.0293 |
| MmugDNA.121.1.S1_at | golgi SNAP receptor complex member 2 | GOSR2 | 3.05 | 0.0435 |
| MmugDNA.17630.1.S1_at | cell division cycle 40 homolog (S. cerevisiae) | CDC40 | 3.05 | 0.0398 |
| MmugDNA.30084.1.S1_at | — | — | 3.05 | 0.0012 |
| MmugDNA.33923.1.S1_at | chromosome 1 open reading frame 79 | C1orf79 | 3.05 | 0.0664 |
| MmugDNA.37503.1.S1_at | ets variant gene 7 (TEL2 oncogene) | ETV7 | 3.05 | 0.0228 |
| MmugDNA.15871.1.S1_at | BSD domain containing 1 | BSDC1 | 3.04 | 0.0107 |
| MmugDNA.32390.1.S1_at | dipeptidyl-peptidase 7 | DPP7 | 3.04 | 0.1328 |
| MmugDNA.41073.1.S1_at | Transcribed locus | — | 3.04 | 0.0000 |
| MmuSTS.2834.1.S1_at | solute carrier family 8 (sodium/calcium exchanger), member 3 | SLC8A3 | 3.04 | 0.0879 |
| MmugDNA.20734.1.S1_at | zinc finger and BTB domain containing 11 | ZBTB11 | 3.04 | 0.0326 |
| MmuSTS.247.1.S1_at | inositol polyphosphate-1-phosphatase | INPP1 | 3.04 | 0.0049 |
| MmugDNA.22134.1.S1_at | SIN3 homolog A, transcription regulator (yeast) | SIN3A | 3.04 | 0.0000 |
| MmugDNA.17708.1.S1_at | torsin A interacting protein 1 | TOR1AIP1 | 3.03 | 0.0001 |
| MmugDNA.42050.1.S1_at | — | — | 3.03 | 0.0980 |
| MmugDNA.30213.1.S1_at | zinc finger, MYM-type 5 | ZMYM5 | 3.03 | 0.0036 |
| MmugDNA.43311.1.S1_at | LDLR-FUT fusion protein (LDLR-FUT) | — | 3.02 | 0.1029 |
| MmugDNA.26409.1.S1_at | hypothetical protein LOC644242 /// hypothetical protein LOC650429 /// hypothetical protein LOC650446 | LOC644242 /// LOC650429 /// LOC650446 | 3.02 | 0.0510 |
| MmuSTS.59.1.S1_at | histone deacetylase 5 | HDAC5 | 3.02 | 0.0063 |
| MmugDNA.34663.1.S1_at | flavin containing monooxygenase 3 | FMO3 | 3.02 | 0.1292 |

-continued

| Probe Set ID | Gene Title | Gene Symbol | Ratio Top verus Bottom | p value Top versus Bottom |
|---|---|---|---|---|
| MmugDNA.40441.1.S1_at | CDNA clone IMAGE:5270500 | — | 3.02 | 0.1493 |
| MmuSTS.1202.1.S1_at | component of oligomeric golgi complex 7 | COG7 | 3.01 | 0.0056 |
| MmugDNA.33076.1.S1_at | Transcribed locus | — | 3.01 | 0.0492 |
| MmuSTS.658.1.S1_at | putative T1 /ST2 receptor binding protein | IL1RL1LG | 3.01 | 0.0153 |
| MmugDNA.26960.1.S1_at | WD repeats and SOF1 domain containing | WDSOF1 | 3.01 | 0.0000 |
| MmugDNA.24887.1.S1_at | tripartite motif-containing 2 | TRIM2 | 3.01 | 0.0073 |
| MmugDNA.26072.1.S1_at | active BCR-related gene | ABR | 3.01 | 0.0038 |
| MmugDNA.28188.1.S1_at | hypothetical gene supported by AK124342 | FLJ42351 | 3.01 | 0.0975 |
| MmugDNA.40888.1.S1_at | taurine upregulated gene 1 | TUG1 | 3.00 | 0.0221 |
| MmugDNA.39101.1.S1_at | — | — | 3.00 | 0.1428 |
| MmuSTS.4591.1.S1_at | thyroid hormone receptor, alpha | THRA | 3.00 | 0.0270 |
| MmugDNA.16168.1.S1_s_at | structural maintenance of chromosomes 3 | SMC3 | 3.00 | 0.0000 |
| MmugDNA.40670.1.S1_at | 3'(2'), 5'-bisphosphate nucleotidase 1 | BPNT1 | 3.00 | 0.0221 |
| MmuSTS.1100.1.S1_at | PAX transcription activation domain interacting protein 1 like | PAXIP1L | 3.00 | 0.0160 |
| MmugDNA.4318.1.S1_at | FLJ12716 protein | FLJ12716 | 3.00 | 0.0565 |
| MmugDNA.28833.1.S1_at | CDNA FLJ41690 fis, clone HCASM2009405 | — | 2.99 | 0.0293 |
| MmugDNA.28320.1.S1_at | CDNA clone IMAGE: 5259419 | — | 2.99 | 0.2149 |
| MmugDNA.19977.1.S1 _at | KIAA1217 | KIAA1217 | 2.99 | 0.0595 |
| MmunewRS.283.1.S1_at | NAD(P) dependent steroid dehydrogenase-like | HSPC105 | 2.99 | 0.1709 |
| MmuSTS.4337.1.S1_at | F-box only protein 25 | FBXO25 | 2.99 | 0.0969 |
| MmugDNA.42396.1.S1_at | germ cell-less | LOC701545 | 2.99 | 0.0783 |
| MmugDNA.23292.1.S1_at | Ras suppressor protein 1 | RSU1 | 2.99 | 0.0016 |
| MmugDNA.17188.1.S1_at | acyl-Coenzyme A dehydrogenase, C-2 to C-3 short chain | ACADS | 2.99 | 0.0453 |
| MmugDNA.8639.1.S1_at | DEAD (Asp-Glu-Ala-Asp) box polypeptide 21 | DDX21 | 2.99 | 0.0027 |
| MmugDNA.6559.1.S1_at | chromosome 9 open reading frame 119 | C9orf119 | 2.99 | 0.0393 |
| MmugDNA.41506.1.S1_at | ankyrin repeat and SOCS box-containing 6 | ASB6 | 2.99 | 0.0077 |
| MmugDNA.13579.1.S1_at | KIAA1712 | KIAA1712 | 2.99 | 0.0879 |
| MmugDNA.19830.1.S1_at | glycoprotein hormone alpha 2 | GPHA2 | 2.99 | 0.0280 |
| Mmu.3556.1.S1_s_at | family with sequence similarity 96, member A isoform a | LOC714217 | 2.98 | 0.0000 |
| MmugDNA.10102.1.S1_s_at | heat shock 70 kDa protein 8 | HSPA8 | 2.98 | 0.0043 |
| MmugDNA.4343.1.S1_at | hypothetical protein FLJ10241 | FLJ10241 | 2.98 | 0.0015 |
| MmugDNA.6426.1.S1_at | CD151 molecule (Raph blood group) | CD151 | 2.98 | 0.0338 |
| MmugDNA.27731.1.S1_at | MRNA from chromosome 5q21-22, clone:843Ex | — | 2.98 | 0.0000 |
| MmugDNA.33252.1.S1_at | protease, serine, 16 (thymus) | PRSS16 | 2.98 | 0.0020 |
| MmugDNA.20450.1.S1_at | chromosome 19 open reading frame 2 | Cl 9orf2 | 2.97 | 0.0001 |
| MmuSTS.3421.1.S1_at | claudin 3 | CLDN3 | 2.97 | 0.0204 |
| MmugDNA.26818.1.S1_at | methyltransferase like 4 | METTL4 | 2.97 | 0.0076 |
| MmugDNA.33099.1.S1_at | KIAA0423 | KIAA0423 | 2.97 | 0.0005 |
| MmuAffx.1252.1.A1 _at | protocadherin alpha (PCDH) mRNA, 3 prime UTR. | AY598414 | 2.96 | 0.1373 |
| MmugDNA.9975.1.S1_at | zinc finger protein 331 | ZNF331 | 2.95 | 0.0596 |
| MmugDNA.41468.1.S1_at | necdin-like 2 | NDNL2 | 2.95 | 0.0006 |
| MmugDNA.17362.1.S1_at | PTD016 protein | LOC51136 | 2.95 | 0.0267 |
| MmugDNA.43033.1.S1_at | HemK methyltransferase family member 2 | HEMK2 | 2.95 | 0.1934 |
| MmugDNA.29141.1.S1_at | UDP-glucose ceramide glucosyltransferase-like 1 | UGCGL1 | 2.95 | 0.0396 |
| MmugDNA.13178.1.S1_at | CDC14 cell division cycle 14 homolog B (S. cerevisiae) | CDC14B | 2.95 | 0.0382 |
| MmugDNA.26142.1.S1_at | coiled-coil domain containing 95 | CCDC95 | 2.95 | 0.0654 |
| MmugDNA.2882.1.S1_at | zinc finger CCCH-type containing 7B | ZC3H7B | 2.95 | 0.0351 |
| MmugDNA.22445.1.S1_at | Ubiquitin-conjugating enzyme E21 (UBC9 homolog, yeast) | UBE2I | 2.95 | 0.0079 |
| MmugDNA.5279.1.S1_at | transmembrane protein 33 | TMEM33 | 2.95 | 0.0097 |
| Mmu.1276.1.S1_at | serine protease inhibitor, Kunitz type, 2 | LOC714755 | 2.94 | 0.0663 |
| MmugDNA.43012.1.S1_at | chromosome 17 open reading frame 28 | C17orf28 | 2.94 | 0.0440 |
| MmuSTS.1982.1.S1_at | CD14 antigen | CD14 | 2.94 | 0.0049 |
| MmugDNA.41964.1.S1_at | hypothetical protein LOC646870 | LOC646870 | 2.94 | 0.0728 |
| MmugDNA.37306.1.S1_at | melanoma antigen family E, 1 | MAGEE1 | 2.94 | 0.0035 |
| MmugDNA.36805.1.S1_at | CDNA clone IMAGE: 5265020 | — | 2.93 | 0.0047 |
| MmugDNA.23752.1.S1_at | Hypothetical gene supported by AK126569 | 230404_at | 2.93 | 0.0014 |
| MmugDNA.7176.1.S1_at | zinc finger protein 508 | ZNF508 | 2.93 | 0.1404 |
| MmugDNA.15639.1.S1_s_at | nuclear distribution gene C homolog (A. nidulans) | NUDC | 2.93 | 0.1171 |
| MmugDNA.23645.1.S1_at | kinase insert domain receptor (a type III receptor tyrosine kinase) | KDR | 2.93 | 0.0526 |
| MmugDNA.28242.1.S1_at | G protein-coupled receptor 82 | GPR82 | 2.92 | 0.0520 |
| MmugDNA.26896.1.S1_at | hypothetical protein LOC285847 | LOC285847 | 2.92 | 0.1348 |
| MmugDNA.33291.1.S1_at | E74-like factor 2 (ets domain transcription factor) | ELF2 | 2.92 | 0.0090 |
| MmugDNA.1352.1.S1_at | 3-hydroxyisobutyryl-Coenzyme A hydrolase | HIBCH | 2.92 | 0.0317 |
| Mmu.14583.1.S1_at | Transcribed locus | — | 2.92 | 0.0000 |
| MmugDNA.23757.1.S1_at | high-mobility group protein 2-like 1 | HMG2L1 | 2.92 | 0.0821 |
| MmugDNA.3973.1.S1_at | TBP-interacting protein | TIP120A | 2.92 | 0.0295 |
| MmugDNA.20292.1.S1_at | breast cancer metastasis suppressor 1 | BRMS1 | 2.92 | 0.0411 |
| MmugDNA.28666.1.S1_at | palmdelphin | PALMD | 2.91 | 0.0451 |
| MmuSTS.2571.1.S1_at | ubiquitin specific peptidase 20 | USP20 | 2.91 | 0.0475 |
| MmugDNA.26331. .S1_at | Mitogen-activated protein kinase kinase kinase 13 | MAP3K13 | 2.91 | 0.0470 |
| MmugDNA.10238. .S1_at | testis expressed sequence 9 | TEX9 | 2.91 | 0.1328 |
| MmunewRS.102.1.S1_at | mRNA for KIAA1979 protein. | gi:18916872 | 2.90 | 0.1195 |
| MmuSTS.3241.1.S1_at | BCL2/adenovirus E1B 19 kDa interacting protein 1 | BNIP1 | 2.90 | 0.0091 |
| MmugDNA.1167.1.S1_at | pyrophosphatase (inorganic) 2 /// ring finger protein 36 | PPA2 /// RNF36 | 2.90 | 0.0008 |

-continued

| Probe Set ID | Gene Title | Gene Symbol | Ratio Top verus Bottom | p value Top versus Bottom |
|---|---|---|---|---|
| MmugDNA.2679.1.S1_at | small nuclear ribonucleoprotein polypeptide A' | SNRPA1 | 2.90 | 0.0215 |
| MmugDNA.29871. .S1_at | NADH dehydrogenase (ubiquinone) Fe-S protein 2, 49 kDa (NADH-coenzyme Q reductase) | NDUFS2 | 2.89 | 0.0192 |
| Mmu.4717.1.S1_at | ankyrin repeat and BTB (POZ) domain containing 1 isoform 2 | LOC710603 | 2.89 | 0.0439 |
| MmugDNA.20718.1.S1_at | heterogeneous nuclear ribonucleoprotein A3 pseudogene 1 /// heterogeneous nuclear ribonucleoprotein A3 | HNRPA3P1 /// HNRPA3 | 2.89 | 0.0013 |
| MmugDNA.28284.1.S1_at | GA binding protein transcription factor, alpha subunit 60 kDa | GABPA | 2.89 | 0.0000 |
| MmuSTS.4752.1.S1_at | vacuolar protein sorting 45 homolog (S. cerevisiae) | VPS45 | 2.89 | 0.0020 |
| MmugDNA.7814.1.S1_at | family with sequence similarity 120A | FAM120A | 2.89 | 0.0377 |
| MmugDNA.43320.1.S1_at | UDP-Gal:betaGlcNAc beta 1,3-galactosyltransferase, polypeptide 4 | B3GALT4 | 2.89 | 0.0379 |
| MmugDNA.38533.1.S1_at | CDNA FLJ11692 fis, clone HEMBA1004983 | — | 2.89 | 0.1672 |
| MmugDNA.37108.1.S1_at | Ribosomal protein L7-like 1 | RPL7L1 | 2.89 | 0.0294 |
| MmugDNA.43087.1.S1_at | choroideremia (Rab escort protein 1) /// hypothetical protein LOC642090 | CHM /// LOC642090 | 2.89 | 0.0003 |
| MmugDNA.37619.1.S1_at | serine/threonine/tyrosine interacting protein /// serine/threonine/tyrosine interacting protein | STYX /// LOC653890 | 2.89 | 0.0039 |
| MmugDNA.6995.1.S1_at | Heterogeneous nuclear ribonucleoprotein A0 | HNRPAO | 2.89 | 0.0419 |
| MmugDNA.33286.1.S1_at | centrosomal protein 57 kDa | CEP57 | 2.88 | 0.0039 |
| MmugDNA.7613.1.S1_at | vitelliform macular dystrophy 2 (Best disease, bestrophin) | VMD2 | 2.88 | 0.0211 |
| MmugDNA.41643.1.S1_at | TPTE and PTEN homologous inositol lipid phosphatase pseudogene /// TPTE and PTEN homologous inositol lipid phosphatase isoform gamma /// TPTE and PTEN homologous inositol lipid phosphatase isoform gamma | LOC374491 /// LOC642904 /// LOC649370 | 2.88 | 0.1625 |
| MmugDNA.17851.1.S1_at | NADH dehydrogenase (ubiquinone) 1, alpha/beta subcomplex, 1, 8 kDa | NDUFAB1 | 2.88 | 0.0718 |
| MmugDNA.35659.1.S1_at | chromosome 9 open reading frame 84 | C9orf84 | 2.88 | 0.1866 |
| MmuSTS.1608.1.S1_at | kelch-like 7 (Drosophila) | KLHL7 | 2.88 | 0.0008 |
| MmugDNA.20882.1.S1_at | hypothetical protein MGC61571 | MGC61571 | 2.88 | 0.0025 |
| MmugDNA.7201.1.S1_at | carboxypeptidase D | CPD | 2.87 | 0.0239 |
| MmugDNA.22156.1.S1_at | LOC166075 | LOC401097 | 2.87 | 0.0185 |
| MmugDNA.18427.1.S1_at | Keratin associated protein 5-11 | KRTAP5-11 | 2.87 | 0.0621 |
| MmugDNA.10502.1.S1_at | dehydrogenase/reductase (SDR family) member 13 | DHRS13 | 2.87 | 0.0613 |
| MmuSTS.2492.1.S1_at | zinc finger protein 509 | ZNF509 | 2.87 | 0.0312 |
| MmugDNA.33371.1.S1_at | chymotrypsin-like | CTRL | 2.87 | 0.0277 |
| MmugDNA.24978.1.S1_at | neuronal PAS domain protein 1 | NPAS1 | 2.87 | 0.1278 |
| MmugDNA.37408.1.S1_at | tyrosyl-tRNA synthetase 2 (mitochondrial) | YARS2 | 2.86 | 0.0023 |
| MmugDNA.27947.1.S1_at | FLJ45244 protein | FLJ45244 | 2.86 | 0.2182 |
| MmugDNA.38426.1.S1_at | KIAA0892 | KIAA0892 | 2.86 | 0.0020 |
| Mmu.12307.1.S1_at | KIAA1008 | KIAA1008 | 2.86 | 0.1271 |
| MmuSTS.534.1.S1_at | UDP-Gal:betaGlcNAc beta 1,4- galactosyltransferase, polypeptide | B4GALT2 | 2.86 | 0.1428 |
| MmugDNA.21102.1.S1_at | hypothetical protein LOC651803 | LOC651803 | 2.86 | 0.0893 |
| MmugDNA.25674.1.S1_at | potassium channel tetramerisation domain containing 14 | KCTD14 | 2.86 | 0.0286 |
| MmugDNA.11321.1.S1_at | FUN14 domain containing 1 | FUNDC1 | 2.86 | 0.0497 |
| MmugDNA.27909.1.S1_at | hypothetical protein FLJ20125 | FLJ20125 | 2.86 | 0.0288 |
| MmugDNA.41621.1.S1_at | tetratricopeptide repeat domain 30B | TTC3OB | 2.85 | 0.0837 |
| MmugDNA.22964.1.S1_at | Transcribed locus | — | 2.85 | 0.1242 |
| MmugDNA.32172.1.S1_at | haloacid dehalogenase-like hydrolase domain containing 2 | HDHD2 | 2.85 | 0.0025 |
| MmugDNA.33685.1.S1_at | chromosome X open reading frame 26 | CXorf26 | 2.85 | 0.0000 |
| MmuSTS.2187.1.S1_at | solute carrier family 41, member 3 | SLC41A3 | 2.85 | 0.0794 |
| MmuSTS.3436.1.S1_at | alpha-methylacyl-CoA racemase | AMACR | 2.85 | 0.0891 |
| MmuSTS.1512.1.S1_at | isoprenylcysteine carboxyl methyltransferase | ICMT | 2.84 | 0.0002 |
| MmuSTS.234.1.S1_at | chromosome 15 open reading frame 40 | C15orf40 | 2.84 | 0.0002 |
| MmunewRS.872.1.S1_at | otopetrin 1 | OTOP1 | 2.84 | 0.0322 |
| MmugDNA.28434.1.S1_at | TROVE domain family, member 2 | TROVE2 | 2.84 | 0.0136 |
| MmugDNA.18405.1.S1_s_at | Suppression of tumorigenicity 7 like | ST7L | 2.84 | 0.0768 |
| MmugDNA.32265.1.S1_at | chromosome 19 open reading frame 52 | C19orf52 | 2.84 | 0.0659 |
| MmugDNA.11590.1.S1_at | chromosome 1 open reading frame 165 | C1orf165 | 2.83 | 0.0087 |
| MmugDNA.12017.1.S1_at | fibronectin type III and ankyrin repeat domains 1 | FANK1 | 2.82 | 0.0001 |
| MmugDNA.8492.1.S1_at | chromosome 6 open reading frame 153 | C6orf153 | 2.82 | 0.0193 |
| MmugDNA.22105.1.S1_at | dynein, axonemal, light intermediate polypeptide 1 | DNALI1 | 2.82 | 0.0264 |
| Mmu.16365.1.S1_at | PRP4 pre-mRNA processing factor 4 homolog B (yeast) (predicted) | LOC709497 /// LOC710193 | 2.82 | 0.0238 |
| MmugDNA.42362.1.S1_at | ornithine decarboxylase antizyme 2 | OAZ2 | 2.82 | 0.0858 |
| MmugDNA.2230.1.S1_at | phosphatidylinositol 4-kinase, catalytic, alpha polypeptide | PIK4CA | 2.82 | 0.0002 |
| MmugDNA.23113.1.S1_at | Midline 2 | MID2 | 2.81 | 0.0018 |
| MmugDNA.9055.1.S1_at | multiple C2 domains, transmembrane 2 | MCTP2 | 2.81 | 0.1229 |
| MmugDNA.28806.1.S1_at | Zinc finger protein 284 | ZNF284 | 2.81 | 0.0754 |
| MmugDNA.6963.1.S1_at | tweety homolog 2 (Drosophila) | TTYH2 | 2.81 | 0.0997 |
| MmugDNA.24592.1.S1_at | CTD (carboxy-terminal domain, RNA polymerase II, polypeptide A) small phosphatase 2 | CTDSP2 | 2.81 | 0.1065 |
| MmugDNA.18857.1.S1_at | KIAA0467 | KIAA0467 | 2.81 | 0.0008 |
| MmugDNA.40098.1.S1_at | hypothetical protein LOCI 44363 | LOCI 44363 | 2.81 | 0.1331 |

-continued

| Probe Set ID | Gene Title | Gene Symbol | Ratio Top verus Bottom | p value Top versus Bottom |
|---|---|---|---|---|
| MmugDNA.23612.1.S1_at | Transcribed locus | — | 2.81 | 0.0728 |
| MmuSTS.1461.1.S1_at | mitogen-activated protein kinase kinase kinase kinase 3 | MAP4K3 | 2.81 | 0.0000 |
| MmuSTS.2022.1.S1_at | prostaglandin D2 synthase, hematopoietic | PGDS | 2.80 | 0.1324 |
| MmugDNA.21008.1.S1_at | ubiquitin specific peptidase 14 (tRNA-guanine transglycosylase) | USP14 | 2.80 | 0.0026 |
| MmugDNA.5481.1.S1_at | Full-length cDNA clone CSODF012YD09 of Fetal brain of Homo sapiens (human) | — | 2.80 | 0.0074 |
| MmuSTS.4011.1.S1_at | solute carrier family 35, member B3 | SLC35B3 | 2.80 | 0.0186 |
| MmugDNA.12978.1.S1_at | phosphoinositide-3-kinase, class 2, alpha polypeptide | PIK3C2A | 2.80 | 0.0138 |
| MmugDNA.25990.1.S1_at | coiled-coil domain containing 123 | CCDC123 | 2.79 | 0.1079 |
| MmugDNA.21323.1.S1_at | CDNA FLJ14181 fis, clone NT2RP2004300 | — | 2.79 | 0.1179 |
| MmugDNA.34194.1.S1_at | chromosome 6 open reading frame 120 | C6orf120 | 2.79 | 0.1196 |
| MmugDNA.1311.1.S1_at | hypothetical protein MGC26733 | MGC26733 | 2.79 | 0.0076 |
| MmugDNA.10629. .S1_at | translocase of inner mitochondrial membrane 17 homolog A (yeast) | TIMM17A | 2.79 | 0.0004 |
| MmugDNA.33991. .S1_at | CDNA: FLJ22539 fis, clone HRC13227 | — | 2.78 | 0.0066 |
| MmugDNA.20536.1.S1_at | transmembrane and tetratricopeptide repeat containing 3 | TMTC3 | 2.78 | 0.0230 |
| MmugDNA.6356.1.S1_at | chromosome 7 open reading frame 28A /// chromosome 7 open reading frame 28B | C7orf28A /// C7orf28B | 2.78 | 0.0024 |
| MmugDNA.6519.1.S1_at | WD repeat domain 39 | WDR39 | 2.78 | 0.0098 |
| MmugDNA.36685.1.S1_at | SET domain, bifurcated 2 | SETDB2 | 2.78 | 0.0199 |
| MmugDNA.22793.1.S1_s_at | tribbles homolog 2 (Drosophila) | TRIB2 | 2.78 | 0.1659 |
| MmugDNA.2623.1.S1_at | prefoldin subunit 4 | PFDN4 | 2.77 | 0.0015 |
| MmuSTS.421.1.S1_at | ORM1-like 3 (S. cerevisiae) | ORMDL3 | 2.77 | 0.0697 |
| MmugDNA.36435. .S1_s_at | histidyl-tRNA synthetase | HARS | 2.77 | 0.0220 |
| MmugDNA.39696. .S1_at | UTP15, U3 small nucleolar ribonucleoprotein, homolog (S. cerevisiae) | UTP15 | 2.77 | 0.1158 |
| MmugDNA.13739. .S1_at | sorting nexin 14 | SNX14 | 2.77 | 0.0059 |
| MmuSTS.1965.1.S _at | frequently rearranged in advanced T-cell lymphomas 2 | FRAT2 | 2.77 | 0.0258 |
| MmugDNA.18514. .S1_at | RNA (guanine-9-) methyltransferase domain containing 2 | RG9MTD2 | 2.77 | 0.0616 |
| MmugDNA.26813. .S1_at | MRNA; cDNA DKFZp762M127 (from clone DKFZp762M127) | — | 2.77 | 0.0023 |
| MmunewRS.1000. .S1_s_at | zinc finger protein 432 | ZNF432 | 2.76 | 0.1958 |
| MmugDNA.22282. .S1_at | WD repeat and FYVE domain containing 1 | WDFY1 | 2.76 | 0.1120 |
| MmuSTS.4631.1.S _at | vascular endothelial growth factor B | VEGFB | 2.76 | 0.0010 |
| MmugDNA.14574. .S1_at | dedicator of cytokinesis 5 | DOCKS | 2.76 | 0.0832 |
| MmugDNA.32208. .S1_at | katanin p80 (WD repeat containing) subunit B 1 | KATNB1 | 2.76 | 0.0202 |
| MmugDNA.7187.1.S1_at | splicing factor, arginine/serine-rich 4 | SFRS4 | 2.76 | 0.0061 |
| MmuSTS.1088.1.S _at | Solute carrier family 43, member 2 | SLC43A1 | 2.76 | 0.0585 |
| MmugDNA.4698.1.S1_at | calcium binding and coiled-coil domain 2 | CALCOCO2 | 2.76 | 0.0099 |
| MmugDNA.11372. .S1_at | Cysteine rich BMP regulator 2 (chordin-like) | CRIM2 | 2.76 | 0.1851 |
| MmugDNA.18070. .S1_at | Kruppel-like factor 9 | KLF9 | 2.76 | 0.0804 |
| MmugDNA.14499. .S1_at | zinc finger protein 596 | ZNF596 | 2.76 | 0.0833 |
| MmugDNA.40758. .S1_at | galactokinase 2 /// retinoblastoma binding protein 8GALK2 /// | RBBP8 | 2.76 | 0.0046 |
| MmugDNA.33141. .S1_at | nitrilase 1 | NIT1 | 2.75 | 0.0000 |
| MmugDNA.42186. .S1_at | hippocampus abundant transcript 1 | HIAT1 | 2.75 | 0.0086 |
| MmugDNA.4834.1.S1_at | aarF domain containing kinase 2 | ADCK2 | 2.75 | 0.0220 |
| MmugDNA.26458. .S1_at | Activating transcription factor 6 | ATF6 | 2.74 | 0.0017 |
| MmugDNA.2646.1.S1_at | atrophin 1 | ATN1 | 2.74 | 0.0001 |
| MmugDNA.40233. .S1_at | X-ray repair complementing defective repair in Chinese hamster cells 1 | XRCC1 | 2.74 | 0.1076 |
| MmugDNA.20861. .S1_at | spermatogenesis associated 13 | LOC721468 | 2.74 | 0.0177 |
| MmugDNA.12752. .S1_s_at | spastic paraplegia 20, spartin (Troyer syndrome) | SPG20 | 2.74 | 0.0000 |
| MmugDNA.41135. .S1_at | Colorectal cancer-related mRNA sequence | — | 2.74 | 0.1356 |
| MmuSTS.4719.1.S _at | tripartite motif-containing 6 | TRIM6 | 2.74 | 0.0029 |
| MmugDNA.4017.1.S1_at | — | — | 2.74 | 0.1313 |
| MmugDNA.27784.1.S1_at | — | — | 2.74 | 0.1942 |
| MmuSTS.4614.1.S1_at | tripartite motif-containing 4 | TRIM4 | 2.74 | 0.0305 |
| MmugDNA.8727.1.S1_at | t-complex 1 | TCP1 | 2.74 | 0.0457 |
| MmugDNA.638.1.S1_at | cytoskeleton associated protein 1 | CKAP1 | 2.74 | 0.1205 |
| MmugDNA.6338.1.S1_at | hypothetical protein FLJ20152 | FLJ20152 | 2.73 | 0.0006 |
| MmuSTS.2636.1.S1_at | family with sequence similarity 3, member A | FAM3A | 2.73 | 0.0019 |
| MmugDNA.33300.1.S1_at | WWC family member 3 | VVWC3 | 2.73 | 0.1279 |
| MmugDNA.18996.1.S1_at | elongation factor Tu GTP binding domain containing 2 | EFTUD2 | 2.73 | 0.0230 |
| MmugDNA.24045.1.S1_s_at | zinc finger protein 292 | ZNF292 | 2.73 | 0.1182 |
| MmugDNA.1299.1.S1_at | CLPTM1-like | CLPTM1L | 2.73 | 0.0121 |
| MmugDNA.22429.1.S1_at | family with sequence similarity 120B | FAM120B | 2.73 | 0.0002 |
| MmugDNA.13037.1.S1_at | chromosome 21 open reading frame 119 | C21orf119 | 2.72 | 0.0357 |
| MmugDNA.20321.1.S1_at | HIR histone cell cycle regulation defective homolog A (S. cerevisiae) | HIRA | 2.72 | 0.0018 |
| MmugDNA.42547.1.S1_at | histidyl-tRNA synthetase-like | HARSL | 2.72 | 0.0116 |
| MmugDNA.1760.1.S1_s_at | COP9 constitutive photomorphogenic homolog subunit 8 (Arabidopsis) | COPS8 | 2.72 | 0.0761 |
| MmugDNA.13758.1.S1_at | COMM domain containing 3 | COMMD3 | 2.72 | 0.0140 |
| MmuSTS.304.1.S1_at | single stranded DNA binding protein 3 | SSBP3 | 2.71 | 0.0862 |
| MmuSTS.2591.1.S1_at | Xenotropic and polytropic retrovirus receptor | XPR1 | 2.71 | 0.0029 |

-continued

| Probe Set ID | Gene Title | Gene Symbol | Ratio Top verus Bottom | p value Top versus Bottom |
|---|---|---|---|---|
| MmugDNA.33009.1.S1_at | zinc finger protein 700 | ZNF700 | 2.71 | 0.0451 |
| MmugDNA.1463.1.S1_s_at | proline rich 14 | PRR14 | 2.71 | 0.0339 |
| MmugDNA.35741.1.S1_at | coiled-coil-helix-coiled-coil-helix domain containing 6 /// coiled-coil-helix-coiled-coil-helix domain containing 6 | CHCHD6 | 2.71 | 0.0482 |
| MmugDNA.4692.1.S1_at | zinc finger RNA binding protein | ZFR | 2.71 | 0.0332 |
| MmugDNA.36934.1.S1_at | zinc finger protein 643 | ZNF643 | 2.71 | 0.1950 |
| MmugDNA.16923.1.S1_at | tumor necrosis factor receptor superfamily, member 13B | TNFRSF13B | 2.71 | 0.1291 |
| MmugDNA.15223.1.S1_at | hypothetical protein FLJ39061 | FLJ39061 | 2.70 | 0.0031 |
| MmuSTS.350.1.S1_at | spectrin repeat containing, nuclear envelope 1 | SYNE1 | 2.70 | 0.1061 |
| MmuSTS.246.1.S1_at | leucine rich repeat containing 42 | LRRC42 | 2.70 | 0.0007 |
| MmuSTS.2186.1.S1_at | zinc finger protein 354B | ZNF354B | 2.70 | 0.0677 |
| Mmu.12802.2.S1_at | chaperonin containing TCP1, subunit 2 | LOC717182 | 2.70 | 0.1220 |
| MmugDNA.6418.1.S1_at | zinc finger protein 83 | ZNF83 | 2.70 | 0.0013 |
| MmuSTS.528.1.S1_at | ATPase, Cu++ transporting, beta polypeptide (Wilson disease) | ATP7B | 2.70 | 0.0280 |
| MmuSTS.727.1.S1_at | cyclin M2 | CNNM2 | 2.70 | 0.1167 |
| MmugDNA.15549.1.S1_s_at | GDP-mannose 4,6-dehydratase | GMDS | 2.70 | 0.0006 |
| MmugDNA.8210.1.S1_at | PR domain containing 16 | PRDM16 | 2.70 | 0.1783 |
| MmuSTS.3743.1.S1_at | RAB26, member RAS onocogene family | RAB26 | 2.69 | 0.0289 |
| MmugDNA.6865.1.S1_at | Transcribed locus, moderately NP_689672.2 hypothetical protein MGC45438 [Homo sapiens] | — | 2.69 | 0.0231 |
| MmuSTS.2292.1.S1_at | protein phosphatase 1, regulatory (inhibitor) subunit 3 | FPPP1 R3F | 2.69 | 0.0001 |
| MmugDNA.34280.1.S1_at | KIAA0683 gene product | KIAA0683 | 2.69 | 0.0352 |
| MmugDNA.13838.1.S1_at | zinc finger protein 502 | ZNF502 | 2.69 | 0.0750 |
| MmuSTS.1404.1.S1_at | potassium inwardly-rectifying channel, subfamily J, member 6 | KCNJ6 | 2.69 | 0.1718 |
| MmugDNA.19168.1.S1_at | enhancer of mRNA decapping 4 | EDC4 | 2.69 | 0.0220 |
| MmugDNA.34757.1.S1_s_at | dynactin 6 | DCTN6 | 2.69 | 0.0000 |
| MmugDNA.8435.1.S1_at | proline synthetase co-transcribed homolog (bacterial) | PROSC | 2.69 | 0.0000 |
| MmugDNA.6197.1.S1_at | chromosome 4 open reading frame 24 | C4orf24 | 2.69 | 0.2130 |
| MmugDNA.3702.1.S1_at | CDNA FLJ46881 fis, clone UTERU3015647, moderately Embigin precursor | — | 2.69 | 0.0653 |
| MmugDNA.12591.1.S1_s_at | dendritic cell-derived ubiquitin-like protein | DC-UbP | 2.68 | 0.0503 |
| MmugDNA.11985.1.S1_at | asparagine-linked glycosylation 2 homolog (S. cerevisiae, alpha-1,3-mannosyltransferase) | ALG2 | 2.68 | 0.0105 |
| MmugDNA.25835.1.S1_at | Homo sapiens, clone IMAGE:4133122, mRNA | — | 2.68 | 0.0342 |
| MmuSTS.3979.1.S1_at | serum/glucocorticoid regulated kinase family, member 3 | SGK3 | 2.68 | 0.0238 |
| MmugDNA.9043.1.S1_at | ADP-ribosylation factor-like 6 interacting protein 2 | ARL6IP2 | 2.68 | 0.0814 |
| Mmu.7150.1.S1_at | Heterogeneous nuclear ribonucleoproteins A2/B1 (hnRNP A2 / hnRNP B1) | HNRPA2B1 | 2.68 | 0.0223 |
| MmugDNA.33865.1.S1_s_at | chromosome 20 open reading frame 7 /// chromosome 20 open reading frame 7 /// transmembrane protein 14B /// transmembrane protein 14B | C20orf7 /// TMEM14B | 2.67 | 0.0426 |
| MmugDNA.3820.1.S1_at | clathrin, light polypeptide (Lcb) | CLTB | 2.67 | 0.2188 |
| MmugDNA.30567.1.S1_at | hypothetical protein BC014011 | LOC116349 | 2.67 | 0.0466 |
| MmugDNA.40707.1.S1_at | zinc finger, X-linked, duplicated B | ZXDB | 2.66 | 0.0300 |
| MmugDNA.43058.1.S1_at | kinesin family member 13A | KIF13A | 2.66 | 0.1629 |
| MmuSTS.4168.1.S1_at | M-phase phosphoprotein 6 | MPHOSPH9 | 2.66 | 0.0283 |
| MmugDNA.3585.1.S1_at | — | — | 2.66 | 0.1649 |
| MmugDNA.37285.1.S1_at | mitochondrial GTPase 1 homolog (S. cerevisiae) | MTG1 | 2.66 | 0.0492 |
| MmugDNA.25292.1.S1_at | jagunal homolog 1 (Drosophila) | JAGN1 | 2.66 | 0.0199 |
| MmugDNA.9421.1.S1_at | mannose-6-phosphate receptor (cation dependent) | M6PR | 2.66 | 0.0305 |
| MmugDNA.18308.1.S1_at | poliovirus receptor-related 2 (herpesvirus entry mediator B) | PVRL2 | 2.65 | 0.1122 |
| MmugDNA.20905.1.S1_at | Chromosome 13 open reading frame 10 | C13orf10 | 2.65 | 0.0168 |
| MmugDNA.34704.1.S1_at | pecanex homolog (Drosophila) | PCNX | 2.65 | 0.1063 |
| MmugDNA.12760.1.S1_at | Fibroblast growth factor 14 | FGF14 | 2.65 | 0.0872 |
| MmugDNA.43498.1.S1_at | NmrA-like family domain containing 1 | NMRAL1 | 2.65 | 0.0479 |
| MmugDNA.21653.1.S1_at | hypothetical protein FLJ30596 | FLJ30596 | 2.65 | 0.0681 |
| MmugDNA.14752.1.S1_at | MRNA; cDNA DKFZp547E193 (from clone DKFZp547E193) | — | 2.65 | 0.1773 |
| MmuSTS.4276.1.S1_at | SREBF chaperone | SCAP | 2.64 | 0.0005 |
| MmugDNA.8363.1.S1_at | tyrosyl-DNA phosphodiesterase 1 | TDP1 | 2.64 | 0.1058 |
| MmugDNA.34065.1.S1_at | uncharacterized hematopoietic stem/progenitor cells protein MDS032 | MDS032 | 2.64 | 0.0254 |
| MmunewRS.641.1.S1_at | selenoprotein S | SELS | 2.64 | 0.0693 |
| MmugDNA.7596.1.S1_at | — | — | 2.64 | 0.2105 |
| MmugDNA.3465.1.S1_at | Full-length cDNA clone CSODI027YJ20 of Placenta Cot 25-normalized of Homo sapiens (human) | — | 2.64 | 0.1052 |
| MmugDNA.13992.1.S1_at | Leo1, Paf1/RNA polymerase II complex component, homolog (S. cerevisiae) | LEO1 | 2.64 | 0.0000 |
| MmugDNA.14603.1.S1_at | bicaudal D homolog 1 (Drosophila) | BICD1 | 2.64 | 0.0314 |
| Mmu.2724.1.S1_at | glutamate dehydrogenase 1 | GLUD1 | 2.63 | 0.0345 |
| MmugDNA.26006.1.S1_at | hypothetical protein MGC16169 | MGC16169 | 2.63 | 0.1844 |
| MmugDNA.34293.1.S1_at | UDP-Gal:betaGlcNAc beta 1,4- galactosyltransferase, polypeptide 5 | B4GALT5 | 2.63 | 0.0018 |
| MmugDNA.5213.1.S1_at | Spleen tyrosine kinase | SYK | 2.63 | 0.0169 |
| MmugDNA.26186.1.S1_at | ankyrin repeat and IBR domain containing 1 | ANKIB1 | 2.63 | 0.0499 |

-continued

| Probe Set ID | Gene Title | Gene Symbol | Ratio Top verus Bottom | p value Top versus Bottom |
|---|---|---|---|---|
| MmugDNA.30722.1.S1_at | tetratricopeptide repeat domain 12 | TTC12 | 2.63 | 0.1383 |
| MmugDNA.20572.1.S1_at | trafficking protein particle complex 6A | TRAPPC6A | 2.63 | 0.1754 |
| MmuSTS.645.1.S1_at | Charcot-Marie-Tooth neuropathy 4B2 (autosomal recessive, with my, in outfolding) | CMT4B2 | 2.63 | 0.0754 |
| MmugDNA.12020.1.S1_at | YTH domain family, member 3 | YTHDF3 | 2.63 | 0.1578 |
| MmugDNA.23364.1.S1_at | Transcribed locus, strongly XP_515572.1 PREDICTED: hypothetical protein XP_515572 [Pan troglodytes] | — | 2.63 | 0.1417 |
| MmugDNA.3150.1.S1_s_at | Cdc42 guanine nucleotide exchange factor (GEF) 9 | ARHGEF9 | 2.63 | 0.0380 |
| MmugDNA.26131.1.S1_at | Nuclear transcription factor, X-box binding-like 1 | NFXL1 | 2.62 | 0.0005 |
| MmugDNA.23082.1.S1_at | nudix (nucleoside diphosphate linked moiety X)-type motif 14 | NUDT14 | 2.62 | 0.0487 |
| MmugDNA.33074.1.S1_at | Transcribed locus, strongly XP_068632.2 PREDICTED: hypothetical protein XP_068632 sapiens+ | — | 2.62 | 0.0003 |
| MmugDNA.30447.1.S1_at | Hermansky-Pudlak syndrome 6 | HPS6 | 2.62 | 0.0431 |
| MmugDNA.37520.1.S1_at | chromosome 1 open reading frame 66 | C1orf66 | 2.62 | 0.0280 |
| MmuSTS.4696.1.S1_at | alanyl-tRNA synthetase | AARS | 2.62 | 0.0110 |
| Mmu.1900.1.S1_s_at | H3 histone, family 3B | LOC693887 /// LOC693939 /// LOC694152 /// LOC695663 /// LOC699443 /// LOC702881 /// LOC707040 /// LOC708847 /// LOC708899 /// LOC709296 /// LOC710748 /// LOC718673 | 2.62 | 0.0092 |
| MmugDNA.3450.1.S1_at | signal recognition particle receptor (docking protein') | SRPR | 2.62 | 0.0000 |
| MmugDNA.20613.1.S1_at | CSL-type zinc finger-containing protein 2 (DeIGEF-interacting protein 1) (DeIGIP1) | ZCSL2 | 2.61 | 0.0000 |
| MmugDNA.26173.1.S1_at | LOC440133 | LOC440133 | 2.61 | 0.1688 |
| MmugDNA.15693.1.S1_at | acyl-Coenzyme A dehydrogenase family, member 11 | ACAD11 | 2.61 | 0.1017 |
| Mmu.14509.2.S1_at | cytosolic malate dehydrogenase | MDH1 | 2.61 | 0.0408 |
| Mmu.967.1.S1_s_at | N-acetylated alpha-linked acidic dipeptidase 2 | — | 2.61 | 0.0338 |
| MmugDNA.33096.1.S1_s_at | coiled-coil domain containing 47 | CCDC47 | 2.61 | 0.0002 |
| MmugDNA.43345.1.S1_at | Family with sequence similarity 98, member B | FAM98B | 2.61 | 0.0000 |
| MmugDNA.20494.1.S1_at | Ewing sarcoma breakpoint region 1 | EWSR1 | 2.61 | 0.0040 |
| MmugDNA.901.1.S1_at | — | — | 2.61 | 0.1627 |
| MmugDNA.18015.1.S1_at | major histocompatibility complex, class II, DM beta /// major histocompatibility complex, class II, DM beta | HLA-DMB | 2.61 | 0.1120 |
| MmugDNA.18688.1.S1_at | FLJ32363 protein | FLJ32363 | 2.61 | 0.1221 |
| MmugDNA.40426.1.S1_at | chromosome 20 open reading frame 42 | C20orf42 | 2.61 | 0.0017 |
| MmugDNA.17109.1.S1_at | zinc finger protein 570 | ZNF570 | 2.61 | 0.0031 |
| MmuSTS.448.1.S1_at | piggyBac transposable element derived 2 | PGBD2 | 2.60 | 0.0847 |
| MmuSTS.2213.1.S1_at | lysosomal trafficking regulator | LYST | 2.60 | 0.0532 |
| MmugDNA.41077.1.S1_at | chromosome 11 open reading frame 10 | C11orf10 | 2.60 | 0.0723 |
| MmugDNA.7760.1.S1_at | Transcribed locus, strongly XP_498525.1 PREDICTED: hypothetical protein XP_498525 [Homo sapiens] | — | 2.60 | 0.0044 |
| MmugDNA.14575.1.S1_at | hypothetical protein FLJ32810 | FLJ32810 | 2.60 | 0.0347 |

The invention claimed is:

1. A method of isolating T1R3 expressing cells comprising:

(i) contacting an impure population of cells containing taste cells with a probe that specifically detects taste cells which express GPR113;

(ii) separating the detected GPR113 expressing taste cells from the impure cell population;

(iii) further detecting among the GPR113 expressing taste cells a subpopulation of taste cells that further express T1R3; and (iv) isolating said subpopulation of taste cells which express both GPR113 and T1R3.

2. The method of claim 1, wherein said isolated cells further express TRPM5.

3. The method of claim 1, wherein said taste cells are immature.

4. The method of claim 1, wherein said detected cells are separated by FACS or magnetic bead cell separation.

5. The method of claim 1, wherein said taste cells are human or macaque taste cells.

6. A purified taste cell population, wherein the purified taste cells all express GPR113 and T1R3.

7. The purified cell population of claim 6, wherein said isolated cells further express TRPM5.

8. The purified cell population of claim 6, wherein said taste cells are immature.

9. The purified cell population of claim 6, wherein purified taste cells are human or macaque taste cells.

* * * * *